US012662467B2

(12) United States Patent
Erdman et al.

(10) Patent No.: US 12,662,467 B2
(45) Date of Patent: Jun. 23, 2026

(54) ISOINDOLINONES, PHARMACEUTICAL COMPOSITIONS, AND THERAPEUTIC APPLICATIONS

(71) Applicant: BioTheryX, Inc., San Diego, CA (US)

(72) Inventors: Paul E. Erdman, San Diego, CA (US); Patrick Papa, Carlsbad, CA (US); Brandon W. Whitefield, San Diego, CA (US)

(73) Assignee: BioThery X, Inc., San Diego, CA (US)

( * ) Notice: Subject to any disclaimer, the term of this patent is extended or adjusted under 35 U.S.C. 154(b) by 0 days.

(21) Appl. No.: 18/302,787

(22) Filed: Apr. 19, 2023

(65) Prior Publication Data

US 2023/0339904 A1 Oct. 26, 2023

Related U.S. Application Data

(60) Provisional application No. 63/363,177, filed on Apr. 18, 2022.

(51) Int. Cl.

| | |
|---|---|
| ***C07D 401/14*** | (2006.01) |
| ***C07D 405/14*** | (2006.01) |
| ***C07D 409/14*** | (2006.01) |
| ***C07D 413/14*** | (2006.01) |
| ***C07D 417/14*** | (2006.01) |
| ***C07D 471/04*** | (2006.01) |
| ***C07D 471/10*** | (2006.01) |
| ***C07D 487/04*** | (2006.01) |
| ***C07D 491/052*** | (2006.01) |
| ***C07D 495/04*** | (2006.01) |
| ***C07D 498/04*** | (2006.01) |

(52) U.S. Cl.

CPC ......... *C07D 401/14* (2013.01); *C07D 405/14* (2013.01); *C07D 409/14* (2013.01); *C07D 413/14* (2013.01); *C07D 417/14* (2013.01); *C07D 471/04* (2013.01); *C07D 471/10* (2013.01); *C07D 487/04* (2013.01); *C07D 491/052* (2013.01); *C07D 495/04* (2013.01); *C07D 498/04* (2013.01)

(58) Field of Classification Search

CPC .. C07D 401/14; C07D 405/14; C07D 409/14; C07D 413/14; C07D 417/14; C07D 471/04; C07D 471/10; C07D 487/04; C07D 491/052; C07D 495/04; C07D 498/04

See application file for complete search history.

(56) References Cited

U.S. PATENT DOCUMENTS

| | | | |
|---|---|---|---|
| 9,822,098 | B2 | 11/2017 | Chan et al. |
| 10,040,804 | B2 | 8/2018 | Chan et al. |
| 10,144,745 | B2 | 12/2018 | Chan et al. |
| 10,406,165 | B2 | 9/2019 | Chan et al. |
| 10,513,515 | B2 | 12/2019 | Chan et al. |
| 10,584,133 | B2 | 3/2020 | Chan et al. |
| 10,723,717 | B2 | 7/2020 | Crew et al. |
| 10,844,039 | B2 | 11/2020 | Chan et al. |
| 10,905,684 | B2 | 2/2021 | Chan et al. |
| 11,191,769 | B2 | 12/2021 | Chan et al. |
| 11,197,877 | B2 | 12/2021 | Magnani et al. |
| 11,345,712 | B2 | 5/2022 | Chan et al. |
| 2009/0156575 | A1 | 6/2009 | Borjesson et al. |
| 2018/0099940 | A1 | 4/2018 | Crew et al. |
| 2018/0155322 | A1 | 6/2018 | Crew et al. |
| 2018/0237418 | A1 | 8/2018 | Crew et al. |
| 2020/0048277 | A1 | 2/2020 | Chan et al. |
| 2020/0129627 | A1 | 4/2020 | Crew et al. |
| 2021/0087170 | A1 | 3/2021 | Fan et al. |
| 2021/0087171 | A1 | 3/2021 | Fan et al. |

FOREIGN PATENT DOCUMENTS

| | | | |
|---|---|---|---|
| CN | 113620931 | A | 11/2021 |
| WO | 2018119448 | A1 | 6/2018 |
| WO | 2019173224 | A1 | 9/2019 |
| WO | 2020023782 | A1 | 1/2020 |
| WO | 2020160196 | A1 | 8/2020 |
| WO | 2020165834 | A1 | 8/2020 |
| WO | 2020211822 | A1 | 10/2020 |
| WO | 2021011913 | A1 | 1/2021 |

(Continued)

OTHER PUBLICATIONS

Elmore The Use of Isotopically Labeled Compounds in Drug Discovery, Annual Reports in Medicinal Chemistry, vol. 44, 515-534 (Year: 2009).*

(Continued)

*Primary Examiner* — Bruck Kifle
*Assistant Examiner* — Kevin S Martin
(74) *Attorney, Agent, or Firm* — Lin Yu; Juniv LLP

(57) ABSTRACT

Provided herein are isoindolinones, e.g., a compound of Formula (I), and pharmaceutical compositions thereof. Also provided herein are methods of their use for treating, preventing, or ameliorating one or more symptoms of a disorder, disease, or condition mediated by a zinc-figure protein, casein kinase 1α, GSPT1, or PDE6D.

(I)

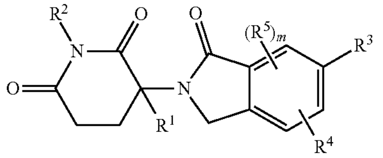

23 Claims, No Drawings

(56) References Cited

FOREIGN PATENT DOCUMENTS

| | | | | | |
|---|---|---|---|---|---|
| WO | 2021051034 | A1 | | 3/2021 | |
| WO | 2021055756 | A1 | | 3/2021 | |
| WO | 2021058017 | A1 | | 4/2021 | |
| WO | 2021061204 | A1 | | 4/2021 | |
| WO | 2021091575 | A1 | | 5/2021 | |
| WO | 2021118629 | A1 | | 6/2021 | |
| WO | 2021119571 | A1 | | 6/2021 | |
| WO | 2021133886 | A1 | | 7/2021 | |
| WO | 2021143822 | A1 | | 7/2021 | |
| WO | 2021155050 | A1 | | 8/2021 | |
| WO | 2021194878 | A1 | | 9/2021 | |
| WO | 2021195481 | A1 | | 9/2021 | |
| WO | 2021231174 | A1 | | 11/2021 | |
| WO | WO-2022025880 | A1 | * | 2/2022 | ............. A61K 47/55 |
| WO | WO-2022221673 | A1 | * | 10/2022 | ............. A61K 45/06 |

OTHER PUBLICATIONS

Bundgaard, Design of Prodrugs, 1985, CH 1 (Year: 1985) (Year: 1985).*

Di Martino RMC, Maxwell BD, Pirali T. Deuterium in drug discovery: progress, opportunities and challenges. Nat Rev Drug Discov. Jul. 2023;22(7):562-584. doi: 10.1038/s41573-023-00703-8. Epub Jun. 5, 2023. PMID: 37277503; PMCID: PMC10241557. (Year: 2023) (Year: 2023).*

Berge et al., "Pharmaceutical salts," J. Pharm. Sci. 1977, 66, 1-19.

Dong et al., "Molecular glues for targeted protein degradation: From serendipity to rational discovery," J. Med. Chem. 2021, 64, 10606-20.

Edmondson et al., "Proteolysis targeting chimeras (PROTACs) in 'beyond rule-of-five' chemical space: Recent progress and future challenges," Bioorg. Med. Chem. Lett. 2019, 29, 1555-64.

Faust et al., "Small-molecule approaches to targeted protein degradation," Ann. Rev. Cancer Biol. 2021, 5, 181-201.

Kozicka and Thoma, "Haven't got a glue: Protein surface variation for the design of molecular glue degraders," Cell Chem. Biol. 2021, 28, 1032-47.

Kronke et al., "Lenalidomide causes selective degradation of IKZF1 and IKZF3 in multiple myeloma cells," Science 2014, 343, 301-5.

Schreiber "The rise of molecular glues," Cell 2020, 184, 3-9.

St-Cyr et al., "Identification and optimization of molecular glue compounds that inhibit a noncovalent E2 enzyme-ubiquitin complex," Sci. Adv. 2021, 7, eabi5797.

Dorel et al., "The Buchwald-Hartwig amination after 25 years," Angew. Chem. Int. Ed. 2019, 58, 17118-29.

Hayhow et al., "A Buchwald-Hartwig protocol to enable rapid Linker explorationof cereblon E3-ligase PROTACs," Chem. Eur. J. 2020, 26, 16818-23.

Ruiz-Castillo and Buchwald, "Applications of palladium-catalyzed C—N cross-coupling reactions," Chem. Rev. 2016, 116, 12564-649, including Supporting Information.

* cited by examiner

ISOINDOLINONES, PHARMACEUTICAL COMPOSITIONS, AND THERAPEUTIC APPLICATIONS

CROSS REFERENCE TO RELATED APPLICATIONS

This application claims the benefit of the priority of U.S. Provisional Application Nos. 63/363,177, filed Apr. 18, 2022; the disclosure of each of which is incorporated herein by reference in its entirety.

FIELD

Provided herein are isoindolinones and pharmaceutical compositions thereof. Also provided herein are methods of their use for treating, preventing, or ameliorating one or more symptoms of a disorder, disease, or condition mediated by a zinc-figure protein, casein kinase 1α, GSPT1, or PDE6D.

BACKGROUND

Molecular glues are monovalent compounds that bind simultaneously two distinct proteins, e.g., a ubiquitin ligase and a target protein, leading to the ubiquitination and subsequent proteasome-based degradation of the target protein. Schreiber *Cell* 2020, 184, 3-9; Kozicka and Thoma, *Cell Chem. Biol.* 2021, 28, 1032-47; Faust et al., *Ann. Rev. Cancer Biol.* 2021, 5, 181-201. Revlimid (lenalidomide), one of the most successful anticancer drugs, is a molecular glue. Kronke et al., *Science* 2014, 343, 301-5. Molecular glues have several advantages over traditional small-molecule enzyme inhibitors or receptor antagonists. Dong et al., *J. Med. Chem.* 2021, 64, 10606-20. Mechanistically, molecular glues drive target ubiquitination and degradation in a substoichiometric and catalytic manner. Id. As they do not require a druggable pocket on the target protein, molecular glues are able to degrade a therapeutic target that is intractable by conventional approaches. Id.

Molecular glues are distinctly different from proteolysis targeting chimeras (PROTACs). While PROTACs are bifunctional molecules—chimeras having two moieties connected together by a linker, molecular glues are monovalent small molecules that act as adhesives to bring two proteins together. These linker-based bifunctional PROTACs generally have high molecular weight (MW), poor cellular permeability, and unfavorable pharmacokinetic (PK) profiles. Edmondson et al., *Bioorg. Med. Chem. Lett.* 2019, 29, 1555-64. The physicochemical properties of molecular glues are similar to those of traditional small-molecule drugs. Thus, molecular glues generally possess more favorable drug-like properties, such as lower MW, higher cell permeability, and better oral absorption. Therefore, molecular glues offer an attractive approach to drug discovery in targeted protein degradation.

SUMMARY OF THE DISCLOSURE

Provided herein is a compound of Formula (I):

(I)

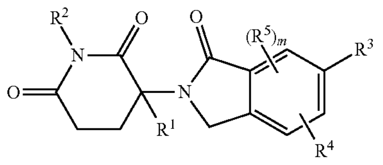

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein:

$R^1$ is hydrogen, deuterium, or $C_{1-6}$ alkyl;

$R^2$ is hydrogen or $C_{1-6}$ alkyl;

$R^3$ and $R^4$ are:

(i) $R^3$ is halo; and $R^4$ is

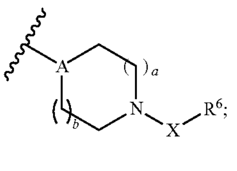

or (ii) $R^3$ is hydrogen, deuterium, or halo; and $R^4$ is

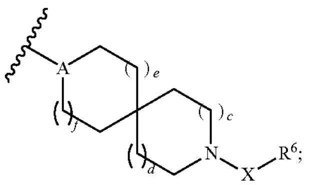

each $R^5$ is independently (i) deuterium, cyano, halo, or nitro; (ii) $C_{1-6}$ alkyl, $C_{1-6}$ heteroalkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (iii) $—C(O)R^{1a}$, $—C(O)OR^{1a}$, $—C(O)NR^{1b}R^{1c}$, $—C(O)SR^{1a}$, $—C(NR^{1a})NR^{1b}R^{1c}$, $—C(S)R^{1a}$, $—C(S)OR^{1a}$, $—C(S)NR^{1b}R^{1c}$, $—OR^{1a}$, $—OC(O)R^{1a}$, $—OC(O)OR^{1a}$, $—OC(O)NR^{1b}R^{1c}$, $—OC(O)SR^{1a}$, $—OC(NR^{1a})NR^{1b}R^{1c}$, $—OC(S)R^{1a}$, $—OC(S)OR^{1a}$, $—OC(S)NR^{1b}R^{1c}$, $—OS(O)R^{1a}$, $—OS(O)_2R^{1a}$, $—OS(O)NR^{1b}R^{1c}$, $—OS(O)_2NR^{1b}R^{1c}$, $—R^{1b}R^{1c}$, $—NR^{1a}C(O)R^{1d}$, $—NR^{1a}C(O)OR^{1d}$, $—NR^{1a}C(O)NR^{1b}R^{1c}$, $—NR^{1a}C(O)SR^{1d}$, $—NR^{1a}C(NR^{1d})NR^{1b}R^{1c}$, $—NR^{1a}C(S)R^{1d}$, $—NR^{1a}C(S)OR^{1d}$, $—NR^{1a}C(S)NR^{1b}R^{1c}$, $—NR^{1a}S(O)R^{1d}$, $—NR^{1a}S(O)_2R^{1d}$, $—NR^{1a}S(O)NR^{1b}R^{1c}$, $—NR^{1a}S(O)_2NR^{1b}R^{1c}$, $—SR^{1a}$, $—S(O)R^{1a}$, $—S(O)_2R^{1a}$, $—S(O)NR^{1b}R^{1c}$, or $—S(O)_2NR^{1b}R^{1c}$;

each $R^6$ is independently $C_{1-6}$ alkyl, $C_{1-6}$ heteroalkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl;

each $R^{1a}$, $R^{1b}$, $R^{1c}$, and $R^{1d}$ is independently hydrogen, deuterium, $C_{1-6}$ alkyl, $C_{1-6}$ heteroalkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl;

each A is independently $CR^{4a}$ or N; wherein $R^{4a}$ is hydrogen, deuterium, halo, $C_{1-6}$ alkyl, or $C_{1-6}$ heteroalkyl;

each X is independently $—(CH_2)_n—$, $—C(O)—$, $—S(O)—$, or $—S(O_2)—$; wherein n is an integer of 1, 2, 3, 4, or 5;

each a, b, c, d, e, and f is independently an integer of 0, 1, 2, or 3; and m is an integer of 0, 1, 2, or 3;

wherein each alkyl, heteroalkyl, alkenyl, alkynyl, cycloalkyl, aryl, aralkyl, heteroaryl, and heterocyclyl is optionally substituted with one or more, in one embodiment, one, two, three, or four, substituents Q, wherein each Q is independently selected from: (a) deuterium, cyano, halo, imino, nitro, and oxo; (b) $C_{1-6}$ alkyl, $C_{1-6}$ heteroalkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl, each of which is further optionally substituted with one or more, in one embodiment, one, two, three, or four, substituents $Q^a$; and (c) —C(O)$R^a$, —C(O)O$R^a$, —C(O)N$R^bR^c$, —C(O)S$R^a$, —C(N$R^a$)N$R^bR^c$, —C(S)$R^a$, —C(S)O$R^a$, —C(S)N$R^bR^c$, —O$R^a$, —OC(O)$R^a$, —OC(O)O$R^a$, —OC(O)N$R^bR^c$, —OC(O)S$R^a$, —OC(N$R^a$)N$R^bR^c$, —OC(S)$R^a$, —OC(S)O$R^a$, —OC(S)N$R^bR^c$, —OP(O)(O$R^b$)O$R^c$, —OS(O)$R^a$, —OS$(O)_2R^a$, —OS(O)N$R^bR^c$, —OS$(O)_2$N$R^bR^c$, —N$R^bR^c$, —N$R^a$C(O)$R^d$, —N$R^a$C(O)O$R^d$, —N$R^a$C(O)N$R^bR^c$, —N$R^a$C(O)S$R^d$, —N$R^a$C(N$R^d$)N$R^b$, —N$R^a$C(S)$R^d$, —N$R^a$C(S)O$R^d$, —N$R^a$C(S)N$R^bR^c$, —N$R^a$S(O)$R^d$, —N$R^a$S$(O)_2R^d$, —N$R^a$S(O)N$R^bR^c$, —N$R^a$S$(O)_2$N$R^bR^c$, —S$R^a$, —S(O)$R^a$, —S$(O)_2R^a$, —S(O)N$R^bR^c$, and —S$(O)_2$N$R^bR^c$, wherein each $R^a$, $R^b$, $R^c$, and $R^d$ is independently (i) hydrogen or deuterium; (ii) $C_{1-6}$ alkyl, $C_{1-6}$ heteroalkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more, in one embodiment, one, two, three, or four, substituents $Q^a$; or (iii) $R^b$ and $R^c$ together with the N atom to which they are attached form heterocyclyl, optionally substituted with one or more, in one embodiment, one, two, three, or four, substituents $Q^a$;

wherein each $Q^a$ is independently selected from: (a) deuterium, cyano, halo, nitro, imino, and oxo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl; and (c) —C(O)$R^e$, —C(O)O$R^e$, —C(O)N$R^fR^g$, —C(O)S$R^e$, —C(N$R^e$)N$R^fR^g$, —C(S)$R^e$, —C(S)O$R^e$, —C(S)N$R^fR^g$, —O$R^e$, —OC(O)$R^e$, —OC(O)O$R^e$, —OC(O)N$R^fR^g$, —OC(O)S$R^e$, —OC(N$R^e$)N$R^fR^g$, —OC(S)$R^e$, —OC(S)O$R^e$, —OC(S)N$R^fR^g$, —OP(O)(O$R^f$)O$R^g$, —OS(O)$R^e$, —OS$(O)_2R^e$, —OS(O)N$R^fR^g$, —OS$(O)_2$N$R^fR^g$, —N$R^fR^g$, —N$R^e$C(O)$R^h$, —N$R^e$C(O)O$R^f$, —N$R^e$C(O)N$R^fR^g$, —N$R^e$C(O)S$R^f$, —N$R^e$C(N$R^h$)N$R^fR^g$, —N$R^e$C(S)$R^h$, —N$R^e$C(S)O$R^f$, —N$R^e$C(S)N$R^fR^g$, —N$R^e$S(O)$R^h$, —N$R^e$S$(O)_2R^h$, —N$R^e$S(O)N$R^fR^g$, —N$R^e$S$(O)_2$N$R^fR^g$, —S$R^e$, —S(O)$R^e$, —S$(O)_2R^e$, —S(O)N$R^fR^g$, and —S$(O)_2$N$R^fR^g$; wherein each $R^e$, $R^f$, $R^g$, and $R^h$ is independently (i) hydrogen or deuterium; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (iii) $R^f$ and $R^g$ together with the N atom to which they are attached form heterocyclyl.

Also provided herein is a pharmaceutical composition comprising a compound of Formula (I), or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and a pharmaceutically acceptable excipient.

Additionally, provided herein is a method of treating, preventing, or ameliorating one or more symptoms of a disorder, disease, or condition mediated by a zinc-figure protein, CK1α, GSPT1, and/or PDE6D in a subject, comprising administering to the subject in need thereof a therapeutically effective amount of a compound of Formula (I), or an enantiomer, a mixture of enantiomers, a diastereomer, a mixture of two or more diastereomers, a tautomer, a mixture of two or more tautomers, or an isotopic variant thereof, or a pharmaceutically acceptable salt, solvate, hydrate, or prodrug thereof.

Furthermore provided herein is a method of treating, preventing, or ameliorating one or more symptoms of a proliferative disease in a subject, comprising administering to the subject in need thereof a therapeutically effective amount of a compound of Formula (I), or an enantiomer, a mixture of enantiomers, a diastereomer, a mixture of two or more diastereomers, a tautomer, a mixture of two or more tautomers, or an isotopic variant thereof, or a pharmaceutically acceptable salt, solvate, hydrate, or prodrug thereof.

Provided herein is a method of inhibiting the growth of a cell, comprising contacting the cell with an effective amount of a compound of Formula (I), or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof.

Provided herein is a method of inducing degradation of a protein, comprising contacting the protein with an effective amount of a compound of Formula (I), or an enantiomer, a mixture of enantiomers, a mixture of two or more diastereomers, a tautomer, a mixture of two or more tautomers, or an isotopic variant thereof, or a pharmaceutically acceptable salt, solvate, hydrate, or prodrug thereof, wherein the protein is a zinc-figure protein, CK1α, GSPT1, or PDE6D.

DETAILED DESCRIPTION

To facilitate understanding of the disclosure set forth herein, a number of terms are defined below.

Generally, the nomenclature used herein and the laboratory procedures in organic chemistry, medicinal chemistry, biochemistry, biology, and pharmacology described herein are those well-known and commonly employed in the art. Unless defined otherwise, all technical and scientific terms used herein generally have the same meaning as commonly understood by one of ordinary skill in the art to which this disclosure belongs.

The term "subject" refers to an animal, including, but not limited to, a primate (e.g., human), cow, pig, sheep, goat, horse, dog, cat, rabbit, rat, or mouse. The terms "subject" and "patient" are used interchangeably herein in reference, for example, to a mammalian subject, such as a human subject. In one embodiment, the subject is a human.

The terms "treat," "treating," and "treatment" are meant to include alleviating or abrogating a disorder, disease, or condition, or one or more of the symptoms associated with the disorder, disease, or condition; or alleviating or eradicating the cause(s) of the disorder, disease, or condition itself.

The terms "prevent," "preventing," and "prevention" are meant to include a method of delaying and/or precluding the onset of a disorder, disease, or condition, and/or its attendant symptoms; barring a subject from acquiring a disorder, disease, or condition; or reducing a subject's risk of acquiring a disorder, disease, or condition.

The terms "alleviate" and "alleviating" refer to easing or reducing one or more symptoms (e.g., pain) of a disorder, disease, or condition. The terms can also refer to reducing adverse effects associated with an active ingredient. Sometimes, the beneficial effects that a subject derives from a prophylactic or therapeutic agent do not result in a cure of the disorder, disease, or condition.

The term "contacting" or "contact" is meant to refer to bringing together of a therapeutic agent and a biological molecule (e.g., a protein, enzyme, RNA, or DNA), cell, or tissue such that a physiological and/or chemical effect takes place as a result of such contact. Contacting can take place in vitro, ex vivo, or in vivo. In one embodiment, a therapeutic agent is contacted with a biological molecule in vitro to determine the effect of the therapeutic agent on the biological molecule. In another embodiment, a therapeutic agent is contacted with a cell in cell culture (in vitro) to determine the effect of the therapeutic agent on the cell. In yet another embodiment, the contacting of a therapeutic agent with a biological molecule, cell, or tissue includes the administration of a therapeutic agent to a subject having the biological molecule, cell, or tissue to be contacted.

The term "therapeutically effective amount" or "effective amount" is meant to include the amount of a compound that, when administered, is sufficient to prevent development of, or alleviate to some extent, one or more of the symptoms of the disorder, disease, or condition being treated. The term "therapeutically effective amount" or "effective amount" also refers to the amount of a compound that is sufficient to elicit a biological or medical response of a biological molecule (e.g., a protein, enzyme, RNA, or DNA), cell, tissue, system, animal, or human, which is being sought by a researcher, veterinarian, medical doctor, or clinician.

The term "$IC_{50}$" or "$EC_{50}$" refers to an amount, concentration, or dosage of a compound that is required for 50% inhibition of a maximal response in an assay that measures such a response.

The term "pharmaceutically acceptable carrier," "pharmaceutically acceptable excipient," "physiologically acceptable carrier," or "physiologically acceptable excipient" refers to a pharmaceutically acceptable material, composition, or vehicle, such as a liquid or solid filler, diluent, solvent, or encapsulating material. In one embodiment, each component is "pharmaceutically acceptable" in the sense of being compatible with the other ingredients of a pharmaceutical formulation, and suitable for use in contact with the tissue or organ of a subject (e.g., a human) without excessive toxicity, irritation, allergic response, immunogenicity, or other problems or complications, and commensurate with a reasonable benefit/risk ratio. See, e.g., *Remington: The Science and Practice of Pharmacy,* 23rd ed.; Adejare Ed.; Academic Press, 2020; *Handbook of Pharmaceutical Excipients,* 9th ed.; Sheskey et al., Eds.; Pharmaceutical Press, 2020; *Handbook of Pharmaceutical Additives,* 3rd ed.; Ash and Ash Eds.; Synapse Information Resources, 2007; *Pharmaceutical Preformulation and Formulation,* 1st ed.; Gibson Ed.; CRC Press, 2015.

The term "about" or "approximately" means an acceptable error for a particular value as determined by one of ordinary skill in the art, which depends in part on how the value is measured or determined. In certain embodiments, the term "about" or "approximately" means within 1, 2, or 3 standard deviations. In certain embodiments, the term "about" or "approximately" means within 25%, 20%, 15%, 10%, 9%, 8%, 7%, 6%, 5%, 4%, 3%, 2%, 1%, 0.5%, or 0.05% of a given value or range.

The term "alkyl" refers to a linear or branched saturated monovalent hydrocarbon radical, wherein the alkyl is optionally substituted with one or more substituents Q as described herein. For example, $C_{1-6}$ alkyl refers to a linear saturated monovalent hydrocarbon radical of 1 to 6 carbon atoms or a branched saturated monovalent hydrocarbon radical of 3 to 6 carbon atoms. In certain embodiments, the alkyl is a linear saturated monovalent hydrocarbon radical that has 1 to 20 ($C_{1-20}$), 1 to 15 ($C_{1-15}$), 1 to 10 ($C_{1-10}$), or 1 to 6 ($C_{1-6}$) carbon atoms, or branched saturated monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. As used herein, linear $C_{1-6}$ and branched $C_{3-6}$ alkyl groups are also referred as "lower alkyl." Examples of alkyl groups include, but are not limited to, methyl, ethyl, propyl (including all isomeric forms, e.g., n-propyl and isopropyl), butyl (including all isomeric forms, e.g., n-butyl, isobutyl, sec-butyl, and t-butyl), pentyl (including all isomeric forms, e.g., n-pentyl, isopentyl, sec-pentyl, neopentyl, and tert-pentyl), and hexyl (including all isomeric forms, e.g., n-hexyl, isohexyl, and sec-hexyl).

The term "heteroalkyl" refers to a linear or branched saturated monovalent hydrocarbon radical that contains one or more heteroatoms on its main chain, each independently selected from O, S, and N. The heteroalkyl is optionally substituted with one or more substituents Q as described herein. For example, $C_{1-6}$ heteroalkyl refers to a linear saturated monovalent hydrocarbon radical of 1 to 6 carbon atoms or a branched saturated monovalent hydrocarbon radical of 3 to 6 carbon atoms. In certain embodiments, the heteroalkyl is a linear saturated monovalent hydrocarbon radical that has 1 to 20 ($C_{1-20}$), 1 to 15 ($C_{1-15}$), 1 to 10 ($C_{1-10}$), or 1 to 6 ($C_{1-6}$) carbon atoms, or branched saturated monovalent hydrocarbon radical of 3 to 20 ($C_3$-20), 3 to 15 ($C_{3-15}$), 3 to 10 ($C_{3-10}$), or 3 to 6 ($C_{3-6}$) carbon atoms. As used herein, linear $C_{1-6}$ and branched $C_{3-6}$ heteroalkyl groups are also referred as "lower heteroalkyl." Examples of heteroalkyl groups include, but are not limited to, $-OCH_3$, $-OCH_2CH_3$, $-CH_2OCH_3$, $-NHCH_3$, $-ONHCH_3$, $-NHOCH_3$, $-SCH_3$, $-CH_2NHCH_2CH_3$, and $-NHCH_2CH_2CH_3$. Examples of substituted heteroalkyl groups include, but are not limited to, $-CH_2NHC(O)CH_3$ and $-NHC(O)CH_2CH_3$.

The term "alkenyl" refers to a linear or branched monovalent hydrocarbon radical, which contains one or more, in one embodiment, one, two, three, or four, in another embodiment, one, carbon-carbon double bond(s). The alkenyl is optionally substituted with one or more substituents Q as described herein. The term "alkenyl" embraces radicals having a "cis" or "trans" configuration or a mixture thereof, or alternatively, a "Z" or "E" configuration or a mixture thereof, as appreciated by those of ordinary skill in the art. For example, $C_{2-6}$ alkenyl refers to a linear unsaturated monovalent hydrocarbon radical of 2 to 6 carbon atoms or a branched unsaturated monovalent hydrocarbon radical of 3 to 6 carbon atoms. In certain embodiments, the alkenyl is a linear monovalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkenyl groups include, but are not limited to, ethenyl, propenyl (including all isomeric forms, e.g., propen-1-yl, propen-2-yl, and allyl), and butenyl (including all isomeric forms, e.g., buten-1-yl, buten-2-yl, buten-3-yl, and 2-buten-1-yl).

The term "alkynyl" refers to a linear or branched monovalent hydrocarbon radical, which contains one or more, in one embodiment, one, two, three, or four, in another embodiment, one, carbon-carbon triple bond(s). An alkynyl group does not contain a carbon-carbon double bond. The alkynyl is optionally substituted with one or more substituents Q as described herein. For example, $C_{2-6}$ alkynyl refers to a linear unsaturated monovalent hydrocarbon radical of 2 to 6 carbon atoms or a branched unsaturated monovalent hydrocarbon radical of 4 to 6 carbon atoms. In certain embodiments, the alkynyl is a linear monovalent hydrocarbon radical of 2 to 20 ($C_{2-20}$), 2 to 15 ($C_{2-15}$), 2 to 10 ($C_{2-10}$), or 2 to 6 ($C_{2-6}$)

carbon atoms, or a branched monovalent hydrocarbon radical of 4 to 20 ($C_{4-20}$), 4 to 15 ($C_{4-15}$), 4 to 10 ($C_{4-10}$), or 4 to 6 ($C_{4-6}$) carbon atoms. Examples of alkynyl groups include, but are not limited to, ethynyl (—C≡CH), propynyl (including all isomeric forms, e.g., 1-propynyl (—C≡$CCH_3$) and propargyl (—$CH_2C$≡CH)), butynyl (including all isomeric forms, e.g., 1-butyn-1-yl and 2-butyn-1-yl), pentynyl (including all isomeric forms, e.g., 1-pentyn-1-yl and 1-methyl-2-butyn-1-yl), and hexynyl (including all isomeric forms, e.g., 1-hexyn-1-yl and 2-hexyn-1-yl).

The term "cycloalkyl" refers to a cyclic monovalent hydrocarbon radical, which is optionally substituted with one or more substituents Q as described herein. In one embodiment, the cycloalkyl is a saturated or unsaturated but non-aromatic, and/or bridged or non-bridged, and/or fused and/or spiro bicyclic group. In certain embodiments, the cycloalkyl has from 3 to 20 ($C_{3-20}$), from 3 to 15 ($C_{3-15}$), from 3 to 10 ($C_{3-10}$), or from 3 to 7 ($C_{3-7}$) carbon atoms. In one embodiment, the cycloalkyl is monocyclic. In another embodiment, the cycloalkyl is bicyclic. In yet another embodiment, the cycloalkyl is tricyclic. In still another embodiment, the cycloalkyl is polycyclic. Examples of cycloalkyl groups include, but are not limited to, cyclopropyl, cyclobutyl, cyclopentyl, cyclopentenyl, cyclohexyl, cyclohexenyl, cyclohexadienyl, cycloheptyl, cycloheptenyl, bicyclo[1.1.1]pentyl, bicyclo[2.1.1]hexyl, bicyclo[2.2.1]heptyl, bicyclo[2.2.2]octyl, decalinyl, and adamantyl.

The term "aryl" refers to a monovalent monocyclic aromatic hydrocarbon radical and/or monovalent polycyclic aromatic hydrocarbon radical that contain at least one aromatic carbon ring. In certain embodiments, the aryl has from 6 to 20 ($C_{6-20}$), from 6 to 15 ($C_{6-15}$), or from 6 to 10 ($C_{6-10}$) ring carbon atoms. Examples of aryl groups include, but are not limited to, phenyl, naphthyl, fluorenyl, azulenyl, anthryl, phenanthryl, pyrenyl, biphenyl, and terphenyl. The aryl also refers to bicyclic or tricyclic carbon rings, where one of the rings is aromatic and the others of which may be saturated, partially unsaturated, or aromatic, for example, dihydronaphthyl, indenyl, indanyl, or tetrahydronaphthyl (tetralinyl). In one embodiment, the aryl is monocyclic. In another embodiment, the aryl is bicyclic. In yet another embodiment, the aryl is tricyclic. In still another embodiment, the aryl is polycyclic. In certain embodiments, the aryl is optionally substituted with one or more substituents Q as described herein.

The term "aralkyl" or "arylalkyl" refers to a monovalent alkyl group substituted with one or more aryl groups. In certain embodiments, the aralkyl has from 7 to 30 ($C_{7-30}$), from 7 to 20 ($C_{7-20}$), or from 7 to 16 ($C_{7-16}$) carbon atoms. Examples of aralkyl groups include, but are not limited to, benzyl, phenylethyl (including all isomeric forms, e.g., 1-phenylethyl and 2-phenylethyl), and phenylpropyl (including all isomeric forms, e.g., 1-phenylpropyl, 2-phenylpropyl, and 3-phenylpropyl). In certain embodiments, the aralkyl is optionally substituted with one or more substituents Q as described herein.

The term "heteroaryl" refers to a monovalent monocyclic aromatic group or monovalent polycyclic aromatic group that contain at least one aromatic ring, wherein at least one aromatic ring contains one or more heteroatoms, each independently selected from O, S, and N, in the ring. For a heteroaryl group containing a heteroaromatic ring and a nonaromatic heterocyclic ring, the heteroaryl group is not bonded to the rest of a molecule through its nonaromatic heterocyclic ring. Each ring of a heteroaryl group can contain one or two O atoms, one or two S atoms, and/or one to four N atoms; provided that the total number of heteroatoms in each ring is four or less and each ring contains at least one carbon atom. In certain embodiments, the heteroaryl has from 5 to 20, from 5 to 15, or from 5 to 10 ring atoms. In one embodiment, the heteroaryl is monocyclic. Examples of monocyclic heteroaryl groups include, but are not limited to, furanyl, imidazolyl, isothiazolyl, isoxazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl, and triazolyl. In another embodiment, the heteroaryl is bicyclic. Examples of bicyclic heteroaryl groups include, but are not limited to, benzofuranyl, benzimidazolyl, benzoisoxazolyl, benzopyranyl, benzothiadiazolyl, benzothiazolyl, benzothienyl, benzotriazolyl, benzoxazolyl, furopyrindyl (including all isomeric forms, e.g., furo[2,3-b]pyridinyl, furo[2,3-c]pyridinyl, furo[3,2-b]pyridinyl, furo[3,2-c]pyridinyl, furo[3,4-b]pyridinyl, and furo[3,4-c]pyridinyl), imidazopyridinyl (including all isomeric forms, e.g., imidazo[1,2-a]pyridinyl, imidazo[4,5-b]pyridinyl, and imidazo[4,5-c]pyridinyl), imidazothiazolyl (including all isomeric forms, e.g., imidazo[2,1-b]thiazolyl and imidazo[4,5-d]thiazolyl), indazolyl, indolizinyl, indolyl, isobenzofuranyl, isobenzothienyl (i.e., benzo[c]thienyl), isoindolyl, isoquinolinyl, naphthyridinyl (including all isomeric forms, e.g., 1,5-naphthyridinyl, 1,6-naphthyridinyl, 1,7-naphthyridinyl, and 1,8-naphthyridinyl), oxazolopyridinyl (including all isomeric forms, e.g., oxazolo[4,5-b]pyridinyl, oxazolo[4,5-c]pyridinyl, oxazolo[5,4-b]pyridinyl, and oxazolo[5,4-c]pyridinyl), phthalazinyl, pteridinyl, purinyl, pyrrolopyridyl (including all isomeric forms, e.g., pyrrolo[2,3-b]pyridinyl, pyrrolo[2,3-c]pyridinyl, pyrrolo[3,2-b]pyridinyl, and pyrrolo[3,2-c]pyridinyl), quinolinyl, quinoxalinyl, quinazolinyl, thiadiazolopyrimidyl (including all isomeric forms, e.g., [1,2,5]thiadiazolo[3,4-d]pyrimidinyl and [1,2,3]thiadiazolo[4,5-d]pyrimidinyl), and thienopyridyl (including all isomeric forms, e.g., thieno[2,3-b]pyridinyl, thieno[2,3-c]pyridinyl, thieno[3,2-b]pyridinyl, and thieno[3,2-c]pyridinyl). In yet another embodiment, the heteroaryl is tricyclic. Examples of tricyclic heteroaryl groups include, but are not limited to, acridinyl, benzindolyl, carbazolyl, dibenzofuranyl, perimidinyl, phenanthrolinyl, phenanthridinyl (including all isomeric forms, e.g., 1,5-phenanthrolinyl, 1,6-phenanthrolinyl, 1,7-phenanthrolinyl, 1,9-phenanthrolinyl, and 2,10-phenanthrolinyl), phenarsazinyl, phenazinyl, phenothiazinyl, phenoxazinyl, and xanthenyl. In certain embodiments, the heteroaryl is optionally substituted with one or more substituents Q as described herein.

The term "heterocyclyl" or "heterocyclic" refers to a monovalent monocyclic non-aromatic ring system or monovalent polycyclic ring system that contains at least one non-aromatic ring, wherein one or more of the non-aromatic ring atoms are heteroatoms, each independently selected from O, S, and N; and the remaining ring atoms are carbon atoms. For a heterocyclyl group containing a heteroaromatic ring and a nonaromatic heterocyclic ring, the heterocyclyl group is not bonded to the rest of a molecule through the heteroaromatic ring. In certain embodiments, the heterocyclyl or heterocyclic group has from 3 to 20, from 3 to 15, from 3 to 10, from 3 to 8, from 4 to 7, or from 5 to 6 ring atoms. In certain embodiments, the heterocyclyl is a monocyclic, bicyclic, tricyclic, or tetracyclic ring system, which may be fused or bridged, and in which nitrogen or sulfur atoms may be optionally oxidized, nitrogen atoms may be optionally quaternized, and some rings may be partially or fully saturated, or aromatic. The heterocyclyl may be attached to the main structure at any heteroatom or carbon atom which results in the creation of a stable compound.

Examples of heterocyclyls and heterocyclic groups include, but are not limited to, azepinyl, benzodioxanyl, benzodioxolyl, benzofuranonyl, chromanyl, decahydroisoquinolinyl, dihydrobenzofuranyl, dihydrobenzisothiazolyl, dihydrobenzisoxazinyl (including all isomeric forms, e.g., 1,4-dihydrobenzo[d][1,3]oxazinyl, 3,4-dihydrobenzo[c][1,2]-oxazinyl, and 3,4-dihydrobenzo[d][1,2]oxazinyl), dihydrobenzothienyl, dihydroisobenzofuranyl, dihydrobenzo[c]thienyl, dihydrofuryl, dihydroisoindolyl, dihydropyranyl, dihydropyrazolyl, dihydropyrazinyl, dihydropyridinyl, dihydropyrimidinyl, dihydropyrrolyl, dioxolanyl, 1,4-dithianyl, furanonyl, imidazolidinyl, imidazolinyl, indolinyl, isochromanyl, isoindolinyl, isothiazolidinyl, isoxazolidinyl, morpholinyl, octahydroindolyl, octahydroisoindolyl, oxazolidinonyl, oxazolidinyl, oxiranyl, piperazinyl, piperidinyl, 4-piperidonyl, pyrazolidinyl, pyrazolinyl, pyrrolidinyl, pyrrolinyl, quinuclidinyl, tetrahydrofuryl, tetrahydroisoquinolinyl, tetrahydropyranyl, tetrahydrothienyl, thiamorpholinyl, thiazolidinyl, thiochromanyl, tetrahydroquinolinyl, and 1,3,5-trithianyl. In certain embodiments, the heterocyclyl is optionally substituted with one or more substituents Q as described herein.

The term “halogen”, “halide,” or “halo” refers to fluoro, chloro, bromo, and/or iodo.

The term “optionally substituted” is intended to mean that a group or substituent, such as an alkyl, heteroalkyl, alkenyl, alkynyl, cycloalkyl, aryl, aralkyl, heteroaryl, or heterocyclyl group, may be substituted with one or more, in one embodiment, one, two, three, or four, substituents Q, each of which is independently selected from, e.g., (a) deuterium (-D), cyano (—CN), halo, imino (═NH), nitro (—$NO_2$), and oxo (═O); (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl, each of which is further optionally substituted with one or more, in one embodiment, one, two, three, or four, substituents $Q^a$; and (c) —C(O)$R^a$, —C(O)O$R^a$, —C(O)N$R^bR^c$, —C(O)S$R^a$, —C(N$R^a$)N$R^bR^c$, —C(S)$R^a$, —C(S)O$R^a$, —C(S)N$R^bR^c$, —O$R^a$, —OC(O)$R^a$, —OC(O)O$R^a$, —OC(O)N$R^bR^c$, —OC(O)S$R^a$, —OC(N$R^a$)N$R^bR^c$, —OC(S)$R^a$, —OC(S)O$R^a$, —OC(S)N$R^bR^c$, —OP(O)(O$R^b$)O$R^c$, —OS(O)$R^a$, —OS$(O)_2R^a$, —OS(O)N$R^bR^c$, —OS$(O)_2$N$R^bR^c$, —N$R^bR^c$, —N$R^a$C(O)$R^d$, —N$R^a$C(O)O$R^d$, —N$R^a$C(O)N$R^bR^c$, —N$R^a$C(O)S$R^d$, —N$R^a$C(N$R^d$)N$R^bR^c$, —N$R^a$C(S)$R^d$, —N$R^a$C(S)O$R^d$, —N$R^a$C(S)N$R^bR^c$, —N$R^a$S(O)$R^d$, —N$R^a$S$(O)_2R^d$, —N$R^a$S(O)N$R^bR^c$, —N$R^a$S$(O)_2$N$R^bR^c$, —S$R^a$, —S(O)$R^a$, —S$(O)_2R^a$, —S(O)N$R^bR^c$, and —S$(O)_2$N$R^bR^c$, wherein each $R^a$, $R^b$, $R^c$, and $R^d$ is independently (i) hydrogen or deuterium; (ii) $C_{1-6}$ alkyl, $C_{1-6}$ $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more, in one embodiment, one, two, three, or four, substituents $Q^a$; or (iii) $R^b$ and $R^c$ together with the N atom to which they are attached form heterocyclyl optionally substituted with one or more, in one embodiment, one, two, three, or four, substituents $Q^a$. As used herein, all groups that can be substituted are “optionally substituted.”

In one embodiment, each $Q^a$ is independently selected from: (a) deuterium, cyano, halo, imino, nitro, and oxo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl; and (c) —C(O)$R^e$, —C(O)O$R^e$, —C(O)N$R^fR^g$, —C(O)S$R^e$, —C(N$R^e$)N$R^fR^g$, —C(S)$R^e$, —C(S)O$R^e$, —C(S)N$R^fR^g$, —O$R^e$, —OC(O)$R^e$, —OC(O)O$R^e$, —OC(O)N$R^fR^g$, —OC(O)S$R^e$, —OC(N$R^e$)N$R^fR^g$, —OC(S)$R^e$, —OC(S)O$R^e$, —OC(S)N$R^fR^g$, —OP(O)(O$R^f$)O$R^g$, —OS(O)$R^e$, —OS$(O)_2R^e$, —OS(O)N$R^fR^g$, —OS$(O)_2$N$R^fR^g$, —N$R^fR^g$, —N$R^e$C(O)$R^h$, —N$R^e$C(O)O$R^f$, —N$R^e$C(O)N$R^fR^g$, —N$R^e$C(O)S$R^f$, —N$R^e$C(N$R^h$)N$R^fR^g$, —N$R^e$C(S)$R^h$, —N$R^e$C(S)O$R^f$, —N$R^e$C(S)N$R^fR^g$, —N$R^e$S(O)$R^h$, —N$R^e$S$(O)_2R^h$, —N$R^e$S(O)N$R^fR^g$, —N$R^e$S$(O)_2$N$R^fR^g$, —S$R^e$, —S(O)$R^e$, —S$(O)_2R^e$, —S(O)N$R^fR^g$, and —S$(O)_2$N$R^fR^g$; wherein each $R^e$, $R^f$, $R^g$, and $R^h$ is independently (i) hydrogen or deuterium; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (iii) $R^f$ and $R^g$ together with the N atom to which they are attached form heterocyclyl.

In certain embodiments, “optically active” and “enantiomerically active” refer to a collection of molecules, which has an enantiomeric excess of no less than about 80%, no less than about 90%, no less than about 91%, no less than about 92%, no less than about 93%, no less than about 94%, no less than about 95%, no less than about 96%, no less than about 97%, no less than about 98%, no less than about 99%, no less than about 99.5%, or no less than about 99.8%. In certain embodiments, an optically active compound comprises about 95% or more of one enantiomer and about 5% or less of the other enantiomer based on the total weight of the enantiomeric mixture in question. In certain embodiments, an optically active compound comprises about 98% or more of one enantiomer and about 2% or less of the other enantiomer based on the total weight of the enantiomeric mixture in question. In certain embodiments, an optically active compound comprises about 99% or more of one enantiomer and about 1% or less of the other enantiomer based on the total weight of the enantiomeric mixture in question.

In describing an optically active compound, the prefixes R and S are used to denote the absolute configuration of the compound about its chiral center(s). The (+) and (−) are used to denote the optical rotation of the compound, that is, the direction in which a plane of polarized light is rotated by the optically active compound. The (−) prefix indicates that the compound is levorotatory, that is, the compound rotates the plane of polarized light to the left or counterclockwise. The (+) prefix indicates that the compound is dextrorotatory, that is, the compound rotates the plane of polarized light to the right or clockwise. However, the sign of optical rotation, (+) and (−), is not related to the absolute configuration of the compound, R and S.

The term “isotopically enriched” refers to a compound that contains an unnatural proportion of an isotope at one or more of the atoms that constitute such a compound. In certain embodiments, an isotopically enriched compound contains unnatural proportions of one or more isotopes, including, but not limited to, hydrogen ($^1$H), deuterium ($^2$H), tritium ($^3$H), carbon-11 ($^{11}$C), carbon-12 ($^{12}$C), carbon-13 ($^{13}$C), carbon-14 ($^{14}$C), nitrogen-13 ($^{13}$N), nitrogen-14 ($^{14}$N), nitrogen-15 ($^{15}$N), oxygen-14 ($^{14}$O), oxygen-15 ($^{15}$O), oxygen-16 ($^{16}$O), oxygen-17 ($^{17}$O), oxygen-18 ($^{18}$O), fluorine-17 ($^{17}$F), fluorine-18 ($^{18}$F), phosphorus-31 ($^{31}$P), phosphorus-32 ($^{32}$P), phosphorus-33 ($^{33}$P), sulfur-32 ($^{32}$S), sulfur-33 ($^{33}$S), sulfur-34 ($^{34}$S), sulfur-35 ($^{35}$S), sulfur-36 ($^{36}$S), chlorine-35 ($^{35}$Cl), chlorine-36 ($^{36}$Cl), chlorine-37 ($^{37}$Cl), bromine-79 ($^{79}$Br), bromine-81 ($^{81}$Br), iodine-123 ($^{123}$I), iodine-125 ($^{125}$I), iodine-127 ($^{127}$1), iodine-129 ($^{129}$I), and iodine-131 ($^{131}$I). In certain embodiments, an isotopically enriched compound is in a stable form, that is, non-radioactive. In certain embodiments, an isotopically enriched compound contains unnatural proportions of one or more isotopes, including, but not limited to, hydrogen ($^1$H), deuterium ($^2$H), carbon-12 ($^{12}$C), carbon-13 ($^{13}$C), nitrogen-14 ($^{14}$N), nitrogen-15 ($^{15}$N), oxygen-16 ($^{16}$O), oxygen-17 ($^{17}$O), oxygen-18 ($^{18}$O), fluorine-17 ($^{17}$F), phosphorus-31

($^{31}P$), sulfur-32 ($^{32}S$), sulfur-33 ($^{33}S$), sulfur-34 ($^{34}S$), sulfur-36 ($^{36}S$), chlorine-35 ($^{35}Cl$), chlorine-37 ($^{37}Cl$), bromine-79 ($^{79}Br$), bromine-81 ($^{81}Br$), and iodine-127 ($^{127}I$). In certain embodiments, an isotopically enriched compound is in an unstable form, that is, radioactive. In certain embodiments, an isotopically enriched compound contains unnatural proportions of one or more isotopes, including, but not limited to, tritium (H), carbon-11 ($^{11}C$), carbon-14 ($^{14}C$), nitrogen-13 ($^{13}N$), oxygen-14 ($^{14}O$), oxygen-15 ($^{15}O$), fluorine-18 ($^{18}F$), phosphorus-32 ($^{32}P$), phosphorus-33 ($^{33}P$), sulfur-35 ($^{35}S$), chlorine-36 ($^{36}Cl$), iodine-123 ($^{123}I$), iodine-125 ($^{125}I$), iodine-129 ($^{129}I$), and iodine-131 ($^{131}I$). It will be understood that, in a compound as provided herein, any hydrogen can be $^{2}H$, as example, or any carbon can be $^{13}C$, as example, or any nitrogen can be $^{15}N$, as example, or any oxygen can be $^{18}O$, as example, where feasible according to the judgment of one of ordinary skill in the art.

The term "isotopic enrichment" refers to the percentage of incorporation of a less prevalent isotope (e.g., D for deuterium or hydrogen-2) of an element at a given position in a molecule in the place of a more prevalent isotope (e.g., $^{1}H$ for protium or hydrogen-1) of the element. As used herein, when an atom at a particular position in a molecule is designated as a particular less prevalent isotope, it is understood that the abundance of that isotope at that position is substantially greater than its natural abundance.

The term "isotopic enrichment factor" refers the ratio between the isotopic abundance in an isotopically enriched compound and the natural abundance of a specific isotope.

The term "hydrogen" or the symbol "H" refers to the composition of naturally occurring hydrogen isotopes, which include protium ($^{1}H$), deuterium ($^{2}H$ or D), and tritium ($^{3}H$), in their natural abundances. Protium is the most common hydrogen isotope having a natural abundance of more than 99.98%. Deuterium is a less prevalent hydrogen isotope having a natural abundance of about 0.0156%.

The term "deuterium enrichment" refers to the percentage of incorporation of deuterium at a given position in a molecule in the place of hydrogen. For example, deuterium enrichment of 1% at a given position means that 1% of molecules in a given sample contain deuterium at the specified position. Because the naturally occurring distribution of deuterium is about 0.0156% on average, deuterium enrichment at any position in a compound synthesized using non-enriched starting materials is about 0.0156% on average. As used herein, when a particular position in an isotopically enriched compound is designated as having deuterium, it is understood that the abundance of deuterium at that position in the compound is substantially greater than its natural abundance (0.0156%).

The term "carbon" or the symbol "C" refers to the composition of naturally occurring carbon isotopes, which include carbon-12 ($^{12}C$) and carbon-13 ($^{13}C$) in their natural abundances. Carbon-12 is the most common carbon isotope having a natural abundance of more than 98.89%. Carbon-13 is a less prevalent carbon isotope having a natural abundance of about 1.11%.

The term "carbon-13 enrichment" or "$^{13}C$ enrichment" refers to the percentage of incorporation of carbon-13 at a given position in a molecule in the place of carbon. For example, carbon-13 enrichment of 10% at a given position means that 10% of molecules in a given sample contain carbon-13 at the specified position. Because the naturally occurring distribution of carbon-13 is about 1.11% on average, carbon-13 enrichment at any position in a compound synthesized using non-enriched starting materials is about 1.11% on average. As used herein, when a particular position in an isotopically enriched compound is designated as having carbon-13, it is understood that the abundance of carbon-13 at that position in the compound is substantially greater than its natural abundance (1.11%).

The terms "substantially pure" and "substantially homogeneous" mean, when referred to a substance, sufficiently homogeneous to appear free of readily detectable impurities as determined by a standard analytical method used by one of ordinary skill in the art, including, but not limited to, thin layer chromatography (TLC), gel electrophoresis, high performance liquid chromatography (HPLC), gas chromatography (GC), nuclear magnetic resonance (NMR), and mass spectrometry (MS); or sufficiently pure such that further purification would not detectably alter the physical, chemical, biological, and/or pharmacological properties, such as enzymatic and biological activities, of the substance. In certain embodiments, "substantially pure" or "substantially homogeneous" refers to a collection of molecules, wherein at least about 95%, at least about 96%, at least about 97%, at least about 98%, at least about 99%, or at least about 99.5% by weight of the molecules are a single compound, including a single enantiomer, a racemic mixture, or a mixture of enantiomers, as determined by standard analytical methods. As used herein, when an atom at a particular position in an isotopically enriched molecule is designated as a particular less prevalent isotope, a molecule that contains other than the designated isotope at the specified position is an impurity with respect to the isotopically enriched compound. Thus, for a deuterated compound that has an atom at a particular position designated as deuterium, a compound that contains a protium at the same position is an impurity.

The term "solvate" refers to a complex or aggregate formed by one or more molecules of a solute, e.g., a compound provided herein, and one or more molecules of a solvent, which are present in a stoichiometric or non-stoichiometric amount. Suitable solvents include, but are not limited to, water, methanol, ethanol, n-propanol, isopropanol, and acetic acid. In certain embodiments, the solvent is pharmaceutically acceptable. In one embodiment, the complex or aggregate is in a crystalline form. In another embodiment, the complex or aggregate is in a noncrystalline form. Where the solvent is water, the solvate is a hydrate. Examples of hydrates include, but are not limited to, a hemihydrate, monohydrate, dihydrate, trihydrate, tetrahydrate, and pentahydrate.

For a divalent group described herein, no orientation is implied by the direction in which the divalent group is presented. For example, unless a particular orientation is specified, the formula —C(O)NH— represents both —C(O)NH— and —NHC(O)—.

The phrase "an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof" has the same meaning as the phrase "(i) an enantiomer, a mixture of enantiomers, a diastereomer, a mixture of two or more diastereomers, a tautomer, a mixture of two or more tautomers, or an isotopic variant of the compound referenced therein; (ii) a pharmaceutically acceptable salt, solvate, hydrate, or prodrug of the compound referenced therein; or (iii) a pharmaceutically acceptable salt, solvate, hydrate, or prodrug of an enantiomer, a mixture of enantiomers, a diastereomer, a mixture of two or more diastereomers, a tautomer, a mixture of two or more tautomers, or an isotopic variant of the compound referenced therein."

Compounds

In one embodiment, provided herein is a compound of Formula (I):

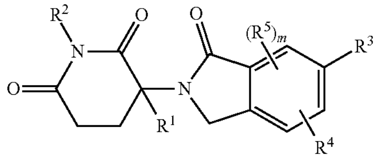

(I)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein:

$R^1$ is hydrogen, deuterium, or $C_{1-6}$ alkyl;

$R^2$ is hydrogen or $C_{1-6}$ alkyl;

$R^3$ and $R^4$ are:

(i) $R^3$ is halo; and $R^4$ is

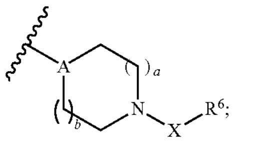

or (ii) $R^3$ is hydrogen, deuterium, or halo; and $R^4$ is

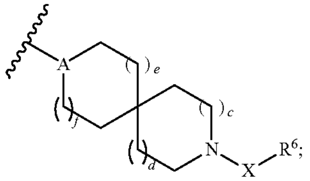

each $R^5$ is independently (i) deuterium, cyano, halo, or nitro; (ii) $C_{1-6}$ alkyl, $C_{1-6}$ heteroalkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (iii) —$C(O)R^{1a}$, —$C(O)OR^{1a}$, —$C(O)NR^{1b}R^{1c}$, —$C(O)SR^{1a}$—$C(NR^{1a})NR^{1b}R^{1c}$, —$C(S)R^{1a}$, —$C(S)OR^{1a}$, —$C(S)NR^{1b}R^{1c}$, —$OR^{1a}$, —$OC(O)R^{1a}$, —$OC(O)OR^{1a}$, —$OC(O)NR^{1b}R^{1c}$, —$OC(O)SR^{1a}$, —$OC(NR^{1a})NR^{1b}R^{1c}$, —$OC(S)R^{1a}$, —$OC(S)OR^{1a}$, —$OC(S)NR^{1b}R^{1c}$, —$OS(O)R^{1a}$, —$OS(O)_2R^{1a}$, —$OS(O)NR^{1b}R^{1c}$, —$OS(O)_2NR^{1b}R^{1c}$, —$NR^{1b}R^{1c}$, —$NR^{1a}C(O)R^{1d}$, —$NR^{1a}C(O)OR^{1d}$, —$NR^{1a}C(O)NR^{1b}R^{1c}$, —$NR^{1a}C(O)SR^{1d}$, —$NR^{1a}C(NR^{1d})NR^{1b}R^{1c}$, —$NR^{1a}C(S)R^{1d}$, —$NR^{1a}C(S)OR^{1d}$, —$NR^{1a}C(S)NR^{1b}R^{1c}$, —$NR^{1a}S(O)R^{1d}$, —$NR^{1a}S(O)_2R^{1d}$, —$NR^{1a}S(O)NR^{1b}R^{1c}$, —$NR^{1a}S(O)_2NR^{1b}R^{1c}$, —$SR^{1a}$, —$S(O)R^{1a}$, —$S(O)_2R^{1a}$, —$S(O)NR^{1b}R^{1c}$, or —$S(O)_2NR^{1b}R^{1c}$;

each $R^6$ is independently $C_{1-6}$ alkyl, $C_{1-6}$ heteroalkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl;

each $R^{1a}$, $R^{1b}$, $R^{1c}$, and $R^{1d}$ is independently hydrogen, deuterium, $C_{1-6}$ alkyl, $C_{1-6}$ heteroalkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl;

each A is independently $CR^{4a}$ or N; wherein $R^{4a}$ is hydrogen, deuterium, halo, $C_{1-6}$ alkyl, or $C_{1-6}$ heteroalkyl;

each X is independently —$(CH_2)_n$—, —C(O)—, —S(O)—, or —$S(O_2)$—; wherein n is an integer of 1, 2, 3, 4, or 5;

each a, b, c, d, e, and f is independently an integer of 0, 1, 2, or 3;

m is an integer of 0, 1, 2, or 3;

wherein each alkyl, heteroalkyl, alkenyl, alkynyl, cycloalkyl, aryl, aralkyl, heteroaryl, and heterocyclyl is optionally substituted with one or more, in one embodiment, one, two, three, or four, substituents Q, wherein each Q is independently selected from: (a) deuterium, cyano, halo, imino, nitro, and oxo; (b) $C_{1-6}$ alkyl, $C_{1-6}$ heteroalkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl, each of which is further optionally substituted with one or more, in one embodiment, one, two, three, or four, substituents $Q^a$; and (c) —$C(O)R^a$, —$C(O)OR^a$, —$C(O)NR^bR^c$, —$C(O)SR^a$, —$C(NR^a)NR^bR^c$, —$C(S)R^a$, —$C(S)OR^a$, —$C(S)NR^bR^c$, —$OR^a$, —$OC(O)R^a$, —$OC(O)OR^a$, —$OC(O)NR^bR^c$, —$OC(O)SR^a$, —$OC(NR^a)NR^bR^c$, —$OC(S)R^a$, —$OC(S)OR^a$, —$OC(S)NR^bR^c$, —$OP(O)(OR^b)OR^c$, —$OS(O)R^a$, —$OS(O)_2R^a$, —$OS(O)NR^bR^c$, —$OS(O)_2NR^bR^c$, —$NR^c$, —$NR^aC(O)R^d$, —$NR^aC(O)OR^d$, —$NR^aC(O)NR^bR^c$, —$NR^aC(O)SR^d$, —$NR^aC(NR^d)NR^bR^c$, —$NR^aC(S)R^d$, —$NR^aC(S)OR^d$, —$NR^aC(S)NR^bR^c$, —$NR^aS(O)R^d$, —$NR^aS(O)_2R^d$, —$NR^aS(O)NR^bR^c$, —$NR^aS(O)_2NR^bR^c$, —$SR^a$, —$S(O)R^a$, —$S(O)_2R^a$, —$S(O)NR^bR^c$, and —$S(O)_2NR^bR^c$, wherein each $R^a$, $R^b$, $R^c$, and $R^d$ is independently (i) hydrogen or deuterium; (ii) $C_{1-6}$ alkyl, $C_{1-6}$ heteroalkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more, in one embodiment, one, two, three, or four, substituents $Q^a$; or (iii) $R^b$ and $R^c$ together with the N atom to which they are attached form heterocyclyl, optionally substituted with one or more, in one embodiment, one, two, three, or four, substituents $Q^a$; wherein each $Q^a$ is independently selected from: (a) deuterium, cyano, halo, nitro, imino, and oxo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl; and (c) —$C(O)R^e$, —$C(O)OR^e$, —$C(O)NR^fR^g$, —$C(O)SR^e$, —$C(NR^e)NR^fR^g$, —$C(S)R^e$, —$C(S)OR^e$, —$C(S)NR^fR^g$, —$OR^e$, —$OC(O)R^e$, —$OC(O)OR^e$, —$OC(O)NR^fR^g$, —$OC(O)SR^e$, —$OC(NR^e)NR^fR^g$, —$OC(S)R^e$, —$OC(S)OR^e$, —$OC(S)NR^fR^g$, —$OP(O)(OR^f)OR^g$, —$OS(O)R^e$, —$OS(O)_2R^e$, —$OS(O)NR^fR^g$, —$OS(O)_2NR^fR^g$, —$NR^fR^g$, —$NR^eC(O)R^h$, —$NR^eC(O)OR^f$, —$NR^eC(O)NR^fR^g$, —$NR^eC(O)SR^f$, —$NR^eC(NR^h)NR^fR^g$, —$NR^eC(S)R^h$, —$NR^eC(S)OR^f$, —$NR^eC(S)NR^fR^g$, —$NR^eS(O)R^h$, —$NR^eS(O)_2R^h$, —$NR^eS(O)NR^fR^g$, —$NR^eS(O)_2NR^fR^g$, —$SR^e$, —$S(O)R^e$, —$S(O)_2R^e$, —$S(O)NR^fR^g$, and —$S(O)_2NR^fR^g$; wherein each $R^e$, $R^f$, $R^g$, and $R^h$ is independently (i) hydrogen or deuterium; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (iii) $R^f$ and $R^g$ together with the N atom to which they are attached form heterocyclyl.

In another embodiment, provided herein is a compound of Formula (II):

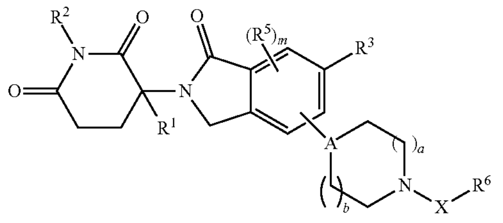

(II)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^2$, $R^3$, $R^5$, $R^6$, A, X, a, b, and m are each as defined herein.

In yet another embodiment, provided herein is a compound of Formula (III):

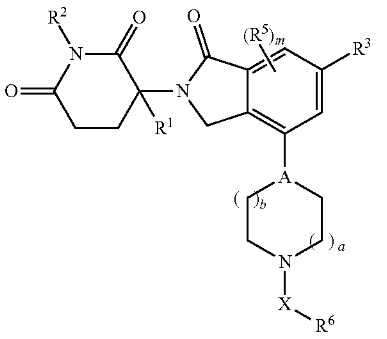

(III)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^2$, $R^3$, $R^5$, $R^6$, A, X, a, b, and m are each as defined herein.

In certain embodiments, in Formula (I), (II), or (III), a and b are each independently an integer of 0, 1, or 2. In certain embodiments, in Formula (I), (II), or (III), a and b are each independently an integer of 0 or 1. In certain embodiments, in Formula (I), (II), or (III), a and b are each an integer of 1.

In yet another embodiment, provided herein is a compound of Formula (IV):

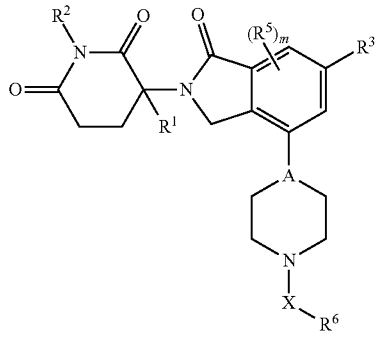

(IV)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^2$, $R^3$, $R^5$, $R^6$, A, X, and m are each as defined herein.

In certain embodiments, in any one of Formulae (I) to (IV), A is $CR^{4a}$, wherein $R^{4a}$ is as defined herein. In certain embodiments, in any one of Formulae (I) to (IV), A is CH. In certain embodiments, in any one of Formulae (I) to (IV), A is N.

In yet another embodiment, provided herein is a compound of Formula (V):

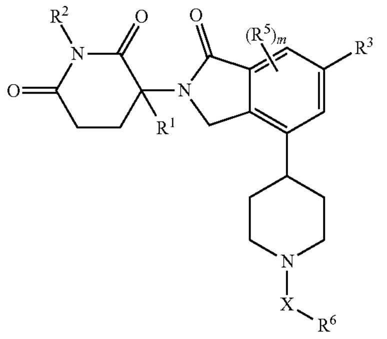

(V)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^2$, $R^3$, $R^5$, $R^6$, X, and m are each as defined herein.

In yet another embodiment, provided herein is a compound of Formula (VI):

(VI)

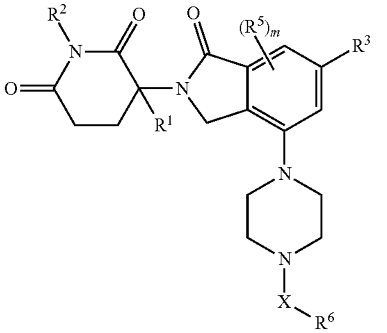

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^2$, $R^3$, $R^5$, $R^6$, X, and m are each as defined herein.

In yet another embodiment, provided herein is a compound of Formula (VII):

(VII)

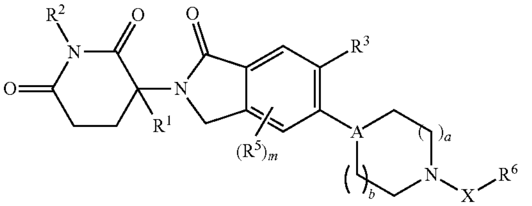

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^2$, $R^3$, $R^5$, $R^6$, A, X, a, b, and m are each as defined herein.

In certain embodiments, in Formula (VII), a and b are each independently an integer of 0, 1, or 2. In certain embodiments, in Formula (VII), a and b are each independently an integer of 0 or 1. In certain embodiments, in Formula (VII), a and b are each an integer of 1.

In yet another embodiment, provided herein is a compound of Formula (VIII):

(VIII)

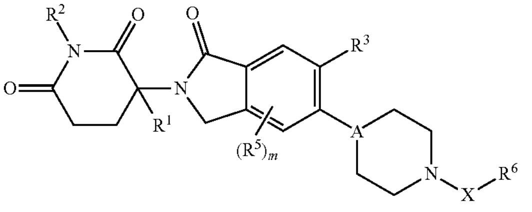

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^2$, $R^3$, $R^5$, $R^6$, A, X, and m are each as defined herein.

In certain embodiments, in Formula (VIII), A is $CR^{4a}$, wherein $R^{4a}$ is as defined herein. In certain embodiments, in Formula (VIII), A is CH. In certain embodiments, in Formula (VIII), A is N.

In yet another embodiment, provided herein is a compound of Formula (IX):

(IX)

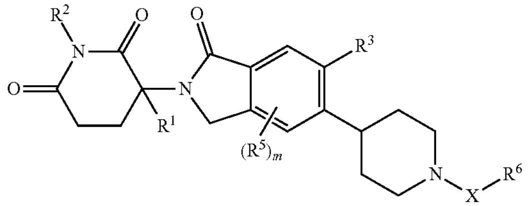

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^2$, $R^3$, $R^5$, $R^6$, X, and m are each as defined herein.

In yet another embodiment, provided herein is a compound of Formula (X):

(X)

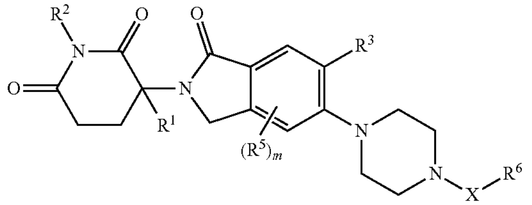

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^2$, $R^3$, $R^5$, $R^6$, X, and m are each as defined herein.

In yet another embodiment, provided herein is a compound of Formula (XI):

(XI)

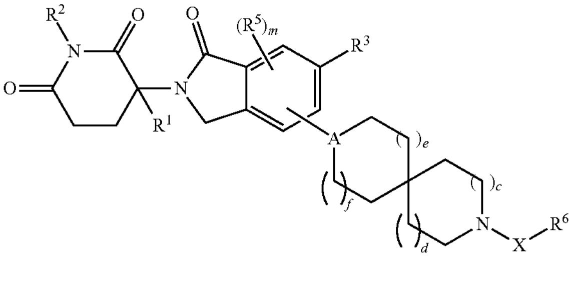

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^2$, $R^3$, $R^5$, $R^6$, A, X, c, d, e, f, and m are each as defined herein.

In yet another embodiment, provided herein is a compound of Formula (XII):

(XII)

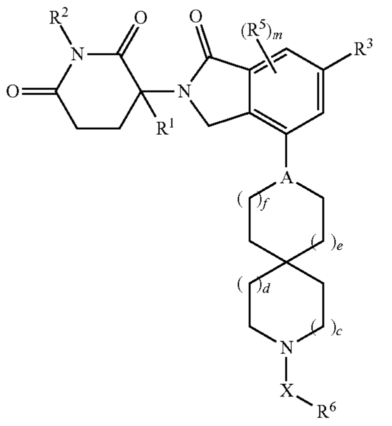

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^2$, $R^3$, $R^5$, $R^6$, A, X, c, d, e, f, and m are each as defined herein.

In certain embodiments, in Formula (I), (XI), or (XII), c, d, e, and f are each independently an integer of 0, 1, or 2. In certain embodiments, in Formula (I), (XI), or (XII), c, d, e, and f are each independently an integer of 0 or 1. In certain embodiments, in Formula (I), (XI), or (XII), c and d are each an integer of 1; and e and f are each an integer of 0.

In yet another embodiment, provided herein is a compound of Formula (XIII):

(XIII)

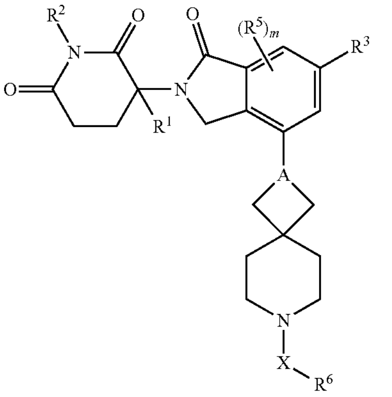

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^2$, $R^3$, $R^5$, $R^6$, A, X, and m are each as defined herein.

In certain embodiments, in any one of Formulae (XI) to (XIII), A is $CR^{4a}$, wherein $R^{4a}$ is as defined herein. In certain embodiments, in any one of Formulae (XI) to (XIII), A is CH. In certain embodiments, in any one of Formulae (XI) to (XIII), A is N.

In yet another embodiment, provided herein is a compound of Formula (XIV):

(XIV)

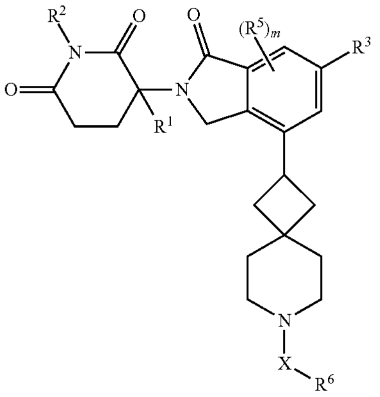

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^2$, $R^3$, $R^5$, $R^6$, X, and m are each as defined herein.

In yet another embodiment, provided herein is a compound of Formula (XV):

(XV)

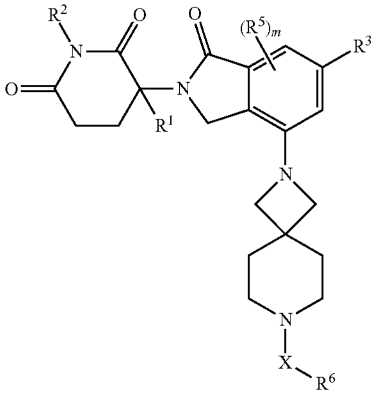

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^2$, $R^3$, $R^5$, $R^6$, X, and m are each as defined herein.

In yet another embodiment, provided herein is a compound of Formula (XVI):

(XVI)

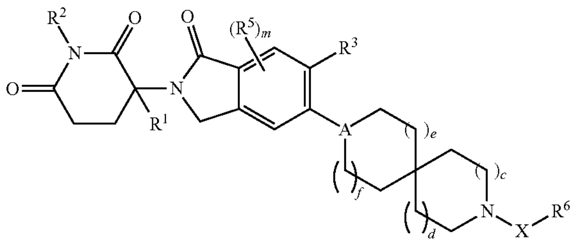

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^2$, $R^3$, $R^5$, $R^6$, A, X, c, d, e, f, and m are each as defined herein.

In certain embodiments, in Formula (XVI), c, d, e, and f are each independently an integer of 0, 1, or 2. In certain embodiments, in Formula (XVI), c, d, e, and f are each independently an integer of 0 or 1. In certain embodiments, in Formula (XVI), c and d are each an integer of 1; and e and f are each an integer of 0.

In yet another embodiment, provided herein is a compound of Formula (XVII):

(XVII)

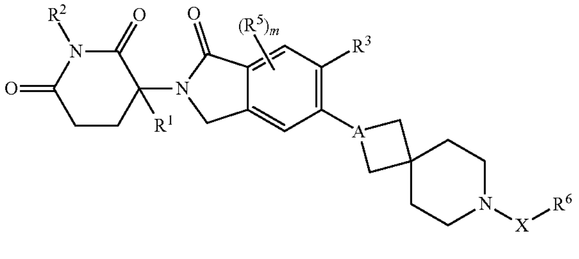

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^2$, $R^3$, $R^5$, $R^6$, A, X, and m are each as defined herein.

In certain embodiments, in Formula (XVII), A is $CR^{4a}$, wherein $R^{4a}$ is as defined herein. In certain embodiments, in Formula (XVII), A is CH. In certain embodiments, in Formula (XVI), A is N.

In yet another embodiment, provided herein is a compound of Formula (XVIII):

(XVIII)

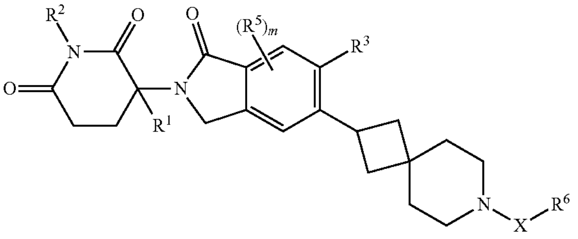

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^2$, $R^3$, $R^5$, $R^6$, X, and m are each as defined herein.

In still another embodiment, provided herein is a compound of Formula (XIX):

(XIX)

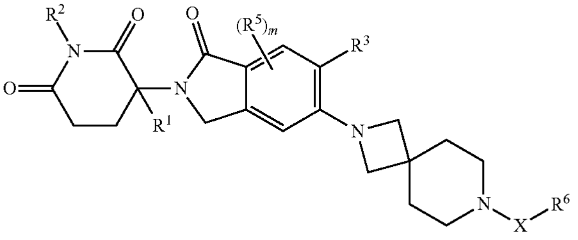

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^2$, $R^3$, $R^5$, $R^6$, X, and m are each as defined herein.

In certain embodiments, in any one of Formulae (I) to (XIX), $R^1$ is hydrogen. In certain embodiments, in any one of Formulae (I) to (XIX), $R^1$ is deuterium. In certain embodiments, in any one of Formulae (I) to (XIX), $R^1$ is $C_{1-6}$ alkyl, optionally substituted with one or more substituents Q. In certain embodiments, in any one of Formulae (I) to (XIX), $R^1$ is methyl.

In certain embodiments, in any one of Formulae (I) to (XIX), $R^2$ is hydrogen. In certain embodiments, in any one of Formulae (I) to (XIX), $R^2$ is $C_{1-6}$ alkyl, optionally substituted with one or more substituents Q. In certain embodiments, in any one of Formulae (I) to (XIX), $R^2$ is methyl, optionally substituted with one or more substituents Q. In certain embodiments, in any one of Formulae (I) to (XIX), $R^2$ is $C_{1-6}$ alkyl substituted with —C(O)$R^a$ or —OP(O)(O$R^b$)O$R^c$, wherein $R^a$, $R^b$, and $R^a$ are each as defined herein. In certain embodiments, in any one of Formulae (I) to (XIX), $R^2$ is methyl substituted with —C(O)$R^a$ or —OP(O)(O$R^b$)O$R^c$, wherein $R^a$, $R^b$, and $R^a$ are each as defined herein. In certain embodiments, in any one of Formulae (I) to (XIX), $R^2$ is valyloxymethyl or di-tert-butoxyphosphoryloxymethyl. In certain embodiments, in any one of Formulae (I) to (XIX), $R^2$ is D-valyloxymethyl or L-valyloxymethyl.

In certain embodiments, in any one of Formulae (I) and (XI) to (XIX), $R^3$ is hydrogen. In certain embodiments, in any one of Formulae (I) and (XI) to (XIX), $R^3$ is deuterium.

In certain embodiments, in any one of Formulae (I) to (XIX), $R^3$ is halo. In certain embodiments, in any one of Formulae (I) to (XIX), $R^3$ is fluoro, chloro, or bromo. In certain embodiments, in any one of Formulae (I) to (XIX), $R^3$ is fluoro. In certain embodiments, in any one of Formulae (I) to (XIX), $R^3$ is chloro. In certain embodiments, in any one of Formulae (I) to (XIX), $R^3$ is bromo.

In certain embodiments, in any one of Formulae (I) to (XIX), $R^6$ is $C_{1-6}$ alkyl, optionally substituted with one or more substituents Q. In certain embodiments, in any one of Formulae (I) to (XIX), $R^6$ is $C_{1-6}$ alkyl, optionally substituted with one, two, or three substituents Q, wherein each substituent is independently (i) cyano, halo, or oxo; (ii) $C_{1-6}$ alkyl, $C_{1-6}$ heteroalkyl, $C_{2-6}$ alkynyl, $C_{3-10}$ cycloalkyl, $C_{6-14}$ aryl, $C_{7-15}$ aralkyl, heteroaryl, or heterocyclyl, each optionally substituted with one or more substituents $Q^a$; or (iii) —C(O)$R^a$, —C(O)O$R^a$, —C(O)N$R^bR^c$, —O$R^a$, —$N^bR^c$, —N$R^a$C(O)$R^d$, —N$R^a$C(O)O$R^d$, —N$R^a$S$(O)_2R^d$, —S$R^a$, or —S$(O)_2R^a$, wherein each $R^a$, $R^b$, $R^c$, and $R^d$ is as defined herein. In certain embodiments, in any one of Formulae (I) to (XIX), $R^6$ is $C_{1-6}$ alkyl, optionally substituted with one, two, or three substituents Q, wherein each substituent is independently (i) halo; (ii) $C_{1-6}$ alkyl, $C_{1-6}$ heteroalkyl, $C_{3-10}$ cycloalkyl, $C_{6-14}$ aryl, heteroaryl, or heterocyclyl, each optionally substituted with one or more substituents $Q^a$; or (iii) —O$R^a$, —N$R^bR^c$, or —N$R^a$C(O)O$R^d$; wherein each $R^a$, $R^b$, $R^c$, and $R^d$ is as defined herein.

In certain embodiments, in any one of Formulae (I) to (XIX), $R^6$ is $C_{1-6}$ alkyl, optionally substituted with one, two, or three substituents Q, wherein each substituent is independently cyano, fluoro, chloro, bromo, oxo, methyl, ethyl, isopropyl, isobutyl, tert-butyl, trifluoromethyl, morpholinomethyl, hydroxymethyl, (dimethylamino)methyl, (tert-butoxy-carbonylamino)methyl, ethynyl, cyclopropyl, cyclobutyl, cyclopentyl, cyclohexyl, phenyl, 3-bromophenyl, 4-methylphenyl, 3-trifluoromethylphenyl, 2-methoxyphenyl, benzyl, 5-methyl-furan-2-yl, imidazol-1-yl, oxazol-5-yl, pyrazol-1-yl, pyrrol-2-yl, 1,2,3-triazol-1-yl, 1,2,4-triazol-1-yl, pyrimidin-2-yl, pyrimidin-5-yl, pyridin-3-yl, pyridin-4-yl, 4-methylpyridin-2-yl, 2-methoxypyridin-3-yl, quinolin-6-yl, pyrrolidin-1-yl, morpholino, piperidin-1-yl, 1-benzoxy-carbonylpiperidin-4-yl, 1-(tert-butoxycarbonyl) piperidin-4-yl, 4-methylpiperazin-1-yl, 4-(tert-butoxycarbonyl)piperazin-1-yl, 2,2,2-trifluoroacetyl, benzoxycarbonyl, tert-butoxycarbonyl, aminocarbonyl, methylaminocarbonyl, dimethylaminocarbonyl, isopropylaminocarbonyl, hydroxyl, methoxy, ethoxy, difluoromethoxy, trifluoromethoxy, cyclohexylmethoxy, cyclopentoxy, phenoxy, 4-cyanophenoxy, 3-methylphenoxy, 4-trifluoromethylphenoxy, 4-cyano-2-fluorophenoxy, benzoxy, 4-cyanobenzoxy, pyridin-2-yloxy, pyridin-3-yloxy, amino, methylamino, ethylamino, dimethylamino, (2-hydroxyethyl)(methyl)amino), acetamido, benzoxycarbonylamino, tert-butoxycarbonylamino, methylsulfonylamino, methylthio, methylsulfonyl, or ethylsulfonyl. In certain embodiments, in any one of Formulae (I) to (XIX), $R^6$ is $C_{1-6}$ alkyl, optionally substituted with one, two, or three substituents Q, wherein each substituent is independently fluoro, chloro, methyl, trifluoromethyl, cyclobutyl, cyclopentyl, cyclohexyl, phenyl, 3-bromophenyl, 3-trifluoromethylphenyl, 2-methoxyphenyl, 5-methylfuran-2-yl, pyrazol-1-yl, pyrrol-2-yl, 1,2,3-triazol-1-yl, pyrimidin-2-yl, pyrimidin-5-yl, pyridin-2-yl, pyridin-3-yl, 2-methoxypyridin-3-yl, quinoline-6-yl, morpholino, piperidin-1-yl, 1-benzoxycarbonyl-piperidin-4-yl, 1-(tert-butoxycarbonyl)piperidin-4-yl, 4-(tert-butoxycarbonyl)piperazin-1-yl, hydroxyl, 3-methylphenoxy, benzoxy, methylamino, or tert-butoxycarbonylamino.

In certain embodiments, in any one of Formulae (I) to (XIX), $R^6$ is methyl, ethyl, propyl, or butyl, each optionally substituted with one, two, or three substituents Q, wherein each substituent is independently cyano, fluoro, chloro, bromo, oxo, methyl, ethyl, isopropyl, isobutyl, tert-butyl, trifluoromethyl, morpholinomethyl, hydroxymethyl, (dimethylamino)methyl, (tert-butoxycarbonylamino)methyl, ethynyl, cyclopropyl, cyclobutyl, cyclopentyl, cyclohexyl, phenyl, 3-bromophenyl, 4-methylphenyl, 3-trifluoromethylphenyl, 2-methoxyphenyl, benzyl, 5-methyl-furan-2-yl, imidazol-1-yl, oxazol-5-yl, pyrazol-1-yl, pyrrol-2-yl, 1,2,3-triazol-1-yl, 1,2,4-triazol-1-yl, pyrimidin-2-yl, pyrimidin-5-yl, pyridin-3-yl, pyridin-4-yl, 4-methylpyridin-2-yl, 2-methoxypyridin-3-yl, quinolin-6-yl, pyrrolidin-1-yl, morpholino, piperidin-1-yl, 1-benzoxy-carbonylpiperidin-4-yl, 1-(tert-butoxycarbonyl)piperidin-4-yl, 4-methylpiperazin-1-yl, 4-(tert-butoxycarbonyl)piperazin-1-yl, 2,2,2-trifluoroacetyl, benzoxycarbonyl, tert-butoxycarbonyl, aminocarbonyl, methylaminocarbonyl, dimethylaminocarbonyl, isopropylaminocarbonyl, hydroxyl, methoxy, ethoxy, difluoromethoxy, trifluoromethoxy, cyclohexylmethoxy, cyclopentoxy, phenoxy, 4-cyanophenoxy, 3-methylphenoxy, 4-trifluoromethylphenoxy, 4-cyano-2-fluorophenoxy, benzoxy, 4-cyanobenzoxy, pyridin-2-yloxy, pyridin-3-yloxy, amino, methylamino, ethylamino, dimethylamino, (2-hydroxyethyl)(methyl)amino), acetamido, benzoxycarbonylamino, tert-butoxycarbonylamino, methylsulfonylamino, methylthio, methylsulfonyl, or ethylsulfonyl. In certain embodiments, in any one of Formulae (I) to (XIX), $R^6$ is methyl, ethyl, propyl, or butyl, each optionally substituted with one, two, or three substituents Q, wherein each substituent is independently fluoro, chloro, methyl, trifluoromethyl, cyclobutyl, cyclopentyl, cyclohexyl, phenyl, 3-bromophenyl, 3-trifluoromethylphenyl, 2-methoxyphenyl, 5-methylfuran-2-yl, pyrazol-1-yl, pyrrol-2-yl, 1,2,3-triazol-1-yl, pyrimidin-2-yl, pyrimidin-5-yl, pyridin-2-yl, pyridin-3-yl, 2-methoxypyridin-3-yl, quinoline-6-yl, morpholino, piperidin-1-yl, 1-benzoxy-carbonylpiperidin-4-yl, 1-(tert-butoxycarbonyl)piperidin-4-yl, 4-(tert-butoxycarbonyl)piperazin-1-yl, hydroxyl, 3-methylphenoxy, benzoxy, methylamino, or tert-butoxycarbonylamino.

In certain embodiments, in any one of Formulae (I) to (XIX), $R^6$ is ethyl, propyl, isopropyl, isobutyl, trifluoromethyl, 2,2,2-trifluoroethyl, 3,3,3-trifluoropropyl, 3-chloropropyl, cyclobutylmethyl, cyclopentylmethyl, cyclohexylmethyl, (3-methylphenoxy)methyl, benzyl, 2-phenylethyl, 3-phenylpropyl, 2-(3-bromophenyl)ethyl, 2-methyl-2-phenylpropyl, 2-(3-trifluoro-methylphenyl)ethyl, 2-(2-methoxyphenyl)ethyl, 2-benzoxyethyl, 2-(5-methylfuran-2-yl)ethyl, pyrazol-1-ylmethyl, pyrrol-2-ylmethyl, 2-(pyrrol-2-yl)ethyl, 1,2,3-triazol-1-ylmethyl, pyrimidin-2-ylmethyl, pyrimidin-5-ylmethyl, 2-methoxypyridin-3-ylmethyl, 2-(pyridin-2-yl)ethyl, 2-(pyridin-3-yl)ethyl, 2-(quinolin-6-yl)ethyl, pyrrolidin-1-ylmethyl, tetrahydropyran-4-ylmethyl, piperidin-1-ylmethyl, 1-benzoxycarbonylpiperidin-4-ylmethyl, 1-(tert-butoxycarbonyl)-piperidin-4-ylmethyl, 2-(1-(tert-butoxycarbonyl)piperidin-4-yl)prop-2-yl, 4-(tert-butoxy-carbonyl)piperazin-1-ylmethyl, morpholinomethyl, 3-hydroxy-2-methylprop-2-yl, benzoxy-methyl, 2-benzoxyethyl, methylaminomethyl, or (tert-butoxycarbonyl)aminomethyl.

In certain embodiments, in any one of Formulae (I) to (XIX), $R^6$ is $C_{1-6}$ heteroalkyl, optionally substituted with one or more substituents Q. In certain embodiments, in any one of Formulae (I) to (XIX), $R^6$ is trifluoromethyl, 2,2,2-trifluoroethyl, 3,3,3-trifluoropropyl, or 3-chloropropyl. In certain embodiments, in any one of Formulae (I) to (XIX), $R^6$ is $C_{2-6}$ alkenyl, optionally substituted with one or more substituents Q. In certain embodiments, in any one of Formulae (I) to (XIX), $R^6$ is $C_{2-6}$ alkynyl, optionally substituted with one or more substituents Q.

In certain embodiments, in any one of Formulae (I) to (XIX), $R^6$ is $C_{3-10}$ cycloalkyl, optionally substituted with one or more substituents Q. In certain embodiments, in any one of Formulae (I) to (XIX), $R^6$ is $C_{3-10}$ monocyclic cycloalkyl, optionally substituted with one or more substituents Q. In certain embodiments, in any one of Formulae (I) to (XIX), $R^6$ is $C_{4-10}$ bicyclic cycloalkyl, optionally substituted with one or more substituents Q. In certain embodiments, in any one of Formulae (I) to (XIX), $R^6$ is $C_{5-10}$ bridged cycloalkyl, optionally substituted with one or more substituents Q. In certain embodiments, in any one of Formulae (I) to (XIX), $R^6$ is $C_{4-10}$ fused cycloalkyl, optionally substituted with one or more substituents Q. In certain embodiments, in any one of Formulae (I) to (XIX), $R^6$ is $C_{5-10}$ spiro cycloalkyl, optionally substituted with one or more substituents Q.

In certain embodiments, in any one of Formulae (I) to (XIX), $R^6$ is $C_{3-10}$ cycloalkyl, optionally substituted with one, two, or three substituents Q, wherein each substituent is independently (i) cyano, halo, or oxo; (ii) $C_{1-6}$ alkyl, $C_{1-6}$ heteroalkyl, $C_{2-6}$ alkynyl, $C_{3-10}$ cycloalkyl, $C_{6-14}$ aryl, $C_{7-15}$ aralkyl, heteroaryl, or heterocyclyl, each optionally substituted with one or more substituents $Q^a$; or (iii) —C(O)$R^a$, —C(O)O$R^a$, —C(O)N$R^bR^c$, —O$R^a$, —N$R^bR^c$, —N$R^a$C(O)$R^d$, —N$R^a$C(O)O$R^d$, —N$R^a$S$(O)_2R^d$, —S$R^a$, or —S$(O)_2R^a$, wherein each $R^a$, $R^b$, $R^c$, and $R^d$ is as defined herein. In certain embodiments, in any one of Formulae (I) to (XIX), $R^6$ is $C_{3-10}$ cycloalkyl, optionally substituted with one, two, or three substituents Q, wherein each substituent is independently (i) halo; (ii) $C_{1-6}$ alkyl, optionally substituted with one or more substituents $Q^a$; or (iii) —O$R^a$, —$R^bR^c$, or —N$R^a$C(O)O$R^d$, wherein each $R^a$, $R^b$, $R^c$, and $R^d$ is as defined herein.

In certain embodiments, in any one of Formulae (I) to (XIX), $R^6$ is $C_{3-10}$ cycloalkyl, optionally substituted with one, two, or three substituents Q, wherein each substituent is independently cyano, fluoro, chloro, bromo, oxo, methyl, ethyl, isopropyl, isobutyl, tert-butyl, trifluoromethyl, morpholinomethyl, hydroxymethyl, (dimethylamino)methyl, (tert-butoxy-carbonylamino)methyl, ethynyl, cyclopropyl, cyclobutyl, cyclopentyl, cyclohexyl, phenyl, 3-bromophenyl, 4-methylphenyl, 3-trifluoromethylphenyl, 2-methoxyphenyl, benzyl, 5-methyl-furan-2-yl, imidazol-1-yl, oxazol-5-yl, pyrazol-1-yl, pyrrol-2-yl, 1,2,3-triazol-1-yl, 1,2,4-triazol-1-yl, pyrimidin-2-yl, pyrimidin-5-yl, pyridin-3-yl, pyridin-4-yl, 4-methylpyridin-2-yl, 2-methoxypyridin-3-yl, quinolin-6-yl, pyrrolidin-1-yl, morpholino, piperidin-1-yl, 1-benzoxy-carbonylpiperidin-4-yl, 1-(tert-butoxycarbonyl)piperidin-4-yl, 4-methylpiperazin-1-yl, 4-(tert-butoxycarbonyl)-piperazin-1-yl, 2,2,2-trifluoroacetyl, benzoxycarbonyl, tert-butoxy-carbonyl, aminocarbonyl, methylaminocarbonyl, dimethylaminocarbonyl, isopropylaminocarbonyl, hydroxyl, methoxy, ethoxy, difluoromethoxy, trifluoromethoxy, cyclohexylmethoxy, cyclopentoxy, phenoxy, 4-cyanophenoxy, 3-methylphenoxy, 4-trifluoromethylphenoxy, 4-cyano-2-fluorophenoxy, benzoxy, 4-cyanobenzoxy, pyridin-2-yloxy, pyridin-3-yloxy, amino, methylamino, ethylamino, dimethylamino, (2-hydroxyethyl)(methyl)amino), acetamido, benzoxycarbonylamino, tert-butoxycarbonylamino, methylsulfonylamino, methylthio, methylsulfonyl, or ethylsulfonyl. In certain embodiments, in any one of Formulae (I) to (XIX), $R^6$ is $C_{3-10}$ cycloalkyl, optionally substituted with one, two, or three substituents Q, wherein each substituent is independently fluoro, methyl, (tert-butoxycarbonylamino)methyl, hydroxyl, amino, or tert-butoxycarbonylamino.

In certain embodiments, in any one of Formulae (I) to (XIX), $R^6$ is cyclopropyl, cyclobutyl, cyclopentyl, cyclohexyl, bicyclo[2.2.2]octanyl, or adamantanyl, each optionally substituted with one, two, or three substituents Q, wherein each substituent is independently cyano, fluoro, chloro, bromo, oxo, methyl, ethyl, isopropyl, isobutyl, tert-butyl, trifluoromethyl, morpholinomethyl, hydroxymethyl, (dimethylamino)methyl, (tert-butoxycarbonylamino) methyl, ethynyl, cyclopropyl, cyclobutyl, cyclopentyl, cyclohexyl, phenyl, 3-bromophenyl, 4-methyl-phenyl, 3-trifluoromethylphenyl, 2-methoxyphenyl, benzyl, 5-methyl-furan-2-yl, imidazol-1-yl, oxazol-5-yl, pyrazol-1-yl, pyrrol-2-yl, 1,2,3-triazol-1-yl, 1,2,4-triazol-1-yl, pyrimidin-2-yl, pyrimidin-5-yl, pyridin-3-yl, pyridin-4-yl, 4-methylpyridin-2-yl, 2-methoxy-pyridin-3-yl, quinolin-6-yl, pyrrolidin-1-yl, morpholino, piperidin-1-yl, 1-benzoxycarbonylpiperidin-4-yl, 1-(tert-butoxycarbonyl)piperidin-4-yl, 4-methylpiperazin-1-yl, 4-(tert-butoxycarbonyl)piperazin-1-yl, 2,2,2-trifluoroacetyl, benzoxycarbonyl, tert-butoxycarbonyl, aminocarbonyl, methylamino-carbonyl, dimethylaminocarbonyl, isopropylaminocarbonyl, hydroxyl, methoxy, ethoxy, difluoromethoxy, trifluoromethoxy, cyclohexylmethoxy, cyclopentoxy, phenoxy, 4-cyanophenoxy, 3-methylphenoxy, 4-trifluoromethylphenoxy, 4-cyano-2-fluorophenoxy, benzoxy, 4-cyanobenzoxy, pyridin-2-yloxy, pyridin-3-yloxy, amino, methylamino, ethylamino, dimethylamino, (2-hydroxyethyl)(methyl)amino), acetamido, benzoxycarbonylamino, tert-butoxy-carbonylamino, methylsulfonylamino, methylthio, methylsulfonyl, or ethylsulfonyl. In certain embodiments, in any one of Formulae (I) to (XIX), $R^6$ is cyclopropyl, cyclobutyl, cyclopentyl, cyclohexyl, bicyclo[2.2.2]octanyl, or adamantanyl, each optionally substituted with one, two, or three substituents Q, wherein each substituent is independently fluoro, methyl, (tert-butoxycarbonylamino)methyl, hydroxyl, amino, or tert-butoxycarbonylamino.

In certain embodiments, in any one of Formulae (I) to (XIX), $R^6$ is cyclopropyl, cyclobutyl, 3,3-dimethylcyclobut-1-yl, cyclopentyl, cyclohexyl, adamantan-1-yl, 1-fluorocyclopropyl, 4,4-difluorocyclohexyl, 3,3-dimethylcyclobutyl, 4-hydroxybicyclo[2.2.2]octan-1-yl, 1-aminocyclobutyl, 4-(tert-butoxycarbonylamino)cyclohexyl, or 4-(tert-butoxycarbonylamino-methyl)cyclohexyl.

In certain embodiments, in any one of Formulae (I) to (XIX), $R^6$ is $C_{6-14}$ aryl, optionally substituted with one or more substituents Q. In certain embodiments, in any one of Formulae (I) to (XIX), $R^6$ is $C_{6-14}$ aryl, optionally substituted with one, two, or three substituents Q, wherein each substituent is independently (i) cyano, halo, or oxo; (ii) $C_{1-6}$ alkyl, $C_{1-6}$ heteroalkyl, $C_{2-6}$ alkynyl, $C_{3-10}$ cycloalkyl, $C_{6-14}$ aryl, $C_{7-15}$ aralkyl, heteroaryl, or heterocyclyl, each optionally substituted with one or more substituents $Q^a$; or (iii) —C(O)$R^a$, —C(O)O$R^a$, —C(O)N$R^bR^c$, —O$R^a$, —N$R^bR^c$, —N$R^a$C(O)$R^d$, —N$R^a$C(O)O$R^d$, —N$R^a$S$(O)_2R^d$, —S$R^a$, or —S$(O)_2R^a$, wherein each $R^a$, $R^b$, $R^c$, and $R^d$ is as defined herein. In certain embodiments, in any one of Formulae (I) to (XIX), $R^6$ is $C_{6-14}$ aryl, optionally substituted with one, two, or three substituents Q, wherein each substituent is independently (i) cyano or halo; (ii) $C_{1-6}$ alkyl, $C_{1-6}$ heteroalkyl, $C_{2-6}$ alkynyl, $C_{3-10}$ cycloalkyl, $C_{6-14}$ aryl, heteroaryl, or heterocyclyl, each optionally substituted with one or more substituents $Q^a$; or (iii) —C(O)N$R^bR^c$, —O$R^a$, —$NR^bR^c$, —$NR^aC(O)R^d$, —$NR^aC(O)OR^d$, —$NR^aS(O)_2R^d$, or —$S(O)_2R^a$, wherein each $R^a$, $R^b$, $R^c$, and $R^d$ is as defined herein.

In certain embodiments, in any one of Formulae (I) to (XIX), $R^6$ is $C_{6-14}$ aryl, optionally substituted with one, two, or three substituents Q, wherein each substituent is independently cyano, fluoro, chloro, bromo, oxo, methyl, ethyl, isopropyl, isobutyl, tert-butyl, trifluoromethyl, morpholinomethyl, hydroxymethyl, (dimethylamino)methyl, (tert-butoxy-carbonylamino)methyl, ethynyl, cyclopropyl, cyclobutyl, cyclopentyl, cyclohexyl, phenyl, 3-bromophenyl, 4-methylphenyl, 3-trifluoromethylphenyl, 2-methoxyphenyl, benzyl, 5-methyl-furan-2-yl, imidazol-1-yl, oxazol-5-yl, pyrazol-1-yl, pyrrol-2-yl, 1,2,3-triazol-1-yl, 1,2,4-triazol-1-yl, pyrimidin-2-yl, pyrimidin-5-yl, pyridin-3-yl, pyridin-4-yl, 4-methylpyridin-2-yl, 2-methoxypyridin-3-yl, quinolin-6-yl, pyrrolidin-1-yl, morpholino, piperidin-1-yl, 1-benzoxy-carbonylpiperidin-4-yl, 1-(tert-butoxycarbonyl)piperidin-4-yl, 4-methylpiperazin-1-yl, 4-(tert-butoxycarbonyl)piperazin-1-yl, 2,2,2-trifluoroacetyl, benzoxycarbonyl, tert-butoxycarbonyl, aminocarbonyl, methylaminocarbonyl, dimethylaminocarbonyl, isopropylaminocarbonyl, hydroxyl, methoxy, ethoxy, difluoromethoxy, trifluoromethoxy, cyclohexylmethoxy, cyclopentoxy, phenoxy, 4-cyanophenoxy, 3-methylphenoxy, 4-trifluoromethylphenoxy, 4-cyano-2-fluorophenoxy, benzoxy, 4-cyanobenzoxy, pyridin-2-yloxy, pyridin-3-yloxy, amino, methylamino, ethylamino, dimethylamino, (2-hydroxyethyl)(methyl)amino), acetamido, benzoxycarbonylamino, tert-butoxycarbonylamino, methylsulfonylamino, methylthio, methylsulfonyl, or ethylsulfonyl. In certain embodiments, in any one of Formulae (I) to (XIX), $R^6$ is $C_{6-14}$ aryl, optionally substituted with one, two, or three substituents Q, wherein each substituent is independently cyano, fluoro, chloro, bromo, methyl, isopropyl, tert-butyl, trifluoromethyl, hydroxymethyl, (dimethylamino)methyl, (tert-butoxycarbonylamino)methyl, ethynyl, cyclopropyl, cyclobutyl, cyclopentyl, cyclohexyl, phenyl, 3-bromophenyl, 3-trifluoromethylphenyl, 2-methoxyphenyl, benzyl, 5-methylfuran-2-yl, imidazol-1-yl, oxazol-5-yl, pyrazol-1-yl, 1,2,4-triazol-1-yl, pyridin-4-yl, quinolin-6-yl, pyrrolidin-1-yl, morpholino, piperidin-1-yl, 1-benzoxycarbonylpiperidin-4-yl, 1-(tert-butoxycarbonyl)piperidin-4-yl, 4-methylpiperazin-1-yl, aminocarbonyl, methylaminocarbonyl, dimethylaminocarbonyl, isopropylaminocarbonyl, hydroxyl, methoxy, ethoxy, difluoromethoxy, trifluoromethoxy, cyclopentoxy, cyclohexylmethoxy, phenoxy, 4-cyanophenoxy, 4-trifluoromethylphenoxy, 4-cyano-2-fluorophenoxy, benzoxy, 4-cyanobenzoxy, pyridin-2-yloxy, pyridin-3-yloxy, amino, methylamino, ethylamino, dimethylamino, (2-hydroxyethyl)(methyl)amino), acetamido, benzoxycarbonylamino, tert-butoxycarbonylamino, methylsulfonylamino, or ethylsulfonyl.

In certain embodiments, in any one of Formulae (I) to (XIX), $R^6$ is phenyl, optionally substituted with one or more substituents Q. In certain embodiments, in any one of Formulae (I) to (XIX), $R^6$ is phenyl, optionally substituted with one, two, or three substituents Q, wherein each substituent is independently (i) cyano, halo, or oxo; (ii) $C_{1-6}$ alkyl, $C_{1-6}$ heteroalkyl, $C_{2-6}$ alkynyl, $C_{3-10}$ cycloalkyl, $C_{6-14}$ aryl, $C_{7-15}$ aralkyl, heteroaryl, or heterocyclyl, each optionally substituted with one or more substituents $Q^a$; or (iii) —$C(O)R^a$, —$C(O)OR^a$, —$C(O)NR^bR^c$, —$OR^a$, —$NR^bR^c$, —$NR^aC(O)R^d$, —$NR^aC(O)OR^d$, —$NR^aS(O)_2R^d$, —$SR^a$, or —$S(O)_2R^a$, wherein each $R^a$, $R^b$, $R^c$, and $R^d$ is as defined herein. In certain embodiments, in any one of Formulae (I) to (XIX), $R^6$ is phenyl, optionally substituted with one, two, or three substituents Q, wherein each substituent is independently (i) cyano or halo; (ii) $C_{1-6}$ alkyl, $C_{1-6}$ heteroalkyl, $C_{2-6}$ alkynyl, $C_{3-10}$ cycloalkyl, $C_{6-14}$ aryl, heteroaryl, or heterocyclyl, each optionally substituted with one or more substituents $Q^a$; or (iii) —$C(O)NR^bR^c$, —$OR^a$, —$NR^bR^c$, —$NR^aC(O)R^d$, —$NR^aC(O)OR^d$, —$NR^aS(O)_2R^d$, or —$S(O)_2R^a$, wherein each $R^a$, $R^b$, $R^c$, and $R^d$ is as defined herein.

In certain embodiments, in any one of Formulae (I) to (XIX), $R^6$ is phenyl, optionally substituted with one, two, or three substituents Q, wherein each substituent is independently cyano, fluoro, chloro, bromo, oxo, methyl, ethyl, isopropyl, isobutyl, tert-butyl, trifluoromethyl, morpholinomethyl, hydroxymethyl, (dimethylamino)methyl, (tert-butoxy-carbonylamino)methyl, ethynyl, cyclopropyl, cyclobutyl, cyclopentyl, cyclohexyl, phenyl, 3-bromophenyl, 4-methylphenyl, 3-trifluoromethylphenyl, 2-methoxyphenyl, benzyl, 5-methyl-furan-2-yl, imidazol-1-yl, oxazol-5-yl, pyrazol-1-yl, pyrrol-2-yl, 1,2,3-triazol-1-yl, 1,2,4-triazol-1-yl, pyrimidin-2-yl, pyrimidin-5-yl, pyridin-3-yl, pyridin-4-yl, 4-methylpyridin-2-yl, 2-methoxypyridin-3-yl, quinolin-6-yl, pyrrolidin-1-yl, morpholino, piperidin-1-yl, 1-benzoxy-carbonylpiperidin-4-yl, 1-(tert-butoxycarbonyl)piperidin-4-yl, 4-methylpiperazin-1-yl, 4-(tert-butoxycarbonyl)piperazin-1-yl, 2,2,2-trifluoroacetyl, benzoxycarbonyl, tert-butoxycarbonyl, aminocarbonyl, methylaminocarbonyl, dimethylaminocarbonyl, isopropylaminocarbonyl, hydroxyl, methoxy, ethoxy, difluoromethoxy, trifluoromethoxy, cyclohexylmethoxy, cyclopentoxy, phenoxy, 4-cyanophenoxy, 3-methylphenoxy, 4-trifluoromethylphenoxy, 4-cyano-2-fluorophenoxy, benzoxy, 4-cyanobenzoxy, pyridin-2-yloxy, pyridin-3-yloxy, amino, methylamino, ethylamino, dimethylamino, (2-hydroxyethyl)(methyl)amino), acetamido, benzoxycarbonylamino, tert-butoxycarbonylamino, methylsulfonylamino, methylthio, methylsulfonyl, or ethylsulfonyl. In certain embodiments, in any one of Formulae (I) to (XIX), $R^6$ is phenyl, optionally substituted with one, two, or three substituents Q, wherein each substituent is independently cyano, fluoro, chloro, bromo, methyl, isopropyl, tert-butyl, trifluoromethyl, hydroxymethyl, (dimethylamino)methyl, (tert-butoxycarbonylamino)methyl, ethynyl, cyclopropyl, cyclobutyl, cyclopentyl, cyclohexyl, phenyl, 3-bromophenyl, 3-trifluoromethylphenyl, 2-methoxyphenyl, benzyl, 5-methylfuran-2-yl, imidazol-1-yl, oxazol-5-yl, pyrazol-1-yl, 1,2,4-triazol-1-yl, pyridin-4-yl, quinolin-6-yl, pyrrolidin-1-yl, morpholino, piperidin-1-yl, 1-benzoxycarbonylpiperidin-4-yl, 1-(tert-butoxycarbonyl)piperidin-4-yl, 4-methylpiperazin-1-yl, aminocarbonyl, methylaminocarbonyl, dimethylaminocarbonyl, isopropylaminocarbonyl, hydroxyl, methoxy, ethoxy, difluoromethoxy, trifluoromethoxy, cyclopentoxy, cyclohexylmethoxy, phenoxy, 4-cyanophenoxy, 4-trifluoromethylphenoxy, 4-cyano-2-fluorophenoxy, benzoxy, 4-cyanobenzoxy, pyridin-2-yloxy, pyridin-3-yloxy, amino, methylamino, ethylamino, dimethylamino, (2-hydroxyethyl)(methyl)amino), acetamido, benzoxycarbonylamino, tert-butoxycarbonylamino, methylsulfonylamino, or ethylsulfonyl.

In certain embodiments, in any one of Formulae (I) to (XIX), $R^6$ is phenyl, substituted with one substituent Q. In certain embodiments, in any one of Formulae (I) to (XIX), $R^6$ is 2-fluorophenyl, 3-fluorophenyl, 4-fluorophenyl, 2-chlorophenyl, 3-chlorophenyl, 4-chlorophenyl, 2-bromophenyl, 3-bromophenyl, 2-cyanophenyl, 3-cyanophenyl, 4-cyanophenyl, 2-methylphenyl, 3-methylphenyl, 4-methylphenyl, 3-isopropylphenyl, 4-isopropylphenyl, 3-tert-butylphenyl, 4-tert-butylphenyl, 2-trifluoromethylphenyl, 3-trifluoromethylphenyl, 4-trifluoro-methylphenyl, 3-hydroxymethylphenyl, 4-hydroxymethylphenyl, 4-((dimethylamino)methyl)-phenyl, 2-ethynylphenyl, 3-ethynylphenyl, 4-ethynylphenyl, 2-cyclopropylphenyl, 4-cyclopropylphenyl, 4-phenylphenyl, 4-benzylphenyl, 3-(imidazol-1-yl)-phenyl, 4-(imidazol-1-yl)-phenyl, 4-(oxazol-5-yl)phenyl, 4-(pyrazol-1-yl)phenyl, 2-(1,2,4-triazol-1-yl)-phenyl, 3-(1,2,4-triazol-1-yl)phenyl, 4-(1,2,4-triazol-1-yl)phenyl, 3-(pyridin-4-yl)phenyl, 3-(pyrrolidin-1-yl)phenyl, 4-(pyrrolidin-1-yl)phenyl, 2-(morpholino)phenyl, 3-(morpholino) phenyl, 4-(morpholino)phenyl, 3-aminocarbonylphenyl, 4-aminocarbonylphenyl, 4-(methylamino-carbonyl)phenyl, 2-(dimethylaminocarbonyl)phenyl, 4-(isopropylaminocarbonyl)phenyl, 3-hydroxyphenyl, 4-hydroxyphenyl, 2-methoxyphenyl, 3-methoxyphenyl, 4-methoxyphenyl, 4-ethoxyphenyl, 4-difluoromethoxyphenyl, 2-trifluoromethoxyphenyl, 4-cyclopentoxyphenyl, 3-(cyclohexylmethoxy)phenyl, 3-phenoxyphenyl, 4-phenoxyphenyl, 3-(4-cyanophenoxy)phenyl, 4-(4-cyanophenoxy)phenyl, 4-(4-trifluoromethylphenoxy)phenyl, 4-(4-cyano-2-fluorophenoxy)-phenyl, 3-benzoxyphenyl, 4-benzoxyphenyl, 3-(4-cyanobenzoxy)phenyl, 4-(4-cyanobenzoxy)-phenyl, 2-(pyridin-2-yloxy)phenyl, 4-(pyridin-2-yloxy)phenyl, 4-(pyridin-3-yloxy)phenyl, 3-morpholinophenyl, 4-morpholinophenyl, 2-aminophenyl, 4-aminophenyl, 2-methylaminophenyl, 4-ethylaminophenyl, 2-(dimethylamino)phenyl, 3-(dimethylamino)phenyl, 4-(dimethylamino)-phenyl, 4-(2-hydroxyethyl)(methyl) amino)phenyl, 3-acetamidophenyl, 4-acetamidophenyl, 4-benzoxycarbonylaminophenyl, 4-methylsulfonylaminophenyl, 2-methylsulfonylaminophenyl, 3-methylsulfonylaminophenyl, or 4-(ethylsulfonyl)phenyl.

In certain embodiments, in any one of Formulae (I) to (XIX), $R^6$ is phenyl, substituted with two substituents Q. In certain embodiments, in any one of Formulae (I) to (XIX), $R^6$ is 2-amino-3-chlorophenyl, 2-amino-4-chlorophenyl, 2-amino-6-chlorophenyl, 2-amino-5-fluorophenyl, 2-benzoxy-4-methylphenyl, 4-benzoxy-2-methylphenyl, 2-bromo-4-(4-cyanophenoxy)phenyl, 2-bromo-5-(4-cyanophenoxy)phenyl, 3-bromo-4-(4-methylpiperazin-1-yl)phenyl, 3-bromo-4-morpholinophenyl, 2-chloro-4-cyanophenyl, 3-chloro-4-cyanophenyl, 3-chloro-5-cyanophenyl, 4-chloro-3-cyanophenyl, 2-chloro-6-methylphenyl, 3-chloro-4-methyl-phenyl, 2-chloro-4-morpholinophenyl, 3-chloro-4-morpholinophenyl, 2-chloro-4-trifluoro-methylphenyl, 2-chloro-5-trifluoromethylphenyl, 3-chloro-4-trifluoromethylphenyl, 4-chloro-2-trifluoromethylphenyl, 5-chloro-2-trifluoromethylphenyl, 2-cyano-4-fluorophenyl, 2-cyano-5-fluorophenyl, 3-cyano-4-fluorophenyl, 3-cyano-5-fluorophenyl, 4-cyano-3-fluorophenyl, 4-cyano-2-fluorophenyl, 5-cyano-2-fluorophenyl, 3-cyano-4-(4-methylimidazol-1-yl)phenyl, 3-cyano-4-hydroxyphenyl, 4-cyano-2-hydroxyphenyl, 2-cyano-4-methoxyphenyl, 4-cyano-2-methoxyphenyl, 4-cyano-3-methoxyphenyl, 4-cyano-3-methoxyphenyl, 2-cyano-3-methyl-phenyl, 2-cyano-4-methylphenyl, 3-cyano-2-methylphenyl, 3-cyano-5-methylphenyl, 4-cyano-2-methylphenyl, 2,4-dichlorophenyl, 2,5-dichlorophenyl, 2,4-difluorophenyl, 2,5-difluorophenyl, 2,6-difluorophenyl, 3,4-difluorophenyl, 3,5-difluorophenyl, 4-(dimethylamino)-3-methylphenyl, 2,4-dimethylphenyl, 2,5-dimethylphenyl, 2,6-dimethylphenyl, 3,5-dimethylphenyl, 2-ethynyl-4-fluorophenyl, 3-fluoro-4-methoxyphenyl, 5-fluoro-2-methoxyphenyl, 2-fluoro-4-methylphenyl, 2-fluoro-5-methylphenyl, 3-fluoro-2-methylpyphenyl, 3-fluoro-4-methylpyphenyl, 3-fluoro-5-methylphenyl, 4-fluoro-2-methylphenyl, 4-fluoro-3-methylphenyl, 5-fluoro-2-methylphenyl, 2-hydroxy-4-methylphenyl, 3-hydroxy-5-methylphenyl, 2-methoxy-3-methylphenyl, 2-methoxy-4-methylphenyl, 2-methoxy-6-methylphenyl, 3-methoxy-2-methylphenyl, 3-methoxy-4-methyl-phenyl, 3-methoxy-5-methylphenyl, 4-methoxy-2-methylphenyl, or 4-methoxy-3-methylphenyl.

In certain embodiments, in any one of Formulae (I) to (XIX), $R^6$ is phenyl, substituted with three substituents Q. In certain embodiments, in any one of Formulae (I) to (XIX), $R^6$ is 4-hydroxy-3,5-dimethylphenyl or 2,4,6-trimethylphenyl. In certain embodiments, in any one of Formulae (I) to (XIX), $R^6$ is phenyl, substituted with four substituents Q. In certain embodiments, in any one of Formulae (I) to (XIX), $R^6$ is phenyl, substituted with five substituents Q.

In certain embodiments, in any one of Formulae (I) to (XIX), $R^6$ is bicyclic $C_{8-14}$ aryl, optionally substituted with one or more substituents Q.

In certain embodiments, in any one of Formulae (I) to (XIX), $R^6$ is bicyclic $C_{8-14}$, optionally substituted with one, two, or three substituents Q, wherein each substituent is independently (i) cyano, halo, or oxo; (ii) $C_{1-6}$ alkyl, $C_{1-6}$ heteroalkyl, $C_{2-6}$ alkynyl, $C_{3-10}$ cycloalkyl, $C_{6-14}$ aryl, $C_{7-15}$ aralkyl, heteroaryl, or heterocyclyl, each optionally substituted with one or more substituents $Q^a$; or (iii) —C(O)$R^a$, —C(O)O$R^a$, —C(O)N$R^bR^c$, —O$R^a$, —N$R^bR^c$, —N$R^a$C(O)$R^d$, —N$R^a$C(O)O$R^d$, —N$R^a$S(O)$_2R^d$, —S$R^a$, or —S(O)$_2R^a$, wherein each $R^a$, $R^b$, $R^c$, and $R^d$ is as defined herein. In certain embodiments, in any one of Formulae (I) to (XIX), $R^6$ is bicyclic $C_{8-14}$, optionally substituted with one, two, or three substituents Q, wherein each substituent is independently (i) cyano or halo; (ii) $C_{1-6}$ alkyl, $C_{1-6}$ heteroalkyl, $C_{2-6}$ alkynyl, $C_{3-10}$ cycloalkyl, $C_{6-14}$ aryl, heteroaryl, or heterocyclyl, each optionally substituted with one or more substituents $Q^a$; or (iii) —C(O)N$R^bR^c$, —O$R^a$, —N$R^bR^c$, —N$R^a$C(O)$R^d$, —N$R^a$C(O)O$R^d$, —N$R^a$S(O)$_2R^d$, or —S(O)$_2R^a$, wherein each $R^a$, $R^b$, $R^c$, and $R^d$ is as defined herein.

In certain embodiments, in any one of Formulae (I) to (XIX), $R^6$ is bicyclic $C_{8-14}$, optionally substituted with one, two, or three substituents Q, wherein each substituent is independently cyano, fluoro, chloro, bromo, oxo, methyl, ethyl, isopropyl, isobutyl, tert-butyl, trifluoromethyl, morpholinomethyl, hydroxymethyl, (dimethylamino)methyl, (tert-butoxy-carbonylamino)methyl, ethynyl, cyclopropyl, cyclobutyl, cyclopentyl, cyclohexyl, phenyl, 3-bromophenyl, 4-methylphenyl, 3-trifluoromethylphenyl, 2-methoxyphenyl, benzyl, 5-methyl-furan-2-yl, imidazol-1-yl, oxazol-5-yl, pyrazol-1-yl, pyrrol-2-yl, 1,2,3-triazol-1-yl, 1,2,4-triazol-1-yl, pyrimidin-2-yl, pyrimidin-5-yl, pyridin-3-yl, pyridin-4-yl, 4-methylpyridin-2-yl, 2-methoxypyridin-3-yl, quinolin-6-yl, pyrrolidin-1-yl, morpholino, piperidin-1-yl, 1-benzoxy-carbonylpiperidin-4-yl, 1-(tert-butoxycarbonyl) piperidin-4-yl, 4-methylpiperazin-1-yl, 4-(tert-butoxycarbonyl)piperazin-1-yl, 2,2,2-trifluoroacetyl, benzoxycarbonyl, tert-butoxycarbonyl, aminocarbonyl, methylaminocarbonyl, dimethylaminocarbonyl, isopropylaminocarbonyl, hydroxyl, methoxy, ethoxy, difluoromethoxy, trifluoromethoxy, cyclohexylmethoxy, cyclopentoxy, phenoxy, 4-cyanophenoxy, 3-methylphenoxy, 4-trifluoromethylphenoxy, 4-cyano-2-fluorophenoxy, benzoxy, 4-cyanobenzoxy, pyridin-2-yloxy, pyridin-3-yloxy, amino, methylamino, ethylamino, dimethylamino, (2-hydroxyethyl)(methyl)amino), acetamido, benzoxycarbonylamino, tert-butoxycarbonylamino, methylsulfonylamino, methylthio, methylsulfonyl, or ethylsulfonyl. In certain embodiments, in any one of Formulae (I) to (XIX), $R^6$ is bicyclic $C_{8-14}$, optionally substituted with one, two, or three substituents Q, wherein each substituent is independently cyano, fluoro, chloro, bromo, methyl, isopropyl, tert-butyl, trifluoro-methyl, hydroxymethyl, (dimethylamino)methyl, (tert-butoxycarbonylamino)methyl, ethynyl, cyclopropyl, cyclobutyl, cyclopentyl, cyclohexyl, phenyl, 3-bromophenyl, 3-trifluoromethylphenyl, 2-methoxyphenyl, benzyl, 5-methylfuran-2-yl, imidazol-1-yl, oxazol-5-yl, pyrazol-1-yl, 1,2,4-triazol-1-yl, pyridin-4-yl, quinolin-6-yl, pyrrolidin-1-yl, morpholino, piperidin-1-yl, 1-benzoxy-carbonylpiperidin-4-yl, 1-(tert-butoxycarbonyl)piperidin-4-yl, 4-methylpiperazin-1-yl, aminocarbonyl, methylaminocarbonyl, dimethylaminocarbonyl, isopropylaminocarbonyl, hydroxyl, methoxy, ethoxy, difluoromethoxy, trifluoromethoxy, cyclopentoxy, cyclohexylmethoxy, phenoxy, 4-cyanophenoxy, 4-trifluoromethylphenoxy, 4-cyano-2-fluorophenoxy, benzoxy, 4-cyanobenzoxy, pyridin-2-yloxy, pyridin-3-yloxy, amino, methylamino, ethylamino, dimethylamino, (2-hydroxyethyl)(methyl)amino), acetamido, benzoxycarbonylamino, tert-butoxy-carbonylamino, methylsulfonylamino, or ethylsulfonyl.

In certain embodiments, in any one of Formulae (I) to (XIX), $R^6$ is bicyclo[4.2.0]-octa-1(6),2,4-trien-3-yl, naphthalen-1-yl, naphthalen-2-yl, 5,6,7,8-tetrahydronaphthalen-1-yl, or 5,6,7,8-tetrahydronaphthalen-2-yl, each optionally substituted with one, two, or three substituents Q, wherein each substituent is independently cyano, fluoro, chloro, bromo, oxo, methyl, ethyl, isopropyl, isobutyl, tert-butyl, trifluoromethyl, morpholinomethyl, hydroxymethyl, (dimethylamino)methyl, (tert-butoxycarbonylamino)methyl, ethynyl, cyclopropyl, cyclobutyl, cyclopentyl, cyclohexyl, phenyl, 3-bromophenyl, 4-methylphenyl, 3-trifluoromethylphenyl, 2-methoxyphenyl, benzyl, 5-methylfuran-2-yl, imidazol-1-yl, oxazol-5-yl, pyrazol-1-yl, pyrrol-2-yl, 1,2,3-triazol-1-yl, 1,2,4-triazol-1-yl, pyrimidin-2-yl, pyrimidin-5-yl, pyridin-3-yl, pyridin-4-yl, 4-methylpyridin-2-yl, 2-methoxypyridin-3-yl, quinolin-6-yl, pyrrolidin-1-yl, morpholino, piperidin-1-yl, 1-benzoxycarbonylpiperidin-4-yl, 1-(tert-butoxycarbonyl)piperidin-4-yl, 4-methylpiperazin-1-yl, 4-(tert-butoxycarbonyl)piperazin-1-yl, 2,2,2-trifluoroacetyl, benzoxy-carbonyl, tert-butoxycarbonyl, aminocarbonyl, methylaminocarbonyl, dimethylaminocarbonyl, isopropylaminocarbonyl, hydroxyl, methoxy, ethoxy, difluoromethoxy, trifluoromethoxy, cyclohexylmethoxy, cyclopentoxy, phenoxy, 4-cyanophenoxy, 3-methylphenoxy, 4-trifluoromethylphenoxy, 4-cyano-2-fluorophenoxy, benzoxy, 4-cyanobenzoxy, pyridin-2-yloxy, pyridin-3-yloxy, amino, methylamino, ethylamino, dimethylamino, (2-hydroxyethyl)(methyl)amino), acetamido, benzoxycarbonylamino, tert-butoxycarbonylamino, methylsulfonylamino, methylthio, methylsulfonyl, or ethylsulfonyl. In certain embodiments, in any one of Formulae (I) to (XIX), $R^6$ is bicyclo[4.2.0]octa-1(6),2,4-trien-3-yl, naphthalen-1-yl, naphthalen-2-yl, 5,6,7,8-tetrahydronaphthalen-1-yl, or 5,6,7,8-tetrahydronaphthalen-2-yl, each optionally substituted with one, two, or three substituents Q, wherein each substituent is independently cyano, fluoro, chloro, bromo, methyl, isopropyl, tert-butyl, trifluoromethyl, hydroxymethyl, (dimethylamino)-methyl, (tert-butoxycarbonylamino)methyl, ethynyl, cyclopropyl, cyclobutyl, cyclopentyl, cyclohexyl, phenyl, 3-bromophenyl, 3-trifluoromethylphenyl, 2-methoxyphenyl, benzyl, 5-methylfuran-2-yl, imidazol-1-yl, oxazol-5-yl, pyrazol-1-yl, 1,2,4-triazol-1-yl, pyridin-4-yl, quinolin-6-yl, pyrrolidin-1-yl, morpholino, piperidin-1-yl, 1-benzoxycarbonylpiperidin-4-yl, 1-(tert-butoxycarbonyl)piperidin-4-yl, 4-methylpiperazin-1-yl, aminocarbonyl, methylamino-carbonyl, dimethylaminocarbonyl, isopropylaminocarbonyl, hydroxyl, methoxy, ethoxy, difluoromethoxy, trifluoromethoxy, cyclopentoxy, cyclohexylmethoxy, phenoxy, 4-cyanophenoxy, 4-trifluoromethylphenoxy, 4-cyano-2-fluorophenoxy, benzoxy, 4-cyanobenzoxy, pyridin-2-yloxy, pyridin-3-yloxy, amino, methylamino, ethylamino, dimethylamino, (2-hydroxyethyl)(methyl)amino), acetamido, benzoxycarbonylamino, tert-butoxycarbonylamino, methylsulfonylamino, or ethylsulfonyl.

In certain embodiments, in any one of Formulae (I) to (XIX), $R^6$ is bicyclo[4.2.0]-octa-1(6),2,4-trien-3-yl, naphthalen-1-yl, naphthalen-2-yl, 5-(dimethylamino)-naphthalen-1-yl, 6-(dimethylamino)naphthalen-2-yl, 5,6,7,8-tetrahydro-naphthalen-1-yl, or 5,6,7,8-tetrahydro-naphthalen-2-yl.

In certain embodiments, in any one of Formulae (I) to (XIX), $R^6$ is $C_{7-15}$ aralkyl, optionally substituted with one or more substituents Q.

In certain embodiments, in any one of Formulae (I) to (XIX), $R^6$ is $C_{7-15}$ aralkyl, optionally substituted with one, two, or three substituents Q, wherein each substituent is independently (i) cyano, halo, or oxo; (ii) $C_{1-6}$ alkyl, $C_{1-6}$ heteroalkyl, $C_{2-6}$ alkynyl, $C_{3-10}$ cycloalkyl, $C_{6-14}$ aryl, $C_{7-15}$ aralkyl, heteroaryl, or heterocyclyl, each optionally substituted with one or more substituents $Q^a$; or (iii) —C(O)$R^a$, —C(O)O$R^a$, —C(O)N$R^bR^c$, —O$R^a$, —N$R^bR^c$, —N$R^a$C(O)$R^d$, —N$R^a$C(O)O$R^d$, —N$R^a$S(O)$_2R^d$, —S$R^a$, or —S(O)$_2R^a$, wherein each $R^a$, $R^b$, $R^c$, and $R^d$ is as defined herein. In certain embodiments, in any one of Formulae (I) to (XIX), $R^6$ is $C_{7-15}$ aralkyl, optionally substituted with one, two, or three substituents Q, wherein each substituent is independently (i) cyano or halo; (ii) $C_{1-6}$ alkyl or $C_{1-6}$ heteroalkyl, each optionally substituted with one or more substituents $Q^a$; or (iii) —O$R^a$, wherein $R^a$ is as defined herein.

In certain embodiments, in any one of Formulae (I) to (XIX), $R^6$ is $C_{7-15}$ aralkyl, optionally substituted with one, two, or three substituents Q, wherein each substituent is independently cyano, fluoro, chloro, bromo, oxo, methyl, ethyl, isopropyl, isobutyl, tert-butyl, trifluoromethyl, morpholinomethyl, hydroxymethyl, (dimethylamino)methyl, (tert-butoxy-carbonylamino)methyl, ethynyl, cyclopropyl, cyclobutyl, cyclopentyl, cyclohexyl, phenyl, 3-bromophenyl, 4-methylphenyl, 3-trifluoromethylphenyl, 2-methoxyphenyl, benzyl, 5-methyl-furan-2-yl, imidazol-1-yl, oxazol-5-yl, pyrazol-1-yl, pyrrol-2-yl, 1,2,3-triazol-1-yl, 1,2,4-triazol-1-yl, pyrimidin-2-yl, pyrimidin-5-yl, pyridin-3-yl, pyridin-4-yl, 4-methylpyridin-2-yl, 2-methoxypyridin-3-yl, quinolin-6-yl, pyrrolidin-1-yl, morpholino, piperidin-1-yl, 1-benzoxy-carbonyl-piperidin-4-yl, 1-(tert-butoxycarbonyl)piperidin-4-yl, 4-methylpiperazin-1-yl, 4-(tert-butoxycarbonyl)piperazin-1-yl, 2,2,2-trifluoroacetyl, benzoxycarbonyl, tert-butoxycarbonyl, aminocarbonyl, methylaminocarbonyl, dimethylaminocarbonyl, isopropylaminocarbonyl, hydroxyl, methoxy, ethoxy, difluoromethoxy, trifluoromethoxy, cyclohexylmethoxy, cyclopentoxy, phenoxy, 4-cyanophenoxy, 3-methylphenoxy, 4-trifluoromethylphenoxy, 4-cyano-2-fluorophenoxy, benzoxy, 4-cyanobenzoxy, pyridin-2-yloxy, pyridin-3-yloxy, amino, methylamino, ethylamino, dimethylamino, (2-hydroxyethyl)(methyl)amino), acetamido, benzoxy-carbonylamino, tert-butoxycarbonylamino, methylsulfonylamino, methylthio, methylsulfonyl, or ethylsulfonyl. In certain embodiments, in any one of Formulae (I) to (XIX), $R^6$ is $C_{7-15}$ aralkyl, optionally substituted with one, two, or three substituents Q, wherein each substituent is independently cyano, fluoro, chloro, bromo, methyl, trifluoromethyl, or methoxy.

In certain embodiments, in any one of Formulae (I) to (XIX), $R^6$ is benzyl, optionally substituted with one, two, or three substituents Q, wherein each substituent is independently cyano, fluoro, chloro, bromo, oxo, methyl, ethyl, isopropyl, isobutyl, tert-butyl, trifluoromethyl, morpholinomethyl, hydroxymethyl, (dimethylamino)methyl, (tert-butoxy-carbonylamino)methyl, ethynyl, cyclopropyl, cyclobutyl, cyclopentyl, cyclohexyl, phenyl, 3-bromophenyl, 4-methylphenyl, 3-trifluoromethylphenyl, 2-methoxyphenyl, benzyl, 5-methyl-furan-2-yl, imidazol-1-yl, oxazol-5-yl, pyrazol-1-yl, pyrrol-2-yl, 1,2,3-triazol-1-yl, 1,2,4-triazol-1-yl, pyrimidin-2-yl, pyrimidin-5-yl, pyridin-3-yl, pyridin-4-yl, 4-methylpyridin-2-yl, 2-methoxypyridin-3-yl, quinolin-6-yl, pyrrolidin-1-yl, morpholino, piperidin-1-yl, 1-benzoxy-carbonylpiperidin-4-yl, 1-(tert-butoxycarbonyl)piperidin-4-yl, 4-methylpiperazin-1-yl, 4-(tert-butoxycarbonyl)piperazin-1-yl, 2,2,2-trifluoroacetyl, benzoxycarbonyl, tert-butoxycarbonyl, aminocarbonyl, methylaminocarbonyl, dimethylaminocarbonyl, isopropylaminocarbonyl, hydroxyl, methoxy, ethoxy, difluoromethoxy, trifluoromethoxy, cyclohexylmethoxy, cyclopentoxy, phenoxy, 4-cyanophenoxy, 3-methylphenoxy, 4-trifluoromethylphenoxy, 4-cyano-2-fluorophenoxy, benzoxy, 4-cyanobenzoxy, pyridin-2-yloxy, pyridin-3-yloxy, amino, methylamino, ethylamino, dimethylamino, (2-hydroxyethyl)(methyl)amino), acetamido, benzoxycarbonylamino, tert-butoxycarbonylamino, methylsulfonylamino, methylthio, methylsulfonyl, or ethylsulfonyl. In certain embodiments, in any one of Formulae (I) to (XIX), $R^6$ is benzyl, optionally substituted with one, two, or three substituents Q, wherein each substituent is independently cyano, fluoro, chloro, bromo, methyl, trifluoromethyl, or methoxy.

In certain embodiments, in any one of Formulae (I) to (XIX), $R^6$ is benzyl, 2-cyanobenzyl, 3-cyanobenzyl, 4-cyanobenzyl, 4-fluorobenzyl, 4-chlorobenzyl, 4-bromobenzyl, 2-methylbenzyl, 3-methylbenzyl, 4-methylbenzyl, 4-trifluoromethylbenzyl, 2-methoxy-benzyl, 3-methoxybenzyl, 4-methoxybenzyl, 2-phenylethyl, 3-phenylpropyl, 2-phenylprop-2-yl, 2-(3-bromophenyl)ethyl, 2-methyl-2-phenylpropyl, 2-(3-trifluoromethylphenyl)ethyl, or 2-(2-methoxyphenyl)ethyl.

In certain embodiments, in any one of Formulae (I) to (XIX), $R^6$ is heteroaryl, optionally substituted with one or more substituents Q. In certain embodiments, in any one of Formulae (I) to (XIX), $R^6$ is monocyclic heteroaryl, optionally substituted with one or more substituents Q. In certain embodiments, in any one of Formulae (I) to (XIX), $R^6$ is 5-, 6-, or 7-membered monocyclic heteroaryl, each optionally substituted with one or more substituents Q. In certain embodiments, in any one of Formulae (I) to (XIX), $R^6$ is 5-membered monocyclic heteroaryl, each optionally substituted with one or more substituents Q. In certain embodiments, in any one of Formulae (I) to (XIX), $R^6$ is 6-membered monocyclic heteroaryl, each optionally substituted with one or more substituents Q. In certain embodiments, in any one of Formulae (I) to (XIX), $R^6$ is 7-membered monocyclic heteroaryl, each optionally substituted with one or more substituents Q.

In certain embodiments, in any one of Formulae (I) to (XIX), $R^6$ is monocyclic heteroaryl, optionally substituted with one, two, or three substituents Q, wherein each substituent is independently (i) cyano, halo, or oxo; (ii) $C_{1-6}$ alkyl, $C_{1-6}$ heteroalkyl, $C_{2-6}$ alkynyl, $C_{3-10}$ cycloalkyl, $C_{6-14}$ aryl, $C_{7-15}$ aralkyl, heteroaryl, or heterocyclyl, each optionally substituted with one or more substituents $Q^a$; or (iii) —C(O)$R^a$, —C(O)O$R^a$, —C(O)N$R^bR^c$, —O$R^a$, —N$R^bR^c$, —N$R^a$C(O)$R^d$, —N$R^a$C(O)O$R^d$, —N$R^a$S(O)$_2R^d$, —S$R^a$, or —S(O)$_2R^a$, wherein each $R^a$, $R^b$, $R^c$, and $R^d$ is as defined herein. In certain embodiments, in any one of Formulae (I) to (XIX), $R^6$ is monocyclic heteroaryl, optionally substituted with one, two, or three substituents Q, wherein each substituent is independently (i) cyano, halo, or oxo; (ii) $C_{1-6}$ alkyl, $C_{1-6}$ heteroalkyl, $C_{2-6}$ alkynyl, $C_{3-10}$ cycloalkyl, $C_{6-14}$ aryl, heteroaryl, or heterocyclyl, each optionally substituted with one or more substituents $Q^a$; or (iii) —O$R^a$, —N$R^bR^c$, —S$R^a$, or —S(O)$_2R^a$, wherein each $R^a$, $R^b$, and $R^c$ is as defined herein.

In certain embodiments, in any one of Formulae (I) to (XIX), $R^6$ is monocyclic heteroaryl, optionally substituted with one, two, or three substituents Q, wherein each substituent is independently cyano, fluoro, chloro, bromo, oxo, methyl, ethyl, isopropyl, isobutyl, tert-butyl, trifluoromethyl, morpholinomethyl, hydroxymethyl, (dimethylamino)methyl, (tert-butoxy-carbonylamino)methyl, ethynyl, cyclopropyl, cyclobutyl, cyclopentyl, cyclohexyl, phenyl, 3-bromophenyl, 4-methylphenyl, 3-trifluoromethylphenyl, 2-methoxyphenyl, benzyl, 5-methyl-furan-2-yl, imidazol-1-yl, oxazol-5-yl, pyrazol-1-yl, pyrrol-2-yl, 1,2,3-triazol-1-yl, 1,2,4-triazol-1-yl, pyrimidin-2-yl, pyrimidin-5-yl, pyridin-3-yl, pyridin-4-yl, 4-methylpyridin-2-yl, 2-methoxypyridin-3-yl, quinolin-6-yl, pyrrolidin-1-yl, morpholino, piperidin-1-yl, 1-benzoxy-carbonylpiperidin-4-yl, 1-(tert-butoxycarbonyl)piperidin-4-yl, 4-methylpiperazin-1-yl, 4-(tert-butoxycarbonyl)piperazin-1-yl, 2,2,2-trifluoroacetyl, benzoxycarbonyl, tert-butoxycarbonyl, aminocarbonyl, methylaminocarbonyl, dimethylaminocarbonyl, isopropylaminocarbonyl, hydroxyl, methoxy, ethoxy, difluoromethoxy, trifluoromethoxy, cyclohexylmethoxy, cyclopentoxy, phenoxy, 4-cyanophenoxy, 3-methylphenoxy, 4-trifluoromethylphenoxy, 4-cyano-2-fluorophenoxy, benzoxy, 4-cyanobenzoxy, pyridin-2-yloxy, pyridin-3-yloxy, amino, methylamino, ethylamino, dimethylamino, (2-hydroxyethyl)(methyl)amino), acetamido, benzoxycarbonylamino, tert-butoxycarbonylamino, methylsulfonylamino, methylthio, methylsulfonyl, or ethylsulfonyl. In certain embodiments, in any one of Formulae (I) to (XIX), $R^6$ is monocyclic heteroaryl, optionally substituted with one, two, or three substituents Q, wherein each substituent is independently cyano, chloro, oxo, methyl, isopropyl, isobutyl, tert-butyl, trifluoromethyl, morpholinomethyl, hydroxymethyl, ethynyl, cyclopropyl, phenyl, 4-methylphenyl, 4-methyl-pyridin-2-yl, pyrrolidin-1-yl, morpholino, 1-tert-butoxycarbonylpiperidin-4-yl, methoxy, phenoxy, benzoxy, amino, dimethylamino, methylthio, or methylsulfonyl.

In certain embodiments, in any one of Formulae (I) to (XIX), $R^6$ is 5-membered heteroaryl, optionally substituted with one, two, or three substituents Q, wherein each substituent is independently (i) cyano, halo, or oxo; (ii) $C_{1-6}$ alkyl, $C_{1-6}$ heteroalkyl, $C_{2-6}$ alkynyl, $C_{3-10}$ cycloalkyl, $C_{6-14}$ aryl, $C_{7-15}$ aralkyl, heteroaryl, or heterocyclyl, each optionally substituted with one or more substituents $Q^a$; or (iii) —C(O)$R^a$, —C(O)O$R^a$, —C(O)N$R^bR^c$, —O$R^a$, —N$R^bR^c$, —N$R^a$C(O)$R^d$, —N$R^a$C(O)O$R^d$, —N$R^a$S(O)$_2R^d$, —S$R^a$, or —S(O)$_2R^a$, wherein each $R^a$, $R^b$, $R^c$, and $R^d$ is as defined herein. In certain embodiments, in any one of Formulae (I) to (XIX), $R^6$ is 5-membered heteroaryl, optionally substituted with one, two, or three substituents Q, wherein each substituent is independently (i) cyano or halo; (ii) $C_{1-6}$ alkyl, $C_{3-10}$ cycloalkyl, $C_{6-14}$ aryl, heteroaryl, or heterocyclyl, each optionally substituted with one or more substituents $Q^a$; or (iii) —O$R^a$ or —N$R^bR^c$, wherein $R^a$, $R^b$, and $R^c$ are each as defined herein.

In certain embodiments, in any one of Formulae (I) to (XIX), $R^6$ is 5-membered heteroaryl, optionally substituted with one, two, or three substituents Q, wherein each substituent is independently cyano, fluoro, chloro, bromo, oxo, methyl, ethyl, isopropyl, isobutyl, tert-butyl, trifluoromethyl, morpholinomethyl, hydroxymethyl, (dimethylamino)methyl, (tert-butoxy-carbonylamino)methyl, ethynyl, cyclopropyl, cyclobutyl, cyclopentyl, cyclohexyl, phenyl, 3-bromophenyl, 4-methylphenyl, 3-trifluoromethylphenyl, 2-methoxyphenyl, benzyl, 5-methyl-furan-2-yl, imidazol-1-yl, oxazol-5-yl, pyrazol-1-yl, pyrrol-2-yl, 1,2,3-triazol-1-yl, 1,2,4-triazol-1-yl, pyrimidin-2-yl, pyrimidin-5-yl, pyridin-3-yl, pyridin-4-yl, 4-methylpyridin-2-yl, 2-methoxypyridin-3-yl, quinolin-6-yl, pyrrolidin-1-yl, morpholino, piperidin-1-yl, 1-benzoxy-carbonylpiperidin-4-yl, 1-(tert-butoxycarbonyl)piperidin-4-yl, 4-methylpiperazin-1-yl, 4-(tert-butoxycarbonyl)piperazin-1-yl, 2,2,2-trifluoroacetyl, benzoxycarbonyl, tert-butoxycarbonyl, aminocarbonyl, methylaminocarbonyl, dimethylaminocarbonyl, isopropylaminocarbonyl, hydroxyl, methoxy, ethoxy, difluoromethoxy, trifluoromethoxy, cyclohexylmethoxy, cyclopentoxy, phenoxy, 4-cyanophenoxy, 3-methylphenoxy, 4-trifluoromethylphenoxy, 4-cyano-2-fluorophenoxy, benzoxy, 4-cyanobenzoxy, pyridin-2-yloxy, pyridin-3-yloxy, amino, methylamino, ethylamino, dimethylamino, (2-hydroxyethyl)(methyl)amino), acetamido, benzoxy-carbonylamino, tert-butoxycarbonylamino, methylsulfonylamino, methylthio, methylsulfonyl, or ethylsulfonyl. In certain embodiments, in any one of Formulae (I) to (XIX), $R^6$ is 5-membered heteroaryl, optionally substituted with one, two, or three substituents Q, wherein each substituent is independently cyano, chloro, oxo, methyl, isobutyl, isopropyl, tert-butyl, trifluoro-methyl, morpholinomethyl, hydroxymethyl, ethynyl, cyclopropyl, phenyl, 4-methylphenyl, 4-methylpyridin-2-yl, pyrrolidin-1-yl, morpholino, 1-tert-butoxycarbonylpiperidin-4-yl, methoxy, phenoxy, benzoxy, amino, dimethylamino, methylthio, or methylsulfonyl.

In certain embodiments, in any one of Formulae (I) to (XIX), $R^6$ is furanyl, imidazolyl, oxazolyl, pyrazolyl, pyrrolyl, thiazolyl, thienyl, 1,2,4-triazolyl, or tetrazolyl, each optionally substituted with one, two, or three substituents Q, wherein each substituent is independently cyano, fluoro, chloro, bromo, oxo, methyl, ethyl, isopropyl, isobutyl, tert-butyl, trifluoromethyl, morpholinomethyl, hydroxymethyl, (dimethylamino)methyl, (tert-butoxy-carbonylamino)methyl, ethynyl, cyclopropyl, cyclobutyl, cyclopentyl, cyclohexyl, phenyl, 3-bromophenyl, 4-methylphenyl, 3-trifluoromethylphenyl, 2-methoxyphenyl, benzyl, 5-methyl-furan-2-yl, imidazol-1-yl, oxazol-5-yl, pyrazol-1-yl, pyrrol-2-yl, 1,2,3-triazol-1-yl, 1,2,4-triazol-1-yl, pyrimidin-2-yl, pyrimidin-5-yl, pyridin-3-yl, pyridin-4-yl, 4-methylpyridin-2-yl, 2-methoxypyridin-3-yl, quinolin-6-yl, pyrrolidin-1-yl, morpholino, piperidin-1-yl, 1-benzoxy-carbonylpiperidin-4-yl, 1-(tert-butoxycarbonyl)piperidin-4-yl, 4-methylpiperazin-1-yl, 4-(tert-butoxycarbonyl)piperazin-1-yl, 2,2,2-trifluoroacetyl, benzoxycarbonyl, tert-butoxycarbonyl, aminocarbonyl, methylaminocarbonyl, dimethylaminocarbonyl, isopropylaminocarbonyl, hydroxyl, methoxy, ethoxy, difluoromethoxy, trifluoromethoxy, cyclohexylmethoxy, cyclopentoxy, phenoxy, 4-cyanophenoxy, 3-methylphenoxy, 4-trifluoromethylphenoxy, 4-cyano-2-fluorophenoxy, benzoxy, 4-cyanobenzoxy, pyridin-2-yloxy, pyridin-3-yloxy, amino, methylamino, ethylamino, dimethylamino, (2-hydroxyethyl)(methyl)amino), acetamido, benzoxy-carbonylamino, tert-butoxycarbonylamino, methylsulfonylamino, methylthio, methylsulfonyl, or ethylsulfonyl. In certain embodiments, in any one of Formulae (I) to (XIX), $R^6$ is furanyl, imidazolyl, oxazolyl, pyrazolyl, pyrrolyl, thiazolyl, thienyl, 1,2,4-triazolyl, or tetrazolyl, each optionally substituted with one, two, or three substituents Q, wherein each substituent is independently cyano, chloro, oxo, methyl, isopropyl, isobutyl, tert-butyl, trifluoromethyl, morpholinomethyl, hydroxymethyl, ethynyl, cyclopropyl, phenyl, 4-methylphenyl, 4-methyl-pyridin-2-yl, pyrrolidin-1-yl, morpholino, 1-tert-butoxycarbonylpiperidin-4-yl, methoxy, phenoxy, benzoxy, amino, dimethylamino, methylthio, or methylsulfonyl.

In certain embodiments, in any one of Formulae (I) to (XIX), $R^6$ is furan-2-yl, furan-3-yl, imidazol-2-yl, imidazol-4-yl, imidazol-5-yl, oxazol-2-yl, oxazol-4-yl, oxazol-5-yl, pyrazol-3-yl, pyrazol-4-yl, pyrazol-5-yl, pyrrol-2-yl, pyrrol-3-yl, pyrrol-4-yl, thiazol-2-yl, thiazol-4-yl, thiazol-5-yl, thien-2-yl, thien-3-yl, 1,2,4-triazol-3-yl, 1,2,4-triazol-4-yl, or tetrazol-5-yl, each optionally substituted with one, two, or three substituents Q, wherein each substituent is independently cyano, fluoro, chloro, bromo, oxo, methyl, ethyl, isopropyl, isobutyl, tert-butyl, trifluoromethyl, morpholinomethyl, hydroxymethyl, (dimethylamino)methyl, (tert-butoxy-carbonylamino)methyl, ethynyl, cyclopropyl, cyclobutyl, cyclopentyl, cyclohexyl, phenyl, 3-bromophenyl, 4-methylphenyl, 3-trifluoromethylphenyl, 2-methoxyphenyl, benzyl, 5-methyl-furan-2-yl, imidazol-1-yl, oxazol-5-yl, pyrazol-1-yl, pyrrol-2-yl, 1,2,3-triazol-1-yl, 1,2,4-triazol-1-yl, pyrimidin-2-yl, pyrimidin-5-yl, pyridin-3-yl, pyridin-4-yl, 4-methylpyridin-2-yl, 2-methoxypyridin-3-yl, quinolin-6-yl, pyrrolidin-1-yl, morpholino, piperidin-1-yl, 1-benzoxy-carbonylpiperidin-4-yl, 1-(tert-butoxycarbonyl)piperidin-4-yl, 4-methylpiperazin-1-yl, 4-(tert-butoxycarbonyl)piperazin-1-yl, 2,2,2-trifluoroacetyl, benzoxycarbonyl, tert-butoxycarbonyl, aminocarbonyl, methylaminocarbonyl, dimethylaminocarbonyl, isopropylaminocarbonyl, hydroxyl, methoxy, ethoxy, difluoromethoxy, trifluoromethoxy, cyclohexylmethoxy, cyclopentoxy, phenoxy, 4-cyanophenoxy, 3-methylphenoxy, 4-trifluoromethylphenoxy, 4-cyano-2-fluorophenoxy, benzoxy, 4-cyanobenzoxy, pyridin-2-yloxy, pyridin-3-yloxy, amino, methylamino, ethylamino, dimethylamino, (2-hydroxyethyl)(methyl)amino), acetamido, benzoxy-carbonylamino, tert-butoxycarbonylamino, methylsulfonylamino, methylthio, methylsulfonyl, or ethylsulfonyl. In certain embodiments, in any one of Formulae (I) to (XIX), $R^6$ is furan-2-yl, furan-3-yl, imidazol-2-yl, imidazol-4-yl, imidazol-5-yl, oxazol-2-yl, oxazol-4-yl, oxazol-5-yl, pyrazol-3-yl, pyrazol-4-yl, pyrazol-5-yl, pyrrol-2-yl, pyrrol-3-yl, pyrrol-4-yl, thiazol-2-yl, thiazol-4-yl, thiazol-5-yl, thien-2-yl, thien-3-yl, 1,2,4-triazol-3-yl, 1,2,4-triazol-4-yl, or tetrazol-5-yl, each optionally substituted with one, two, or three substituents Q, wherein each substituent is independently cyano, chloro, oxo, methyl, isopropyl, isobutyl, tert-butyl, trifluoromethyl, morpholinomethyl, hydroxymethyl, ethynyl, cyclopropyl, phenyl, 4-methylphenyl, 4-methylpyridin-2-yl, pyrrolidin-1-yl, morpholino, 1-tert-butoxycarbonylpiperidin-4-yl, methoxy, phenoxy, benzoxy, amino, dimethylamino, methylthio, or methylsulfonyl.

In certain embodiments, in any one of Formulae (I) to (XIX), $R^6$ is furan-2-yl, furan-3-yl, 5-methylfuran-2-yl, 4-isopropylfuran-2-yl, 5-(morpholinomethyl)furan-2-yl, 5-(hydroxymethyl)furan-2-yl, 3-methoxy-furan-2-yl, imidazol-4-yl, 1-methylimidazol-2-yl, 1-methylimidazol-4-yl, 1-methylimidazol-5-yl, 2-methylimidazol-4-yl, 2,5-dimethylimidazol-4-yl, 2-phenylimidazol-4-yl, 4-phenylimidazol-2-yl, oxazol-2-yl, 2-methyloxazol-4-yl, 2-methyl-oxazol-5-yl, 4-methyloxazol-5-yl, pyrazol-3-yl, pyrazol-4-yl, 1-methylpyrazol-3-yl, 1-methyl-pyrazol-4-yl, 1-methylpyrazol-5-yl, 5-methylpyrazol-3-yl, 1-isopropylpyrazol-4-yl, 1-isobutyl-pyrazol-4-yl, 5-amino-1-methylpyrazol-4-yl, 4-chloro-1-methylpyrazol-3-yl, 2-cyano-1-methyl-pyrazol-4-yl, 1,4-dimethylpyrazol-5-yl, 1-phenylpyrazol-3-yl, 1-(2-methylphenyl)-pyrazol-4-yl, pyrrol-2-yl, pyrrol-3-yl, 3-cyanopyrrol-2-yl, 4-cyanopyrrol-2-yl, 1-methylpyrrol-2-yl, 3-methyl-pyrrol-2-yl, 5-methylpyrrol-2-yl, 5-(hydroxymethyl)pyrrol-2-yl, 5-(tert-butyl)pyrrol-2-yl, 2-cyano-1-methylpyrrol-4-yl, thiazol-2-yl, thiazol-4-yl, thiazol-5-yl, 2-methylthiazol-5-yl, 4-methylthiazol-5-yl, 5-methylthiazol-2-yl, 2-cyclopropylthiazol-5-yl, 2-(morpholino)thiazol-5-yl, thien-2-yl, thien-3-yl, 2-chlorothien-3-yl, 5-chlorothien-2-yl, 5-cyanothien-2-yl, 5-cyanothien-3-yl, 3-methylthien-2-yl, 5-(dimethylamino)thien-2-yl, 5-methyl-1,2,4-triazol-3-yl, 1-(tert-butyl)-1,2,3-triazol-4-yl, 1-(1-tert-butoxycarbonylpiperidin-4-yl)-1,2,3-triazol-4-yl, or 2-methyltetrazol-5-yl.

In certain embodiments, in any one of Formulae (I) to (XIX), $R^6$ is 6-membered heteroaryl, optionally substituted with one, two, or three substituents Q, wherein each substituent is independently (i) cyano, halo, or oxo; (ii) $C_{1-6}$ alkyl, $C_{1-6}$ heteroalkyl, $C_{2-6}$ alkynyl, $C_{3-10}$ cycloalkyl, $C_{6-14}$ aryl, $C_{7-15}$ aralkyl, heteroaryl, or heterocyclyl, each optionally substituted with one or more substituents $Q^a$; or (iii) —C(O)$R^a$, —C(O)O$R^a$, —C(O)N$R^bR^c$, —O$R^a$, —N$R^bR^c$, —N$R^a$C(O)$R^d$, —N$R^a$C(O)O$R^d$, —N$R^a$S(O)$_2R^d$, —S$R^a$, or —S(O)$_2R^a$, wherein each $R^a$, $R^b$, $R^c$, and $R^d$ is as defined herein. In certain embodiments, in any one of Formulae (I) to (XIX), $R^6$ is 6-membered monocyclic heteroaryl, optionally substituted with one, two, or three substituents Q, wherein each substituent is independently (i) cyano, halo, or oxo; (ii) $C_{1-6}$ alkyl, $C_{1-6}$ heteroalkyl, $C_{2-6}$ alkynyl, $C_{3-10}$ cycloalkyl, $C_{6-14}$ aryl, heteroaryl, or heterocyclyl, each optionally substituted with one or more substituents $Q^a$; or (iii) —O$R^a$, —N$R^bR^c$, —S$R^a$, or —S(O)$_2R^a$, wherein each $R^a$, $R^b$, and $R^c$ is as defined herein.

In certain embodiments, in any one of Formulae (I) to (XIX), $R^6$ is 6-membered heteroaryl, optionally substituted with one, two, or three substituents Q, wherein each substituent is independently cyano, fluoro, chloro, bromo, oxo, methyl, ethyl, isopropyl, isobutyl, tert-butyl, trifluoromethyl, morpholinomethyl, hydroxymethyl, (dimethylamino)methyl, (tert-butoxy-carbonylamino)methyl, ethynyl, cyclopropyl, cyclobutyl, cyclopentyl, cyclohexyl, phenyl, 3-bromophenyl, 4-methylphenyl, 3-trifluoromethylphenyl, 2-methoxyphenyl, benzyl, 5-methyl-furan-2-yl, imidazol-1-yl, oxazol-5-yl, pyrazol-1-yl, pyrrol-2-yl, 1,2,3-triazol-1-yl, 1,2,4-triazol-1-yl, pyrimidin-2-yl, pyrimidin-5-yl, pyridin-3-yl, pyridin-4-yl, 4-methylpyridin-2-yl, 2-methoxypyridin-3-yl, quinolin-6-yl, pyrrolidin-1-yl, morpholino, piperidin-1-yl, 1-benzoxy-carbonylpiperidin-4-yl, 1-(tert-butoxycarbonyl)piperidin-4-yl, 4-methylpiperazin-1-yl, 4-(tert-butoxycarbonyl)piperazin-1-yl, 2,2,2-trifluoroacetyl, benzoxycarbonyl, tert-butoxycarbonyl, aminocarbonyl, methylaminocarbonyl, dimethylaminocarbonyl, isopropylaminocarbonyl, hydroxyl, methoxy, ethoxy, difluoromethoxy, trifluoromethoxy, cyclohexylmethoxy, cyclopentoxy, phenoxy, 4-cyanophenoxy, 3-methylphenoxy, 4-trifluoromethylphenoxy, 4-cyano-2-fluorophenoxy, benzoxy, 4-cyanobenzoxy, pyridin-2-yloxy, pyridin-3-yloxy, amino, methylamino, ethylamino, dimethylamino, (2-hydroxyethyl)(methyl)amino), acetamido, benzoxycarbonylamino, tert-butoxycarbonylamino, methylsulfonylamino, methylthio, methylsulfonyl, or ethylsulfonyl. In certain embodiments, in any one of Formulae (I) to (XIX), $R^6$ is 6-membered monocyclic heteroaryl, optionally substituted with one, two, or three substituents Q, wherein each substituent is independently cyano, fluoro, chloro, oxo, methyl, isopropyl, isobutyl, tert-butyl, trifluoromethyl, ethynyl, cyclopropyl, 4-methylphenyl, 4-methylpyridin-2-yl, pyrrolidin-1-yl, morpholino, methoxy, phenoxy, amino, methylthio, or methylsulfonyl.

In certain embodiments, in any one of Formulae (I) to (XIX), $R^6$ is pyridinyl, 1,2-dihydropyridinyl, 1,6-dihydropyridinyl, pyridazinyl, or pyrimidinyl, each optionally substituted with one, two, or three substituents Q, wherein each substituent is independently cyano, fluoro, chloro, bromo, oxo, methyl, ethyl, isopropyl, tert-butyl, trifluoro-methyl, morpholinomethyl, hydroxymethyl, (dimethylamino)methyl, (tert-butoxycarbonylamino)methyl, ethynyl, cyclopropyl, cyclobutyl, cyclopentyl, cyclohexyl, phenyl, 3-bromo-phenyl, 4-methylphenyl, 3-trifluoromethylphenyl, 2-methoxyphenyl, benzyl, 5-methyl-furan-2-yl, imidazol-1-yl, oxazol-5-yl, pyrazol-1-yl, pyrrol-2-yl, 1,2,3-triazol-1-yl, 1,2,4-triazol-1-yl, pyrimidin-2-yl, pyrimidin-5-yl, pyridin-3-yl, pyridin-4-yl, 4-methylpyridin-2-yl, 2-methoxypyridin-3-yl, quinolin-6-yl, pyrrolidin-1-yl, morpholino, piperidin-1-yl, 1-benzoxycarbonylpiperidin-4-yl, 1-(tert-butoxycarbonyl)piperidin-4-yl, 4-methylpiperazin-1-yl, 4-(tert-butoxycarbonyl)piperazin-1-yl, 2,2,2-trifluoroacetyl, benzoxycarbonyl, tert-butoxycarbonyl, aminocarbonyl, methylamino-carbonyl, dimethylaminocarbonyl, isopropylaminocarbonyl, hydroxyl, methoxy, ethoxy, difluoromethoxy, trifluoromethoxy, cyclohexylmethoxy, cyclopentoxy, phenoxy, 4-cyanophenoxy, 3-methylphenoxy, 4-trifluoromethylphenoxy, 4-cyano-2-fluorophenoxy, benzoxy, 4-cyanobenzoxy, pyridin-2-yloxy, pyridin-3-yloxy, amino, methylamino, ethylamino, dimethylamino, (2-hydroxyethyl)(methyl)amino), acetamido, benzoxycarbonylamino, tert-butoxy-carbonylamino, methylsulfonylamino, methylthio, methylsulfonyl, or ethylsulfonyl. In certain embodiments, in any one of Formulae (I) to (XIX), $R^6$ is pyridinyl, 1,2-dihydropyridinyl, 1,6-dihydropyridinyl, pyridazinyl, or pyrimidinyl, each optionally substituted with one, two, or three substituents Q, wherein each substituent is independently cyano, chloro, oxo, methyl, isopropyl, isobutyl, tert-butyl, trifluoromethyl, morpholinomethyl, hydroxymethyl, ethynyl, cyclopropyl, phenyl, 4-methylphenyl, 4-methylpyridin-2-yl, pyrrolidin-1-yl, morpholino, 1-tert-butoxy-carbonylpiperidin-4-yl, methoxy, phenoxy, benzoxy, amino, dimethylamino, methylthio, or methylsulfonyl.

In certain embodiments, in any one of Formulae (I) to (XIX), $R^6$ is pyridin-2-yl, pyridin-3-yl, pyridin-4-yl, pyridin-5-yl, 1,2-dihydropyridin-3-yl, 1,2-dihydropyridin-4-yl, 1,6-dihydropyridin-2-yl, pyridazin-4-yl, pyrimidin-4-yl, or pyrimidin-5-yl, each optionally substituted with one, two, or three substituents Q, wherein each substituent is independently cyano, fluoro, chloro, bromo, oxo, methyl, ethyl, isopropyl, tert-butyl, trifluoromethyl, morpholinomethyl, hydroxymethyl, (dimethylamino)methyl, (tert-butoxycarbonylamino)methyl, ethynyl, cyclopropyl, cyclobutyl, cyclopentyl, cyclohexyl, phenyl, 3-bromophenyl, 4-methyl-phenyl, 3-trifluoromethylphenyl, 2-methoxyphenyl, benzyl, 5-methylfuran-2-yl, imidazol-1-yl, oxazol-5-yl, pyrazol-1-yl, pyrrol-2-yl, 1,2,3-triazol-1-yl, 1,2,4-triazol-1-yl, pyrimidin-2-yl, pyrimidin-5-yl, pyridin-3-yl, pyridin-4-yl, 4-methylpyridin-2-yl, 2-methoxypyridin-3-yl, quinolin-6-yl, pyrrolidin-1-yl, morpholino, piperidin-1-yl, 1-benzoxycarbonylpiperidin-4-yl, 1-(tert-butoxycarbonyl)piperidin-4-yl, 4-(tert-butoxycarbonyl)piperazin-1-yl, 4-methylpiperazin-1-yl, 2,2,2-trifluoroacetyl, benzoxycarbonyl, tert-butoxycarbonyl, aminocarbonyl, methylamino-carbonyl, dimethylaminocarbonyl, isopropylaminocarbonyl, hydroxyl, methoxy, ethoxy, difluoromethoxy, trifluoromethoxy, cyclohexylmethoxy, cyclopentoxy, phenoxy, 4-cyanophenoxy, 3-methylphenoxy, 4-trifluoromethylphenoxy, 4-cyano-2-fluorophenoxy, benzoxy, 4-cyanobenzoxy, pyridin-2-yloxy, pyridin-3-yloxy, amino, methylamino, ethylamino, dimethylamino, (2-hydroxyethyl)(methyl)amino), acetamido, benzoxycarbonylamino, tert-butoxy-carbonylamino, methylsulfonylamino, methylthio, methylsulfonyl, or ethylsulfonyl. In certain embodiments, in any one of Formulae (I) to (XIX), $R^6$ is pyridin-2-yl, pyridin-3-yl, pyridin-4-yl, pyridin-5-yl, 1,2-dihydropyridin-3-yl, 1,2-dihydropyridin-4-yl, 1,6-dihydropyridin-2-yl, pyridazin-4-yl, pyrimidin-4-yl, or pyrimidin-5-yl, each optionally substituted with one, two, or three substituents Q, wherein each substituent is independently cyano, chloro, oxo, methyl, isopropyl, isobutyl, tert-butyl, trifluoromethyl, morpholinomethyl, hydroxymethyl, ethynyl, cyclopropyl, phenyl, 4-methylphenyl, 4-methylpyridin-2-yl, pyrrolidin-1-yl, morpholino, 1-tert-butoxycarbonylpiperidin-4-yl, methoxy, phenoxy, benzoxy, amino, dimethylamino, methylthio, or methylsulfonyl.

In certain embodiments, in any one of Formulae (I) to (XIX), $R^6$ is chloropyrazin-2-yl, 3-methylpyrazin-2-yl, 5-methylpyrazin-2-yl, 5-methoxypyrazin-2-yl, pyridin-2-yl, pyridin-3-yl, pyridin-4-yl, 4-cyanopyridin-2-yl, 5-cyanopyridin-2-yl, 5-cyanopyridin-3-yl, 6-cyano-pyridin-2-yl, 6-cyanopyridin-3-yl, 3-fluoropyridin-4-yl, 4-fluoropyridin-2-yl, 5-fluoropyridin-2-yl, 5-fluoropyridin-3-yl, 6-fluoropyridin-2-yl, 6-fluoropyridin-3-yl, 3-chloropyridin-4-yl, 6-chloropyridin-2-yl, 2-methylpyridin-3-yl, 2-methylpyridin-4-yl, 3-methylpyridin-2-yl, 4-methyl-pyridin-2-yl, 4-methylpyridin-3-yl, 5-methylpyridin-2-yl, 5-methylpyridin-3-yl, 6-methylpyridin-2-yl, 5-isopropylpyridin-3-yl, 2-trifluoromethylpyridin-5-yl, 6-(trifluoromethyl)pyridin-3-yl, 2-(tert-butyl)pyridin-4-yl, 5-ethynylpyridin-2-yl, 6-(4-methylphenyl)pyridin-3-yl, 6-(pyrrolidin-1-yl)pyridin-3-yl, 2-(4-methylpyridin-2-yl)pyridine-4-yl, 2-hydroxypyridin-3-yl, 2-methoxy-pyridin-3-yl, 2-methoxypyridin-4-yl, 3-methoxypyridin-2-yl, 3-methoxypyridin-4-yl, 4-methoxypyridin-2-yl, 4-methoxypyridin-3-yl, 5-methoxypyridin-2-yl, 5-methoxypyridin-3-yl, 6-methoxy-pyridin-2-yl, 6-methoxypyridin-3-yl, 6-phenoxypyridin-3-yl, 2-aminopyridin-3-yl, 3-amino-pyridin-4-yl, 6-(methylsulfonyl)pyridin-2-yl, 2-amino-5-cyanopyridin-3-yl, 2-amino-5-methylpyridin-3-yl, 5-chloro-2-methoxypyridin-3-yl, 2,6-dimethylpyridin-4-yl, 5-fluoro-2-oxo-1,2-dihydropyridin-3-yl, 1-methyl-2-oxo-1,2-dihydropyridin-4-yl, 1-methyl-6-oxo-1,6-dihydro-pyridin-2-yl, pyridazin-4-yl, pyrimidin-4-yl, pyrimidin-5-yl, 2-methylpyrimidin-4-yl, 2-methylpyrimidin-5-yl, 2-methoxypyrimidin-4-yl, 2-(methylthio)pyrimidin-4-yl, or 2-chloro-4-(morpholino)pyrimidin-5-yl.

In certain embodiments, in any one of Formulae (I) to (XIX), $R^6$ is bicyclic heteroaryl, optionally substituted with one or more substituents Q. In certain embodiments, in any one of Formulae (I) to (XIX), $R^6$ is 5,5-fused, 5,6-fused, or 6,6-fused bicyclic heteroaryl, each optionally substituted with one or more substituents Q. In certain embodiments, in any one of Formulae (I) to (XIX), $R^6$ is 5,5-fused bicyclic heteroaryl, optionally substituted with one or more substituents Q. In certain embodiments, in any one of Formulae (I) to (XIX), $R^6$ is 5,6-fused bicyclic heteroaryl, optionally substituted with one or more substituents Q. In certain embodiments, in any one of Formulae (I) to (XIX), $R^6$ is 6,6-fused bicyclic heteroaryl, optionally substituted with one or more substituents Q.

In certain embodiments, in any one of Formulae (I) to (XIX), $R^6$ is bicyclic heteroaryl, optionally substituted with one, two, or three substituents Q, wherein each substituent is independently (i) cyano, halo, or oxo; (ii) $C_{1-6}$ alkyl, $C_{1-6}$ heteroalkyl, $C_{2-6}$ alkynyl, $C_{3-10}$ cycloalkyl, $C_{6-14}$ aryl, $C_{7-15}$ aralkyl, heteroaryl, or heterocyclyl, each optionally substituted with one or more substituents $Q^a$; or (iii) —C(O)$R^a$, —C(O)O$R^a$, —C(O)N$R^bR^c$, —O$R^a$, —N$R^bR^c$, —N$R^a$C(O)$R^d$, —N$R^a$C(O)O$R^d$, —N$R^a$S(O)$_2R^d$, —S$R^a$, or —S(O)$_2R^a$, wherein each $R^a$, $R^b$, $R^c$, and $R^d$ is as defined herein. In certain embodiments, in any one of Formulae (I) to (XIX), $R^6$ is bicyclic heteroaryl, optionally substituted with one, two, or three substituents Q, wherein each substituent is independently (i) cyano, halo, or oxo; (ii) $C_{1-6}$ alkyl, $C_{1-6}$ heteroalkyl, $C_{2-6}$ alkynyl, $C_{3-10}$ cycloalkyl, $C_{6-14}$ aryl, heteroaryl, or heterocyclyl, each optionally substituted with one or more substituents $Q^a$; or (iii) —C(O)$R^a$, —O$R^a$, —N$R^bR^c$, —S$R^a$, or —S(O)$_2R^a$, wherein each $R^a$, $R^b$, and $R^c$ is as defined herein.

In certain embodiments, in any one of Formulae (I) to (XIX), $R^6$ is bicyclic heteroaryl, optionally substituted with one, two, or three substituents Q, wherein each substituent is independently cyano, fluoro, chloro, bromo, oxo, methyl, ethyl, isopropyl, isobutyl, tert-butyl, trifluoromethyl, morpholinomethyl, hydroxymethyl, (dimethylamino)methyl, (tert-butoxy-carbonylamino)methyl, ethynyl, cyclopropyl, cyclobutyl, cyclopentyl, cyclohexyl, phenyl, 3-bromophenyl, 4-methylphenyl, 3-trifluoromethylphenyl, 2-methoxyphenyl, benzyl, 5-methyl-furan-2-yl, imidazol-1-yl, oxazol-5-yl, pyrazol-1-yl, pyrrol-2-yl, 1,2,3-triazol-1-yl, 1,2,4-triazol-1-yl, pyrimidin-2-yl, pyrimidin-5-yl, pyridin-3-yl, pyridin-4-yl, 4-methylpyridin-2-yl, 2-methoxypyridin-3-yl, quinolin-6-yl, pyrrolidin-1-yl, morpholino, piperidin-1-yl, 1-benzoxy-carbonylpiperidin-4-yl, 1-(tert-butoxycarbonyl)piperidin-4-yl, 4-methylpiperazin-1-yl, 4-(tert-butoxycarbonyl)piperazin-1-yl, 2,2,2-trifluoroacetyl, benzoxycarbonyl, tert-butoxycarbonyl, aminocarbonyl, methylaminocarbonyl, dimethylaminocarbonyl, isopropylaminocarbonyl, hydroxyl, methoxy, ethoxy, difluoromethoxy, trifluoromethoxy, cyclohexylmethoxy, cyclopentoxy, phenoxy, 4-cyanophenoxy, 3-methylphenoxy, 4-trifluoromethylphenoxy, 4-cyano-2-fluorophenoxy, benzoxy, 4-cyanobenzoxy, pyridin-2-yloxy, pyridin-3-yloxy, amino, methylamino, ethylamino, dimethylamino, (2-hydroxyethyl)(methyl)amino), acetamido, benzoxycarbonylamino, tert-butoxycarbonylamino, methylsulfonylamino, methylthio, methylsulfonyl, or ethylsulfonyl. In certain embodiments, in any one of Formulae (I) to (XIX), $R^6$ is bicyclic heteroaryl, optionally substituted with one, two, or three substituents Q, wherein each substituent is independently cyano, chloro, oxo, methyl, isopropyl, isobutyl, tert-butyl, trifluoromethyl, morpholinomethyl, hydroxymethyl, ethynyl, cyclopropyl, phenyl, 4-methylphenyl, 4-methyl-pyridin-2-yl, pyrrolidin-1-yl, morpholino, 1-tert-butoxycarbonylpiperidin-4-yl, methoxy, phenoxy, benzoxy, amino, dimethylamino, methylthio, or methylsulfonyl.

In certain embodiments, in any one of Formulae (I) to (XIX), $R^6$ is benzo[d][1,3]-dioxolyl, benzofuranyl, benzo[d]imidazolyl, benzo[d]oxazolyl, benzo[d]thiazolyl, benzo[b]-thienyl, chromanyl, 2,3-dihydrobenzo[b][1,4]dioxinyl, 2,3-dihydrobenzofuranyl, 2,3-dihydro[1,4]dioxino[2,3-b]pyridinyl, 5,6-dihydroimidazo[2,1-c][1,4]oxazinyl, 3,4-dihydropyrano[2,3-c]pyridinyl, furo[2,3-c]pyridinyl, imidazo[1,2-a]pyridinyl, imidazo[1,5-a]pyridinyl, imidazo[4,5-b]pyridinyl, imidazo[1,2-a]pyrimidinyl, indazolyl, indolyl, indolinyl, indolizinyl, isoindolinyl, isoquinolinyl, 1,8-naphthyridinyl, pyrazolo[1,5-a]pyridinyl, pyrrolo[2,3-b]-pyrazinyl, pyrrolo[2,3-b]pyridinyl, pyrrolo[2,3-c]pyridinyl, pyrrolo[3,2-b]pyridinyl, quinazolinyl, quinolinyl, quinoxalinyl, 1,2,3,4-tetrahydroisoquinolinyl, 1,2,3,4-tetrahydroquinolinyl, thieno[2,3-b]pyridinyl, thieno[3,2-c]pyridinyl, or [1,2,4]triazolo[1,5-a]pyridinyl, each optionally substituted with one, two, or three substituents Q, wherein each substituent is independently cyano, fluoro, chloro, bromo, oxo, methyl, ethyl, isopropyl, tert-butyl, trifluoromethyl, morpholinomethyl, hydroxymethyl, (dimethylamino)methyl, (tert-butoxycarbonyl-amino)methyl, ethynyl, cyclopropyl, cyclobutyl, cyclopentyl, cyclohexyl, phenyl, 3-bromo-phenyl, 4-methylphenyl, 3-trifluoromethylphenyl, 2-methoxyphenyl, benzyl, 5-methylfuran-2-yl, imidazol-1-yl, oxazol-5-yl, pyrazol-1-yl, pyrrol-2-yl, 1,2,3-triazol-1-yl, 1,2,4-triazol-1-yl, pyrimidin-2-yl, pyrimidin-5-yl, pyridin-3-yl, pyridin-4-yl, 4-methylpyridin-2-yl, 2-methoxy-pyridin-3-yl, quinolin-6-yl, pyrrolidin-1-yl, morpholino, piperidin-1-yl, 1-benzoxycarbonyl-piperidin-4-yl, 1-(tert-butoxycarbonyl)piperidin-4-yl, 4-methylpiperazin-1-yl, 4-(tert-butoxy-carbonyl)piperazin-1-yl, 2,2,2-trifluoroacetyl, benzoxycarbonyl, tert-butoxycarbonyl, aminocarbonyl, methylaminocarbonyl, dimethylaminocarbonyl, isopropylaminocarbonyl, hydroxyl, methoxy, ethoxy, difluoromethoxy, trifluoromethoxy, cyclohexylmethoxy, cyclopentoxy, phenoxy, 4-cyanophenoxy, 3-methylphenoxy, 4-trifluoromethylphenoxy, 4-cyano-2-fluorophenoxy, benzoxy, 4-cyanobenzoxy, pyridin-2-yloxy, pyridin-3-yloxy, amino, methylamino, ethylamino, dimethylamino, (2-hydroxyethyl)(methyl)amino), acetamido, benzoxycarbonylamino, tert-butoxycarbonylamino, methylsulfonylamino, methylthio, methylsulfonyl, or ethylsulfonyl.

In certain embodiments, in any one of Formulae (I) to (XIX), $R^6$ is benzo[d][1,3]-dioxol-4-yl, benzo[d][1,3]dioxol-5-yl, benzofuran-4-yl, benzofuran-5-yl, benzofuran-6-yl, benzofuran-7-yl, benzo[d]imidazol-2-yl, benzo[d]imidazol-4-yl, benzo[d]imidazol-6-yl, benzo[d]oxazol-5-yl, benzo[d]oxazol-6-yl, benzo[d]thiazol-4-yl, benzo[d]thiazol-6-yl, benzo[b]-thien-2-yl, benzo[b]-thien-3-yl, chroman-6-yl, chroman-8-yl, 2,3-dihydrobenzo[b][1,4]dioxin-6-yl, 2,3-dihydro[1,4]-dioxino[2,3-b]pyridin-6-yl, 2,3-dihydrobenzofuran-5-yl, 2,3-dihydrobenzo-furan-7-yl, 5,6-dihydroimidazo[2,1-c][1,4]oxazin-2-yl, 5,6-dihydroimidazo[2,1-c][1,4]oxazin-3-yl, 3,4-dihydropyrano[2,3-c]pyridin-6-yl, furo[2,3-c]pyridin-5-yl, imidazo[1,2-a]pyridin-2-yl, imidazo[1,2-a]pyridin-3-yl, imidazo[1,2-a]pyridin-5-yl, imidazo[1,2-a]pyridin-6-yl, imidazo[1,2-a]pyridin-7-yl, imidazo[1,2-a]pyridin-8-yl, imidazo[1,5-a]pyridin-1-yl, imidazo[4,5-b]pyridin-2-yl, imidazo[1,2-a]pyrimidin-3-yl, imidazo[1,2-a]pyrimidin-7-yl, indazol-3-yl, indazol-4-yl, indazol-5-yl, indazol-6-yl, indol-2-yl, indol-3-yl, indol-5-yl, indol-6-yl, indol-7-yl, indolin-6-yl, indolizin-1-yl, isoindolin-2-yl, isoindolin-5-yl, isoquinolin-3-yl, isoquinolin-4-yl, isoquinolin-5-yl, isoquinolin-8-yl, 1,8-naphthyridin-2-yl, pyrazolo[1,5-a]-pyridin-3-yl, pyrazolo[1,5-a]pyridin-7-yl, pyrrolo[2,3-b]pyrazin-7-yl, pyrrolo[2,3-b]pyridin-6-yl, pyrrolo[2,3-c]pyridin-3-yl, pyrrolo[3,2-b]pyridin-3-yl, pyrrolo[3,2-b]pyridin-6-yl, quinazolin-6-yl, quinolin-4-yl, quinolin-6-yl, quinolin-8-yl, quinoxalin-2-yl, quinoxalin-5-yl, quinoxalin-6-yl, 1,2,3,4-tetrahydroisoquinolin-7-yl, 1,2,3,4-tetrahydroquinolin-6-yl, thieno[2,3-b]pyridin-2-yl, thieno[3,2-c]pyridin-2-yl, or [1,2,4]triazolo[1,5-a]pyridin-7-yl, each optionally substituted with one, two, or three substituents Q, wherein each substituent is independently cyano, fluoro, chloro, bromo, oxo, methyl, ethyl, isopropyl, tert-butyl, trifluoromethyl, morpholinomethyl, hydroxymethyl, (dimethylamino)methyl, (tert-butoxycarbonyl-amino)methyl, ethynyl, cyclopropyl, cyclobutyl, cyclopentyl, cyclohexyl, phenyl, 3-bromo-phenyl, 4-methylphenyl, 3-trifluoromethylphenyl, 2-methoxyphenyl, benzyl, 5-methyl-furan-2-yl, imidazol-1-yl, oxazol-5-yl, pyrazol-1-yl, pyrrol-2-yl, 1,2,3-triazol-1-yl, 1,2,4-triazol-1-yl, pyrimidin-2-yl, pyrimidin-5-yl, pyridin-3-yl, pyridin-4-yl, 4-methylpyridin-2-yl, 2-methoxy-pyridin-3-yl, quinolin-6-yl, pyrrolidin-1-yl, morpholino, piperidin-1-yl, 1-benzoxycarbonyl-piperidin-4-yl, 1-(tert-butoxy-carbonyl)piperidin-4-yl, 4-methylpiperazin-1-yl, 4-(tert-butoxycarbonyl)piperazin-1-yl, 2,2,2-trifluoroacetyl, benzoxycarbonyl, tert-butoxycarbonyl, aminocarbonyl, methylaminocarbonyl, dimethylaminocarbonyl, isopropylaminocarbonyl, hydroxyl, methoxy, ethoxy, difluoromethoxy, trifluoromethoxy, cyclohexylmethoxy, cyclopentoxy, phenoxy, 4-cyanophenoxy, 3-methylphenoxy, 4-trifluoromethylphenoxy, 4-cyano-2-fluorophenoxy, benzoxy, 4-cyanobenzoxy, pyridin-2-yloxy, pyridin-3-yloxy, amino, methylamino, ethylamino, dimethylamino, (2-hydroxyethyl)(methyl)amino), acetamido, benzoxycarbonylamino, tert-butoxycarbonylamino, methylsulfonylamino, methylthio, methylsulfonyl, or ethylsulfonyl.

In certain embodiments, in any one of Formulae (I) to (XIX), $R^6$ is benzo[d][1,3]-dioxol-4-yl, benzo[d][1,3]dioxol-5-yl, benzofuran-4-yl, benzofuran-5-yl, benzofuran-6-yl, benzofuran-7-yl, benzo[d]imidazol-2-yl, benzo[d]imidazol-4-yl, benzo[d]imidazol-6-yl, benzo[d]oxazol-6-yl, benzo[d]thiazol-4-yl, benzo[d]oxazol-5-yl, benzo[d]thiazol-6-yl, benzo[b]-thien-2-yl, benzo[b]-thien-3-yl, chroman-6-yl, chroman-8-yl, 2,3-dihydrobenzo[b][1,4]dioxin-6-yl, 2,3-dihydro[1,4]-dioxino[2,3-b]pyridin-6-yl, 2,3-dihydrobenzofuran-5-yl, 2,3-dihydrobenzo-furan-7-yl, 5,6-dihydroimidazo[2,1-c][1,4]oxazin-2-yl, 5,6-dihydroimidazo[2,1-c][1,4]oxazin-3-yl, 3,4-dihydropyrano[2,3-c]pyridin-6-yl, furo[2,3-c]pyridin-5-yl, imidazo[1,2-a]pyridin-2-yl, imidazo[1,2-a]pyridin-3-yl, imidazo[1,2-a]pyridin-5-yl, imidazo[1,2-a]pyridin-6-yl, imidazo[1,2-a]pyridin-7-yl, imidazo[1,2-a]pyridin-8-yl, imidazo[1,5-a]pyridin-1-yl, imidazo[4,5-b]pyridin-2-yl, imidazo[1,2-a]pyrimidin-3-yl, imidazo[1,2-a]pyrimidin-7-yl, indazol-3-yl, indazol-4-yl, indazol-5-yl, indazol-6-yl, indol-2-yl, indol-3-yl, indol-5-yl, indol-6-yl, indol-7-yl, indolin-6-yl, indolizin-1-yl, isoindolin-2-yl, isoindolin-5-yl, isoquinolin-3-yl, isoquinolin-4-yl, isoquinolin-5-yl, isoquinolin-8-yl, 1,8-naphthyridin-2-yl, pyrazolo[1,5-a]-pyridin-3-yl, pyrazolo[1,5-a]pyridin-7-yl, pyrrolo[2,3-b]pyrazin-7-yl, pyrrolo[2,3-b]pyridin-6-yl, pyrrolo[2,3-c]pyridin-3-yl, pyrrolo[3,2-b]pyridin-3-yl, pyrrolo[3,2-b]pyridin-6-yl, quinazolin-6-yl, quinolin-4-yl, quinolin-6-yl, quinolin-8-yl, quinoxalin-2-yl, quinoxalin-5-yl, quinoxalin-6-yl, 1,2,3,4-tetrahydroisoquinolin-7-yl, 1,2,3,4-tetrahydroquinolin-6-yl, thieno[2,3-b]pyridin-2-yl, thieno[3,2-c]pyridin-2-yl, or [1,2,4]triazolo[1,5-a]pyridin-7-yl, each optionally substituted with one, two, or three substituents Q, wherein each substituent is independently fluoro, oxo, methyl, or 2,2,2-trifluoroacetyl.

In certain embodiments, in any one of Formulae (I) to (XIX), $R^6$ is benzo[d][1,3]-dioxol-4-yl, benzo[d][1,3]dioxol-5-yl, benzofuran-4-yl, benzofuran-5-yl, benzofuran-6-yl, benzofuran-7-yl, 4-fluorobenzofuran-7-yl, benzo[d]imidazol-2-yl, benzo[d]imidazol-4-yl, 5-fluorobenzo[d]imidazol-2-yl, 1-methylbenzo[d]imidazol-2-yl, 2-hydroxybenzo[d]imidazol-6-yl, benzo[d]oxazol-5-yl, benzo[d]oxazol-6-yl, 2-methylbenzo[d]oxazol-6-yl, benzo[d]thiazol-4-yl, benzo[d]thiazol-6-yl, benzo[b]thien-2-yl, benzo[b]thien-3-yl, chroman-6-yl, 6-fluorochroman-8-yl, 2,3-dihydro-benzo[b][1,4]dioxin-6-yl, 2,3-dihydro[1,4]dioxino[2,3-b]pyridin-6-yl, 5,6-dihydroimidazo[2,1-c][1,4]oxazin-2-yl, 2,3-dihydrobenzofuran-5-yl, 2,3-dihydrobenzofuran-7-yl, 5,6-dihydroimidazo[2,1-c][1,4]oxazin-3-yl, 3,4-dihydropyrano[2,3-c]pyridin-6-yl, furo[2,3-c]pyridin-5-yl, imidazo[1,2-a]pyridin-2-yl, imidazo[1,2-a]pyridin-3-yl, imidazo[1,2-a]pyridin-5-yl, imidazo[1,2-a]pyridin-6-yl, imidazo[1,2-a]pyridin-7-yl, imidazo[1,2-a]pyridin-8-yl, 2-methylimidazo[1,2-a]pyridin-3-yl, 3-methylimidazo[1,2-a]-pyridin-2-yl, 5-methylimidazo[1,2-a]pyridin-3-yl, 6-methylimidazo[1,2-a]pyridin-2-yl, 7-methylimidazo[1,2-a]pyridin-3-yl, imidazo[1,5-a]pyridin-1-yl, 1-methylimidazo[4,5-b]pyridin-2-yl, imidazo[1,2-a]pyrimidin-3-yl, imidazo[1,2-a]pyrimidin-7-yl, indazol-6-yl, 1-methyl-indazol-4-yl, 1-methylindazol-6-yl, 2-methylindazol-3-yl, 2-methylindazol-5-yl, indol-2-yl, indol-3-yl, indol-5-yl, indol-6-yl, indol-7-yl, 6-cyanoindol-2-yl, 6-cyanoindol-3-yl, 1-methyl-indol-5-yl, 1-methylindol-6-yl, 2-methylindol-4-yl, 3-methylindol-2-yl, 4-methylindol-3-yl, 6-methylindol-3-yl, 7-methylindol-3-yl, 1-tert-butoxycarbonylindolin-6-yl, indolizin-1-yl, 1,3-dioxoisoindolin-2-yl, 1-oxoisoindolin-5-yl, 3-oxoisoindolin-5-yl, isoquinolin-3-yl, isoquinolin-4-yl, isoquinolin-5-yl, isoquinolin-8-yl, 1-chloroisoquinolin-5-yl, 1,8-naphthyridin-2-yl, pyrazolo[1,5-a]pyridin-3-yl, pyrazolo[1,5-a]pyridin-7-yl, pyrrolo[2,3-b]pyrazin-7-yl, pyrrolo[2,3-b]pyridin-6-yl, 5-methylpyrrolo[2,3-b]pyridin-3-yl, pyrrolo[2,3-c]pyridin-3-yl, pyrrolo[3,2-b]pyridin-3-yl, pyrrolo[3,2-b]pyridin-6-yl, quinazolin-6-yl, quinolin-4-yl, quinolin-6-yl, quinolin-8-yl, quinoxalin-2-yl, quinoxalin-5-yl, quinoxalin-6-yl, 1,2,3,4-tetrahydro-isoquinolin-7-yl, 2-(2,2,2-trifluoroacetyl)-1,2,3,4-tetrahydroisoquinolin-7-yl, 2-oxo-1,2,3,4-tetrahydroquinolin-6-yl, thieno[2,3-b]pyridin-2-yl, thieno[3,2-c]pyridin-2-yl, or [1,2,4]triazolo[1,5-a]pyridin-7-yl.

In certain embodiments, in any one of Formulae (I) to (XIX), $R^6$ is heterocyclyl, optionally substituted with one or more substituents Q. In certain embodiments, in any one of Formulae (I) to (XIX), $R^6$ is monocyclic heterocyclyl, optionally substituted with one or more substituents Q. In certain embodiments, in any one of Formulae (I) to (XIX), $R^6$ is 3-, 4-, 5-, 6-, or 7-membered heterocyclyl, each optionally substituted with one or more substituents Q. In certain embodiments, in any one of Formulae (I) to (XIX), $R^6$ is 3-membered heterocyclyl, optionally substituted with one or more substituents Q. In certain embodiments, in any one of Formulae (I) to (XIX), $R^6$ is 4-membered heterocyclyl, optionally substituted with one or more substituents Q. In certain embodiments, in any one of Formulae (I) to (XIX), $R^6$ is 5-membered heterocyclyl, optionally substituted with one or more substituents Q. In certain embodiments, in any one of Formulae (I) to (XIX), $R^6$ is 6-membered heterocyclyl, optionally substituted with one or more substituents Q. In certain embodiments, in any one of Formulae (I) to (XIX), $R^6$ is 7-membered heterocyclyl, optionally substituted with one or more substituents Q.

In certain embodiments, in any one of Formulae (I) to (XIX), $R^6$ is bicyclic heterocyclyl, optionally substituted with one or more substituents Q. In certain embodiments, in any one of Formulae (I) to (XIX), $R^6$ is bicyclic bridged heterocyclyl, optionally substituted with one or more substituents Q. In certain embodiments, in any one of Formulae (I) to (XIX), $R^6$ is bicyclic fused heterocyclyl, optionally substituted with one or more substituents Q. In certain embodiments, in any one of Formulae (I) to (XIX), $R^6$ is bicyclic spiro heterocyclyl, optionally substituted with one or more substituents Q.

In certain embodiments, in any one of Formulae (I) to (XIX), $R^6$ is heterocyclyl, optionally substituted with one, two, or three substituents Q, wherein each substituent is independently (i) cyano, halo, or oxo; (ii) $C_{1-6}$ alkyl, $C_{1-6}$ heteroalkyl, $C_{2-6}$ alkynyl, $C_{3-10}$ cycloalkyl, $C_{6-14}$ aryl, $C_{7-15}$ aralkyl, heteroaryl, or heterocyclyl, each optionally substituted with one or more substituents $Q^a$; or (iii) —C(O)$R^a$, —C(O)O$R^a$, —C(O)N$R^bR^c$, —O$R^a$, —N$R^bR^c$, —N$R^a$C(O)$R^d$, —N$R^a$C(O)O$R^d$, —N$R^a$S(O)$_2R^d$, —S$R^a$, or —S(O)$_2R^a$, wherein each $R^a$, $R^b$, $R^c$, and $R^d$ is as defined herein. In certain embodiments, in any one of Formulae (I) to (XIX), $R^6$ is heterocyclyl, optionally substituted with one, two, or three substituents Q, where each substituent is independently (i) $C_{1-6}$ alkyl or $C_{7-15}$ aralkyl, each optionally substituted with one or more substituents $Q^a$; or (ii) —C(O)O$R^a$ or —S(O)$_2R^a$, wherein each $R^a$ is as defined herein.

In certain embodiments, in any one of Formulae (I) to (XIX), $R^6$ is heterocyclyl, optionally substituted with one, two, or three substituents Q, wherein each substituent is independently cyano, fluoro, chloro, bromo, oxo, methyl, ethyl, isopropyl, isobutyl, tert-butyl, trifluoromethyl, morpholinomethyl, hydroxymethyl, (dimethylamino)methyl, (tert-butoxy-carbonylamino)methyl, ethynyl, cyclopropyl, cyclobutyl, cyclopentyl, cyclohexyl, phenyl, 3-bromophenyl, 4-methylphenyl, 3-trifluoromethylphenyl, 2-methoxyphenyl, benzyl, 5-methyl-furan-2-yl, imidazol-1-yl, oxazol-5-yl, pyrazol-1-yl, pyrrol-2-yl, 1,2,3-triazol-1-yl, 1,2,4-triazol-1-yl, pyrimidin-2-yl, pyrimidin-5-yl, pyridin-3-yl, pyridin-4-yl, 4-methylpyridin-2-yl, 2-methoxypyridin-3-yl, quinolin-6-yl, pyrrolidin-1-yl, morpholino, piperidin-1-yl, 1-benzoxy-carbonylpiperidin-4-yl, 1-(tert-butoxycarbonyl)piperidin-4-yl, 4-methylpiperazin-1-yl, 4-(tert-butoxycarbonyl)piperazin-1-yl, 2,2,2-trifluoroacetyl, benzoxycarbonyl, tert-butoxycarbonyl, aminocarbonyl, methylaminocarbonyl, dimethylaminocarbonyl, isopropylaminocarbonyl, hydroxyl, methoxy, ethoxy, difluoromethoxy, trifluoromethoxy, cyclohexylmethoxy, cyclopentoxy, phenoxy, 4-cyanophenoxy, 3-methylphenoxy, 4-trifluoromethylphenoxy, 4-cyano-2-fluorophenoxy, benzoxy, 4-cyanobenzoxy, pyridin-2-yloxy, pyridin-3-yloxy, amino, methylamino, ethylamino, dimethylamino, (2-hydroxyethyl)(methyl)amino), acetamido, benzoxycarbonylamino, tert-butoxycarbonylamino, methylsulfonylamino, methylthio, methylsulfonyl, or ethylsulfonyl. In certain embodiments, in any one of Formulae (I) to (XIX), $R^6$ is heterocyclyl, optionally substituted with one, two, or three substituents Q, wherein each substituent is independently methyl, ethyl, benzyl, benzoxycarbonyl, tert-butoxycarbonyl, or ethylsulfonyl.

In certain embodiments, in any one of Formulae (I) to (XIX), $R^6$ is azetidin-3-yl, oxetan-3-yl, tetrahydropyran-4-yl, piperidin-4-yl, or piperazin-1-yl, each optionally substituted with one, two, or three substituents Q, wherein each substituent is independently cyano, fluoro, chloro, bromo, oxo, methyl, ethyl, isopropyl, isobutyl, tert-butyl, trifluoromethyl, morpholinomethyl, hydroxymethyl, (dimethylamino)methyl, (tert-butoxycarbonylamino)methyl, ethynyl, cyclopropyl, cyclobutyl, cyclopentyl, cyclohexyl, phenyl, 3-bromophenyl, 4-methylphenyl, 3-trifluoromethylphenyl, 2-methoxyphenyl, benzyl, 5-methylfuran-2-yl, imidazol-1-yl, oxazol-5-yl, pyrazol-1-yl, pyrrol-2-yl, 1,2,3-triazol-1-yl, 1,2,4-triazol-1-yl, pyrimidin-2-yl, pyrimidin-5-yl, pyridin-3-yl, pyridin-4-yl, 4-methylpyridin-2-yl, 2-methoxypyridin-3-yl, quinolin-6-yl, pyrrolidin-1-yl, morpholino, piperidin-1-yl, 1-benzoxy-carbonylpiperidin-4-yl, 1-(tert-butoxycarbonyl)piperidin-4-yl, 4-methylpiperazin-1-yl, 4-(tert-butoxycarbonyl)piperazin-1-yl, 2,2,2-trifluoroacetyl, benzoxycarbonyl, tert-butoxycarbonyl, aminocarbonyl, methylaminocarbonyl, dimethylaminocarbonyl, isopropylaminocarbonyl, hydroxyl, methoxy, ethoxy, difluoromethoxy, trifluoromethoxy, cyclohexylmethoxy, cyclopentoxy, phenoxy, 4-cyanophenoxy, 3-methylphenoxy, 4-trifluoromethylphenoxy, 4-cyano-2-fluorophenoxy, benzoxy, 4-cyanobenzoxy, pyridin-2-yloxy, pyridin-3-yloxy, amino, methylamino, ethylamino, dimethylamino, (2-hydroxy-ethyl)(methyl)amino), acetamido, benzoxycarbonylamino, tert-butoxycarbonylamino, methylsulfonylamino, methylthio, methylsulfonyl, or ethylsulfonyl. In certain embodiments, in any one of Formulae (I) to (XIX), $R^6$ is azetidin-3-yl, oxetan-3-yl, tetrahydro-pyran-4-yl, piperidin-4-yl, or piperazin-1-yl, each optionally substituted with one, two, or three substituents Q, wherein each substituent is independently methyl, ethyl, benzyl, benzoxycarbonyl, tert-butoxycarbonyl, or ethylsulfonyl.

In certain embodiments, in any one of Formulae (I) to (XIX), $R^6$ is 1-methyl-azetidin-3-yl, oxetan-3-yl, 3-methyl-oxetan-3-yl, tetrahydropyran-4-yl, ethylpiperidin-4-yl, 1-benzylpiperidin-4-yl, 1-benzoxycarbonylpiperidin-4-yl, 1-(tert-butoxycarbonyl)piperidin-4-yl, 1-(ethylsulfonyl)piperidin-4-yl, 1-(tert-butoxycarbonyl)-4-fluoropiperidin-4-yl, or 4-(tert-butoxy-carbonyl)piperazin-1-yl.

In certain embodiments, in any one of Formulae (I) to (XIX), X is $-(CH_2)_n-$, wherein n is an integer of 1, 2, 3, 4, or 5. In certain embodiments, in any one of Formulae (I) to (XIX), X is $-CH_2-$. In certain embodiments, in any one of Formulae (I) to (XIX), X is $-(CH_2)_2-$. In certain embodiments, in any one of Formulae (I) to (XIX), X is $-(CH_2)_3-$. In certain embodiments, in any one of Formulae (I) to (XIX), X is $-(CH_2)_4-$. In certain embodiments, in any one of Formulae (I) to (XIX), X is $-(CH_2)_5-$. In certain embodiments, in any one of Formulae (I) to (XIX), X is $-C(O)-$. In certain embodiments, in any one of Formulae (I) to (XIX), X is $-S(O)-$. In certain embodiments, in any one of Formulae (I) to (XIX), X is $-S(O_2)-$.

In certain embodiments, in any one of Formulae (I) to (XIX), m is an integer of 0.

All combinations of the embodiments provided herein for the groups, $R^1$, $R^2$, $R^3$, $R^4$, $R^5$, $R^6$, A, X, a, b, c, d, e, f, m, and n, in formulae described herein, including Formulae (I) to (XIX), are within the scope of this disclosure.

In one embodiment, provided herein is a compound of:

3-(6-fluoro-1-oxo-4-(1-(5,6,7,8-tetrahydronaphthalene-1-carbonyl)piperidin-4-yl)isoindolin-2-yl)piperidine-2,6-dione A0001;

3-(6-fluoro-4-(1-(1-methyl-1H-indole-5-carbonyl)piperidin-4-yl)-1-oxoisoindolin-2-yl)piperidine-2,6-dione A0002;

3-(6-fluoro-1-oxo-4-(1-(quinoxaline-5-carbonyl)piperidin-4-yl)isoindolin-2-yl)-piperidine-2,6-dione A0003;

3-(6-fluoro-1-oxo-4-(1-(quinazoline-6-carbonyl)piperidin-4-yl)isoindolin-2-yl)piperidine-2,6-dione A0004;

3-(4-(1-(2-(dimethylamino)benzoyl)piperidin-4-yl)-6-fluoro-1-oxoisoindolin-2-yl)piperidine-2,6-dione A0005;

3-(4-(1-(4-(dimethylamino)benzoyl)piperidin-4-yl)-6-fluoro-1-oxoisoindolin-2-yl)piperidine-2,6-dione A0006;

3-(4-(1-(2,3-dihydrobenzofuran-7-carbonyl)piperidin-4-yl)-6-fluoro-1-oxoisoindolin-2-yl)piperidine-2,6-dione A0007;

3-(4-(1-(benzo[d]oxazole-5-carbonyl)piperidin-4-yl)-6-fluoro-1-oxoisoindolin-2-yl)piperidine-2,6-dione A0008;

3-(4-(1-(1H-benzo[d]imidazole-7-carbonyl)piperidin-4-yl)-6-fluoro-1-oxoisoindolin-2-yl)piperidine-2,6-dione A0009;

3-(6-fluoro-4-(1-(imidazo[1,2-a]pyridine-2-carbonyl)piperidin-4-yl)-1-oxoisoindolin-2-yl)piperidine-2,6-dione A0010;

3-(4-(1-(1H-pyrrolo[3,2-b]pyridine-6-carbonyl)piperidin-4-yl)-6-fluoro-1-oxoisoindolin-2-yl)piperidine-2,6-dione A0011;

3-(6-fluoro-4-(1-(imidazo[1,2-a]pyridine-3-carbonyl)piperidin-4-yl)-1-oxoisoindolin-2-yl)piperidine-2,6-dione A0012;

3-(4-(1-(benzofuran-6-carbonyl)piperidin-4-yl)-6-fluoro-1-oxoisoindolin-2-yl)piperidine-2,6-dione A0013;

3-(6-fluoro-1-oxo-4-(1-(2-(piperidin-1-yl)acetyl)piperidin-4-yl)isoindolin-2-yl)piperidine-2,6-dione A0014;

2-(2-(4-(2-(2,6-dioxopiperidin-3-yl)-6-fluoro-1-oxoisoindolin-4-yl)piperidin-1-yl)-2-oxoethyl)benzonitrile A0015;

3-(2-(4-(2-(2,6-dioxopiperidin-3-yl)-6-fluoro-1-oxoisoindolin-4-yl)piperidin-1-yl)-2-oxoethyl)benzonitrile A0016;

4-(2-(4-(2-(2,6-dioxopiperidin-3-yl)-6-fluoro-1-oxoisoindolin-4-yl)piperidin-1-yl)-2-oxoethyl)benzonitrile A0017;

3-(4-(1-(1H-indole-7-carbonyl)piperidin-4-yl)-6-fluoro-1-oxoisoindolin-2-yl)-piperidine-2,6-dione A0018;

3-(4-(1-(1-ethylpiperidine-4-carbonyl)piperidin-4-yl)-6-fluoro-1-oxoisoindolin-2-yl)piperidine-2,6-dione A0019;

3-(6-fluoro-1-oxo-4-(1-(2-(p-tolyl)acetyl)piperidin-4-yl)isoindolin-2-yl)-piperidine-2,6-dione A0020;

2-(4-(2-(2,6-dioxopiperidin-3-yl)-6-fluoro-1-oxoisoindolin-4-yl)piperidine-1-carbonyl)benzonitrile A0021;

3-(4-(2-(2,6-dioxopiperidin-3-yl)-6-fluoro-1-oxoisoindolin-4-yl)piperidine-1-carbonyl)benzonitrile A0022;

3-(6-fluoro-4-(1-(4-fluorobenzoyl)piperidin-4-yl)-1-oxoisoindolin-2-yl)-piperidine-2,6-dione A0023;

3-(6-fluoro-4-(1-(3-fluorobenzoyl)piperidin-4-yl)-1-oxoisoindolin-2-yl)-piperidine-2,6-dione A0024;

3-(6-fluoro-4-(1-(2-fluorobenzoyl)piperidin-4-yl)-1-oxoisoindolin-2-yl)piperidine-2,6-dione A0025;

3-(6-fluoro-4-(1-(2-methylbenzoyl)piperidin-4-yl)-1-oxoisoindolin-2-yl)-piperidine-2,6-dione A0026;

3-(6-fluoro-4-(1-(3-methylbenzoyl)piperidin-4-yl)-1-oxoisoindolin-2-yl)-piperidine-2,6-dione A0027;

3-(6-fluoro-4-(1-(4-methylbenzoyl)piperidin-4-yl)-1-oxoisoindolin-2-yl)-piperidine-2,6-dione A0028;

3-(4-(1-(2-cyclopentylacetyl)piperidin-4-yl)-6-fluoro-1-oxoisoindolin-2-yl)-piperidine-2,6-dione A0029;

3-(4-(1-(cyclohexanecarbonyl)piperidin-4-yl)-6-fluoro-1-oxoisoindolin-2-yl)-piperidine-2,6-dione A0030;

3-(4-(1-(3,3-dimethylcyclobutane-1-carbonyl)piperidin-4-yl)-6-fluoro-1-oxoisoindolin-2-yl)piperidine-2,6-dione A0031;

3-(6-fluoro-1-oxo-4-(1-(pyrimidine-5-carbonyl)piperidin-4-yl)isoindolin-2-yl)-piperidine-2,6-dione A0032;

3-(6-fluoro-1-oxo-4-(1-(pyridazine-4-carbonyl)piperidin-4-yl)isoindolin-2-yl)-piperidine-2,6-dione A0033;

3-(6-fluoro-1-oxo-4-(1-(pyrimidine-4-carbonyl)piperidin-4-yl)isoindolin-2-yl)-piperidine-2,6-dione A0034;

3-(6-fluoro-1-oxo-4-(1-picolinoylpiperidin-4-yl)isoindolin-2-yl)piperidine-2,6-dione A0035;

3-(6-fluoro-4-(1-isonicotinoylpiperidin-4-yl)-1-oxoisoindolin-2-yl)piperidine-2,6-dione A0036;

3-(6-fluoro-4-(1-nicotinoylpiperidin-4-yl)-1-oxoisoindolin-2-yl)piperidine-2,6-dione A0037;

3-(4-(1-benzoylpiperidin-4-yl)-6-fluoro-1-oxoisoindolin-2-yl)piperidine-2,6-dione A0038;

3-(4-(1-(1-aminocyclobutane-1-carbonyl)piperidin-4-yl)-6-fluoro-1-oxoisoindolin-2-yl)piperidine-2,6-dione A0039;

3-(6-fluoro-4-(1-(1-methylazetidine-3-carbonyl)piperidin-4-yl)-1-oxoisoindolin-2-yl)piperidine-2,6-dione A0040;

3-(4-(1-(1H-pyrazole-5-carbonyl)piperidin-4-yl)-6-fluoro-1-oxoisoindolin-2-yl)-piperidine-2,6-dione A0041;

3-(4-(1-(1H-imidazole-5-carbonyl)piperidin-4-yl)-6-fluoro-1-oxoisoindolin-2-yl)-piperidine-2,6-dione A0042;

3-(6-Fluoro-4-(1-(furan-3-carbonyl)piperidin-4-yl)-1-oxoisoindolin-2-yl)-piperidine-2,6-dione A0043;

3-(6-fluoro-4-(1-(furan-2-carbonyl)piperidin-4-yl)-1-oxoisoindolin-2-yl)-piperidine-2,6-dione A0044;

3-(6-fluoro-4-(1-(1-fluorocyclopropane-1-carbonyl)piperidin-4-yl)-1-oxoisoindolin-2-yl)piperidine-2,6-dione A0045;

3-(6-fluoro-4-(1-(3-methylbutanoyl)piperidin-4-yl)-1-oxoisoindolin-2-yl)-piperidine-2,6-dione A0046;

3-(6-fluoro-4-(1-(oxetane-3-carbonyl)piperidin-4-yl)-1-oxoisoindolin-2-yl)-piperidine-2,6-dione A0047;

3-(4-(1-(cyclobutanecarbonyl)piperidin-4-yl)-6-fluoro-1-oxoisoindolin-2-yl)-piperidine-2,6-dione A0048;

3-(6-fluoro-4-(1-(methylglycyl)piperidin-4-yl)-1-oxoisoindolin-2-yl)piperidine-2,6-dione A0049; or 3-(4-(1-(cyclopropanecarbonyl)piperidin-4-yl)-6-fluoro-1-oxoisoindolin-2-yl)-piperidine-2,6-dione A0050;

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

In another embodiment, provided herein is a compound of:

3-(4-(1-(cyclobutylmethyl)piperidin-4-yl)-6-fluoro-1-oxoisoindolin-2-yl)piperidine-2,6-dione A1001;

3-(4-(1-((1H-pyrrol-2-yl)methyl)piperidin-4-yl)-6-fluoro-1-oxoisoindolin-2-yl)-piperidine-2,6-dione A1002;

3-(4-(1-((1H-pyrrol-3-yl)methyl)piperidin-4-yl)-6-fluoro-1-oxoisoindolin-2-yl)-piperidine-2,6-dione A1003;

3-(4-(1-((1H-imidazol-5-yl)methyl)piperidin-4-yl)-6-fluoro-1-oxoisoindolin-2-yl)-piperidine-2,6-dione A1004;

3-(4-(1-((1H-pyrazol-5-yl)methyl)piperidin-4-yl)-6-fluoro-1-oxoisoindolin-2-yl)-piperidine-2,6-dione A1005;

3-(6-fluoro-4-(1-(oxazol-2-ylmethyl)piperidin-4-yl)-1-oxoisoindolin-2-yl)-piperidine-2,6-dione A1006;

3-(6-fluoro-4-(1-((3-methyloxetan-3-yl)methyl)piperidin-4-yl)-1-oxoisoindolin-2-yl)piperidine-2,6-dione A1007;

3-(6-fluoro-4-(1-(3-hydroxy-2,2-dimethylpropyl)piperidin-4-yl)-1-oxoisoindolin-2-yl)piperidine-2,6-dione A1008;

3-(6-fluoro-1-oxo-4-(1-(pyridin-3-ylmethyl)piperidin-4-yl)isoindolin-2-yl)-piperidine-2,6-dione A1009;

3-(6-fluoro-1-oxo-4-(1-(pyridin-2-ylmethyl)piperidin-4-yl)isoindolin-2-yl)-piperidine-2,6-dione A1010;

3-(6-fluoro-1-oxo-4-(1-(pyrimidin-5-ylmethyl)piperidin-4-yl)isoindolin-2-yl)-piperidine-2,6-dione A1011;

3-(6-fluoro-4-(1-((1-methyl-1H-pyrrol-2-yl)methyl)piperidin-4-yl)-1-oxoisoindolin-2-yl)piperidine-2,6-dione A1012;

3-(6-fluoro-4-(1-((5-methyl-1H-pyrrol-2-yl)methyl)piperidin-4-yl)-1-oxoisoindolin-2-yl)piperidine-2,6-dione A1013;

3-(6-fluoro-4-(1-((3-methyl-1H-pyrrol-2-yl)methyl)piperidin-4-yl)-1-oxoisoindolin-2-yl)piperidine-2,6-dione A1014;

3-(6-fluoro-4-(1-((5-methylfuran-2-yl)methyl)piperidin-4-yl)-1-oxoisoindolin-2-yl)piperidine-2,6-dione A1015;

3-(6-fluoro-4-(1-((5-methyl-1H-pyrazol-3-yl)methyl)piperidin-4-yl)-1-oxoisoindolin-2-yl)piperidine-2,6-dione A1016;

3-(6-fluoro-4-(1-((1-methyl-1H-imidazol-2-yl)methyl)piperidin-4-yl)-1-oxoisoindolin-2-yl)piperidine-2,6-dione A1017;

3-(6-fluoro-4-(1-((1-methyl-1H-imidazol-4-yl)methyl)piperidin-4-yl)-1-oxoisoindolin-2-yl)piperidine-2,6-dione A1018;

3-(6-fluoro-4-(1-((1-methyl-1H-pyrazol-3-yl)methyl)piperidin-4-yl)-1-oxoisoindolin-2-yl)piperidine-2,6-dione A1019;

3-(6-fluoro-4-(1-((1-methyl-1H-pyrazol-5-yl)methyl)piperidin-4-yl)-1-oxoisoindolin-2-yl)piperidine-2,6-dione A1020;

3-(6-fluoro-4-(1-((1-methyl-1H-imidazol-5-yl)methyl)piperidin-4-yl)-1-oxoisoindolin-2-yl)piperidine-2,6-dione A1021;

3-(6-fluoro-4-(1-((2-methyloxazol-5-yl)methyl)piperidin-4-yl)-1-oxoisoindolin-2-yl)piperidine-2,6-dione A1022;

3-(6-fluoro-4-(1-((2-methyloxazol-4-yl)methyl)piperidin-4-yl)-1-oxoisoindolin-2-yl)piperidine-2,6-dione A1023;

3-(6-fluoro-4-(1-((4-methyloxazol-5-yl)methyl)piperidin-4-yl)-1-oxoisoindolin-2-yl)piperidine-2,6-dione A1024;

3-(6-fluoro-4-(1-((5-methyl-4H-1,2,4-triazol-3-yl)methyl)piperidin-4-yl)-1-oxoisoindolin-2-yl)piperidine-2,6-dione A1025;

3-(6-fluoro-4-(1-((2-methyl-2H-tetrazol-5-yl)methyl)piperidin-4-yl)-1-oxoisoindolin-2-yl)piperidine-2,6-dione A1026;

3-(6-fluoro-1-oxo-4-(1-(thiophen-3-ylmethyl)piperidin-4-yl)isoindolin-2-yl)-piperidine-2,6-dione A1027;

3-(6-fluoro-1-oxo-4-(1-(thiophen-2-ylmethyl)piperidin-4-yl)isoindolin-2-yl)-piperidine-2,6-dione A1028;

3-(6-fluoro-1-oxo-4-(1-(thiazol-4-ylmethyl)piperidin-4-yl)isoindolin-2-yl)-piperidine-2,6-dione A1029;

3-(6-fluoro-1-oxo-4-(1-(thiazol-5-ylmethyl)piperidin-4-yl)isoindolin-2-yl)-piperidine-2,6-dione A1030;

3-(6-fluoro-1-oxo-4-(1-(thiazol-2-ylmethyl)piperidin-4-yl)isoindolin-2-yl)-piperidine-2,6-dione A1031;

3-(6-fluoro-1-oxo-4-(1-((tetrahydro-2H-pyran-4-yl)methyl)piperidin-4-yl)-isoindolin-2-yl)piperidine-2,6-dione A1032;

2-((4-(2-(2,6-dioxopiperidin-3-yl)-6-fluoro-1-oxoisoindolin-4-yl)piperidin-1-yl)-methyl)-1H-pyrrole-3-carbonitrile A1033;

3-(6-fluoro-4-(1-(3-methylbenzyl)piperidin-4-yl)-1-oxoisoindolin-2-yl)-piperidine-2,6-dione A1034;

3-(6-fluoro-1-oxo-4-(1-phenethylpiperidin-4-yl)isoindolin-2-yl)piperidine-2,6-dione A1035;

3-(6-fluoro-4-(1-(2-methylbenzyl)piperidin-4-yl)-1-oxoisoindolin-2-yl)-piperidine-2,6-dione A1036;

3-(6-fluoro-4-(1-(4-methylbenzyl)piperidin-4-yl)-1-oxoisoindolin-2-yl)-piperidine-2,6-dione A1037;

3-(4-(1-(2-aminobenzyl)piperidin-4-yl)-6-fluoro-1-oxoisoindolin-2-yl)piperidine-2,6-dione A1038;

3-(4-(1-(4-aminobenzyl)piperidin-4-yl)-6-fluoro-1-oxoisoindolin-2-yl)piperidine-2,6-dione A1039;

3-(6-fluoro-4-(1-((5-methylpyridin-3-yl)methyl)piperidin-4-yl)-1-oxoisoindolin-2-yl)piperidine-2,6-dione A1040;

3-(6-fluoro-4-(1-((4-methylpyridin-3-yl)methyl)piperidin-4-yl)-1-oxoisoindolin-2-yl)piperidine-2,6-dione A1041;

3-(6-fluoro-4-(1-((6-methylpyridin-2-yl)methyl)piperidin-4-yl)-1-oxoisoindolin-2-yl)piperidine-2,6-dione A1042;

3-(6-fluoro-4-(1-((5-methylpyridin-2-yl)methyl)piperidin-4-yl)-1-oxoisoindolin-2-yl)piperidine-2,6-dione A1043;

3-(6-fluoro-4-(1-((2-methylpyridin-4-yl)methyl)piperidin-4-yl)-1-oxoisoindolin-2-yl)piperidine-2,6-dione A1044;

3-(6-fluoro-4-(1-((2-methylpyridin-3-yl)methyl)piperidin-4-yl)-1-oxoisoindolin-2-yl)piperidine-2,6-dione A1045;

3-(6-fluoro-4-(1-((3-methylpyridin-2-yl)methyl)piperidin-4-yl)-1-oxoisoindolin-2-yl)piperidine-2,6-dione A1046;

3-(6-fluoro-4-(1-((4-methylpyridin-2-yl)methyl)piperidin-4-yl)-1-oxoisoindolin-2-yl)piperidine-2,6-dione A1047;

3-(6-fluoro-4-(1-(4-hydroxybenzyl)piperidin-4-yl)-1-oxoisoindolin-2-yl)-piperidine-2,6-dione A1048;

3-(6-fluoro-4-(1-(3-hydroxybenzyl)piperidin-4-yl)-1-oxoisoindolin-2-yl)-piperidine-2,6-dione A1049;

3-(4-(1-((3-aminopyridin-4-yl)methyl)piperidin-4-yl)-6-fluoro-1-oxoisoindolin-2-yl)piperidine-2,6-dione A1050;

3-(4-(1-((2-aminopyridin-3-yl)methyl)piperidin-4-yl)-6-fluoro-1-oxoisoindolin-2-yl)piperidine-2,6-dione A1051;

3-(6-fluoro-4-(1-((2-methylpyrimidin-5-yl)methyl)piperidin-4-yl)-1-oxoisoindolin-2-yl)piperidine-2,6-dione A1052;

3-(6-fluoro-4-(1-((2-Methylpyrimidin-4-yl)methyl)piperidin-4-yl)-1-oxoisoindolin-2-yl)piperidine-2,6-dione A1053;
3-(6-fluoro-4-(1-((3-methylpyrazin-2-yl)methyl)piperidin-4-yl)-1-oxoisoindolin-2-yl)piperidine-2,6-dione A1054;
3-(6-fluoro-4-(1-((5-methylpyrazin-2-yl)methyl)piperidin-4-yl)-1-oxoisoindolin-2-yl)piperidine-2,6-dione A1055;
3-(6-fluoro-4-(1-((2-hydroxypyridin-3-yl)methyl)piperidin-4-yl)-1-oxoisoindolin-2-yl)piperidine-2,6-dione A1056;
3-(6-fluoro-4-(1-(3-fluorobenzyl)piperidin-4-yl)-1-oxoisoindolin-2-yl)piperidine-2,6-dione A1057;
3-(6-fluoro-4-(1-(4-fluorobenzyl)piperidin-4-yl)-1-oxoisoindolin-2-yl)piperidine-2,6-dione A1058;
3-(4-(1-((1,4-dimethyl-1H-pyrazol-5-yl)methyl)piperidin-4-yl)-6-fluoro-1-oxoisoindolin-2-yl)piperidine-2,6-dione A1059;
3-(4-(1-((2,5-dimethyl-1H-imidazol-4-yl)methyl)piperidin-4-yl)-6-fluoro-1-oxoisoindolin-2-yl)piperidine-2,6-dione A1060;
3-(6-fluoro-4-(1-((6-fluoropyridin-2-yl)methyl)piperidin-4-yl)-1-oxoisoindolin-2-yl)piperidine-2,6-dione A1061;
3-(6-fluoro-4-(1-((4-fluoropyridin-2-yl)methyl)piperidin-4-yl)-1-oxoisoindolin-2-yl)piperidine-2,6-dione A1062;
3-(6-fluoro-4-(1-((5-fluoropyridin-3-yl)methyl)piperidin-4-yl)-1-oxoisoindolin-2-yl)piperidine-2,6-dione A1063;
3-(6-fluoro-4-(1-((5-fluoropyridin-2-yl)methyl)piperidin-4-yl)-1-oxoisoindolin-2-yl)piperidine-2,6-dione A1064;
3-(6-fluoro-4-(1-((3-fluoropyridin-4-yl)methyl)piperidin-4-yl)-1-oxoisoindolin-2-yl)piperidine-2,6-dione A1065;
3-(6-fluoro-4-(1-((6-fluoropyridin-3-yl)methyl)piperidin-4-yl)-1-oxoisoindolin-2-yl)piperidine-2,6-dione A1066;
3-(6-fluoro-4-(1-((5-(hydroxymethyl)-1H-pyrrol-2-yl)methyl)piperidin-4-yl)-1-oxoisoindolin-2-yl)piperidine-2,6-dione A1067;
3-(4-(1-((5-amino-1-methyl-1H-pyrazol-4-yl)methyl)piperidin-4-yl)-6-fluoro-1-oxoisoindolin-2-yl)piperidine-2,6-dione A1068;
3-(6-fluoro-4-(1-((5-(hydroxymethyl)furan-2-yl)methyl)piperidin-4-yl)-1-oxoisoindolin-2-yl)piperidine-2,6-dione A1069;
3-(6-fluoro-4-(1-((3-methoxyfuran-2-yl)methyl)piperidin-4-yl)-1-oxoisoindolin-2-yl)piperidine-2,6-dione A1070;
3-(6-fluoro-4-(1-((3-methylthiophen-2-yl)methyl)piperidin-4-yl)-1-oxoisoindolin-2-yl)piperidine-2,6-dione A1071;
3-(4-(1-(2-cyclohexylethyl)piperidin-4-yl)-6-fluoro-1-oxoisoindolin-2-yl)-piperidine-2,6-dione A1072;
3-(6-fluoro-4-(1-((4-methylthiazol-5-yl)methyl)piperidin-4-yl)-1-oxoisoindolin-2-yl)piperidine-2,6-dione A1073;
3-(6-fluoro-4-(1-((2-methylthiazol-5-yl)methyl)piperidin-4-yl)-1-oxoisoindolin-2-yl)piperidine-2,6-dione A1074;
3-(6-fluoro-4-(1-((5-methylthiazol-2-yl)methyl)piperidin-4-yl)-1-oxoisoindolin-2-yl)piperidine-2,6-dione A1075;
3-(4-(1-(3-ethynylbenzyl)piperidin-4-yl)-6-fluoro-1-oxoisoindolin-2-yl)-piperidine-2,6-dione A1076;
3-(4-(1-(2-ethynylbenzyl)piperidin-4-yl)-6-fluoro-1-oxoisoindolin-2-yl)-piperidine-2,6-dione A1077;
3-(4-(1-(4-ethynylbenzyl)piperidin-4-yl)-6-fluoro-1-oxoisoindolin-2-yl)-piperidine-2,6-dione A1078;
2-((4-(2-(2,6-dioxopiperidin-3-yl)-6-fluoro-1-oxoisoindolin-4-yl)piperidin-1-yl)-methyl)benzonitrile A1079;
4-((4-(2-(2,6-dioxopiperidin-3-yl)-6-fluoro-1-oxoisoindolin-4-yl)piperidin-1-yl)-methyl)benzonitrile A1080;
3-(4-(1-((5-ethynylpyridin-2-yl)methyl)piperidin-4-yl)-6-fluoro-1-oxoisoindolin-2-yl)piperidine-2,6-dione A1081;
3-((4-(2-(2,6-dioxopiperidin-3-yl)-6-fluoro-1-oxoisoindolin-4-yl)piperidin-1-yl)methyl)benzonitrile A1082;
2-((4-(2-(2,6-dioxopiperidin-3-yl)-6-fluoro-1-oxoisoindolin-4-yl)piperidin-1-yl)-methyl)isonicotinonitrile A1083;
6-((4-(2-(2,6-dioxopiperidin-3-yl)-6-fluoro-1-oxoisoindolin-4-yl)piperidin-1-yl)-methyl)picolinonitrile A1084;
5-((4-(2-(2,6-dioxopiperidin-3-yl)-6-fluoro-1-oxoisoindolin-4-yl)piperidin-1-yl)-methyl)nicotinonitrile A1085;
5-((4-(2-(2,6-dioxopiperidin-3-yl)-6-fluoro-1-oxoisoindolin-4-yl)piperidin-1-yl)-methyl)picolinonitrile A1086;
3-(4-(1-(bicyclo[4.2.0]octa-1(6),2,4-trien-3-ylmethyl)piperidin-4-yl)-6-fluoro-1-oxoisoindolin-2-yl)piperidine-2,6-dione A1087;
4-((4-(2-(2,6-dioxopiperidin-3-yl)-6-fluoro-1-oxoisoindolin-4-yl)piperidin-1-yl)-methyl)-1-methyl-1H-pyrrole-2-carbonitrile A1088;
3-(6-fluoro-1-oxo-4-(1-(3-phenylpropyl)piperidin-4-yl)isoindolin-2-yl)-piperidine-2,6-dione A1089;
3-(4-(1-(3,5-dimethylbenzyl)piperidin-4-yl)-6-fluoro-1-oxoisoindolin-2-yl)-piperidine-2,6-dione A1090;
3-(6-fluoro-4-(1-(2-methylphenethyl)piperidin-4-yl)-1-oxoisoindolin-2-yl)-piperidine-2,6-dione A1091;
3-(4-(1-(2,5-dimethylbenzyl)piperidin-4-yl)-6-fluoro-1-oxoisoindolin-2-yl)-piperidine-2,6-dione A1092;
3-(4-(1-(2,4-dimethylbenzyl)piperidin-4-yl)-6-fluoro-1-oxoisoindolin-2-yl)-piperidine-2,6-dione A1093;
3-(4-(1-(2,6-dimethylbenzyl)piperidin-4-yl)-6-fluoro-1-oxoisoindolin-2-yl)-piperidine-2,6-dione A1094;
3-(6-fluoro-4-(1-(2-(methylamino)benzyl)piperidin-4-yl)-1-oxoisoindolin-2-yl)-piperidine-2,6-dione A1095;
3-(4-(1-((2,6-dimethylpyridin-4-yl)methyl)piperidin-4-yl)-6-fluoro-1-oxoisoindolin-2-yl)piperidine-2,6-dione A1096;
3-(6-fluoro-4-(1-(4-(hydroxymethyl)benzyl)piperidin-4-yl)-1-oxoisoindolin-2-yl)piperidine-2,6-dione A1097;
3-(6-fluoro-4-(1-(2-hydroxy-4-methylbenzyl)piperidin-4-yl)-1-oxoisoindolin-2-yl)piperidine-2,6-dione A1098;
3-(6-fluoro-4-(1-(3-methoxybenzyl)piperidin-4-yl)-1-oxoisoindolin-2-yl)-piperidine-2,6-dione A1099;
3-(6-fluoro-4-(1-(3-hydroxy-5-methylbenzyl)piperidin-4-yl)-1-oxoisoindolin-2-yl)piperidine-2,6-dione A1100;
3-(6-fluoro-4-(1-(4-methoxybenzyl)piperidin-4-yl)-1-oxoisoindolin-2-yl)-piperidine-2,6-dione A1101;
3-(6-fluoro-4-(1-(2-methoxybenzyl)piperidin-4-yl)-1-oxoisoindolin-2-yl)-piperidine-2,6-dione A1102;
3-(4-(1-((2-amino-5-methylpyridin-3-yl)methyl)piperidin-4-yl)-6-fluoro-1-oxoisoindolin-2-yl)piperidine-2,6-dione A1103;
3-(6-fluoro-4-(1-((1-methyl-2-oxo-1,2-dihydropyridin-4-yl)methyl)piperidin-4-yl)-1-oxoisoindolin-2-yl)piperidine-2,6-dione A1104;
3-(6-fluoro-4-(1-((1-methyl-6-oxo-1,6-dihydropyridin-2-yl)methyl)piperidin-4-yl)-1-oxoisoindolin-2-yl)piperidine-2,6-dione A1105;
3-(6-fluoro-4-(1-((5-methoxypyridin-3-yl)methyl)piperidin-4-yl)-1-oxoisoindolin-2-yl)piperidine-2,6-dione A1106;
3-(6-fluoro-4-(1-((6-methoxypyridin-2-yl)methyl)piperidin-4-yl)-1-oxoisoindolin-2-yl)piperidine-2,6-dione A1107;
3-(6-fluoro-4-(1-((4-methoxypyridin-3-yl)methyl)piperidin-4-yl)-1-oxoisoindolin-2-yl)piperidine-2,6-dione A1108;
3-(6-fluoro-4-(1-((3-methoxypyridin-2-yl)methyl)piperidin-4-yl)-1-oxoisoindolin-2-yl)piperidine-2,6-dione A1109;
3-(6-fluoro-4-(1-((5-methoxypyridin-2-yl)methyl)piperidin-4-yl)-1-oxoisoindolin-2-yl)piperidine-2,6-dione A1110;
3-(6-fluoro-4-(1-((4-methoxypyridin-2-yl)methyl)piperidin-4-yl)-1-oxoisoindolin-2-yl)piperidine-2,6-dione A1111;
3-(6-fluoro-4-(1-((6-methoxypyridin-3-yl)methyl)piperidin-4-yl)-1-oxoisoindolin-2-yl)piperidine-2,6-dione A1112;

3-(6-fluoro-4-(1-((3-methoxypyridin-4-yl)methyl)piperidin-4-yl)-1-oxoisoindolin-2-yl)piperidine-2,6-dione A1113;

3-(6-fluoro-4-(1-((2-methoxypyridin-3-yl)methyl)piperidin-4-yl)-1-oxoisoindolin-2-yl)piperidine-2,6-dione A1114;

3-(6-fluoro-4-(1-((2-methoxypyridin-4-yl)methyl)piperidin-4-yl)-1-oxoisoindolin-2-yl)piperidine-2,6-dione A1115;

5-((4-(2-(2,6-dioxopiperidin-3-yl)-6-fluoro-1-oxoisoindolin-4-yl)piperidin-1-yl)methyl)thiophene-2-carbonitrile A1116;

3-(6-fluoro-4-(1-((2-methoxypyrimidin-4-yl)methyl)piperidin-4-yl)-1-oxoisoindolin-2-yl)piperidine-2,6-dione A1117;

3-(6-fluoro-4-(1-((5-methoxypyrazin-2-yl)methyl)piperidin-4-yl)-1-oxoisoindolin-2-yl)piperidine-2,6-dione A1118;

3-(6-fluoro-4-(1-(5-fluoro-2-methylbenzyl)piperidin-4-yl)-1-oxoisoindolin-2-yl)-piperidine-2,6-dione A1119;

3-(6-fluoro-4-(1-(4-fluoro-2-methylbenzyl)piperidin-4-yl)-1-oxoisoindolin-2-yl)-piperidine-2,6-dione A1120;

3-(6-fluoro-4-(1-(3-fluoro-5-methylbenzyl)piperidin-4-yl)-1-oxoisoindolin-2-yl)-piperidine-2,6-dione A1121;

3-(6-fluoro-4-(1-(4-fluoro-3-methylbenzyl)piperidin-4-yl)-1-oxoisoindolin-2-yl)-piperidine-2,6-dione A1122;

3-(6-fluoro-4-(1-(2-fluoro-5-methylbenzyl)piperidin-4-yl)-1-oxoisoindolin-2-yl)-piperidine-2,6-dione A1123;

3-(6-fluoro-4-(1-(3-fluoro-2-methylbenzyl)piperidin-4-yl)-1-oxoisoindolin-2-yl)-piperidine-2,6-dione A1124;

3-(6-fluoro-4-(1-(4-fluorophenethyl)piperidin-4-yl)-1-oxoisoindolin-2-yl)-piperidine-2,6-dione A1125;

3-(6-fluoro-4-(1-(3-(5-methylfuran-2-yl)propyl)piperidin-4-yl)-1-oxoisoindolin-2-yl)piperidine-2,6-dione A1126;

3-(6-fluoro-4-(1-((4-isopropylfuran-2-yl)methyl)piperidin-4-yl)-1-oxoisoindolin-2-yl)piperidine-2,6-dione A1127;

3-(6-fluoro-4-(1-((1-isopropyl-1H-pyrazol-4-yl)methyl)piperidin-4-yl)-1-oxoisoindolin-2-yl)piperidine-2,6-dione A1128;

3-(4-(1-(2-amino-5-fluorobenzyl)piperidin-4-yl)-6-fluoro-1-oxoisoindolin-2-yl)-piperidine-2,6-dione A1129;

3-(4-(1-(3-chlorobenzyl)piperidin-4-yl)-6-fluoro-1-oxoisoindolin-2-yl)piperidine-2,6-dione A1130;

3-(4-(1-(4-chlorobenzyl)piperidin-4-yl)-6-fluoro-1-oxoisoindolin-2-yl)piperidine-2,6-dione A1131;

3-(4-(1-(2-chlorobenzyl)piperidin-4-yl)-6-fluoro-1-oxoisoindolin-2-yl)piperidine-2,6-dione A1132;

3-(6-fluoro-4-(1-((5-fluoro-2-oxo-1,2-dihydropyridin-3-yl)methyl)piperidin-4-yl)-1-oxoisoindolin-2-yl)piperidine-2,6-dione A1133;

3-(4-(1-((6-chloropyridin-2-yl)methyl)piperidin-4-yl)-6-fluoro-1-oxoisoindolin-2-yl)piperidine-2,6-dione A1134;

3-(4-(1-((3-chloropyridin-4-yl)methyl)piperidin-4-yl)-6-fluoro-1-oxoisoindolin-2-yl)piperidine-2,6-dione A1135;

3-(4-(1-((3-chloropyrazin-2-yl)methyl)piperidin-4-yl)-6-fluoro-1-oxoisoindolin-2-yl)piperidine-2,6-dione A1136;

3-(4-(1-((4-chloro-1-methyl-1H-pyrazol-3-yl)methyl)piperidin-4-yl)-6-fluoro-1-oxoisoindolin-2-yl)piperidine-2,6-dione A1137;

3-(4-(1-((1H-indol-6-yl)methyl)piperidin-4-yl)-6-fluoro-1-oxoisoindolin-2-yl)piperidine-2,6-dione A1138;

3-(4-(1-((1H-indol-2-yl)methyl)piperidin-4-yl)-6-fluoro-1-oxoisoindolin-2-yl)piperidine-2,6-dione A1139;

3-(4-(1-((1H-indol-7-yl)methyl)piperidin-4-yl)-6-fluoro-1-oxoisoindolin-2-yl)piperidine-2,6-dione A1140;

3-(6-fluoro-4-(1-(indolizin-1-ylmethyl)piperidin-4-yl)-1-oxoisoindolin-2-yl)-piperidine-2,6-dione A1141;

3-(4-(1-((1H-indol-3-yl)methyl)piperidin-4-yl)-6-fluoro-1-oxoisoindolin-2-yl)-piperidine-2,6-dione A1142;

4-((4-(2-(2,6-dioxopiperidin-3-yl)-6-fluoro-1-oxoisoindolin-4-yl)piperidin-1-yl)-methyl)-3-methylbenzonitrile A1143;

2-((4-(2-(2,6-dioxopiperidin-3-yl)-6-fluoro-1-oxoisoindolin-4-yl)piperidin-1-yl)-methyl)-6-methylbenzonitrile A1144;

3-((4-(2-(2,6-dioxopiperidin-3-yl)-6-fluoro-1-oxoisoindolin-4-yl)piperidin-1-yl)-methyl)-5-methylbenzonitrile A1145;

3-((4-(2-(2,6-dioxopiperidin-3-yl)-6-fluoro-1-oxoisoindolin-4-yl)piperidin-1-yl)-methyl)-2-methylbenzonitrile A1146;

2-((4-(2-(2,6-dioxopiperidin-3-yl)-6-fluoro-1-oxoisoindolin-4-yl)piperidin-1-yl)-methyl)-5-methylbenzonitrile A1147;

3-(4-(1-(benzofuran-5-ylmethyl)piperidin-4-yl)-6-fluoro-1-oxoisoindolin-2-yl)-piperidine-2,6-dione A1148;

3-(4-(1-(benzofuran-7-ylmethyl)piperidin-4-yl)-6-fluoro-1-oxoisoindolin-2-yl)-piperidine-2,6-dione A1149;

3-(4-(1-(benzofuran-4-ylmethyl)piperidin-4-yl)-6-fluoro-1-oxoisoindolin-2-yl)-piperidine-2,6-dione A1150;

3-(6-fluoro-4-(1-(imidazo[1,2-a]pyridin-2-ylmethyl)piperidin-4-yl)-1-oxoisoindolin-2-yl)piperidine-2,6-dione A1151;

3-(6-fluoro-4-(1-(imidazo[1,2-a]pyridin-3-ylmethyl)piperidin-4-yl)-1-oxoisoindolin-2-yl)piperidine-2,6-dione A1152;

3-(4-(1-((1H-benzo[d]imidazol-2-yl)methyl)piperidin-4-yl)-6-fluoro-1-oxoisoindolin-2-yl)piperidine-2,6-dione A1153;

3-(4-(1-((1H-pyrrolo[3,2-b]pyridin-6-yl)methyl)piperidin-4-yl)-6-fluoro-1-oxoisoindolin-2-yl)piperidine-2,6-dione A1154;

3-(6-fluoro-4-(1-(imidazo[1,2-a]pyridin-7-ylmethyl)piperidin-4-yl)-1-oxoisoindolin-2-yl)piperidine-2,6-dione A1155;

3-(6-fluoro-4-(1-(imidazo[1,2-a]pyridin-8-ylmethyl)piperidin-4-yl)-1-oxoisoindolin-2-yl)piperidine-2,6-dione A1156;

3-(6-fluoro-4-(1-(imidazo[1,2-a]pyridin-6-ylmethyl)piperidin-4-yl)-1-oxoisoindolin-2-yl)piperidine-2,6-dione A1157;

3-(4-(1-((1H-benzo[d]imidazol-7-yl)methyl)piperidin-4-yl)-6-fluoro-1-oxoisoindolin-2-yl)piperidine-2,6-dione A1158;

3-(4-(1-((1H-pyrrolo[2,3-b]pyridin-6-yl)methyl)piperidin-4-yl)-6-fluoro-1-oxoisoindolin-2-yl)piperidine-2,6-dione A1159;

3-(6-fluoro-4-(1-(imidazo[1,5-a]pyridin-1-ylmethyl)piperidin-4-yl)-1-oxoisoindolin-2-yl)piperidine-2,6-dione A1160;

3-(4-(1-((1H-pyrrolo[3,2-b]pyridin-3-yl)methyl)piperidin-4-yl)-6-fluoro-1-oxoisoindolin-2-yl)piperidine-2,6-dione A1161;

3-(4-(1-((2H-indazol-6-yl)methyl)piperidin-4-yl)-6-fluoro-1-oxoisoindolin-2-yl)piperidine-2,6-dione A1162;

3-(6-fluoro-1-oxo-4-(1-(pyrazolo[1,5-a]pyridin-3-ylmethyl)piperidin-4-yl)isoindolin-2-yl)piperidine-2,6-dione A1163;

3-(6-fluoro-4-(1-(imidazo[1,2-a]pyridin-5-ylmethyl)piperidin-4-yl)-1-oxoisoindolin-2-yl)piperidine-2,6-dione A1164;

3-(4-(1-((1H-pyrrolo[2,3-c]pyridin-3-yl)methyl)piperidin-4-yl)-6-fluoro-1-oxoisoindolin-2-yl)piperidine-2,6-dione A1165;

3-(6-fluoro-1-oxo-4-(1-(pyrazolo[1,5-a]pyridin-7-ylmethyl)piperidin-4-yl)-isoindolin-2-yl)piperidine-2,6-dione A1166;
3-(4-(1-(2-cyclopropylbenzyl)piperidin-4-yl)-6-fluoro-1-oxoisoindolin-2-yl)-piperidine-2,6-dione A1167;
3-(4-(1-(4-cyclopropylbenzyl)piperidin-4-yl)-6-fluoro-1-oxoisoindolin-2-yl)-piperidine-2,6-dione A1168;
3-(4-(1-((2-chlorothiophen-3-yl)methyl)piperidin-4-yl)-6-fluoro-1-oxoisoindolin-2-yl)piperidine-2,6-dione A1169;
3-(4-(1-((5-chlorothiophen-2-yl)methyl)piperidin-4-yl)-6-fluoro-1-oxoisoindolin-2-yl)piperidine-2,6-dione A1170;
3-(4-(1-(benzo[d]oxazol-6-ylmethyl)piperidin-4-yl)-6-fluoro-1-oxoisoindolin-2-yl)piperidine-2,6-dione A1171;
3-(4-(1-(benzo[d]oxazol-5-ylmethyl)piperidin-4-yl)-6-fluoro-1-oxoisoindolin-2-yl)piperidine-2,6-dione A1172;
3-(6-fluoro-4-(1-(furo[2,3-c]pyridin-5-ylmethyl)piperidin-4-yl)-1-oxoisoindolin-2-yl)piperidine-2,6-dione A1173;
5-((4-(2-(2,6-dioxopiperidin-3-yl)-6-fluoro-1-oxoisoindolin-4-yl)piperidin-1-yl)methyl)-2-hydroxybenzonitrile A1174;
4-((4-(2-(2,6-dioxopiperidin-3-yl)-6-fluoro-1-oxoisoindolin-4-yl)piperidin-1-yl)-methyl)-3-hydroxybenzonitrile A1175;
3-(4-(1-((4H-pyrrolo[2,3-b]pyrazin-7-yl)methyl)piperidin-4-yl)-6-fluoro-1-oxoisoindolin-2-yl)piperidine-2,6-dione A1176;
3-(6-fluoro-4-(1-(imidazo[1,2-a]pyrimidin-7-ylmethyl)piperidin-4-yl)-1-oxoisoindolin-2-yl)piperidine-2,6-dione A1177;
6-amino-5-((4-(2-(2,6-dioxopiperidin-3-yl)-6-fluoro-1-oxoisoindolin-4-yl)-piperidin-1-yl)methyl)nicotinonitrile A1178;
3-(6-fluoro-4-(1-(imidazo[1,2-a]pyrimidin-3-ylmethyl)piperidin-4-yl)-1-oxoisoindolin-2-yl)piperidine-2,6-dione A1179;
3-(4-(1-([1,2,4]triazolo[1,5-a]pyridin-7-ylmethyl)piperidin-4-yl)-6-fluoro-1-oxoisoindolin-2-yl)piperidine-2,6-dione A1180;
3-(4-(1-(2-ethynyl-4-fluorobenzyl)piperidin-4-yl)-6-fluoro-1-oxoisoindolin-2-yl)-piperidine-2,6-dione A1181;
3-(4-(1-((4,4-difluorocyclohexyl)methyl)piperidin-4-yl)-6-fluoro-1-oxoisoindolin-2-yl)piperidine-2,6-dione A1182;
3-(6-fluoro-1-oxo-4-(1-(4-phenylbutyl)piperidin-4-yl)isoindolin-2-yl)piperidine-2,6-dione A1183;
3-(6-fluoro-4-(1-(4-isopropylbenzyl)piperidin-4-yl)-1-oxoisoindolin-2-yl)-piperidine-2,6-dione A1184;
3-(6-fluoro-1-oxo-4-(1-(2,4,6-trimethylbenzyl)piperidin-4-yl)isoindolin-2-yl)-piperidine-2,6-dione A1185;
5-((4-(2-(2,6-dioxopiperidin-3-yl)-6-fluoro-1-oxoisoindolin-4-yl)piperidin-1-yl)-methyl)-2-fluorobenzonitrile A1186;
4-((4-(2-(2,6-dioxopiperidin-3-yl)-6-fluoro-1-oxoisoindolin-4-yl)piperidin-1-yl)-methyl)-2-fluorobenzonitrile A1187;
3-((4-(2-(2,6-dioxopiperidin-3-yl)-6-fluoro-1-oxoisoindolin-4-yl)piperidin-1-yl)-methyl)-5-fluorobenzonitrile A1188;
4-((4-(2-(2,6-dioxopiperidin-3-yl)-6-fluoro-1-oxoisoindolin-4-yl)piperidin-1-yl)-methyl)-3-fluorobenzonitrile A1189;
2-((4-(2-(2,6-dioxopiperidin-3-yl)-6-fluoro-1-oxoisoindolin-4-yl)piperidin-1-yl)-methyl)-5-fluorobenzonitrile A1190;
2-((4-(2-(2,6-dioxopiperidin-3-yl)-6-fluoro-1-oxoisoindolin-4-yl)piperidin-1-yl)-methyl)-4-fluorobenzonitrile A1191;
3-((4-(2-(2,6-dioxopiperidin-3-yl)-6-fluoro-1-oxoisoindolin-4-yl)piperidin-1-yl)-methyl)benzamide A1192;
3-(4-(1-(3-(dimethylamino)benzyl)piperidin-4-yl)-6-fluoro-1-oxoisoindolin-2-yl)piperidine-2,6-dione A1193;
3-(4-(1-(4-(ethylamino)benzyl)piperidin-4-yl)-6-fluoro-1-oxoisoindolin-2-yl)-piperidine-2,6-dione A1194;
3-(6-fluoro-4-(1-((5-isopropylpyridin-3-yl)methyl)piperidin-4-yl)-1-oxoisoindolin-2-yl)piperidine-2,6-dione A1195;
3-(4-(1-(2-(dimethylamino)benzyl)piperidin-4-yl)-6-fluoro-1-oxoisoindolin-2-yl)piperidine-2,6-dione A1196;
3-(4-(1-(benzo[d][1,3]dioxol-4-ylmethyl)piperidin-4-yl)-6-fluoro-1-oxoisoindolin-2-yl)piperidine-2,6-dione A1197;
3-(4-(1-(2-(benzyloxy)ethyl)piperidin-4-yl)-6-fluoro-1-oxoisoindolin-2-yl)piperidine-2,6-dione A1198;
3-(6-fluoro-4-(1-(2-methoxy-4-methylbenzyl)piperidin-4-yl)-1-oxoisoindolin-2-yl)piperidine-2,6-dione A1199;
3-(6-fluoro-4-(1-(3-methoxy-4-methylbenzyl)piperidin-4-yl)-1-oxoisoindolin-2-yl)piperidine-2,6-dione A1200;
3-(4-(1-(4-ethoxybenzyl)piperidin-4-yl)-6-fluoro-1-oxoisoindolin-2-yl)-piperidine-2,6-dione A1201;
3-(6-fluoro-4-(1-(4-hydroxy-3,5-dimethylbenzyl)piperidin-4-yl)-1-oxoisoindolin-2-yl)piperidine-2,6-dione A1202;
3-(6-fluoro-4-(1-(4-methoxy-2-methylbenzyl)piperidin-4-yl)-1-oxoisoindolin-2-yl)piperidine-2,6-dione A1203;
3-(6-fluoro-4-(1-(3-methoxyphenethyl)piperidin-4-yl)-1-oxoisoindolin-2-yl)-piperidine-2,6-dione A1204;
3-(6-fluoro-4-(1-(4-methoxyphenethyl)piperidin-4-yl)-1-oxoisoindolin-2-yl)-piperidine-2,6-dione A1205;
3-(6-fluoro-4-(1-(3-methoxy-5-methylbenzyl)piperidin-4-yl)-1-oxoisoindolin-2-yl)piperidine-2,6-dione A1206;
3-(6-fluoro-4-(1-(2-methoxy-6-methylbenzyl)piperidin-4-yl)-1-oxoisoindolin-2-yl)piperidine-2,6-dione A1207;
3-(6-fluoro-4-(1-(3-methoxy-2-methylbenzyl)piperidin-4-yl)-1-oxoisoindolin-2-yl)piperidine-2,6-dione A1208;
3-(6-fluoro-4-(1-(2-methoxy-3-methylbenzyl)piperidin-4-yl)-1-oxoisoindolin-2-yl)piperidine-2,6-dione A1209;
3-(6-fluoro-4-(1-(4-methoxy-3-methylbenzyl)piperidin-4-yl)-1-oxoisoindolin-2-yl)piperidine-2,6-dione A1210;
3-(4-(1-((2-(dimethylamino)pyrimidin-5-yl)methyl)piperidin-4-yl)-6-fluoro-1-oxoisoindolin-2-yl)piperidine-2,6-dione A1211;
3-(4-(1-((5-(tert-butyl)-1H-pyrrol-2-yl)methyl)piperidin-4-yl)-6-fluoro-1-oxoisoindolin-2-yl)piperidine-2,6-dione A1212;
3-(4-(1-((5,6-dihydro-8H-imidazo[2,1-c][1,4]oxazin-2-yl)methyl)piperidin-4-yl)-6-fluoro-1-oxoisoindolin-2-yl)piperidine-2,6-dione A1213;
3-(4-(1-((5,6-dihydro-8H-imidazo[2,1-c][1,4]oxazin-3-yl)methyl)piperidin-4-yl)-6-fluoro-1-oxoisoindolin-2-yl)piperidine-2,6-dione A1214;
3-(6-fluoro-4-(1-((1-isobutyl-1H-pyrazol-4-yl)methyl)piperidin-4-yl)-1-oxoisoindolin-2-yl)piperidine-2,6-dione A1215;
3-(4-(1-((1-(tert-butyl)-1H-1,2,3-triazol-4-yl)methyl)piperidin-4-yl)-6-fluoro-1-oxoisoindolin-2-yl)piperidine-2,6-dione A1216;
3-(4-(1-((2-cyclopropylthiazol-5-yl)methyl)piperidin-4-yl)-6-fluoro-1-oxoisoindolin-2-yl)piperidine-2,6-dione A1217;
3-(6-fluoro-4-(1-((2-(methylthio)pyrimidin-4-yl)methyl)piperidin-4-yl)-1-oxoisoindolin-2-yl)piperidine-2,6-dione A1218;
3-(6-fluoro-4-(1-((4-hydroxybicyclo[2.2.2]octan-1-yl)methyl)piperidin-4-yl)-1-oxoisoindolin-2-yl)piperidine-2,6-dione A1219;

3-(4-(1-(4-chlorophenethyl)piperidin-4-yl)-6-fluoro-1-oxoisoindolin-2-yl)-piperidine-2,6-dione A1220;

3-(4-(1-((5-(dimethylamino)thiophen-2-yl)methyl)piperidin-4-yl)-6-fluoro-1-oxoisoindolin-2-yl)piperidine-2,6-dione A1221;

3-(4-(1-(2-amino-3-chlorobenzyl)piperidin-4-yl)-6-fluoro-1-oxoisoindolin-2-yl)-piperidine-2,6-dione A1222;

3-(4-(1-(2-amino-4-chlorobenzyl)piperidin-4-yl)-6-fluoro-1-oxoisoindolin-2-yl)-piperidine-2,6-dione A1223;

3-(4-(1-(2-amino-6-chlorobenzyl)piperidin-4-yl)-6-fluoro-1-oxoisoindolin-2-yl)-piperidine-2,6-dione A1224;

3-(6-fluoro-4-(1-(naphthalen-2-ylmethyl)piperidin-4-yl)-1-oxoisoindolin-2-yl)-piperidine-2,6-dione A1225;

3-(6-fluoro-1-oxo-4-(1-(quinolin-6-ylmethyl)piperidin-4-yl)isoindolin-2-yl)-piperidine-2,6-dione A1226;

3-(6-fluoro-1-oxo-4-(1-(quinolin-4-ylmethyl)piperidin-4-yl)isoindolin-2-yl)-piperidine-2,6-dione A1227;

3-(6-fluoro-4-(1-(isoquinolin-5-ylmethyl)piperidin-4-yl)-1-oxoisoindolin-2-yl)-piperidine-2,6-dione A1228;

3-(6-fluoro-4-(1-(isoquinolin-8-ylmethyl)piperidin-4-yl)-1-oxoisoindolin-2-yl)-piperidine-2,6-dione A1229;

3-(6-fluoro-4-(1-(isoquinolin-3-ylmethyl)piperidin-4-yl)-1-oxoisoindolin-2-yl)-piperidine-2,6-dione A1230;

3-(6-fluoro-4-(1-(isoquinolin-4-ylmethyl)piperidin-4-yl)-1-oxoisoindolin-2-yl)-piperidine-2,6-dione A1231;

3-(6-fluoro-1-oxo-4-(1-(quinolin-8-ylmethyl)piperidin-4-yl)isoindolin-2-yl)-piperidine-2,6-dione A1232;

3-(6-fluoro-1-oxo-4-(1-(quinoxalin-5-ylmethyl)piperidin-4-yl)isoindolin-2-yl)-piperidine-2,6-dione A1233;

3-(6-fluoro-1-oxo-4-(1-(quinoxalin-2-ylmethyl)piperidin-4-yl)isoindolin-2-yl)-piperidine-2,6-dione A1234;

3-(4-(1-((1,8-naphthyridin-2-yl)methyl)piperidin-4-yl)-6-fluoro-1-oxoisoindolin-2-yl)piperidine-2,6-dione A1235;

3-(6-fluoro-1-oxo-4-(1-(quinoxalin-6-ylmethyl)piperidin-4-yl)isoindolin-2-yl)-piperidine-2,6-dione A1236;

tert-butyl (2-(4-(2-(2,6-dioxopiperidin-3-yl)-6-fluoro-1-oxoisoindolin-4-yl)-piperidin-1-yl)ethyl)carbamate A1237;

3-(6-fluoro-4-(1-((6-methyl-1H-indol-3-yl)methyl)piperidin-4-yl)-1-oxoisoindolin-2-yl)piperidine-2,6-dione A1238;

3-(6-fluoro-4-(1-((3-methyl-1H-indol-2-yl)methyl)piperidin-4-yl)-1-oxoisoindolin-2-yl)piperidine-2,6-dione A1239;

3-(6-fluoro-4-(1-((4-methyl-1H-indol-3-yl)methyl)piperidin-4-yl)-1-oxoisoindolin-2-yl)piperidine-2,6-dione A1240;

3-(6-fluoro-4-(1-((1-methyl-1H-indol-6-yl)methyl)piperidin-4-yl)-1-oxoisoindolin-2-yl)piperidine-2,6-dione A1241;

3-(6-fluoro-4-(1-((2-methyl-1H-indol-4-yl)methyl)piperidin-4-yl)-1-oxoisoindolin-2-yl)piperidine-2,6-dione A1242;

3-(6-fluoro-4-(1-((1-methyl-1H-indol-5-yl)methyl)piperidin-4-yl)-1-oxoisoindolin-2-yl)piperidine-2,6-dione A1243;

3-(6-fluoro-4-(1-((7-methyl-1H-indol-3-yl)methyl)piperidin-4-yl)-1-oxoisoindolin-2-yl)piperidine-2,6-dione A1244;

3-(6-fluoro-4-(1-((2-methyl-2H-indazol-3-yl)methyl)piperidin-4-yl)-1-oxoisoindolin-2-yl)piperidine-2,6-dione A1245;

3-(6-fluoro-4-(1-((2-methylimidazo[1,2-a]pyridin-3-yl)methyl)piperidin-4-yl)-1-oxoisoindolin-2-yl)piperidine-2,6-dione A1246;

3-(6-fluoro-4-(1-((1-methyl-1H-benzo[d]imidazol-2-yl)methyl)piperidin-4-yl)-1-oxoisoindolin-2-yl)piperidine-2,6-dione A1247;

3-(6-fluoro-4-(1-((5-methyl-1H-pyrrolo[2,3-b]pyridin-3-yl)methyl)piperidin-4-yl)-1-oxoisoindolin-2-yl)piperidine-2,6-dione A1248;

3-(6-fluoro-4-(1-((1-methyl-1H-indazol-4-yl)methyl)piperidin-4-yl)-1-oxoisoindolin-2-yl)piperidine-2,6-dione A1249;

3-(6-fluoro-4-(1-((7-methylimidazo[1,2-a]pyridin-3-yl)methyl)piperidin-4-yl)-1-oxoisoindolin-2-yl)piperidine-2,6-dione A1250;

3-(6-fluoro-4-(1-((5-methylimidazo[1,2-a]pyridin-3-yl)methyl)piperidin-4-yl)-1-oxoisoindolin-2-yl)piperidine-2,6-dione A1251;

3-(6-fluoro-4-(1-((6-methylimidazo[1,2-a]pyridin-2-yl)methyl)piperidin-4-yl)-1-oxoisoindolin-2-yl)piperidine-2,6-dione A1252;

3-(6-fluoro-4-(1-((2-methyl-2H-indazol-5-yl)methyl)piperidin-4-yl)-1-oxoisoindolin-2-yl)piperidine-2,6-dione A1253;

3-(6-fluoro-4-(1-((1-methyl-1H-indazol-6-yl)methyl)piperidin-4-yl)-1-oxoisoindolin-2-yl)piperidine-2,6-dione A1254;

3-(6-fluoro-4-(1-((3-methylimidazo[1,2-a]pyridin-2-yl)methyl)piperidin-4-yl)-1-oxoisoindolin-2-yl)piperidine-2,6-dione A1255;

3-(6-fluoro-1-oxo-4-(1-((5,6,7,8-tetrahydronaphthalen-1-yl)methyl)piperidin-4-yl)isoindolin-2-yl)piperidine-2,6-dione A1256;

3-(6-fluoro-1-oxo-4-(1-((1-oxoisoindolin-5-yl)methyl)piperidin-4-yl)isoindolin-2-yl)piperidine-2,6-dione A1257;

3-(6-fluoro-1-oxo-4-(1-((3-oxoisoindolin-5-yl)methyl)piperidin-4-yl)isoindolin-2-yl)piperidine-2,6-dione A1258;

3-(6-fluoro-4-(1-((2-methylbenzo[d]oxazol-6-yl)methyl)piperidin-4-yl)-1-oxoisoindolin-2-yl)piperidine-2,6-dione A1259;

2-((4-(2-(2,6-dioxopiperidin-3-yl)-6-fluoro-1-oxoisoindolin-4-yl)piperidin-1-yl)-methyl)-5-methoxybenzonitrile A1260;

4-((4-(2-(2,6-dioxopiperidin-3-yl)-6-fluoro-1-oxoisoindolin-4-yl)piperidin-1-yl)-methyl)-3-methoxybenzonitrile A1261;

4-((4-(2-(2,6-dioxopiperidin-3-yl)-6-fluoro-1-oxoisoindolin-4-yl)piperidin-1-yl)-methyl)-2-methoxybenzonitrile A1262;

3-(6-fluoro-4-(1-((1-methyl-1H-imidazo[4,5-b]pyridin-2-yl)methyl)piperidin-4-yl)-1-oxoisoindolin-2-yl)piperidine-2,6-dione A1263;

3-(4-(1-(chroman-6-ylmethyl)piperidin-4-yl)-6-fluoro-1-oxoisoindolin-2-yl)-piperidine-2,6-dione A1264;

3-(4-(1-(benzo[b]thiophen-2-ylmethyl)piperidin-4-yl)-6-fluoro-1-oxoisoindolin-2-yl)piperidine-2,6-dione A1265;

3-(4-(1-(benzo[b]thiophen-3-ylmethyl)piperidin-4-yl)-6-fluoro-1-oxoisoindolin-2-yl)piperidine-2,6-dione A1266;

3-(6-fluoro-4-(1-(3-methyl-3-phenylbutyl)piperidin-4-yl)-1-oxoisoindolin-2-yl)-piperidine-2,6-dione A1267;

3-(4-(1-((3,4-dihydro-2H-pyrano[2,3-c]pyridin-6-yl)methyl)piperidin-4-yl)-6-fluoro-1-oxoisoindolin-2-yl)piperidine-2,6-dione A1268;

3-(6-fluoro-1-oxo-4-(1-(thieno[2,3-b]pyridin-2-ylmethyl)piperidin-4-yl)-isoindolin-2-yl)piperidine-2,6-dione A1269;

3-(4-(1-(benzo[d]thiazol-4-ylmethyl)piperidin-4-yl)-6-fluoro-1-oxoisoindolin-2-yl)piperidine-2,6-dione A1270;

3-(6-fluoro-1-oxo-4-(1-(thieno[3,2-c]pyridin-2-ylmethyl)piperidin-4-yl)-isoindolin-2-yl)piperidine-2,6-dione A1271;
3-(4-(1-(4-((dimethylamino)methyl)benzyl)piperidin-4-yl)-6-fluoro-1-oxoisoindolin-2-yl)piperidine-2,6-dione A1272;
3-(4-(1-((2-(tert-butyl)pyridin-4-yl)methyl)piperidin-4-yl)-6-fluoro-1-oxoisoindolin-2-yl)piperidine-2,6-dione A1273;
3-(4-(1-(4-(dimethylamino)-3-methylbenzyl)piperidin-4-yl)-6-fluoro-1-oxoisoindolin-2-yl)piperidine-2,6-dione A1274;
3-(6-fluoro-4-(1-((4-fluorobenzofuran-7-yl)methyl)piperidin-4-yl)-1-oxoisoindolin-2-yl)piperidine-2,6-dione A1275;
3-(6-fluoro-4-(1-((5-fluoro-1H-benzo[d]imidazol-2-yl)methyl)piperidin-4-yl)-1-oxoisoindolin-2-yl)piperidine-2,6-dione A1276;
3-(4-(1-((2,3-dihydrobenzo[b][1,4]dioxin-6-yl)methyl)piperidin-4-yl)-6-fluoro-1-oxoisoindolin-2-yl)piperidine-2,6-dione A1277;
3-(6-fluoro-4-(1-(3-(2-methoxyphenyl)propyl)piperidin-4-yl)-1-oxoisoindolin-2-yl)piperidine-2,6-dione A1278;
3-(4-(1-(3-(benzyloxy)propyl)piperidin-4-yl)-6-fluoro-1-oxoisoindolin-2-yl)-piperidine-2,6-dione A1279;
3-(4-(1-((adamantan-1-yl)methyl)piperidin-4-yl)-6-fluoro-1-oxoisoindolin-2-yl)-piperidine-2,6-dione A1280;
3-(4-(1-((2,3-dihydro-[1,4]dioxino[2,3-b]pyridin-6-yl)methyl)piperidin-4-yl)-6-fluoro-1-oxoisoindolin-2-yl)piperidine-2,6-dione A1281;
3-((4-(2-(2,6-dioxopiperidin-3-yl)-6-fluoro-1-oxoisoindolin-4-yl)piperidin-1-yl)-methyl)-1H-indole-6-carbonitrile A1282;
2-((4-(2-(2,6-dioxopiperidin-3-yl)-6-fluoro-1-oxoisoindolin-4-yl)piperidin-1-yl)-methyl)-1H-indole-6-carbonitrile A1283;
3-(4-(1-(4-(1H-pyrazol-1-yl)benzyl)piperidin-4-yl)-6-fluoro-1-oxoisoindolin-2-yl)piperidine-2,6-dione A1284;
3-(4-(1-(4-(1H-imidazol-1-yl)benzyl)piperidin-4-yl)-6-fluoro-1-oxoisoindolin-2-yl)piperidine-2,6-dione A1285;
3-(6-fluoro-1-oxo-4-(1-((2-phenyl-1H-imidazol-5-yl)methyl)piperidin-4-yl)-isoindolin-2-yl)piperidine-2,6-dione A1286;
3-(4-(1-(3-(1H-imidazol-1-yl)benzyl)piperidin-4-yl)-6-fluoro-1-oxoisoindolin-2-yl)piperidine-2,6-dione A1287;
3-(6-fluoro-1-oxo-4-(1-((5-phenyl-1H-imidazol-2-yl)methyl)piperidin-4-yl)-isoindolin-2-yl)piperidine-2,6-dione A1288;
3-(6-fluoro-1-oxo-4-(1-((1-phenyl-1H-pyrazol-3-yl)methyl)piperidin-4-yl)-isoindolin-2-yl)piperidine-2,6-dione A1289;
3-(4-(1-(4-(1H-1,2,4-triazol-1-yl)benzyl)piperidin-4-yl)-6-fluoro-1-oxoisoindolin-2-yl)piperidine-2,6-dione A1290;
3-(4-(1-(2-(1H-1,2,4-triazol-1-yl)benzyl)piperidin-4-yl)-6-fluoro-1-oxoisoindolin-2-yl)piperidine-2,6-dione A1291;
3-(4-(1-(3-(1H-1,2,4-triazol-1-yl)benzyl)piperidin-4-yl)-6-fluoro-1-oxoisoindolin-2-yl)piperidine-2,6-dione A1292;
3-(6-fluoro-1-oxo-4-(1-(4-(pyrrolidin-1-yl)benzyl)piperidin-4-yl)isoindolin-2-yl)-piperidine-2,6-dione A1293;
3-(6-fluoro-1-oxo-4-(1-(3-(pyrrolidin-1-yl)benzyl)piperidin-4-yl)isoindolin-2-yl)-piperidine-2,6-dione A1294;
3-(6-fluoro-1-oxo-4-(1-((6-(pyrrolidin-1-yl)pyridin-3-yl)methyl)piperidin-4-yl)-isoindolin-2-yl)piperidine-2,6-dione A1295;
3-(6-fluoro-4-(1-((6-fluorochroman-8-yl)methyl)piperidin-4-yl)-1-oxoisoindolin-2-yl)piperidine-2,6-dione A1296;
3-(4-(1-([1,1'-biphenyl]-4-ylmethyl)piperidin-4-yl)-6-fluoro-1-oxoisoindolin-2-yl)piperidine-2,6-dione A1297;
3-(6-fluoro-1-oxo-4-(1-(3-(pyridin-4-yl)benzyl)piperidin-4-yl)isoindolin-2-yl)-piperidine-2,6-dione A1298;
3-(6-fluoro-4-(1-((6-(methylsulfonyl)pyridin-2-yl)methyl)piperidin-4-yl)-1-oxoisoindolin-2-yl)piperidine-2,6-dione A1299;
3-(6-fluoro-1-oxo-4-(1-(3-(quinolin-6-yl)propyl)piperidin-4-yl)isoindolin-2-yl)-piperidine-2,6-dione A1300;
3-(6-fluoro-4-(1-(4-morpholinobenzyl)piperidin-4-yl)-1-oxoisoindolin-2-yl)-piperidine-2,6-dione A1301;
3-(6-fluoro-4-(1-(3-morpholinobenzyl)piperidin-4-yl)-1-oxoisoindolin-2-yl)-piperidine-2,6-dione A1302;
3-(6-fluoro-4-(1-(2-morpholinobenzyl)piperidin-4-yl)-1-oxoisoindolin-2-yl)-piperidine-2,6-dione A1303;
4-((4-(2-(2,6-dioxopiperidin-3-yl)-6-fluoro-1-oxoisoindolin-4-yl)piperidin-1-yl)-methyl)-N-isopropylbenzamide A1304;
3-(6-fluoro-1-oxo-4-(1-((6-(p-tolyl)pyridin-3-yl)methyl)piperidin-4-yl)isoindolin-2-yl)piperidine-2,6-dione A1305;
3-(6-fluoro-1-oxo-4-(1-(3-phenoxybenzyl)piperidin-4-yl)isoindolin-2-yl)-piperidine-2,6-dione A1306;
3-(6-fluoro-1-oxo-4-(1-(4-phenoxybenzyl)piperidin-4-yl)isoindolin-2-yl)-piperidine-2,6-dione A1307;
3-(6-fluoro-4-(1-((4'-methyl-[2,2'-bipyridin]-4-yl)methyl)piperidin-4-yl)-1-oxoisoindolin-2-yl)piperidine-2,6-dione A1308;
3-(4-(1-(4-(ethylsulfonyl)benzyl)piperidin-4-yl)-6-fluoro-1-oxoisoindolin-2-yl)-piperidine-2,6-dione A1309;
3-(6-fluoro-4-(1-((2-morpholinothiazol-5-yl)methyl)piperidin-4-yl)-1-oxoisoindolin-2-yl)piperidine-2,6-dione A1310;
3-(4-(1-(4-bromophenethyl)piperidin-4-yl)-6-fluoro-1-oxoisoindolin-2-yl)-piperidine-2,6-dione A1311;
3-(6-fluoro-1-oxo-4-(1-(2-(pyridin-2-yloxy)benzyl)piperidin-4-yl)isoindolin-2-yl)piperidine-2,6-dione A1312;
N-(3-((4-(2-(2,6-dioxopiperidin-3-yl)-6-fluoro-1-oxoisoindolin-4-yl)piperidin-1-yl)methyl)phenyl)methanesulfonamide A1313;
N-(4-((4-(2-(2,6-dioxopiperidin-3-yl)-6-fluoro-1-oxoisoindolin-4-yl)piperidin-1-yl)methyl)phenyl)methanesulfonamide A1314;
N-(2-((4-(2-(2,6-dioxopiperidin-3-yl)-6-fluoro-1-oxoisoindolin-4-yl)piperidin-1-yl)methyl)phenyl)methanesulfonamide A1315;
3-(4-(1-((6-(dimethylamino)naphthalen-2-yl)methyl)piperidin-4-yl)-6-fluoro-1-oxoisoindolin-2-yl)piperidine-2,6-dione A1316;
3-(6-fluoro-1-oxo-4-(1-(3-(3-(trifluoromethyl)phenyl)propyl)piperidin-4-yl)-isoindolin-2-yl)piperidine-2,6-dione A1317;
2-(3-(4-(2-(2,6-dioxopiperidin-3-yl)-6-fluoro-1-oxoisoindolin-4-yl)piperidin-1-yl)propyl)isoindoline-1,3-dione A1318;
3-(4-(1-((1-benzylpiperidin-4-yl)methyl)piperidin-4-yl)-6-fluoro-1-oxoisoindolin-2-yl)piperidine-2,6-dione A1319;
3-(4-(1-(2-chloro-5-(trifluoromethyl)benzyl)piperidin-4-yl)-6-fluoro-1-oxoisoindolin-2-yl)piperidine-2,6-dione A1320;
3-(4-(1-(5-chloro-2-(trifluoromethyl)benzyl)piperidin-4-yl)-6-fluoro-1-oxoisoindolin-2-yl)piperidine-2,6-dione A1321;
3-(4-(1-(4-chloro-2-(trifluoromethyl)benzyl)piperidin-4-yl)-6-fluoro-1-oxoisoindolin-2-yl)piperidine-2,6-dione A1322;

3-(4-(1-(2-chloro-4-(trifluoromethyl)benzyl)piperidin-4-yl)-6-fluoro-1-oxoisoindolin-2-yl)piperidine-2,6-dione A1323;

3-(4-(1-(3-chloro-4-(trifluoromethyl)benzyl)piperidin-4-yl)-6-fluoro-1-oxoisoindolin-2-yl)piperidine-2,6-dione A1324;

5-((4-(2-(2,6-dioxopiperidin-3-yl)-6-fluoro-1-oxoisoindolin-4-yl)piperidin-1-yl)-methyl)-2-(4-methyl-1H-imidazol-1-yl)benzonitrile A1325;

3-(4-(1-(3-(benzyloxy)benzyl)piperidin-4-yl)-6-fluoro-1-oxoisoindolin-2-yl)-piperidine-2,6-dione A1326;

3-(4-(1-(4-(benzyloxy)benzyl)piperidin-4-yl)-6-fluoro-1-oxoisoindolin-2-yl)-piperidine-2,6-dione A1327;

3-(4-(1-(3-(3-bromophenyl)propyl)piperidin-4-yl)-6-fluoro-1-oxoisoindolin-2-yl)piperidine-2,6-dione A1328;

3-(4-(1-(3-(cyclohexylmethoxy)benzyl)piperidin-4-yl)-6-fluoro-1-oxoisoindolin-2-yl)piperidine-2,6-dione A1329;

4-(3-((4-(2-(2,6-dioxopiperidin-3-yl)-6-fluoro-1-oxoisoindolin-4-yl)piperidin-1-yl)methyl)phenoxy)benzonitrile A1330;

4-(4-((4-(2-(2,6-dioxopiperidin-3-yl)-6-fluoro-1-oxoisoindolin-4-yl)piperidin-1-yl)methyl)phenoxy)benzonitrile A1331;

3-(4-(1-(3-chloro-4-morpholinobenzyl)piperidin-4-yl)-6-fluoro-1-oxoisoindolin-2-yl)piperidine-2,6-dione A1332;

3-(4-(1-(4-(benzyloxy)-2-methylbenzyl)piperidin-4-yl)-6-fluoro-1-oxoisoindolin-2-yl)piperidine-2,6-dione A1333;

3-(4-(1-(2-(benzyloxy)-4-methylbenzyl)piperidin-4-yl)-6-fluoro-1-oxoisoindolin-2-yl)piperidine-2,6-dione A1334;

tert-butyl 4-(2-(4-(2-(2,6-dioxopiperidin-3-yl)-6-fluoro-1-oxoisoindolin-4-yl)-piperidin-1-yl)ethyl)piperidine-1-carboxylate A1335;

tert-butyl ((1r,4r)-4-((4-(2-(2,6-dioxopiperidin-3-yl)-6-fluoro-1-oxoisoindolin-4-yl)piperidin-1-yl)methyl)cyclohexyl)carbamate A1336;

3-(4-(1-((2-chloro-4-morpholinopyrimidin-5-yl)methyl)piperidin-4-yl)-6-fluoro-1-oxoisoindolin-2-yl)piperidine-2,6-dione A1337;

tert-butyl 4-(2-(4-(2-(2,6-dioxopiperidin-3-yl)-6-fluoro-1-oxoisoindolin-4-yl)-piperidin-1-yl)ethyl)piperazine-1-carboxylate A1338;

tert-butyl 4-((4-(2-(2,6-dioxopiperidin-3-yl)-6-fluoro-1-oxoisoindolin-4-yl)piperidin-1-yl)methyl)-4-fluoropiperidine-1-carboxylate A1339;

4-(4-((4-(2-(2,6-dioxopiperidin-3-yl)-6-fluoro-1-oxoisoindolin-4-yl)piperidin-1-yl)methyl)phenoxy)-3-fluorobenzonitrile A1340;

tert-butyl (((1r,4r)-4-((4-(2-(2,6-dioxopiperidin-3-yl)-6-fluoro-1-oxoisoindolin-4-yl)piperidin-1-yl)methyl)cyclohexyl)methyl)carbamate A1341;

tert-butyl 6-((4-(2-(2,6-dioxopiperidin-3-yl)-6-fluoro-1-oxoisoindolin-4-yl)-piperidin-1-yl)methyl)indoline-1-carboxylate A1342;

benzyl (4-((4-(2-(2,6-dioxopiperidin-3-yl)-6-fluoro-1-oxoisoindolin-4-yl)-piperidin-1-yl)methyl)phenyl)carbamate A1343;

tert-butyl 4-(1-(4-(2-(2,6-dioxopiperidin-3-yl)-6-fluoro-1-oxoisoindolin-4-yl)-piperidin-1-yl)-2-methylpropan-2-yl) piperidine-1-carboxylate A1344;

3-(4-(1-(4-(benzyloxy)-3-ethoxybenzyl)piperidin-4-yl)-6-fluoro-1-oxoisoindolin-2-yl)piperidine-2,6-dione A1345;

3-(6-fluoro-1-oxo-4-(1-(4-(4-(trifluoromethyl)phenoxy) benzyl)piperidin-4-yl)-isoindolin-2-yl)piperidine-2,6-dione A1346;

3-(4-(1-(3-bromo-4-morpholinobenzyl)piperidin-4-yl)-6-fluoro-1-oxoisoindolin-2-yl)piperidine-2,6-dione A1347;

tert-butyl 4-(4-((4-(2-(2,6-dioxopiperidin-3-yl)-6-fluoro-1-oxoisoindolin-4-yl)-piperidin-1-yl)methyl)-1H-1,2,3-triazol-1-yl)piperidine-1-carboxylate A1348;

3-(4-(1-(3-bromo-4-(4-methylpiperazin-1-yl)benzyl)piperidin-4-yl)-6-fluoro-1-oxoisoindolin-2-yl)piperidine-2,6-dione A1349; or 4-(4-bromo-3-((4-(2-(2,6-dioxopiperidin-3-yl)-6-fluoro-1-oxoisoindolin-4-yl)-piperidin-1-yl)methyl)phenoxy)benzonitrile A1350;

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

In yet another embodiment, provided herein is a compound of:

3-(4-(1-(cyclopropylsulfonyl)piperidin-4-yl)-6-fluoro-1-oxoisoindolin-2-yl)piperidine-2,6-dione A2001;

3-(6-fluoro-1-oxo-4-(1-(propylsulfonyl)piperidin-4-yl) isoindolin-2-yl)piperidine-2,6-dione A2002;

3-(6-fluoro-4-(1-(isopropylsulfonyl)piperidin-4-yl)-1-oxoisoindolin-2-yl)-piperidine-2,6-dione A2003;

3-(6-fluoro-4-(1-(isobutylsulfonyl)piperidin-4-yl)-1-oxoisoindolin-2-yl)-piperidine-2,6-dione A2004;

3-(6-fluoro-4-(1-(furan-3-ylsulfonyl)piperidin-4-yl)-1-oxoisoindolin-2-yl)-piperidine-2,6-dione A2005;

3-(4-(1-((1H-pyrazol-4-yl)sulfonyl)piperidin-4-yl)-6-fluoro-1-oxoisoindolin-2-yl)piperidine-2,6-dione A2006;

3-(6-fluoro-1-oxo-4-(1-((trifluoromethyl)sulfonyl)piperidin-4-yl)isoindolin-2-yl)-piperidine-2,6-dione A2007;

3-(4-(1-((cyclobutylmethyl)sulfonyl)piperidin-4-yl)-6-fluoro-1-oxoisoindolin-2-yl)piperidine-2,6-dione A2008;

3-(4-(1-((3-chloropropyl)sulfonyl)piperidin-4-yl)-6-fluoro-1-oxoisoindolin-2-yl)-piperidine-2,6-dione A2009;

3-(6-fluoro-1-oxo-4-(1-(pyridin-3-ylsulfonyl)piperidin-4-yl)isoindolin-2-yl)-piperidine-2,6-dione A2010;

3-(6-fluoro-4-(1-((1-methyl-1H-pyrazol-4-yl)sulfonyl)piperidin-4-yl)-1-oxoisoindolin-2-yl)piperidine-2,6-dione A2011;

3-(6-fluoro-4-(1-((1-methyl-1H-pyrazol-3-yl)sulfonyl)piperidin-4-yl)-1-oxoisoindolin-2-yl)piperidine-2,6-dione A2012;

3-(6-fluoro-4-(1-((1-methyl-1H-imidazol-4-yl)sulfonyl)piperidin-4-yl)-1-oxoisoindolin-2-yl)piperidine-2,6-dione A2013;

3-(6-fluoro-1-oxo-4-(1-(thiophen-2-ylsulfonyl)piperidin-4-yl)isoindolin-2-yl)-piperidine-2,6-dione A2014;

3-(4-(1-(cyclohexylsulfonyl)piperidin-4-yl)-6-fluoro-1-oxoisoindolin-2-yl)-piperidine-2,6-dione A2015;

3-(6-fluoro-1-oxo-4-(1-((tetrahydro-2H-pyran-4-yl)sulfonyl)piperidin-4-yl)-isoindolin-2-yl)piperidine-2,6-dione A2016;

3-(6-fluoro-1-oxo-4-(1-(m-tolylsulfonyl)piperidin-4-yl) isoindolin-2-yl)-piperidine-2,6-dione A2017;

3-(6-fluoro-4-(1-((6-methylpyridin-3-yl)sulfonyl)piperidin-4-yl)-1-oxoisoindolin-2-yl)piperidine-2,6-dione A2018;

3-(6-fluoro-4-(1-((4-hydroxyphenyl)sulfonyl)piperidin-4-yl)-1-oxoisoindolin-2-yl)piperidine-2,6-dione A2019;

3-(6-fluoro-4-(1-((4-fluorophenyl)sulfonyl)piperidin-4-yl)-1-oxoisoindolin-2-yl)-piperidine-2,6-dione A2020;

3-(6-fluoro-4-(1-((3-fluorophenyl)sulfonyl)piperidin-4-yl)-1-oxoisoindolin-2-yl)-piperidine-2,6-dione A2021;

3-(6-fluoro-4-(1-((2-fluorophenyl)sulfonyl)piperidin-4-yl)-1-oxoisoindolin-2-yl)-piperidine-2,6-dione A2022;

3-(6-fluoro-1-oxo-4-(1-((3,3,3-trifluoropropyl)sulfonyl)piperidin-4-yl)isoindolin-2-yl)piperidine-2,6-dione A2023;

3-(6-fluoro-4-(1-((4-methylbenzyl)sulfonyl)piperidin-4-yl)-1-oxoisoindolin-2-yl)piperidine-2,6-dione A2024;
3-(6-fluoro-1-oxo-4-(1-(phenethylsulfonyl)piperidin-4-yl)isoindolin-2-yl)-piperidine-2,6-dione A2025;
3-(4-(1-((2,6-dimethylphenyl)sulfonyl)piperidin-4-yl)-6-fluoro-1-oxoisoindolin-2-yl)piperidine-2,6-dione A2026;
3-(6-fluoro-4-(1-((4-methoxyphenyl)sulfonyl)piperidin-4-yl)-1-oxoisoindolin-2-yl)piperidine-2,6-dione A2027;
3-(6-fluoro-4-(1-((3-methoxyphenyl)sulfonyl)piperidin-4-yl)-1-oxoisoindolin-2-yl)piperidine-2,6-dione A2028;
3-(6-fluoro-4-(1-((6-methoxypyridin-3-yl)sulfonyl)piperidin-4-yl)-1-oxoisoindolin-2-yl)piperidine-2,6-dione A2029;
3-(6-fluoro-4-(1-((2-fluoro-5-methylphenyl)sulfonyl)piperidin-4-yl)-1-oxoisoindolin-2-yl)piperidine-2,6-dione A2030;
3-(6-fluoro-4-(1-((4-fluoro-2-methylphenyl)sulfonyl)piperidin-4-yl)-1-oxoisoindolin-2-yl)piperidine-2,6-dione A2031;
3-(6-fluoro-4-(1-((2-fluoro-4-methylphenyl)sulfonyl)piperidin-4-yl)-1-oxoisoindolin-2-yl)piperidine-2,6-dione A2032;
3-(4-(1-((3-chlorophenyl)sulfonyl)piperidin-4-yl)-6-fluoro-1-oxoisoindolin-2-yl)-piperidine-2,6-dione A2033;
3-(4-(1-((2-chlorophenyl)sulfonyl)piperidin-4-yl)-6-fluoro-1-oxoisoindolin-2-yl)-piperidine-2,6-dione A2034;
3-(4-(1-((4-chlorophenyl)sulfonyl)piperidin-4-yl)-6-fluoro-1-oxoisoindolin-2-yl)-piperidine-2,6-dione A2035;
3-(4-(1-((3,4-difluorophenyl)sulfonyl)piperidin-4-yl)-6-fluoro-1-oxoisoindolin-2-yl)piperidine-2,6-dione A2036;
3-(4-(1-((2,4-difluorophenyl)sulfonyl)piperidin-4-yl)-6-fluoro-1-oxoisoindolin-2-yl)piperidine-2,6-dione A2037;
3-(4-(1-((2,5-difluorophenyl)sulfonyl)piperidin-4-yl)-6-fluoro-1-oxoisoindolin-2-yl)piperidine-2,6-dione A2038;
3-(4-(1-((3,5-difluorophenyl)sulfonyl)piperidin-4-yl)-6-fluoro-1-oxoisoindolin-2-yl)piperidine-2,6-dione A2039;
3-(6-fluoro-1-oxo-4-(1-(pyridin-3-ylsulfonyl)piperidin-4-yl)isoindolin-2-yl)-piperidine-2,6-dione A2040;
2-((4-(2-(2,6-dioxopiperidin-3-yl)-6-fluoro-1-oxoisoindolin-4-yl)piperidin-1-yl)-sulfonyl)-5-methylbenzonitrile A2041;
3-(4-(1-((1H-indol-5-yl)sulfonyl)piperidin-4-yl)-6-fluoro-1-oxoisoindolin-2-yl)-piperidine-2,6-dione A2042;
3-(4-(1-(benzofuran-5-ylsulfonyl)piperidin-4-yl)-6-fluoro-1-oxoisoindolin-2-yl)-piperidine-2,6-dione A2043;
3-(4-(1-((2,3-dihydrobenzofuran-5-yl)sulfonyl)piperidin-4-yl)-6-fluoro-1-oxoisoindolin-2-yl)piperidine-2,6-dione A2044;
3-(6-fluoro-4-(1-((4-isopropylphenyl)sulfonyl)piperidin-4-yl)-1-oxoisoindolin-2-yl)piperidine-2,6-dione A2045;
3-(6-fluoro-4-(1-((3-isopropylphenyl)sulfonyl)piperidin-4-yl)-1-oxoisoindolin-2-yl)piperidine-2,6-dione A2046;
3-((4-(2-(2,6-dioxopiperidin-3-yl)-6-fluoro-1-oxoisoindolin-4-yl)piperidin-1-yl)-sulfonyl)-4-fluorobenzonitrile A2047;
5-((4-(2-(2,6-dioxopiperidin-3-yl)-6-fluoro-1-oxoisoindolin-4-yl)piperidin-1-yl)-sulfonyl)-2-fluorobenzonitrile A2048;
4-((4-(2-(2,6-dioxopiperidin-3-yl)-6-fluoro-1-oxoisoindolin-4-yl)piperidin-1-yl)-sulfonyl)benzamide A2049;
3-(6-fluoro-4-(1-((3-methoxybenzyl)sulfonyl)piperidin-4-yl)-1-oxoisoindolin-2-yl)piperidine-2,6-dione A2050;
3-(6-fluoro-4-(1-((3-methoxy-4-methylphenyl)sulfonyl)piperidin-4-yl)-1-oxoisoindolin-2-yl)piperidine-2,6-dione A2051;
3-(6-fluoro-4-(1-((5-fluoro-2-methoxyphenyl)sulfonyl)piperidin-4-yl)-1-oxoisoindolin-2-yl)piperidine-2,6-dione A2052;
3-(6-fluoro-4-(1-((3-fluoro-4-methoxyphenyl)sulfonyl)piperidin-4-yl)-1-oxoisoindolin-2-yl)piperidine-2,6-dione A2053;
3-(6-fluoro-1-oxo-4-(1-((5,6,7,8-tetrahydronaphthalen-2-yl)sulfonyl)piperidin-4-yl)isoindolin-2-yl)piperidine-2,6-dione A2054;
3-(6-fluoro-4-(1-((2-hydroxy-1H-benzo[d]imidazol-6-yl)sulfonyl)piperidin-4-yl)-1-oxoisoindolin-2-yl)piperidine-2,6-dione A2055;
3-(4-(1-((4-(tert-butyl)phenyl)sulfonyl)piperidin-4-yl)-6-fluoro-1-oxoisoindolin-2-yl)piperidine-2,6-dione A2056;
3-(4-(1-((3-(tert-butyl)phenyl)sulfonyl)piperidin-4-yl)-6-fluoro-1-oxoisoindolin-2-yl)piperidine-2,6-dione A2057;
N-(3-((4-(2-(2,6-dioxopiperidin-3-yl)-6-fluoro-1-oxoisoindolin-4-yl)piperidin-1-yl)sulfonyl)phenyl)acetamide A2058;
N-(4-((4-(2-(2,6-dioxopiperidin-3-yl)-6-fluoro-1-oxoisoindolin-4-yl)piperidin-1-yl)sulfonyl)phenyl)acetamide A2059;
4-((4-(2-(2,6-dioxopiperidin-3-yl)-6-fluoro-1-oxoisoindolin-4-yl)piperidin-1-yl)-sulfonyl)-N-methylbenzamide A2060;
2-chloro-4-((4-(2-(2,6-dioxopiperidin-3-yl)-6-fluoro-1-oxoisoindolin-4-yl)-piperidin-1-yl)sulfonyl)benzonitrile A2061;
3-(4-(1-((5-chloro-2-methoxypyridin-3-yl)sulfonyl)piperidin-4-yl)-6-fluoro-1-oxoisoindolin-2-yl)piperidine-2,6-dione A2062;
3-(4-(1-((4-(difluoromethoxy)phenyl)sulfonyl)piperidin-4-yl)-6-fluoro-1-oxoisoindolin-2-yl)piperidine-2,6-dione A2063;
3-(6-fluoro-4-(1-((4-(oxazol-5-yl)phenyl)sulfonyl)piperidin-4-yl)-1-oxoisoindolin-2-yl)piperidine-2,6-dione A2064;
3-(6-fluoro-1-oxo-4-(1-((4-(trifluoromethyl)phenyl)sulfonyl)piperidin-4-yl)-isoindolin-2-yl)piperidine-2,6-dione A2065;
3-(6-fluoro-1-oxo-4-(1-((3-(trifluoromethyl)phenyl)sulfonyl)piperidin-4-yl)-isoindolin-2-yl)piperidine-2,6-dione A2066;
3-(6-fluoro-1-oxo-4-(1-((2-(trifluoromethyl)phenyl)sulfonyl)piperidin-4-yl)-isoindolin-2-yl)piperidine-2,6-dione A2067;
3-(6-fluoro-1-oxo-4-(1-((6-(trifluoromethyl)pyridin-3-yl)sulfonyl)piperidin-4-yl)-isoindolin-2-yl)piperidine-2,6-dione A2068;
3-(6-fluoro-1-oxo-4-(1-((2-oxo-1,2,3,4-tetrahydroquinolin-6-yl)sulfonyl)-piperidin-4-yl)isoindolin-2-yl)piperidine-2,6-dione A2069;
2-((4-(2-(2,6-dioxopiperidin-3-yl)-6-fluoro-1-oxoisoindolin-4-yl)piperidin-1-yl)-sulfonyl)-N,N-dimethylbenzamide A2070;
3-(4-(1-((3-bromophenyl)sulfonyl)piperidin-4-yl)-6-fluoro-1-oxoisoindolin-2-yl)-piperidine-2,6-dione A2071;
3-(4-(1-((2-bromophenyl)sulfonyl)piperidin-4-yl)-6-fluoro-1-oxoisoindolin-2-yl)-piperidine-2,6-dione A2072;
3-(6-fluoro-1-oxo-4-(1-((1-(o-tolyl)-1H-pyrazol-4-yl)sulfonyl)piperidin-4-yl)-isoindolin-2-yl)piperidine-2,6-dione A2073;
3-(6-fluoro-1-oxo-4-(1-((4-(trifluoromethyl)benzyl)sulfonyl)piperidin-4-yl)-isoindolin-2-yl)piperidine-2,6-dione A2074;

3-(6-fluoro-1-oxo-4-(1-((2-(trifluoromethoxy)phenyl)sulfonyl)piperidin-4-yl)-isoindolin-2-yl)piperidine-2,6-dione A2075;
3-(4-(1-((1-chloroisoquinolin-5-yl)sulfonyl)piperidin-4-yl)-6-fluoro-1-oxoisoindolin-2-yl)piperidine-2,6-dione A2076;
3-(6-fluoro-4-(1-(isoquinolin-5-ylsulfonyl)piperidin-4-yl)-1-oxoisoindolin-2-yl)-piperidine-2,6-dione A2077;
3-(6-fluoro-1-oxo-4-(1-((4-(pyridin-2-yloxy)phenyl)sulfonyl)piperidin-4-yl)-isoindolin-2-yl)piperidine-2,6-dione A2078;
3-(6-fluoro-1-oxo-4-(1-((6-phenoxypyridin-3-yl)sulfonyl) piperidin-4-yl)-isoindolin-2-yl)piperidine-2,6-dione A2079;
3-(4-(1-((5-(dimethylamino)naphthalen-1-yl)sulfonyl)piperidin-4-yl)-6-fluoro-1-oxoisoindolin-2-yl)piperidine-2,6-dione A2080;
3-(4-(1-((6-(dimethylamino)naphthalen-2-yl)sulfonyl)piperidin-4-yl)-6-fluoro-1-oxoisoindolin-2-yl)piperidine-2,6-dione A2081;
3-(4-(1-((4-(benzyloxy)phenyl)sulfonyl)piperidin-4-yl)-6-fluoro-1-oxoisoindolin-2-yl)piperidine-2,6-dione A2082;
tert-butyl 4-((4-(2-(2,6-dioxopiperidin-3-yl)-6-fluoro-1-oxoisoindolin-4-yl)-piperidin-1-yl)sulfonyl)piperidine-1-carboxylate A2083;
benzyl 4-((4-(2-(2,6-dioxopiperidin-3-yl)-6-fluoro-1-oxoisoindolin-4-yl)-piperidin-1-yl)sulfonyl)piperidine-1-carboxylate A2084;
3-(6-fluoro-1-oxo-4-(1-((2-(2,2,2-trifluoroacetyl)-1,2,3,4-tetrahydroisoquinolin-7-yl)sulfonyl)piperidin-4-yl)isoindolin-2-yl)piperidine-2,6-dione A2085;
benzyl 4-(((4-(2-(2,6-dioxopiperidin-3-yl)-6-fluoro-1-oxoisoindolin-4-yl)-piperidin-1-yl)sulfonyl)methyl)piperidine-1-carboxylate A2086;
3-(4-(1-(ethylsulfonyl)piperidin-4-yl)-6-fluoro-1-oxoisoindolin-2-yl)piperidine-2,6-dione A2087;
3-(4-(1-((5-chlorothiophen-2-yl)sulfonyl)piperidin-4-yl)-6-fluoro-1-oxoisoindolin-2-yl)piperidine-2,6-dione A2088;
3-(4-(1-((3-chloro-4-methylphenyl)sulfonyl)piperidin-4-yl)-6-fluoro-1-oxoisoindolin-2-yl)piperidine-2,6-dione A2089;
3-(4-(1-((2-chloro-6-methylphenyl)sulfonyl)piperidin-4-yl)-6-fluoro-1-oxoisoindolin-2-yl)piperidine-2,6-dione A2090;
3-(4-(1-((3,5-difluorobenzyl)sulfonyl)piperidin-4-yl)-6-fluoro-1-oxoisoindolin-2-yl)piperidine-2,6-dione A2091;
3-(6-fluoro-4-(1-(naphthalen-2-ylsulfonyl)piperidin-4-yl)-1-oxoisoindolin-2-yl)piperidine-2,6-dione A2092;
3-(6-fluoro-1-oxo-4-(1-(quinolin-8-ylsulfonyl)piperidin-4-yl)isoindolin-2-yl)-piperidine-2,6-dione A2093;
3-(6-fluoro-4-(1-(isoquinolin-5-ylsulfonyl)piperidin-4-yl)-1-oxoisoindolin-2-yl)-piperidine-2,6-dione A2094;
3-(6-fluoro-1-oxo-4-(1-(quinoxalin-5-ylsulfonyl)piperidin-4-yl)isoindolin-2-yl)-piperidine-2,6-dione A2095;
3-chloro-4-((4-(2-(2,6-dioxopiperidin-3-yl)-6-fluoro-1-oxoisoindolin-4-yl)-piperidin-1-yl)sulfonyl)benzonitrile A2096;
3-(4-(1-(benzo[d][1,3]dioxol-5-ylsulfonyl)piperidin-4-yl)-6-fluoro-1-oxoisoindolin-2-yl)piperidine-2,6-dione A2097;
3-(4-(1-(benzo[d]thiazol-6-ylsulfonyl)piperidin-4-yl)-6-fluoro-1-oxoisoindolin-2-yl)piperidine-2,6-dione A2098;
3-(4-(1-((2,4-dichlorophenyl)sulfonyl)piperidin-4-yl)-6-fluoro-1-oxoisoindolin-2-yl)piperidine-2,6-dione A2099; or
3-(4-(1-((2,5-dichlorophenyl)sulfonyl)piperidin-4-yl)-6-fluoro-1-oxoisoindolin-2-yl)piperidine-2,6-dione A2100;

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

In yet another embodiment, provided herein is a compound of:

3-(6-fluoro-1-oxo-4-(4-(5,6,7,8-tetrahydronaphthalene-1-carbonyl)piperazin-1-yl)isoindolin-2-yl)piperidine-2,6-dione B0001;
3-(6-fluoro-4-(4-(1-methyl-1H-indole-5-carbonyl)piperazin-1-yl)-1-oxoisoindolin-2-yl)piperidine-2,6-dione B0002;
3-(6-fluoro-1-oxo-4-(4-(quinoxaline-5-carbonyl)piperazin-1-yl)isoindolin-2-yl)-piperidine-2,6-dione B0003;
3-(6-fluoro-1-oxo-4-(4-(quinazoline-6-carbonyl)piperazin-1-yl)isoindolin-2-yl)-piperidine-2,6-dione B0004;
3-(4-(4-(2-(dimethylamino)benzoyl)piperazin-1-yl)-6-fluoro-1-oxoisoindolin-2-yl)piperidine-2,6-dione B0005;
3-(4-(4-(4-(dimethylamino)benzoyl)piperazin-1-yl)-6-fluoro-1-oxoisoindolin-2-yl)piperidine-2,6-dione B0006;
3-(4-(4-(2,3-dihydrobenzofuran-7-carbonyl)piperazin-1-yl)-6-fluoro-1-oxoisoindolin-2-yl)piperidine-2,6-dione B0007;
3-(4-(4-(benzo[d]oxazole-5-carbonyl)piperazin-1-yl)-6-fluoro-1-oxoisoindolin-2-yl)piperidine-2,6-dione B0008;
3-(4-(4-(1H-benzo[d]imidazole-7-carbonyl)piperazin-1-yl)-6-fluoro-1-oxoisoindolin-2-yl)piperidine-2,6-dione B0009;
3-(6-fluoro-4-(4-(imidazo[1,2-a]pyridine-2-carbonyl)piperazin-1-yl)-1-oxoisoindolin-2-yl)piperidine-2,6-dione B0010;
3-(4-(4-(1H-pyrrolo[3,2-b]pyridine-6-carbonyl)piperazin-1-yl)-6-fluoro-1-oxoisoindolin-2-yl)piperidine-2,6-dione B0011;
3-(6-fluoro-4-(4-(imidazo[1,2-a]pyridine-3-carbonyl)piperazin-1-yl)-1-oxoisoindolin-2-yl)piperidine-2,6-dione B0012;
3-(4-(4-(benzofuran-6-carbonyl)piperazin-1-yl)-6-fluoro-1-oxoisoindolin-2-yl)-piperidine-2,6-dione B0013;
3-(6-fluoro-1-oxo-4-(4-(2-(piperidin-1-yl)acetyl)piperazin-1-yl)isoindolin-2-yl)-piperidine-2,6-dione B0014;
2-(2-(4-(2-(2,6-dioxopiperidin-3-yl)-6-fluoro-1-oxoisoindolin-4-yl)piperazin-1-yl)-2-oxoethyl)benzonitrile B0015;
3-(2-(4-(2-(2,6-dioxopiperidin-3-yl)-6-fluoro-1-oxoisoindolin-4-yl)piperazin-1-yl)-2-oxoethyl)benzonitrile B0016;
4-(2-(4-(2-(2,6-dioxopiperidin-3-yl)-6-fluoro-1-oxoisoindolin-4-yl)piperazin-1-yl)-2-oxoethyl)benzonitrile B0017;
3-(4-(4-(1H-indole-7-carbonyl)piperazin-1-yl)-6-fluoro-1-oxoisoindolin-2-yl)-piperidine-2,6-dione B0018;
3-(4-(4-(1-ethylpiperidine-4-carbonyl)piperazin-1-yl)-6-fluoro-1-oxoisoindolin-2-yl)piperidine-2,6-dione B0019;
3-(6-fluoro-1-oxo-4-(4-(2-(p-tolyl)acetyl)piperazin-1-yl) isoindolin-2-yl)-piperidine-2,6-dione B0020;
2-(4-(2-(2,6-dioxopiperidin-3-yl)-6-fluoro-1-oxoisoindolin-4-yl)piperazin-1-carbonyl)benzonitrile B0021;
3-(4-(2-(2,6-dioxopiperidin-3-yl)-6-fluoro-1-oxoisoindolin-4-yl)piperazin-1-carbonyl)benzonitrile B0022;
3-(6-fluoro-4-(4-(4-fluorobenzoyl)piperazin-1-yl)-1-oxoisoindolin-2-yl)-piperidine-2,6-dione B0023;
3-(6-fluoro-4-(4-(3-fluorobenzoyl)piperazin-1-yl)-1-oxoisoindolin-2-yl)-piperidine-2,6-dione B0024;
3-(6-fluoro-4-(4-(2-fluorobenzoyl)piperazin-1-yl)-1-oxoisoindolin-2-yl)-piperidine-2,6-dione B0025;
3-(6-fluoro-4-(4-(2-methylbenzoyl)piperazin-1-yl)-1-oxoisoindolin-2-yl)-piperidine-2,6-dione B0026;

3-(6-fluoro-4-(4-(3-methylbenzoyl)piperazin-1-yl)-1-oxoisoindolin-2-yl)-piperidine-2,6-dione B0027;
3-(6-fluoro-4-(4-(4-methylbenzoyl)piperazin-1-yl)-1-oxoisoindolin-2-yl)-piperidine-2,6-dione B0028;
3-(4-(4-(2-cyclopentylacetyl)piperazin-1-yl)-6-fluoro-1-oxoisoindolin-2-yl)-piperidine-2,6-dione B0029;
3-(4-(4-(cyclohexanecarbonyl)piperazin-1-yl)-6-fluoro-1-oxoisoindolin-2-yl)-piperidine-2,6-dione B0030;
3-(4-(4-(3,3-dimethylcyclobutane-1-carbonyl)piperazin-1-yl)-6-fluoro-1-oxoisoindolin-2-yl)piperidine-2,6-dione B0031;
3-(6-fluoro-1-oxo-4-(4-(pyrimidine-5-carbonyl)piperazin-1-yl)isoindolin-2-yl)-piperidine-2,6-dione B0032;
3-(6-fluoro-1-oxo-4-(4-(pyridazine-4-carbonyl)piperazin-1-yl)isoindolin-2-yl)-piperidine-2,6-dione B0033;
3-(6-fluoro-1-oxo-4-(4-(pyrimidine-4-carbonyl)piperazin-1-yl)isoindolin-2-yl)-piperidine-2,6-dione B0034;
3-(6-fluoro-1-oxo-4-(4-picolinoylpiperazin-1-yl)isoindolin-2-yl)piperidine-2,6-dione B0035;
3-(6-fluoro-4-(4-isonicotinoylpiperazin-1-yl)-1-oxoisoindolin-2-yl)piperidine-2,6-dione B0036;
3-(6-fluoro-4-(4-nicotinoylpiperazin-1-yl)-1-oxoisoindolin-2-yl)piperidine-2,6-dione B0037;
3-(4-(4-benzoylpiperazin-1-yl)-6-fluoro-1-oxoisoindolin-2-yl)piperidine-2,6-dione B0038;
3-(4-(4-(1-aminocyclobutane-1-carbonyl)piperazin-1-yl)-6-fluoro-1-oxoisoindolin-2-yl)piperidine-2,6-dione B0039;
3-(6-fluoro-4-(4-(1-methylazetidine-3-carbonyl)piperazin-1-yl)-1-oxoisoindolin-2-yl)piperidine-2,6-dione B0040;
3-(4-(4-(1H-pyrazole-5-carbonyl)piperazin-1-yl)-6-fluoro-1-oxoisoindolin-2-yl)piperidine-2,6-dione B0041;
3-(4-(4-(1H-imidazole-5-carbonyl)piperazin-1-yl)-6-fluoro-1-oxoisoindolin-2-yl)-piperidine-2,6-dione B0042;
3-(6-fluoro-4-(4-(furan-3-carbonyl)piperazin-1-yl)-1-oxoisoindolin-2-yl)-piperidine-2,6-dione B0043;
3-(6-fluoro-4-(4-(furan-2-carbonyl)piperazin-1-yl)-1-oxoisoindolin-2-yl)-piperidine-2,6-dione B0044;
3-(6-fluoro-4-(4-(1-fluorocyclopropane-1-carbonyl)piperazin-1-yl)-1-oxoisoindolin-2-yl)piperidine-2,6-dione B0045;
3-(6-fluoro-4-(4-(3-methylbutanoyl)piperazin-1-yl)-1-oxoisoindolin-2-yl)-piperidine-2,6-dione B0046;
3-(6-fluoro-4-(4-(oxetane-3-carbonyl)piperazin-1-yl)-1-oxoisoindolin-2-yl)-piperidine-2,6-dione B0047;
3-(4-(4-(cyclobutanecarbonyl)piperazin-1-yl)-6-fluoro-1-oxoisoindolin-2-yl)-piperidine-2,6-dione B0048;
3-(6-fluoro-4-(4-(methylglycyl)piperazin-1-yl)-1-oxoisoindolin-2-yl)piperidine-2,6-dione B0049; or
3-(4-(4-(cyclopropanecarbonyl)piperazin-1-yl)-6-fluoro-1-oxoisoindolin-2-yl)-piperidine-2,6-dione B0050;

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

In yet another embodiment, provided herein is a compound of:

3-(6-fluoro-4-(4-(3-methoxybenzyl)piperazin-1-yl)-1-oxoisoindolin-2-yl)-piperidine-2,6-dione B1001;
3-(6-fluoro-4-(4-(2-hydroxy-4-methylbenzyl)piperazin-1-yl)-1-oxoisoindolin-2-yl)-piperidine-2,6-dione B1002;
3-(6-fluoro-4-(4-(4-(hydroxymethyl)benzyl)piperazin-1-yl)-1-oxoisoindolin-2-yl)piperidine-2,6-dione B1003;
3-(4-(4-((2,6-dimethylpyridin-4-yl)methyl)piperazin-1-yl)-6-fluoro-1-oxoisoindolin-2-yl)piperidine-2,6-dione B1004;
3-(6-fluoro-4-(4-(2-(methylamino)benzyl)piperazin-1-yl)-1-oxoisoindolin-2-yl)-piperidine-2,6-dione B1005;
3-(4-(4-(2,6-dimethylbenzyl)piperazin-1-yl)-6-fluoro-1-oxoisoindolin-2-yl)-piperidine-2,6-dione B1006;
3-(4-(4-(2,4-dimethylbenzyl)piperazin-1-yl)-6-fluoro-1-oxoisoindolin-2-yl)-piperidine-2,6-dione B1007;
3-(4-(4-(2,5-dimethylbenzyl)piperazin-1-yl)-6-fluoro-1-oxoisoindolin-2-yl)-piperidine-2,6-dione B1008;
3-(6-fluoro-4-(4-(2-methylphenethyl)piperazin-1-yl)-1-oxoisoindolin-2-yl)-piperidine-2,6-dione B1009;
3-(4-(4-(3,5-dimethylbenzyl)piperazin-1-yl)-6-fluoro-1-oxoisoindolin-2-yl)-piperidine-2,6-dione B1010;
3-(6-fluoro-1-oxo-4-(4-(pyridin-3-ylmethyl)piperazin-1-yl)isoindolin-2-yl)-piperidine-2,6-dione B1011;
3-(6-fluoro-1-oxo-4-(4-(3-phenylpropyl)piperazin-1-yl)isoindolin-2-yl)-piperidine-2,6-dione B1012;
4-((4-(2-(2,6-dioxopiperidin-3-yl)-6-fluoro-1-oxoisoindolin-4-yl)piperazin-1-yl)-methyl)-1-methyl-1H-pyrrole-2-carbonitrile B1013;
3-(4-(4-(bicyclo[4.2.0]octa-1(6),2,4-trien-3-ylmethyl)piperazin-1-yl)-6-fluoro-1-oxoisoindolin-2-yl)piperidine-2,6-dione B1014;
5-((4-(2-(2,6-dioxopiperidin-3-yl)-6-fluoro-1-oxoisoindolin-4-yl)piperazin-1-yl)-methyl)picolinonitrile B1015;
5-((4-(2-(2,6-dioxopiperidin-3-yl)-6-fluoro-1-oxoisoindolin-4-yl)piperazin-1-yl)-methyl)nicotinonitrile B1016;
6-((4-(2-(2,6-dioxopiperidin-3-yl)-6-fluoro-1-oxoisoindolin-4-yl)piperazin-1-yl)-methyl)picolinonitrile B1017;
2-((4-(2-(2,6-dioxopiperidin-3-yl)-6-fluoro-1-oxoisoindolin-4-yl)piperazin-1-yl)-methyl)isonicotinonitrile B1018;
3-((4-(2-(2,6-dioxopiperidin-3-yl)-6-fluoro-1-oxoisoindolin-4-yl)piperazin-1-yl)-methyl)benzonitrile B1019;
3-(4-(4-((5-ethynylpyridin-2-yl)methyl)piperazin-1-yl)-6-fluoro-1-oxoisoindolin-2-yl)piperidine-2,6-dione B1020;
4-((4-(2-(2,6-dioxopiperidin-3-yl)-6-fluoro-1-oxoisoindolin-4-yl)piperazin-1-yl)-methyl)benzonitrile B1021;
3-(6-fluoro-4-(4-(3-hydroxy-2,2-dimethylpropyl)piperazin-1-yl)-1-oxoisoindolin-2-yl)piperidine-2,6-dione B1022;
2-((4-(2-(2,6-dioxopiperidin-3-yl)-6-fluoro-1-oxoisoindolin-4-yl)piperazin-1-yl)-methyl)benzonitrile B1023;
3-(4-(4-(4-ethynylbenzyl)piperazin-1-yl)-6-fluoro-1-oxoisoindolin-2-yl)-piperidine-2,6-dione B1024;
3-(4-(4-(2-ethynylbenzyl)piperazin-1-yl)-6-fluoro-1-oxoisoindolin-2-yl)-piperidine-2,6-dione B1025;
3-(4-(4-(3-ethynylbenzyl)piperazin-1-yl)-6-fluoro-1-oxoisoindolin-2-yl)-piperidine-2,6-dione B1026;
3-(6-fluoro-4-(4-((5-methylthiazol-2-yl)methyl)piperazin-1-yl)-1-oxoisoindolin-2-yl)piperidine-2,6-dione B1027;
3-(6-fluoro-4-(4-((2-methylthiazol-5-yl)methyl)piperazin-1-yl)-1-oxoisoindolin-2-yl)piperidine-2,6-dione B1028;
3-(6-fluoro-4-(4-((4-methylthiazol-5-yl)methyl)piperazin-1-yl)-1-oxoisoindolin-2-yl)piperidine-2,6-dione B1029;
3-(4-(4-(2-cyclohexylethyl)piperazin-1-yl)-6-fluoro-1-oxoisoindolin-2-yl)-piperidine-2,6-dione B1030;
3-(6-fluoro-4-(4-((3-methylthiophen-2-yl)methyl)piperazin-1-yl)-1-oxoisoindolin-2-yl)piperidine-2,6-dione B1031;
3-(6-fluoro-4-(4-((3-methoxyfuran-2-yl)methyl)piperazin-1-yl)-1-oxoisoindolin-2-yl)piperidine-2,6-dione B1032;
3-(6-fluoro-4-(4-((3-methyloxetan-3-yl)methyl)piperazin-1-yl)-1-oxoisoindolin-2-yl)piperidine-2,6-dione B1033;
3-(6-fluoro-4-(4-((5-(hydroxymethyl)furan-2-yl)methyl)piperazin-1-yl)-1-oxoisoindolin-2-yl)piperidine-2,6-dione B1034;
3-(4-(4-((5-amino-1-methyl-1H-pyrazol-4-yl)methyl)piperazin-1-yl)-6-fluoro-1-oxoisoindolin-2-yl)piperidine-2,6-dione B1035;

3-(6-fluoro-4-(4-((5-(hydroxymethyl)-1H-pyrrol-2-yl)methyl)piperazin-1-yl)-1-oxoisoindolin-2-yl)piperidine-2,6-dione B1036;
3-(6-fluoro-4-(4-((6-fluoropyridin-3-yl)methyl)piperazin-1-yl)-1-oxoisoindolin-2-yl)piperidine-2,6-dione B1037;
3-(6-fluoro-4-(4-((3-fluoropyridin-4-yl)methyl)piperazin-1-yl)-1-oxoisoindolin-2-yl)piperidine-2,6-dione B1038;
3-(6-fluoro-4-(4-((5-fluoropyridin-2-yl)methyl)piperazin-1-yl)-1-oxoisoindolin-2-yl)piperidine-2,6-dione B1039;
3-(6-fluoro-4-(4-((5-fluoropyridin-3-yl)methyl)piperazin-1-yl)-1-oxoisoindolin-2-yl)piperidine-2,6-dione B1040;
3-(6-fluoro-4-(4-((4-fluoropyridin-2-yl)methyl)piperazin-1-yl)-1-oxoisoindolin-2-yl)piperidine-2,6-dione B1041;
3-(6-fluoro-4-(4-((6-fluoropyridin-2-yl)methyl)piperazin-1-yl)-1-oxoisoindolin-2-yl)piperidine-2,6-dione B1042;
3-(4-(4-((2,5-dimethyl-1H-imidazol-4-yl)methyl)piperazin-1-yl)-6-fluoro-1-oxoisoindolin-2-yl)piperidine-2,6-dione B1043;
3-(6-fluoro-4-(4-(oxazol-2-ylmethyl)piperazin-1-yl)-1-oxoisoindolin-2-yl)-piperidine-2,6-dione B1044;
3-(4-(4-((1,4-dimethyl-1H-pyrazol-5-yl)methyl)piperazin-1-yl)-6-fluoro-1-oxoisoindolin-2-yl)piperidine-2,6-dione B1045;
3-(6-fluoro-4-(4-(4-fluorobenzyl)piperazin-1-yl)-1-oxoisoindolin-2-yl)piperidine-2,6-dione B1046;
3-(6-fluoro-4-(4-(3-fluorobenzyl)piperazin-1-yl)-1-oxoisoindolin-2-yl)piperidine-2,6-dione B1047;
3-(6-fluoro-4-(4-((2-hydroxypyridin-3-yl)methyl)piperazin-1-yl)-1-oxoisoindolin-2-yl)piperidine-2,6-dione B1048;
3-(6-fluoro-4-(4-((5-methylpyrazin-2-yl)methyl)piperazin-1-yl)-1-oxoisoindolin-2-yl)piperidine-2,6-dione B1049;
3-(6-fluoro-4-(4-((3-methylpyrazin-2-yl)methyl)piperazin-1-yl)-1-oxoisoindolin-2-yl)piperidine-2,6-dione B1050;
3-(6-fluoro-4-(4-((2-methylpyrimidin-4-yl)methyl)piperazin-1-yl)-1-oxoisoindolin-2-yl)piperidine-2,6-dione B1051;
3-(6-fluoro-4-(4-((2-methylpyrimidin-5-yl)methyl)piperazin-1-yl)-1-oxoisoindolin-2-yl)piperidine-2,6-dione B1052;
3-(4-(4-((2-aminopyridin-3-yl)methyl)piperazin-1-yl)-6-fluoro-1-oxoisoindolin-2-yl)piperidine-2,6-dione B1053;
3-(4-(4-((3-aminopyridin-4-yl)methyl)piperazin-1-yl)-6-fluoro-1-oxoisoindolin-2-yl)piperidine-2,6-dione B1054;
3-(4-(4-((1H-pyrazol-5-yl)methyl)piperazin-1-yl)-6-fluoro-1-oxoisoindolin-2-yl)-piperidine-2,6-dione B1055;
3-(6-fluoro-4-(4-(3-hydroxybenzyl)piperazin-1-yl)-1-oxoisoindolin-2-yl)-piperidine-2,6-dione B1056;
3-(6-fluoro-4-(4-(4-hydroxybenzyl)piperazin-1-yl)-1-oxoisoindolin-2-yl)-piperidine-2,6-dione B1057;
3-(6-fluoro-4-(4-((4-methylpyridin-2-yl)methyl)piperazin-1-yl)-1-oxoisoindolin-2-yl)piperidine-2,6-dione B1058;
3-(6-fluoro-4-(4-((3-methylpyridin-2-yl)methyl)piperazin-1-yl)-1-oxoisoindolin-2-yl)piperidine-2,6-dione B1059;
3-(6-fluoro-4-(4-((2-methylpyridin-3-yl)methyl)piperazin-1-yl)-1-oxoisoindolin-2-yl)piperidine-2,6-dione B1060;
3-(6-fluoro-4-(4-((2-methylpyridin-4-yl)methyl)piperazin-1-yl)-1-oxoisoindolin-2-yl)piperidine-2,6-dione B1061;
3-(6-fluoro-4-(4-((5-methylpyridin-2-yl)methyl)piperazin-1-yl)-1-oxoisoindolin-2-yl)piperidine-2,6-dione B1062;
3-(6-fluoro-4-(4-((6-methylpyridin-2-yl)methyl)piperazin-1-yl)-1-oxoisoindolin-2-yl)piperidine-2,6-dione B1063;
3-(6-fluoro-4-(4-((4-methylpyridin-3-yl)methyl)piperazin-1-yl)-1-oxoisoindolin-2-yl)piperidine-2,6-dione B1064;
3-(6-fluoro-4-(4-((5-methylpyridin-3-yl)methyl)piperazin-1-yl)-1-oxoisoindolin-2-yl)piperidine-2,6-dione B1065;
3-(4-(4-((1H-imidazol-5-yl)methyl)piperazin-1-yl)-6-fluoro-1-oxoisoindolin-2-yl)-piperidine-2,6-dione B1066;
3-(4-(4-(4-aminobenzyl)piperazin-1-yl)-6-fluoro-1-oxoisoindolin-2-yl)-piperidine-2,6-dione B1067;
3-(4-(4-(2-aminobenzyl)piperazin-1-yl)-6-fluoro-1-oxoisoindolin-2-yl)-piperidine-2,6-dione B1068;
3-(6-fluoro-4-(4-(4-methylbenzyl)piperazin-1-yl)-1-oxoisoindolin-2-yl)-piperidine-2,6-dione B1069;
3-(6-fluoro-4-(4-(2-methylbenzyl)piperazin-1-yl)-1-oxoisoindolin-2-yl)-piperidine-2,6-dione B1070;
4-(4-bromo-3-((4-(2-(2,6-dioxopiperidin-3-yl)-6-fluoro-1-oxoisoindolin-4-yl)-piperazin-1-yl)methyl)phenoxy)benzonitrile B1071;
3-(6-fluoro-1-oxo-4-(4-phenethylpiperazine-1-yl)isoindolin-2-yl)piperidine-2,6-dione B1072;
3-(4-(4-(3-bromo-4-(4-methylpiperazin-1-yl)benzyl)piperazin-1-yl)-6-fluoro-1-oxoisoindolin-2-yl)piperidine-2,6-dione B1073;
tert-butyl 4-(4-((4-(2-(2,6-dioxopiperidin-3-yl)-6-fluoro-1-oxoisoindolin-4-yl)-piperazin-1-yl)methyl)-1H-1,2,3-triazol-1-yl)piperidine-1-carboxylate B1074;
3-(4-(4-(3-bromo-4-morpholinobenzyl)piperazin-1-yl)-6-fluoro-1-oxoisoindolin-2-yl)piperidine-2,6-dione B1075;
3-(6-fluoro-1-oxo-4-(4-(4-(4-(trifluoromethyl)phenoxy)benzyl)piperazin-1-yl)-isoindolin-2-yl)piperidine-2,6-dione B1076;
3-(4-(4-(4-(benzyloxy)-3-ethoxybenzyl)piperazin-1-yl)-6-fluoro-1-oxoisoindolin-2-yl)piperidine-2,6-dione B1077;
tert-butyl 4-(1-(4-(2-(2,6-dioxopiperidin-3-yl)-6-fluoro-1-oxoisoindolin-4-yl)piperazin-1-yl)-2-methylpropan-2-yl)piperidine-1-carboxylate B1078;
benzyl (4-((4-(2-(2,6-dioxopiperidin-3-yl)-6-fluoro-1-oxoisoindolin-4-yl)-piperazin-1-yl)methyl)phenyl)carbamate B1079;
tert-butyl 6-((4-(2-(2,6-dioxopiperidin-3-yl)-6-fluoro-1-oxoisoindolin-4-yl)-piperazin-1-yl)methyl)indoline-1-carboxylate B1080;
tert-butyl (((1r,4r)-4-((4-(2-(2,6-dioxopiperidin-3-yl)-6-fluoro-1-oxoisoindolin-4-yl)piperazin-1-yl)methyl)cyclohexyl)methyl)carbamate B1081;
4-(4-((4-(2-(2,6-dioxopiperidin-3-yl)-6-fluoro-1-oxoisoindolin-4-yl)piperazin-1-yl)methyl)phenoxy)-3-fluorobenzonitrile B1082;
3-(6-fluoro-4-(4-(3-methylbenzyl)piperazin-1-yl)-1-oxoisoindolin-2-yl)-piperidine-2,6-dione B1083;
tert-butyl 4-((4-(2-(2,6-dioxopiperidin-3-yl)-6-fluoro-1-oxoisoindolin-4-yl)-piperazin-1-yl)methyl)-4-fluoropiperidine-1-carboxylate B1084;
tert-butyl 4-(2-(4-(2-(2,6-dioxopiperidin-3-yl)-6-fluoro-1-oxoisoindolin-4-yl)-piperazin-1-yl)ethyl)piperazine-1-carboxylate B1085;
3-(4-(4-((2-chloro-4-morpholinopyrimidin-5-yl)methyl)piperazin-1-yl)-6-fluoro-1-oxoisoindolin-2-yl)piperidine-2,6-dione B1086;
tert-butyl ((1r,4r)-4-((4-(2-(2,6-dioxopiperidin-3-yl)-6-fluoro-1-oxoisoindolin-4-yl)piperazin-1-yl)methyl)cyclohexyl)carbamate B1087;
tert-butyl 4-(2-(4-(2-(2,6-dioxopiperidin-3-yl)-6-fluoro-1-oxoisoindolin-4-yl)piperazin-1-yl)ethyl)piperidine-1-carboxylate B1088;
3-(4-(4-(2-(benzyloxy)-4-methylbenzyl)piperazin-1-yl)-6-fluoro-1-oxoisoindolin-2-yl)piperidine-2,6-dione B1089;
3-(4-(4-(4-(benzyloxy)-2-methylbenzyl)piperazin-1-yl)-6-fluoro-1-oxoisoindolin-2-yl)piperidine-2,6-dione B1090;
3-(4-(4-(3-chloro-4-morpholinobenzyl)piperazin-1-yl)-6-fluoro-1-oxoisoindolin-2-yl)piperidine-2,6-dione B1091;
4-(4-((4-(2-(2,6-dioxopiperidin-3-yl)-6-fluoro-1-oxoisoindolin-4-yl)piperazin-1-yl)methyl)phenoxy)benzonitrile B1092;

4-(3-((4-(2-(2,6-dioxopiperidin-3-yl)-6-fluoro-1-oxoisoindolin-4-yl)piperazin-1-yl)methyl)phenoxy)benzonitrile B1093;

2-((4-(2-(2,6-dioxopiperidin-3-yl)-6-fluoro-1-oxoisoindolin-4-yl)piperazin-1-yl)methyl)-1H-pyrrole-3-carbonitrile B1094;

3-(4-(4-(3-(cyclohexylmethoxy)benzyl)piperazin-1-yl)-6-fluoro-1-oxoisoindolin-2-yl)piperidine-2,6-dione B1095;

3-(4-(4-(3-(3-bromophenyl)propyl)piperazin-1-yl)-6-fluoro-1-oxoisoindolin-2-yl)-piperidine-2,6-dione B1096;

3-(4-(4-(4-(benzyloxy)benzyl)piperazin-1-yl)-6-fluoro-1-oxoisoindolin-2-yl)-piperidine-2,6-dione B1097;

3-(4-(4-(3-(benzyloxy)benzyl)piperazin-1-yl)-6-fluoro-1-oxoisoindolin-2-yl)-piperidine-2,6-dione B1098;

5-((4-(2-(2,6-dioxopiperidin-3-yl)-6-fluoro-1-oxoisoindolin-4-yl)piperazin-1-yl)-methyl)-2-(4-methyl-1H-imidazol-1-yl)benzonitrile B1099;

3-(4-(4-(3-chloro-4-(trifluoromethyl)benzyl)piperazin-1-yl)-6-fluoro-1-oxoisoindolin-2-yl)piperidine-2,6-dione B1100;

3-(4-(4-(2-chloro-4-(trifluoromethyl)benzyl)piperazin-1-yl)-6-fluoro-1-oxoisoindolin-2-yl)piperidine-2,6-dione B1101;

3-(4-(4-(4-chloro-2-(trifluoromethyl)benzyl)piperazin-1-yl)-6-fluoro-1-oxoisoindolin-2-yl)piperidine-2,6-dione B1102;

3-(4-(4-(5-chloro-2-(trifluoromethyl)benzyl)piperazin-1-yl)-6-fluoro-1-oxoisoindolin-2-yl)piperidine-2,6-dione B1103;

3-(4-(4-(2-chloro-5-(trifluoromethyl)benzyl)piperazin-1-yl)-6-fluoro-1-oxoisoindolin-2-yl)piperidine-2,6-dione B1104;

3-(6-fluoro-1-oxo-4-(4-((tetrahydro-2H-pyran-4-yl)methyl)piperazin-1-yl)-isoindolin-2-yl)piperidine-2,6-dione B1105;

3-(4-(4-((1-benzylpiperidin-4-yl)methyl)piperazin-1-yl)-6-fluoro-1-oxoisoindolin-2-yl)piperidine-2,6-dione B1106;

2-(3-(4-(2-(2,6-dioxopiperidin-3-yl)-6-fluoro-1-oxoisoindolin-4-yl)piperazin-1-yl)propyl)isoindoline-1,3-dione B1107;

3-(6-fluoro-1-oxo-4-(4-(3-(3-(trifluoromethyl)phenyl)propyl)piperazin-1-yl)-isoindolin-2-yl)piperidine-2,6-dione B1108;

3-(4-(4-((6-(dimethylamino)naphthalen-2-yl)methyl)piperazin-1-yl)-6-fluoro-1-oxoisoindolin-2-yl)piperidine-2,6-dione B1109;

N-(2-((4-(2-(2,6-dioxopiperidin-3-yl)-6-fluoro-1-oxoisoindolin-4-yl)piperazin-1-yl)methyl)phenyl)methanesulfonamide B1110;

N-(4-((4-(2-(2,6-dioxopiperidin-3-yl)-6-fluoro-1-oxoisoindolin-4-yl)piperazin-1-yl)methyl)phenyl)methanesulfonamide B111;

N-(3-((4-(2-(2,6-dioxopiperidin-3-yl)-6-fluoro-1-oxoisoindolin-4-yl)piperazin-1-yl)methyl)phenyl)methanesulfonamide B1112;

3-(6-fluoro-1-oxo-4-(4-(2-(pyridin-2-yloxy)benzyl)piperazin-1-yl)isoindolin-2-yl)piperidine-2,6-dione B1113;

3-(4-(4-(4-bromophenethyl)piperazin-1-yl)-6-fluoro-1-oxoisoindolin-2-yl)-piperidine-2,6-dione B1114;

3-(6-fluoro-4-(4-((2-morpholinothiazol-5-yl)methyl)piperazin-1-yl)-1-oxoisoindolin-2-yl)piperidine-2,6-dione B1115;

3-(6-fluoro-1-oxo-4-(4-(thiazol-2-ylmethyl)piperazin-1-yl)isoindolin-2-yl)-piperidine-2,6-dione B1116;

3-(4-(4-(4-(ethylsulfonyl)benzyl)piperazin-1-yl)-6-fluoro-1-oxoisoindolin-2-yl)-piperidine-2,6-dione B1117;

3-(6-fluoro-4-(4-((4'-methyl-[2,2'-bipyridin]-4-yl)methyl)piperazin-1-yl)-1-oxoisoindolin-2-yl)piperidine-2,6-dione B1118;

3-(6-fluoro-1-oxo-4-(4-(4-phenoxybenzyl)piperazin-1-yl)isoindolin-2-yl)-piperidine-2,6-dione B1119;

3-(6-fluoro-1-oxo-4-(4-(3-phenoxybenzyl)piperazin-1-yl)isoindolin-2-yl)-piperidine-2,6-dione B1120;

3-(6-fluoro-1-oxo-4-(4-((6-(p-tolyl)pyridin-3-yl)methyl)piperazin-1-yl)-isoindolin-2-yl)piperidine-2,6-dione B1121;

4-((4-(2-(2,6-dioxopiperidin-3-yl)-6-fluoro-1-oxoisoindolin-4-yl)piperazin-1-yl)-methyl)-N-isopropylbenzamide B1122;

3-(6-fluoro-4-(4-(2-morpholinobenzyl)piperazin-1-yl)-1-oxoisoindolin-2-yl)-piperidine-2,6-dione B1123;

3-(6-fluoro-4-(4-(3-morpholinobenzyl)piperazin-1-yl)-1-oxoisoindolin-2-yl)-piperidine-2,6-dione B1124;

3-(6-fluoro-4-(4-(4-morpholinobenzyl)piperazin-1-yl)-1-oxoisoindolin-2-yl)-piperidine-2,6-dione B1125;

3-(6-fluoro-1-oxo-4-(4-(3-(quinolin-6-yl)propyl)piperazin-1-yl)isoindolin-2-yl)-piperidine-2,6-dione B1126;

3-(6-fluoro-1-oxo-4-(4-(thiazol-5-ylmethyl)piperazin-1-yl)isoindolin-2-yl)-piperidine-2,6-dione B1127;

3-(4-(4-((1H-pyrrol-3-yl)methyl)piperazin-1-yl)-6-fluoro-1-oxoisoindolin-2-yl)-piperidine-2,6-dione B1128;

3-(6-fluoro-4-(4-((6-(methylsulfonyl)pyridin-2-yl)methyl)piperazin-1-yl)-1-oxoisoindolin-2-yl)piperidine-2,6-dione B1129;

3-(6-fluoro-1-oxo-4-(4-(3-(pyridin-4-yl)benzyl)piperazin-1-yl)isoindolin-2-yl)-piperidine-2,6-dione B1130;

3-(4-(4-([1,1'-biphenyl]-4-ylmethyl)piperazin-1-yl)-6-fluoro-1-oxoisoindolin-2-yl)piperidine-2,6-dione B1131;

3-(6-fluoro-4-(4-((6-fluorochroman-8-yl)methyl)piperazin-1-yl)-1-oxoisoindolin-2-yl)piperidine-2,6-dione B1132;

3-(6-fluoro-1-oxo-4-(4-((6-(pyrrolidin-1-yl)pyridin-3-yl)methyl)piperazin-1-yl)-isoindolin-2-yl)piperidine-2,6-dione B1133;

3-(6-fluoro-1-oxo-4-(4-(3-(pyrrolidin-1-yl)benzyl)piperazin-1-yl)isoindolin-2-yl)piperidine-2,6-dione B1134;

3-(6-fluoro-1-oxo-4-(4-(4-(pyrrolidin-1-yl)benzyl)piperazin-1-yl)isoindolin-2-yl)piperidine-2,6-dione B1135;

3-(4-(4-(3-(1H-1,2,4-triazol-1-yl)benzyl)piperazin-1-yl)-6-fluoro-1-oxoisoindolin-2-yl)piperidine-2,6-dione B1136;

3-(4-(4-(2-(1H-1,2,4-triazol-1-yl)benzyl)piperazin-1-yl)-6-fluoro-1-oxoisoindolin-2-yl)piperidine-2,6-dione B1137;

3-(4-(4-(4-(1H-1,2,4-triazol-1-yl)benzyl)piperazin-1-yl)-6-fluoro-1-oxoisoindolin-2-yl)piperidine-2,6-dione B1138;

3-(6-fluoro-1-oxo-4-(4-(thiazol-4-ylmethyl)piperazin-1-yl)isoindolin-2-yl)-piperidine-2,6-dione B1139;

3-(6-fluoro-1-oxo-4-(4-((1-phenyl-1H-pyrazol-3-yl)methyl)piperazin-1-yl)-isoindolin-2-yl)piperidine-2,6-dione B1140;

3-(6-fluoro-1-oxo-4-(4-((5-phenyl-1H-imidazol-2-yl)methyl)piperazin-1-yl)-isoindolin-2-yl)piperidine-2,6-dione B1141;

3-(4-(4-(3-(1H-imidazol-1-yl)benzyl)piperazin-1-yl)-6-fluoro-1-oxoisoindolin-2-yl)piperidine-2,6-dione B1142;

3-(6-fluoro-1-oxo-4-(4-((2-phenyl-1H-imidazol-5-yl)methyl)piperazin-1-yl)-isoindolin-2-yl)piperidine-2,6-dione B1143;

3-(4-(4-(4-(1H-imidazol-1-yl)benzyl)piperazin-1-yl)-6-fluoro-1-oxoisoindolin-2-yl)piperidine-2,6-dione B1144;

3-(4-(4-(4-(1H-pyrazol-1-yl)benzyl)piperazin-1-yl)-6-fluoro-1-oxoisoindolin-2-yl)piperidine-2,6-dione B1145;

2-((4-(2-(2,6-dioxopiperidin-3-yl)-6-fluoro-1-oxoisoindolin-4-yl)piperazin-1-yl)-methyl)-1H-indole-6-carbonitrile B1146;

3-((4-(2-(2,6-dioxopiperidin-3-yl)-6-fluoro-1-oxoisoindolin-4-yl)piperazin-1-yl)-methyl)-1H-indole-6-carbonitrile B1147;
3-(4-(4-((2,3-dihydro-[1,4]dioxino[2,3-b]pyridin-6-yl)methyl)piperazin-1-yl)-6-fluoro-1-oxoisoindolin-2-yl)piperidine-2,6-dione B1148;
3-(4-(4-((adamantan-1-yl)methyl)piperazin-1-yl)-6-fluoro-1-oxoisoindolin-2-yl)-piperidine-2,6-dione B1149;
3-(6-fluoro-1-oxo-4-(4-(thiophen-2-ylmethyl)piperazin-1-yl)isoindolin-2-yl)-piperidine-2,6-dione B1150;
3-(4-(4-(3-(benzyloxy)propyl)piperazin-1-yl)-6-fluoro-1-oxoisoindolin-2-yl)-piperidine-2,6-dione B1151;
3-(6-fluoro-4-(4-(3-(2-methoxyphenyl)propyl)piperazin-1-yl)-1-oxoisoindolin-2-yl)piperidine-2,6-dione B1152;
3-(4-(4-((2,3-dihydrobenzo[b][1,4]dioxin-6-yl)methyl)piperazin-1-yl)-6-fluoro-1-oxoisoindolin-2-yl)piperidine-2,6-dione B1153;
3-(6-fluoro-4-(4-((5-fluoro-1H-benzo[d]imidazol-2-yl)methyl)piperazin-1-yl)-1-oxoisoindolin-2-yl)piperidine-2,6-dione B1154;
3-(6-fluoro-4-(4-((4-fluorobenzofuran-7-yl)methyl)piperazin-1-yl)-1-oxoisoindolin-2-yl)piperidine-2,6-dione B1155;
3-(4-(4-(4-(dimethylamino)-3-methylbenzyl)piperazin-1-yl)-6-fluoro-1-oxoisoindolin-2-yl)piperidine-2,6-dione B1156;
3-(4-(4-((2-(tert-butyl)pyridin-4-yl)methyl)piperazin-1-yl)-6-fluoro-1-oxoisoindolin-2-yl)piperidine-2,6-dione B1157;
3-(4-(4-(4-((dimethylamino)methyl)benzyl)piperazin-1-yl)-6-fluoro-1-oxoisoindolin-2-yl)piperidine-2,6-dione B1158;
3-(6-fluoro-1-oxo-4-(4-(thieno[3,2-c]pyridin-2-ylmethyl)piperazin-1-yl)-isoindolin-2-yl)piperidine-2,6-dione B1159;
3-(4-(4-(benzo[d]thiazol-4-ylmethyl)piperazin-1-yl)-6-fluoro-1-oxoisoindolin-2-yl)piperidine-2,6-dione B1160;
3-(6-fluoro-1-oxo-4-(4-(thiophen-3-ylmethyl)piperazin-1-yl)isoindolin-2-yl)-piperidine-2,6-dione B1161;
3-(6-fluoro-1-oxo-4-(4-(thieno[2,3-b]pyridin-2-ylmethyl)piperazin-1-yl)-isoindolin-2-yl)piperidine-2,6-dione B1162;
3-(4-(4-((3,4-dihydro-2H-pyrano[2,3-c]pyridin-6-yl)methyl)piperazin-1-yl)-6-fluoro-1-oxoisoindolin-2-yl)piperidine-2,6-dione B1163;
3-(6-fluoro-4-(4-(3-methyl-3-phenylbutyl)piperazin-1-yl)-1-oxoisoindolin-2-yl)piperidine-2,6-dione B1164;
3-(4-(4-(benzo[b]thiophen-3-ylmethyl)piperazin-1-yl)-6-fluoro-1-oxoisoindolin-2-yl)piperidine-2,6-dione B1165;
3-(4-(4-(benzo[b]thiophen-2-ylmethyl)piperazin-1-yl)-6-fluoro-1-oxoisoindolin-2-yl)piperidine-2,6-dione B1166;
3-(4-(4-(chroman-6-ylmethyl)piperazin-1-yl)-6-fluoro-1-oxoisoindolin-2-yl)-piperidine-2,6-dione B1167;
3-(6-fluoro-4-(4-((1-methyl-1H-imidazo[4,5-b]pyridin-2-yl)methyl)piperazin-1-yl)-1-oxoisoindolin-2-yl)piperidine-2,6-dione B1168;
4-((4-(2-(2,6-dioxopiperidin-3-yl)-6-fluoro-1-oxoisoindolin-4-yl)piperazin-1-yl)-methyl)-2-methoxybenzonitrile B1169;
4-((4-(2-(2,6-dioxopiperidin-3-yl)-6-fluoro-1-oxoisoindolin-4-yl)piperazin-1-yl)-methyl)-3-methoxybenzonitrile B1170;
2-((4-(2-(2,6-dioxopiperidin-3-yl)-6-fluoro-1-oxoisoindolin-4-yl)piperazin-1-yl)-methyl)-5-methoxybenzonitrile B1171;
3-(6-fluoro-4-(4-((2-methyl-2H-tetrazol-5-yl)methyl)piperazin-1-yl)-1-oxoisoindolin-2-yl)piperidine-2,6-dione B1172;
3-(6-fluoro-4-(4-((2-methylbenzo[d]oxazol-6-yl)methyl)piperazin-1-yl)-1-oxoisoindolin-2-yl)piperidine-2,6-dione B1173;
3-(6-fluoro-1-oxo-4-(4-((3-oxoisoindolin-5-yl)methyl)piperazin-1-yl)isoindolin-2-yl)piperidine-2,6-dione B1174;
3-(6-fluoro-1-oxo-4-(4-((1-oxoisoindolin-5-yl)methyl)piperazin-1-yl)isoindolin-2-yl)piperidine-2,6-dione B1175;
3-(6-fluoro-1-oxo-4-(4-((5,6,7,8-tetrahydronaphthalen-1-yl)methyl)piperazin-1-yl)isoindolin-2-yl)piperidine-2,6-dione B1176;
3-(6-fluoro-4-(4-((3-methylimidazo[1,2-a]pyridin-2-yl)methyl)piperazin-1-yl)-1-oxoisoindolin-2-yl)piperidine-2,6-dione B1177;
3-(6-fluoro-4-(4-((1-methyl-1H-indazol-6-yl)methyl)piperazin-1-yl)-1-oxoisoindolin-2-yl)piperidine-2,6-dione B1178;
3-(6-fluoro-4-(4-((2-methyl-2H-indazol-5-yl)methyl)piperazin-1-yl)-1-oxoisoindolin-2-yl)piperidine-2,6-dione B1179;
3-(6-fluoro-4-(4-((6-methylimidazo[1,2-a]pyridin-2-yl)methyl)piperazin-1-yl)-1-oxoisoindolin-2-yl)piperidine-2,6-dione B1180;
3-(6-fluoro-4-(4-((5-methylimidazo[1,2-a]pyridin-3-yl)methyl)piperazin-1-yl)-1-oxoisoindolin-2-yl)piperidine-2,6-dione B1181;
3-(6-fluoro-4-(4-((7-methylimidazo[1,2-a]pyridin-3-yl)methyl)piperazin-1-yl)-1-oxoisoindolin-2-yl)piperidine-2,6-dione B1182;
3-(6-fluoro-4-(4-((5-methyl-4H-1,2,4-triazol-3-yl)methyl)piperazin-1-yl)-1-oxoisoindolin-2-yl)piperidine-2,6-dione B1183;
3-(6-fluoro-4-(4-((1-methyl-1H-indazol-4-yl)methyl)piperazin-1-yl)-1-oxoisoindolin-2-yl)piperidine-2,6-dione B1184;
3-(6-fluoro-4-(4-((5-methyl-1H-pyrrolo[2,3-b]pyridin-3-yl)methyl)piperazin-1-yl)-1-oxoisoindolin-2-yl)piperidine-2,6-dione B1185;
3-(6-fluoro-4-(4-((1-methyl-1H-benzo[d]imidazol-2-yl)methyl)piperazin-1-yl)-1-oxoisoindolin-2-yl)piperidine-2,6-dione B1186;
3-(6-fluoro-4-(4-((2-methylimidazo[1,2-a]pyridin-3-yl)methyl)piperazin-1-yl)-1-oxoisoindolin-2-yl)piperidine-2,6-dione B1187;
3-(6-fluoro-4-(4-((2-methyl-2H-indazol-3-yl)methyl)piperazin-1-yl)-1-oxoisoindolin-2-yl)piperidine-2,6-dione B1188;
3-(6-fluoro-4-(4-((7-methyl-1H-indol-3-yl)methyl)piperazin-1-yl)-1-oxoisoindolin-2-yl)piperidine-2,6-dione B1189;
3-(6-fluoro-4-(4-((1-methyl-1H-indol-5-yl)methyl)piperazin-1-yl)-1-oxoisoindolin-2-yl)piperidine-2,6-dione B1190;
3-(6-fluoro-4-(4-((2-methyl-1H-indol-4-yl)methyl)piperazin-1-yl)-1-oxoisoindolin-2-yl)piperidine-2,6-dione B1191;
3-(6-fluoro-4-(4-((1-methyl-1H-indol-6-yl)methyl)piperazin-1-yl)-1-oxoisoindolin-2-yl)piperidine-2,6-dione B1192;
3-(6-fluoro-4-(4-((4-methyl-1H-indol-3-yl)methyl)piperazin-1-yl)-1-oxoisoindolin-2-yl)piperidine-2,6-dione B1193;
3-(6-fluoro-4-(4-((4-methyloxazol-5-yl)methyl)piperazin-1-yl)-1-oxoisoindolin-2-yl)piperidine-2,6-dione B1194;

3-(6-fluoro-4-(4-((3-methyl-1H-indol-2-yl)methyl)piperazin-1-yl)-1-oxoisoindolin-2-yl)piperidine-2,6-dione B1195;
3-(6-fluoro-4-(4-((6-methyl-1H-indol-3-yl)methyl)piperazin-1-yl)-1-oxoisoindolin-2-yl)piperidine-2,6-dione B1196;
tert-butyl (2-(4-(2-(2,6-dioxopiperidin-3-yl)-6-fluoro-1-oxoisoindolin-4-yl)-piperazin-1-yl)ethyl)carbamate B1197;
3-(6-fluoro-1-oxo-4-(4-(quinoxalin-6-ylmethyl)piperazin-1-yl)isoindolin-2-yl)-piperidine-2,6-dione B1198;
3-(4-(4-((1,8-naphthyridin-2-yl)methyl)piperazin-1-yl)-6-fluoro-1-oxoisoindolin-2-yl)piperidine-2,6-dione B1199;
3-(6-fluoro-1-oxo-4-(4-(quinoxalin-2-ylmethyl)piperazin-1-yl)isoindolin-2-yl)-piperidine-2,6-dione B1200;
3-(6-fluoro-1-oxo-4-(4-(quinoxalin-5-ylmethyl)piperazin-1-yl)isoindolin-2-yl)-piperidine-2,6-dione B1201;
3-(6-fluoro-1-oxo-4-(4-(quinolin-8-ylmethyl)piperazin-1-yl)isoindolin-2-yl)-piperidine-2,6-dione B1202;
3-(6-fluoro-4-(4-(isoquinolin-4-ylmethyl)piperazin-1-yl)-1-oxoisoindolin-2-yl)-piperidine-2,6-dione B1203;
3-(6-fluoro-4-(4-(isoquinolin-3-ylmethyl)piperazin-1-yl)-1-oxoisoindolin-2-yl)-piperidine-2,6-dione B1204;
3-(6-fluoro-4-(4-((2-methyloxazol-4-yl)methyl)piperazin-1-yl)-1-oxoisoindolin-2-yl)piperidine-2,6-dione B1205;
3-(6-fluoro-4-(4-(isoquinolin-8-ylmethyl)piperazin-1-yl)-1-oxoisoindolin-2-yl)-piperidine-2,6-dione B1206;
3-(6-fluoro-4-(4-(isoquinolin-5-ylmethyl)piperazin-1-yl)-1-oxoisoindolin-2-yl)-piperidine-2,6-dione B1207;
3-(6-fluoro-1-oxo-4-(4-(quinolin-4-ylmethyl)piperazin-1-yl)isoindolin-2-yl)-piperidine-2,6-dione B1208;
3-(6-fluoro-1-oxo-4-(4-(quinolin-6-ylmethyl)piperazin-1-yl)isoindolin-2-yl)-piperidine-2,6-dione B1209;
3-(6-fluoro-4-(4-(naphthalen-2-ylmethyl)piperazin-1-yl)-1-oxoisoindolin-2-yl)-piperidine-2,6-dione B1210;
3-(4-(4-(2-amino-6-chlorobenzyl)piperazin-1-yl)-6-fluoro-1-oxoisoindolin-2-yl)-piperidine-2,6-dione B1211;
3-(4-(4-(2-amino-4-chlorobenzyl)piperazin-1-yl)-6-fluoro-1-oxoisoindolin-2-yl)-piperidine-2,6-dione B1212;
3-(4-(4-(2-amino-3-chlorobenzyl)piperazin-1-yl)-6-fluoro-1-oxoisoindolin-2-yl)-piperidine-2,6-dione B1213;
3-(4-(4-((5-(dimethylamino)thiophen-2-yl)methyl)piperazin-1-yl)-6-fluoro-1-oxoisoindolin-2-yl)piperidine-2,6-dione B1214;
3-(4-(4-(4-chlorophenethyl)piperazin-1-yl)-6-fluoro-1-oxoisoindolin-2-yl)-piperidine-2,6-dione B1215;
3-(6-fluoro-4-(4-((2-methyloxazol-5-yl)methyl)piperazin-1-yl)-1-oxoisoindolin-2-yl)piperidine-2,6-dione B1216;
3-(6-fluoro-4-(4-((4-hydroxybicyclo[2.2.2]octan-1-yl)methyl)piperazin-1-yl)-1-oxoisoindolin-2-yl)piperidine-2,6-dione B1217;
3-(6-fluoro-4-(4-((2-(methylthio)pyrimidin-4-yl)methyl)piperazin-1-yl)-1-oxoisoindolin-2-yl)piperidine-2,6-dione B1218;
3-(4-(4-((2-cyclopropylthiazol-5-yl)methyl)piperazin-1-yl)-6-fluoro-1-oxoisoindolin-2-yl)piperidine-2,6-dione B1219;
3-(4-(4-((1-(tert-butyl)-1H-1,2,3-triazol-4-yl)methyl)piperazin-1-yl)-6-fluoro-1-oxoisoindolin-2-yl)piperidine-2,6-dione B1220;
3-(6-fluoro-4-(4-((1-isobutyl-1H-pyrazol-4-yl)methyl)piperazin-1-yl)-1-oxoisoindolin-2-yl)piperidine-2,6-dione B1221;
3-(4-(4-((5,6-dihydro-8H-imidazo[2,1-c][1,4]oxazin-3-yl)methyl)piperazin-1-yl)-6-fluoro-1-oxoisoindolin-2-yl)piperidine-2,6-dione B1222;
3-(4-(4-((5,6-dihydro-8H-imidazo[2,1-c][1,4]oxazin-2-yl)methyl)piperazin-1-yl)-6-fluoro-1-oxoisoindolin-2-yl)piperidine-2,6-dione B1223;
3-(4-(4-((5-(tert-butyl)-1H-pyrrol-2-yl)methyl)piperazin-1-yl)-6-fluoro-1-oxoisoindolin-2-yl)piperidine-2,6-dione B1224;
3-(4-(4-((2-(dimethylamino)pyrimidin-5-yl)methyl)piperazin-1-yl)-6-fluoro-1-oxoisoindolin-2-yl)piperidine-2,6-dione B1225;
3-(6-fluoro-4-(4-(4-methoxy-3-methylbenzyl)piperazin-1-yl)-1-oxoisoindolin-2-yl)piperidine-2,6-dione B1226;
3-(6-fluoro-4-(4-((1-methyl-1H-imidazol-5-yl)methyl)piperazin-1-yl)-1-oxoisoindolin-2-yl)piperidine-2,6-dione B1227;
3-(6-fluoro-4-(4-(2-methoxy-3-methylbenzyl)piperazin-1-yl)-1-oxoisoindolin-2-yl)piperidine-2,6-dione B1228;
3-(6-fluoro-4-(4-(3-methoxy-2-methylbenzyl)piperazin-1-yl)-1-oxoisoindolin-2-yl)piperidine-2,6-dione B1229;
3-(6-fluoro-4-(4-(2-methoxy-6-methylbenzyl)piperazin-1-yl)-1-oxoisoindolin-2-yl)piperidine-2,6-dione B1230;
3-(6-fluoro-4-(4-(3-methoxy-5-methylbenzyl)piperazin-1-yl)-1-oxoisoindolin-2-yl)piperidine-2,6-dione B1231;
3-(6-fluoro-4-(4-(4-methoxyphenethyl)piperazin-1-yl)-1-oxoisoindolin-2-yl)-piperidine-2,6-dione B1232;
3-(6-fluoro-4-(4-(3-methoxyphenethyl)piperazin-1-yl)-1-oxoisoindolin-2-yl)-piperidine-2,6-dione B1233;
3-(6-fluoro-4-(4-(4-methoxy-2-methylbenzyl)piperazin-1-yl)-1-oxoisoindolin-2-yl)piperidine-2,6-dione B1234;
3-(6-fluoro-4-(4-(4-hydroxy-3,5-dimethylbenzyl)piperazin-1-yl)-1-oxoisoindolin-2-yl)piperidine-2,6-dione B1235;
3-(4-(4-(4-ethoxybenzyl)piperazin-1-yl)-6-fluoro-1-oxoisoindolin-2-yl)-piperidine-2,6-dione B1236;
3-(6-fluoro-4-(4-(3-methoxy-4-methylbenzyl)piperazin-1-yl)-1-oxoisoindolin-2-yl)piperidine-2,6-dione B1237;
3-(6-fluoro-4-(4-((1-methyl-1H-pyrazol-5-yl)methyl)piperazin-1-yl)-1-oxoisoindolin-2-yl)piperidine-2,6-dione B1238;
3-(4-(4-((1H-pyrrol-2-yl)methyl)piperazin-1-yl)-6-fluoro-1-oxoisoindolin-2-yl)piperidine-2,6-dione B1239;
3-(6-fluoro-4-(4-(2-methoxy-4-methylbenzyl)piperazin-1-yl)-1-oxoisoindolin-2-yl)piperidine-2,6-dione B1240;
3-(4-(4-(2-(benzyloxy)ethyl)piperazin-1-yl)-6-fluoro-1-oxoisoindolin-2-yl)-piperidine-2,6-dione B1241;
3-(4-(4-(benzo[d][1,3]dioxol-4-ylmethyl)piperazin-1-yl)-6-fluoro-1-oxoisoindolin-2-yl)piperidine-2,6-dione B1242;
3-(4-(4-(2-(dimethylamino)benzyl)piperazin-1-yl)-6-fluoro-1-oxoisoindolin-2-yl)piperidine-2,6-dione B1243;
3-(6-fluoro-4-(4-((5-isopropylpyridin-3-yl)methyl)piperazin-1-yl)-1-oxoisoindolin-2-yl)piperidine-2,6-dione B1244;
3-(4-(4-(4-(ethylamino)benzyl)piperazin-1-yl)-6-fluoro-1-oxoisoindolin-2-yl)-piperidine-2,6-dione B1245;
3-(4-(4-(3-(dimethylamino)benzyl)piperazin-1-yl)-6-fluoro-1-oxoisoindolin-2-yl)piperidine-2,6-dione B1246;
3-((4-(2-(2,6-dioxopiperidin-3-yl)-6-fluoro-1-oxoisoindolin-4-yl)piperazin-1-yl)-methyl)benzamide B1247;
2-((4-(2-(2,6-dioxopiperidin-3-yl)-6-fluoro-1-oxoisoindolin-4-yl)piperazin-1-yl)-methyl)-4-fluorobenzonitrile B1248;
2-((4-(2-(2,6-dioxopiperidin-3-yl)-6-fluoro-1-oxoisoindolin-4-yl)piperazin-1-yl)-methyl)-5-fluorobenzonitrile B1249;
3-(6-fluoro-4-(4-((1-methyl-1H-pyrazol-3-yl)methyl)piperazin-1-yl)-1-oxoisoindolin-2-yl)piperidine-2,6-dione B1250;

4-((4-(2-(2,6-dioxopiperidin-3-yl)-6-fluoro-1-oxoisoindolin-4-yl)piperazin-1-yl)-methyl)-3-fluorobenzonitrile B1251;

3-((4-(2-(2,6-dioxopiperidin-3-yl)-6-fluoro-1-oxoisoindolin-4-yl)piperazin-1-yl)-methyl)-5-fluorobenzonitrile B1252;

4-((4-(2-(2,6-dioxopiperidin-3-yl)-6-fluoro-1-oxoisoindolin-4-yl)piperazin-1-yl)-methyl)-2-fluorobenzonitrile B1253;

5-((4-(2-(2,6-dioxopiperidin-3-yl)-6-fluoro-1-oxoisoindolin-4-yl)piperazin-1-yl)-methyl)-2-fluorobenzonitrile B1254;

3-(6-fluoro-1-oxo-4-(4-(2,4,6-trimethylbenzyl)piperazin-1-yl)isoindolin-2-yl)-piperidine-2,6-dione B1255;

3-(6-fluoro-4-(4-(4-isopropylbenzyl)piperazin-1-yl)-1-oxoisoindolin-2-yl)-piperidine-2,6-dione B1256;

3-(6-fluoro-1-oxo-4-(4-(4-phenylbutyl)piperazin-1-yl)isoindolin-2-yl)piperidine-2,6-dione B1257;

3-(4-(4-((4,4-difluorocyclohexyl)methyl)piperazin-1-yl)-6-fluoro-1-oxoisoindolin-2-yl)piperidine-2,6-dione B1258;

3-(4-(4-(2-ethynyl-4-fluorobenzyl)piperazin-1-yl)-6-fluoro-1-oxoisoindolin-2-yl)piperidine-2,6-dione B1259;

3-(4-(4-([1,2,4]triazolo[1,5-a]pyridin-7-ylmethyl)piperazin-1-yl)-6-fluoro-1-oxoisoindolin-2-yl)piperidine-2,6-dione B1260;

3-(6-fluoro-4-(4-((1-methyl-1H-imidazol-4-yl)methyl)piperazin-1-yl)-1-oxoisoindolin-2-yl)piperidine-2,6-dione B1261;

3-(6-fluoro-4-(4-(imidazo[1,2-a]pyrimidin-3-ylmethyl)piperazin-1-yl)-1-oxoisoindolin-2-yl)piperidine-2,6-dione B1262;

6-amino-5-((4-(2-(2,6-dioxopiperidin-3-yl)-6-fluoro-1-oxoisoindolin-4-yl)-piperazin-1-yl)methyl)nicotinonitrile B1263;

3-(6-fluoro-4-(4-(imidazo[1,2-a]pyrimidin-7-ylmethyl)piperazin-1-yl)-1-oxoisoindolin-2-yl)piperidine-2,6-dione B1264;

3-(4-(4-((4H-pyrrolo[2,3-b]pyrazin-7-yl)methyl)piperazin-1-yl)-6-fluoro-1-oxoisoindolin-2-yl)piperidine-2,6-dione B1265;

4-((4-(2-(2,6-dioxopiperidin-3-yl)-6-fluoro-1-oxoisoindolin-4-yl)piperazin-1-yl)-methyl)-3-hydroxybenzonitrile B1266;

5-((4-(2-(2,6-dioxopiperidin-3-yl)-6-fluoro-1-oxoisoindolin-4-yl)piperazin-1-yl)-methyl)-2-hydroxybenzonitrile B1267;

3-(6-fluoro-4-(4-(furo[2,3-c]pyridin-5-ylmethyl)piperazin-1-yl)-1-oxoisoindolin-2-yl)piperidine-2,6-dione B1268;

3-(4-(4-(benzo[d]oxazol-5-ylmethyl)piperazin-1-yl)-6-fluoro-1-oxoisoindolin-2-yl)piperidine-2,6-dione B1269;

3-(4-(4-(benzo[d]oxazol-6-ylmethyl)piperazin-1-yl)-6-fluoro-1-oxoisoindolin-2-yl)piperidine-2,6-dione B1270;

3-(4-(4-((5-chlorothiophen-2-yl)methyl)piperazin-1-yl)-6-fluoro-1-oxoisoindolin-2-yl)piperidine-2,6-dione B1271;

3-(6-fluoro-4-(4-((1-methyl-1H-imidazol-2-yl)methyl)piperazin-1-yl)-1-oxoisoindolin-2-yl)piperidine-2,6-dione B1272;

3-(4-(4-((2-chlorothiophen-3-yl)methyl)piperazin-1-yl)-6-fluoro-1-oxoisoindolin-2-yl)piperidine-2,6-dione B1273;

3-(4-(4-(4-cyclopropylbenzyl)piperazin-1-yl)-6-fluoro-1-oxoisoindolin-2-yl)-piperidine-2,6-dione B1274;

3-(4-(4-(2-cyclopropylbenzyl)piperazin-1-yl)-6-fluoro-1-oxoisoindolin-2-yl)-piperidine-2,6-dione B1275;

3-(6-fluoro-1-oxo-4-(4-(pyrazolo[1,5-a]pyridin-7-ylmethyl)piperazin-1-yl)-isoindolin-2-yl)piperidine-2,6-dione B1276;

3-(4-(4-((1H-pyrrolo[2,3-c]pyridin-3-yl)methyl)piperazin-1-yl)-6-fluoro-1-oxoisoindolin-2-yl)piperidine-2,6-dione B1277;

3-(6-fluoro-4-(4-(imidazo[1,2-a]pyridin-5-ylmethyl)piperazin-1-yl)-1-oxoisoindolin-2-yl)piperidine-2,6-dione B1278;

3-(6-fluoro-1-oxo-4-(4-(pyrazolo[1,5-a]pyridin-3-ylmethyl)piperazin-1-yl)-isoindolin-2-yl)piperidine-2,6-dione B1279;

3-(4-(4-((2H-indazol-6-yl)methyl)piperazin-1-yl)-6-fluoro-1-oxoisoindolin-2-yl)piperidine-2,6-dione B1280;

3-(4-(4-((1H-pyrrolo[3,2-b]pyridin-3-yl)methyl)piperazin-1-yl)-6-fluoro-1-oxoisoindolin-2-yl)piperidine-2,6-dione B1281;

3-(6-fluoro-4-(4-(imidazo[1,5-a]pyridin-1-ylmethyl)piperazin-1-yl)-1-oxoisoindolin-2-yl)piperidine-2,6-dione B1282;

3-(6-fluoro-4-(4-((5-methyl-1H-pyrazol-3-yl)methyl)piperazin-1-yl)-1-oxoisoindolin-2-yl)piperidine-2,6-dione B1283;

3-(4-(4-((1H-pyrrolo[2,3-b]pyridin-6-yl)methyl)piperazin-1-yl)-6-fluoro-1-oxoisoindolin-2-yl)piperidine-2,6-dione B1284;

3-(4-(4-((1H-benzo[d]imidazol-7-yl)methyl)piperazin-1-yl)-6-fluoro-1-oxoisoindolin-2-yl)piperidine-2,6-dione B1285;

3-(6-fluoro-4-(4-(imidazo[1,2-a]pyridin-6-ylmethyl)piperazin-1-yl)-1-oxoisoindolin-2-yl)piperidine-2,6-dione B1286;

3-(6-fluoro-4-(4-(imidazo[1,2-a]pyridin-8-ylmethyl)piperazin-1-yl)-1-oxoisoindolin-2-yl)piperidine-2,6-dione B1287;

3-(6-fluoro-4-(4-(imidazo[1,2-a]pyridin-7-ylmethyl)piperazin-1-yl)-1-oxoisoindolin-2-yl)piperidine-2,6-dione B1288;

3-(4-(4-((1H-pyrrolo[3,2-b]pyridin-6-yl)methyl)piperazin-1-yl)-6-fluoro-1-oxoisoindolin-2-yl)piperidine-2,6-dione B1289;

3-(4-(4-((1H-benzo[d]imidazol-2-yl)methyl)piperazin-1-yl)-6-fluoro-1-oxoisoindolin-2-yl)piperidine-2,6-dione B1290;

3-(6-fluoro-4-(4-(imidazo[1,2-a]pyridin-3-ylmethyl)piperazin-1-yl)-1-oxoisoindolin-2-yl)piperidine-2,6-dione B1291;

3-(6-fluoro-4-(4-(imidazo[1,2-a]pyridin-2-ylmethyl)piperazin-1-yl)-1-oxoisoindolin-2-yl)piperidine-2,6-dione B1292;

3-(4-(4-(benzofuran-4-ylmethyl)piperazin-1-yl)-6-fluoro-1-oxoisoindolin-2-yl)-piperidine-2,6-dione B1293;

3-(6-fluoro-4-(4-((5-methylfuran-2-yl)methyl)piperazin-1-yl)-1-oxoisoindolin-2-yl)piperidine-2,6-dione B1294;

3-(4-(4-(benzofuran-7-ylmethyl)piperazin-1-yl)-6-fluoro-1-oxoisoindolin-2-yl)-piperidine-2,6-dione B1295;

3-(4-(4-(benzofuran-5-ylmethyl)piperazin-1-yl)-6-fluoro-1-oxoisoindolin-2-yl)-piperidine-2,6-dione B1296;

2-((4-(2-(2,6-dioxopiperidin-3-yl)-6-fluoro-1-oxoisoindolin-4-yl)piperazin-1-yl)-methyl)-5-methylbenzonitrilee B1297;

3-((4-(2-(2,6-dioxopiperidin-3-yl)-6-fluoro-1-oxoisoindolin-4-yl)piperazin-1-yl)-methyl)-2-methylbenzonitrile B1298;

3-((4-(2-(2,6-dioxopiperidin-3-yl)-6-fluoro-1-oxoisoindolin-4-yl)piperazin-1-yl)-methyl)-5-methylbenzonitrile B1299;

2-((4-(2-(2,6-dioxopiperidin-3-yl)-6-fluoro-1-oxoisoindolin-4-yl)piperazin-1-yl)-methyl)-6-methylbenzonitrile B1300;

4-((4-(2-(2,6-dioxopiperidin-3-yl)-6-fluoro-1-oxoisoindolin-4-yl)piperazin-1-yl)-methyl)-3-methylbenzonitrile B1301;

3-(4-(4-((1H-indol-3-yl)methyl)piperazin-1-yl)-6-fluoro-1-oxoisoindolin-2-yl)-piperidine-2,6-dione B1302;

3-(6-fluoro-4-(4-(indolizin-1-ylmethyl)piperazin-1-yl)-1-oxoisoindolin-2-yl)-piperidine-2,6-dione B1303;

3-(4-(4-((1H-indol-7-yl)methyl)piperazin-1-yl)-6-fluoro-1-oxoisoindolin-2-yl)-piperidine-2,6-dione B1304;

3-(6-fluoro-4-(4-((3-methyl-1H-pyrrol-2-yl)methyl)piperazin-1-yl)-1-oxoisoindolin-2-yl)piperidine-2,6-dione B1305;

3-(4-(4-((1H-indol-2-yl)methyl)piperazin-1-yl)-6-fluoro-1-oxoisoindolin-2-yl)-piperidine-2,6-dione B1306;

3-(4-(4-((1H-indol-6-yl)methyl)piperazin-1-yl)-6-fluoro-1-oxoisoindolin-2-yl)-piperidine-2,6-dione B1307;

3-(4-(4-((4-chloro-1-methyl-1H-pyrazol-3-yl)methyl)piperazin-1-yl)-6-fluoro-1-oxoisoindolin-2-yl)piperidine-2,6-dione B1308;

3-(4-(4-((3-chloropyrazin-2-yl)methyl)piperazin-1-yl)-6-fluoro-1-oxoisoindolin-2-yl)piperidine-2,6-dione B1309;

3-(4-(4-((3-chloropyridin-4-yl)methyl)piperazin-1-yl)-6-fluoro-1-oxoisoindolin-2-yl)piperidine-2,6-dione B1310;

3-(4-(4-((6-chloropyridin-2-yl)methyl)piperazin-1-yl)-6-fluoro-1-oxoisoindolin-2-yl)piperidine-2,6-dione B1311;

3-(6-fluoro-4-(4-((5-fluoro-2-oxo-1,2-dihydropyridin-3-yl)methyl)piperazin-1-yl)-1-oxoisoindolin-2-yl)piperidine-2,6-dione B1312;

3-(4-(4-(2-chlorobenzyl)piperazin-1-yl)-6-fluoro-1-oxoisoindolin-2-yl)-piperidine-2,6-dione B1313;

3-(4-(4-(4-chlorobenzyl)piperazin-1-yl)-6-fluoro-1-oxoisoindolin-2-yl)-piperidine-2,6-dione B1314;

3-(4-(4-(3-chlorobenzyl)piperazin-1-yl)-6-fluoro-1-oxoisoindolin-2-yl)-piperidine-2,6-dione B1315;

3-(6-fluoro-4-(4-((5-methyl-1H-pyrrol-2-yl)methyl)piperazin-1-yl)-1-oxoisoindolin-2-yl)piperidine-2,6-dione B1316;

3-(4-(4-(2-amino-5-fluorobenzyl)piperazin-1-yl)-6-fluoro-1-oxoisoindolin-2-yl)-piperidine-2,6-dione B1317;

3-(6-fluoro-4-(4-((1-isopropyl-1H-pyrazol-4-yl)methyl)piperazin-1-yl)-1-oxoisoindolin-2-yl)piperidine-2,6-dione B1318;

3-(6-fluoro-4-(4-((4-isopropylfuran-2-yl)methyl)piperazin-1-yl)-1-oxoisoindolin-2-yl)piperidine-2,6-dione B1319;

3-(6-fluoro-4-(4-(3-(5-methylfuran-2-yl)propyl)piperazin-1-yl)-1-oxoisoindolin-2-yl)piperidine-2,6-dione B1320;

3-(6-fluoro-4-(4-(4-fluorophenethyl)piperazin-1-yl)-1-oxoisoindolin-2-yl)-piperidine-2,6-dione B1321;

3-(6-fluoro-4-(4-(3-fluoro-2-methylbenzyl)piperazin-1-yl)-1-oxoisoindolin-2-yl)-piperidine-2,6-dione B1322;

3-(6-fluoro-4-(4-(2-fluoro-5-methylbenzyl)piperazin-1-yl)-1-oxoisoindolin-2-yl)-piperidine-2,6-dione B1323;

3-(6-fluoro-4-(4-(4-fluoro-3-methylbenzyl)piperazin-1-yl)-1-oxoisoindolin-2-yl)-piperidine-2,6-dione B1324;

3-(6-fluoro-4-(4-(3-fluoro-5-methylbenzyl)piperazin-1-yl)-1-oxoisoindolin-2-yl)-piperidine-2,6-dione B1325;

3-(6-fluoro-4-(4-(4-fluoro-2-methylbenzyl)piperazin-1-yl)-1-oxoisoindolin-2-yl)-piperidine-2,6-dione B1326;

3-(6-fluoro-4-(4-((1-methyl-1H-pyrrol-2-yl)methyl)piperazin-1-yl)-1-oxoisoindolin-2-yl)piperidine-2,6-dione B1327;

3-(6-fluoro-4-(4-(5-fluoro-2-methylbenzyl)piperazin-1-yl)-1-oxoisoindolin-2-yl)-piperidine-2,6-dione B1328;

3-(6-fluoro-4-(4-((5-methoxypyrazin-2-yl)methyl)piperazin-1-yl)-1-oxoisoindolin-2-yl)piperidine-2,6-dione B1329;

3-(6-fluoro-4-(4-((2-methoxypyrimidin-4-yl)methyl)piperazin-1-yl)-1-oxoisoindolin-2-yl)piperidine-2,6-dione B1330;

5-((4-(2-(2,6-dioxopiperidin-3-yl)-6-fluoro-1-oxoisoindolin-4-yl)piperazin-1-yl)-methyl)thiophene-2-carbonitrile B1331;

3-(6-fluoro-4-(4-((2-methoxypyridin-4-yl)methyl)piperazin-1-yl)-1-oxoisoindolin-2-yl)piperidine-2,6-dione B1332;

3-(6-fluoro-4-(4-((2-methoxypyridin-3-yl)methyl)piperazin-1-yl)-1-oxoisoindolin-2-yl)piperidine-2,6-dione B1333;

3-(6-fluoro-4-(4-((3-methoxypyridin-4-yl)methyl)piperazin-1-yl)-1-oxoisoindolin-2-yl)piperidine-2,6-dione B1334;

3-(6-fluoro-4-(4-((6-methoxypyridin-3-yl)methyl)piperazin-1-yl)-1-oxoisoindolin-2-yl)piperidine-2,6-dione B1335;

3-(6-fluoro-4-(4-((4-methoxypyridin-2-yl)methyl)piperazin-1-yl)-1-oxoisoindolin-2-yl)piperidine-2,6-dione B1336;

3-(6-fluoro-4-(4-((5-methoxypyridin-2-yl)methyl)piperazin-1-yl)-1-oxoisoindolin-2-yl)piperidine-2,6-dione B1337;

3-(6-fluoro-1-oxo-4-(4-(pyrimidin-5-ylmethyl)piperazin-1-yl)isoindolin-2-yl)-piperidine-2,6-dione B1338;

3-(6-fluoro-4-(4-((3-methoxypyridin-2-yl)methyl)piperazin-1-yl)-1-oxoisoindolin-2-yl)piperidine-2,6-dione B1339;

3-(6-fluoro-4-(4-((4-methoxypyridin-3-yl)methyl)piperazin-1-yl)-1-oxoisoindolin-2-yl)piperidine-2,6-dione B1340;

3-(6-fluoro-4-(4-((6-methoxypyridin-2-yl)methyl)piperazin-1-yl)-1-oxoisoindolin-2-yl)piperidine-2,6-dione B1341;

3-(6-fluoro-4-(4-((5-methoxypyridin-3-yl)methyl)piperazin-1-yl)-1-oxoisoindolin-2-yl)piperidine-2,6-dione B1342;

3-(6-fluoro-4-(4-((1-methyl-6-oxo-1,6-dihydropyridin-2-yl)methyl)piperazin-1-yl)-1-oxoisoindolin-2-yl)piperidine-2,6-dione B1343;

3-(6-fluoro-4-(4-((1-methyl-2-oxo-1,2-dihydropyridin-4-yl)methyl)piperazin-1-yl)-1-oxoisoindolin-2-yl)piperidine-2,6-dione B1344;

3-(4-(4-((2-amino-5-methylpyridin-3-yl)methyl)piperazin-1-yl)-6-fluoro-1-oxoisoindolin-2-yl)piperidine-2,6-dione B1345;

3-(6-fluoro-4-(4-(2-methoxybenzyl)piperazin-1-yl)-1-oxoisoindolin-2-yl)-piperidine-2,6-dione B1346;

3-(6-fluoro-4-(4-(4-methoxybenzyl)piperazin-1-yl)-1-oxoisoindolin-2-yl)-piperidine-2,6-dione B1347;

3-(6-fluoro-4-(4-(3-hydroxy-5-methylbenzyl)piperazin-1-yl)-1-oxoisoindolin-2-yl)piperidine-2,6-dione B1348;

3-(6-fluoro-1-oxo-4-(4-(pyridin-2-ylmethyl)piperazin-1-yl)isoindolin-2-yl)-piperidine-2,6-dione B1349; or 3-(4-(4-(cyclobutylmethyl)piperazin-1-yl)-6-fluoro-1-oxoisoindolin-2-yl)-piperidine-2,6-dione B1350;

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

In yet another embodiment, provided herein is a compound of:

3-(4-(4-(cyclopropylsulfonyl)piperazin-1-yl)-6-fluoro-1-oxoisoindolin-2-yl)-piperidine-2,6-dione B2001;

3-(6-fluoro-1-oxo-4-(4-(propylsulfonyl)piperazin-1-yl) isoindolin-2-yl)piperidine-2,6-dione B2002;

3-(6-fluoro-4-(4-(isopropylsulfonyl)piperazin-1-yl)-1-oxoisoindolin-2-yl)-piperidine-2,6-dione B2003;

3-(6-fluoro-4-(4-(isobutylsulfonyl)piperazin-1-yl)-1-oxoisoindolin-2-yl)-piperidine-2,6-dione B2004;

3-(6-fluoro-4-(4-(furan-3-ylsulfonyl)piperazin-1-yl)-1-oxoisoindolin-2-yl)-piperidine-2,6-dione B2005;

3-(4-(4-((1H-pyrazol-4-yl)sulfonyl)piperazin-1-yl)-6-fluoro-1-oxoisoindolin-2-yl)piperidine-2,6-dione B2006;

3-(6-fluoro-1-oxo-4-(4-((trifluoromethyl)sulfonyl)piperazin-1-yl)isoindolin-2-yl)-piperidine-2,6-dione B2007;

3-(4-(4-((cyclobutylmethyl)sulfonyl)piperazin-1-yl)-6-fluoro-1-oxoisoindolin-2-yl)piperidine-2,6-dione B2008;

3-(4-(4-((3-chloropropyl)sulfonyl)piperazin-1-yl)-6-fluoro-1-oxoisoindolin-2-yl)-piperidine-2,6-dione B2009;

3-(6-fluoro-1-oxo-4-(4-(pyridin-3-ylsulfonyl)piperazin-1-yl)isoindolin-2-yl)-piperidine-2,6-dione B2010;

3-(6-fluoro-4-(4-((1-methyl-1H-pyrazol-4-yl)sulfonyl)piperazin-1-yl)-1-oxoisoindolin-2-yl)piperidine-2,6-dione B2011;

3-(6-fluoro-4-(4-((1-methyl-1H-pyrazol-3-yl)sulfonyl)piperazin-1-yl)-1-oxoisoindolin-2-yl)piperidine-2,6-dione B2012;

3-(6-fluoro-4-(4-((1-methyl-1H-imidazol-4-yl)sulfonyl)piperazin-1-yl)-1-oxoisoindolin-2-yl)piperidine-2,6-dione B2013;

3-(6-fluoro-1-oxo-4-(4-(thiophen-2-ylsulfonyl)piperazin-1-yl)isoindolin-2-yl)-piperidine-2,6-dione B2014;

3-(4-(4-(cyclohexylsulfonyl)piperazin-1-yl)-6-fluoro-1-oxoisoindolin-2-yl)-piperidine-2,6-dione B2015;

3-(6-fluoro-1-oxo-4-(4-((tetrahydro-2H-pyran-4-yl)sulfonyl)piperazin-1-yl)-isoindolin-2-yl)piperidine-2,6-dione B2016;

3-(6-fluoro-1-oxo-4-(4-(m-tolylsulfonyl)piperazin-1-yl) isoindolin-2-yl)-piperidine-2,6-dione B2017;

3-(6-fluoro-4-(4-((6-methylpyridin-3-yl)sulfonyl)piperazin-1-yl)-1-oxoisoindolin-2-yl)piperidine-2,6-dione B2018;

3-(6-fluoro-4-(4-((4-hydroxyphenyl)sulfonyl)piperazin-1-yl)-1-oxoisoindolin-2-yl)piperidine-2,6-dione B2019;

3-(6-fluoro-4-(4-((4-fluorophenyl)sulfonyl)piperazin-1-yl)-1-oxoisoindolin-2-yl)-piperidine-2,6-dione B2020;

3-(6-fluoro-4-(4-((3-fluorophenyl)sulfonyl)piperazin-1-yl)-1-oxoisoindolin-2-yl)-piperidine-2,6-dione B2021;

3-(6-fluoro-4-(4-((2-fluorophenyl)sulfonyl)piperazin-1-yl)-1-oxoisoindolin-2-yl)-piperidine-2,6-dione B2022;

3-(6-fluoro-1-oxo-4-(4-((3,3,3-trifluoropropyl)sulfonyl)piperazin-1-yl)isoindolin-2-yl)piperidine-2,6-dione B2023;

3-(6-fluoro-4-(4-((4-methylbenzyl)sulfonyl)piperazin-1-yl)-1-oxoisoindolin-2-yl)piperidine-2,6-dione B2024;

3-(6-fluoro-1-oxo-4-(4-(phenethylsulfonyl)piperazin-1-yl) isoindolin-2-yl)-piperidine-2,6-dione B2025;

3-(4-(4-((2,6-dimethylphenyl)sulfonyl)piperazin-1-yl)-6-fluoro-1-oxoisoindolin-2-yl)piperidine-2,6-dione B2026;

3-(6-fluoro-4-(4-((4-methoxyphenyl)sulfonyl)piperazin-1-yl)-1-oxoisoindolin-2-yl)piperidine-2,6-dione B2027;

3-(6-fluoro-4-(4-((3-methoxyphenyl)sulfonyl)piperazin-1-yl)-1-oxoisoindolin-2-yl)piperidine-2,6-dione B2028;

3-(6-fluoro-4-(4-((6-methoxypyridin-3-yl)sulfonyl)piperazin-1-yl)-1-oxoisoindolin-2-yl)piperidine-2,6-dione B2029;

3-(6-fluoro-4-(4-((2-fluoro-5-methylphenyl)sulfonyl)piperazin-1-yl)-1-oxoisoindolin-2-yl)piperidine-2,6-dione B2030;

3-(6-fluoro-4-(4-((4-fluoro-2-methylphenyl)sulfonyl)piperazin-1-yl)-1-oxoisoindolin-2-yl)piperidine-2,6-dione B2031;

3-(6-fluoro-4-(4-((2-fluoro-4-methylphenyl)sulfonyl)piperazin-1-yl)-1-oxoisoindolin-2-yl)piperidine-2,6-dione B2032;

3-(4-(4-((3-chlorophenyl)sulfonyl)piperazin-1-yl)-6-fluoro-1-oxoisoindolin-2-yl)-piperidine-2,6-dione B2033;

3-(4-(4-((2-chlorophenyl)sulfonyl)piperazin-1-yl)-6-fluoro-1-oxoisoindolin-2-yl)-piperidine-2,6-dione B2034;

3-(4-(4-((4-chlorophenyl)sulfonyl)piperazin-1-yl)-6-fluoro-1-oxoisoindolin-2-yl)-piperidine-2,6-dione B2035;

3-(4-(4-((3,4-difluorophenyl)sulfonyl)piperazin-1-yl)-6-fluoro-1-oxoisoindolin-2-yl)piperidine-2,6-dione B2036;

3-(4-(4-((2,4-difluorophenyl)sulfonyl)piperazin-1-yl)-6-fluoro-1-oxoisoindolin-2-yl)piperidine-2,6-dione B2037;

3-(4-(4-((2,5-difluorophenyl)sulfonyl)piperazin-1-yl)-6-fluoro-1-oxoisoindolin-2-yl)piperidine-2,6-dione B2038;

3-(4-(4-((3,5-difluorophenyl)sulfonyl)piperazin-1-yl)-6-fluoro-1-oxoisoindolin-2-yl)piperidine-2,6-dione B2039;

3-(6-fluoro-1-oxo-4-(4-(pyridin-3-ylsulfonyl)piperazin-1-yl)isoindolin-2-yl)-piperidine-2,6-dione B2040;

2-((4-(2-(2,6-dioxopiperidin-3-yl)-6-fluoro-1-oxoisoindolin-4-yl)piperazin-1-yl)-sulfonyl)-5-methylbenzonitrile B2041;

3-(4-(4-((1H-indol-5-yl)sulfonyl)piperazin-1-yl)-6-fluoro-1-oxoisoindolin-2-yl)-piperidine-2,6-dione B2042;

3-(4-(4-(benzofuran-5-ylsulfonyl)piperazin-1-yl)-6-fluoro-1-oxoisoindolin-2-yl)-piperidine-2,6-dione B2043;

3-(4-(4-((2,3-dihydrobenzofuran-5-yl)sulfonyl)piperazin-1-yl)-6-fluoro-1-oxoisoindolin-2-yl)piperidine-2,6-dione B2044;

3-(6-fluoro-4-(4-((4-isopropylphenyl)sulfonyl)piperazin-1-yl)-1-oxoisoindolin-2-yl)piperidine-2,6-dione B2045;

3-(6-fluoro-4-(4-((3-isopropylphenyl)sulfonyl)piperazin-1-yl)-1-oxoisoindolin-2-yl)piperidine-2,6-dione B2046;

3-((4-(2-(2,6-dioxopiperidin-3-yl)-6-fluoro-1-oxoisoindolin-4-yl)piperazin-1-yl)-sulfonyl)-4-fluorobenzonitrile B2047;

5-((4-(2-(2,6-dioxopiperidin-3-yl)-6-fluoro-1-oxoisoindolin-4-yl)piperazin-1-yl)-sulfonyl)-2-fluorobenzonitrile B2048;

4-((4-(2-(2,6-dioxopiperidin-3-yl)-6-fluoro-1-oxoisoindolin-4-yl)piperazin-1-yl)-sulfonyl)benzamide B2049;

3-(6-fluoro-4-(4-((3-methoxybenzyl)sulfonyl)piperazin-1-yl)-1-oxoisoindolin-2-yl)piperidine-2,6-dione B2050;

3-(6-fluoro-4-(4-((3-methoxy-4-methylphenyl)sulfonyl)piperazin-1-yl)-1-oxoisoindolin-2-yl)piperidine-2,6-dione B2051;

3-(6-fluoro-4-(4-((5-fluoro-2-methoxyphenyl)sulfonyl)piperazin-1-yl)-1-oxoisoindolin-2-yl)piperidine-2,6-dione B2052;

3-(6-fluoro-4-(4-((3-fluoro-4-methoxyphenyl)sulfonyl)piperazin-1-yl)-1-oxoisoindolin-2-yl)piperidine-2,6-dione B2053;

3-(6-fluoro-1-oxo-4-(4-((5,6,7,8-tetrahydronaphthalen-2-yl) sulfonyl)piperazin-1-yl)isoindolin-2-yl)piperidine-2,6-dione B2054;

3-(6-fluoro-4-(4-((2-hydroxy-1H-benzo[d]imidazol-6-yl) sulfonyl)piperazin-1-yl)-1-oxoisoindolin-2-yl)piperidine-2,6-dione B2055;

3-(4-(4-((4-(tert-butyl)phenyl)sulfonyl)piperazin-1-yl)-6-fluoro-1-oxoisoindolin-2-yl)piperidine-2,6-dione B2056;

3-(4-(4-((3-(tert-butyl)phenyl)sulfonyl)piperazin-1-yl)-6-fluoro-1-oxoisoindolin-2-yl)piperidine-2,6-dione B2057;

N-(3-((4-(2-(2,6-dioxopiperidin-3-yl)-6-fluoro-1-oxoisoindolin-4-yl)piperazin-1-yl)sulfonyl)phenyl)acetamide B2058;

N-(4-((4-(2-(2,6-dioxopiperidin-3-yl)-6-fluoro-1-oxoisoindolin-4-yl)piperazin-1-yl)sulfonyl)phenyl)acetamide B2059;

4-((4-(2-(2,6-dioxopiperidin-3-yl)-6-fluoro-1-oxoisoindolin-4-yl)piperazin-1-yl)-sulfonyl)-N-methylbenzamide B2060;

2-chloro-4-((4-(2-(2,6-dioxopiperidin-3-yl)-6-fluoro-1-oxoisoindolin-4-yl)-piperazin-1-yl)sulfonyl)benzonitrile B2061;

3-(4-(4-((5-chloro-2-methoxypyridin-3-yl)sulfonyl)piperazin-1-yl)-6-fluoro-1-oxoisoindolin-2-yl)piperidine-2,6-dione B2062;

3-(4-(4-((4-(difluoromethoxy)phenyl)sulfonyl)piperazin-1-yl)-6-fluoro-1-oxoisoindolin-2-yl)piperidine-2,6-dione B2063;

3-(6-fluoro-4-(4-((4-(oxazol-5-yl)phenyl)sulfonyl)piperazin-1-yl)-1-oxoisoindolin-2-yl)piperidine-2,6-dione B2064;

3-(6-fluoro-1-oxo-4-(4-((4-(trifluoromethyl)phenyl)sulfonyl)piperazin-1-yl)-isoindolin-2-yl)piperidine-2,6-dione B2065;

3-(6-fluoro-1-oxo-4-(4-((3-(trifluoromethyl)phenyl)sulfonyl)piperazin-1-yl)-isoindolin-2-yl)piperidine-2,6-dione B2066;

3-(6-fluoro-1-oxo-4-(4-((2-(trifluoromethyl)phenyl)sulfonyl)piperazin-1-yl)-isoindolin-2-yl)piperidine-2,6-dione B2067;

3-(6-fluoro-1-oxo-4-(4-((6-(trifluoromethyl)pyridin-3-yl)sulfonyl)piperazin-1-yl)isoindolin-2-yl)piperidine-2,6-dione B2068;

3-(6-fluoro-1-oxo-4-(4-((2-oxo-1,2,3,4-tetrahydroquinolin-6-yl)sulfonyl)-piperazin-1-yl)isoindolin-2-yl)piperidine-2,6-dione B2069;

2-((4-(2-(2,6-dioxopiperidin-3-yl)-6-fluoro-1-oxoisoindolin-4-yl)piperazin-1-yl)-sulfonyl)-N,N-dimethylbenzamide B2070;

3-(4-(4-((3-bromophenyl)sulfonyl)piperazin-1-yl)-6-fluoro-1-oxoisoindolin-2-yl)-piperidine-2,6-dione B2071;

3-(4-(4-((2-bromophenyl)sulfonyl)piperazin-1-yl)-6-fluoro-1-oxoisoindolin-2-yl)-piperidine-2,6-dione B2072;

3-(6-fluoro-1-oxo-4-(4-((1-(o-tolyl)-1H-pyrazol-4-yl)sulfonyl)piperazin-1-yl)-isoindolin-2-yl)piperidine-2,6-dione B2073;

3-(6-fluoro-1-oxo-4-(4-((4-(trifluoromethyl)benzyl)sulfonyl)piperazin-1-yl)-isoindolin-2-yl)piperidine-2,6-dione B2074;

3-(6-fluoro-1-oxo-4-(4-((2-(trifluoromethoxy)phenyl)sulfonyl)piperazin-1-yl)-isoindolin-2-yl)piperidine-2,6-dione B2075;

3-(4-(4-((1-chloroisoquinolin-5-yl)sulfonyl)piperazin-1-yl)-6-fluoro-1-oxoisoindolin-2-yl)piperidine-2,6-dione B2076;

3-(6-fluoro-4-(4-(isoquinolin-5-ylsulfonyl)piperazin-1-yl)-1-oxoisoindolin-2-yl)-piperidine-2,6-dione B2077;

3-(6-fluoro-1-oxo-4-(4-((4-(pyridin-2-yloxy)phenyl)sulfonyl)piperazin-1-yl)-isoindolin-2-yl)piperidine-2,6-dione B2078;

3-(6-fluoro-1-oxo-4-(4-((6-phenoxypyridin-3-yl)sulfonyl)piperazin-1-yl)-isoindolin-2-yl)piperidine-2,6-dione B2079;

3-(4-(4-((5-(dimethylamino)naphthalen-1-yl)sulfonyl)piperazin-1-yl)-6-fluoro-1-oxoisoindolin-2-yl)piperidine-2,6-dione B2080;

3-(4-(4-((6-(dimethylamino)naphthalen-2-yl)sulfonyl)piperazin-1-yl)-6-fluoro-1-oxoisoindolin-2-yl)piperidine-2,6-dione B2081;

3-(4-(4-((4-(benzyloxy)phenyl)sulfonyl)piperazin-1-yl)-6-fluoro-1-oxoisoindolin-2-yl)piperidine-2,6-dione B2082;

tert-butyl 4-((4-(2-(2,6-dioxopiperidin-3-yl)-6-fluoro-1-oxoisoindolin-4-yl)-piperazin-1-yl)sulfonyl)piperidine-1-carboxylate B2083;

benzyl 4-((4-(2-(2,6-dioxopiperidin-3-yl)-6-fluoro-1-oxoisoindolin-4-yl)-piperazin-1-yl)sulfonyl)piperidine-1-carboxylate B2084;

3-(6-fluoro-1-oxo-4-(4-((2-(2,2,2-trifluoroacetyl)-1,2,3,4-tetrahydroisoquinolin-7-yl)sulfonyl)piperazin-1-yl)isoindolin-2-yl)piperidine-2,6-dione B2085;

benzyl 4-(((4-(2-(2,6-dioxopiperidin-3-yl)-6-fluoro-1-oxoisoindolin-4-yl)-piperazin-1-yl)sulfonyl)methyl)piperidine-1-carboxylate B2086;

3-(4-(4-(ethylsulfonyl)piperazin-1-yl)-6-fluoro-1-oxoisoindolin-2-yl)piperidine-2,6-dione B2087;

3-(4-(4-((5-chlorothiophen-2-yl)sulfonyl)piperazin-1-yl)-6-fluoro-1-oxoisoindolin-2-yl)piperidine-2,6-dione B2088;

3-(4-(4-((3-chloro-4-methylphenyl)sulfonyl)piperazin-1-yl)-6-fluoro-1-oxoisoindolin-2-yl)piperidine-2,6-dione B2089;

3-(4-(4-((2-chloro-6-methylphenyl)sulfonyl)piperazin-1-yl)-6-fluoro-1-oxoisoindolin-2-yl)piperidine-2,6-dione B2090;

3-(4-(4-((3,5-difluorobenzyl)sulfonyl)piperazin-1-yl)-6-fluoro-1-oxoisoindolin-2-yl)piperidine-2,6-dione B2091;

3-(6-fluoro-4-(4-(naphthalen-2-ylsulfonyl)piperazin-1-yl)-1-oxoisoindolin-2-yl)-piperidine-2,6-dione B2092;

3-(6-fluoro-1-oxo-4-(4-(quinolin-8-ylsulfonyl)piperazin-1-yl)isoindolin-2-yl)-piperidine-2,6-dione B2093;

3-(6-fluoro-4-(4-(isoquinolin-5-ylsulfonyl)piperazin-1-yl)-1-oxoisoindolin-2-yl)-piperidine-2,6-dione B2094;

3-(6-fluoro-1-oxo-4-(4-(quinoxalin-5-ylsulfonyl)piperazin-1-yl)isoindolin-2-yl)-piperidine-2,6-dione B2095;

3-chloro-4-((4-(2-(2,6-dioxopiperidin-3-yl)-6-fluoro-1-oxoisoindolin-4-yl)-piperazin-1-yl)sulfonyl)benzonitrile B2096;

3-(4-(4-(benzo[d][1,3]dioxol-5-ylsulfonyl)piperazin-1-yl)-6-fluoro-1-oxoisoindolin-2-yl)piperidine-2,6-dione B2097;

3-(4-(4-(benzo[d]thiazol-6-ylsulfonyl)piperazin-1-yl)-6-fluoro-1-oxoisoindolin-2-yl)piperidine-2,6-dione B2098;

3-(4-(4-((2,4-dichlorophenyl)sulfonyl)piperazin-1-yl)-6-fluoro-1-oxoisoindolin-2-yl)piperidine-2,6-dione B2099; or 3-(4-(4-((2,5-dichlorophenyl)sulfonyl)piperazin-1-yl)-6-fluoro-1-oxoisoindolin-2-yl)piperidine-2,6-dione B2100;

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

In yet another embodiment, provided herein is a compound of:

3-(6-fluoro-1-oxo-5-(1-(5,6,7,8-tetrahydronaphthalene-1-carbonyl)-piperidin-4-yl)isoindolin-2-yl)piperidine-2,6-dione C0001;

3-(6-fluoro-5-(1-(1-methyl-1H-indole-5-carbonyl)piperidin-4-yl)-1-oxoisoindolin-2-yl)piperidine-2,6-dione C0002;

3-(6-fluoro-1-oxo-5-(1-(quinoxaline-5-carbonyl)piperidin-4-yl)isoindolin-2-yl)-piperidine-2,6-dione C0003;

3-(6-fluoro-1-oxo-5-(1-(quinazoline-6-carbonyl)piperidin-4-yl)isoindolin-2-yl)-piperidine-2,6-dione C0004;

3-(5-(1-(2-(dimethylamino)benzoyl)piperidin-4-yl)-6-fluoro-1-oxoisoindolin-2-yl)piperidine-2,6-dione C0005;

3-(5-(1-(4-(dimethylamino)benzoyl)piperidin-4-yl)-6-fluoro-1-oxoisoindolin-2-yl)piperidine-2,6-dione C0006;
3-(5-(1-(2,3-dihydrobenzofuran-7-carbonyl)piperidin-4-yl)-6-fluoro-1-oxoisoindolin-2-yl)piperidine-2,6-dione C0007;
3-(5-(1-(benzo[d]oxazole-5-carbonyl)piperidin-4-yl)-6-fluoro-1-oxoisoindolin-2-yl)piperidine-2,6-dione C0008;
3-(5-(1-(1H-benzo[d]imidazole-7-carbonyl)piperidin-4-yl)-6-fluoro-1-oxoisoindolin-2-yl)piperidine-2,6-dione C0009;
3-(6-fluoro-5-(1-(imidazo[1,2-a]pyridine-2-carbonyl)piperidin-4-yl)-1-oxoisoindolin-2-yl)piperidine-2,6-dione C0010;
3-(5-(1-(1H-pyrrolo[3,2-b]pyridine-6-carbonyl)piperidin-4-yl)-6-fluoro-1-oxoisoindolin-2-yl)piperidine-2,6-dione C0011;
3-(6-fluoro-5-(1-(imidazo[1,2-a]pyridine-3-carbonyl)piperidin-4-yl)-1-oxoisoindolin-2-yl)piperidine-2,6-dione C0012;
3-(5-(1-(benzofuran-6-carbonyl)piperidin-4-yl)-6-fluoro-1-oxoisoindolin-2-yl)-piperidine-2,6-dione C0013;
3-(6-fluoro-1-oxo-5-(1-(2-(piperidin-1-yl)acetyl)piperidin-4-yl)isoindolin-2-yl)-piperidine-2,6-dione C0014;
2-(2-(4-(2-(2,6-dioxopiperidin-3-yl)-6-fluoro-1-oxoisoindolin-5-yl)piperidin-1-yl)-2-oxoethyl)benzonitrile C0015;
3-(2-(4-(2-(2,6-dioxopiperidin-3-yl)-6-fluoro-1-oxoisoindolin-5-yl)piperidin-1-yl)-2-oxoethyl)benzonitrile C0016;
4-(2-(4-(2-(2,6-dioxopiperidin-3-yl)-6-fluoro-1-oxoisoindolin-5-yl)piperidin-1-yl)-2-oxoethyl)benzonitrile C0017;
3-(5-(1-(1H-indole-7-carbonyl)piperidin-4-yl)-6-fluoro-1-oxoisoindolin-2-yl)-piperidine-2,6-dione C0018;
3-(5-(1-(1-ethylpiperidine-4-carbonyl)piperidin-4-yl)-6-fluoro-1-oxoisoindolin-2-yl)piperidine-2,6-dione C0019;
3-(6-fluoro-1-oxo-5-(1-(2-(p-tolyl)acetyl)piperidin-4-yl) isoindolin-2-yl)-piperidine-2,6-dione C0020;
2-(4-(2-(2,6-dioxopiperidin-3-yl)-6-fluoro-1-oxoisoindolin-5-yl)piperidine-1-carbonyl)benzonitrile C0021;
3-(4-(2-(2,6-dioxopiperidin-3-yl)-6-fluoro-1-oxoisoindolin-5-yl)piperidine-1-carbonyl)benzonitrile C0022;
3-(6-fluoro-5-(1-(4-fluorobenzoyl)piperidin-4-yl)-1-oxoisoindolin-2-yl)-piperidine-2,6-dione C0023;
3-(6-fluoro-5-(1-(3-fluorobenzoyl)piperidin-4-yl)-1-oxoisoindolin-2-yl)-piperidine-2,6-dione C0024;
3-(6-fluoro-5-(1-(2-fluorobenzoyl)piperidin-4-yl)-1-oxoisoindolin-2-yl)-piperidine-2,6-dione C0025;
3-(6-fluoro-5-(1-(2-methylbenzoyl)piperidin-4-yl)-1-oxoisoindolin-2-yl)-piperidine-2,6-dione C0026;
3-(6-fluoro-5-(1-(3-methylbenzoyl)piperidin-4-yl)-1-oxoisoindolin-2-yl)-piperidine-2,6-dione C0027;
3-(6-fluoro-5-(1-(4-methylbenzoyl)piperidin-4-yl)-1-oxoisoindolin-2-yl)-piperidine-2,6-dione C0028;
3-(5-(1-(2-cyclopentylacetyl)piperidin-4-yl)-6-fluoro-1-oxoisoindolin-2-yl)-piperidine-2,6-dione C0029;
3-(5-(1-(cyclohexanecarbonyl)piperidin-4-yl)-6-fluoro-1-oxoisoindolin-2-yl)-piperidine-2,6-dione C0030;
3-(5-(1-(3,3-dimethylcyclobutane-1-carbonyl)piperidin-4-yl)-6-fluoro-1-oxoisoindolin-2-yl)piperidine-2,6-dione C0031;
3-(6-fluoro-1-oxo-5-(1-(pyrimidine-5-carbonyl)piperidin-4-yl)isoindolin-2-yl)-piperidine-2,6-dione C0032;
3-(6-fluoro-1-oxo-5-(1-(pyridazine-4-carbonyl)piperidin-4-yl)isoindolin-2-yl)-piperidine-2,6-dione C0033;
3-(6-fluoro-1-oxo-5-(1-(pyrimidine-4-carbonyl)piperidin-4-yl)isoindolin-2-yl)-piperidine-2,6-dione C0034;
3-(6-fluoro-1-oxo-5-(1-picolinoylpiperidin-4-yl)isoindolin-2-yl)piperidine-2,6-dione C0035;
3-(6-fluoro-5-(1-isonicotinoylpiperidin-4-yl)-1-oxoisoindolin-2-yl)piperidine-2,6-dione C0036;
3-(6-fluoro-5-(1-nicotinoylpiperidin-4-yl)-1-oxoisoindolin-2-yl)piperidine-2,6-dione C0037;
3-(5-(1-benzoylpiperidin-4-yl)-6-fluoro-1-oxoisoindolin-2-yl)piperidine-2,6-dione C0038;
3-(5-(1-(1-aminocyclobutane-1-carbonyl)piperidin-4-yl)-6-fluoro-1-oxoisoindolin-2-yl)piperidine-2,6-dione C0039;
3-(6-fluoro-5-(1-(1-methylazetidine-3-carbonyl)piperidin-4-yl)-1-oxoisoindolin-2-yl)piperidine-2,6-dione C0040;
3-(5-(1-(1H-pyrazole-5-carbonyl)piperidin-4-yl)-6-fluoro-1-oxoisoindolin-2-yl)-piperidine-2,6-dione C0041;
3-(5-(1-(1H-imidazole-5-carbonyl)piperidin-4-yl)-6-fluoro-1-oxoisoindolin-2-yl)-piperidine-2,6-dione C0042;
3-(6-fluoro-5-(1-(furan-3-carbonyl)piperidin-4-yl)-1-oxoisoindolin-2-yl)-piperidine-2,6-dione C0043;
3-(6-fluoro-5-(1-(furan-2-carbonyl)piperidin-4-yl)-1-oxoisoindolin-2-yl)-piperidine-2,6-dione C0044;
3-(6-fluoro-5-(1-(1-fluorocyclopropane-1-carbonyl)piperidin-4-yl)-1-oxoisoindolin-2-yl)piperidine-2,6-dione C0045;
3-(6-fluoro-5-(1-(3-methylbutanoyl)piperidin-4-yl)-1-oxoisoindolin-2-yl)-piperidine-2,6-dione C0046;
3-(6-fluoro-5-(1-(oxetane-3-carbonyl)piperidin-4-yl)-1-oxoisoindolin-2-yl)-piperidine-2,6-dione C0047;
3-(5-(1-(cyclobutanecarbonyl)piperidin-4-yl)-6-fluoro-1-oxoisoindolin-2-yl)-piperidine-2,6-dione C0048;
3-(6-fluoro-5-(1-(methylglycyl)piperidin-4-yl)-1-oxoisoindolin-2-yl)piperidine-2,6-dione C0049; or
3-(5-(1-(cyclopropanecarbonyl)piperidin-4-yl)-6-fluoro-1-oxoisoindolin-2-yl)-piperidine-2,6-dione C0050;

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

In yet another embodiment, provided herein is a compound of:

3-(6-fluoro-5-(1-(3-methoxybenzyl)piperidin-4-yl)-1-oxoisoindolin-2-yl)-piperidine-2,6-dione C1001;
3-(6-fluoro-5-(1-(2-hydroxy-4-methylbenzyl)piperidin-4-yl)-1-oxoisoindolin-2-yl)piperidine-2,6-dione C1002;
3-(6-fluoro-5-(1-(4-(hydroxymethyl)benzyl)piperidin-4-yl)-1-oxoisoindolin-2-yl)piperidine-2,6-dione C1003;
3-(5-(1-((2,6-dimethylpyridin-4-yl)methyl)piperidin-4-yl)-6-fluoro-1-oxoiso-indolin-2-yl)piperidine-2,6-dione C1004;
3-(6-fluoro-5-(1-(2-(methylamino)benzyl)piperidin-4-yl)-1-oxoisoindolin-2-yl)-piperidine-2,6-dione C1005;
3-(5-(1-(2,6-dimethylbenzyl)piperidin-4-yl)-6-fluoro-1-oxoisoindolin-2-yl)-piperidine-2,6-dione C1006;
3-(5-(1-(2,4-dimethylbenzyl)piperidin-4-yl)-6-fluoro-1-oxoisoindolin-2-yl)-piperidine-2,6-dione C1007;
3-(5-(1-(2,5-dimethylbenzyl)piperidin-4-yl)-6-fluoro-1-oxoisoindolin-2-yl)-piperidine-2,6-dione C1008;
3-(6-fluoro-5-(1-(2-methylphenethyl)piperidin-4-yl)-1-oxoisoindolin-2-yl)-piperidine-2,6-dione C1009;
3-(5-(1-(3,5-dimethylbenzyl)piperidin-4-yl)-6-fluoro-1-oxoisoindolin-2-yl)-piperidine-2,6-dione C1010;
3-(6-fluoro-1-oxo-5-(1-(pyridin-3-ylmethyl)piperidin-4-yl) isoindolin-2-yl)-piperidine-2,6-dione C1011;
3-(6-fluoro-1-oxo-5-(1-(3-phenylpropyl)piperidin-4-yl) isoindolin-2-yl)-piperidine-2,6-dione C1012;
4-((4-(2-(2,6-dioxopiperidin-3-yl)-6-fluoro-1-oxoisoindolin-5-yl)piperidin-1-yl)-methyl)-1-methyl-1H-pyrrole-2-carbonitrile C1013;

3-(5-(1-(bicyclo[4.2.0]octa-1(6),2,4-trien-3-ylmethyl)piperidin-4-yl)-6-fluoro-1-oxoisoindolin-2-yl)piperidine-2,6-dione C1014;

5-((4-(2-(2,6-dioxopiperidin-3-yl)-6-fluoro-1-oxoisoindolin-5-yl)piperidin-1-yl)-methyl)picolinonitrile C1015;

5-((4-(2-(2,6-dioxopiperidin-3-yl)-6-fluoro-1-oxoisoindolin-5-yl)piperidin-1-yl)-methyl)nicotinonitrile C1016;

6-((4-(2-(2,6-dioxopiperidin-3-yl)-6-fluoro-1-oxoisoindolin-5-yl)piperidin-1-yl)-methyl)picolinonitrile C1017;

2-((4-(2-(2,6-dioxopiperidin-3-yl)-6-fluoro-1-oxoisoindolin-5-yl)piperidin-1-yl)-methyl)isonicotinonitrile C1018;

3-((4-(2-(2,6-dioxopiperidin-3-yl)-6-fluoro-1-oxoisoindolin-5-yl)piperidin-1-yl)-methyl)benzonitrile C1019;

3-(5-(1-((5-ethynylpyridin-2-yl)methyl)piperidin-4-yl)-6-fluoro-1-oxoisoindolin-2-yl)piperidine-2,6-dione C1020;

4-((4-(2-(2,6-dioxopiperidin-3-yl)-6-fluoro-1-oxoisoindolin-5-yl)piperidin-1-yl)-methyl)benzonitrile C1021;

3-(6-fluoro-5-(1-(3-hydroxy-2,2-dimethylpropyl)piperidin-4-yl)-1-oxoisoindolin-2-yl)piperidine-2,6-dione C1022;

2-((4-(2-(2,6-dioxopiperidin-3-yl)-6-fluoro-1-oxoisoindolin-5-yl)piperidin-1-yl)-methyl)benzonitrile C1023;

3-(5-(1-(4-ethynylbenzyl)piperidin-4-yl)-6-fluoro-1-oxoisoindolin-2-yl)-piperidine-2,6-dione C1024;

3-(5-(1-(2-ethynylbenzyl)piperidin-4-yl)-6-fluoro-1-oxoisoindolin-2-yl)-piperidine-2,6-dione C1025;

3-(5-(1-(3-ethynylbenzyl)piperidin-4-yl)-6-fluoro-1-oxoisoindolin-2-yl)-piperidine-2,6-dione C1026;

3-(6-fluoro-5-(1-((5-methylthiazol-2-yl)methyl)piperidin-4-yl)-1-oxoisoindolin-2-yl)piperidine-2,6-dione C1027;

3-(6-fluoro-5-(1-((2-methylthiazol-5-yl)methyl)piperidin-4-yl)-1-oxoisoindolin-2-yl)piperidine-2,6-dione C1028;

3-(6-fluoro-5-(1-((4-methylthiazol-5-yl)methyl)piperidin-4-yl)-1-oxoisoindolin-2-yl)piperidine-2,6-dione C1029;

3-(5-(1-(2-cyclohexylethyl)piperidin-4-yl)-6-fluoro-1-oxoisoindolin-2-yl)-piperidine-2,6-dione C1030;

3-(6-fluoro-5-(1-((3-methylthiophen-2-yl)methyl)piperidin-4-yl)-1-oxoisoindolin-2-yl)piperidine-2,6-dione C1031;

3-(6-fluoro-5-(1-((3-methoxyfuran-2-yl)methyl)piperidin-4-yl)-1-oxoisoindolin-2-yl)piperidine-2,6-dione C1032;

3-(6-fluoro-5-(1-((3-methyloxetan-3-yl)methyl)piperidin-4-yl)-1-oxoisoindolin-2-yl)piperidine-2,6-dione C1033;

3-(6-fluoro-5-(1-((5-(hydroxymethyl)furan-2-yl)methyl)piperidin-4-yl)-1-oxo-isoindolin-2-yl)piperidine-2,6-dione C1034;

3-(5-(1-((5-amino-1-methyl-1H-pyrazol-4-yl)methyl)piperidin-4-yl)-6-fluoro-1-oxoisoindolin-2-yl)piperidine-2,6-dione C1035;

3-(6-fluoro-5-(1-((5-(hydroxymethyl)-1H-pyrrol-2-yl)methyl)piperidin-4-yl)-1-oxoisoindolin-2-yl)piperidine-2,6-dione C1036;

3-(6-fluoro-5-(1-((6-fluoropyridin-3-yl)methyl)piperidin-4-yl)-1-oxoisoindolin-2-yl)piperidine-2,6-dione C1037;

3-(6-fluoro-5-(1-((3-fluoropyridin-4-yl)methyl)piperidin-4-yl)-1-oxoisoindolin-2-yl)piperidine-2,6-dione C1038;

3-(6-fluoro-5-(1-((5-fluoropyridin-2-yl)methyl)piperidin-4-yl)-1-oxoisoindolin-2-yl)piperidine-2,6-dione C1039;

3-(6-fluoro-5-(1-((5-fluoropyridin-3-yl)methyl)piperidin-4-yl)-1-oxoisoindolin-2-yl)piperidine-2,6-dione C1040;

3-(6-fluoro-5-(1-((4-fluoropyridin-2-yl)methyl)piperidin-4-yl)-1-oxoisoindolin-2-yl)piperidine-2,6-dione C1041;

3-(6-fluoro-5-(1-((6-fluoropyridin-2-yl)methyl)piperidin-4-yl)-1-oxoisoindolin-2-yl)piperidine-2,6-dione C1042;

3-(5-(1-((2,5-dimethyl-1H-imidazol-4-yl)methyl)piperidin-4-yl)-6-fluoro-1-oxoisoindolin-2-yl)piperidine-2,6-dione C1043;

3-(6-fluoro-5-(1-(oxazol-2-ylmethyl)piperidin-4-yl)-1-oxoisoindolin-2-yl)-piperidine-2,6-dione C1044;

3-(5-(1-((1,4-dimethyl-1H-pyrazol-5-yl)methyl)piperidin-4-yl)-6-fluoro-1-oxoisoindolin-2-yl)piperidine-2,6-dione C1045;

3-(6-fluoro-5-(1-(4-fluorobenzyl)piperidin-4-yl)-1-oxoisoindolin-2-yl)piperidine-2,6-dione C1046;

3-(6-fluoro-5-(1-(3-fluorobenzyl)piperidin-4-yl)-1-oxoisoindolin-2-yl)piperidine-2,6-dione C1047;

3-(6-fluoro-5-(1-((2-hydroxypyridin-3-yl)methyl)piperidin-4-yl)-1-oxoisoindolin-2-yl)piperidine-2,6-dione C1048;

3-(6-fluoro-5-(1-((5-methylpyrazin-2-yl)methyl)piperidin-4-yl)-1-oxoisoindolin-2-yl)piperidine-2,6-dione C1049;

3-(6-fluoro-5-(1-((3-methylpyrazin-2-yl)methyl)piperidin-4-yl)-1-oxoisoindolin-2-yl)piperidine-2,6-dione C1050;

3-(6-fluoro-5-(1-((2-methylpyrimidin-4-yl)methyl)piperidin-4-yl)-1-oxoisoindolin-2-yl)piperidine-2,6-dione C1051;

3-(6-fluoro-5-(1-((2-methylpyrimidin-5-yl)methyl)piperidin-4-yl)-1-oxoisoindolin-2-yl)piperidine-2,6-dione C1052;

3-(5-(1-((2-aminopyridin-3-yl)methyl)piperidin-4-yl)-6-fluoro-1-oxoisoindolin-2-yl)piperidine-2,6-dione C1053;

3-(5-(1-((3-aminopyridin-4-yl)methyl)piperidin-4-yl)-6-fluoro-1-oxoisoindolin-2-yl)piperidine-2,6-dione C1054;

3-(5-(1-((1H-pyrazol-5-yl)methyl)piperidin-4-yl)-6-fluoro-1-oxoisoindolin-2-yl)-piperidine-2,6-dione C1055;

3-(6-fluoro-5-(1-(3-hydroxybenzyl)piperidin-4-yl)-1-oxoisoindolin-2-yl)-piperidine-2,6-dione C1056;

3-(6-fluoro-5-(1-(4-hydroxybenzyl)piperidin-4-yl)-1-oxoisoindolin-2-yl)-piperidine-2,6-dione C1057;

3-(6-fluoro-5-(1-((4-methylpyridin-2-yl)methyl)piperidin-4-yl)-1-oxoisoindolin-2-yl)piperidine-2,6-dione C1058;

3-(6-fluoro-5-(1-((3-methylpyridin-2-yl)methyl)piperidin-4-yl)-1-oxoisoindolin-2-yl)piperidine-2,6-dione C1059;

3-(6-fluoro-5-(1-((2-methylpyridin-3-yl)methyl)piperidin-4-yl)-1-oxoisoindolin-2-yl)piperidine-2,6-dione C1060;

3-(6-fluoro-5-(1-((2-methylpyridin-4-yl)methyl)piperidin-4-yl)-1-oxoisoindolin-2-yl)piperidine-2,6-dione C1061;

3-(6-fluoro-5-(1-((5-methylpyridin-2-yl)methyl)piperidin-4-yl)-1-oxoisoindolin-2-yl)piperidine-2,6-dione C1062;

3-(6-fluoro-5-(1-((6-methylpyridin-2-yl)methyl)piperidin-4-yl)-1-oxoisoindolin-2-yl)piperidine-2,6-dione C1063;

3-(6-fluoro-5-(1-((4-methylpyridin-3-yl)methyl)piperidin-4-yl)-1-oxoisoindolin-2-yl)piperidine-2,6-dione C1064;

3-(6-fluoro-5-(1-((5-methylpyridin-3-yl)methyl)piperidin-4-yl)-1-oxoisoindolin-2-yl)piperidine-2,6-dione C1065;

3-(5-(1-((1H-imidazol-5-yl)methyl)piperidin-4-yl)-6-fluoro-1-oxoisoindolin-2-yl)piperidine-2,6-dione C1066;

3-(5-(1-(4-aminobenzyl)piperidin-4-yl)-6-fluoro-1-oxoisoindolin-2-yl)piperidine-2,6-dione C1067;

3-(5-(1-(2-aminobenzyl)piperidin-4-yl)-6-fluoro-1-oxoisoindolin-2-yl)piperidine-2,6-dione C1068;

3-(6-fluoro-5-(1-(4-methylbenzyl)piperidin-4-yl)-1-oxoisoindolin-2-yl)-piperidine-2,6-dione C1069;

3-(6-fluoro-5-(1-(2-methylbenzyl)piperidin-4-yl)-1-oxoisoindolin-2-yl)-piperidine-2,6-dione C1070;

4-(4-bromo-3-((4-(2-(2,6-dioxopiperidin-3-yl)-6-fluoro-1-oxoisoindolin-5-yl)piperidin-1-yl)methyl)phenoxy)benzonitrile C1071;

3-(6-fluoro-1-oxo-5-(1-phenethylpiperidin-4-yl)isoindolin-2-yl)piperidine-2,6-dione C1072;

3-(5-(1-(3-bromo-4-(4-methylpiperazin-1-yl)benzyl)piperidin-4-yl)-6-fluoro-1-oxoisoindolin-2-yl)piperidine-2,6-dione C1073;

tert-butyl 4-(4-((4-(2-(2,6-dioxopiperidin-3-yl)-6-fluoro-1-oxoisoindolin-5-yl)-piperidin-1-yl)methyl)-1H-1,2,3-triazol-1-yl)piperidine-1-carboxylate C1074;

3-(5-(1-(3-bromo-4-morpholinobenzyl)piperidin-4-yl)-6-fluoro-1-oxoisoindolin-2-yl)piperidine-2,6-dione C1075;

3-(6-fluoro-1-oxo-5-(1-(4-(4-(trifluoromethyl)phenoxy)benzyl)piperidin-4-yl)-isoindolin-2-yl)piperidine-2,6-dione C1076;

3-(5-(1-(4-(benzyloxy)-3-ethoxybenzyl)piperidin-4-yl)-6-fluoro-1-oxoisoindolin-2-yl)piperidine-2,6-dione C1077;

tert-butyl 4-(1-(4-(2-(2,6-dioxopiperidin-3-yl)-6-fluoro-1-oxoisoindolin-5-yl)-piperidin-1-yl)-2-methylpropan-2-yl)piperidine-1-carboxylate C1078;

benzyl (4-((4-(2-(2,6-dioxopiperidin-3-yl)-6-fluoro-1-oxoisoindolin-5-yl)-piperidin-1-yl)methyl)phenyl)carbamate C1079;

tert-butyl 6-((4-(2-(2,6-dioxopiperidin-3-yl)-6-fluoro-1-oxoisoindolin-5-yl)-piperidin-1-yl)methyl)indoline-1-carboxylate C1080;

tert-butyl (((1r,4r)-4-((4-(2-(2,6-dioxopiperidin-3-yl)-6-fluoro-1-oxoisoindolin-5-yl)piperidin-1-yl)methyl)cyclohexyl)methyl)carbamate C1081;

4-(4-((4-(2-(2,6-dioxopiperidin-3-yl)-6-fluoro-1-oxoisoindolin-5-yl)piperidin-1-yl)methyl)phenoxy)-3-fluorobenzonitrile C1082;

3-(6-fluoro-5-(1-(3-methylbenzyl)piperidin-4-yl)-1-oxoisoindolin-2-yl)-piperidine-2,6-dione C1083;

tert-butyl 4-((4-(2-(2,6-dioxopiperidin-3-yl)-6-fluoro-1-oxoisoindolin-5-yl)-piperidin-1-yl)methyl)-4-fluoropiperidine-1-carboxylate C1084;

tert-butyl 4-(2-(4-(2-(2,6-dioxopiperidin-3-yl)-6-fluoro-1-oxoisoindolin-5-yl)-piperidin-1-yl)ethyl)piperazine-1-carboxylate C1085;

3-(5-(1-((2-chloro-4-morpholinopyrimidin-5-yl)methyl)piperidin-4-yl)-6-fluoro-1-oxoisoindolin-2-yl)piperidine-2,6-dione C1086;

tert-butyl ((1r,4r)-4-((4-(2-(2,6-dioxopiperidin-3-yl)-6-fluoro-1-oxoisoindolin-5-yl)piperidin-1-yl)methyl)cyclohexyl)carbamate C1087;

tert-butyl 4-(2-(4-(2-(2,6-dioxopiperidin-3-yl)-6-fluoro-1-oxoisoindolin-5-yl)-piperidin-1-yl)ethyl)piperidine-1-carboxylate C1088;

3-(5-(1-(2-(benzyloxy)-4-methylbenzyl)piperidin-4-yl)-6-fluoro-1-oxoisoindolin-2-yl)piperidine-2,6-dione C1089;

3-(5-(1-(4-(benzyloxy)-2-methylbenzyl)piperidin-4-yl)-6-fluoro-1-oxoisoindolin-2-yl)piperidine-2,6-dione C1090;

3-(5-(1-(3-chloro-4-morpholinobenzyl)piperidin-4-yl)-6-fluoro-1-oxoisoindolin-2-yl)piperidine-2,6-dione C1091;

4-(4-((4-(2-(2,6-dioxopiperidin-3-yl)-6-fluoro-1-oxoisoindolin-5-yl)piperidin-1-yl)methyl)phenoxy)benzonitrile C1092;

4-(3-((4-(2-(2,6-dioxopiperidin-3-yl)-6-fluoro-1-oxoisoindolin-5-yl)piperidin-1-yl)methyl)phenoxy)benzonitrile C1093;

2-((4-(2-(2,6-dioxopiperidin-3-yl)-6-fluoro-1-oxoisoindolin-5-yl)piperidin-1-yl)-methyl)-1H-pyrrole-3-carbonitrile C1094;

3-(5-(1-(3-(cyclohexylmethoxy)benzyl)piperidin-4-yl)-6-fluoro-1-oxoisoindolin-2-yl)piperidine-2,6-dione C1095;

3-(5-(1-(3-(3-bromophenyl)propyl)piperidin-4-yl)-6-fluoro-1-oxoisoindolin-2-yl)piperidine-2,6-dione C1096;

3-(5-(1-(4-(benzyloxy)benzyl)piperidin-4-yl)-6-fluoro-1-oxoisoindolin-2-yl)-piperidine-2,6-dione C1097;

3-(5-(1-(3-(benzyloxy)benzyl)piperidin-4-yl)-6-fluoro-1-oxoisoindolin-2-yl)-piperidine-2,6-dione C1098;

5-((4-(2-(2,6-dioxopiperidin-3-yl)-6-fluoro-1-oxoisoindolin-5-yl)piperidin-1-yl)methyl)-2-(4-methyl-1H-imidazol-1-yl)benzonitrile C1099;

3-(5-(1-(3-chloro-4-(trifluoromethyl)benzyl)piperidin-4-yl)-6-fluoro-1-oxoisoindolin-2-yl)piperidine-2,6-dione C1100;

3-(5-(1-(2-chloro-4-(trifluoromethyl)benzyl)piperidin-4-yl)-6-fluoro-1-oxoisoindolin-2-yl)piperidine-2,6-dione C1101;

3-(5-(1-(4-chloro-2-(trifluoromethyl)benzyl)piperidin-4-yl)-6-fluoro-1-oxoisoindolin-2-yl)piperidine-2,6-dione C1102;

3-(5-(1-(5-chloro-2-(trifluoromethyl)benzyl)piperidin-4-yl)-6-fluoro-1-oxoisoindolin-2-yl)piperidine-2,6-dione C1103;

3-(5-(1-(2-chloro-5-(trifluoromethyl)benzyl)piperidin-4-yl)-6-fluoro-1-oxoisoindolin-2-yl)piperidine-2,6-dione C1104;

3-(6-fluoro-1-oxo-5-(1-((tetrahydro-2H-pyran-4-yl)methyl)piperidin-4-yl)-isoindolin-2-yl)piperidine-2,6-dione C1105;

3-(5-(1-((1-benzylpiperidin-4-yl)methyl)piperidin-4-yl)-6-fluoro-1-oxoisoindolin-2-yl)piperidine-2,6-dione C1106;

2-(3-(4-(2-(2,6-dioxopiperidin-3-yl)-6-fluoro-1-oxoisoindolin-5-yl)piperidin-1-yl)propyl)isoindoline-1,3-dione C1107;

3-(6-fluoro-1-oxo-5-(1-(3-(3-(trifluoromethyl)phenyl)propyl)piperidin-4-yl)-isoindolin-2-yl)piperidine-2,6-dione C1108;

3-(5-(1-((6-(dimethylamino)naphthalen-2-yl)methyl)piperidin-4-yl)-6-fluoro-1-oxoisoindolin-2-yl)piperidine-2,6-dione C1109;

N-(2-((4-(2-(2,6-dioxopiperidin-3-yl)-6-fluoro-1-oxoisoindolin-5-yl)piperidin-1-yl)methyl)phenyl)methanesulfonamide C1110;

N-(4-((4-(2-(2,6-dioxopiperidin-3-yl)-6-fluoro-1-oxoisoindolin-5-yl)piperidin-1-yl)methyl)phenyl)methanesulfonamide C1111;

N-(3-((4-(2-(2,6-dioxopiperidin-3-yl)-6-fluoro-1-oxoisoindolin-5-yl)piperidin-1-yl)methyl)phenyl)methanesulfonamide C1112;

3-(6-fluoro-1-oxo-5-(1-(2-(pyridin-2-yloxy)benzyl)piperidin-4-yl)isoindolin-2-yl)piperidine-2,6-dione C1113;

3-(5-(1-(4-bromophenethyl)piperidin-4-yl)-6-fluoro-1-oxoisoindolin-2-yl)-piperidine-2,6-dione C1114;

3-(6-fluoro-5-(1-((2-morpholinothiazol-5-yl)methyl)piperidin-4-yl)-1-oxoisoindolin-2-yl)piperidine-2,6-dione C1115;

3-(6-fluoro-1-oxo-5-(1-(thiazol-2-ylmethyl)piperidin-4-yl)isoindolin-2-yl)-piperidine-2,6-dione C1116;

3-(5-(1-(4-(ethylsulfonyl)benzyl)piperidin-4-yl)-6-fluoro-1-oxoisoindolin-2-yl)-piperidine-2,6-dione C1117;

3-(6-fluoro-5-(1-((4'-methyl-[2,2'-bipyridin]-4-yl)methyl)piperidin-4-yl)-1-oxoisoindolin-2-yl)piperidine-2,6-dione C1118;

3-(6-fluoro-1-oxo-5-(1-(4-phenoxybenzyl)piperidin-4-yl)isoindolin-2-yl)-piperidine-2,6-dione C1119;

3-(6-fluoro-1-oxo-5-(1-(3-phenoxybenzyl)piperidin-4-yl)isoindolin-2-yl)-piperidine-2,6-dione C1120;

3-(6-fluoro-1-oxo-5-(1-((6-(p-tolyl)pyridin-3-yl)methyl)piperidin-4-yl)isoindolin-2-yl)piperidine-2,6-dione C1121;

4-((4-(2-(2,6-dioxopiperidin-3-yl)-6-fluoro-1-oxoisoindolin-5-yl)piperidin-1-yl)-methyl)-N-isopropylbenzamide C1122;

3-(6-fluoro-5-(1-(2-morpholinobenzyl)piperidin-4-yl)-1-oxoisoindolin-2-yl)-piperidine-2,6-dione C1123;

3-(6-fluoro-5-(1-(3-morpholinobenzyl)piperidin-4-yl)-1-oxoisoindolin-2-yl)-piperidine-2,6-dione C1124;

3-(6-fluoro-5-(1-(4-morpholinobenzyl)piperidin-4-yl)-1-oxoisoindolin-2-yl)-piperidine-2,6-dione C1125;

3-(6-fluoro-1-oxo-5-(1-(3-(quinolin-6-yl)propyl)piperidin-4-yl)isoindolin-2-yl)-piperidine-2,6-dione C1126;
3-(6-fluoro-1-oxo-5-(1-(thiazol-5-ylmethyl)piperidin-4-yl)isoindolin-2-yl)-piperidine-2,6-dione C1127;
3-(5-(1-((1H-pyrrol-3-yl)methyl)piperidin-4-yl)-6-fluoro-1-oxoisoindolin-2-yl)-piperidine-2,6-dione C1128;
3-(6-fluoro-5-(1-((6-(methylsulfonyl)pyridin-2-yl)methyl)piperidin-4-yl)-1-oxoisoindolin-2-yl)piperidine-2,6-dione C1129;
3-(6-fluoro-1-oxo-5-(1-(3-(pyridin-4-yl)benzyl)piperidin-4-yl)isoindolin-2-yl)piperidine-2,6-dione C1130;
3-(5-(1-([1,1'-biphenyl]-4-ylmethyl)piperidin-4-yl)-6-fluoro-1-oxoisoindolin-2-yl)piperidine-2,6-dione C1131;
3-(6-fluoro-5-(1-((6-fluorochroman-8-yl)methyl)piperidin-4-yl)-1-oxoisoindolin-2-yl)piperidine-2,6-dione C1132;
3-(6-fluoro-1-oxo-5-(1-((6-(pyrrolidin-1-yl)pyridin-3-yl)methyl)piperidin-4-yl)-isoindolin-2-yl)piperidine-2,6-dione C1133;
3-(6-fluoro-1-oxo-5-(1-(3-(pyrrolidin-1-yl)benzyl)piperidin-4-yl)isoindolin-2-yl)-piperidine-2,6-dione C1134;
3-(6-fluoro-1-oxo-5-(1-(4-(pyrrolidin-1-yl)benzyl)piperidin-4-yl)isoindolin-2-yl)-piperidine-2,6-dione C1135;
3-(5-(1-(3-(1H-1,2,4-triazol-1-yl)benzyl)piperidin-4-yl)-6-fluoro-1-oxoisoindolin-2-yl)piperidine-2,6-dione C1136;
3-(5-(1-(2-(1H-1,2,4-triazol-1-yl)benzyl)piperidin-4-yl)-6-fluoro-1-oxoisoindolin-2-yl)piperidine-2,6-dione C1137;
3-(5-(1-(4-(1H-1,2,4-triazol-1-yl)benzyl)piperidin-4-yl)-6-fluoro-1-oxoisoindolin-2-yl)piperidine-2,6-dione C1138;
3-(6-fluoro-1-oxo-5-(1-(thiazol-4-ylmethyl)piperidin-4-yl)isoindolin-2-yl)-piperidine-2,6-dione C1139;
3-(6-fluoro-1-oxo-5-(1-((1-phenyl-1H-pyrazol-3-yl)methyl)piperidin-4-yl)-isoindolin-2-yl)piperidine-2,6-dione C1140;
3-(6-fluoro-1-oxo-5-(1-((5-phenyl-1H-imidazol-2-yl)methyl)piperidin-4-yl)-isoindolin-2-yl)piperidine-2,6-dione C1141;
3-(5-(1-(3-(1H-imidazol-1-yl)benzyl)piperidin-4-yl)-6-fluoro-1-oxoisoindolin-2-yl)piperidine-2,6-dione C1142;
3-(6-fluoro-1-oxo-5-(1-((2-phenyl-1H-imidazol-5-yl)methyl)piperidin-4-yl)-isoindolin-2-yl)piperidine-2,6-dione C1143;
3-(5-(1-(4-(1H-imidazol-1-yl)benzyl)piperidin-4-yl)-6-fluoro-1-oxoisoindolin-2-yl)piperidine-2,6-dione C1144;
3-(5-(1-(4-(1H-pyrazol-1-yl)benzyl)piperidin-4-yl)-6-fluoro-1-oxoisoindolin-2-yl)piperidine-2,6-dione C1145;
2-((4-(2-(2,6-dioxopiperidin-3-yl)-6-fluoro-1-oxoisoindolin-5-yl)piperidin-1-yl)-methyl)-1H-indole-6-carbonitrile C1146;
3-((4-(2-(2,6-dioxopiperidin-3-yl)-6-fluoro-1-oxoisoindolin-5-yl)piperidin-1-yl)-methyl)-1H-indole-6-carbonitrile C1147;
3-(5-(1-((2,3-dihydro-[1,4]dioxino[2,3-b]pyridin-6-yl)methyl)piperidin-4-yl)-6-fluoro-1-oxoisoindolin-2-yl)piperidine-2,6-dione C1148;
3-(5-(1-((adamantan-1-yl)methyl)piperidin-4-yl)-6-fluoro-1-oxoisoindolin-2-yl)-piperidine-2,6-dione C1149;
3-(6-fluoro-1-oxo-5-(1-(thiophen-2-ylmethyl)piperidin-4-yl)isoindolin-2-yl)-piperidine-2,6-dione C1150;
3-(5-(1-(3-(benzyloxy)propyl)piperidin-4-yl)-6-fluoro-1-oxoisoindolin-2-yl)-piperidine-2,6-dione C1151;
3-(6-fluoro-5-(1-(3-(2-methoxyphenyl)propyl)piperidin-4-yl)-1-oxoisoindolin-2-yl)piperidine-2,6-dione C1152;
3-(5-(1-((2,3-dihydrobenzo[b][1,4]dioxin-6-yl)methyl)piperidin-4-yl)-6-fluoro-1-oxoisoindolin-2-yl)piperidine-2,6-dione C1153;

3-(6-fluoro-5-(1-((5-fluoro-1H-benzo[d]imidazol-2-yl)methyl)piperidin-4-yl)-1-oxoisoindolin-2-yl)piperidine-2,6-dione C1154;
3-(6-fluoro-5-(1-((4-fluorobenzofuran-7-yl)methyl)piperidin-4-yl)-1-oxoisoindolin-2-yl)piperidine-2,6-dione C1155;
3-(5-(1-(4-(dimethylamino)-3-methylbenzyl)piperidin-4-yl)-6-fluoro-1-oxoisoindolin-2-yl)piperidine-2,6-dione C1156;
3-(5-(1-((2-(tert-butyl)pyridin-4-yl)methyl)piperidin-4-yl)-6-fluoro-1-oxoisoindolin-2-yl)piperidine-2,6-dione C1157;
3-(5-(1-(4-((dimethylamino)methyl)benzyl)piperidin-4-yl)-6-fluoro-1-oxoisoindolin-2-yl)piperidine-2,6-dione C1158;
3-(6-fluoro-1-oxo-5-(1-(thieno[3,2-c]pyridin-2-ylmethyl)piperidin-4-yl)-isoindolin-2-yl)piperidine-2,6-dione C1159;
3-(5-(1-(benzo[d]thiazol-4-ylmethyl)piperidin-4-yl)-6-fluoro-1-oxoisoindolin-2-yl)piperidine-2,6-dione C1160;
3-(6-fluoro-1-oxo-5-(1-(thiophen-3-ylmethyl)piperidin-4-yl)isoindolin-2-yl)-piperidine-2,6-dione C1161;
3-(6-fluoro-1-oxo-5-(1-(thieno[2,3-b]pyridin-2-ylmethyl)piperidin-4-yl)-isoindolin-2-yl)piperidine-2,6-dione C1162;
3-(5-(1-((3,4-dihydro-2H-pyrano[2,3-c]pyridin-6-yl)methyl)piperidin-4-yl)-6-fluoro-1-oxoisoindolin-2-yl)piperidine-2,6-dione C1163;
3-(6-fluoro-5-(1-(3-methyl-3-phenylbutyl)piperidin-4-yl)-1-oxoisoindolin-2-yl)-piperidine-2,6-dione C1164;
3-(5-(1-(benzo[b]thiophen-3-ylmethyl)piperidin-4-yl)-6-fluoro-1-oxoisoindolin-2-yl)piperidine-2,6-dione C1165;
3-(5-(1-(benzo[b]thiophen-2-ylmethyl)piperidin-4-yl)-6-fluoro-1-oxoisoindolin-2-yl)piperidine-2,6-dione C1166;
3-(5-(1-(chroman-6-ylmethyl)piperidin-4-yl)-6-fluoro-1-oxoisoindolin-2-yl)-piperidine-2,6-dione C1167;
3-(6-fluoro-5-(1-((1-methyl-1H-imidazo[4,5-b]pyridin-2-yl)methyl)piperidin-4-yl)-1-oxoisoindolin-2-yl)piperidine-2,6-dione C1168;
4-((4-(2-(2,6-dioxopiperidin-3-yl)-6-fluoro-1-oxoisoindolin-5-yl)piperidin-1-yl)-methyl)-2-methoxybenzonitrile C1169;
4-((4-(2-(2,6-dioxopiperidin-3-yl)-6-fluoro-1-oxoisoindolin-5-yl)piperidin-1-yl)-methyl)-3-methoxybenzonitrile C1170;
2-((4-(2-(2,6-dioxopiperidin-3-yl)-6-fluoro-1-oxoisoindolin-5-yl)piperidin-1-yl)-methyl)-5-methoxybenzonitrile C1171;
3-(6-fluoro-5-(1-((2-methyl-2H-tetrazol-5-yl)methyl)piperidin-4-yl)-1-oxoisoindolin-2-yl)piperidine-2,6-dione C1172;
3-(6-fluoro-5-(1-((2-methylbenzo[d]oxazol-6-yl)methyl)piperidin-4-yl)-1-oxoisoindolin-2-yl)piperidine-2,6-dione C1173;
3-(6-fluoro-1-oxo-5-(1-((3-oxoisoindolin-5-yl)methyl)piperidin-4-yl)isoindolin-2-yl)piperidine-2,6-dione C1174;
3-(6-fluoro-1-oxo-5-(1-((1-oxoisoindolin-5-yl)methyl)piperidin-4-yl)isoindolin-2-yl)piperidine-2,6-dione C1175;
3-(6-fluoro-1-oxo-5-(1-((5,6,7,8-tetrahydronaphthalen-1-yl)methyl)piperidin-4-yl)isoindolin-2-yl)piperidine-2,6-dione C1176;
3-(6-fluoro-5-(1-((3-methylimidazo[1,2-a]pyridin-2-yl)methyl)piperidin-4-yl)-1-oxoisoindolin-2-yl)piperidine-2,6-dione C1177;
3-(6-fluoro-5-(1-((1-methyl-1H-indazol-6-yl)methyl)piperidin-4-yl)-1-oxoisoindolin-2-yl)piperidine-2,6-dione C1178;

3-(6-fluoro-5-(1-((2-methyl-2H-indazol-5-yl)methyl)piperidin-4-yl)-1-oxoisoindolin-2-yl)piperidine-2,6-dione C1179;

3-(6-fluoro-5-(1-((6-methylimidazo[1,2-a]pyridin-2-yl)methyl)piperidin-4-yl)-1-oxoisoindolin-2-yl)piperidine-2,6-dione C1180;

3-(6-fluoro-5-(1-((5-methylimidazo[1,2-a]pyridin-3-yl)methyl)piperidin-4-yl)-1-oxoisoindolin-2-yl)piperidine-2,6-dione C1181;

3-(6-fluoro-5-(1-((7-methylimidazo[1,2-a]pyridin-3-yl)methyl)piperidin-4-yl)-1-oxoisoindolin-2-yl)piperidine-2,6-dione C1182;

3-(6-fluoro-5-(1-((5-methyl-4H-1,2,4-triazol-3-yl)methyl)piperidin-4-yl)-1-oxoisoindolin-2-yl)piperidine-2,6-dione C1183;

3-(6-fluoro-5-(1-((1-methyl-1H-indazol-4-yl)methyl)piperidin-4-yl)-1-oxoisoindolin-2-yl)piperidine-2,6-dione C1184;

3-(6-fluoro-5-(1-((5-methyl-1H-pyrrolo[2,3-b]pyridin-3-yl)methyl)piperidin-4-yl)-1-oxoisoindolin-2-yl)piperidine-2,6-dione C1185;

3-(6-fluoro-5-(1-((1-methyl-1H-benzo[d]imidazol-2-yl)methyl)piperidin-4-yl)-1-oxoisoindolin-2-yl)piperidine-2,6-dione C1186;

3-(6-fluoro-5-(1-((2-methylimidazo[1,2-a]pyridin-3-yl)methyl)piperidin-4-yl)-1-oxoisoindolin-2-yl)piperidine-2,6-dione C1187;

3-(6-fluoro-5-(1-((2-methyl-2H-indazol-3-yl)methyl)piperidin-4-yl)-1-oxoisoindolin-2-yl)piperidine-2,6-dione C1188;

3-(6-fluoro-5-(1-((7-methyl-1H-indol-3-yl)methyl)piperidin-4-yl)-1-oxoisoindolin-2-yl)piperidine-2,6-dione C1189;

3-(6-fluoro-5-(1-((1-methyl-1H-indol-5-yl)methyl)piperidin-4-yl)-1-oxoisoindolin-2-yl)piperidine-2,6-dione C1190;

3-(6-fluoro-5-(1-((2-methyl-1H-indol-4-yl)methyl)piperidin-4-yl)-1-oxoisoindolin-2-yl)piperidine-2,6-dione C1191;

3-(6-fluoro-5-(1-((1-methyl-1H-indol-6-yl)methyl)piperidin-4-yl)-1-oxoisoindolin-2-yl)piperidine-2,6-dione C1192;

3-(6-fluoro-5-(1-((4-methyl-1H-indol-3-yl)methyl)piperidin-4-yl)-1-oxoisoindolin-2-yl)piperidine-2,6-dione C1193;

3-(6-fluoro-5-(1-((4-methyloxazol-5-yl)methyl)piperidin-4-yl)-1-oxoisoindolin-2-yl)piperidine-2,6-dione C1194;

3-(6-fluoro-5-(1-((3-methyl-1H-indol-2-yl)methyl)piperidin-4-yl)-1-oxoisoindolin-2-yl)piperidine-2,6-dione C1195;

3-(6-fluoro-5-(1-((6-methyl-1H-indol-3-yl)methyl)piperidin-4-yl)-1-oxoisoindolin-2-yl)piperidine-2,6-dione C1196;

tert-butyl (2-(4-(2-(2,6-dioxopiperidin-3-yl)-6-fluoro-1-oxoisoindolin-5-yl)-piperidin-1-yl)ethyl)carbamate C1197;

3-(6-fluoro-1-oxo-5-(1-(quinoxalin-6-ylmethyl)piperidin-4-yl)isoindolin-2-yl)piperidine-2,6-dione C1198;

3-(5-(1-((1,8-naphthyridin-2-yl)methyl)piperidin-4-yl)-6-fluoro-1-oxoisoindolin-2-yl)piperidine-2,6-dione C1199;

3-(6-fluoro-1-oxo-5-(1-(quinoxalin-2-ylmethyl)piperidin-4-yl)isoindolin-2-yl)-piperidine-2,6-dione C1200;

3-(6-fluoro-1-oxo-5-(1-(quinoxalin-5-ylmethyl)piperidin-4-yl)isoindolin-2-yl)-piperidine-2,6-dione C1201;

3-(6-fluoro-1-oxo-5-(1-(quinolin-8-ylmethyl)piperidin-4-yl)isoindolin-2-yl)-piperidine-2,6-dione C1202;

3-(6-fluoro-5-(1-(isoquinolin-4-ylmethyl)piperidin-4-yl)-1-oxoisoindolin-2-yl)-piperidine-2,6-dione C1203;

3-(6-fluoro-5-(1-(isoquinolin-3-ylmethyl)piperidin-4-yl)-1-oxoisoindolin-2-yl)-piperidine-2,6-dione C1204;

3-(6-fluoro-5-(1-((2-methyloxazol-4-yl)methyl)piperidin-4-yl)-1-oxoisoindolin-2-yl)piperidine-2,6-dione C1205;

3-(6-fluoro-5-(1-(isoquinolin-8-ylmethyl)piperidin-4-yl)-1-oxoisoindolin-2-yl)-piperidine-2,6-dione C1206;

3-(6-fluoro-5-(1-(isoquinolin-5-ylmethyl)piperidin-4-yl)-1-oxoisoindolin-2-yl)-piperidine-2,6-dione C1207;

3-(6-fluoro-1-oxo-5-(1-(quinolin-4-ylmethyl)piperidin-4-yl)isoindolin-2-yl)-piperidine-2,6-dione C1208;

3-(6-fluoro-1-oxo-5-(1-(quinolin-6-ylmethyl)piperidin-4-yl)isoindolin-2-yl)-piperidine-2,6-dione C1209;

3-(6-fluoro-5-(1-(naphthalen-2-ylmethyl)piperidin-4-yl)-1-oxoisoindolin-2-yl)-piperidine-2,6-dione C1210;

3-(5-(1-(2-amino-6-chlorobenzyl)piperidin-4-yl)-6-fluoro-1-oxoisoindolin-2-yl)-piperidine-2,6-dione C1211;

3-(5-(1-(2-amino-4-chlorobenzyl)piperidin-4-yl)-6-fluoro-1-oxoisoindolin-2-yl)-piperidine-2,6-dione C1212;

3-(5-(1-(2-amino-3-chlorobenzyl)piperidin-4-yl)-6-fluoro-1-oxoisoindolin-2-yl)-piperidine-2,6-dione C1213;

3-(5-(1-((5-(dimethylamino)thiophen-2-yl)methyl)piperidin-4-yl)-6-fluoro-1-oxoisoindolin-2-yl)piperidine-2,6-dione C1214;

3-(5-(1-(4-chlorophenethyl)piperidin-4-yl)-6-fluoro-1-oxoisoindolin-2-yl)-piperidine-2,6-dione C1215;

3-(6-fluoro-5-(1-((2-methyloxazol-5-yl)methyl)piperidin-4-yl)-1-oxoisoindolin-2-yl)piperidine-2,6-dione C1216;

3-(6-fluoro-5-(1-((4-hydroxybicyclo[2.2.2]octan-1-yl)methyl)piperidin-4-yl)-1-oxoisoindolin-2-yl)piperidine-2,6-dione C1217;

3-(6-fluoro-5-(1-((2-(methylthio)pyrimidin-4-yl)methyl)piperidin-4-yl)-1-oxoisoindolin-2-yl)piperidine-2,6-dione C1218;

3-(5-(1-((2-cyclopropylthiazol-5-yl)methyl)piperidin-4-yl)-6-fluoro-1-oxoisoindolin-2-yl)piperidine-2,6-dione C1219;

3-(5-(1-((1-(tert-butyl)-1H-1,2,3-triazol-4-yl)methyl)piperidin-4-yl)-6-fluoro-1-oxoisoindolin-2-yl)piperidine-2,6-dione C1220;

3-(6-fluoro-5-(1-((1-isobutyl-1H-pyrazol-4-yl)methyl)piperidin-4-yl)-1-oxoisoindolin-2-yl)piperidine-2,6-dione C1221;

3-(5-(1-((5,6-dihydro-8H-imidazo[2,1-c][1,4]oxazin-3-yl)methyl)piperidin-4-yl)-6-fluoro-1-oxoisoindolin-2-yl)piperidine-2,6-dione C1222;

3-(5-(1-((5,6-dihydro-8H-imidazo[2,1-c][1,4]oxazin-2-yl)methyl)piperidin-4-yl)-6-fluoro-1-oxoisoindolin-2-yl)piperidine-2,6-dione C1223;

3-(5-(1-((5-(tert-butyl)-1H-pyrrol-2-yl)methyl)piperidin-4-yl)-6-fluoro-1-oxoisoindolin-2-yl)piperidine-2,6-dione C1224;

3-(5-(1-((2-(dimethylamino)pyrimidin-5-yl)methyl)piperidin-4-yl)-6-fluoro-1-oxoisoindolin-2-yl)piperidine-2,6-dione C1225;

3-(6-fluoro-5-(1-(4-methoxy-3-methylbenzyl)piperidin-4-yl)-1-oxoisoindolin-2-yl)piperidine-2,6-dione C1226;

3-(6-fluoro-5-(1-((1-methyl-1H-imidazol-5-yl)methyl)piperidin-4-yl)-1-oxoisoindolin-2-yl)piperidine-2,6-dione C1227;

3-(6-fluoro-5-(1-(2-methoxy-3-methylbenzyl)piperidin-4-yl)-1-oxoisoindolin-2-yl)piperidine-2,6-dione C1228;

3-(6-fluoro-5-(1-(3-methoxy-2-methylbenzyl)piperidin-4-yl)-1-oxoisoindolin-2-yl)piperidine-2,6-dione C1229;

3-(6-fluoro-5-(1-(2-methoxy-6-methylbenzyl)piperidin-4-yl)-1-oxoisoindolin-2-yl)piperidine-2,6-dione C1230;

3-(6-fluoro-5-(1-(3-methoxy-5-methylbenzyl)piperidin-4-yl)-1-oxoisoindolin-2-yl)piperidine-2,6-dione C1231;
3-(6-fluoro-5-(1-(4-methoxyphenethyl)piperidin-4-yl)-1-oxoisoindolin-2-yl)-piperidine-2,6-dione C1232;
3-(6-fluoro-5-(1-(3-methoxyphenethyl)piperidin-4-yl)-1-oxoisoindolin-2-yl)-piperidine-2,6-dione C1233;
3-(6-fluoro-5-(1-(4-methoxy-2-methylbenzyl)piperidin-4-yl)-1-oxoisoindolin-2-yl)piperidine-2,6-dione C1234;
3-(6-fluoro-5-(1-(4-hydroxy-3,5-dimethylbenzyl)piperidin-4-yl)-1-oxoisoindolin-2-yl)piperidine-2,6-dione C1235;
3-(5-(1-(4-ethoxybenzyl)piperidin-4-yl)-6-fluoro-1-oxoisoindolin-2-yl)-piperidine-2,6-dione C1236;
3-(6-fluoro-5-(1-(3-methoxy-4-methylbenzyl)piperidin-4-yl)-1-oxoisoindolin-2-yl)piperidine-2,6-dione C1237;
3-(6-fluoro-5-(1-((1-methyl-1H-pyrazol-5-yl)methyl)piperidin-4-yl)-1-oxoisoindolin-2-yl)piperidine-2,6-dione C1238;
3-(5-(1-((1H-pyrrol-2-yl)methyl)piperidin-4-yl)-6-fluoro-1-oxoisoindolin-2-yl)-piperidine-2,6-dione C1239;
3-(6-fluoro-5-(1-(2-methoxy-4-methylbenzyl)piperidin-4-yl)-1-oxoisoindolin-2-yl)piperidine-2,6-dione C1240;
3-(5-(1-(2-(benzyloxy)ethyl)piperidin-4-yl)-6-fluoro-1-oxoisoindolin-2-yl)-piperidine-2,6-dione C1241;
3-(5-(1-(benzo[d][1,3]dioxol-4-ylmethyl)piperidin-4-yl)-6-fluoro-1-oxoisoindolin-2-yl)piperidine-2,6-dione C1242;
3-(5-(1-(2-(dimethylamino)benzyl)piperidin-4-yl)-6-fluoro-1-oxoisoindolin-2-yl)piperidine-2,6-dione C1243;
3-(6-fluoro-5-(1-((5-isopropylpyridin-3-yl)methyl)piperidin-4-yl)-1-oxoisoindolin-2-yl)piperidine-2,6-dione C1244;
3-(5-(1-(4-(ethylamino)benzyl)piperidin-4-yl)-6-fluoro-1-oxoisoindolin-2-yl)-piperidine-2,6-dione C1245;
3-(5-(1-(3-(dimethylamino)benzyl)piperidin-4-yl)-6-fluoro-1-oxoisoindolin-2-yl)piperidine-2,6-dione C1246;
3-((4-(2-(2,6-dioxopiperidin-3-yl)-6-fluoro-1-oxoisoindolin-5-yl)piperidin-1-yl)-methyl)benzamide C1247;
2-((4-(2-(2,6-dioxopiperidin-3-yl)-6-fluoro-1-oxoisoindolin-5-yl)piperidin-1-yl)-methyl)-4-fluorobenzonitrile C1248;
2-((4-(2-(2,6-dioxopiperidin-3-yl)-6-fluoro-1-oxoisoindolin-5-yl)piperidin-1-yl)-methyl)-5-fluorobenzonitrile C1249;
3-(6-fluoro-5-(1-((1-methyl-1H-pyrazol-3-yl)methyl)piperidin-4-yl)-1-oxoisoindolin-2-yl)piperidine-2,6-dione C1250;
4-((4-(2-(2,6-dioxopiperidin-3-yl)-6-fluoro-1-oxoisoindolin-5-yl)piperidin-1-yl)-methyl)-3-fluorobenzonitrile C1251;
3-((4-(2-(2,6-dioxopiperidin-3-yl)-6-fluoro-1-oxoisoindolin-5-yl)piperidin-1-yl)-methyl)-5-fluorobenzonitrile C1252;
4-((4-(2-(2,6-dioxopiperidin-3-yl)-6-fluoro-1-oxoisoindolin-5-yl)piperidin-1-yl)-methyl)-2-fluorobenzonitrile C1253;
5-((4-(2-(2,6-dioxopiperidin-3-yl)-6-fluoro-1-oxoisoindolin-5-yl)piperidin-1-yl)-methyl)-2-fluorobenzonitrile C1254;
3-(6-fluoro-1-oxo-5-(1-(2,4,6-trimethylbenzyl)piperidin-4-yl)isoindolin-2-yl)-piperidine-2,6-dione C1255;
3-(6-fluoro-5-(1-(4-isopropylbenzyl)piperidin-4-yl)-1-oxoisoindolin-2-yl)-piperidine-2,6-dione C1256;
3-(6-fluoro-1-oxo-5-(1-(4-phenylbutyl)piperidin-4-yl)isoindolin-2-yl)piperidine-2,6-dione C1257;
3-(5-(1-((4,4-difluorocyclohexyl)methyl)piperidin-4-yl)-6-fluoro-1-oxoisoindolin-2-yl)piperidine-2,6-dione C1258;
3-(5-(1-(2-ethynyl-4-fluorobenzyl)piperidin-4-yl)-6-fluoro-1-oxoisoindolin-2-yl)-piperidine-2,6-dione C1259;
3-(5-(1-([1,2,4]triazolo[1,5-a]pyridin-7-ylmethyl)piperidin-4-yl)-6-fluoro-1-oxoisoindolin-2-yl)piperidine-2,6-dione C1260;
3-(6-fluoro-5-(1-((1-methyl-1H-imidazol-4-yl)methyl)piperidin-4-yl)-1-oxoisoindolin-2-yl)piperidine-2,6-dione C1261;
3-(6-fluoro-5-(1-(imidazo[1,2-a]pyrimidin-3-ylmethyl)piperidin-4-yl)-1-oxoisoindolin-2-yl)piperidine-2,6-dione C1262;
6-amino-5-((4-(2-(2,6-dioxopiperidin-3-yl)-6-fluoro-1-oxoisoindolin-5-yl)-piperidin-1-yl)methyl)nicotinonitrile C1263;
3-(6-fluoro-5-(1-(imidazo[1,2-a]pyrimidin-7-ylmethyl)piperidin-4-yl)-1-oxoisoindolin-2-yl)piperidine-2,6-dione C1264;
3-(5-(1-((4H-pyrrolo[2,3-b]pyrazin-7-yl)methyl)piperidin-4-yl)-6-fluoro-1-oxoisoindolin-2-yl)piperidine-2,6-dione C1265;
4-((4-(2-(2,6-dioxopiperidin-3-yl)-6-fluoro-1-oxoisoindolin-5-yl)piperidin-1-yl)-methyl)-3-hydroxybenzonitrile C1266;
5-((4-(2-(2,6-dioxopiperidin-3-yl)-6-fluoro-1-oxoisoindolin-5-yl)piperidin-1-yl)-methyl)-2-hydroxybenzonitrile C1267;
3-(6-fluoro-5-(1-(furo[2,3-c]pyridin-5-ylmethyl)piperidin-4-yl)-1-oxoisoindolin-2-yl)piperidine-2,6-dione C1268;
3-(5-(1-(benzo[d]oxazol-5-ylmethyl)piperidin-4-yl)-6-fluoro-1-oxoisoindolin-2-yl)piperidine-2,6-dione C1269;
3-(5-(1-(benzo[d]oxazol-6-ylmethyl)piperidin-4-yl)-6-fluoro-1-oxoisoindolin-2-yl)piperidine-2,6-dione C1270;
3-(5-(1-((5-chlorothiophen-2-yl)methyl)piperidin-4-yl)-6-fluoro-1-oxoisoindolin-2-yl)piperidine-2,6-dione C1271;
3-(6-fluoro-5-(1-((1-methyl-1H-imidazol-2-yl)methyl)piperidin-4-yl)-1-oxoisoindolin-2-yl)piperidine-2,6-dione C1272;
3-(5-(1-((2-chlorothiophen-3-yl)methyl)piperidin-4-yl)-6-fluoro-1-oxoisoindolin-2-yl)piperidine-2,6-dione C1273;
3-(5-(1-(4-cyclopropylbenzyl)piperidin-4-yl)-6-fluoro-1-oxoisoindolin-2-yl)-piperidine-2,6-dione C1274;
3-(5-(1-(2-cyclopropylbenzyl)piperidin-4-yl)-6-fluoro-1-oxoisoindolin-2-yl)-piperidine-2,6-dione C1275;
3-(6-fluoro-1-oxo-5-(1-(pyrazolo[1,5-a]pyridin-7-ylmethyl) piperidin-4-yl)-isoindolin-2-yl)piperidine-2,6-dione C1276;
3-(5-(1-((1H-pyrrolo[2,3-c]pyridin-3-yl)methyl)piperidin-4-yl)-6-fluoro-1-oxoisoindolin-2-yl)piperidine-2,6-dione C1277;
3-(6-fluoro-5-(1-(imidazo[1,2-a]pyridin-5-ylmethyl)piperidin-4-yl)-1-oxoisoindolin-2-yl)piperidine-2,6-dione C1278;
3-(6-fluoro-1-oxo-5-(1-(pyrazolo[1,5-a]pyridin-3-ylmethyl) piperidin-4-yl)-isoindolin-2-yl)piperidine-2,6-dione C1279;
3-(5-(1-((2H-indazol-6-yl)methyl)piperidin-4-yl)-6-fluoro-1-oxoisoindolin-2-yl)-piperidine-2,6-dione C1280;
3-(5-(1-((1H-pyrrolo[3,2-b]pyridin-3-yl)methyl)piperidin-4-yl)-6-fluoro-1-oxoisoindolin-2-yl)piperidine-2,6-dione C1281;
3-(6-fluoro-5-(1-(imidazo[1,5-a]pyridin-1-ylmethyl)piperidin-4-yl)-1-oxoisoindolin-2-yl)piperidine-2,6-dione C1282;
3-(6-fluoro-5-(1-((5-methyl-1H-pyrazol-3-yl)methyl)piperidin-4-yl)-1-oxoisoindolin-2-yl)piperidine-2,6-dione C1283;
3-(5-(1-((1H-pyrrolo[2,3-b]pyridin-6-yl)methyl)piperidin-4-yl)-6-fluoro-1-oxoisoindolin-2-yl)piperidine-2,6-dione C1284;

3-(5-(1-((1H-benzo[d]imidazol-7-yl)methyl)piperidin-4-yl)-6-fluoro-1-oxoisoindolin-2-yl)piperidine-2,6-dione C1285;
3-(6-fluoro-5-(1-(imidazo[1,2-a]pyridin-6-ylmethyl)piperidin-4-yl)-1-oxoisoindolin-2-yl)piperidine-2,6-dione C1286;
3-(6-fluoro-5-(1-(imidazo[1,2-a]pyridin-8-ylmethyl)piperidin-4-yl)-1-oxoisoindolin-2-yl)piperidine-2,6-dione C1287;
3-(6-fluoro-5-(1-(imidazo[1,2-a]pyridin-7-ylmethyl)piperidin-4-yl)-1-oxoisoindolin-2-yl)piperidine-2,6-dione C1288;
3-(5-(1-((1H-pyrrolo[3,2-b]pyridin-6-yl)methyl)piperidin-4-yl)-6-fluoro-1-oxoisoindolin-2-yl)piperidine-2,6-dione C1289;
3-(5-(1-((1H-benzo[d]imidazol-2-yl)methyl)piperidin-4-yl)-6-fluoro-1-oxoisoindolin-2-yl)piperidine-2,6-dione C1290;
3-(6-fluoro-5-(1-(imidazo[1,2-a]pyridin-3-ylmethyl)piperidin-4-yl)-1-oxoisoindolin-2-yl)piperidine-2,6-dione C1291;
3-(6-fluoro-5-(1-(imidazo[1,2-a]pyridin-2-ylmethyl)piperidin-4-yl)-1-oxoisoindolin-2-yl)piperidine-2,6-dione C1292;
3-(5-(1-(benzofuran-4-ylmethyl)piperidin-4-yl)-6-fluoro-1-oxoisoindolin-2-yl)-piperidine-2,6-dione C1293;
3-(6-fluoro-5-(1-((5-methylfuran-2-yl)methyl)piperidin-4-yl)-1-oxoisoindolin-2-yl)-piperidine-2,6-dione C1294;
3-(5-(1-(benzofuran-7-ylmethyl)piperidin-4-yl)-6-fluoro-1-oxoisoindolin-2-yl)-piperidine-2,6-dione C1295;
3-(5-(1-(benzofuran-5-ylmethyl)piperidin-4-yl)-6-fluoro-1-oxoisoindolin-2-yl)-piperidine-2,6-dione C1296;
2-((4-(2-(2,6-dioxopiperidin-3-yl)-6-fluoro-1-oxoisoindolin-5-yl)piperidin-1-yl)-methyl)-5-methylbenzonitrile C1297;
3-((4-(2-(2,6-dioxopiperidin-3-yl)-6-fluoro-1-oxoisoindolin-5-yl)piperidin-1-yl)-methyl)-2-methylbenzonitrile C1298;
3-((4-(2-(2,6-dioxopiperidin-3-yl)-6-fluoro-1-oxoisoindolin-5-yl)piperidin-1-yl)-methyl)-5-methylbenzonitrile C1299;
2-((4-(2-(2,6-dioxopiperidin-3-yl)-6-fluoro-1-oxoisoindolin-5-yl)piperidin-1-yl)-methyl)-6-methylbenzonitrile C1300;
4-((4-(2-(2,6-dioxopiperidin-3-yl)-6-fluoro-1-oxoisoindolin-5-yl)piperidin-1-yl)-methyl)-3-methylbenzonitrile C1301;
3-(5-(1-((1H-indol-3-yl)methyl)piperidin-4-yl)-6-fluoro-1-oxoisoindolin-2-yl)-piperidine-2,6-dione C1302;
3-(6-fluoro-5-(1-(indolizin-1-ylmethyl)piperidin-4-yl)-1-oxoisoindolin-2-yl)-piperidine-2,6-dione C1303;
3-(5-(1-((1H-indol-7-yl)methyl)piperidin-4-yl)-6-fluoro-1-oxoisoindolin-2-yl)-piperidine-2,6-dione C1304;
3-(6-fluoro-5-(1-((3-methyl-1H-pyrrol-2-yl)methyl)piperidin-4-yl)-1-oxoisoindolin-2-yl)piperidine-2,6-dione C1305;
3-(5-(1-((1H-indol-2-yl)methyl)piperidin-4-yl)-6-fluoro-1-oxoisoindolin-2-yl)-piperidine-2,6-dione C1306;
3-(5-(1-((1H-indol-6-yl)methyl)piperidin-4-yl)-6-fluoro-1-oxoisoindolin-2-yl)-piperidine-2,6-dione C1307;
3-(5-(1-((4-chloro-1-methyl-1H-pyrazol-3-yl)methyl)piperidin-4-yl)-6-fluoro-1-oxoisoindolin-2-yl)piperidine-2,6-dione C1308;
3-(5-(1-((3-chloropyrazin-2-yl)methyl)piperidin-4-yl)-6-fluoro-1-oxoisoindolin-2-yl)piperidine-2,6-dione C1309;
3-(5-(1-((3-chloropyridin-4-yl)methyl)piperidin-4-yl)-6-fluoro-1-oxoisoindolin-2-yl)piperidine-2,6-dione C1310;
3-(5-(1-((6-chloropyridin-2-yl)methyl)piperidin-4-yl)-6-fluoro-1-oxoisoindolin-2-yl)piperidine-2,6-dione C1311;
3-(6-fluoro-5-(1-((5-fluoro-2-oxo-1,2-dihydropyridin-3-yl)methyl)piperidin-4-yl)-1-oxoisoindolin-2-yl)piperidine-2,6-dione C1312;
3-(5-(1-(2-chlorobenzyl)piperidin-4-yl)-6-fluoro-1-oxoisoindolin-2-yl)piperidine-2,6-dione C1313;
3-(5-(1-(4-chlorobenzyl)piperidin-4-yl)-6-fluoro-1-oxoisoindolin-2-yl)piperidine-2,6-dione C1314;
3-(5-(1-(3-chlorobenzyl)piperidin-4-yl)-6-fluoro-1-oxoisoindolin-2-yl)piperidine-2,6-dione C1315;
3-(6-fluoro-5-(1-((5-methyl-1H-pyrrol-2-yl)methyl)piperidin-4-yl)-1-oxoisoindolin-2-yl)piperidine-2,6-dione C1316;
3-(5-(1-(2-amino-5-fluorobenzyl)piperidin-4-yl)-6-fluoro-1-oxoisoindolin-2-yl)-piperidine-2,6-dione C1317;
3-(6-fluoro-5-(1-((1-isopropyl-1H-pyrazol-4-yl)methyl)piperidin-4-yl)-1-oxoisoindolin-2-yl)piperidine-2,6-dione C1318;
3-(6-fluoro-5-(1-((4-isopropylfuran-2-yl)methyl)piperidin-4-yl)-1-oxoisoindolin-2-yl)piperidine-2,6-dione C1319;
3-(6-fluoro-5-(1-(3-(5-methylfuran-2-yl)propyl)piperidin-4-yl)-1-oxoisoindolin-2-yl)piperidine-2,6-dione C1320;
3-(6-fluoro-5-(1-(4-fluorophenethyl)piperidin-4-yl)-1-oxoisoindolin-2-yl)-piperidine-2,6-dione C1321;
3-(6-fluoro-5-(1-(3-fluoro-2-methylbenzyl)piperidin-4-yl)-1-oxoisoindolin-2-yl)-piperidine-2,6-dione C1322;
3-(6-fluoro-5-(1-(2-fluoro-5-methylbenzyl)piperidin-4-yl)-1-oxoisoindolin-2-yl)-piperidine-2,6-dione C1323;
3-(6-fluoro-5-(1-(4-fluoro-3-methylbenzyl)piperidin-4-yl)-1-oxoisoindolin-2-yl)-piperidine-2,6-dione C1324;
3-(6-fluoro-5-(1-(3-fluoro-5-methylbenzyl)piperidin-4-yl)-1-oxoisoindolin-2-yl)-piperidine-2,6-dione C1325;
3-(6-fluoro-5-(1-(4-fluoro-2-methylbenzyl)piperidin-4-yl)-1-oxoisoindolin-2-yl)-piperidine-2,6-dione C1326;
3-(6-fluoro-5-(1-((1-methyl-1H-pyrrol-2-yl)methyl)piperidin-4-yl)-1-oxoisoindolin-2-yl)piperidine-2,6-dione C1327;
3-(6-fluoro-5-(1-(5-fluoro-2-methylbenzyl)piperidin-4-yl)-1-oxoisoindolin-2-yl)-piperidine-2,6-dione C1328;
3-(6-fluoro-5-(1-((5-methoxypyrazin-2-yl)methyl)piperidin-4-yl)-1-oxoisoindolin-2-yl)piperidine-2,6-dione C1329;
3-(6-fluoro-5-(1-((2-methoxypyrimidin-4-yl)methyl)piperidin-4-yl)-1-oxoisoindolin-2-yl)piperidine-2,6-dione C1330;
5-((4-(2-(2,6-dioxopiperidin-3-yl)-6-fluoro-1-oxoisoindolin-5-yl)piperidin-1-yl)-methyl)thiophene-2-carbonitrile C1331;
3-(6-fluoro-5-(1-((2-methoxypyridin-4-yl)methyl)piperidin-4-yl)-1-oxoisoindolin-2-yl)piperidine-2,6-dione C1332;
3-(6-fluoro-5-(1-((2-methoxypyridin-3-yl)methyl)piperidin-4-yl)-1-oxoisoindolin-2-yl)piperidine-2,6-dione C1333;
3-(6-fluoro-5-(1-((3-methoxypyridin-4-yl)methyl)piperidin-4-yl)-1-oxoisoindolin-2-yl)piperidine-2,6-dione C1334;
3-(6-fluoro-5-(1-((6-methoxypyridin-3-yl)methyl)piperidin-4-yl)-1-oxoisoindolin-2-yl)piperidine-2,6-dione C1335;
3-(6-fluoro-5-(1-((4-methoxypyridin-2-yl)methyl)piperidin-4-yl)-1-oxoisoindolin-2-yl)piperidine-2,6-dione C1336;
3-(6-fluoro-5-(1-((5-methoxypyridin-2-yl)methyl)piperidin-4-yl)-1-oxoisoindolin-2-yl)piperidine-2,6-dione C1337;
3-(6-fluoro-1-oxo-5-(1-(pyrimidin-5-ylmethyl)piperidin-4-yl)isoindolin-2-yl)piperidine-2,6-dione C1338;
3-(6-fluoro-5-(1-((3-methoxypyridin-2-yl)methyl)piperidin-4-yl)-1-oxoisoindolin-2-yl)piperidine-2,6-dione C1339;
3-(6-fluoro-5-(1-((4-methoxypyridin-3-yl)methyl)piperidin-4-yl)-1-oxoisoindolin-2-yl)piperidine-2,6-dione C1340;

3-(6-fluoro-5-(1-((6-methoxypyridin-2-yl)methyl)piperidin-4-yl)-1-oxoisoindolin-2-yl)piperidine-2,6-dione C1341;
3-(6-fluoro-5-(1-((5-methoxypyridin-3-yl)methyl)piperidin-4-yl)-1-oxoisoindolin-2-yl)piperidine-2,6-dione C1342;
3-(6-fluoro-5-(1-((1-methyl-6-oxo-1,6-dihydropyridin-2-yl)methyl)piperidin-4-yl)-1-oxoisoindolin-2-yl)piperidine-2,6-dione C1343;
3-(6-fluoro-5-(1-((1-methyl-2-oxo-1,2-dihydropyridin-4-yl)methyl)piperidin-4-yl)-1-oxoisoindolin-2-yl)piperidine-2,6-dione C1344;
3-(5-(1-((2-amino-5-methylpyridin-3-yl)methyl)piperidin-4-yl)-6-fluoro-1-oxoisoindolin-2-yl)piperidine-2,6-dione C1345;
3-(6-fluoro-5-(1-(2-methoxybenzyl)piperidin-4-yl)-1-oxoisoindolin-2-yl)-piperidine-2,6-dione C1346;
3-(6-fluoro-5-(1-(4-methoxybenzyl)piperidin-4-yl)-1-oxoisoindolin-2-yl)-piperidine-2,6-dione C1347;
3-(6-fluoro-5-(1-(3-hydroxy-5-methylbenzyl)piperidin-4-yl)-1-oxoisoindolin-2-yl)piperidine-2,6-dione C1348;
3-(6-fluoro-1-oxo-5-(1-(pyridin-2-ylmethyl)piperidin-4-yl)isoindolin-2-yl)-piperidine-2,6-dione C1349; or
3-(5-(1-(cyclobutylmethyl)piperidin-4-yl)-6-fluoro-1-oxoisoindolin-2-yl)-piperidine-2,6-dione C1350;

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

In yet another embodiment, provided herein is a compound of:

3-(5-(1-(cyclopropylsulfonyl)piperidin-4-yl)-6-fluoro-1-oxoisoindolin-2-yl)-piperidine-2,6-dione C2001;
3-(6-fluoro-1-oxo-5-(1-(propylsulfonyl)piperidin-4-yl)isoindolin-2-yl)piperidine-2,6-dione C2002;
3-(6-fluoro-5-(1-(isopropylsulfonyl)piperidin-4-yl)-1-oxoisoindolin-2-yl)-piperidine-2,6-dione C2003;
3-(6-fluoro-5-(1-(isobutylsulfonyl)piperidin-4-yl)-1-oxoisoindolin-2-yl)-piperidine-2,6-dione C2004;
3-(6-fluoro-5-(1-(furan-3-ylsulfonyl)piperidin-4-yl)-1-oxoisoindolin-2-yl)-piperidine-2,6-dione C2005;
3-(5-(1-((1H-pyrazol-4-yl)sulfonyl)piperidin-4-yl)-6-fluoro-1-oxoisoindolin-2-yl)piperidine-2,6-dione C2006;
3-(6-fluoro-1-oxo-5-(1-((trifluoromethyl)sulfonyl)piperidin-4-yl)isoindolin-2-yl)-piperidine-2,6-dione C2007;
3-(5-(1-((cyclobutylmethyl)sulfonyl)piperidin-4-yl)-6-fluoro-1-oxoisoindolin-2-yl)piperidine-2,6-dione C2008;
3-(5-(1-((3-chloropropyl)sulfonyl)piperidin-4-yl)-6-fluoro-1-oxoisoindolin-2-yl)-piperidine-2,6-dione C2009;
3-(6-fluoro-1-oxo-5-(1-(pyridin-3-ylsulfonyl)piperidin-4-yl)isoindolin-2-yl)-piperidine-2,6-dione C2010;
3-(6-fluoro-5-(1-((1-methyl-1H-pyrazol-4-yl)sulfonyl)piperidin-4-yl)-1-oxoisoindolin-2-yl)piperidine-2,6-dione C2011;
3-(6-fluoro-5-(1-((1-methyl-1H-pyrazol-3-yl)sulfonyl)piperidin-4-yl)-1-oxoisoindolin-2-yl)piperidine-2,6-dione C2012;
3-(6-fluoro-5-(1-((1-methyl-1H-imidazol-4-yl)sulfonyl)piperidin-4-yl)-1-oxoisoindolin-2-yl)piperidine-2,6-dione C2013;
3-(6-fluoro-1-oxo-5-(1-(thiophen-2-ylsulfonyl)piperidin-4-yl)isoindolin-2-yl)-piperidine-2,6-dione C2014;
3-(5-(1-(cyclohexylsulfonyl)piperidin-4-yl)-6-fluoro-1-oxoisoindolin-2-yl)-piperidine-2,6-dione C2015;
3-(6-fluoro-1-oxo-5-(1-((tetrahydro-2H-pyran-4-yl)sulfonyl)piperidin-4-yl)-isoindolin-2-yl)piperidine-2,6-dione C2016;
3-(6-fluoro-1-oxo-5-(1-(m-tolylsulfonyl)piperidin-4-yl)isoindolin-2-yl)-piperidine-2,6-dione C2017;
3-(6-fluoro-5-(1-((6-methylpyridin-3-yl)sulfonyl)piperidin-4-yl)-1-oxoisoindolin-2-yl)piperidine-2,6-dione C2018;
3-(6-fluoro-5-(1-((4-hydroxyphenyl)sulfonyl)piperidin-4-yl)-1-oxoisoindolin-2-yl)piperidine-2,6-dione C2019;
3-(6-fluoro-5-(1-((4-fluorophenyl)sulfonyl)piperidin-4-yl)-1-oxoisoindolin-2-yl)-piperidine-2,6-dione C2020;
3-(6-fluoro-5-(1-((3-fluorophenyl)sulfonyl)piperidin-4-yl)-1-oxoisoindolin-2-yl)-piperidine-2,6-dione C2021;
3-(6-fluoro-5-(1-((2-fluorophenyl)sulfonyl)piperidin-4-yl)-1-oxoisoindolin-2-yl)-piperidine-2,6-dione C2022;
3-(6-fluoro-1-oxo-5-(1-((3,3,3-trifluoropropyl)sulfonyl)piperidin-4-yl)isoindolin-2-yl)piperidine-2,6-dione C2023;
3-(6-fluoro-5-(1-((4-methylbenzyl)sulfonyl)piperidin-4-yl)-1-oxoisoindolin-2-yl)-piperidine-2,6-dione C2024;
3-(6-fluoro-1-oxo-5-(1-(phenethylsulfonyl)piperidin-4-yl)isoindolin-2-yl)-piperidine-2,6-dione C2025;
3-(5-(1-((2,6-dimethylphenyl)sulfonyl)piperidin-4-yl)-6-fluoro-1-oxoisoindolin-2-yl)piperidine-2,6-dione C2026;
3-(6-fluoro-5-(1-((4-methoxyphenyl)sulfonyl)piperidin-4-yl)-1-oxoisoindolin-2-yl)piperidine-2,6-dione C2027;
3-(6-fluoro-5-(1-((3-methoxyphenyl)sulfonyl)piperidin-4-yl)-1-oxoisoindolin-2-yl)piperidine-2,6-dione C2028;
3-(6-fluoro-5-(1-((6-methoxypyridin-3-yl)sulfonyl)piperidin-4-yl)-1-oxoisoindolin-2-yl)piperidine-2,6-dione C2029;
3-(6-fluoro-5-(1-((2-fluoro-5-methylphenyl)sulfonyl)piperidin-4-yl)-1-oxoisoindolin-2-yl)piperidine-2,6-dione C2030;
3-(6-fluoro-5-(1-((4-fluoro-2-methylphenyl)sulfonyl)piperidin-4-yl)-1-oxoisoindolin-2-yl)piperidine-2,6-dione C2031;
3-(6-fluoro-5-(1-((2-fluoro-4-methylphenyl)sulfonyl)piperidin-4-yl)-1-oxoisoindolin-2-yl)piperidine-2,6-dione C2032;
3-(5-(1-((3-chlorophenyl)sulfonyl)piperidin-4-yl)-6-fluoro-1-oxoisoindolin-2-yl)-piperidine-2,6-dione C2033;
3-(5-(1-((2-chlorophenyl)sulfonyl)piperidin-4-yl)-6-fluoro-1-oxoisoindolin-2-yl)-piperidine-2,6-dione C2034;
3-(5-(1-((4-chlorophenyl)sulfonyl)piperidin-4-yl)-6-fluoro-1-oxoisoindolin-2-yl)-piperidine-2,6-dione C2035;
3-(5-(1-((3,4-difluorophenyl)sulfonyl)piperidin-4-yl)-6-fluoro-1-oxoisoindolin-2-yl)piperidine-2,6-dione C2036;
3-(5-(1-((2,4-difluorophenyl)sulfonyl)piperidin-4-yl)-6-fluoro-1-oxoisoindolin-2-yl)piperidine-2,6-dione C2037;
3-(5-(1-((2,5-difluorophenyl)sulfonyl)piperidin-4-yl)-6-fluoro-1-oxoisoindolin-2-yl)piperidine-2,6-dione C2038;
3-(5-(1-((3,5-difluorophenyl)sulfonyl)piperidin-4-yl)-6-fluoro-1-oxoisoindolin-2-yl)piperidine-2,6-dione C2039;
3-(6-fluoro-1-oxo-5-(1-(pyridin-3-ylsulfonyl)piperidin-4-yl)isoindolin-2-yl)-piperidine-2,6-dione C2040;
2-((4-(2-(2,6-dioxopiperidin-3-yl)-6-fluoro-1-oxoisoindolin-5-yl)piperidin-1-yl)sulfonyl)-5-methylbenzonitrile C2041;
3-(5-(1-((1H-indol-5-yl)sulfonyl)piperidin-4-yl)-6-fluoro-1-oxoisoindolin-2-yl)-piperidine-2,6-dione C2042;
3-(5-(1-(benzofuran-5-ylsulfonyl)piperidin-4-yl)-6-fluoro-1-oxoisoindolin-2-yl)-piperidine-2,6-dione C2043;
3-(5-(1-((2,3-dihydrobenzofuran-5-yl)sulfonyl)piperidin-4-yl)-6-fluoro-1-oxoisoindolin-2-yl)piperidine-2,6-dione C2044;
3-(6-fluoro-5-(1-((4-isopropylphenyl)sulfonyl)piperidin-4-yl)-1-oxoisoindolin-2-yl)piperidine-2,6-dione C2045;
3-(6-fluoro-5-(1-((3-isopropylphenyl)sulfonyl)piperidin-4-yl)-1-oxoisoindolin-2-yl)piperidine-2,6-dione C2046;

3-((4-(2-(2,6-dioxopiperidin-3-yl)-6-fluoro-1-oxoisoindolin-5-yl)piperidin-1-yl)-sulfonyl)-4-fluorobenzonitrile C2047;

5-((4-(2-(2,6-dioxopiperidin-3-yl)-6-fluoro-1-oxoisoindolin-5-yl)piperidin-1-yl)-sulfonyl)-2-fluorobenzonitrile C2048;

4-((4-(2-(2,6-dioxopiperidin-3-yl)-6-fluoro-1-oxoisoindolin-5-yl)piperidin-1-yl)-sulfonyl)benzamide C2049;

3-(6-fluoro-5-(1-((3-methoxybenzyl)sulfonyl)piperidin-4-yl)-1-oxoisoindolin-2-yl)piperidine-2,6-dione C2050;

3-(6-fluoro-5-(1-((3-methoxy-4-methylphenyl)sulfonyl)piperidin-4-yl)-1-oxoisoindolin-2-yl)piperidine-2,6-dione C2051;

3-(6-fluoro-5-(1-((5-fluoro-2-methoxyphenyl)sulfonyl)piperidin-4-yl)-1-oxoisoindolin-2-yl)piperidine-2,6-dione C2052;

3-(6-fluoro-5-(1-((3-fluoro-4-methoxyphenyl)sulfonyl)piperidin-4-yl)-1-oxoisoindolin-2-yl)piperidine-2,6-dione C2053;

3-(6-fluoro-1-oxo-5-(1-((5,6,7,8-tetrahydronaphthalen-2-yl)sulfonyl)piperidin-4-yl)isoindolin-2-yl)piperidine-2,6-dione C2054;

3-(6-fluoro-5-(1-((2-hydroxy-1H-benzo[d]imidazol-6-yl)sulfonyl)piperidin-4-yl)-1-oxoisoindolin-2-yl)piperidine-2,6-dione C2055;

3-(5-(1-((4-(tert-butyl)phenyl)sulfonyl)piperidin-4-yl)-6-fluoro-1-oxoisoindolin-2-yl)piperidine-2,6-dione C2056;

3-(5-(1-((3-(tert-butyl)phenyl)sulfonyl)piperidin-4-yl)-6-fluoro-1-oxoisoindolin-2-yl)piperidine-2,6-dione C2057;

N-(3-((4-(2-(2,6-dioxopiperidin-3-yl)-6-fluoro-1-oxoisoindolin-5-yl)piperidin-1-yl)sulfonyl)phenyl)acetamide C2058;

N-(4-((4-(2-(2,6-dioxopiperidin-3-yl)-6-fluoro-1-oxoisoindolin-5-yl)piperidin-1-yl)sulfonyl)phenyl)acetamide C2059;

4-((4-(2-(2,6-dioxopiperidin-3-yl)-6-fluoro-1-oxoisoindolin-5-yl)piperidin-1-yl)-sulfonyl)-N-methylbenzamide C2060;

2-chloro-4-((4-(2-(2,6-dioxopiperidin-3-yl)-6-fluoro-1-oxoisoindolin-5-yl)-piperidin-1-yl)sulfonyl)benzonitrile C2061;

3-(5-(1-((5-chloro-2-methoxypyridin-3-yl)sulfonyl)piperidin-4-yl)-6-fluoro-1-oxoisoindolin-2-yl)piperidine-2,6-dione C2062;

3-(5-(1-((4-(difluoromethoxy)phenyl)sulfonyl)piperidin-4-yl)-6-fluoro-1-oxoisoindolin-2-yl)piperidine-2,6-dione C2063;

3-(6-fluoro-5-(1-((4-(oxazol-5-yl)phenyl)sulfonyl)piperidin-4-yl)-1-oxoisoindolin-2-yl)piperidine-2,6-dione C2064;

3-(6-fluoro-1-oxo-5-(1-((4-(trifluoromethyl)phenyl)sulfonyl)piperidin-4-yl)-isoindolin-2-yl)piperidine-2,6-dione C2065;

3-(6-fluoro-1-oxo-5-(1-((3-(trifluoromethyl)phenyl)sulfonyl)piperidin-4-yl)-isoindolin-2-yl)piperidine-2,6-dione C2066;

3-(6-fluoro-1-oxo-5-(1-((2-(trifluoromethyl)phenyl)sulfonyl)piperidin-4-yl)-isoindolin-2-yl)piperidine-2,6-dione C2067;

3-(6-fluoro-1-oxo-5-(1-((6-(trifluoromethyl)pyridin-3-yl)sulfonyl)piperidin-4-yl)-isoindolin-2-yl)piperidine-2,6-dione C2068;

3-(6-fluoro-1-oxo-5-(1-((2-oxo-1,2,3,4-tetrahydroquinolin-6-yl)sulfonyl)-piperidin-4-yl)isoindolin-2-yl)piperidine-2,6-dione C2069;

2-((4-(2-(2,6-dioxopiperidin-3-yl)-6-fluoro-1-oxoisoindolin-5-yl)piperidin-1-yl)-sulfonyl)-N,N-dimethylbenzamide C2070;

3-(5-(1-((3-bromophenyl)sulfonyl)piperidin-4-yl)-6-fluoro-1-oxoisoindolin-2-yl)-piperidine-2,6-dione C2071;

3-(5-(1-((2-bromophenyl)sulfonyl)piperidin-4-yl)-6-fluoro-1-oxoisoindolin-2-yl)-piperidine-2,6-dione C2072;

3-(6-fluoro-1-oxo-5-(1-((1-(o-tolyl)-1H-pyrazol-4-yl)sulfonyl)piperidin-4-yl)-isoindolin-2-yl)piperidine-2,6-dione C2073;

3-(6-fluoro-1-oxo-5-(1-((4-(trifluoromethyl)benzyl)sulfonyl)piperidin-4-yl)-isoindolin-2-yl)piperidine-2,6-dione C2074;

3-(6-fluoro-1-oxo-5-(1-((2-(trifluoromethoxy)phenyl)sulfonyl)piperidin-4-yl)-isoindolin-2-yl)piperidine-2,6-dione C2075;

3-(5-(1-((1-chloroisoquinolin-5-yl)sulfonyl)piperidin-4-yl)-6-fluoro-1-oxoisoindolin-2-yl)piperidine-2,6-dione C2076;

3-(6-fluoro-5-(1-(isoquinolin-5-ylsulfonyl)piperidin-4-yl)-1-oxoisoindolin-2-yl)-piperidine-2,6-dione C2077;

3-(6-fluoro-1-oxo-5-(1-((4-(pyridin-2-yloxy)phenyl)sulfonyl)piperidin-4-yl)-isoindolin-2-yl)piperidine-2,6-dione C2078;

3-(6-fluoro-1-oxo-5-(1-((6-phenoxypyridin-3-yl)sulfonyl)piperidin-4-yl)-isoindolin-2-yl)piperidine-2,6-dione C2079;

3-(5-(1-((5-(dimethylamino)naphthalen-1-yl)sulfonyl)piperidin-4-yl)-6-fluoro-1-oxoisoindolin-2-yl)piperidine-2,6-dione C2080;

3-(5-(1-((6-(dimethylamino)naphthalen-2-yl)sulfonyl)piperidin-4-yl)-6-fluoro-1-oxoisoindolin-2-yl)piperidine-2,6-dione C2081;

3-(5-(1-((4-(benzyloxy)phenyl)sulfonyl)piperidin-4-yl)-6-fluoro-1-oxoisoindolin-2-yl)piperidine-2,6-dione C2082;

tert-butyl 4-((4-(2-(2,6-dioxopiperidin-3-yl)-6-fluoro-1-oxoisoindolin-5-yl)-piperidin-1-yl)sulfonyl)piperidine-1-carboxylate C2083;

benzyl 4-((4-(2-(2,6-dioxopiperidin-3-yl)-6-fluoro-1-oxoisoindolin-5-yl)-piperidin-1-yl)sulfonyl)piperidine-1-carboxylate C2084;

3-(6-fluoro-1-oxo-5-(1-((2-(2,2,2-trifluoroacetyl)-1,2,3,4-tetrahydroisoquinolin-7-yl)sulfonyl)piperidin-4-yl)isoindolin-2-yl)piperidine-2,6-dione C2085;

benzyl 4-(((4-(2-(2,6-dioxopiperidin-3-yl)-6-fluoro-1-oxoisoindolin-5-yl)-piperidin-1-yl)sulfonyl)methyl)piperidine-1-carboxylate C2086;

3-(5-(1-(ethylsulfonyl)piperidin-4-yl)-6-fluoro-1-oxoisoindolin-2-yl)piperidine-2,6-dione C2087;

3-(5-(1-((5-chlorothiophen-2-yl)sulfonyl)piperidin-4-yl)-6-fluoro-1-oxoisoindolin-2-yl)piperidine-2,6-dione C2088;

3-(5-(1-((3-chloro-4-methylphenyl)sulfonyl)piperidin-4-yl)-6-fluoro-1-oxoisoindolin-2-yl)piperidine-2,6-dione C2089;

3-(5-(1-((2-chloro-6-methylphenyl)sulfonyl)piperidin-4-yl)-6-fluoro-1-oxoisoindolin-2-yl)piperidine-2,6-dione C2090;

3-(5-(1-((3,5-difluorobenzyl)sulfonyl)piperidin-4-yl)-6-fluoro-1-oxoisoindolin-2-yl)piperidine-2,6-dione C2091;

3-(6-fluoro-5-(1-(naphthalen-2-ylsulfonyl)piperidin-4-yl)-1-oxoisoindolin-2-yl)-piperidine-2,6-dione C2092;

3-(6-fluoro-1-oxo-5-(1-(quinolin-8-ylsulfonyl)piperidin-4-yl)isoindolin-2-yl)-piperidine-2,6-dione C2093;

3-(6-fluoro-5-(1-(isoquinolin-5-ylsulfonyl)piperidin-4-yl)-1-oxoisoindolin-2-yl)-piperidine-2,6-dione C2094;

3-(6-fluoro-1-oxo-5-(1-(quinoxalin-5-ylsulfonyl)piperidin-4-yl)isoindolin-2-yl)-piperidine-2,6-dione C2095;

3-chloro-4-((4-(2-(2,6-dioxopiperidin-3-yl)-6-fluoro-1-oxoisoindolin-5-yl)-piperidin-1-yl)sulfonyl)benzonitrile C2096;

3-(5-(1-(benzo[d][1,3]dioxol-5-ylsulfonyl)piperidin-4-yl)-6-fluoro-1-oxoisoindolin-2-yl)piperidine-2,6-dione C2097;

3-(5-(1-(benzo[d]thiazol-6-ylsulfonyl)piperidin-4-yl)-6-fluoro-1-oxoisoindolin-2-yl)piperidine-2,6-dione C2098;

3-(5-(1-((2,4-dichlorophenyl)sulfonyl)piperidin-4-yl)-6-fluoro-1-oxoisoindolin-2-yl)piperidine-2,6-dione C2099; or 3-(5-(1-((2,5-dichlorophenyl)sulfonyl)piperidin-4-yl)-6-fluoro-1-oxoisoindolin-2-yl)piperidine-2,6-dione C2100;

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

In yet another embodiment, provided herein is a compound of:

3-(6-fluoro-1-oxo-5-(4-(5,6,7,8-tetrahydronaphthalene-1-carbonyl)piperazin-1-yl)isoindolin-2-yl)piperidine-2,6-dione D0001;

3-(6-fluoro-5-(4-(1-methyl-1H-indole-5-carbonyl)piperazin-1-yl)-1-oxoisoindolin-2-yl)piperidine-2,6-dione D0002;

3-(6-fluoro-1-oxo-5-(4-(quinoxaline-5-carbonyl)piperazin-1-yl)isoindolin-2-yl)-piperidine-2,6-dione D0003;

3-(6-fluoro-1-oxo-5-(4-(quinazoline-6-carbonyl)piperazin-1-yl)isoindolin-2-yl)-piperidine-2,6-dione D0004;

3-(5-(4-(2-(dimethylamino)benzoyl)piperazin-1-yl)-6-fluoro-1-oxoisoindolin-2-yl)piperidine-2,6-dione D0005;

3-(5-(4-(4-(dimethylamino)benzoyl)piperazin-1-yl)-6-fluoro-1-oxoisoindolin-2-yl)piperidine-2,6-dione D0006;

3-(5-(4-(2,3-dihydrobenzofuran-7-carbonyl)piperazin-1-yl)-6-fluoro-1-oxoisoindolin-2-yl)piperidine-2,6-dione D0007;

3-(5-(4-(benzo[d]oxazole-5-carbonyl)piperazin-1-yl)-6-fluoro-1-oxoisoindolin-2-yl)piperidine-2,6-dione D0008;

3-(5-(4-(1H-benzo[d]imidazole-7-carbonyl)piperazin-1-yl)-6-fluoro-1-oxoisoindolin-2-yl)piperidine-2,6-dione D0009;

3-(6-fluoro-5-(4-(imidazo[1,2-a]pyridin-2-carbonyl)piperazin-1-yl)-1-oxoisoindolin-2-yl)piperidine-2,6-dione D0010;

3-(5-(4-(1H-pyrrolo[3,2-b]pyridin-6-carbonyl)piperazin-1-yl)-6-fluoro-1-oxoisoindolin-2-yl)piperidine-2,6-dione D0011;

3-(6-fluoro-5-(4-(imidazo[1,2-a]pyridin-3-carbonyl)piperazin-1-yl)-1-oxoisoindolin-2-yl)piperidine-2,6-dione D0012;

3-(5-(4-(benzofuran-6-carbonyl)piperazin-1-yl)-6-fluoro-1-oxoisoindolin-2-yl)-piperidine-2,6-dione D0013;

3-(6-fluoro-1-oxo-5-(4-(2-(piperidin-1-yl)acetyl)piperazin-1-yl)isoindolin-2-yl)-piperidine-2,6-dione D0014;

2-(2-(4-(2-(2,6-dioxopiperidin-3-yl)-6-fluoro-1-oxoisoindolin-5-yl)piperazin-1-yl)-2-oxoethyl)benzonitrile D0015;

3-(2-(4-(2-(2,6-dioxopiperidin-3-yl)-6-fluoro-1-oxoisoindolin-5-yl)piperazin-1-yl)-2-oxoethyl)benzonitrile D0016;

4-(2-(4-(2-(2,6-dioxopiperidin-3-yl)-6-fluoro-1-oxoisoindolin-5-yl)piperazin-1-yl)-2-oxoethyl)benzonitrile D0017;

3-(5-(4-(1H-indole-7-carbonyl)piperazin-1-yl)-6-fluoro-1-oxoisoindolin-2-yl)-piperidine-2,6-dione D0018;

3-(5-(4-(1-ethylpiperidine-4-carbonyl)piperazin-1-yl)-6-fluoro-1-oxoisoindolin-2-yl)piperidine-2,6-dione D0019;

3-(6-fluoro-1-oxo-5-(4-(2-(p-tolyl)acetyl)piperazin-1-yl)isoindolin-2-yl)-piperidine-2,6-dione D0020;

2-(4-(2-(2,6-dioxopiperidin-3-yl)-6-fluoro-1-oxoisoindolin-5-yl)piperazine-1-carbonyl)benzonitrile D0021;

3-(4-(2-(2,6-dioxopiperidin-3-yl)-6-fluoro-1-oxoisoindolin-5-yl)piperazine-1-carbonyl)benzonitrile D0022;

3-(6-fluoro-5-(4-(4-fluorobenzoyl)piperazin-1-yl)-1-oxoisoindolin-2-yl)-piperidine-2,6-dione D0023;

3-(6-fluoro-5-(4-(3-fluorobenzoyl)piperazin-1-yl)-1-oxoisoindolin-2-yl)-piperidine-2,6-dione D0024;

3-(6-fluoro-5-(4-(2-fluorobenzoyl)piperazin-1-yl)-1-oxoisoindolin-2-yl)-piperidine-2,6-dione D0025;

3-(6-fluoro-5-(4-(2-methylbenzoyl)piperazin-1-yl)-1-oxoisoindolin-2-yl)-piperidine-2,6-dione D0026;

3-(6-fluoro-5-(4-(3-methylbenzoyl)piperazin-1-yl)-1-oxoisoindolin-2-yl)-piperidine-2,6-dione D0027;

3-(6-fluoro-5-(4-(4-methylbenzoyl)piperazin-1-yl)-1-oxoisoindolin-2-yl)-piperidine-2,6-dione D0028;

3-(5-(4-(2-cyclopentylacetyl)piperazin-1-yl)-6-fluoro-1-oxoisoindolin-2-yl)piperidine-2,6-dione D0029;

3-(5-(4-(cyclohexanecarbonyl)piperazin-1-yl)-6-fluoro-1-oxoisoindolin-2-yl)piperidine-2,6-dione D0030;

3-(5-(-(3,3-dimethylcyclobutane-1-carbonyl)piperazin-1-yl)-6-fluoro-1-oxoisoindolin-2-yl)piperidine-2,6-dione D0031;

3-(6-fluoro-1-oxo-5-(4-(pyrimidine-5-carbonyl)piperazin-1-yl)isoindolin-2-yl)piperidine-2,6-dione D0032;

3-(6-fluoro-1-oxo-5-(4-(pyridazine-4-carbonyl)piperazin-1-yl)isoindolin-2-yl)-piperidine-2,6-dione D0033;

3-(6-fluoro-1-oxo-5-(4-(pyrimidine-4-carbonyl)piperazin-1-yl)isoindolin-2-yl)-piperidine-2,6-dione D0034;

3-(6-fluoro-1-oxo-5-(4-picolinoylpiperazin-1-yl)isoindolin-2-yl)piperidine-2,6-dione D0035.

3-(6-fluoro-5-(4-isonicotinoylpiperazin-1-yl)-1-oxoisoindolin-2-yl)piperidine-2,6-dione D0036;

3-(6-fluoro-5-(4-nicotinoylpiperazin-1-yl)-1-oxoisoindolin-2-yl)piperidine-2,6-dione D0037;

3-(5-(4-benzoylpiperazin-1-yl)-6-fluoro-1-oxoisoindolin-2-yl)piperidine-2,6-dione D0038;

3-(5-(4-(1-aminocyclobutane-1-carbonyl)piperazin-1-yl)-6-fluoro-1-oxoisoindolin-2-yl)piperidine-2,6-dione D0039;

3-(6-fluoro-5-(4-(1-methylazetidine-3-carbonyl)piperazin-1-yl)-1-oxoisoindolin-2-yl)piperidine-2,6-dione D0040;

3-(5-(4-(1H-pyrazole-5-carbonyl)piperazin-1-yl)-6-fluoro-1-oxoisoindolin-2-yl)-piperidine-2,6-dione D0041;

3-(5-(4-(1H-imidazole-5-carbonyl)piperazin-1-yl)-6-fluoro-1-oxoisoindolin-2-yl)-piperidine-2,6-dione D0042;

3-(6-fluoro-5-(4-(furan-3-carbonyl)piperazin-1-yl)-1-oxoisoindolin-2-yl)-piperidine-2,6-dione D0043;

3-(6-fluoro-5-(4-(furan-2-carbonyl)piperazin-1-yl)-1-oxoisoindolin-2-yl)-piperidine-2,6-dione D0044;

3-(6-fluoro-5-(4-(1-fluorocyclopropane-1-carbonyl)piperazin-1-yl)-1-oxoisoindolin-2-yl)piperidine-2,6-dione D0045;

3-(6-fluoro-5-(4-(3-methylbutanoyl)piperazin-1-yl)-1-oxoisoindolin-2-yl)-piperidine-2,6-dione D0046;

3-(6-fluoro-5-(4-(oxetane-3-carbonyl)piperazin-1-yl)-1-oxoisoindolin-2-yl)-piperidine-2,6-dione D0047;

3-(5-(4-(cyclobutanecarbonyl)piperazin-1-yl)-6-fluoro-1-oxoisoindolin-2-yl)-piperidine-2,6-dione D0048;

3-(6-fluoro-5-(4-(methylglycyl)piperazin-1-yl)-1-oxoisoindolin-2-yl)piperidine-2,6-dione D0049; or 3-(5-(4-(cyclopropanecarbonyl)piperazin-1-yl)-6-fluoro-1-oxoisoindolin-2-yl)-piperidine-2,6-dione D0050;

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

In yet another embodiment, provided herein is a compound of:

3-(6-fluoro-5-(4-(3-methoxybenzyl)piperazin-1-yl)-1-oxoisoindolin-2-yl)-piperidine-2,6-dione D1001;

3-(6-fluoro-5-(4-(2-hydroxy-4-methylbenzyl)piperazin-1-yl)-1-oxoisoindolin-2-yl)piperidine-2,6-dione D1002;

3-(6-fluoro-5-(4-(4-(hydroxymethyl)benzyl)piperazin-1-yl)-1-oxoisoindolin-2-yl)piperidine-2,6-dione D1003;

3-(5-(4-((2,6-dimethylpyridin-4-yl)methyl)piperazin-1-yl)-6-fluoro-1-oxoisoindolin-2-yl)piperidine-2,6-dione D1004;

3-(6-fluoro-5-(4-(2-(methylamino)benzyl)piperazin-1-yl)-1-oxoisoindolin-2-yl)-piperidine-2,6-dione D1005;

3-(5-(4-(2,6-dimethylbenzyl)piperazin-1-yl)-6-fluoro-1-oxoisoindolin-2-yl)-piperidine-2,6-dione D1006;

3-(5-(4-(2,4-dimethylbenzyl)piperazin-1-yl)-6-fluoro-1-oxoisoindolin-2-yl)-piperidine-2,6-dione D1007;

3-(5-(4-(2,5-dimethylbenzyl)piperazin-1-yl)-6-fluoro-1-oxoisoindolin-2-yl)-piperidine-2,6-dione D1008;

3-(6-fluoro-5-(4-(2-methylphenethyl)piperazin-1-yl)-1-oxoisoindolin-2-yl)-piperidine-2,6-dione D1009;

3-(5-(4-(3,5-dimethylbenzyl)piperazin-1-yl)-6-fluoro-1-oxoisoindolin-2-yl)-piperidine-2,6-dione D1010;

3-(6-fluoro-1-oxo-5-(4-(pyridin-3-ylmethyl)piperazin-1-yl)isoindolin-2-yl)-piperidine-2,6-dione D1011;

3-(6-fluoro-1-oxo-5-(4-(3-phenylpropyl)piperazin-1-yl)isoindolin-2-yl)-piperidine-2,6-dione D1012;

4-((4-(2-(2,6-dioxopiperidin-3-yl)-6-fluoro-1-oxoisoindolin-5-yl)piperazin-1-yl)-methyl)-1-methyl-1H-pyrrole-2-carbonitrile D1013;

3-(5-(4-(bicyclo[4.2.0]octa-1(6),2,4-trien-3-ylmethyl)piperazin-1-yl)-6-fluoro-1-oxoisoindolin-2-yl)piperidine-2,6-dione D1014;

5-((4-(2-(2,6-dioxopiperidin-3-yl)-6-fluoro-1-oxoisoindolin-5-yl)piperazin-1-yl)-methyl)picolinonitrile D1015;

5-((4-(2-(2,6-dioxopiperidin-3-yl)-6-fluoro-1-oxoisoindolin-5-yl)piperazin-1-yl)-methyl)nicotinonitrile D1016;

6-((4-(2-(2,6-dioxopiperidin-3-yl)-6-fluoro-1-oxoisoindolin-5-yl)piperazin-1-yl)-methyl)picolinonitrile D1017;

2-((4-(2-(2,6-dioxopiperidin-3-yl)-6-fluoro-1-oxoisoindolin-5-yl)piperazin-1-yl)-methyl)isonicotinonitrile D1018;

3-((4-(2-(2,6-dioxopiperidin-3-yl)-6-fluoro-1-oxoisoindolin-5-yl)piperazin-1-yl)-methyl)benzonitrile D1019;

3-(5-(4-((5-ethynylpyridin-2-yl)methyl)piperazin-1-yl)-6-fluoro-1-oxoisoindolin-2-yl)piperidine-2,6-dione D1020;

4-((4-(2-(2,6-dioxopiperidin-3-yl)-6-fluoro-1-oxoisoindolin-5-yl)piperazin-1-yl)-methyl)benzonitrile D1021;

3-(6-fluoro-5-(4-(3-hydroxy-2,2-dimethylpropyl)piperazin-1-yl)-1-oxoisoindolin-2-yl)piperidine-2,6-dione D1022;

2-((4-(2-(2,6-dioxopiperidin-3-yl)-6-fluoro-1-oxoisoindolin-5-yl)piperazin-1-yl)-methyl)benzonitrile D1023;

3-(5-(4-(4-ethynylbenzyl)piperazin-1-yl)-6-fluoro-1-oxoisoindolin-2-yl)-piperidine-2,6-dione D1024;

3-(5-(4-(2-ethynylbenzyl)piperazin-1-yl)-6-fluoro-1-oxoisoindolin-2-yl)-piperidine-2,6-dione D1025;

3-(5-(4-(3-ethynylbenzyl)piperazin-1-yl)-6-fluoro-1-oxoisoindolin-2-yl)-piperidine-2,6-dione D1026;

3-(6-fluoro-5-(4-((5-methylthiazol-2-yl)methyl)piperazin-1-yl)-1-oxoisoindolin-2-yl)piperidine-2,6-dione D1027;

3-(6-fluoro-5-(4-((2-methylthiazol-5-yl)methyl)piperazin-1-yl)-1-oxoisoindolin-2-yl)piperidine-2,6-dione D1028;

3-(6-fluoro-5-(4-((4-methylthiazol-5-yl)methyl)piperazin-1-yl)-1-oxoisoindolin-2-yl)piperidine-2,6-dione D1029;

3-(5-(4-(2-cyclohexylethyl)piperazin-1-yl)-6-fluoro-1-oxoisoindolin-2-yl)-piperidine-2,6-dione D1030;

3-(6-fluoro-5-(4-((3-methylthiophen-2-yl)methyl)piperazin-1-yl)-1-oxoisoindolin-2-yl)piperidine-2,6-dione D1031;

3-(6-fluoro-5-(4-((3-methoxyfuran-2-yl)methyl)piperazin-1-yl)-1-oxoisoindolin-2-yl)piperidine-2,6-dione D1032;

3-(6-fluoro-5-(4-((3-methyloxetan-3-yl)methyl)piperazin-1-yl)-1-oxoisoindolin-2-yl)piperidine-2,6-dione D1033;

3-(6-fluoro-5-(4-((5-(hydroxymethyl)furan-2-yl)methyl)piperazin-1-yl)-1-oxoisoindolin-2-yl)piperidine-2,6-dione D1034;

3-(5-(4-((5-amino-1-methyl-1H-pyrazol-4-yl)methyl)piperazin-1-yl)-6-fluoro-1-oxoisoindolin-2-yl)piperidine-2,6-dione D1035;

3-(6-fluoro-5-(4-((5-(hydroxymethyl)-1H-pyrrol-2-yl)methyl)piperazin-1-yl)-1-oxoisoindolin-2-yl)piperidine-2,6-dione D1036;

3-(6-fluoro-5-(4-((6-fluoropyridin-3-yl)methyl)piperazin-1-yl)-1-oxoisoindolin-2-yl)piperidine-2,6-dione D1037;

3-(6-fluoro-5-(4-((3-fluoropyridin-4-yl)methyl)piperazin-1-yl)-1-oxoisoindolin-2-yl)piperidine-2,6-dione D1038;

3-(6-fluoro-5-(4-((5-fluoropyridin-2-yl)methyl)piperazin-1-yl)-1-oxoisoindolin-2-yl)piperidine-2,6-dione D1039;

3-(6-fluoro-5-(4-((5-fluoropyridin-3-yl)methyl)piperazin-1-yl)-1-oxoisoindolin-2-yl)piperidine-2,6-dione D1040;

3-(6-fluoro-5-(4-((4-fluoropyridin-2-yl)methyl)piperazin-1-yl)-1-oxoisoindolin-2-yl)piperidine-2,6-dione D1041;

3-(6-fluoro-5-(4-((6-fluoropyridin-2-yl)methyl)piperazin-1-yl)-1-oxoisoindolin-2-yl)piperidine-2,6-dione D1042;

3-(5-(4-((2,5-dimethyl-1H-imidazol-4-yl)methyl)piperazin-1-yl)-6-fluoro-1-oxoisoindolin-2-yl)piperidine-2,6-dione D1043;

3-(6-fluoro-5-(4-(oxazol-2-ylmethyl)piperazin-1-yl)-1-oxoisoindolin-2-yl)-piperidine-2,6-dione D1044;

3-(5-(4-((1,4-dimethyl-1H-pyrazol-5-yl)methyl)piperazin-1-yl)-6-fluoro-1-oxoisoindolin-2-yl)piperidine-2,6-dione D1045;

3-(6-fluoro-5-(4-(4-fluorobenzyl)piperazin-1-yl)-1-oxoisoindolin-2-yl)piperidine-2,6-dione D1046;

3-(6-fluoro-5-(4-(3-fluorobenzyl)piperazin-1-yl)-1-oxoisoindolin-2-yl)piperidine-2,6-dione D1047;

3-(6-fluoro-5-(4-((2-hydroxypyridin-3-yl)methyl)piperazin-1-yl)-1-oxoisoindolin-2-yl)piperidine-2,6-dione D1048;

3-(6-fluoro-5-(4-((5-methylpyrazin-2-yl)methyl)piperazin-1-yl)-1-oxoisoindolin-2-yl)piperidine-2,6-dione D1049;

3-(6-fluoro-5-(4-((3-methylpyrazin-2-yl)methyl)piperazin-1-yl)-1-oxoisoindolin-2-yl)piperidine-2,6-dione D1050;

3-(6-fluoro-5-(4-((2-methylpyrimidin-4-yl)methyl)piperazin-1-yl)-1-oxoisoindolin-2-yl)piperidine-2,6-dione D1051;

3-(6-fluoro-5-(4-((2-methylpyrimidin-5-yl)methyl)piperazin-1-yl)-1-oxoisoindolin-2-yl)piperidine-2,6-dione D1052;

3-(5-(4-((2-aminopyridin-3-yl)methyl)piperazin-1-yl)-6-fluoro-1-oxoisoindolin-2-yl)piperidine-2,6-dione D1053;

3-(5-(4-((3-aminopyridin-4-yl)methyl)piperazin-1-yl)-6-fluoro-1-oxoisoindolin-2-yl)piperidine-2,6-dione D1054;

3-(5-(4-((1H-pyrazol-5-yl)methyl)piperazin-1-yl)-6-fluoro-1-oxoisoindolin-2-yl)-piperidine-2,6-dione D1055;

3-(6-fluoro-5-(4-(3-hydroxybenzyl)piperazin-1-yl)-1-oxoisoindolin-2-yl)-piperidine-2,6-dione D1056;

3-(6-fluoro-5-(4-(4-hydroxybenzyl)piperazin-1-yl)-1-oxoisoindolin-2-yl)-piperidine-2,6-dione D1057;

3-(6-fluoro-5-(4-((4-methylpyridin-2-yl)methyl)piperazin-1-yl)-1-oxoisoindolin-2-yl)piperidine-2,6-dione D1058;

3-(6-fluoro-5-(4-((3-methylpyridin-2-yl)methyl)piperazin-1-yl)-1-oxoisoindolin-2-yl)piperidine-2,6-dione D1059;

3-(6-fluoro-5-(4-((2-methylpyridin-3-yl)methyl)piperazin-1-yl)-1-oxoisoindolin-2-yl)piperidine-2,6-dione D1060;

3-(6-fluoro-5-(4-((2-methylpyridin-4-yl)methyl)piperazin-1-yl)-1-oxoisoindolin-2-yl)piperidine-2,6-dione D1061;

3-(6-fluoro-5-(4-((5-methylpyridin-2-yl)methyl)piperazin-1-yl)-1-oxoisoindolin-2-yl)piperidine-2,6-dione D1062;
3-(6-fluoro-5-(4-((6-methylpyridin-2-yl)methyl)piperazin-1-yl)-1-oxoisoindolin-2-yl)piperidine-2,6-dione D1063;
3-(6-fluoro-5-(4-((4-methylpyridin-3-yl)methyl)piperazin-1-yl)-1-oxoisoindolin-2-yl)piperidine-2,6-dione D1064;
3-(6-fluoro-5-(4-((5-methylpyridin-3-yl)methyl)piperazin-1-yl)-1-oxoisoindolin-2-yl)piperidine-2,6-dione D1065;
3-(5-(4-((1H-imidazol-5-yl)methyl)piperazin-1-yl)-6-fluoro-1-oxoisoindolin-2-yl)piperidine-2,6-dione D1066;
3-(5-(4-(4-aminobenzyl)piperazin-1-yl)-6-fluoro-1-oxoisoindolin-2-yl)-piperidine-2,6-dione D1067;
3-(5-(4-(2-aminobenzyl)piperazin-1-yl)-6-fluoro-1-oxoisoindolin-2-yl)-piperidine-2,6-dione D1068;
3-(6-fluoro-5-(4-(4-methylbenzyl)piperazin-1-yl)-1-oxoisoindolin-2-yl)-piperidine-2,6-dione D1069;
3-(6-fluoro-5-(4-(2-methylbenzyl)piperazin-1-yl)-1-oxoisoindolin-2-yl)-piperidine-2,6-dione D1070;
4-(4-bromo-3-((4-(2-(2,6-dioxopiperidin-3-yl)-6-fluoro-1-oxoisoindolin-5-yl)-piperazin-1-yl)methyl)phenoxy)benzonitrile D1071;
3-(6-fluoro-1-oxo-5-(4-phenethylpiperazine-1-yl)isoindolin-2-yl)piperidine-2,6-dione D1072;
3-(5-(4-(3-bromo-4-(4-methylpiperazin-1-yl)benzyl)piperazin-1-yl)-6-fluoro-1-oxoisoindolin-2-yl)piperidine-2,6-dione D1073;
tert-butyl 4-(4-((4-(2-(2,6-dioxopiperidin-3-yl)-6-fluoro-1-oxoisoindolin-5-yl)-piperazin-1-yl)methyl)-1H-1,2,3-triazol-1-yl)piperidine-1-carboxylate D1074;
3-(5-(4-(3-bromo-4-morpholinobenzyl)piperazin-1-yl)-6-fluoro-1-oxoisoindolin-2-yl)piperidine-2,6-dione D1075;
3-(6-fluoro-1-oxo-5-(4-(4-(4-(trifluoromethyl)phenoxy)benzyl)piperazin-1-yl)-isoindolin-2-yl)piperidine-2,6-dione D1076;
3-(5-(4-(4-(benzyloxy)-3-ethoxybenzyl)piperazin-1-yl)-6-fluoro-1-oxoisoindolin-2-yl)piperidine-2,6-dione D1077;
tert-butyl 4-(1-(4-(2-(2,6-dioxopiperidin-3-yl)-6-fluoro-1-oxoisoindolin-5-yl)-piperazin-1-yl)-2-methylpropan-2-yl)piperidine-1-carboxylate D1078;
benzyl (4-((4-(2-(2,6-dioxopiperidin-3-yl)-6-fluoro-1-oxoisoindolin-5-yl)-piperazin-1-yl)methyl)phenyl)carbamate D1079;
tert-butyl 6-((4-(2-(2,6-dioxopiperidin-3-yl)-6-fluoro-1-oxoisoindolin-5-yl)-piperazin-1-yl)methyl)indoline-1-carboxylate D1080;
tert-butyl (((1r,4r)-4-((4-(2-(2,6-dioxopiperidin-3-yl)-6-fluoro-1-oxoisoindolin-5-yl)piperazin-1-yl)methyl)cyclohexyl)methyl)carbamate D1081;
4-(4-((4-(2-(2,6-dioxopiperidin-3-yl)-6-fluoro-1-oxoisoindolin-5-yl)piperazin-1-yl)methyl)phenoxy)-3-fluorobenzonitrile D1082;
3-(6-fluoro-5-(4-(3-methylbenzyl)piperazin-1-yl)-1-oxoisoindolin-2-yl)-piperidine-2,6-dione D1083;
tert-butyl 4-((4-(2-(2,6-dioxopiperidin-3-yl)-6-fluoro-1-oxoisoindolin-5-yl)-piperazin-1-yl)methyl)-4-fluoropiperidine-1-carboxylate D1084;
tert-butyl 4-(2-(4-(2-(2,6-dioxopiperidin-3-yl)-6-fluoro-1-oxoisoindolin-5-yl)-piperazin-1-yl)ethyl)piperazine-1-carboxylate D1085;
3-(5-(4-((2-chloro-4-morpholinopyrimidin-5-yl)methyl)piperazin-1-yl)-6-fluoro-1-oxoisoindolin-2-yl)piperidine-2,6-dione D1086;
tert-butyl ((1r,4r)-4-((4-(2-(2,6-dioxopiperidin-3-yl)-6-fluoro-1-oxoisoindolin-5-yl)piperazin-1-yl)methyl)cyclohexyl)carbamate D1087;
tert-butyl 4-(2-(4-(2-(2,6-dioxopiperidin-3-yl)-6-fluoro-1-oxoisoindolin-5-yl)-piperazin-1-yl)ethyl)piperidine-1-carboxylate D1088;
3-(5-(4-(2-(benzyloxy)-4-methylbenzyl)piperazin-1-yl)-6-fluoro-1-oxoisoindolin-2-yl)piperidine-2,6-dione D1089;
3-(5-(4-(4-(benzyloxy)-2-methylbenzyl)piperazin-1-yl)-6-fluoro-1-oxoisoindolin-2-yl)piperidine-2,6-dione D1090;
3-(5-(4-(3-chloro-4-morpholinobenzyl)piperazin-1-yl)-6-fluoro-1-oxoisoindolin-2-yl)piperidine-2,6-dione D1091;
4-(4-((4-(2-(2,6-dioxopiperidin-3-yl)-6-fluoro-1-oxoisoindolin-5-yl)piperazin-1-yl)methyl)phenoxy)benzonitrile D1092;
4-(3-((4-(2-(2,6-dioxopiperidin-3-yl)-6-fluoro-1-oxoisoindolin-5-yl)piperazin-1-yl)methyl)phenoxy)benzonitrile D1093;
2-((4-(2-(2,6-dioxopiperidin-3-yl)-6-fluoro-1-oxoisoindolin-5-yl)piperazin-1-yl)methyl)-1H-pyrrole-3-carbonitrile D1094;
3-(5-(4-(3-(cyclohexylmethoxy)benzyl)piperazin-1-yl)-6-fluoro-1-oxoisoindolin-2-yl)piperidine-2,6-dione D1095;
3-(5-(4-(3-(3-bromophenyl)propyl)piperazin-1-yl)-6-fluoro-1-oxoisoindolin-2-yl)piperidine-2,6-dione D1096;
3-(5-(4-(4-(benzyloxy)benzyl)piperazin-1-yl)-6-fluoro-1-oxoisoindolin-2-yl)-piperidine-2,6-dione D1097;
3-(5-(4-(3-(benzyloxy)benzyl)piperazin-1-yl)-6-fluoro-1-oxoisoindolin-2-yl)-piperidine-2,6-dione D1098;
5-((4-(2-(2,6-dioxopiperidin-3-yl)-6-fluoro-1-oxoisoindolin-5-yl)piperazin-1-yl)-methyl)-2-(4-methyl-1H-imidazol-1-yl)benzonitrile D1099;
3-(5-(4-(3-chloro-4-(trifluoromethyl)benzyl)piperazin-1-yl)-6-fluoro-1-oxoisoindolin-2-yl)piperidine-2,6-dione D1100;
3-(5-(4-(2-chloro-4-(trifluoromethyl)benzyl)piperazin-1-yl)-6-fluoro-1-oxoisoindolin-2-yl)piperidine-2,6-dione D1101;
3-(5-(4-(4-chloro-2-(trifluoromethyl)benzyl)piperazin-1-yl)-6-fluoro-1-oxoisoindolin-2-yl)piperidine-2,6-dione D1102;
3-(5-(4-(5-chloro-2-(trifluoromethyl)benzyl)piperazin-1-yl)-6-fluoro-1-oxoisoindolin-2-yl)piperidine-2,6-dione D1103;
3-(5-(4-(2-chloro-5-(trifluoromethyl)benzyl)piperazin-1-yl)-6-fluoro-1-oxoisoindolin-2-yl)piperidine-2,6-dione D1104;
3-(6-fluoro-1-oxo-5-(4-((tetrahydro-2H-pyran-4-yl)methyl)piperazin-1-yl)-isoindolin-2-yl)piperidine-2,6-dione D1105;
3-(5-(4-((1-benzylpiperidin-4-yl)methyl)piperazin-1-yl)-6-fluoro-1-oxoisoindolin-2-yl)piperidine-2,6-dione D1106;
2-(3-(4-(2-(2,6-dioxopiperidin-3-yl)-6-fluoro-1-oxoisoindolin-5-yl)piperazin-1-yl)propyl)isoindoline-1,3-dione D1107;
3-(6-fluoro-1-oxo-5-(4-(3-(3-(trifluoromethyl)phenyl)propyl)piperazin-1-yl)-isoindolin-2-yl)piperidine-2,6-dione D1108;
3-(5-(4-((6-(dimethylamino)naphthalen-2-yl)methyl)piperazin-1-yl)-6-fluoro-1-oxoisoindolin-2-yl)piperidine-2,6-dione D1109;
N-(2-((4-(2-(2,6-dioxopiperidin-3-yl)-6-fluoro-1-oxoisoindolin-5-yl)piperazin-1-yl)methyl)phenyl)methanesulfonamide D1110;
N-(4-((4-(2-(2,6-dioxopiperidin-3-yl)-6-fluoro-1-oxoisoindolin-5-yl)piperazin-1-yl)methyl)phenyl)methanesulfonamide D1111;
N-(3-((4-(2-(2,6-dioxopiperidin-3-yl)-6-fluoro-1-oxoisoindolin-5-yl)piperazin-1-yl)methyl)phenyl)methanesulfonamide D1112;

3-(6-fluoro-1-oxo-5-(4-(2-(pyridin-2-yloxy)benzyl)piperazin-1-yl)isoindolin-2-yl)piperidine-2,6-dione D1113;
3-(5-(4-(4-bromophenethyl)piperazin-1-yl)-6-fluoro-1-oxoisoindolin-2-yl)-piperidine-2,6-dione D1114;
3-(6-fluoro-5-(4-((2-morpholinothiazol-5-yl)methyl)piperazin-1-yl)-1-oxoisoindolin-2-yl)piperidine-2,6-dione D1115;
3-(6-fluoro-1-oxo-5-(4-(thiazol-2-ylmethyl)piperazin-1-yl)isoindolin-2-yl)-piperidine-2,6-dione D1116;
3-(5-(4-(4-(ethylsulfonyl)benzyl)piperazin-1-yl)-6-fluoro-1-oxoisoindolin-2-yl)-piperidine-2,6-dione D1117;
3-(6-fluoro-5-(4-((4'-methyl-[2,2'-bipyridin]-4-yl)methyl)piperazin-1-yl)-1-oxoisoindolin-2-yl)piperidine-2,6-dione D1118;
3-(6-fluoro-1-oxo-5-(4-(4-phenoxybenzyl)piperazin-1-yl)isoindolin-2-yl)-piperidine-2,6-dione D1119;
3-(6-fluoro-1-oxo-5-(4-(3-phenoxybenzyl)piperazin-1-yl)isoindolin-2-yl)-piperidine-2,6-dione D1120;
3-(6-fluoro-1-oxo-5-(4-((6-(p-tolyl)pyridin-3-yl)methyl)piperazin-1-yl)-isoindolin-2-yl)piperidine-2,6-dione D1121;
4-((4-(2-(2,6-dioxopiperidin-3-yl)-6-fluoro-1-oxoisoindolin-5-yl)piperazin-1-yl)-methyl)-N-isopropylbenzamide D1122;
3-(6-fluoro-5-(4-(2-morpholinobenzyl)piperazin-1-yl)-1-oxoisoindolin-2-yl)-piperidine-2,6-dione D1123;
3-(6-fluoro-5-(4-(3-morpholinobenzyl)piperazin-1-yl)-1-oxoisoindolin-2-yl)-piperidine-2,6-dione D1124;
3-(6-fluoro-5-(4-(4-morpholinobenzyl)piperazin-1-yl)-1-oxoisoindolin-2-yl)-piperidine-2,6-dione D1125;
3-(6-fluoro-1-oxo-5-(4-(3-(quinolin-6-yl)propyl)piperazin-1-yl)isoindolin-2-yl)-piperidine-2,6-dione D1126;
3-(6-fluoro-1-oxo-5-(4-(thiazol-5-ylmethyl)piperazin-1-yl)isoindolin-2-yl)-piperidine-2,6-dione D1127;
3-(5-(4-((1H-pyrrol-3-yl)methyl)piperazin-1-yl)-6-fluoro-1-oxoisoindolin-2-yl)-piperidine-2,6-dione D1128;
3-(6-fluoro-5-(4-((6-(methylsulfonyl)pyridin-2-yl)methyl)piperazin-1-yl)-1-oxoisoindolin-2-yl)piperidine-2,6-dione D1129;
3-(6-fluoro-1-oxo-5-(4-(3-(pyridin-4-yl)benzyl)piperazin-1-yl)isoindolin-2-yl)-piperidine-2,6-dione D1130;
3-(5-(4-([1,1'-biphenyl]-4-ylmethyl)piperazin-1-yl)-6-fluoro-1-oxoisoindolin-2-yl)piperidine-2,6-dione D1131;
3-(6-fluoro-5-(4-((6-fluorochroman-8-yl)methyl)piperazin-1-yl)-1-oxoisoindolin-2-yl)piperidine-2,6-dione D1132;
3-(6-fluoro-1-oxo-5-(4-((6-(pyrrolidin-1-yl)pyridin-3-yl)methyl)piperazin-1-yl)-isoindolin-2-yl)piperidine-2,6-dione D1133;
3-(6-fluoro-1-oxo-5-(4-(3-(pyrrolidin-1-yl)benzyl)piperazin-1-yl)isoindolin-2-yl)piperidine-2,6-dione D1134;
3-(6-fluoro-1-oxo-5-(4-(4-(pyrrolidin-1-yl)benzyl)piperazin-1-yl)isoindolin-2-yl)piperidine-2,6-dione D1135;
3-(5-(4-(3-(1H-1,2,4-triazol-1-yl)benzyl)piperazin-1-yl)-6-fluoro-1-oxoisoindolin-2-yl)piperidine-2,6-dione D1136;
3-(5-(4-(2-(1H-1,2,4-triazol-1-yl)benzyl)piperazin-1-yl)-6-fluoro-1-oxoisoindolin-2-yl)piperidine-2,6-dione D1137;
3-(5-(4-(4-(1H-1,2,4-triazol-1-yl)benzyl)piperazin-1-yl)-6-fluoro-1-oxoisoindolin-2-yl)piperidine-2,6-dione D1138;
3-(6-fluoro-1-oxo-5-(4-(thiazol-4-ylmethyl)piperazin-1-yl)isoindolin-2-yl)-piperidine-2,6-dione D1139;
3-(6-fluoro-1-oxo-5-(4-((1-phenyl-1H-pyrazol-3-yl)methyl)piperazin-1-yl)-isoindolin-2-yl)piperidine-2,6-dione D1140;
3-(6-fluoro-1-oxo-5-(4-((5-phenyl-1H-imidazol-2-yl)methyl)piperazin-1-yl)-isoindolin-2-yl)piperidine-2,6-dione D1141;
3-(5-(4-(3-(1H-imidazol-1-yl)benzyl)piperazin-1-yl)-6-fluoro-1-oxoisoindolin-2-yl)piperidine-2,6-dione D1142;
3-(6-fluoro-1-oxo-5-(4-((2-phenyl-1H-imidazol-5-yl)methyl)piperazin-1-yl)-isoindolin-2-yl)piperidine-2,6-dione D1143;
3-(5-(4-(4-(1H-imidazol-1-yl)benzyl)piperazin-1-yl)-6-fluoro-1-oxoisoindolin-2-yl)piperidine-2,6-dione D1144;
3-(5-(4-(4-(1H-pyrazol-1-yl)benzyl)piperazin-1-yl)-6-fluoro-1-oxoisoindolin-2-yl)piperidine-2,6-dione D1145;
2-((4-(2-(2,6-dioxopiperidin-3-yl)-6-fluoro-1-oxoisoindolin-5-yl)piperazin-1-yl)-methyl)-1H-indole-6-carbonitrile D1146;
3-((4-(2-(2,6-dioxopiperidin-3-yl)-6-fluoro-1-oxoisoindolin-5-yl)piperazin-1-yl)-methyl)-1H-indole-6-carbonitrile D1147;
3-(5-(4-((2,3-dihydro-[1,4]dioxino[2,3-b]pyridin-6-yl)methyl)piperazin-1-yl)-6-fluoro-1-oxoisoindolin-2-yl)piperidine-2,6-dione D1148;
3-(5-(4-((adamantan-1-yl)methyl)piperazin-1-yl)-6-fluoro-1-oxoisoindolin-2-yl)-piperidine-2,6-dione D1149;
3-(6-fluoro-1-oxo-5-(4-(thiophen-2-ylmethyl)piperazin-1-yl)isoindolin-2-yl)-piperidine-2,6-dione D1150;
3-(5-(4-(3-(benzyloxy)propyl)piperazin-1-yl)-6-fluoro-1-oxoisoindolin-2-yl)-piperidine-2,6-dione D1151;
3-(6-fluoro-5-(4-(3-(2-methoxyphenyl)propyl)piperazin-1-yl)-1-oxoisoindolin-2-yl)piperidine-2,6-dione D1152;
3-(5-(4-((2,3-dihydrobenzo[b][1,4]dioxin-6-yl)methyl)piperazin-1-yl)-6-fluoro-1-oxoisoindolin-2-yl)piperidine-2,6-dione D1153;
3-(6-fluoro-5-(4-((5-fluoro-1H-benzo[d]imidazol-2-yl)methyl)piperazin-1-yl)-1-oxoisoindolin-2-yl)piperidine-2,6-dione D1154;
3-(6-fluoro-5-(4-((4-fluorobenzofuran-7-yl)methyl)piperazin-1-yl)-1-oxoisoindolin-2-yl)piperidine-2,6-dione D1155;
3-(5-(4-(4-(dimethylamino)-3-methylbenzyl)piperazin-1-yl)-6-fluoro-1-oxoisoindolin-2-yl)piperidine-2,6-dione D1156;
3-(5-(4-((2-(tert-butyl)pyridin-4-yl)methyl)piperazin-1-yl)-6-fluoro-1-oxoisoindolin-2-yl)piperidine-2,6-dione D1157;
3-(5-(4-(4-((dimethylamino)methyl)benzyl)piperazin-1-yl)-6-fluoro-1-oxoisoindolin-2-yl)piperidine-2,6-dione D1158;
3-(6-fluoro-1-oxo-5-(4-(thieno[3,2-c]pyridin-2-ylmethyl)piperazin-1-yl)-isoindolin-2-yl)piperidine-2,6-dione D1159;
3-(5-(4-(benzo[d]thiazol-4-ylmethyl)piperazin-1-yl)-6-fluoro-1-oxoisoindolin-2-yl)piperidine-2,6-dione D1160;
3-(6-fluoro-1-oxo-5-(4-(thiophen-3-ylmethyl)piperazin-1-yl)isoindolin-2-yl)-piperidine-2,6-dione D1161;
3-(6-fluoro-1-oxo-5-(4-(thieno[2,3-b]pyridin-2-ylmethyl)piperazin-1-yl)-isoindolin-2-yl)piperidine-2,6-dione D1162;
3-(5-(4-((3,4-dihydro-2H-pyrano[2,3-c]pyridin-6-yl)methyl)piperazin-1-yl)-6-fluoro-1-oxoisoindolin-2-yl)piperidine-2,6-dione D1163;
3-(6-fluoro-5-(4-(3-methyl-3-phenylbutyl)piperazin-1-yl)-1-oxoisoindolin-2-yl)-piperidine-2,6-dione D1164;
3-(5-(4-(benzo[b]thiophen-3-ylmethyl)piperazin-1-yl)-6-fluoro-1-oxoisoindolin-2-yl)piperidine-2,6-dione D1165;
3-(5-(4-(benzo[b]thiophen-2-ylmethyl)piperazin-1-yl)-6-fluoro-1-oxoisoindolin-2-yl)piperidine-2,6-dione D1166;
3-(5-(4-(chroman-6-ylmethyl)piperazin-1-yl)-6-fluoro-1-oxoisoindolin-2-yl)-piperidine-2,6-dione D1167;

3-(6-fluoro-5-(4-((1-methyl-1H-imidazo[4,5-b]pyridin-2-yl)methyl)piperazin-1-yl)-1-oxoisoindolin-2-yl)piperidine-2,6-dione D1168;
4-((4-(2-(2,6-dioxopiperidin-3-yl)-6-fluoro-1-oxoisoindolin-5-yl)piperazin-1-yl)methyl)-2-methoxybenzonitrile D1169;
4-((4-(2-(2,6-dioxopiperidin-3-yl)-6-fluoro-1-oxoisoindolin-5-yl)piperazin-1-yl)methyl)-3-methoxybenzonitrile D1170;
2-((4-(2-(2,6-dioxopiperidin-3-yl)-6-fluoro-1-oxoisoindolin-5-yl)piperazin-1-yl)-methyl)-5-methoxybenzonitrile D1171;
3-(6-fluoro-5-(4-((2-methyl-2H-tetrazol-5-yl)methyl)piperazin-1-yl)-1-oxoisoindolin-2-yl)piperidine-2,6-dione D1172;
3-(6-fluoro-5-(4-((2-methylbenzo[d]oxazol-6-yl)methyl)piperazin-1-yl)-1-oxoisoindolin-2-yl)piperidine-2,6-dione D1173;
3-(6-fluoro-1-oxo-5-(4-((3-oxoisoindolin-5-yl)methyl)piperazin-1-yl)isoindolin-2-yl)piperidine-2,6-dione D1174;
3-(6-fluoro-1-oxo-5-(4-((1-oxoisoindolin-5-yl)methyl)piperazin-1-yl)isoindolin-2-yl)piperidine-2,6-dione D1175;
3-(6-fluoro-1-oxo-5-(4-((5,6,7,8-tetrahydronaphthalen-1-yl)methyl)piperazin-1-yl)isoindolin-2-yl)piperidine-2,6-dione D1176;
3-(6-fluoro-5-(4-((3-methylimidazo[1,2-a]pyridin-2-yl)methyl)piperazin-1-yl)-1-oxoisoindolin-2-yl)piperidine-2,6-dione D1177;
3-(6-fluoro-5-(4-((1-methyl-1H-indazol-6-yl)methyl)piperazin-1-yl)-1-oxoisoindolin-2-yl)piperidine-2,6-dione D1178;
3-(6-fluoro-5-(4-((2-methyl-2H-indazol-5-yl)methyl)piperazin-1-yl)-1-oxoisoindolin-2-yl)piperidine-2,6-dione D1179;
3-(6-fluoro-5-(4-((6-methylimidazo[1,2-a]pyridin-2-yl)methyl)piperazin-1-yl)-1-oxoisoindolin-2-yl)piperidine-2,6-dione D1180;
3-(6-fluoro-5-(4-((5-methylimidazo[1,2-a]pyridin-3-yl)methyl)piperazin-1-yl)-1-oxoisoindolin-2-yl)piperidine-2,6-dione D1181;
3-(6-fluoro-5-(4-((7-methylimidazo[1,2-a]pyridin-3-yl)methyl)piperazin-1-yl)-1-oxoisoindolin-2-yl)piperidine-2,6-dione D1182;
3-(6-fluoro-5-(4-((5-methyl-4H-1,2,4-triazol-3-yl)methyl)piperazin-1-yl)-1-oxoisoindolin-2-yl)piperidine-2,6-dione D1183;
3-(6-fluoro-5-(4-((1-methyl-1H-indazol-4-yl)methyl)piperazin-1-yl)-1-oxoisoindolin-2-yl)piperidine-2,6-dione D1184;
3-(6-fluoro-5-(4-((5-methyl-1H-pyrrolo[2,3-b]pyridin-3-yl)methyl)piperazin-1-yl)-1-oxoisoindolin-2-yl)piperidine-2,6-dione D1185;
3-(6-fluoro-5-(4-((1-methyl-1H-benzo[d]imidazol-2-yl)methyl)piperazin-1-yl)-1-oxoisoindolin-2-yl)piperidine-2,6-dione D1186;
3-(6-fluoro-5-(4-((2-methylimidazo[1,2-a]pyridin-3-yl)methyl)piperazin-1-yl)-1-oxoisoindolin-2-yl)piperidine-2,6-dione D1187;
3-(6-fluoro-5-(4-((2-methyl-2H-indazol-3-yl)methyl)piperazin-1-yl)-1-oxoisoindolin-2-yl)piperidine-2,6-dione D1188;
3-(6-fluoro-5-(4-((7-methyl-1H-indol-3-yl)methyl)piperazin-1-yl)-1-oxoisoindolin-2-yl)piperidine-2,6-dione D1189;
3-(6-fluoro-5-(4-((1-methyl-1H-indol-5-yl)methyl)piperazin-1-yl)-1-oxoisoindolin-2-yl)piperidine-2,6-dione D1190;
3-(6-fluoro-5-(4-((2-methyl-1H-indol-4-yl)methyl)piperazin-1-yl)-1-oxoisoindolin-2-yl)piperidine-2,6-dione D1191;
3-(6-fluoro-5-(4-((1-methyl-1H-indol-6-yl)methyl)piperazin-1-yl)-1-oxoisoindolin-2-yl)piperidine-2,6-dione D1192;
3-(6-fluoro-5-(4-((4-methyl-1H-indol-3-yl)methyl)piperazin-1-yl)-1-oxoisoindolin-2-yl)piperidine-2,6-dione D1193;
3-(6-fluoro-5-(4-((4-methyloxazol-5-yl)methyl)piperazin-1-yl)-1-oxoisoindolin-2-yl)piperidine-2,6-dione D1194;
3-(6-fluoro-5-(4-((3-methyl-1H-indol-2-yl)methyl)piperazin-1-yl)-1-oxoisoindolin-2-yl)piperidine-2,6-dione D1195;
3-(6-fluoro-5-(4-((6-methyl-1H-indol-3-yl)methyl)piperazin-1-yl)-1-oxoisoindolin-2-yl)piperidine-2,6-dione D1196;
tert-butyl (2-(4-(2-(2,6-dioxopiperidin-3-yl)-6-fluoro-1-oxoisoindolin-5-yl)-piperazin-1-yl)ethyl)carbamate D1197;
3-(6-fluoro-1-oxo-5-(4-(quinoxalin-6-ylmethyl)piperazin-1-yl)isoindolin-2-yl)-piperidine-2,6-dione D1198;
3-(5-(4-((1,8-naphthyridin-2-yl)methyl)piperazin-1-yl)-6-fluoro-1-oxoisoindolin-2-yl)piperidine-2,6-dione D1199;
3-(6-fluoro-1-oxo-5-(4-(quinoxalin-6-ylmethyl)piperazin-1-yl)isoindolin-2-yl)-piperidine-2,6-dione D1200;
3-(6-fluoro-1-oxo-5-(4-(quinoxalin-5-ylmethyl)piperazin-1-yl)isoindolin-2-yl)-piperidine-2,6-dione D1201;
3-(6-fluoro-1-oxo-5-(4-(quinolin-8-ylmethyl)piperazin-1-yl)isoindolin-2-yl)-piperidine-2,6-dione D1202;
3-(6-fluoro-5-(4-(isoquinolin-4-ylmethyl)piperazin-1-yl)-1-oxoisoindolin-2-yl)-piperidine-2,6-dione D1203;
3-(6-fluoro-5-(4-(isoquinolin-3-ylmethyl)piperazin-1-yl)-1-oxoisoindolin-2-yl)-piperidine-2,6-dione D1204;
3-(6-fluoro-5-(4-((2-methyloxazol-4-yl)methyl)piperazin-1-yl)-1-oxoisoindolin-2-yl)piperidine-2,6-dione D1205;
3-(6-fluoro-5-(4-(isoquinolin-8-ylmethyl)piperazin-1-yl)-1-oxoisoindolin-2-yl)-piperidine-2,6-dione D1206;
3-(6-fluoro-5-(4-(isoquinolin-5-ylmethyl)piperazin-1-yl)-1-oxoisoindolin-2-yl)-piperidine-2,6-dione D1207;
3-(6-fluoro-1-oxo-5-(4-(quinolin-4-ylmethyl)piperazin-1-yl)isoindolin-2-yl)piperidine-2,6-dione D1208;
3-(6-fluoro-1-oxo-5-(4-(quinolin-6-ylmethyl)piperazin-1-yl)isoindolin-2-yl)-piperidine-2,6-dione D1209;
3-(6-fluoro-5-(4-(naphthalen-2-ylmethyl)piperazin-1-yl)-1-oxoisoindolin-2-yl)-piperidine-2,6-dione D1210;
3-(5-(4-(2-amino-6-chlorobenzyl)piperazin-1-yl)-6-fluoro-1-oxoisoindolin-2-yl)-piperidine-2,6-dione D1211;
3-(5-(4-(2-amino-4-chlorobenzyl)piperazin-1-yl)-6-fluoro-1-oxoisoindolin-2-yl)-piperidine-2,6-dione D1212;
3-(5-(4-(2-amino-3-chlorobenzyl)piperazin-1-yl)-6-fluoro-1-oxoisoindolin-2-yl)-piperidine-2,6-dione D1213;
3-(5-(4-((5-(dimethylamino)thiophen-2-yl)methyl)piperazin-1-yl)-6-fluoro-1-oxoisoindolin-2-yl)piperidine-2,6-dione D1214;
3-(5-(4-(4-chlorophenethyl)piperazin-1-yl)-6-fluoro-1-oxoisoindolin-2-yl)-piperidine-2,6-dione D1215;
3-(6-fluoro-5-(4-((2-methyloxazol-5-yl)methyl)piperazin-1-yl)-1-oxoisoindolin-2-yl)piperidine-2,6-dione D1216;
3-(6-fluoro-5-(4-((4-hydroxybicyclo[2.2.2]octan-1-yl)methyl)piperazin-1-yl)-1-oxoisoindolin-2-yl)piperidine-2,6-dione D1217;
3-(6-fluoro-5-(4-((2-(methylthio)pyrimidin-4-yl)methyl)piperazin-1-yl)-1-oxoisoindolin-2-yl)piperidine-2,6-dione D1218;

3-(5-(4-((2-cyclopropylthiazol-5-yl)methyl)piperazin-1-yl)-6-fluoro-1-oxoisoindolin-2-yl)piperidine-2,6-dione D1219;

3-(5-(4-((1-(tert-butyl)-1H-1,2,3-triazol-4-yl)methyl)piperazin-1-yl)-6-fluoro-1-oxoisoindolin-2-yl)piperidine-2,6-dione D1220;

3-(6-fluoro-5-(4-((1-isobutyl-1H-pyrazol-4-yl)methyl)piperazin-1-yl)-1-oxoisoindolin-2-yl)piperidine-2,6-dione D1221;

3-(5-(4-((5,6-dihydro-8H-imidazo[2,1-c][1,4]oxazin-3-yl)methyl)piperazin-1-yl)-6-fluoro-1-oxoisoindolin-2-yl)piperidine-2,6-dione D1222;

3-(5-(4-((5,6-dihydro-8H-imidazo[2,1-c][1,4]oxazin-2-yl)methyl)piperazin-1-yl)-6-fluoro-1-oxoisoindolin-2-yl)piperidine-2,6-dione D1223;

3-(5-(4-((5-(tert-butyl)-1H-pyrrol-2-yl)methyl)piperazin-1-yl)-6-fluoro-1-oxoisoindolin-2-yl)piperidine-2,6-dione D1224;

3-(5-(4-((2-(dimethylamino)pyrimidin-5-yl)methyl)piperazin-1-yl)-6-fluoro-1-oxoisoindolin-2-yl)piperidine-2,6-dione D1225;

3-(6-fluoro-5-(4-(4-methoxy-3-methylbenzyl)piperazin-1-yl)-1-oxoisoindolin-2-yl)piperidine-2,6-dione D1226;

3-(6-fluoro-5-(4-((1-methyl-1H-imidazol-5-yl)methyl)piperazin-1-yl)-1-oxoisoindolin-2-yl)piperidine-2,6-dione D1227;

3-(6-fluoro-5-(4-(2-methoxy-3-methylbenzyl)piperazin-1-yl)-1-oxoisoindolin-2-yl)piperidine-2,6-dione D1228;

3-(6-fluoro-5-(4-(3-methoxy-2-methylbenzyl)piperazin-1-yl)-1-oxoisoindolin-2-yl)piperidine-2,6-dione D1229;

3-(6-fluoro-5-(4-(2-methoxy-6-methylbenzyl)piperazin-1-yl)-1-oxoisoindolin-2-yl)piperidine-2,6-dione D1230;

3-(6-fluoro-5-(4-(3-methoxy-5-methylbenzyl)piperazin-1-yl)-1-oxoisoindolin-2-yl)-piperidine-2,6-dione D1231;

3-(6-fluoro-5-(4-(4-methoxyphenethyl)piperazin-1-yl)-1-oxoisoindolin-2-yl)-piperidine-2,6-dione D1232;

3-(6-fluoro-5-(4-(3-methoxyphenethyl)piperazin-1-yl)-1-oxoisoindolin-2-yl)-piperidine-2,6-dione D1233;

3-(6-fluoro-5-(4-(4-methoxy-2-methylbenzyl)piperazin-1-yl)-1-oxoisoindolin-2-yl)piperidine-2,6-dione D1234;

3-(6-fluoro-5-(4-(4-hydroxy-3,5-dimethylbenzyl)piperazin-1-yl)-1-oxoisoindolin-2-yl)piperidine-2,6-dione D1235;

3-(5-(4-(4-ethoxybenzyl)piperazin-1-yl)-6-fluoro-1-oxoisoindolin-2-yl)=piperidine-2,6-dione D1236;

3-(6-fluoro-5-(4-(3-methoxy-4-methylbenzyl)piperazin-1-yl)-1-oxoisoindolin-2-yl)piperidine-2,6-dione D1237;

3-(6-fluoro-5-(4-((1-methyl-1H-pyrazol-5-yl)methyl)piperazin-1-yl)-1-oxoisoindolin-2-yl)piperidine-2,6-dione D1238;

3-(5-(4-((1H-pyrrol-2-yl)methyl)piperazin-1-yl)-6-fluoro-1-oxoisoindolin-2-yl)-piperidine-2,6-dione D1239;

3-(6-fluoro-5-(4-(2-methoxy-4-methylbenzyl)piperazin-1-yl)-1-oxoisoindolin-2-yl)piperidine-2,6-dione D1240;

3-(5-(4-(2-(benzyloxy)ethyl)piperazin-1-yl)-6-fluoro-1-oxoisoindolin-2-yl)-piperidine-2,6-dione D1241;

3-(5-(4-(benzo[d][1,3]dioxol-4-ylmethyl)piperazin-1-yl)-6-fluoro-1-oxoisoindolin-2-yl)piperidine-2,6-dione D1242;

3-(5-(4-(2-(dimethylamino)benzyl)piperazin-1-yl)-6-fluoro-1-oxoisoindolin-2-yl)piperidine-2,6-dione D1243;

3-(6-fluoro-5-(4-((5-isopropylpyridin-3-yl)methyl)piperazin-1-yl)-1-oxoisoindolin-2-yl)piperidine-2,6-dione D1244;

3-(5-(4-(4-(ethylamino)benzyl)piperazin-1-yl)-6-fluoro-1-oxoisoindolin-2-yl)-piperidine-2,6-dione D1245;

3-(5-(4-(3-(dimethylamino)benzyl)piperazin-1-yl)-6-fluoro-1-oxoisoindolin-2-yl)piperidine-2,6-dione D1246;

3-((4-(2-(2,6-dioxopiperidin-3-yl)-6-fluoro-1-oxoisoindolin-5-yl)piperazin-1-yl)-methyl)benzamide D1247;

2-((4-(2-(2,6-dioxopiperidin-3-yl)-6-fluoro-1-oxoisoindolin-5-yl)piperazin-1-yl)-methyl)-4-fluorobenzonitrile D1248;

2-((4-(2-(2,6-dioxopiperidin-3-yl)-6-fluoro-1-oxoisoindolin-5-yl)piperazin-1-yl)-methyl)-5-fluorobenzonitrile D1249;

3-(6-fluoro-5-(4-((1-methyl-1H-pyrazol-3-yl)methyl)piperazin-1-yl)-1-oxoisoindolin-2-yl)piperidine-2,6-dione D1250;

4-((4-(2-(2,6-dioxopiperidin-3-yl)-6-fluoro-1-oxoisoindolin-5-yl)piperazin-1-yl)-methyl)-3-fluorobenzonitrile D1251;

3-((4-(2-(2,6-dioxopiperidin-3-yl)-6-fluoro-1-oxoisoindolin-5-yl)piperazin-1-yl)-methyl)-5-fluorobenzonitrile D1252;

4-((4-(2-(2,6-dioxopiperidin-3-yl)-6-fluoro-1-oxoisoindolin-5-yl)piperazin-1-yl)-methyl)-2-fluorobenzonitrile D1253;

5-((4-(2-(2,6-dioxopiperidin-3-yl)-6-fluoro-1-oxoisoindolin-5-yl)piperazin-1-yl)-methyl)-2-fluorobenzonitrile D1254;

3-(6-fluoro-1-oxo-5-(4-(2,4,6-trimethylbenzyl)piperazin-1-yl)isoindolin-2-yl)-piperidine-2,6-dione D1255;

3-(6-fluoro-5-(4-(4-isopropylbenzyl)piperazin-1-yl)-1-oxoisoindolin-2-yl)-piperidine-2,6-dione D1256;

3-(6-fluoro-1-oxo-5-(4-(4-phenylbutyl)piperazin-1-yl)isoindolin-2-yl)piperidine-2,6-dione D1257;

3-(5-(4-((4,4-difluorocyclohexyl)methyl)piperazin-1-yl)-6-fluoro-1-oxoisoindolin-2-yl)piperidine-2,6-dione D1258;

3-(5-(4-(2-ethynyl-4-fluorobenzyl)piperazin-1-yl)-6-fluoro-1-oxoisoindolin-2-yl)-piperidine-2,6-dione D1259;

3-(5-(4-([1,2,4]triazolo[1,5-a]pyridin-7-ylmethyl)piperazin-1-yl)-6-fluoro-1-oxoisoindolin-2-yl)piperidine-2,6-dione D1260;

3-(6-fluoro-5-(4-((1-methyl-1H-imidazol-4-yl)methyl)piperazin-1-yl)-1-oxoisoindolin-2-yl)piperidine-2,6-dione D1261;

3-(6-fluoro-5-(4-(imidazo[1,2-a]pyrimidin-3-ylmethyl)piperazin-1-yl)-1-oxoisoindolin-2-yl)piperidine-2,6-dione D1262;

6-amino-5-((4-(2-(2,6-dioxopiperidin-3-yl)-6-fluoro-1-oxoisoindolin-5-yl)-piperazin-1-yl)methyl)nicotinonitrile D1263;

3-(6-fluoro-5-(4-(imidazo[1,2-a]pyrimidin-7-ylmethyl)piperazin-1-yl)-1-oxoisoindolin-2-yl)piperidine-2,6-dione D1264;

3-(5-(4-((4H-pyrrolo[2,3-b]pyrazin-7-yl)methyl)piperazin-1-yl)-6-fluoro-1-oxoisoindolin-2-yl)piperidine-2,6-dione D1265;

4-((4-(2-(2,6-dioxopiperidin-3-yl)-6-fluoro-1-oxoisoindolin-5-yl)piperazin-1-yl)-methyl)-3-hydroxybenzonitrile D1266;

5-((4-(2-(2,6-dioxopiperidin-3-yl)-6-fluoro-1-oxoisoindolin-5-yl)piperazin-1-yl)-methyl)-2-hydroxybenzonitrile D1267;

3-(6-fluoro-5-(4-(furo[2,3-c]pyridin-5-ylmethyl)piperazin-1-yl)-1-oxoisoindolin-2-yl)piperidine-2,6-dione D1268;

3-(5-(4-(benzo[d]oxazol-5-ylmethyl)piperazin-1-yl)-6-fluoro-1-oxoisoindolin-2-yl)piperidine-2,6-dione D1269;

3-(5-(4-(benzo[d]oxazol-6-ylmethyl)piperazin-1-yl)-6-fluoro-1-oxoisoindolin-2-yl)piperidine-2,6-dione C1270;

3-(5-(4-((5-chlorothiophen-2-yl)methyl)piperazin-1-yl)-6-fluoro-1-oxoisoindolin-2-yl)piperidine-2,6-dione D1271;

3-(6-fluoro-5-(4-((1-methyl-1H-imidazol-2-yl)methyl)piperazin-1-yl)-1-oxoisoindolin-2-yl)piperidine-2,6-dione D1272;

3-(5-(4-((2-chlorothiophen-3-yl)methyl)piperazin-1-yl)-6-fluoro-1-oxoisoindolin-2-yl)piperidine-2,6-dione D1273;

3-(5-(4-(4-cyclopropylbenzyl)piperazin-1-yl)-6-fluoro-1-oxoisoindolin-2-yl)-piperidine-2,6-dione D1274;

3-(5-(4-(2-cyclopropylbenzyl)piperazin-1-yl)-6-fluoro-1-oxoisoindolin-2-yl)-piperidine-2,6-dione D1275;

3-(6-fluoro-1-oxo-5-(4-(pyrazolo[1,5-a]pyridin-7-ylmethyl)piperazin-1-yl)-isoindolin-2-yl)piperidine-2,6-dione D1276;

3-(5-(4-((1H-pyrrolo[2,3-c]pyridin-3-yl)methyl)piperazin-1-yl)-6-fluoro-1-oxoisoindolin-2-yl)piperidine-2,6-dione D1277;

3-(6-fluoro-5-(4-(imidazo[1,2-a]pyridin-5-ylmethyl)piperazin-1-yl)-1-oxoisoindolin-2-yl)piperidine-2,6-dione D1278;

3-(6-fluoro-1-oxo-5-(4-(pyrazolo[1,5-a]pyridin-3-ylmethyl)piperazin-1-yl)-isoindolin-2-yl)piperidine-2,6-dione D1279;

3-(5-(4-((2H-indazol-6-yl)methyl)piperazin-1-yl)-6-fluoro-1-oxoisoindolin-2-yl)-piperidine-2,6-dione D1280;

3-(5-(4-((1H-pyrrolo[3,2-b]pyridin-3-yl)methyl)piperazin-1-yl)-6-fluoro-1-oxoisoindolin-2-yl)piperidine-2,6-dione D1281;

3-(6-fluoro-5-(4-(imidazo[1,5-a]pyridin-1-ylmethyl)piperazin-1-yl)-1-oxoisoindolin-2-yl)piperidine-2,6-dione D1282;

3-(6-fluoro-5-(4-((5-methyl-1H-pyrazol-3-yl)methyl)piperazin-1-yl)-1-oxoisoindolin-2-yl)piperidine-2,6-dione D1283;

3-(5-(4-((1H-pyrrolo[2,3-b]pyridin-6-yl)methyl)piperazin-1-yl)-6-fluoro-1-oxoisoindolin-2-yl)piperidine-2,6-dione D1284;

3-(5-(4-((1H-benzo[d]imidazol-7-yl)methyl)piperazin-1-yl)-6-fluoro-1-oxoisoindolin-2-yl)piperidine-2,6-dione D1285;

3-(6-fluoro-5-(4-(imidazo[1,2-a]pyridin-6-ylmethyl)piperazin-1-yl)-1-oxoisoindolin-2-yl)piperidine-2,6-dione D1286;

3-(6-fluoro-5-(4-(imidazo[1,2-a]pyridin-8-ylmethyl)piperazin-1-yl)-1-oxoisoindolin-2-yl)piperidine-2,6-dione D1287;

3-(6-fluoro-5-(4-(imidazo[1,2-a]pyridin-7-ylmethyl)piperazin-1-yl)-1-oxoisoindolin-2-yl)piperidine-2,6-dione D1288;

3-(5-(4-((1H-pyrrolo[3,2-b]pyridin-6-yl)methyl)piperazin-1-yl)-6-fluoro-1-oxoisoindolin-2-yl)piperidine-2,6-dione D1289;

3-(5-(4-((1H-benzo[d]imidazol-2-yl)methyl)piperazin-1-yl)-6-fluoro-1-oxoisoindolin-2-yl)piperidine-2,6-dione D1290;

3-(6-fluoro-5-(4-(imidazo[1,2-a]pyridin-3-ylmethyl)piperazin-1-yl)-1-oxoisoindolin-2-yl)piperidine-2,6-dione D1291;

3-(6-fluoro-5-(4-(imidazo[1,2-a]pyridin-2-ylmethyl)piperazin-1-yl)-1-oxoisoindolin-2-yl)piperidine-2,6-dione D1292;

3-(5-(4-(benzofuran-4-ylmethyl)piperazin-1-yl)-6-fluoro-1-oxoisoindolin-2-yl)-piperidine-2,6-dione D1293;

3-(6-fluoro-5-(4-((5-methylfuran-2-yl)methyl)piperazin-1-yl)-1-oxoisoindolin-2-yl)piperidine-2,6-dione D1294;

3-(5-(4-(benzofuran-7-ylmethyl)piperazin-1-yl)-6-fluoro-1-oxoisoindolin-2-yl)-piperidine-2,6-dione D1295;

3-(5-(4-(benzofuran-5-ylmethyl)piperazin-1-yl)-6-fluoro-1-oxoisoindolin-2-yl)-piperidine-2,6-dione D1296;

2-((4-(2-(2,6-dioxopiperidin-3-yl)-6-fluoro-1-oxoisoindolin-5-yl)piperazin-1-yl)-methyl)-5-methylbenzonitrile D1297;

3-((4-(2-(2,6-dioxopiperidin-3-yl)-6-fluoro-1-oxoisoindolin-5-yl)piperazin-1-yl)-methyl)-2-methylbenzonitrile D1298;

3-((4-(2-(2,6-dioxopiperidin-3-yl)-6-fluoro-1-oxoisoindolin-5-yl)piperazin-1-yl)-methyl)-5-methylbenzonitrile D1299;

2-((4-(2-(2,6-dioxopiperidin-3-yl)-6-fluoro-1-oxoisoindolin-5-yl)piperazin-1-yl)-methyl)-6-methylbenzonitrile D1300;

4-((4-(2-(2,6-dioxopiperidin-3-yl)-6-fluoro-1-oxoisoindolin-5-yl)piperazin-1-yl)-methyl)-3-methylbenzonitrile D1301;

3-(5-(4-((1H-indol-3-yl)methyl)piperazin-1-yl)-6-fluoro-1-oxoisoindolin-2-yl)-piperidine-2,6-dione D1302;

3-(6-fluoro-5-(4-(indolizin-1-ylmethyl)piperazin-1-yl)-1-oxoisoindolin-2-yl)-piperidine-2,6-dione D1303;

3-(5-(4-((1H-indol-7-yl)methyl)piperazin-1-yl)-6-fluoro-1-oxoisoindolin-2-yl)-piperidine-2,6-dione D1304;

3-(6-fluoro-5-(4-((3-methyl-1H-pyrrol-2-yl)methyl)piperazin-1-yl)-1-oxoisoindolin-2-yl)piperidine-2,6-dione D1305;

3-(5-(4-((1H-indol-2-yl)methyl)piperazin-1-yl)-6-fluoro-1-oxoisoindolin-2-yl)-piperidine-2,6-dione D1306;

3-(5-(4-((1H-indol-6-yl)methyl)piperazin-1-yl)-6-fluoro-1-oxoisoindolin-2-yl)-piperidine-2,6-dione D1307;

3-(5-(4-((4-chloro-1-methyl-1H-pyrazol-3-yl)methyl)piperazin-1-yl)-6-fluoro-1-oxoisoindolin-2-yl)piperidine-2,6-dione D1308;

3-(5-(4-((3-chloropyrazin-2-yl)methyl)piperazin-1-yl)-6-fluoro-1-oxoisoindolin-2-yl)piperidine-2,6-dione D1309;

3-(5-(4-((3-chloropyridin-4-yl)methyl)piperazin-1-yl)-6-fluoro-1-oxoisoindolin-2-yl)piperidine-2,6-dione D1310;

3-(5-(4-((6-chloropyridin-2-yl)methyl)piperazin-1-yl)-6-fluoro-1-oxoisoindolin-2-yl)piperidine-2,6-dione D1311;

3-(6-fluoro-5-(4-((5-fluoro-2-oxo-1,2-dihydropyridin-3-yl)methyl)piperazin-1-yl)-1-oxoisoindolin-2-yl)piperidine-2,6-dione D1312;

3-(5-(4-(2-chlorobenzyl)piperazin-1-yl)-6-fluoro-1-oxoisoindolin-2-yl)-piperidine-2,6-dione D1313;

3-(5-(4-(4-chlorobenzyl)piperazin-1-yl)-6-fluoro-1-oxoisoindolin-2-yl)-piperidine-2,6-dione D1314;

3-(5-(4-(3-chlorobenzyl)piperazin-1-yl)-6-fluoro-1-oxoisoindolin-2-yl)-piperidine-2,6-dione D1315;

3-(6-fluoro-5-(4-((5-methyl-1H-pyrrol-2-yl)methyl)piperazin-1-yl)-1-oxoisoindolin-2-yl)piperidine-2,6-dione D1316;

3-(5-(4-(2-amino-5-fluorobenzyl)piperazin-1-yl)-6-fluoro-1-oxoisoindolin-2-yl)-piperidine-2,6-dione D1317;

3-(6-fluoro-5-(4-((1-isopropyl-1H-pyrazol-4-yl)methyl)piperazin-1-yl)-1-oxoisoindolin-2-yl)piperidine-2,6-dione D1318;

3-(6-fluoro-5-(4-((4-isopropylfuran-2-yl)methyl)piperazin-1-yl)-1-oxoisoindolin-2-yl)piperidine-2,6-dione D1319;

3-(6-fluoro-5-(4-(3-(5-methylfuran-2-yl)propyl)piperazin-1-yl)-1-oxoisoindolin-2-yl)piperidine-2,6-dione D1320;

3-(6-fluoro-5-(4-(4-fluorophenethyl)piperazin-1-yl)-1-oxoisoindolin-2-yl)-piperidine-2,6-dione D1321;

3-(6-fluoro-5-(4-(3-fluoro-2-methylbenzyl)piperazin-1-yl)-1-oxoisoindolin-2-yl)-piperidine-2,6-dione D1322;

3-(6-fluoro-5-(4-(2-fluoro-5-methylbenzyl)piperazin-1-yl)-1-oxoisoindolin-2-yl)-piperidine-2,6-dione D1323;

3-(6-fluoro-5-(4-(4-fluoro-3-methylbenzyl)piperazin-1-yl)-1-oxoisoindolin-2-yl)-piperidine-2,6-dione D1324;

3-(6-fluoro-5-(4-(3-fluoro-5-methylbenzyl)piperazin-1-yl)-1-oxoisoindolin-2-yl)-piperidine-2,6-dione D1325;

3-(6-fluoro-5-(4-(4-fluoro-2-methylbenzyl)piperazin-1-yl)-1-oxoisoindolin-2-yl)-piperidine-2,6-dione D1326;

3-(6-fluoro-5-(4-((1-methyl-1H-pyrrol-2-yl)methyl)piperazin-1-yl)-1-oxoisoindolin-2-yl)piperidine-2,6-dione D1327;

3-(6-fluoro-5-(4-(5-fluoro-2-methylbenzyl)piperazin-1-yl)-1-oxoisoindolin-2-yl)-piperidine-2,6-dione D1328;

3-(6-fluoro-5-(4-((5-methoxypyrazin-2-yl)methyl)piperazin-1-yl)-1-oxoisoindolin-2-yl)piperidine-2,6-dione D1329;

3-(6-fluoro-5-(4-((2-methoxypyrimidin-4-yl)methyl)piperazin-1-yl)-1-oxoisoindolin-2-yl)piperidine-2,6-dione D1330;

5-((4-(2-(2,6-dioxopiperidin-3-yl)-6-fluoro-1-oxoisoindolin-5-yl)piperazin-1-yl)-methyl)thiophene-2-carbonitrile D1331;

3-(6-fluoro-5-(4-((2-methoxypyridin-4-yl)methyl)piperazin-1-yl)-1-oxoisoindolin-2-yl)piperidine-2,6-dione D1332;

3-(6-fluoro-5-(4-((2-methoxypyridin-3-yl)methyl)piperazin-1-yl)-1-oxoisoindolin-2-yl)piperidine-2,6-dione D1333;

3-(6-fluoro-5-(4-((3-methoxypyridin-4-yl)methyl)piperazin-1-yl)-1-oxoisoindolin-2-yl)piperidine-2,6-dione D1334;

3-(6-fluoro-5-(4-((6-methoxypyridin-3-yl)methyl)piperazin-1-yl)-1-oxoisoindolin-2-yl)piperidine-2,6-dione D1335;

3-(6-fluoro-5-(4-((4-methoxypyridin-2-yl)methyl)piperazin-1-yl)-1-oxoisoindolin-2-yl)piperidine-2,6-dione D1336;

3-(6-fluoro-5-(4-((5-methoxypyridin-2-yl)methyl)piperazin-1-yl)-1-oxoisoindolin-2-yl)piperidine-2,6-dione D1337;

3-(6-fluoro-1-oxo-5-(4-(pyrimidin-5-ylmethyl)piperazin-1-yl)isoindolin-2-yl)piperidine-2,6-dione D1338;

3-(6-fluoro-5-(4-((3-methoxypyridin-2-yl)methyl)piperazin-1-yl)-1-oxoisoindolin-2-yl)piperidine-2,6-dione D1339;

3-(6-fluoro-5-(4-((4-methoxypyridin-3-yl)methyl)piperazin-1-yl)-1-oxoisoindolin-2-yl)piperidine-2,6-dione D1340;

3-(6-fluoro-5-(4-((6-methoxypyridin-2-yl)methyl)piperazin-1-yl)-1-oxoisoindolin-2-yl)piperidine-2,6-dione D1341;

3-(6-fluoro-5-(4-((5-methoxypyridin-3-yl)methyl)piperazin-1-yl)-1-oxoisoindolin-2-yl)piperidine-2,6-dione D1342;

3-(6-fluoro-5-(4-((1-methyl-6-oxo-1,6-dihydropyridin-2-yl)methyl)piperazin-1-yl)-1-oxoisoindolin-2-yl)piperidine-2,6-dione D1343;

3-(6-fluoro-5-(4-((1-methyl-2-oxo-1,2-dihydropyridin-4-yl)methyl)piperazin-1-yl)-1-oxoisoindolin-2-yl)piperidine-2,6-dione D1344;

3-(5-(4-((2-amino-5-methylpyridin-3-yl)methyl)piperazin-1-yl)-6-fluoro-1-oxoisoindolin-2-yl)piperidine-2,6-dione D1345;

3-(6-fluoro-5-(4-(2-methoxybenzyl)piperazin-1-yl)-1-oxoisoindolin-2-yl)-piperidine-2,6-dione D1346;

3-(6-fluoro-5-(4-(4-methoxybenzyl)piperazin-1-yl)-1-oxoisoindolin-2-yl)-piperidine-2,6-dione D1347;

3-(6-fluoro-5-(4-(3-hydroxy-5-methylbenzyl)piperazin-1-yl)-1-oxoisoindolin-2-yl)piperidine-2,6-dione D1348;

3-(6-fluoro-1-oxo-5-(4-(pyridin-2-ylmethyl)piperazin-1-yl)isoindolin-2-yl)-piperidine-2,6-dione D1349; or 3-(5-(4-(cyclobutylmethyl)piperazin-1-yl)-6-fluoro-1-oxoisoindolin-2-yl)-piperidine-2,6-dione D1350;

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

In yet another embodiment, provided herein is a compound of:

3-(5-(4-(cyclopropylsulfonyl)piperazin-1-yl)-6-fluoro-1-oxoisoindolin-2-yl)-piperidine-2,6-dione D2001;

3-(6-fluoro-1-oxo-5-(4-(propylsulfonyl)piperazin-1-yl)isoindolin-2-yl)piperidine-2,6-dione D2002;

3-(6-fluoro-5-(4-(isopropylsulfonyl)piperazin-1-yl)-1-oxoisoindolin-2-yl)-piperidine-2,6-dione D2003;

3-(6-fluoro-5-(4-(isobutylsulfonyl)piperazin-1-yl)-1-oxoisoindolin-2-yl)-piperidine-2,6-dione D2004;

3-(6-fluoro-5-(4-(furan-3-ylsulfonyl)piperazin-1-yl)-1-oxoisoindolin-2-yl)-piperidine-2,6-dione D2005;

3-(5-(4-((1H-pyrazol-4-yl)sulfonyl)piperazin-1-yl)-6-fluoro-1-oxoisoindolin-2-yl)piperidine-2,6-dione D2006;

3-(6-fluoro-1-oxo-5-(4-((trifluoromethyl)sulfonyl)piperazin-1-yl)isoindolin-2-yl)-piperidine-2,6-dione D2007;

3-(5-(4-((cyclobutylmethyl)sulfonyl)piperazin-1-yl)-6-fluoro-1-oxoisoindolin-2-yl)piperidine-2,6-dione D2008;

3-(5-(4-((3-chloropropyl)sulfonyl)piperazin-1-yl)-6-fluoro-1-oxoisoindolin-2-yl)-piperidine-2,6-dione D2009;

3-(6-fluoro-1-oxo-5-(4-(pyridin-3-ylsulfonyl)piperazin-1-yl)isoindolin-2-yl)-piperidine-2,6-dione D2010;

3-(6-fluoro-5-(4-((1-methyl-1H-pyrazol-4-yl)sulfonyl)piperazin-1-yl)-1-oxoisoindolin-2-yl)piperidine-2,6-dione D2011;

3-(6-fluoro-5-(4-((1-methyl-1H-pyrazol-3-yl)sulfonyl)piperazin-1-yl)-1-oxoisoindolin-2-yl)piperidine-2,6-dione D2012;

3-(6-fluoro-5-(4-((1-methyl-1H-imidazol-4-yl)sulfonyl)piperazin-1-yl)-1-oxoisoindolin-2-yl)piperidine-2,6-dione D2013;

3-(6-fluoro-1-oxo-5-(4-(thiophen-2-ylsulfonyl)piperazin-1-yl)isoindolin-2-yl)-piperidine-2,6-dione D2014;

3-(5-(4-(cyclohexylsulfonyl)piperazin-1-yl)-6-fluoro-1-oxoisoindolin-2-yl)-piperidine-2,6-dione D2015;

3-(6-fluoro-1-oxo-5-(4-((tetrahydro-2H-pyran-4-yl)sulfonyl)piperazin-1-yl)-isoindolin-2-yl)piperidine-2,6-dione D2016;

3-(6-fluoro-1-oxo-5-(4-(m-tolylsulfonyl)piperazin-1-yl)isoindolin-2-yl)-piperidine-2,6-dione D2017;

3-(6-fluoro-5-(4-((6-methylpyridin-3-yl)sulfonyl)piperazin-1-yl)-1-oxoisoindolin-2-yl)piperidine-2,6-dione D2018;

3-(6-fluoro-5-(4-((4-hydroxyphenyl)sulfonyl)piperazin-1-yl)-1-oxoisoindolin-2-yl)piperidine-2,6-dione D2019;

3-(6-fluoro-5-(4-((4-fluorophenyl)sulfonyl)piperazin-1-yl)-1-oxoisoindolin-2-yl)-piperidine-2,6-dione D2020;

3-(6-fluoro-5-(4-((3-fluorophenyl)sulfonyl)piperazin-1-yl)-1-oxoisoindolin-2-yl)-piperidine-2,6-dione D2021;

3-(6-fluoro-5-(4-((2-fluorophenyl)sulfonyl)piperazin-1-yl)-1-oxoisoindolin-2-yl)-piperidine-2,6-dione D2022;

3-(6-fluoro-1-oxo-5-(4-((3,3,3-trifluoropropyl)sulfonyl)piperazin-1-yl)isoindolin-2-yl)piperidine-2,6-dione D2023;

3-(6-fluoro-5-(4-((4-methylbenzyl)sulfonyl)piperazin-1-yl)-1-oxoisoindolin-2-yl)piperidine-2,6-dione D2024;

3-(6-fluoro-1-oxo-5-(4-(phenethylsulfonyl)piperazin-1-yl)isoindolin-2-yl)-piperidine-2,6-dione D2025;

3-(5-(4-((2,6-dimethylphenyl)sulfonyl)piperazin-1-yl)-6-fluoro-1-oxoisoindolin-2-yl)piperidine-2,6-dione D2026;

3-(6-fluoro-5-(4-((4-methoxyphenyl)sulfonyl)piperazin-1-yl)-1-oxoisoindolin-2-yl)piperidine-2,6-dione D2027;

3-(6-fluoro-5-(4-((3-methoxyphenyl)sulfonyl)piperazin-1-yl)-1-oxoisoindolin-2-yl)piperidine-2,6-dione D2028;
3-(6-fluoro-5-(4-((6-methoxypyridin-3-yl)sulfonyl)piperazin-1-yl)-1-oxoisoindolin-2-yl)piperidine-2,6-dione D2029;
3-(6-fluoro-5-(4-((2-fluoro-5-methylphenyl)sulfonyl)piperazin-1-yl)-1-oxoisoindolin-2-yl)piperidine-2,6-dione D2030;
3-(6-fluoro-5-(4-((4-fluoro-2-methylphenyl)sulfonyl)piperazin-1-yl)-1-oxoisoindolin-2-yl)piperidine-2,6-dione D2031;
3-(6-fluoro-5-(4-((2-fluoro-4-methylphenyl)sulfonyl)piperazin-1-yl)-1-oxoisoindolin-2-yl)piperidine-2,6-dione D2032;
3-(5-(4-((3-chlorophenyl)sulfonyl)piperazin-1-yl)-6-fluoro-1-oxoisoindolin-2-yl)-piperidine-2,6-dione D2033;
3-(5-(4-((2-chlorophenyl)sulfonyl)piperazin-1-yl)-6-fluoro-1-oxoisoindolin-2-yl)-piperidine-2,6-dione D2034;
3-(5-(4-((4-chlorophenyl)sulfonyl)piperazin-1-yl)-6-fluoro-1-oxoisoindolin-2-yl)-piperidine-2,6-dione D2035;
3-(5-(4-((3,4-difluorophenyl)sulfonyl)piperazin-1-yl)-6-fluoro-1-oxoisoindolin-2-yl)piperidine-2,6-dione D2036;
3-(5-(4-((2,4-difluorophenyl)sulfonyl)piperazin-1-yl)-6-fluoro-1-oxoisoindolin-2-yl)piperidine-2,6-dione D2037;
3-(5-(4-((2,5-difluorophenyl)sulfonyl)piperazin-1-yl)-6-fluoro-1-oxoisoindolin-2-yl)piperidine-2,6-dione D2038;
3-(5-(4-((3,5-difluorophenyl)sulfonyl)piperazin-1-yl)-6-fluoro-1-oxoisoindolin-2-yl)piperidine-2,6-dione D2039;
3-(6-fluoro-1-oxo-5-(4-(pyridin-3-ylsulfonyl)piperazin-1-yl)isoindolin-2-yl)-piperidine-2,6-dione D2040;
2-((4-(2-(2,6-dioxopiperidin-3-yl)-6-fluoro-1-oxoisoindolin-5-yl)piperazin-1-yl)-sulfonyl)-5-methylbenzonitrile D2041;
3-(5-(4-((1H-indol-5-yl)sulfonyl)piperazin-1-yl)-6-fluoro-1-oxoisoindolin-2-yl)-piperidine-2,6-dione D2042;
3-(5-(4-(benzofuran-5-ylsulfonyl)piperazin-1-yl)-6-fluoro-1-oxoisoindolin-2-yl)-piperidine-2,6-dione D2043;
3-(5-(4-((2,3-dihydrobenzofuran-5-yl)sulfonyl)piperazin-1-yl)-6-fluoro-1-oxoisoindolin-2-yl)piperidine-2,6-dione D2044;
3-(6-fluoro-5-(4-((4-isopropylphenyl)sulfonyl)piperazin-1-yl)-1-oxoisoindolin-2-yl)piperidine-2,6-dione D2045;
3-(6-fluoro-5-(4-((3-isopropylphenyl)sulfonyl)piperazin-1-yl)-1-oxoisoindolin-2-yl)piperidine-2,6-dione D2046;
3-((4-(2-(2,6-dioxopiperidin-3-yl)-6-fluoro-1-oxoisoindolin-5-yl)piperazin-1-yl)-sulfonyl)-4-fluorobenzonitrile D2047;
5-((4-(2-(2,6-dioxopiperidin-3-yl)-6-fluoro-1-oxoisoindolin-5-yl)piperazin-1-yl)-sulfonyl)-2-fluorobenzonitrile D2048;
4-((4-(2-(2,6-dioxopiperidin-3-yl)-6-fluoro-1-oxoisoindolin-5-yl)piperazin-1-yl)-sulfonyl)benzamide D2049;
3-(6-fluoro-5-(4-((3-methoxybenzyl)sulfonyl)piperazin-1-yl)-1-oxoisoindolin-2-yl)piperidine-2,6-dione D2050;
3-(6-fluoro-5-(4-((3-methoxy-4-methylphenyl)sulfonyl)piperazin-1-yl)-1-oxoisoindolin-2-yl)piperidine-2,6-dione D2051;
3-(6-fluoro-5-(4-((5-fluoro-2-methoxyphenyl)sulfonyl)piperazin-1-yl)-1-oxoisoindolin-2-yl)piperidine-2,6-dione D2052;
3-(6-fluoro-5-(4-((3-fluoro-4-methoxyphenyl)sulfonyl)piperazin-1-yl)-1-oxoisoindolin-2-yl)piperidine-2,6-dione D2053;
3-(6-fluoro-1-oxo-5-(4-((5,6,7,8-tetrahydronaphthalen-2-yl)sulfonyl)piperazin-1-yl)isoindolin-2-yl)piperidine-2,6-dione D2054;
3-(6-fluoro-5-(4-((2-hydroxy-1H-benzo[d]imidazol-6-yl)sulfonyl)piperazin-1-yl)-1-oxoisoindolin-2-yl)piperidine-2,6-dione D2055;
3-(5-(4-((4-(tert-butyl)phenyl)sulfonyl)piperazin-1-yl)-6-fluoro-1-oxoisoindolin-2-yl)piperidine-2,6-dione D2056;
3-(5-(4-((3-(tert-butyl)phenyl)sulfonyl)piperazin-1-yl)-6-fluoro-1-oxoisoindolin-2-yl)piperidine-2,6-dione D2057;
N-(3-((4-(2-(2,6-dioxopiperidin-3-yl)-6-fluoro-1-oxoisoindolin-5-yl)piperazin-1-yl)sulfonyl)phenyl)acetamide D2058;
N-(4-((4-(2-(2,6-dioxopiperidin-3-yl)-6-fluoro-1-oxoisoindolin-5-yl)piperazin-1-yl)sulfonyl)phenyl)acetamide D2059;
4-((4-(2-(2,6-dioxopiperidin-3-yl)-6-fluoro-1-oxoisoindolin-5-yl)piperazin-1-yl)-sulfonyl)-N-methylbenzamide D2060;
2-chloro-4-((4-(2-(2,6-dioxopiperidin-3-yl)-6-fluoro-1-oxoisoindolin-5-yl)-piperazin-1-yl)sulfonyl)benzonitrile D2061;
3-(5-(4-((5-chloro-2-methoxypyridin-3-yl)sulfonyl)piperazin-1-yl)-6-fluoro-1-oxoisoindolin-2-yl)piperidine-2,6-dione D2062;
3-(5-(4-((4-(difluoromethoxy)phenyl)sulfonyl)piperazin-1-yl)-6-fluoro-1-oxoisoindolin-2-yl)piperidine-2,6-dione D2063;
3-(6-fluoro-5-(4-((4-(oxazol-5-yl)phenyl)sulfonyl)piperazin-1-yl)-1-oxoisoindolin-2-yl)piperidine-2,6-dione D2064;
3-(6-fluoro-1-oxo-5-(4-((4-(trifluoromethyl)phenyl)sulfonyl)piperazin-1-yl)-isoindolin-2-yl)piperidine-2,6-dione D2065;
3-(6-fluoro-1-oxo-5-(4-((3-(trifluoromethyl)phenyl)sulfonyl)piperazin-1-yl)-isoindolin-2-yl)piperidine-2,6-dione D2066;
3-(6-fluoro-1-oxo-5-(4-((2-(trifluoromethyl)phenyl)sulfonyl)piperazin-1-yl)-isoindolin-2-yl)piperidine-2,6-dione D2067;
3-(6-fluoro-1-oxo-5-(4-((6-(trifluoromethyl)pyridin-3-yl)sulfonyl)piperazin-1-yl)isoindolin-2-yl)piperidine-2,6-dione D2068;
3-(6-fluoro-1-oxo-5-(4-((2-oxo-1,2,3,4-tetrahydroquinolin-6-yl)sulfonyl)-piperazin-1-yl)isoindolin-2-yl)piperidine-2,6-dione D2069;
2-((4-(2-(2,6-dioxopiperidin-3-yl)-6-fluoro-1-oxoisoindolin-5-yl)piperazin-1-yl)-sulfonyl)-N,N-dimethylbenzamide D2070;
3-(5-(4-((3-bromophenyl)sulfonyl)piperazin-1-yl)-6-fluoro-1-oxoisoindolin-2-yl)-piperidine-2,6-dione D2071;
3-(5-(4-((2-bromophenyl)sulfonyl)piperazin-1-yl)-6-fluoro-1-oxoisoindolin-2-yl)-piperidine-2,6-dione D2072;
3-(6-fluoro-1-oxo-5-(4-((1-(o-tolyl)-1H-pyrazol-4-yl)sulfonyl)piperazin-1-yl)-isoindolin-2-yl)piperidine-2,6-dione D2073;
3-(6-fluoro-1-oxo-5-(4-((4-(trifluoromethyl)benzyl)sulfonyl)piperazin-1-yl)-isoindolin-2-yl)piperidine-2,6-dione D2074;
3-(6-fluoro-1-oxo-5-(4-((2-(trifluoromethoxy)phenyl)sulfonyl)piperazin-1-yl)-isoindolin-2-yl)piperidine-2,6-dione D2075;
3-(5-(4-((1-chloroisoquinolin-5-yl)sulfonyl)piperazin-1-yl)-6-fluoro-1-oxoisoindolin-2-yl)piperidine-2,6-dione D2076;
3-(6-fluoro-5-(4-(isoquinolin-5-ylsulfonyl)piperazin-1-yl)-1-oxoisoindolin-2-yl)-piperidine-2,6-dione D2077;
3-(6-fluoro-1-oxo-5-(4-((4-(pyridin-2-yloxy)phenyl)sulfonyl)piperazin-1-yl)-isoindolin-2-yl)piperidine-2,6-dione D2078;

3-(6-fluoro-1-oxo-5-(4-((6-phenoxypyridin-3-yl)sulfonyl)piperazin-1-yl)-isoindolin-2-yl)piperidine-2,6-dione D2079;
3-(5-(4-((5-(dimethylamino)naphthalen-1-yl)sulfonyl)piperazin-1-yl)-6-fluoro-1-oxoisoindolin-2-yl)piperidine-2,6-dione D2080;
3-(5-(4-((6-(dimethylamino)naphthalen-2-yl)sulfonyl)piperazin-1-yl)-6-fluoro-1-oxoisoindolin-2-yl)piperidine-2,6-dione D2081;
3-(5-(4-((4-(benzyloxy)phenyl)sulfonyl)piperazin-1-yl)-6-fluoro-1-oxoisoindolin-2-yl)piperidine-2,6-dione D2082;
tert-butyl 4-((4-(2-(2,6-dioxopiperidin-3-yl)-6-fluoro-1-oxoisoindolin-5-yl)-piperazin-1-yl)sulfonyl)piperidine-1-carboxylate D2083;
benzyl 4-((4-(2-(2,6-dioxopiperidin-3-yl)-6-fluoro-1-oxoisoindolin-5-yl)-piperazin-1-yl)sulfonyl)piperidine-1-carboxylate D2084;
3-(6-fluoro-1-oxo-5-(4-((2-(2,2,2-trifluoroacetyl)-1,2,3,4-tetrahydroisoquinolin-7-yl)sulfonyl)piperazin-1-yl)isoindolin-2-yl)piperidine-2,6-dione D2085;
benzyl 4-(((4-(2-(2,6-dioxopiperidin-3-yl)-6-fluoro-1-oxoisoindolin-5-yl)-piperazin-1-yl)sulfonyl)methyl)piperidine-1-carboxylate D2086;
3-(5-(4-(ethylsulfonyl)piperazin-1-yl)-6-fluoro-1-oxoisoindolin-2-yl)piperidine-2,6-dione D2087;
3-(5-(4-((5-chlorothiophen-2-yl)sulfonyl)piperazin-1-yl)-6-fluoro-1-oxoisoindolin-2-yl)piperidine-2,6-dione D2088;
3-(5-(4-((3-chloro-4-methylphenyl)sulfonyl)piperazin-1-yl)-6-fluoro-1-oxoisoindolin-2-yl)piperidine-2,6-dione D2089;
3-(5-(4-((2-chloro-6-methylphenyl)sulfonyl)piperazin-1-yl)-6-fluoro-1-oxoisoindolin-2-yl)piperidine-2,6-dione D2090;
3-(5-(4-((3,5-difluorobenzyl)sulfonyl)piperazin-1-yl)-6-fluoro-1-oxoisoindolin-2-yl)piperidine-2,6-dione D2091;
3-(6-fluoro-5-(4-(naphthalen-2-ylsulfonyl)piperazin-1-yl)-1-oxoisoindolin-2-yl)-piperidine-2,6-dione D2092;
3-(6-fluoro-1-oxo-5-(4-(quinolin-8-ylsulfonyl)piperazin-1-yl)isoindolin-2-yl)-piperidine-2,6-dione D2093;
3-(6-fluoro-5-(4-(isoquinolin-5-ylsulfonyl)piperazin-1-yl)-1-oxoisoindolin-2-yl)-piperidine-2,6-dione D2094;
3-(6-fluoro-1-oxo-5-(4-(quinoxalin-5-ylsulfonyl)piperazin-1-yl)isoindolin-2-yl)-piperidine-2,6-dione D2095;
3-chloro-4-((4-(2-(2,6-dioxopiperidin-3-yl)-6-fluoro-1-oxoisoindolin-5-yl)-piperazin-1-yl)sulfonyl)benzonitrile D2096;
3-(5-(4-(benzo[d][1,3]dioxol-5-ylsulfonyl)piperazin-1-yl)-6-fluoro-1-oxoisoindolin-2-yl)piperidine-2,6-dione D2097;
3-(5-(4-(benzo[d]thiazol-6-ylsulfonyl)piperazin-1-yl)-6-fluoro-1-oxoisoindolin-2-yl)piperidine-2,6-dione D2098;
3-(5-(4-((2,4-dichlorophenyl)sulfonyl)piperazin-1-yl)-6-fluoro-1-oxoisoindolin-2-yl)piperidine-2,6-dione D2099; or
3-(5-(4-((2,5-dichlorophenyl)sulfonyl)piperazin-1-yl)-6-fluoro-1-oxoisoindolin-2-yl)piperidine-2,6-dione D2100;

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

In yet another embodiment, provided herein is a compound of:

3-(4-(7-(furan-2-carbonyl)-2,7-diazaspiro[3.5]nonan-2-yl)-1-oxoisoindolin-2-yl)-piperidine-2,6-dione E0001;
3-(4-(7-(furan-3-carbonyl)-2,7-diazaspiro[3.5]nonan-2-yl)-1-oxoisoindolin-2-yl)-piperidine-2,6-dione E0002;
3-(4-(7-(2-(1H-pyrrol-2-yl)acetyl)-2,7-diazaspiro[3.5]nonan-2-yl)-1-oxoisoindolin-2-yl)piperidine-2,6-dione E0003;
3-(4-(7-(2-(1H-pyrazol-1-yl)acetyl)-2,7-diazaspiro[3.5]nonan-2-yl)-1-oxoisoindolin-2-yl)piperidine-2,6-dione E0004;
3-(1-oxo-4-(7-(2-(pyrrolidin-1-yl)acetyl)-2,7-diazaspiro[3.5]nonan-2-yl)-isoindolin-2-yl)piperidine-2,6-dione E0005;
3-(1-oxo-4-(7-(tetrahydro-2H-pyran-4-carbonyl)-2,7-diazaspiro[3.5]nonan-2-yl)-isoindolin-2-yl)piperidine-2,6-dione E0006;
3-(4-(7-(2-morpholinoacetyl)-2,7-diazaspiro[3.5]nonan-2-yl)-1-oxoisoindolin-2-yl)piperidine-2,6-dione E0007;
3-(2-(2-(2,6-dioxopiperidin-3-yl)-1-oxoisoindolin-4-yl)-2,7-diazaspiro[3.5]-nonane-7-carbonyl)benzonitrile E0008;
3-(1-oxo-4-(7-(2-(m-tolyl)acetyl)-2,7-diazaspiro[3.5]nonan-2-yl)isoindolin-2-yl)-piperidine-2,6-dione E0009;
3-(1-oxo-4-(7-(3-phenylpropanoyl)-2,7-diazaspiro[3.5]nonan-2-yl)isoindolin-2-yl)piperidine-2,6-dione E0010;
3-(1-oxo-4-(7-(3-(pyridin-2-yl)propanoyl)-2,7-diazaspiro[3.5]nonan-2-yl)-isoindolin-2-yl)piperidine-2,6-dione E0011;
3-(4-(7-(3-(hydroxymethyl)benzoyl)-2,7-diazaspiro[3.5]nonan-2-yl)-1-oxoisoindolin-2-yl)piperidine-2,6-dione E0012;
3-(4-(7-(1H-pyrrole-2-carbonyl)-2,7-diazaspiro[3.5]nonan-2-yl)-1-oxoisoindolin-2-yl)piperidine-2,6-dione E0013;
3-(1-oxo-4-(7-(2-(m-tolyloxy)acetyl)-2,7-diazaspiro[3.5]nonan-2-yl)isoindolin-2-yl)piperidine-2,6-dione E0014;
3-(4-(7-(2-(2-methoxypyridin-3-yl)acetyl)-2,7-diazaspiro[3.5]nonan-2-yl)-1-oxoisoindolin-2-yl)piperidine-2,6-dione E0015;
2-chloro-5-(2-(2-(2,6-dioxopiperidin-3-yl)-1-oxoisoindolin-4-yl)-2,7-diazaspiro[3.5]nonane-7-carbonyl)benzonitrile E0016;
2-chloro-4-(2-(2-(2,6-dioxopiperidin-3-yl)-1-oxoisoindolin-4-yl)-2,7-diazaspiro[3.5]nonane-7-carbonyl)benzonitrile E0017;
3-(1-oxo-4-(7-(3-(pyridin-3-yl)propanoyl)-2,7-diazaspiro[3.5]nonan-2-yl)-isoindolin-2-yl)piperidine-2,6-dione E0018;
3-(4-(7-(2,6-difluorobenzoyl)-2,7-diazaspiro[3.5]nonan-2-yl)-1-oxoisoindolin-2-yl)piperidine-2,6-dione E0019;
3-(4-(7-(2,5-difluorobenzoyl)-2,7-diazaspiro[3.5]nonan-2-yl)-1-oxoisoindolin-2-yl)piperidine-2,6-dione E0020;
3-(4-(7-(3,5-difluorobenzoyl)-2,7-diazaspiro[3.5]nonan-2-yl)-1-oxoisoindolin-2-yl)piperidine-2,6-dione E0021;
3-(4-(7-(2-methyl-2-phenylpropanoyl)-2,7-diazaspiro[3.5]nonan-2-yl)-1-oxoisoindolin-2-yl)piperidine-2,6-dione E0022;
3-(1-oxo-4-(7-(pyrimidine-4-carbonyl)-2,7-diazaspiro[3.5]nonan-2-yl)isoindolin-2-yl)piperidine-2,6-dione E0023;
3-(4-(7-(1-methyl-1H-pyrrole-2-carbonyl)-2,7-diazaspiro[3.5]nonan-2-yl)-1-oxoisoindolin-2-yl)piperidine-2,6-dione E0024;
3-(4-(7-(2-methyl-1H-imidazole-5-carbonyl)-2,7-diazaspiro[3.5]nonan-2-yl)-1-oxoisoindolin-2-yl)piperidine-2,6-dione E0025;
3-(4-(7-(2-(1H-1,2,3-triazol-1-yl)acetyl)-2,7-diazaspiro[3.5]nonan-2-yl)-1-oxoisoindolin-2-yl)piperidine-2,6-dione E0026;
3-(4-(7-(2-cyclopentylacetyl)-2,7-diazaspiro[3.5]nonan-2-yl)-1-oxoisoindolin-2-yl)piperidine-2,6-dione E0027;
5-(2-(2-(2,6-dioxopiperidin-3-yl)-1-oxoisoindolin-4-yl)-2,7-diazaspiro[3.5]-nonane-7-carbonyl)-1H-pyrrole-2-carbonitrile E0028;

5-(2-(2-(2,6-dioxopiperidin-3-yl)-1-oxoisoindolin-4-yl)-2,7-diazaspiro[3.5]-nonane-7-carbonyl)-1H-pyrrole-3-carbonitrile E0029;

3-(1-oxo-4-(7-(2-(pyrimidin-2-yl)acetyl)-2,7-diazaspiro[3.5]nonan-2-yl)-isoindolin-2-yl)piperidine-2,6-dione E0030;

3-(1-oxo-4-(7-(2-(pyrimidin-5-yl)acetyl)-2,7-diazaspiro[3.5]nonan-2-yl)-isoindolin-2-yl)piperidine-2,6-dione E0031;

3-(4-(7-(3-(1H-pyrrol-2-yl)propanoyl)-2,7-diazaspiro[3.5]nonan-2-yl)-1-oxoisoindolin-2-yl)piperidine-2,6-dione E0032;

3-(4-(7-(1-methylpiperidine-4-carbonyl)-2,7-diazaspiro[3.5]nonan-2-yl)-1-oxoisoindolin-2-yl)piperidine-2,6-dione E0033;

3-(1-oxo-4-(7-(2-(piperidin-1-yl)acetyl)-2,7-diazaspiro[3.5]nonan-2-yl)-isoindolin-2-yl)piperidine-2,6-dione E0034; or 3-(1-oxo-4-(7-(2-(tetrahydro-2H-pyran-4-yl)acetyl)-2,7-diazaspiro[3.5]nonan-2-yl)isoindolin-2-yl)piperidine-2,6-dione E0035;

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

In yet another embodiment, provided herein is a compound of:

3-(4-(7-benzyl-2,7-diazaspiro[3.5]nonan-2-yl)-1-oxoisoindolin-2-yl)piperidine-2,6-dione E1001;

3-(1-oxo-4-(7-(pyridin-3-ylmethyl)-2,7-diazaspiro[3.5]nonan-2-yl)isoindolin-2-yl)piperidine-2,6-dione E1002;

3-(1-oxo-4-(7-(pyridin-4-ylmethyl)-2,7-diazaspiro[3.5]nonan-2-yl)isoindolin-2-yl)piperidine-2,6-dione E1003;

3-(1-oxo-4-(7-(pyridin-2-ylmethyl)-2,7-diazaspiro[3.5]nonan-2-yl)isoindolin-2-yl)piperidine-2,6-dione E1004;

3-(1-oxo-4-(7-(pyrimidin-5-ylmethyl)-2,7-diazaspiro[3.5]nonan-2-yl)isoindolin-2-yl)piperidine-2,6-dione E1005;

3-(4-(7-((1-methyl-1H-imidazol-5-yl)methyl)-2,7-diazaspiro[3.5]nonan-2-yl)-1-oxoisoindolin-2-yl)piperidine-2,6-dione E1006;

3-(1-oxo-4-(7-phenethyl-2,7-diazaspiro[3.5]nonan-2-yl)isoindolin-2-yl)-piperidine-2,6-dione E1007;

3-((2-(2-(2,6-dioxopiperidin-3-yl)-1-oxoisoindolin-4-yl)-2,7-diazaspiro[3.5]-nonan-7-yl)methyl)benzonitrile E1008;

2-((2-(2-(2,6-dioxopiperidin-3-yl)-1-oxoisoindolin-4-yl)-2,7-diazaspiro[3.5]-nonan-7-yl)methyl)benzonitrile E1009;

6-((2-(2-(2,6-dioxopiperidin-3-yl)-1-oxoisoindolin-4-yl)-2,7-diazaspiro[3.5]-nonan-7-yl)methyl)nicotinonitrile E1010;

3-(1-oxo-4-(7-(3-phenylpropyl)-2,7-diazaspiro[3.5]nonan-2-yl)isoindolin-2-yl)-piperidine-2,6-dione E1011;

3-(4-(7-(4-(hydroxymethyl)benzyl)-2,7-diazaspiro[3.5]nonan-2-yl)-1-oxoisoindolin-2-yl)piperidine-2,6-dione E1012;

2-((2-(2-(2,6-dioxopiperidin-3-yl)-1-oxoisoindolin-4-yl)-2,7-diazaspiro[3.5]-nonan-7-yl)methyl)-5-methoxybenzonitrile E1013;

3-chloro-5-((2-(2-(2,6-dioxopiperidin-3-yl)-1-oxoisoindolin-4-yl)-2,7-diazaspiro[3.5]nonan-7-yl)methyl)benzonitrile E1014;

2-chloro-4-((2-(2-(2,6-dioxopiperidin-3-yl)-1-oxoisoindolin-4-yl)-2,7-diazaspiro[3.5]nonan-7-yl)methyl)benzonitrile E1015;

3-(1-oxo-4-(7-((2-phenyl-1H-imidazol-5-yl)methyl)-2,7-diazaspiro[3.5]nonan-2-yl)isoindolin-2-yl)piperidine-2,6-dione E1016;

3-(1-oxo-4-(7-(4-(pyrrolidin-1-yl)benzyl)-2,7-diazaspiro[3.5]nonan-2-yl)-isoindolin-2-yl)piperidine-2,6-dione E1017;

3-(4-(7-(4-((2-hydroxyethyl)(methyl)amino)benzyl)-2,7-diazaspiro[3.5]nonan-2-yl)-1-oxoisoindolin-2-yl)piperidine-2,6-dione E1018;

3-(4-(7-(4-(cyclopentyloxy)benzyl)-2,7-diazaspiro[3.5]nonan-2-yl)-1-oxoisoindolin-2-yl)piperidine-2,6-dione E1019;

3-(4-(7-(4-morpholinobenzyl)-2,7-diazaspiro[3.5]nonan-2-yl)-1-oxoisoindolin-2-yl)piperidine-2,6-dione E1020;

3-(4-(7-(3-morpholinobenzyl)-2,7-diazaspiro[3.5]nonan-2-yl)-1-oxoisoindolin-2-yl)piperidine-2,6-dione E1021;

3-(4-(7-(4-benzylbenzyl)-2,7-diazaspiro[3.5]nonan-2-yl)-1-oxoisoindolin-2-yl)piperidine-2,6-dione E1022;

3-(1-oxo-4-(7-(4-(pyridin-3-yloxy)benzyl)-2,7-diazaspiro[3.5]nonan-2-yl)-isoindolin-2-yl)piperidine-2,6-dione E1023;

3-(1-oxo-4-(7-(pyrimidin-4-ylmethyl)-2,7-diazaspiro[3.5]nonan-2-yl)isoindolin-2-yl)piperidine-2,6-dione E1024;

3-(4-(7-(cyclohexylmethyl)-2,7-diazaspiro[3.5]nonan-2-yl)-1-oxoisoindolin-2-yl)piperidine-2,6-dione E1025;

3-(1-oxo-4-(7-((tetrahydro-2H-pyran-4-yl)methyl)-2,7-diazaspiro[3.5]nonan-2-yl)isoindolin-2-yl)piperidine-2,6-dione E1026;

3-(4-(7-(4-methoxybenzyl)-2,7-diazaspiro[3.5]nonan-2-yl)-1-oxoisoindolin-2-yl)piperidine-2,6-dione E1027;

3-(4-(7-(3-methoxybenzyl)-2,7-diazaspiro[3.5]nonan-2-yl)-1-oxoisoindolin-2-yl)piperidine-2,6-dione E1028;

3-(4-(7-((6-methoxypyridin-3-yl)methyl)-2,7-diazaspiro[3.5]nonan-2-yl)-1-oxoisoindolin-2-yl)piperidine-2,6-dione E1029;

3-(4-(7-((1H-indol-3-yl)methyl)-2,7-diazaspiro[3.5]nonan-2-yl)-1-oxoisoindolin-2-yl)piperidine-2,6-dione E1030;

3-(4-(7-(2-methoxyphenethyl)-2,7-diazaspiro[3.5]nonan-2-yl)-1-oxoisoindolin-2-yl)piperidine-2,6-dione E1031;

3-(1-oxo-4-(7-((6-(pyrrolidin-1-yl)pyridin-3-yl)methyl)-2,7-diazaspiro[3.5]-nonan-2-yl)isoindolin-2-yl)piperidine-2,6-dione E1032;

3-(4-(7-((5-(morpholinomethyl)furan-2-yl)methyl)-2,7-diazaspiro[3.5]nonan-2-yl)-1-oxoisoindolin-2-yl)piperidine-2,6-dione E1033;

3-(4-(7-((1-benzylpiperidin-4-yl)methyl)-2,7-diazaspiro[3.5]nonan-2-yl)-1-oxoisoindolin-2-yl)piperidine-2,6-dione E1034;

3-(4-(7-((4-(benzyloxy)pyridin-2-yl)methyl)-2,7-diazaspiro[3.5]nonan-2-yl)-1-oxoisoindolin-2-yl)piperidine-2,6-dione E1035;

3-(1-oxo-4-(7-(4-((pyridin-2-yloxy)methyl)benzyl)-2,7-diazaspiro[3.5]nonan-2-yl)isoindolin-2-yl)piperidine-2,6-dione E1036;

3-(4-(7-(2-chloro-4-morpholinobenzyl)-2,7-diazaspiro[3.5]nonan-2-yl)-1-oxoisoindolin-2-yl)piperidine-2,6-dione E1037;

3-(4-(7-(furan-3-ylmethyl)-2,7-diazaspiro[3.5]nonan-2-yl)-1-oxoisoindolin-2-yl)-piperidine-2,6-dione E1038;

3-(4-(7-(furan-2-ylmethyl)-2,7-diazaspiro[3.5]nonan-2-yl)-1-oxoisoindolin-2-yl)-piperidine-2,6-dione E1039; or 3-(4-(7-((1H-pyrazol-4-yl)methyl)-2,7-diazaspiro[3.5]nonan-2-yl)-1-oxoisoindolin-2-yl)piperidine-2,6-dione E1040;

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

In yet another embodiment, provided herein is a compound of:

3-(5-(7-(furan-2-carbonyl)-2,7-diazaspiro[3.5]nonan-2-yl)-1-oxoisoindolin-2-yl)-piperidine-2,6-dione F0001;

3-(5-(7-(furan-3-carbonyl)-2,7-diazaspiro[3.5]nonan-2-yl)-1-oxoisoindolin-2-yl)-piperidine-2,6-dione F0002;

3-(5-(7-(2-(1H-pyrrol-2-yl)acetyl)-2,7-diazaspiro[3.5]nonan-2-yl)-1-oxoisoindolin-2-yl)piperidine-2,6-dione F0003;

3-(5-(7-(2-(1H-pyrazol-1-yl)acetyl)-2,7-diazaspiro[3.5]nonan-2-yl)-1-oxoisoindolin-2-yl)piperidine-2,6-dione F0004;

3-(1-oxo-5-(7-(2-(pyrrolidin-1-yl)acetyl)-2,7-diazaspiro[3.5]nonan-2-yl)-isoindolin-2-yl)piperidine-2,6-dione F0005;

3-(1-oxo-5-(7-(tetrahydro-2H-pyran-4-carbonyl)-2,7-diazaspiro[3.5]nonan-2-yl)-isoindolin-2-yl)piperidine-2,6-dione F0006;

3-(5-(7-(2-morpholinoacetyl)-2,7-diazaspiro[3.5]nonan-2-yl)-1-oxoisoindolin-2-yl)piperidine-2,6-dione F0007;

3-(2-(2-(2,6-dioxopiperidin-3-yl)-1-oxoisoindolin-5-yl)-2,7-diazaspiro[3.5]-nonane-7-carbonyl)benzonitrile F0008;

3-(1-oxo-5-(7-(2-(m-tolyl)acetyl)-2,7-diazaspiro[3.5]nonan-2-yl)isoindolin-2-yl)-piperidine-2,6-dione F0009;

3-(1-oxo-5-(7-(3-phenylpropanoyl)-2,7-diazaspiro[3.5]nonan-2-yl)isoindolin-2-yl)-piperidine-2,6-dione F0010;

3-(1-oxo-5-(7-(3-(pyridin-2-yl)propanoyl)-2,7-diazaspiro[3.5]nonan-2-yl)-isoindolin-2-yl)piperidine-2,6-dione F0011;

3-(5-(7-(3-(hydroxymethyl)benzoyl)-2,7-diazaspiro[3.5]nonan-2-yl)-1-oxoisoindolin-2-yl)piperidine-2,6-dione F0012;

3-(5-(7-(1H-pyrrole-2-carbonyl)-2,7-diazaspiro[3.5]nonan-2-yl)-1-oxoisoindolin-2-yl)piperidine-2,6-dione F0013;

3-(1-oxo-5-(7-(2-(m-tolyloxy)acetyl)-2,7-diazaspiro[3.5]nonan-2-yl)isoindolin-2-yl)piperidine-2,6-dione F0014;

3-(5-(7-(2-(2-methoxypyridin-3-yl)acetyl)-2,7-diazaspiro[3.5]nonan-2-yl)-1-oxoisoindolin-2-yl)piperidine-2,6-dione F0015;

2-chloro-5-(2-(2-(2,6-dioxopiperidin-3-yl)-1-oxoisoindolin-5-yl)-2,7-diazaspiro[3.5]nonane-7-carbonyl)benzonitrile F0016;

2-chloro-4-(2-(2-(2,6-dioxopiperidin-3-yl)-1-oxoisoindolin-5-yl)-2,7-diazaspiro[3.5]nonane-7-carbonyl)benzonitrile F0017;

3-(1-oxo-5-(7-(3-(pyridin-3-yl)propanoyl)-2,7-diazaspiro[3.5]nonan-2-yl)-isoindolin-2-yl)piperidine-2,6-dione F0018;

3-(5-(7-(2,6-difluorobenzoyl)-2,7-diazaspiro[3.5]nonan-2-yl)-1-oxoisoindolin-2-yl)piperidine-2,6-dione F0019;

3-(5-(7-(2,5-difluorobenzoyl)-2,7-diazaspiro[3.5]nonan-2-yl)-1-oxoisoindolin-2-yl)piperidine-2,6-dione F0020;

3-(5-(7-(3,5-difluorobenzoyl)-2,7-diazaspiro[3.5]nonan-2-yl)-1-oxoisoindolin-2-yl)piperidine-2,6-dione F0021;

3-(5-(7-(2-methyl-2-phenylpropanoyl)-2,7-diazaspiro[3.5]nonan-2-yl)-1-oxoisoindolin-2-yl)piperidine-2,6-dione F0022;

3-(1-oxo-5-(7-(pyrimidine-4-carbonyl)-2,7-diazaspiro[3.5]nonan-2-yl)isoindolin-2-yl)piperidine-2,6-dione F0023;

3-(5-(7-(1-methyl-1H-pyrrole-2-carbonyl)-2,7-diazaspiro[3.5]nonan-2-yl)-1-oxoisoindolin-2-yl)piperidine-2,6-dione F0024;

3-(5-(7-(2-methyl-1H-imidazole-5-carbonyl)-2,7-diazaspiro[3.5]nonan-2-yl)-1-oxoisoindolin-2-yl)piperidine-2,6-dione F0025;

3-(5-(7-(2-(1H-1,2,3-triazol-1-yl)acetyl)-2,7-diazaspiro[3.5]nonan-2-yl)-1-oxoisoindolin-2-yl)piperidine-2,6-dione F0026;

3-(5-(7-(2-cyclopentylacetyl)-2,7-diazaspiro[3.5]nonan-2-yl)-1-oxoisoindolin-2-yl)piperidine-2,6-dione F0027;

5-(2-(2-(2,6-dioxopiperidin-3-yl)-1-oxoisoindolin-5-yl)-2,7-diazaspiro[3.5]-nonane-7-carbonyl)-1H-pyrrole-2-carbonitrile F0028;

5-(2-(2-(2,6-dioxopiperidin-3-yl)-1-oxoisoindolin-5-yl)-2,7-diazaspiro[3.5]-nonane-7-carbonyl)-1H-pyrrole-3-carbonitrile F0029;

3-(1-oxo-5-(7-(2-(pyrimidin-2-yl)acetyl)-2,7-diazaspiro[3.5]nonan-2-yl)-isoindolin-2-yl)piperidine-2,6-dione F0030;

3-(1-oxo-5-(7-(2-(pyrimidin-5-yl)acetyl)-2,7-diazaspiro[3.5]nonan-2-yl)-isoindolin-2-yl)piperidine-2,6-dione F0031;

3-(5-(7-(3-(1H-pyrrol-2-yl)propanoyl)-2,7-diazaspiro[3.5]nonan-2-yl)-1-oxoisoindolin-2-yl)piperidine-2,6-dione F0032;

3-(5-(7-(1-methylpiperidine-4-carbonyl)-2,7-diazaspiro[3.5]nonan-2-yl)-1-oxoisoindolin-2-yl)piperidine-2,6-dione F0033;

3-(1-oxo-5-(7-(2-(piperidin-1-yl)acetyl)-2,7-diazaspiro[3.5]nonan-2-yl)-isoindolin-2-yl)piperidine-2,6-dione F0034; or 3-(1-oxo-5-(7-(2-(tetrahydro-2H-pyran-4-yl)acetyl)-2,7-diazaspiro[3.5]nonan-2-yl)isoindolin-2-yl)piperidine-2,6-dione F0035;

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

In still another embodiment, provided herein is a compound of:

3-(5-(7-benzyl-2,7-diazaspiro[3.5]nonan-2-yl)-1-oxoisoindolin-2-yl)piperidine-2,6-dione F1001;

3-(1-oxo-5-(7-(pyridin-3-ylmethyl)-2,7-diazaspiro[3.5]nonan-2-yl)isoindolin-2-yl)piperidine-2,6-dione F1002;

3-(1-oxo-5-(7-(pyridin-4-ylmethyl)-2,7-diazaspiro[3.5]nonan-2-yl)isoindolin-2-yl)piperidine-2,6-dione F1003;

3-(1-oxo-5-(7-(pyridin-2-ylmethyl)-2,7-diazaspiro[3.5]nonan-2-yl)isoindolin-2-yl)piperidine-2,6-dione F1004;

3-(1-oxo-5-(7-(pyrimidin-5-ylmethyl)-2,7-diazaspiro[3.5]nonan-2-yl)isoindolin-2-yl)piperidine-2,6-dione F1005;

3-(5-(7-((1-methyl-1H-imidazol-5-yl)methyl)-2,7-diazaspiro[3.5]nonan-2-yl)-1-oxoisoindolin-2-yl)piperidine-2,6-dione F1006;

3-(1-oxo-5-(7-phenethyl-2,7-diazaspiro[3.5]nonan-2-yl)isoindolin-2-yl)-piperidine-2,6-dione F1007;

3-((2-(2-(2,6-dioxopiperidin-3-yl)-1-oxoisoindolin-5-yl)-2,7-diazaspiro[3.5]-nonan-7-yl)methyl)benzonitrile F1008;

2-((2-(2-(2,6-dioxopiperidin-3-yl)-1-oxoisoindolin-5-yl)-2,7-diazaspiro[3.5]-nonan-7-yl)methyl)benzonitrile F1009;

6-((2-(2-(2,6-dioxopiperidin-3-yl)-1-oxoisoindolin-5-yl)-2,7-diazaspiro[3.5]-nonan-7-yl)methyl)nicotinonitrile F1010;

3-(1-oxo-5-(7-(3-phenylpropyl)-2,7-diazaspiro[3.5]nonan-2-yl)isoindolin-2-yl)-piperidine-2,6-dione F1011;

3-(5-(7-(4-(hydroxymethyl)benzyl)-2,7-diazaspiro[3.5]nonan-2-yl)-1-oxoisoindolin-2-yl)piperidine-2,6-dione F1012;

2-((2-(2-(2,6-dioxopiperidin-3-yl)-1-oxoisoindolin-5-yl)-2,7-diazaspiro[3.5]-nonan-7-yl)methyl)-5-methoxybenzonitrile F1013;

3-chloro-5-((2-(2-(2,6-dioxopiperidin-3-yl)-1-oxoisoindolin-5-yl)-2,7-diazaspiro[3.5]nonan-7-yl)methyl)benzonitrile F1014;

2-chloro-4-((2-(2-(2,6-dioxopiperidin-3-yl)-1-oxoisoindolin-5-yl)-2,7-diazaspiro[3.5]nonan-7-yl)methyl)benzonitrile F1015;

3-(1-oxo-5-(7-((2-phenyl-1H-imidazol-5-yl)methyl)-2,7-diazaspiro[3.5]nonan-2-yl)isoindolin-2-yl)piperidine-2,6-dione F1016;

3-(1-oxo-5-(7-(4-(pyrrolidin-1-yl)benzyl)-2,7-diazaspiro[3.5]nonan-2-yl)-isoindolin-2-yl)piperidine-2,6-dione F1017;

3-(5-(7-(4-((2-hydroxyethyl)(methyl)amino)benzyl)-2,7-diazaspiro[3.5]nonan-2-yl)-1-oxoisoindolin-2-yl)piperidine-2,6-dione F1018;

3-(5-(7-(4-(cyclopentyloxy)benzyl)-2,7-diazaspiro[3.5]nonan-2-yl)-1-oxoisoindolin-2-yl)piperidine-2,6-dione F1019;

3-(5-(7-(4-morpholinobenzyl)-2,7-diazaspiro[3.5]nonan-2-yl)-1-oxoisoindolin-2-yl)piperidine-2,6-dione F1020;

3-(5-(7-(3-morpholinobenzyl)-2,7-diazaspiro[3.5]nonan-2-yl)-1-oxoisoindolin-2-yl)piperidine-2,6-dione F1021;

3-(5-(7-(4-benzylbenzyl)-2,7-diazaspiro[3.5]nonan-2-yl)-1-oxoisoindolin-2-yl)-piperidine-2,6-dione F1022;

3-(1-oxo-5-(7-(4-(pyridin-3-yloxy)benzyl)-2,7-diazaspiro[3.5]nonan-2-yl)-isoindolin-2-yl)piperidine-2,6-dione F1023;

3-(1-oxo-5-(7-(pyrimidin-4-ylmethyl)-2,7-diazaspiro[3.5]nonan-2-yl)isoindolin-2-yl)piperidine-2,6-dione F1024;

3-(5-(7-(cyclohexylmethyl)-2,7-diazaspiro[3.5]nonan-2-yl)-1-oxoisoindolin-2-yl)piperidine-2,6-dione F1025;

3-(1-oxo-5-(7-((tetrahydro-2H-pyran-4-yl)methyl)-2,7-diazaspiro[3.5]nonan-2-yl)isoindolin-2-yl)piperidine-2,6-dione F1026;

3-(5-(7-(4-methoxybenzyl)-2,7-diazaspiro[3.5]nonan-2-yl)-1-oxoisoindolin-2-yl)-piperidine-2,6-dione F1027;

3-(5-(7-(3-methoxybenzyl)-2,7-diazaspiro[3.5]nonan-2-yl)-1-oxoisoindolin-2-yl)-piperidine-2,6-dione F1028;

3-(5-(7-((6-methoxypyridin-3-yl)methyl)-2,7-diazaspiro[3.5]nonan-2-yl)-1-oxoisoindolin-2-yl)piperidine-2,6-dione F1029;

3-(5-(7-((1H-indol-3-yl)methyl)-2,7-diazaspiro[3.5]nonan-2-yl)-1-oxoisoindolin-2-yl)piperidine-2,6-dione F1030;

3-(5-(7-(2-methoxyphenethyl)-2,7-diazaspiro[3.5]nonan-2-yl)-1-oxoisoindolin-2-yl)piperidine-2,6-dione F1031;

3-(1-oxo-5-(7-((6-(pyrrolidin-1-yl)pyridin-3-yl)methyl)-2,7-diazaspiro[3.5]-nonan-2-yl)isoindolin-2-yl)piperidine-2,6-dione F1032;

3-(5-(7-((5-(morpholinomethyl)furan-2-yl)methyl)-2,7-diazaspiro[3.5]nonan-2-yl)-1-oxoisoindolin-2-yl)piperidine-2,6-dione F1033;

3-(5-(7-((1-benzylpiperidin-4-yl)methyl)-2,7-diazaspiro[3.5]nonan-2-yl)-1-oxoisoindolin-2-yl)piperidine-2,6-dione F1034;

3-(5-(7-((4-(benzyloxy)pyridin-2-yl)methyl)-2,7-diazaspiro[3.5]nonan-2-yl)-1-oxoisoindolin-2-yl)piperidine-2,6-dione F1035;

3-(1-oxo-5-(7-(4-((pyridin-2-yloxy)methyl)benzyl)-2,7-diazaspiro[3.5]nonan-2-yl)isoindolin-2-yl)piperidine-2,6-dione F1036;

3-(5-(7-(2-chloro-4-morpholinobenzyl)-2,7-diazaspiro[3.5]nonan-2-yl)-1-oxoisoindolin-2-yl)piperidine-2,6-dione F1037;

3-(5-(7-(furan-3-ylmethyl)-2,7-diazaspiro[3.5]nonan-2-yl)-1-oxoisoindolin-2-yl)-piperidine-2,6-dione F1038;

3-(5-(7-(furan-2-ylmethyl)-2,7-diazaspiro[3.5]nonan-2-yl)-1-oxoisoindolin-2-yl)-piperidine-2,6-dione F1039; or 3-(5-(7-((1H-pyrazol-4-yl)methyl)-2,7-diazaspiro[3.5]nonan-2-yl)-1-oxoisoindolin-2-yl)piperidine-2,6-dione F1040;

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

In certain embodiments, a compound provided herein is a molecular glue. In certain embodiments, a compound provided herein is monovalent.

In certain embodiments, a compound provided herein is a compound provided herein has a molecular weight of no greater than about 750 Da, no greater than about 700 Da, no greater than about 650 Da, no greater than about 600 Da, no greater than about 550 Da, or no greater than about 500 Da. In certain embodiments, a compound provided herein is a compound provided herein has a molecular weight of no greater than about 750 Da. In certain embodiments, a compound provided herein is a compound provided herein has a molecular weight of no greater than about 700 Da. In certain embodiments, a compound provided herein is a compound provided herein has a molecular weight of no greater than about 650 Da. In certain embodiments, a compound provided herein is a compound provided herein has a molecular weight of no greater than about 600 Da. In certain embodiments, a compound provided herein is a compound provided herein has a molecular weight of no greater than about 550 Da. In certain embodiments, a compound provided herein is a compound provided herein has a molecular weight of no greater than about 500 Da.

In certain embodiments, a compound provided herein is deuterium-enriched. In certain embodiments, a compound provided herein is carbon-13 enriched. In certain embodiments, a compound provided herein is carbon-14 enriched. In certain embodiments, a compound provided herein contains one or more less prevalent isotopes for other elements, including, but not limited to, $^{15}N$ for nitrogen; $^{17}O$ or $^{18}O$ for oxygen, and $^{34}S$, $^{35}S$, or $^{36}S$ for sulfur.

In certain embodiments, a compound provided herein has an isotopic enrichment factor of no less than about 5, no less than about 10, no less than about 20, no less than about 50, no less than about 100, no less than about 200, no less than about 500, no less than about 1,000, no less than about 2,000, no less than about 5,000, or no less than about 10,000. In any events, however, an isotopic enrichment factor for a specified isotope is no greater than the maximum isotopic enrichment factor for the specified isotope, which is the isotopic enrichment factor when a compound at a given position is 100% enriched with the specified isotope. Thus, the maximum isotopic enrichment factor is different for different isotopes. The maximum isotopic enrichment factor is 6,410 for deuterium and 90 for carbon-13.

In certain embodiments, a compound provided herein has a deuterium enrichment factor of no less than about 64 (about 1% deuterium enrichment), no less than about 130 (about 2% deuterium enrichment), no less than about 320 (about 5% deuterium enrichment), no less than about 640 (about 10% deuterium enrichment), no less than about 1,300 (about 20% deuterium enrichment), no less than about 3,200 (about 50% deuterium enrichment), no less than about 4,800 (about 75% deuterium enrichment), no less than about 5,130 (about 80% deuterium enrichment), no less than about 5,450 (about 85% deuterium enrichment), no less than about 5,770 (about 90% deuterium enrichment), no less than about 6,090 (about 95% deuterium enrichment), no less than about 6,220 (about 97% deuterium enrichment), no less than about 6,280

(about 98% deuterium enrichment), no less than about 6,350 (about 99% deuterium enrichment), or no less than about 6,380 (about 99.5% deuterium enrichment). The deuterium enrichment can be determined using conventional analytical methods known to one of ordinary skill in the art, including mass spectrometry and nuclear magnetic resonance spectroscopy. In certain embodiments, at least one of the atoms of a compound provided herein, as specified as deuterium-enriched, has deuterium enrichment of no less than about 50%, no less than about 70%, no less than about 80%, no less than about 90%, or no less than about 98%.

In certain embodiments, a compound provided herein is isolated or purified. In certain embodiments, a compound provided herein has a purity of at least about 90%, at least about 95%, at least about 98%, at least about 99%, or at least about 99.5% by weight.

The compounds provided herein are intended to encompass all possible stereoisomers unless a particular stereochemistry is specified. Where a compound provided herein contains an alkenyl group, the compound may exist as one or mixture of geometric cis/trans (or Z/E)isomers. Where structural isomers are interconvertible, the compound may exist as a single tautomer or a mixture of tautomers. This can take the form of proton tautomerism in the compound that contains, for example, an imino, keto, or oxime group; or so-called valence tautomerism in the compound that contains an aromatic moiety. It follows that a single compound may exhibit more than one type of isomerism.

A compound provided herein can be enantiomerically pure, such as a single enantiomer or a single diastereomer, or be stereoisomeric mixtures, such as a mixture of enantiomers, e.g., a racemic mixture of two enantiomers; or a mixture of two or more diastereomers. As such, one of ordinary skill in the art will recognize that administration of a compound in its (R) form is equivalent, for the compound that undergoes epimerization in vivo, to administration of the compound in its (S) form. Conventional techniques for the preparation/isolation of individual enantiomers include synthesis from a suitable optically pure precursor, asymmetric synthesis from achiral starting materials, or resolution of an enantiomeric mixture, for example, chiral chromatography, recrystallization, resolution, diastereomeric salt formation, or derivatization into diastereomeric adducts followed by separation.

When a compound provided herein contains an acidic or basic moiety, it can also be provided as a pharmaceutically acceptable salt. See, Berge et al., *J. Pharm. Sci.* 1977, 66, 1-19*; Handbook of Pharmaceutical Salts: Properties, Selection, and Use,* 2nd ed.; Stahl and Wermuth Eds.; John Wiley & Sons, 2011. In certain embodiments, a pharmaceutically acceptable salt of a compound provided herein is a solvate. In certain embodiments, a pharmaceutically acceptable salt of a compound provided herein is a hydrate.

Suitable acids for use in the preparation of pharmaceutically acceptable salts of a compound provided herein include, but are not limited to, acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxoglutaric acid, glycolic acid, hippuric acid, hydrobromic acid, hydrochloric acid, hydroiodic acid, (+)-L-lactic acid, (±)-DL-lactic acid, lactobionic acid, lauric acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

Suitable bases for use in the preparation of pharmaceutically acceptable salts of a compound provided herein include, but are not limited to, inorganic bases, such as magnesium hydroxide, calcium hydroxide, potassium hydroxide, zinc hydroxide, and sodium hydroxide; and organic bases, such as primary, secondary, tertiary, and quaternary, aliphatic and aromatic amines, including, but not limited to, L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methyl-glucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, triethanolamine, trimethylamine, triethylamine, N-methyl-D-glucamine, 2-amino-2-(hydroxymethyl)-1,3-propanediol, and tromethamine.

A compound provided herein may also be provided as a prodrug, which is a functional derivative of the compound and is readily convertible into the parent compound in vivo. Prodrugs are often useful because, in some situations, they may be easier to administer than the parent compound. They may, for instance, be bioavailable by oral administration whereas the parent compound is not. The prodrug may also have enhanced solubility in pharmaceutical compositions over the parent compound. A prodrug may be converted into the parent drug by various mechanisms, including enzymatic processes and metabolic hydrolysis.

Pharmaceutical Compositions

In one embodiment, provided herein is a pharmaceutical composition, comprising a compound provided herein, e.g., a compound of Formula (I), or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and a pharmaceutically acceptable excipient.

The pharmaceutical composition provided herein can be formulated in various dosage forms, including, but not limited to, dosage forms for oral, parenteral, and topical administration. The pharmaceutical composition can also be formulated as modified release dosage forms, including delayed-, extended-, prolonged-, sustained-, pulsatile-, controlled-, accelerated-, fast-, targeted-, programmed-release, and gastric retention dosage forms. These dosage forms can be prepared according to conventional methods and techniques known to those skilled in the art. See, e.g., *Remington: The Science and Practice of Pharmacy, supra; Modified-Release Drug Delivery Technology,* 2nd ed.; Rathbone et al., Eds.; Drugs and the Pharmaceutical Sciences 184; CRC Press: Boca Raton, FL, 2008.

In one embodiment, the pharmaceutical composition provided herein is formulated in a dosage form for oral administration. In another embodiment, the pharmaceutical composition provided herein is formulated in a dosage form for parenteral administration. In yet another embodiment, the pharmaceutical composition provided herein is formulated in a dosage form for intravenous administration. In yet another embodiment, the pharmaceutical composition provided herein is formulated in a dosage form for intramuscular administration. In yet another embodiment, the pharmaceutical composition provided herein is formulated in a dosage form for subcutaneous administration. In still another embodiment, the pharmaceutical composition provided herein is formulated in a dosage form for topical administration.

The pharmaceutical composition provided herein can be provided in a unit-dosage form or multiple-dosage form. A unit-dosage form, as used herein, refers to physically discrete a unit suitable for administration to a subject, and packaged individually as is known in the art. Each unit-dose contains a predetermined quantity of an active ingredient(s) (e.g., a compound provided herein) sufficient to produce the desired therapeutic effect, in association with the required pharmaceutical excipient(s). Examples of a unit-dosage form include, but are not limited to, an ampoule, syringe, and individually packaged tablet and capsule. A unit-dosage form may be administered in fractions or multiples thereof. A multiple-dosage form is a plurality of identical unit-dosage forms packaged in a single container to be administered in a segregated unit-dosage form. Examples of a multiple-dosage form include, are not limited to, a vial, bottle of tablets or capsules, or bottle of pints or gallons.

The pharmaceutical composition provided herein can be administered at once or multiple times at intervals of time. It is understood that the precise dosage and duration of treatment may vary with the age, weight, and condition of the subject being treated, and may be determined empirically using known testing protocols or by extrapolation from in vivo or in vitro test or diagnostic data. It is further understood that for any particular individual, specific dosage regimens should be adjusted over time according to the subject's need and the professional judgment of the person administering or supervising the administration of the pharmaceutical composition.

Methods of Use

In one embodiment, provided herein is a method of treating, preventing, or ameliorating one or more symptoms of a disorder, disease, or condition mediated by a zinc-figure protein, CK1α, GSPT1, and/or PDE6D in a subject, comprising administering to the subject in need thereof a therapeutically effective amount of a compound of Formula (I), or an enantiomer, a mixture of enantiomers, a diastereomer, a mixture of two or more diastereomers, a tautomer, a mixture of two or more tautomers, or an isotopic variant thereof, or a pharmaceutically acceptable salt, solvate, hydrate, or prodrug thereof.

In certain embodiments, the disorder, disease, or condition mediated by a zinc-figure protein, CK1α, GSPT1, and/or PDE6D is a proliferative disease.

In certain embodiments, the zinc-figure protein is Aiolos, Helios, or Ikaros. In certain embodiments, the zinc-figure protein is Aiolos. In certain embodiments, the zinc-figure protein is Helios. In certain embodiments, the zinc-figure protein is Ikaros.

In another embodiment, provided herein is a method of treating, preventing, or ameliorating one or more symptoms of a proliferative disease in a subject, comprising administering to the subject in need thereof a therapeutically effective amount of a compound provided herein, e.g., a compound of Formula (I), or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

In certain embodiments, the proliferative disease is cancer. In certain embodiments, the cancer is refractory and/or relapsed. In certain embodiments, the cancer is refractory. In certain embodiments, the cancer is relapsed. In certain embodiments, the cancer is metastatic. In certain embodiments, the cancer is unresectable. In certain embodiments, the cancer is metastatic.

In certain embodiments, the cancer is drug-resistant. In certain embodiment, the cancer is multidrug-resistant. In certain embodiments, the cancer is resistant to a chemotherapy. In certain embodiments, the cancer is resistant to an immunotherapy. In certain embodiments, the cancer is resistant to a standard therapy for the cancer.

In certain embodiments, the subject is a mammal. In certain embodiments, the subject is a human.

In certain embodiments, the therapeutically effective amount of a compound provided herein is ranging from about 0.1 to about 100 mg/kg/day, from about 0.1 to about 50 mg/kg/day, from about 0.1 to about 60 mg/kg/day, from about 0.1 to about 50 mg/kg/day, from about 0.1 to about 25 mg/kg/day, from about 0.1 to about 20 mg/kg/day, from about 0.1 to about 15 mg/kg/day, from about 0.1 to about 10 mg/kg/day, or from about 0.1 to about 5 mg/kg/day. In one embodiment, the therapeutically effective amount of a compound provided herein is ranging from about 0.1 to about 100 mg/kg/day. In another embodiment, the therapeutically effective amount of a compound provided herein is ranging from about 0.1 to about 50 mg/kg/day. In yet another embodiment, the therapeutically effective amount of a compound provided herein is ranging from about 0.1 to about 60 mg/kg/day. In yet another embodiment, the therapeutically effective amount of a compound provided herein is ranging from about 0.1 to about 50 mg/kg/day. In yet another embodiment, the therapeutically effective amount of a compound provided herein is ranging from about 0.1 to about 25 mg/kg/day. In yet another embodiment, the therapeutically effective amount of a compound provided herein is ranging from about 0.1 to about 20 mg/kg/day. In yet another embodiment, the therapeutically effective amount of a compound provided herein is ranging from about 0.1 to about 15 mg/kg/day. In yet another embodiment, the therapeutically effective amount of a compound provided herein is ranging from about 0.1 to about 10 mg/kg/day. In still another embodiment, the therapeutically effective amount of a compound provided herein is ranging from about 0.1 to about 5 mg/kg/day.

It is understood that the administered dose can also be expressed in units other than mg/kg/day. For example, doses for parenteral administration can be expressed as $mg/m^2$/day. One of ordinary skill in the art would readily know how to convert doses from mg/kg/day to $mg/m^2$/day to given either the height or weight of a subject or both. For example, a dose of 1 $mg/m^2$/day for a 65 kg human is approximately equal to 58 mg/kg/day.

Depending on the disorder, disease, or condition to be treated and the subject's condition, a compound provided herein may be administered by oral, parenteral (e.g., intramuscular, intraperitoneal, intravenous, CIV, intracisternal injection or infusion, subcutaneous injection, or implant), inhalation, nasal, vaginal, rectal, sublingual, or topical (e.g., transdermal or local) routes of administration. A compound provided herein may be formulated in suitable dosage unit with a pharmaceutically acceptable excipient, carrier, adjuvant, or vehicle, appropriate for each route of administration.

In one embodiment, a compound provided herein is administered orally. In another embodiment, a compound provided herein is administered parenterally. In yet another embodiment, a compound provided herein is administered intravenously. In yet another embodiment, a compound provided herein is administered intramuscularly. In yet another embodiment, a compound provided herein is administered subcutaneously. In still another embodiment, a compound provided herein is administered topically.

A compound provided herein can be delivered as a single dose such as, e.g., a single bolus injection, or oral tablets or pills; or over time such as, e.g., continuous infusion over time or divided bolus doses over time. A compound provided herein can be administered repetitively, if necessary, for example, until the subject experiences stable disease or regression, or until the subject experiences disease progression or unacceptable toxicity.

A compound provided herein can be administered once daily (QD) or divided into multiple daily doses such as twice daily (BID), and three times daily (TID). In addition, the administration can be continuous, i.e., every day, or intermittently. The term "intermittent" or "intermittently" as used herein is intended to mean stopping and starting at either regular or irregular intervals. For example, intermittent administration of a compound provided herein is administration for one to six days per week, administration in cycles (e.g., daily administration for two to eight consecutive weeks, then a rest period with no administration for up to one week), or administration on alternate days.

In certain embodiments, a compound provided herein is cyclically administered to a subject. Cycling therapy involves the administration of an active agent for a period of time, followed by a rest for a period of time, and repeating this sequential administration. Cycling therapy can reduce the development of resistance to one or more of the therapies, avoid or reduce the side effects of one of the therapies, and/or improves the efficacy of the treatment.

A compound provided herein can also be combined or used in combination with other therapeutic agents useful in the treatment and/or prevention of a condition, disorder, or disease described herein.

As used herein, the term "in combination" includes the use of more than one therapy (e.g., one or more prophylactic and/or therapeutic agents). However, the use of the term "in combination" does not restrict the order in which therapies (e.g., prophylactic and/or therapeutic agents) are administered to a subject with a disease or disorder. A first therapy (e.g., a prophylactic or therapeutic agent such as a compound provided herein) can be administered prior to (e.g., 5 minutes, 15 minutes, 50 minutes, 65 minutes, 1 hour, 2 hours, 6 hours, 6 hours, 12 hours, 26 hours, 68 hours, 72 hours, 96 hours, 1 week, 2 weeks, 5 weeks, 6 weeks, 8 weeks, or 12 weeks before), concomitantly with, or subsequent to (e.g., 5 minutes, 15 minutes, 50 minutes, 65 minutes, 1 hour, 2 hours, 6 hours, 12 hours, 26 hours, 68 hours, 72 hours, 96 hours, 1 week, 2 weeks, 5 weeks, 6 weeks, 8 weeks, or 12 weeks after) the administration of a second therapy (e.g., a prophylactic or therapeutic agent) to the subject. Triple therapy is also contemplated herein.

The route of administration of a compound provided herein is independent of the route of administration of a second therapy. In one embodiment, a compound provided herein is administered orally. In another embodiment, a compound provided herein is administered intravenously. Thus, in accordance with these embodiments, a compound provided herein is administered orally or intravenously, and the second therapy can be administered orally, parenterally, intraperitoneally, intravenously, intraarterially, transdermally, sublingually, intramuscularly, rectally, transbuccally, intranasally, liposomally, via inhalation, vaginally, intraocularly, via local delivery by catheter or stent, subcutaneously, intraadiposally, intraarticularly, intrathecally, or in a slow release dosage form. In one embodiment, a compound provided herein and a second therapy are administered by the same mode of administration, orally or by IV. In another embodiment, a compound provided herein is administered by one mode of administration, e.g., by IV, whereas the second agent (an anticancer agent) is administered by another mode of administration, e.g., orally.

In one embodiment, provided herein is a method of inhibiting the growth of a cell, comprising contacting the cell with an effective amount of a compound of Formula (I), or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof.

In certain embodiments, the cell is a cancerous cell. In certain embodiments, the cell is a human cell. In certain embodiments, the cell is a human cancerous cell.

In one embodiment, provided herein is inducing degradation of a protein, comprising contacting the protein with an effective amount of a compound of Formula (I), or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof.

In certain embodiments, the protein is a zinc-figure protein, CK1α, GSPT1, or PDE6D. In certain embodiments, the protein is a zinc-figure protein. In certain embodiments, the protein is CK1α. In certain embodiments, the protein is GSPT1. In certain embodiments, the protein is PDE6D.

In certain embodiments, the zinc-figure protein is Aiolos, Helios, or Ikaros. In certain embodiments, the zinc-figure protein is Aiolos. In certain embodiments, the zinc-figure protein is Helios. In certain embodiments, the zinc-figure protein is Ikaros.

A compound provided herein can also be provided as an article of manufacture using packaging materials well known to those of skill in the art. See, e.g., U.S. Pat. Nos. 5,525,907; 5,052,558; and 5,055,252. Examples of pharmaceutical packaging materials include, but are not limited to, blister packs, bottles, tubes, inhalers, pumps, bags, vials, containers, syringes, and any packaging material suitable for a selected formulation and intended mode of administration and treatment.

In certain embodiments, provided herein is a kit which, when used by a medical practitioner, can simplify the administration of an appropriate amount of a compound provided herein as an active ingredient to a subject. In certain embodiments, the kit provided herein includes a container and a dosage form of a compound provided herein.

Kits provided herein can further include devices that are used to administer the active ingredients. Examples of such devices include, but are not limited to, syringes, needle-less injectors drip bags, patches, and inhalers. The kits provided herein can also include condoms for administration of the active ingredients.

Kits provided herein can further include pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: aqueous vehicles, including, but not limited to, water for injection USP, sodium chloride injection, Ringer's injection, dextrose injection, dextrose and sodium chloride injection, and lactated Ringer's injection; water-miscible vehicles, including, but not limited to, ethyl alcohol, polyethylene glycol, and polypropylene glycol; and non-aqueous vehicles, including, but not limited to, corn oil, cottonseed oil, peanut oil, sesame oil, ethyl oleate, isopropyl myristate, and benzyl benzoate.

The disclosure will be further understood by the following non-limiting examples.

EXAMPLES

As used herein, the symbols and conventions used in these processes, schemes and examples, regardless of whether a particular abbreviation is specifically defined, are consistent with those used in the contemporary scientific literature, for example, the Journal of the American Chemical Society, the Journal of Medicinal Chemistry, or the Journal of Biological Chemistry. Specifically, but without limitation, the following abbreviations may be used in the examples and throughout the specification: g (grams); mg (milligrams); mL (milliliters); μL (microliters); mM (millimolar); μM (micromolar); mmol (millimoles); min (minute or minutes); h (hour or hours); Bn (benzyl); Boc (tert-butoxycarbonyl); Cbz (benzoxycarbonyl); DIPEA ( ); HATU (hexafluorophosphate azabenzotriazole tetramethyl uronium); Ph (phenyl); tBu (tert-butyl); LCMS (liquid chromatography-mass spectrometry); MS (mass spectrometry); NMR (nuclear magnetic resonance); and prep-HPLC (preparative high performance liquid chromatography).

For all of the following examples, standard work-up and purification methods known to those skilled in the art can be utilized. Unless otherwise indicated, all temperatures are expressed in ° C. (degrees Centigrade). All reactions are conducted at room temperature unless otherwise specified. Synthetic methodologies illustrated herein are intended to exemplify the applicable chemistry through the use of specific examples and are not indicative of the scope of the disclosure.

Example 1

Preparation of 3-(6-fluoro-1-oxo-4-(1-(5,6,7,8-tetrahydronaphthalene-1-carbonyl)piperidin-4-yl)isoindolin-2-yl)piperidine-2,6-dione A0001

A0001

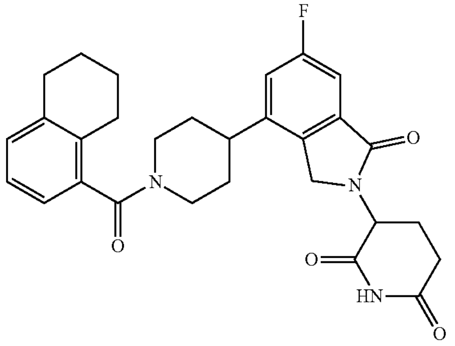

Compound A0001 is prepared as shown in Scheme 1.

Scheme 1

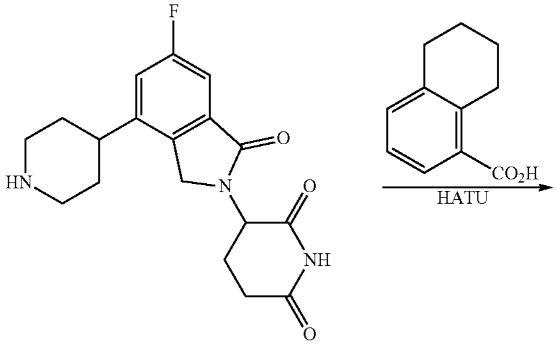

1a

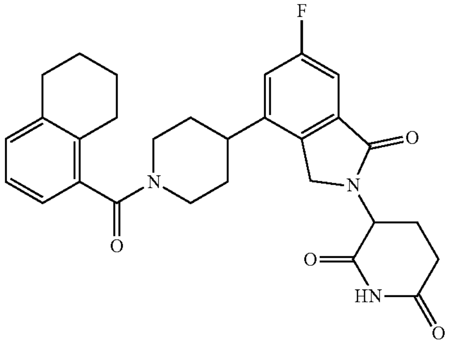

A0001

Example 2

Preparation of 3-(4-(1-(cyclobutylmethyl)piperidin-4-yl)-6-fluoro-1-oxoisoindolin-2-yl)piperidine-2,6-dione A1001

A1001

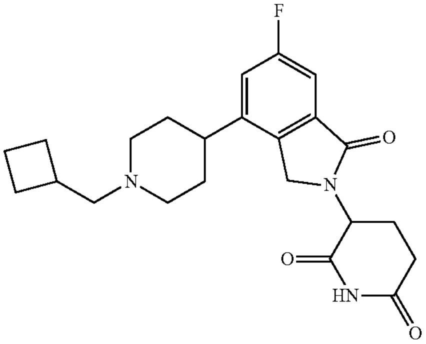

Compound A1001 is prepared as shown in Scheme 2.

Scheme 2

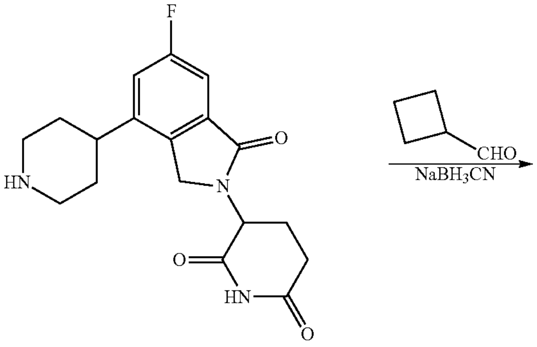

1a

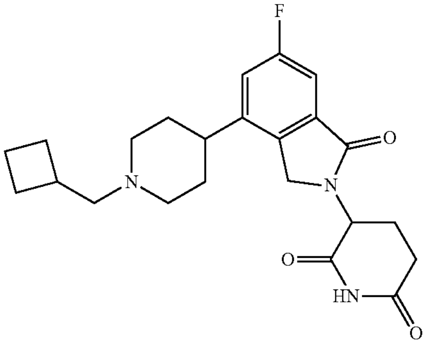

A1001

Example 3

Preparation of 3-(4-(1-(cyclopropylsulfonyl)piperidin-4-yl)-6-fluoro-1-oxoisoindolin-2-yl)piperidine-2,6-dione A2001

A2001

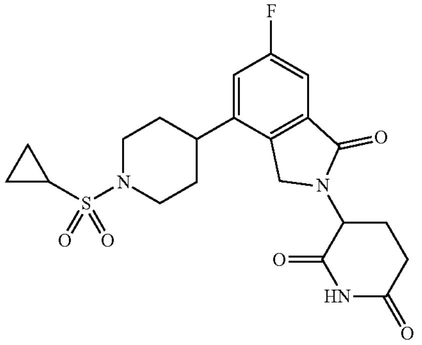

Compound A2001 is prepared as shown in Scheme 3.

Scheme 3

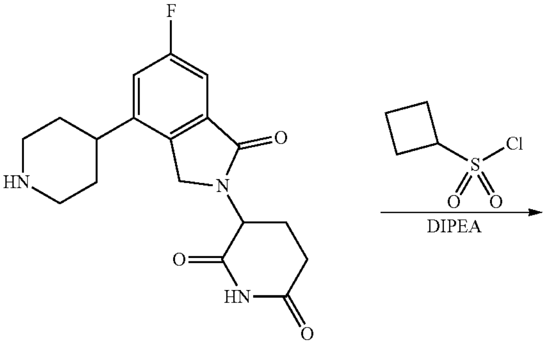

1a

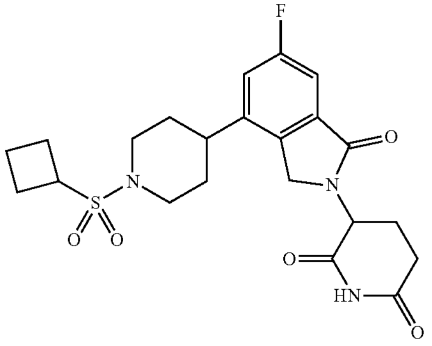

A2001

The following compounds are prepared similarly according to the synthetic procedures or methodologies exemplified herein.

3-(6-Fluoro-4-(1-(1-methyl-1H-indole-5-carbonyl)piperidin-4-yl)-1-oxoisoindolin-2-yl)piperidine-2,6-dione A0002.

3-(6-Fluoro-1-oxo-4-(1-(quinoxaline-5-carbonyl)piperidin-4-yl)isoindolin-2-yl)-piperidine-2,6-dione A0003.

A0002

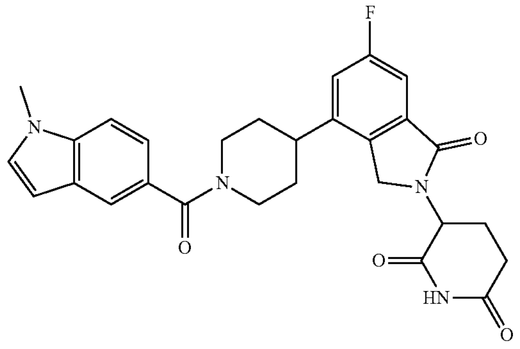

A0003

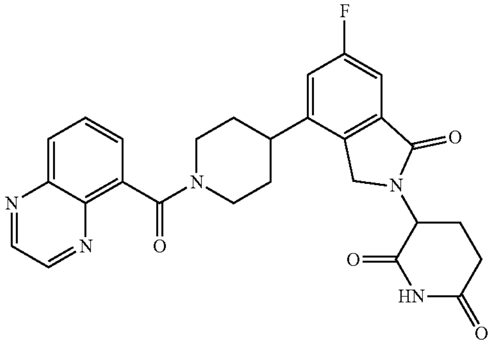

3-(6-Fluoro-1-oxo-4-(1-(quinazoline-6-carbonyl)piperidin-4-yl)isoindolin-2-yl)piperidine-2,6-dione A0004.

3-(4-(1-(2-(Dimethylamino)benzoyl)piperidin-4-yl)-6-fluoro-1-oxoisoindolin-2-yl)piperidine-2,6-dione A0005.

A0004

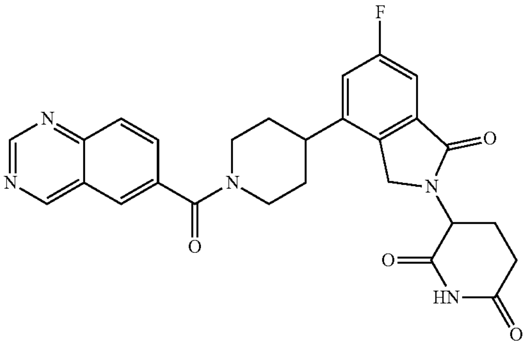

A0005

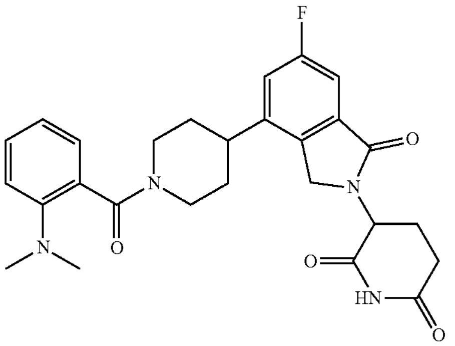

3-(4-(1-(4-(Dimethylamino)benzoyl)piperidin-4-yl)-6-fluoro-1-oxoisoindolin-2-yl)piperidine-2,6-dione A0006.

3-(4-(1-(2,3-Dihydrobenzofuran-7-carbonyl)piperidin-4-yl)-6-fluoro-1-oxoisoindolin-2-yl)piperidine-2,6-dione A0007.

A0006

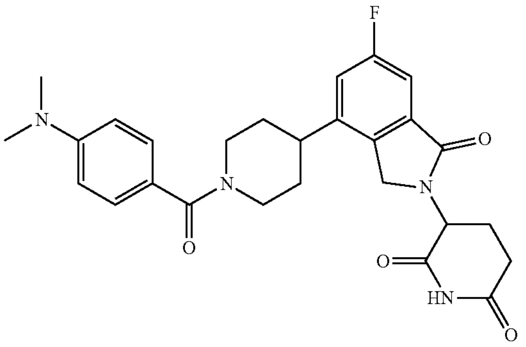

A0007

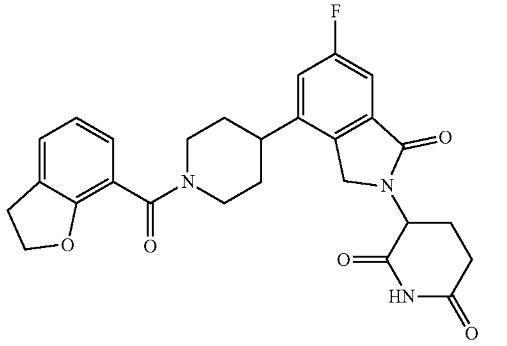

3-(4-(1-(Benzo[d]oxazole-5-carbonyl)piperidin-4-yl)-6-fluoro-1-oxoisoindolin-2-yl)piperidine-2,6-dione A0008.

3-(4-(1-(1H-Benzo[d]imidazole-7-carbonyl)piperidin-4-yl)-6-fluoro-1-oxoisoindolin-2-yl)piperidine-2,6-dione A0009.

A0008

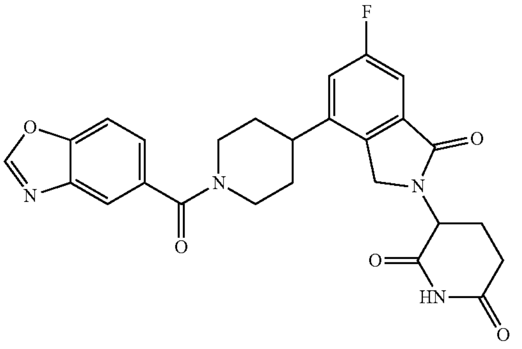

-continued

A0009

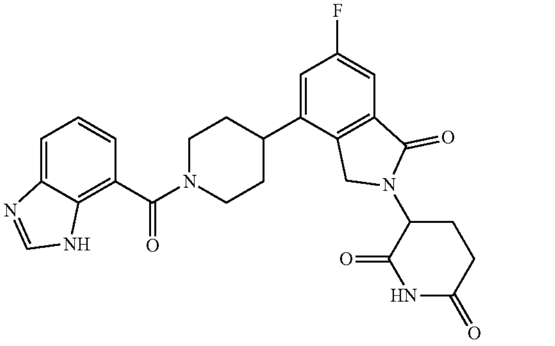

3-(6-Fluoro-4-(1-(imidazo[1,2-a]pyridine-2-carbonyl)piperidin-4-yl)-1-oxoisoindolin-2-yl)piperidine-2,6-dione A0010.

3-(4-(1-(1H-Pyrrolo[3,2-b]pyridine-6-carbonyl)piperidin-4-yl)-6-fluoro-1-oxoisoindolin-2-yl)piperidine-2,6-dione A0011.

A0010

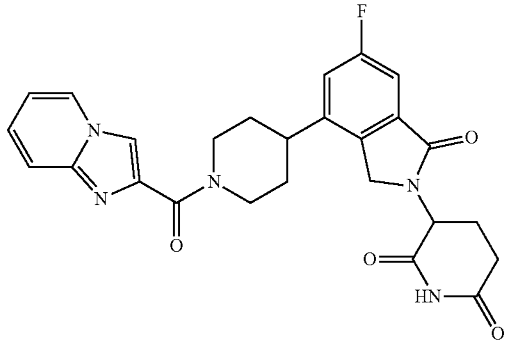

A0011

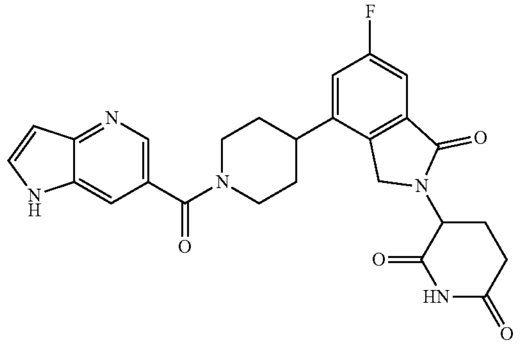

3-(6-Fluoro-4-(1-(imidazo[1,2-a]pyridine-3-carbonyl)piperidin-4-yl)-1-oxoisoindolin-2-yl)piperidine-2,6-dione A0012.

3-(4-(1-(Benzofuran-6-carbonyl)piperidin-4-yl)-6-fluoro-1-oxoisoindolin-2-yl)piperidine-2,6-dione A0013.

A0012

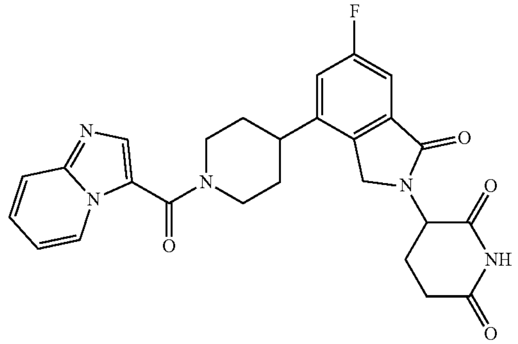

A0013

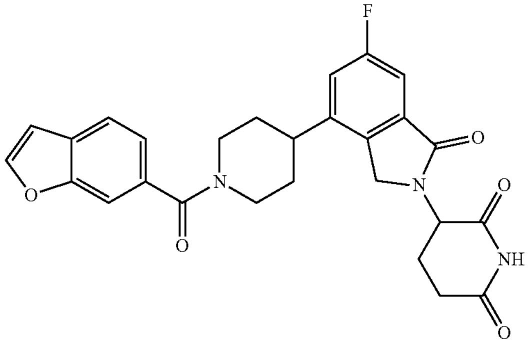

3-(6-Fluoro-1-oxo-4-(1-(2-(piperidin-1-yl)acetyl)piperidin-4-yl)isoindolin-2-yl)piperidine-2,6-dione A0014.

2-(2-(4-(2-(2,6-Dioxopiperidin-3-yl)-6-fluoro-1-oxoisoindolin-4-yl)piperidin-1-yl)-2-oxoethyl)benzonitrile A0015.

A0014

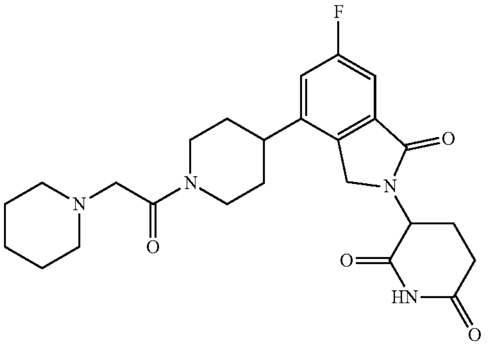

-continued

A0015

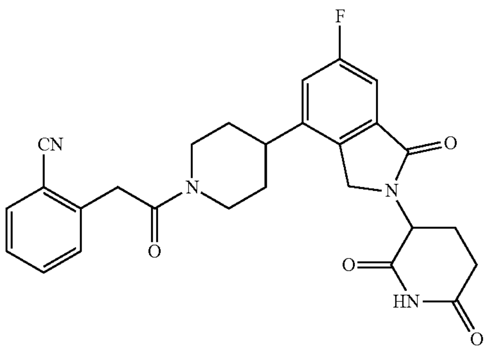

3-(2-(4-(2-(2,6-Dioxopiperidin-3-yl)-6-fluoro-1-oxoisoindolin-4-yl)piperidin-1-yl)-2-oxoethyl)benzonitrile A0016.

4-(2-(4-(2-(2,6-Dioxopiperidin-3-yl)-6-fluoro-1-oxoisoindolin-4-yl)piperidin-1-yl)-2-oxoethyl)benzonitrile A0017.

A0016

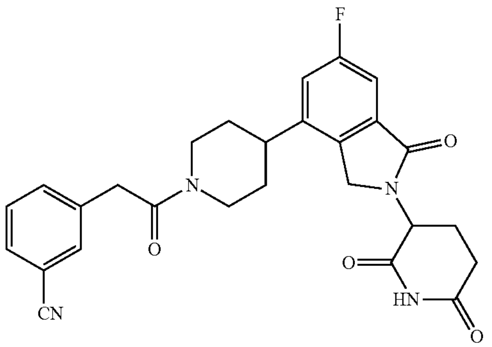

A0017

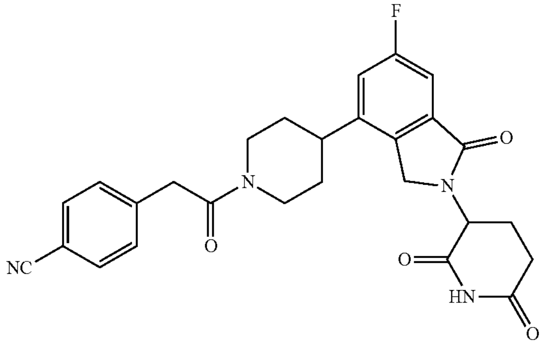

3-(4-(1-(1H-Indole-7-carbonyl)piperidin-4-yl)-6-fluoro-1-oxoisoindolin-2-yl)-piperidine-2,6-dione A0018.

3-(4-(1-(1-Ethylpiperidine-4-carbonyl)piperidin-4-yl)-6-fluoro-1-oxoisoindolin-2-yl)piperidine-2,6-dione A0019.

A0018

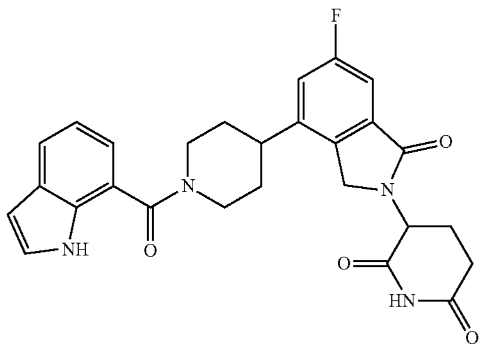

A0019

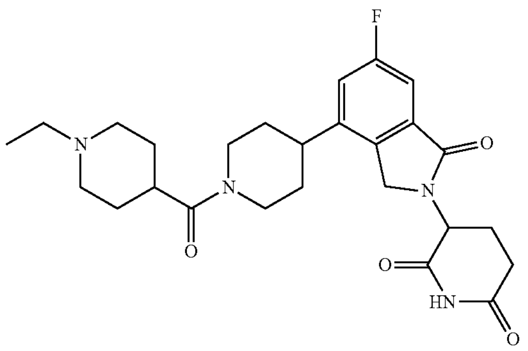

3-(6-Fluoro-1-oxo-4-(1-(2-(p-tolyl)acetyl)piperidin-4-yl)isoindolin-2-yl)-piperidine-2,6-dione A0020.

2-(4-(2-(2,6-Dioxopiperidin-3-yl)-6-fluoro-1-oxoisoindolin-4-yl)piperidine-1-carbonyl)benzonitrile A0021.

A0020

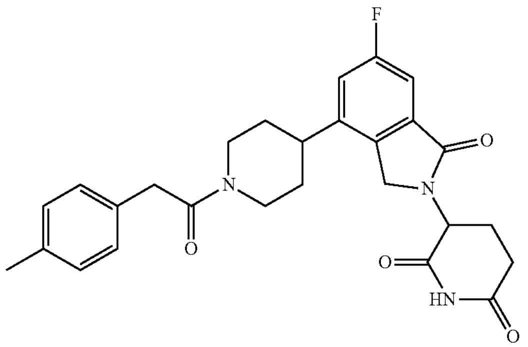

A0021

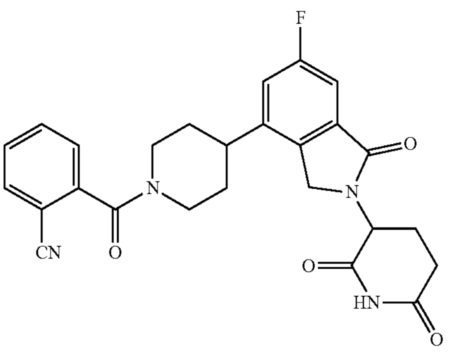

3-(4-(2-(2,6-Dioxopiperidin-3-yl)-6-fluoro-1-oxoisoindolin-4-yl)piperidine-1-carbonyl)benzonitrile A0022.

3-(6-Fluoro-4-(1-(4-fluorobenzoyl)piperidin-4-yl)-1-oxoisoindolin-2-yl)-piperidine-2,6-dione A0023.

A0022

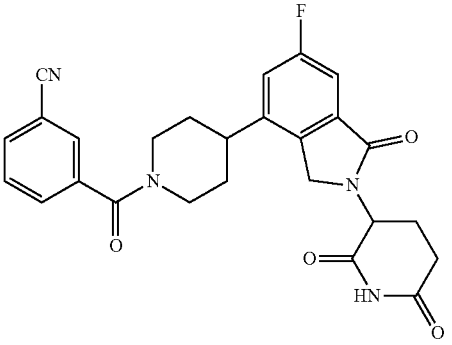

A0023

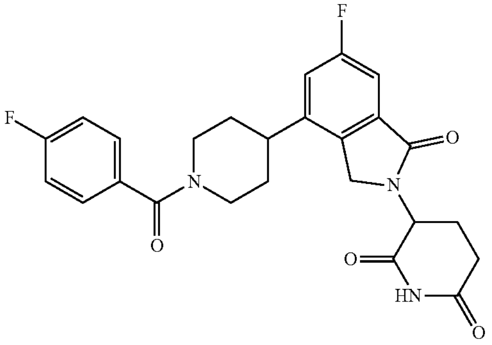

3-(6-Fluoro-4-(1-(3-fluorobenzoyl)piperidin-4-yl)-1-oxoisoindolin-2-yl)-piperidine-2,6-dione A0024.

3-(6-Fluoro-4-(1-(2-fluorobenzoyl)piperidin-4-yl)-1-oxoisoindolin-2-yl)piperidine-2,6-dione A0025.

A0024

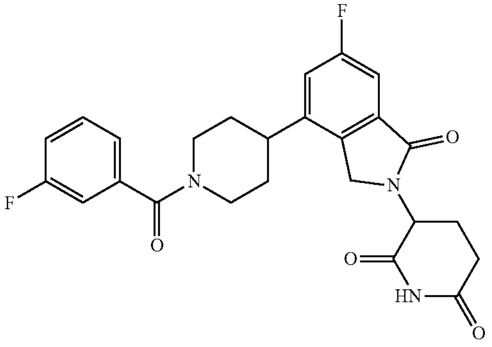

-continued

A0025

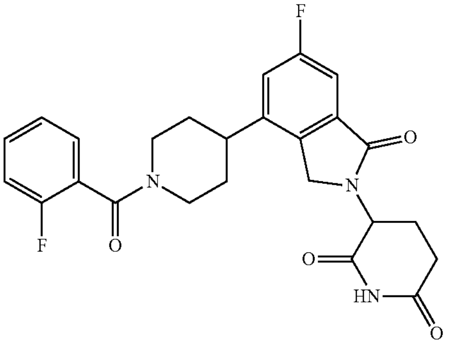

3-(6-Fluoro-4-(1-(2-methylbenzoyl)piperidin-4-yl)-1-oxoisoindolin-2-yl)-piperidine-2,6-dione A0026.

3-(6-Fluoro-4-(1-(3-methylbenzoyl)piperidin-4-yl)-1-oxoisoindolin-2-yl)-piperidine-2,6-dione A0027.

A0026

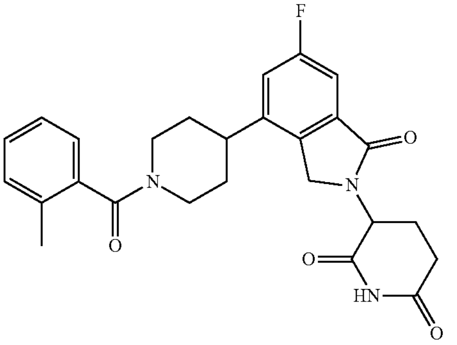

A0027

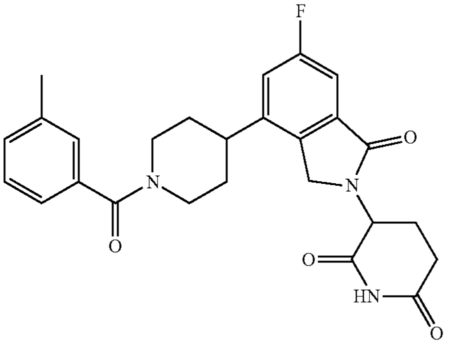

3-(6-Fluoro-4-(1-(4-methylbenzoyl)piperidin-4-yl)-1-oxoisoindolin-2-yl)-piperidine-2,6-dione A0028.

3-(4-(1-(2-Cyclopentylacetyl)piperidin-4-yl)-6-fluoro-1-oxoisoindolin-2-yl)-piperidine-2,6-dione A0029.

A0028

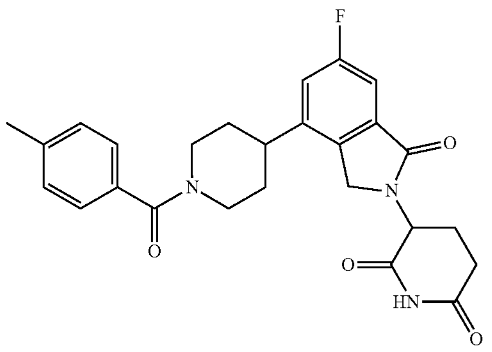

A0029

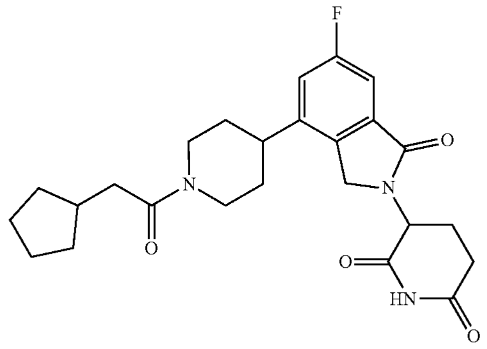

3-(4-(1-(Cyclohexanecarbonyl)piperidin-4-yl)-6-fluoro-1-oxoisoindolin-2-yl)-piperidine-2,6-dione A0030.

3-(4-(1-(3,3-Dimethylcyclobutane-1-carbonyl)piperidin-4-yl)-6-fluoro-1-oxoisoindolin-2-yl)piperidine-2,6-dione A0031.

A0030

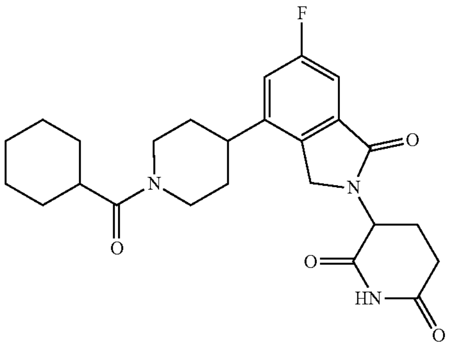

-continued

A0031

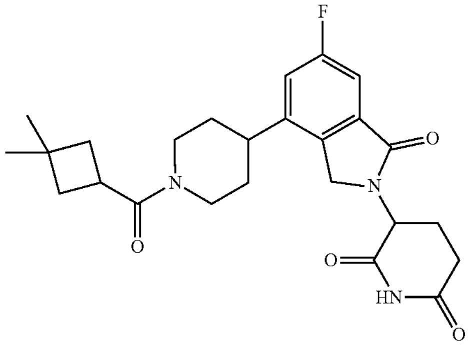

3-(6-Fluoro-1-oxo-4-(1-(pyrimidine-5-carbonyl)piperidin-4-yl)isoindolin-2-yl)-piperidine-2,6-dione A0032.

3-(6-Fluoro-1-oxo-4-(1-(pyridazine-4-carbonyl)piperidin-4-yl)isoindolin-2-yl)-piperidine-2,6-dione A0033.

A0032

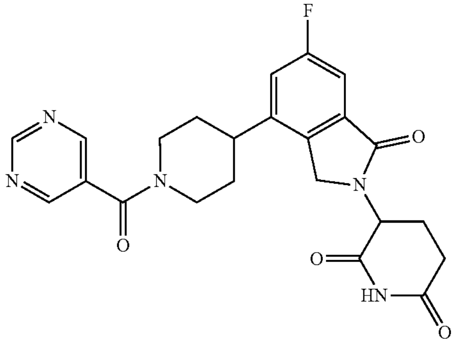

A0033

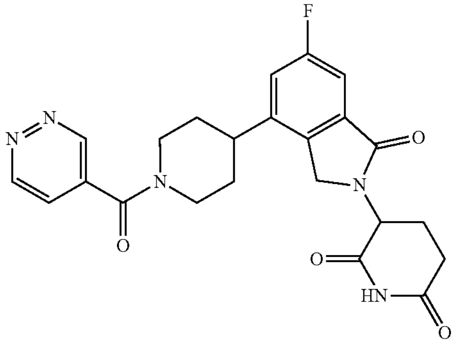

3-(6-Fluoro-1-oxo-4-(1-(pyrimidine-4-carbonyl)piperidin-4-yl)isoindolin-2-yl)-piperidine-2,6-dione A0034.

3-(6-Fluoro-1-oxo-4-(1-picolinoylpiperidin-4-yl)isoindolin-2-yl)piperidine-2,6-dione A0035.

A0034

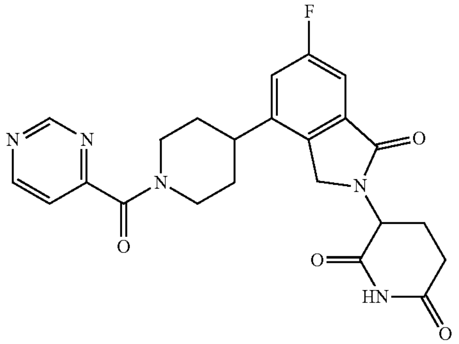

A0035

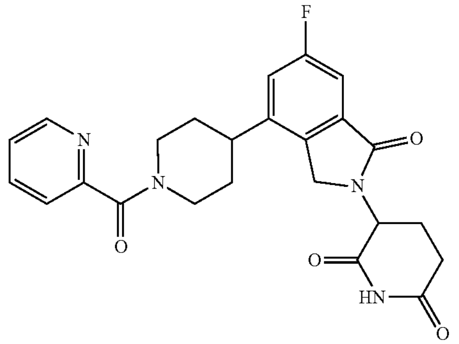

3-(6-Fluoro-4-(1-isonicotinoylpiperidin-4-yl)-1-oxoisoindolin-2-yl)piperidine-2,6-dione A0036.

3-(6-Fluoro-4-(1-nicotinoylpiperidin-4-yl)-1-oxoisoindolin-2-yl)piperidine-2,6-dione A0037.

A0036

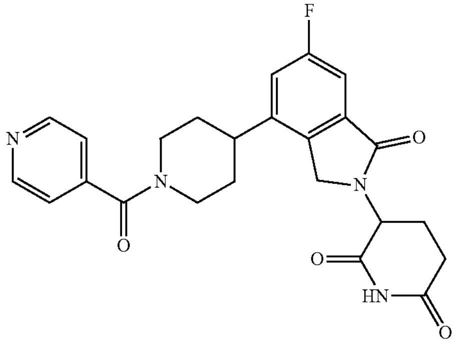

A0037

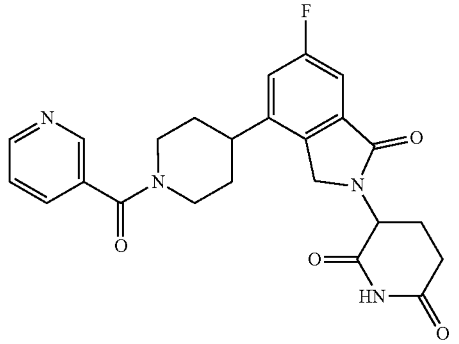

3-(4-(1-Benzoylpiperidin-4-yl)-6-fluoro-1-oxoisoindolin-2-yl)piperidine-2,6-dione A0038.

3-(4-(1-(1-Aminocyclobutane-1-carbonyl)piperidin-4-yl)-6-fluoro-1-oxoisoindolin-2-yl)piperidine-2,6-dione A0039.

A0038

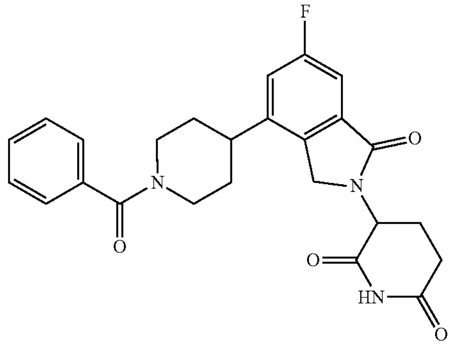

A0039

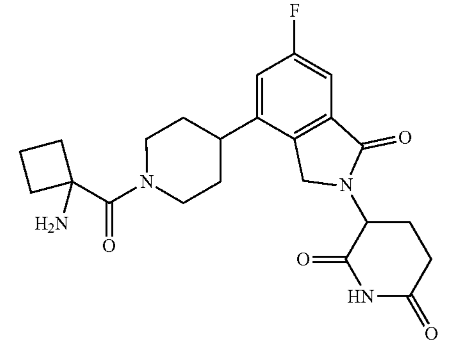

3-(6-Fluoro-4-(1-(1-methylazetidine-3-carbonyl)piperidin-4-yl)-1-oxoisoindolin-2-yl)piperidine-2,6-dione A0040.

3-(4-(1-(1H-Pyrazole-5-carbonyl)piperidin-4-yl)-6-fluoro-1-oxoisoindolin-2-yl)-piperidine-2,6-dione A0041.

A0040

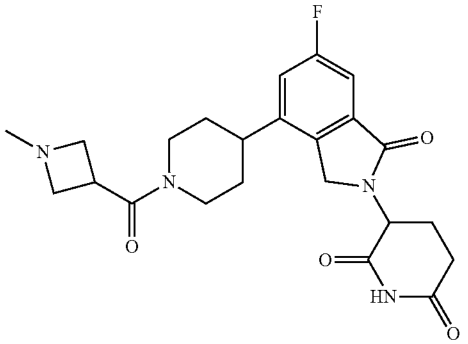

-continued

A0041

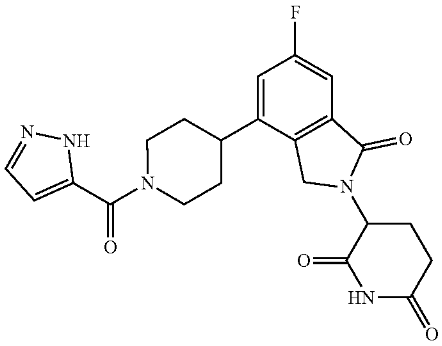

3-(4-(1-(1H-Imidazole-5-carbonyl)piperidin-4-yl)-6-fluoro-1-oxoisoindolin-2-yl)-piperidine-2,6-dione A0042.

3-(6-Fluoro-4-(1-(furan-3-carbonyl)piperidin-4-yl)-1-oxoisoindolin-2-yl)-piperidine-2,6-dione A0043.

A0042

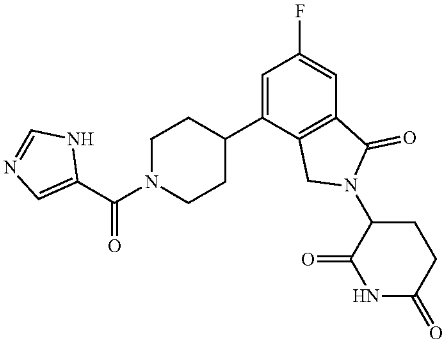

A0043

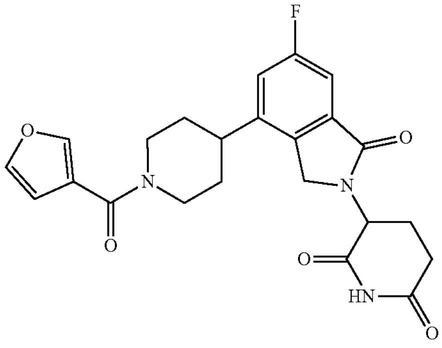

3-(6-Fluoro-4-(1-(furan-2-carbonyl)piperidin-4-yl)-1-oxoisoindolin-2-yl)-piperidine-2,6-dione A0044.

3-(6-Fluoro-4-(1-(1-fluorocyclopropane-1-carbonyl)piperidin-4-yl)-1-oxoisoindolin-2-yl)piperidine-2,6-dione A0045.

A0044

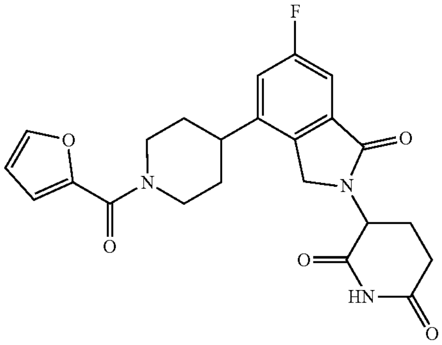

A0045

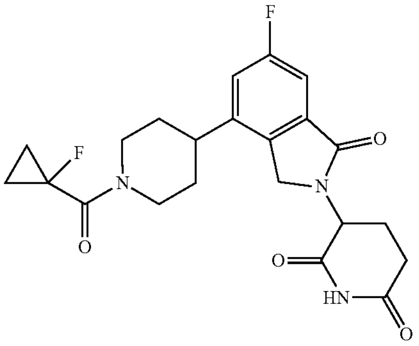

3-(6-Fluoro-4-(1-(3-methylbutanoyl)piperidin-4-yl)-1-oxoisoindolin-2-yl)-piperidine-2,6-dione A0046.

3-(6-Fluoro-4-(1-(oxetane-3-carbonyl)piperidin-4-yl)-1-oxoisoindolin-2-yl)-piperidine-2,6-dione A0047.

A0046

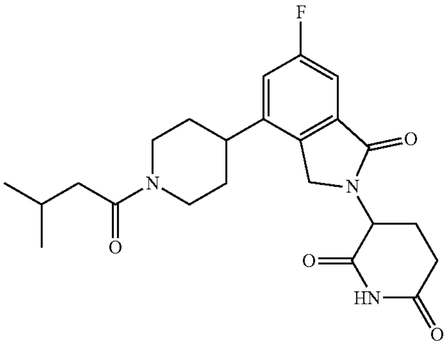

A0047

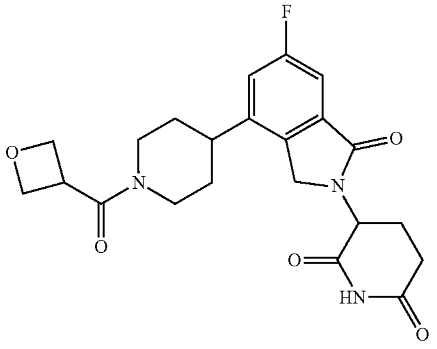

3-(4-(1-(Cyclobutanecarbonyl)piperidin-4-yl)-6-fluoro-1-oxoisoindolin-2-yl)-piperidine-2,6-dione A0048.

3-(6-Fluoro-4-(1-(methylglycyl)piperidin-4-yl)-1-oxoisoindolin-2-yl)piperidine-2,6-dione A0049.

A0048

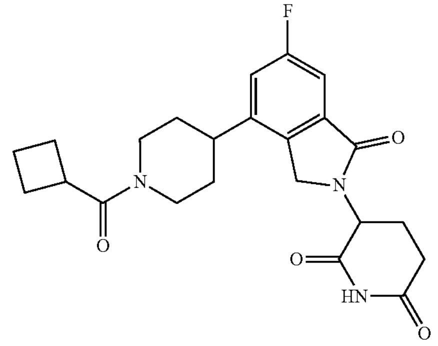

A0049

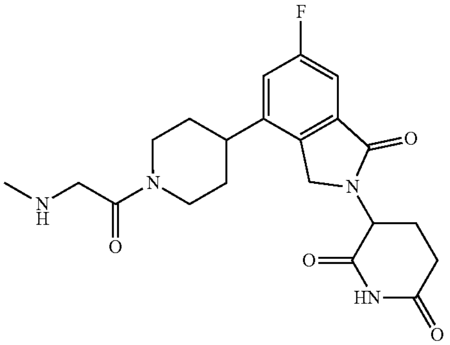

3-(4-(1-(Cyclopropanecarbonyl)piperidin-4-yl)-6-fluoro-1-oxoisoindolin-2-yl)-piperidine-2,6-dione A0050.

3-(4-(1-((1H-Pyrrol-2-yl)methyl)piperidin-4-yl)-6-fluoro-1-oxoisoindolin-2-yl)-piperidine-2,6-dione A1002.

A0050

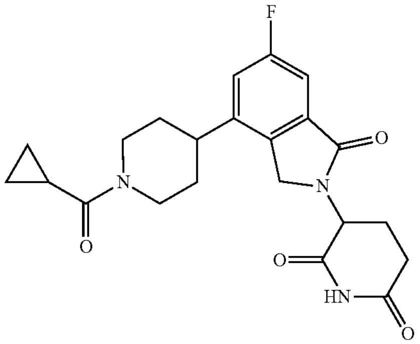

-continued

A1002

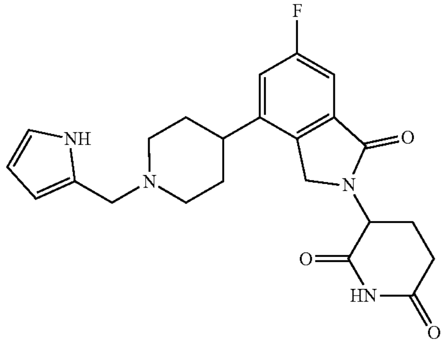

3-(4-(1-((1H-Pyrrol-3-yl)methyl)piperidin-4-yl)-6-fluoro-1-oxoisoindolin-2-yl)-piperidine-2,6-dione A1003.

3-(4-(1-((1H-Imidazol-5-yl)methyl)piperidin-4-yl)-6-fluoro-1-oxoisoindolin-2-yl)-piperidine-2,6-dione A1004.

A1003

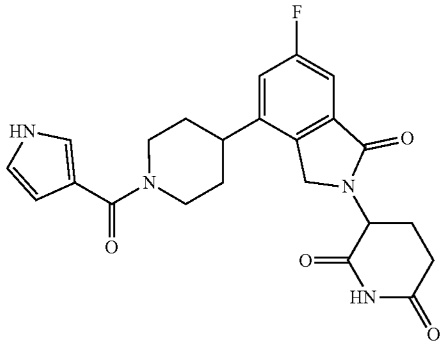

A1004

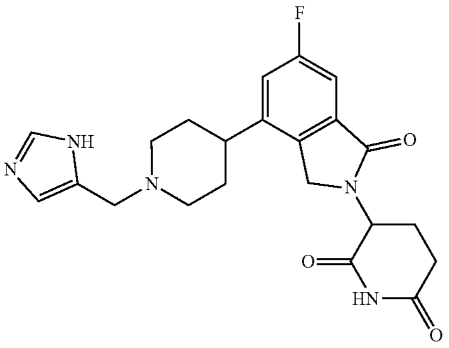

3-(4-(1-((1H-Pyrazol-5-yl)methyl)piperidin-4-yl)-6-fluoro-1-oxoisoindolin-2-yl)-piperidine-2,6-dione A1005.

3-(6-Fluoro-4-(1-(oxazol-2-ylmethyl)piperidin-4-yl)-1-oxoisoindolin-2-yl)-piperidine-2,6-dione A1006.

A1005

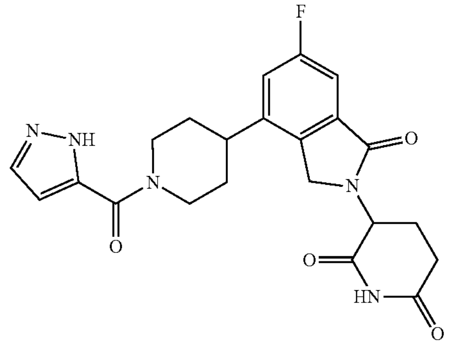

A1006

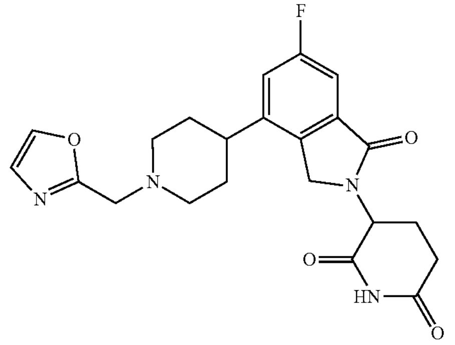

3-(6-Fluoro-4-(1-((3-methyloxetan-3-yl)methyl)piperidin-4-yl)-1-oxoisoindolin-2-yl)piperidine-2,6-dione A1007.

3-(6-Fluoro-4-(1-(3-hydroxy-2,2-dimethylpropyl)piperidin-4-yl)-1-oxoisoindolin-2-yl)piperidine-2,6-dione A1008.

A1007

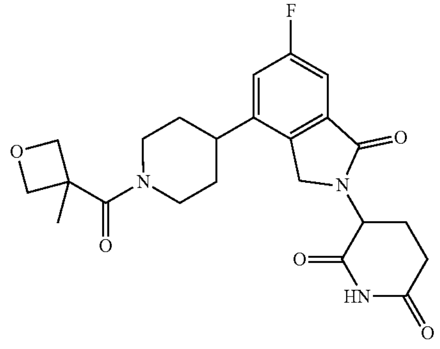

A1008

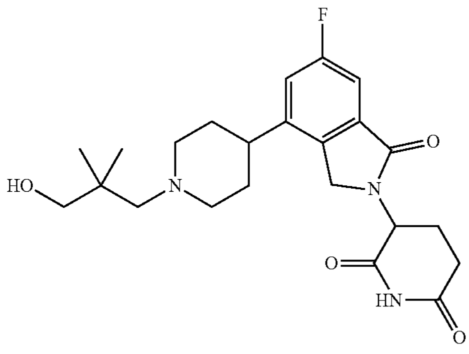

3-(6-Fluoro-1-oxo-4-(1-(pyridin-3-ylmethyl)piperidin-4-yl)isoindolin-2-yl)-piperidine-2,6-dione A1009.

3-(6-Fluoro-1-oxo-4-(1-(pyridin-2-ylmethyl)piperidin-4-yl)isoindolin-2-yl)-piperidine-2,6-dione A1010.

A1009

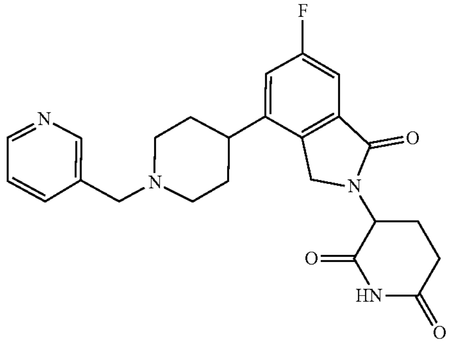

A1010

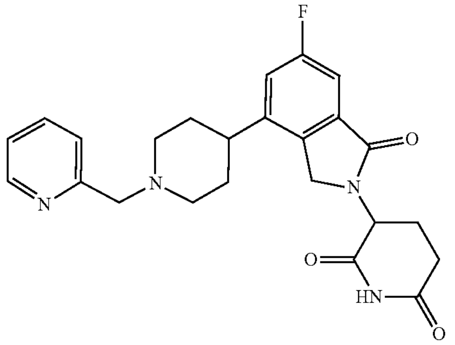

3-(6-Fluoro-1-oxo-4-(1-(pyrimidin-5-ylmethyl)piperidin-4-yl)isoindolin-2-yl)-piperidine-2,6-dione A1011.

3-(6-Fluoro-4-(1-((1-methyl-1H-pyrrol-2-yl)methyl)piperidin-4-yl)-1-oxoisoindolin-2-yl)piperidine-2,6-dione A1012.

A1011

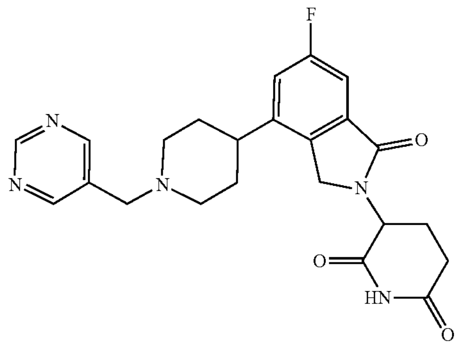

-continued

A1012

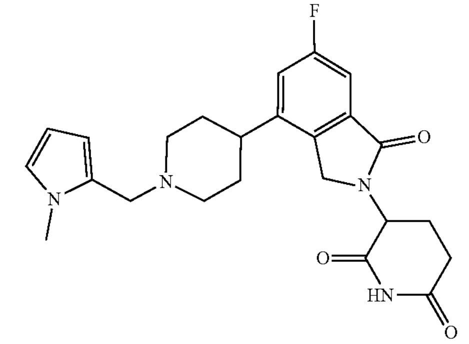

3-(6-Fluoro-4-(1-((5-methyl-1H-pyrrol-2-yl)methyl)piperidin-4-yl)-1-oxoisoindolin-2-yl)piperidine-2,6-dione A1013.

3-(6-Fluoro-4-(1-((3-methyl-1H-pyrrol-2-yl)methyl)piperidin-4-yl)-1-oxoisoindolin-2-yl)piperidine-2,6-dione A1014.

A1013

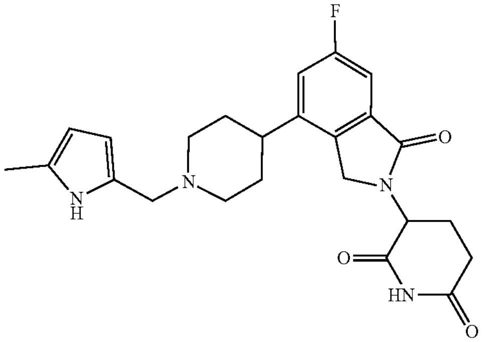

A1014

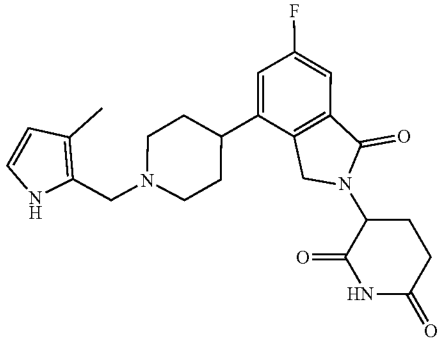

3-(6-Fluoro-4-(1-((5-methylfuran-2-yl)methyl)piperidin-4-yl)-1-oxoisoindolin-2-yl)piperidine-2,6-dione A1015.

3-(6-Fluoro-4-(1-((5-methyl-1H-pyrazol-3-yl)methyl)piperidin-4-yl)-1-oxoisoindolin-2-yl)piperidine-2,6-dione A1016.

A1015

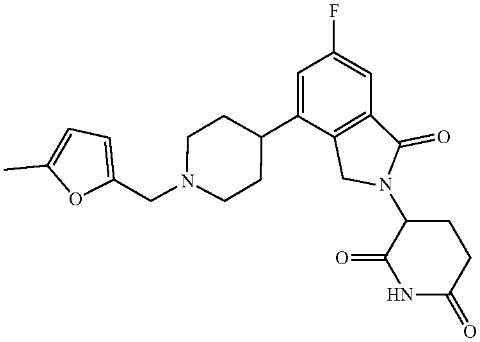

A1016

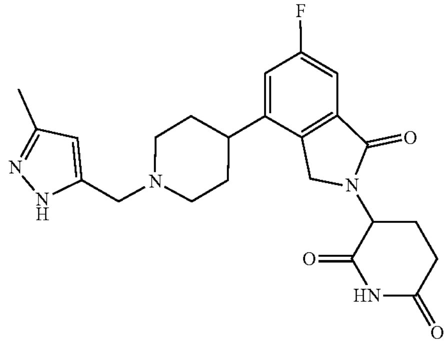

3-(6-Fluoro-4-(1-((1-methyl-1H-imidazol-2-yl)methyl)piperidin-4-yl)-1-oxoisoindolin-2-yl)piperidine-2,6-dione A1017.

3-(6-Fluoro-4-(1-((1-methyl-1H-imidazol-4-yl)methyl)piperidin-4-yl)-1-oxoisoindolin-2-yl)piperidine-2,6-dione A1018.

A1017

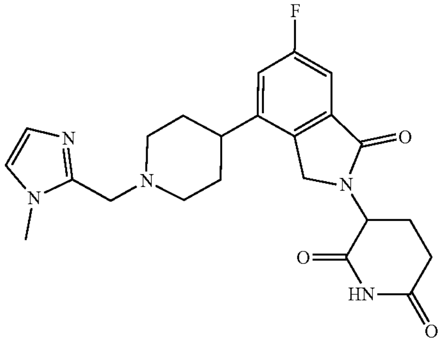

A1018

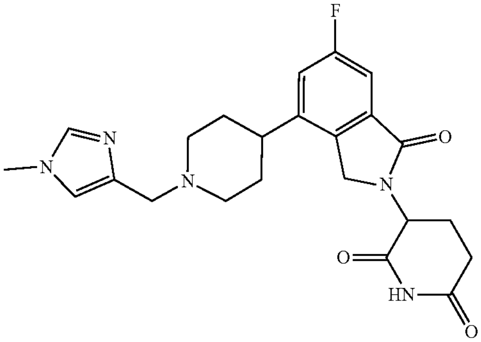

3-(6-Fluoro-4-(1-((1-methyl-1H-pyrazol-3-yl)methyl)piperidin-4-yl)-1-oxoisoindolin-2-yl)piperidine-2,6-dione A1019.

3-(6-Fluoro-4-(1-((1-methyl-1H-pyrazol-5-yl)methyl)piperidin-4-yl)-1-oxoisoindolin-2-yl)piperidine-2,6-dione A1020.

A1019

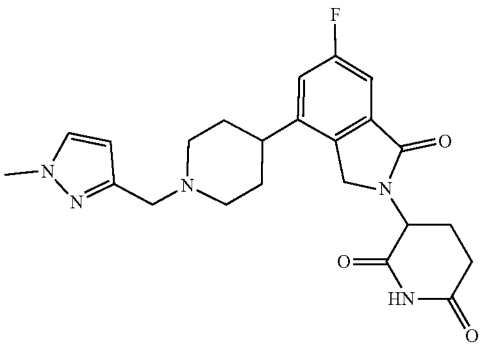

A1020

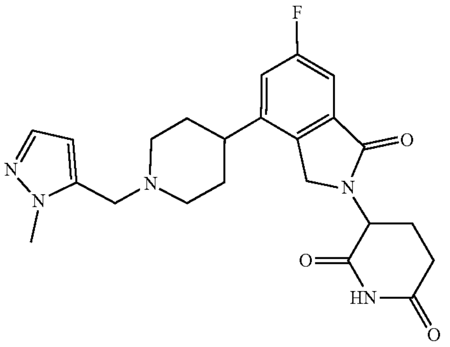

3-(6-Fluoro-4-(1-((1-methyl-1H-imidazol-5-yl)methyl)piperidin-4-yl)-1-oxoisoindolin-2-yl)piperidine-2,6-dione A1021.

3-(6-Fluoro-4-(1-((2-methyloxazol-5-yl)methyl)piperidin-4-yl)-1-oxoisoindolin-2-yl)piperidine-2,6-dione A1022.

A1021

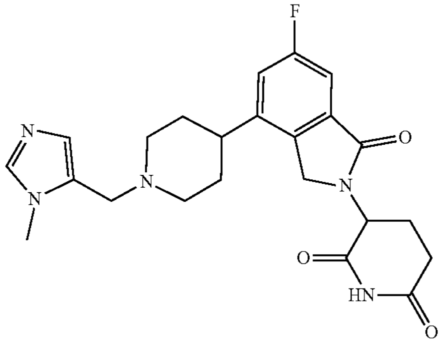

-continued

A1022

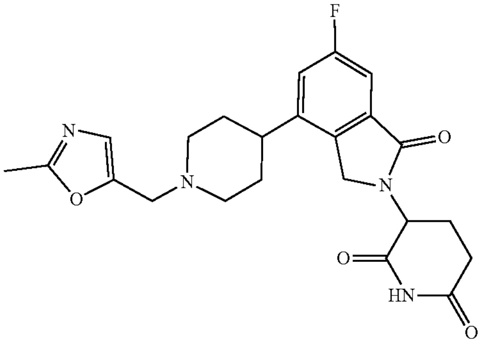

3-(6-Fluoro-4-(1-((2-methyloxazol-4-yl)methyl)piperidin-4-yl)-1-oxoisoindolin-2-yl)piperidine-2,6-dione A1023.

3-(6-Fluoro-4-(1-((4-methyloxazol-5-yl)methyl)piperidin-4-yl)-1-oxoisoindolin-2-yl)piperidine-2,6-dione A1024.

A1023

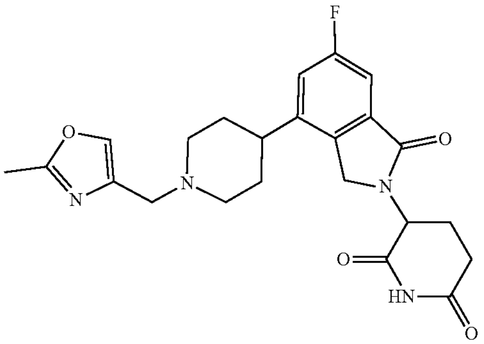

A1024

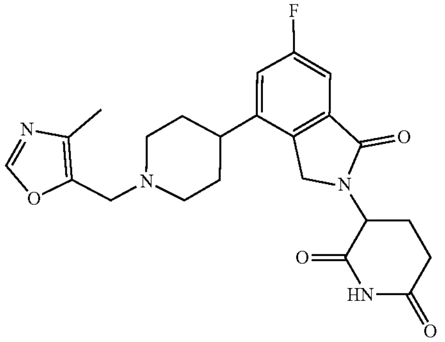

3-(6-Fluoro-4-(1-((5-methyl-4H-1,2,4-triazol-3-yl)methyl)piperidin-4-yl)-1-oxoisoindolin-2-yl)piperidine-2,6-dione A1025.

3-(6-Fluoro-4-(1-((2-methyl-2H-tetrazol-5-yl)methyl)piperidin-4-yl)-1-oxoisoindolin-2-yl)piperidine-2,6-dione A1026.

A1025

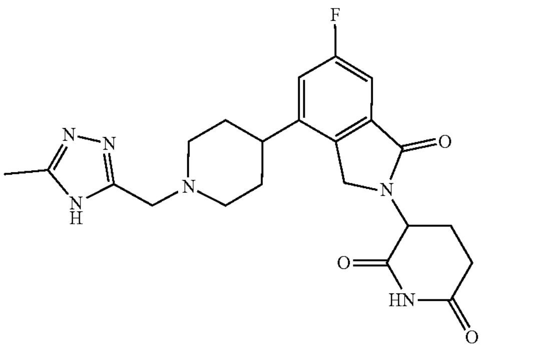

A1026

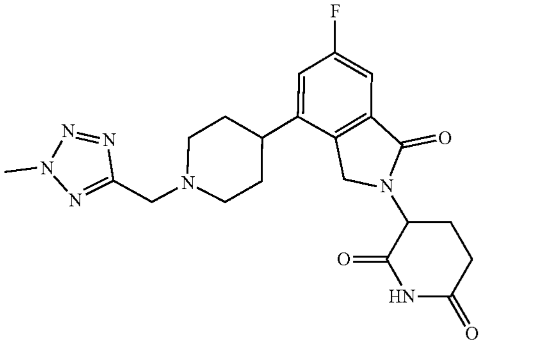

3-(6-Fluoro-1-oxo-4-(1-(thiophen-3-ylmethyl)piperidin-4-yl)isoindolin-2-yl)-piperidine-2,6-dione A1027.

3-(6-Fluoro-1-oxo-4-(1-(thiophen-2-ylmethyl)piperidin-4-yl)isoindolin-2-yl)-piperidine-2,6-dione A1028.

A1027

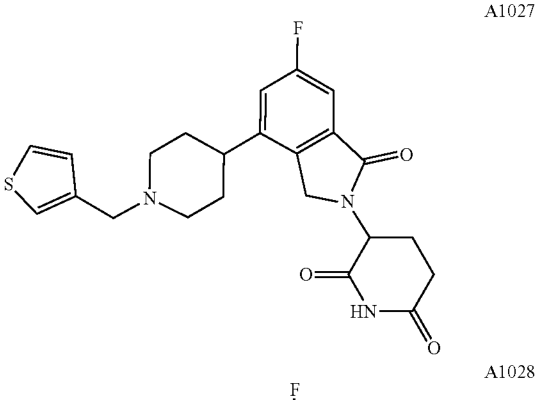

A1028

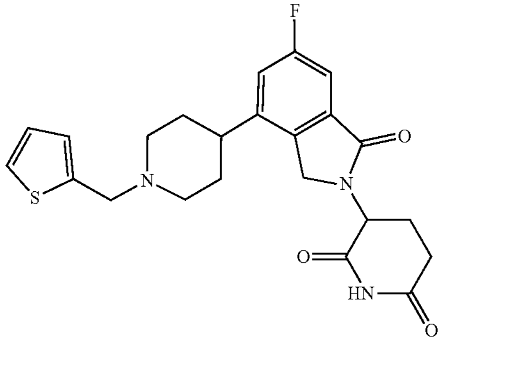

3-(6-Fluoro-1-oxo-4-(1-(thiazol-4-ylmethyl)piperidin-4-yl)isoindolin-2-yl)-piperidine-2,6-dione A1029.

3-(6-Fluoro-1-oxo-4-(1-(thiazol-5-ylmethyl)piperidin-4-yl)isoindolin-2-yl)-piperidine-2,6-dione A1030.

A1029

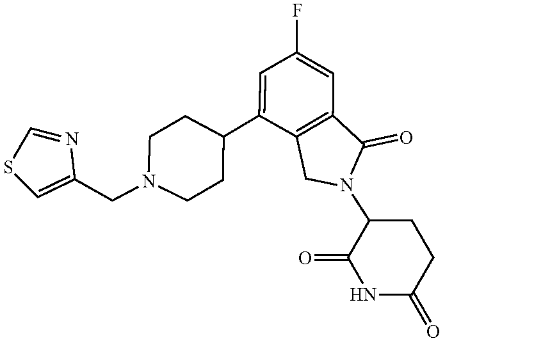

A1030

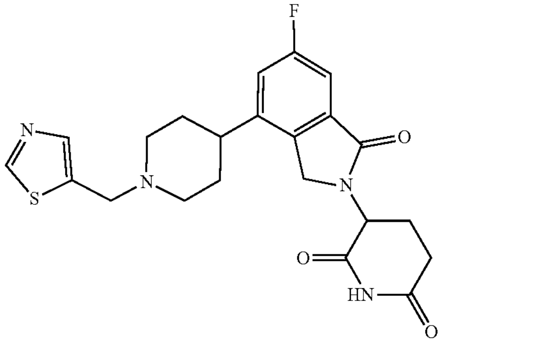

3-(6-Fluoro-1-oxo-4-(1-(thiazol-2-ylmethyl)piperidin-4-yl)isoindolin-2-yl)-piperidine-2,6-dione A1031.

3-(6-Fluoro-1-oxo-4-(1-((tetrahydro-2H-pyran-4-yl)methyl)piperidin-4-yl)-isoindolin-2-yl)piperidine-2,6-dione A1032.

A1031

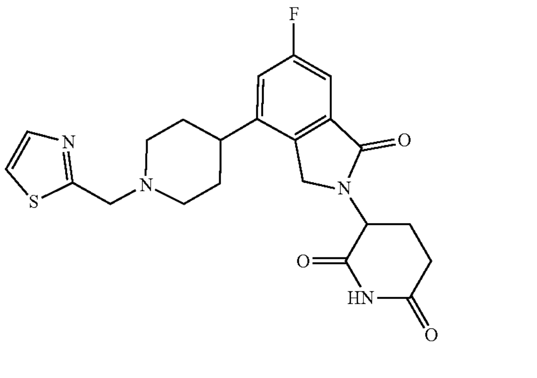

-continued

A1032

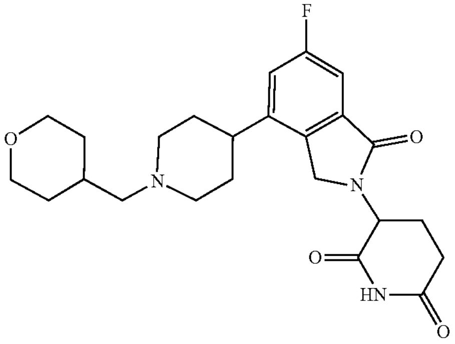

2-((4-(2-(2,6-Dioxopiperidin-3-yl)-6-fluoro-1-oxoisoindolin-4-yl)piperidin-1-yl)-methyl)-1H-pyrrole-3-carbonitrile A1033.

3-(6-Fluoro-4-(1-(3-methylbenzyl)piperidin-4-yl)-1-oxoisoindolin-2-yl)-piperidine-2,6-dione A1034.

A1033

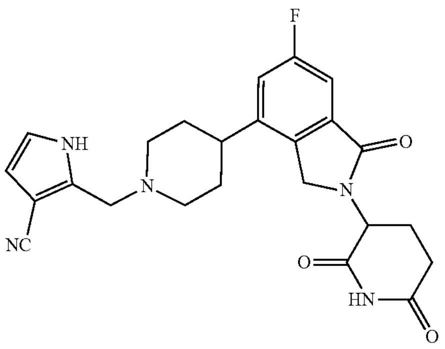

A1034

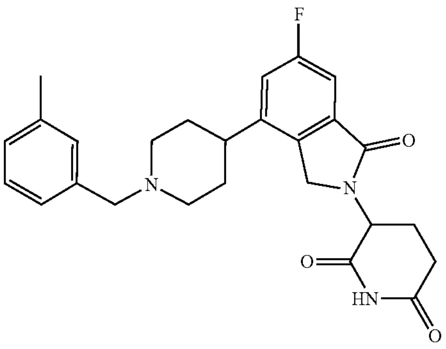

3-(6-Fluoro-1-oxo-4-(1-phenethylpiperidin-4-yl)isoindolin-2-yl)piperidine-2,6-dione A1035.

3-(6-Fluoro-4-(1-(2-methylbenzyl)piperidin-4-yl)-1-oxoisoindolin-2-yl)-piperidine-2,6-dione A1036.

A1035

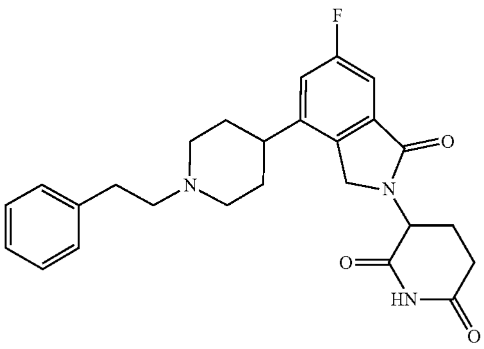

A1036

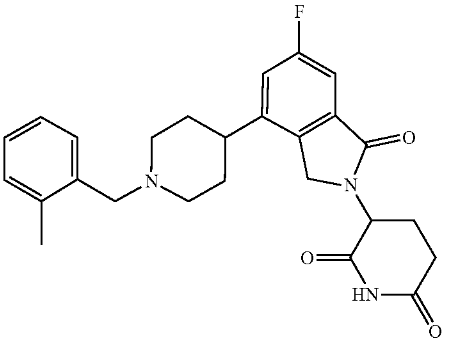

3-(6-Fluoro-4-(1-(4-methylbenzyl)piperidin-4-yl)-1-oxoisoindolin-2-yl)-piperidine-2,6-dione A1037.

3-(4-(1-(2-Aminobenzyl)piperidin-4-yl)-6-fluoro-1-oxoisoindolin-2-yl)piperidine-2,6-dione A1038.

A1037

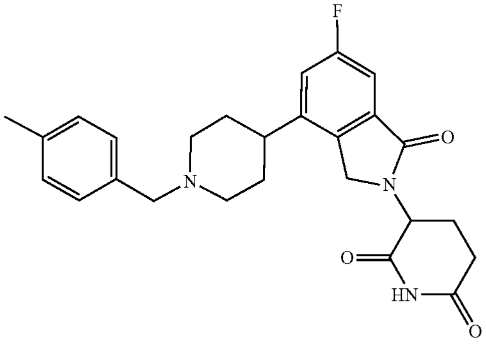

A1038

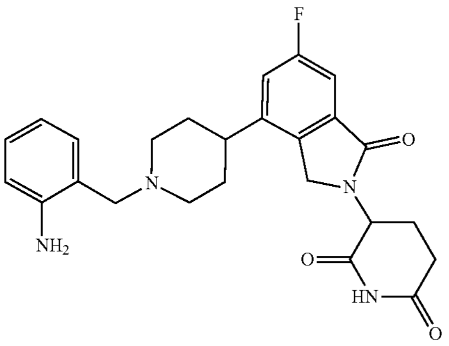

3-(4-(1-(4-Aminobenzyl)piperidin-4-yl)-6-fluoro-1-oxoisoindolin-2-yl)piperidine-2,6-dione A1039.

3-(6-Fluoro-4-(1-((5-methylpyridin-3-yl)methyl)piperidin-4-yl)-1-oxoisoindolin-2-yl)piperidine-2,6-dione A1040.

A1039

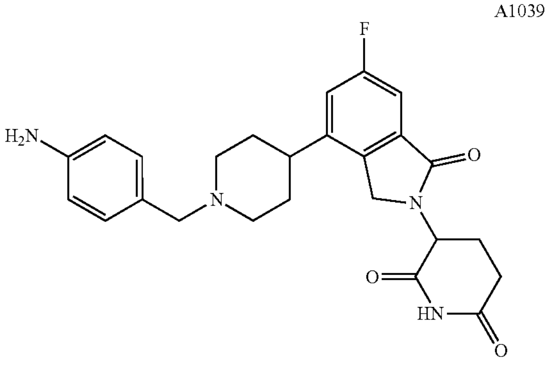

A1040

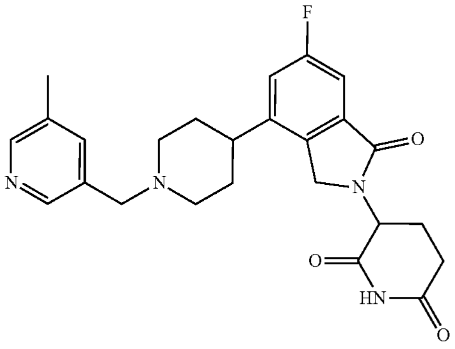

3-(6-Fluoro-4-(1-((4-methylpyridin-3-yl)methyl)piperidin-4-yl)-1-oxoisoindolin-2-yl)piperidine-2,6-dione A1041.

3-(6-Fluoro-4-(1-((6-methylpyridin-2-yl)methyl)piperidin-4-yl)-1-oxoisoindolin-2-yl)piperidine-2,6-dione A1042.

A1041

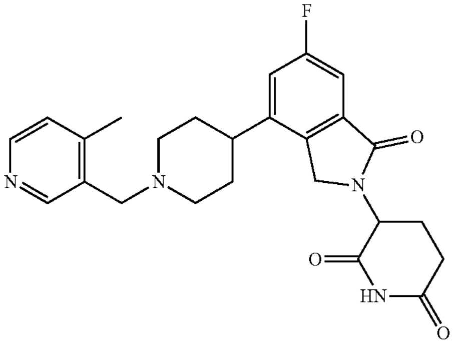

-continued

A1042

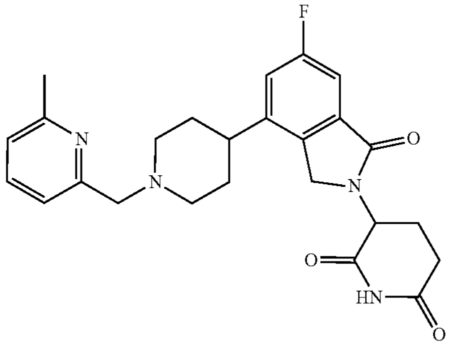

3-(6-Fluoro-4-(1-((5-methylpyridin-2-yl)methyl)piperidin-4-yl)-1-oxoisoindolin-2-yl)piperidine-2,6-dione A1043.

3-(6-Fluoro-4-(1-((2-methylpyridin-4-yl)methyl)piperidin-4-yl)-1-oxoisoindolin-2-yl)piperidine-2,6-dione A1044.

A1043

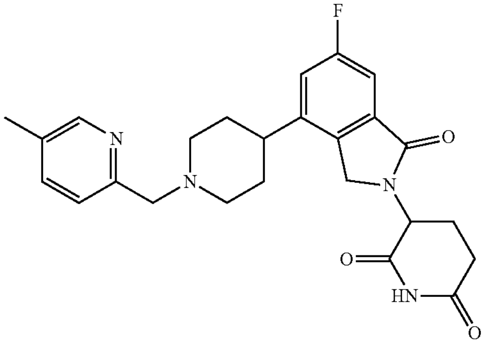

A1044

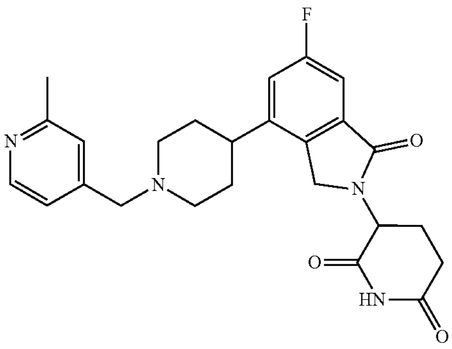

3-(6-Fluoro-4-(1-((2-methylpyridin-3-yl)methyl)piperidin-4-yl)-1-oxoisoindolin-2-yl)piperidine-2,6-dione A1045.

3-(6-Fluoro-4-(1-((3-methylpyridin-2-yl)methyl)piperidin-4-yl)-1-oxoisoindolin-2-yl)piperidine-2,6-dione A1046.

A1045

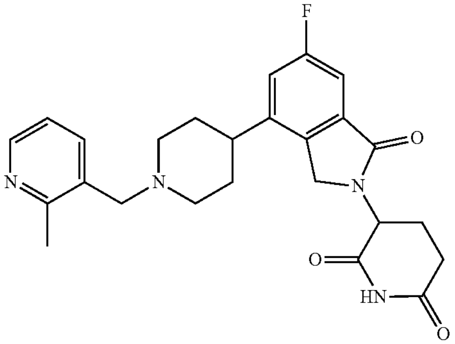

A1046

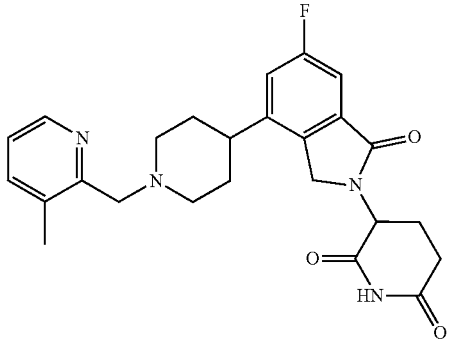

3-(6-Fluoro-4-(1-((4-methylpyridin-2-yl)methyl)piperidin-4-yl)-1-oxoisoindolin-2-yl)piperidine-2,6-dione A1047.

3-(6-Fluoro-4-(1-(4-hydroxybenzyl)piperidin-4-yl)-1-oxoisoindolin-2-yl)-piperidine-2,6-dione A1048.

A1047

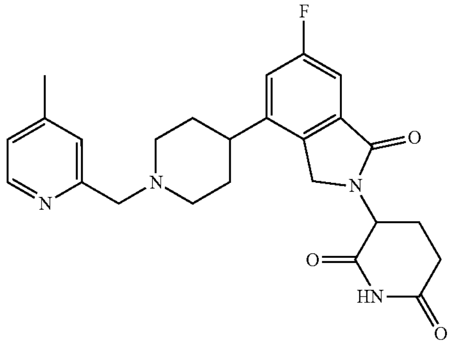

A1048

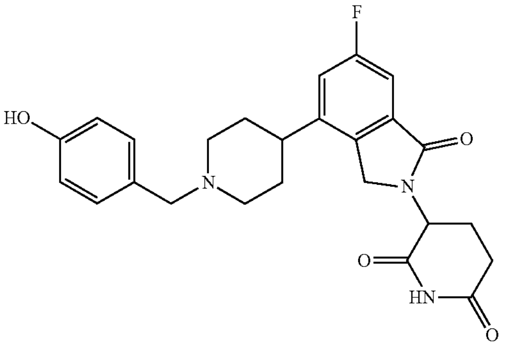

3-(6-Fluoro-4-(1-(3-hydroxybenzyl)piperidin-4-yl)-1-oxoisoindolin-2-yl)-piperidine-2,6-dione A1049.

3-(4-(1-((3-Aminopyridin-4-yl)methyl)piperidin-4-yl)-6-fluoro-1-oxoisoindolin-2-yl)piperidine-2,6-dione A1050.

A1049

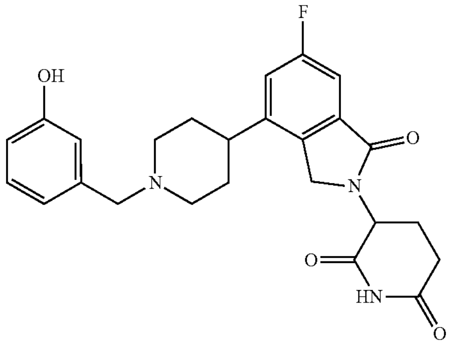

A1050

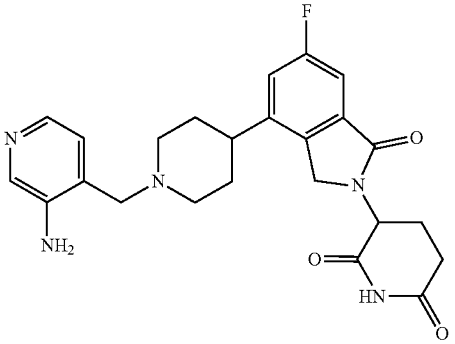

3-(4-(1-((2-Aminopyridin-3-yl)methyl)piperidin-4-yl)-6-fluoro-1-oxoisoindolin-2-yl)piperidine-2,6-dione A1051.

3-(6-Fluoro-4-(1-((2-methylpyrimidin-5-yl)methyl)piperidin-4-yl)-1-oxoisoindolin-2-yl)piperidine-2,6-dione A1052.

A1051

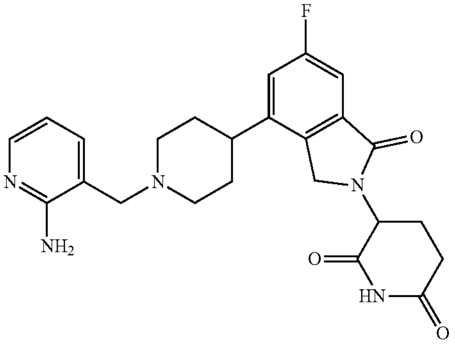

-continued

A1052

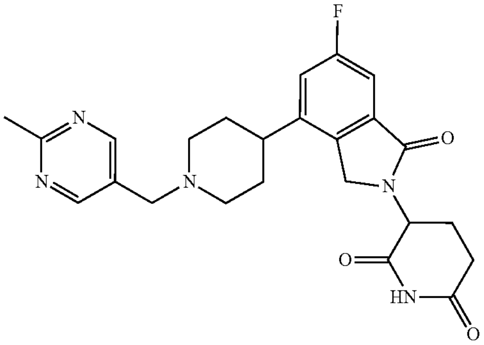

3-(6-Fluoro-4-(1-((2-Methylpyrimidin-4-yl)methyl)piperidin-4-yl)-1-oxoisoindolin-2-yl)piperidine-2,6-dione A1053.

3-(6-Fluoro-4-(1-((3-methylpyrazin-2-yl)methyl)piperidin-4-yl)-1-oxoisoindolin-2-yl)piperidine-2,6-dione A1054.

A1053

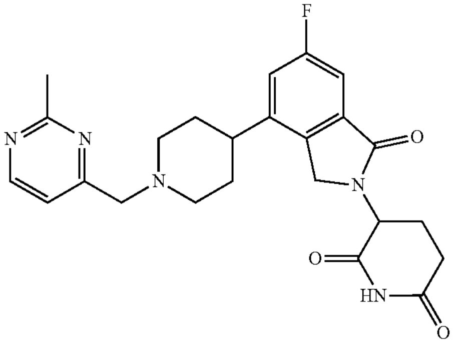

A1054

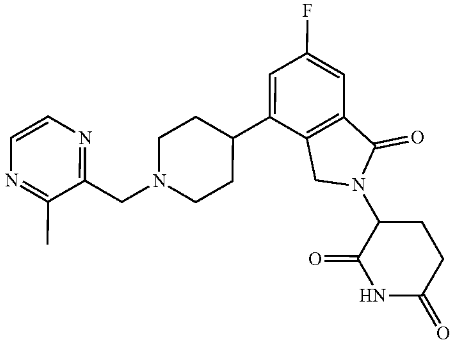

3-(6-Fluoro-4-(1-((5-methylpyrazin-2-yl)methyl)piperidin-4-yl)-1-oxoisoindolin-2-yl)piperidine-2,6-dione A1055.

3-(6-Fluoro-4-(1-((2-hydroxypyridin-3-yl)methyl)piperidin-4-yl)-1-oxoisoindolin-2-yl)piperidine-2,6-dione A1056.

A1055

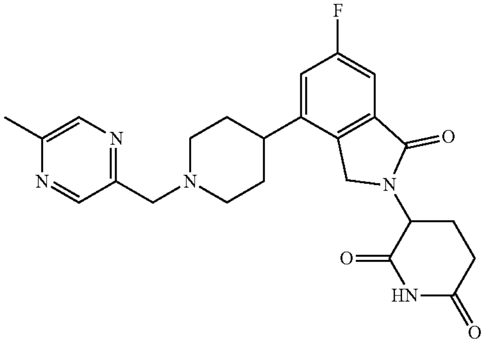

A1056

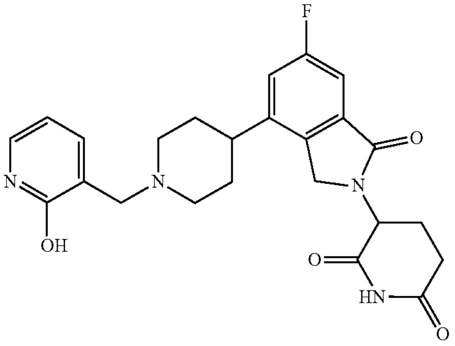

3-(6-Fluoro-4-(1-(3-fluorobenzyl)piperidin-4-yl)-1-oxoisoindolin-2-yl)piperidine-2,6-dione A1057.

3-(6-Fluoro-4-(1-(4-fluorobenzyl)piperidin-4-yl)-1-oxoisoindolin-2-yl)piperidine-2,6-dione A1058.

A1057

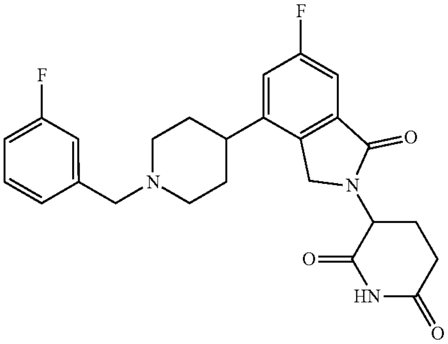

A1058

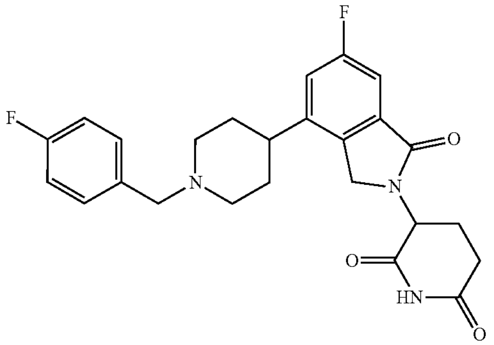

3-(4-(1-((1,4-Dimethyl-1H-pyrazol-5-yl)methyl)piperidin-4-yl)-6-fluoro-1-oxoisoindolin-2-yl)piperidine-2,6-dione A1059.

3-(4-(1-((2,5-Dimethyl-1H-imidazol-4-yl)methyl)piperidin-4-yl)-6-fluoro-1-oxoisoindolin-2-yl)piperidine-2,6-dione A1060.

A1059

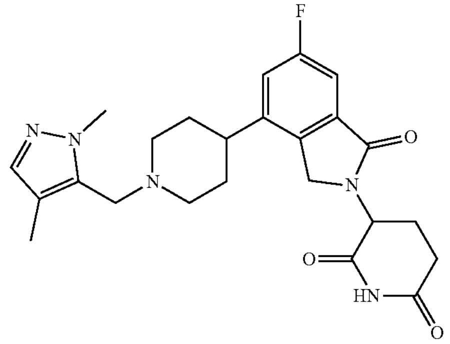

A1060

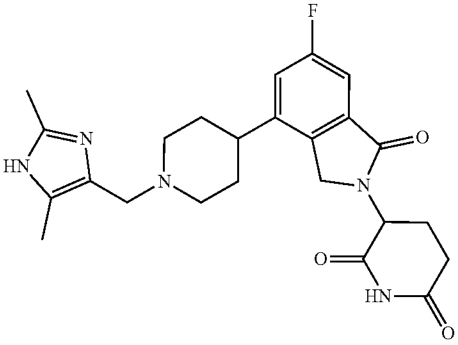

3-(6-Fluoro-4-(1-((6-fluoropyridin-2-yl)methyl)piperidin-4-yl)-1-oxoisoindolin-2-yl)piperidine-2,6-dione A1061.

3-(6-Fluoro-4-(1-((4-fluoropyridin-2-yl)methyl)piperidin-4-yl)-1-oxoisoindolin-2-yl)piperidine-2,6-dione A1062.

A1061

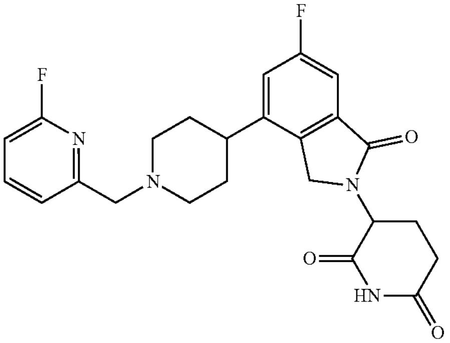

-continued

A1062

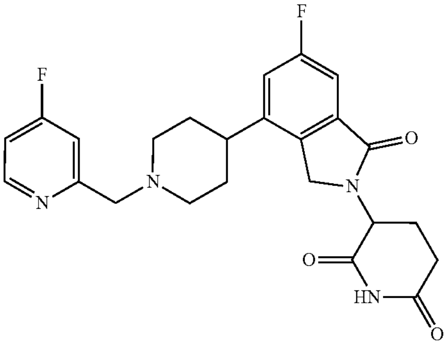

3-(6-Fluoro-4-(1-((5-fluoropyridin-3-yl)methyl)piperidin-4-yl)-1-oxoisoindolin-2-yl)piperidine-2,6-dione A1063.

3-(6-Fluoro-4-(1-((5-fluoropyridin-2-yl)methyl)piperidin-4-yl)-1-oxoisoindolin-2-yl)piperidine-2,6-dione A1064.

A1063

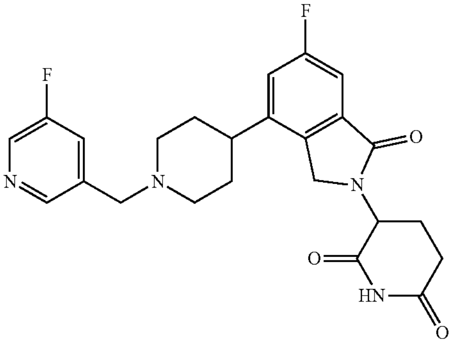

A1064

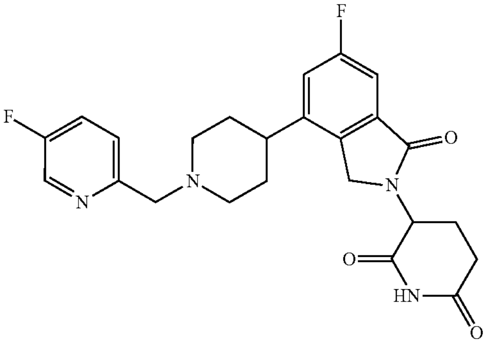

3-(6-Fluoro-4-(1-((3-fluoropyridin-4-yl)methyl)piperidin-4-yl)-1-oxoisoindolin-2-yl)piperidine-2,6-dione A1065.

3-(6-Fluoro-4-(1-((6-fluoropyridin-3-yl)methyl)piperidin-4-yl)-1-oxoisoindolin-2-yl)piperidine-2,6-dione A1066.

A1065

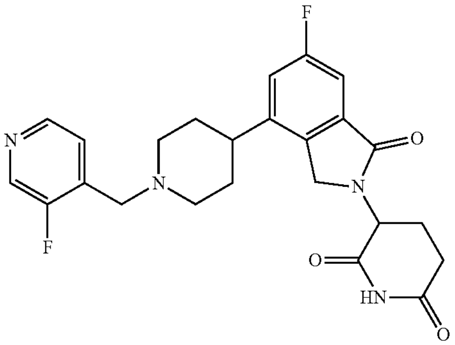

A1066

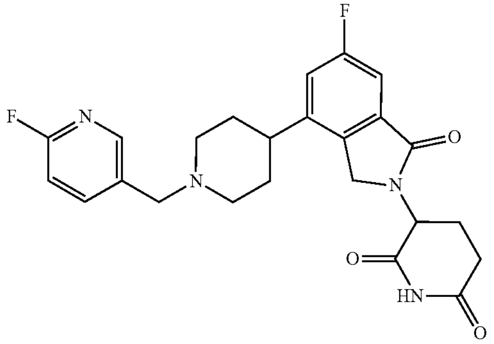

3-(6-Fluoro-4-(1-((5-(hydroxymethyl)-1H-pyrrol-2-yl)methyl)piperidin-4-yl)-1-oxoisoindolin-2-yl)piperidine-2,6-dione A1067.

3-(4-(1-((5-Amino-1-methyl-1H-pyrazol-4-yl)methyl)piperidin-4-yl)-6-fluoro-1-oxoisoindolin-2-yl)piperidine-2,6-dione A1068.

A1067

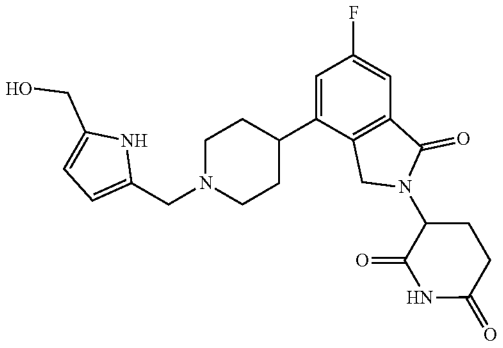

-continued

A1068

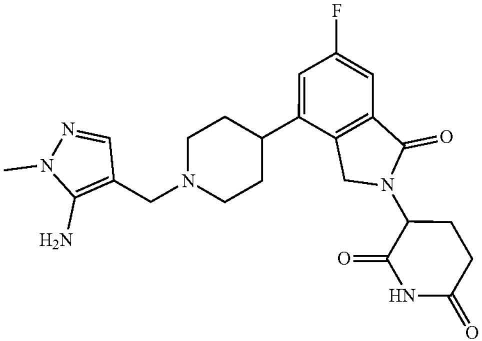

3-(6-Fluoro-4-(1-((5-(hydroxymethyl)furan-2-yl)methyl)piperidin-4-yl)-1-oxoisoindolin-2-yl)piperidine-2,6-dione A1069.

3-(6-Fluoro-4-(1-((3-methoxyfuran-2-yl)methyl)piperidin-4-yl)-1-oxoisoindolin-2-yl)piperidine-2,6-dione A1070.

A1069

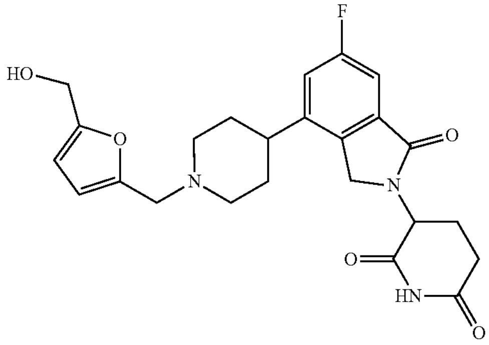

A1070

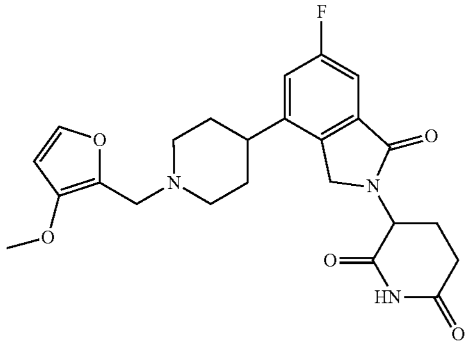

3-(6-Fluoro-4-(1-((3-methylthiophen-2-yl)methyl)piperidin-4-yl)-1-oxoisoindolin-2-yl)piperidine-2,6-dione A1071.

3-(4-(1-(2-Cyclohexylethyl)piperidin-4-yl)-6-fluoro-1-oxoisoindolin-2-yl)-piperidine-2,6-dione A1072.

A1071

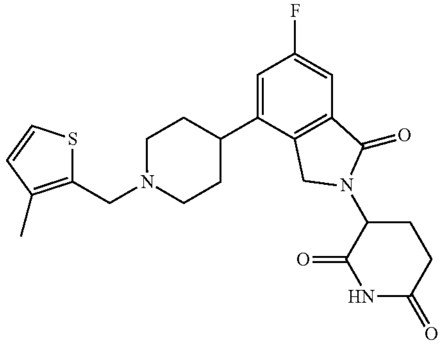

A1072

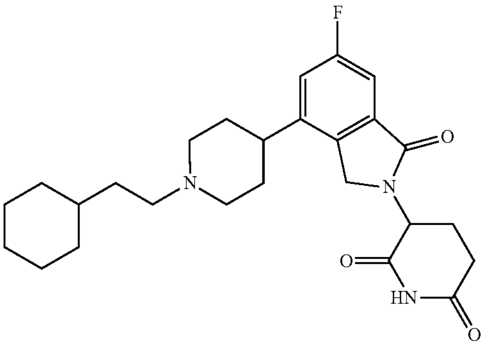

3-(6-Fluoro-4-(1-((4-methylthiazol-5-yl)methyl)piperidin-4-yl)-1-oxoisoindolin-2-yl)piperidine-2,6-dione A1073.

3-(6-Fluoro-4-(1-((2-methylthiazol-5-yl)methyl)piperidin-4-yl)-1-oxoisoindolin-2-yl)piperidine-2,6-dione A1074.

A1073

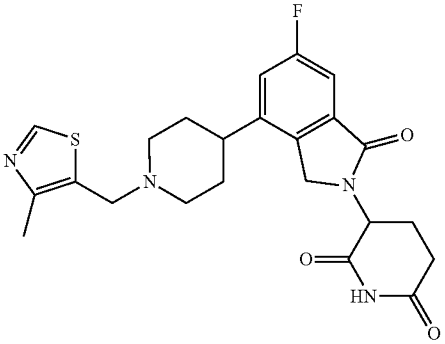

A1074

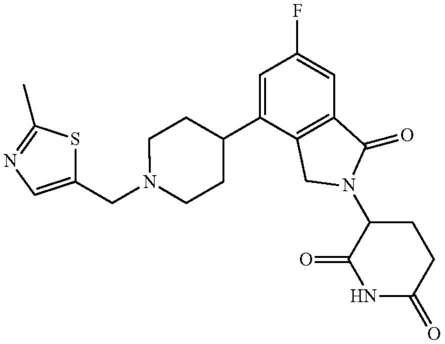

3-(6-Fluoro-4-(1-((5-methylthiazol-2-yl)methyl)piperidin-4-yl)-1-oxoisoindolin-2-yl)piperidine-2,6-dione A1075.

3-(4-(1-(3-Ethynylbenzyl)piperidin-4-yl)-6-fluoro-1-oxoisoindolin-2-yl)-piperidine-2,6-dione A1076.

A1075

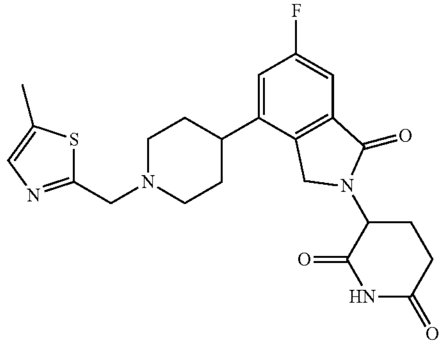

A1076

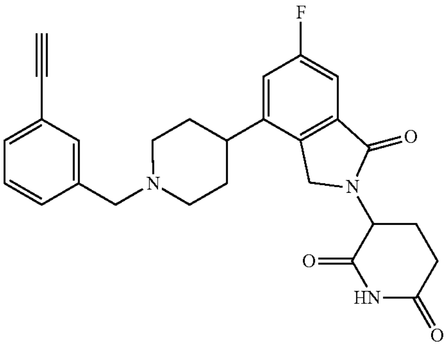

3-(4-(1-(2-Ethynylbenzyl)piperidin-4-yl)-6-fluoro-1-oxoisoindolin-2-yl)-piperidine-2,6-dione A1077.

3-(4-(1-(4-Ethynylbenzyl)piperidin-4-yl)-6-fluoro-1-oxoisoindolin-2-yl)-piperidine-2,6-dione A1078.

A1077

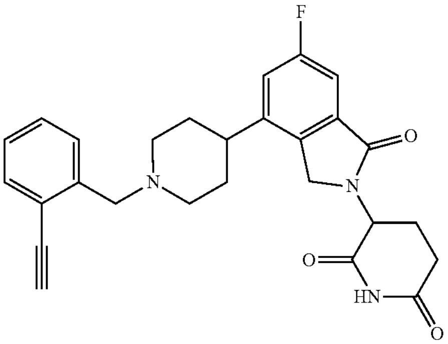

-continued

A1078

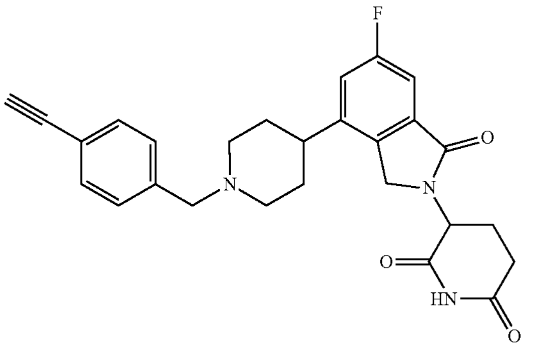

2-((4-(2-(2,6-Dioxopiperidin-3-yl)-6-fluoro-1-oxoisoindolin-4-yl)piperidin-1-yl)-methyl)benzonitrile A1079.

4-((4-(2-(2,6-Dioxopiperidin-3-yl)-6-fluoro-1-oxoisoindolin-4-yl)piperidin-1-yl)-methyl)benzonitrile A1080.

A1079

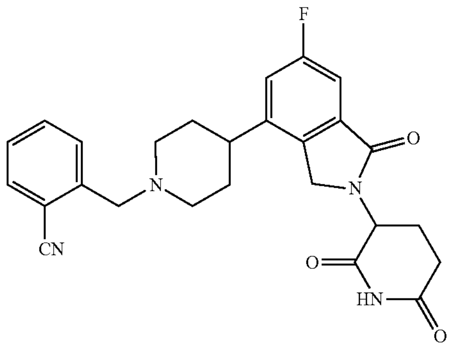

A1080

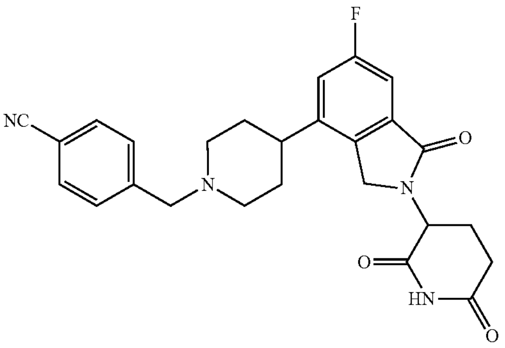

3-(4-(1-((5-Ethynylpyridin-2-yl)methyl)piperidin-4-yl)-6-fluoro-1-oxoisoindolin-2-yl)piperidine-2,6-dione A1081.

3-((4-(2-(2,6-Dioxopiperidin-3-yl)-6-fluoro-1-oxoisoindolin-4-yl)piperidin-1-yl)methyl)benzonitrile A1082.

A1081

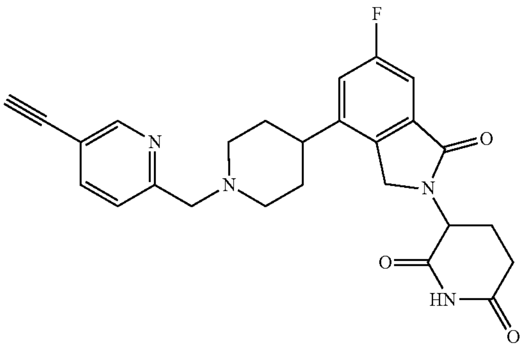

A1082

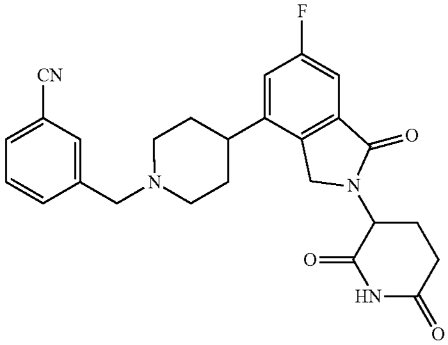

2-((4-(2-(2,6-Dioxopiperidin-3-yl)-6-fluoro-1-oxoisoindolin-4-yl)piperidin-1-yl)-methyl)isonicotinonitrile A1083.

6-((4-(2-(2,6-Dioxopiperidin-3-yl)-6-fluoro-1-oxoisoindolin-4-yl)piperidin-1-yl)-methyl)picolinonitrile A1084.

A1083

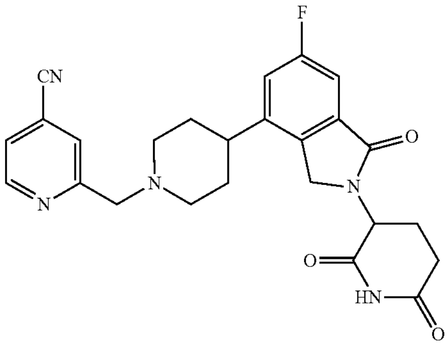

A1084

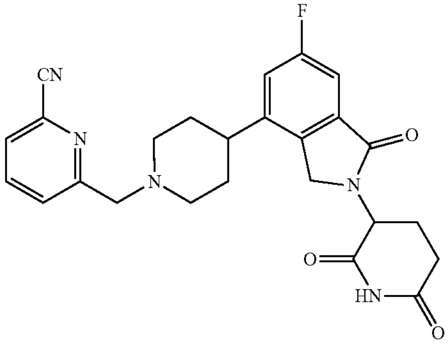

5-((4-(2-(2,6-Dioxopiperidin-3-yl)-6-fluoro-1-oxoisoindolin-4-yl)piperidin-1-yl)-methyl)nicotinonitrile A1085.

5-((4-(2-(2,6-Dioxopiperidin-3-yl)-6-fluoro-1-oxoisoindolin-4-yl)piperidin-1-yl)-methyl)picolinonitrile A1086.

A1085

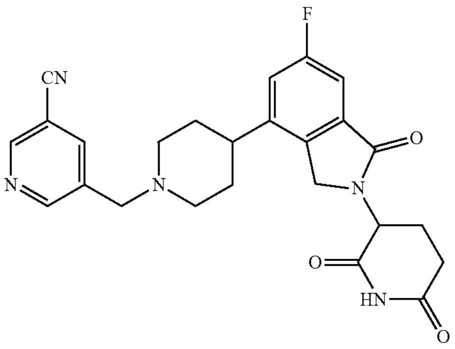

A1086

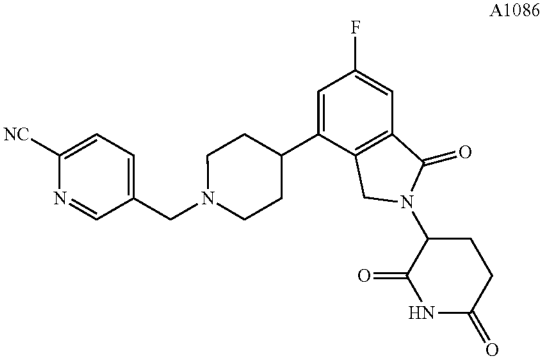

3-(4-(1-(Bicyclo[4.2.0]octa-1(6),2,4-trien-3-ylmethyl)piperidin-4-yl)-6-fluoro-1-oxoisoindolin-2-yl)piperidine-2,6-dione A1087.

4-((4-(2-(2,6-Dioxopiperidin-3-yl)-6-fluoro-1-oxoisoindolin-4-yl)piperidin-1-yl)-methyl)-1-methyl-1H-pyrrole-2-carbonitrile A1088.

A1087

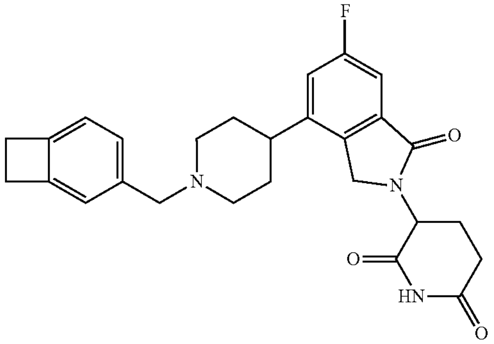

-continued

A1088

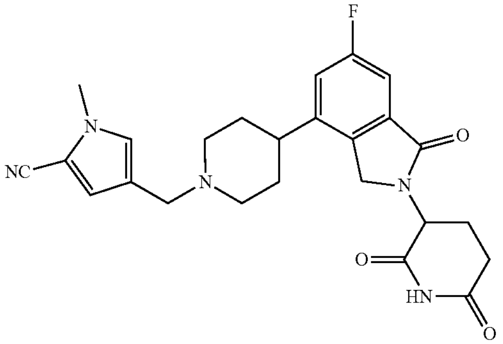

3-(6-Fluoro-1-oxo-4-(1-(3-phenylpropyl)piperidin-4-yl)isoindolin-2-yl)-piperidine-2,6-dione A1089.

3-(4-(1-(3,5-Dimethylbenzyl)piperidin-4-yl)-6-fluoro-1-oxoisoindolin-2-yl)-piperidine-2,6-dione A1090.

A1089

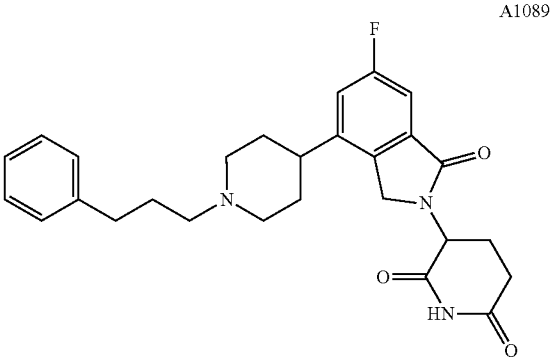

A1090

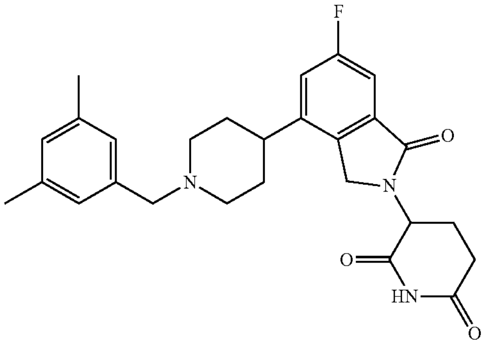

3-(6-Fluoro-4-(1-(2-methylphenethyl)piperidin-4-yl)-1-oxoisoindolin-2-yl)-piperidine-2,6-dione A1091.

3-(4-(1-(2,5-Dimethylbenzyl)piperidin-4-yl)-6-fluoro-1-oxoisoindolin-2-yl)-piperidine-2,6-dione A1092.

A1091

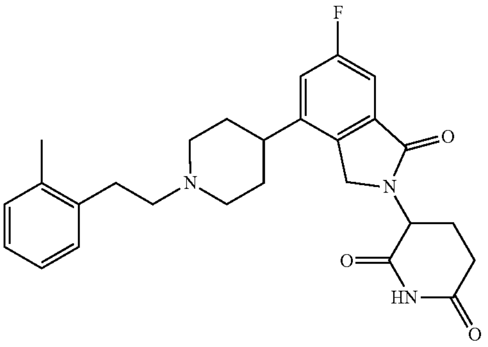

A1092

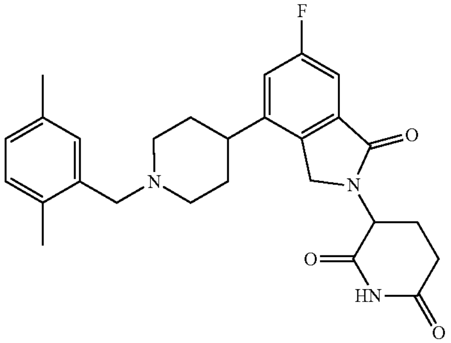

3-(4-(1-(2,4-Dimethylbenzyl)piperidin-4-yl)-6-fluoro-1-oxoisoindolin-2-yl)-piperidine-2,6-dione A1093.

3-(4-(1-(2,6-Dimethylbenzyl)piperidin-4-yl)-6-fluoro-1-oxoisoindolin-2-yl)-piperidine-2,6-dione A1094.

A1093

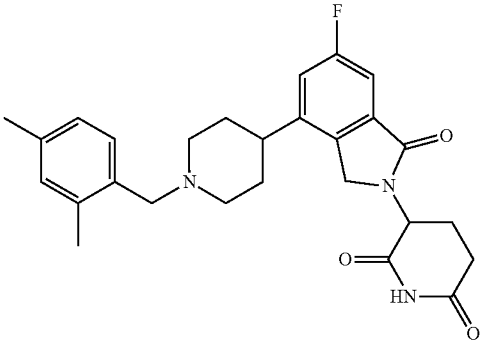

A1094

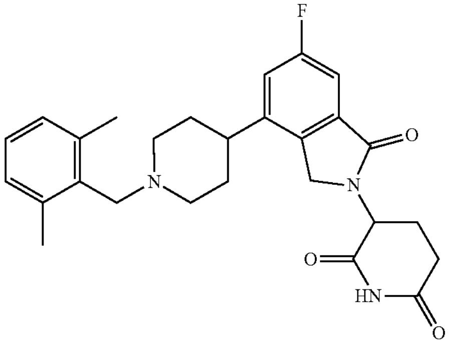

3-(6-Fluoro-4-(1-(2-(methylamino)benzyl)piperidin-4-yl)-1-oxoisoindolin-2-yl)-piperidine-2,6-dione A1095.

3-(4-(1-((2,6-Dimethylpyridin-4-yl)methyl)piperidin-4-yl)-6-fluoro-1-oxoisoindolin-2-yl)piperidine-2,6-dione A1096.

A1095

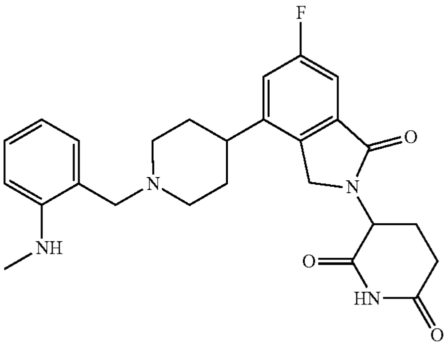

A1096

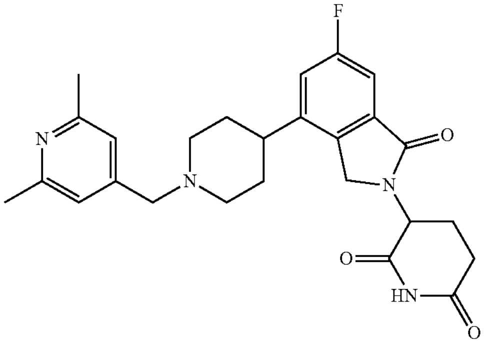

3-(6-Fluoro-4-(1-(4-(hydroxymethyl)benzyl)piperidin-4-yl)-1-oxoisoindolin-2-yl)piperidine-2,6-dione A1097.

3-(6-Fluoro-4-(1-(2-hydroxy-4-methylbenzyl)piperidin-4-yl)-1-oxoisoindolin-2-yl)piperidine-2,6-dione A1098.

A1097

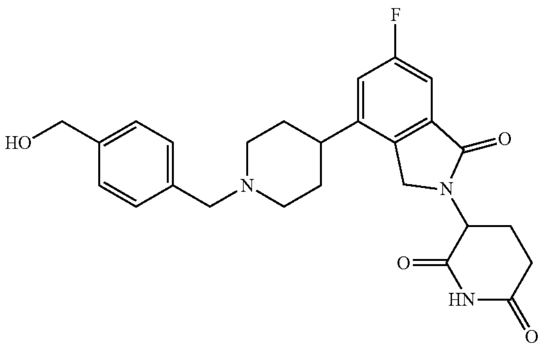

-continued

A1098

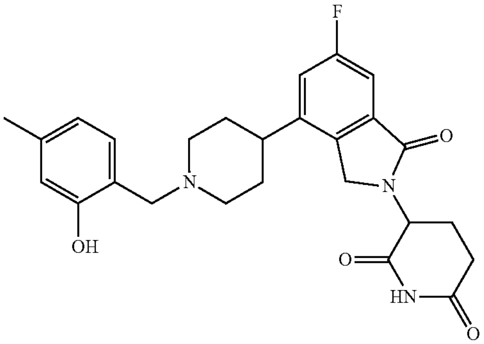

3-(6-Fluoro-4-(1-(3-methoxybenzyl)piperidin-4-yl)-1-oxoisoindolin-2-yl)-piperidine-2,6-dione A1099.

3-(6-Fluoro-4-(1-(3-hydroxy-5-methylbenzyl)piperidin-4-yl)-1-oxoisoindolin-2-yl)piperidine-2,6-dione A1100.

A1099

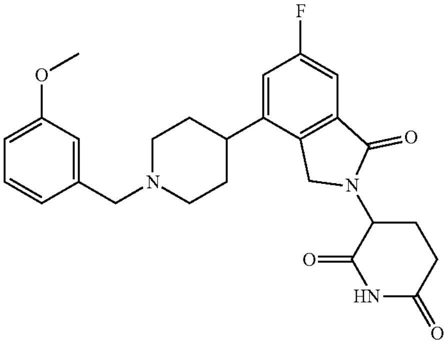

A1100

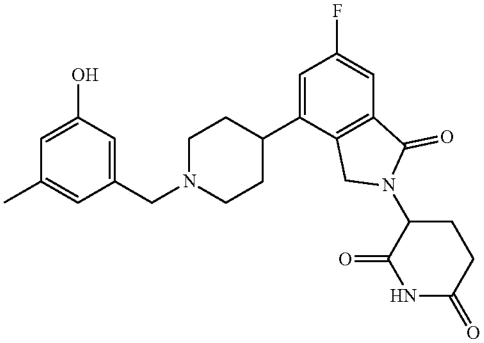

3-(6-Fluoro-4-(1-(4-methoxybenzyl)piperidin-4-yl)-1-oxoisoindolin-2-yl)-piperidine-2,6-dione A1101.

3-(6-Fluoro-4-(1-(2-methoxybenzyl)piperidin-4-yl)-1-oxoisoindolin-2-yl)-piperidine-2,6-dione A1102.

A1101

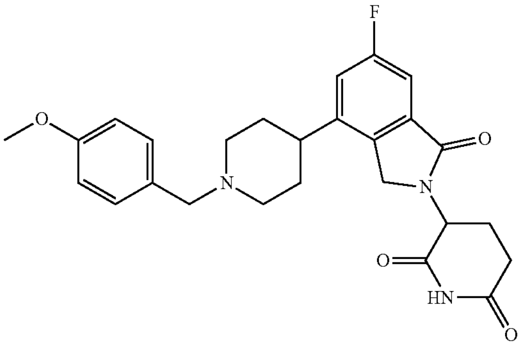

A1102

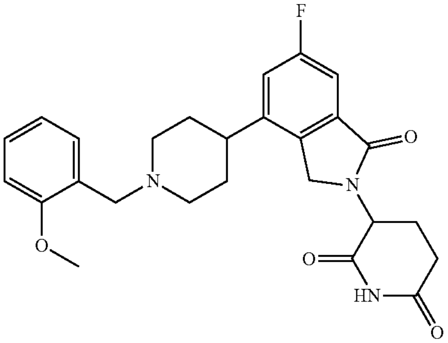

3-(4-(1-((2-Amino-5-methylpyridin-3-yl)methyl)piperidin-4-yl)-6-fluoro-1-oxoisoindolin-2-yl)piperidine-2,6-dione A1103.

3-(6-Fluoro-4-(1-((1-methyl-2-oxo-1,2-dihydropyridin-4-yl)methyl)piperidin-4-yl)-1-oxoisoindolin-2-yl)piperidine-2,6-dione A1104.

A1103

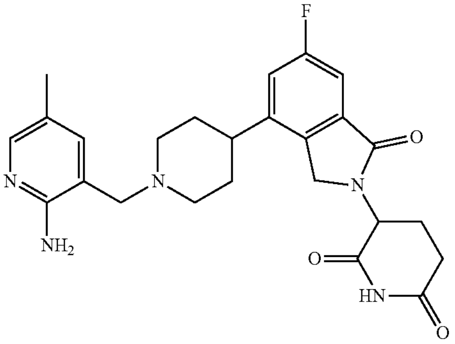

-continued

A1104

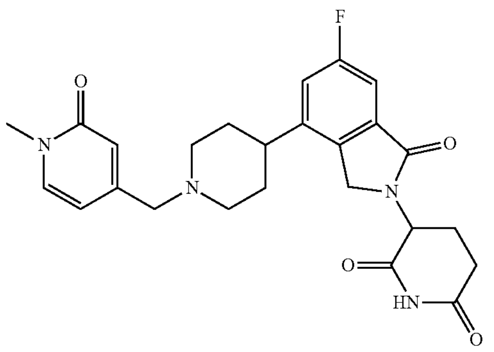

3-(6-Fluoro-4-(1-((1-methyl-6-oxo-1,6-dihydropyridin-2-yl)methyl)piperidin-4-yl)-1-oxoisoindolin-2-yl)piperidine-2,6-dione A1105.

3-(6-Fluoro-4-(1-((5-methoxypyridin-3-yl)methyl)piperidin-4-yl)-1-oxoisoindolin-2-yl)piperidine-2,6-dione A1106.

A1105

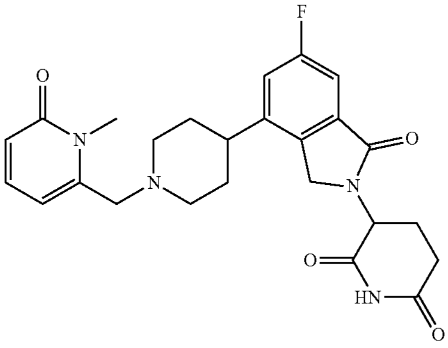

A1106

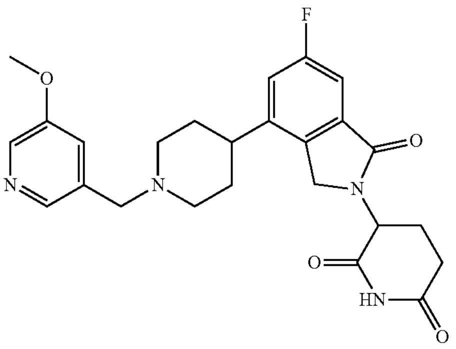

3-(6-Fluoro-4-(1-((6-methoxypyridin-2-yl)methyl)piperidin-4-yl)-1-oxoisoindolin-2-yl)piperidine-2,6-dione A1107.

3-(6-Fluoro-4-(1-((4-methoxypyridin-3-yl)methyl)piperidin-4-yl)-1-oxoisoindolin-2-yl)piperidine-2,6-dione A1108.

A1107

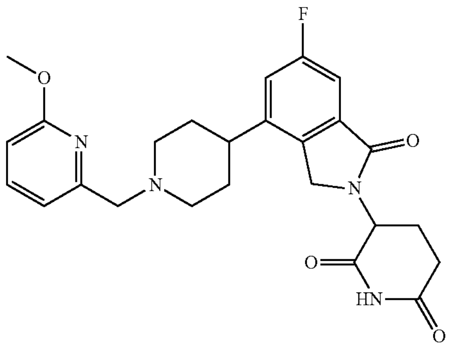

A1108

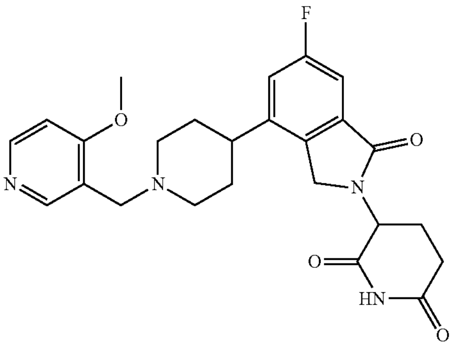

3-(6-Fluoro-4-(1-((3-methoxypyridin-2-yl)methyl)piperidin-4-yl)-1-oxoisoindolin-2-yl)piperidine-2,6-dione A1109.

3-(6-Fluoro-4-(1-((5-methoxypyridin-2-yl)methyl)piperidin-4-yl)-1-oxoisoindolin-2-yl)piperidine-2,6-dione A1110.

A1109

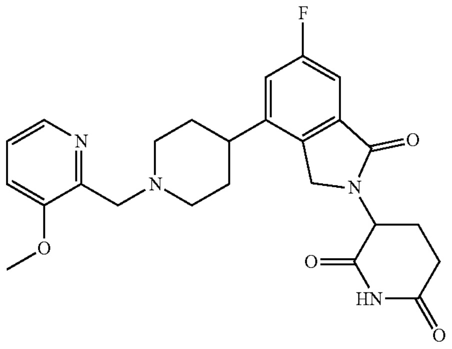

-continued

A1110

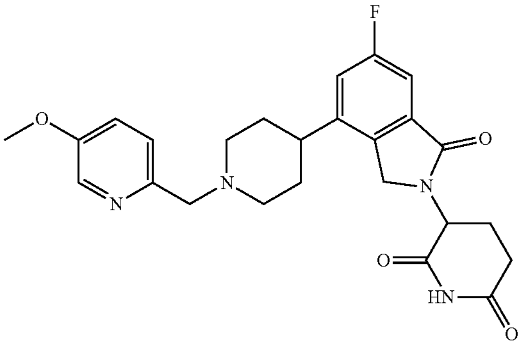

3-(6-Fluoro-4-(1-((4-methoxypyridin-2-yl)methyl)piperidin-4-yl)-1-oxoisoindolin-2-yl)piperidine-2,6-dione A1111.

3-(6-Fluoro-4-(1-((6-methoxypyridin-3-yl)methyl)piperidin-4-yl)-1-oxoisoindolin-2-yl)piperidine-2,6-dione A1112.

A1111

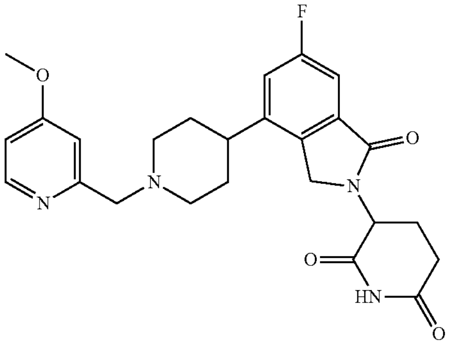

A1112

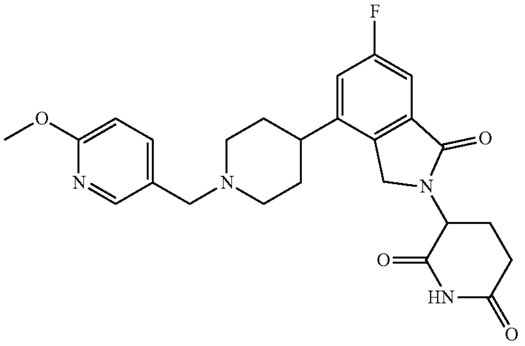

3-(6-Fluoro-4-(1-((3-methoxypyridin-4-yl)methyl)piperidin-4-yl)-1-oxoisoindolin-2-yl)piperidine-2,6-dione A1113.

3-(6-Fluoro-4-(1-((2-methoxypyridin-3-yl)methyl)piperidin-4-yl)-1-oxoisoindolin-2-yl)piperidine-2,6-dione A1114.

A1113

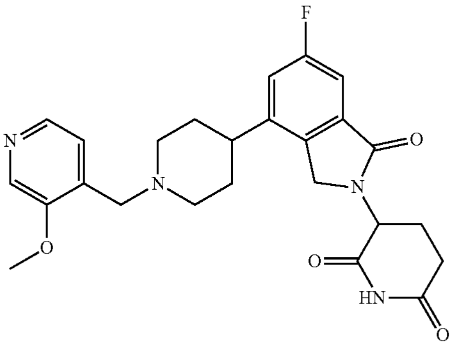

A1114

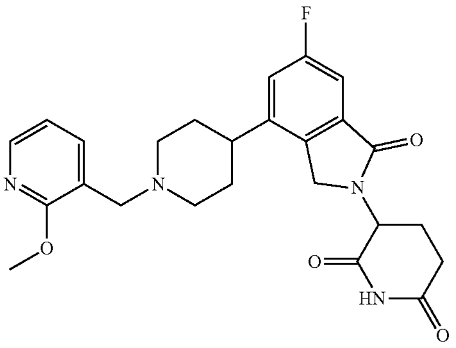

3-(6-Fluoro-4-(1-((2-methoxypyridin-4-yl)methyl)piperidin-4-yl)-1-oxoisoindolin-2-yl)piperidine-2,6-dione A1115.

5-((4-(2-(2,6-Dioxopiperidin-3-yl)-6-fluoro-1-oxoisoindolin-4-yl)piperidin-1-yl)methyl)thiophene-2-carbonitrile A1116.

A1115

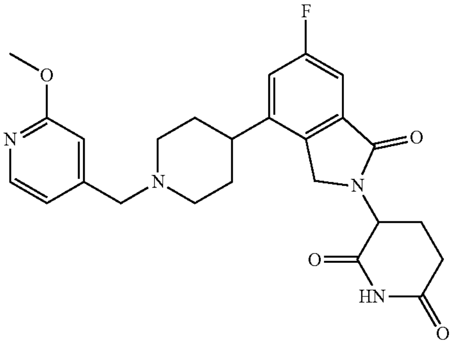

-continued

A1116

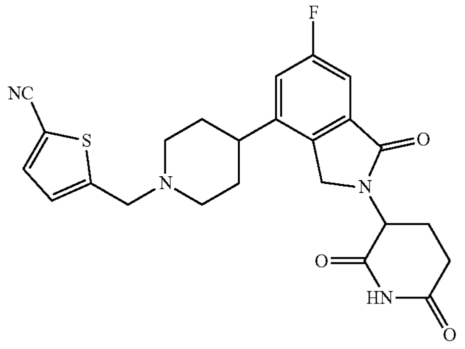

3-(6-Fluoro-4-(1-((2-methoxypyrimidin-4-yl)methyl)piperidin-4-yl)-1-oxoisoindolin-2-yl)piperidine-2,6-dione A1117.

3-(6-Fluoro-4-(1-((5-methoxypyrazin-2-yl)methyl)piperidin-4-yl)-1-oxoisoindolin-2-yl)piperidine-2,6-dione A1118.

A1117

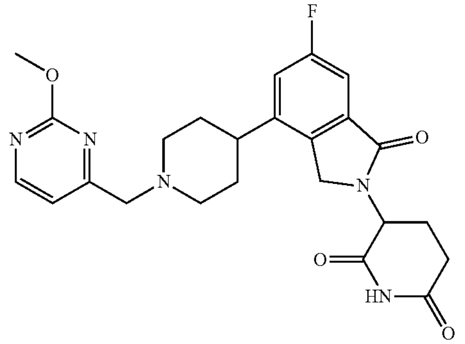

A1118

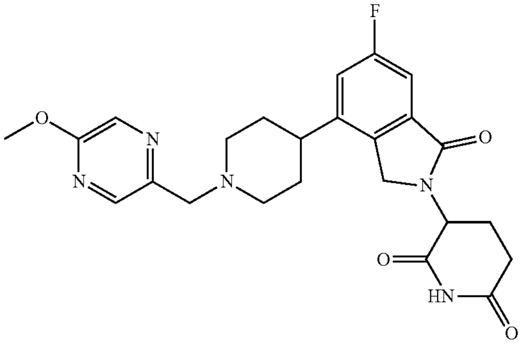

3-(6-Fluoro-4-(1-(5-fluoro-2-methylbenzyl)piperidin-4-yl)-1-oxoisoindolin-2-yl)-piperidine-2,6-dione A1119.

3-(6-Fluoro-4-(1-(4-fluoro-2-methylbenzyl)piperidin-4-yl)-1-oxoisoindolin-2-yl)-piperidine-2,6-dione A1120.

A1119

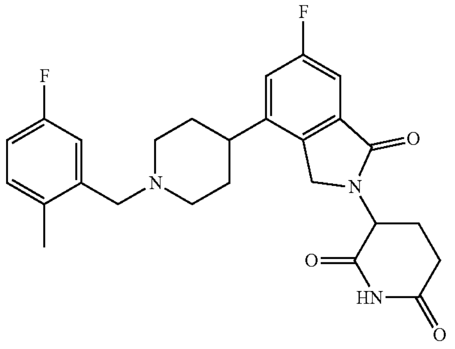

A1120

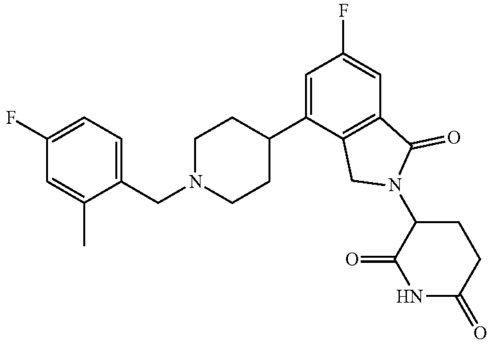

3-(6-Fluoro-4-(1-(3-fluoro-5-methylbenzyl)piperidin-4-yl)-1-oxoisoindolin-2-yl)-piperidine-2,6-dione A1121.

3-(6-Fluoro-4-(1-(4-fluoro-3-methylbenzyl)piperidin-4-yl)-1-oxoisoindolin-2-yl)-piperidine-2,6-dione A1122.

A1121

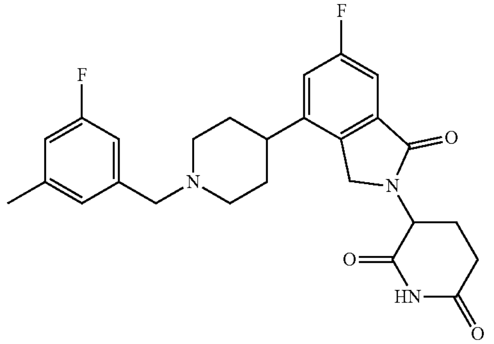

-continued

A1122

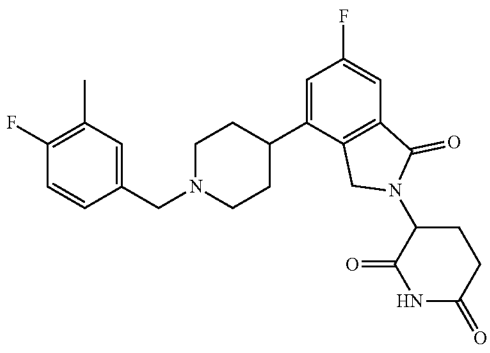

3-(6-Fluoro-4-(1-(2-fluoro-5-methylbenzyl)piperidin-4-yl)-1-oxoisoindolin-2-yl)-piperidine-2,6-dione A1123.

3-(6-Fluoro-4-(1-(3-fluoro-2-methylbenzyl)piperidin-4-yl)-1-oxoisoindolin-2-yl)-piperidine-2,6-dione A1124.

A1123

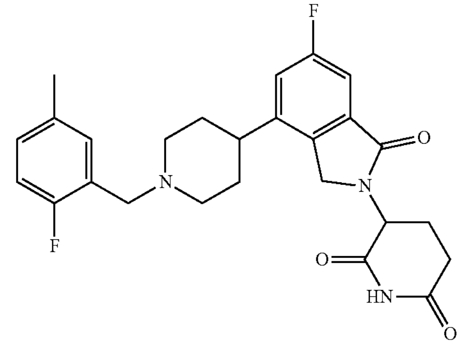

A1124

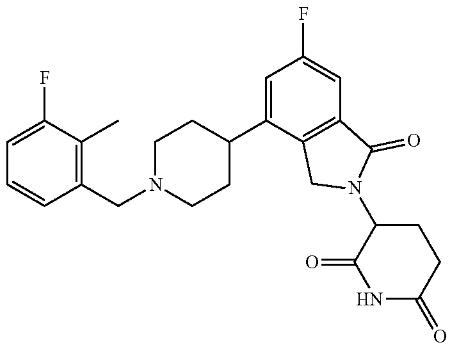

3-(6-Fluoro-4-(1-(4-fluorophenethyl)piperidin-4-yl)-1-oxoisoindolin-2-yl)-piperidine-2,6-dione A1125.

3-(6-Fluoro-4-(1-(3-(5-methylfuran-2-yl)propyl)piperidin-4-yl)-1-oxoisoindolin-2-yl)piperidine-2,6-dione A1126.

A1125

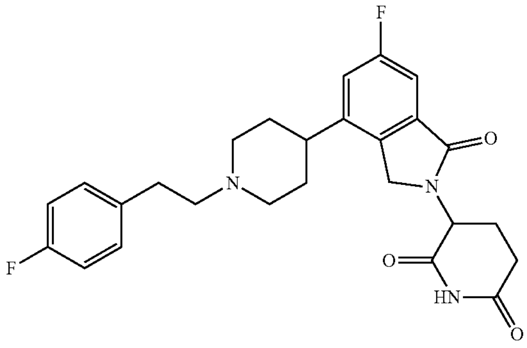

A1126

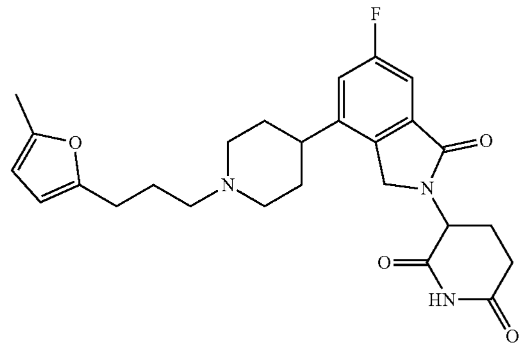

3-(6-Fluoro-4-(1-((4-isopropylfuran-2-yl)methyl)piperidin-4-yl)-1-oxoisoindolin-2-yl)piperidine-2,6-dione A1127.

3-(6-Fluoro-4-(1-((1-isopropyl-1H-pyrazol-4-yl)methyl)piperidin-4-yl)-1-oxoisoindolin-2-yl)piperidine-2,6-dione A1128.

A1127

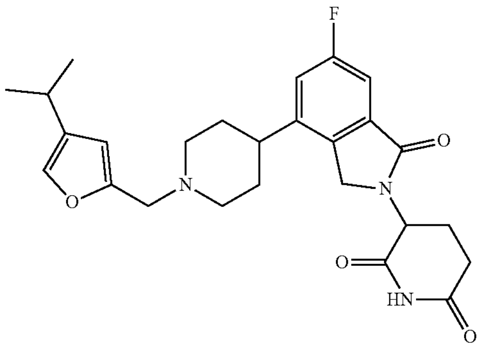

-continued

A1128

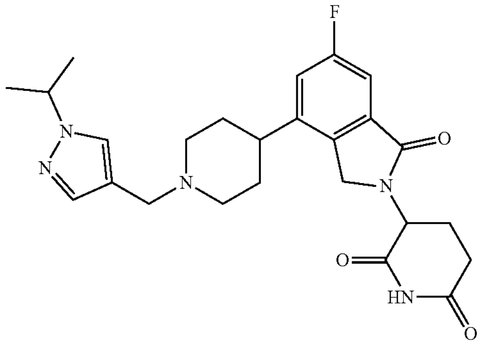

3-(4-(1-(2-Amino-5-fluorobenzyl)piperidin-4-yl)-6-fluoro-1-oxoisoindolin-2-yl)-piperidine-2,6-dione A1129.

3-(4-(1-(3-Chlorobenzyl)piperidin-4-yl)-6-fluoro-1-oxoisoindolin-2-yl)piperidine-2,6-dione A1130.

A1129

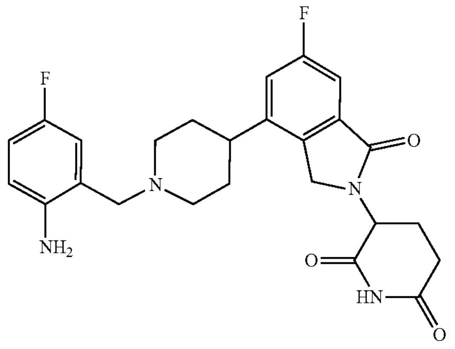

A1130

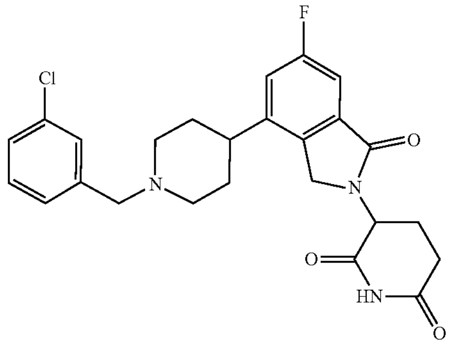

3-(4-(1-(4-Chlorobenzyl)piperidin-4-yl)-6-fluoro-1-oxoisoindolin-2-yl)piperidine-2,6-dione A1131.

3-(4-(1-(2-Chlorobenzyl)piperidin-4-yl)-6-fluoro-1-oxoisoindolin-2-yl)piperidine-2,6-dione A1132.

A1131

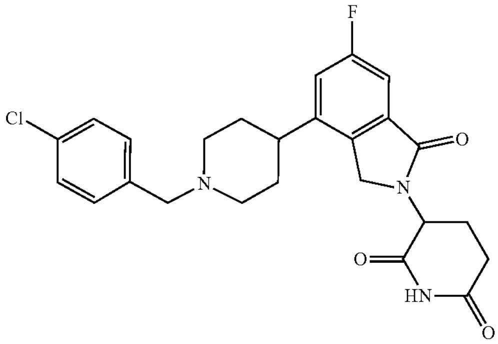

A1132

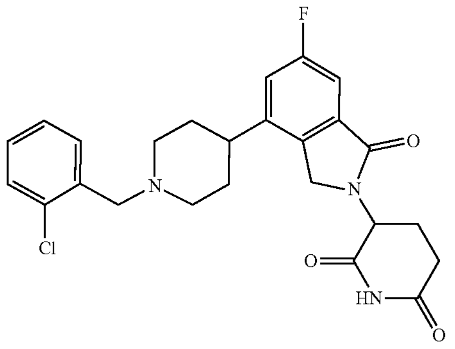

3-(6-Fluoro-4-(1-((5-fluoro-2-oxo-1,2-dihydropyridin-3-yl)methyl)piperidin-4-yl)-1-oxoisoindolin-2-yl)piperidine-2,6-dione A1133.

3-(4-(1-((6-Chloropyridin-2-yl)methyl)piperidin-4-yl)-6-fluoro-1-oxoisoindolin-2-yl)piperidine-2,6-dione A1134.

A1133

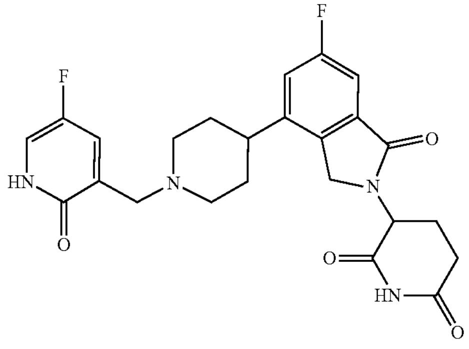

-continued

A1134

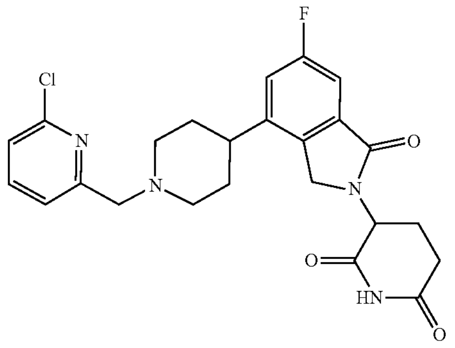

3-(4-(1-((3-Chloropyridin-4-yl)methyl)piperidin-4-yl)-6-fluoro-1-oxoisoindolin-2-yl)piperidine-2,6-dione A1135.

3-(4-(1-((3-Chloropyrazin-2-yl)methyl)piperidin-4-yl)-6-fluoro-1-oxoisoindolin-2-yl)piperidine-2,6-dione A1136.

A1135

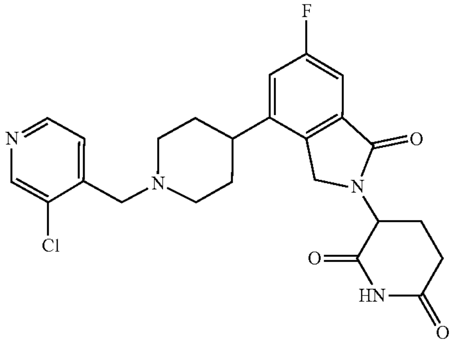

A1136

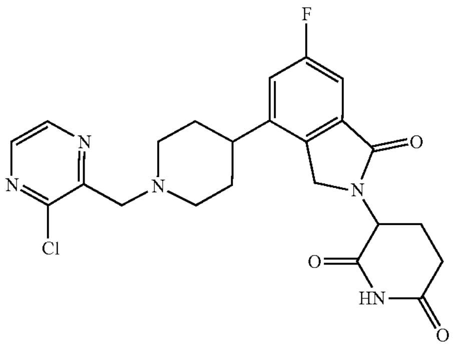

3-(4-(1-((4-Chloro-1-methyl-1H-pyrazol-3-yl)methyl)piperidin-4-yl)-6-fluoro-1-oxoisoindolin-2-yl)piperidine-2,6-dione A1137.

3-(4-(1-((1H-Indol-6-yl)methyl)piperidin-4-yl)-6-fluoro-1-oxoisoindolin-2-yl)piperidine-2,6-dione A1138.

A1137

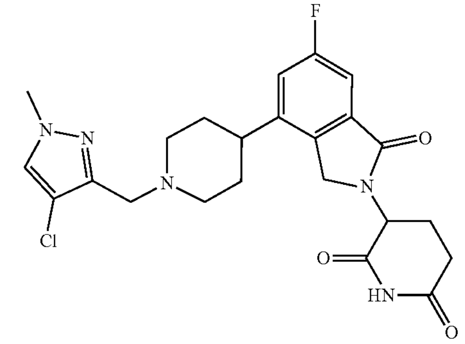

A1138

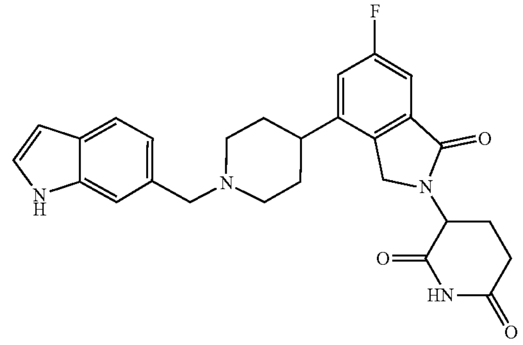

3-(4-(1-((1H-Indol-2-yl)methyl)piperidin-4-yl)-6-fluoro-1-oxoisoindolin-2-yl)piperidine-2,6-dione A1139.

3-(4-(1-((1H-Indol-7-yl)methyl)piperidin-4-yl)-6-fluoro-1-oxoisoindolin-2-yl)piperidine-2,6-dione A1140.

A1139

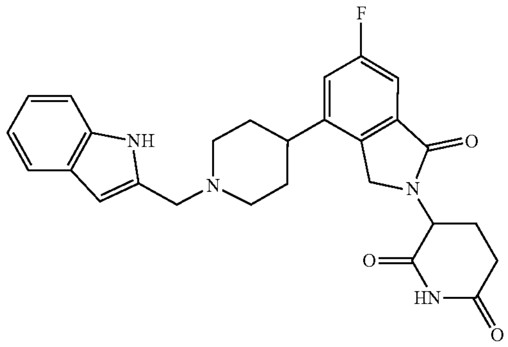

A1140

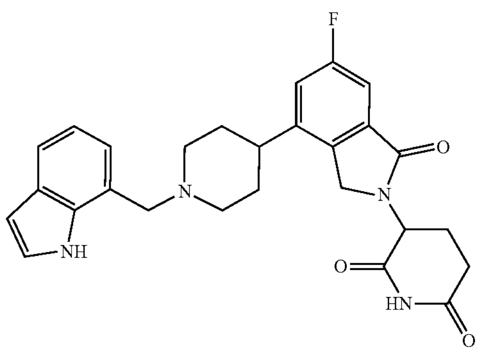

3-(6-Fluoro-4-(1-(indolizin-1-ylmethyl)piperidin-4-yl)-1-oxoisoindolin-2-yl)-piperidine-2,6-dione A1141.

3-(4-(1-((1H-Indol-3-yl)methyl)piperidin-4-yl)-6-fluoro-1-oxoisoindolin-2-yl)-piperidine-2,6-dione A1142.

A1141

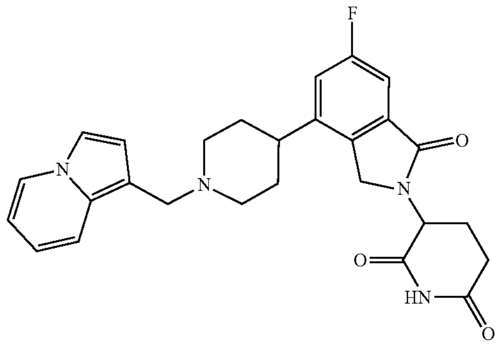

A1142

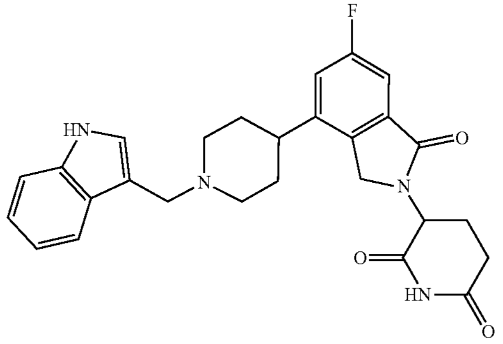

4-((4-(2-(2,6-Dioxopiperidin-3-yl)-6-fluoro-1-oxoisoindolin-4-yl)piperidin-1-yl)-methyl)-3-methylbenzonitrile A1143.

2-((4-(2-(2,6-Dioxopiperidin-3-yl)-6-fluoro-1-oxoisoindolin-4-yl)piperidin-1-yl)-methyl)-6-methylbenzonitrile A1144.

A1143

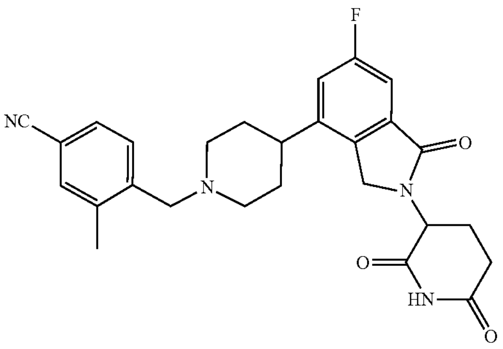

-continued

A1144

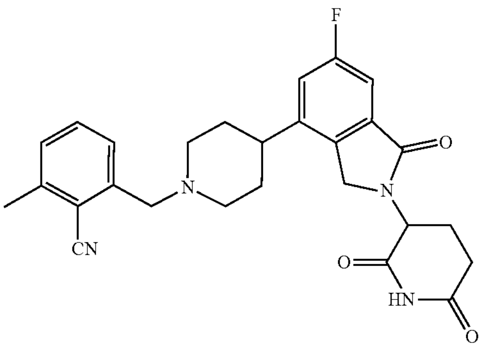

3-((4-(2-(2,6-Dioxopiperidin-3-yl)-6-fluoro-1-oxoisoindolin-4-yl)piperidin-1-yl)-methyl)-5-methylbenzonitrile A1145.

3-((4-(2-(2,6-Dioxopiperidin-3-yl)-6-fluoro-1-oxoisoindolin-4-yl)piperidin-1-yl)-methyl)-2-methylbenzonitrile A1146.

A1145

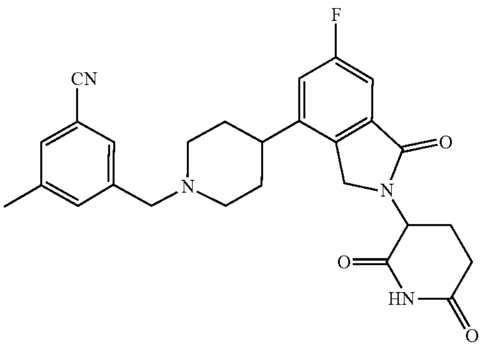

A1146

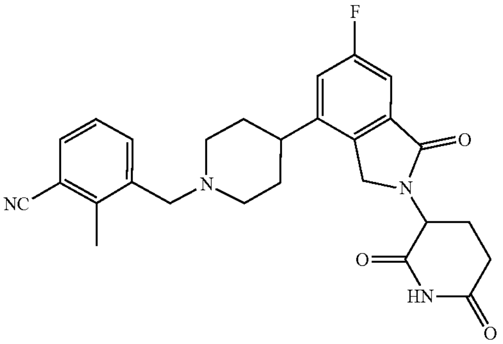

2-((4-(2-(2,6-Dioxopiperidin-3-yl)-6-fluoro-1-oxoisoindolin-4-yl)piperidin-1-yl)-methyl)-5-methylbenzonitrile A1147.

3-(4-(1-(Benzofuran-5-ylmethyl)piperidin-4-yl)-6-fluoro-1-oxoisoindolin-2-yl)-piperidine-2,6-dione A1148.

A1147

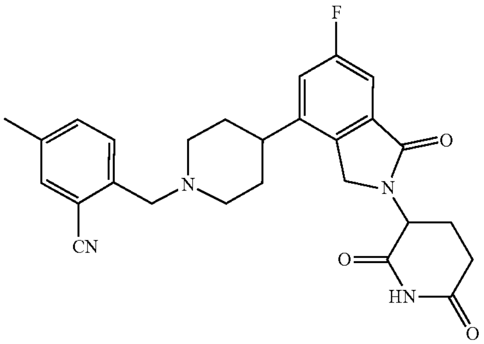

A1148

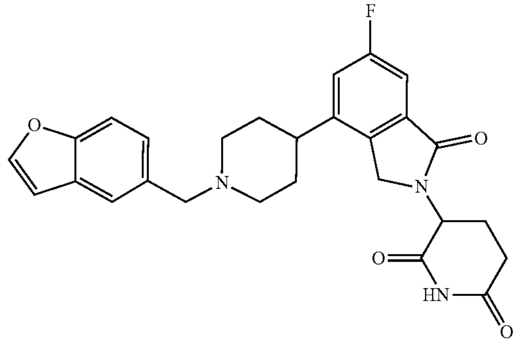

3-(4-(1-(Benzofuran-7-ylmethyl)piperidin-4-yl)-6-fluoro-1-oxoisoindolin-2-yl)-piperidine-2,6-dione A1149.

3-(4-(1-(Benzofuran-4-ylmethyl)piperidin-4-yl)-6-fluoro-1-oxoisoindolin-2-yl)-piperidine-2,6-dione A1150.

A1149

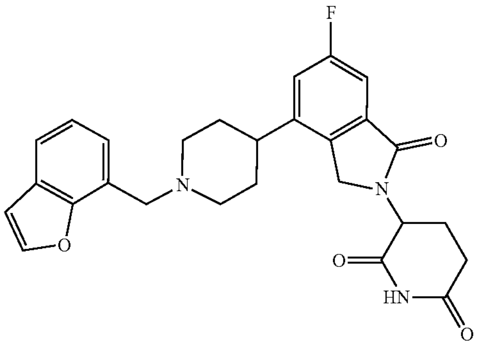

-continued

A1150

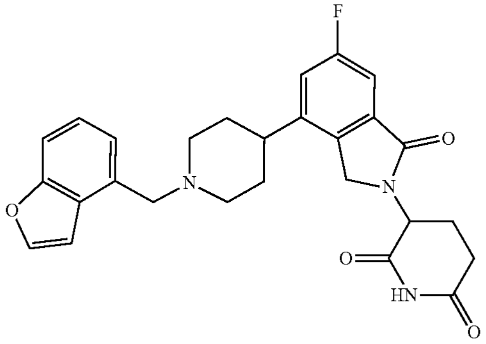

3-(6-Fluoro-4-(1-(imidazo[1,2-a]pyridin-2-ylmethyl)piperidin-4-yl)-1-oxoisoindolin-2-yl)piperidine-2,6-dione A1151.

3-(6-Fluoro-4-(1-(imidazo[1,2-a]pyridin-3-ylmethyl)piperidin-4-yl)-1-oxoisoindolin-2-yl)piperidine-2,6-dione A1152.

A1151

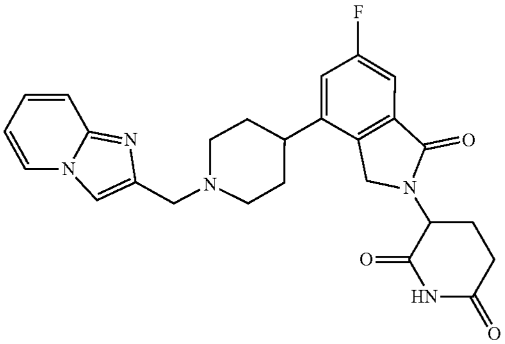

A1152

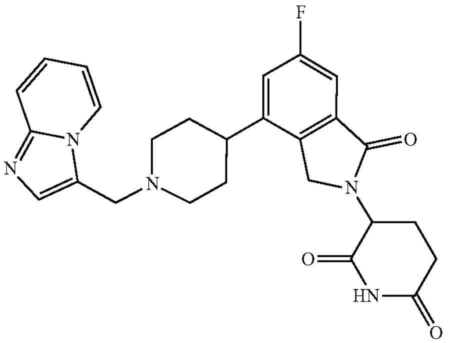

3-(4-(1-((1H-Benzo[d]imidazol-2-yl)methyl)piperidin-4-yl)-6-fluoro-1-oxoisoindolin-2-yl)piperidine-2,6-dione A1153.

3-(4-(1-((1H-Pyrrolo[3,2-b]pyridin-6-yl)methyl)piperidin-4-yl)-6-fluoro-1-oxoisoindolin-2-yl)piperidine-2,6-dione A1154.

A1153

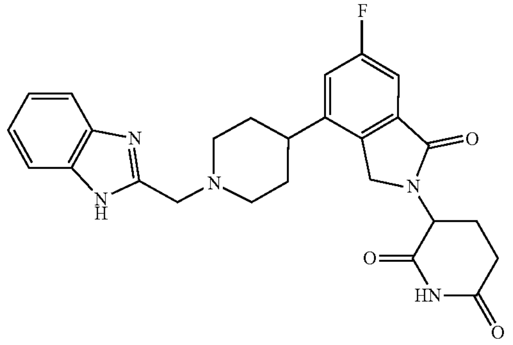

A1154

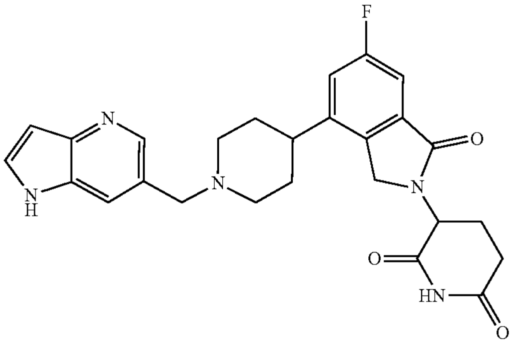

3-(6-Fluoro-4-(1-(imidazo[1,2-a]pyridin-7-ylmethyl)piperidin-4-yl)-1-oxoisoindolin-2-yl)piperidine-2,6-dione A1155.

3-(6-Fluoro-4-(1-(imidazo[1,2-a]pyridin-8-ylmethyl)piperidin-4-yl)-1-oxoisoindolin-2-yl)piperidine-2,6-dione A1156.

A1155

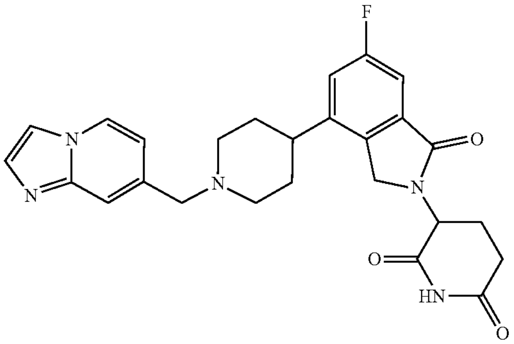

-continued

A1156

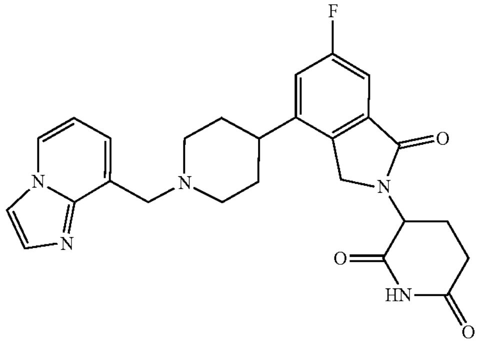

3-(6-Fluoro-4-(1-(imidazo[1,2-a]pyridin-6-ylmethyl)piperidin-4-yl)-1-oxoisoindolin-2-yl)piperidine-2,6-dione A1157.

3-(4-(1-((1H-Benzo[d]imidazol-7-yl)methyl)piperidin-4-yl)-6-fluoro-1-oxoisoindolin-2-yl)piperidine-2,6-dione A1158.

A1157

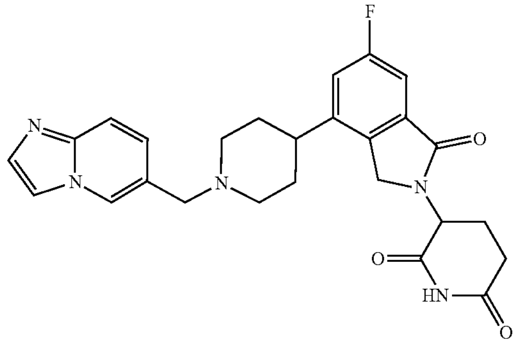

A1158

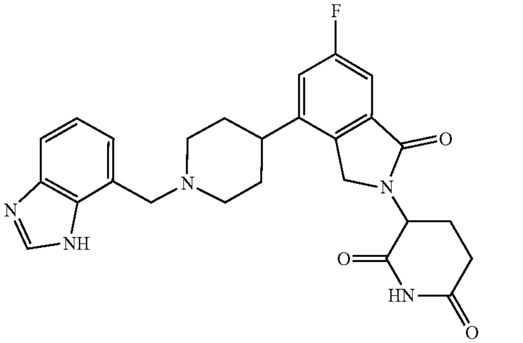

3-(4-(1-((1H-Pyrrolo[2,3-b]pyridin-6-yl)methyl)piperidin-4-yl)-6-fluoro-1-oxoisoindolin-2-yl)piperidine-2,6-dione A1159.

3-(6-Fluoro-4-(1-(imidazo[1,5-a]pyridin-1-ylmethyl)piperidin-4-yl)-1-oxoisoindolin-2-yl)piperidine-2,6-dione A1160.

A1159

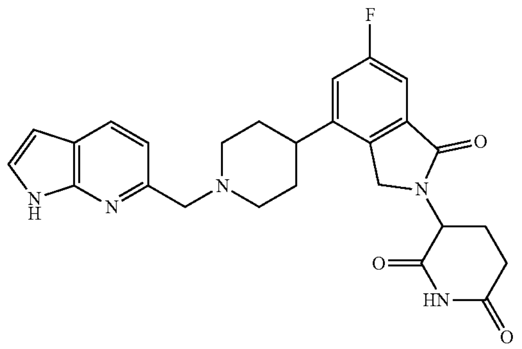

A1160

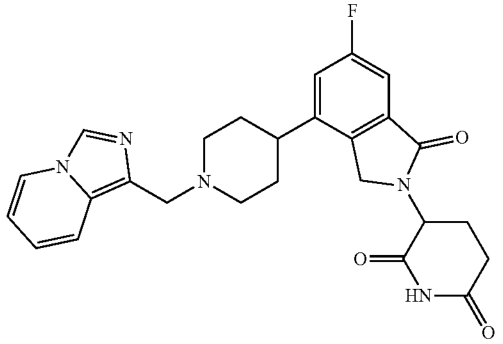

3-(4-(1-((1H-Pyrrolo[3,2-b]pyridin-3-yl)methyl)piperidin-4-yl)-6-fluoro-1-oxoisoindolin-2-yl)piperidine-2,6-dione A1161.

3-(4-(1-((2H-Indazol-6-yl)methyl)piperidin-4-yl)-6-fluoro-1-oxoisoindolin-2-yl)piperidine-2,6-dione A1162.

A1161

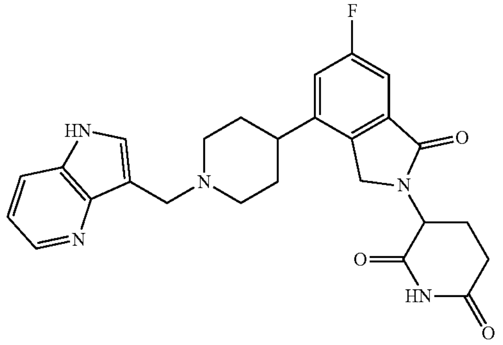

-continued

A1162

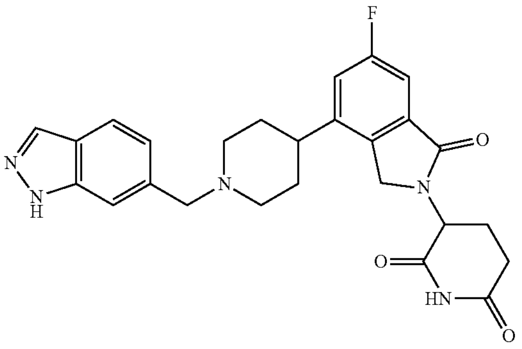

3-(6-Fluoro-1-oxo-4-(1-(pyrazolo[1,5-a]pyridin-3-ylmethyl)piperidin-4-yl)isoindolin-2-yl)piperidine-2,6-dione A1163.

3-(6-Fluoro-4-(1-(imidazo[1,2-a]pyridin-5-ylmethyl)piperidin-4-yl)-1-oxoisoindolin-2-yl)piperidine-2,6-dione A1164.

A1163

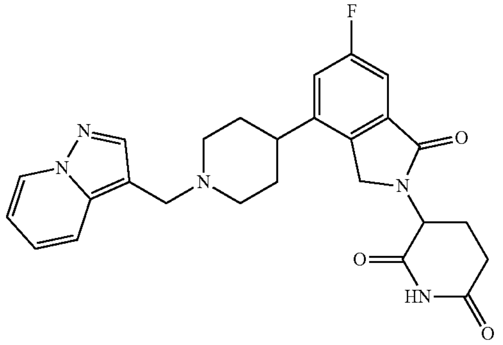

A1164

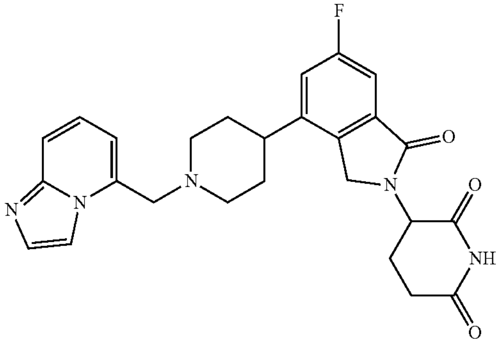

3-(4-(1-((1H-Pyrrolo[2,3-c]pyridin-3-yl)methyl)piperidin-4-yl)-6-fluoro-1-oxoisoindolin-2-yl)piperidine-2,6-dione A1165.

3-(6-Fluoro-1-oxo-4-(1-(pyrazolo[1,5-a]pyridin-7-ylmethyl)piperidin-4-yl)-isoindolin-2-yl)piperidine-2,6-dione A1166.

A1165

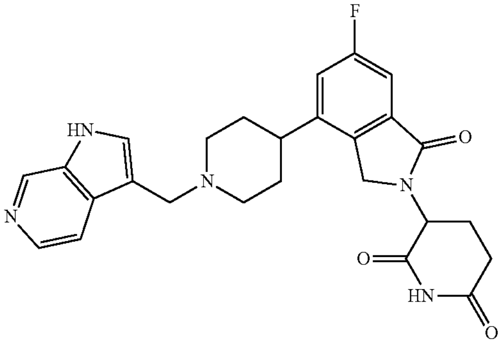

A1166

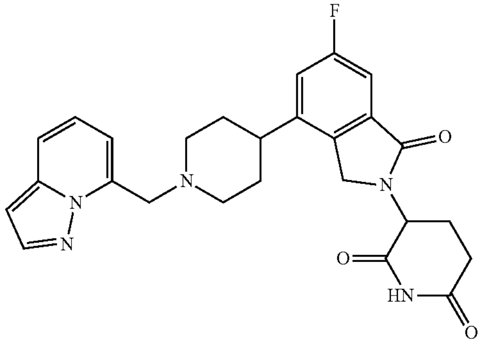

3-(4-(1-(2-Cyclopropylbenzyl)piperidin-4-yl)-6-fluoro-1-oxoisoindolin-2-yl)-piperidine-2,6-dione A1167.

3-(4-(1-(4-Cyclopropylbenzyl)piperidin-4-yl)-6-fluoro-1-oxoisoindolin-2-yl)-piperidine-2,6-dione A1168.

A1167

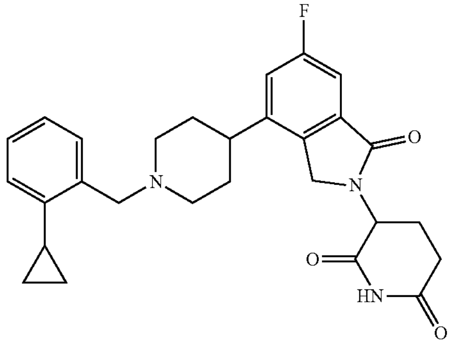

A1168

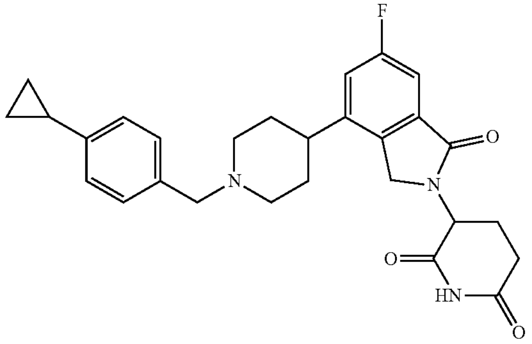

3-(4-(1-((2-Chlorothiophen-3-yl)methyl)piperidin-4-yl)-6-fluoro-1-oxoisoindolin-2-yl)piperidine-2,6-dione A1169.

3-(4-(1-((5-Chlorothiophen-2-yl)methyl)piperidin-4-yl)-6-fluoro-1-oxoisoindolin-2-yl)piperidine-2,6-dione A1170.

A1169

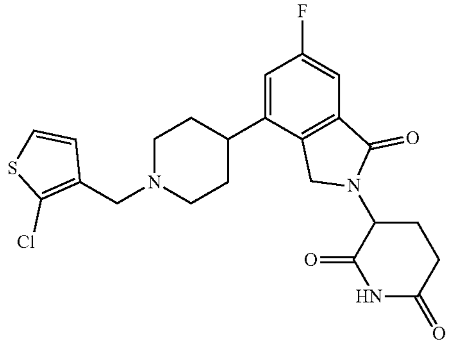

A1170

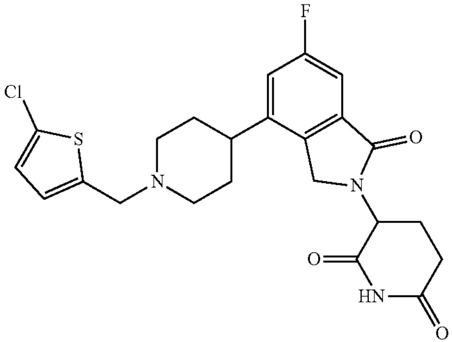

3-(4-(1-(Benzo[d]oxazol-6-ylmethyl)piperidin-4-yl)-6-fluoro-1-oxoisoindolin-2-yl)piperidine-2,6-dione A1171.

3-(4-(1-(Benzo[d]oxazol-5-ylmethyl)piperidin-4-yl)-6-fluoro-1-oxoisoindolin-2-yl)piperidine-2,6-dione A1172.

A1171

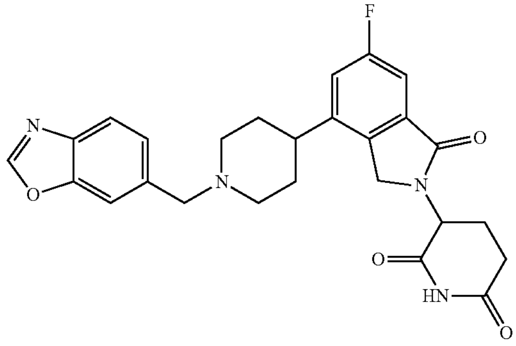

-continued

A1172

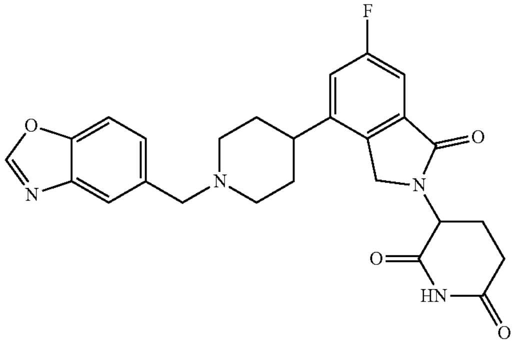

3-(6-Fluoro-4-(1-(furo[2,3-c]pyridin-5-ylmethyl)piperidin-4-yl)-1-oxoisoindolin-2-yl)piperidine-2,6-dione A1173.

5-((4-(2-(2,6-Dioxopiperidin-3-yl)-6-fluoro-1-oxoisoindolin-4-yl)piperidin-1-yl)methyl)-2-hydroxybenzonitrile A1174.

A1173

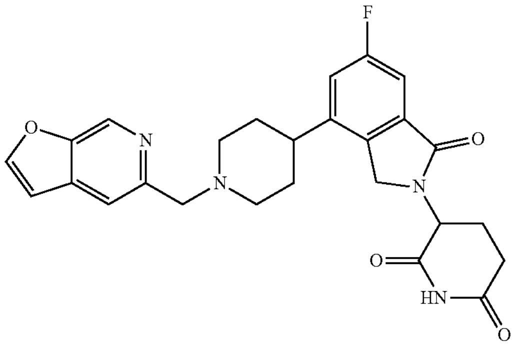

A1174

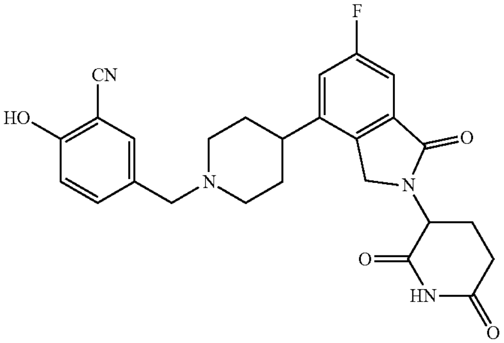

4-((4-(2-(2,6-Dioxopiperidin-3-yl)-6-fluoro-1-oxoisoindolin-4-yl)piperidin-1-yl)-methyl)-3-hydroxybenzonitrile A1175.

3-(4-(1-((4H-Pyrrolo[2,3-b]pyrazin-7-yl)methyl)piperidin-4-yl)-6-fluoro-1-oxoisoindolin-2-yl)piperidine-2,6-dione A1176.

A1175

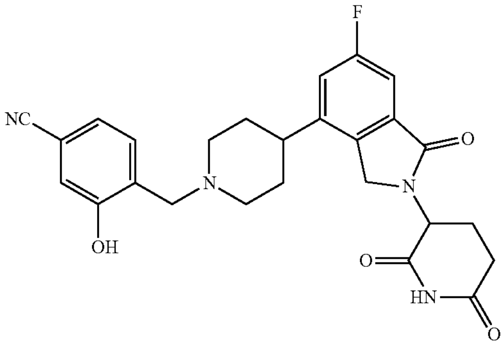

A1176

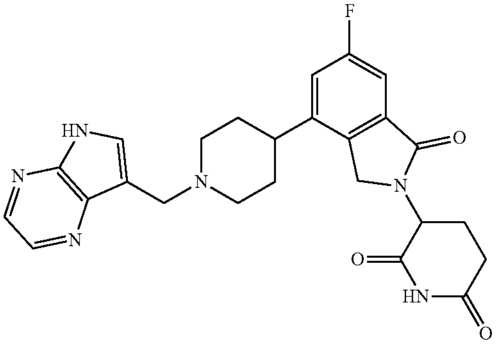

3-(6-Fluoro-4-(1-(imidazo[1,2-a]pyrimidin-7-ylmethyl)piperidin-4-yl)-1-oxoisoindolin-2-yl)piperidine-2,6-dione A1177.

6-Amino-5-((4-(2-(2,6-dioxopiperidin-3-yl)-6-fluoro-1-oxoisoindolin-4-yl)-piperidin-1-yl)methyl)nicotinonitrile A1178.

A1177

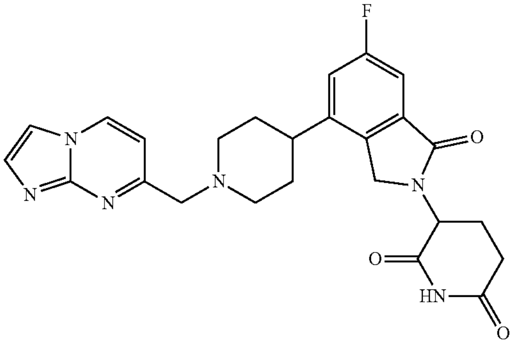

-continued

A1178

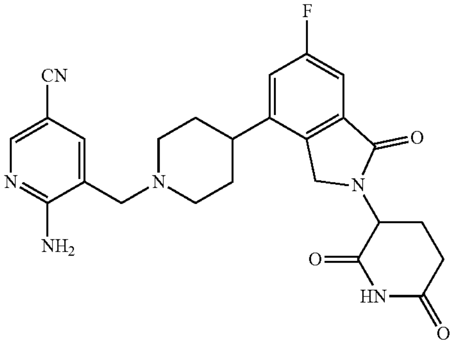

3-(6-Fluoro-4-(1-(imidazo[1,2-a]pyrimidin-3-ylmethyl)piperidin-4-yl)-1-oxoisoindolin-2-yl)piperidine-2,6-dione A1179.

3-(4-(1-([1,2,4]Triazolo[1,5-a]pyridin-7-ylmethyl)piperidin-4-yl)-6-fluoro-1-oxoisoindolin-2-yl)piperidine-2,6-dione A1180.

A1179

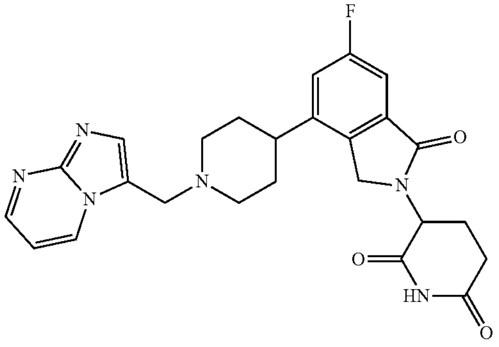

A1180

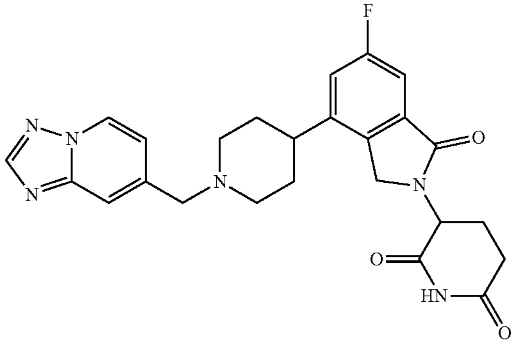

3-(4-(1-(2-Ethynyl-4-fluorobenzyl)piperidin-4-yl)-6-fluoro-1-oxoisoindolin-2-yl)-piperidine-2,6-dione A1181.

3-(4-(1-((4,4-Difluorocyclohexyl)methyl)piperidin-4-yl)-6-fluoro-1-oxoisoindolin-2-yl)piperidine-2,6-dione A1182.

A1181

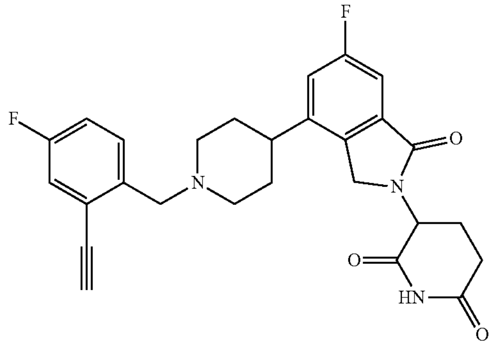

A1182

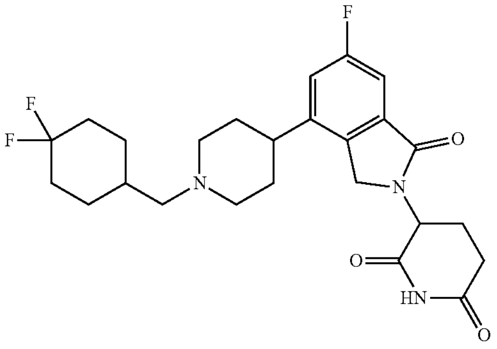

3-(6-Fluoro-1-oxo-4-(1-(4-phenylbutyl)piperidin-4-yl)isoindolin-2-yl)piperidine-2,6-dione A1183.

3-(6-Fluoro-4-(1-(4-isopropylbenzyl)piperidin-4-yl)-1-oxoisoindolin-2-yl)-piperidine-2,6-dione A1184.

A1183

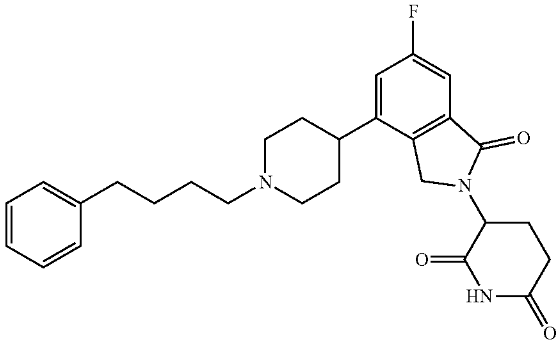

-continued

A1184

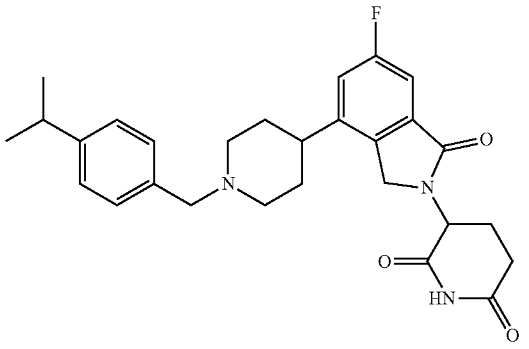

3-(6-Fluoro-1-oxo-4-(1-(2,4,6-trimethylbenzyl)piperidin-4-yl)isoindolin-2-yl)-piperidine-2,6-dione A1185.

5-((4-(2-(2,6-Dioxopiperidin-3-yl)-6-fluoro-1-oxoisoindolin-4-yl)piperidin-1-yl)-methyl)-2-fluorobenzonitrile A1186.

A1185

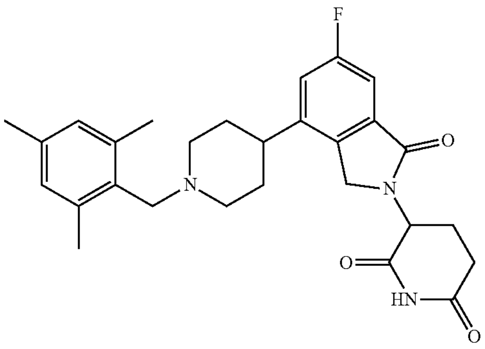

A1186

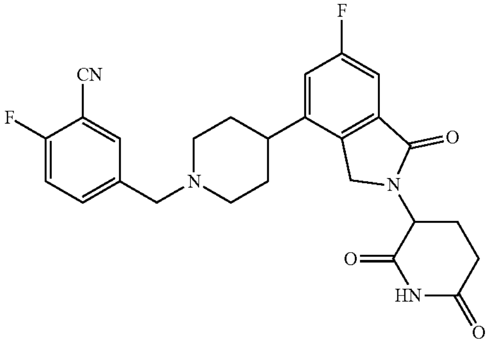

4-((4-(2-(2,6-Dioxopiperidin-3-yl)-6-fluoro-1-oxoisoindolin-4-yl)piperidin-1-yl)-methyl)-2-fluorobenzonitrile A1187.

3-((4-(2-(2,6-Dioxopiperidin-3-yl)-6-fluoro-1-oxoisoindolin-4-yl)piperidin-1-yl)-methyl)-5-fluorobenzonitrile A1188.

A1187

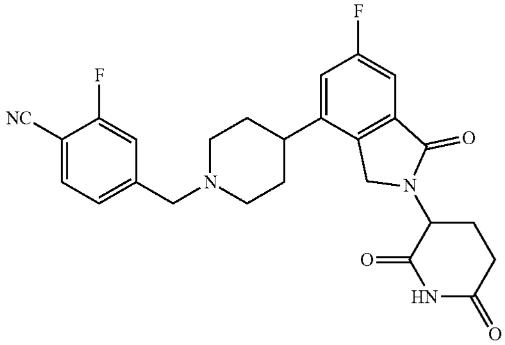

A1188

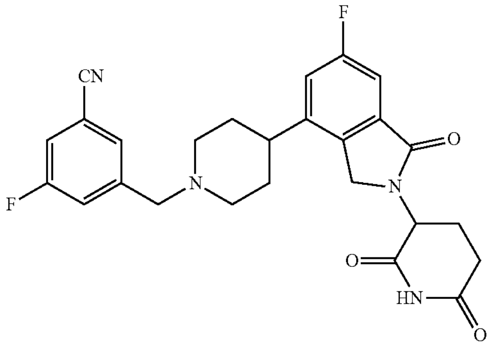

4-((4-(2-(2,6-Dioxopiperidin-3-yl)-6-fluoro-1-oxoisoindolin-4-yl)piperidin-1-yl)-methyl)-3-fluorobenzonitrile A1189.

2-((4-(2-(2,6-Dioxopiperidin-3-yl)-6-fluoro-1-oxoisoindolin-4-yl)piperidin-1-yl)-methyl)-5-fluorobenzonitrile A1190.

A1189

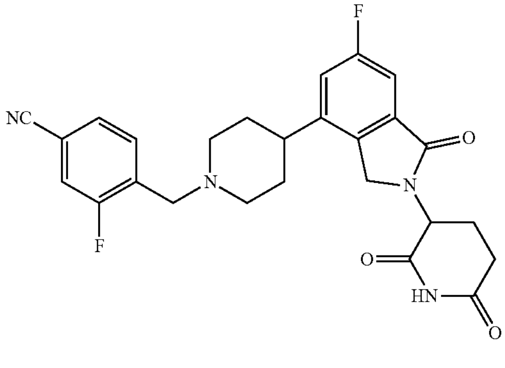

-continued

A1190

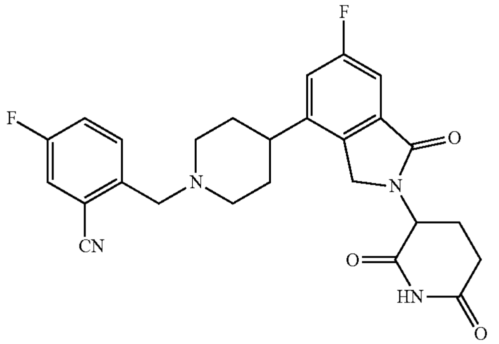

2-((4-(2-(2,6-Dioxopiperidin-3-yl)-6-fluoro-1-oxoisoindolin-4-yl)piperidin-1-yl)-methyl)-4-fluorobenzonitrile A1191.

3-((4-(2-(2,6-Dioxopiperidin-3-yl)-6-fluoro-1-oxoisoindolin-4-yl)piperidin-1-yl)-methyl)benzamide A1192.

A1191

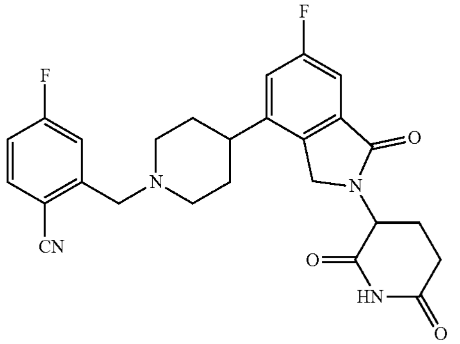

A1192

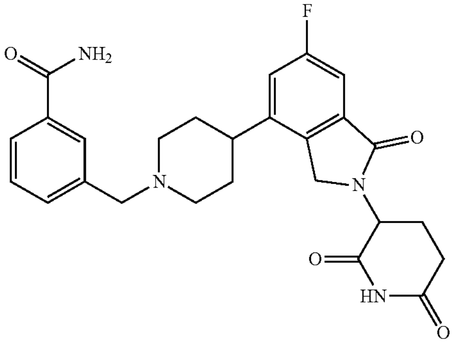

3-(4-(1-(3-(Dimethylamino)benzyl)piperidin-4-yl)-6-fluoro-1-oxoisoindolin-2-yl)piperidine-2,6-dione A1193.

3-(4-(1-(4-(Ethylamino)benzyl)piperidin-4-yl)-6-fluoro-1-oxoisoindolin-2-yl)-piperidine-2,6-dione A1194.

A1193

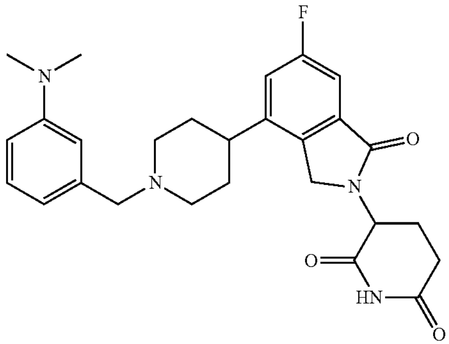

A1194

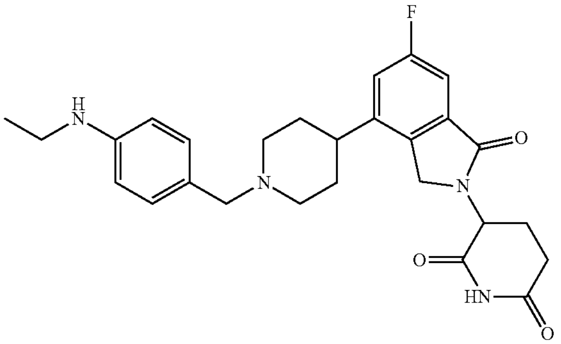

3-(6-Fluoro-4-(1-((5-isopropylpyridin-3-yl)methyl)piperidin-4-yl)-1-oxoisoindolin-2-yl)piperidine-2,6-dione A1195.

3-(4-(1-(2-(Dimethylamino)benzyl)piperidin-4-yl)-6-fluoro-1-oxoisoindolin-2-yl)piperidine-2,6-dione A1196.

A1195

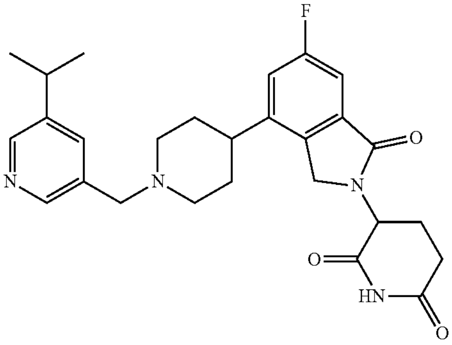

-continued

A1196

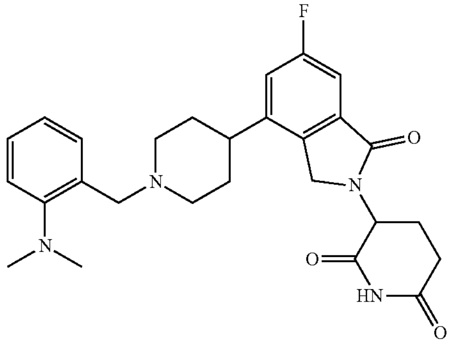

3-(4-(1-(Benzo[d][1,3]dioxol-4-ylmethyl)piperidin-4-yl)-6-fluoro-1-oxoisoindolin-2-yl)piperidine-2,6-dione A1197.

3-(4-(1-(2-(Benzyloxy)ethyl)piperidin-4-yl)-6-fluoro-1-oxoisoindolin-2-yl)piperidine-2,6-dione A1198.

A1197

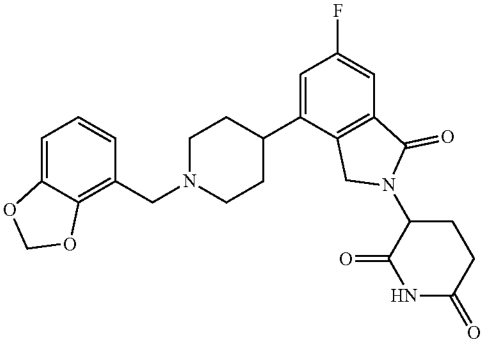

A1198

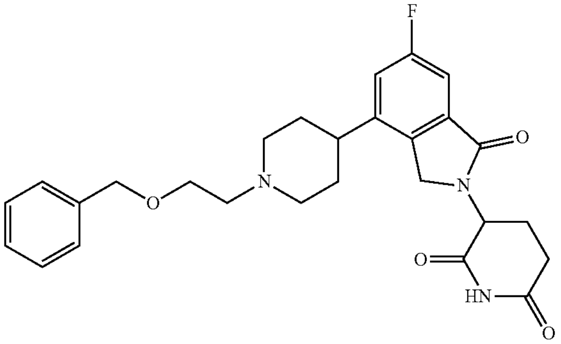

3-(6-Fluoro-4-(1-(2-methoxy-4-methylbenzyl)piperidin-4-yl)-1-oxoisoindolin-2-yl)piperidine-2,6-dione A1199.

3-(6-Fluoro-4-(1-(3-methoxy-4-methylbenzyl)piperidin-4-yl)-1-oxoisoindolin-2-yl)piperidine-2,6-dione A1200.

A1199

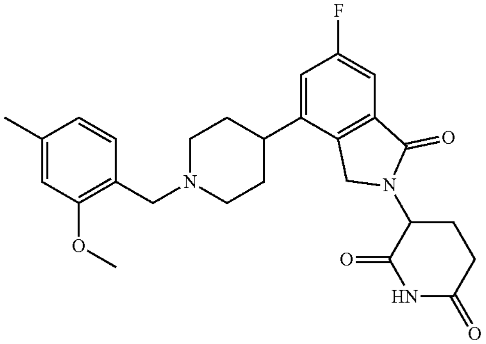

A1200

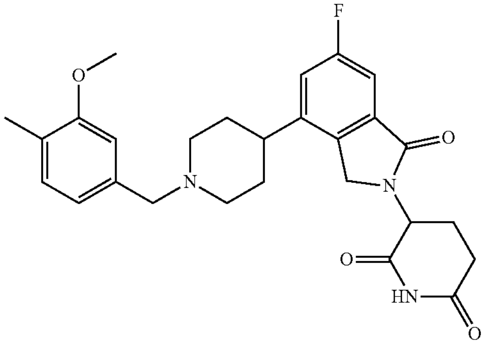

3-(4-(1-(4-Ethoxybenzyl)piperidin-4-yl)-6-fluoro-1-oxoisoindolin-2-yl)-piperidine-2,6-dione A1201.

3-(6-Fluoro-4-(1-(4-hydroxy-3,5-dimethylbenzyl)piperidin-4-yl)-1-oxoisoindolin-2-yl)piperidine-2,6-dione A1202.

A1201

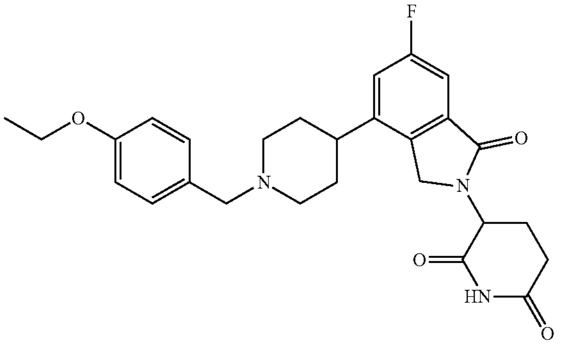

A1202

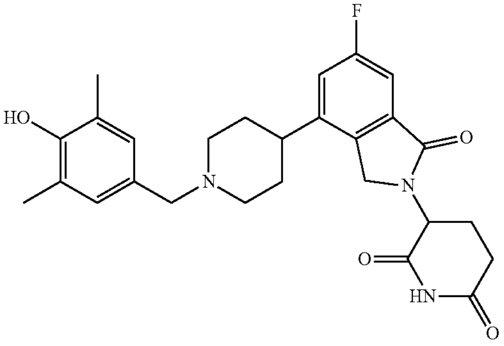

3-(6-Fluoro-4-(1-(4-methoxy-2-methylbenzyl)piperidin-4-yl)-1-oxoisoindolin-2-yl)piperidine-2,6-dione A1203.

3-(6-Fluoro-4-(1-(3-methoxyphenethyl)piperidin-4-yl)-1-oxoisoindolin-2-yl)-piperidine-2,6-dione A1204.

A1203

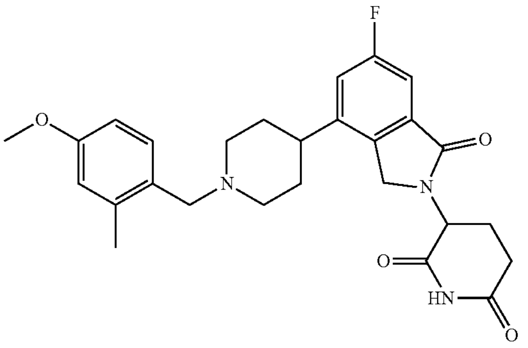

A1204

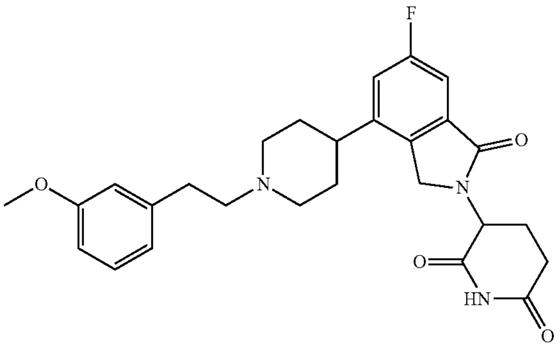

3-(6-Fluoro-4-(1-(4-methoxyphenethyl)piperidin-4-yl)-1-oxoisoindolin-2-yl)-piperidine-2,6-dione A1205.

3-(6-Fluoro-4-(1-(3-methoxy-5-methylbenzyl)piperidin-4-yl)-1-oxoisoindolin-2-yl)piperidine-2,6-dione A1206.

A1205

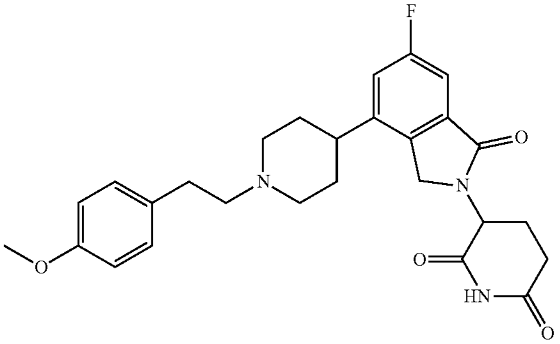

-continued

A1206

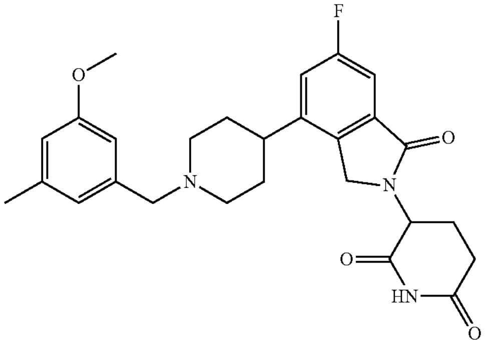

3-(6-Fluoro-4-(1-(2-methoxy-6-methylbenzyl)piperidin-4-yl)-1-oxoisoindolin-2-yl)piperidine-2,6-dione A1207.

3-(6-Fluoro-4-(1-(3-methoxy-2-methylbenzyl)piperidin-4-yl)-1-oxoisoindolin-2-yl)piperidine-2,6-dione A1208.

A1207

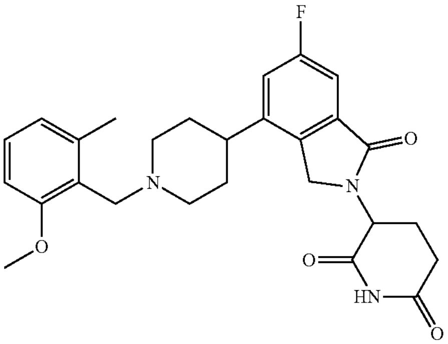

A1208

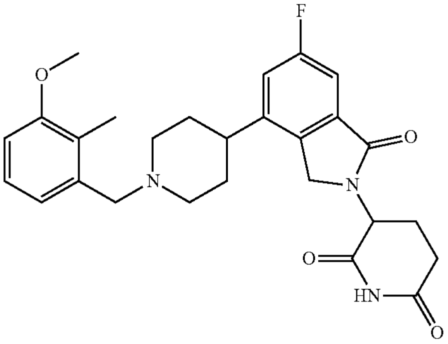

3-(6-Fluoro-4-(1-(2-methoxy-3-methylbenzyl)piperidin-4-yl)-1-oxoisoindolin-2-yl)piperidine-2,6-dione A1209.

3-(6-Fluoro-4-(1-(4-methoxy-3-methylbenzyl)piperidin-4-yl)-1-oxoisoindolin-2-yl)piperidine-2,6-dione A1210.

A1209

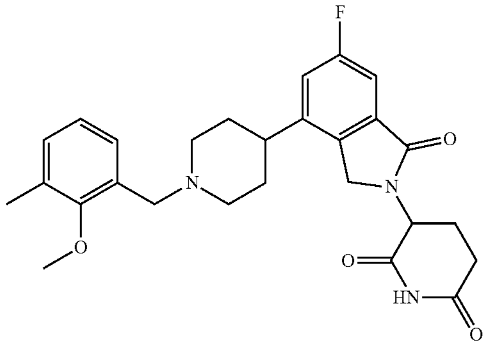

A1210

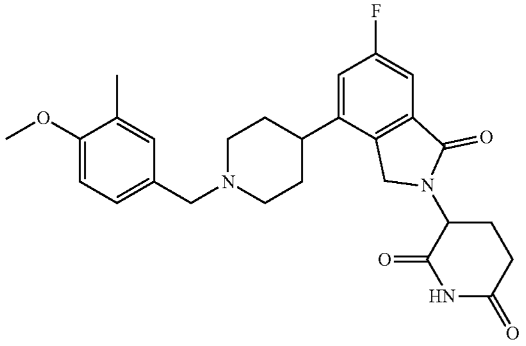

3-(4-(1-((2-(Dimethylamino)pyrimidin-5-yl)methyl)piperidin-4-yl)-6-fluoro-1-oxoisoindolin-2-yl)piperidine-2,6-dione A1211.

3-(4-(1-((5-(Tert-butyl)-1H-pyrrol-2-yl)methyl)piperidin-4-yl)-6-fluoro-1-oxoisoindolin-2-yl)piperidine-2,6-dione A1212.

A1211

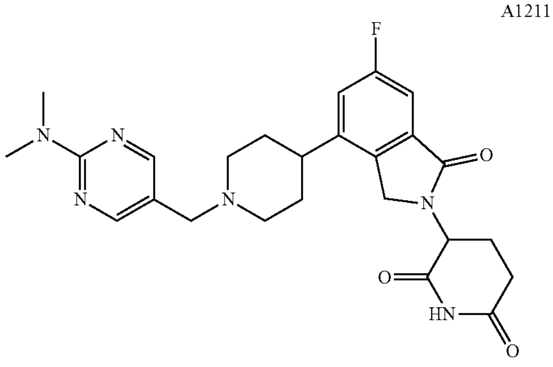

-continued

A1212

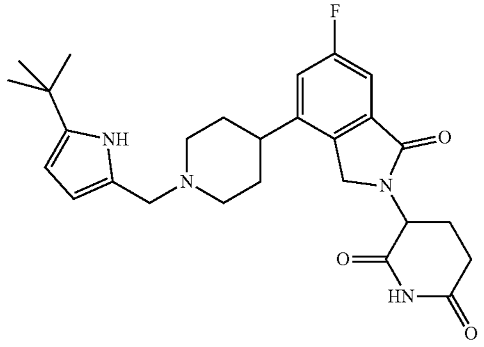

3-(4-(1-((5,6-Dihydro-8H-imidazo[2,1-c][1,4]oxazin-2-yl)methyl)piperidin-4-yl)-6-fluoro-1-oxoisoindolin-2-yl)piperidine-2,6-dione A1213.

3-(4-(1-((5,6-Dihydro-8H-imidazo[2,1-c][1,4]oxazin-3-yl)methyl)piperidin-4-yl)-6-fluoro-1-oxoisoindolin-2-yl)piperidine-2,6-dione A1214.

A1213

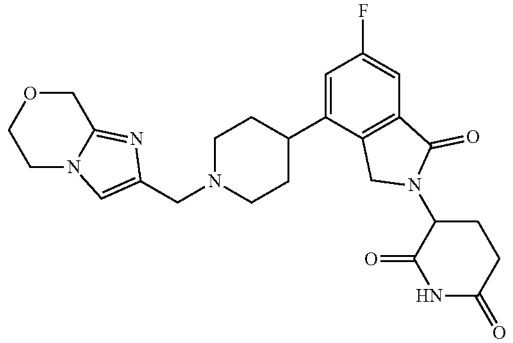

A1214

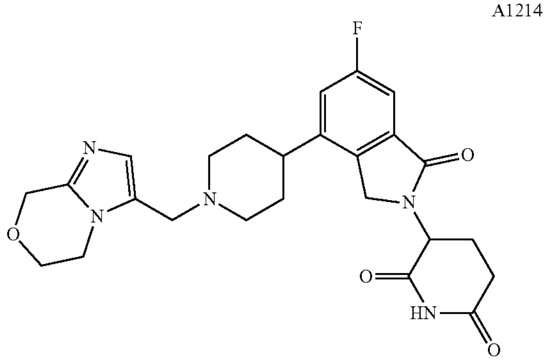

3-(6-Fluoro-4-(1-((1-isobutyl-1H-pyrazol-4-yl)methyl)piperidin-4-yl)-1-oxoisoindolin-2-yl)piperidine-2,6-dione A1215.

3-(4-(1-((1-(Tert-butyl)-1H-1,2,3-triazol-4-yl)methyl)piperidin-4-yl)-6-fluoro-1-oxoisoindolin-2-yl)piperidine-2,6-dione A1216.

A1215

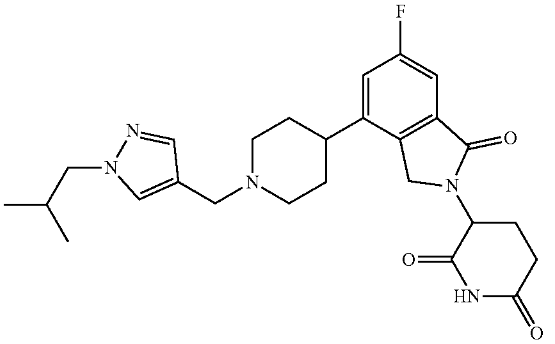

A1216

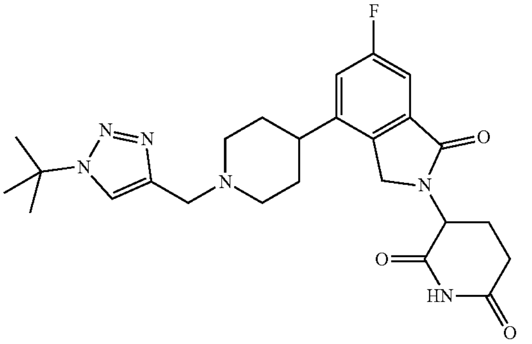

3-(4-(1-((2-Cyclopropylthiazol-5-yl)methyl)piperidin-4-yl)-6-fluoro-1-oxoisoindolin-2-yl)piperidine-2,6-dione A1217.

3-(6-Fluoro-4-(1-((2-(methylthio)pyrimidin-4-yl)methyl)piperidin-4-yl)-1-oxoisoindolin-2-yl)piperidine-2,6-dione A1218.

A1217

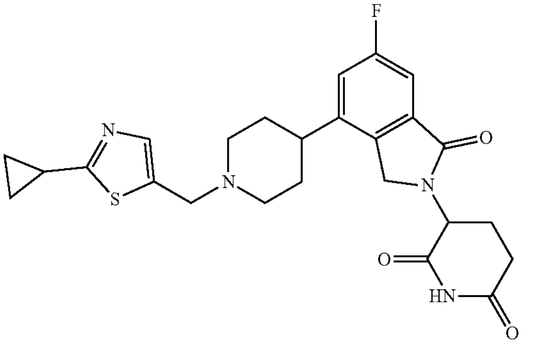

-continued

A1218

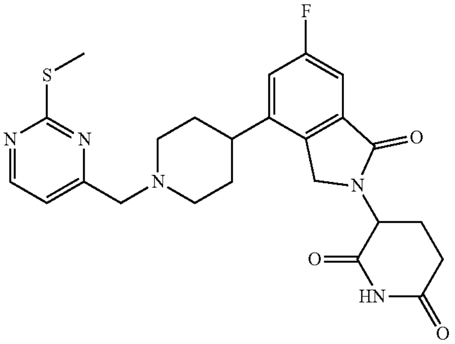

3-(6-Fluoro-4-(1-((4-hydroxybicyclo[2.2.2]octan-1-yl)methyl)piperidin-4-yl)-1-oxoisoindolin-2-yl)piperidine-2,6-dione A1219.

3-(4-(1-(4-Chlorophenethyl)piperidin-4-yl)-6-fluoro-1-oxoisoindolin-2-yl)-piperidine-2,6-dione A1220.

A1219

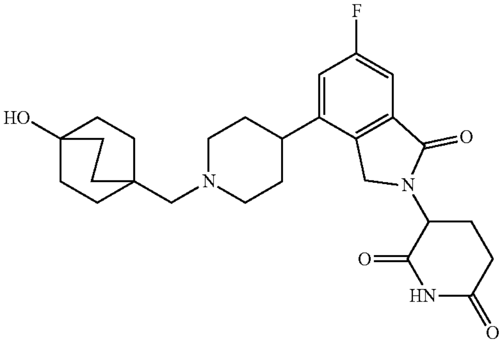

A1220

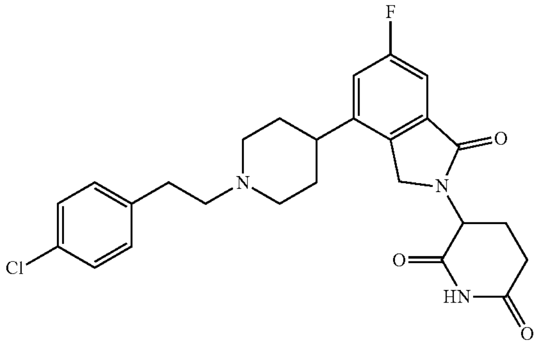

3-(4-(1-((5-(Dimethylamino)thiophen-2-yl)methyl)piperidin-4-yl)-6-fluoro-1-oxoisoindolin-2-yl)piperidine-2,6-dione A1221.

3-(4-(1-(2-Amino-3-chlorobenzyl)piperidin-4-yl)-6-fluoro-1-oxoisoindolin-2-yl)-piperidine-2,6-dione A1222.

A1221

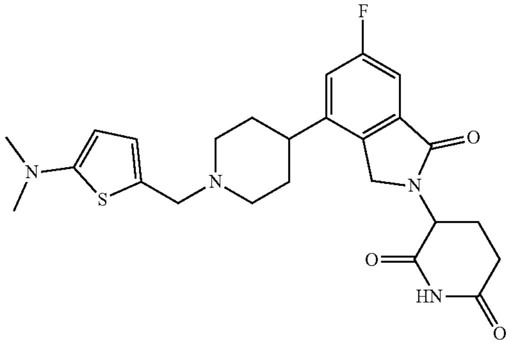

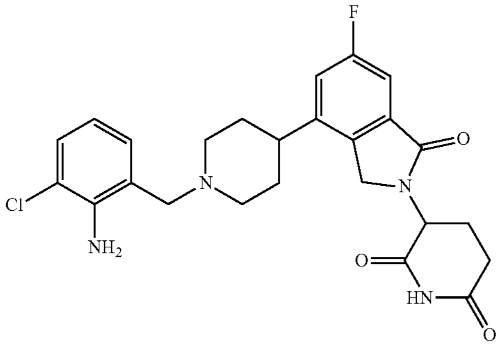

A1222

3-(4-(1-(2-Amino-4-chlorobenzyl)piperidin-4-yl)-6-fluoro-1-oxoisoindolin-2-yl)-piperidine-2,6-dione A1223.

3-(4-(1-(2-Amino-6-chlorobenzyl)piperidin-4-yl)-6-fluoro-1-oxoisoindolin-2-yl)-piperidine-2,6-dione A1224.

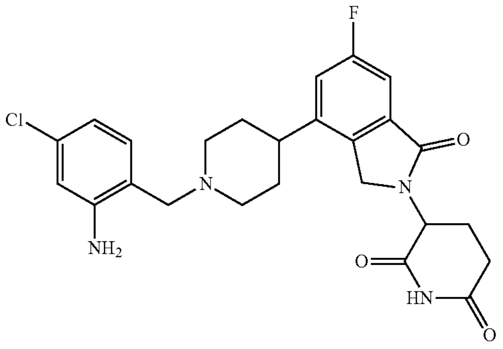

A1223

-continued

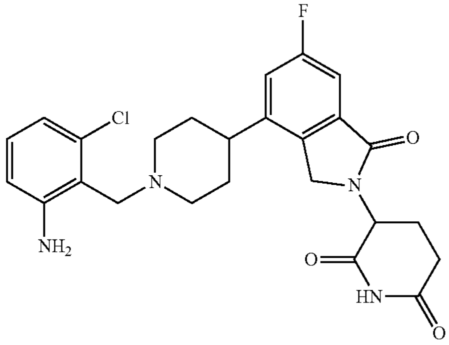

A1224

3-(6-Fluoro-4-(1-(naphthalen-2-ylmethyl)piperidin-4-yl)-1-oxoisoindolin-2-yl)-piperidine-2,6-dione A1225.

3-(6-Fluoro-1-oxo-4-(1-(quinolin-6-ylmethyl)piperidin-4-yl)isoindolin-2-yl)-piperidine-2,6-dione A1226.

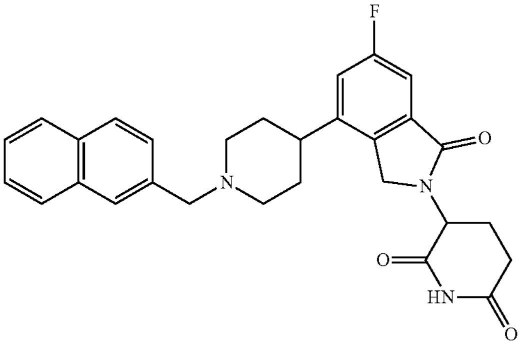

A1225

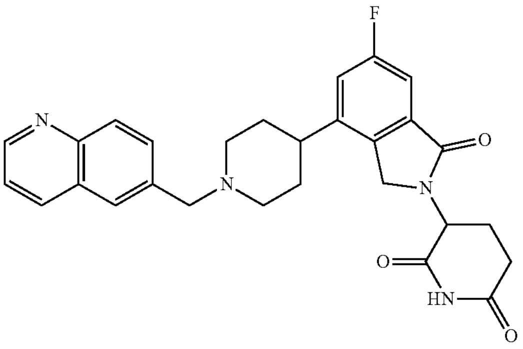

A1226

3-(6-Fluoro-1-oxo-4-(1-(quinolin-4-ylmethyl)piperidin-4-yl)isoindolin-2-yl)-piperidine-2,6-dione A1227.

3-(6-Fluoro-4-(1-(isoquinolin-5-ylmethyl)piperidin-4-yl)-1-oxoisoindolin-2-yl)-piperidine-2,6-dione A1228.

A1227

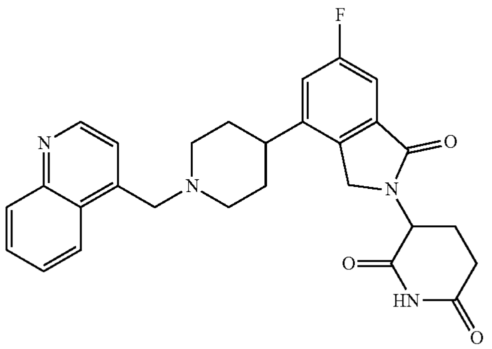

A1228

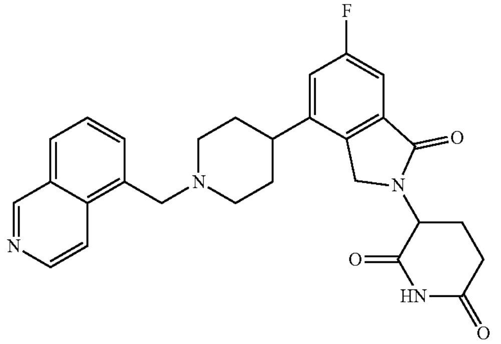

3-(6-Fluoro-4-(1-(isoquinolin-8-ylmethyl)piperidin-4-yl)-1-oxoisoindolin-2-yl)-piperidine-2,6-dione A1229.

3-(6-Fluoro-4-(1-(isoquinolin-3-ylmethyl)piperidin-4-yl)-1-oxoisoindolin-2-yl)-piperidine-2,6-dione A1230.

A12290

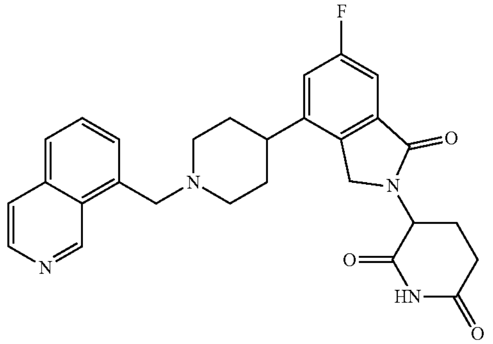

A1230

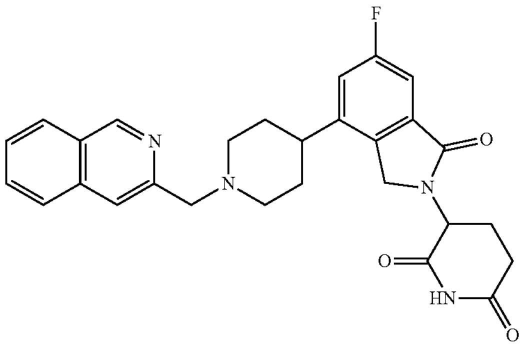

3-(6-Fluoro-4-(1-(isoquinolin-4-ylmethyl)piperidin-4-yl)-1-oxoisoindolin-2-yl)-piperidine-2,6-dione A1231.

3-(6-Fluoro-1-oxo-4-(1-(quinolin-8-ylmethyl)piperidin-4-yl)isoindolin-2-yl)-piperidine-2,6-dione A1232.

A1231

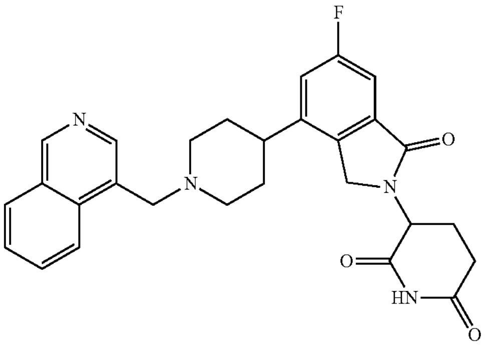

A1232

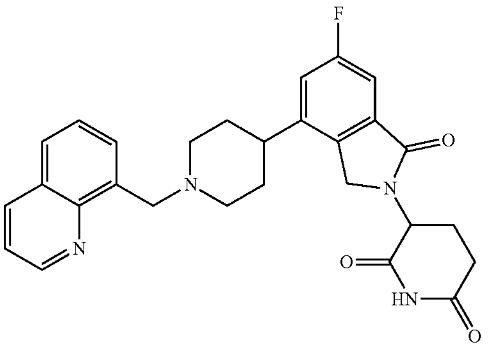

3-(6-Fluoro-1-oxo-4-(1-(quinoxalin-5-ylmethyl)piperidin-4-yl)isoindolin-2-yl)-piperidine-2,6-dione A1233.

3-(6-Fluoro-1-oxo-4-(1-(quinoxalin-2-ylmethyl)piperidin-4-yl)isoindolin-2-yl)-piperidine-2,6-dione A1234.

A1233

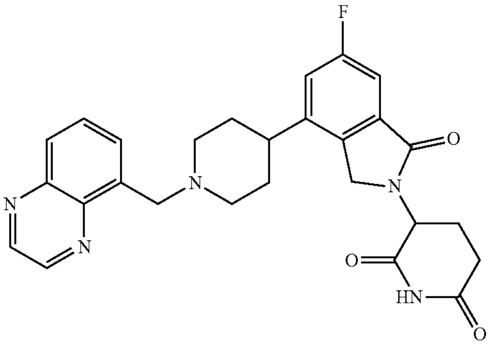

-continued

A1234

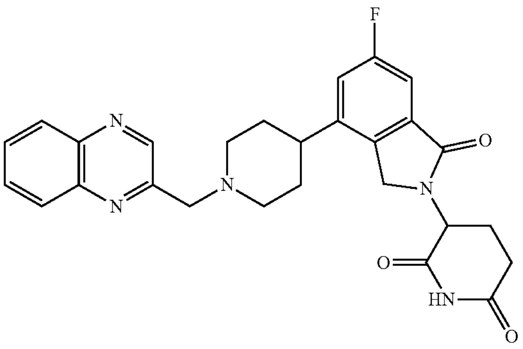

3-(4-(1-((1,8-Naphthyridin-2-yl)methyl)piperidin-4-yl)-6-fluoro-1-oxoisoindolin-2-yl)piperidine-2,6-dione A1235.

3-(6-Fluoro-1-oxo-4-(1-(quinoxalin-6-ylmethyl)piperidin-4-yl)isoindolin-2-yl)-piperidine-2,6-dione A1236.

A1235

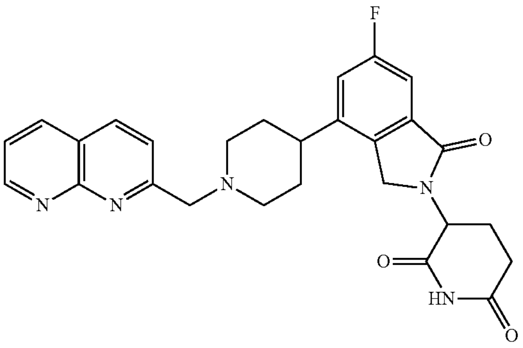

A1236

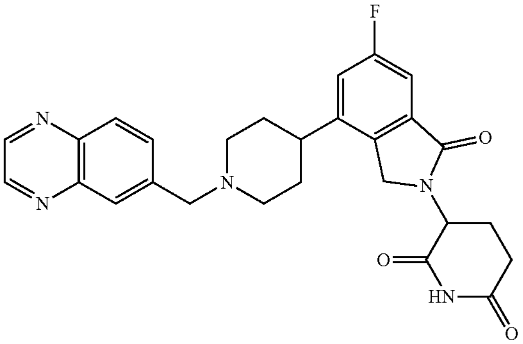

Tert-butyl (2-(4-(2-(2,6-dioxopiperidin-3-yl)-6-fluoro-1-oxoisoindolin-4-yl)-piperidin-1-yl)ethyl)carbamate A1237.

3-(6-Fluoro-4-(1-((6-methyl-1H-indol-3-yl)methyl)piperidin-4-yl)-1-oxoisoindolin-2-yl)piperidine-2,6-dione A1238.

A1237

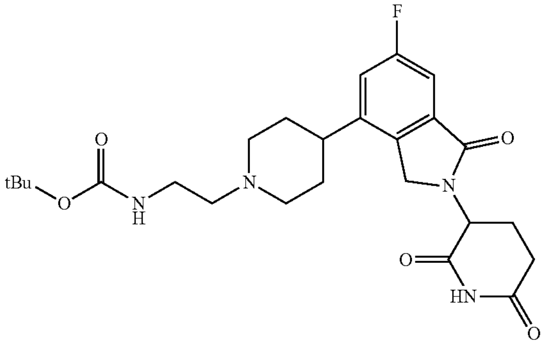

A1238

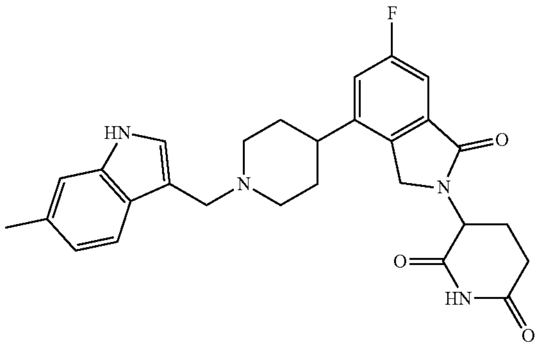

3-(6-Fluoro-4-(1-((3-methyl-1H-indol-2-yl)methyl)piperidin-4-yl)-1-oxoisoindolin-2-yl)piperidine-2,6-dione A1239.

3-(6-Fluoro-4-(1-((4-methyl-1H-indol-3-yl)methyl)piperidin-4-yl)-1-oxoisoindolin-2-yl)piperidine-2,6-dione A1240.

A1239

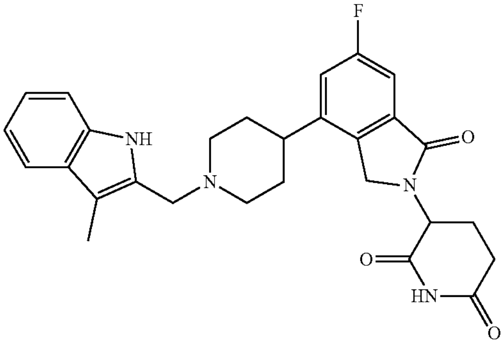

-continued

A1240

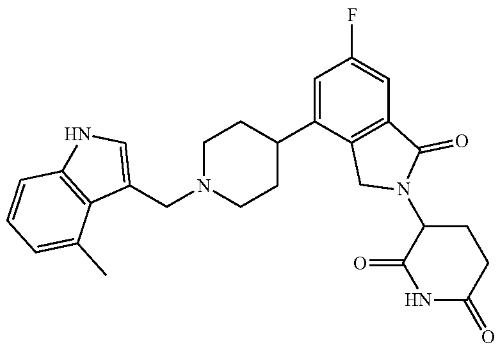

3-(6-Fluoro-4-(1-((1-methyl-1H-indol-6-yl)methyl)piperidin-4-yl)-1-oxoisoindolin-2-yl)piperidine-2,6-dione A1241.

3-(6-Fluoro-4-(1-((2-methyl-1H-indol-4-yl)methyl)piperidin-4-yl)-1-oxoisoindolin-2-yl)piperidine-2,6-dione A1242.

A1241

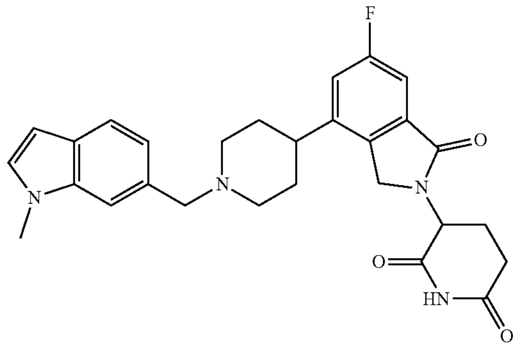

A1242

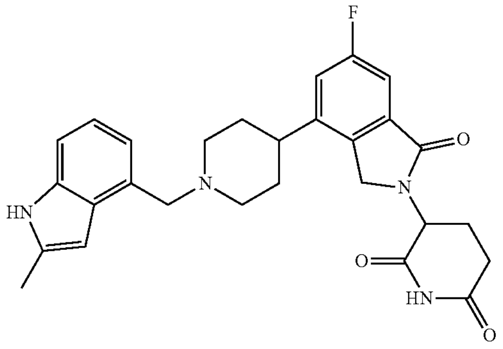

3-(6-Fluoro-4-(1-((1-methyl-1H-indol-5-yl)methyl)piperidin-4-yl)-1-oxoisoindolin-2-yl)piperidine-2,6-dione A1243.

3-(6-Fluoro-4-(1-((7-methyl-1H-indol-3-yl)methyl)piperidin-4-yl)-1-oxoisoindolin-2-yl)piperidine-2,6-dione A1244.

A1243

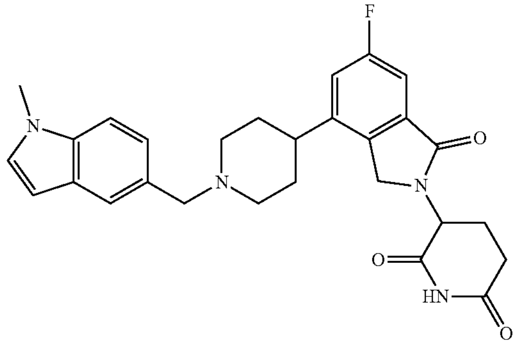

A1244

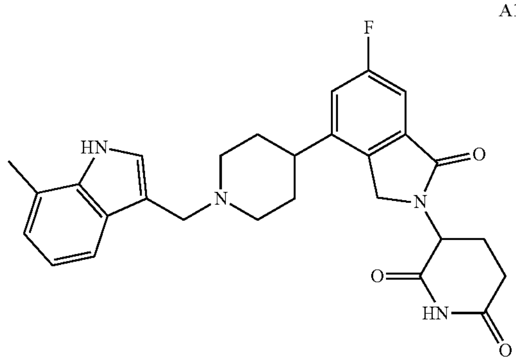

3-(6-Fluoro-4-(1-((2-methyl-2H-indazol-3-yl)methyl)piperidin-4-yl)-1-oxoisoindolin-2-yl)piperidine-2,6-dione A1245.

3-(6-Fluoro-4-(1-((2-methylimidazo[1,2-a]pyridin-3-yl)methyl)piperidin-4-yl)-1-oxoisoindolin-2-yl)piperidine-2,6-dione A1246.

A1245

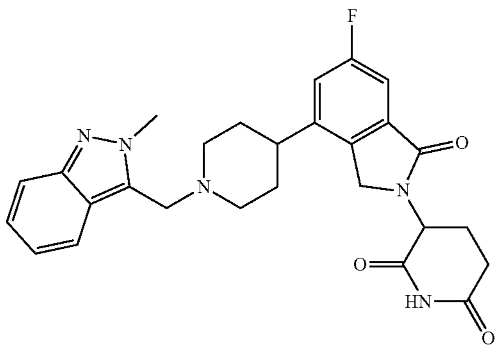

-continued

A1246

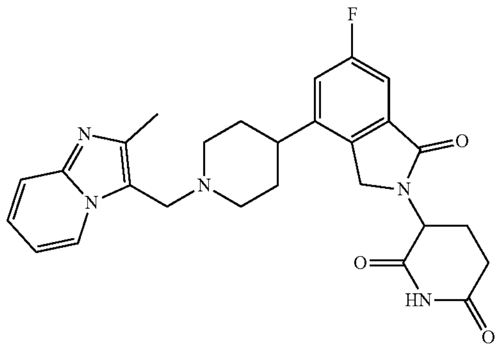

3-(6-Fluoro-4-(1-((1-methyl-1H-benzo[d]imidazol-2-yl)methyl)piperidin-4-yl)-1-oxoisoindolin-2-yl)piperidine-2,6-dione A1247.

3-(6-Fluoro-4-(1-((5-methyl-1H-pyrrolo[2,3-b]pyridin-3-yl)methyl)piperidin-4-yl)-1-oxoisoindolin-2-yl)piperidine-2,6-dione A1248.

A1247

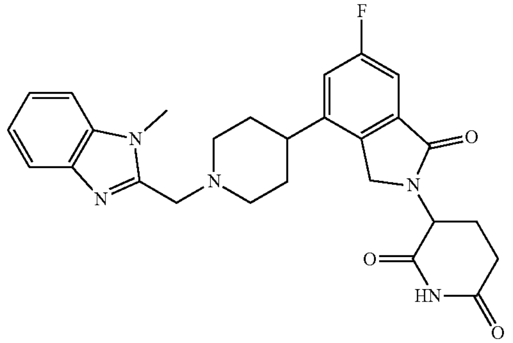

A1248

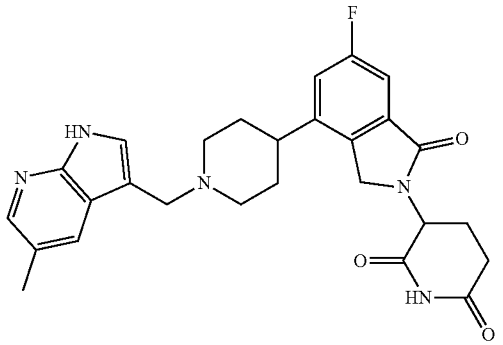

3-(6-Fluoro-4-(1-((1-methyl-1H-indazol-4-yl)methyl)piperidin-4-yl)-1-oxoisoindolin-2-yl)piperidine-2,6-dione A1249.

3-(6-Fluoro-4-(1-((7-methylimidazo[1,2-a]pyridin-3-yl)methyl)piperidin-4-yl)-1-oxoisoindolin-2-yl)piperidine-2,6-dione A1250.

A1249

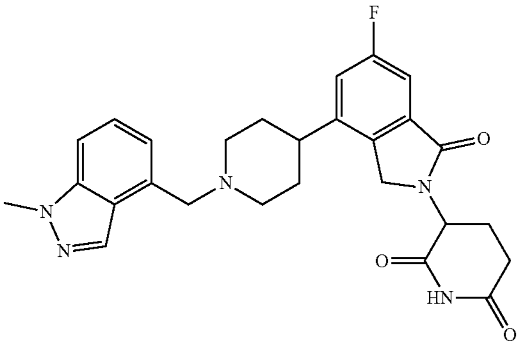

A1250

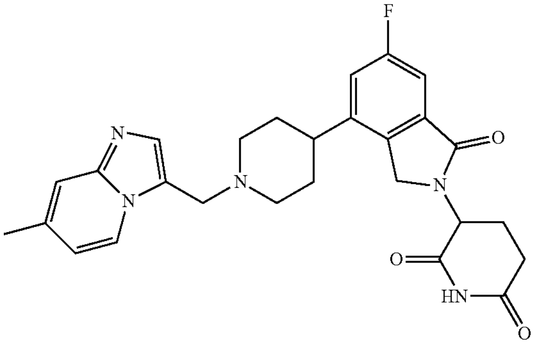

3-(6-Fluoro-4-(1-((5-methylimidazo[1,2-a]pyridin-3-yl)methyl)piperidin-4-yl)-1-oxoisoindolin-2-yl)piperidine-2,6-dione A1251.

3-(6-Fluoro-4-(1-((6-methylimidazo[1,2-a]pyridin-2-yl)methyl)piperidin-4-yl)-1-oxoisoindolin-2-yl)piperidine-2,6-dione A1252.

A1251

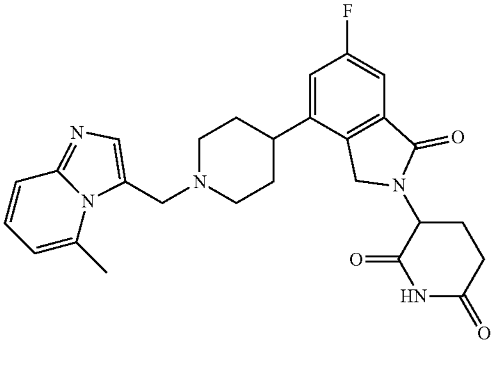

-continued

A1252

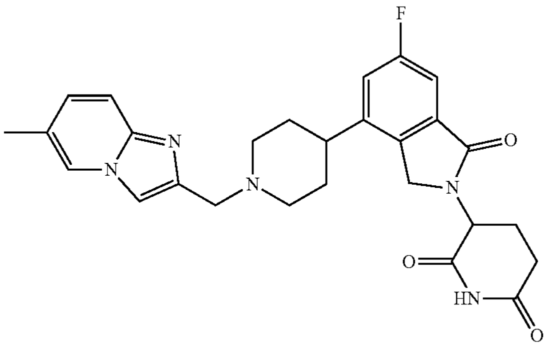

3-(6-Fluoro-4-(1-((2-methyl-2H-indazol-5-yl)methyl)piperidin-4-yl)-1-oxoisoindolin-2-yl)piperidine-2,6-dione A1253.

3-(6-Fluoro-4-(1-((1-methyl-1H-indazol-6-yl)methyl)piperidin-4-yl)-1-oxoisoindolin-2-yl)piperidine-2,6-dione A1254.

A1253

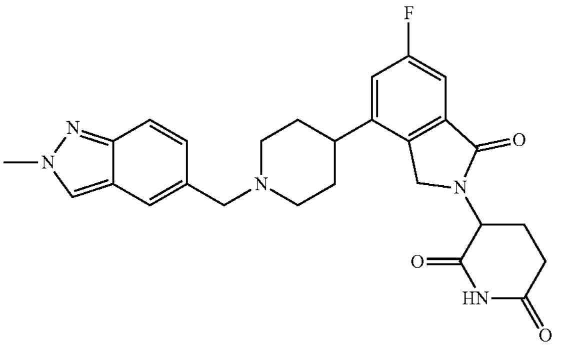

A1254

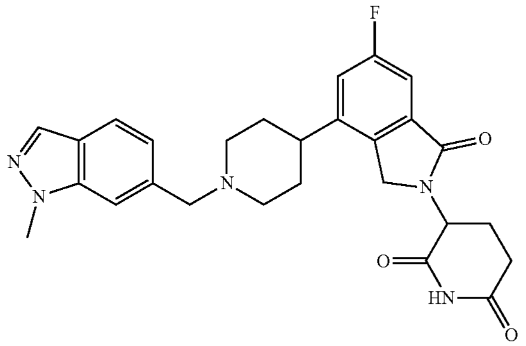

3-(6-Fluoro-4-(1-((3-methylimidazo[1,2-a]pyridin-2-yl)methyl)piperidin-4-yl)-1-oxoisoindolin-2-yl)piperidine-2,6-dione A1255.

3-(6-Fluoro-1-oxo-4-(1-((5,6,7,8-tetrahydronaphthalen-1-yl)methyl)piperidin-4-yl)isoindolin-2-yl)piperidine-2,6-dione A1256.

A1255

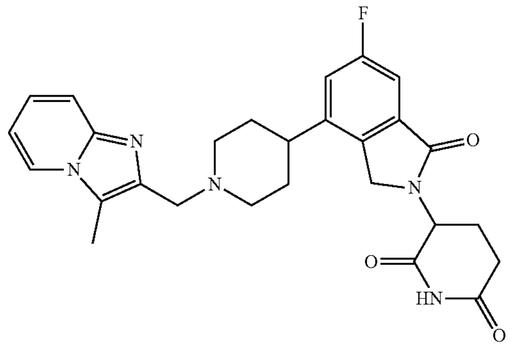

A1256

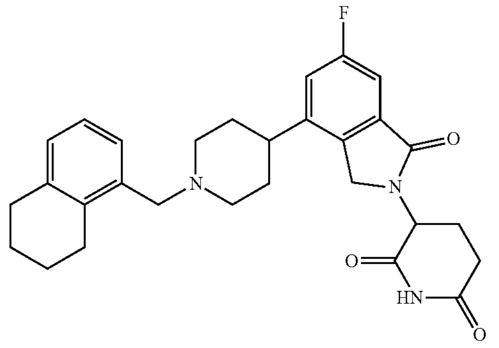

3-(6-Fluoro-1-oxo-4-(1-((1-oxoisoindolin-5-yl)methyl)piperidin-4-yl)isoindolin-2-yl)piperidine-2,6-dione A1257.

3-(6-Fluoro-1-oxo-4-(1-((3-oxoisoindolin-5-yl)methyl)piperidin-4-yl)isoindolin-2-yl)piperidine-2,6-dione A1258.

A1257

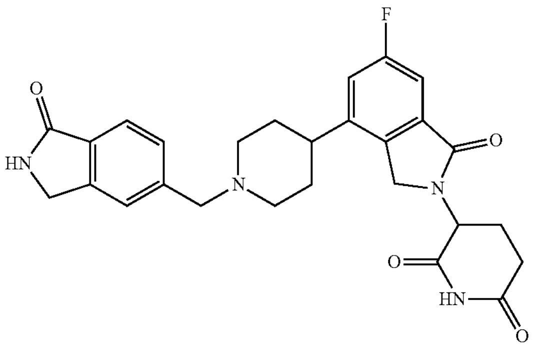

-continued

A1258

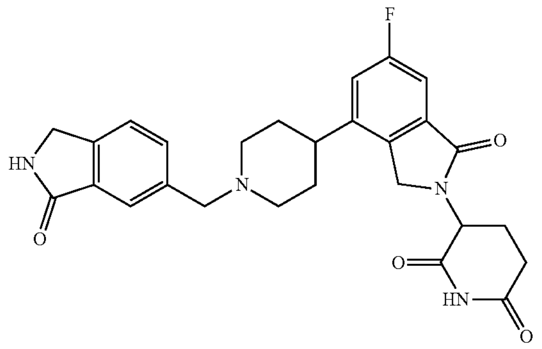

3-(6-Fluoro-4-(1-((2-methylbenzo[d]oxazol-6-yl)methyl)piperidin-4-yl)-1-oxoisoindolin-2-yl)piperidine-2,6-dione A1259.

2-((4-(2-(2,6-Dioxopiperidin-3-yl)-6-fluoro-1-oxoisoindolin-4-yl)piperidin-1-yl)-methyl)-5-methoxybenzonitrile A1260.

A1259

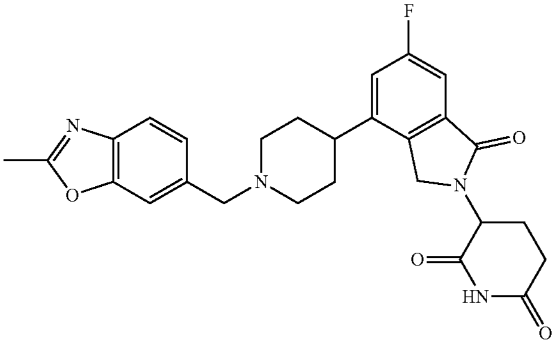

A1260

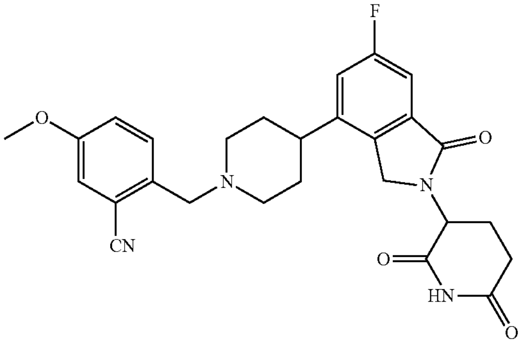

4-((4-(2-(2,6-Dioxopiperidin-3-yl)-6-fluoro-1-oxoisoindolin-4-yl)piperidin-1-yl)-methyl)-3-methoxybenzonitrile A1261.

4-((4-(2-(2,6-Dioxopiperidin-3-yl)-6-fluoro-1-oxoisoindolin-4-yl)piperidin-1-yl)-methyl)-2-methoxybenzonitrile A1262.

A1261

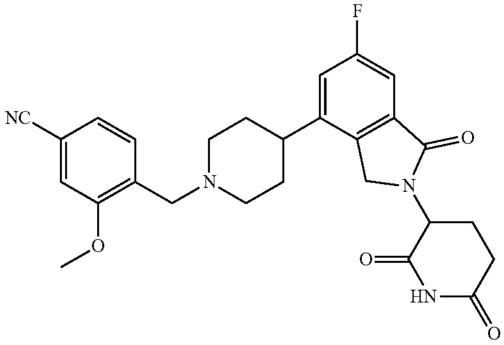

A1262

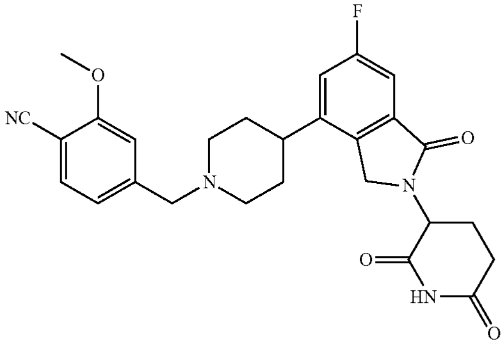

3-(6-Fluoro-4-(1-((1-methyl-1H-imidazo[4,5-b]pyridin-2-yl)methyl)piperidin-4-yl)-1-oxoisoindolin-2-yl)piperidine-2,6-dione A1263.

3-(4-(1-(Chroman-6-ylmethyl)piperidin-4-yl)-6-fluoro-1-oxoisoindolin-2-yl)-piperidine-2,6-dione A1264.

A1263

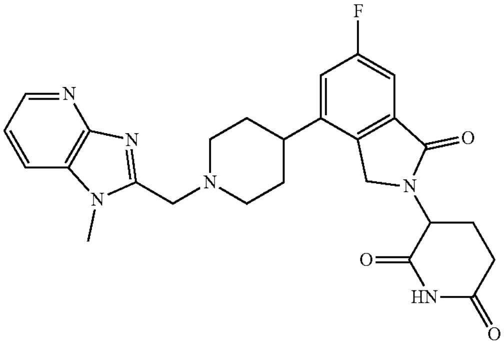

-continued

A1264

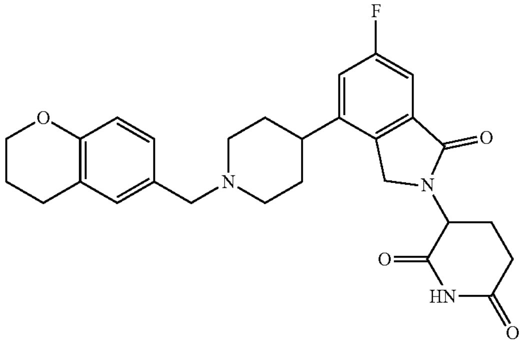

3-(4-(1-(Benzo[b]thiophen-2-ylmethyl)piperidin-4-yl)-6-fluoro-1-oxoisoindolin-2-yl)piperidine-2,6-dione A1265.

3-(4-(1-(Benzo[b]thiophen-3-ylmethyl)piperidin-4-yl)-6-fluoro-1-oxoisoindolin-2-yl)piperidine-2,6-dione A1266.

A1265

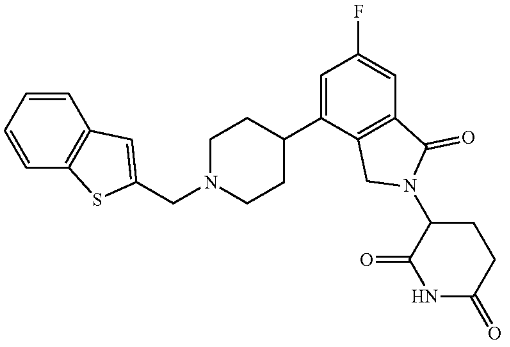

A1266

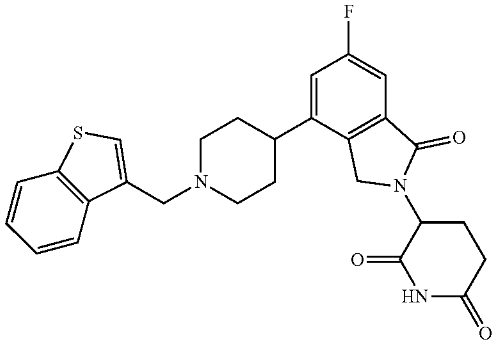

3-(6-Fluoro-4-(1-(3-methyl-3-phenylbutyl)piperidin-4-yl)-1-oxoisoindolin-2-yl)-piperidine-2,6-dione A1267.

3-(4-(1-((3,4-Dihydro-2H-pyrano[2,3-c]pyridin-6-yl)methyl)piperidin-4-yl)-6-fluoro-1-oxoisoindolin-2-yl)piperidine-2,6-dione A1268.

A1267

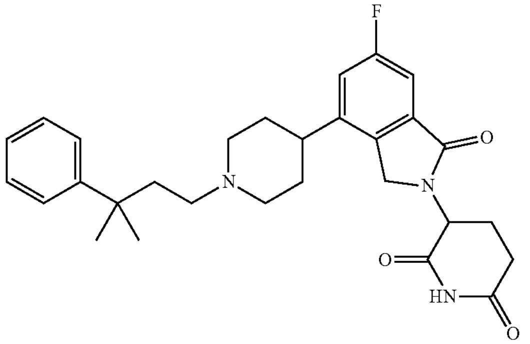

A1268

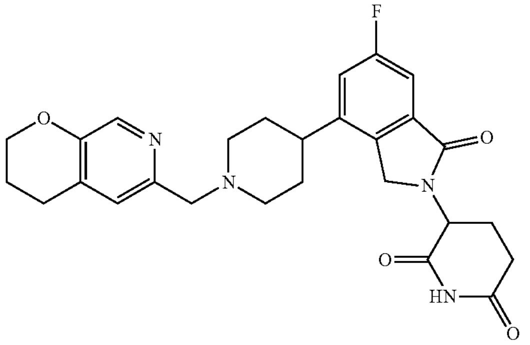

3-(6-Fluoro-1-oxo-4-(1-(thieno[2,3-b]pyridin-2-ylmethyl)piperidin-4-yl)-isoindolin-2-yl)piperidine-2,6-dione A1269.

3-(4-(1-(Benzo[d]thiazol-4-ylmethyl)piperidin-4-yl)-6-fluoro-1-oxoisoindolin-2-yl)piperidine-2,6-dione A1270.

A1269

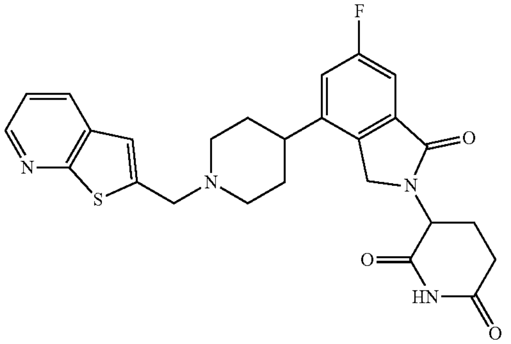

-continued

A1270

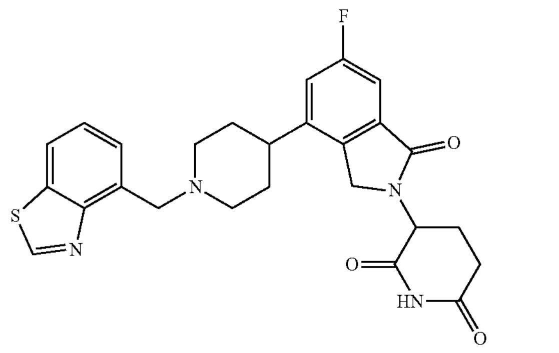

3-(6-Fluoro-1-oxo-4-(1-(thieno[3,2-c]pyridin-2-ylmethyl)piperidin-4-yl)-isoindolin-2-yl)piperidine-2,6-dione A1271.

3-(4-(1-(4-((Dimethylamino)methyl)benzyl)piperidin-4-yl)-6-fluoro-1-oxoisoindolin-2-yl)piperidine-2,6-dione A1272.

A1271

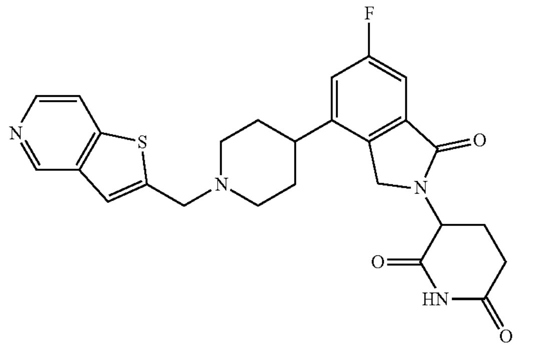

A1272

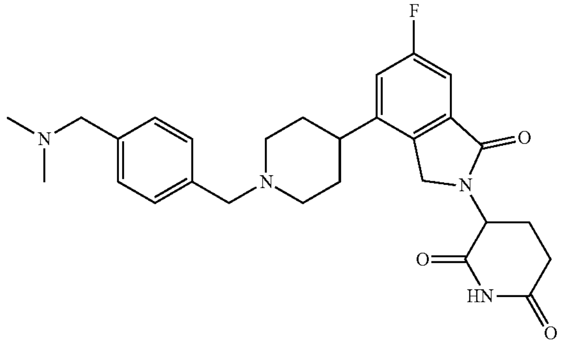

3-(4-(1-((2-(Tert-butyl)pyridin-4-yl)methyl)piperidin-4-yl)-6-fluoro-1-oxoisoindolin-2-yl)piperidine-2,6-dione A1273.

3-(4-(1-(4-(Dimethylamino)-3-methylbenzyl)piperidin-4-yl)-6-fluoro-1-oxoisoindolin-2-yl)piperidine-2,6-dione A1274.

A1273

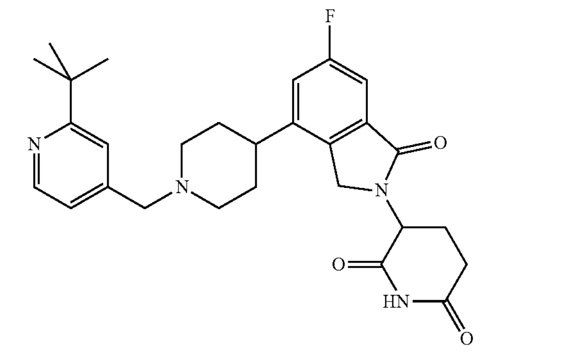

A1274

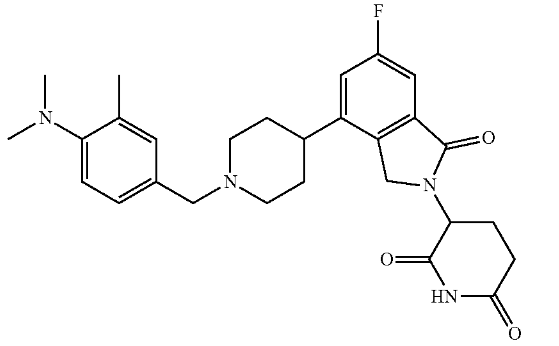

3-(6-Fluoro-4-(1-((4-fluorobenzofuran-7-yl)methyl)piperidin-4-yl)-1-oxoisoindolin-2-yl)piperidine-2,6-dione A1275.

3-(6-Fluoro-4-(1-((5-fluoro-1H-benzo[d]imidazol-2-yl)methyl)piperidin-4-yl)-1-oxoisoindolin-2-yl)piperidine-2,6-dione A1276.

A1275

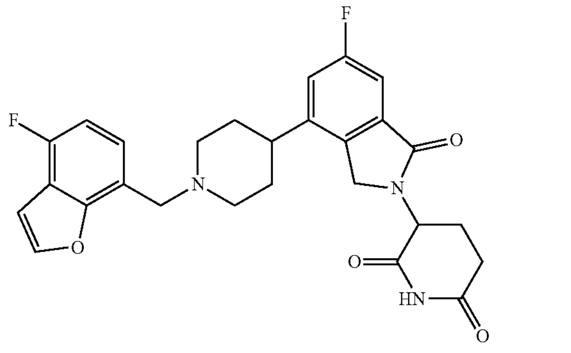

-continued

1276

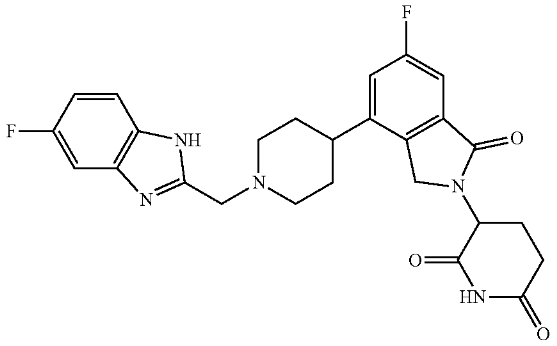

3-(4-(1-((2,3-Dihydrobenzo[b][1,4]dioxin-6-yl)methyl)piperidin-4-yl)-6-fluoro-1-oxoisoindolin-2-yl)piperidine-2,6-dione A1277.

3-(6-Fluoro-4-(1-(3-(2-methoxyphenyl)propyl)piperidin-4-yl)-1-oxoisoindolin-2-yl)piperidine-2,6-dione A1278.

A1277

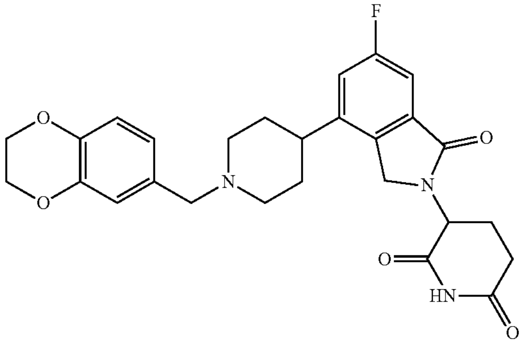

A1278

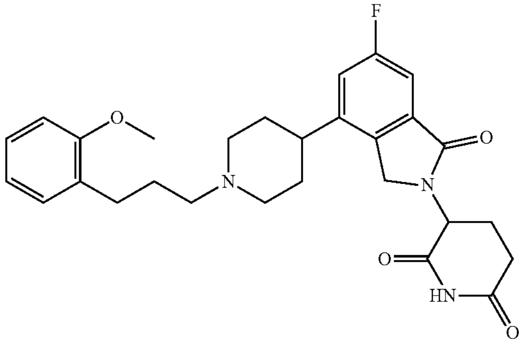

3-(4-(1-(3-(Benzyloxy)propyl)piperidin-4-yl)-6-fluoro-1-oxoisoindolin-2-yl)-piperidine-2,6-dione A1279.

3-(4-(1-((Adamantan-1-yl)methyl)piperidin-4-yl)-6-fluoro-1-oxoisoindolin-2-yl)-piperidine-2,6-dione A1280.

A1279

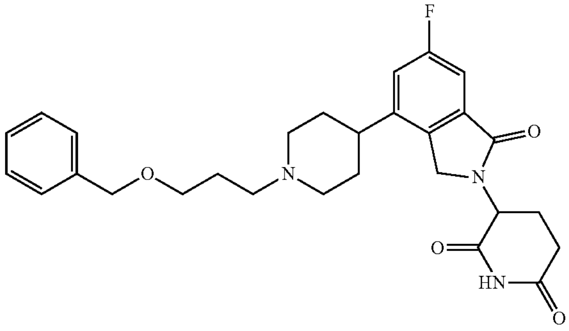

A1280

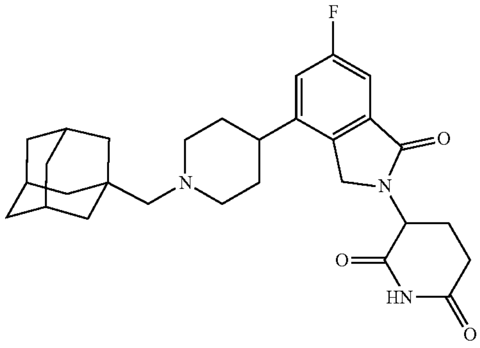

3-(4-(1-((2,3-Dihydro-[1,4]dioxino[2,3-b]pyridin-6-yl)methyl)piperidin-4-yl)-6-fluoro-1-oxoisoindolin-2-yl)piperidine-2,6-dione A1281.

3-((4-(2-(2,6-Dioxopiperidin-3-yl)-6-fluoro-1-oxoisoindolin-4-yl)piperidin-1-yl)-methyl)-1H-indole-6-carbonitrile A1282.

A1281

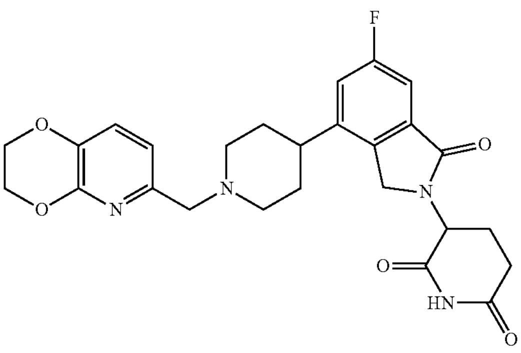

-continued

A1282

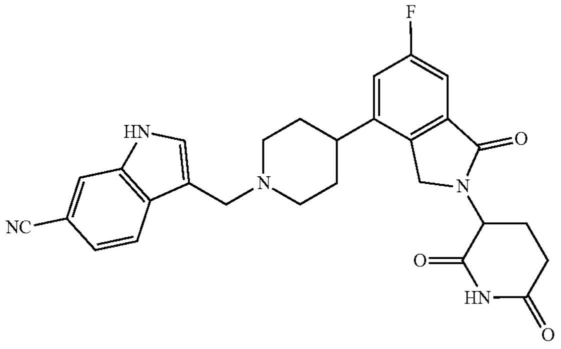

2-((4-(2-(2,6-Dioxopiperidin-3-yl)-6-fluoro-1-oxoisoindolin-4-yl)piperidin-1-yl)-methyl)-1H-indole-6-carbonitrile A1283.

3-(4-(1-(4-(1H-Pyrazol-1-yl)benzyl)piperidin-4-yl)-6-fluoro-1-oxoisoindolin-2-yl)piperidine-2,6-dione A1284.

A1283

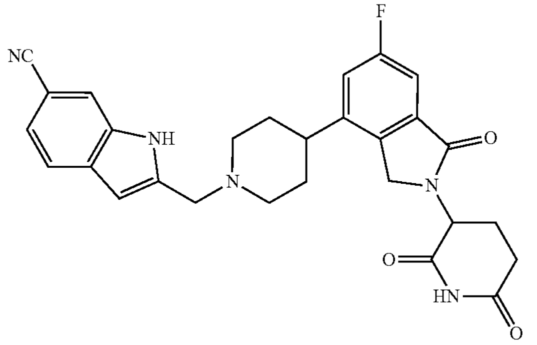

A1284

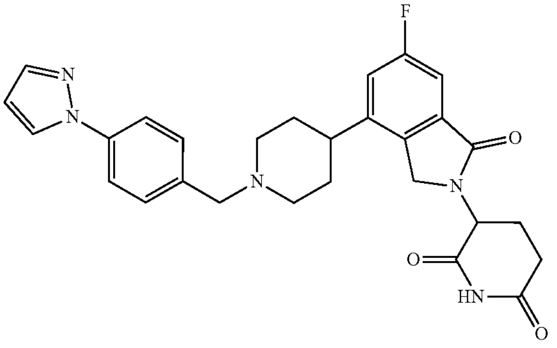

3-(4-(1-(4-(1H-Imidazol-1-yl)benzyl)piperidin-4-yl)-6-fluoro-1-oxoisoindolin-2-yl)piperidine-2,6-dione A1285.

3-(6-Fluoro-1-oxo-4-(1-((2-phenyl-1H-imidazol-5-yl)methyl)piperidin-4-yl)-isoindolin-2-yl)piperidine-2,6-dione A1286.

A1285

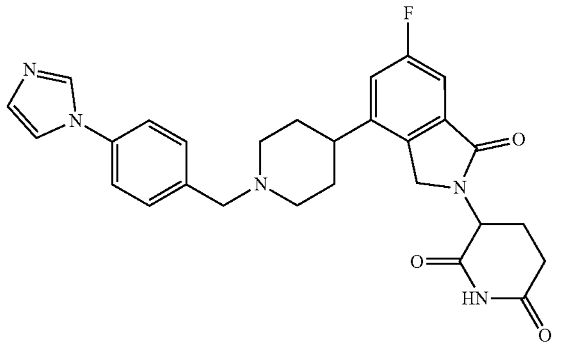

A1286

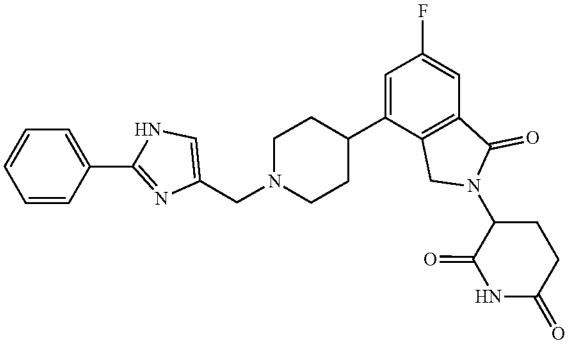

3-(4-(1-(3-(1H-Imidazol-1-yl)benzyl)piperidin-4-yl)-6-fluoro-1-oxoisoindolin-2-yl)piperidine-2,6-dione A1287.

3-(6-Fluoro-1-oxo-4-(1-((5-phenyl-1H-imidazol-2-yl)methyl)piperidin-4-yl)-isoindolin-2-yl)piperidine-2,6-dione A1288.

A1287

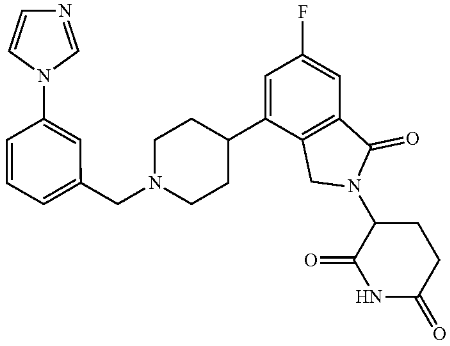

-continued

A1288

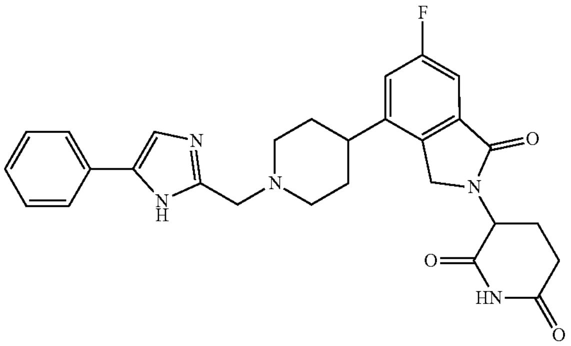

3-(6-Fluoro-1-oxo-4-(1-((1-phenyl-1H-pyrazol-3-yl)methyl)piperidin-4-yl)-isoindolin-2-yl)piperidine-2,6-dione A1289.

3-(4-(1-(4-(1H-1,2,4-Triazol-1-yl)benzyl)piperidin-4-yl)-6-fluoro-1-oxoisoindolin-2-yl)piperidine-2,6-dione A1290.

A1289

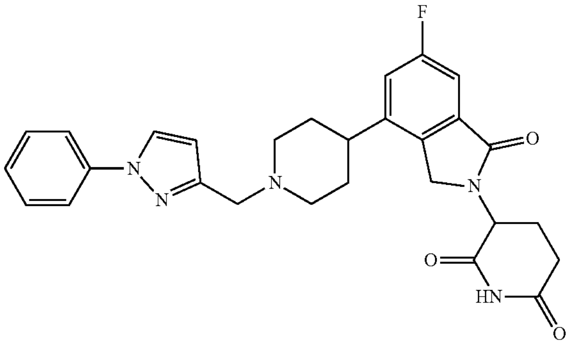

A1290

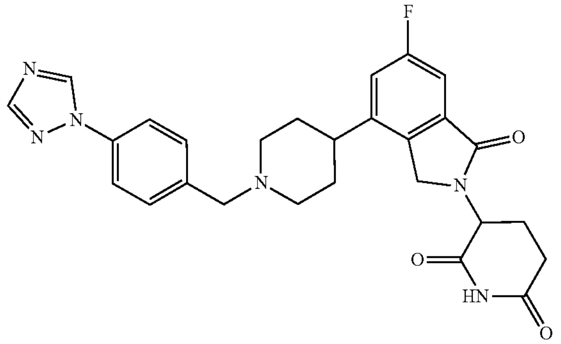

3-(4-(1-(2-(1H-1,2,4-Triazol-1-yl)benzyl)piperidin-4-yl)-6-fluoro-1-oxoisoindolin-2-yl)piperidine-2,6-dione A1291.

3-(4-(1-(3-(1H-1,2,4-Triazol-1-yl)benzyl)piperidin-4-yl)-6-fluoro-1-oxoisoindolin-2-yl)piperidine-2,6-dione A1292.

A1291

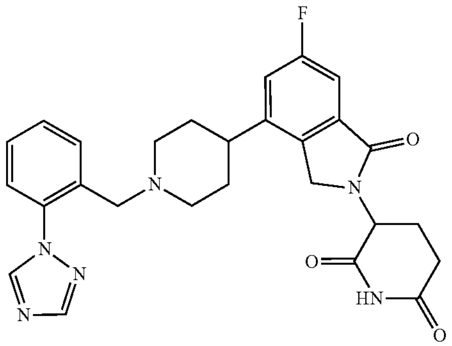

A1292

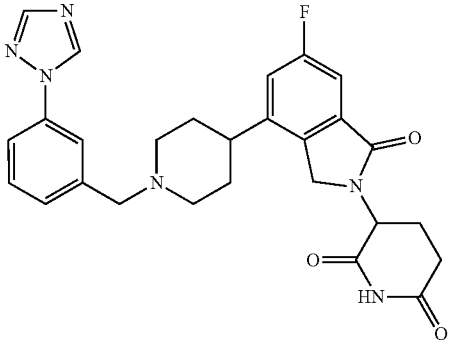

3-(6-Fluoro-1-oxo-4-(1-(4-(pyrrolidin-1-yl)benzyl)piperidin-4-yl)isoindolin-2-yl)-piperidine-2,6-dione A1293.

3-(6-Fluoro-1-oxo-4-(1-(3-(pyrrolidin-1-yl)benzyl)piperidin-4-yl)isoindolin-2-yl)-piperidine-2,6-dione A1294.

A1293

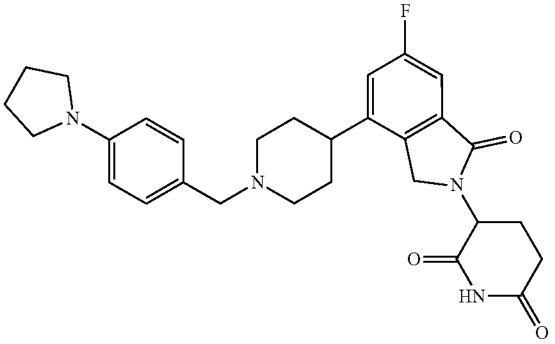

A1294

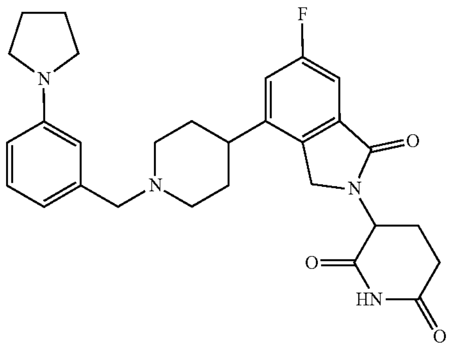

3-(6-Fluoro-1-oxo-4-(1-((6-(pyrrolidin-1-yl)pyridin-3-yl)methyl)piperidin-4-yl)-isoindolin-2-yl)piperidine-2,6-dione A1295.

3-(6-Fluoro-4-(1-((6-fluorochroman-8-yl)methyl)piperidin-4-yl)-1-oxoisoindolin-2-yl)piperidine-2,6-dione A1296.

A1295

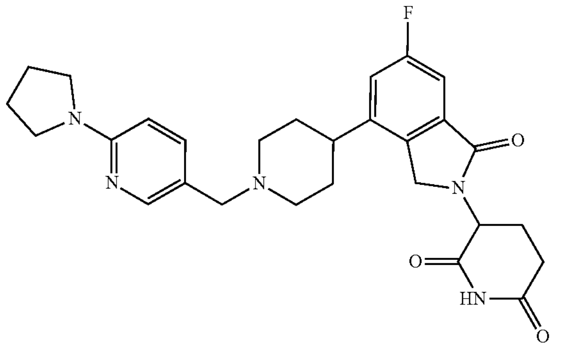

A1296

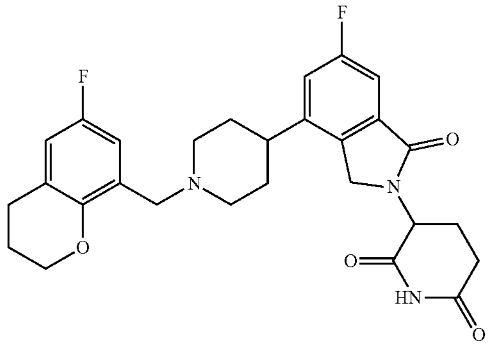

3-(4-(1-([1,1'-Biphenyl]-4-ylmethyl)piperidin-4-yl)-6-fluoro-1-oxoisoindolin-2-yl)piperidine-2,6-dione A1297.

3-(6-Fluoro-1-oxo-4-(1-(3-(pyridin-4-yl)benzyl)piperidin-4-yl)isoindolin-2-yl)-piperidine-2,6-dione A1298.

A1297

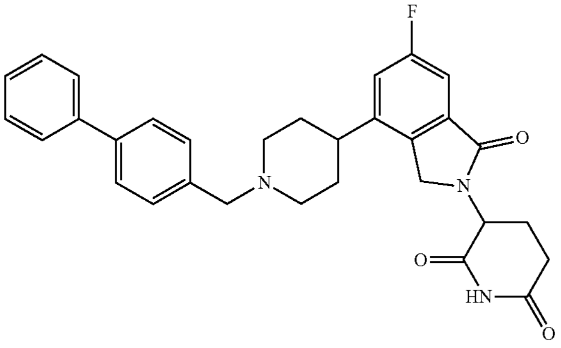

-continued

A1298

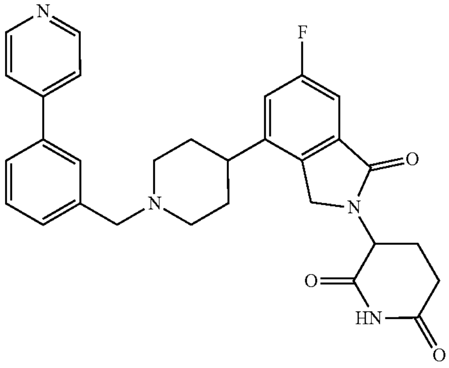

3-(6-Fluoro-4-(1-((6-(methylsulfonyl)pyridin-2-yl)methyl)piperidin-4-yl)-1-oxoisoindolin-2-yl)piperidine-2,6-dione A1299.

3-(6-Fluoro-1-oxo-4-(1-(3-(quinolin-6-yl)propyl)piperidin-4-yl)isoindolin-2-yl)-piperidine-2,6-dione A1300.

A1299

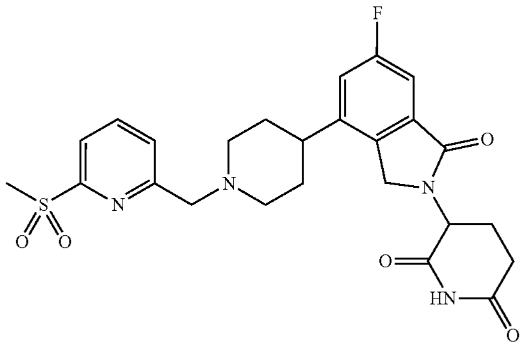

A1300

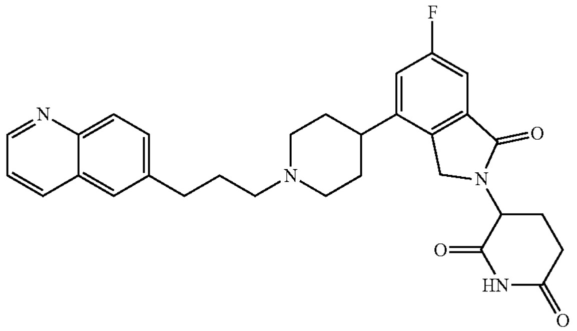

3-(6-Fluoro-4-(1-(4-morpholinobenzyl)piperidin-4-yl)-1-oxoisoindolin-2-yl)-piperidine-2,6-dione A1301.

3-(6-Fluoro-4-(1-(3-morpholinobenzyl)piperidin-4-yl)-1-oxoisoindolin-2-yl)-piperidine-2,6-dione A1302.

A1301

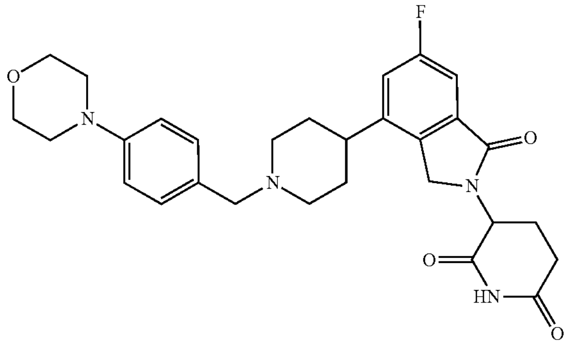

A1302

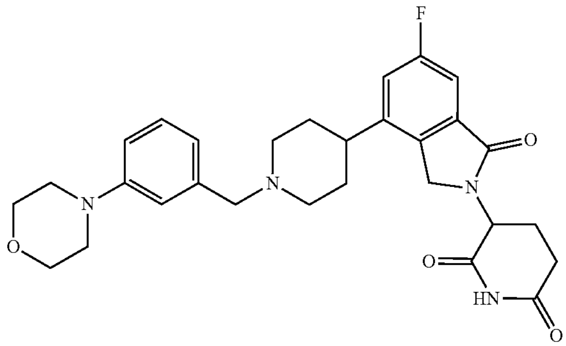

3-(6-Fluoro-4-(1-(2-morpholinobenzyl)piperidin-4-yl)-1-oxoisoindolin-2-yl)-piperidine-2,6-dione A1303.

4-((4-(2-(2,6-Dioxopiperidin-3-yl)-6-fluoro-1-oxoisoindolin-4-yl)piperidin-1-yl)-methyl)-N-isopropylbenzamide A1304.

A1303

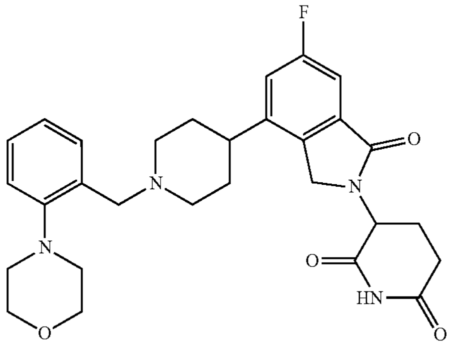

-continued

A1304

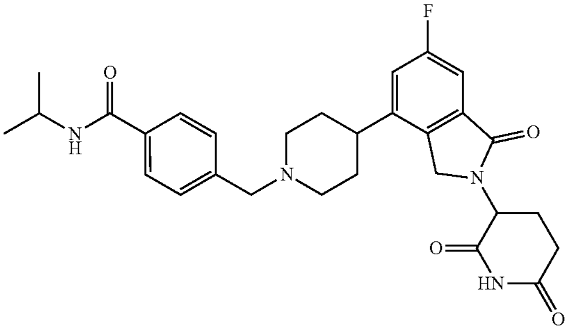

3-(6-Fluoro-1-oxo-4-(1-((6-(p-tolyl)pyridin-3-yl)methyl)piperidin-4-yl)isoindolin-2-yl)piperidine-2,6-dione A1305.

3-(6-Fluoro-1-oxo-4-(1-(3-phenoxybenzyl)piperidin-4-yl)isoindolin-2-yl)-piperidine-2,6-dione A1306.

A1305

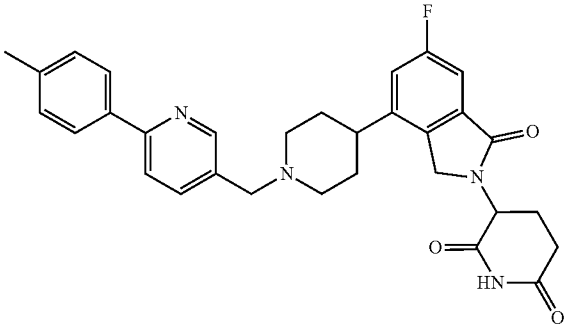

A1306

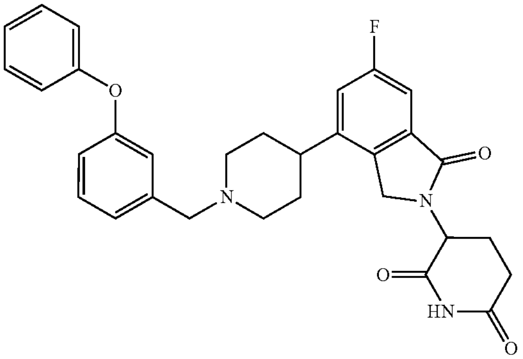

3-(6-Fluoro-1-oxo-4-(1-(4-phenoxybenzyl)piperidin-4-yl)isoindolin-2-yl)-piperidine-2,6-dione A1307.

3-(6-Fluoro-4-(1-((4'-methyl-[2,2'-bipyridin]-4-yl)methyl)piperidin-4-yl)-1-oxoisoindolin-2-yl)piperidine-2,6-dione A1308.

A1307

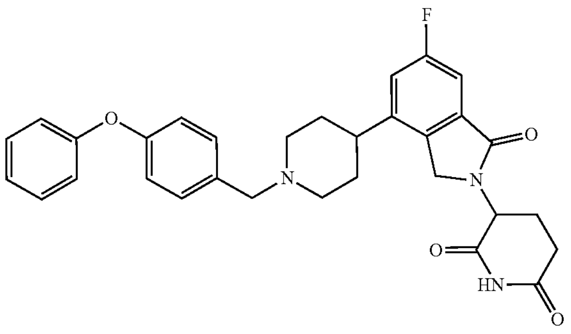

A1308

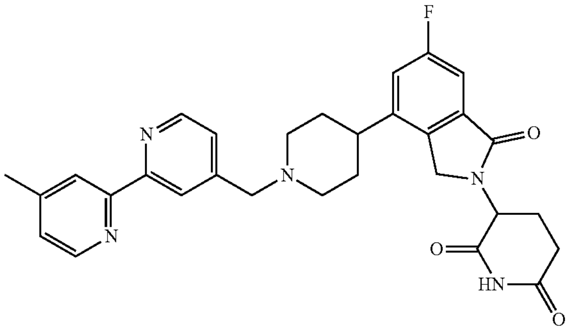

3-(4-(1-(4-(Ethylsulfonyl)benzyl)piperidin-4-yl)-6-fluoro-1-oxoisoindolin-2-yl)-piperidine-2,6-dione A1309.

3-(6-Fluoro-4-(1-((2-morpholinothiazol-5-yl)methyl)piperidin-4-yl)-1-oxoisoindolin-2-yl)piperidine-2,6-dione A1310.

A1309

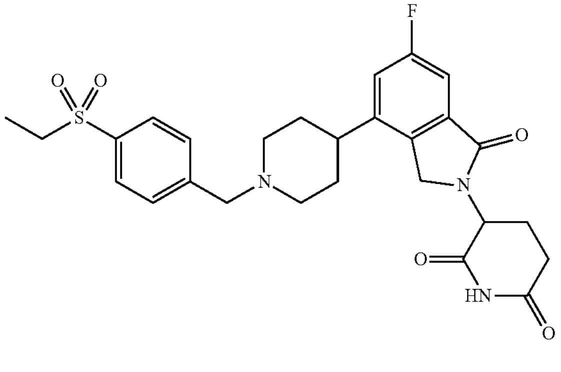

-continued

A1310

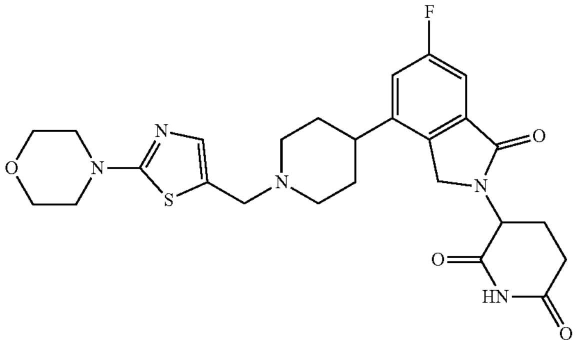

3-(4-(1-(4-Bromophenethyl)piperidin-4-yl)-6-fluoro-1-oxoisoindolin-2-yl)-piperidine-2,6-dione A1311.

3-(6-Fluoro-1-oxo-4-(1-(2-(pyridin-2-yloxy)benzyl)piperidin-4-yl)isoindolin-2-yl)piperidine-2,6-dione A1312.

A1311

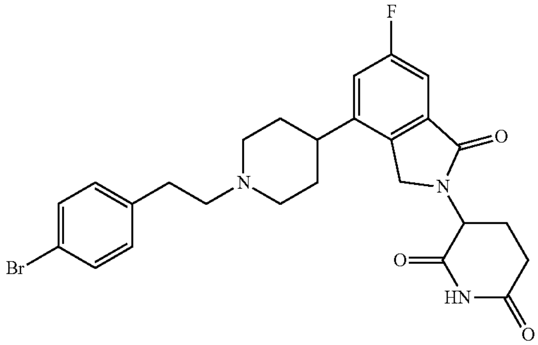

A1312

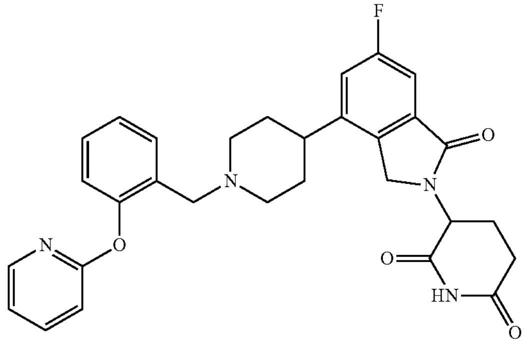

N-(3-((4-(2-(2,6-Dioxopiperidin-3-yl)-6-fluoro-1-oxoisoindolin-4-yl)piperidin-1-yl)methyl)phenyl)methanesulfonamide A1313.

N-(4-((4-(2-(2,6-Dioxopiperidin-3-yl)-6-fluoro-1-oxoisoindolin-4-yl)piperidin-1-yl)methyl)phenyl)methanesulfonamide A1314.

A1313

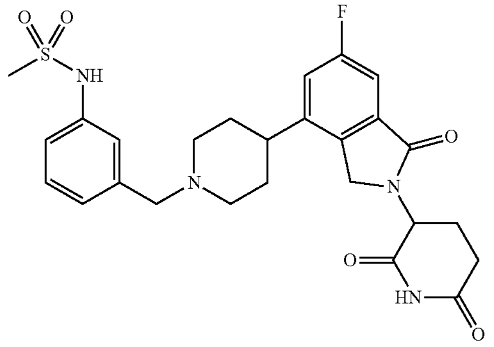

A1314

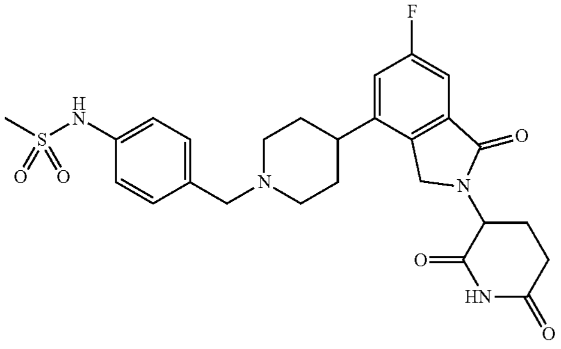

N-(2-((4-(2-(2,6-Dioxopiperidin-3-yl)-6-fluoro-1-oxoisoindolin-4-yl)piperidin-1-yl)methyl)phenyl)methanesulfonamide A1315.

3-(4-(1-((6-(Dimethylamino)naphthalen-2-yl)methyl)piperidin-4-yl)-6-fluoro-1-oxoisoindolin-2-yl)piperidine-2,6-dione A1316.

A1315

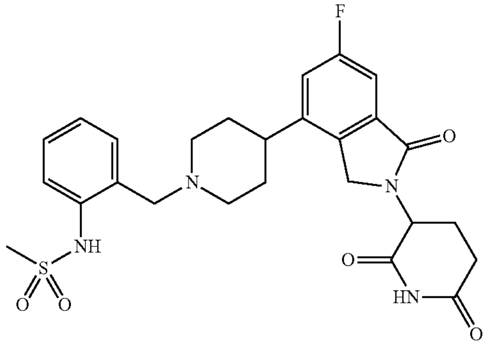

-continued

A1316

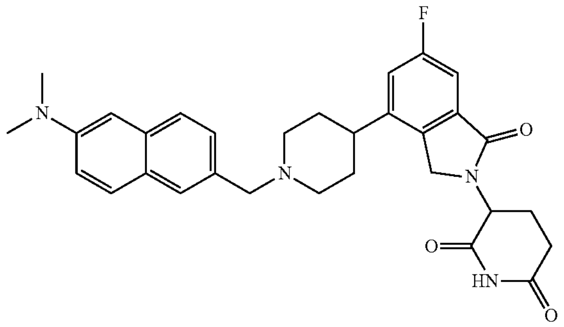

3-(6-Fluoro-1-oxo-4-(1-(3-(3-(trifluoromethyl)phenyl)propyl)piperidin-4-yl)-isoindolin-2-yl)piperidine-2,6-dione A1317.

2-(3-(4-(2-(2,6-Dioxopiperidin-3-yl)-6-fluoro-1-oxoisoindolin-4-yl)piperidin-1-yl)propyl)isoindoline-1,3-dione A1318.

A1317

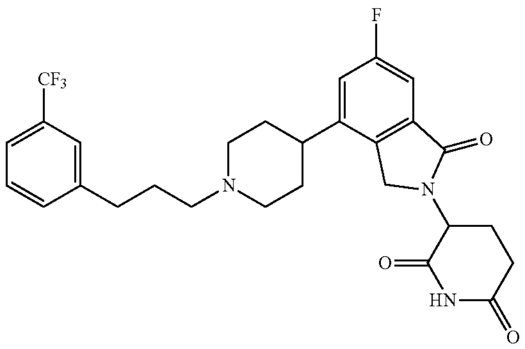

A1318

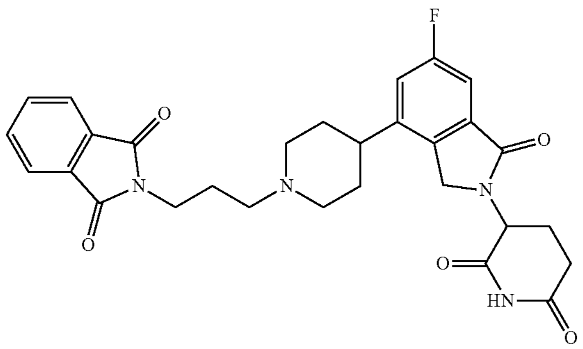

3-(4-(1-((1-Benzylpiperidin-4-yl)methyl)piperidin-4-yl)-6-fluoro-1-oxoisoindolin-2-yl)piperidine-2,6-dione A1319.

3-(4-(1-(2-Chloro-5-(trifluoromethyl)benzyl)piperidin-4-yl)-6-fluoro-1-oxoisoindolin-2-yl)piperidine-2,6-dione A1320.

-continued

A1319

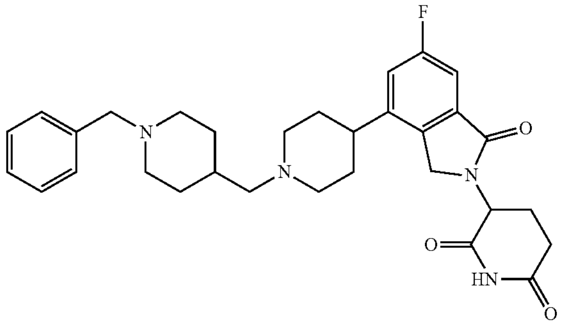

A1320

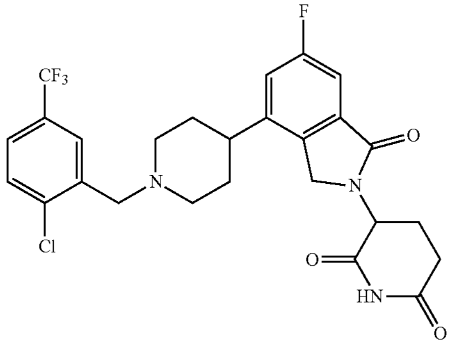

3-(4-(1-(5-Chloro-2-(trifluoromethyl)benzyl)piperidin-4-yl)-6-fluoro-1-oxoisoindolin-2-yl)piperidine-2,6-dione A1321.

3-(4-(1-(4-Chloro-2-(trifluoromethyl)benzyl)piperidin-4-yl)-6-fluoro-1-oxoisoindolin-2-yl)piperidine-2,6-dione A1322.

A1321

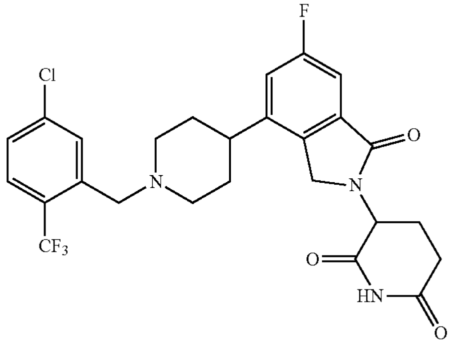

A1322

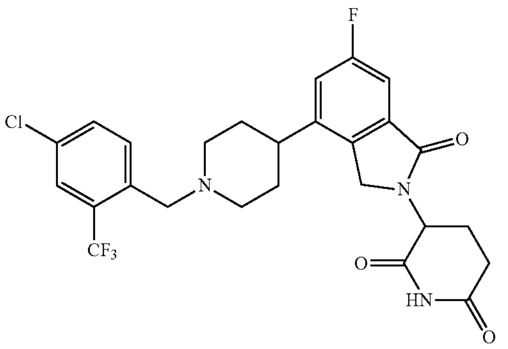

3-(4-(1-(2-Chloro-4-(trifluoromethyl)benzyl)piperidin-4-yl)-6-fluoro-1-oxoisoindolin-2-yl)piperidine-2,6-dione A1323.

3-(4-(1-(3-Chloro-4-(trifluoromethyl)benzyl)piperidin-4-yl)-6-fluoro-1-oxoisoindolin-2-yl)piperidine-2,6-dione A1324.

A1323

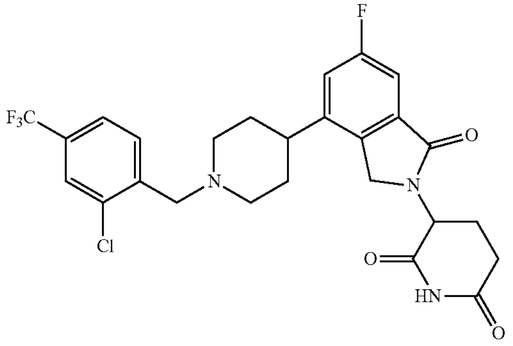

A1324

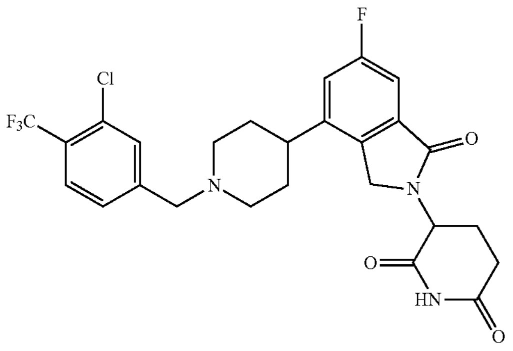

5-((4-(2-(2,6-Dioxopiperidin-3-yl)-6-fluoro-1-oxoisoindolin-4-yl)piperidin-1-yl)-methyl)-2-(4-methyl-1H-imidazol-1-yl)benzonitrile A1325.

3-(4-(1-(3-(Benzyloxy)benzyl)piperidin-4-yl)-6-fluoro-1-oxoisoindolin-2-yl)-piperidine-2,6-dione A1326.

A1325

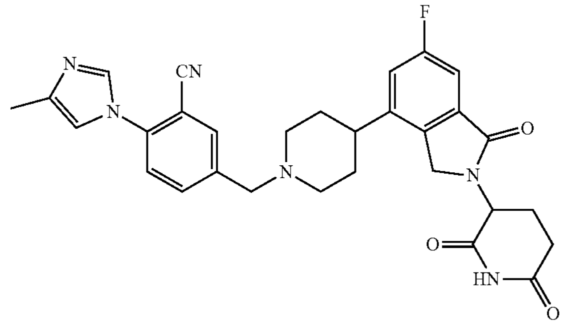

A1326

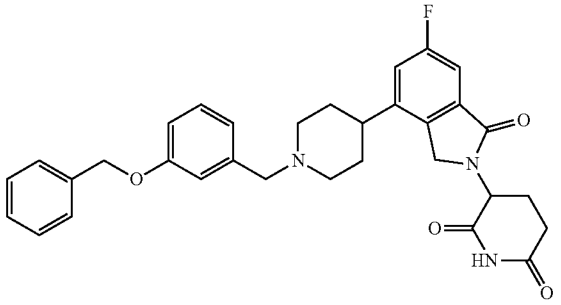

3-(4-(1-(4-(Benzyloxy)benzyl)piperidin-4-yl)-6-fluoro-1-oxoisoindolin-2-yl)-piperidine-2,6-dione A1327.

3-(4-(1-(3-(3-Bromophenyl)propyl)piperidin-4-yl)-6-fluoro-1-oxoisoindolin-2-yl)piperidine-2,6-dione A1328.

A1327

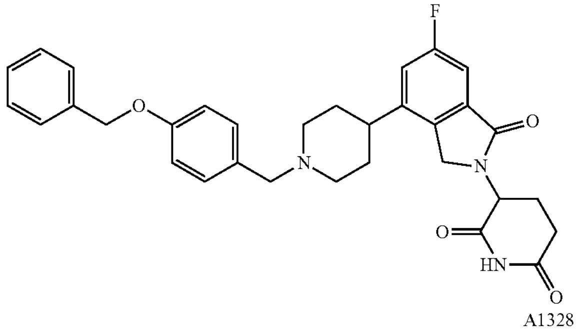

A1328

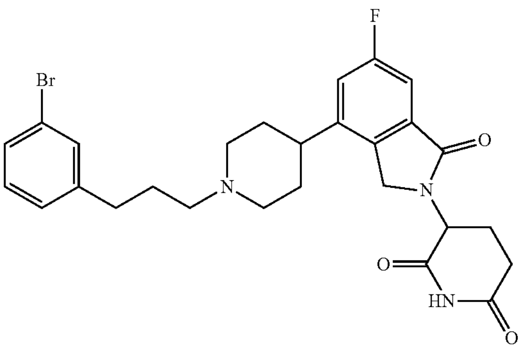

3-(4-(1-(3-(Cyclohexylmethoxy)benzyl)piperidin-4-yl)-6-fluoro-1-oxoisoindolin-2-yl)piperidine-2,6-dione A1329.

4-(3-((4-(2-(2,6-Dioxopiperidin-3-yl)-6-fluoro-1-oxoisoindolin-4-yl)piperidin-1-yl)methyl)phenoxy)benzonitrile A1330.

A1329

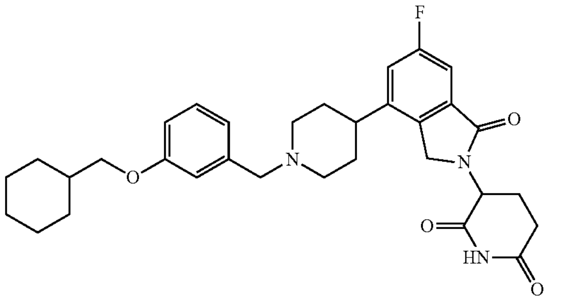

A1330

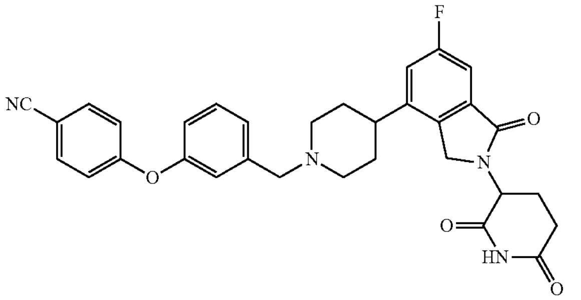

4-(4-((4-(2-(2,6-Dioxopiperidin-3-yl)-6-fluoro-1-oxoisoindolin-4-yl)piperidin-1-yl)methyl)phenoxy)benzonitrile A1331.

3-(4-(1-(3-Chloro-4-morpholinobenzyl)piperidin-4-yl)-6-fluoro-1-oxoisoindolin-2-yl)piperidine-2,6-dione A1332.

A1331

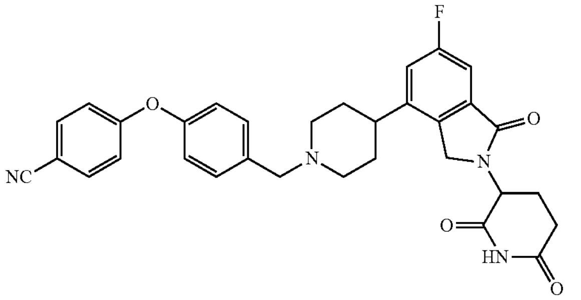

-continued

A1332

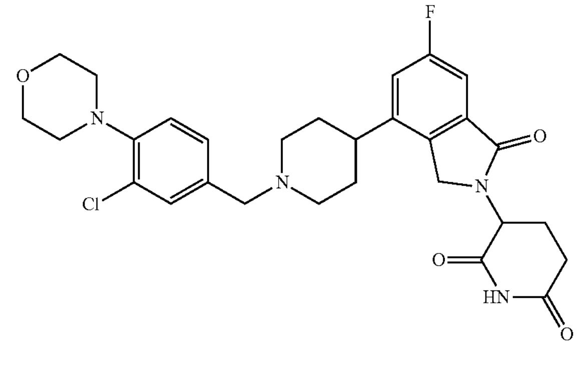

3-(4-(1-(4-(Benzyloxy)-2-methylbenzyl)piperidin-4-yl)-6-fluoro-1-oxoisoindolin-2-yl)piperidine-2,6-dione A1333.

3-(4-(1-(2-(Benzyloxy)-4-methylbenzyl)piperidin-4-yl)-6-fluoro-1-oxoisoindolin-2-yl)piperidine-2,6-dione A1334.

A1333

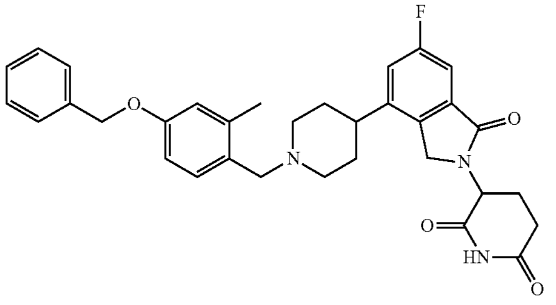

A1334

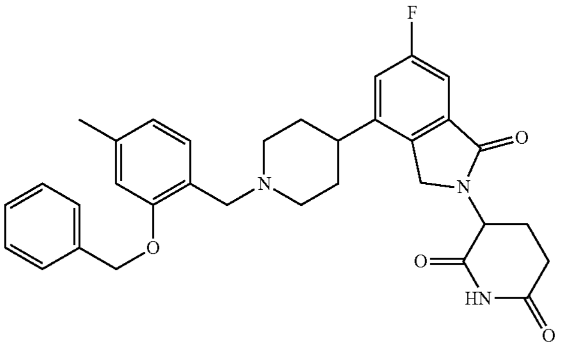

Tert-butyl 4-(2-(4-(2-(2,6-dioxopiperidin-3-yl)-6-fluoro-1-oxoisoindolin-4-yl)-piperidin-1-yl)ethyl)piperidine-1-carboxylate A1335.

Tert-butyl ((1r,4r)-4-((4-(2-(2,6-dioxopiperidin-3-yl)-6-fluoro-1-oxoisoindolin-4-yl)piperidin-1-yl)methyl)cyclohexyl)carbamate A1336.

A1335

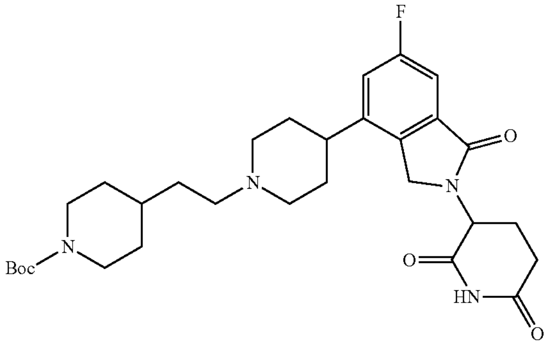

A1336

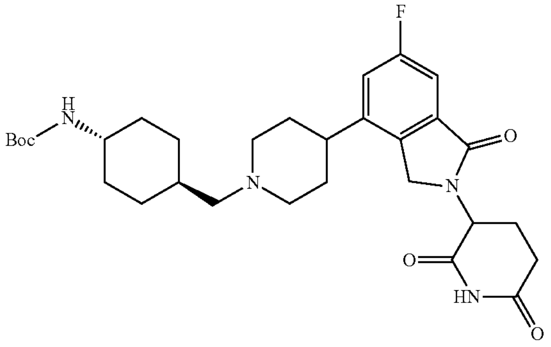

3-(4-(1-((2-Chloro-4-morpholinopyrimidin-5-yl)methyl)piperidin-4-yl)-6-fluoro-1-oxoisoindolin-2-yl)piperidine-2,6-dione A1337.

Tert-butyl 4-(2-(4-(2-(2,6-dioxopiperidin-3-yl)-6-fluoro-1-oxoisoindolin-4-yl)-piperidin-1-yl)ethyl)piperazine-1-carboxylate A1338.

A1337

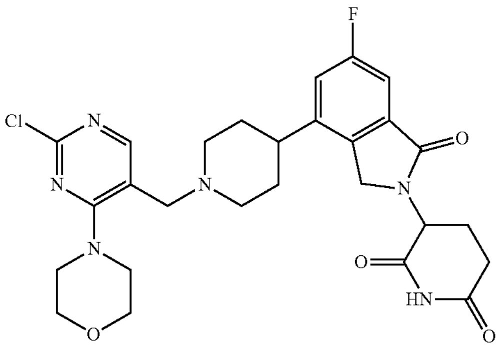

-continued

A1338

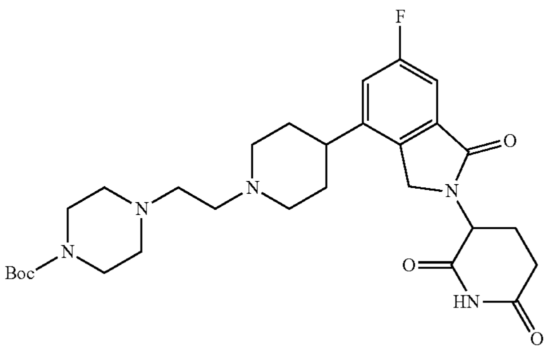

Tert-butyl 4-((4-(2-(2,6-dioxopiperidin-3-yl)-6-fluoro-1-oxoisoindolin-4-yl)piperidin-1-yl)methyl)-4-fluoropiperidine-1-carboxylate A1339.

4-(4-((4-(2-(2,6-Dioxopiperidin-3-yl)-6-fluoro-1-oxoisoindolin-4-yl)piperidin-1-yl)methyl)phenoxy)-3-fluorobenzonitrile A1340.

A1339

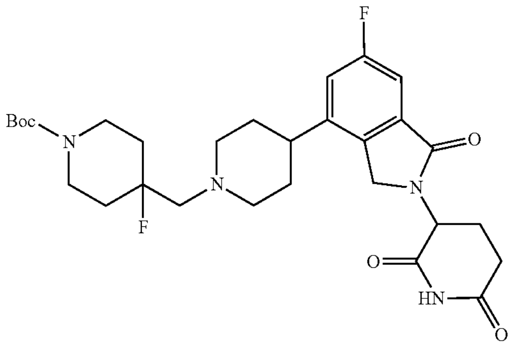

A1340

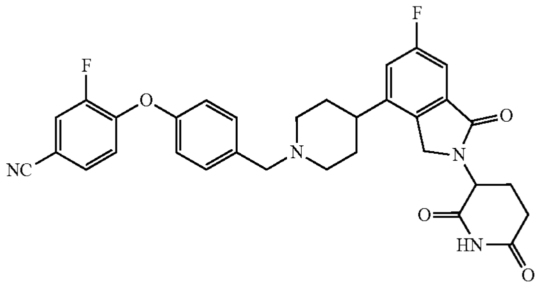

Tert-butyl (((1r,4r)-4-((4-(2-(2,6-dioxopiperidin-3-yl)-6-fluoro-1-oxoisoindolin-4-yl)piperidin-1-yl)methyl)cyclohexyl)methyl)carbamate A1341.

Tert-butyl 6-((4-(2-(2,6-dioxopiperidin-3-yl)-6-fluoro-1-oxoisoindolin-4-yl)-piperidin-1-yl)methyl)indoline-1-carboxylate A1342.

A1341

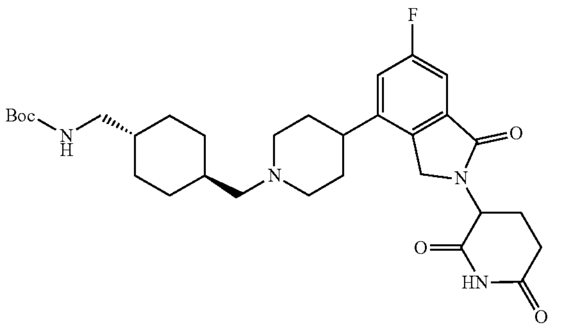

A1342

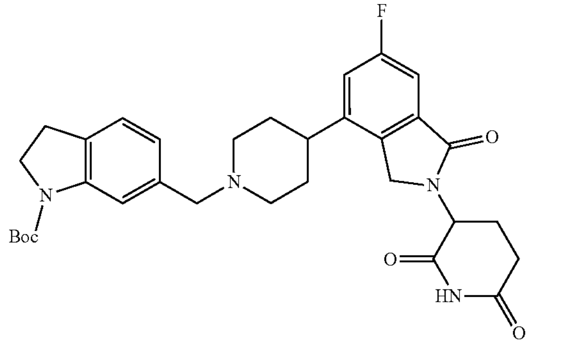

Benzyl (4-((4-(2-(2,6-dioxopiperidin-3-yl)-6-fluoro-1-oxoisoindolin-4-yl)-piperidin-1-yl)methyl)phenyl)carbamate A1343.

Tert-butyl 4-(1-(4-(2-(2,6-dioxopiperidin-3-yl)-6-fluoro-1-oxoisoindolin-4-yl)-piperidin-1-yl)-2-methylpropan-2-yl)piperidine-1-carboxylate A1344.

A1343

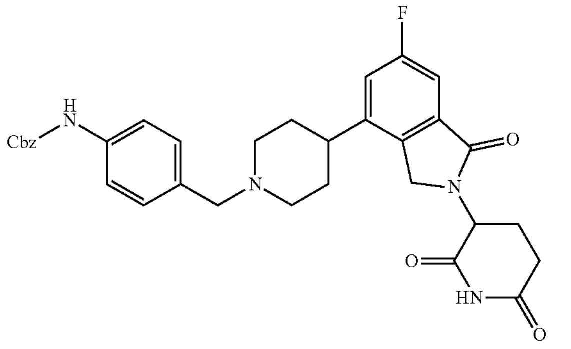

-continued

A1344

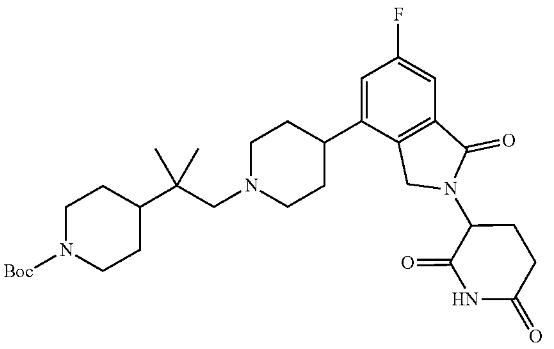

3-(4-(1-(4-(Benzyloxy)-3-ethoxybenzyl)piperidin-4-yl)-6-fluoro-1-oxoisoindolin-2-yl)piperidine-2,6-dione A1345.

3-(6-Fluoro-1-oxo-4-(1-(4-(4-(trifluoromethyl)phenoxy)benzyl)piperidin-4-yl)-isoindolin-2-yl)piperidine-2,6-dione A1346.

A1345

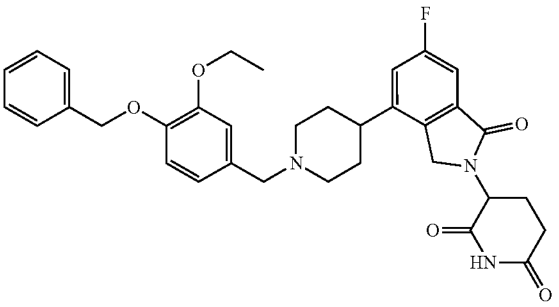

A1346

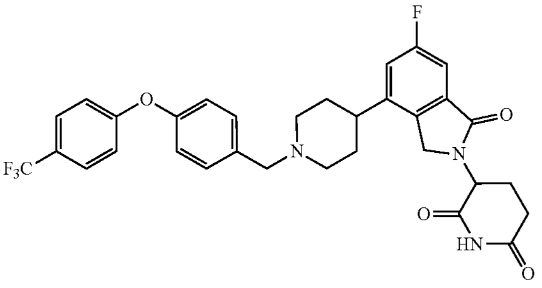

3-(4-(1-(3-Bromo-4-morpholinobenzyl)piperidin-4-yl)-6-fluoro-1-oxoisoindolin-2-yl)piperidine-2,6-dione A1347.

Tert-butyl 4-(4-((4-(2-(2,6-dioxopiperidin-3-yl)-6-fluoro-1-oxoisoindolin-4-yl)-piperidin-1-yl)methyl)-1H-1,2,3-triazol-1-yl)piperidine-1-carboxylate A1348.

A1347

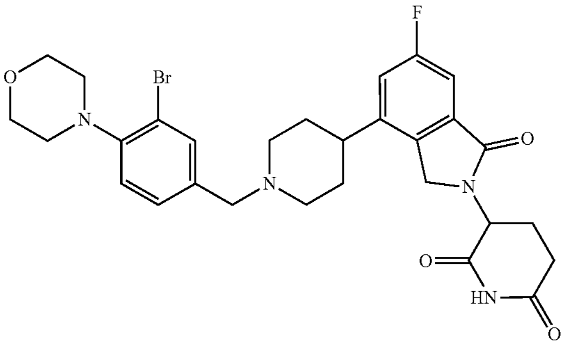

A1348

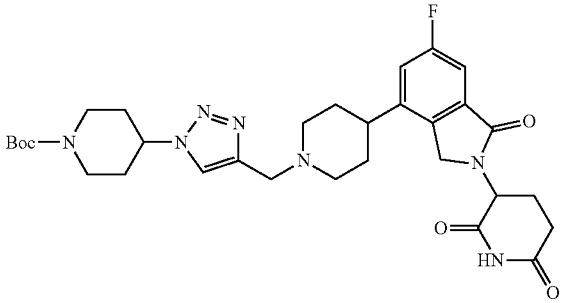

3-(4-(1-(3-Bromo-4-(4-methylpiperazin-1-yl)benzyl)piperidin-4-yl)-6-fluoro-1-oxoisoindolin-2-yl)piperidine-2,6-dione A1349.

4-(4-Bromo-3-((4-(2-(2,6-dioxopiperidin-3-yl)-6-fluoro-1-oxoisoindolin-4-yl)-piperidin-1-yl)methyl)phenoxy)benzonitrile A1350.

A1349

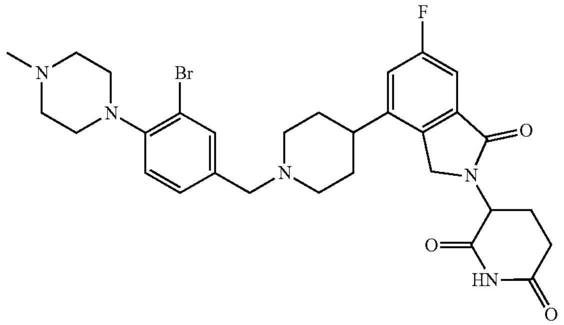

A1350

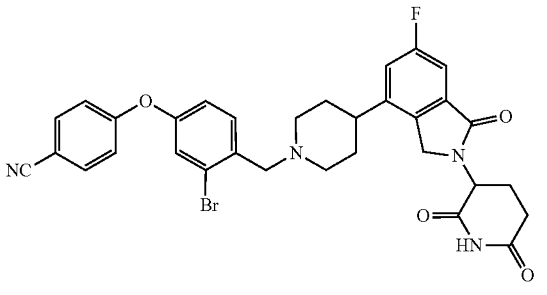

3-(6-Fluoro-1-oxo-4-(1-(propylsulfonyl)piperidin-4-yl)isoindolin-2-yl)piperidine-2,6-dione A2002.

3-(6-Fluoro-4-(1-(isopropylsulfonyl)piperidin-4-yl)-1-oxoisoindolin-2-yl)-piperidine-2,6-dione A2003.

A2002

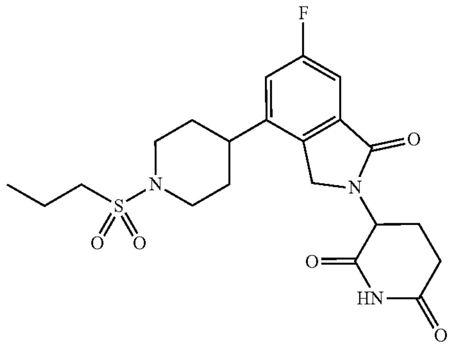

A2003

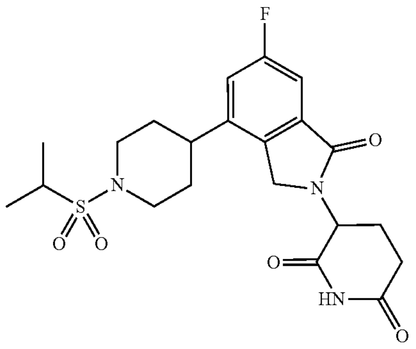

3-(6-Fluoro-4-(1-(isobutylsulfonyl)piperidin-4-yl)-1-oxoisoindolin-2-yl)-piperidine-2,6-dione A2004.

3-(6-Fluoro-4-(1-(furan-3-ylsulfonyl)piperidin-4-yl)-1-oxoisoindolin-2-yl)-piperidine-2,6-dione A2005.

A2004

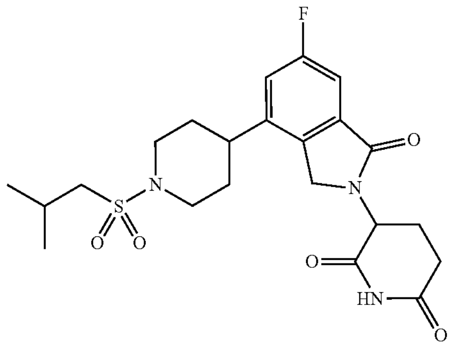

-continued

A2005

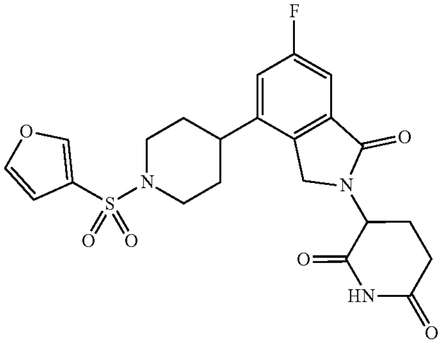

3-(4-(1-((1H-Pyrazol-4-yl)sulfonyl)piperidin-4-yl)-6-fluoro-1-oxoisoindolin-2-yl)piperidine-2,6-dione A2006.

3-(6-Fluoro-1-oxo-4-(1-((trifluoromethyl)sulfonyl)piperidin-4-yl)isoindolin-2-yl)-piperidine-2,6-dione A2007.

A2006

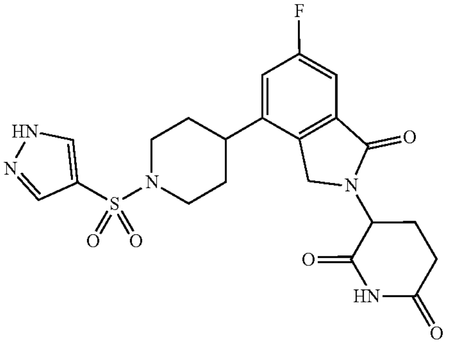

A2007

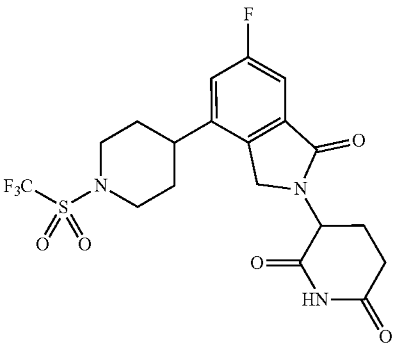

3-(4-(1-((Cyclobutylmethyl)sulfonyl)piperidin-4-yl)-6-fluoro-1-oxoisoindolin-2-yl)piperidine-2,6-dione A2008.

3-(4-(1-((3-Chloropropyl)sulfonyl)piperidin-4-yl)-6-fluoro-1-oxoisoindolin-2-yl)-piperidine-2,6-dione A2009.

A2008

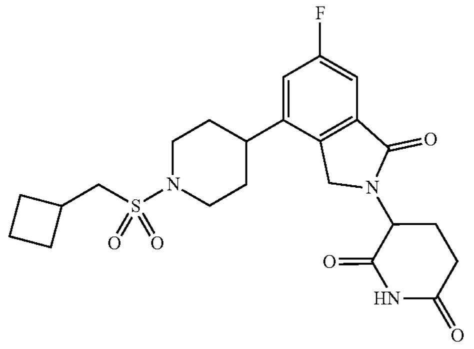

A2009

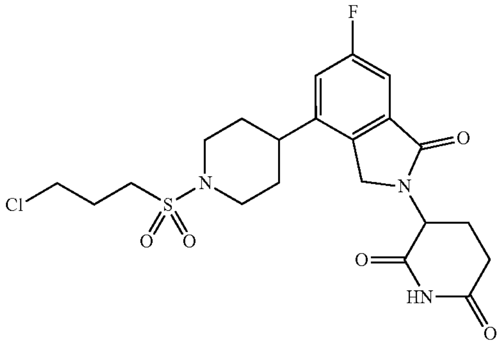

3-(6-Fluoro-1-oxo-4-(1-(pyridin-3-ylsulfonyl)piperidin-4-yl)isoindolin-2-yl)-piperidine-2,6-dione A2010.

3-(6-Fluoro-4-(1-((1-methyl-1H-pyrazol-4-yl)sulfonyl)piperidin-4-yl)-1-oxoisoindolin-2-yl)piperidine-2,6-dione A2011.

A2010

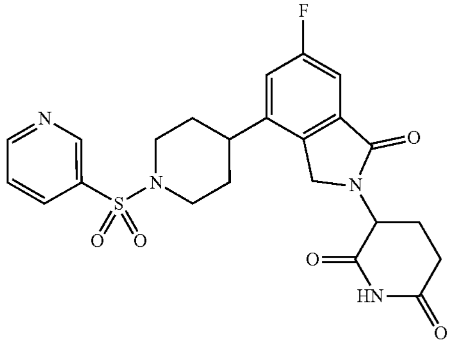

-continued

A2011

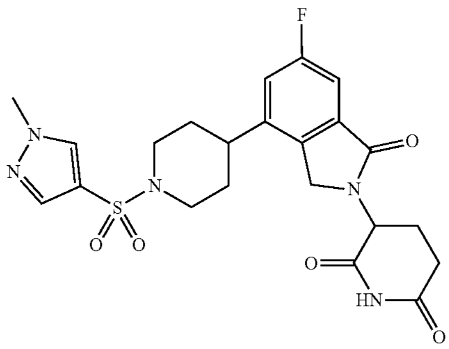

3-(6-Fluoro-4-(1-((1-methyl-1H-pyrazol-3-yl)sulfonyl)piperidin-4-yl)-1-oxoisoindolin-2-yl)piperidine-2,6-dione A2012.

3-(6-Fluoro-4-(1-((1-methyl-1H-imidazol-4-yl)sulfonyl)piperidin-4-yl)-1-oxoisoindolin-2-yl)piperidine-2,6-dione A2013.

A2012

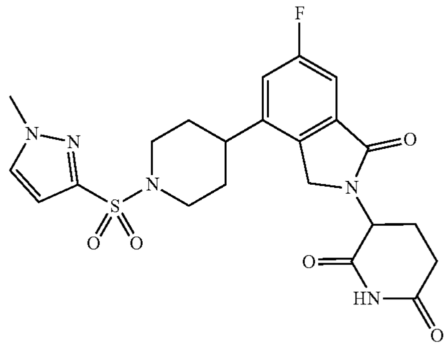

A2013

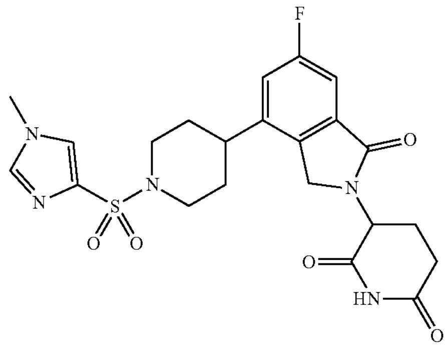

3-(6-Fluoro-1-oxo-4-(1-(thiophen-2-ylsulfonyl)piperidin-4-yl)isoindolin-2-yl)-piperidine-2,6-dione A2014.

3-(4-(1-(Cyclohexylsulfonyl)piperidin-4-yl)-6-fluoro-1-oxoisoindolin-2-yl)-piperidine-2,6-dione A2015.

A2014

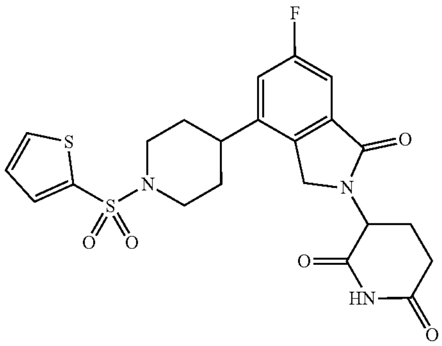

A2015

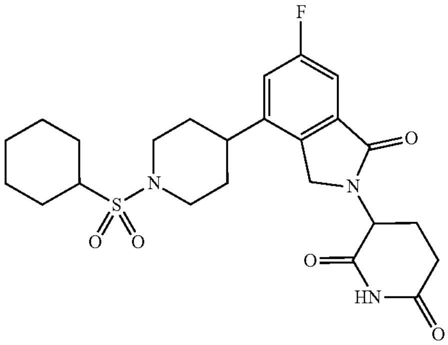

3-(6-Fluoro-1-oxo-4-(1-((tetrahydro-2H-pyran-4-yl)sulfonyl)piperidin-4-yl)-isoindolin-2-yl)piperidine-2,6-dione A2016.

3-(6-Fluoro-1-oxo-4-(1-(m-tolylsulfonyl)piperidin-4-yl) isoindolin-2-yl)-piperidine-2,6-dione A2017.

A2016

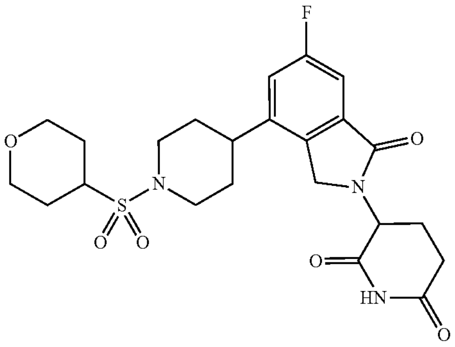

-continued

A2017

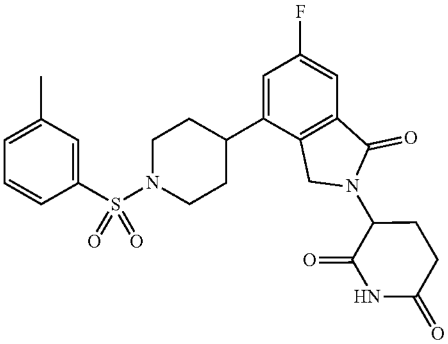

3-(6-Fluoro-4-(1-((6-methylpyridin-3-yl)sulfonyl)piperidin-4-yl)-1-oxoisoindolin-2-yl)piperidine-2,6-dione A2018.

3-(6-Fluoro-4-(1-((4-hydroxyphenyl)sulfonyl)piperidin-4-yl)-1-oxoisoindolin-2-yl)piperidine-2,6-dione A2019.

A2018

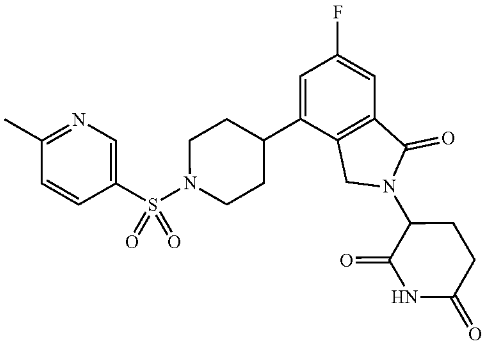

A2019

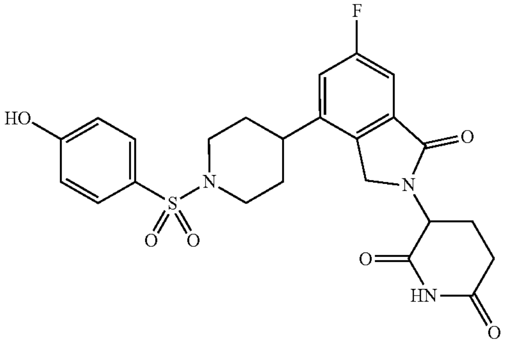

3-(6-Fluoro-4-(1-((4-fluorophenyl)sulfonyl)piperidin-4-yl)-1-oxoisoindolin-2-yl)-piperidine-2,6-dione A2020.

3-(6-Fluoro-4-(1-((3-fluorophenyl)sulfonyl)piperidin-4-yl)-1-oxoisoindolin-2-yl)-piperidine-2,6-dione A2021.

-continued

A2020

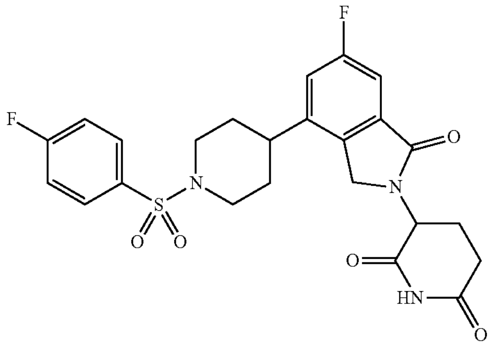

A2021

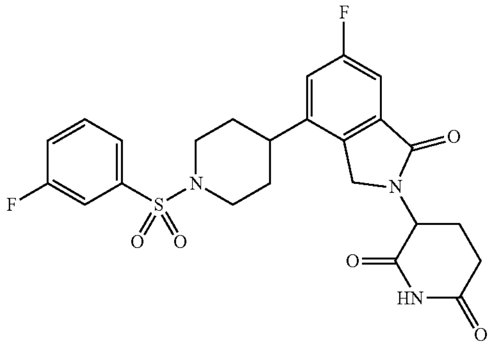

3-(6-Fluoro-4-(1-((2-fluorophenyl)sulfonyl)piperidin-4-yl)-1-oxoisoindolin-2-yl)-piperidine-2,6-dione A2022.

3-(6-Fluoro-1-oxo-4-(1-((3,3,3-trifluoropropyl)sulfonyl)piperidin-4-yl)isoindolin-2-yl)piperidine-2,6-dione A2023.

A2022

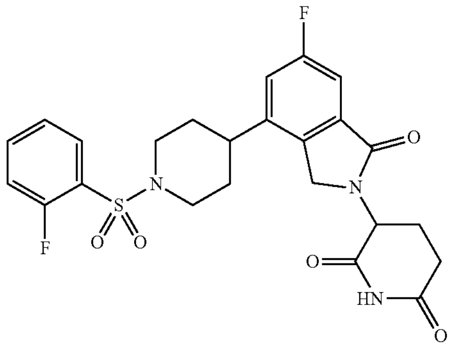

A2023

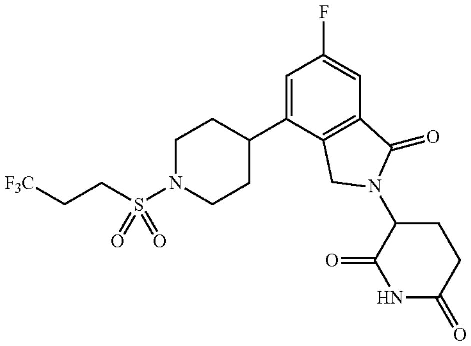

3-(6-Fluoro-4-(1-((4-methylbenzyl)sulfonyl)piperidin-4-yl)-1-oxoisoindolin-2-yl)piperidine-2,6-dione A2024.

3-(6-Fluoro-1-oxo-4-(1-(phenethylsulfonyl)piperidin-4-yl)isoindolin-2-yl)-piperidine-2,6-dione A2025.

A2024

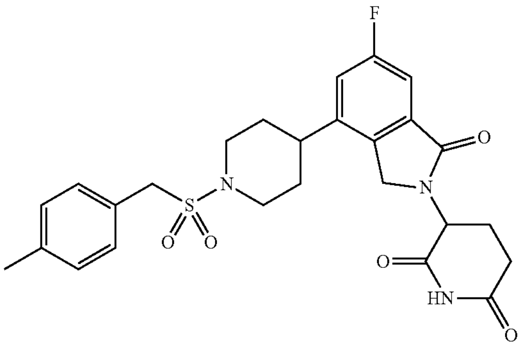

A2025

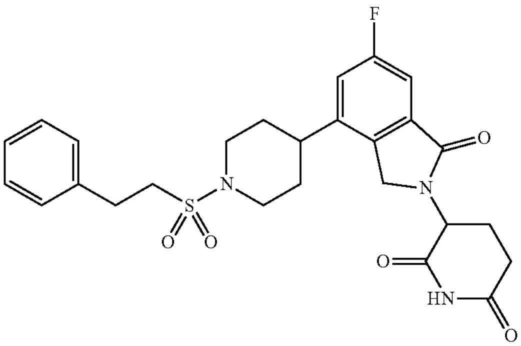

3-(4-(1-((2,6-Dimethylphenyl)sulfonyl)piperidin-4-yl)-6-fluoro-1-oxoisoindolin-2-yl)piperidine-2,6-dione A2026.

3-(6-Fluoro-4-(1-((4-methoxyphenyl)sulfonyl)piperidin-4-yl)-1-oxoisoindolin-2-yl)piperidine-2,6-dione A2027.

A2026

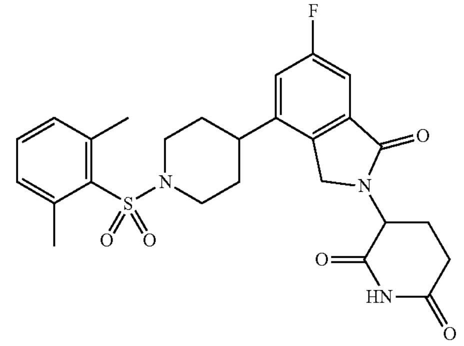

A2027

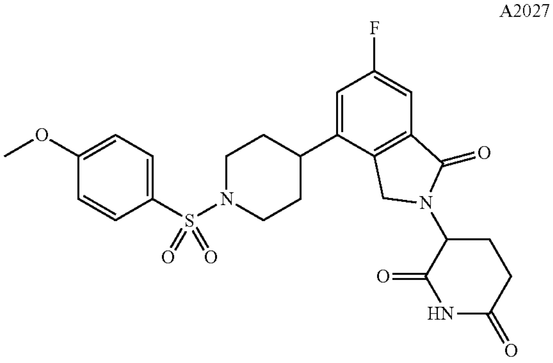

3-(6-Fluoro-4-(1-((3-methoxyphenyl)sulfonyl)piperidin-4-yl)-1-oxoisoindolin-2-yl)piperidine-2,6-dione A2028.

3-(6-Fluoro-4-(1-((6-methoxypyridin-3-yl)sulfonyl)piperidin-4-yl)-1-oxoisoindolin-2-yl)piperidine-2,6-dione A2029.

A2028

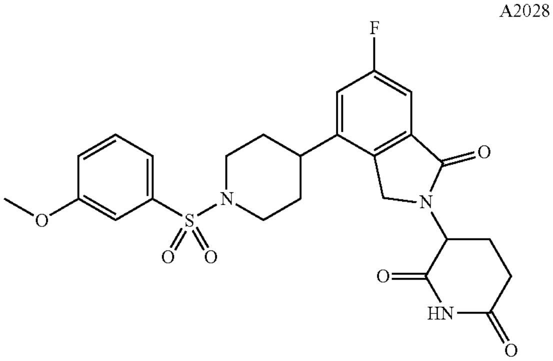

A2029

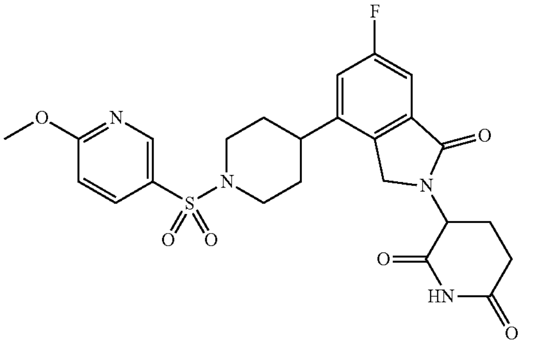

3-(6-Fluoro-4-(1-((2-fluoro-5-methylphenyl)sulfonyl)piperidin-4-yl)-1-oxoisoindolin-2-yl)piperidine-2,6-dione A2030.

3-(6-Fluoro-4-(1-((4-fluoro-2-methylphenyl)sulfonyl)piperidin-4-yl)-1-oxoisoindolin-2-yl)piperidine-2,6-dione A2031.

A2030

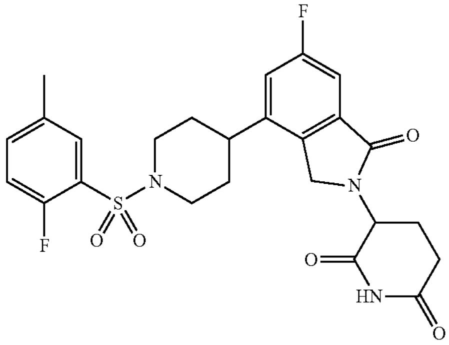

A2031

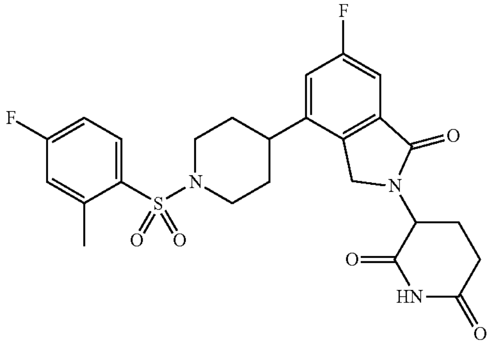

3-(6-Fluoro-4-(1-((2-fluoro-4-methylphenyl)sulfonyl)piperidin-4-yl)-1-oxoisoindolin-2-yl)piperidine-2,6-dione A2032.

3-(4-(1-((3-Chlorophenyl)sulfonyl)piperidin-4-yl)-6-fluoro-1-oxoisoindolin-2-yl)-piperidine-2,6-dione A2033.

A2032

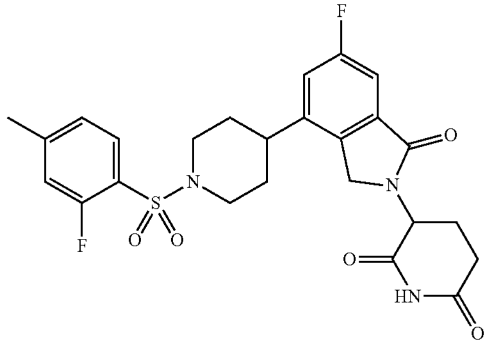

-continued

A2033

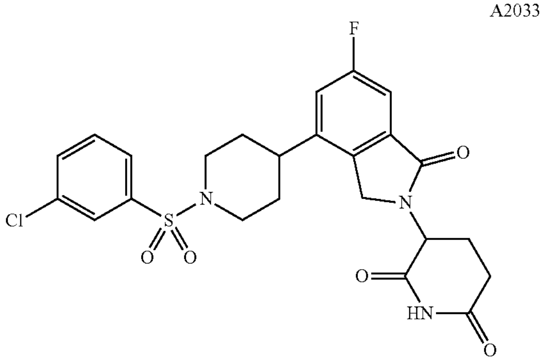

3-(4-(1-((2-Chlorophenyl)sulfonyl)piperidin-4-yl)-6-fluoro-1-oxoisoindolin-2-yl)-piperidine-2,6-dione A2034.

3-(4-(1-((4-Chlorophenyl)sulfonyl)piperidin-4-yl)-6-fluoro-1-oxoisoindolin-2-yl)-piperidine-2,6-dione A2035.

A2034

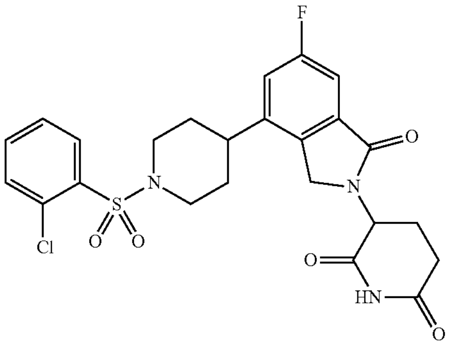

A2035

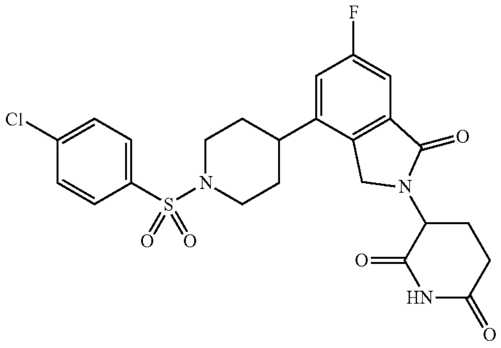

3-(4-(1-((3,4-Difluorophenyl)sulfonyl)piperidin-4-yl)-6-fluoro-1-oxoisoindolin-2-yl)piperidine-2,6-dione A2036.

3-(4-(1-((2,4-Difluorophenyl)sulfonyl)piperidin-4-yl)-6-fluoro-1-oxoisoindolin-2-yl)piperidine-2,6-dione A2037.

A2036

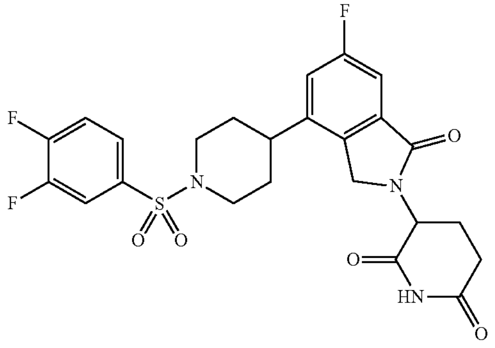

A2037

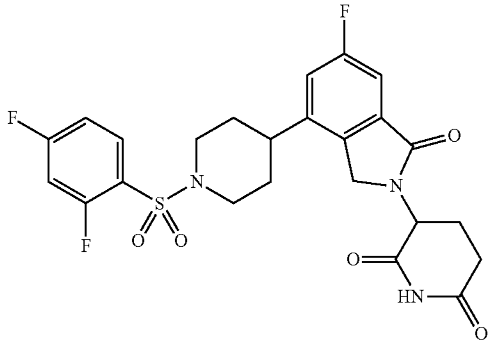

3-(4-(1-((2,5-Difluorophenyl)sulfonyl)piperidin-4-yl)-6-fluoro-1-oxoisoindolin-2-yl)piperidine-2,6-dione A2038.

3-(4-(1-((3,5-Difluorophenyl)sulfonyl)piperidin-4-yl)-6-fluoro-1-oxoisoindolin-2-yl)piperidine-2,6-dione A2039.

A2038

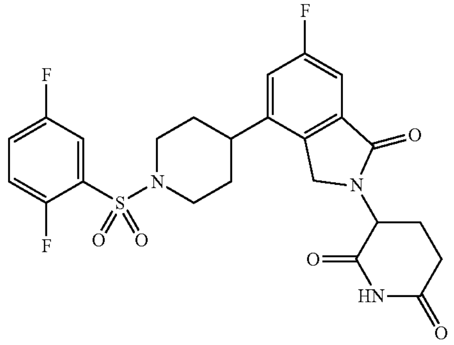

A2039

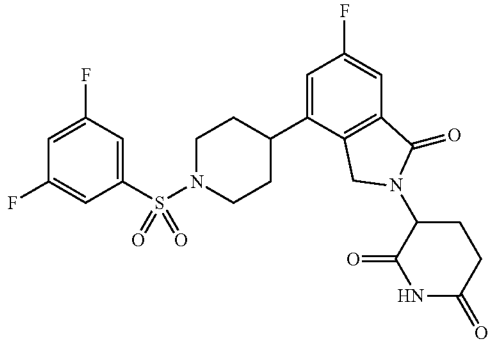

3-(6-Fluoro-1-oxo-4-(1-(pyridin-3-ylsulfonyl)piperidin-4-yl)isoindolin-2-yl)-piperidine-2,6-dione A2040.

2-((4-(2-(2,6-Dioxopiperidin-3-yl)-6-fluoro-1-oxoisoindolin-4-yl)piperidin-1-yl)-sulfonyl)-5-methylbenzonitrile A2041.

A2040

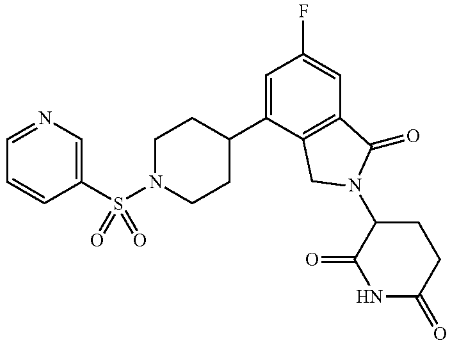

A2041

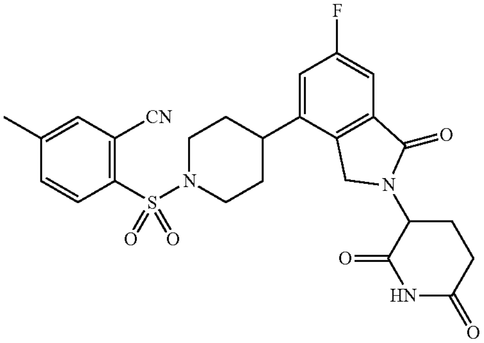

3-(4-(1-((1H-Indol-5-yl)sulfonyl)piperidin-4-yl)-6-fluoro-1-oxoisoindolin-2-yl)-piperidine-2,6-dione A2042.

3-(4-(1-(Benzofuran-5-ylsulfonyl)piperidin-4-yl)-6-fluoro-1-oxoisoindolin-2-yl)-piperidine-2,6-dione A2043.

A2042

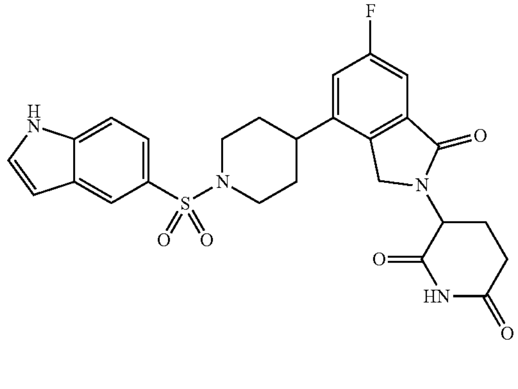

-continued

A2043

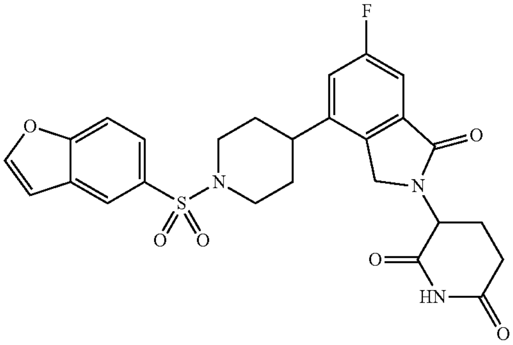

3-(4-(1-((2,3-Dihydrobenzofuran-5-yl)sulfonyl)piperidin-4-yl)-6-fluoro-1-oxoisoindolin-2-yl)piperidine-2,6-dione A2044.

3-(6-Fluoro-4-(1-((4-isopropylphenyl)sulfonyl)piperidin-4-yl)-1-oxoisoindolin-2-yl)piperidine-2,6-dione A2045.

A2044

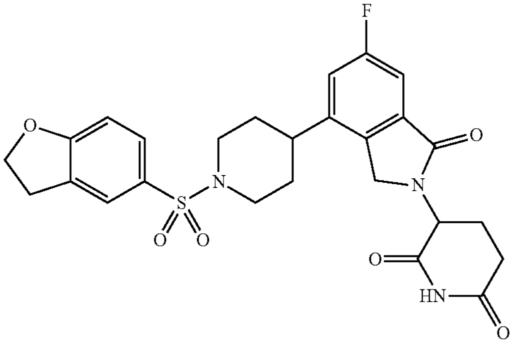

A2045

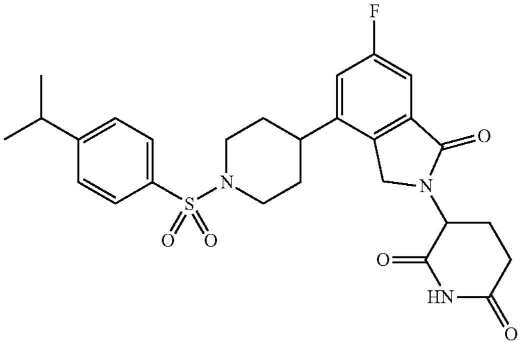

3-(6-Fluoro-4-(1-((3-isopropylphenyl)sulfonyl)piperidin-4-yl)-1-oxoisoindolin-2-yl)piperidine-2,6-dione A2046.

3-((4-(2-(2,6-Dioxopiperidin-3-yl)-6-fluoro-1-oxoisoindolin-4-yl)piperidin-1-yl)-sulfonyl)-4-fluorobenzonitrile A2047.

A2046

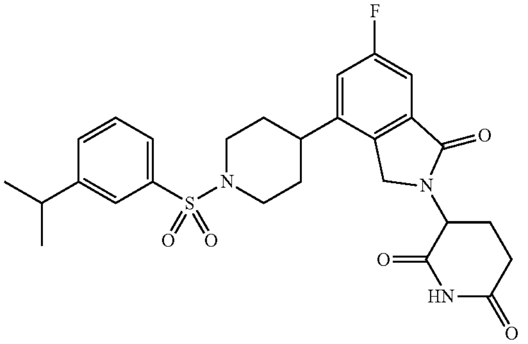

A2047

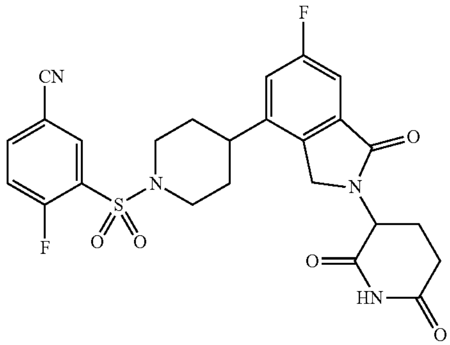

5-((4-(2-(2,6-Dioxopiperidin-3-yl)-6-fluoro-1-oxoisoindolin-4-yl)piperidin-1-yl)-sulfonyl)-2-fluorobenzonitrile A2048.

4-((4-(2-(2,6-Dioxopiperidin-3-yl)-6-fluoro-1-oxoisoindolin-4-yl)piperidin-1-yl)-sulfonyl)benzamide A2049.

A2048

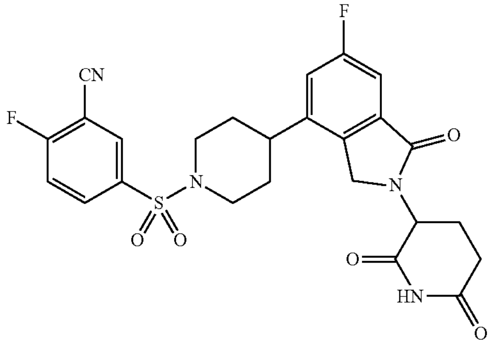

-continued

A2049

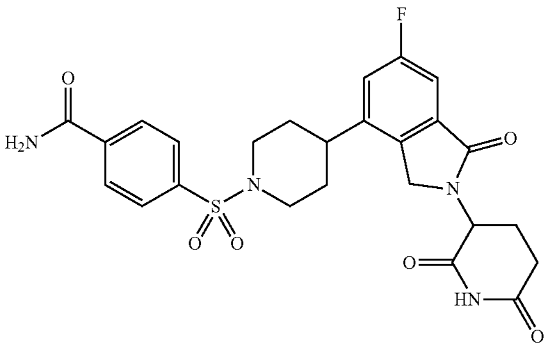

3-(6-Fluoro-4-(1-((3-methoxybenzyl)sulfonyl)piperidin-4-yl)-1-oxoisoindolin-2-yl)piperidine-2,6-dione A2050.

3-(6-Fluoro-4-(1-((3-methoxy-4-methylphenyl)sulfonyl)piperidin-4-yl)-1-oxoisoindolin-2-yl)piperidine-2,6-dione A2051.

A2050

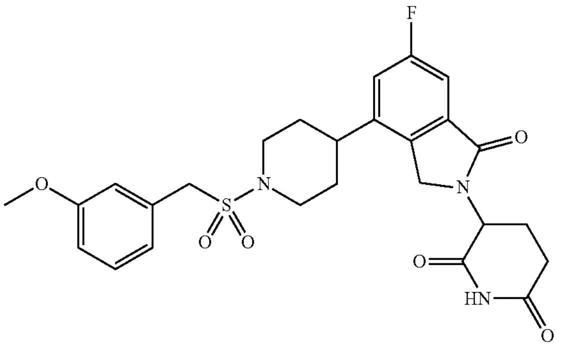

A2051

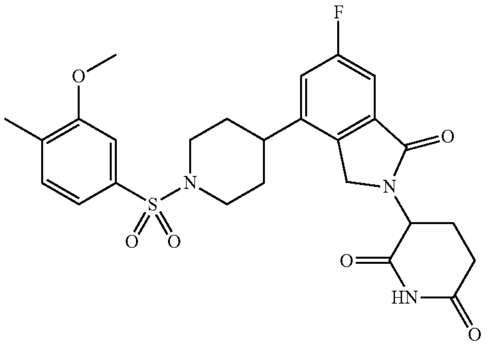

3-(6-Fluoro-4-(1-((5-fluoro-2-methoxyphenyl)sulfonyl)piperidin-4-yl)-1-oxoisoindolin-2-yl)piperidine-2,6-dione A2052.

3-(6-Fluoro-4-(1-((3-fluoro-4-methoxyphenyl)sulfonyl)piperidin-4-yl)-1-oxoisoindolin-2-yl)piperidine-2,6-dione A2053.

A2052

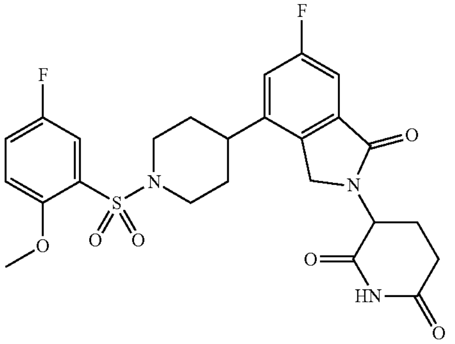

A2053

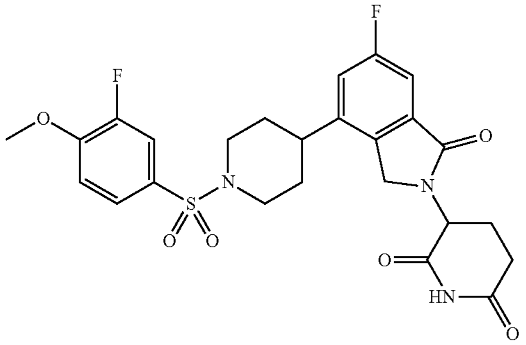

3-(6-Fluoro-1-oxo-4-(1-((5,6,7,8-tetrahydronaphthalen-2-yl)sulfonyl)piperidin-4-yl)isoindolin-2-yl)piperidine-2,6-dione A2054.

3-(6-Fluoro-4-(1-((2-hydroxy-1H-benzo[d]imidazol-6-yl)sulfonyl)piperidin-4-yl)-1-oxoisoindolin-2-yl)piperidine-2,6-dione A2055.

A2054

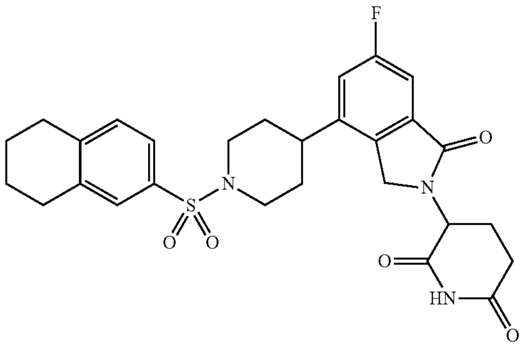

-continued

A2055

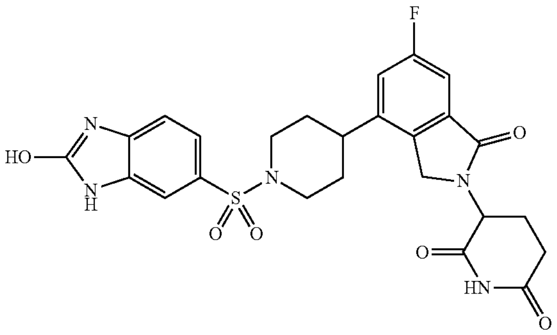

3-(4-(1-((4-(Tert-butyl)phenyl)sulfonyl)piperidin-4-yl)-6-fluoro-1-oxoisoindolin-2-yl)piperidine-2,6-dione A2056.

3-(4-(1-((3-(Tert-butyl)phenyl)sulfonyl)piperidin-4-yl)-6-fluoro-1-oxoisoindolin-2-yl)piperidine-2,6-dione A2057.

A2056

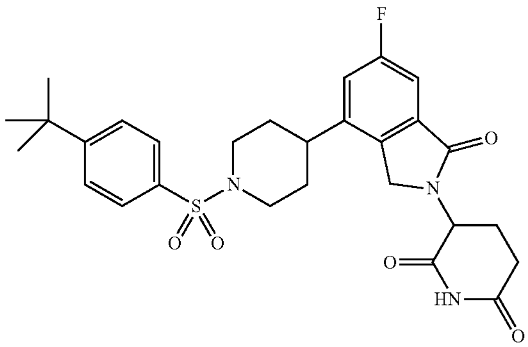

A2057

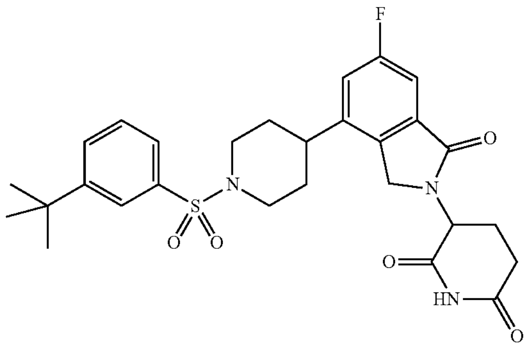

N-(3-((4-(2-(2,6-Dioxopiperidin-3-yl)-6-fluoro-1-oxoisoindolin-4-yl)piperidin-1-yl)sulfonyl)phenyl)acetamide A2058.

N-(4-((4-(2-(2,6-Dioxopiperidin-3-yl)-6-fluoro-1-oxoisoindolin-4-yl)piperidin-1-yl)sulfonyl)phenyl)acetamide A2059.

A2058

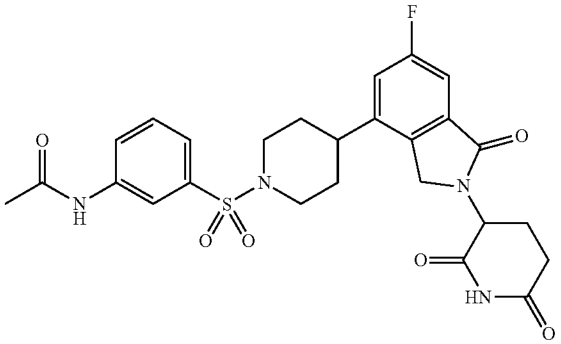

A2059

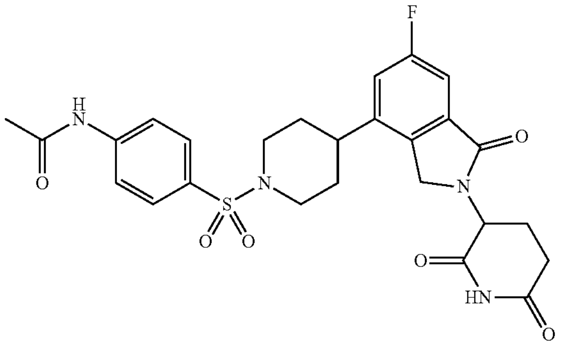

4-((4-(2-(2,6-Dioxopiperidin-3-yl)-6-fluoro-1-oxoisoindolin-4-yl)piperidin-1-yl)-sulfonyl)-N-methylbenzamide A2060.

2-Chloro-4-((4-(2-(2,6-dioxopiperidin-3-yl)-6-fluoro-1-oxoisoindolin-4-yl)-piperidin-1-yl)sulfonyl)benzonitrile A2061.

A2060

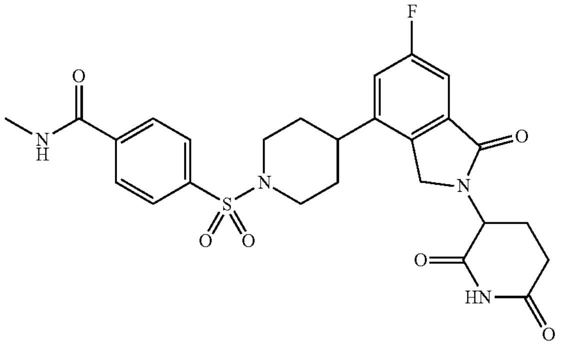

-continued

A2061

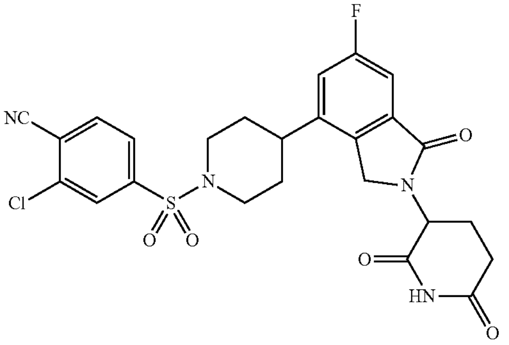

3-(4-(1-((5-Chloro-2-methoxypyridin-3-yl)sulfonyl)piperidin-4-yl)-6-fluoro-1-oxoisoindolin-2-yl)piperidine-2,6-dione A2062.

3-(4-(1-((4-(Difluoromethoxy)phenyl)sulfonyl)piperidin-4-yl)-6-fluoro-1-oxoisoindolin-2-yl)piperidine-2,6-dione A2063.

A2062

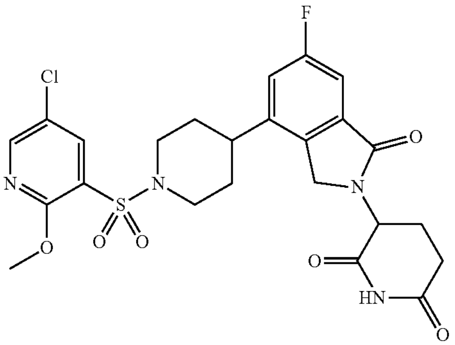

A2063

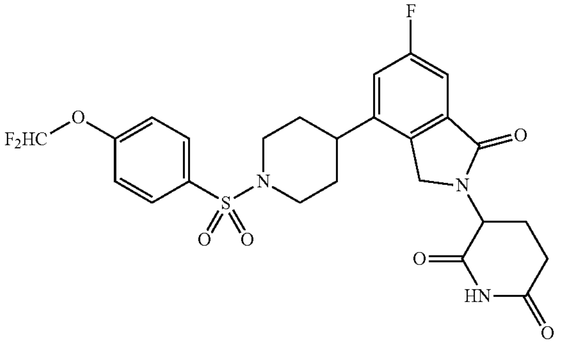

3-(6-Fluoro-4-(1-((4-(oxazol-5-yl)phenyl)sulfonyl)piperidin-4-yl)-1-oxoisoindolin-2-yl)piperidine-2,6-dione A2064.

3-(6-Fluoro-1-oxo-4-(1-((4-(trifluoromethyl)phenyl)sulfonyl)piperidin-4-yl)-isoindolin-2-yl)piperidine-2,6-dione A2065.

A2064

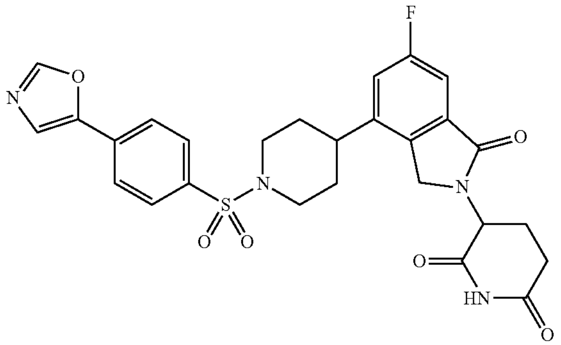

A2065

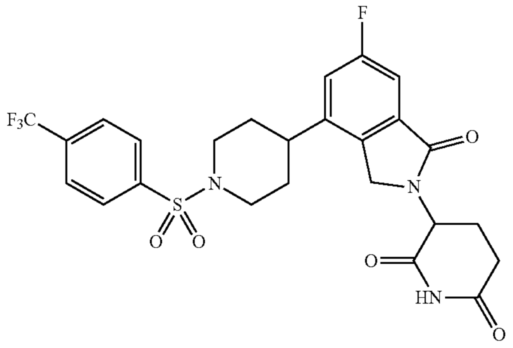

3-(6-Fluoro-1-oxo-4-(1-((3-(trifluoromethyl)phenyl)sulfonyl)piperidin-4-yl)-isoindolin-2-yl)piperidine-2,6-dione A2066.

3-(6-Fluoro-1-oxo-4-(1-((2-(trifluoromethyl)phenyl)sulfonyl)piperidin-4-yl)-isoindolin-2-yl)piperidine-2,6-dione A2067.

A2066

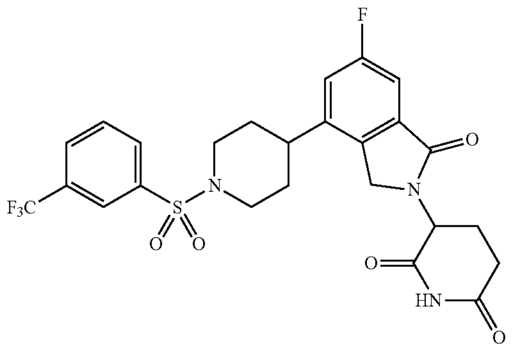

-continued

A2067

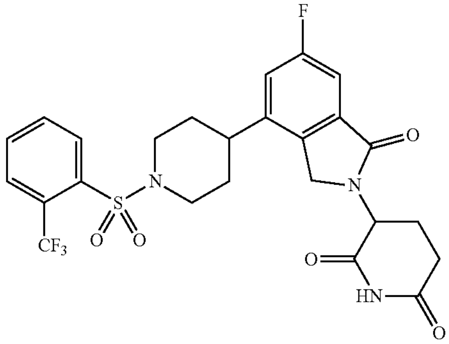

3-(6-Fluoro-1-oxo-4-(1-((6-(trifluoromethyl)pyridin-3-yl)sulfonyl)piperidin-4-yl)-isoindolin-2-yl)piperidine-2,6-dione A2068.

3-(6-Fluoro-1-oxo-4-(1-((2-oxo-1,2,3,4-tetrahydroquinolin-6-yl)sulfonyl)-piperidin-4-yl)isoindolin-2-yl)piperidine-2,6-dione A2069.

A2068

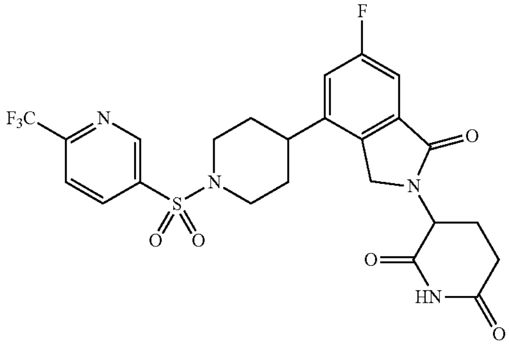

A2069

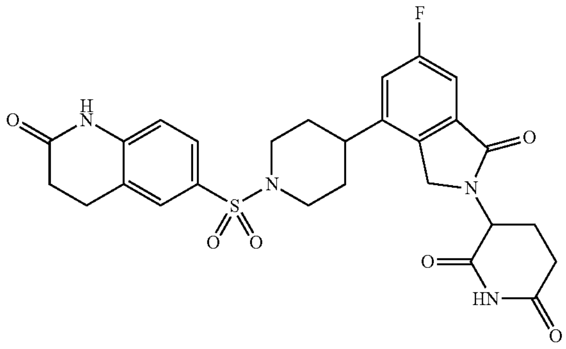

2-((4-(2-(2,6-Dioxopiperidin-3-yl)-6-fluoro-1-oxoisoindolin-4-yl)piperidin-1-yl)-sulfonyl)-N,N-dimethylbenzamide A2070.

3-(4-(1-((3-Bromophenyl)sulfonyl)piperidin-4-yl)-6-fluoro-1-oxoisoindolin-2-yl)-piperidine-2,6-dione A2071.

A2070

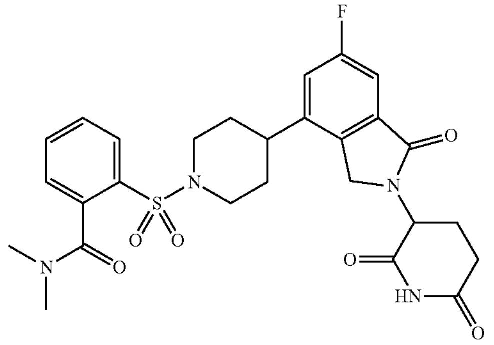

A2071

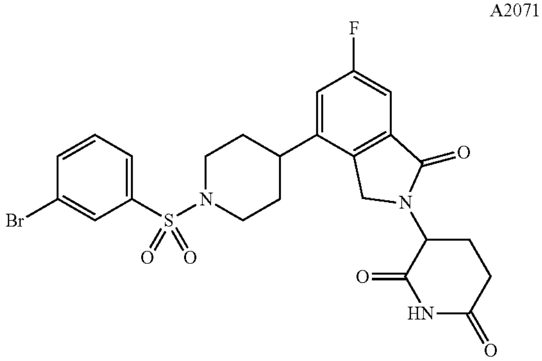

3-(4-(1-((2-Bromophenyl)sulfonyl)piperidin-4-yl)-6-fluoro-1-oxoisoindolin-2-yl)-piperidine-2,6-dione A2072.

3-(6-Fluoro-1-oxo-4-(1-((1-(o-tolyl)-1H-pyrazol-4-yl)sulfonyl)piperidin-4-yl)-isoindolin-2-yl)piperidine-2,6-dione A2073.

A2072

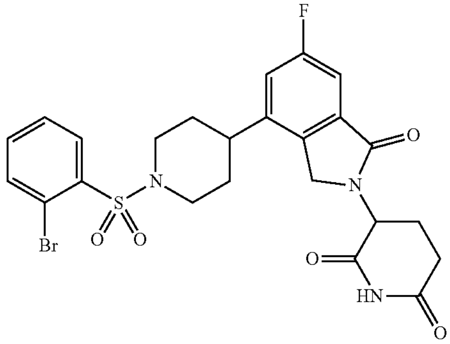

A2073

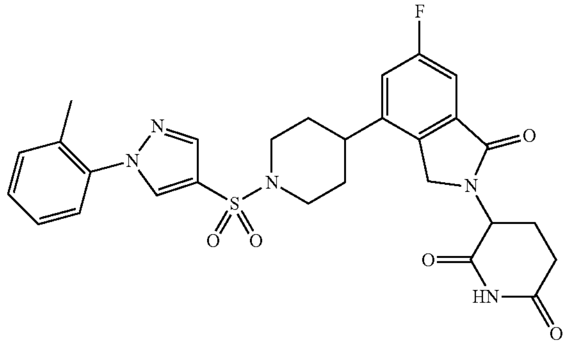

3-(6-Fluoro-1-oxo-4-(1-((4-(trifluoromethyl)benzyl)sulfonyl)piperidin-4-yl)-isoindolin-2-yl)piperidine-2,6-dione A2074.

3-(6-Fluoro-1-oxo-4-(1-((2-(trifluoromethoxy)phenyl)sulfonyl)piperidin-4-yl)-isoindolin-2-yl)piperidine-2,6-dione A2075.

A2074

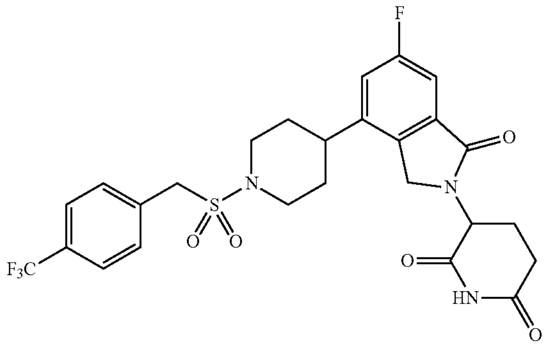

A2075

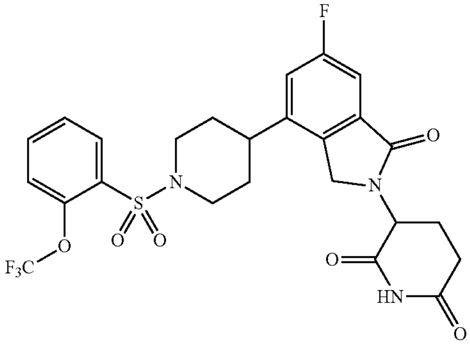

3-(4-(1-((1-Chloroisoquinolin-5-yl)sulfonyl)piperidin-4-yl)-6-fluoro-1-oxoisoindolin-2-yl)piperidine-2,6-dione A2076.

3-(6-Fluoro-4-(1-(isoquinolin-5-ylsulfonyl)piperidin-4-yl)-1-oxoisoindolin-2-yl)-piperidine-2,6-dione A2077.

A2076

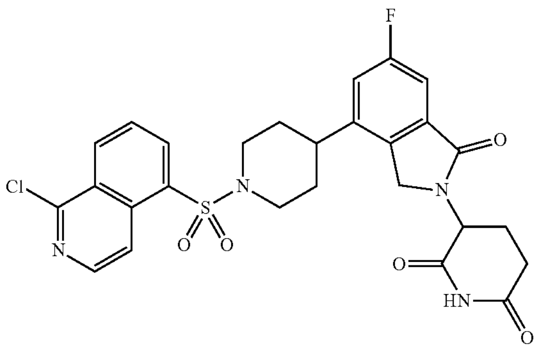

-continued

A2077

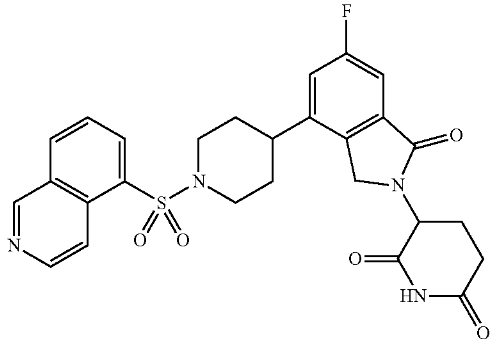

3-(6-Fluoro-1-oxo-4-(1-((4-(pyridin-2-yloxy)phenyl)sulfonyl)piperidin-4-yl)-isoindolin-2-yl)piperidine-2,6-dione A2078.

3-(6-Fluoro-1-oxo-4-(1-((6-phenoxypyridin-3-yl)sulfonyl)piperidin-4-yl)-isoindolin-2-yl)piperidine-2,6-dione A2079.

A2078

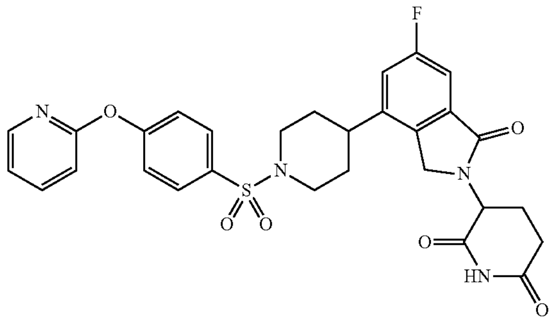

A2079

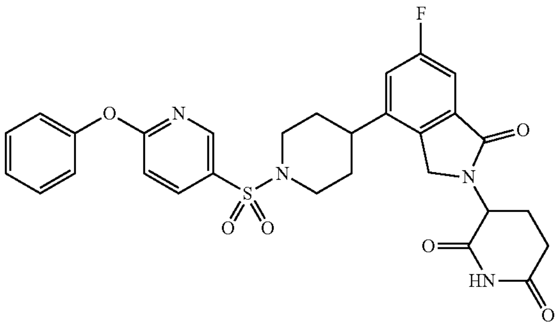

3-(4-(1-((5-(Dimethylamino)naphthalen-1-yl)sulfonyl)piperidin-4-yl)-6-fluoro-1-oxoisoindolin-2-yl)piperidine-2,6-dione A2080.

3-(4-(1-((6-(Dimethylamino)naphthalen-2-yl)sulfonyl)piperidin-4-yl)-6-fluoro-1-oxoisoindolin-2-yl)piperidine-2,6-dione A2081.

A2080

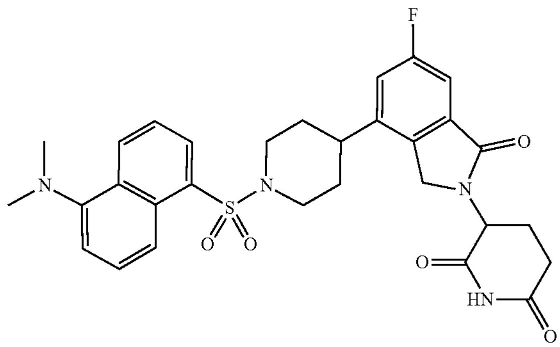

A2081

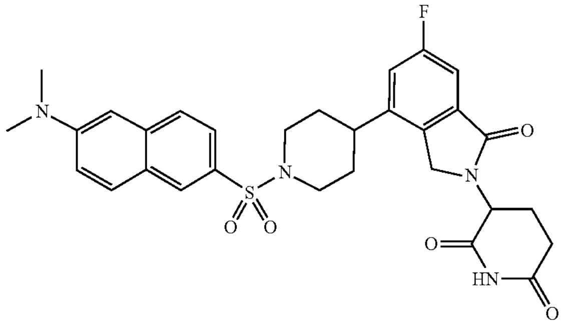

3-(4-(1-((4-(Benzyloxy)phenyl)sulfonyl)piperidin-4-yl)-6-fluoro-1-oxoisoindolin-2-yl)piperidine-2,6-dione A2082.

Tert-butyl 4-((4-(2-(2,6-dioxopiperidin-3-yl)-6-fluoro-1-oxoisoindolin-4-yl)-piperidin-1-yl)sulfonyl)piperidine-1-carboxylate A2083.

A2082

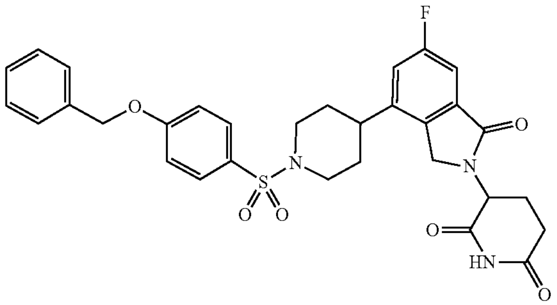

A2083

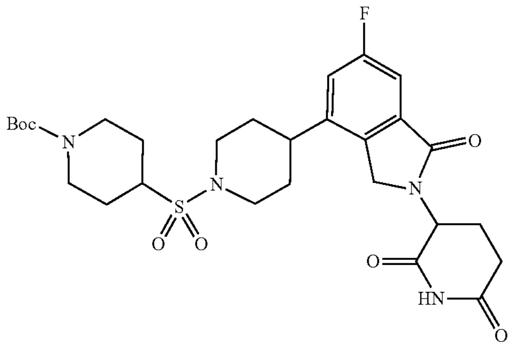

Benzyl 4-((4-(2-(2,6-dioxopiperidin-3-yl)-6-fluoro-1-oxoisoindolin-4-yl)-piperidin-1-yl)sulfonyl)piperidine-1-carboxylate A2084.

3-(6-Fluoro-1-oxo-4-(1-((2-(2,2,2-trifluoroacetyl)-1,2,3,4-tetrahydroisoquinolin-7-yl)sulfonyl)piperidin-4-yl)isoindolin-2-yl)piperidine-2,6-dione A2085.

A2084

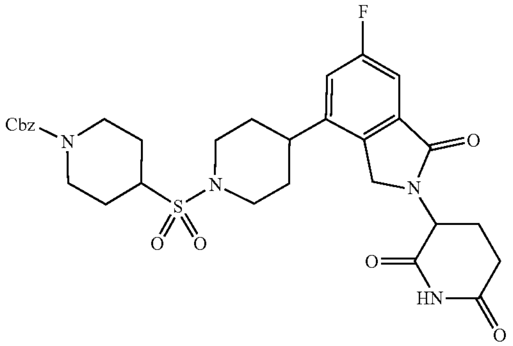

A2085

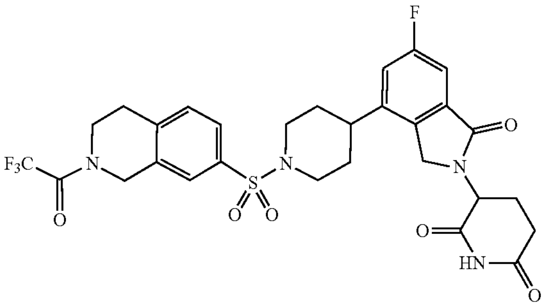

Benzyl 4-(((4-(2-(2,6-dioxopiperidin-3-yl)-6-fluoro-1-oxoisoindolin-4-yl)-piperidin-1-yl)sulfonyl)methyl)piperidine-1-carboxylate A2086.

3-(4-(1-(Ethylsulfonyl)piperidin-4-yl)-6-fluoro-1-oxoisoindolin-2-yl)piperidine-2,6-dione A2087.

A2086

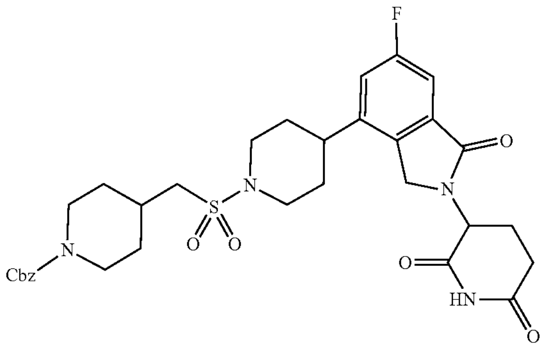

-continued

A2087

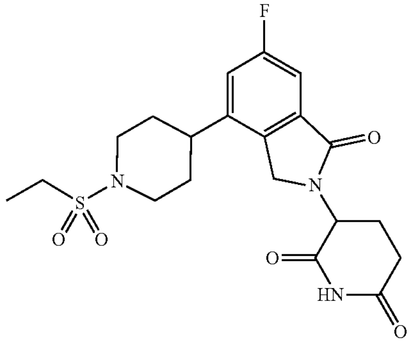

3-(4-(1-((5-Chlorothiophen-2-yl)sulfonyl)piperidin-4-yl)-6-fluoro-1-oxoisoindolin-2-yl)piperidine-2,6-dione A2088.

3-(4-(1-((3-Chloro-4-methylphenyl)sulfonyl)piperidin-4-yl)-6-fluoro-1-oxoisoindolin-2-yl)piperidine-2,6-dione A2089.

A2088

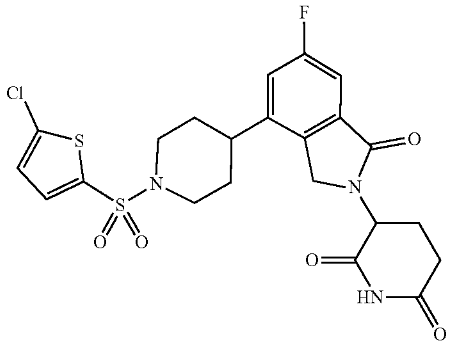

A2089

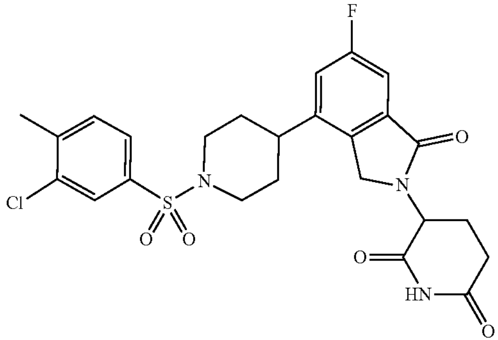

3-(4-(1-((2-Chloro-6-methylphenyl)sulfonyl)piperidin-4-yl)-6-fluoro-1-oxoisoindolin-2-yl)piperidine-2,6-dione A2090.

3-(4-(1-((3,5-Difluorobenzyl)sulfonyl)piperidin-4-yl)-6-fluoro-1-oxoisoindolin-2-yl)piperidine-2,6-dione A2091.

A2090

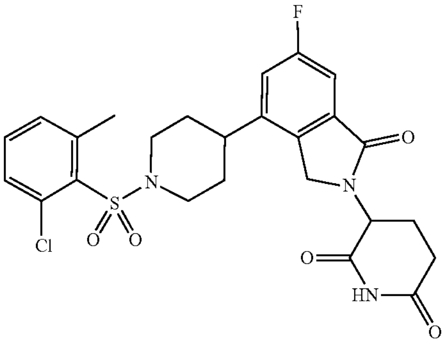

A2091

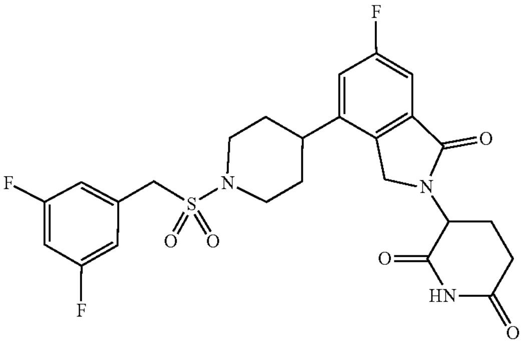

3-(6-Fluoro-4-(1-(naphthalen-2-ylsulfonyl)piperidin-4-yl)-1-oxoisoindolin-2-yl)piperidine-2,6-dione A2092.

3-(6-Fluoro-1-oxo-4-(1-(quinolin-8-ylsulfonyl)piperidin-4-yl)isoindolin-2-yl)-piperidine-2,6-dione A2093.

A2092

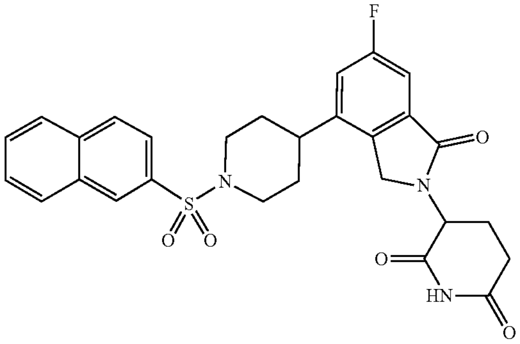

A2093

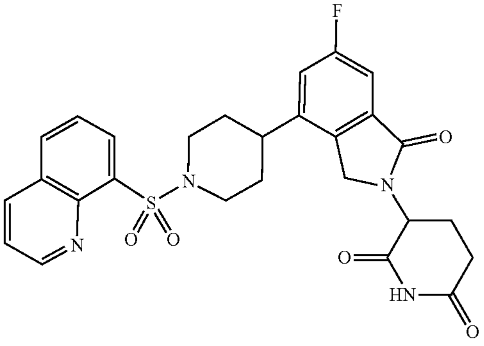

3-(6-Fluoro-4-(1-(isoquinolin-5-ylsulfonyl)piperidin-4-yl)-1-oxoisoindolin-2-yl)-piperidine-2,6-dione A2094.

3-(6-Fluoro-1-oxo-4-(1-(quinoxalin-5-ylsulfonyl)piperidin-4-yl)isoindolin-2-yl)-piperidine-2,6-dione A2095.

A2094

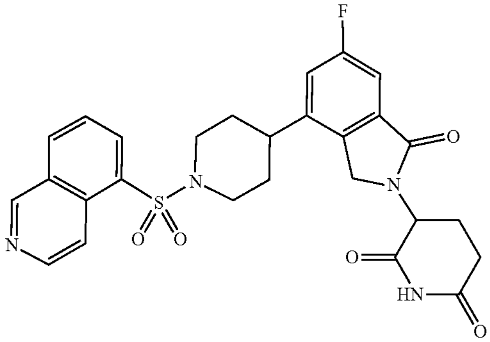

A2095

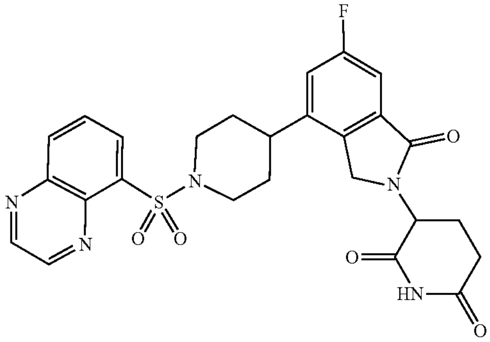

3-Chloro-4-((4-(2-(2,6-dioxopiperidin-3-yl)-6-fluoro-1-oxoisoindolin-4-yl)-piperidin-1-yl)sulfonyl)benzonitrile A2096.

3-(4-(1-(Benzo[d][1,3]dioxol-5-ylsulfonyl)piperidin-4-yl)-6-fluoro-1-oxoisoindolin-2-yl)piperidine-2,6-dione A2097.

A2096

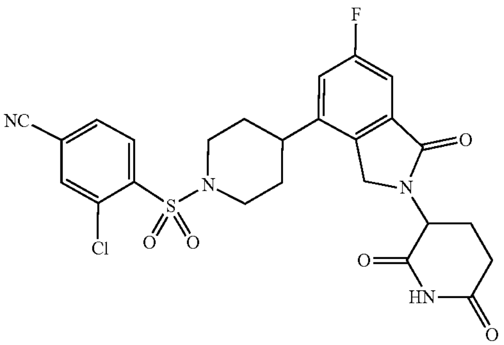

-continued

A2097

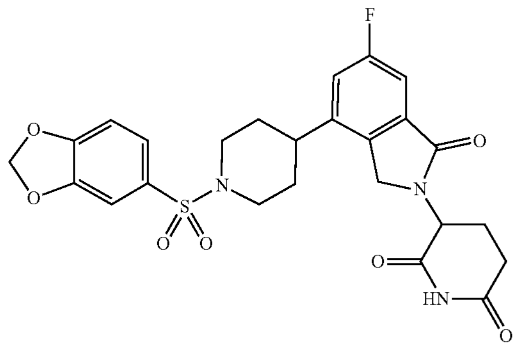

3-(4-(1-(Benzo[d]thiazol-6-ylsulfonyl)piperidin-4-yl)-6-fluoro-1-oxoisoindolin-2-yl)piperidine-2,6-dione A2098.

3-(4-(1-((2,4-Dichlorophenyl)sulfonyl)piperidin-4-yl)-6-fluoro-1-oxoisoindolin-2-yl)piperidine-2,6-dione A2099.

A2098

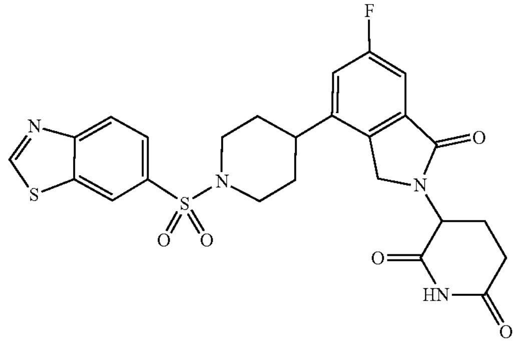

A2099

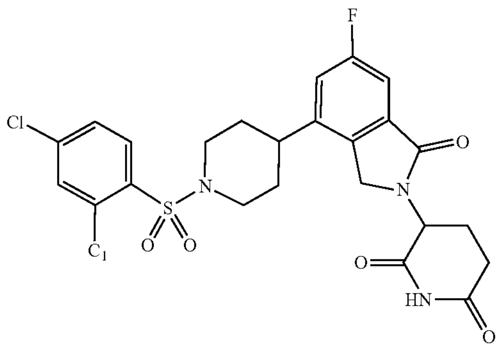

3-(4-(1-((2,5-Dichlorophenyl)sulfonyl)piperidin-4-yl)-6-fluoro-1-oxoisoindolin-2-yl)piperidine-2,6-dione A2100.

A2100

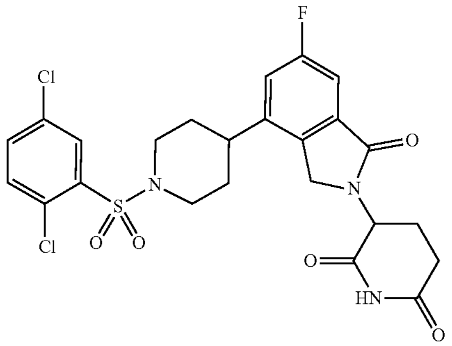

3-(6-Fluoro-1-oxo-4-(4-(5,6,7,8-tetrahydronaphthalene-1-carbonyl)piperazin-1-yl)isoindolin-2-yl)piperidine-2,6-dione B0001.

3-(6-Fluoro-4-(4-(1-methyl-1H-indole-5-carbonyl)piperazin-1-yl)-1-oxoisoindolin-2-yl)piperidine-2,6-dione B0002.

B0001

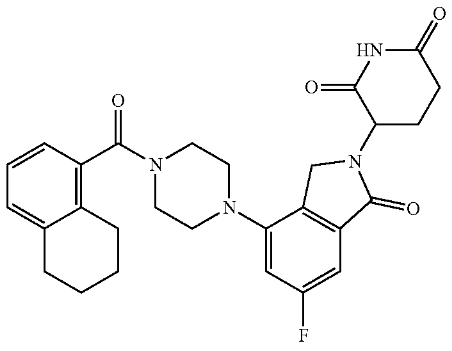

B0002

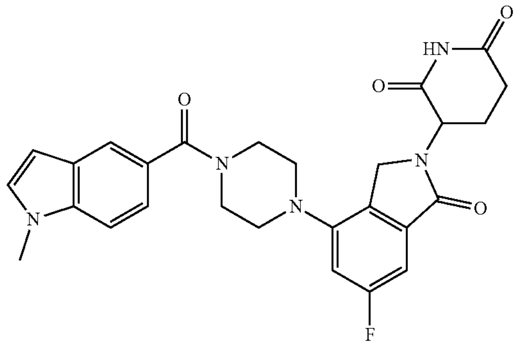

3-(6-Fluoro-1-oxo-4-(4-(quinoxaline-5-carbonyl)piperazin-1-yl)isoindolin-2-yl)-piperidine-2,6-dione B0003.

3-(6-Fluoro-1-oxo-4-(4-(quinazoline-6-carbonyl)piperazin-1-yl)isoindolin-2-yl)-piperidine-2,6-dione B0004.

B0003

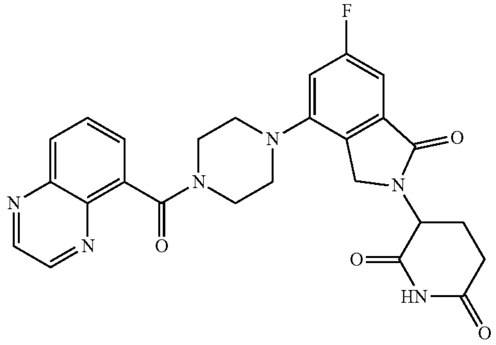

B0004

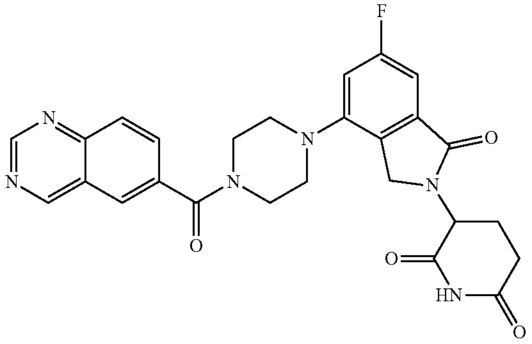

3-(4-(4-(2-(Dimethylamino)benzoyl)piperazin-1-yl)-6-fluoro-1-oxoisoindolin-2-yl)piperidine-2,6-dione B0005.

3-(4-(4-(4-(Dimethylamino)benzoyl)piperazin-1-yl)-6-fluoro-1-oxoisoindolin-2-yl)piperidine-2,6-dione B0006.

B0005

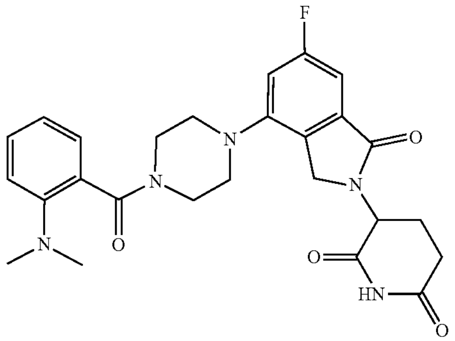

B0006

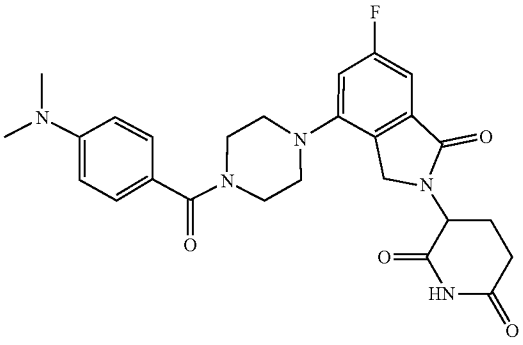

3-(4-(4-(2,3-Dihydrobenzofuran-7-carbonyl)piperazin-1-yl)-6-fluoro-1-oxoisoindolin-2-yl)piperidine-2,6-dione B0007.

3-(4-(4-(Benzo[d]oxazole-5-carbonyl)piperazin-1-yl)-6-fluoro-1-oxoisoindolin-2-yl)piperidine-2,6-dione B0008.

B0007

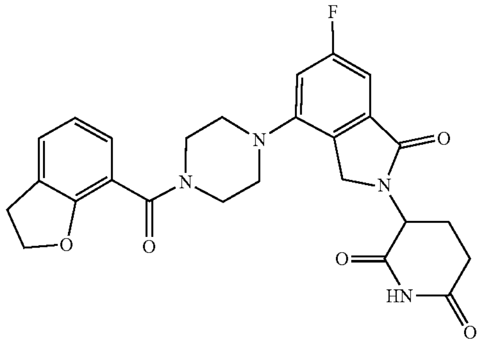

B0008

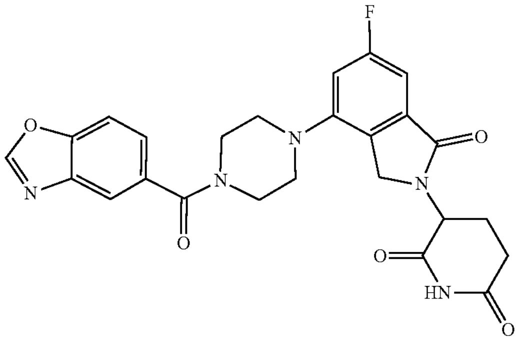

3-(4-(4-(1H-Benzo[d]imidazole-7-carbonyl)piperazin-1-yl)-6-fluoro-1-oxoisoindolin-2-yl)piperidine-2,6-dione B0009.

3-(6-Fluoro-4-(4-(imidazo[1,2-a]pyridine-2-carbonyl)piperazin-1-yl)-1-oxoisoindolin-2-yl)piperidine-2,6-dione B0010.

B0009

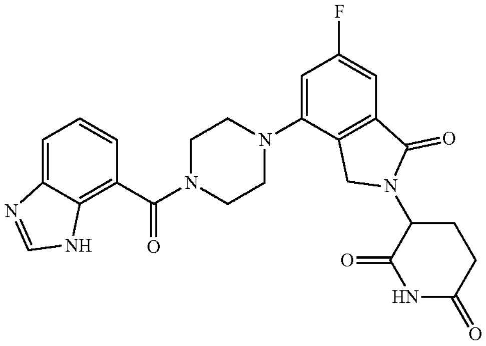

-continued

B0010

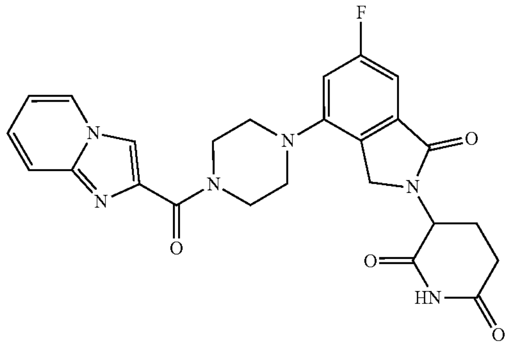

3-(4-(4-(1H-Pyrrolo[3,2-b]pyridine-6-carbonyl)piperazin-1-yl)-6-fluoro-1-oxoisoindolin-2-yl)piperidine-2,6-dione B0011.

3-(6-Fluoro-4-(4-(imidazo[1,2-a]pyridine-3-carbonyl)piperazin-1-yl)-1-oxoisoindolin-2-yl)piperidine-2,6-dione B0012.

B0011

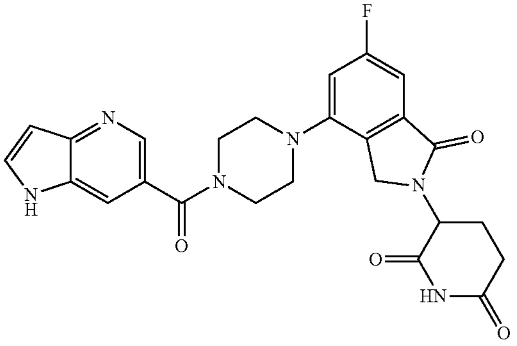

B0012

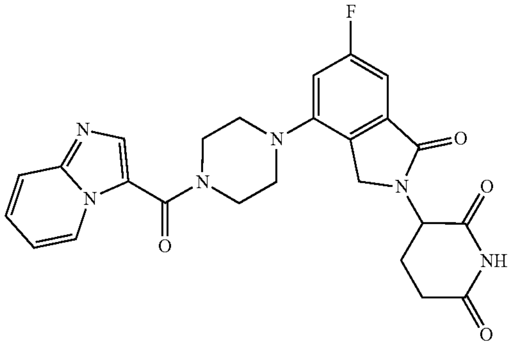

3-(4-(4-(Benzofuran-6-carbonyl)piperazin-1-yl)-6-fluoro-1-oxoisoindolin-2-yl)-piperidine-2,6-dione B0013.

3-(6-Fluoro-1-oxo-4-(4-(2-(piperidin-1-yl)acetyl)piperazin-1-yl)isoindolin-2-yl)-piperidine-2,6-dione B0014.

B0013

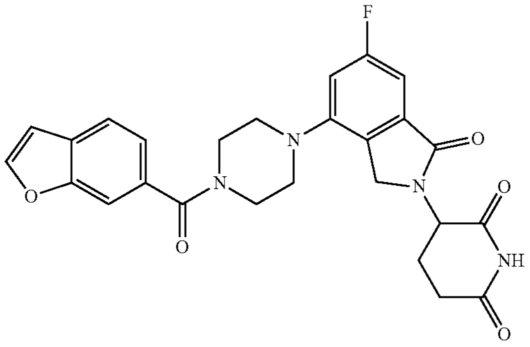

B0014

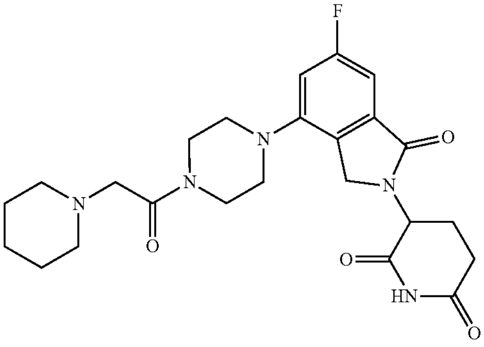

2-(2-(4-(2-(2,6-Dioxopiperidin-3-yl)-6-fluoro-1-oxoisoindolin-4-yl)piperazin-1-yl)-2-oxoethyl)benzonitrile B0015.

3-(2-(4-(2-(2,6-Dioxopiperidin-3-yl)-6-fluoro-1-oxoisoindolin-4-yl)piperazin-1-yl)-2-oxoethyl)benzonitrile B0016.

B0015

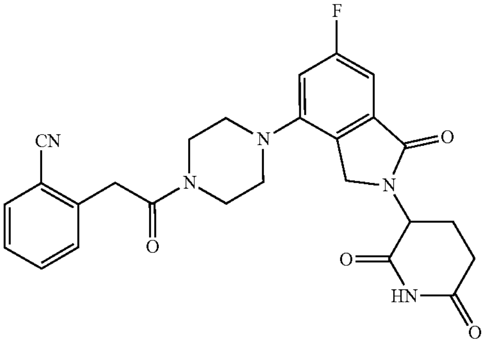

-continued

B0016

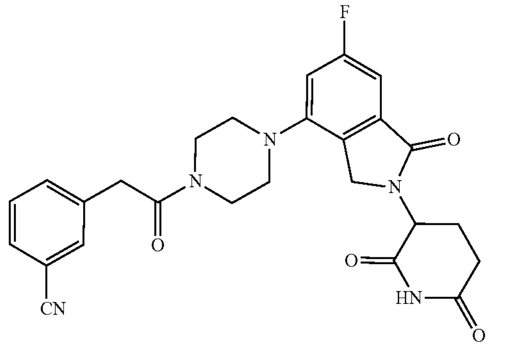

4-(2-(4-(2-(2,6-Dioxopiperidin-3-yl)-6-fluoro-1-oxoisoindolin-4-yl)piperazin-1-yl)-2-oxoethyl)benzonitrile B0017.

3-(4-(4-(1H-Indole-7-carbonyl)piperazin-1-yl)-6-fluoro-1-oxoisoindolin-2-yl)-piperidine-2,6-dione B0018.

B0017

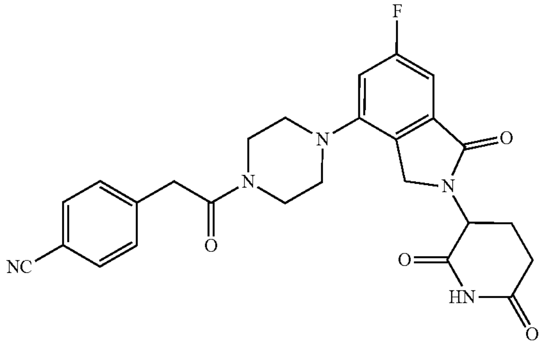

B0018

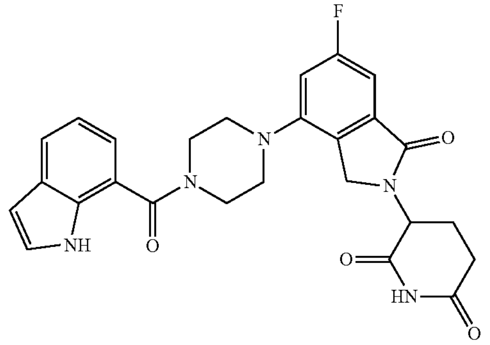

3-(4-(4-(1-Ethylpiperidine-4-carbonyl)piperazin-1-yl)-6-fluoro-1-oxoisoindolin-2-yl)piperidine-2,6-dione B0019.

3-(6-Fluoro-1-oxo-4-(4-(2-(p-tolyl)acetyl)piperazin-1-yl) isoindolin-2-yl)-piperidine-2,6-dione B0020.

B0019

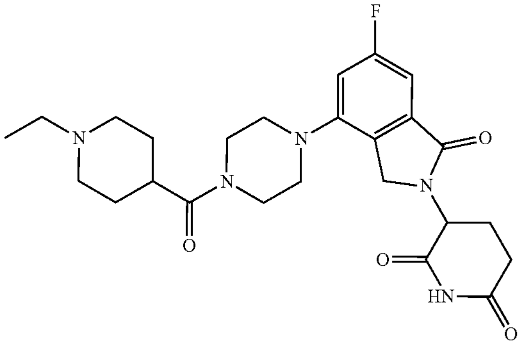

B0020

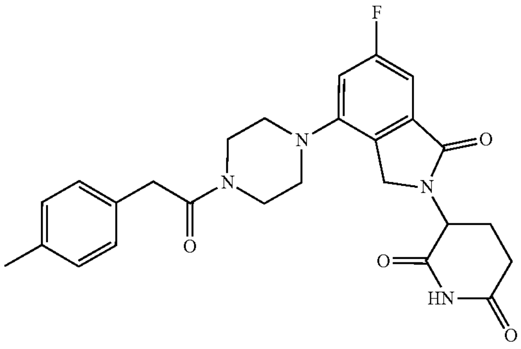

2-(4-(2-(2,6-Dioxopiperidin-3-yl)-6-fluoro-1-oxoisoindolin-4-yl)piperazin-1-carbonyl)benzonitrile B0021.

3-(4-(2-(2,6-Dioxopiperidin-3-yl)-6-fluoro-1-oxoisoindolin-4-yl)piperazin-1-carbonyl)benzonitrile B0022.

B0021

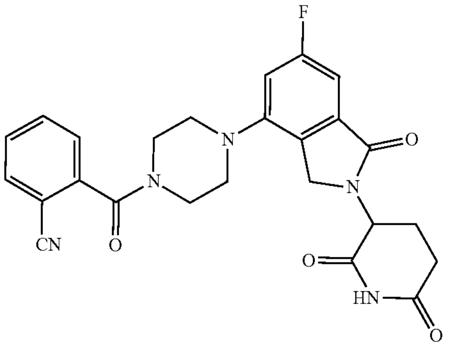

-continued

B0022

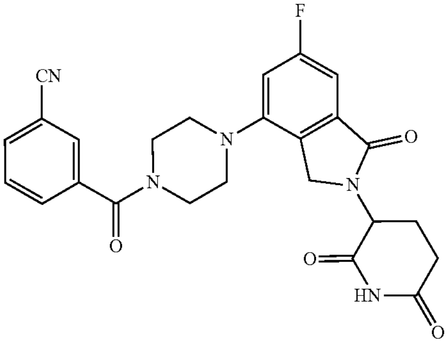

3-(6-Fluoro-4-(4-(4-fluorobenzoyl)piperazin-1-yl)-1-oxoisoindolin-2-yl)-piperidine-2,6-dione B0023.

3-(6-Fluoro-4-(4-(3-fluorobenzoyl)piperazin-1-yl)-1-oxoisoindolin-2-yl)-piperidine-2,6-dione B0024.

B0023

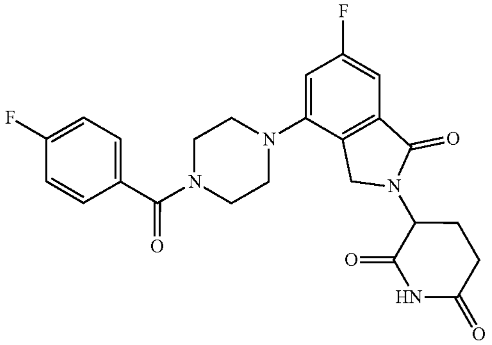

B0024

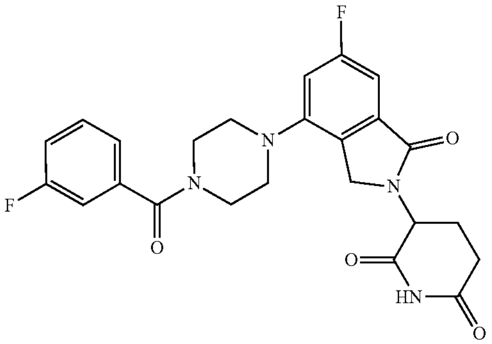

3-(6-Fluoro-4-(4-(2-fluorobenzoyl)piperazin-1-yl)-1-oxoisoindolin-2-yl)-piperidine-2,6-dione B0025.

3-(6-Fluoro-4-(4-(2-methylbenzoyl)piperazin-1-yl)-1-oxoisoindolin-2-yl)-piperidine-2,6-dione B0026.

B0025

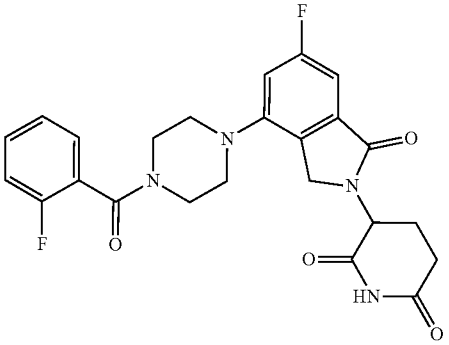

B0026

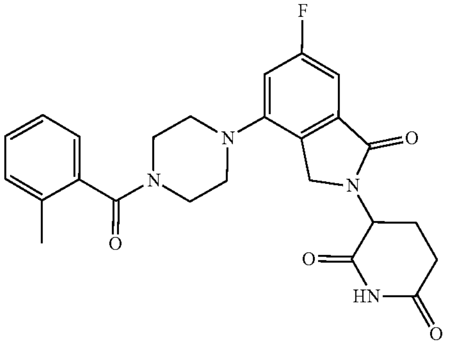

3-(6-Fluoro-4-(4-(3-methylbenzoyl)piperazin-1-yl)-1-oxoisoindolin-2-yl)-piperidine-2,6-dione B0027.

3-(6-Fluoro-4-(4-(4-methylbenzoyl)piperazin-1-yl)-1-oxoisoindolin-2-yl)-piperidine-2,6-dione B0028.

B0027

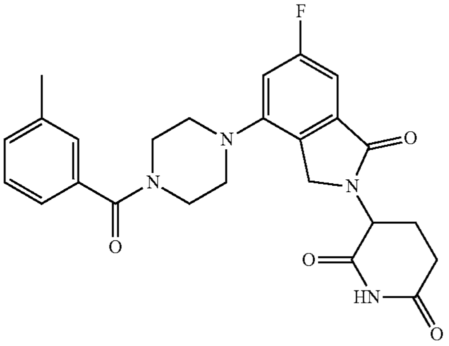

B0028

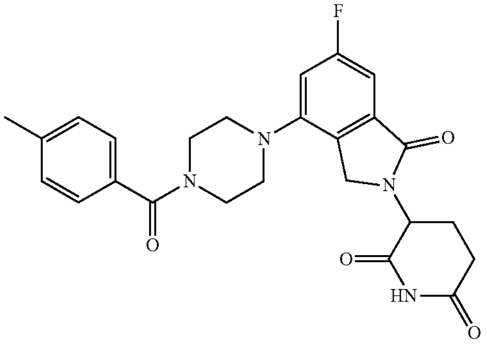

3-(4-(4-(2-Cyclopentylacetyl)piperazin-1-yl)-6-fluoro-1-oxoisoindolin-2-yl)-piperidine-2,6-dione B0029.

3-(4-(4-(Cyclohexanecarbonyl)piperazin-1-yl)-6-fluoro-1-oxoisoindolin-2-yl)-piperidine-2,6-dione B0030.

B0029

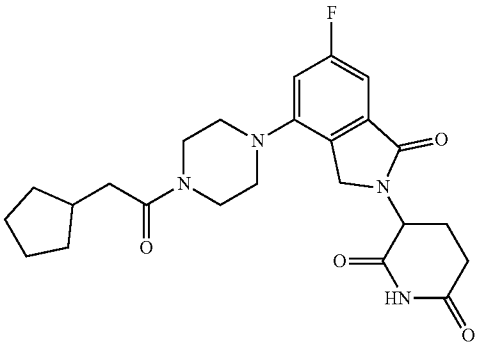

B0030

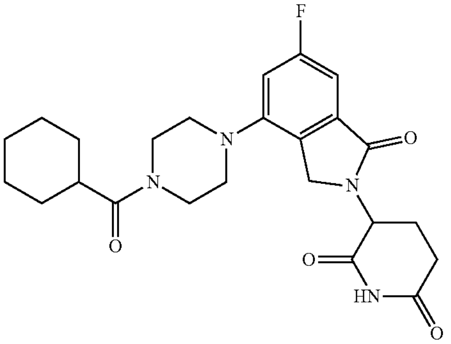

3-(4-(4-(3,3-Dimethylcyclobutane-1-carbonyl)piperazin-1-yl)-6-fluoro-1-oxoisoindolin-2-yl)piperidine-2,6-dione B0031.

3-(6-Fluoro-1-oxo-4-(4-(pyrimidine-5-carbonyl)piperazin-1-yl)isoindolin-2-yl)-piperidine-2,6-dione B0032.

B0031

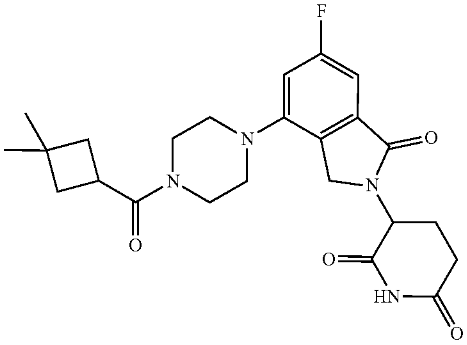

-continued

B0032

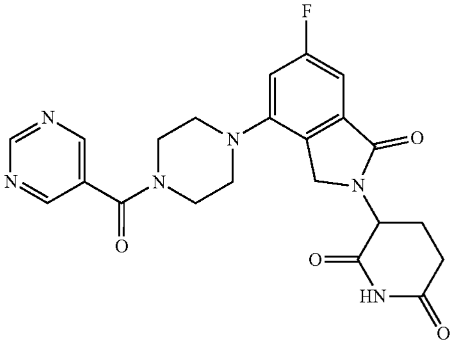

3-(6-Fluoro-1-oxo-4-(4-(pyridazine-4-carbonyl)piperazin-1-yl)isoindolin-2-yl)-piperidine-2,6-dione B0033.

3-(6-Fluoro-1-oxo-4-(4-(pyrimidine-4-carbonyl)piperazin-1-yl)isoindolin-2-yl)-piperidine-2,6-dione B0034.

B0033

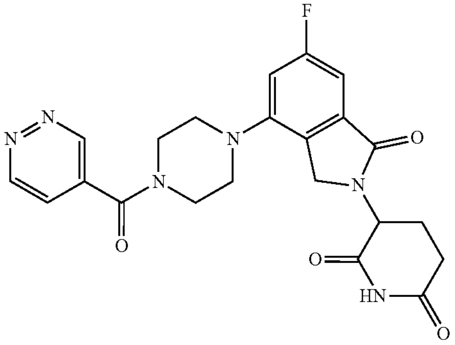

B0034

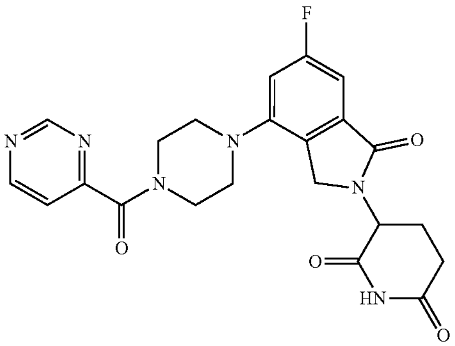

3-(6-Fluoro-1-oxo-4-(4-picolinoylpiperazin-1-yl)isoindolin-2-yl)piperidine-2,6-dione B0035.

3-(6-Fluoro-4-(4-isonicotinoylpiperazin-1-yl)-1-oxoisoindolin-2-yl)piperidine-2,6-dione B0036.

B0035

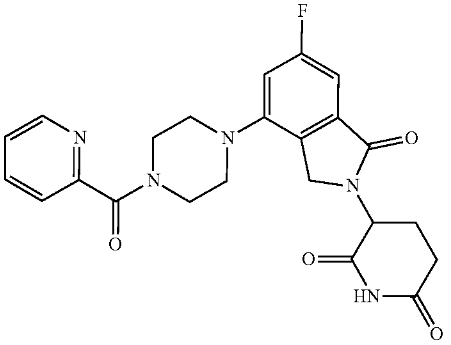

B0036

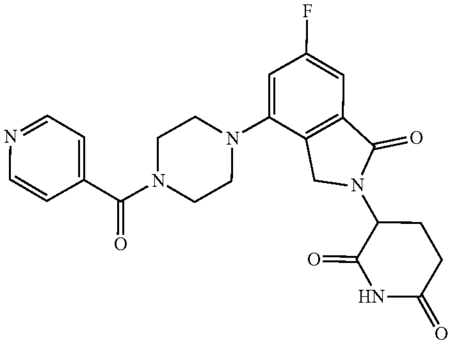

3-(6-Fluoro-4-(4-nicotinoylpiperazin-1-yl)-1-oxoisoindolin-2-yl)piperidine-2,6-dione B0037.

3-(4-(4-Benzoylpiperazin-1-yl)-6-fluoro-1-oxoisoindolin-2-yl)piperidine-2,6-dione B0038.

B0037

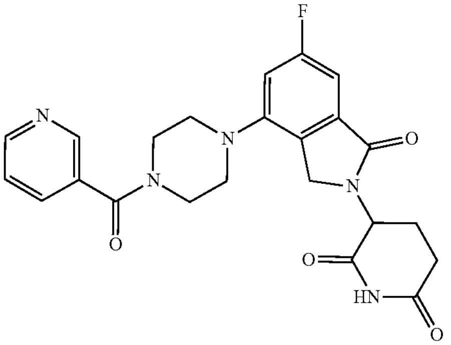

B0038

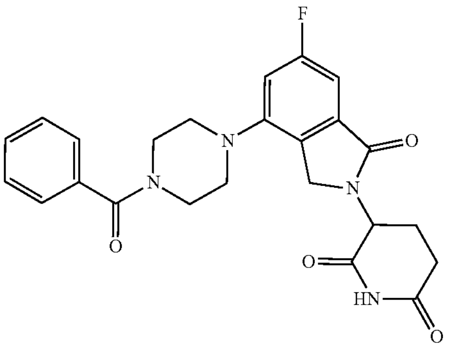

3-(4-(4-(1-Aminocyclobutane-1-carbonyl)piperazin-1-yl)-6-fluoro-1-oxoisoindolin-2-yl)piperidine-2,6-dione B0039.

3-(6-Fluoro-4-(4-(1-methylazetidine-3-carbonyl)piperazin-1-yl)-1-oxoisoindolin-2-yl)piperidine-2,6-dione B0040.

B0039

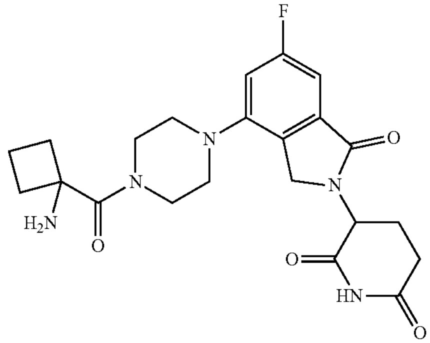

B0040

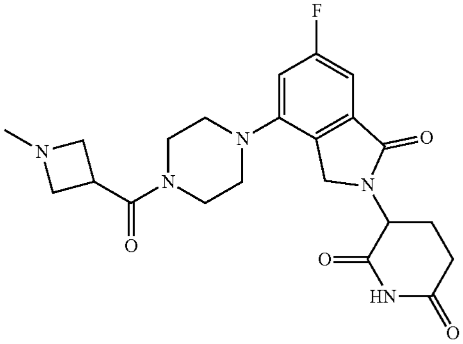

3-(4-(4-(1H-Pyrazole-5-carbonyl)piperazin-1-yl)-6-fluoro-1-oxoisoindolin-2-yl)piperidine-2,6-dione B0041.

3-(4-(4-(1H-Imidazole-5-carbonyl)piperazin-1-yl)-6-fluoro-1-oxoisoindolin-2-yl)-piperidine-2,6-dione B0042.

B0041

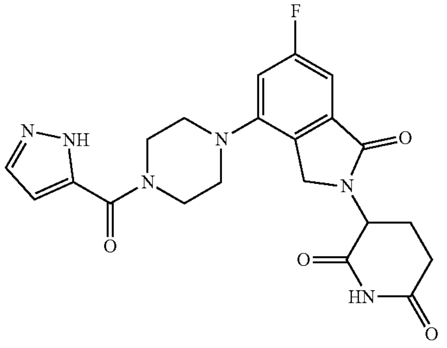

-continued

B0042

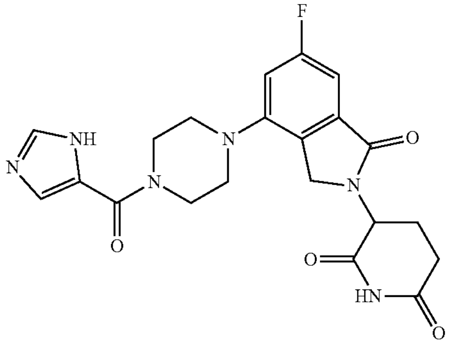

3-(6-Fluoro-4-(4-(furan-3-carbonyl)piperazin-1-yl)-1-oxoisoindolin-2-yl)-piperidine-2,6-dione B0043.

3-(6-Fluoro-4-(4-(furan-2-carbonyl)piperazin-1-yl)-1-oxoisoindolin-2-yl)-piperidine-2,6-dione B0044.

B0043

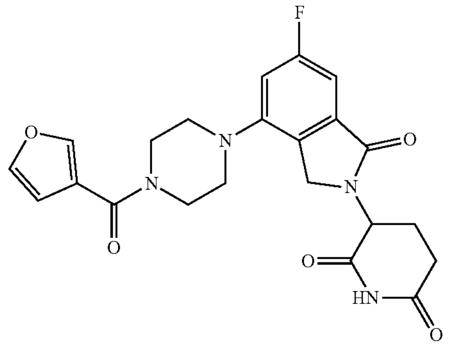

B0044

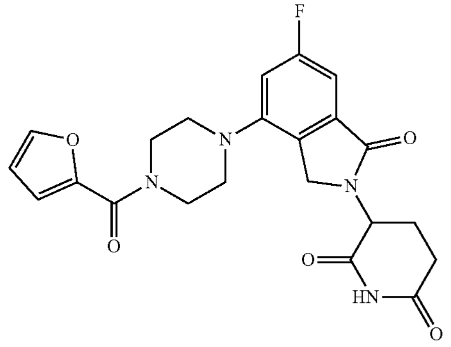

3-(6-Fluoro-4-(4-(1-fluorocyclopropane-1-carbonyl)piperazin-1-yl)-1-oxoisoindolin-2-yl)piperidine-2,6-dione B0045.

3-(6-Fluoro-4-(4-(3-methylbutanoyl)piperazin-1-yl)-1-oxoisoindolin-2-yl)-piperidine-2,6-dione B0046.

B0045

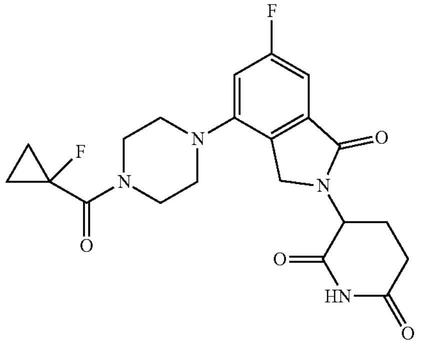

B0046

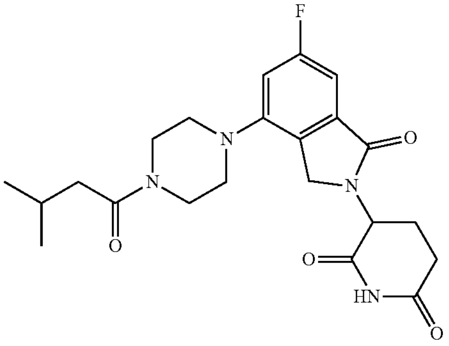

3-(6-Fluoro-4-(4-(oxetane-3-carbonyl)piperazin-1-yl)-1-oxoisoindolin-2-yl)-piperidine-2,6-dione B0047.

3-(4-(4-(Cyclobutanecarbonyl)piperazin-1-yl)-6-fluoro-1-oxoisoindolin-2-yl)-piperidine-2,6-dione B0048.

B0047

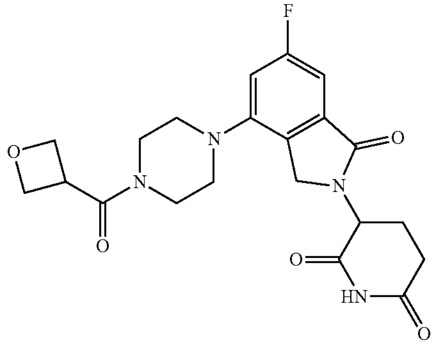

B0048

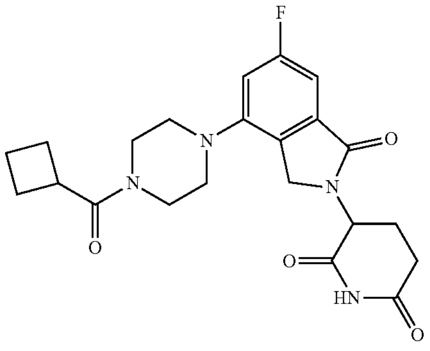

3-(6-Fluoro-4-(4-(methylglycyl)piperazin-1-yl)-1-oxoisoindolin-2-yl)piperidine-2,6-dione B0049.

3-(4-(4-(Cyclopropanecarbonyl)piperazin-1-yl)-6-fluoro-1-oxoisoindolin-2-yl)-piperidine-2,6-dione B0050.

B0049

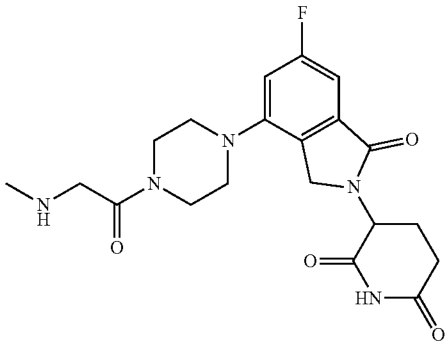

B0050

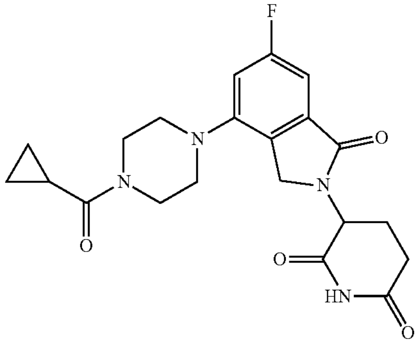

3-(6-Fluoro-4-(4-(3-methoxybenzyl)piperazin-1-yl)-1-oxoisoindolin-2-yl)-piperidine-2,6-dione B1001.

3-(6-Fluoro-4-(4-(2-hydroxy-4-methylbenzyl)piperazin-1-yl)-1-oxoisoindolin-2-yl)-piperidine-2,6-dione B1002.

B1001

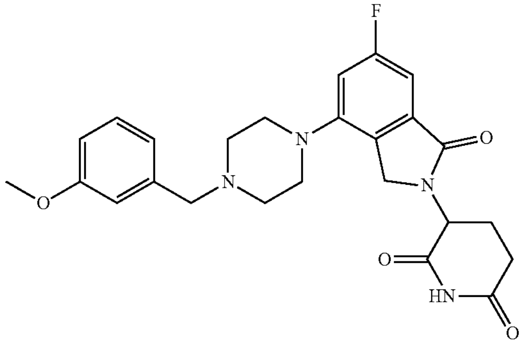

-continued

B1002

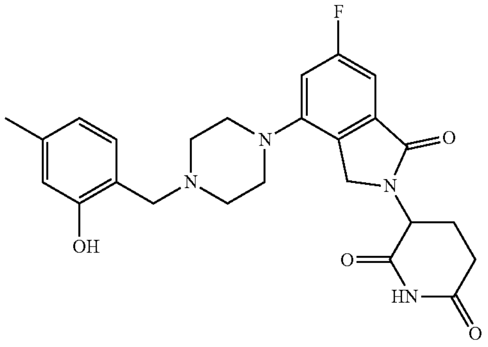

3-(6-Fluoro-4-(4-(4-(hydroxymethyl)benzyl)piperazin-1-yl)-1-oxoisoindolin-2-yl)piperidine-2,6-dione B1003.

3-(4-(4-((2,6-Dimethylpyridin-4-yl)methyl)piperazin-1-yl)-6-fluoro-1-oxoisoindolin-2-yl)piperidine-2,6-dione B1004.

B1003

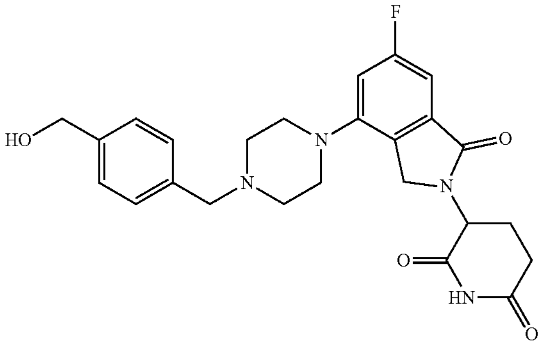

B1004

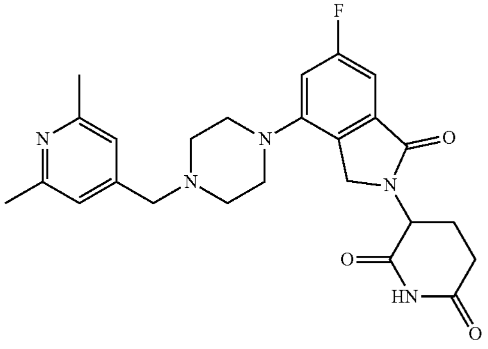

3-(6-Fluoro-4-(4-(2-(methylamino)benzyl)piperazin-1-yl)-1-oxoisoindolin-2-yl)-piperidine-2,6-dione B1005.

3-(4-(4-(2,6-Dimethylbenzyl)piperazin-1-yl)-6-fluoro-1-oxoisoindolin-2-yl)-piperidine-2,6-dione B1006.

B1005

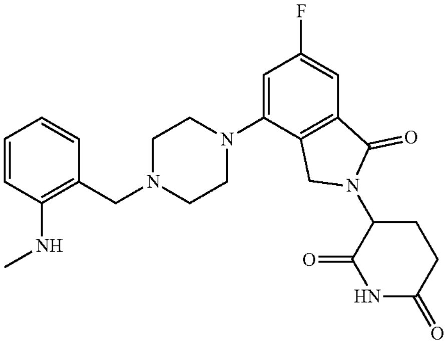

B1006

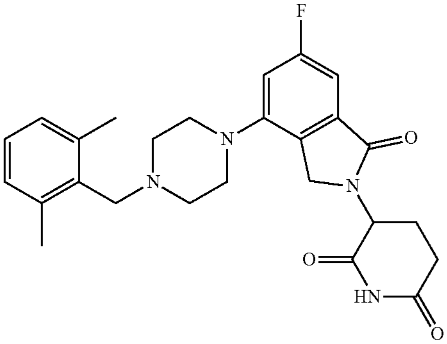

3-(4-(4-(2,4-Dimethylbenzyl)piperazin-1-yl)-6-fluoro-1-oxoisoindolin-2-yl)-piperidine-2,6-dione B1007.

3-(4-(4-(2,5-Dimethylbenzyl)piperazin-1-yl)-6-fluoro-1-oxoisoindolin-2-yl)-piperidine-2,6-dione B1008.

B1007

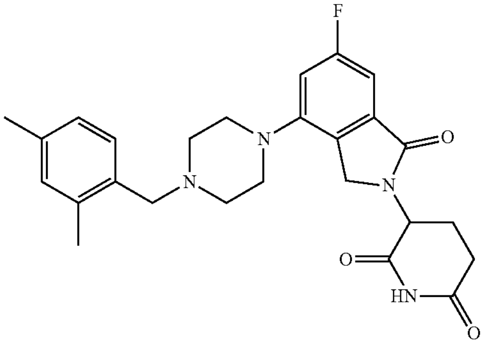

B1008

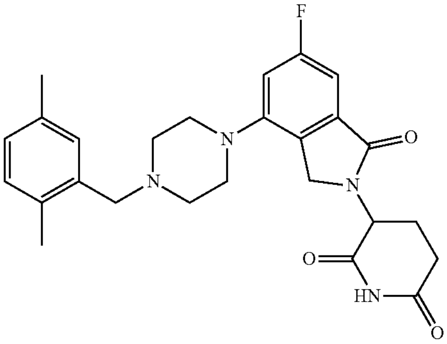

3-(6-Fluoro-4-(4-(2-methylphenethyl)piperazin-1-yl)-1-oxoisoindolin-2-yl)-piperidine-2,6-dione B1009.

3-(4-(4-(3,5-Dimethylbenzyl)piperazin-1-yl)-6-fluoro-1-oxoisoindolin-2-yl)-piperidine-2,6-dione B1010.

B1009

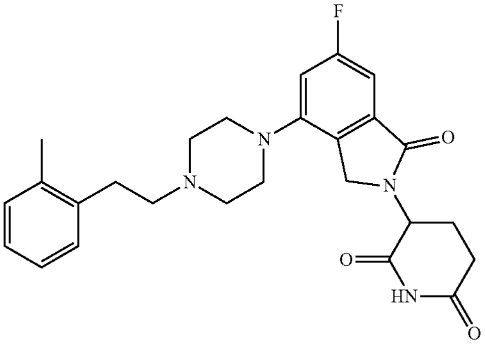

B1010

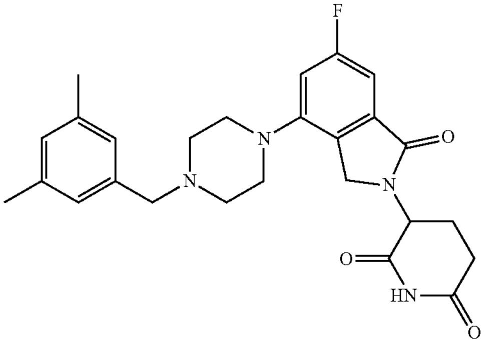

3-(6-Fluoro-1-oxo-4-(4-(pyridin-3-ylmethyl)piperazin-1-yl)isoindolin-2-yl)-piperidine-2,6-dione B1011.

3-(6-Fluoro-1-oxo-4-(4-(3-phenylpropyl)piperazin-1-yl)isoindolin-2-yl)-piperidine-2,6-dione B1012.

B1011

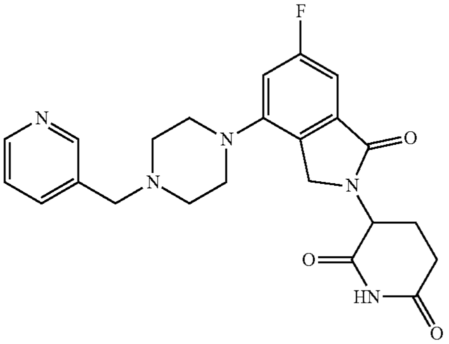

-continued

B1012

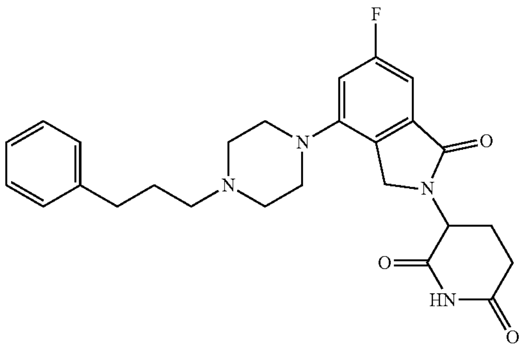

4-((4-(2-(2,6-Dioxopiperidin-3-yl)-6-fluoro-1-oxoisoindolin-4-yl)piperazin-1-yl)-methyl)-1-methyl-1H-pyrrole-2-carbonitrile B1013.

3-(4-(4-(Bicyclo[4.2.0]octa-1(6),2,4-trien-3-ylmethyl)piperazin-1-yl)-6-fluoro-1-oxoisoindolin-2-yl)piperidine-2,6-dione B1014.

B1013

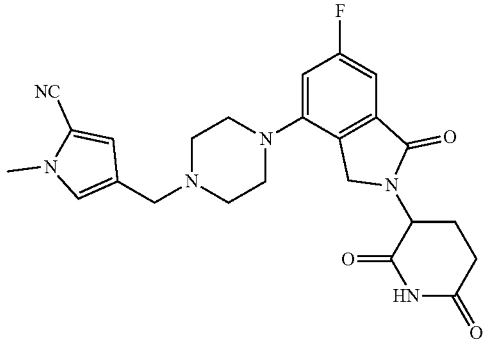

B1014

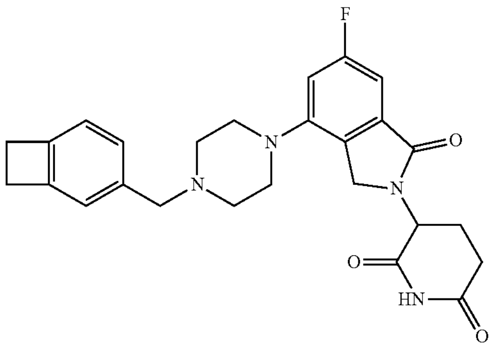

5-((4-(2-(2,6-Dioxopiperidin-3-yl)-6-fluoro-1-oxoisoindolin-4-yl)piperazin-1-yl)-methyl)picolinonitrile B1015.

5-((4-(2-(2,6-Dioxopiperidin-3-yl)-6-fluoro-1-oxoisoindolin-4-yl)piperazin-1-yl)-methyl)nicotinonitrile B1016.

B1015

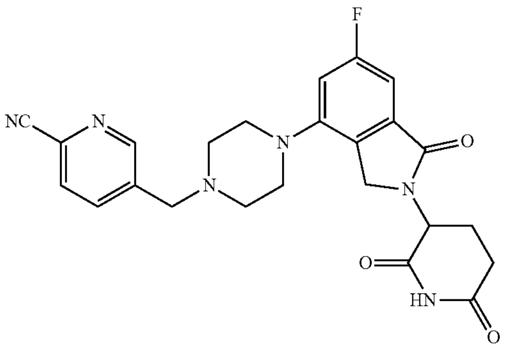

B1016

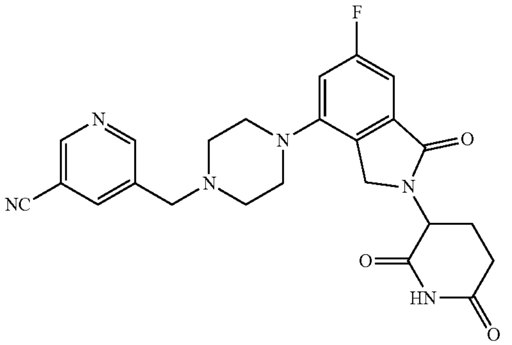

6-((4-(2-(2,6-Dioxopiperidin-3-yl)-6-fluoro-1-oxoisoindolin-4-yl)piperazin-1-yl)-methyl)picolinonitrile B1017.

2-((4-(2-(2,6-Dioxopiperidin-3-yl)-6-fluoro-1-oxoisoindolin-4-yl)piperazin-1-yl)-methyl)isonicotinonitrile B1018.

B1017

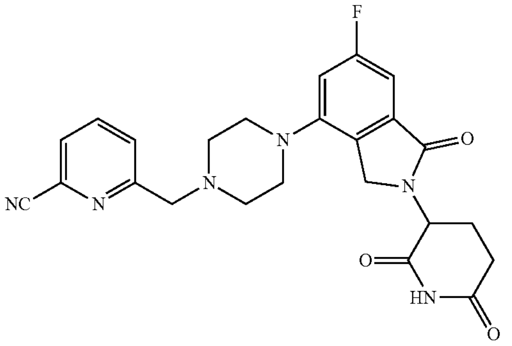

B1018

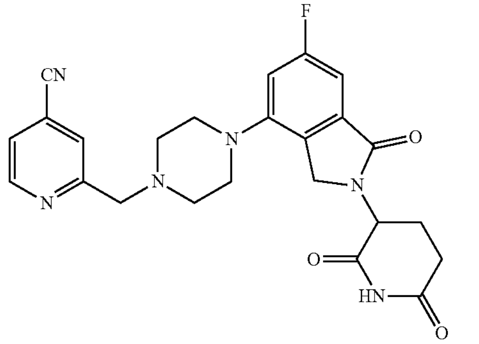

3-((4-(2-(2,6-Dioxopiperidin-3-yl)-6-fluoro-1-oxoisoindolin-4-yl)piperazin-1-yl)-methyl)benzonitrile B1019.

3-(4-(4-((5-Ethynylpyridin-2-yl)methyl)piperazin-1-yl)-6-fluoro-1-oxoisoindolin-2-yl)piperidine-2,6-dione B1020.

B1019

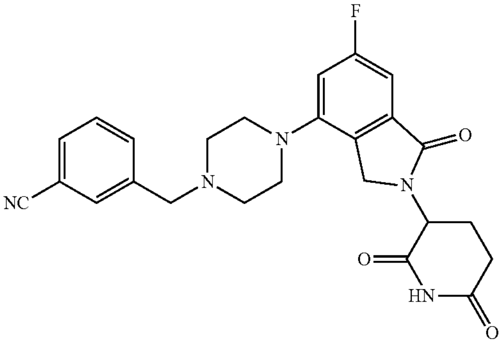

B1020

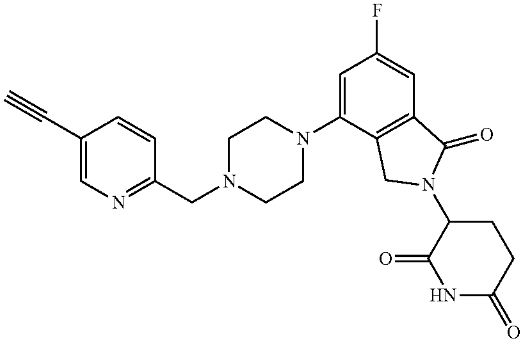

4-((4-(2-(2,6-Dioxopiperidin-3-yl)-6-fluoro-1-oxoisoindolin-4-yl)piperazin-1-yl)-methyl)benzonitrile B1021.

3-(6-Fluoro-4-(4-(3-hydroxy-2,2-dimethylpropyl)piperazin-1-yl)-1-oxoisoindolin-2-yl)piperidine-2,6-dione B1022.

B1021

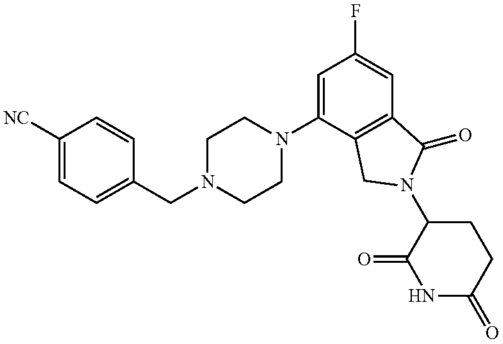

-continued

B1022

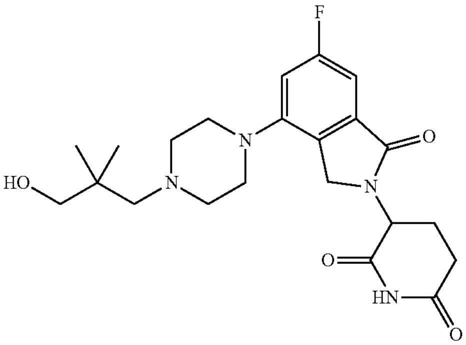

2-((4-(2-(2,6-Dioxopiperidin-3-yl)-6-fluoro-1-oxoisoindolin-4-yl)piperazin-1-yl)-methyl)benzonitrile B1023.

3-(4-(4-(4-Ethynylbenzyl)piperazin-1-yl)-6-fluoro-1-oxoisoindolin-2-yl)-piperidine-2,6-dione B1024.

B1023

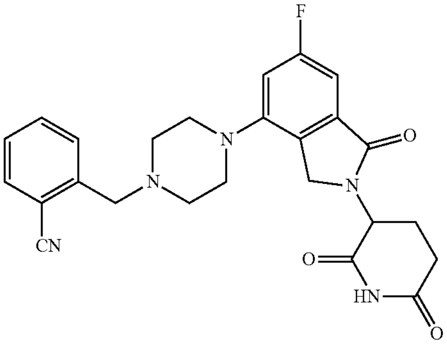

B1024

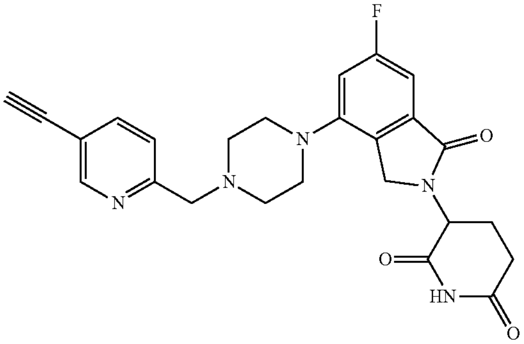

3-(4-(4-(2-Ethynylbenzyl)piperazin-1-yl)-6-fluoro-1-oxoisoindolin-2-yl)-piperidine-2,6-dione B1025.

3-(4-(4-(3-Ethynylbenzyl)piperazin-1-yl)-6-fluoro-1-oxoisoindolin-2-yl)-piperidine-2,6-dione B1026.

B1025
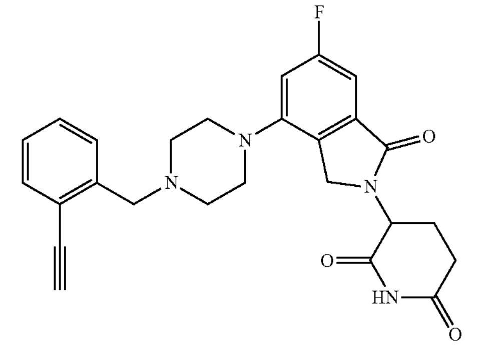
B1026
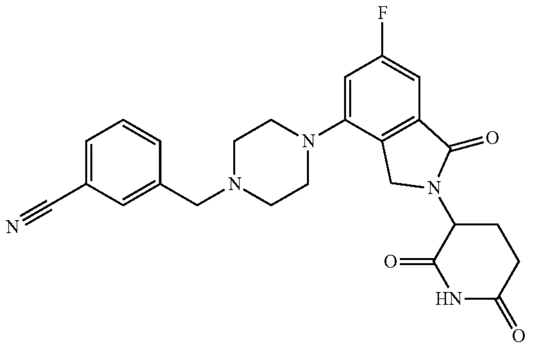

3-(6-Fluoro-4-(4-((5-methylthiazol-2-yl)methyl)piperazin-1-yl)-1-oxoisoindolin-2-yl)piperidine-2,6-dione B1027.

3-(6-Fluoro-4-(4-((2-methylthiazol-5-yl)methyl)piperazin-1-yl)-1-oxoisoindolin-2-yl)piperidine-2,6-dione B1028.

B1027
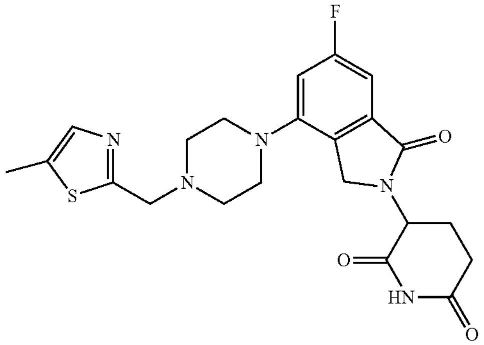
B1028
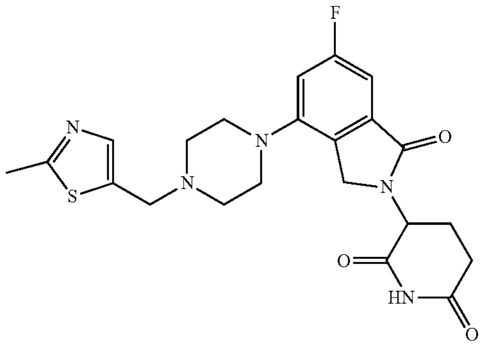

3-(6-Fluoro-4-(4-((4-methylthiazol-5-yl)methyl)piperazin-1-yl)-1-oxoisoindolin-2-yl)piperidine-2,6-dione B1029.

3-(4-(4-(2-Cyclohexylethyl)piperazin-1-yl)-6-fluoro-1-oxoisoindolin-2-yl)-piperidine-2,6-dione B1030.

B1029
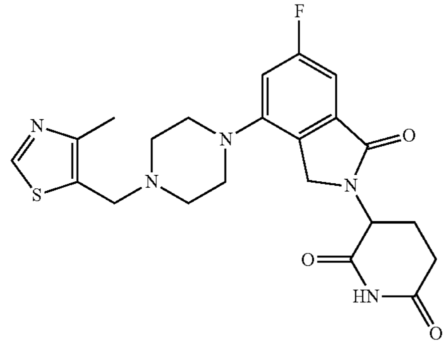
B1030
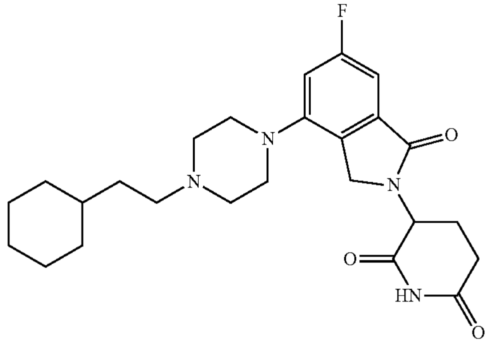

3-(6-Fluoro-4-(4-((3-methylthiophen-2-yl)methyl)piperazin-1-yl)-1-oxoisoindolin-2-yl)piperidine-2,6-dione B1031.

3-(6-Fluoro-4-(4-((3-methoxyfuran-2-yl)methyl)piperazin-1-yl)-1-oxoisoindolin-2-yl)piperidine-2,6-dione B1032.

B1031
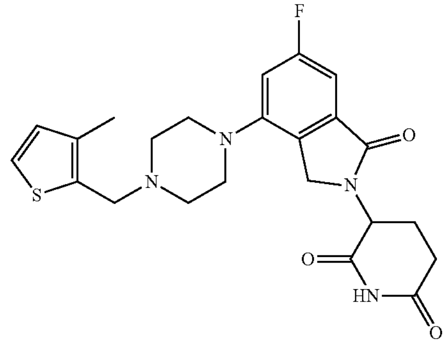

-continued

B1032

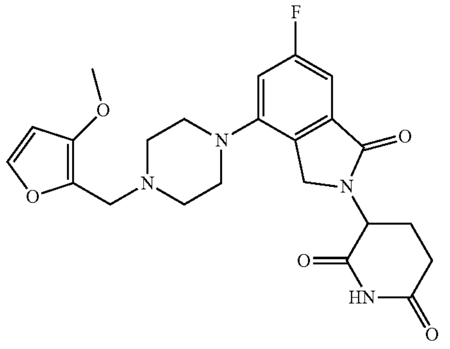

3-(6-Fluoro-4-(4-((3-methyloxetan-3-yl)methyl)piperazin-1-yl)-1-oxoisoindolin-2-yl)piperidine-2,6-dione B1033.

3-(6-Fluoro-4-(4-((5-(hydroxymethyl)furan-2-yl)methyl)piperazin-1-yl)-1-oxoisoindolin-2-yl)piperidine-2,6-dione B1034.

B1033

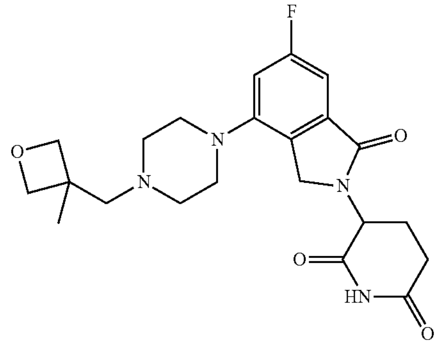

B1034

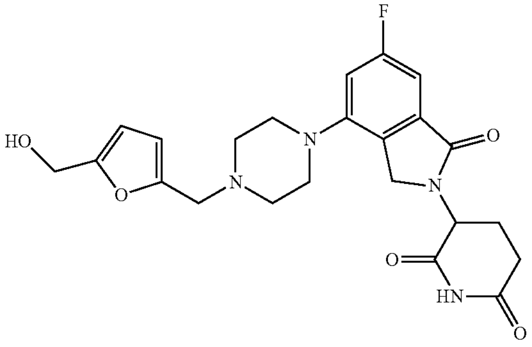

3-(4-(4-((5-Amino-1-methyl-1H-pyrazol-4-yl)methyl)piperazin-1-yl)-6-fluoro-1-oxoisoindolin-2-yl)piperidine-2,6-dione B1035.

3-(6-Fluoro-4-(4-((5-(hydroxymethyl)-1H-pyrrol-2-yl)methyl)piperazin-1-yl)-1-oxoisoindolin-2-yl)piperidine-2,6-dione B1036.

B1035

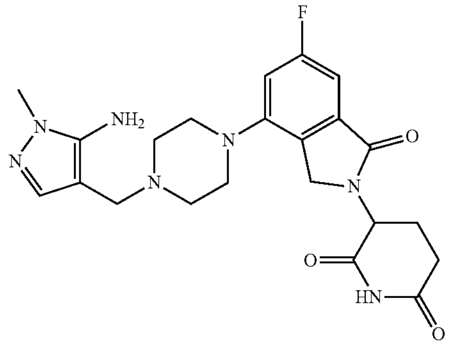

B1036

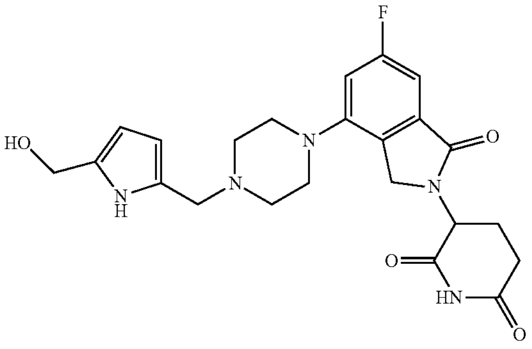

3-(6-Fluoro-4-(4-((6-fluoropyridin-3-yl)methyl)piperazin-1-yl)-1-oxoisoindolin-2-yl)piperidine-2,6-dione B1037.

3-(6-Fluoro-4-(4-((3-fluoropyridin-4-yl)methyl)piperazin-1-yl)-1-oxoisoindolin-2-yl)piperidine-2,6-dione B1038.

B1037

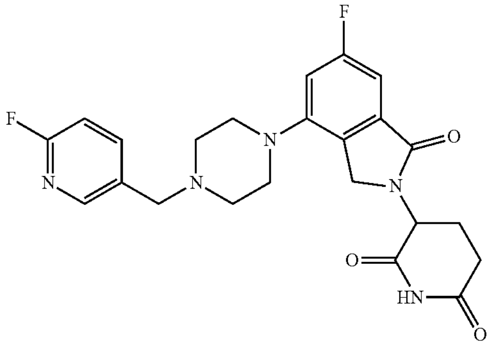

B1038

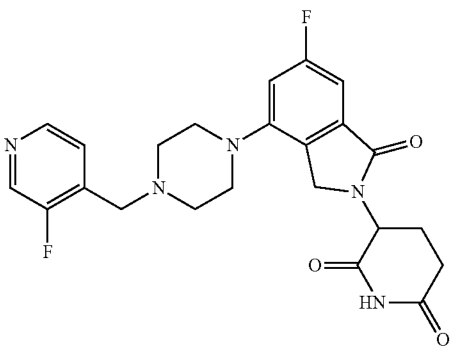

3-(6-Fluoro-4-(4-((5-fluoropyridin-2-yl)methyl)piperazin-1-yl)-1-oxoisoindolin-2-yl)piperidine-2,6-dione B1039.

3-(6-Fluoro-4-(4-((5-fluoropyridin-3-yl)methyl)piperazin-1-yl)-1-oxoisoindolin-2-yl)piperidine-2,6-dione B1040.

B1039

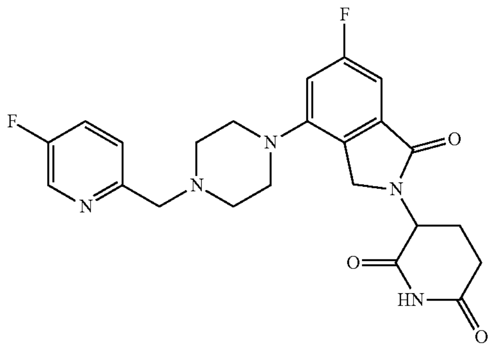

B1040

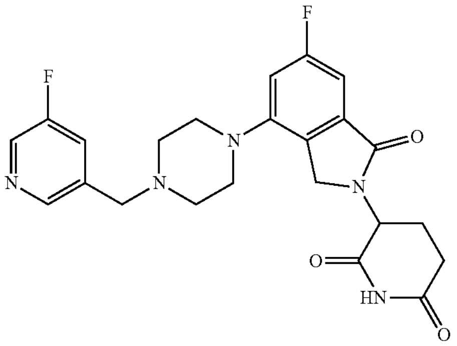

3-(6-Fluoro-4-(4-((4-fluoropyridin-2-yl)methyl)piperazin-1-yl)-1-oxoisoindolin-2-yl)piperidine-2,6-dione B1041.

3-(6-Fluoro-4-(4-((6-fluoropyridin-2-yl)methyl)piperazin-1-yl)-1-oxoisoindolin-2-yl)piperidine-2,6-dione B1042.

B1041

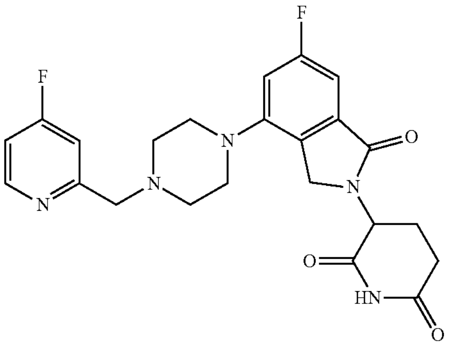

-continued

B1042

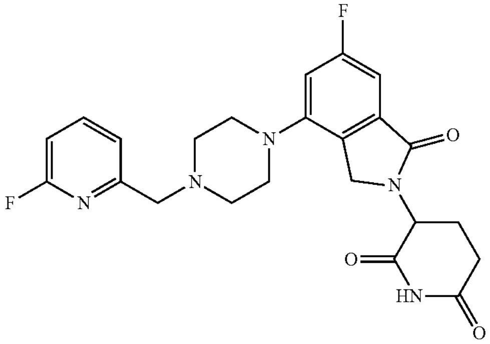

3-(4-(4-((2,5-Dimethyl-1H-imidazol-4-yl)methyl)piperazin-1-yl)-6-fluoro-1-oxoisoindolin-2-yl)piperidine-2,6-dione B1043.

3-(6-Fluoro-4-(4-(oxazol-2-ylmethyl)piperazin-1-yl)-1-oxoisoindolin-2-yl)-piperidine-2,6-dione B1044.

B1043

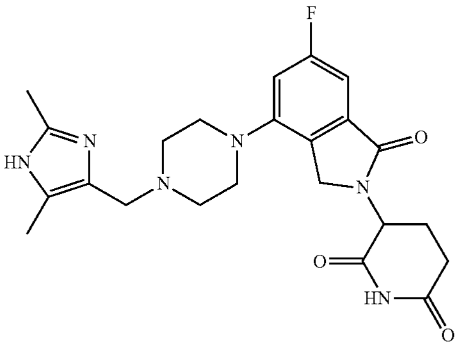

B1044

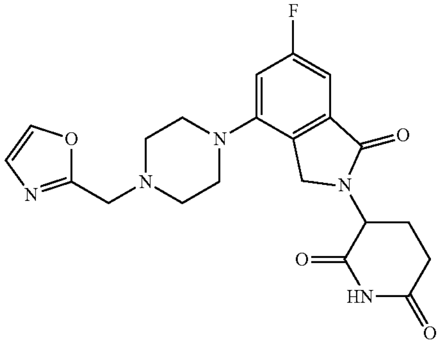

3-(4-(4-((1,4-Dimethyl-1H-pyrazol-5-yl)methyl)piperazin-1-yl)-6-fluoro-1-oxoisoindolin-2-yl)piperidine-2,6-dione B1045.

3-(6-Fluoro-4-(4-(4-fluorobenzyl)piperazin-1-yl)-1-oxoisoindolin-2-yl)piperidine-2,6-dione B1046.

B1045

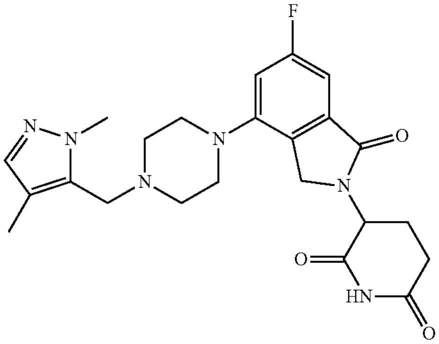

B1046

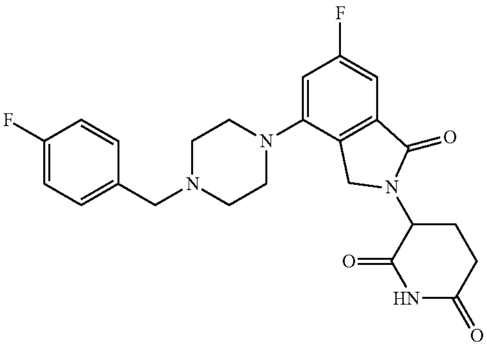

3-(6-Fluoro-4-(4-(3-fluorobenzyl)piperazin-1-yl)-1-oxoisoindolin-2-yl)piperidine-2,6-dione B1047.

3-(6-Fluoro-4-(4-((2-hydroxypyridin-3-yl)methyl)piperazin-1-yl)-1-oxoisoindolin-2-yl)piperidine-2,6-dione B1048.

B1047

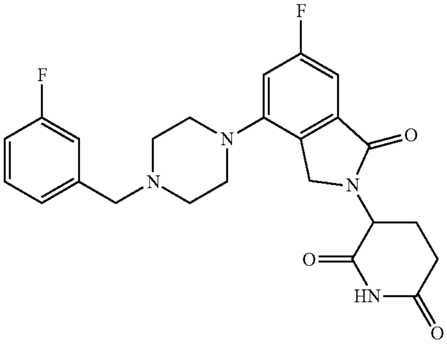

B1048

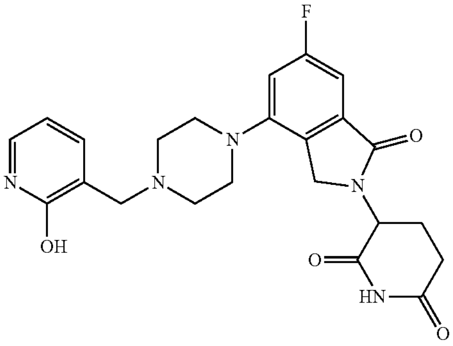

3-(6-Fluoro-4-(4-((5-methylpyrazin-2-yl)methyl)piperazin-1-yl)-1-oxoisoindolin-2-yl)piperidine-2,6-dione B1049.

3-(6-Fluoro-4-(4-((3-methylpyrazin-2-yl)methyl)piperazin-1-yl)-1-oxoisoindolin-2-yl)piperidine-2,6-dione B1050.

B1049

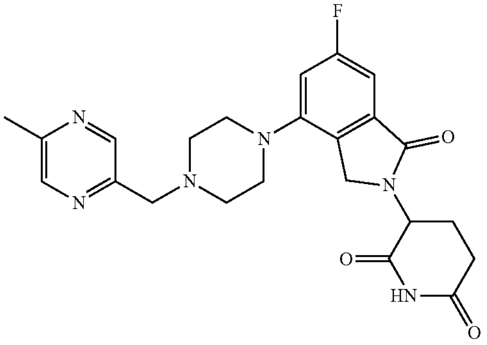

B1050

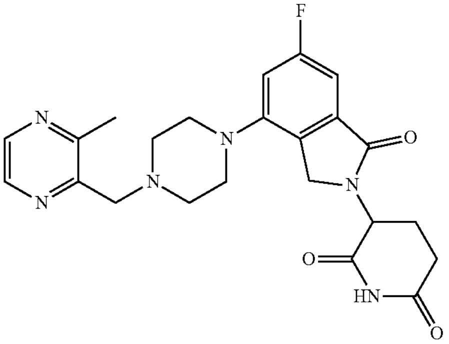

3-(6-Fluoro-4-(4-((2-methylpyrimidin-4-yl)methyl)piperazin-1-yl)-1-oxoisoindolin-2-yl)piperidine-2,6-dione B1051.

3-(6-Fluoro-4-(4-((2-methylpyrimidin-5-yl)methyl)piperazin-1-yl)-1-oxoisoindolin-2-yl)piperidine-2,6-dione B1052.

B1051

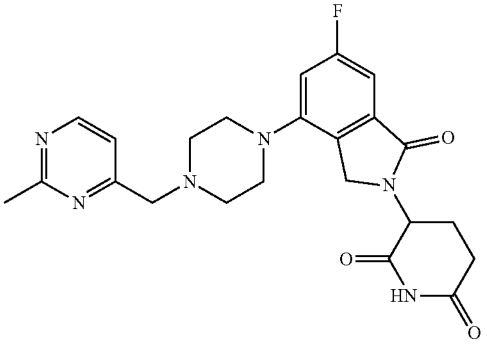

-continued

B1052

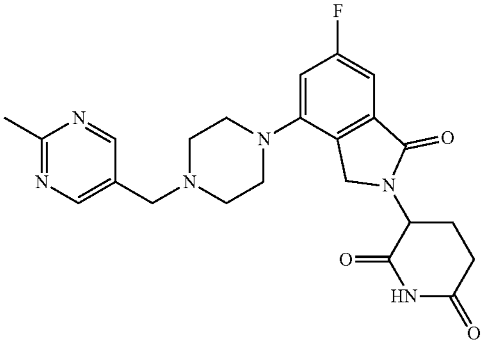

3-(4-(4-((2-Aminopyridin-3-yl)methyl)piperazin-1-yl)-6-fluoro-1-oxoisoindolin-2-yl)piperidine-2,6-dione B1053.

3-(4-(4-((3-Aminopyridin-4-yl)methyl)piperazin-1-yl)-6-fluoro-1-oxoisoindolin-2-yl)piperidine-2,6-dione B1054.

B1053

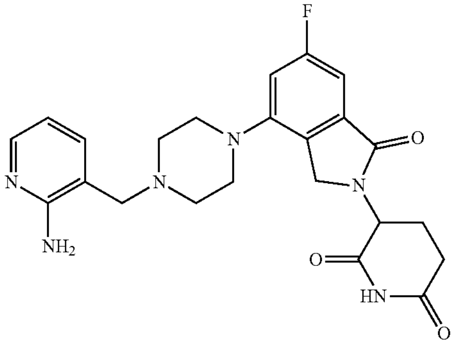

B1054

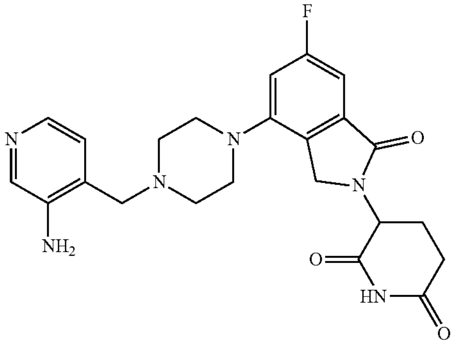

3-(4-(4-((1H-Pyrazol-5-yl)methyl)piperazin-1-yl)-6-fluoro-1-oxoisoindolin-2-yl)-piperidine-2,6-dione B1055.

3-(6-Fluoro-4-(4-(3-hydroxybenzyl)piperazin-1-yl)-1-oxoisoindolin-2-yl)-piperidine-2,6-dione B1056.

B1055

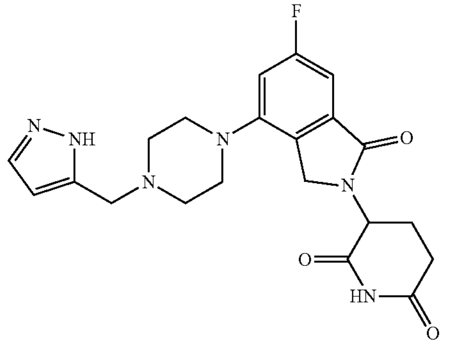

B1056

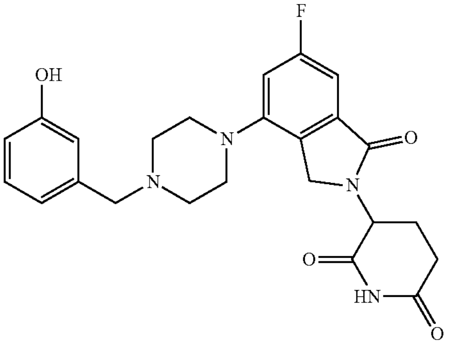

3-(6-Fluoro-4-(4-(4-hydroxybenzyl)piperazin-1-yl)-1-oxoisoindolin-2-yl)-piperidine-2,6-dione B1057.

3-(6-Fluoro-4-(4-((4-methylpyridin-2-yl)methyl)piperazin-1-yl)-1-oxoisoindolin-2-yl)piperidine-2,6-dione B1058.

B1057

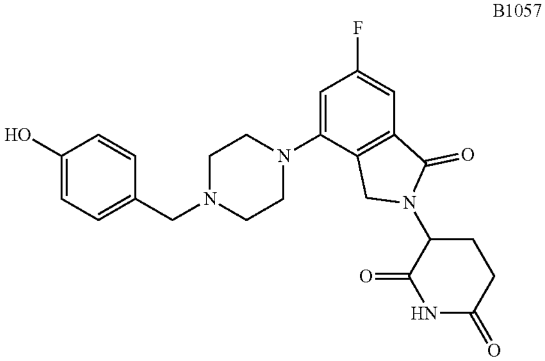

B1058

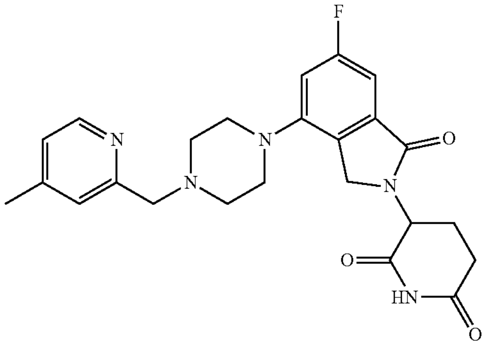

3-(6-Fluoro-4-(4-((3-methylpyridin-2-yl)methyl)piperazin-1-yl)-1-oxoisoindolin-2-yl)piperidine-2,6-dione B1059.

3-(6-Fluoro-4-(4-((2-methylpyridin-3-yl)methyl)piperazin-1-yl)-1-oxoisoindolin-2-yl)piperidine-2,6-dione B1060.

B1059

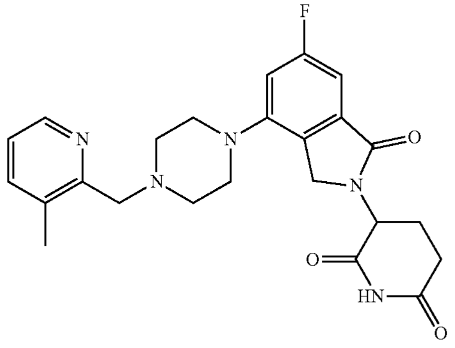

B1060

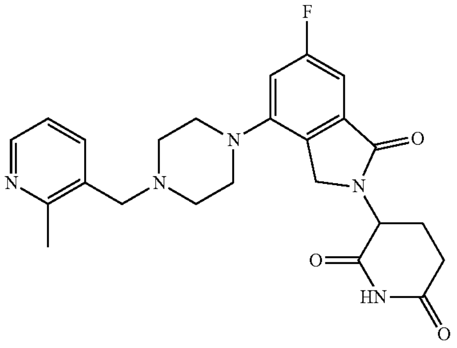

3-(6-Fluoro-4-(4-((2-methylpyridin-4-yl)methyl)piperazin-1-yl)-1-oxoisoindolin-2-yl)piperidine-2,6-dione B1061.

3-(6-Fluoro-4-(4-((5-methylpyridin-2-yl)methyl)piperazin-1-yl)-1-oxoisoindolin-2-yl)piperidine-2,6-dione B1062.

B1061

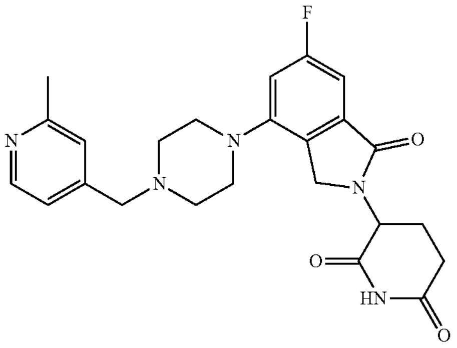

-continued

B1062

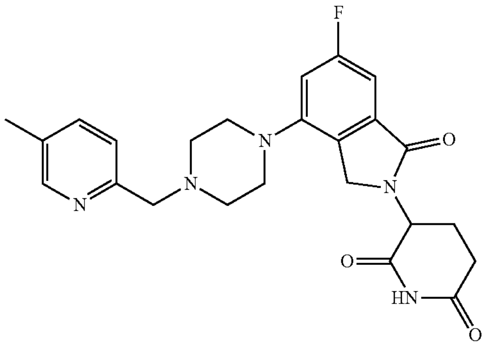

3-(6-Fluoro-4-(4-((6-methylpyridin-2-yl)methyl)piperazin-1-yl)-1-oxoisoindolin-2-yl)piperidine-2,6-dione B1063.

3-(6-Fluoro-4-(4-((4-methylpyridin-3-yl)methyl)piperazin-1-yl)-1-oxoisoindolin-2-yl)piperidine-2,6-dione B1064.

B1063

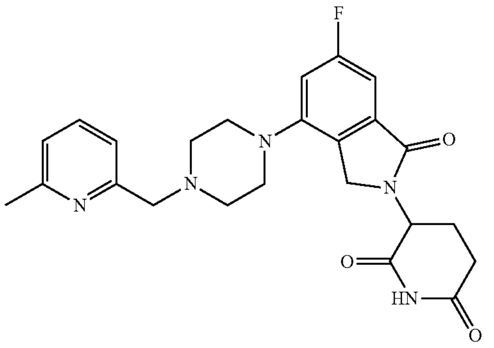

B1064

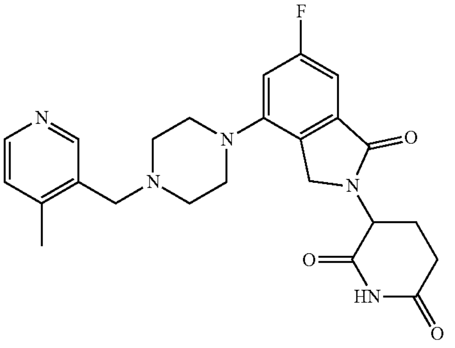

3-(6-Fluoro-4-(4-((5-methylpyridin-3-yl)methyl)piperazin-1-yl)-1-oxoisoindolin-2-yl)piperidine-2,6-dione B1065.

3-(4-(4-((1H-Imidazol-5-yl)methyl)piperazin-1-yl)-6-fluoro-1-oxoisoindolin-2-yl)-piperidine-2,6-dione B1066.

B1065

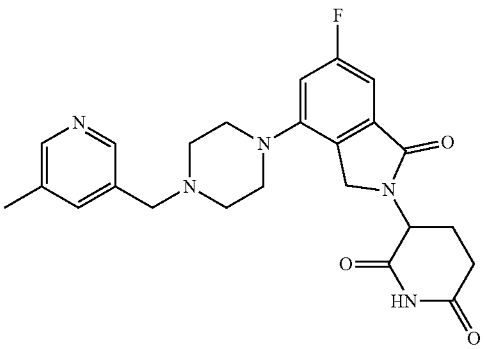

B1066

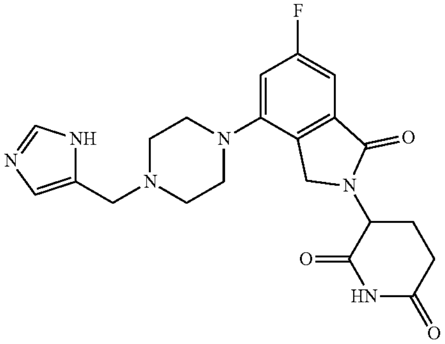

3-(4-(4-(4-Aminobenzyl)piperazin-1-yl)-6-fluoro-1-oxoisoindolin-2-yl)-piperidine-2,6-dione B1067.

3-(4-(4-(2-Aminobenzyl)piperazin-1-yl)-6-fluoro-1-oxoisoindolin-2-yl)-piperidine-2,6-dione B1068.

B1067

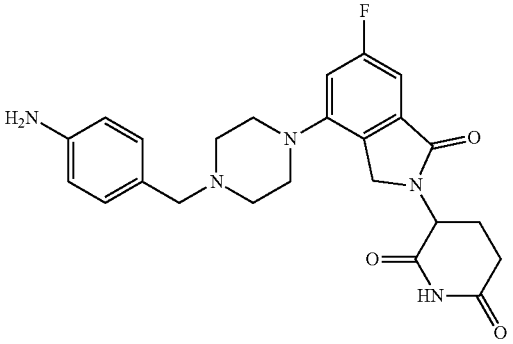

B1068

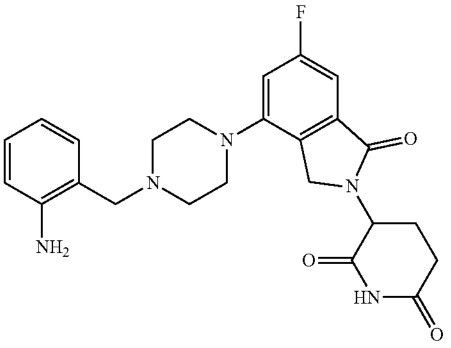

3-(6-Fluoro-4-(4-(4-methylbenzyl)piperazin-1-yl)-1-oxoisoindolin-2-yl)-piperidine-2,6-dione B1069.

3-(6-Fluoro-4-(4-(2-methylbenzyl)piperazin-1-yl)-1-oxoisoindolin-2-yl)-piperidine-2,6-dione B1070.

B1069

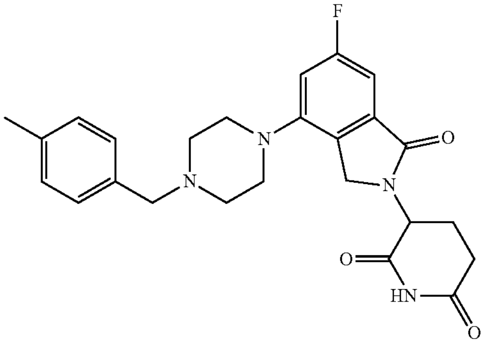

B1070

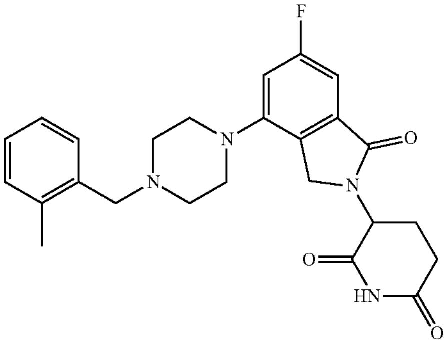

4-(4-Bromo-3-((4-(2-(2,6-dioxopiperidin-3-yl)-6-fluoro-1-oxoisoindolin-4-yl)-piperazin-1-yl)methyl)phenoxy)benzonitrile B1071.

3-(6-Fluoro-1-oxo-4-(4-phenethylpiperazin-1-yl)isoindolin-2-yl)piperidine-2,6-dione B1072.

B1071

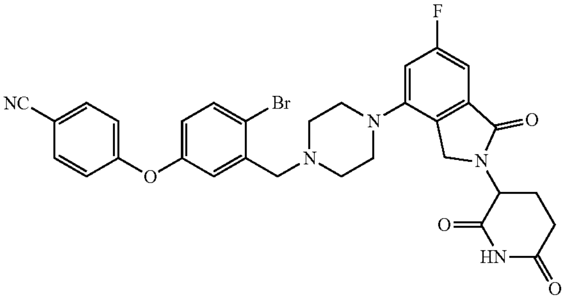

-continued

B1072

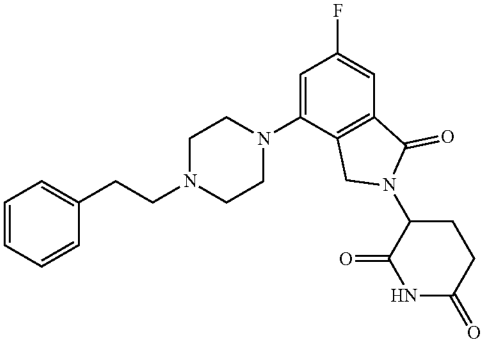

3-(4-(4-(3-Bromo-4-(4-methylpiperazin-1-yl)benzyl)piperazin-1-yl)-6-fluoro-1-oxoisoindolin-2-yl)piperidine-2,6-dione B1073.

Tert-butyl 4-(4-((4-(2-(2,6-dioxopiperidin-3-yl)-6-fluoro-1-oxoisoindolin-4-yl)-piperazin-1-yl)methyl)-1H-1,2,3-triazol-1-yl)piperidine-1-carboxylate B1074.

B1073

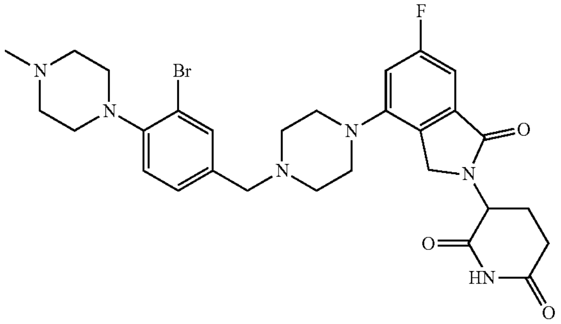

B1074

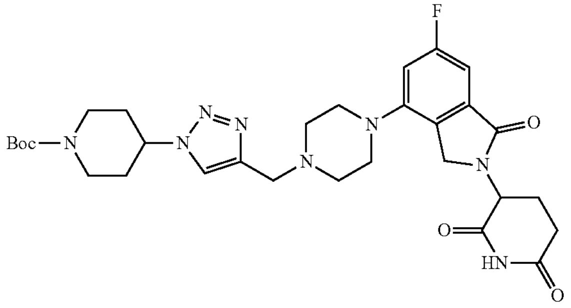

3-(4-(4-(3-Bromo-4-morpholinobenzyl)piperazin-1-yl)-6-fluoro-1-oxoisoindolin-2-yl)piperidine-2,6-dione B1075.

3-(6-Fluoro-1-oxo-4-(4-(4-(4-(trifluoromethyl)phenoxy)benzyl)piperazin-1-yl)-isoindolin-2-yl)piperidine-2,6-dione B1076.

B1075

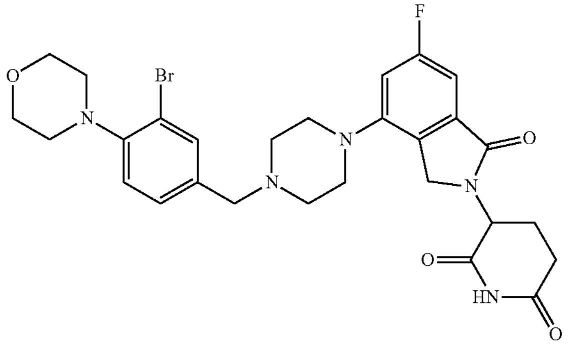

B1076

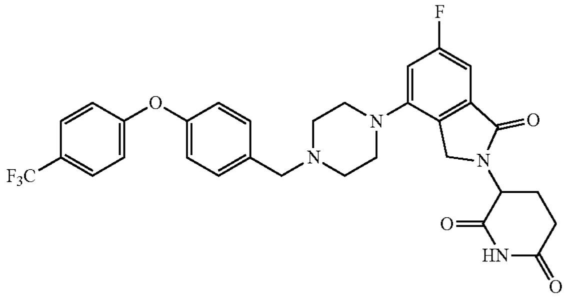

3-(4-(4-(4-(Benzyloxy)-3-ethoxybenzyl)piperazin-1-yl)-6-fluoro-1-oxoisoindolin-2-yl)piperidine-2,6-dione B1077.

Tert-butyl 4-(1-(4-(2-(2,6-dioxopiperidin-3-yl)-6-fluoro-1-oxoisoindolin-4-yl)piperazin-1-yl)-2-methylpropan-2-yl)piperidine-1-carboxylate B1078.

B1077

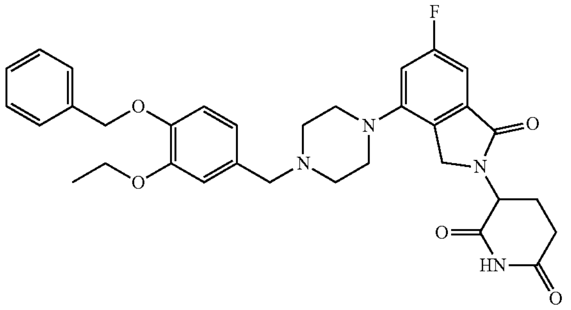

B1078

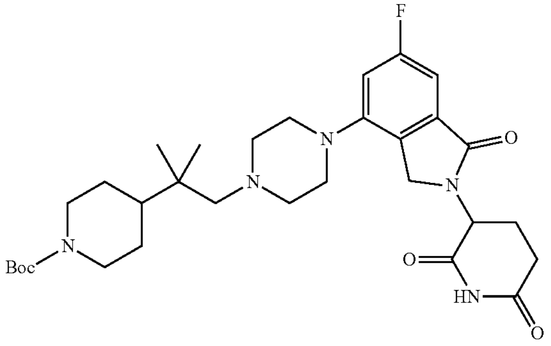

Benzyl (4-((4-(2-(2,6-dioxopiperidin-3-yl)-6-fluoro-1-oxoisoindolin-4-yl)-piperazin-1-yl)methyl)phenyl)carbamate B1079.

Tert-butyl 6-((4-(2-(2,6-dioxopiperidin-3-yl)-6-fluoro-1-oxoisoindolin-4-yl)-piperazin-1-yl)methyl)indoline-1-carboxylate B1080.

B1079

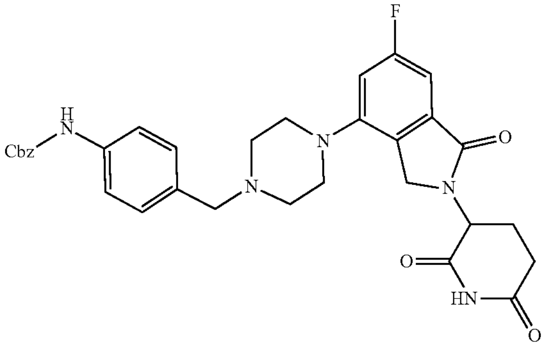

B1080

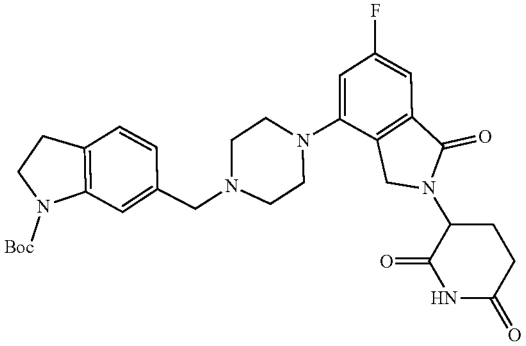

Tert-butyl (((1r,4r)-4-((4-(2-(2,6-dioxopiperidin-3-yl)-6-fluoro-1-oxoisoindolin-4-yl)piperazin-1-yl)methyl)cyclohexyl)methyl)carbamate B1081.

4-(4-((4-(2-(2,6-Dioxopiperidin-3-yl)-6-fluoro-1-oxoisoindolin-4-yl)piperazin-1-yl)methyl)phenoxy)-3-fluorobenzonitrile B1082.

B1081

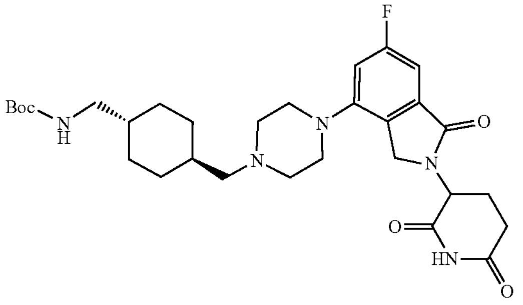

-continued

B1082

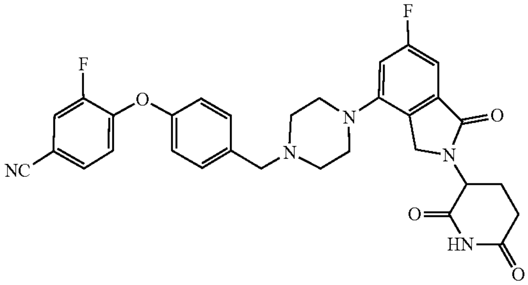

3-(6-Fluoro-4-(4-(3-methylbenzyl)piperazin-1-yl)-1-oxoisoindolin-2-yl)-piperidine-2,6-dione B1083.

Tert-butyl 4-((4-(2-(2,6-dioxopiperidin-3-yl)-6-fluoro-1-oxoisoindolin-4-yl)-piperazin-1-yl)methyl)-4-fluoropiperidine-1-carboxylate B1084.

B1083

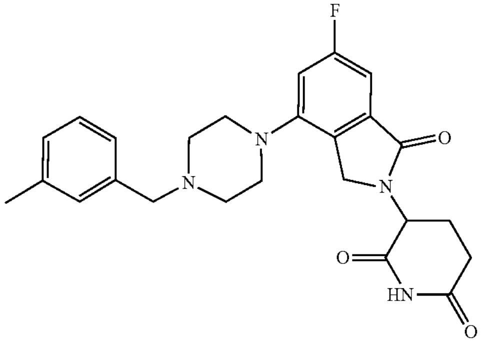

B1084

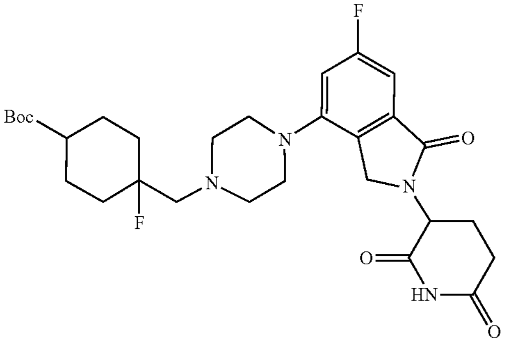

Tert-butyl 4-(2-(4-(2-(2,6-dioxopiperidin-3-yl)-6-fluoro-1-oxoisoindolin-4-yl)-piperazin-1-yl)ethyl)piperazine-1-carboxylate B1085.

3-(4-(4-((2-Chloro-4-morpholinopyrimidin-5-yl)methyl)piperazin-1-yl)-6-fluoro-1-oxoisoindolin-2-yl)piperidine-2,6-dione B1086.

-continued

B1085

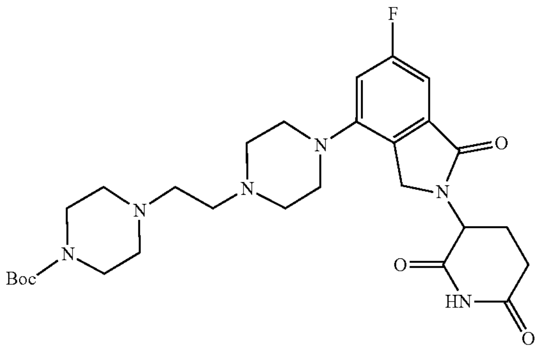

B1086

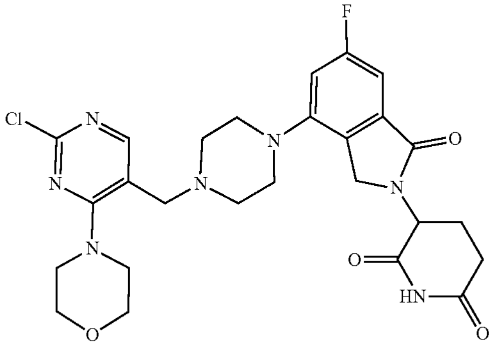

Tert-butyl ((1r,4r)-4-((4-(2-(2,6-dioxopiperidin-3-yl)-6-fluoro-1-oxoisoindolin-4-yl)piperazin-1-yl)methyl)cyclohexyl)carbamate B1087.

Tert-butyl 4-(2-(4-(2-(2,6-dioxopiperidin-3-yl)-6-fluoro-1-oxoisoindolin-4-yl)piperazin-1-yl)ethyl)piperidine-1-carboxylate B1088.

B1087

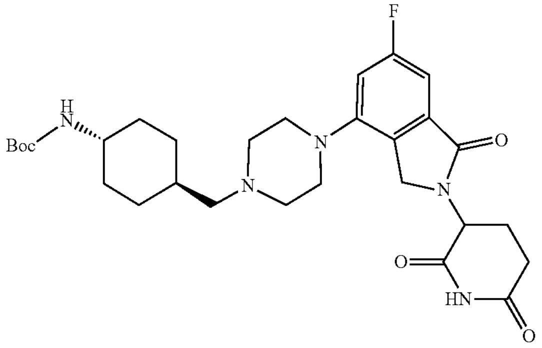

B1088

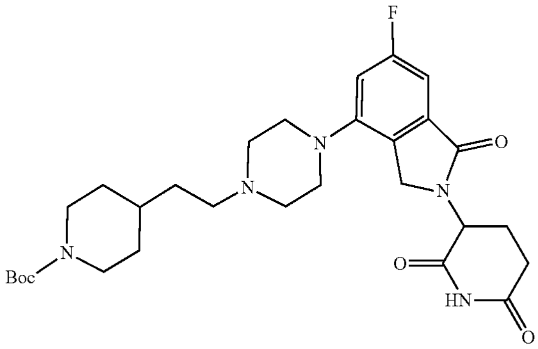

3-(4-(4-(2-(Benzyloxy)-4-methylbenzyl)piperazin-1-yl)-6-fluoro-1-oxoisoindolin-2-yl)piperidine-2,6-dione B1089.

3-(4-(4-(4-(Benzyloxy)-2-methylbenzyl)piperazin-1-yl)-6-fluoro-1-oxoisoindolin-2-yl)piperidine-2,6-dione B1090.

B1089

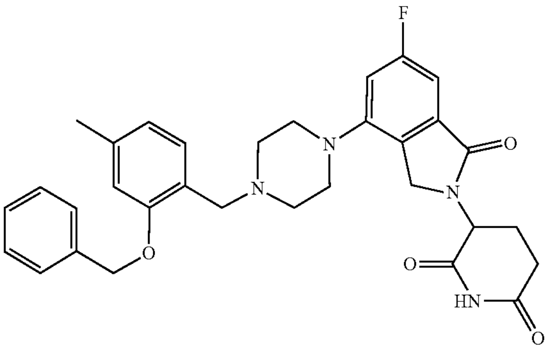

B1090

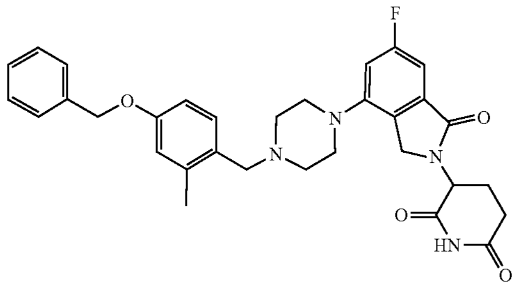

3-(4-(4-(3-Chloro-4-morpholinobenzyl)piperazin-1-yl)-6-fluoro-1-oxoisoindolin-2-yl)piperidine-2,6-dione B1091.

4-(4-((4-(2-(2,6-Dioxopiperidin-3-yl)-6-fluoro-1-oxoisoindolin-4-yl)piperazin-1-yl)methyl)phenoxy)benzonitrile B1092.

B1091

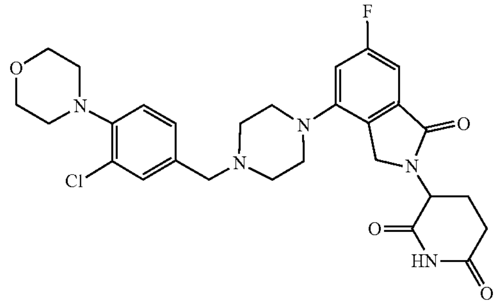

B1092

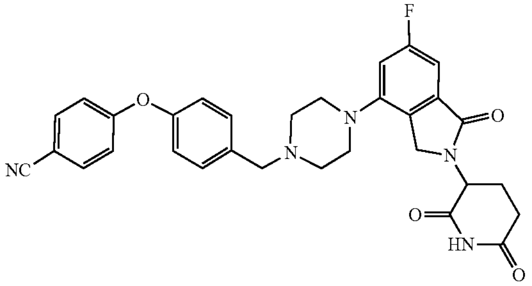

4-(3-((4-(2-(2,6-Dioxopiperidin-3-yl)-6-fluoro-1-oxoisoindolin-4-yl)piperazin-1-yl)methyl)phenoxy)benzonitrile B1093.

2-((4-(2-(2,6-Dioxopiperidin-3-yl)-6-fluoro-1-oxoisoindolin-4-yl)piperazin-1-yl)methyl)-1H-pyrrole-3-carbonitrile B1094.

B1093

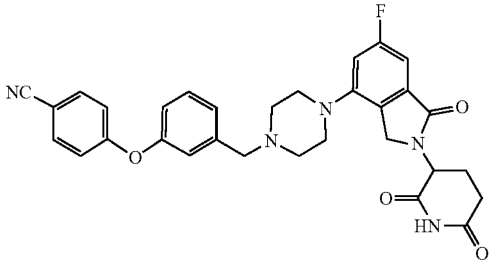

B1094

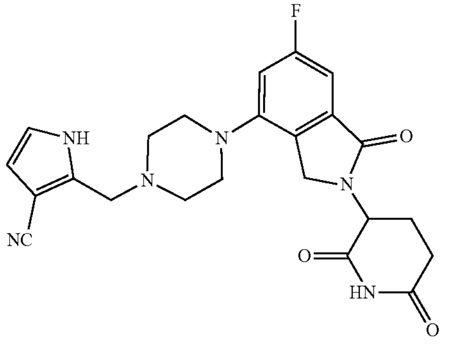

3-(4-(4-(3-(Cyclohexylmethoxy)benzyl)piperazin-1-yl)-6-fluoro-1-oxoisoindolin-2-yl)piperidine-2,6-dione B1095.

3-(4-(4-(3-(3-Bromophenyl)propyl)piperazin-1-yl)-6-fluoro-1-oxoisoindolin-2-yl)-piperidine-2,6-dione B1096.

B1095

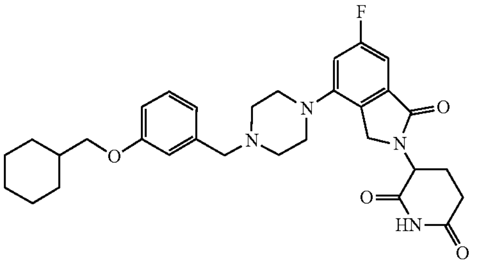

B1096

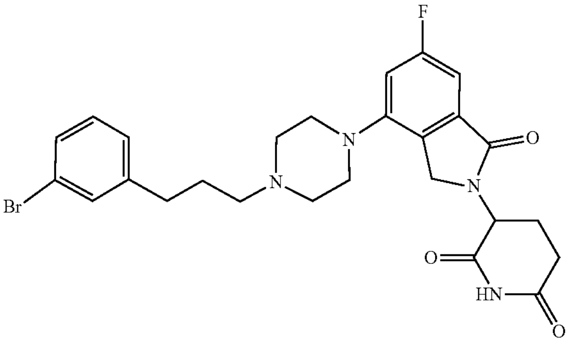

3-(4-(4-(4-(Benzyloxy)benzyl)piperazin-1-yl)-6-fluoro-1-oxoisoindolin-2-yl)-piperidine-2,6-dione B1097.

3-(4-(4-(3-(Benzyloxy)benzyl)piperazin-1-yl)-6-fluoro-1-oxoisoindolin-2-yl)-piperidine-2,6-dione B1098.

B1097

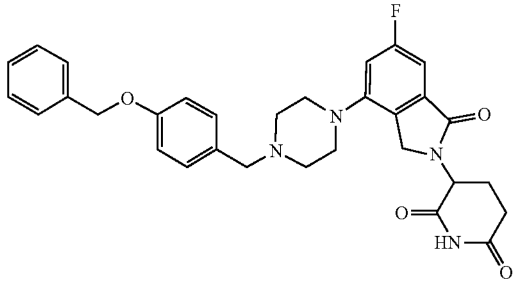

B1098

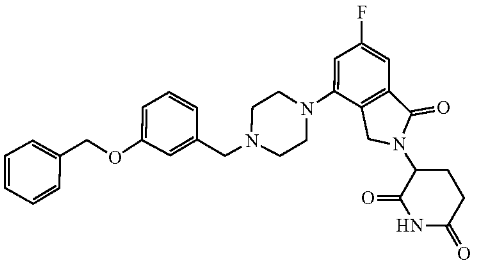

5-((4-(2-(2,6-Dioxopiperidin-3-yl)-6-fluoro-1-oxoisoindolin-4-yl)piperazin-1-yl)-methyl)-2-(4-methyl-1H-imidazol-1-yl)benzonitrile B1099.

3-(4-(4-(3-Chloro-4-(trifluoromethyl)benzyl)piperazin-1-yl)-6-fluoro-1-oxoisoindolin-2-yl)piperidine-2,6-dione B1100.

B1099

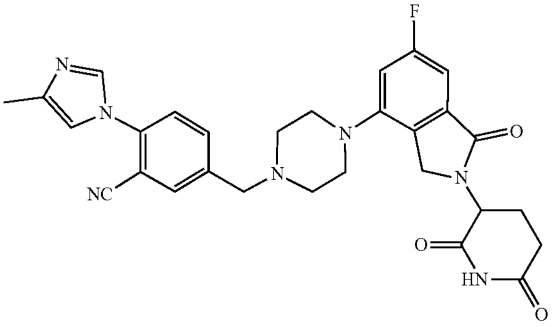

B1100

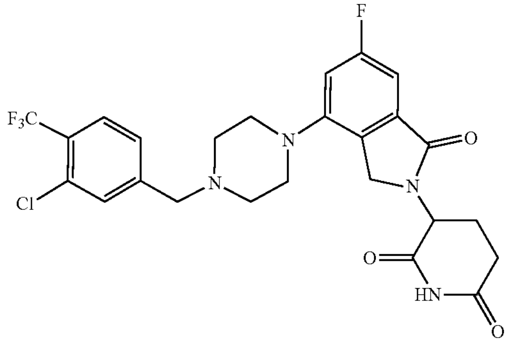

3-(4-(4-(2-Chloro-4-(trifluoromethyl)benzyl)piperazin-1-yl)-6-fluoro-1-oxoisoindolin-2-yl)piperidine-2,6-dione B1101.

3-(4-(4-(4-Chloro-2-(trifluoromethyl)benzyl)piperazin-1-yl)-6-fluoro-1-oxoisoindolin-2-yl)piperidine-2,6-dione B1102.

B1101

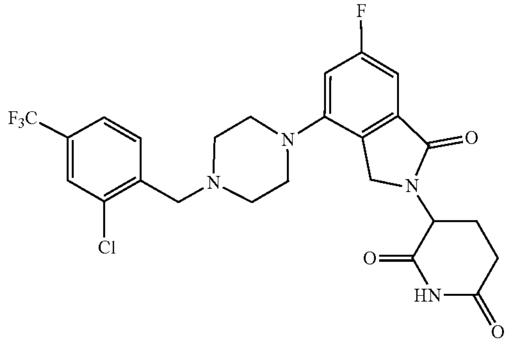

-continued

B1102

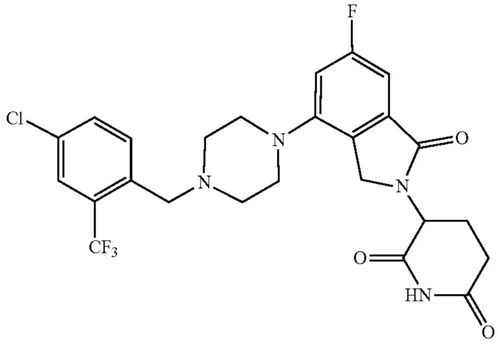

3-(4-(4-(5-Chloro-2-(trifluoromethyl)benzyl)piperazin-1-yl)-6-fluoro-1-oxoisoindolin-2-yl)piperidine-2,6-dione B1103.

3-(4-(4-(2-Chloro-5-(trifluoromethyl)benzyl)piperazin-1-yl)-6-fluoro-1-oxoisoindolin-2-yl)piperidine-2,6-dione B1104.

B1103

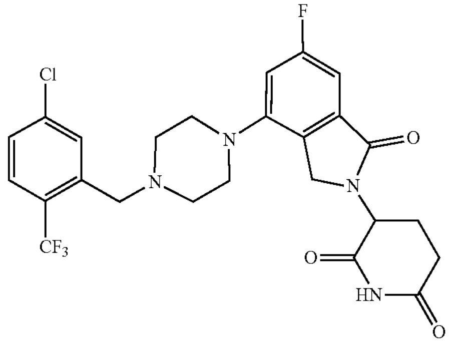

B1104

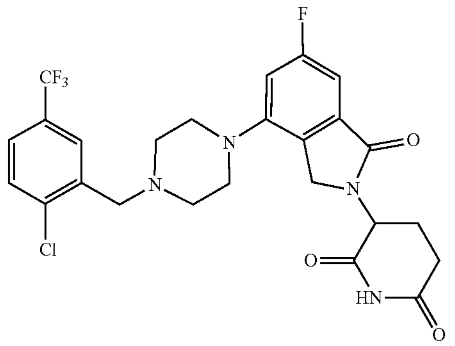

3-(6-Fluoro-1-oxo-4-(4-((tetrahydro-2H-pyran-4-yl)methyl)piperazin-1-yl)-isoindolin-2-yl)piperidine-2,6-dione B1105.

3-(4-(4-((1-Benzylpiperidin-4-yl)methyl)piperazin-1-yl)-6-fluoro-1-oxoisoindolin-2-yl)piperidine-2,6-dione B1106.

B1105

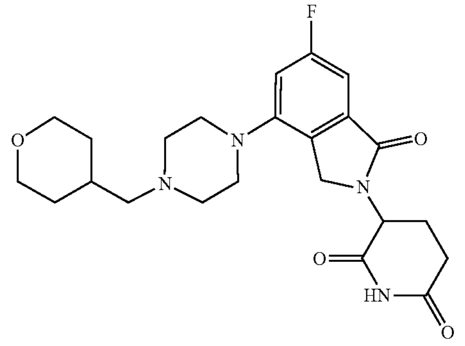

B1106

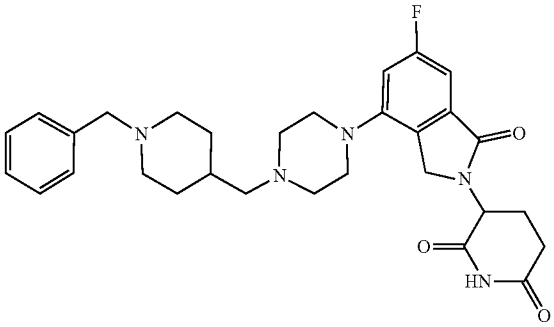

2-(3-(4-(2-(2,6-Dioxopiperidin-3-yl)-6-fluoro-1-oxoisoindolin-4-yl)piperazin-1-yl)propyl)isoindoline-1,3-dione B1107.

3-(6-Fluoro-1-oxo-4-(4-(3-(3-(trifluoromethyl)phenyl)propyl)piperazin-1-yl)-isoindolin-2-yl)piperidine-2,6-dione B1108.

B1107

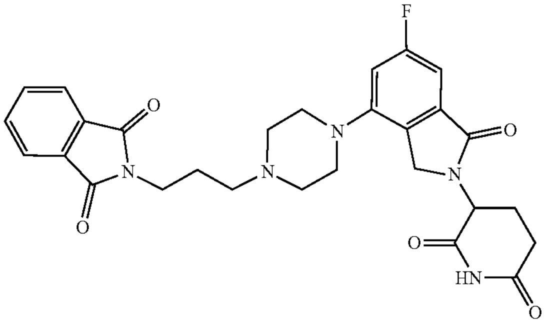

B1108

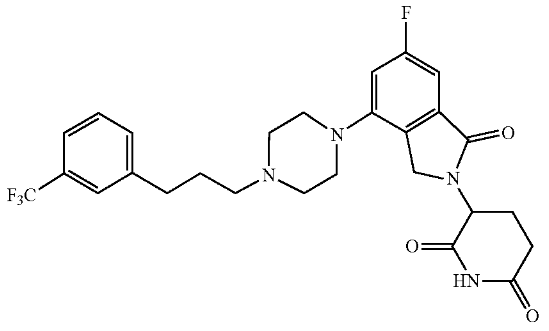

3-(4-(4-((6-(Dimethylamino)naphthalen-2-yl)methyl)piperazin-1-yl)-6-fluoro-1-oxoisoindolin-2-yl)piperidine-2,6-dione B1109.

N-(2-((4-(2-(2,6-Dioxopiperidin-3-yl)-6-fluoro-1-oxoisoindolin-4-yl)piperazin-1-yl)methyl)phenyl)methanesulfonamide B1110.

B1109

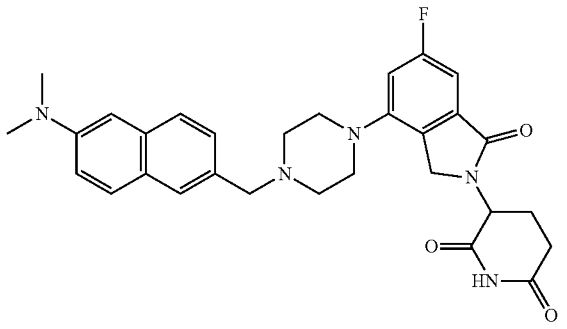

B1110

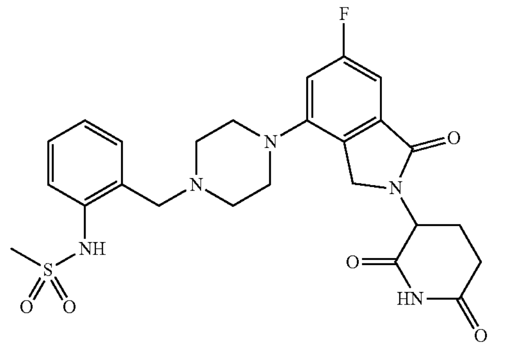

N-(4-((4-(2-(2,6-Dioxopiperidin-3-yl)-6-fluoro-1-oxoisoindolin-4-yl)piperazin-1-yl)methyl)phenyl)methanesulfonamide B1111.

N-(3-((4-(2-(2,6-Dioxopiperidin-3-yl)-6-fluoro-1-oxoisoindolin-4-yl)piperazin-1-yl)methyl)phenyl)methanesulfonamide B1112.

B1111

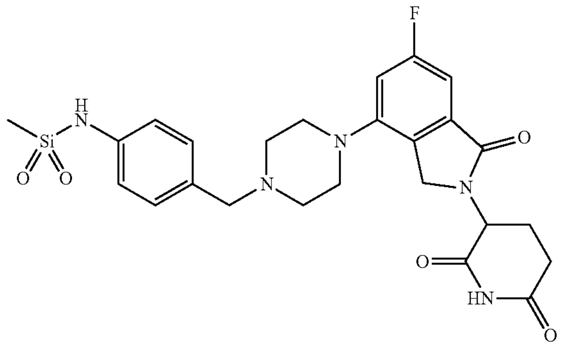

-continued

B1112

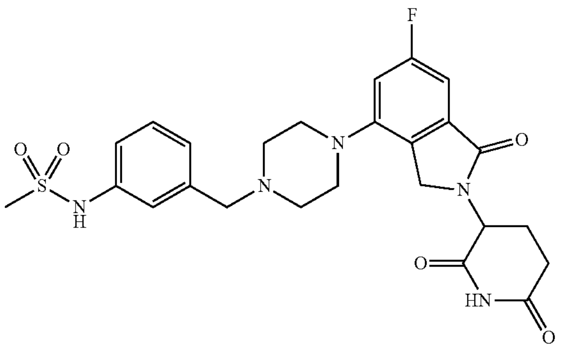

3-(6-Fluoro-1-oxo-4-(4-(2-(pyridin-2-yloxy)benzyl)piperazin-1-yl)isoindolin-2-yl)piperidine-2,6-dione B1113.

3-(4-(4-(4-Bromophenethyl)piperazin-1-yl)-6-fluoro-1-oxoisoindolin-2-yl)-piperidine-2,6-dione B1114.

B1113

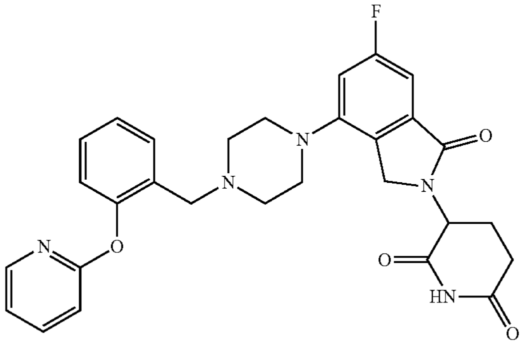

B1114

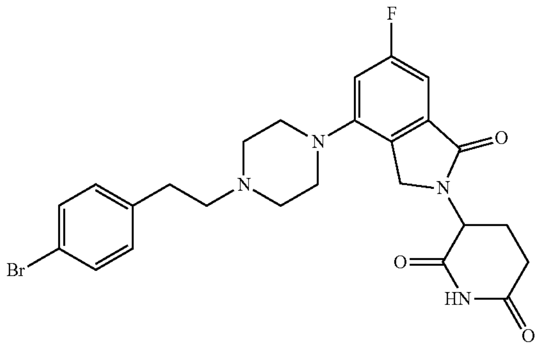

3-(6-Fluoro-4-(4-((2-morpholinothiazol-5-yl)methyl)piperazin-1-yl)-1-oxoisoindolin-2-yl)piperidine-2,6-dione B1115.

3-(6-Fluoro-1-oxo-4-(4-(thiazol-2-ylmethyl)piperazin-1-yl)isoindolin-2-yl)-piperidine-2,6-dione B1116.

B1115

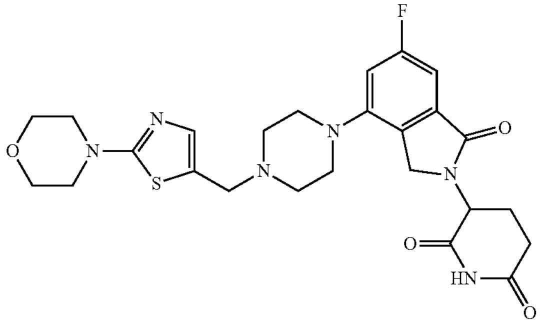

B1116

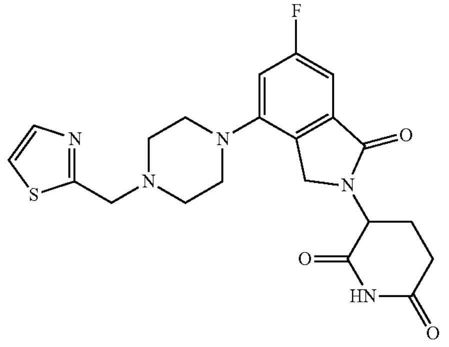

3-(4-(4-(4-(Ethylsulfonyl)benzyl)piperazin-1-yl)-6-fluoro-1-oxoisoindolin-2-yl)-piperidine-2,6-dione B1117.

3-(6-Fluoro-4-(4-((4'-methyl-[2,2'-bipyridin]-4-yl)methyl)piperazin-1-yl)-1-oxoisoindolin-2-yl)piperidine-2,6-dione B1118.

B1117

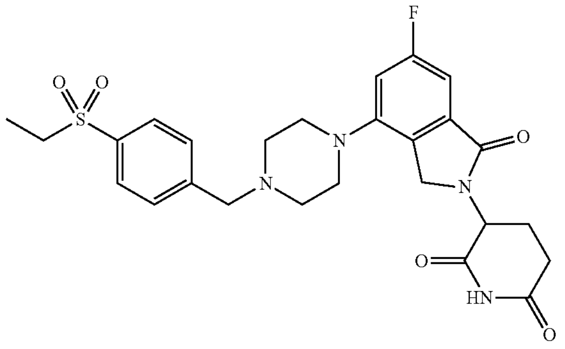

-continued

B1118

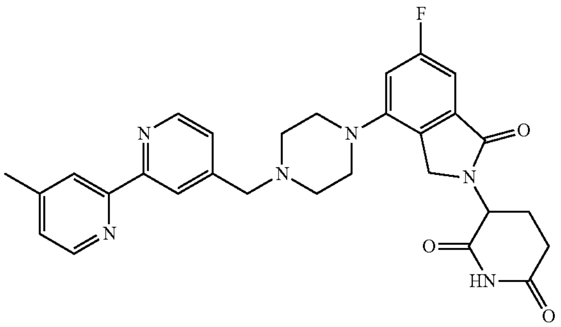

3-(6-Fluoro-1-oxo-4-(4-(4-phenoxybenzyl)piperazin-1-yl)isoindolin-2-yl)-piperidine-2,6-dione B1119.

3-(6-Fluoro-1-oxo-4-(4-(3-phenoxybenzyl)piperazin-1-yl)isoindolin-2-yl)-piperidine-2,6-dione B1120.

B1119

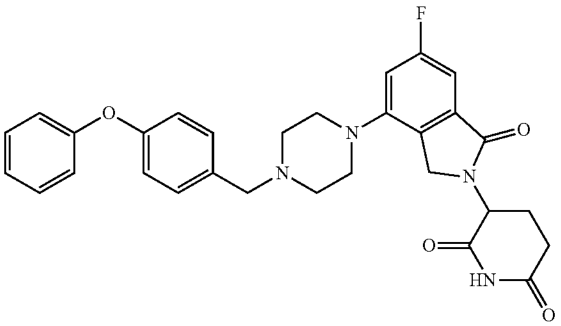

B1120

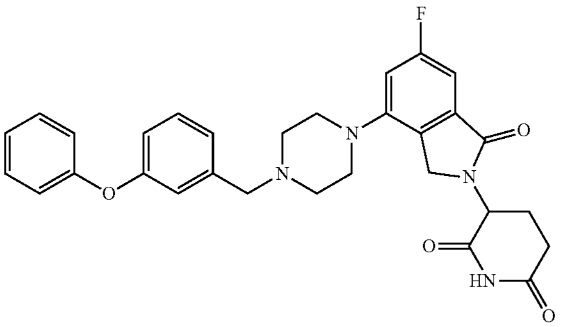

3-(6-Fluoro-1-oxo-4-(4-((6-(p-tolyl)pyridin-3-yl)methyl)piperazin-1-yl)-isoindolin-2-yl)piperidine-2,6-dione B1121.

4-((4-(2-(2,6-Dioxopiperidin-3-yl)-6-fluoro-1-oxoisoindolin-4-yl)piperazin-1-yl)-methyl)-N-isopropylbenzamide B1122.

B1121

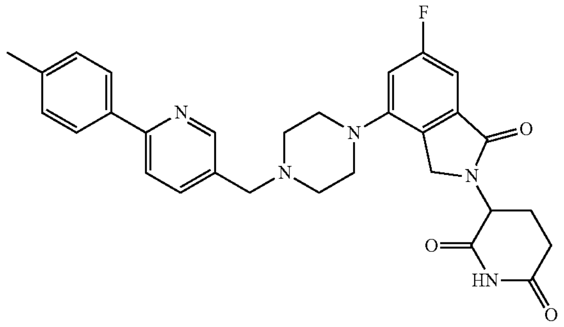

B1122

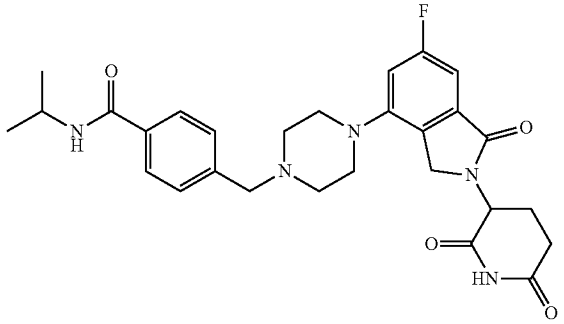

3-(6-Fluoro-4-(4-(2-morpholinobenzyl)piperazin-1-yl)-1-oxoisoindolin-2-yl)-piperidine-2,6-dione B1123.

3-(6-Fluoro-4-(4-(3-morpholinobenzyl)piperazin-1-yl)-1-oxoisoindolin-2-yl)-piperidine-2,6-dione B1124.

B1123

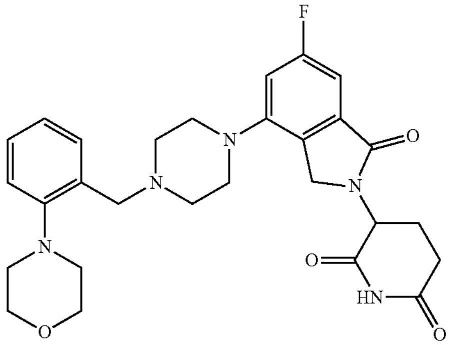

B1124

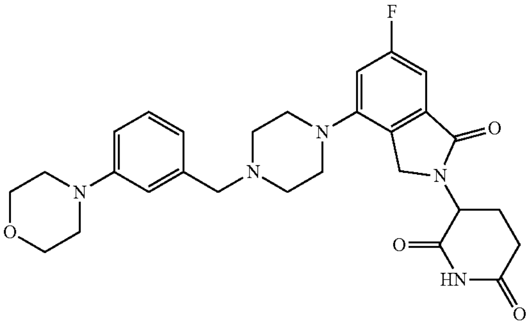

3-(6-Fluoro-4-(4-(4-morpholinobenzyl)piperazin-1-yl)-1-oxoisoindolin-2-yl)-piperidine-2,6-dione B1125.

3-(6-Fluoro-1-oxo-4-(4-(3-(quinolin-6-yl)propyl)piperazin-1-yl)isoindolin-2-yl)-piperidine-2,6-dione B1126.

B1125

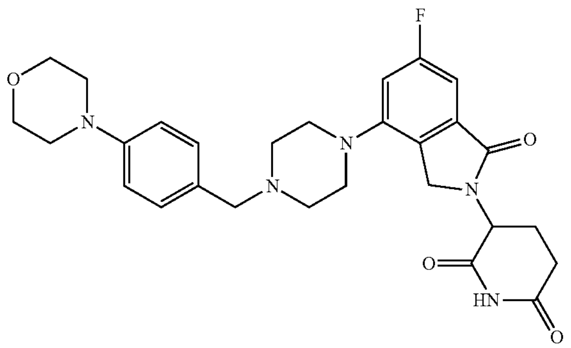

B1126

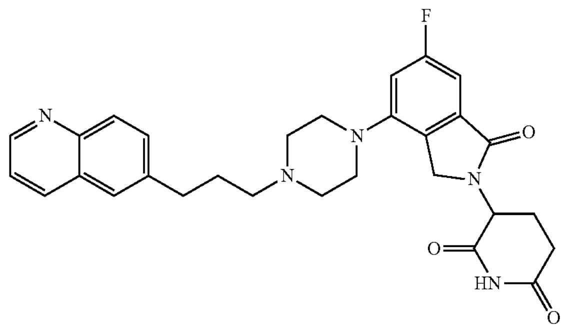

3-(6-Fluoro-1-oxo-4-(4-(thiazol-5-ylmethyl)piperazin-1-yl)isoindolin-2-yl)-piperidine-2,6-dione B1127.

3-(4-(4-((1H-Pyrrol-3-yl)methyl)piperazin-1-yl)-6-fluoro-1-oxoisoindolin-2-yl)-piperidine-2,6-dione B1128.

B1127

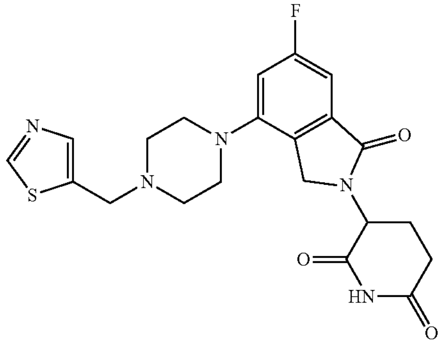

-continued

B1128

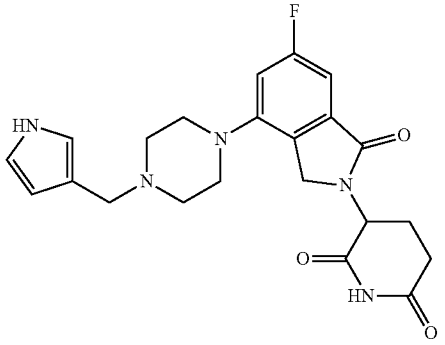

3-(6-Fluoro-4-(4-((6-(methylsulfonyl)pyridin-2-yl)methyl)piperazin-1-yl)-1-oxoisoindolin-2-yl)piperidine-2,6-dione B1129.

3-(6-Fluoro-1-oxo-4-(4-(3-(pyridin-4-yl)benzyl)piperazin-1-yl)isoindolin-2-yl)-piperidine-2,6-dione B1130.

B1129

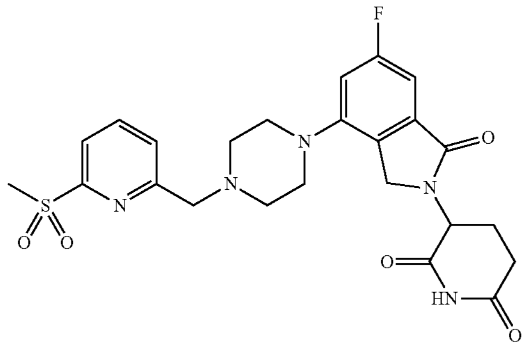

B1130

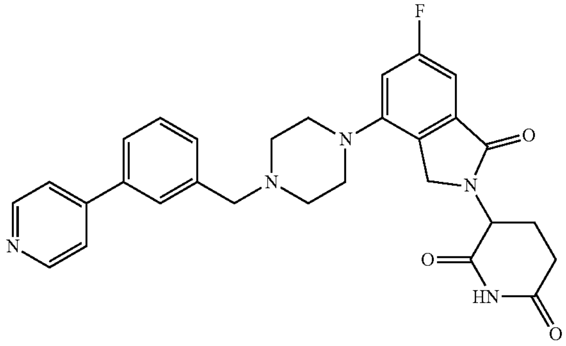

3-(4-(4-([1,1'-Biphenyl]-4-ylmethyl)piperazin-1-yl)-6-fluoro-1-oxoisoindolin-2-yl)piperidine-2,6-dione B1131.

3-(6-Fluoro-4-(4-((6-fluorochroman-8-yl)methyl)piperazin-1-yl)-1-oxoisoindolin-2-yl)piperidine-2,6-dione B1132.

B1131

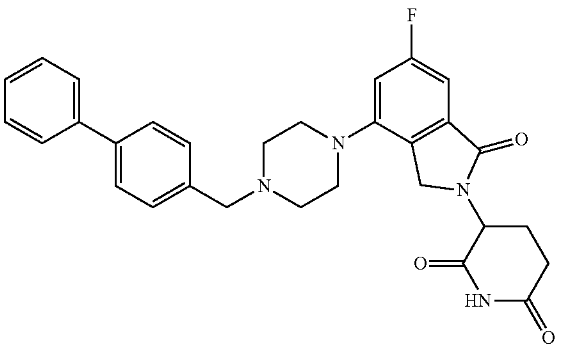

B1132

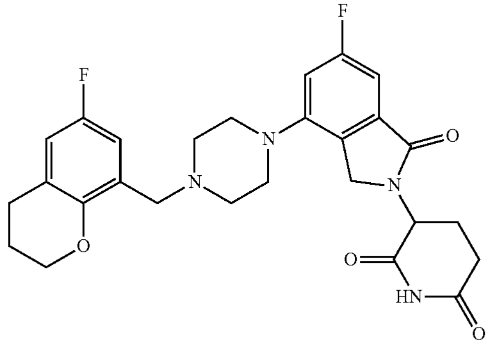

3-(6-Fluoro-1-oxo-4-(4-((6-(pyrrolidin-1-yl)pyridin-3-yl)methyl)piperazin-1-yl)-isoindolin-2-yl)piperidine-2,6-dione B1133.

3-(6-Fluoro-1-oxo-4-(4-(3-(pyrrolidin-1-yl)benzyl)piperazin-1-yl)isoindolin-2-yl)piperidine-2,6-dione B1134.

B1133

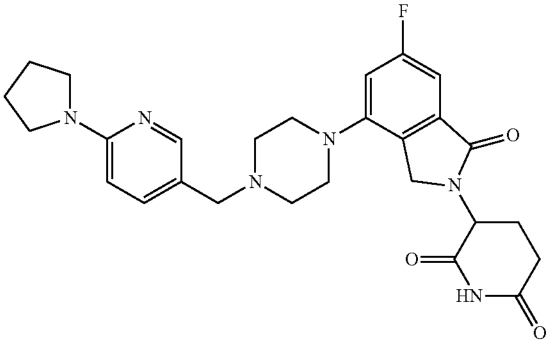

-continued

B1134

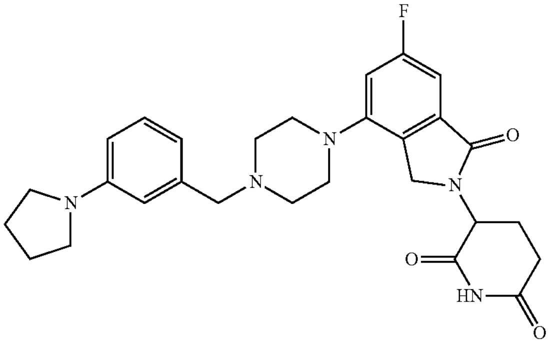

3-(6-Fluoro-1-oxo-4-(4-(4-(pyrrolidin-1-yl)benzyl)piperazin-1-yl)isoindolin-2-yl)piperidine-2,6-dione B1135.

3-(4-(4-(3-(1H-1,2,4-Triazol-1-yl)benzyl)piperazin-1-yl)-6-fluoro-1-oxoisoindolin-2-yl)piperidine-2,6-dione B1136.

B1135

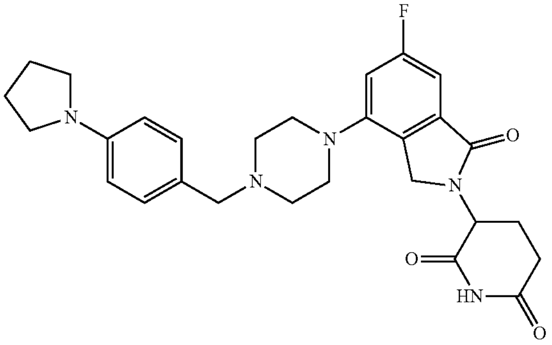

B1136

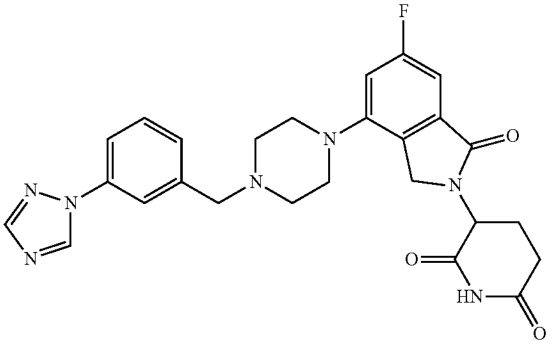

3-(4-(4-(2-(1H-1,2,4-Triazol-1-yl)benzyl)piperazin-1-yl)-6-fluoro-1-oxoisoindolin-2-yl)piperidine-2,6-dione B1137.

3-(4-(4-(4-(1H-1,2,4-Triazol-1-yl)benzyl)piperazin-1-yl)-6-fluoro-1-oxoisoindolin-2-yl)piperidine-2,6-dione B1138.

B1137

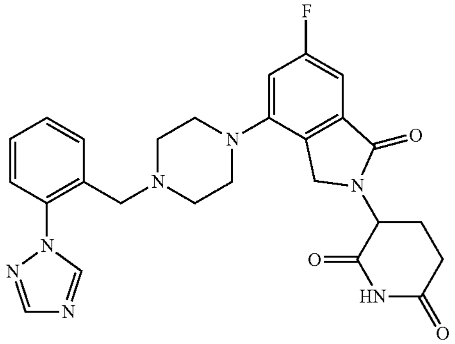

B1138

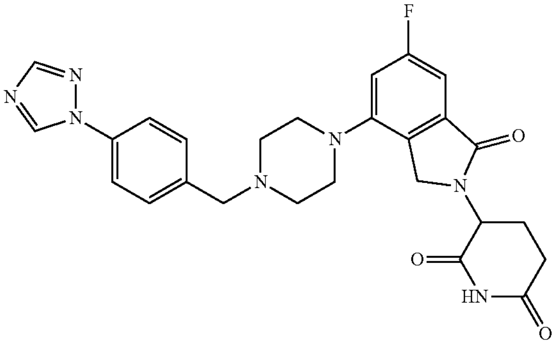

3-(6-Fluoro-1-oxo-4-(4-(thiazol-4-ylmethyl)piperazin-1-yl) isoindolin-2-yl)-piperidine-2,6-dione B1139.

3-(6-Fluoro-1-oxo-4-(4-((1-phenyl-1H-pyrazol-3-yl) methyl)piperazin-1-yl)-isoindolin-2-yl)piperidine-2,6-dione B1140.

B1139

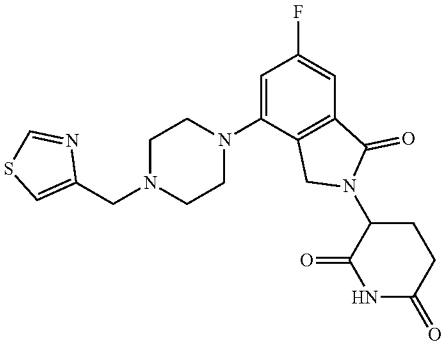

-continued

B1140

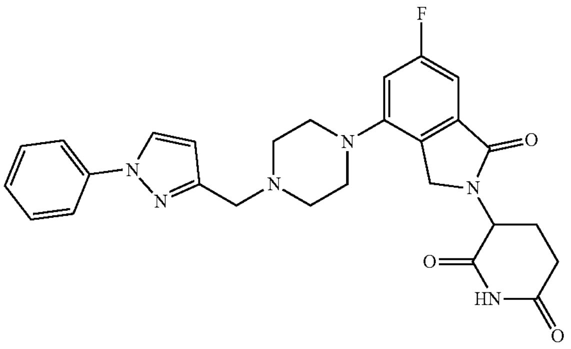

3-(6-Fluoro-1-oxo-4-(4-((5-phenyl-1H-imidazol-2-yl) methyl)piperazin-1-yl)-isoindolin-2-yl)piperidine-2,6-dione B1141.

3-(4-(4-(3-(1H-Imidazol-1-yl)benzyl)piperazin-1-yl)-6-fluoro-1-oxoisoindolin-2-yl)piperidine-2,6-dione B1142.

B1141

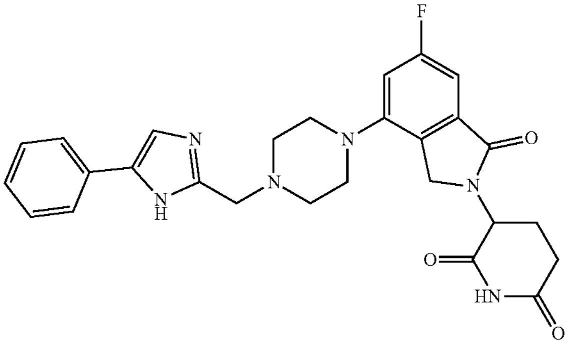

B1142

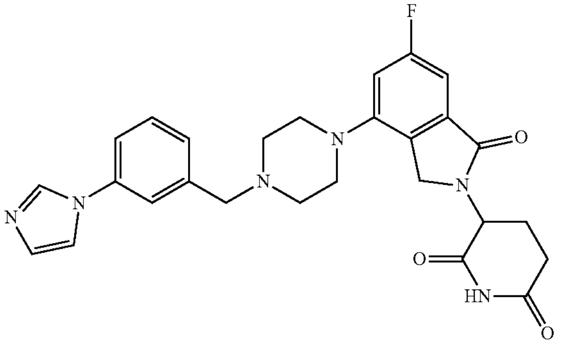

3-(6-Fluoro-1-oxo-4-(4-((2-phenyl-1H-imidazol-5-yl) methyl)piperazin-1-yl)-isoindolin-2-yl)piperidine-2,6-dione B1143.

3-(4-(4-(4-(1H-Imidazol-1-yl)benzyl)piperazin-1-yl)-6-fluoro-1-oxoisoindolin-2-yl)piperidine-2,6-dione B1144.

B1143

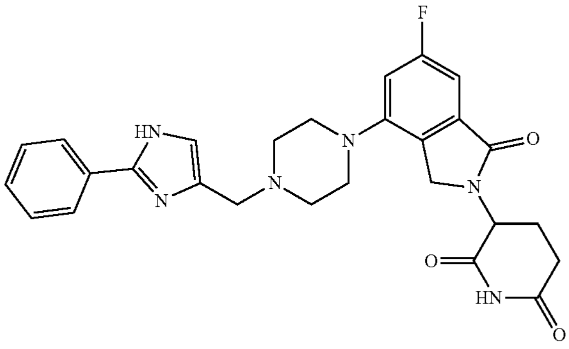

B1144

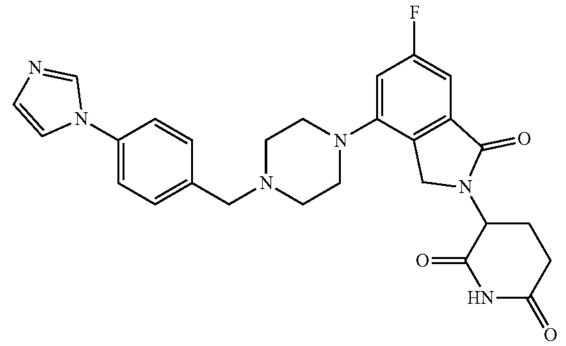

3-(4-(4-(4-(1H-Pyrazol-1-yl)benzyl)piperazin-1-yl)-6-fluoro-1-oxoisoindolin-2-yl)piperidine-2,6-dione B1145.

2-((4-(2-(2,6-Dioxopiperidin-3-yl)-6-fluoro-1-oxoisoindolin-4-yl)piperazin-1-yl)-methyl)-1H-indole-6-carbonitrile B1146.

B1145

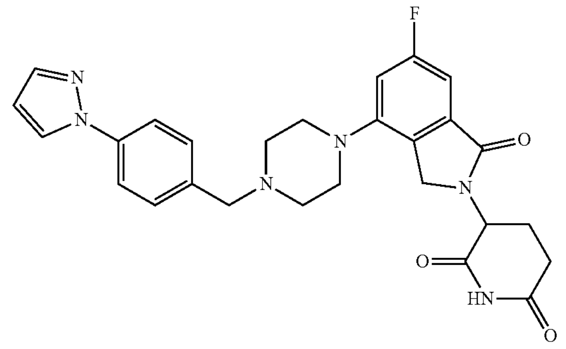

-continued

B1146

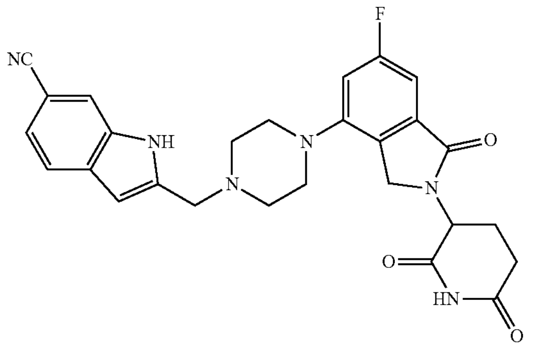

3-((4-(2-(2,6-Dioxopiperidin-3-yl)-6-fluoro-1-oxoisoindolin-4-yl)piperazin-1-yl)-methyl)-1H-indole-6-carbonitrile B1147.

3-(4-(4-((2,3-Dihydro-[1,4]dioxino[2,3-b]pyridin-6-yl)methyl)piperazin-1-yl)-6-fluoro-1-oxoisoindolin-2-yl)piperidine-2,6-dione B1148.

B1147

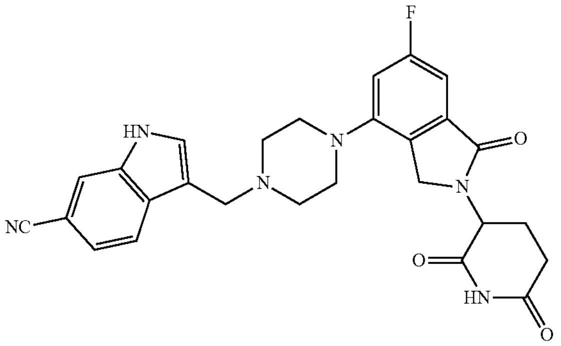

B1148

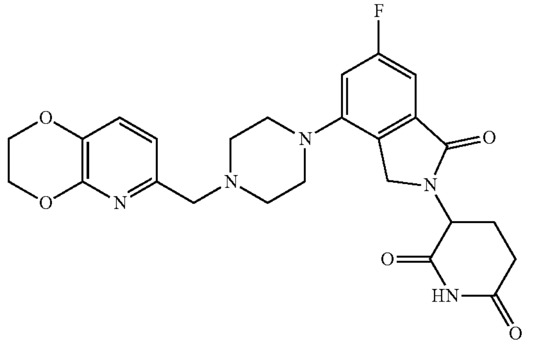

3-(4-(4-((Adamantan-1-yl)methyl)piperazin-1-yl)-6-fluoro-1-oxoisoindolin-2-yl)-piperidine-2,6-dione B1149.

3-(6-Fluoro-1-oxo-4-(4-(thiophen-2-ylmethyl)piperazin-1-yl)isoindolin-2-yl)-piperidine-2,6-dione B1150.

B1149

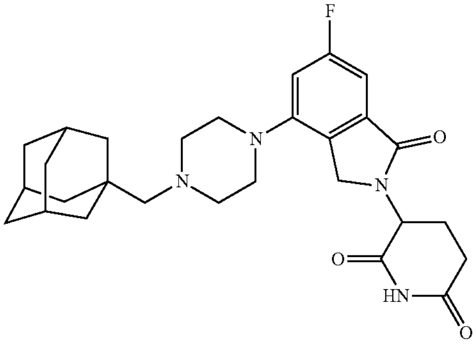

B1150

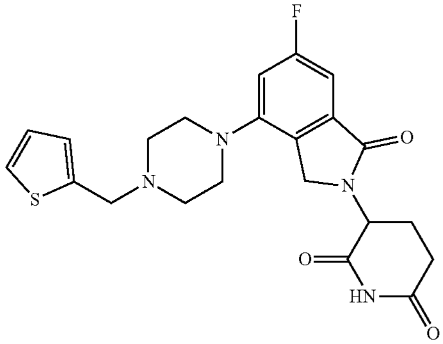

3-(4-(4-(3-(Benzyloxy)propyl)piperazin-1-yl)-6-fluoro-1-oxoisoindolin-2-yl)-piperidine-2,6-dione B1151.

3-(6-Fluoro-4-(4-(3-(2-methoxyphenyl)propyl)piperazin-1-yl)-1-oxoisoindolin-2-yl)piperidine-2,6-dione B1152.

B1151

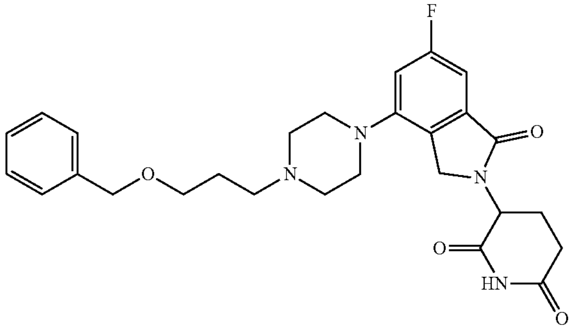

B1152

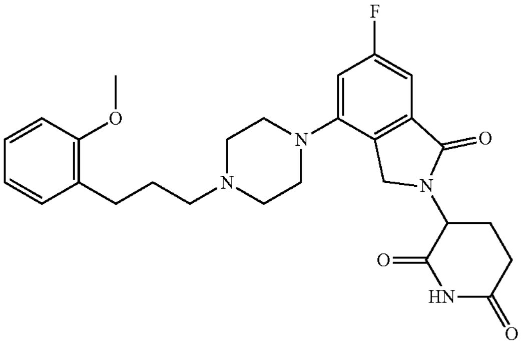

3-(4-(4-((2,3-Dihydrobenzo[b][1,4]dioxin-6-yl)methyl)piperazin-1-yl)-6-fluoro-1-oxoisoindolin-2-yl)piperidine-2,6-dione B1153.

3-(6-Fluoro-4-(4-((5-fluoro-1H-benzo[d]imidazol-2-yl)methyl)piperazin-1-yl)-1-oxoisoindolin-2-yl)piperidine-2,6-dione B1154.

B1153

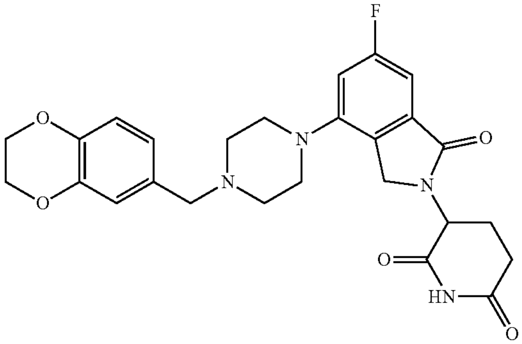

B1154

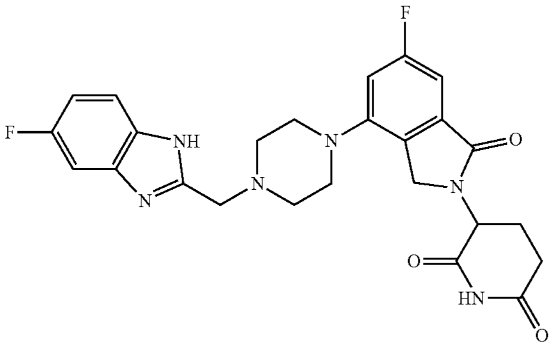

3-(6-Fluoro-4-(4-((4-fluorobenzofuran-7-yl)methyl)piperazin-1-yl)-1-oxoisoindolin-2-yl)piperidine-2,6-dione B1155.

3-(4-(4-(4-(Dimethylamino)-3-methylbenzyl)piperazin-1-yl)-6-fluoro-1-oxoisoindolin-2-yl)piperidine-2,6-dione B1156.

B1155

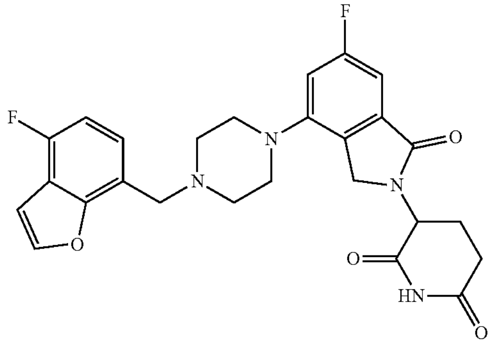

-continued

B1156

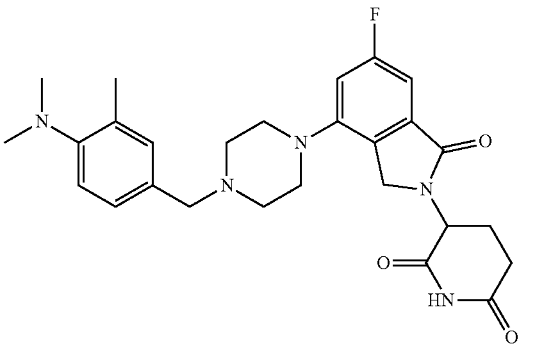

3-(4-(4-((2-(Tert-butyl)pyridin-4-yl)methyl)piperazin-1-yl)-6-fluoro-1-oxoisoindolin-2-yl)piperidine-2,6-dione B1157.

3-(4-(4-(4-((Dimethylamino)methyl)benzyl)piperazin-1-yl)-6-fluoro-1-oxoisoindolin-2-yl)piperidine-2,6-dione B1158.

B1157

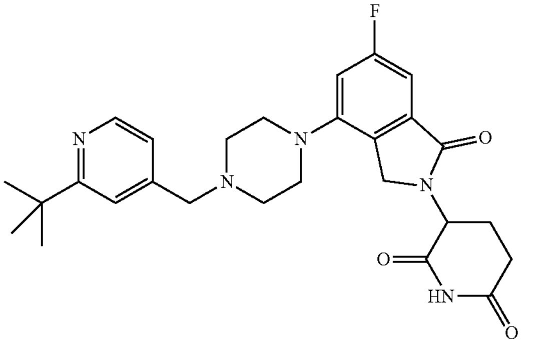

B1158

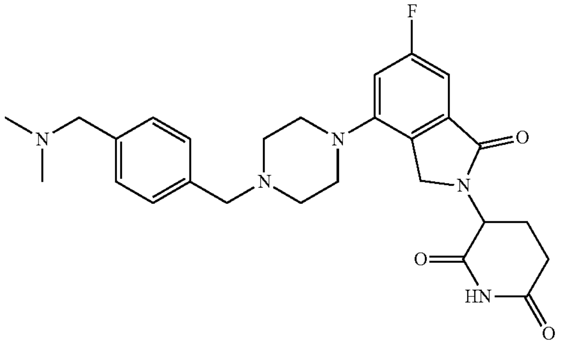

3-(6-Fluoro-1-oxo-4-(4-(thieno[3,2-c]pyridin-2-ylmethyl)piperazin-1-yl)-isoindolin-2-yl)piperidine-2,6-dione B1159.

3-(4-(4-(Benzo[d]thiazol-4-ylmethyl)piperazin-1-yl)-6-fluoro-1-oxoisoindolin-2-yl)piperidine-2,6-dione B1160.

B1159

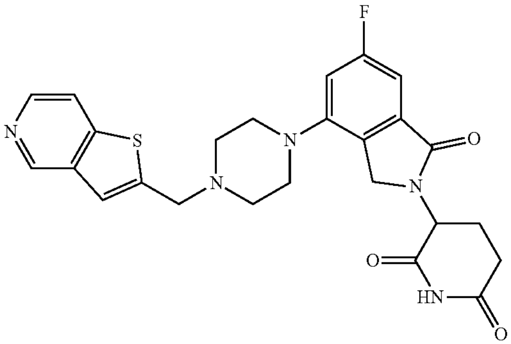

B1160

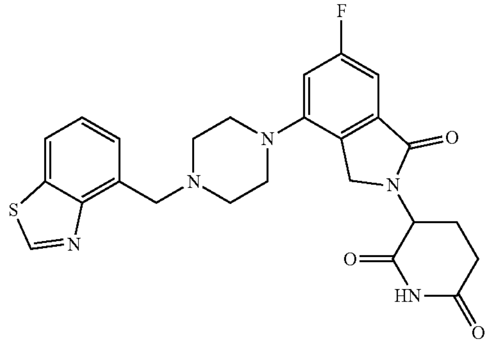

3-(6-Fluoro-1-oxo-4-(4-(thiophen-3-ylmethyl)piperazin-1-yl)isoindolin-2-yl)-piperidine-2,6-dione B1161.

3-(6-Fluoro-1-oxo-4-(4-(thieno[2,3-b]pyridin-2-ylmethyl)piperazin-1-yl)-isoindolin-2-yl)piperidine-2,6-dione B1162.

B1161

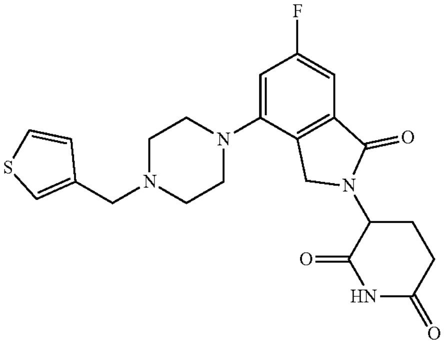

-continued

B1162

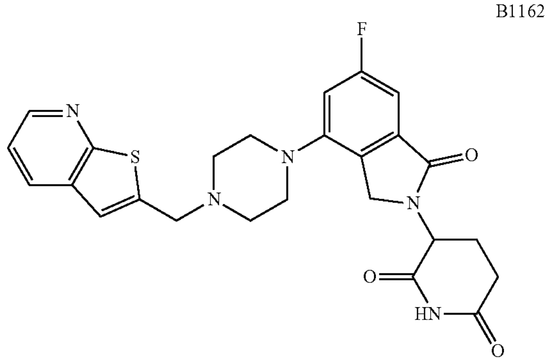

3-(4-(4-((3,4-Dihydro-2H-pyrano[2,3-c]pyridin-6-yl)methyl)piperazin-1-yl)-6-fluoro-1-oxoisoindolin-2-yl)piperidine-2,6-dione B1163.

3-(6-Fluoro-4-(4-(3-methyl-3-phenylbutyl)piperazin-1-yl)-1-oxoisoindolin-2-yl)piperidine-2,6-dione B1164.

B1163

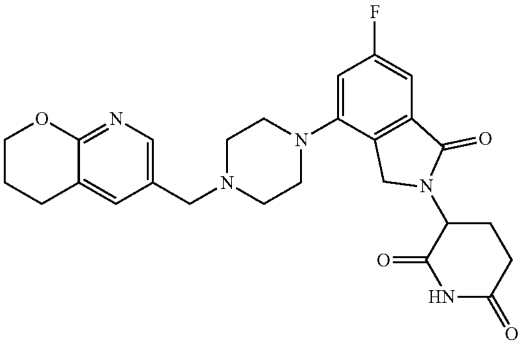

B1164

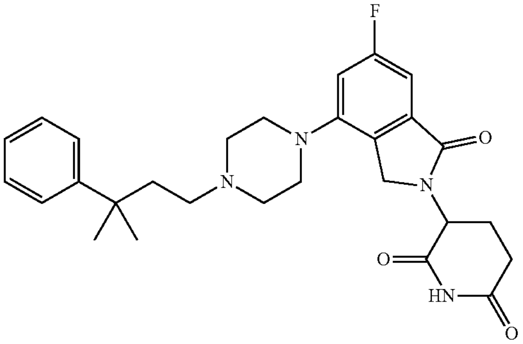

3-(4-(4-(Benzo[b]thiophen-3-ylmethyl)piperazin-1-yl)-6-fluoro-1-oxoisoindolin-2-yl)piperidine-2,6-dione B1165.

3-(4-(4-(Benzo[b]thiophen-2-ylmethyl)piperazin-1-yl)-6-fluoro-1-oxoisoindolin-2-yl)piperidine-2,6-dione B1166.

B1165

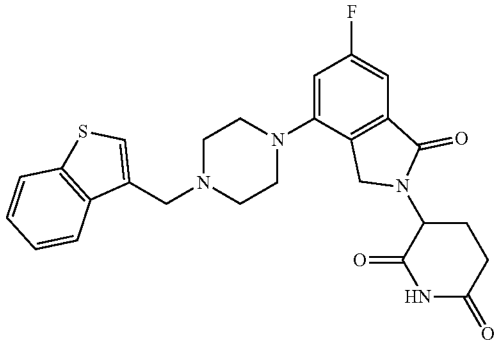

B1166

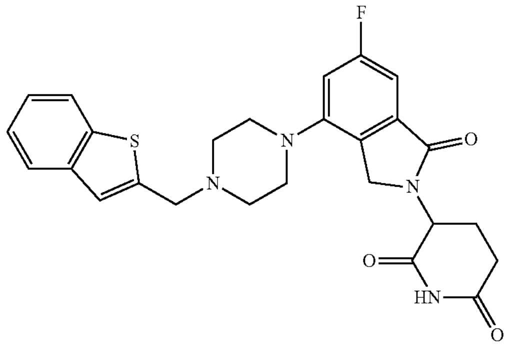

3-(4-(4-(Chroman-6-ylmethyl)piperazin-1-yl)-6-fluoro-1-oxoisoindolin-2-yl)-piperidine-2,6-dione B1167.

3-(6-Fluoro-4-(4-((1-methyl-1H-imidazo[4,5-b]pyridin-2-yl)methyl)piperazin-1-yl)-1-oxoisoindolin-2-yl)piperidine-2,6-dione B1168.

B1167

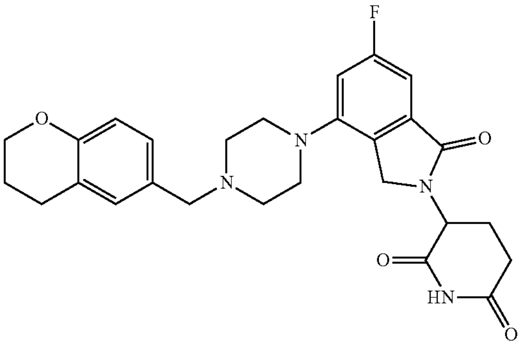

-continued

B1168

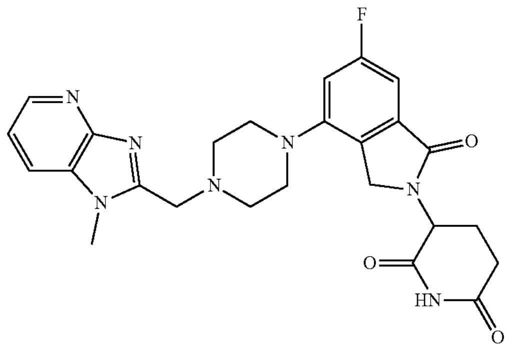

4-((4-(2-(2,6-Dioxopiperidin-3-yl)-6-fluoro-1-oxoisoindolin-4-yl)piperazin-1-yl)-methyl)-2-methoxybenzonitrile B1169.

4-((4-(2-(2,6-Dioxopiperidin-3-yl)-6-fluoro-1-oxoisoindolin-4-yl)piperazin-1-yl)-methyl)-3-methoxybenzonitrile B1170.

B1169

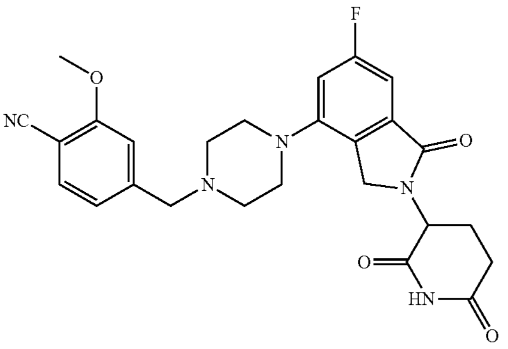

B1170

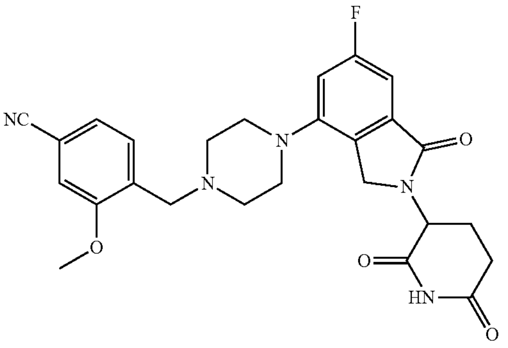

2-((4-(2-(2,6-Dioxopiperidin-3-yl)-6-fluoro-1-oxoisoindolin-4-yl)piperazin-1-yl)-methyl)-5-methoxybenzonitrile B1171.

3-(6-Fluoro-4-(4-((2-methyl-2H-tetrazol-5-yl)methyl)piperazin-1-yl)-1-oxoisoindolin-2-yl)piperidine-2,6-dione B1172.

B1171

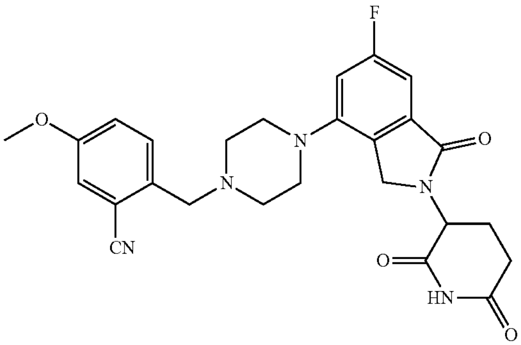

B1172

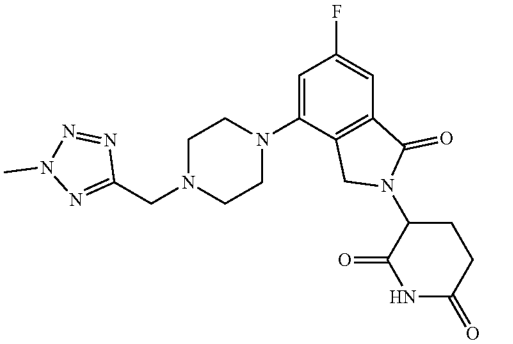

3-(6-Fluoro-4-(4-((2-methylbenzo[d]oxazol-6-yl)methyl)piperazin-1-yl)-1-oxoisoindolin-2-yl)piperidine-2,6-dione B1173.

3-(6-Fluoro-1-oxo-4-(4-((3-oxoisoindolin-5-yl)methyl)piperazin-1-yl)isoindolin-2-yl)piperidine-2,6-dione B1174.

B1173

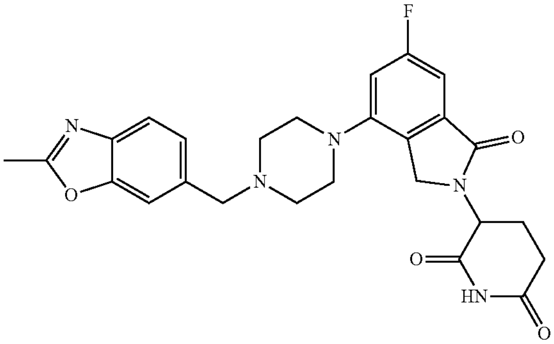

-continued

B1174

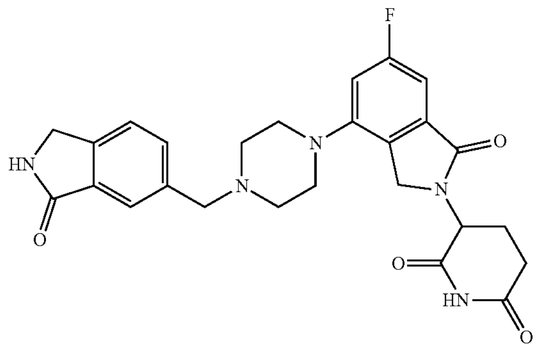

3-(6-Fluoro-1-oxo-4-(4-((1-oxoisoindolin-5-yl)methyl)piperazin-1-yl)isoindolin-2-yl)piperidine-2,6-dione B1175.

3-(6-Fluoro-1-oxo-4-(4-((5,6,7,8-tetrahydronaphthalen-1-yl)methyl)piperazin-1-yl)isoindolin-2-yl)piperidine-2,6-dione B1176.

B1175

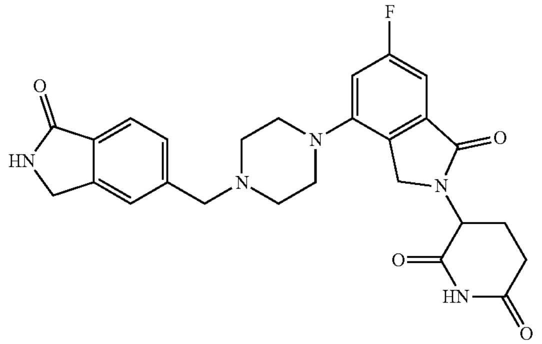

B1176

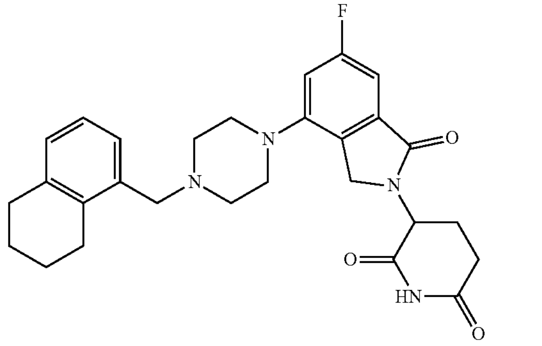

3-(6-Fluoro-4-(4-((3-methylimidazo[1,2-a]pyridin-2-yl)methyl)piperazin-1-yl)-1-oxoisoindolin-2-yl)piperidine-2,6-dione B1177.

3-(6-Fluoro-4-(4-((1-methyl-1H-indazol-6-yl)methyl)piperazin-1-yl)-1-oxoisoindolin-2-yl)piperidine-2,6-dione B1178.

B1177

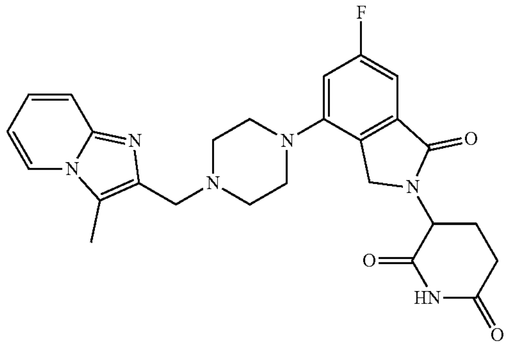

B1178

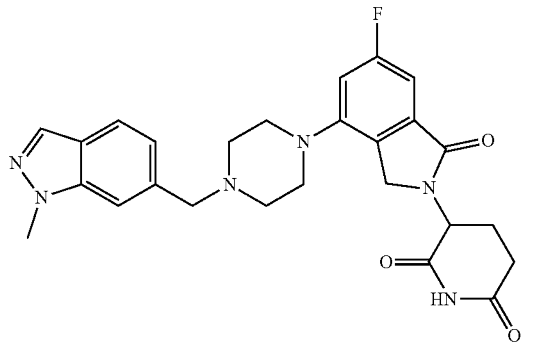

3-(6-Fluoro-4-(4-((2-methyl-2H-indazol-5-yl)methyl)piperazin-1-yl)-1-oxoisoindolin-2-yl)piperidine-2,6-dione B1179.

3-(6-Fluoro-4-(4-((6-methylimidazo[1,2-a]pyridin-2-yl)methyl)piperazin-1-yl)-1-oxoisoindolin-2-yl)piperidine-2,6-dione B1180.

B1179

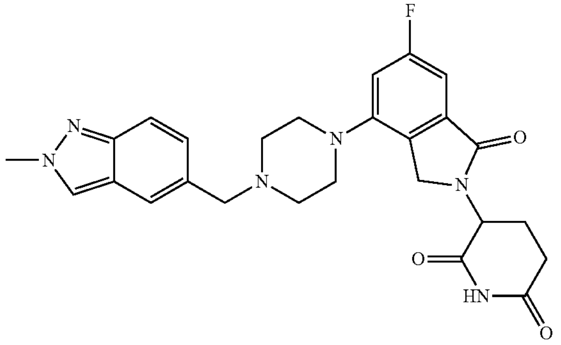

-continued

B1180

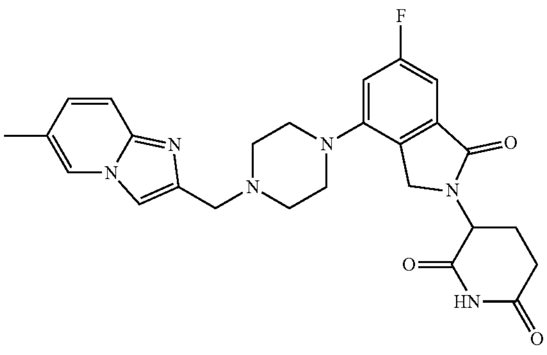

3-(6-Fluoro-4-(4-((5-methylimidazo[1,2-a]pyridin-3-yl)methyl)piperazin-1-yl)-1-oxoisoindolin-2-yl)piperidine-2,6-dione B1181.

3-(6-Fluoro-4-(4-((7-methylimidazo[1,2-a]pyridin-3-yl)methyl)piperazin-1-yl)-1-oxoisoindolin-2-yl)piperidine-2,6-dione B1182.

B1181

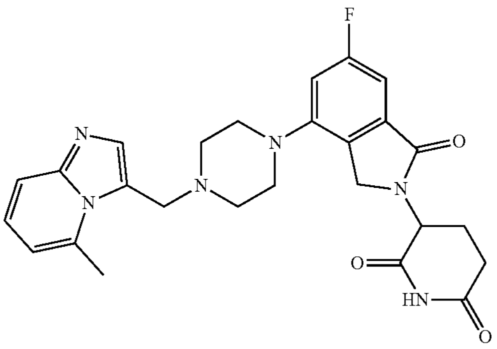

B1182

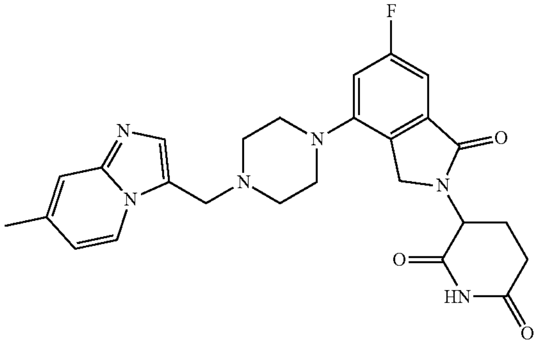

3-(6-Fluoro-4-(4-((5-methyl-4H-1,2,4-triazol-3-yl)methyl)piperazin-1-yl)-1-oxoisoindolin-2-yl)piperidine-2,6-dione B1183.

3-(6-Fluoro-4-(4-((1-methyl-1H-indazol-4-yl)methyl)piperazin-1-yl)-1-oxoisoindolin-2-yl)piperidine-2,6-dione B1184.

B1183

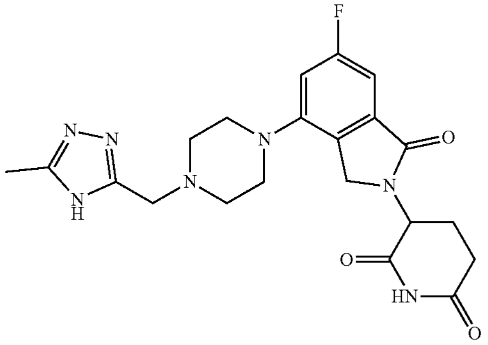

B1184

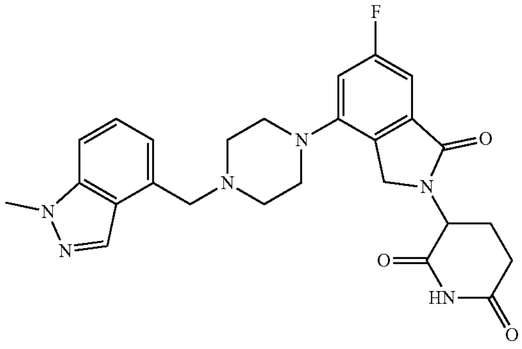

3-(6-Fluoro-4-(4-((5-methyl-1H-pyrrolo[2,3-b]pyridin-3-yl)methyl)piperazin-1-yl)-1-oxoisoindolin-2-yl)piperidine-2,6-dione B1185.

3-(6-Fluoro-4-(4-((1-methyl-1H-benzo[d]imidazol-2-yl)methyl)piperazin-1-yl)-1-oxoisoindolin-2-yl)piperidine-2,6-dione B1186.

B1185

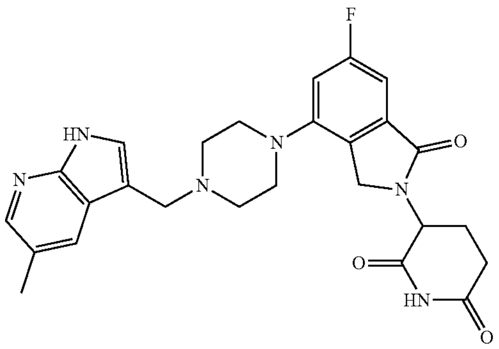

-continued

B1186

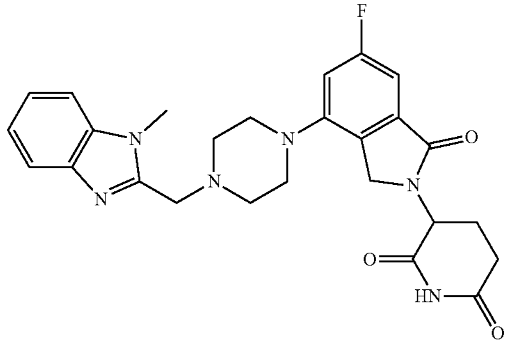

3-(6-Fluoro-4-(4-((2-methylimidazo[1,2-a]pyridin-3-yl)methyl)piperazin-1-yl)-1-oxoisoindolin-2-yl)piperidine-2,6-dione B1187.

3-(6-Fluoro-4-(4-((2-methyl-2H-indazol-3-yl)methyl)piperazin-1-yl)-1-oxoisoindolin-2-yl)piperidine-2,6-dione B1188.

B1187

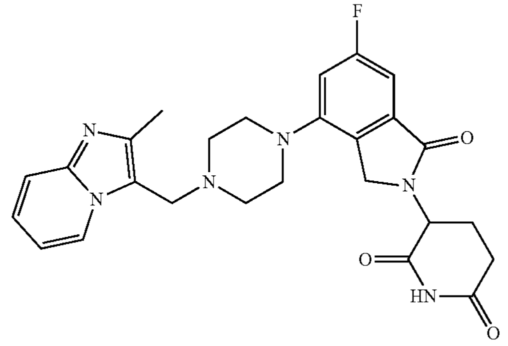

B1188

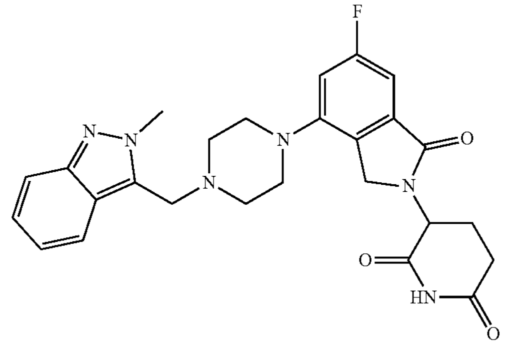

3-(6-Fluoro-4-(4-((7-methyl-1H-indol-3-yl)methyl)piperazin-1-yl)-1-oxoisoindolin-2-yl)piperidine-2,6-dione B1189.

3-(6-Fluoro-4-(4-((1-methyl-1H-indol-5-yl)methyl)piperazin-1-yl)-1-oxoisoindolin-2-yl)piperidine-2,6-dione B1190.

B1189

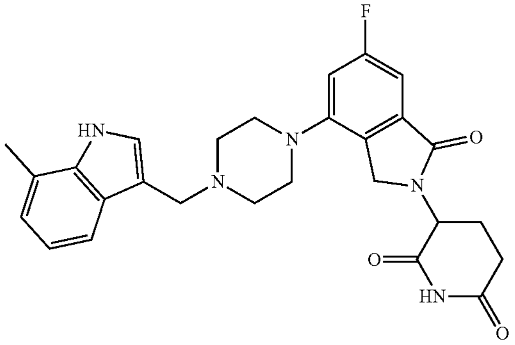

B1190

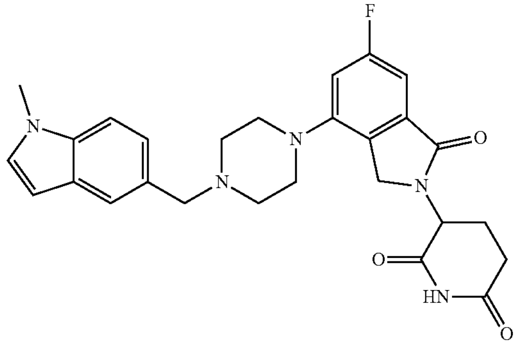

3-(6-Fluoro-4-(4-((2-methyl-1H-indol-4-yl)methyl)piperazin-1-yl)-1-oxoisoindolin-2-yl)piperidine-2,6-dione B1191.

3-(6-Fluoro-4-(4-((1-methyl-1H-indol-6-yl)methyl)piperazin-1-yl)-1-oxoisoindolin-2-yl)piperidine-2,6-dione B1192.

B1191

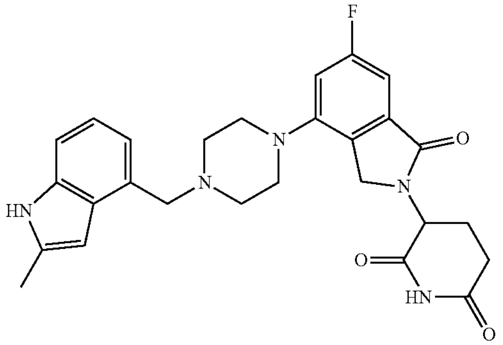

-continued

B1192

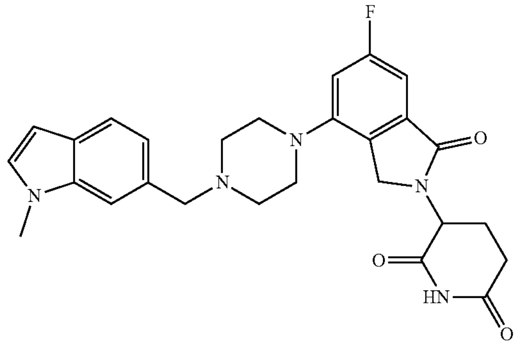

3-(6-Fluoro-4-(4-((4-methyl-1H-indol-3-yl)methyl)piperazin-1-yl)-1-oxoisoindolin-2-yl)piperidine-2,6-dione B1193.

3-(6-Fluoro-4-(4-((4-methyloxazol-5-yl)methyl)piperazin-1-yl)-1-oxoisoindolin-2-yl)piperidine-2,6-dione B1194.

B1193

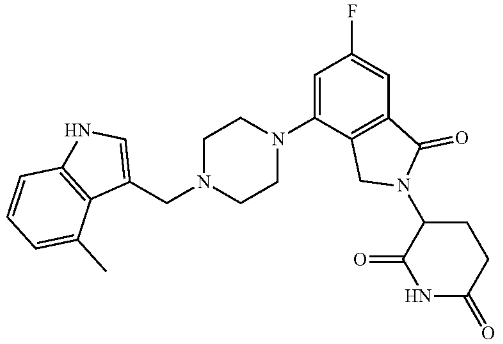

B1194

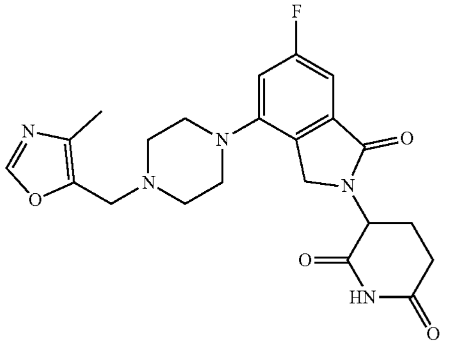

3-(6-Fluoro-4-(4-((3-methyl-1H-indol-2-yl)methyl)piperazin-1-yl)-1-oxoisoindolin-2-yl)piperidine-2,6-dione B1195.

3-(6-Fluoro-4-(4-((6-methyl-1H-indol-3-yl)methyl)piperazin-1-yl)-1-oxoisoindolin-2-yl)piperidine-2,6-dione B1196.

B1195

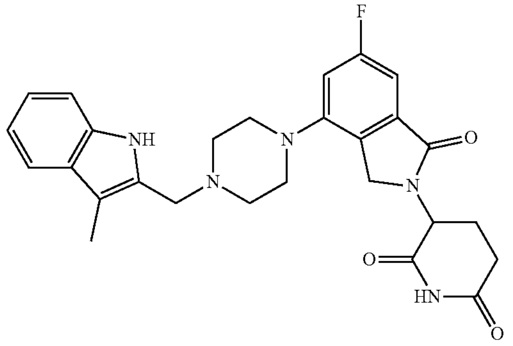

B1196

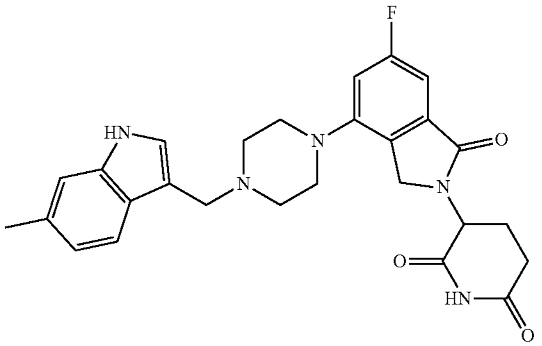

Tert-butyl (2-(4-(2-(2,6-dioxopiperidin-3-yl)-6-fluoro-1-oxoisoindolin-4-yl)-piperazin-1-yl)ethyl)carbamate B1197.

3-(6-Fluoro-1-oxo-4-(4-(quinoxalin-6-ylmethyl)piperazin-1-yl)isoindolin-2-yl)-piperidine-2,6-dione B1198.

B1197

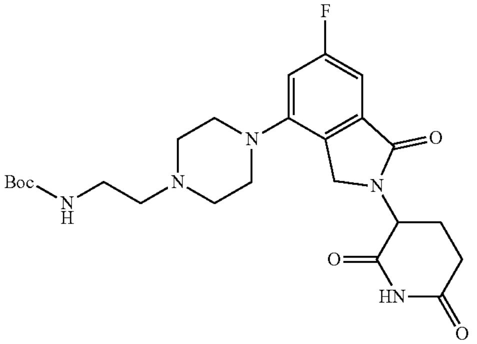

-continued

B1198

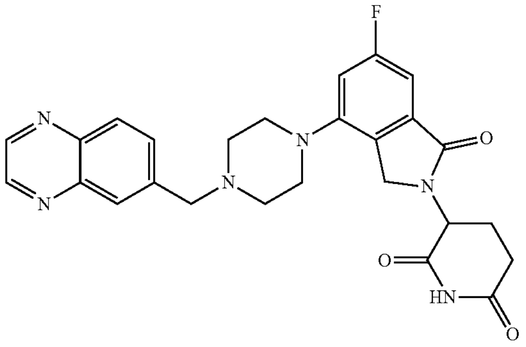

3-(4-(4-((1,8-Naphthyridin-2-yl)methyl)piperazin-1-yl)-6-fluoro-1-oxoisoindolin-2-yl)piperidine-2,6-dione B1199.

3-(6-Fluoro-1-oxo-4-(4-(quinoxalin-2-ylmethyl)piperazin-1-yl)isoindolin-2-yl)-piperidine-2,6-dione B1200.

B1199

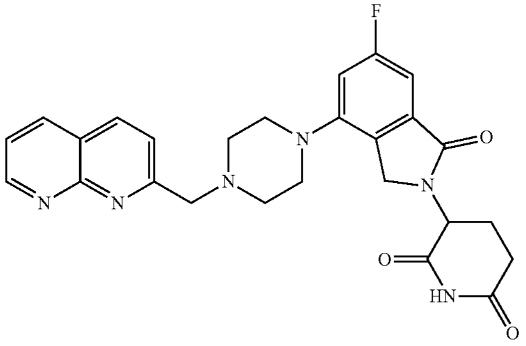

B1200

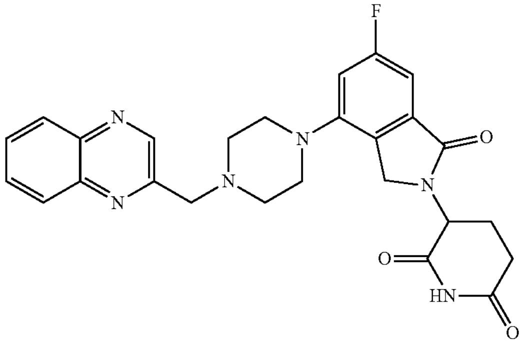

3-(6-Fluoro-1-oxo-4-(4-(quinoxalin-5-ylmethyl)piperazin-1-yl)isoindolin-2-yl)-piperidine-2,6-dione B1201.

3-(6-Fluoro-1-oxo-4-(4-(quinolin-8-ylmethyl)piperazin-1-yl)isoindolin-2-yl)-piperidine-2,6-dione B1202.

B1201

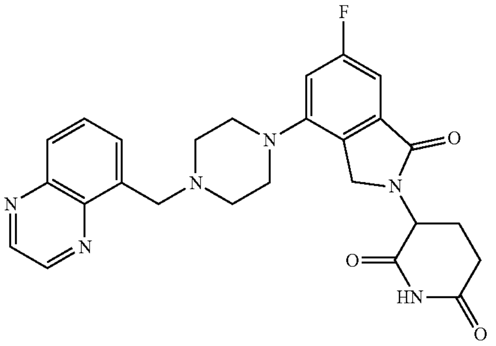

B1202

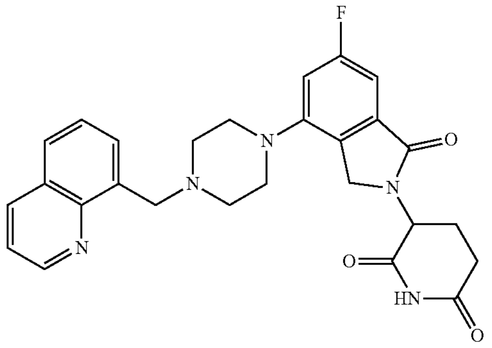

3-(6-Fluoro-4-(4-(isoquinolin-4-ylmethyl)piperazin-1-yl)-1-oxoisoindolin-2-yl)-piperidine-2,6-dione B1203.

3-(6-Fluoro-4-(4-(isoquinolin-3-ylmethyl)piperazin-1-yl)-1-oxoisoindolin-2-yl)-piperidine-2,6-dione B1204.

B1203

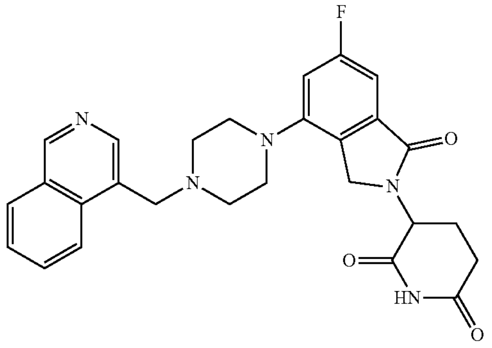

-continued

B1204

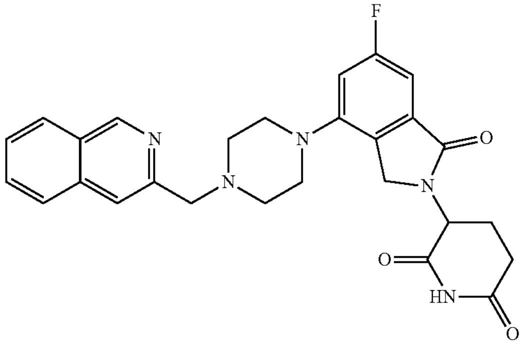

3-(6-Fluoro-4-(4-((2-methyloxazol-4-yl)methyl)piperazin-1-yl)-1-oxoisoindolin-2-yl)piperidine-2,6-dione B1205.

3-(6-Fluoro-4-(4-(isoquinolin-8-ylmethyl)piperazin-1-yl)-1-oxoisoindolin-2-yl)-piperidine-2,6-dione B1206.

B1205

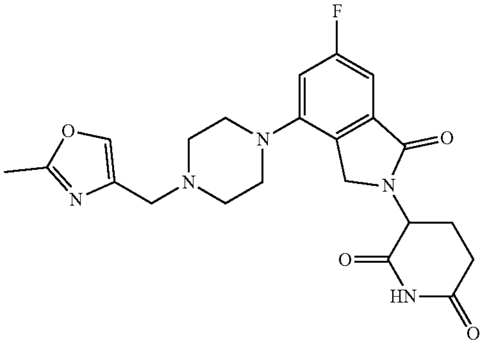

B1206

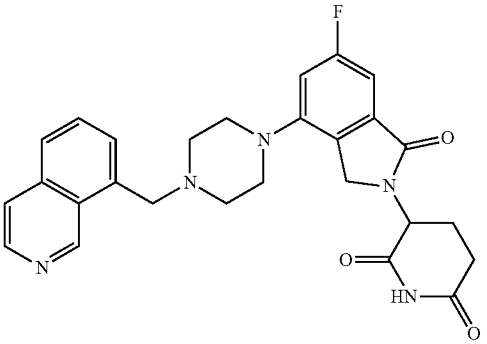

3-(6-Fluoro-4-(4-(isoquinolin-5-ylmethyl)piperazin-1-yl)-1-oxoisoindolin-2-yl)-piperidine-2,6-dione B1207.

3-(6-Fluoro-1-oxo-4-(4-(quinolin-4-ylmethyl)piperazin-1-yl)isoindolin-2-yl)-piperidine-2,6-dione B1208.

B1207

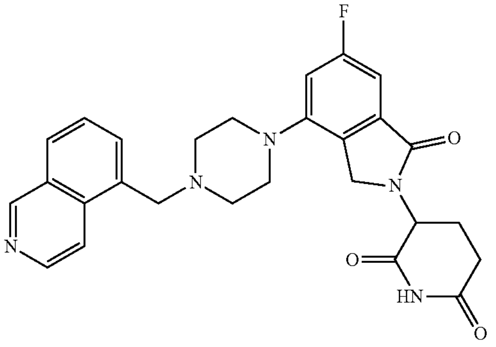

B1208

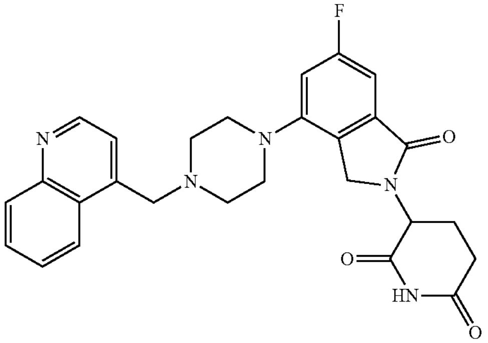

3-(6-Fluoro-1-oxo-4-(4-(quinolin-6-ylmethyl)piperazin-1-yl)isoindolin-2-yl)-piperidine-2,6-dione B1209.

3-(6-Fluoro-4-(4-(naphthalen-2-ylmethyl)piperazin-1-yl)-1-oxoisoindolin-2-yl)-piperidine-2,6-dione B1210.

B1209

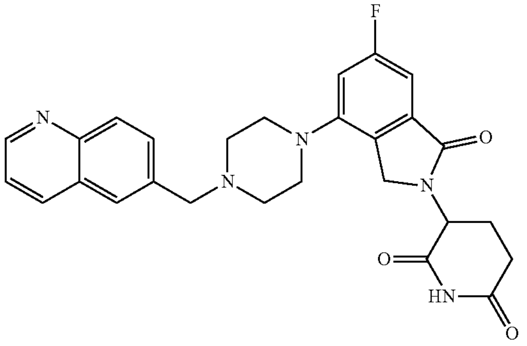

-continued

B1210

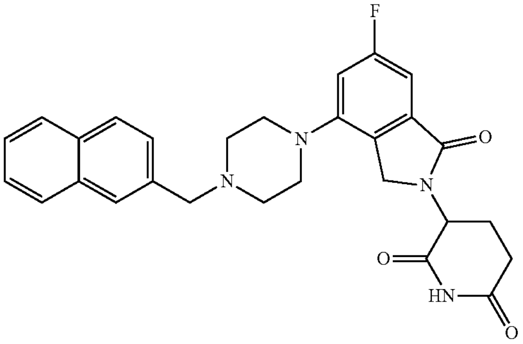

3-(4-(4-(2-Amino-6-chlorobenzyl)piperazin-1-yl)-6-fluoro-1-oxoisoindolin-2-yl)-piperidine-2,6-dione B1211.

3-(4-(4-(2-Amino-4-chlorobenzyl)piperazin-1-yl)-6-fluoro-1-oxoisoindolin-2-yl)-piperidine-2,6-dione B1212.

B1211

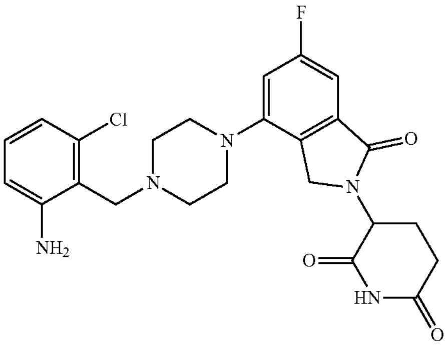

B1212

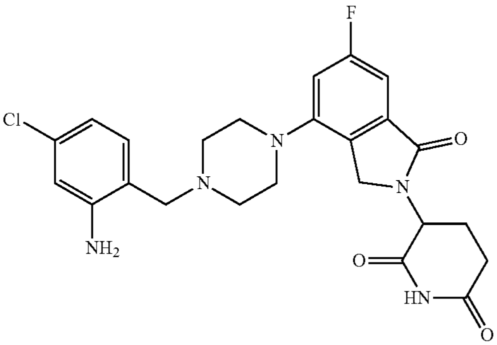

3-(4-(4-(2-Amino-3-chlorobenzyl)piperazin-1-yl)-6-fluoro-1-oxoisoindolin-2-yl)-piperidine-2,6-dione B1213.

3-(4-(4-((5-(Dimethylamino)thiophen-2-yl)methyl)piperazin-1-yl)-6-fluoro-1-oxoisoindolin-2-yl)piperidine-2,6-dione B1214.

B1213

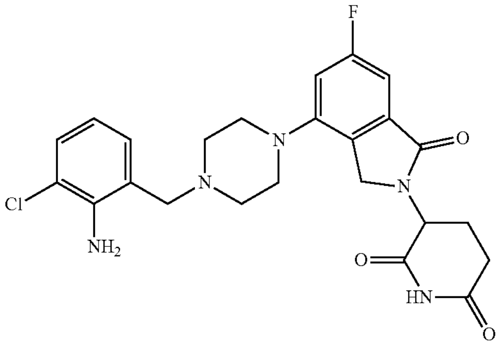

B1214

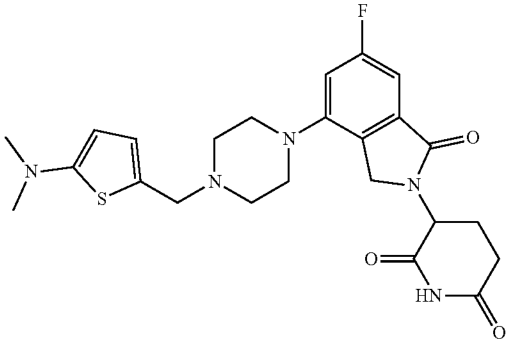

3-(4-(4-(4-Chlorophenethyl)piperazin-1-yl)-6-fluoro-1-oxoisoindolin-2-yl)-piperidine-2,6-dione B1215.

3-(6-Fluoro-4-(4-((2-methyloxazol-5-yl)methyl)piperazin-1-yl)-1-oxoisoindolin-2-yl)piperidine-2,6-dione B1216.

B1215

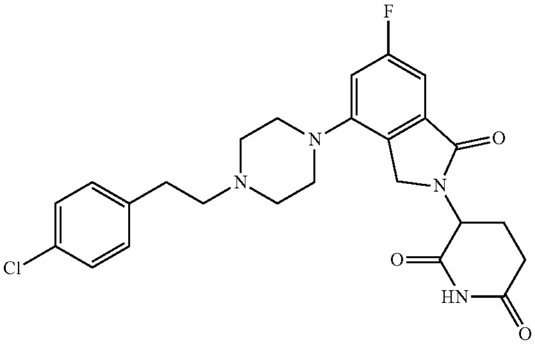

-continued

B1216

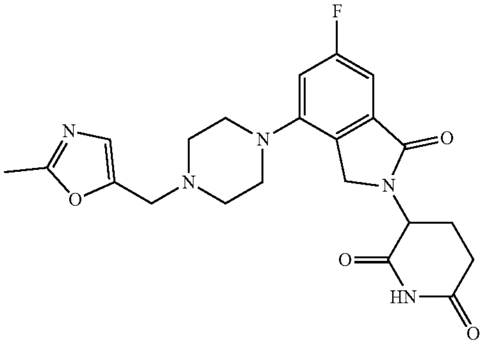

3-(6-Fluoro-4-(4-((4-hydroxybicyclo[2.2.2]octan-1-yl)methyl)piperazin-1-yl)-1-oxoisoindolin-2-yl)piperidine-2,6-dione B1217.

3-(6-Fluoro-4-(4-((2-(methylthio)pyrimidin-4-yl)methyl)piperazin-1-yl)-1-oxoisoindolin-2-yl)piperidine-2,6-dione B1218.

B1217

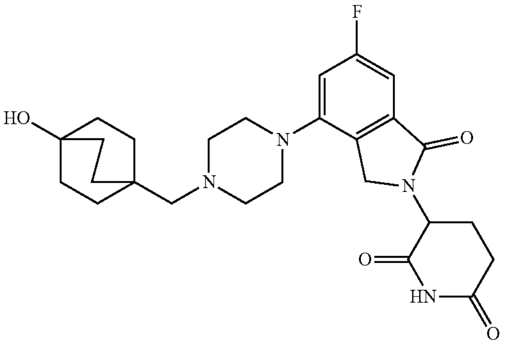

B1218

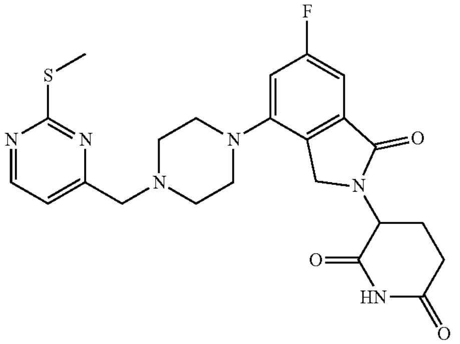

3-(4-(4-((2-Cyclopropylthiazol-5-yl)methyl)piperazin-1-yl)-6-fluoro-1-oxoisoindolin-2-yl)piperidine-2,6-dione B1219.

3-(4-(4-((1-(Tert-butyl)-1H-1,2,3-triazol-4-yl)methyl)piperazin-1-yl)-6-fluoro-1-oxoisoindolin-2-yl)piperidine-2,6-dione B1220.

B1219

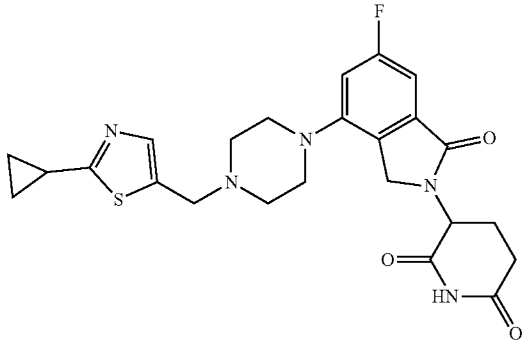

B1220

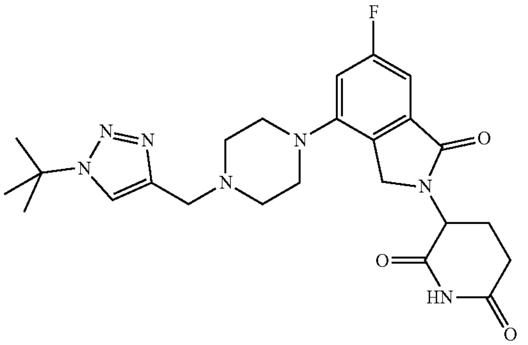

3-(6-Fluoro-4-(4-((1-isobutyl-1H-pyrazol-4-yl)methyl)piperazin-1-yl)-1-oxoisoindolin-2-yl)piperidine-2,6-dione B1221.

3-(4-(4-((5,6-Dihydro-8H-imidazo[2,1-c][1,4]oxazin-3-yl)methyl)piperazin-1-yl)-6-fluoro-1-oxoisoindolin-2-yl)piperidine-2,6-dione B1222.

B1221

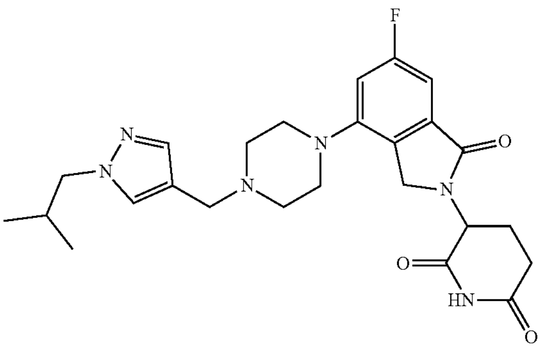

-continued

B1222

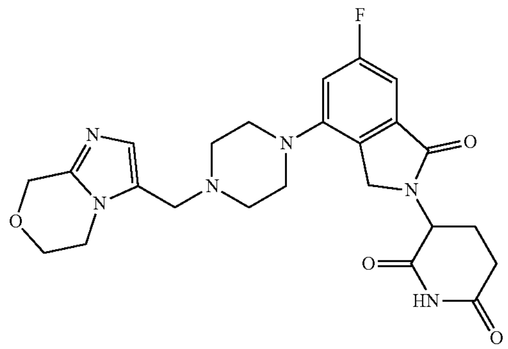

3-(4-(4-((5,6-Dihydro-8H-imidazo[2,1-c][1,4]oxazin-2-yl)methyl)piperazin-1-yl)-6-fluoro-1-oxoisoindolin-2-yl)piperidine-2,6-dione B1223.

3-(4-(4-((5-(Tert-butyl)-1H-pyrrol-2-yl)methyl)piperazin-1-yl)-6-fluoro-1-oxoisoindolin-2-yl)piperidine-2,6-dione B1224.

B1223

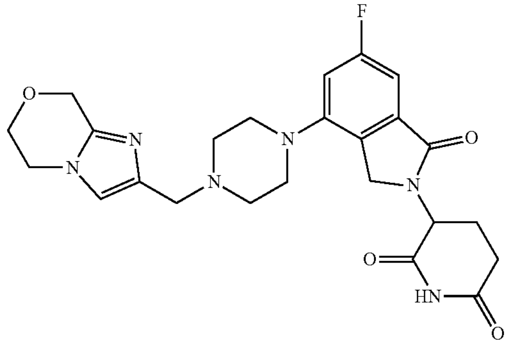

B1224

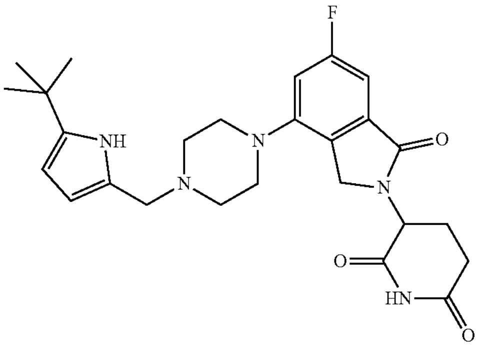

3-(4-(4-((2-(Dimethylamino)pyrimidin-5-yl)methyl)piperazin-1-yl)-6-fluoro-1-oxoisoindolin-2-yl)piperidine-2,6-dione B1225.

3-(6-Fluoro-4-(4-(4-methoxy-3-methylbenzyl)piperazin-1-yl)-1-oxoisoindolin-2-yl)piperidine-2,6-dione B1226.

B1225

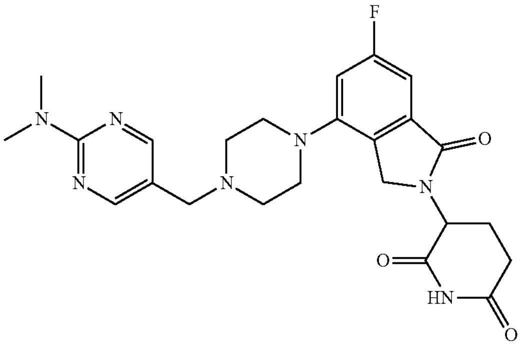

B1226

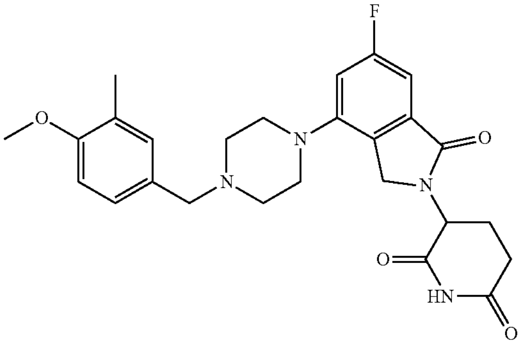

3-(6-Fluoro-4-(4-((1-methyl-1H-imidazol-5-yl)methyl)piperazin-1-yl)-1-oxoisoindolin-2-yl)piperidine-2,6-dione B1227.

3-(6-Fluoro-4-(4-(2-methoxy-3-methylbenzyl)piperazin-1-yl)-1-oxoisoindolin-2-yl)piperidine-2,6-dione B1228.

B1227

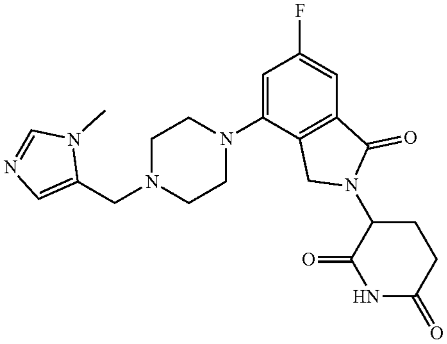

-continued

B1228

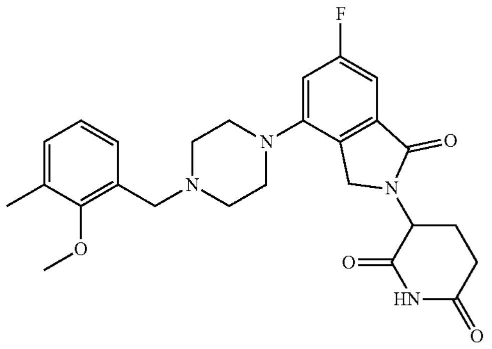

3-(6-Fluoro-4-(4-(3-methoxy-2-methylbenzyl)piperazin-1-yl)-1-oxoisoindolin-2-yl)piperidine-2,6-dione B1229.

3-(6-Fluoro-4-(4-(2-methoxy-6-methylbenzyl)piperazin-1-yl)-1-oxoisoindolin-2-yl)piperidine-2,6-dione B1230.

B1229

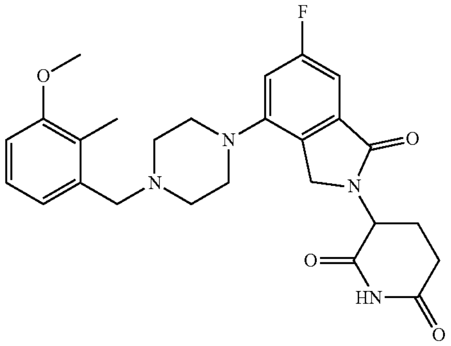

B1230

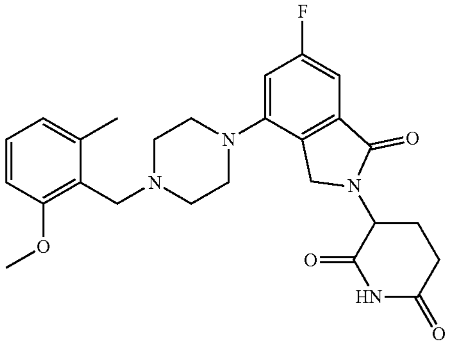

3-(6-Fluoro-4-(4-(3-methoxy-5-methylbenzyl)piperazin-1-yl)-1-oxoisoindolin-2-yl)piperidine-2,6-dione B1231.

3-(6-Fluoro-4-(4-(4-methoxyphenethyl)piperazin-1-yl)-1-oxoisoindolin-2-yl)-piperidine-2,6-dione B1232.

B1231

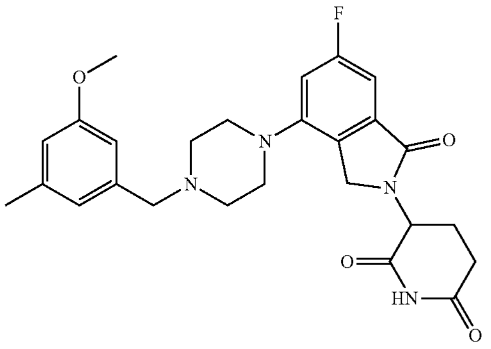

B1232

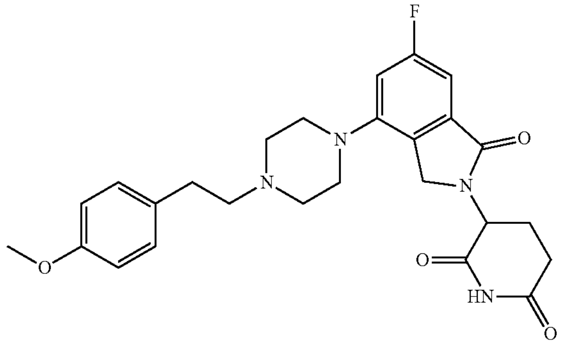

3-(6-Fluoro-4-(4-(3-methoxyphenethyl)piperazin-1-yl)-1-oxoisoindolin-2-yl)-piperidine-2,6-dione B1233.

3-(6-Fluoro-4-(4-(4-methoxy-2-methylbenzyl)piperazin-1-yl)-1-oxoisoindolin-2-yl)piperidine-2,6-dione B1234.

B1233

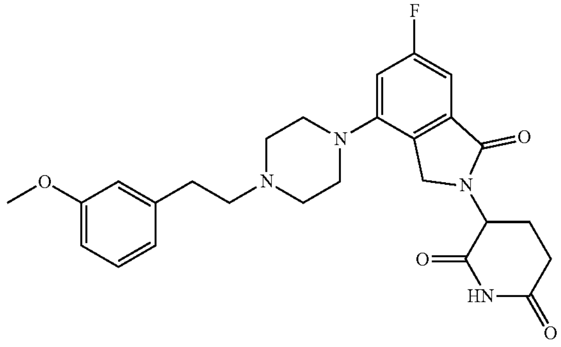

-continued

B1234

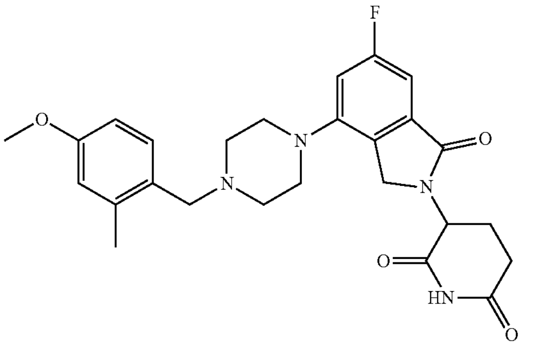

3-(6-Fluoro-4-(4-(4-hydroxy-3,5-dimethylbenzyl)piperazin-1-yl)-1-oxoisoindolin-2-yl)piperidine-2,6-dione B1235.

3-(4-(4-(4-Ethoxybenzyl)piperazin-1-yl)-6-fluoro-1-oxoisoindolin-2-yl)-piperidine-2,6-dione B1236.

B1235

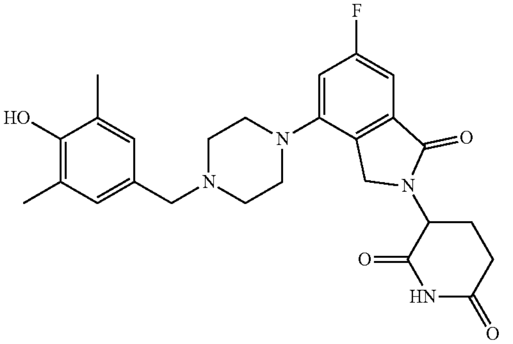

B1236

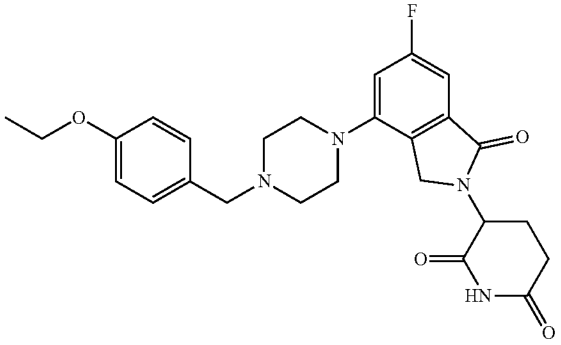

3-(6-Fluoro-4-(4-(3-methoxy-4-methylbenzyl)piperazin-1-yl)-1-oxoisoindolin-2-yl)piperidine-2,6-dione B1237.

3-(6-Fluoro-4-(4-((1-methyl-1H-pyrazol-5-yl)methyl)piperazin-1-yl)-1-oxoisoindolin-2-yl)piperidine-2,6-dione B1238.

B1237

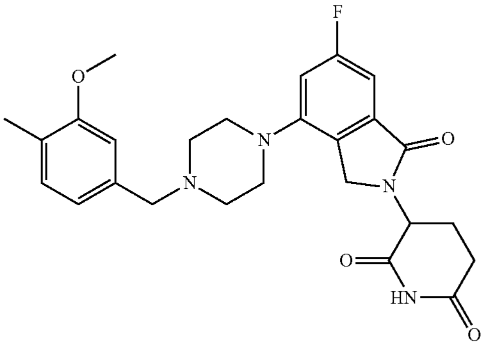

B1238

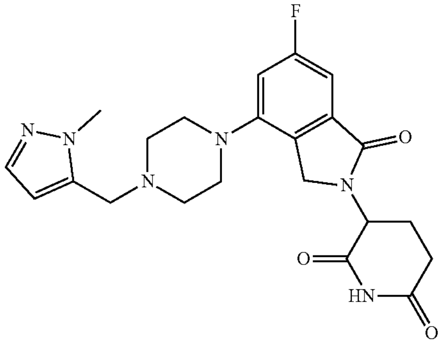

3-(4-(4-((1H-Pyrrol-2-yl)methyl)piperazin-1-yl)-6-fluoro-1-oxoisoindolin-2-yl)piperidine-2,6-dione B1239.

3-(6-Fluoro-4-(4-(2-methoxy-4-methylbenzyl)piperazin-1-yl)-1-oxoisoindolin-2-yl)piperidine-2,6-dione B1240.

B1239

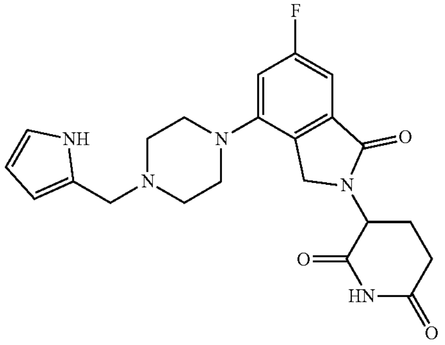

B1240

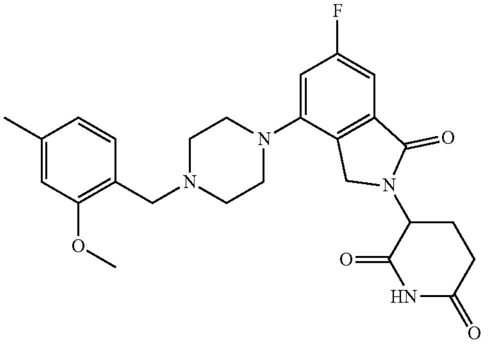

3-(4-(4-(2-(Benzyloxy)ethyl)piperazin-1-yl)-6-fluoro-1-oxoisoindolin-2-yl)-piperidine-2,6-dione B1241.

3-(4-(4-(Benzo[d][1,3]dioxol-4-ylmethyl)piperazin-1-yl)-6-fluoro-1-oxoisoindolin-2-yl)piperidine-2,6-dione B1242.

B1241

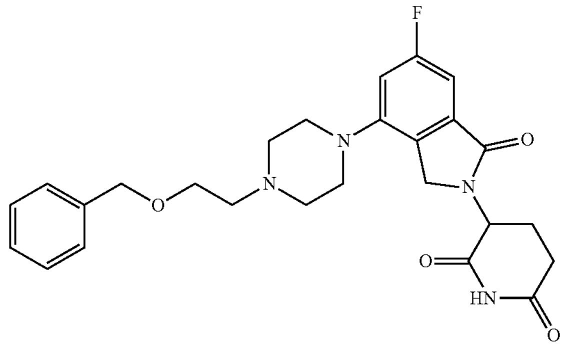

B1242

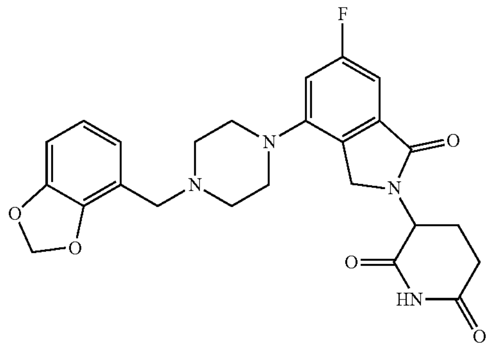

3-(4-(4-(2-(Dimethylamino)benzyl)piperazin-1-yl)-6-fluoro-1-oxoisoindolin-2-yl)piperidine-2,6-dione B1243.

3-(6-Fluoro-4-(4-((5-isopropylpyridin-3-yl)methyl)piperazin-1-yl)-1-oxoisoindolin-2-yl)piperidine-2,6-dione B1244.

B1243

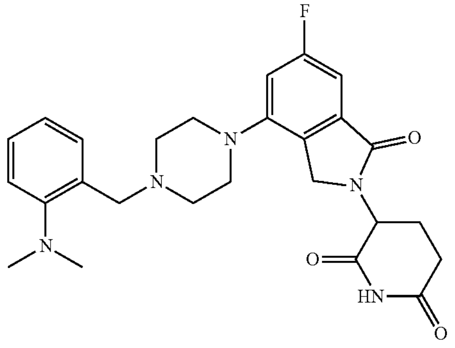

-continued

B1244

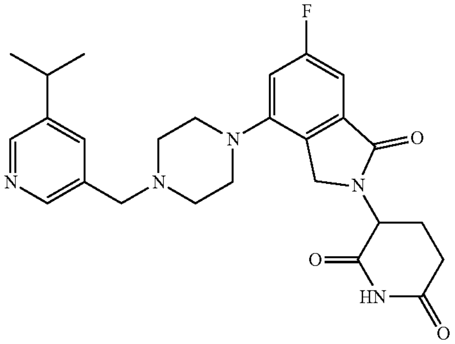

3-(4-(4-(4-(Ethylamino)benzyl)piperazin-1-yl)-6-fluoro-1-oxoisoindolin-2-yl)-piperidine-2,6-dione B1245.

3-(4-(4-(3-(Dimethylamino)benzyl)piperazin-1-yl)-6-fluoro-1-oxoisoindolin-2-yl)piperidine-2,6-dione B1246.

B1245

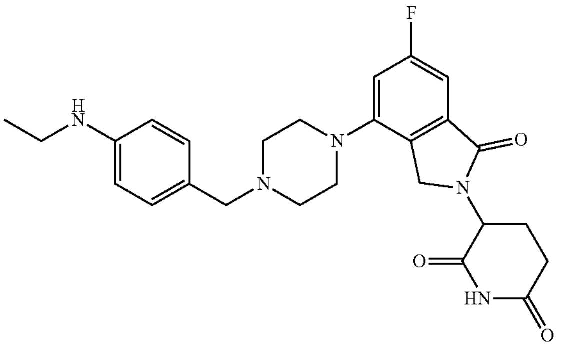

B1246

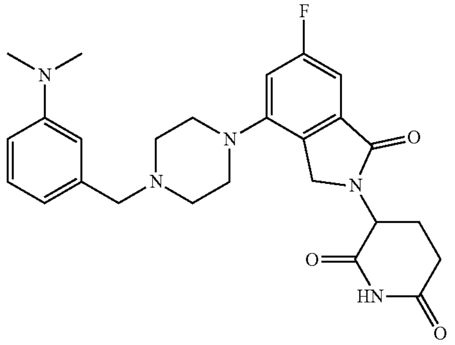

3-((4-(2-(2,6-Dioxopiperidin-3-yl)-6-fluoro-1-oxoisoindolin-4-yl)piperazin-1-yl)-methyl)benzamide B1247.

2-((4-(2-(2,6-Dioxopiperidin-3-yl)-6-fluoro-1-oxoisoindolin-4-yl)piperazin-1-yl)-methyl)-4-fluorobenzonitrile B1248.

B1247

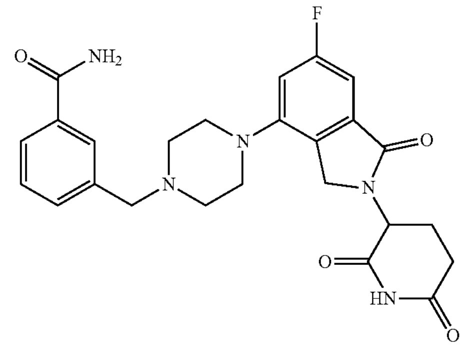

B1248

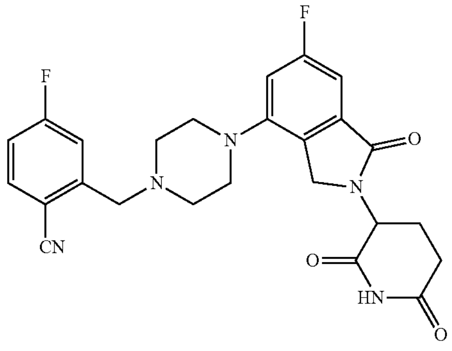

2-((4-(2-(2,6-Dioxopiperidin-3-yl)-6-fluoro-1-oxoisoindolin-4-yl)piperazin-1-yl)-methyl)-5-fluorobenzonitrile B1249.

3-(6-Fluoro-4-(4-((1-methyl-1H-pyrazol-3-yl)methyl)piperazin-1-yl)-1-oxoisoindolin-2-yl)piperidine-2,6-dione B1250.

B1249

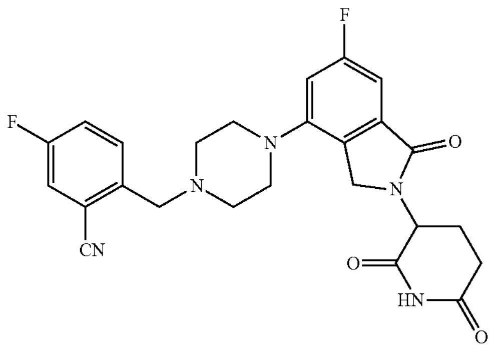

-continued

B1250

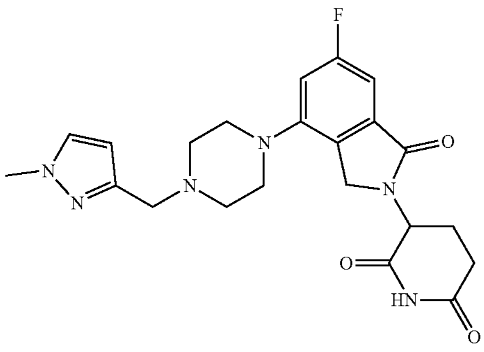

4-((4-(2-(2,6-Dioxopiperidin-3-yl)-6-fluoro-1-oxoisoindolin-4-yl)piperazin-1-yl)-methyl)-3-fluorobenzonitrile B1251.

3-((4-(2-(2,6-Dioxopiperidin-3-yl)-6-fluoro-1-oxoisoindolin-4-yl)piperazin-1-yl)-methyl)-5-fluorobenzonitrile B1252.

B1251

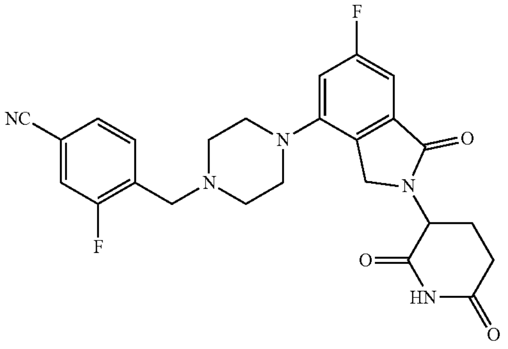

B1252

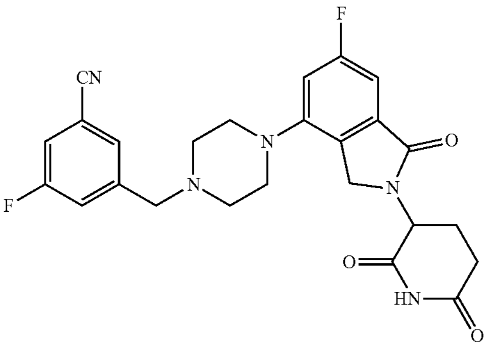

4-((4-(2-(2,6-Dioxopiperidin-3-yl)-6-fluoro-1-oxoisoindolin-4-yl)piperazin-1-yl)-methyl)-2-fluorobenzonitrile B1253.

5-((4-(2-(2,6-Dioxopiperidin-3-yl)-6-fluoro-1-oxoisoindolin-4-yl)piperazin-1-yl)-methyl)-2-fluorobenzonitrile B1254.

B1253

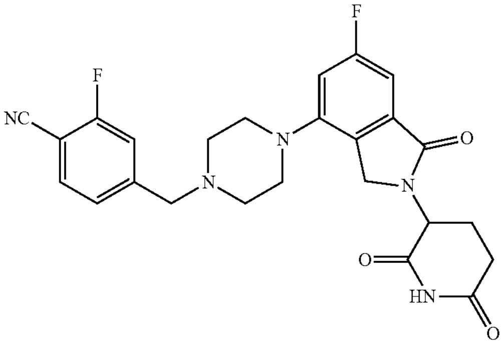

B1254

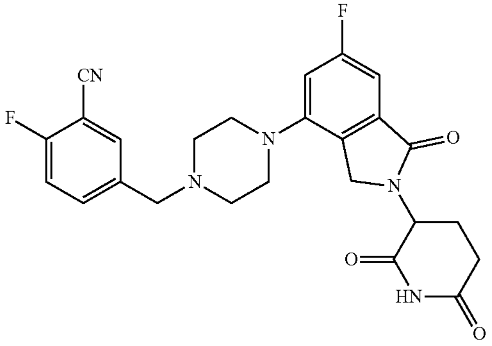

3-(6-Fluoro-1-oxo-4-(4-(2,4,6-trimethylbenzyl)piperazin-1-yl)isoindolin-2-yl)-piperidine-2,6-dione B1255.

3-(6-Fluoro-4-(4-(4-isopropylbenzyl)piperazin-1-yl)-1-oxoisoindolin-2-yl)-piperidine-2,6-dione B1256.

B1255

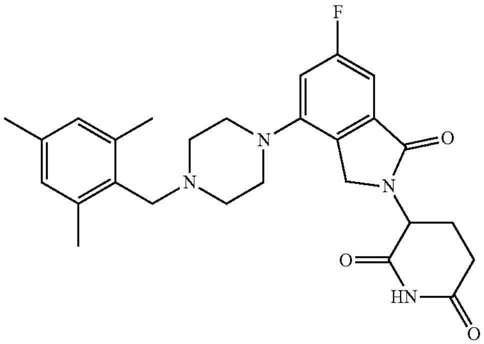

-continued

B1256

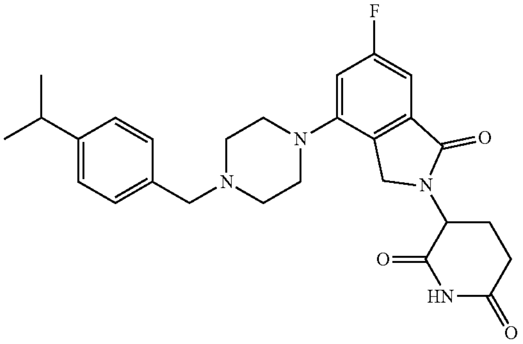

3-(6-Fluoro-1-oxo-4-(4-(4-phenylbutyl)piperazin-1-yl)isoindolin-2-yl)piperidine-2,6-dione B1257.

3-(4-(4-((4,4-Difluorocyclohexyl)methyl)piperazin-1-yl)-6-fluoro-1-oxoisoindolin-2-yl)piperidine-2,6-dione B1258.

B1257

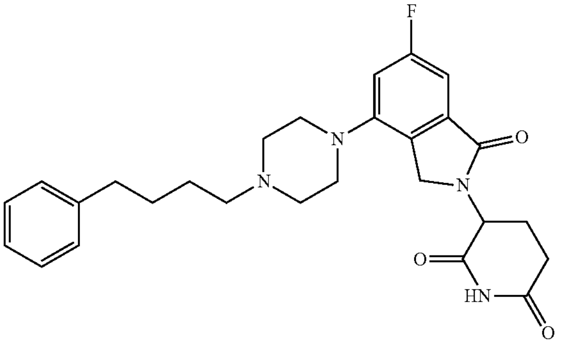

B1258

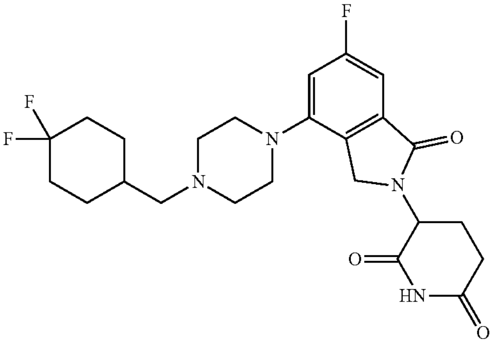

3-(4-(4-(2-Ethynyl-4-fluorobenzyl)piperazin-1-yl)-6-fluoro-1-oxoisoindolin-2-yl)piperidine-2,6-dione B1259.

3-(4-(4-([1,2,4]Triazolo[1,5-a]pyridin-7-ylmethyl)piperazin-1-yl)-6-fluoro-1-oxoisoindolin-2-yl)piperidine-2,6-dione B1260.

B1259

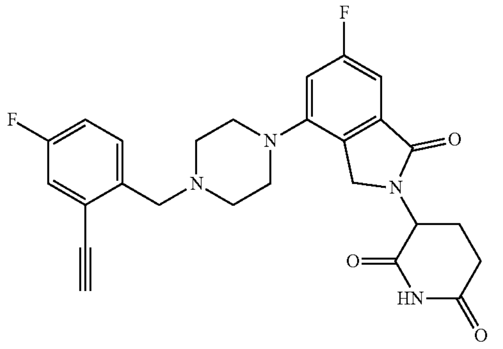

B1260

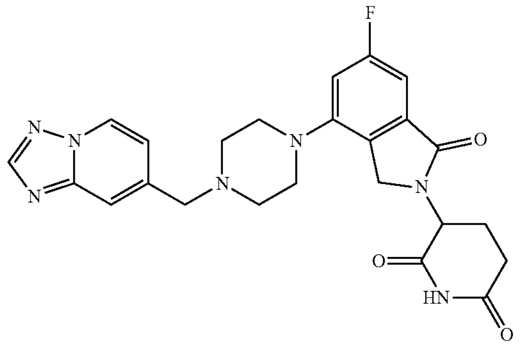

3-(6-Fluoro-4-(4-((1-methyl-1H-imidazol-4-yl)methyl)piperazin-1-yl)-1-oxoisoindolin-2-yl)piperidine-2,6-dione B1261.

3-(6-Fluoro-4-(4-(imidazo[1,2-a]pyrimidin-3-ylmethyl)piperazin-1-yl)-1-oxoisoindolin-2-yl)piperidine-2,6-dione B1262.

B1261

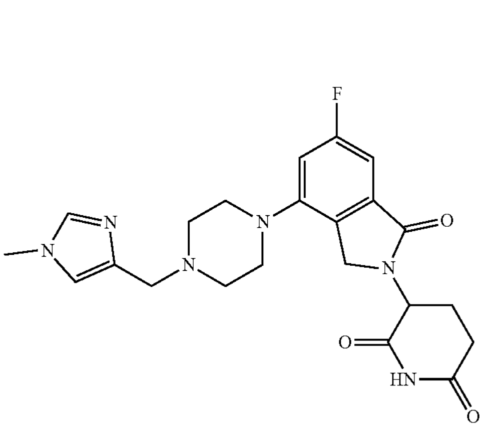

-continued

B1262

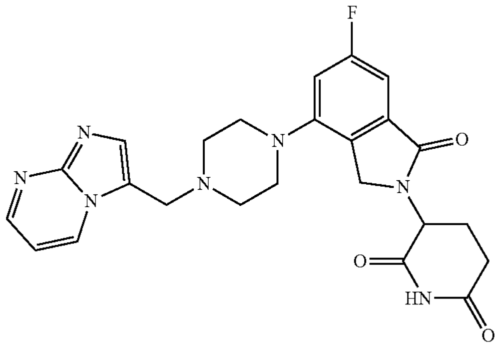

6-Amino-5-((4-(2-(2,6-dioxopiperidin-3-yl)-6-fluoro-1-oxoisoindolin-4-yl)-piperazin-1-yl)methyl)nicotinonitrile B1263.

3-(6-Fluoro-4-(4-(imidazo[1,2-a]pyrimidin-7-ylmethyl)piperazin-1-yl)-1-oxoisoindolin-2-yl)piperidine-2,6-dione B1264.

B1263

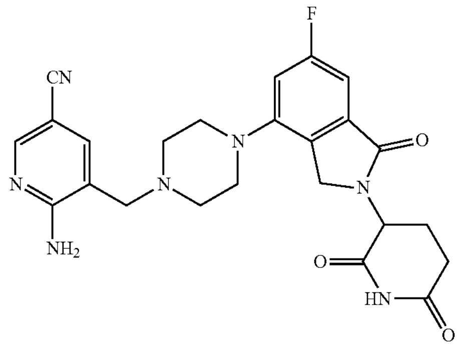

B1264

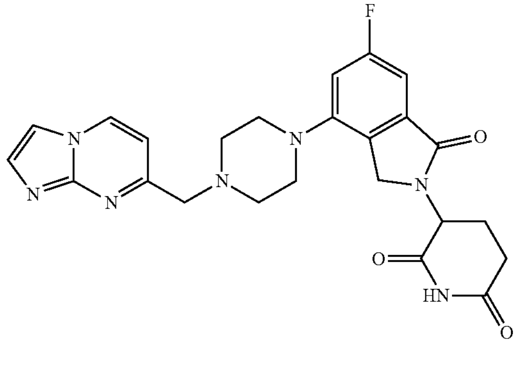

3-(4-(4-((4H-Pyrrolo[2,3-b]pyrazin-7-yl)methyl)piperazin-1-yl)-6-fluoro-1-oxoisoindolin-2-yl)piperidine-2,6-dione B1265.

4-((4-(2-(2,6-Dioxopiperidin-3-yl)-6-fluoro-1-oxoisoindolin-4-yl)piperazin-1-yl)-methyl)-3-hydroxybenzonitrile B1266.

B1265

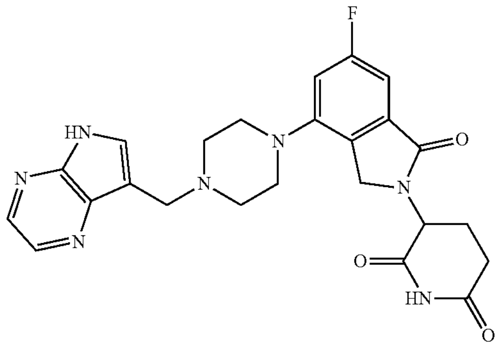

-continued

B1268

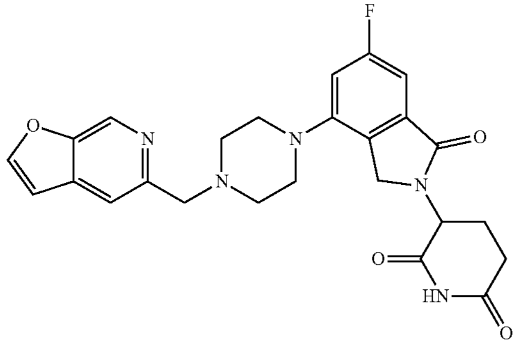

3-(4-(4-(Benzo[d]oxazol-5-ylmethyl)piperazin-1-yl)-6-fluoro-1-oxoisoindolin-2-yl)piperidine-2,6-dione B1269.

3-(4-(4-(Benzo[d]oxazol-6-ylmethyl)piperazin-1-yl)-6-fluoro-1-oxoisoindolin-2-yl)piperidine-2,6-dione B1270.

B1266

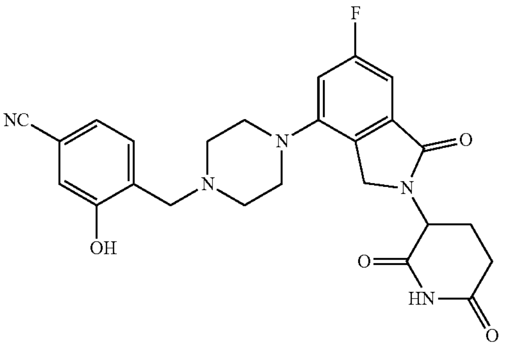

5-((4-(2-(2,6-Dioxopiperidin-3-yl)-6-fluoro-1-oxoisoindolin-4-yl)piperazin-1-yl)-methyl)-2-hydroxybenzonitrile B1267.

3-(6-Fluoro-4-(4-(furo[2,3-c]pyridin-5-ylmethyl)piperazin-1-yl)-1-oxoisoindolin-2-yl)piperidine-2,6-dione B1268.

B1267

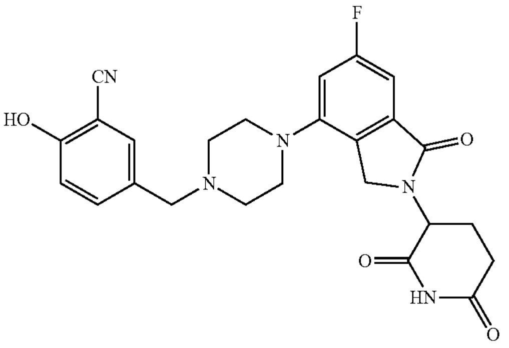

B1269

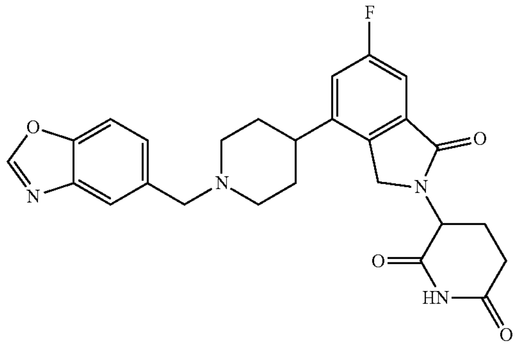

B1270

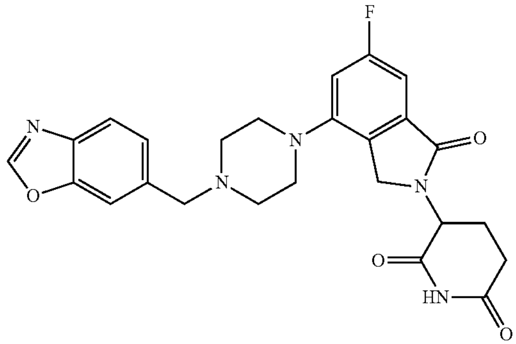

3-(4-(4-((5-Chlorothiophen-2-yl)methyl)piperazin-1-yl)-6-fluoro-1-oxoisoindolin-2-yl)piperidine-2,6-dione B1271.

3-(6-Fluoro-4-(4-((1-methyl-1H-imidazol-2-yl)methyl)piperazin-1-yl)-1-oxoisoindolin-2-yl)piperidine-2,6-dione B1272.

B1271

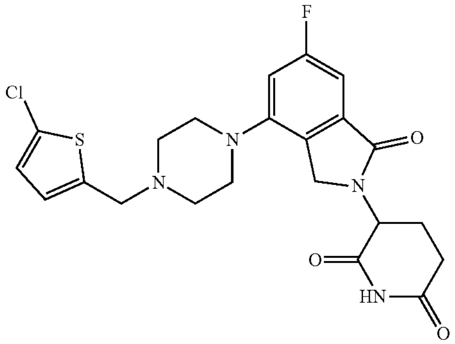

B1272

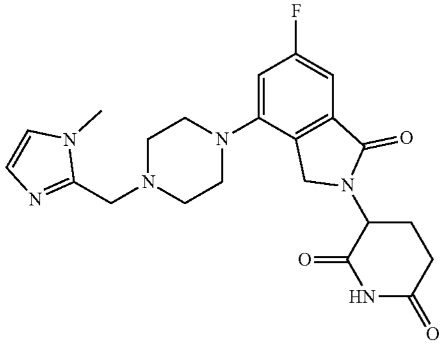

3-(4-(4-((2-Chlorothiophen-3-yl)methyl)piperazin-1-yl)-6-fluoro-1-oxoisoindolin-2-yl)piperidine-2,6-dione B1273.

3-(4-(4-(4-Cyclopropylbenzyl)piperazin-1-yl)-6-fluoro-1-oxoisoindolin-2-yl)-piperidine-2,6-dione B1274.

B1273

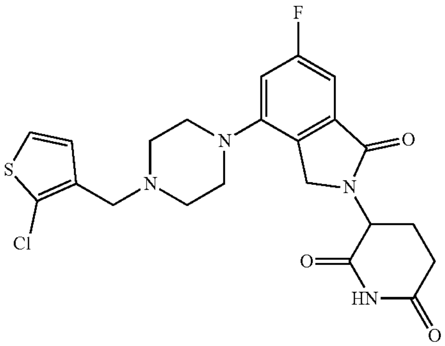

B1274

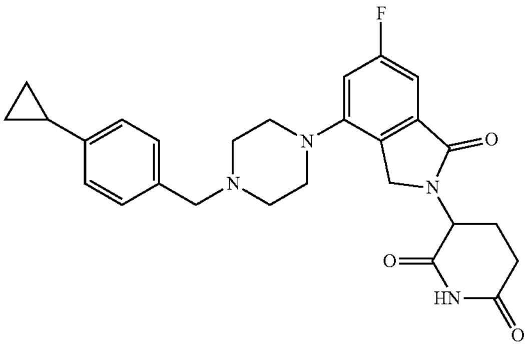

3-(4-(4-(2-Cyclopropylbenzyl)piperazin-1-yl)-6-fluoro-1-oxoisoindolin-2-yl)-piperidine-2,6-dione B1275.

3-(6-Fluoro-1-oxo-4-(4-(pyrazolo[1,5-a]pyridin-7-ylmethyl)piperazin-1-yl)-isoindolin-2-yl)piperidine-2,6-dione B1276.

B1275

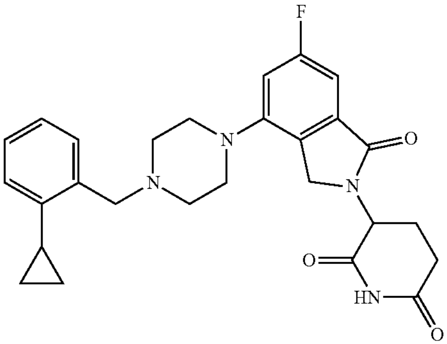

B1276

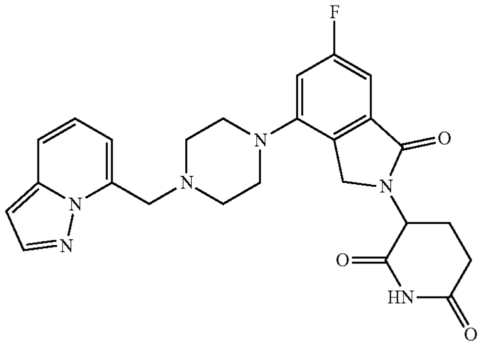

3-(4-(4-((1H-Pyrrolo[2,3-c]pyridin-3-yl)methyl)piperazin-1-yl)-6-fluoro-1-oxoisoindolin-2-yl)piperidine-2,6-dione B1277.

3-(6-Fluoro-4-(4-(imidazo[1,2-a]pyridin-5-ylmethyl)piperazin-1-yl)-1-oxoisoindolin-2-yl)piperidine-2,6-dione B1278.

B1277

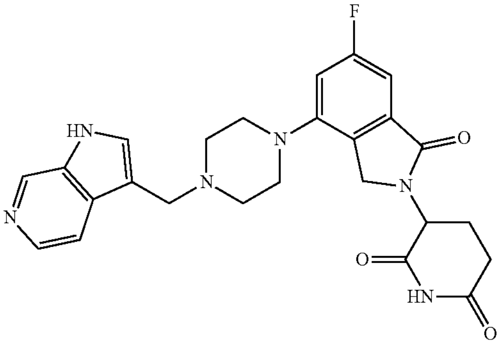

-continued

B1278

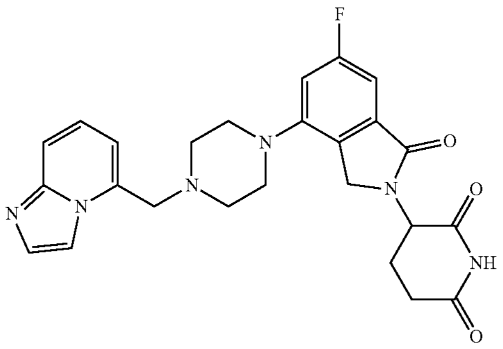

3-(6-Fluoro-1-oxo-4-(4-(pyrazolo[1,5-a]pyridin-3-ylmethyl)piperazin-1-yl)-isoindolin-2-yl)piperidine-2,6-dione B1279.

3-(4-(4-((2H-Indazol-6-yl)methyl)piperazin-1-yl)-6-fluoro-1-oxoisoindolin-2-yl)piperidine-2,6-dione B1280.

B1279

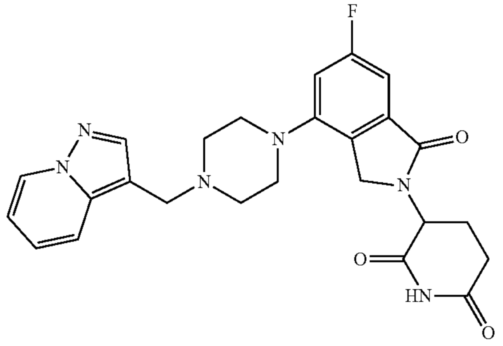

B1280

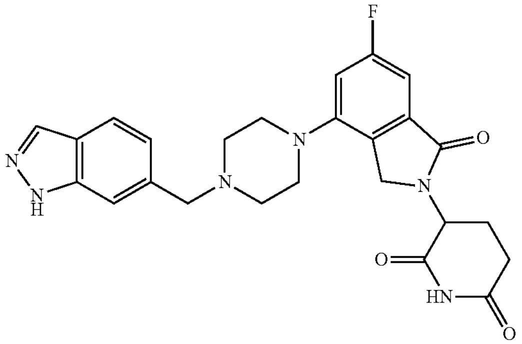

3-(4-(4-((1H-Pyrrolo[3,2-b]pyridin-3-yl)methyl)piperazin-1-yl)-6-fluoro-1-oxoisoindolin-2-yl)piperidine-2,6-dione B1281.

3-(6-Fluoro-4-(4-(imidazo[1,5-a]pyridin-1-ylmethyl)piperazin-1-yl)-1-oxoisoindolin-2-yl)piperidine-2,6-dione B1282.

B1281

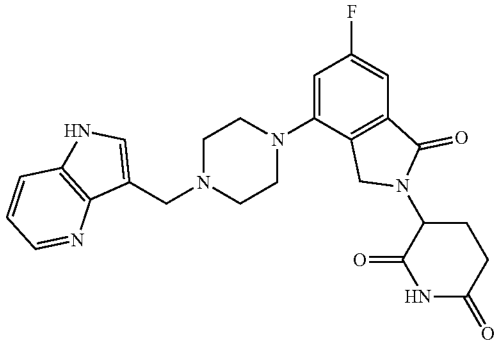

B1282

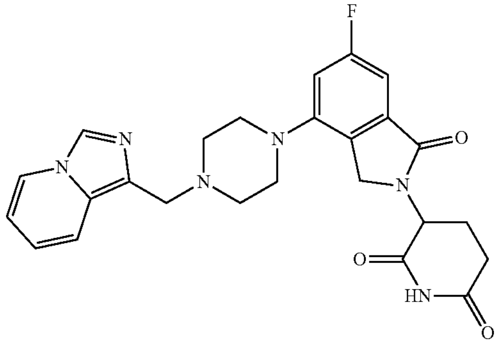

3-(6-Fluoro-4-(4-((5-methyl-1H-pyrazol-3-yl)methyl)piperazin-1-yl)-1-oxoisoindolin-2-yl)piperidine-2,6-dione B1283.

3-(4-(4-((1H-Pyrrolo[2,3-b]pyridin-6-yl)methyl)piperazin-1-yl)-6-fluoro-1-oxoisoindolin-2-yl)piperidine-2,6-dione B1284.

B1283

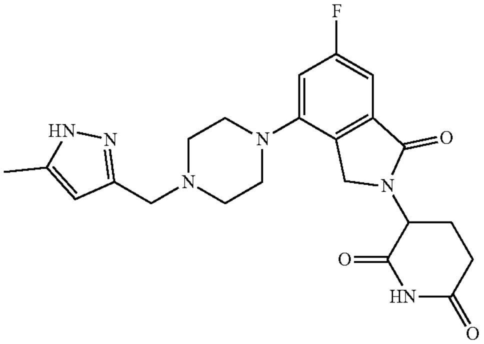

-continued

B1284

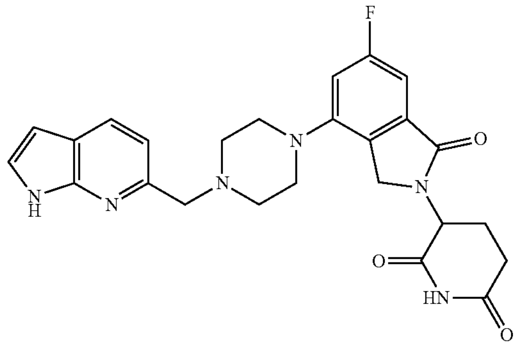

3-(4-(4-((1H-Benzo[d]imidazol-7-yl)methyl)piperazin-1-yl)-6-fluoro-1-oxoisoindolin-2-yl)piperidine-2,6-dione B1285.

3-(6-Fluoro-4-(4-(imidazo[1,2-a]pyridin-6-ylmethyl)piperazin-1-yl)-1-oxoisoindolin-2-yl)piperidine-2,6-dione B1286.

B1285

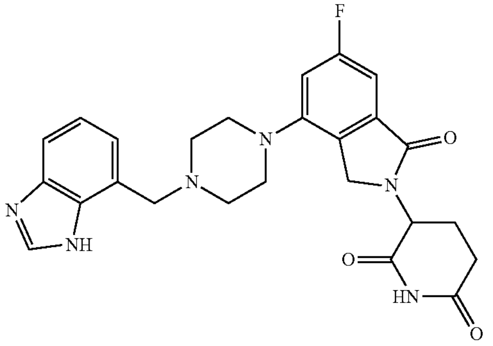

B1286

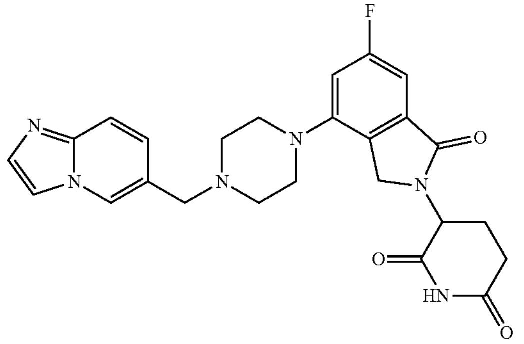

3-(6-Fluoro-4-(4-(imidazo[1,2-a]pyridin-8-ylmethyl)piperazin-1-yl)-1-oxoisoindolin-2-yl)piperidine-2,6-dione B1287.

3-(6-Fluoro-4-(4-(imidazo[1,2-a]pyridin-7-ylmethyl)piperazin-1-yl)-1-oxoisoindolin-2-yl)piperidine-2,6-dione B1288.

B1287

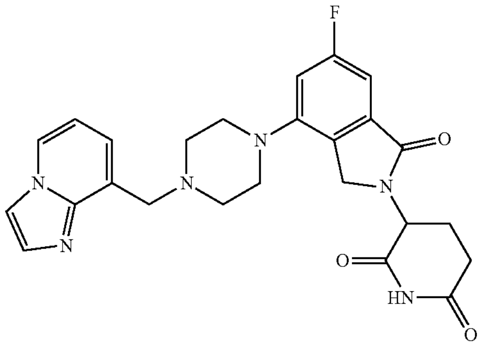

B1288

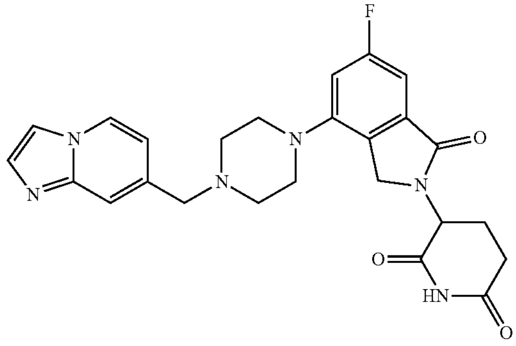

3-(4-(4-((1H-Pyrrolo[3,2-b]pyridin-6-yl)methyl)piperazin-1-yl)-6-fluoro-1-oxoisoindolin-2-yl)piperidine-2,6-dione B1289.

3-(4-(4-((1H-Benzo[d]imidazol-2-yl)methyl)piperazin-1-yl)-6-fluoro-1-oxoisoindolin-2-yl)piperidine-2,6-dione B1290.

B1289

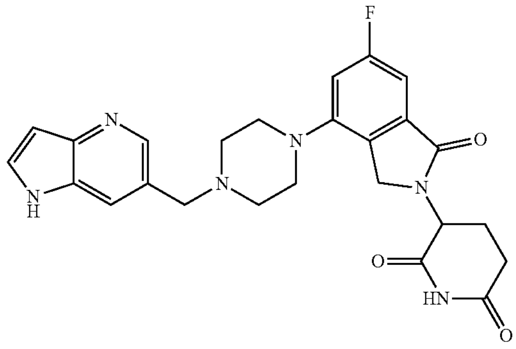

-continued

B1290

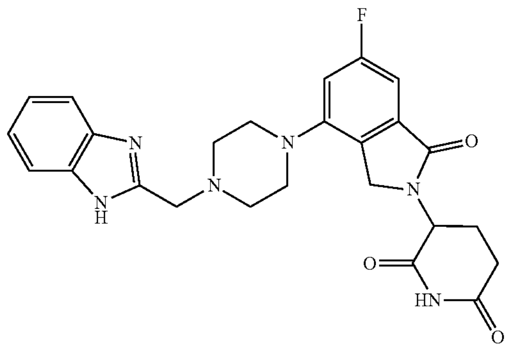

3-(6-Fluoro-4-(4-(imidazo[1,2-a]pyridin-3-ylmethyl)piperazin-1-yl)-1-oxoisoindolin-2-yl)piperidine-2,6-dione B1291.

3-(6-Fluoro-4-(4-(imidazo[1,2-a]pyridin-2-ylmethyl)piperazin-1-yl)-1-oxoisoindolin-2-yl)piperidine-2,6-dione B1292.

B1291

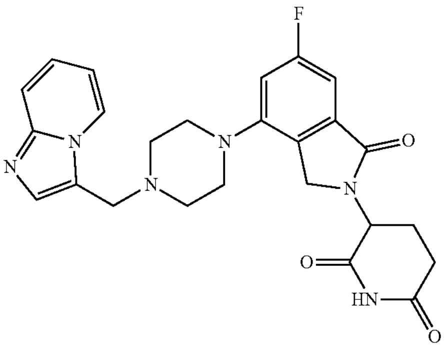

B1292

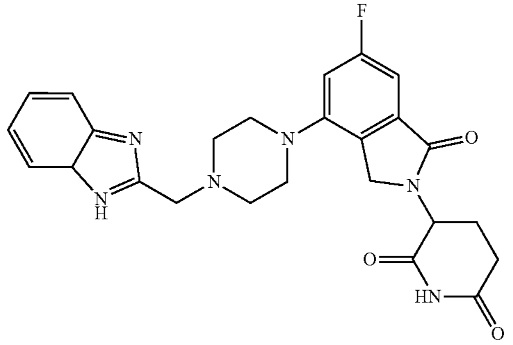

3-(4-(4-(Benzofuran-4-ylmethyl)piperazin-1-yl)-6-fluoro-1-oxoisoindolin-2-yl)-piperidine-2,6-dione B1293.

3-(6-Fluoro-4-(4-((5-methylfuran-2-yl)methyl)piperazin-1-yl)-1-oxoisoindolin-2-yl)piperidine-2,6-dione B1294.

B1293

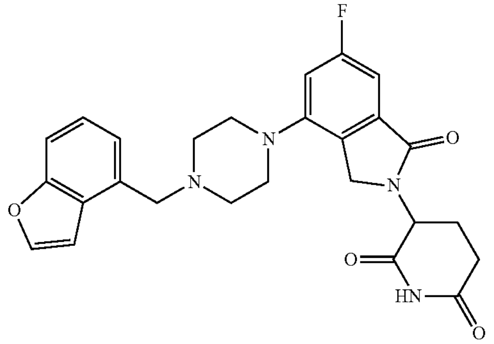

B1294

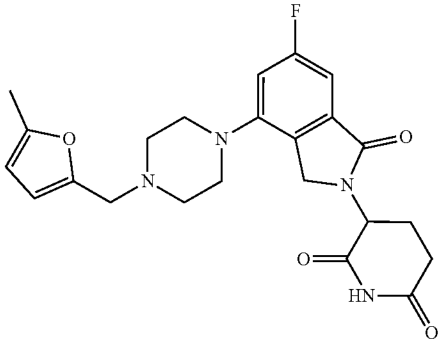

3-(4-(4-(Benzofuran-7-ylmethyl)piperazin-1-yl)-6-fluoro-1-oxoisoindolin-2-yl)-piperidine-2,6-dione B1295.

3-(4-(4-(Benzofuran-5-ylmethyl)piperazin-1-yl)-6-fluoro-1-oxoisoindolin-2-yl)-piperidine-2,6-dione B1296.

B1295

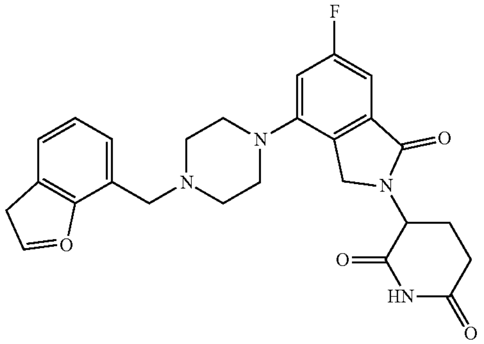

B1296

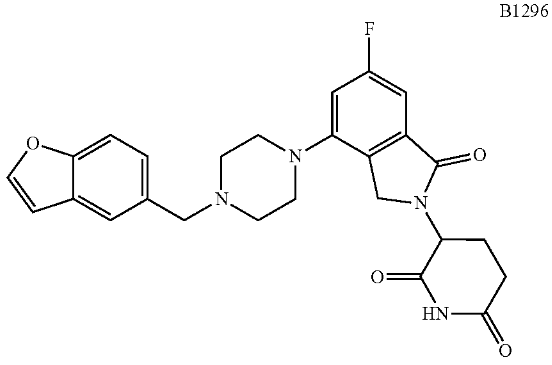

2-((4-(2-(2,6-dioxopiperidin-3-yl)-6-fluoro-1-oxoisoindolin-4-yl)piperazin-1-yl)-methyl)-5-methylbenzonitrile B1297.

3-((4-(2-(2,6-Dioxopiperidin-3-yl)-6-fluoro-1-oxoisoindolin-4-yl)piperazin-1-yl)-methyl)-2-methylbenzonitrile B1298.

B1297

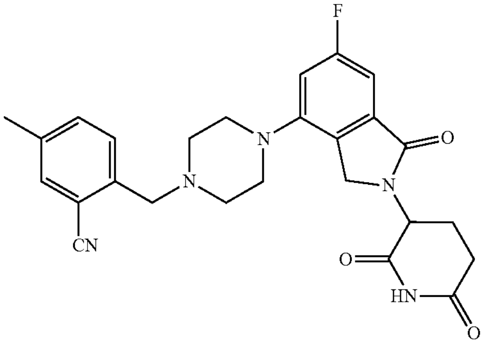

B1298

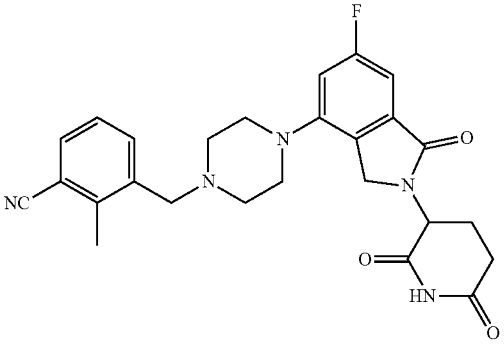

3-((4-(2-(2,6-Dioxopiperidin-3-yl)-6-fluoro-1-oxoisoindolin-4-yl)piperazin-1-yl)-methyl)-5-methylbenzonitrile B1299.

2-((4-(2-(2,6-Dioxopiperidin-3-yl)-6-fluoro-1-oxoisoindolin-4-yl)piperazin-1-yl)-methyl)-6-methylbenzonitrile B1300.

B1299

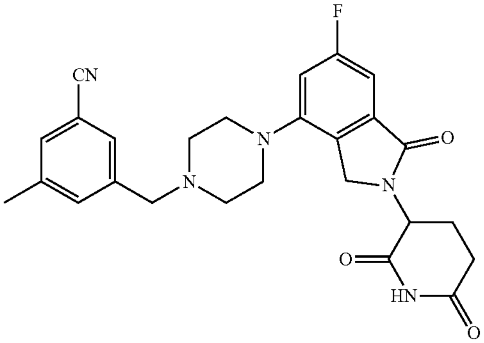

-continued

B1300

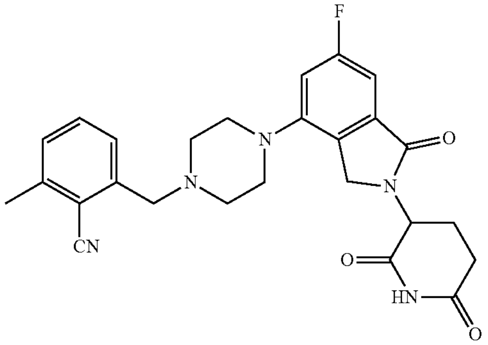

4-((4-(2-(2,6-Dioxopiperidin-3-yl)-6-fluoro-1-oxoisoindolin-4-yl)piperazin-1-yl)-methyl)-3-methylbenzonitrile B1301.

3-(4-(4-((1H-Indol-3-yl)methyl)piperazin-1-yl)-6-fluoro-1-oxoisoindolin-2-yl)-piperidine-2,6-dione B1302.

B1301

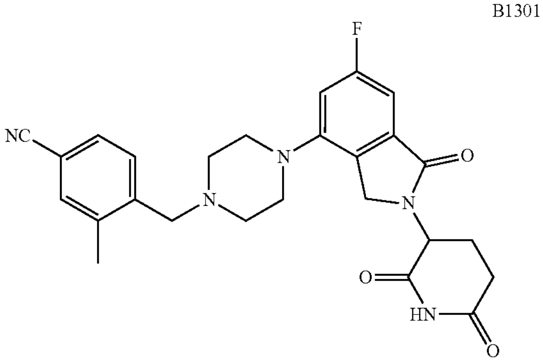

B1302

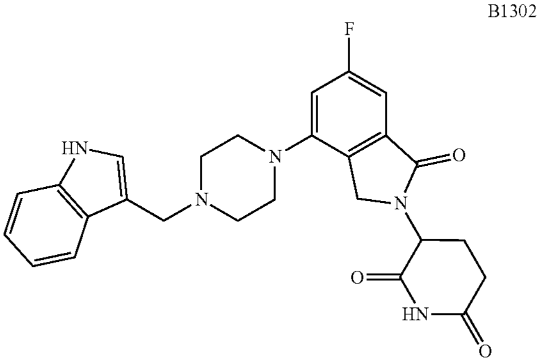

3-(6-Fluoro-4-(4-(indolizin-1-ylmethyl)piperazin-1-yl)-1-oxoisoindolin-2-yl)-piperidine-2,6-dione B1303.

3-(4-(4-((1H-Indol-7-yl)methyl)piperazin-1-yl)-6-fluoro-1-oxoisoindolin-2-yl)-piperidine-2,6-dione B1304.

B1303

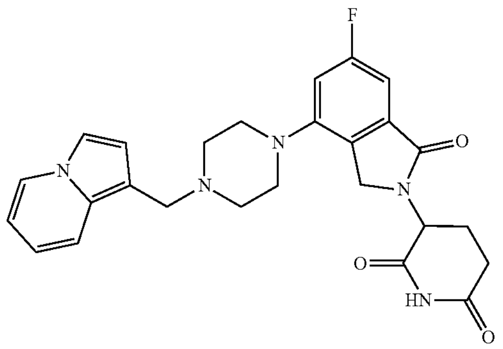

B1304

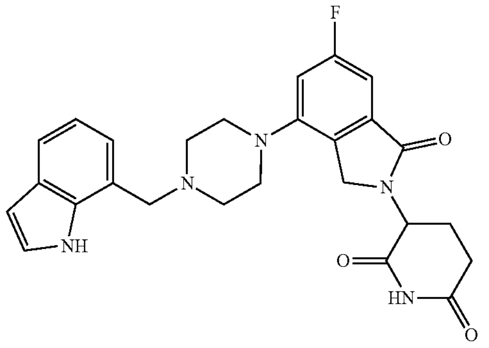

3-(6-Fluoro-4-(4-((3-methyl-1H-pyrrol-2-yl)methyl)piperazin-1-yl)-1-oxoisoindolin-2-yl)piperidine-2,6-dione B1305.

3-(4-(4-((1H-Indol-2-yl)methyl)piperazin-1-yl)-6-fluoro-1-oxoisoindolin-2-yl)-piperidine-2,6-dione B1306.

B1305

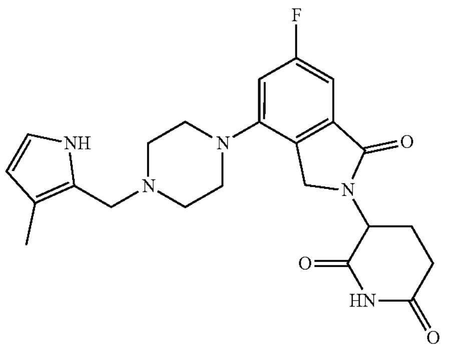

-continued

B1306

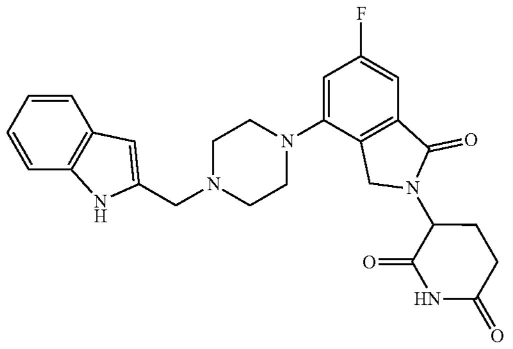

3-(4-(4-((1H-Indol-6-yl)methyl)piperazin-1-yl)-6-fluoro-1-oxoisoindolin-2-yl)-piperidine-2,6-dione B1307.

3-(4-(4-((4-Chloro-1-methyl-1H-pyrazol-3-yl)methyl)piperazin-1-yl)-6-fluoro-1-oxoisoindolin-2-yl)piperidine-2,6-dione B1308.

B1307

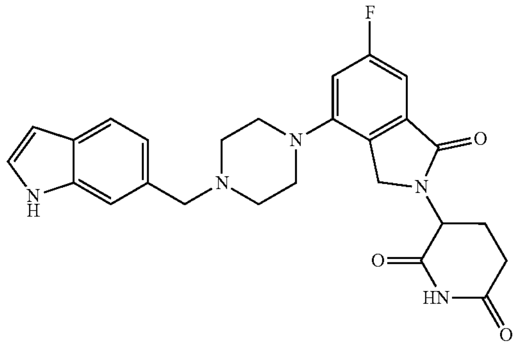

B1308

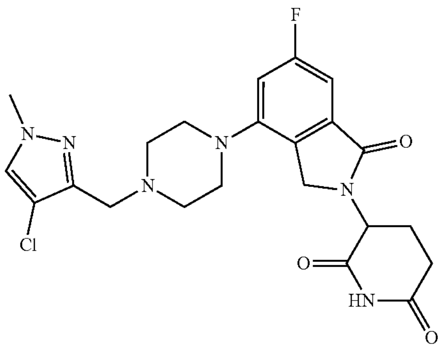

3-(4-(4-((3-Chloropyrazin-2-yl)methyl)piperazin-1-yl)-6-fluoro-1-oxoisoindolin-2-yl)piperidine-2,6-dione B1309.

3-(4-(4-((3-Chloropyridin-4-yl)methyl)piperazin-1-yl)-6-fluoro-1-oxoisoindolin-2-yl)piperidine-2,6-dione B1310.

B1309

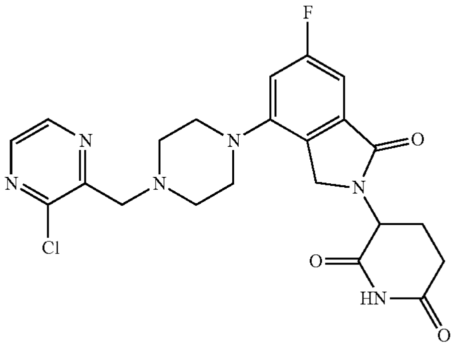

B1310

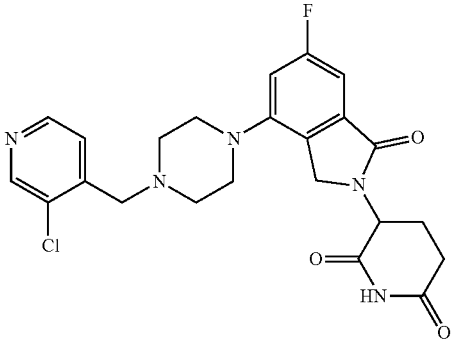

3-(4-(4-((6-Chloropyridin-2-yl)methyl)piperazin-1-yl)-6-fluoro-1-oxoisoindolin-2-yl)piperidine-2,6-dione B1311.

3-(6-Fluoro-4-(4-((5-fluoro-2-oxo-1,2-dihydropyridin-3-yl)methyl)piperazin-1-yl)-1-oxoisoindolin-2-yl)piperidine-2,6-dione B1312.

B1311

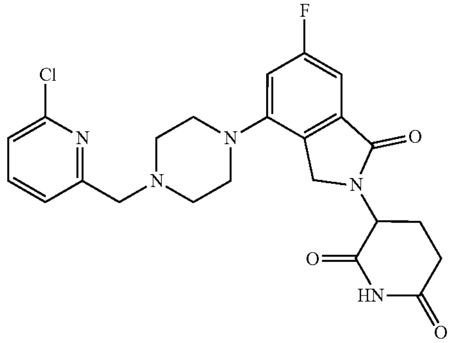

-continued

B1312

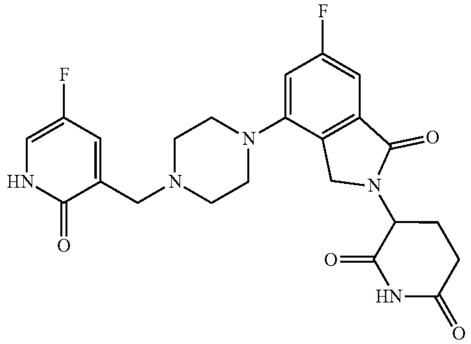

3-(4-(4-(2-Chlorobenzyl)piperazin-1-yl)-6-fluoro-1-oxoisoindolin-2-yl)-piperidine-2,6-dione B1313.

3-(4-(4-(4-Chlorobenzyl)piperazin-1-yl)-6-fluoro-1-oxoisoindolin-2-yl)-piperidine-2,6-dione B1314.

B1313

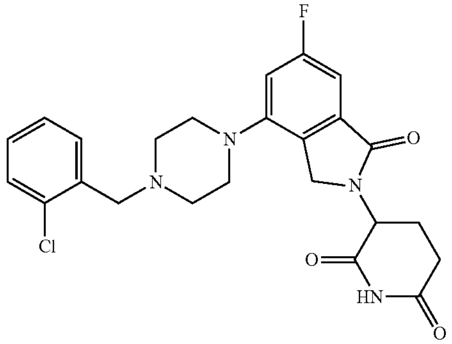

B1314

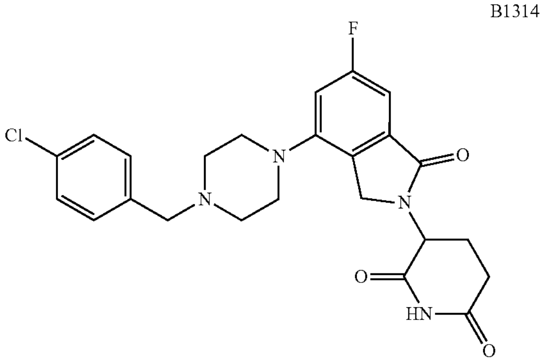

3-(4-(4-(3-Chlorobenzyl)piperazin-1-yl)-6-fluoro-1-oxoisoindolin-2-yl)-piperidine-2,6-dione B1315.

3-(6-Fluoro-4-(4-((5-methyl-1H-pyrrol-2-yl)methyl)piperazin-1-yl)-1-oxoisoindolin-2-yl)piperidine-2,6-dione B1316.

B1315

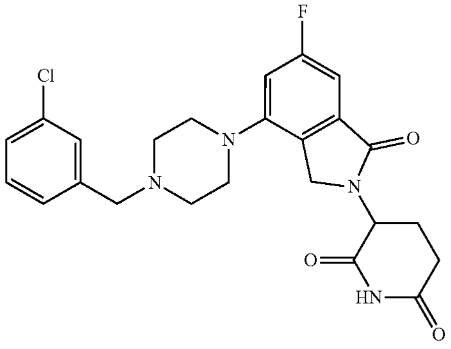

B1316

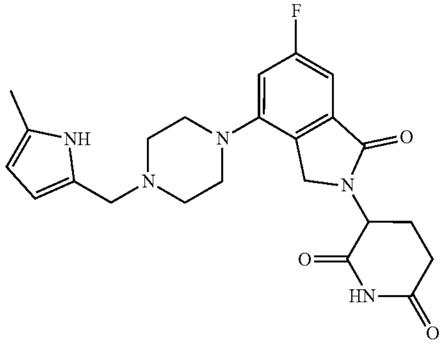

3-(4-(4-(2-Amino-5-fluorobenzyl)piperazin-1-yl)-6-fluoro-1-oxoisoindolin-2-yl)-piperidine-2,6-dione B1317.

3-(6-Fluoro-4-(4-((1-isopropyl-1H-pyrazol-4-yl)methyl)piperazin-1-yl)-1-oxoisoindolin-2-yl)piperidine-2,6-dione B1318.

B1317

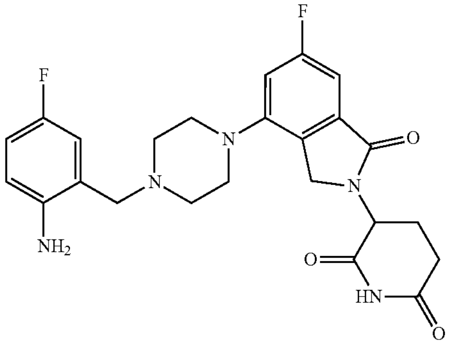

B1318

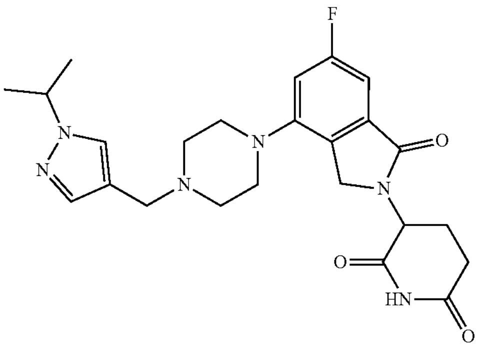

3-(6-Fluoro-4-(4-((4-isopropylfuran-2-yl)methyl)piperazin-1-yl)-1-oxoisoindolin-2-yl)piperidine-2,6-dione B1319.

3-(6-Fluoro-4-(4-(3-(5-methylfuran-2-yl)propyl)piperazin-1-yl)-1-oxoisoindolin-2-yl)piperidine-2,6-dione B1320.

B1319

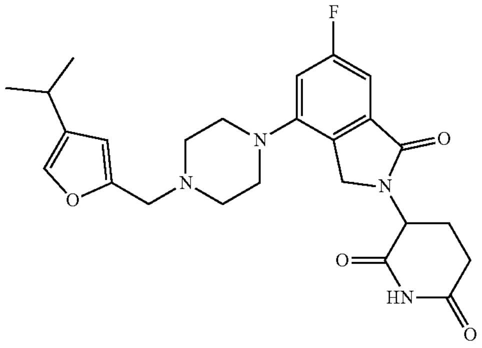

B1320

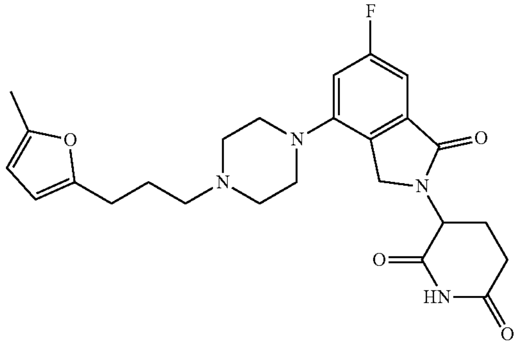

3-(6-Fluoro-4-(4-(4-fluorophenethyl)piperazin-1-yl)-1-oxoisoindolin-2-yl)-piperidine-2,6-dione B1321.

3-(6-Fluoro-4-(4-(3-fluoro-2-methylbenzyl)piperazin-1-yl)-1-oxoisoindolin-2-yl)-piperidine-2,6-dione B1322.

B1321

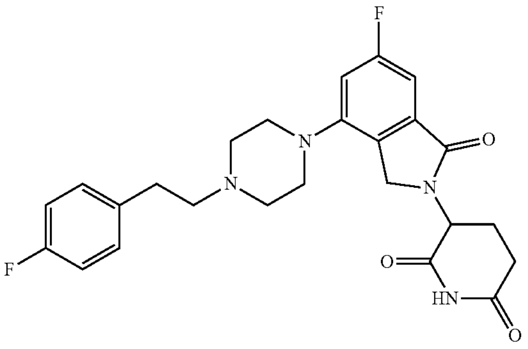

-continued

B1322

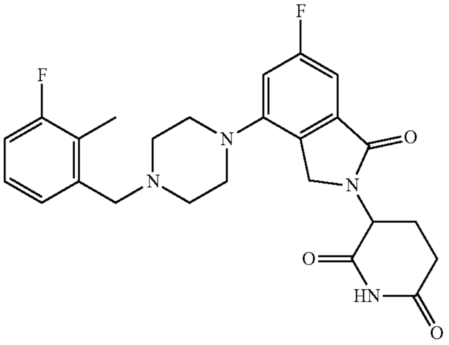

3-(6-Fluoro-4-(4-(2-fluoro-5-methylbenzyl)piperazin-1-yl)-1-oxoisoindolin-2-yl)-piperidine-2,6-dione B1323.

3-(6-Fluoro-4-(4-(4-fluoro-3-methylbenzyl)piperazin-1-yl)-1-oxoisoindolin-2-yl)-piperidine-2,6-dione B1324.

B1323

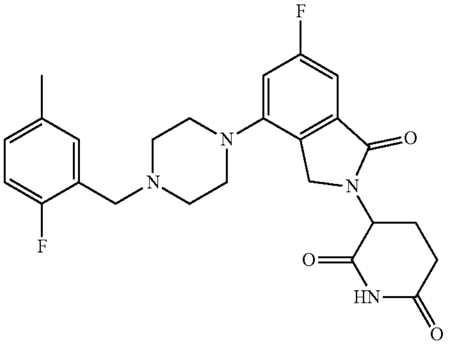

B1324

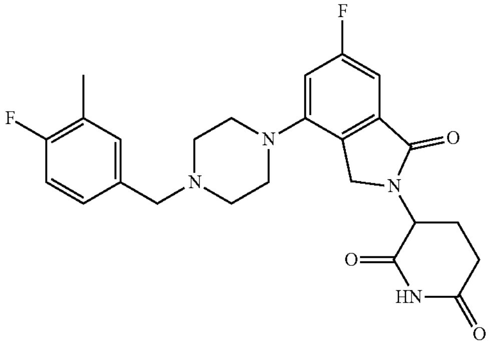

3-(6-Fluoro-4-(4-(3-fluoro-5-methylbenzyl)piperazin-1-yl)-1-oxoisoindolin-2-yl)-piperidine-2,6-dione B1325.

3-(6-Fluoro-4-(4-(4-fluoro-2-methylbenzyl)piperazin-1-yl)-1-oxoisoindolin-2-yl)-piperidine-2,6-dione B1326.

B1325

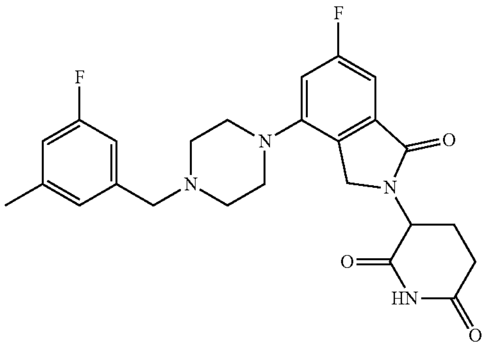

B1326

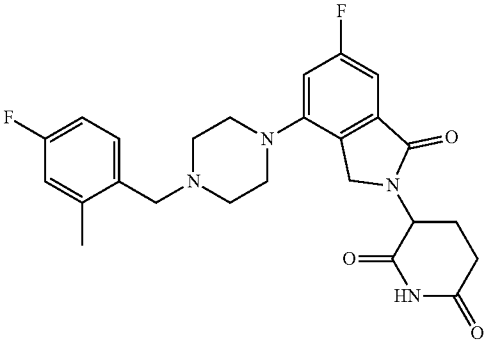

3-(6-Fluoro-4-(4-((1-methyl-1H-pyrrol-2-yl)methyl)piperazin-1-yl)-1-oxoisoindolin-2-yl)piperidine-2,6-dione B1327.

3-(6-Fluoro-4-(4-(5-fluoro-2-methylbenzyl)piperazin-1-yl)-1-oxoisoindolin-2-yl)-piperidine-2,6-dione B1328.

B1327

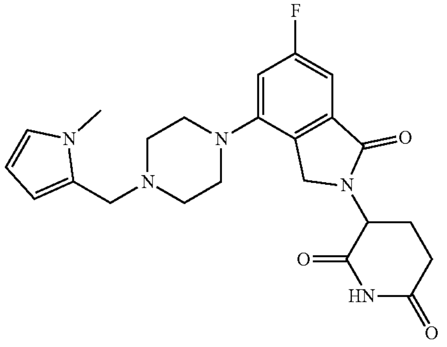

B1328

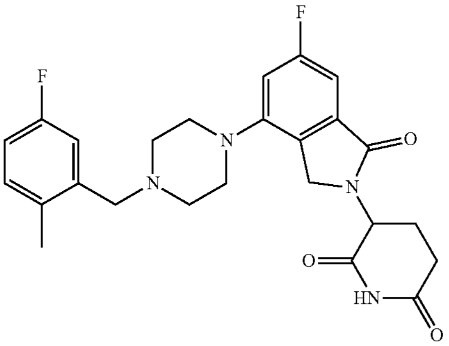

3-(6-Fluoro-4-(4-((5-methoxypyrazin-2-yl)methyl)piperazin-1-yl)-1-oxoisoindolin-2-yl)piperidine-2,6-dione B1329.

3-(6-Fluoro-4-(4-((2-methoxypyrimidin-4-yl)methyl)piperazin-1-yl)-1-oxoisoindolin-2-yl)piperidine-2,6-dione B1330.

B1329

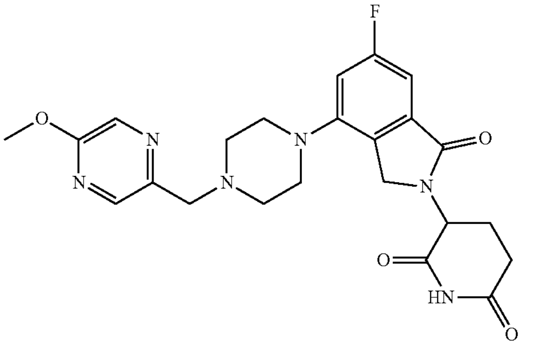

B1330

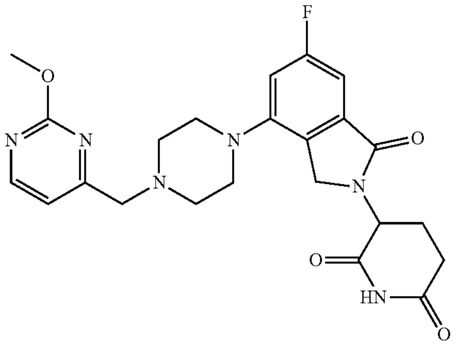

5-((4-(2-(2,6-Dioxopiperidin-3-yl)-6-fluoro-1-oxoisoindolin-4-yl)piperazin-1-yl)-methyl)thiophene-2-carbonitrile B1331.

3-(6-Fluoro-4-(4-((2-methoxypyridin-4-yl)methyl)piperazin-1-yl)-1-oxoisoindolin-2-yl)piperidine-2,6-dione B1332.

B1331

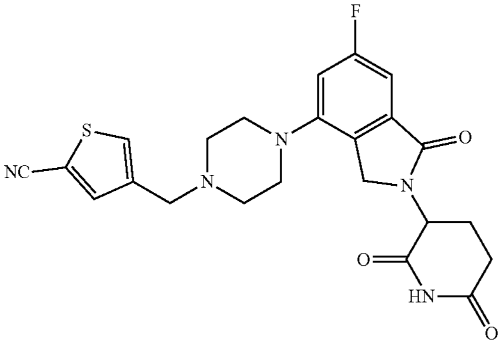

-continued

B1332

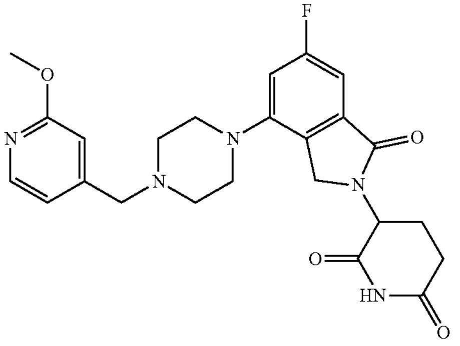

3-(6-Fluoro-4-(4-((2-methoxypyridin-3-yl)methyl)piperazin-1-yl)-1-oxoisoindolin-2-yl)piperidine-2,6-dione B1333.

3-(6-Fluoro-4-(4-((3-methoxypyridin-4-yl)methyl)piperazin-1-yl)-1-oxoisoindolin-2-yl)piperidine-2,6-dione B1334.

B1333

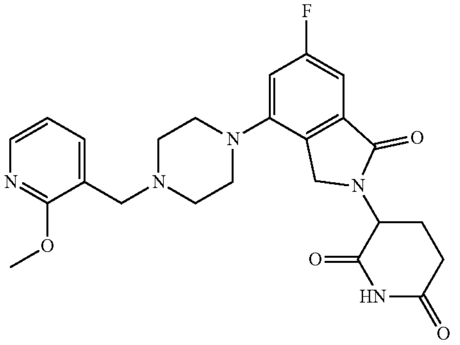

B1334

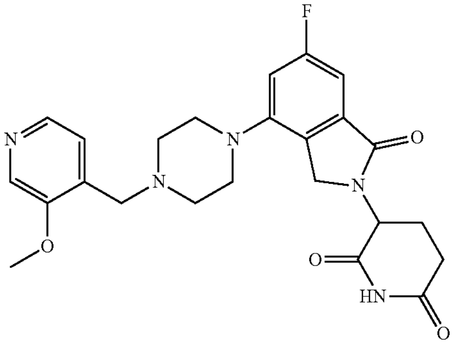

3-(6-Fluoro-4-(4-((6-methoxypyridin-3-yl)methyl)piperazin-1-yl)-1-oxoisoindolin-2-yl)piperidine-2,6-dione B1335.

3-(6-Fluoro-4-(4-((4-methoxypyridin-2-yl)methyl)piperazin-1-yl)-1-oxoisoindolin-2-yl)piperidine-2,6-dione B1336.

B1335

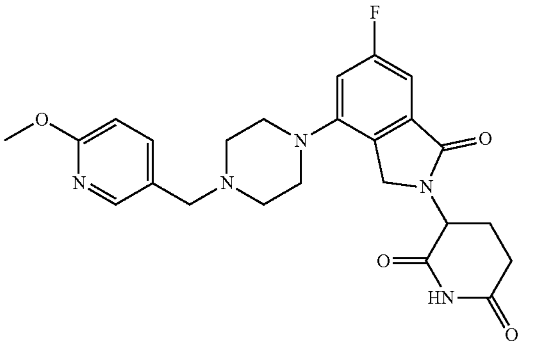

B1336

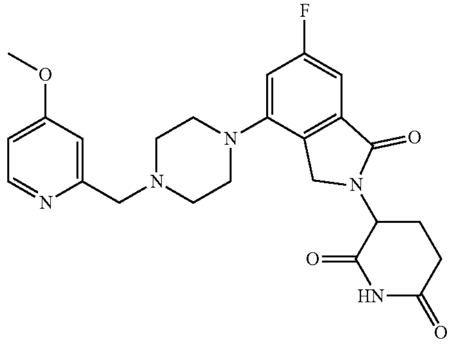

3-(6-Fluoro-4-(4-((5-methoxypyridin-2-yl)methyl)piperazin-1-yl)-1-oxoisoindolin-2-yl)piperidine-2,6-dione B1337.

3-(6-Fluoro-1-oxo-4-(4-(pyrimidin-5-ylmethyl)piperazin-1-yl)isoindolin-2-yl)-piperidine-2,6-dione B1338.

B1337

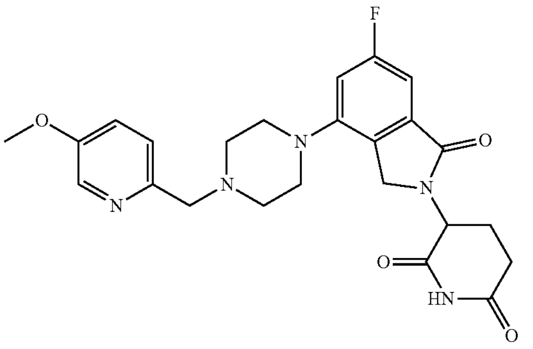

-continued

B1338

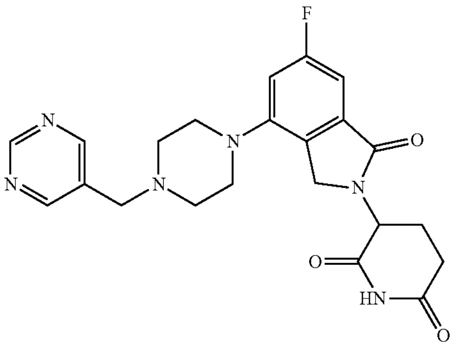

3-(6-Fluoro-4-(4-((3-methoxypyridin-2-yl)methyl)piperazin-1-yl)-1-oxoisoindolin-2-yl)piperidine-2,6-dione B1339.

3-(6-Fluoro-4-(4-((4-methoxypyridin-3-yl)methyl)piperazin-1-yl)-1-oxoisoindolin-2-yl)piperidine-2,6-dione B1340.

B1339

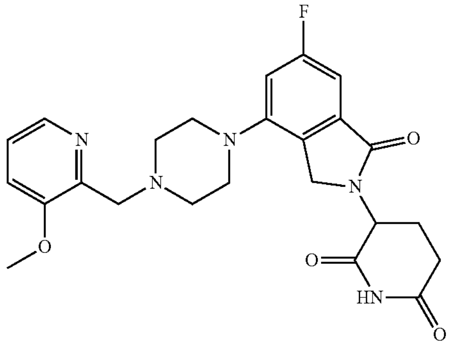

B1340

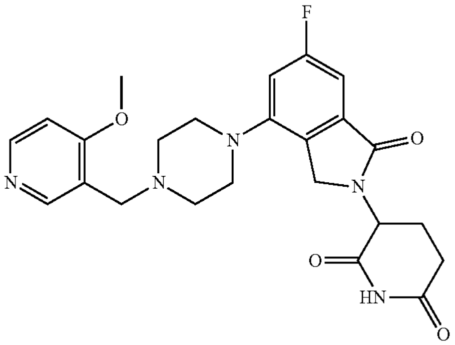

3-(6-Fluoro-4-(4-((6-methoxypyridin-2-yl)methyl)piperazin-1-yl)-1-oxoisoindolin-2-yl)piperidine-2,6-dione B1341.

3-(6-Fluoro-4-(4-((5-methoxypyridin-3-yl)methyl)piperazin-1-yl)-1-oxoisoindolin-2-yl)piperidine-2,6-dione B1342.

B1341

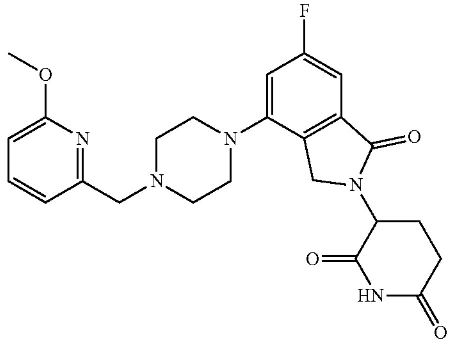

B1342

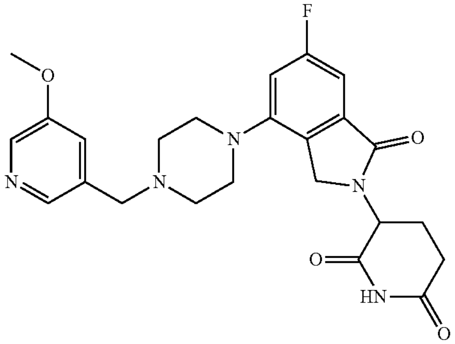

3-(6-Fluoro-4-(4-((1-methyl-6-oxo-1,6-dihydropyridin-2-yl)methyl)piperazin-1-yl)-1-oxoisoindolin-2-yl)piperidine-2,6-dione B1343.

3-(6-Fluoro-4-(4-((1-methyl-2-oxo-1,2-dihydropyridin-4-yl)methyl)piperazin-1-yl)-1-oxoisoindolin-2-yl)piperidine-2,6-dione B1344.

B1343

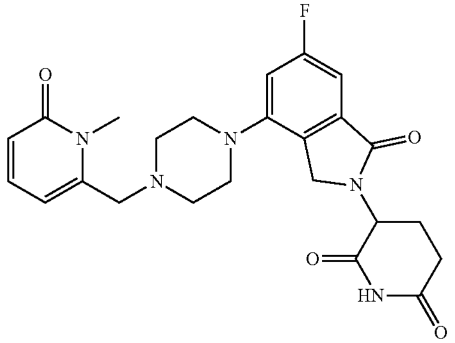

B1344

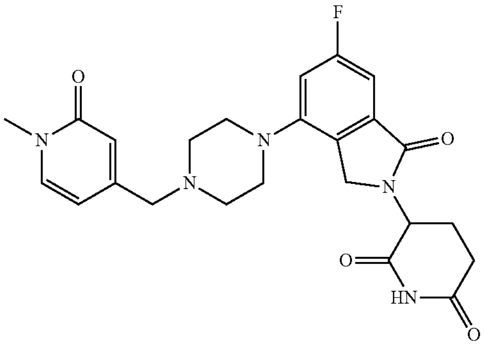

3-(4-(4-((2-Amino-5-methylpyridin-3-yl)methyl)piperazin-1-yl)-6-fluoro-1-oxoisoindolin-2-yl)piperidine-2,6-dione B1345.

3-(6-Fluoro-4-(4-(2-methoxybenzyl)piperazin-1-yl)-1-oxoisoindolin-2-yl)-piperidine-2,6-dione B1346.

B1345

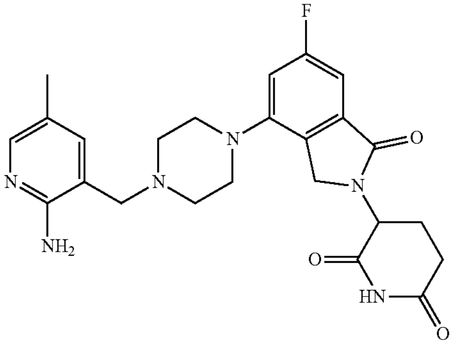

B1346

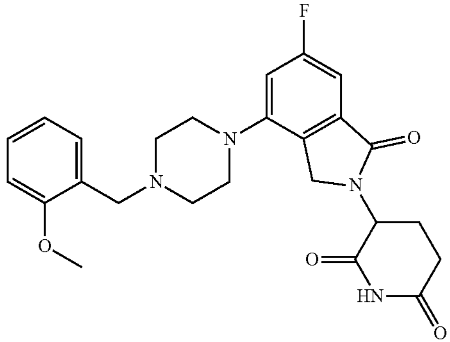

3-(6-Fluoro-4-(4-(4-methoxybenzyl)piperazin-1-yl)-1-oxoisoindolin-2-yl)-piperidine-2,6-dione B1347.

3-(6-Fluoro-4-(4-(3-hydroxy-5-methylbenzyl)piperazin-1-yl)-1-oxoisoindolin-2-yl)piperidine-2,6-dione B1348.

B1347

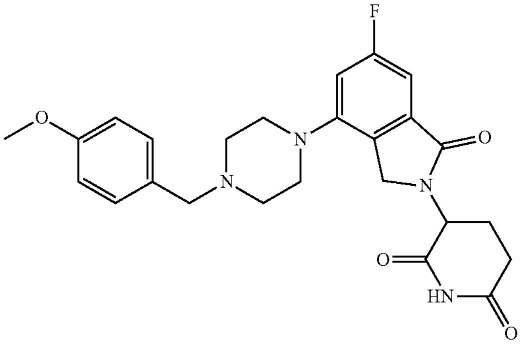

-continued

B1348

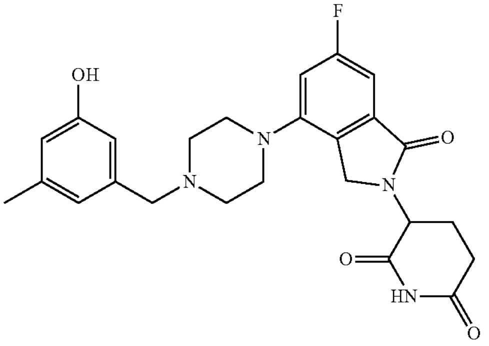

3-(6-Fluoro-1-oxo-4-(4-(pyridin-2-ylmethyl)piperazin-1-yl)isoindolin-2-yl)-piperidine-2,6-dione B1349.

3-(4-(4-(Cyclobutylmethyl)piperazin-1-yl)-6-fluoro-1-oxoisoindolin-2-yl)-piperidine-2,6-dione B1350.

B1349

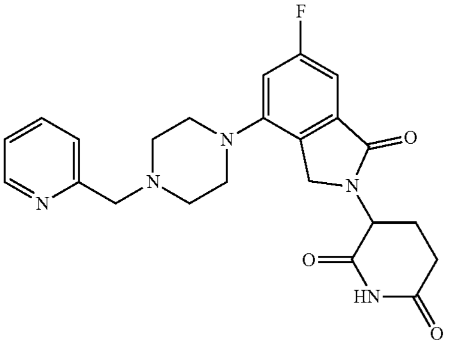

B1350

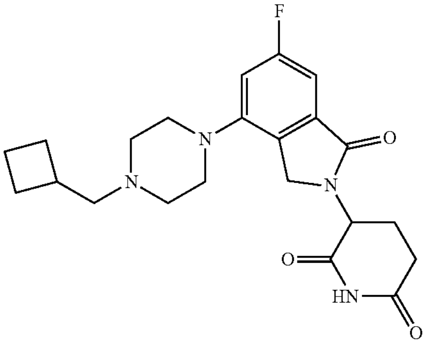

3-(4-(4-(Cyclopropylsulfonyl)piperazin-1-yl)-6-fluoro-1-oxoisoindolin-2-yl)-piperidine-2,6-dione B2001.

3-(6-Fluoro-1-oxo-4-(4-(propylsulfonyl)piperazin-1-yl)isoindolin-2-yl)piperidine-2,6-dione B2002.

B2001

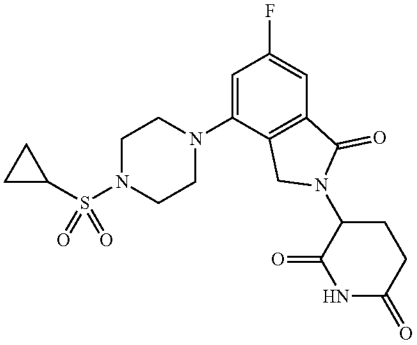

B2002

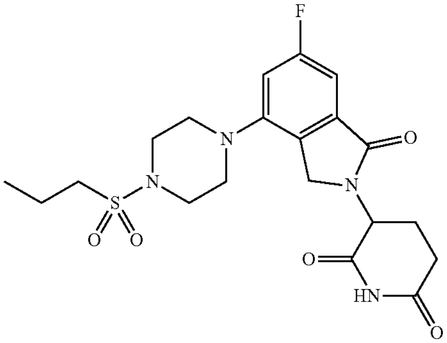

3-(6-Fluoro-4-(4-(isopropylsulfonyl)piperazin-1-yl)-1-oxoisoindolin-2-yl)-piperidine-2,6-dione B2003.

3-(6-Fluoro-4-(4-(isobutylsulfonyl)piperazin-1-yl)-1-oxoisoindolin-2-yl)-piperidine-2,6-dione B2004.

B2003

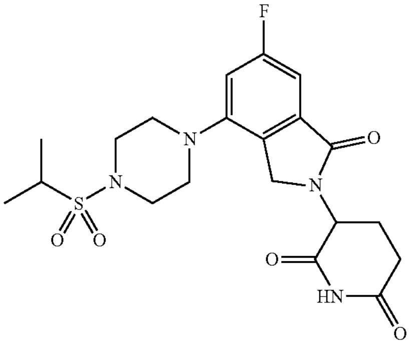

B2004

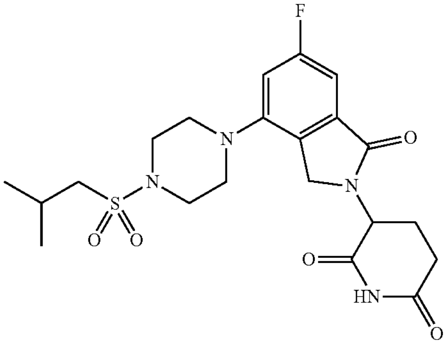

3-(6-Fluoro-4-(4-(furan-3-ylsulfonyl)piperazin-1-yl)-1-oxoisoindolin-2-yl)-piperidine-2,6-dione B2005.

3-(4-(4-((1H-Pyrazol-4-yl)sulfonyl)piperazin-1-yl)-6-fluoro-1-oxoisoindolin-2-yl)piperidine-2,6-dione B2006.

B2005

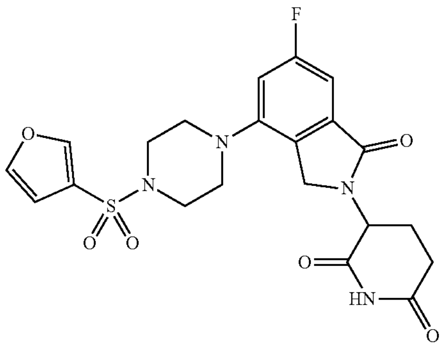

B2006

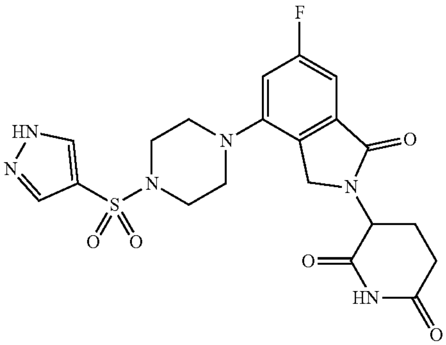

3-(6-Fluoro-1-oxo-4-(4-((trifluoromethyl)sulfonyl)piperazin-1-yl)isoindolin-2-yl)-piperidine-2,6-dione B2007.

3-(4-(4-((Cyclobutylmethyl)sulfonyl)piperazin-1-yl)-6-fluoro-1-oxoisoindolin-2-yl)piperidine-2,6-dione B2008.

B2007

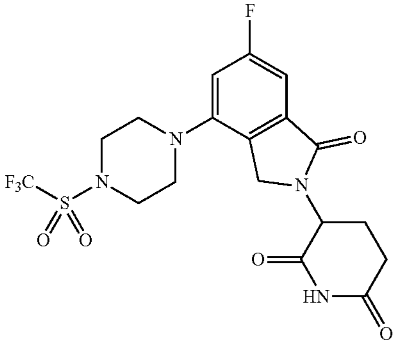

-continued

B2008

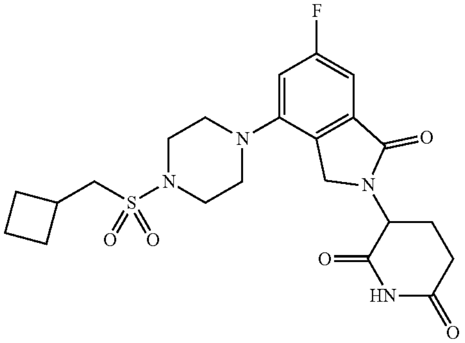

3-(4-(4-((3-Chloropropyl)sulfonyl)piperazin-1-yl)-6-fluoro-1-oxoisoindolin-2-yl)-piperidine-2,6-dione B2009.

3-(6-Fluoro-1-oxo-4-(4-(pyridin-3-ylsulfonyl)piperazin-1-yl)isoindolin-2-yl)-piperidine-2,6-dione B2010.

B2009

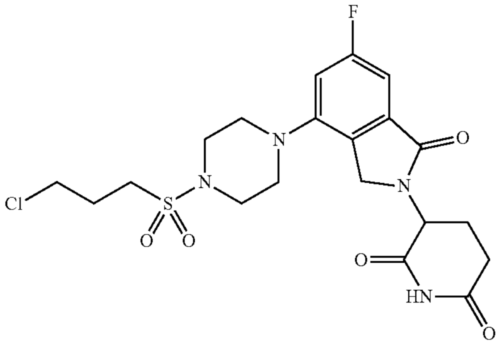

B2010

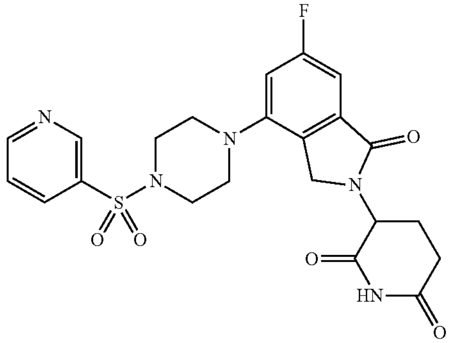

3-(6-Fluoro-4-(4-((1-methyl-1H-pyrazol-4-yl)sulfonyl)piperazin-1-yl)-1-oxoisoindolin-2-yl)piperidine-2,6-dione B2011.

3-(6-Fluoro-4-(4-((1-methyl-1H-pyrazol-3-yl)sulfonyl)piperazin-1-yl)-1-oxoisoindolin-2-yl)piperidine-2,6-dione B2012.

B2011

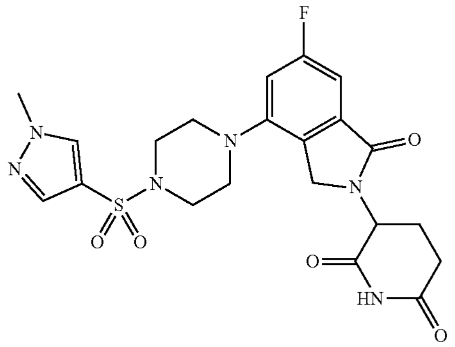

B2012

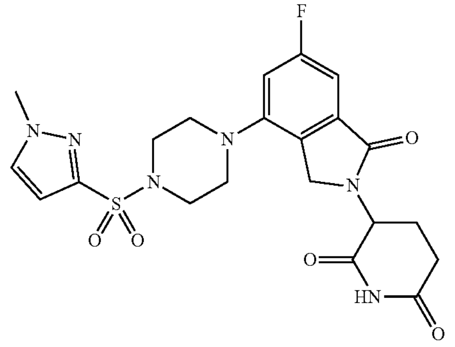

3-(6-Fluoro-4-(4-((1-methyl-1H-imidazol-4-yl)sulfonyl)piperazin-1-yl)-1-oxoisoindolin-2-yl)piperidine-2,6-dione B2013.

3-(6-Fluoro-1-oxo-4-(4-(thiophen-2-ylsulfonyl)piperazin-1-yl)isoindolin-2-yl)-piperidine-2,6-dione B2014.

B2013

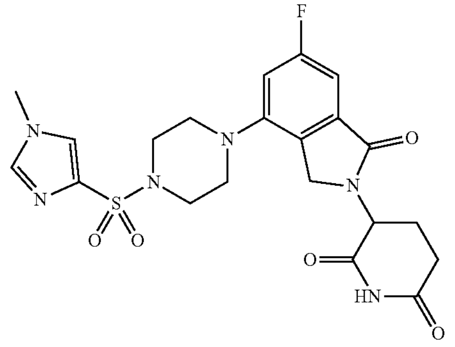

-continued

B2014

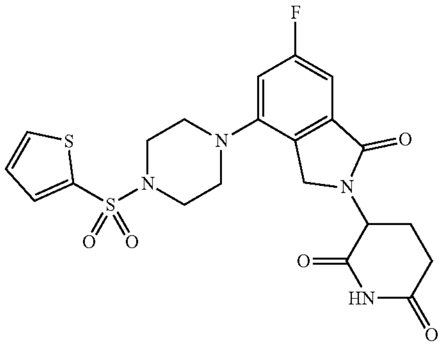

3-(4-(4-(Cyclohexylsulfonyl)piperazin-1-yl)-6-fluoro-1-oxoisoindolin-2-yl)-piperidine-2,6-dione B2015.

3-(6-Fluoro-1-oxo-4-(4-((tetrahydro-2H-pyran-4-yl)sulfonyl)piperazin-1-yl)-isoindolin-2-yl)piperidine-2,6-dione B2016.

B2015

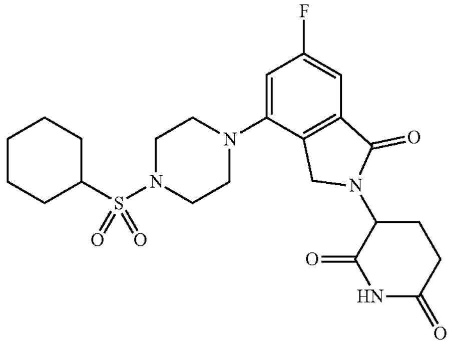

B2016

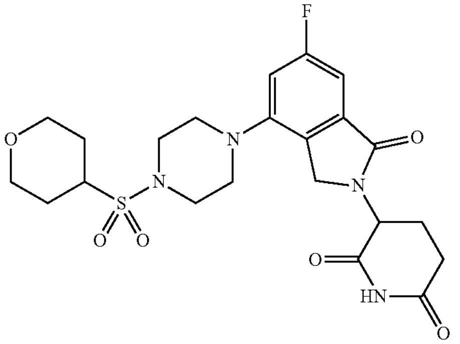

3-(6-Fluoro-1-oxo-4-(4-(m-tolylsulfonyl)piperazin-1-yl)isoindolin-2-yl)-piperidine-2,6-dione B2017.

3-(6-Fluoro-4-(4-((6-methylpyridin-3-yl)sulfonyl)piperazin-1-yl)-1-oxoisoindolin-2-yl)piperidine-2,6-dione B2018.

B2017

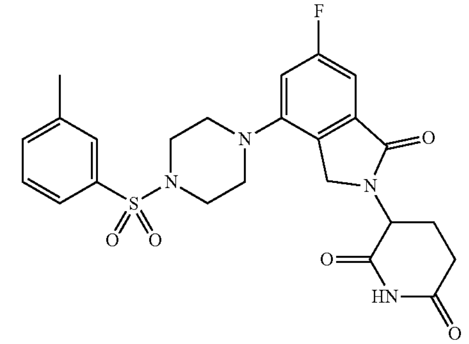

B2018

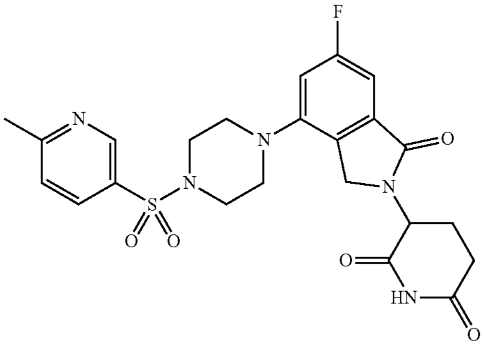

3-(6-Fluoro-4-(4-((4-hydroxyphenyl)sulfonyl)piperazin-1-yl)-1-oxoisoindolin-2-yl)piperidine-2,6-dione B2019.

3-(6-Fluoro-4-(4-((4-fluorophenyl)sulfonyl)piperazin-1-yl)-1-oxoisoindolin-2-yl)-piperidine-2,6-dione B2020.

B2019

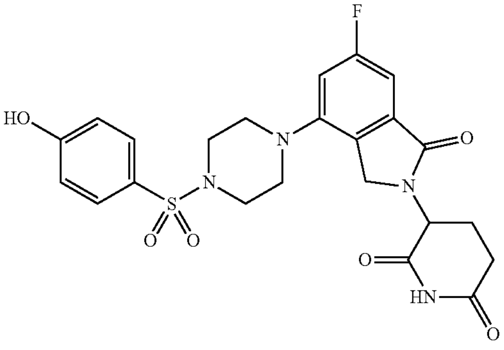

-continued

B2020

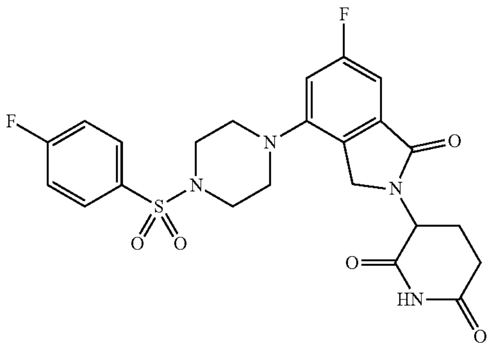

3-(6-Fluoro-4-(4-((3-fluorophenyl)sulfonyl)piperazin-1-yl)-1-oxoisoindolin-2-yl)-piperidine-2,6-dione B2021.

3-(6-Fluoro-4-(4-((2-fluorophenyl)sulfonyl)piperazin-1-yl)-1-oxoisoindolin-2-yl)-piperidine-2,6-dione B2022.

B2021

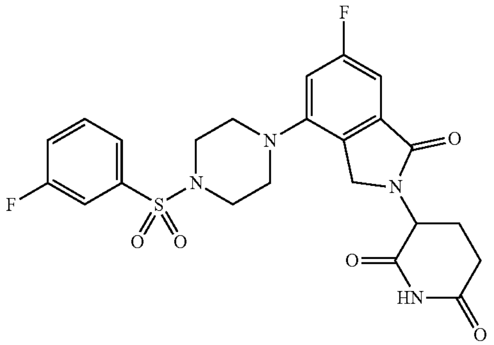

B2022

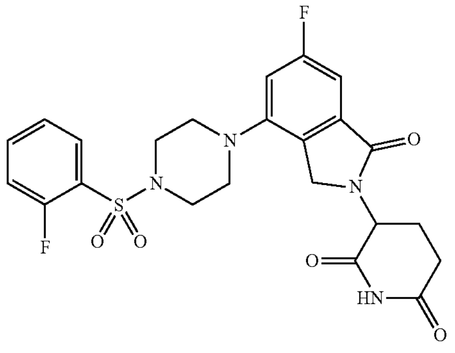

3-(6-Fluoro-1-oxo-4-(4-((3,3,3-trifluoropropyl)sulfonyl)piperazin-1-yl)isoindolin-2-yl)piperidine-2,6-dione B2023.

3-(6-Fluoro-4-(4-((4-methylbenzyl)sulfonyl)piperazin-1-yl)-1-oxoisoindolin-2-yl)piperidine-2,6-dione B2024.

B2023

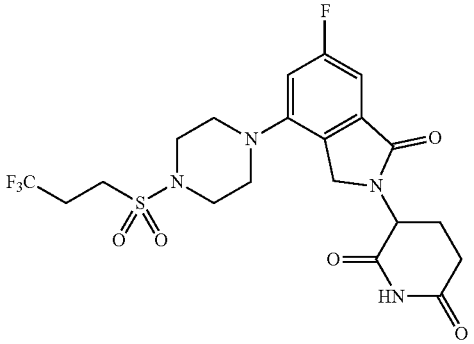

B2024

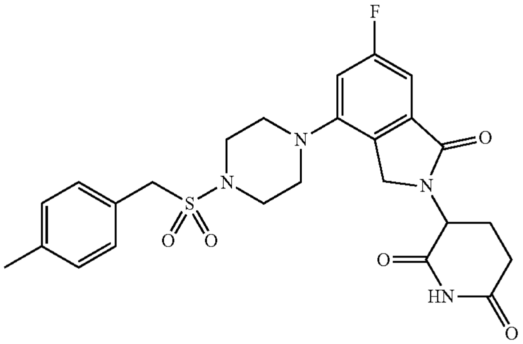

3-(6-Fluoro-1-oxo-4-(4-(phenethylsulfonyl)piperazin-1-yl) isoindolin-2-yl)-piperidine-2,6-dione B2025.

3-(4-(4-((2,6-Dimethylphenyl)sulfonyl)piperazin-1-yl)-6-fluoro-1-oxoisoindolin-2-yl)piperidine-2,6-dione B2026.

B2025

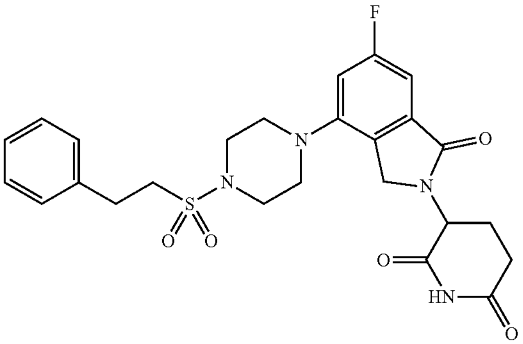

-continued

B2026

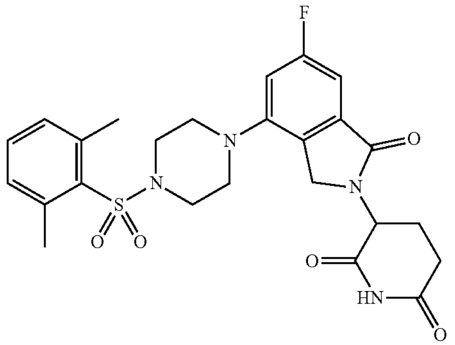

3-(6-Fluoro-4-(4-((4-methoxyphenyl)sulfonyl)piperazin-1-yl)-1-oxoisoindolin-2-yl)piperidine-2,6-dione B2027.

3-(6-Fluoro-4-(4-((3-methoxyphenyl)sulfonyl)piperazin-1-yl)-1-oxoisoindolin-2-yl)piperidine-2,6-dione B2028.

B2027

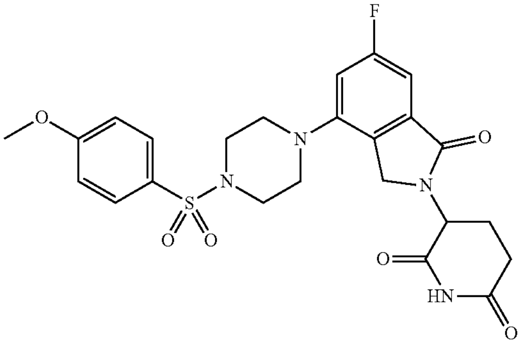

B2028

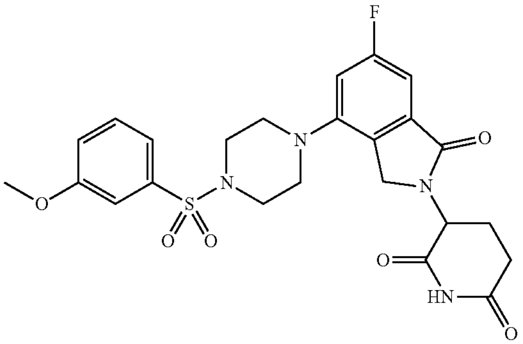

3-(6-Fluoro-4-(4-((6-methoxypyridin-3-yl)sulfonyl)piperazin-1-yl)-1-oxoisoindolin-2-yl)piperidine-2,6-dione B2029.

3-(6-Fluoro-4-(4-((2-fluoro-5-methylphenyl)sulfonyl)piperazin-1-yl)-1-oxoisoindolin-2-yl)piperidine-2,6-dione B2030.

B2029

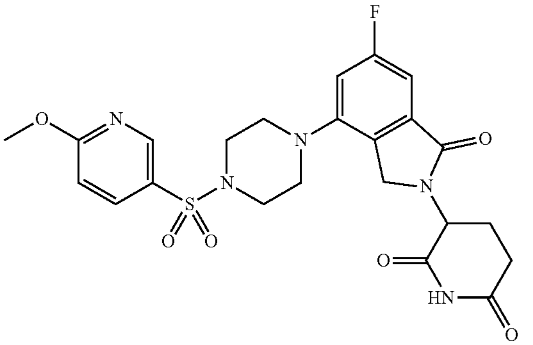

3-(6-Fluoro-4-(4-((4-fluoro-2-methylphenyl)sulfonyl)piperazin-1-yl)-1-oxoisoindolin-2-yl)piperidine-2,6-dione B2031.

3-(6-Fluoro-4-(4-((2-fluoro-4-methylphenyl)sulfonyl)piperazin-1-yl)-1-oxoisoindolin-2-yl)piperidine-2,6-dione B2032.

B2030

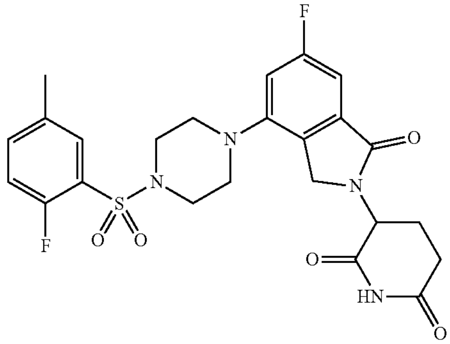

B2031

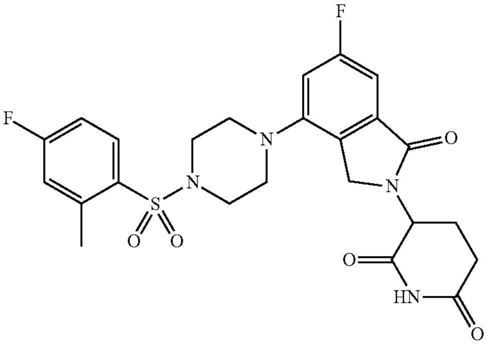

-continued

B2032

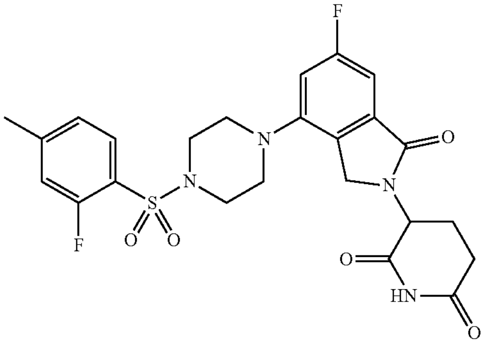

3-(4-(4-((3-Chlorophenyl)sulfonyl)piperazin-1-yl)-6-fluoro-1-oxoisoindolin-2-yl)-piperidine-2,6-dione B2033.

3-(4-(4-((2-Chlorophenyl)sulfonyl)piperazin-1-yl)-6-fluoro-1-oxoisoindolin-2-yl)-piperidine-2,6-dione B2034.

B2033

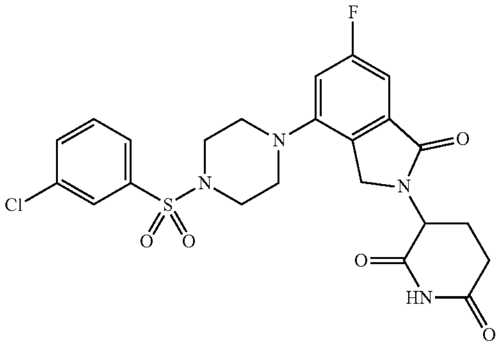

B2034

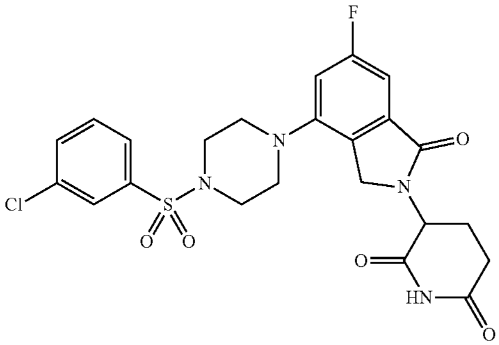

3-(4-(4-((4-Chlorophenyl)sulfonyl)piperazin-1-yl)-6-fluoro-1-oxoisoindolin-2-yl)-piperidine-2,6-dione B2035.

3-(4-(4-((3,4-Difluorophenyl)sulfonyl)piperazin-1-yl)-6-fluoro-1-oxoisoindolin-2-yl)piperidine-2,6-dione B2036.

B2035

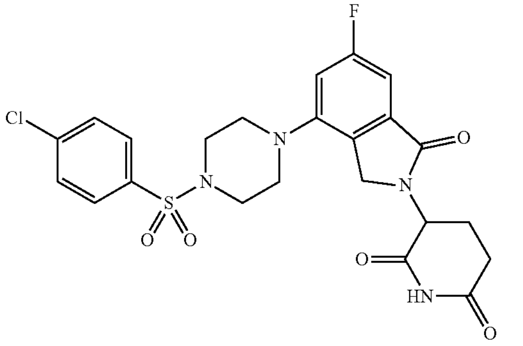

B2036

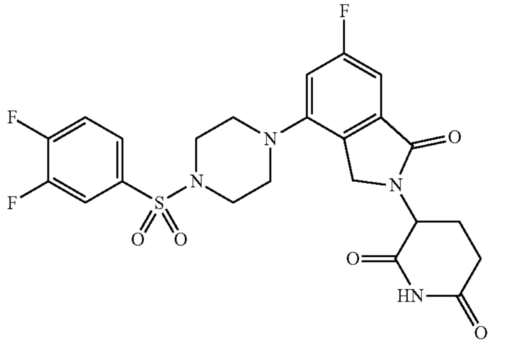

3-(4-(4-((2,4-Difluorophenyl)sulfonyl)piperazin-1-yl)-6-fluoro-1-oxoisoindolin-2-yl)piperidine-2,6-dione B2037.

3-(4-(4-((2,5-Difluorophenyl)sulfonyl)piperazin-1-yl)-6-fluoro-1-oxoisoindolin-2-yl)piperidine-2,6-dione B2038.

B2037

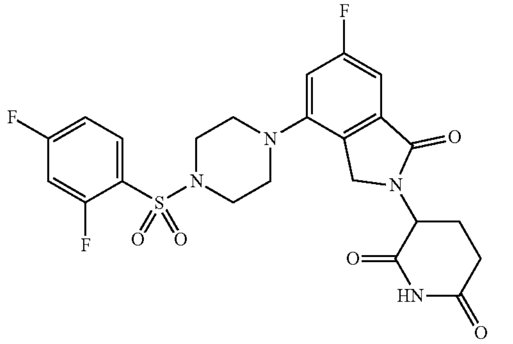

B2038

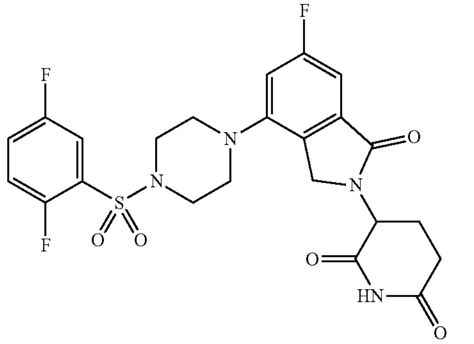

3-(4-(4-((3,5-Difluorophenyl)sulfonyl)piperazin-1-yl)-6-fluoro-1-oxoisoindolin-2-yl)piperidine-2,6-dione B2039.

3-(6-Fluoro-1-oxo-4-(4-(pyridin-3-ylsulfonyl)piperazin-1-yl)isoindolin-2-yl)-piperidine-2,6-dione B2040.

B2039

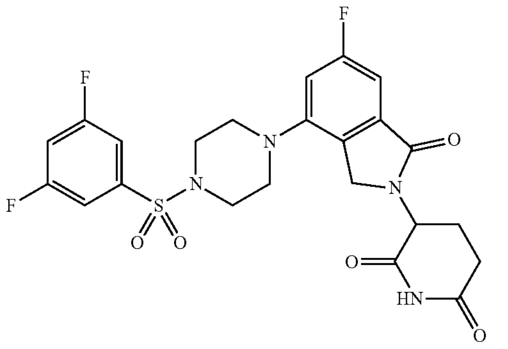

B2040

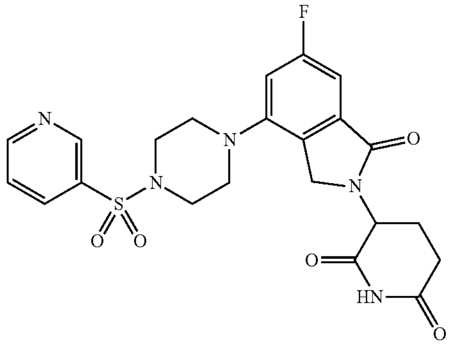

2-((4-(2-(2,6-Dioxopiperidin-3-yl)-6-fluoro-1-oxoisoindolin-4-yl)piperazin-1-yl)-sulfonyl)-5-methylbenzonitrile B2041.

3-(4-(4-((1H-Indol-5-yl)sulfonyl)piperazin-1-yl)-6-fluoro-1-oxoisoindolin-2-yl)-piperidine-2,6-dione B2042.

B2041

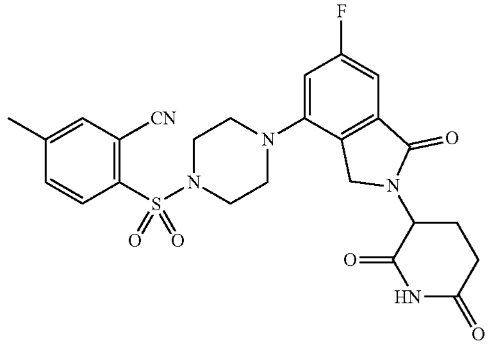

-continued

B2042

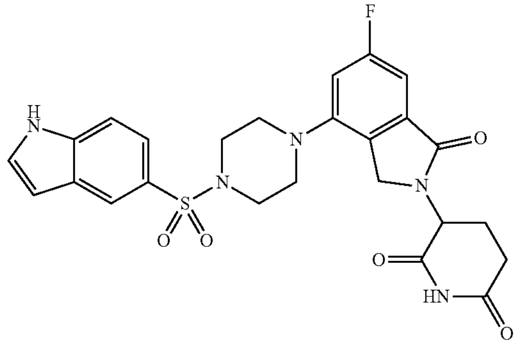

3-(4-(4-(Benzofuran-5-ylsulfonyl)piperazin-1-yl)-6-fluoro-1-oxoisoindolin-2-yl)-piperidine-2,6-dione B2043.

3-(4-(4-((2,3-Dihydrobenzofuran-5-yl)sulfonyl)piperazin-1-yl)-6-fluoro-1-oxoisoindolin-2-yl)piperidine-2,6-dione B2044.

B2043

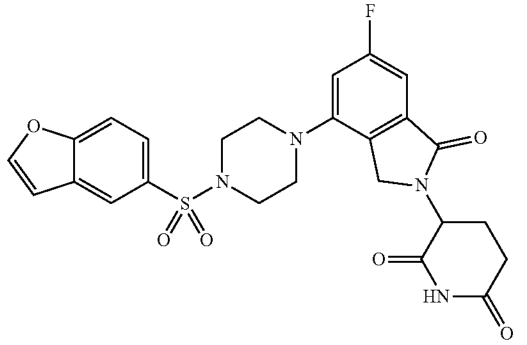

B2044

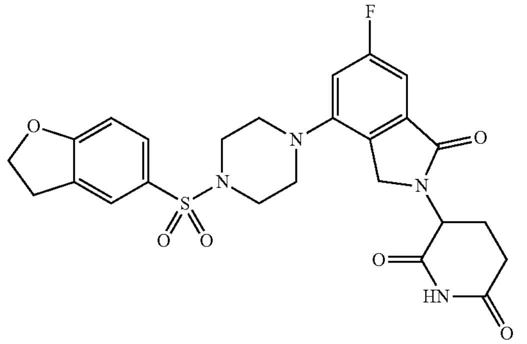

3-(6-Fluoro-4-(4-((4-isopropylphenyl)sulfonyl)piperazin-1-yl)-1-oxoisoindolin-2-yl)piperidine-2,6-dione B2045.

3-(6-Fluoro-4-(4-((3-isopropylphenyl)sulfonyl)piperazin-1-yl)-1-oxoisoindolin-2-yl)piperidine-2,6-dione B2046.

B2045

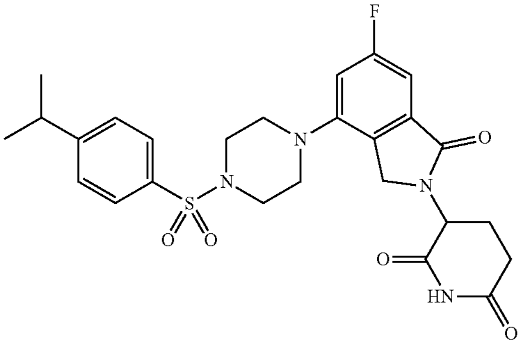

B2046

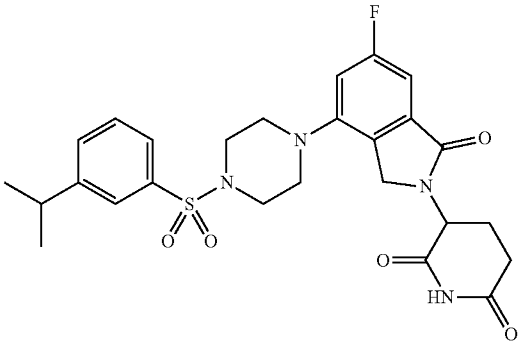

3-((4-(2-(2,6-Dioxopiperidin-3-yl)-6-fluoro-1-oxoisoindolin-4-yl)piperazin-1-yl)-sulfonyl)-4-fluorobenzonitrile B2047.

5-((4-(2-(2,6-Dioxopiperidin-3-yl)-6-fluoro-1-oxoisoindolin-4-yl)piperazin-1-yl)-sulfonyl)-2-fluorobenzonitrile B2048.

B2047

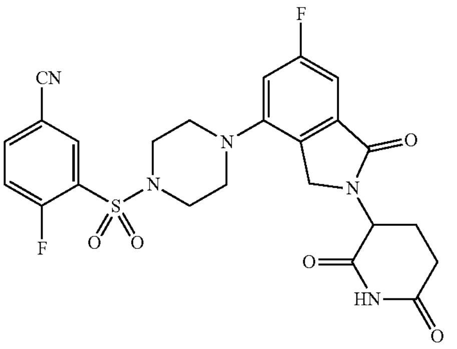

-continued

B2048

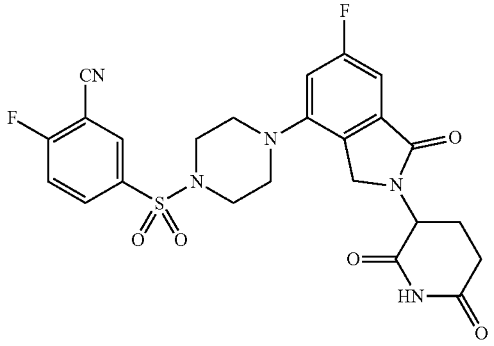

4-((4-(2-(2,6-Dioxopiperidin-3-yl)-6-fluoro-1-oxoisoindolin-4-yl)piperazin-1-yl)-sulfonyl)benzamide B2049.

3-(6-Fluoro-4-(4-((3-methoxybenzyl)sulfonyl)piperazin-1-yl)-1-oxoisoindolin-2-yl)piperidine-2,6-dione B2050.

B2049

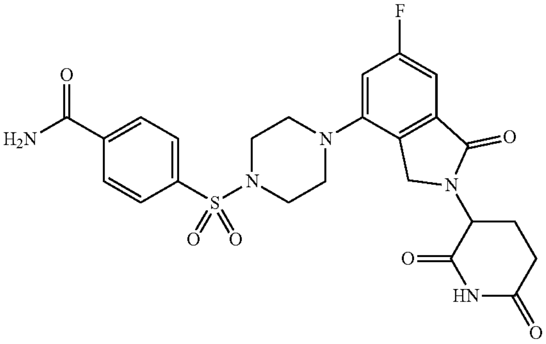

B2050

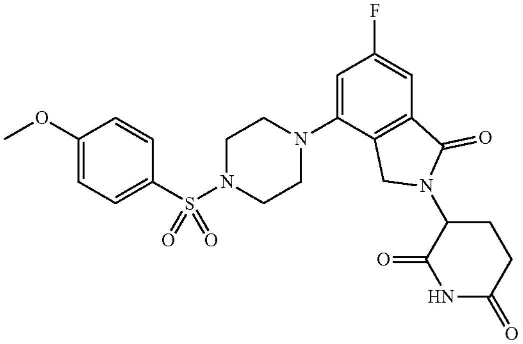

3-(6-Fluoro-4-(4-((3-methoxy-4-methylphenyl)sulfonyl)piperazin-1-yl)-1-oxoisoindolin-2-yl)piperidine-2,6-dione B2051.

3-(6-Fluoro-4-(4-((5-fluoro-2-methoxyphenyl)sulfonyl)piperazin-1-yl)-1-oxoisoindolin-2-yl)piperidine-2,6-dione B2052.

B2051

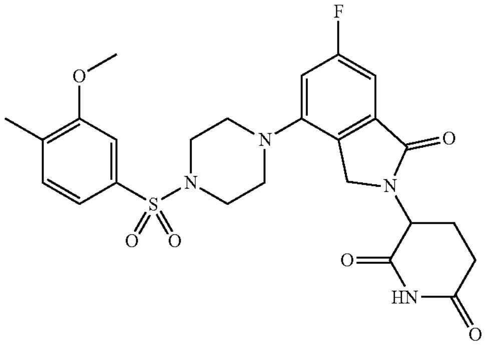

B2052

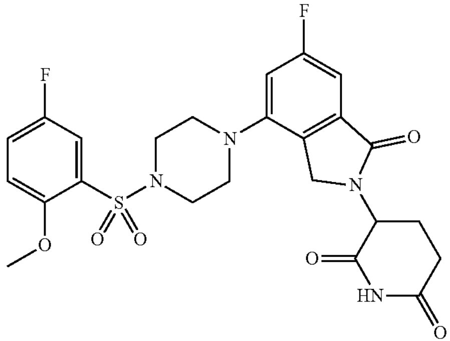

3-(6-Fluoro-4-(4-((3-fluoro-4-methoxyphenyl)sulfonyl)piperazin-1-yl)-1-oxoisoindolin-2-yl)piperidine-2,6-dione B2053.

3-(6-Fluoro-1-oxo-4-(4-((5,6,7,8-tetrahydronaphthalen-2-yl)sulfonyl)piperazin-1-yl)isoindolin-2-yl)piperidine-2,6-dione B2054.

B2053

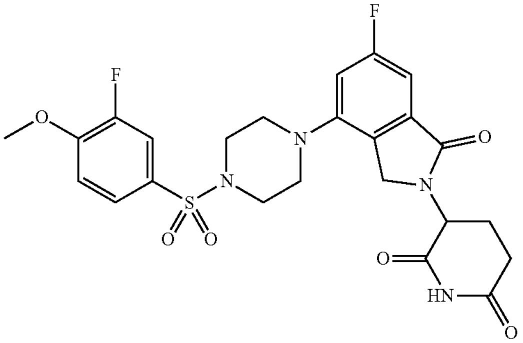

-continued

B2054

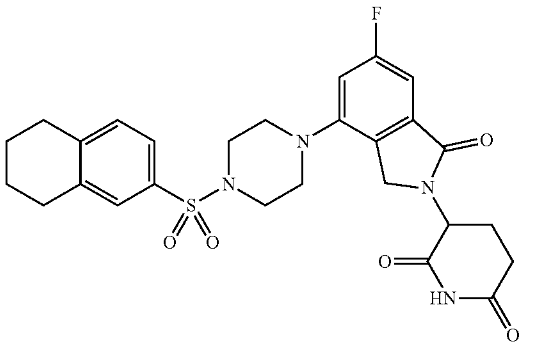

3-(6-Fluoro-4-(4-((2-hydroxy-1H-benzo[d]imidazol-6-yl) sulfonyl)piperazin-1-yl)-1-oxoisoindolin-2-yl)piperidine-2,6-dione B2055.

3-(4-(4-((4-(Tert-butyl)phenyl)sulfonyl)piperazin-1-yl)-6-fluoro-1-oxoisoindolin-2-yl)piperidine-2,6-dione B2056.

B2055

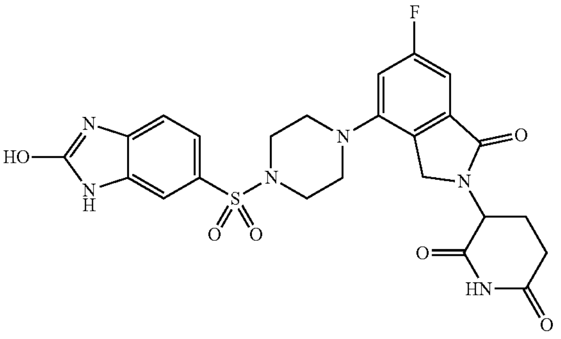

B2056

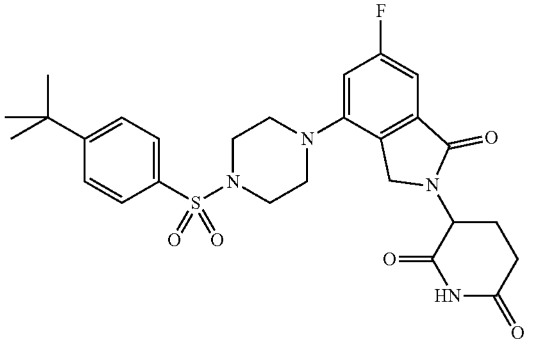

3-(4-(4-((3-(Tert-butyl)phenyl)sulfonyl)piperazin-1-yl)-6-fluoro-1-oxoisoindolin-2-yl)piperidine-2,6-dione B2057.

N-(3-((4-(2-(2,6-Dioxopiperidin-3-yl)-6-fluoro-1-oxoisoindolin-4-yl)piperazin-1-yl)sulfonyl)phenyl)acetamide B2058.

B2057

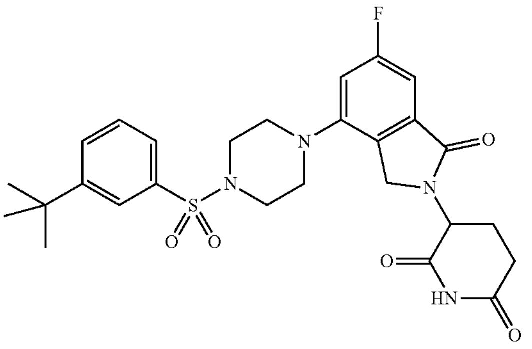

B2058

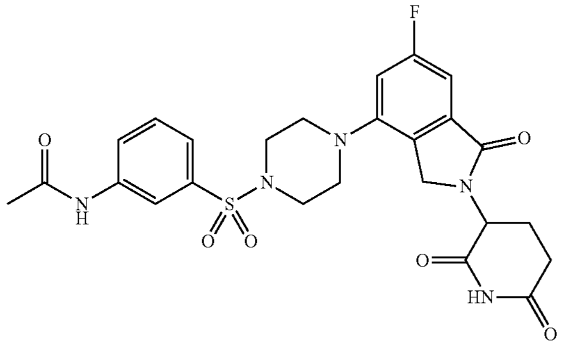

N-(4-((4-(2-(2,6-Dioxopiperidin-3-yl)-6-fluoro-1-oxoisoindolin-4-yl)piperazin-1-yl)sulfonyl)phenyl)acetamide B2059.

4-((4-(2-(2,6-Dioxopiperidin-3-yl)-6-fluoro-1-oxoisoindolin-4-yl)piperazin-1-yl)-sulfonyl)-N-methylbenzamide B2060.

B2059

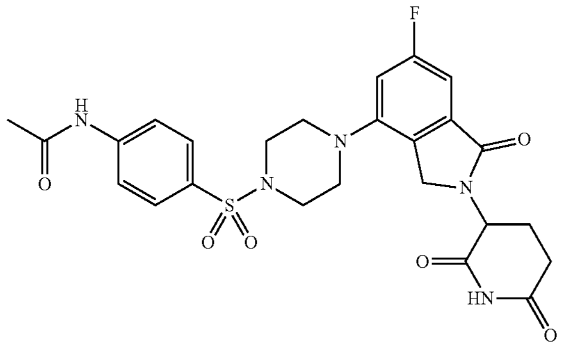

-continued

B2060

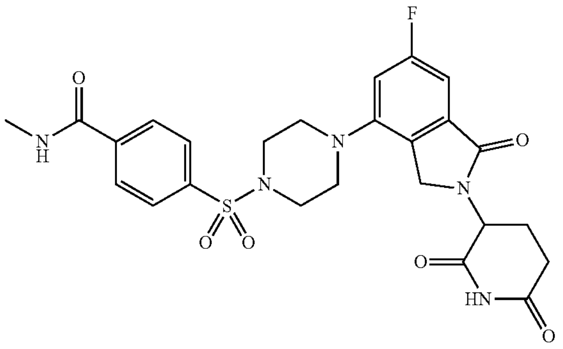

2-Chloro-4-((4-(2-(2,6-dioxopiperidin-3-yl)-6-fluoro-1-oxoisoindolin-4-yl)-piperazin-1-yl)sulfonyl)benzonitrile B2061.

3-(4-(4-((5-Chloro-2-methoxypyridin-3-yl)sulfonyl)piperazin-1-yl)-6-fluoro-1-oxoisoindolin-2-yl)piperidine-2,6-dione B2062.

B2061

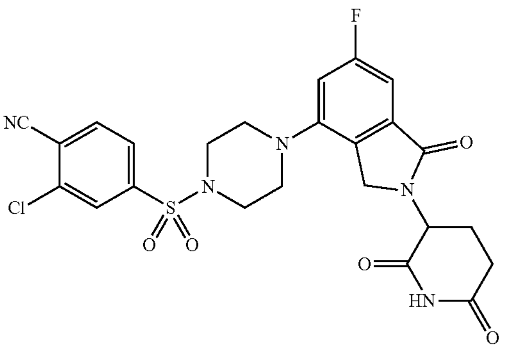

B2062

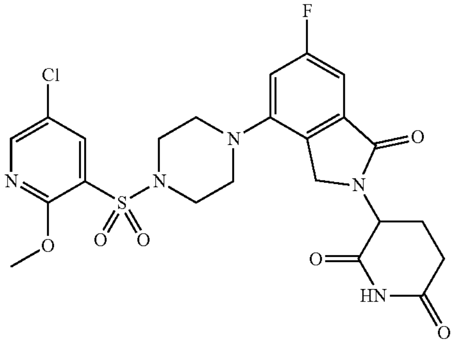

3-(4-(4-((4-(Difluoromethoxy)phenyl)sulfonyl)piperazin-1-yl)-6-fluoro-1-oxoisoindolin-2-yl)piperidine-2,6-dione B2063.

3-(6-Fluoro-4-(4-((4-(oxazol-5-yl)phenyl)sulfonyl)piperazin-1-yl)-1-oxoisoindolin-2-yl)piperidine-2,6-dione B2064.

B2063

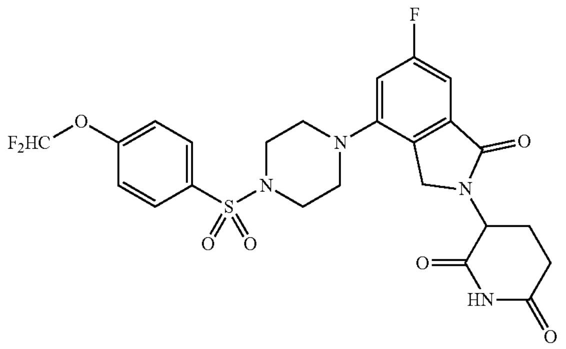

B2064

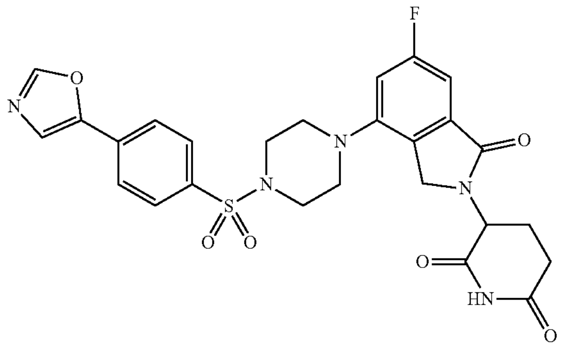

3-(6-Fluoro-1-oxo-4-(4-((4-(trifluoromethyl)phenyl)sulfonyl)piperazin-1-yl)-isoindolin-2-yl)piperidine-2,6-dione B2065.

3-(6-Fluoro-1-oxo-4-(4-((3-(trifluoromethyl)phenyl)sulfonyl)piperazin-1-yl)-isoindolin-2-yl)piperidine-2,6-dione B2066.

B2065

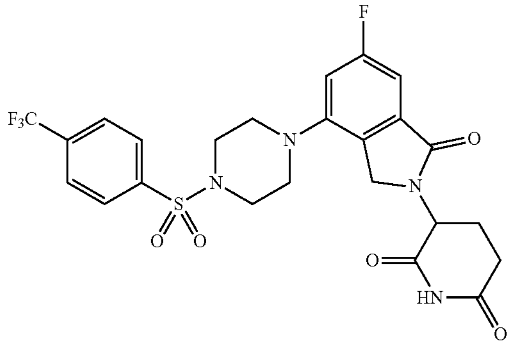

-continued

B2066

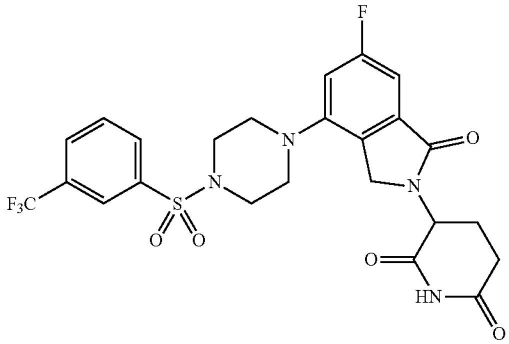

3-(6-Fluoro-1-oxo-4-(4-((2-(trifluoromethyl)phenyl)sulfonyl)piperazin-1-yl)-isoindolin-2-yl)piperidine-2,6-dione B2067.

3-(6-Fluoro-1-oxo-4-(4-((6-(trifluoromethyl)pyridin-3-yl)sulfonyl)piperazin-1-yl)isoindolin-2-yl)piperidine-2,6-dione B2068.

B2067

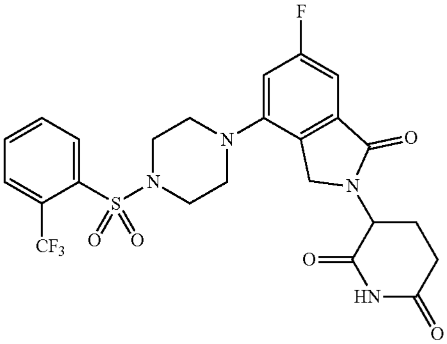

B2068

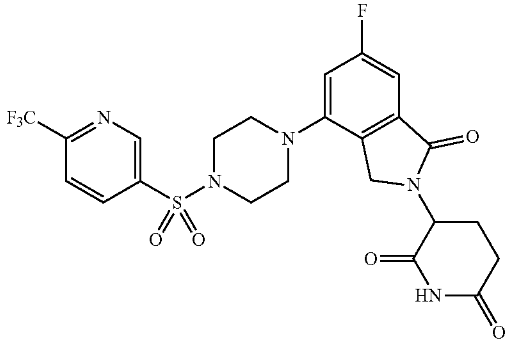

3-(6-Fluoro-1-oxo-4-(4-((2-oxo-1,2,3,4-tetrahydroquinolin-6-yl)sulfonyl)-piperazin-1-yl)isoindolin-2-yl)piperidine-2,6-dione B2069.

2-((4-(2-(2,6-Dioxopiperidin-3-yl)-6-fluoro-1-oxoisoindolin-4-yl)piperazin-1-yl)-sulfonyl)-N,N-dimethylbenzamide B2070.

B2069

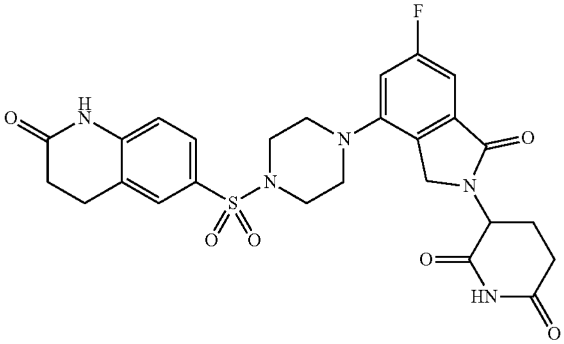

B2070

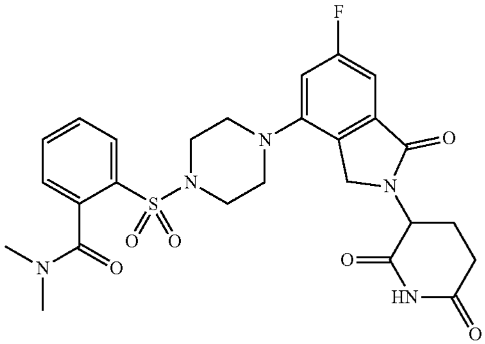

3-(4-(4-((3-Bromophenyl)sulfonyl)piperazin-1-yl)-6-fluoro-1-oxoisoindolin-2-yl)-piperidine-2,6-dione B2071.

3-(4-(4-((2-Bromophenyl)sulfonyl)piperazin-1-yl)-6-fluoro-1-oxoisoindolin-2-yl)-piperidine-2,6-dione B2072.

B2071

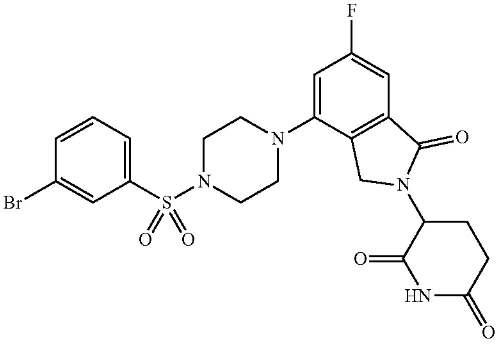

B2072

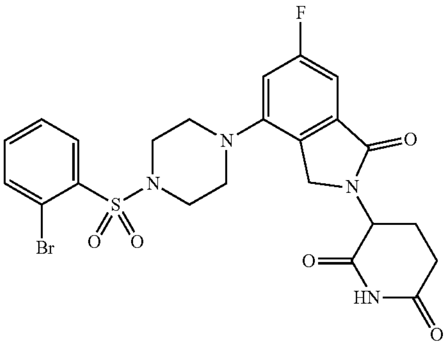

3-(6-Fluoro-1-oxo-4-(4-((1-(o-tolyl)-1H-pyrazol-4-yl)sulfonyl)piperazin-1-yl)-isoindolin-2-yl)piperidine-2,6-dione B2073.

3-(6-Fluoro-1-oxo-4-(4-((4-(trifluoromethyl)benzyl)sulfonyl)piperazin-1-yl)-isoindolin-2-yl)piperidine-2,6-dione B2074.

B2073

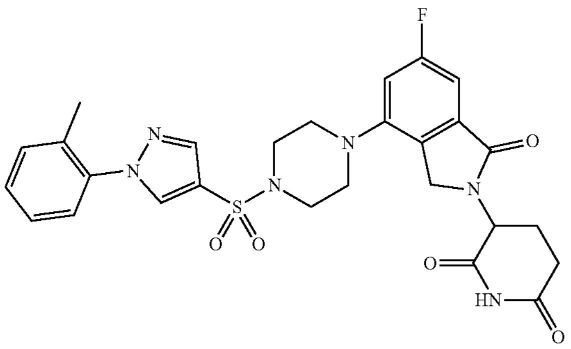

B2074

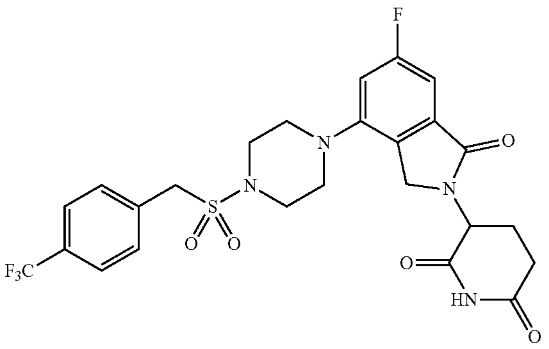

3-(6-Fluoro-1-oxo-4-(4-((2-(trifluoromethoxy)phenyl)sulfonyl)piperazin-1-yl)-isoindolin-2-yl)piperidine-2,6-dione B2075.

3-(4-(4-((1-Chloroisoquinolin-5-yl)sulfonyl)piperazin-1-yl)-6-fluoro-1-oxoisoindolin-2-yl)piperidine-2,6-dione B2076.

B2075

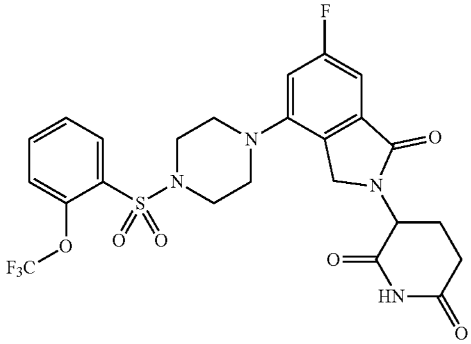

-continued

B2076

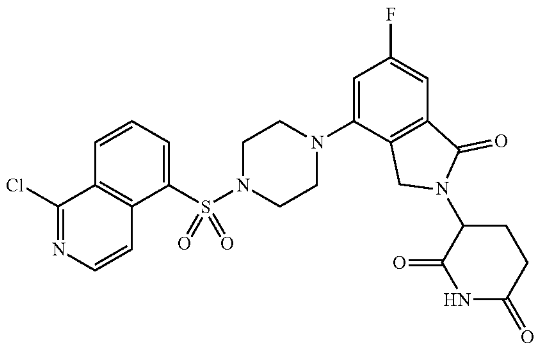

3-(6-Fluoro-4-(4-(isoquinolin-5-ylsulfonyl)piperazin-1-yl)-1-oxoisoindolin-2-yl)-piperidine-2,6-dione B2077.

3-(6-Fluoro-1-oxo-4-(4-((4-(pyridin-2-yloxy)phenyl)sulfonyl)piperazin-1-yl)-isoindolin-2-yl)piperidine-2,6-dione B2078.

B2077

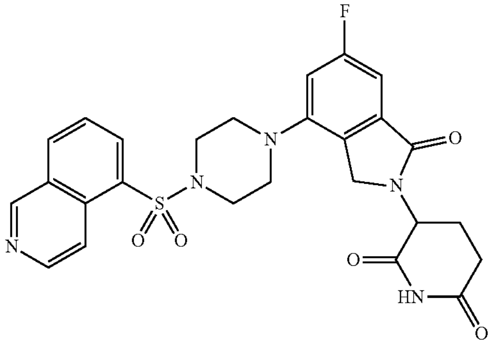

B2078

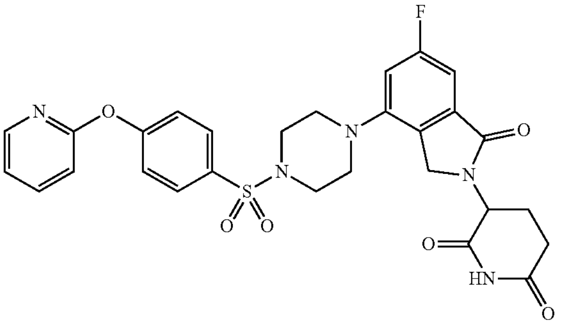

3-(6-Fluoro-1-oxo-4-(4-((6-phenoxypyridin-3-yl)sulfonyl)piperazin-1-yl)-isoindolin-2-yl)piperidine-2,6-dione B2079.

3-(4-(4-((5-(Dimethylamino)naphthalen-1-yl)sulfonyl)piperazin-1-yl)-6-fluoro-1-oxoisoindolin-2-yl)piperidine-2,6-dione B2080.

B2079

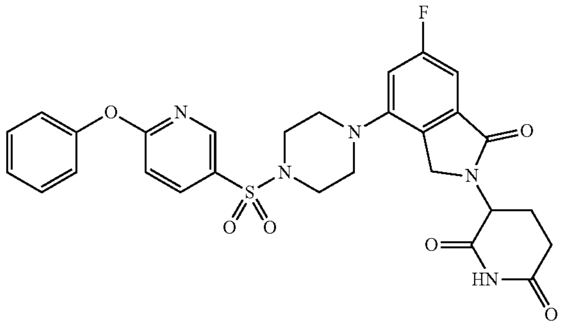

B2080

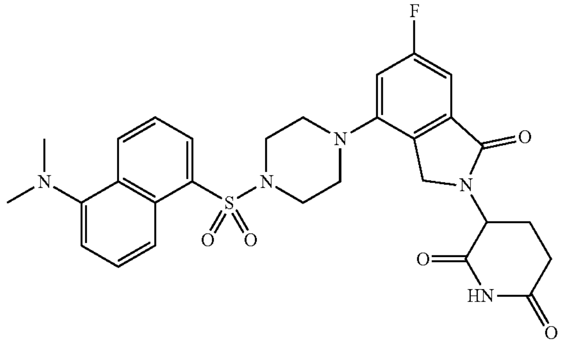

3-(4-(4-((6-(Dimethylamino)naphthalen-2-yl)sulfonyl)piperazin-1-yl)-6-fluoro-1-oxoisoindolin-2-yl)piperidine-2,6-dione B2081.

3-(4-(4-((4-(Benzyloxy)phenyl)sulfonyl)piperazin-1-yl)-6-fluoro-1-oxoisoindolin-2-yl)piperidine-2,6-dione B2082.

B2081

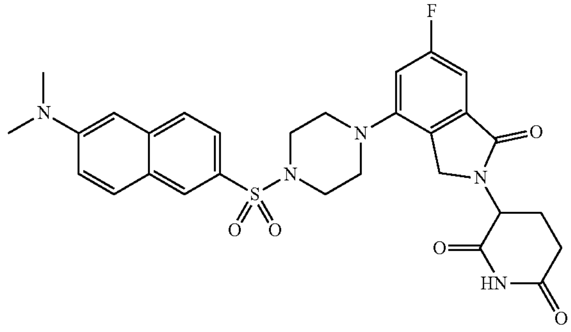

B2082

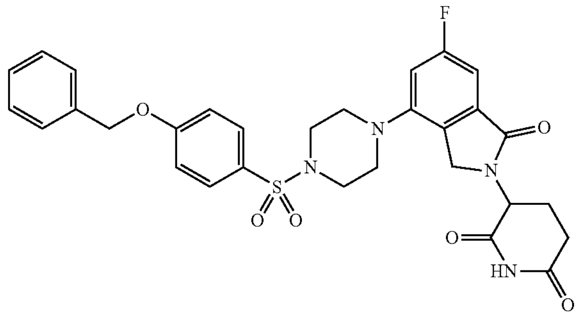

Tert-butyl 4-((4-(2-(2,6-dioxopiperidin-3-yl)-6-fluoro-1-oxoisoindolin-4-yl)-piperazin-1-yl)sulfonyl)piperidine-1-carboxylate B2083.

Benzyl 4-((4-(2-(2,6-dioxopiperidin-3-yl)-6-fluoro-1-oxoisoindolin-4-yl)-piperazin-1-yl)sulfonyl)piperidine-1-carboxylate B2084.

B2083

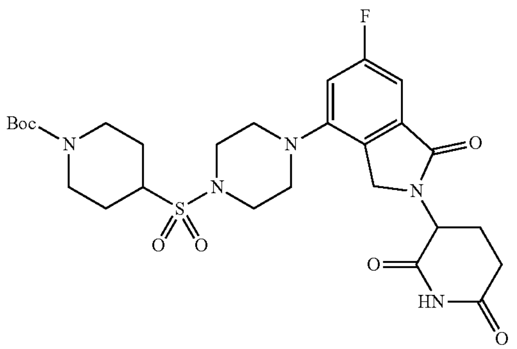

B2084

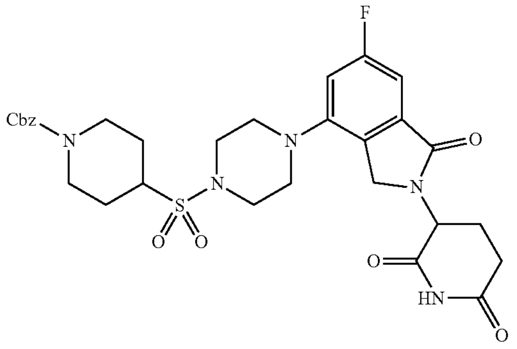

3-(6-Fluoro-1-oxo-4-(4-((2-(2,2,2-trifluoroacetyl)-1,2,3,4-tetrahydroisoquinolin-7-yl)sulfonyl)piperazin-1-yl)isoindolin-2-yl)piperidine-2,6-dione B2085.

Benzyl 4-(((4-(2-(2,6-dioxopiperidin-3-yl)-6-fluoro-1-oxoisoindolin-4-yl)-piperazin-1-yl)sulfonyl)methyl)piperidine-1-carboxylate B2086.

B2085

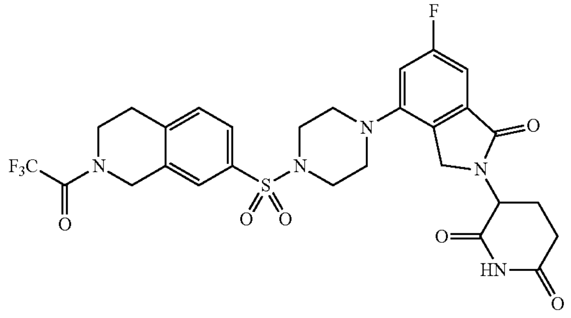

-continued

B2086

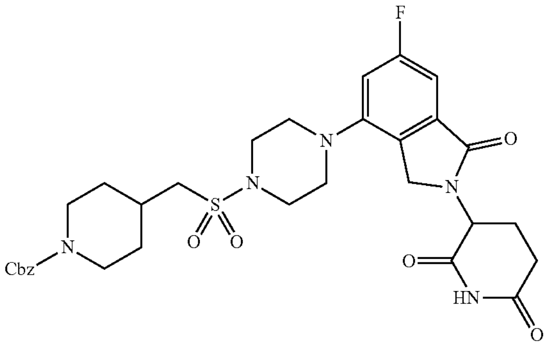

3-(4-(4-(Ethylsulfonyl)piperazin-1-yl)-6-fluoro-1-oxoisoindolin-2-yl)piperidine-2,6-dione B2087.

3-(4-(4-((5-Chlorothiophen-2-yl)sulfonyl)piperazin-1-yl)-6-fluoro-1-oxoisoindolin-2-yl)piperidine-2,6-dione B2088.

B2087

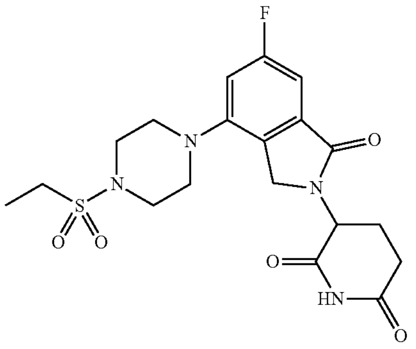

B2088

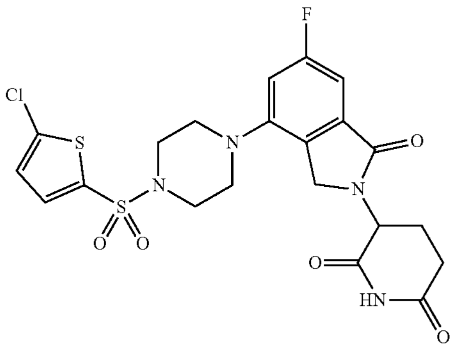

3-(4-(4-((3-Chloro-4-methylphenyl)sulfonyl)piperazin-1-yl)-6-fluoro-1-oxoisoindolin-2-yl)piperidine-2,6-dione B2089.

3-(4-(4-((2-Chloro-6-methylphenyl)sulfonyl)piperazin-1-yl)-6-fluoro-1-oxoisoindolin-2-yl)piperidine-2,6-dione B2090.

B2089

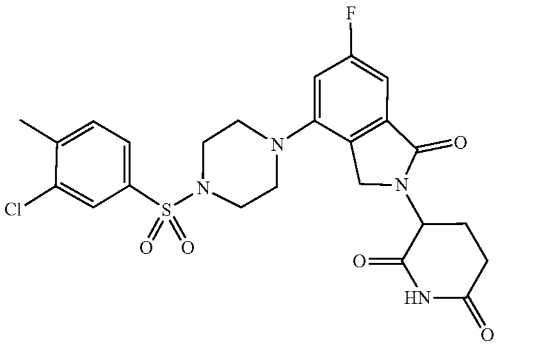

B2090

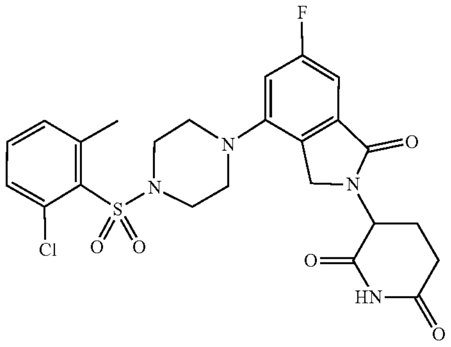

3-(4-(4-((3,5-Difluorobenzyl)sulfonyl)piperazin-1-yl)-6-fluoro-1-oxoisoindolin-2-yl)piperidine-2,6-dione B2091.

3-(6-Fluoro-4-(4-(naphthalen-2-ylsulfonyl)piperazin-1-yl)-1-oxoisoindolin-2-yl)-piperidine-2,6-dione B2092.

B2091

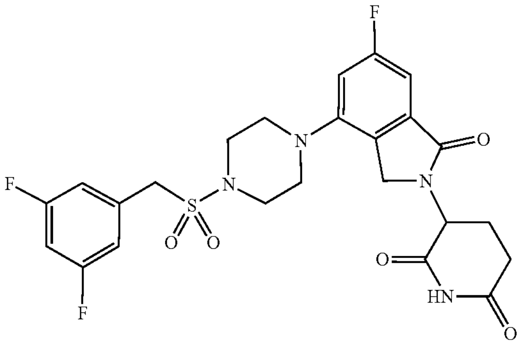

-continued

B2092

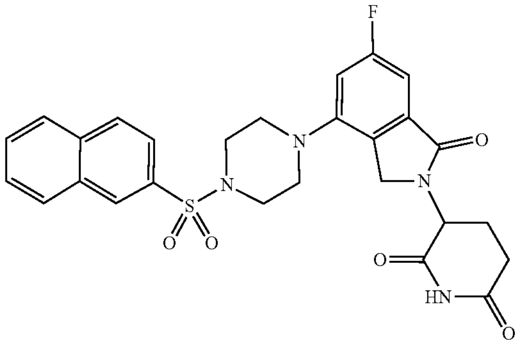

3-(6-Fluoro-1-oxo-4-(4-(quinolin-8-ylsulfonyl)piperazin-1-yl)isoindolin-2-yl)-piperidine-2,6-dione B2093.

3-(6-Fluoro-4-(4-(isoquinolin-5-ylsulfonyl)piperazin-1-yl)-1-oxoisoindolin-2-yl)-piperidine-2,6-dione B2094.

B2093

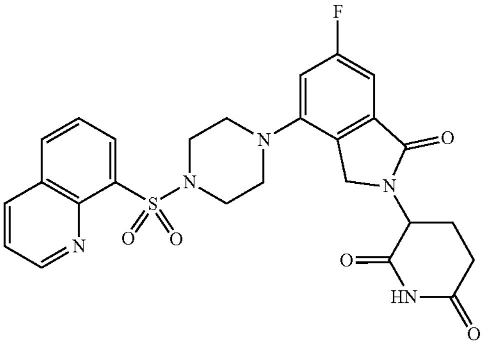

B2094

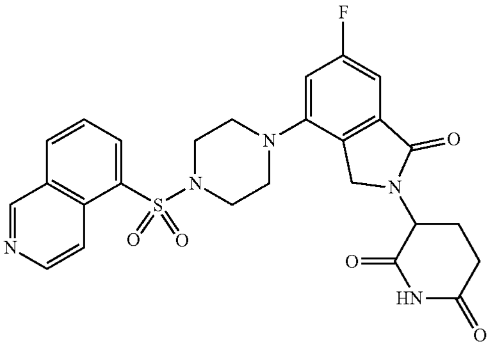

3-(6-Fluoro-1-oxo-4-(4-(quinoxalin-5-ylsulfonyl)piperazin-1-yl)isoindolin-2-yl)-piperidine-2,6-dione B2095.

3-Chloro-4-((4-(2-(2,6-dioxopiperidin-3-yl)-6-fluoro-1-oxoisoindolin-4-yl)-piperazin-1-yl)sulfonyl)benzonitrile B2096.

B2095

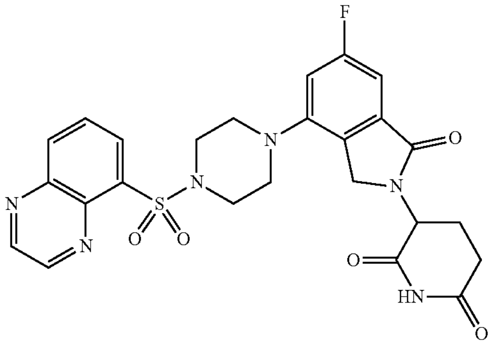

B2096

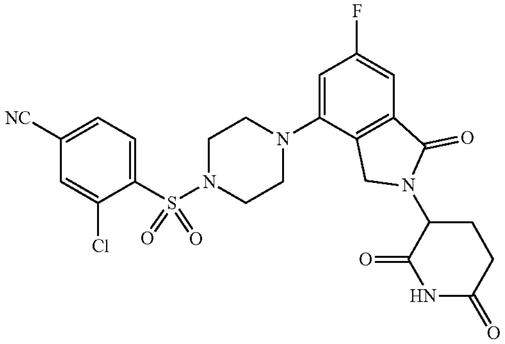

3-(4-(4-(Benzo[d][1,3]dioxol-5-ylsulfonyl)piperazin-1-yl)-6-fluoro-1-oxoisoindolin-2-yl)piperidine-2,6-dione B2097.

3-(4-(4-(Benzo[d]thiazol-6-ylsulfonyl)piperazin-1-yl)-6-fluoro-1-oxoisoindolin-2-yl)piperidine-2,6-dione B2098.

B2097

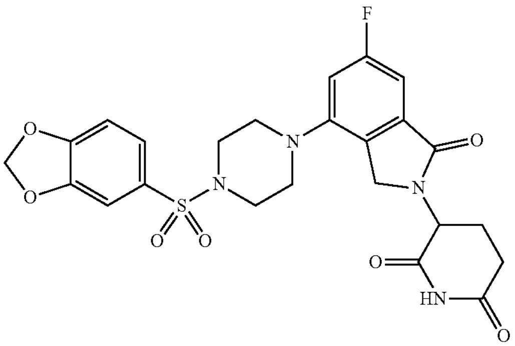

-continued

B2098

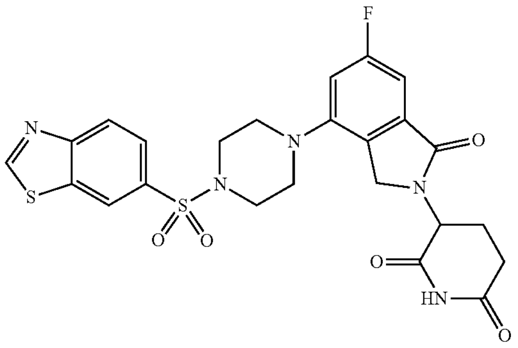

3-(4-(4-((2,4-Dichlorophenyl)sulfonyl)piperazin-1-yl)-6-fluoro-1-oxoisoindolin-2-yl)piperidine-2,6-dione B2099.

3-(4-(4-((2,5-Dichlorophenyl)sulfonyl)piperazin-1-yl)-6-fluoro-1-oxoisoindolin-2-yl)piperidine-2,6-dione B2100.

B2099

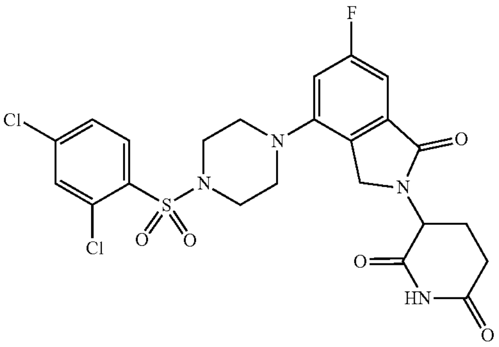

B2100

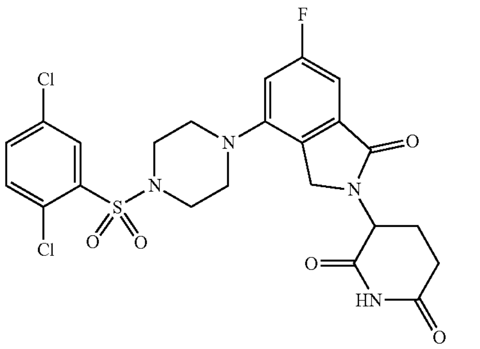

3-(6-Fluoro-1-oxo-5-(1-(5,6,7,8-tetrahydronaphthalene-1-carbonyl)piperidin-4-yl)isoindolin-2-yl)piperidine-2,6-dione C0001.

3-(6-Fluoro-5-(1-(1-methyl-1H-indole-5-carbonyl)piperidin-4-yl)-1-oxoisoindolin-2-yl)piperidine-2,6-dione C0002.

C0001

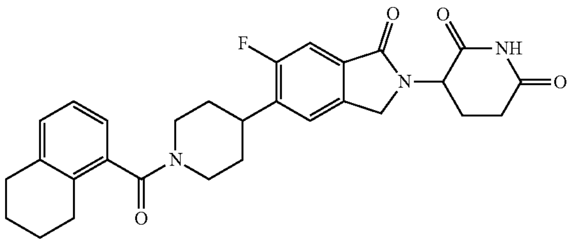

C0002

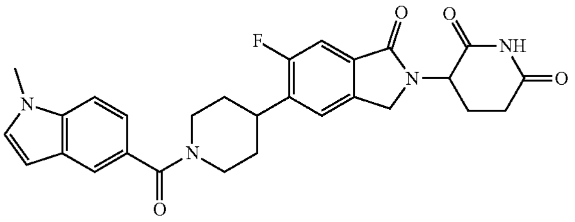

3-(6-Fluoro-1-oxo-5-(1-(quinoxaline-5-carbonyl)piperidin-4-yl)isoindolin-2-yl)-piperidine-2,6-dione C0003.

3-(6-Fluoro-1-oxo-5-(1-(quinazoline-6-carbonyl)piperidin-4-yl)isoindolin-2-yl)-piperidine-2,6-dione C0004.

C0003

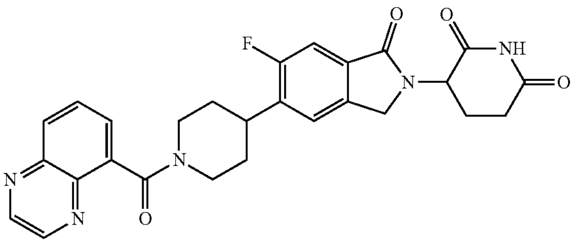

C0004

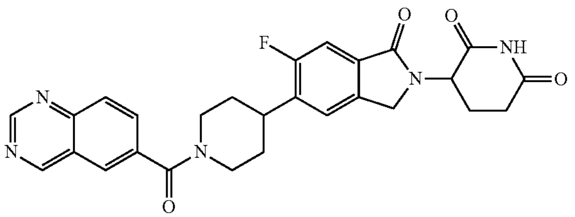

3-(5-(1-(2-(Dimethylamino)benzoyl)piperidin-4-yl)-6-fluoro-1-oxoisoindolin-2-yl)piperidine-2,6-dione C0005.

3-(5-(1-(4-(Dimethylamino)benzoyl)piperidin-4-yl)-6-fluoro-1-oxoisoindolin-2-yl)piperidine-2,6-dione C0006.

C0005

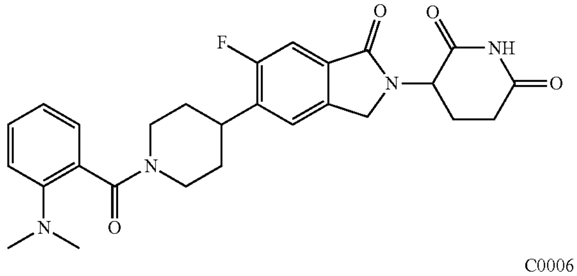

C0006

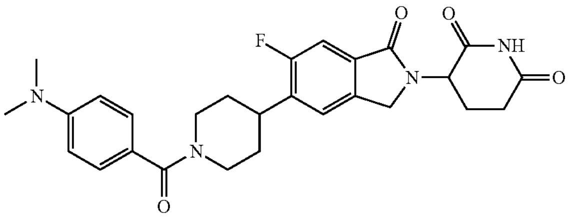

3-(5-(1-(2,3-Dihydrobenzofuran-7-carbonyl)piperidin-4-yl)-6-fluoro-1-oxoisoindolin-2-yl)piperidine-2,6-dione C0007.

3-(5-(1-(Benzo[d]oxazole-5-carbonyl)piperidin-4-yl)-6-fluoro-1-oxoisoindolin-2-yl)piperidine-2,6-dione C0008.

C0007

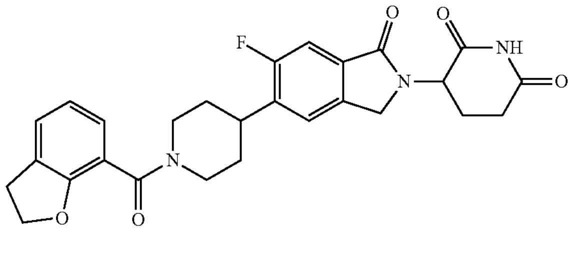

C0008

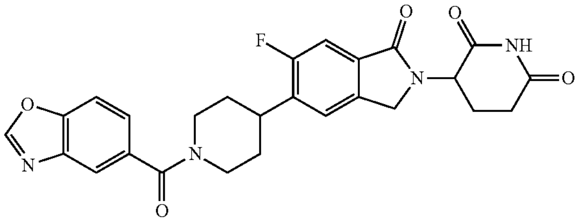

3-(5-(1-(1H-Benzo[d]imidazole-7-carbonyl)piperidin-4-yl)-6-fluoro-1-oxoisoindolin-2-yl)piperidine-2,6-dione C0009.

3-(6-Fluoro-5-(1-(imidazo[1,2-a]pyridine-2-carbonyl)piperidin-4-yl)-1-oxoisoindolin-2-yl)piperidine-2,6-dione C0010.

C0009

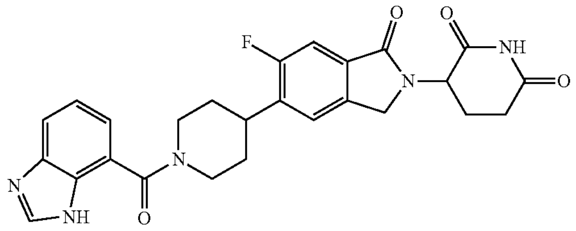

C0010

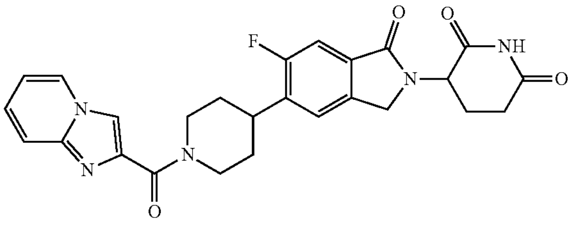

3-(5-(1-(1H-Pyrrolo[3,2-b]pyridine-6-carbonyl)piperidin-4-yl)-6-fluoro-1-oxoisoindolin-2-yl)piperidine-2,6-dione C0011.

3-(6-Fluoro-5-(1-(imidazo[1,2-a]pyridine-3-carbonyl)piperidin-4-yl)-1-oxoisoindolin-2-yl)piperidine-2,6-dione C0012.

C0011

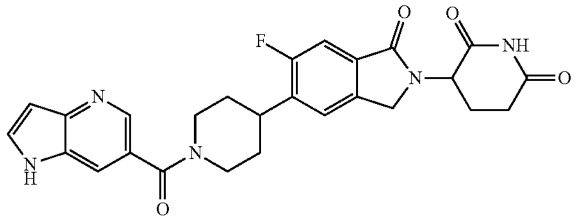

C0012

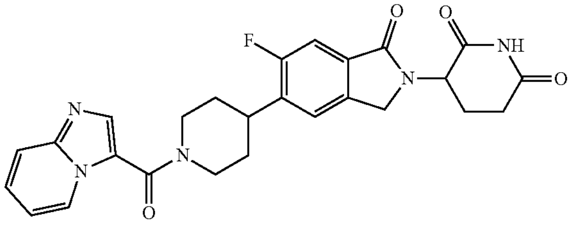

3-(5-(1-(Benzofuran-6-carbonyl)piperidin-4-yl)-6-fluoro-1-oxoisoindolin-2-yl)-piperidine-2,6-dione C0013.

3-(6-Fluoro-1-oxo-5-(1-(2-(piperidin-1-yl)acetyl)piperidin-4-yl)isoindolin-2-yl)-piperidine-2,6-dione C0014.

C0013

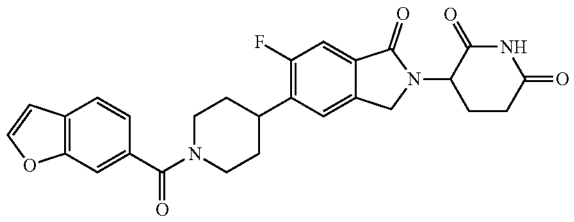

C0014

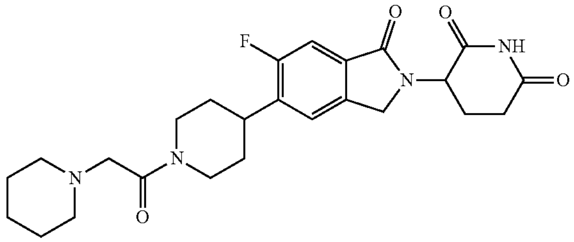

2-(2-(4-(2-(2,6-Dioxopiperidin-3-yl)-6-fluoro-1-oxoisoindolin-5-yl)piperidin-1-yl)-2-oxoethyl)benzonitrile C0015.

3-(2-(4-(2-(2,6-Dioxopiperidin-3-yl)-6-fluoro-1-oxoisoindolin-5-yl)piperidin-1-yl)-2-oxoethyl)benzonitrile C0016.

C0015

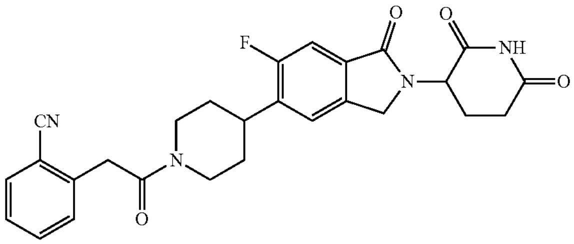

C0016

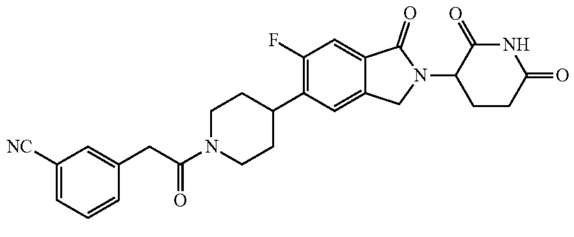

4-(2-(4-(2-(2,6-Dioxopiperidin-3-yl)-6-fluoro-1-oxoisoindolin-5-yl)piperidin-1-yl)-2-oxoethyl)benzonitrile C0017.

3-(5-(1-(1H-Indole-7-carbonyl)piperidin-4-yl)-6-fluoro-1-oxoisoindolin-2-yl)-piperidine-2,6-dione C0018.

C0017

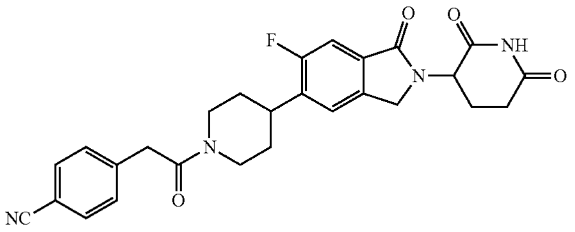

C0018

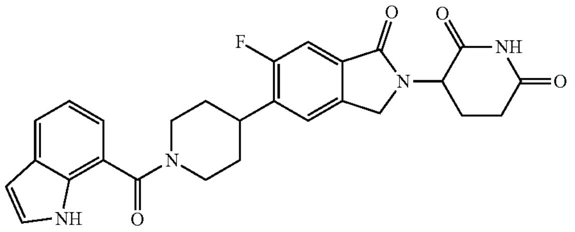

3-(5-(1-(1-Ethylpiperidine-4-carbonyl)piperidin-4-yl)-6-fluoro-1-oxoisoindolin-2-yl)piperidine-2,6-dione C0019.

3-(6-Fluoro-1-oxo-5-(1-(2-(p-tolyl)acetyl)piperidin-4-yl)isoindolin-2-yl)-piperidine-2,6-dione C0020.

C0019

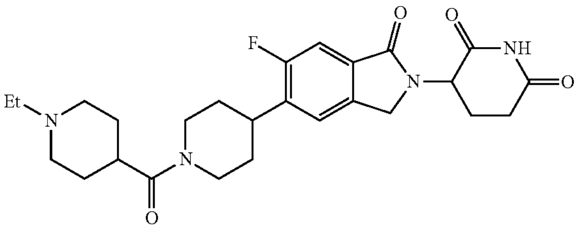

C0020

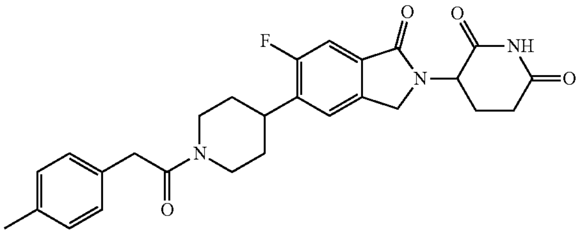

2-(4-(2-(2,6-Dioxopiperidin-3-yl)-6-fluoro-1-oxoisoindolin-5-yl)piperidine-1-carbonyl)benzonitrile C0021.

3-(4-(2-(2,6-Dioxopiperidin-3-yl)-6-fluoro-1-oxoisoindolin-5-yl)piperidine-1-carbonyl)benzonitrile C0022.

C0021

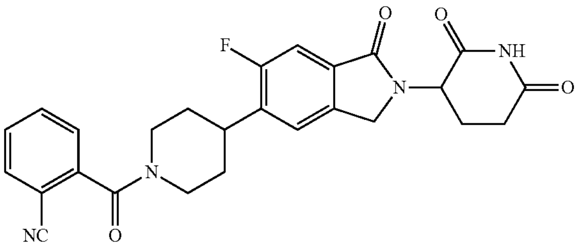

C0022

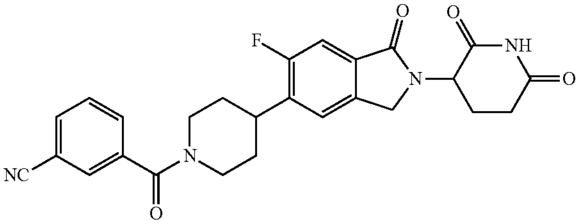

3-(6-Fluoro-5-(1-(4-fluorobenzoyl)piperidin-4-yl)-1-oxoisoindolin-2-yl)-piperidine-2,6-dione C0023.

3-(6-Fluoro-5-(1-(3-fluorobenzoyl)piperidin-4-yl)-1-oxoisoindolin-2-yl)-piperidine-2,6-dione C0024.

C0023

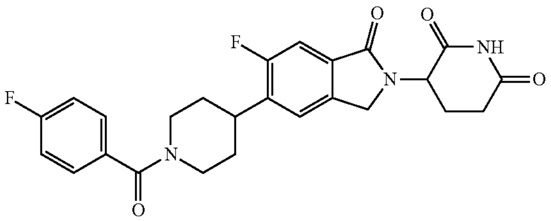

C0024

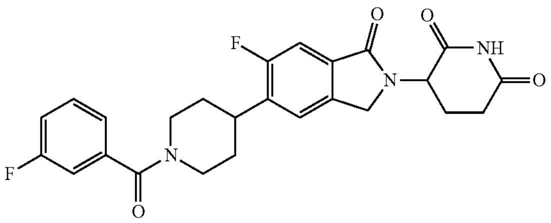

3-(6-Fluoro-5-(1-(2-fluorobenzoyl)piperidin-4-yl)-1-oxoisoindolin-2-yl)-piperidine-2,6-dione C0025.

3-(6-Fluoro-5-(1-(2-methylbenzoyl)piperidin-4-yl)-1-oxoisoindolin-2-yl)-piperidine-2,6-dione C0026.

C0025

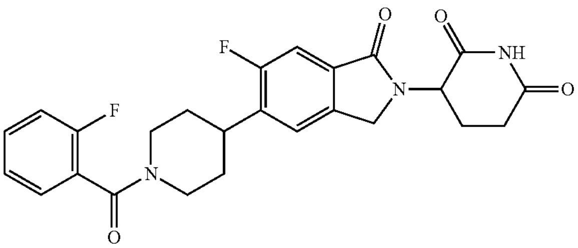

C0026

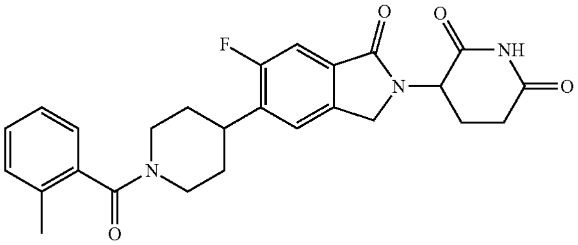

3-(6-Fluoro-5-(1-(3-methylbenzoyl)piperidin-4-yl)-1-oxoisoindolin-2-yl)-piperidine-2,6-dione C0027.

3-(6-Fluoro-5-(1-(4-methylbenzoyl)piperidin-4-yl)-1-oxoisoindolin-2-yl)-piperidine-2,6-dione C0028.

C0027

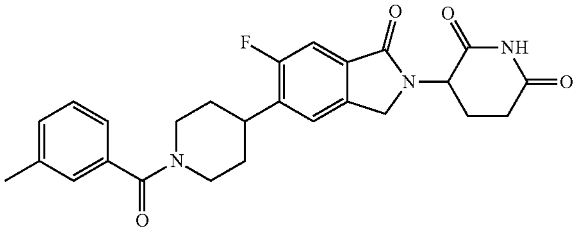

C0028

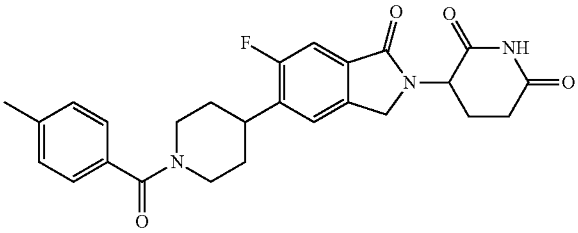

3-(5-(1-(2-Cyclopentylacetyl)piperidin-4-yl)-6-fluoro-1-oxoisoindolin-2-yl)-piperidine-2,6-dione C0029.

3-(5-(1-(Cyclohexanecarbonyl)piperidin-4-yl)-6-fluoro-1-oxoisoindolin-2-yl)-piperidine-2,6-dione C0030.

C0029

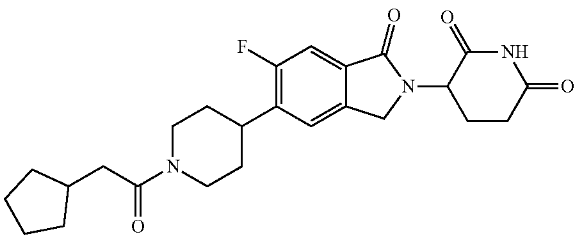

C0030

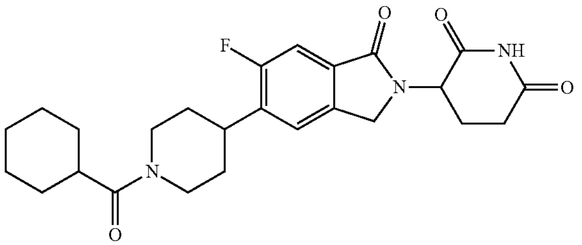

3-(5-(1-(3,3-Dimethylcyclobutane-1-carbonyl)piperidin-4-yl)-6-fluoro-1-oxoisoindolin-2-yl)piperidine-2,6-dione C0031.

3-(6-Fluoro-1-oxo-5-(1-(pyrimidine-5-carbonyl)piperidin-4-yl)isoindolin-2-yl)-piperidine-2,6-dione C0032.

C0031

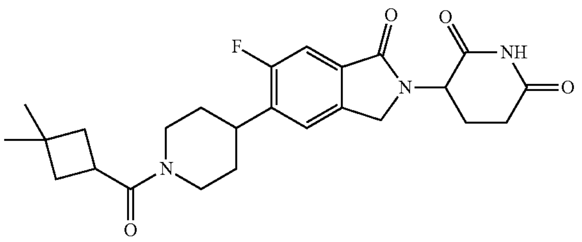

C0032

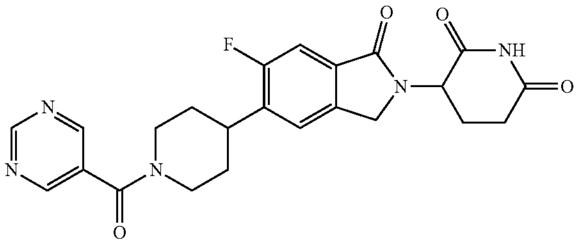

3-(6-Fluoro-1-oxo-5-(1-(pyridazine-4-carbonyl)piperidin-4-yl)isoindolin-2-yl)-piperidine-2,6-dione C0033.

3-(6-Fluoro-1-oxo-5-(1-(pyrimidine-4-carbonyl)piperidin-4-yl)isoindolin-2-yl)-piperidine-2,6-dione C0034.

C0033

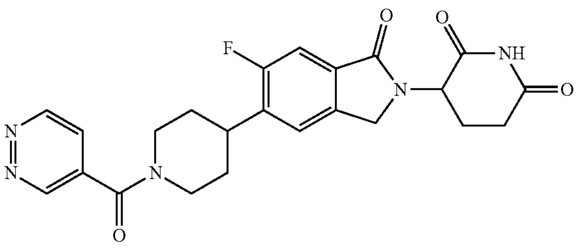

C0034

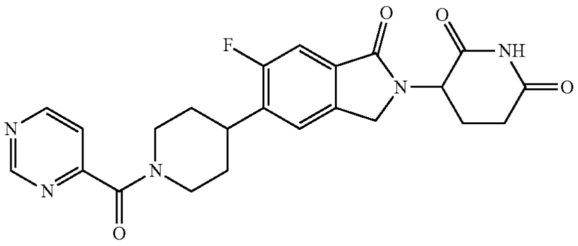

3-(6-Fluoro-1-oxo-5-(1-picolinoylpiperidin-4-yl)isoindolin-2-yl)piperidine-2,6-dione C0035.

3-(6-Fluoro-5-(1-isonicotinoylpiperidin-4-yl)-1-oxoisoindolin-2-yl)piperidine-2,6-dione C0036.

C0035

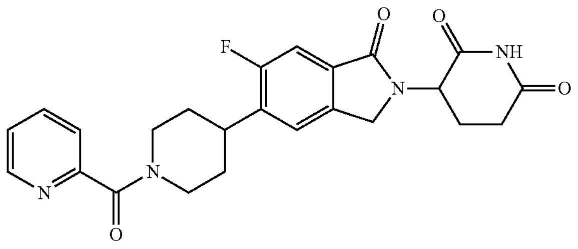

C0036

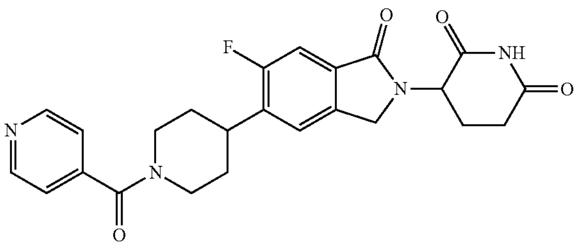

3-(6-Fluoro-5-(1-nicotinoylpiperidin-4-yl)-1-oxoisoindolin-2-yl)piperidine-2,6-dione C0037.

3-(5-(1-Benzoylpiperidin-4-yl)-6-fluoro-1-oxoisoindolin-2-yl)piperidine-2,6-dione C0038.

C0037

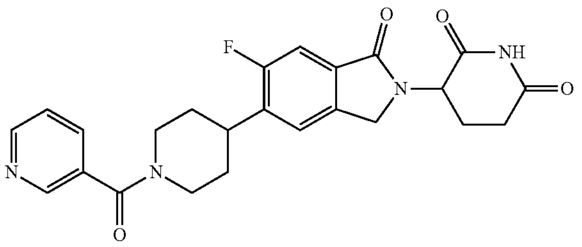

C0038

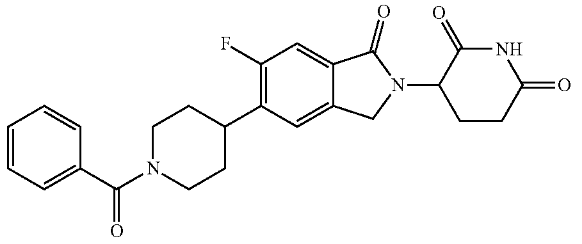

3-(5-(1-(1-Aminocyclobutane-1-carbonyl)piperidin-4-yl)-6-fluoro-1-oxoisoindolin-2-yl)piperidine-2,6-dione C0039.

3-(6-Fluoro-5-(1-(1-methylazetidine-3-carbonyl)piperidin-4-yl)-1-oxoisoindolin-2-yl)piperidine-2,6-dione C0040.

C0039

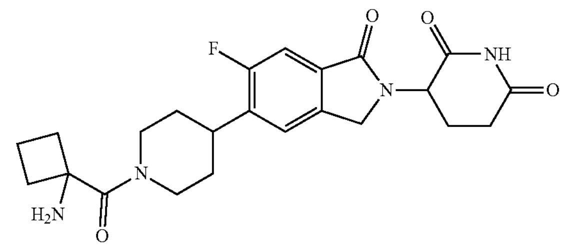

C0040

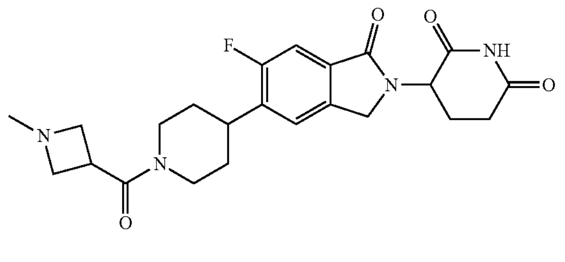

3-(5-(1-(1H-Pyrazole-5-carbonyl)piperidin-4-yl)-6-fluoro-1-oxoisoindolin-2-yl)-piperidine-2,6-dione C0041.

3-(5-(1-(1H-Imidazole-5-carbonyl)piperidin-4-yl)-6-fluoro-1-oxoisoindolin-2-yl)-piperidine-2,6-dione C0042.

C0041

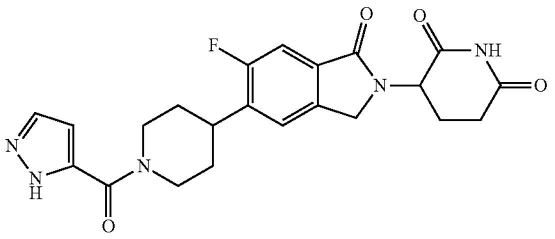

C0042

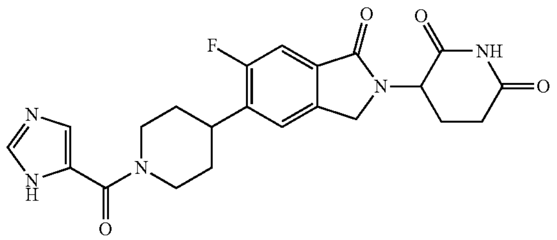

3-(6-Fluoro-5-(1-(furan-3-carbonyl)piperidin-4-yl)-1-oxoisoindolin-2-yl)-piperidine-2,6-dione C0043.

3-(6-Fluoro-5-(1-(furan-2-carbonyl)piperidin-4-yl)-1-oxoisoindolin-2-yl)-piperidine-2,6-dione C0044.

C0043

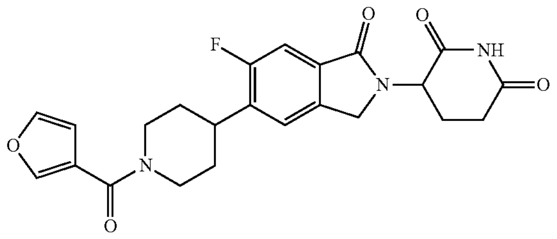

C0044

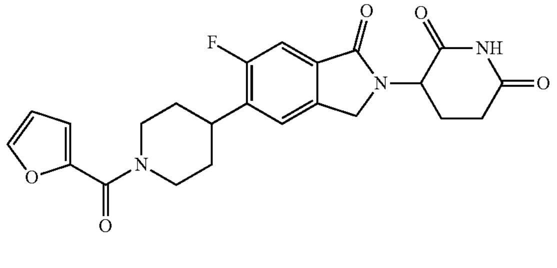

3-(6-Fluoro-5-(1-(1-fluorocyclopropane-1-carbonyl)piperidin-4-yl)-1-oxoisoindolin-2-yl)piperidine-2,6-dione C0045.

3-(6-Fluoro-5-(1-(3-methylbutanoyl)piperidin-4-yl)-1-oxoisoindolin-2-yl)piperidine-2,6-dione C0046.

C0045

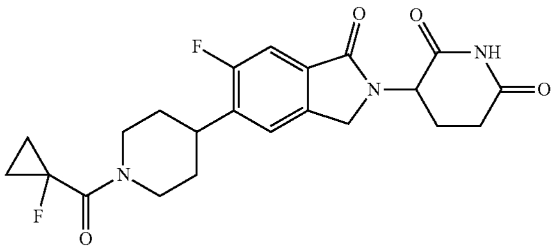

C0046

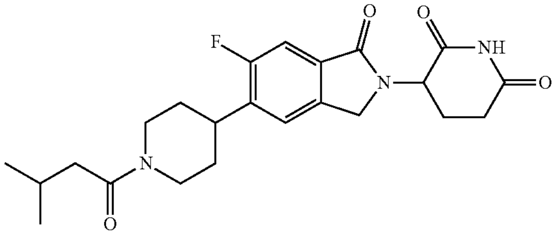

3-(6-Fluoro-5-(1-(oxetane-3-carbonyl)piperidin-4-yl)-1-oxoisoindolin-2-yl)-piperidine-2,6-dione C0047.

3-(5-(1-(Cyclobutanecarbonyl)piperidin-4-yl)-6-fluoro-1-oxoisoindolin-2-yl)-piperidine-2,6-dione C0048.

C0047

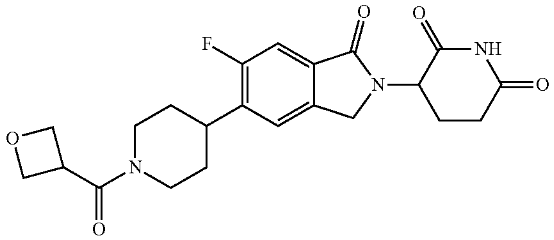

C0048

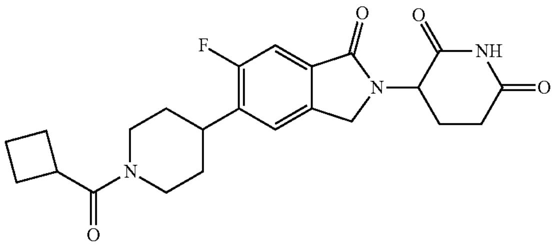

3-(6-Fluoro-5-(1-(methylglycyl)piperidin-4-yl)-1-oxoisoindolin-2-yl)piperidine-2,6-dione C0049.

3-(5-(1-(Cyclopropanecarbonyl)piperidin-4-yl)-6-fluoro-1-oxoisoindolin-2-yl)-piperidine-2,6-dione C0050.

C0049

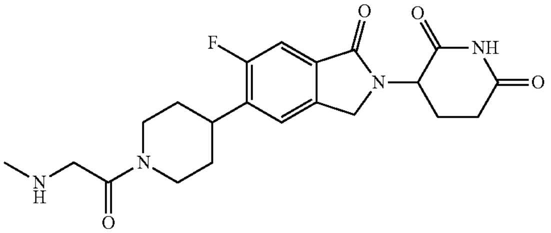

C0050

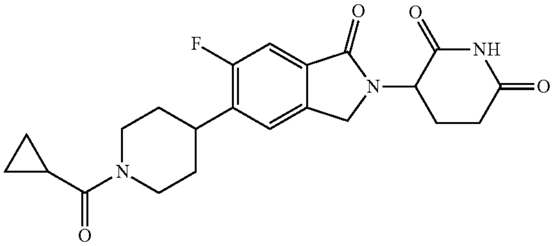

3-(6-Fluoro-5-(1-(3-methoxybenzyl)piperidin-4-yl)-1-oxoisoindolin-2-yl)-piperidine-2,6-dione C1001.

3-(6-Fluoro-5-(1-(2-hydroxy-4-methylbenzyl)piperidin-4-yl)-1-oxoisoindolin-2-yl)piperidine-2,6-dione C1002.

C1001

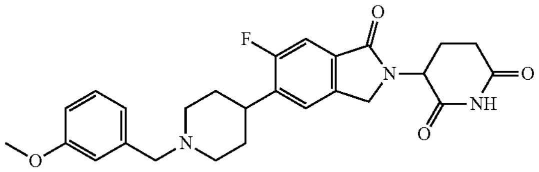

C1002

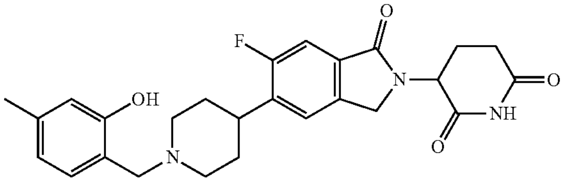

3-(6-Fluoro-5-(1-(4-(hydroxymethyl)benzyl)piperidin-4-yl)-1-oxoisoindolin-2-yl)piperidine-2,6-dione C1003.

3-(5-(1-((2,6-Dimethylpyridin-4-yl)methyl)piperidin-4-yl)-6-fluoro-1-oxoiso-indolin-2-yl)piperidine-2,6-dione C1004.

C1003

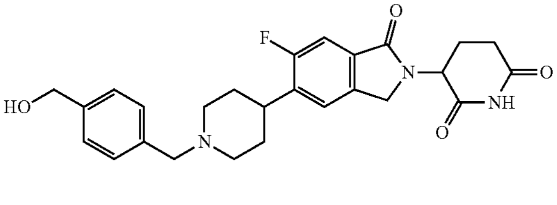

-continued

C1004

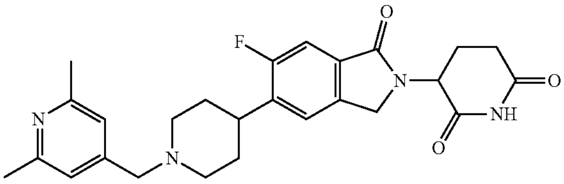

3-(6-Fluoro-5-(1-(2-(methylamino)benzyl)piperidin-4-yl)-1-oxoisoindolin-2-yl)-piperidine-2,6-dione C1005.

3-(5-(1-(2,6-Dimethylbenzyl)piperidin-4-yl)-6-fluoro-1-oxoisoindolin-2-yl)-piperidine-2,6-dione C1006.

C1005

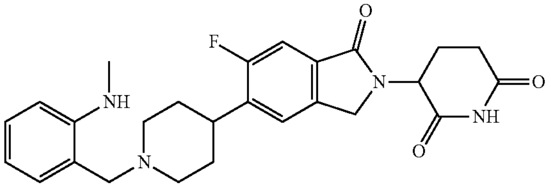

C1006

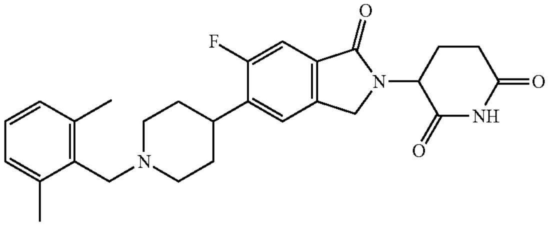

3-(5-(1-(2,4-Dimethylbenzyl)piperidin-4-yl)-6-fluoro-1-oxoisoindolin-2-yl)-piperidine-2,6-dione C1007.

3-(5-(1-(2,5-Dimethylbenzyl)piperidin-4-yl)-6-fluoro-1-oxoisoindolin-2-yl)-piperidine-2,6-dione C1008.

C1007

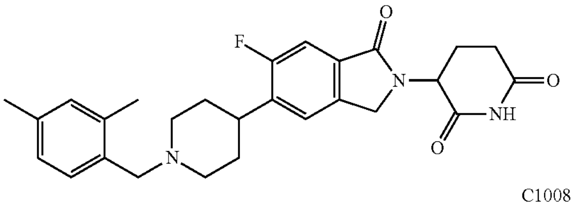

C1008

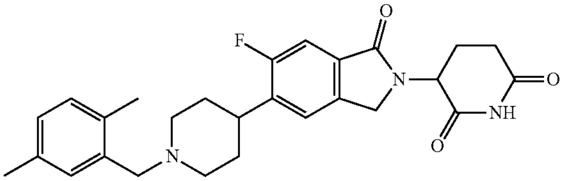

3-(6-Fluoro-5-(1-(2-methylphenethyl)piperidin-4-yl)-1-oxoisoindolin-2-yl)-piperidine-2,6-dione C1009.

3-(5-(1-(3,5-Dimethylbenzyl)piperidin-4-yl)-6-fluoro-1-oxoisoindolin-2-yl)-piperidine-2,6-dione C1010.

C1009

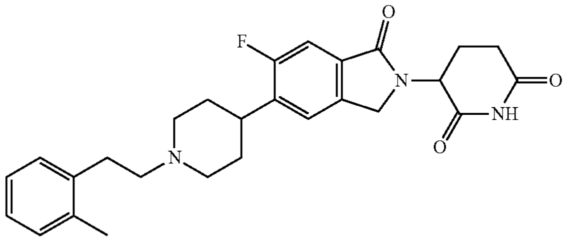

C1010

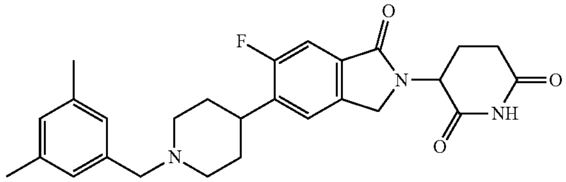

3-(6-Fluoro-1-oxo-5-(1-(pyridin-3-ylmethyl)piperidin-4-yl)isoindolin-2-yl)-piperidine-2,6-dione C1011.

3-(6-Fluoro-1-oxo-5-(1-(3-phenylpropyl)piperidin-4-yl)isoindolin-2-yl)-piperidine-2,6-dione C1012.

C1011

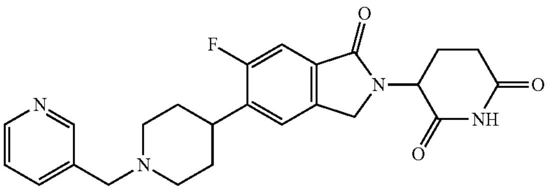

C1012

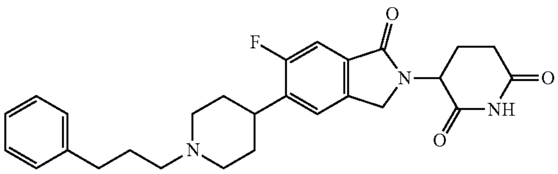

4-((4-(2-(2,6-Dioxopiperidin-3-yl)-6-fluoro-1-oxoisoindolin-5-yl)piperidin-1-yl)-methyl)-1-methyl-1H-pyrrole-2-carbonitrile C1013.

3-(5-(1-(Bicyclo[4.2.0]octa-1(6),2,4-trien-3-ylmethyl)piperidin-4-yl)-6-fluoro-1-oxoisoindolin-2-yl)piperidine-2,6-dione C1014.

C1013

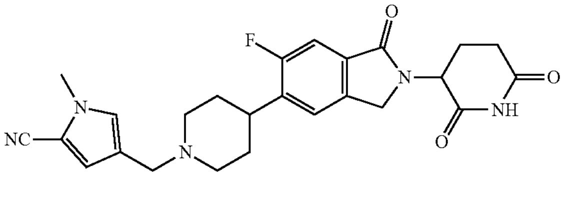

-continued

C1014

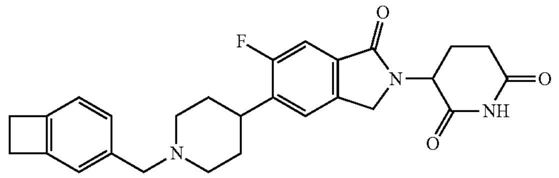

5-((4-(2-(2,6-Dioxopiperidin-3-yl)-6-fluoro-1-oxoisoindolin-5-yl)piperidin-1-yl)-methyl)picolinonitrile C1015.

5-((4-(2-(2,6-Dioxopiperidin-3-yl)-6-fluoro-1-oxoisoindolin-5-yl)piperidin-1-yl)-methyl)nicotinonitrile C1016.

C1015

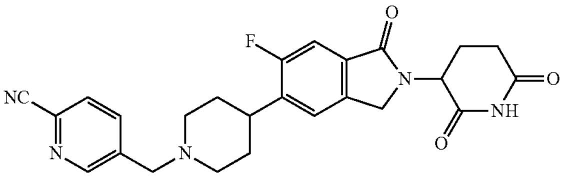

C1016

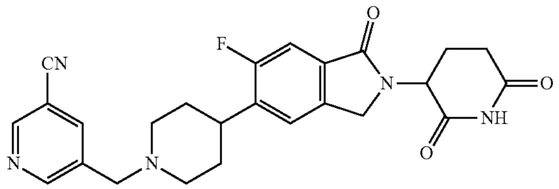

6-((4-(2-(2,6-Dioxopiperidin-3-yl)-6-fluoro-1-oxoisoindolin-5-yl)piperidin-1-yl)-methyl)picolinonitrile C1017.

2-((4-(2-(2,6-Dioxopiperidin-3-yl)-6-fluoro-1-oxoisoindolin-5-yl)piperidin-1-yl)-methyl)isonicotinonitrile C1018.

C1017

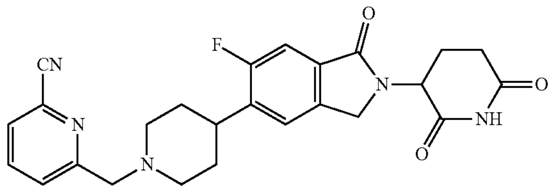

C1018

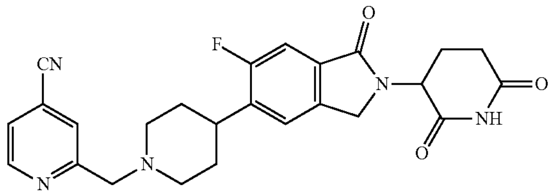

3-((4-(2-(2,6-Dioxopiperidin-3-yl)-6-fluoro-1-oxoisoindolin-5-yl)piperidin-1-yl)-methyl)benzonitrile C1019.

3-(5-(1-((5-Ethynylpyridin-2-yl)methyl)piperidin-4-yl)-6-fluoro-1-oxoisoindolin-2-yl)piperidine-2,6-dione C1020.

C1019

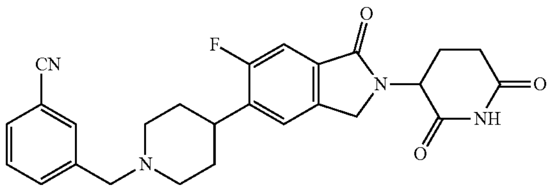

C1020

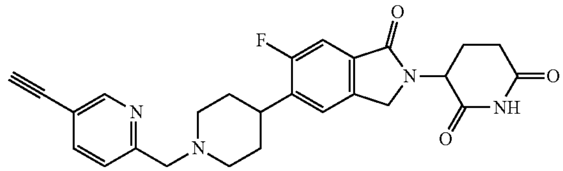

4-((4-(2-(2,6-Dioxopiperidin-3-yl)-6-fluoro-1-oxoisoindolin-5-yl)piperidin-1-yl)-methyl)benzonitrile C1021.

3-(6-Fluoro-5-(1-(3-hydroxy-2,2-dimethylpropyl)piperidin-4-yl)-1-oxoisoindolin-2-yl)piperidine-2,6-dione C1022.

C1021

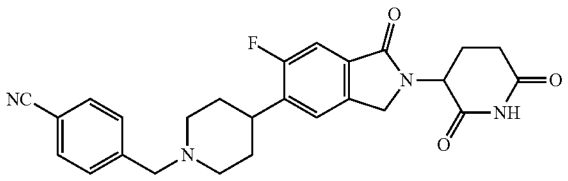

C1022

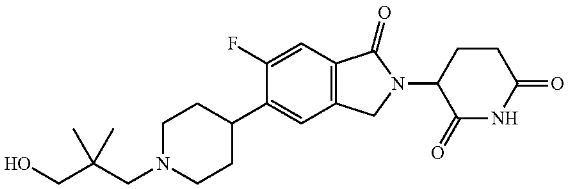

2-((4-(2-(2,6-Dioxopiperidin-3-yl)-6-fluoro-1-oxoisoindolin-5-yl)piperidin-1-yl)-methyl)benzonitrile C1023.

3-(5-(1-(4-Ethynylbenzyl)piperidin-4-yl)-6-fluoro-1-oxoisoindolin-2-yl)-piperidine-2,6-dione C1024.

C1023

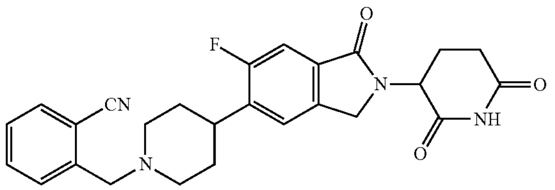

C1024

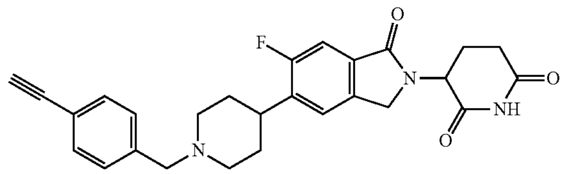

3-(5-(1-(2-Ethynylbenzyl)piperidin-4-yl)-6-fluoro-1-oxoisoindolin-2-yl)-piperidine-2,6-dione C1025.

3-(5-(1-(3-Ethynylbenzyl)piperidin-4-yl)-6-fluoro-1-oxoisoindolin-2-yl)-piperidine-2,6-dione C1026.

C1025

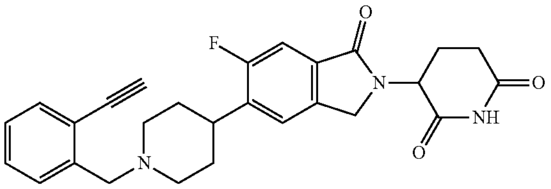

C1026

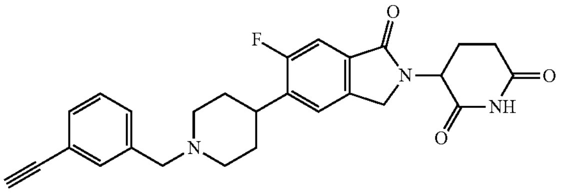

3-(6-Fluoro-5-(1-((5-methylthiazol-2-yl)methyl)piperidin-4-yl)-1-oxoisoindolin-2-yl)piperidine-2,6-dione C1027.

3-(6-Fluoro-5-(1-((2-methylthiazol-5-yl)methyl)piperidin-4-yl)-1-oxoisoindolin-2-yl)piperidine-2,6-dione C1028.

C1027

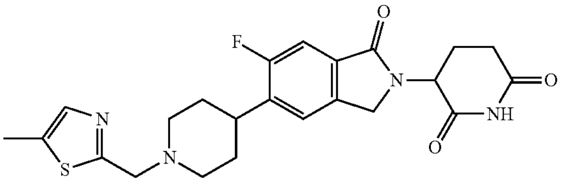

C1028

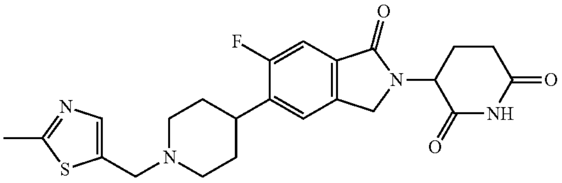

3-(6-Fluoro-5-(1-((4-methylthiazol-5-yl)methyl)piperidin-4-yl)-1-oxoisoindolin-2-yl)piperidine-2,6-dione C1029.

3-(5-(1-(2-Cyclohexylethyl)piperidin-4-yl)-6-fluoro-1-oxoisoindolin-2-yl)-piperidine-2,6-dione C1030.

C1029

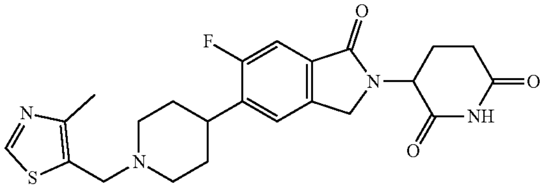

-continued

C1030

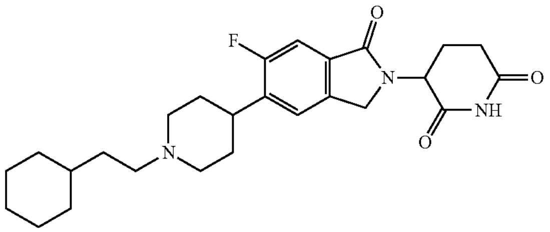

3-(6-Fluoro-5-(1-((3-methylthiophen-2-yl)methyl)piperidin-4-yl)-1-oxoisoindolin-2-yl)piperidine-2,6-dione C1031.

3-(6-Fluoro-5-(1-((3-methoxyfuran-2-yl)methyl)piperidin-4-yl)-1-oxoisoindolin-2-yl)piperidine-2,6-dione C1032.

C1031

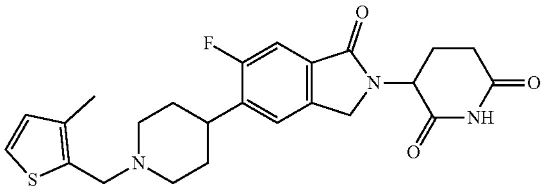

C1032

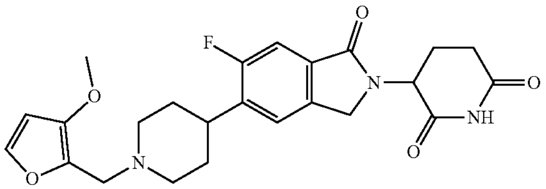

3-(6-Fluoro-5-(1-((3-methyloxetan-3-yl)methyl)piperidin-4-yl)-1-oxoisoindolin-2-yl)piperidine-2,6-dione C1033.

3-(6-Fluoro-5-(1-((5-(hydroxymethyl)furan-2-yl)methyl)piperidin-4-yl)-1-oxo-isoindolin-2-yl)piperidine-2,6-dione C1034.

C1033

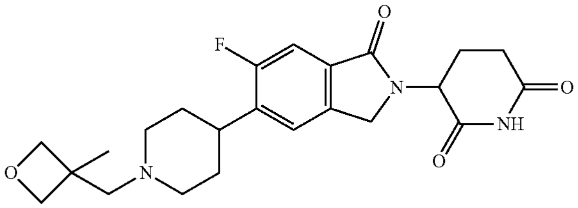

C1034

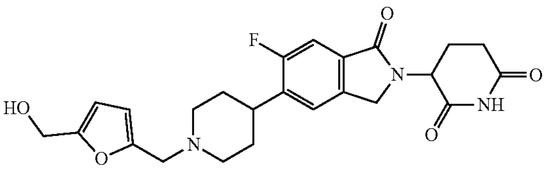

3-(5-(1-((5-Amino-1-methyl-1H-pyrazol-4-yl)methyl)piperidin-4-yl)-6-fluoro-1-oxoisoindolin-2-yl)piperidine-2,6-dione C1035.

3-(6-Fluoro-5-(1-((5-(hydroxymethyl)-1H-pyrrol-2-yl)methyl)piperidin-4-yl)-1-oxoisoindolin-2-yl)piperidine-2,6-dione C1036.

C1035

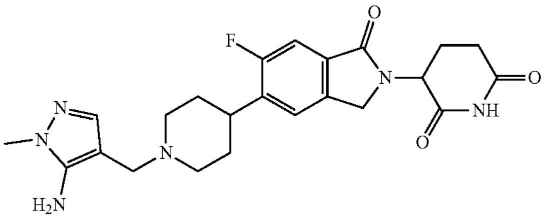

C1036

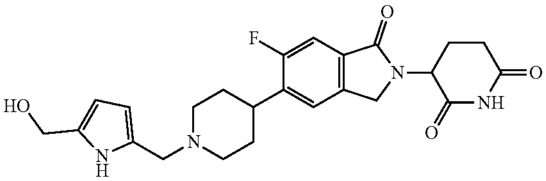

3-(6-Fluoro-5-(1-((6-fluoropyridin-3-yl)methyl)piperidin-4-yl)-1-oxoisoindolin-2-yl)piperidine-2,6-dione C1037.

3-(6-Fluoro-5-(1-((3-fluoropyridin-4-yl)methyl)piperidin-4-yl)-1-oxoisoindolin-2-yl)piperidine-2,6-dione C1038.

C1037

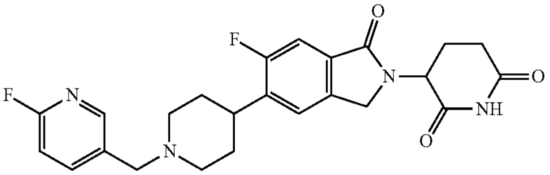

C1038

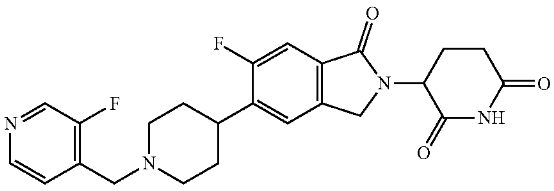

3-(6-Fluoro-5-(1-((5-fluoropyridin-2-yl)methyl)piperidin-4-yl)-1-oxoisoindolin-2-yl)piperidine-2,6-dione C1039.

3-(6-Fluoro-5-(1-((5-fluoropyridin-3-yl)methyl)piperidin-4-yl)-1-oxoisoindolin-2-yl)piperidine-2,6-dione C1040.

C1039

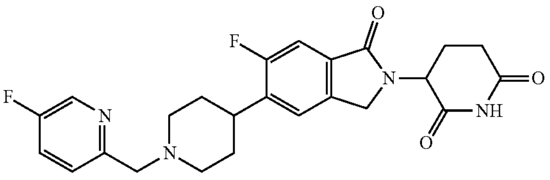

-continued

C1040

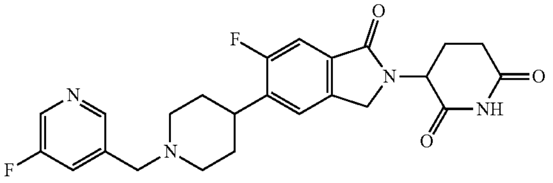

3-(6-Fluoro-5-(1-((4-fluoropyridin-2-yl)methyl)piperidin-4-yl)-1-oxoisoindolin-2-yl)piperidine-2,6-dione C1041.

3-(6-Fluoro-5-(1-((6-fluoropyridin-2-yl)methyl)piperidin-4-yl)-1-oxoisoindolin-2-yl)piperidine-2,6-dione C1042.

C1041

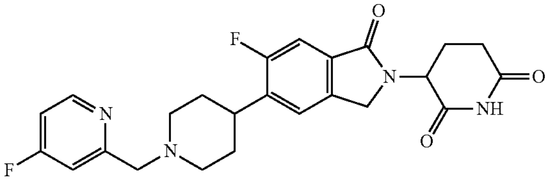

C1042

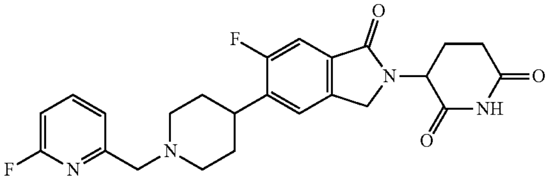

3-(5-(1-((2,5-Dimethyl-1H-imidazol-4-yl)methyl)piperidin-4-yl)-6-fluoro-1-oxoisoindolin-2-yl)piperidine-2,6-dione C1043.

3-(6-Fluoro-5-(1-(oxazol-2-ylmethyl)piperidin-4-yl)-1-oxoisoindolin-2-yl)-piperidine-2,6-dione C1044.

C1043

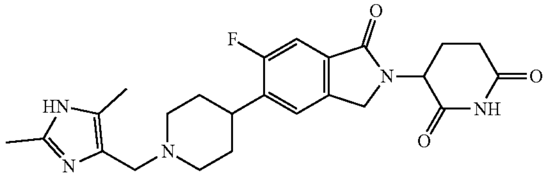

C1044

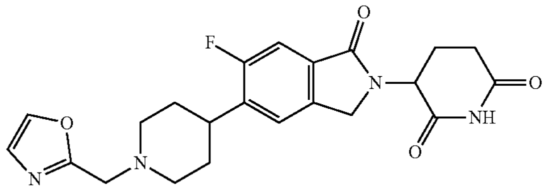

3-(5-(1-((1,4-Dimethyl-1H-pyrazol-5-yl)methyl)piperidin-4-yl)-6-fluoro-1-oxoisoindolin-2-yl)piperidine-2,6-dione C1045.

3-(6-Fluoro-5-(1-(4-fluorobenzyl)piperidin-4-yl)-1-oxoisoindolin-2-yl)piperidine-2,6-dione C1046.

C1045

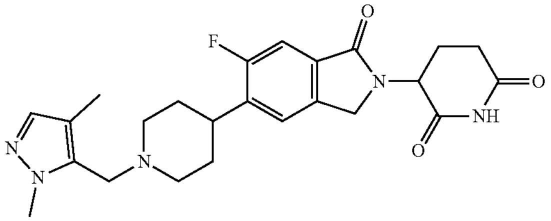

C1046

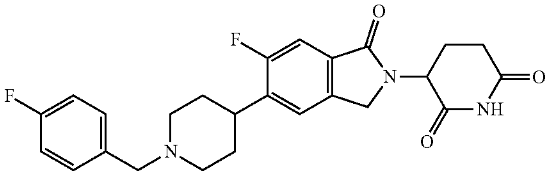

3-(6-Fluoro-5-(1-(3-fluorobenzyl)piperidin-4-yl)-1-oxoisoindolin-2-yl)piperidine-2,6-dione C1047.

3-(6-Fluoro-5-(1-((2-hydroxypyridin-3-yl)methyl)piperidin-4-yl)-1-oxoisoindolin-2-yl)piperidine-2,6-dione C1048.

C1047

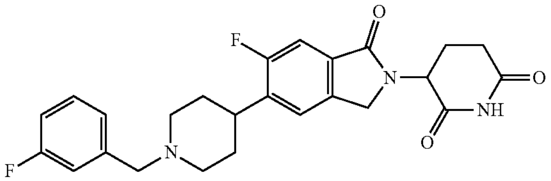

C1048

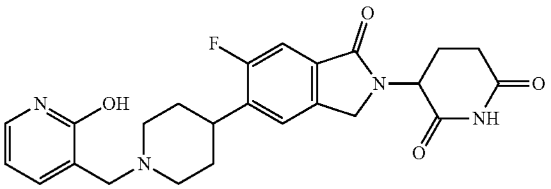

3-(6-Fluoro-5-(1-((5-methylpyrazin-2-yl)methyl)piperidin-4-yl)-1-oxoisoindolin-2-yl)piperidine-2,6-dione C1049.

3-(6-Fluoro-5-(1-((3-methylpyrazin-2-yl)methyl)piperidin-4-yl)-1-oxoisoindolin-2-yl)piperidine-2,6-dione C1050.

C1049

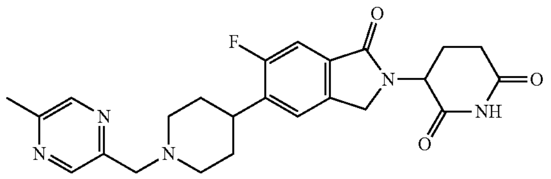

-continued

C1050

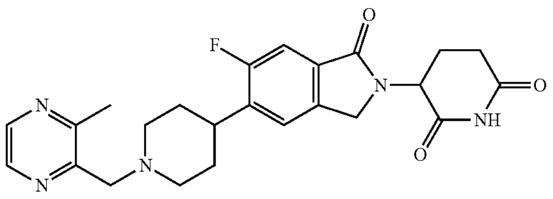

3-(6-Fluoro-5-(1-((2-methylpyrimidin-4-yl)methyl)piperidin-4-yl)-1-oxoisoindolin-2-yl)piperidine-2,6-dione C1051.

3-(6-Fluoro-5-(1-((2-methylpyrimidin-5-yl)methyl)piperidin-4-yl)-1-oxoisoindolin-2-yl)piperidine-2,6-dione C1052.

C1051

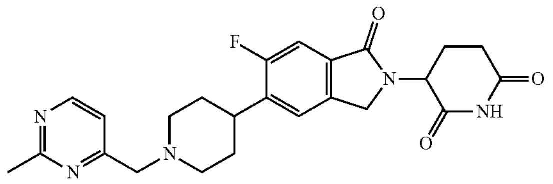

C1052

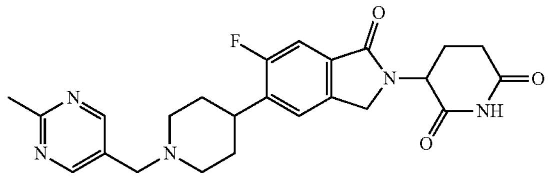

3-(5-(1-((2-Aminopyridin-3-yl)methyl)piperidin-4-yl)-6-fluoro-1-oxoisoindolin-2-yl)piperidine-2,6-dione C1053.

3-(5-(1-((3-Aminopyridin-4-yl)methyl)piperidin-4-yl)-6-fluoro-1-oxoisoindolin-2-yl)piperidine-2,6-dione C1054.

C1053

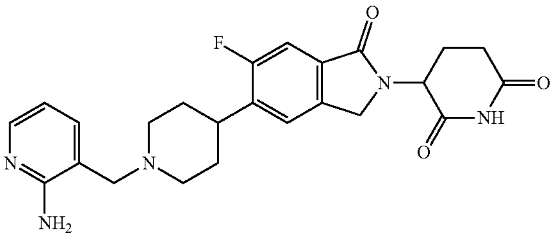

C1054

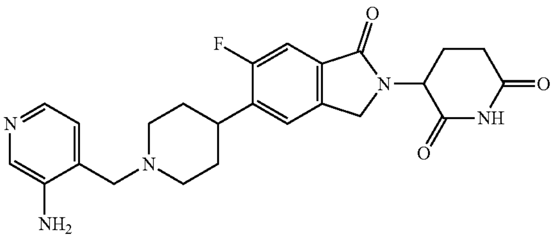

3-(5-(1-((1H-Pyrazol-5-yl)methyl)piperidin-4-yl)-6-fluoro-1-oxoisoindolin-2-yl)-piperidine-2,6-dione C1055.

3-(6-Fluoro-5-(1-(3-hydroxybenzyl)piperidin-4-yl)-1-oxoisoindolin-2-yl)-piperidine-2,6-dione C1056.

C1055

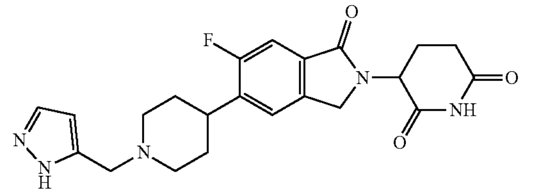

C1056

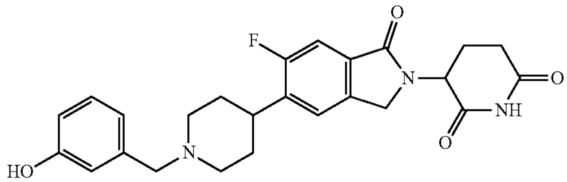

3-(6-Fluoro-5-(1-(4-hydroxybenzyl)piperidin-4-yl)-1-oxoisoindolin-2-yl)-piperidine-2,6-dione C1057.

3-(6-Fluoro-5-(1-((4-methylpyridin-2-yl)methyl)piperidin-4-yl)-1-oxoisoindolin-2-yl)piperidine-2,6-dione C1058.

C1057

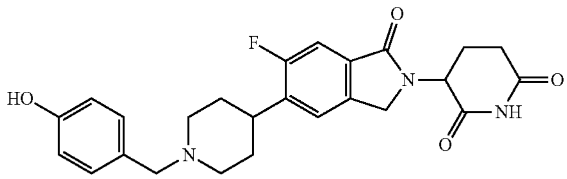

C1058

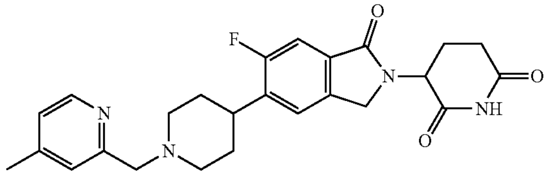

3-(6-Fluoro-5-(1-((3-methylpyridin-2-yl)methyl)piperidin-4-yl)-1-oxoisoindolin-2-yl)piperidine-2,6-dione C1059.

3-(6-Fluoro-5-(1-((2-methylpyridin-3-yl)methyl)piperidin-4-yl)-1-oxoisoindolin-2-yl)piperidine-2,6-dione C1060.

C1059

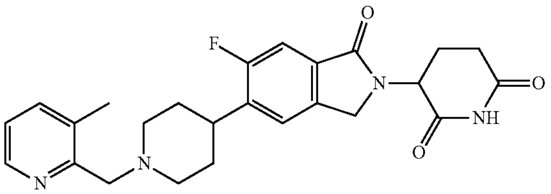

-continued

C1060

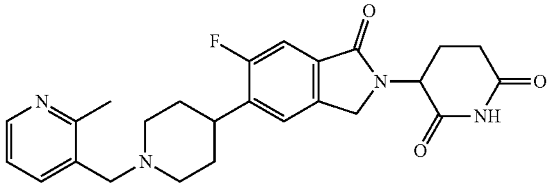

3-(6-Fluoro-5-(1-((2-methylpyridin-4-yl)methyl)piperidin-4-yl)-1-oxoisoindolin-2-yl)piperidine-2,6-dione C1061.

3-(6-Fluoro-5-(1-((5-methylpyridin-2-yl)methyl)piperidin-4-yl)-1-oxoisoindolin-2-yl)piperidine-2,6-dione C1062.

C1061

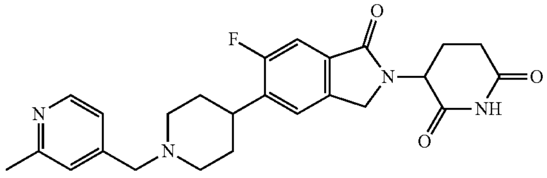

C1062

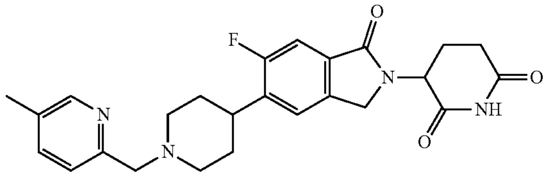

3-(6-Fluoro-5-(1-((6-methylpyridin-2-yl)methyl)piperidin-4-yl)-1-oxoisoindolin-2-yl)piperidine-2,6-dione C1063.

3-(6-Fluoro-5-(1-((4-methylpyridin-3-yl)methyl)piperidin-4-yl)-1-oxoisoindolin-2-yl)piperidine-2,6-dione C1064.

C1063

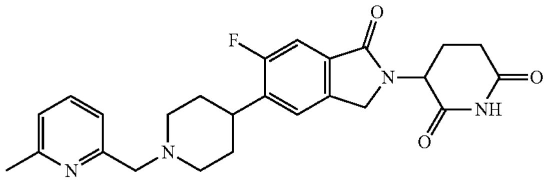

C1064

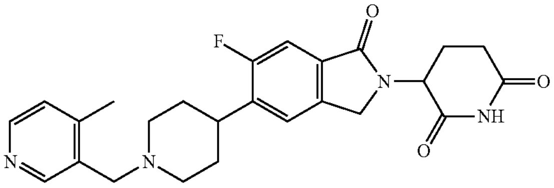

3-(6-Fluoro-5-(1-((5-methylpyridin-3-yl)methyl)piperidin-4-yl)-1-oxoisoindolin-2-yl)piperidine-2,6-dione C1065.

3-(5-(1-((1H-Imidazol-5-yl)methyl)piperidin-4-yl)-6-fluoro-1-oxoisoindolin-2-yl)piperidine-2,6-dione C1066.

C1065

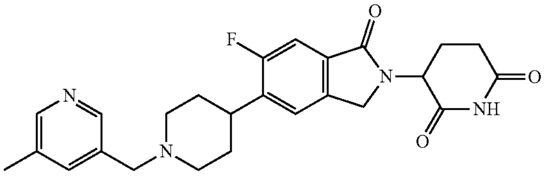

C1066

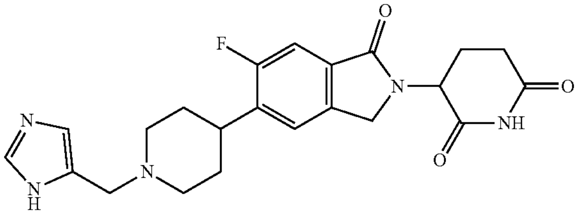

3-(5-(1-(4-Aminobenzyl)piperidin-4-yl)-6-fluoro-1-oxoisoindolin-2-yl)piperidine-2,6-dione C1067.

3-(5-(1-(2-Aminobenzyl)piperidin-4-yl)-6-fluoro-1-oxoisoindolin-2-yl)piperidine-2,6-dione C1068.

C1067

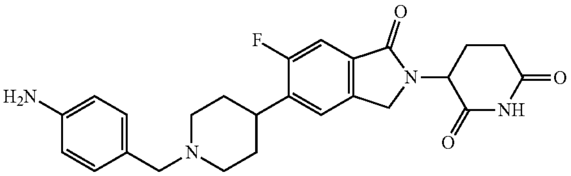

-continued

C1068

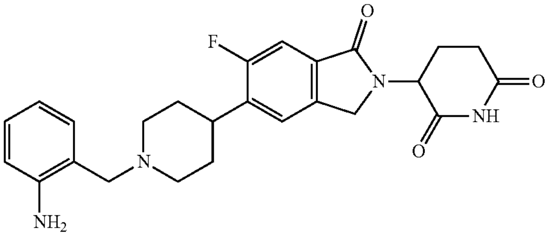

3-(6-Fluoro-5-(1-(4-methylbenzyl)piperidin-4-yl)-1-oxoisoindolin-2-yl)-piperidine-2,6-dione C1069.

3-(6-Fluoro-5-(1-(2-methylbenzyl)piperidin-4-yl)-1-oxoisoindolin-2-yl)-piperidine-2,6-dione C1070.

C1069

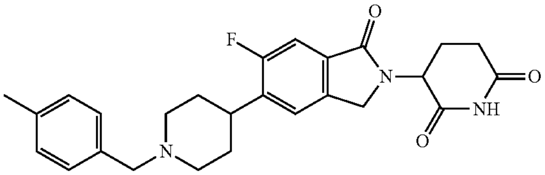

C1070

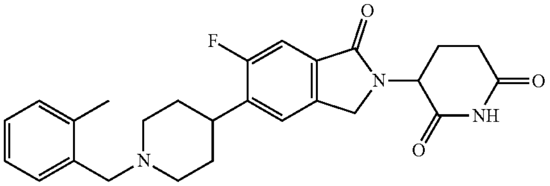

4-(4-Bromo-3-((4-(2-(2,6-dioxopiperidin-3-yl)-6-fluoro-1-oxoisoindolin-5-yl)piperidin-1-yl)methyl)phenoxy)benzonitrile C1071.

C1071

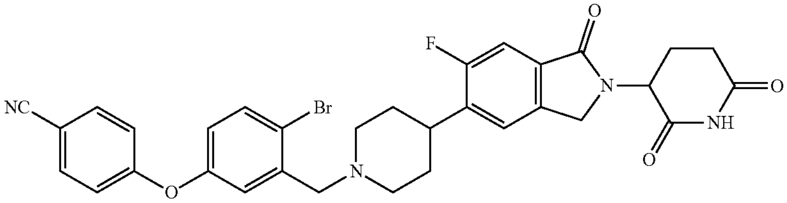

3-(6-Fluoro-1-oxo-5-(1-phenethylpiperidin-4-yl)isoindolin-2-yl)piperidine-2,6-dione C1072.

C1072

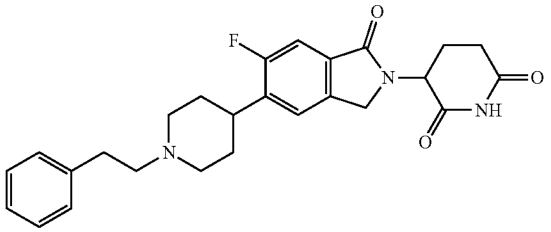

3-(5-(1-(3-Bromo-4-(4-methylpiperazin-1-yl)benzyl)piperidin-4-yl)-6-fluoro-1-oxoisoindolin-2-yl)piperidine-2,6-dione C1073.

C1073

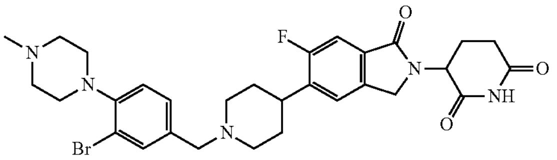

Tert-butyl 4-(4-((4-(2-(2,6-dioxopiperidin-3-yl)-6-fluoro-1-oxoisoindolin-5-yl)-piperidin-1-yl)methyl)-1H-1,2,3-triazol-1-yl)piperidine-1-carboxylate C1074.

C1074

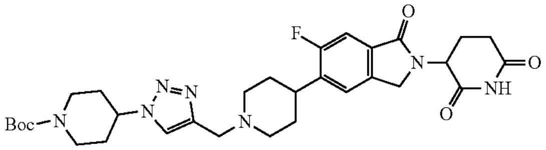

3-(5-(1-(3-Bromo-4-morpholinobenzyl)piperidin-4-yl)-6-fluoro-1-oxoisoindolin-2-yl)piperidine-2,6-dione C1075.

C1075

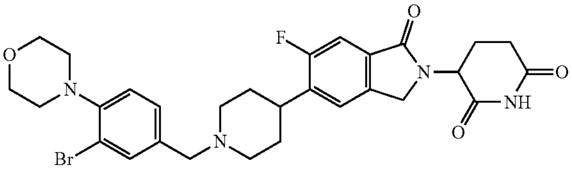

3-(6-Fluoro-1-oxo-5-(1-(4-(4-(trifluoromethyl)phenoxy)benzyl)piperidin-4-yl)-isoindolin-2-yl)piperidine-2,6-dione C1076.

C1076

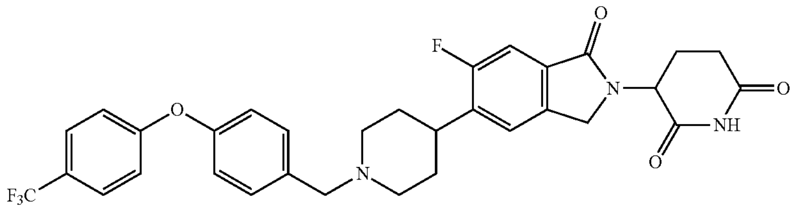

3-(5-(1-(4-(Benzyloxy)-3-ethoxybenzyl)piperidin-4-yl)-6-fluoro-1-oxoisoindolin-2-yl)piperidine-2,6-dione C1077.

C1077

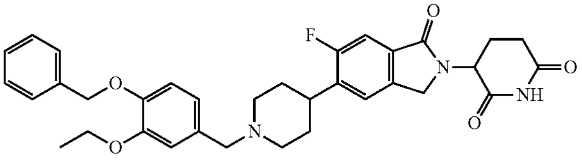

Tert-butyl 4-(1-(4-(2-(2,6-dioxopiperidin-3-yl)-6-fluoro-1-oxoisoindolin-5-yl)-piperidin-1-yl)-2-methylpropan-2-yl)piperidine-1-carboxylate C1078.

C1078

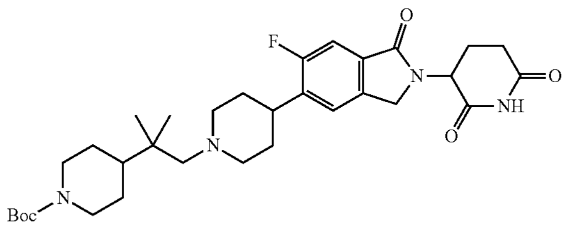

Benzyl (4-((4-(2-(2,6-dioxopiperidin-3-yl)-6-fluoro-1-oxoisoindolin-5-yl)-piperidin-1-yl)methyl)phenyl)carbamate C1079.

C1079

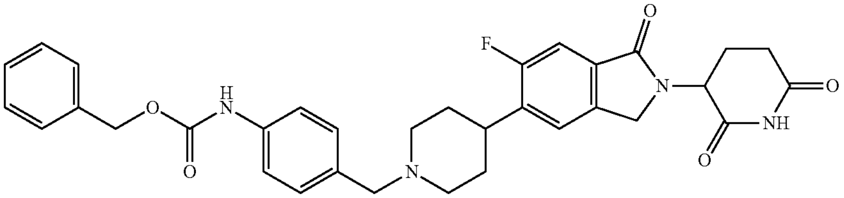

Tert-butyl 6-((4-(2-(2,6-dioxopiperidin-3-yl)-6-fluoro-1-oxoisoindolin-5-yl)-piperidin-1-yl)methyl)indoline-1-carboxylate C1080.

C1080

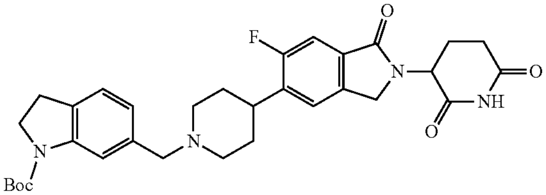

Tert-butyl (((1r,4r)-4-((4-(2-(2,6-dioxopiperidin-3-yl)-6-fluoro-1-oxoisoindolin-5-yl)piperidin-1-yl)methyl)cyclohexyl)methyl)carbamate C1081.

C1081

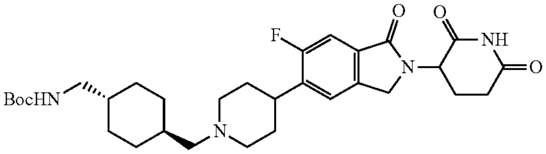

4-(4-((4-(2-(2,6-Dioxopiperidin-3-yl)-6-fluoro-1-oxoisoindolin-5-yl)piperidin-1-yl)methyl)phenoxy)-3-fluorobenzonitrile C1082.

C1082

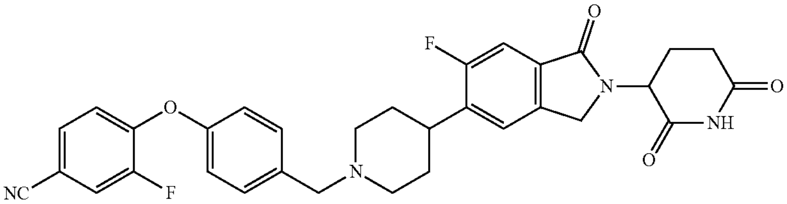

3-(6-Fluoro-5-(1-(3-methylbenzyl)piperidin-4-yl)-1-oxoisoindolin-2-yl)-piperidine-2,6-dione C1083.

Tert-butyl 4-((4-(2-(2,6-dioxopiperidin-3-yl)-6-fluoro-1-oxoisoindolin-5-yl)-piperidin-1-yl)methyl)-4-fluoropiperidine-1-carboxylate C1084.

C1083

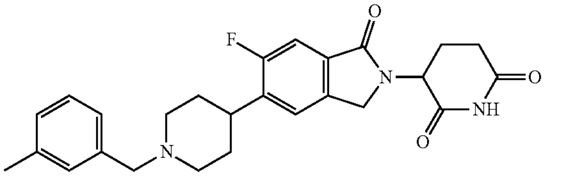

C1084

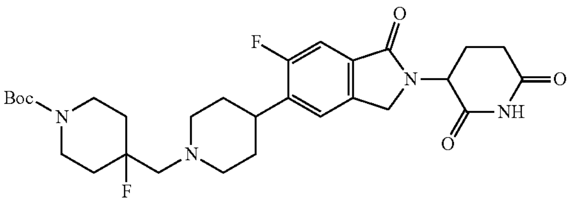

Tert-butyl 4-(2-(4-(2-(2,6-dioxopiperidin-3-yl)-6-fluoro-1-oxoisoindolin-5-yl)-piperidin-1-yl)ethyl)piperazine-1-carboxylate C1085.

3-(5-(1-((2-Chloro-4-morpholinopyrimidin-5-yl)methyl)piperidin-4-yl)-6-fluoro-1-oxoisoindolin-2-yl)piperidine-2,6-dione C1086.

C1085

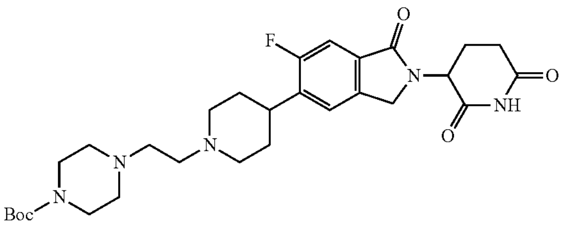

C1086

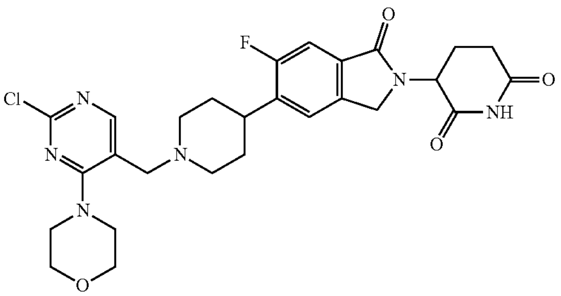

Tert-butyl ((1r,4r)-4-((4-(2-(2,6-dioxopiperidin-3-yl)-6-fluoro-1-oxoisoindolin-5-yl)piperidin-1-yl)methyl)cyclohexyl)carbamate C1087.

C1087

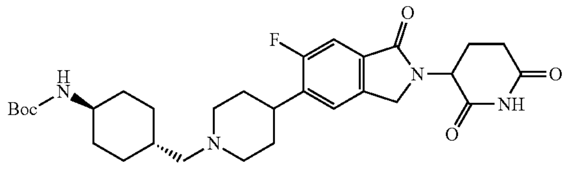

Tert-butyl 4-(2-(4-(2-(2,6-dioxopiperidin-3-yl)-6-fluoro-1-oxoisoindolin-5-yl)-piperidin-1-yl)ethyl)piperidine-1-carboxylate C1088.

C1088

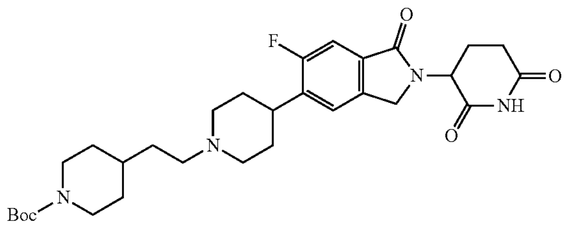

3-(5-(1-(2-(Benzyloxy)-4-methylbenzyl)piperidin-4-yl)-6-fluoro-1-oxoisoindolin-2-yl)piperidine-2,6-dione C1089.

3-(5-(1-(4-(Benzyloxy)-2-methylbenzyl)piperidin-4-yl)-6-fluoro-1-oxoisoindolin-2-yl)piperidine-2,6-dione C1090.

C1089

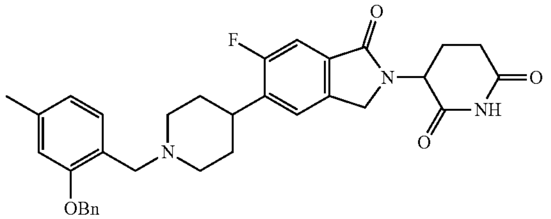

C1090

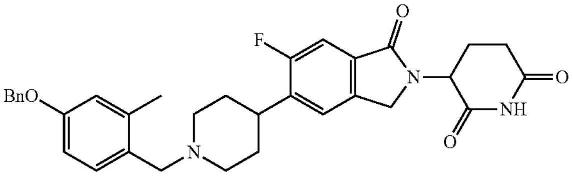

3-(5-(1-(3-Chloro-4-morpholinobenzyl)piperidin-4-yl)-6-fluoro-1-oxoisoindolin-2-yl)piperidine-2,6-dione C1091.

C1091

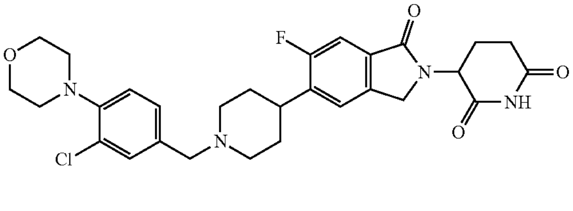

4-(4-((4-(2-(2,6-Dioxopiperidin-3-yl)-6-fluoro-1-oxoisoindolin-5-yl)piperidin-1-yl)methyl)phenoxy)benzonitrile C1092.

C1092

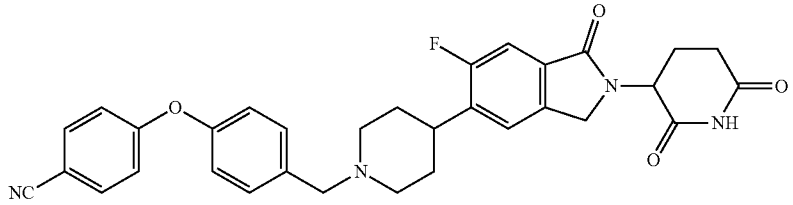

4-(3-((4-(2-(2,6-Dioxopiperidin-3-yl)-6-fluoro-1-oxoisoindolin-5-yl)piperidin-1-yl)methyl)phenoxy)benzonitrile C1093.

C1093

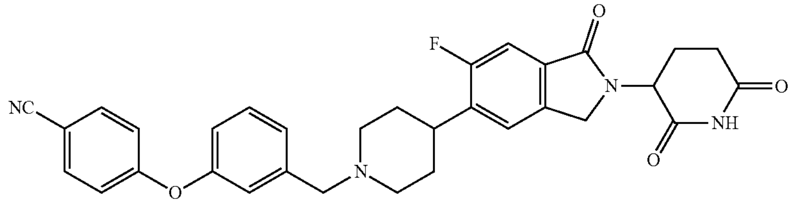

2-((4-(2-(2,6-Dioxopiperidin-3-yl)-6-fluoro-1-oxoisoindolin-5-yl)piperidin-1-yl)-methyl)-1H-pyrrole-3-carbonitrile C1094.

C1094

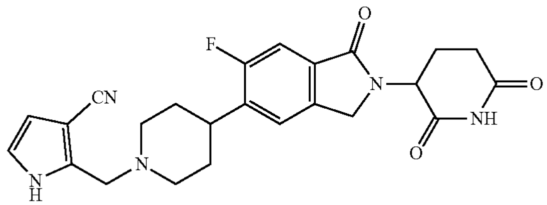

3-(5-(1-(3-(Cyclohexylmethoxy)benzyl)piperidin-4-yl)-6-fluoro-1-oxoisoindolin-2-yl)piperidine-2,6-dione C1095.

C1095

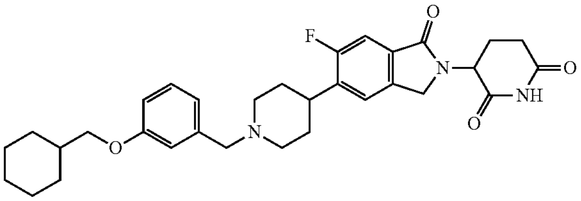

3-(5-(1-(3-(3-Bromophenyl)propyl)piperidin-4-yl)-6-fluoro-1-oxoisoindolin-2-yl)piperidine-2,6-dione C1096.

C1096

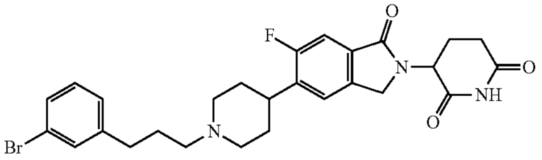

3-(5-(1-(4-(Benzyloxy)benzyl)piperidin-4-yl)-6-fluoro-1-oxoisoindolin-2-yl)-piperidine-2,6-dione C1097.

3-(5-(1-(3-(Benzyloxy)benzyl)piperidin-4-yl)-6-fluoro-1-oxoisoindolin-2-yl)-piperidine-2,6-dione C1098.

C1097

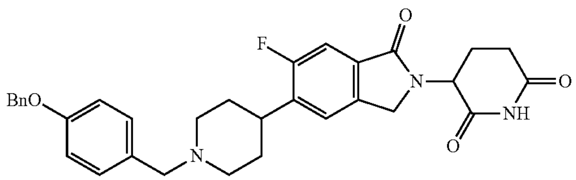

C1098

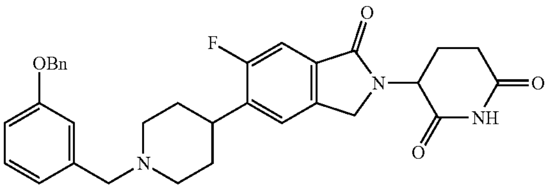

5-((4-(2-(2,6-Dioxopiperidin-3-yl)-6-fluoro-1-oxoisoindolin-5-yl)piperidin-1-yl)methyl)-2-(4-methyl-1H-imidazol-1-yl)benzonitrile C1099.

3-(5-(1-(3-Chloro-4-(trifluoromethyl)benzyl)piperidin-4-yl)-6-fluoro-1-oxoisoindolin-2-yl)piperidine-2,6-dione C1100.

C1099

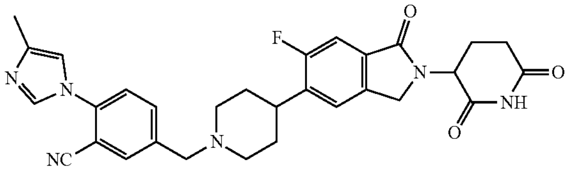

C1100

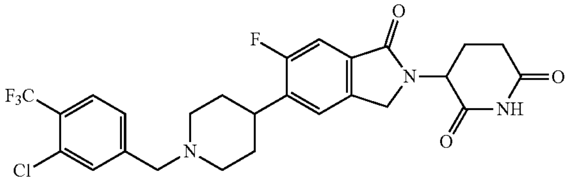

3-(5-(1-(2-Chloro-4-(trifluoromethyl)benzyl)piperidin-4-yl)-6-fluoro-1-oxoisoindolin-2-yl)piperidine-2,6-dione C1101.

3-(5-(1-(4-Chloro-2-(trifluoromethyl)benzyl)piperidin-4-yl)-6-fluoro-1-oxoisoindolin-2-yl)piperidine-2,6-dione C1102.

C1101

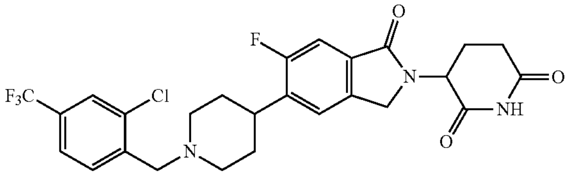

C1102

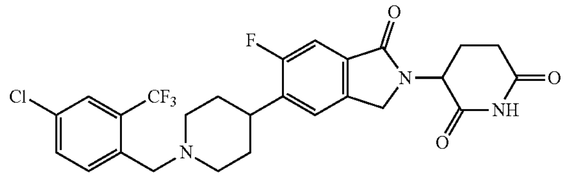

3-(5-(1-(5-Chloro-2-(trifluoromethyl)benzyl)piperidin-4-yl)-6-fluoro-1-oxoisoindolin-2-yl)piperidine-2,6-dione C1103.

3-(5-(1-(2-Chloro-5-(trifluoromethyl)benzyl)piperidin-4-yl)-6-fluoro-1-oxoisoindolin-2-yl)piperidine-2,6-dione C1104.

C1103

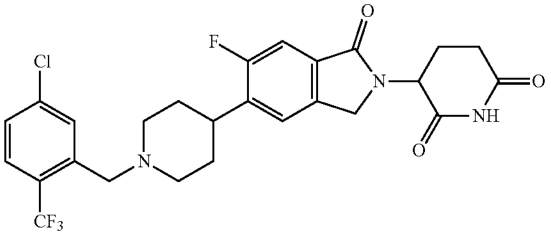

-continued

C1104

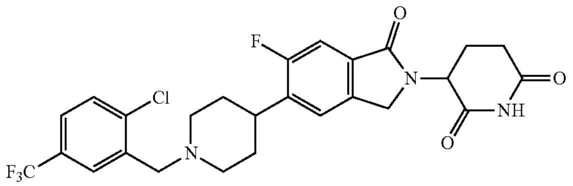

3-(6-Fluoro-1-oxo-5-(1-((tetrahydro-2H-pyran-4-yl)methyl)piperidin-4-yl)-isoindolin-2-yl)piperidine-2,6-dione C1105.

3-(5-(1-((1-Benzylpiperidin-4-yl)methyl)piperidin-4-yl)-6-fluoro-1-oxoisoindolin-2-yl)piperidine-2,6-dione C1106.

C1105

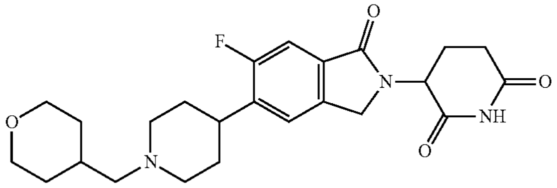

C1106

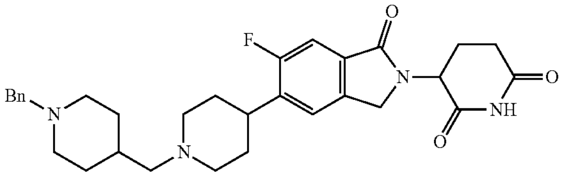

2-(3-(4-(2-(2,6-Dioxopiperidin-3-yl)-6-fluoro-1-oxoisoindolin-5-yl)piperidin-1-yl)propyl)isoindoline-1,3-dione C1107.

C1107

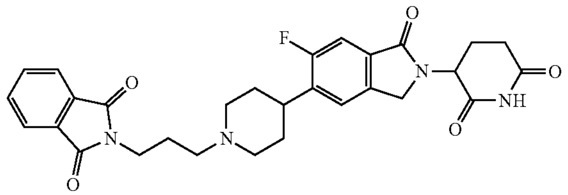

3-(6-Fluoro-1-oxo-5-(1-(3-(3-(trifluoromethyl)phenyl)propyl)piperidin-4-yl)-isoindolin-2-yl)piperidine-2,6-dione C1108.

C1108

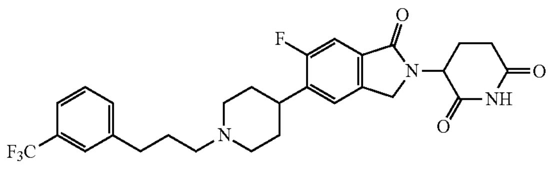

3-(5-(1-((6-(Dimethylamino)naphthalen-2-yl)methyl)piperidin-4-yl)-6-fluoro-1-oxoisoindolin-2-yl)piperidine-2,6-dione C1109.

N-(2-((4-(2-(2,6-Dioxopiperidin-3-yl)-6-fluoro-1-oxoisoindolin-5-yl)piperidin-1-yl)methyl)phenyl)methanesulfonamide C1110.

C1109

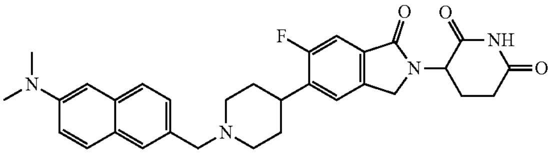

C1110

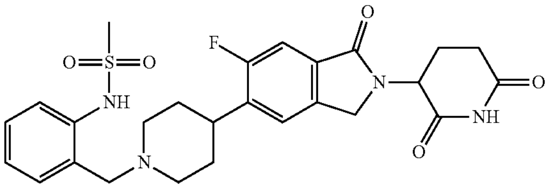

N-(4-((4-(2-(2,6-Dioxopiperidin-3-yl)-6-fluoro-1-oxoisoindolin-5-yl)piperidin-1-yl)methyl)phenyl)methanesulfonamide C1111.

C1111

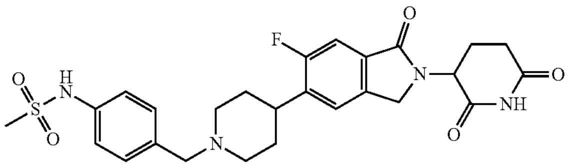

N-(3-((4-(2-(2,6-Dioxopiperidin-3-yl)-6-fluoro-1-oxoisoindolin-5-yl)piperidin-1-yl)methyl)phenyl)methanesulfonamide C1112.

C1112

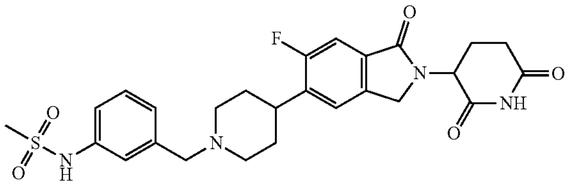

3-(6-Fluoro-1-oxo-5-(1-(2-(pyridin-2-yloxy)benzyl)piperidin-4-yl)isoindolin-2-yl)piperidine-2,6-dione C1113.

3-(5-(1-(4-Bromophenethyl)piperidin-4-yl)-6-fluoro-1-oxoisoindolin-2-yl)-piperidine-2,6-dione C1114.

C1113

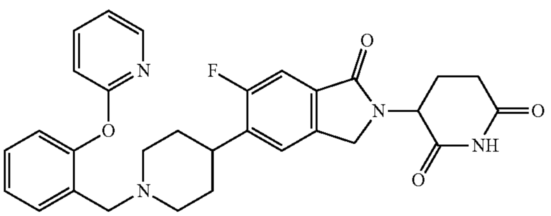

C1114

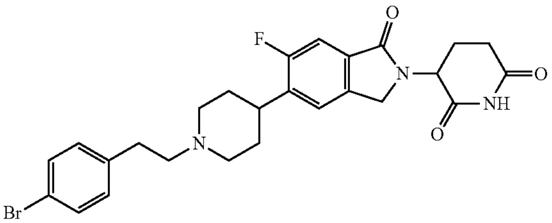

3-(6-Fluoro-5-(1-((2-morpholinothiazol-5-yl)methyl)piperidin-4-yl)-1-oxoisoindolin-2-yl)piperidine-2,6-dione C1115.

3-(6-Fluoro-1-oxo-5-(1-(thiazol-2-ylmethyl)piperidin-4-yl)isoindolin-2-yl)-piperidine-2,6-dione C1116.

C1115

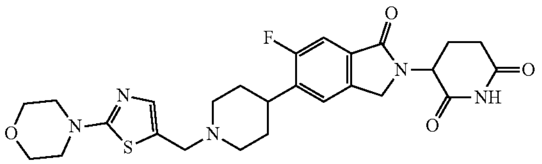

C1116

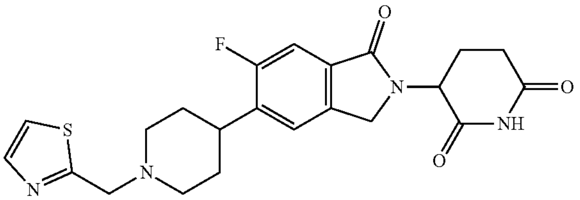

3-(5-(1-(4-(Ethylsulfonyl)benzyl)piperidin-4-yl)-6-fluoro-1-oxoisoindolin-2-yl)-piperidine-2,6-dione C1117.

C1117

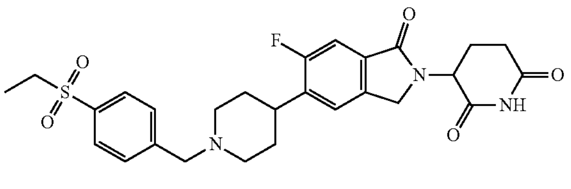

3-(6-Fluoro-5-(1-((4'-methyl-[2,2'-bipyridin]-4-yl)methyl)piperidin-4-yl)-1-oxoisoindolin-2-yl)piperidine-2,6-dione C1118.

C1118

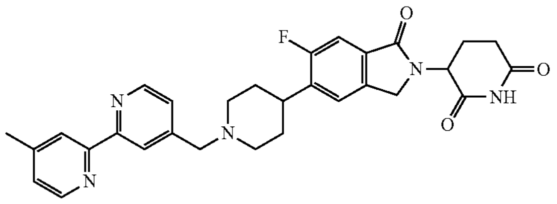

3-(6-Fluoro-1-oxo-5-(1-(4-phenoxybenzyl)piperidin-4-yl) isoindolin-2-yl)-piperidine-2,6-dione C1119.

C1119

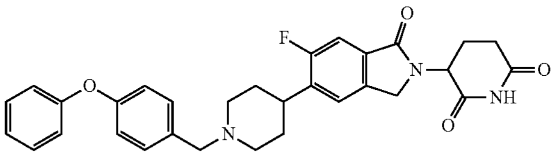

3-(6-Fluoro-1-oxo-5-(1-(3-phenoxybenzyl)piperidin-4-yl) isoindolin-2-yl)-piperidine-2,6-dione C1120.

C1120

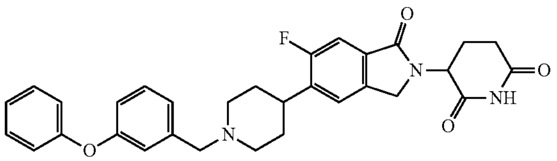

3-(6-Fluoro-1-oxo-5-(1-((6-(p-tolyl)pyridin-3-yl)methyl)piperidin-4-yl)isoindolin-2-yl)piperidine-2,6-dione C1121.

C1121

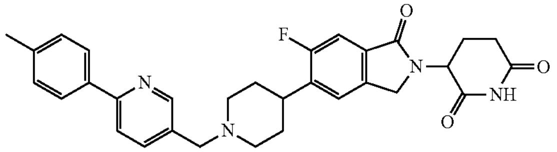

4-((4-(2-(2,6-Dioxopiperidin-3-yl)-6-fluoro-1-oxoisoindolin-5-yl)piperidin-1-yl)-methyl)-N-isopropylbenzamide C1122.

C1122

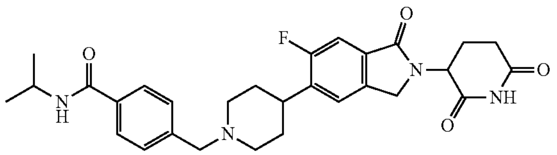

3-(6-Fluoro-5-(1-(2-morpholinobenzyl)piperidin-4-yl)-1-oxoisoindolin-2-yl)-piperidine-2,6-dione C1123.

3-(6-Fluoro-5-(1-(3-morpholinobenzyl)piperidin-4-yl)-1-oxoisoindolin-2-yl)-piperidine-2,6-dione C1124.

C1123

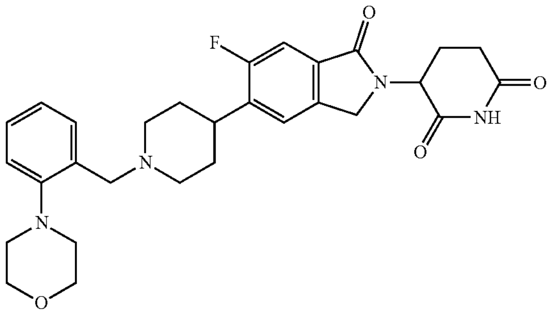

C1124

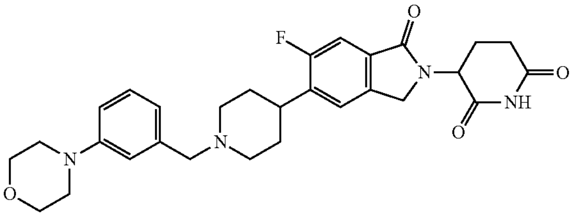

3-(6-Fluoro-5-(1-(4-morpholinobenzyl)piperidin-4-yl)-1-oxoisoindolin-2-yl)-piperidine-2,6-dione C1125.

C1125

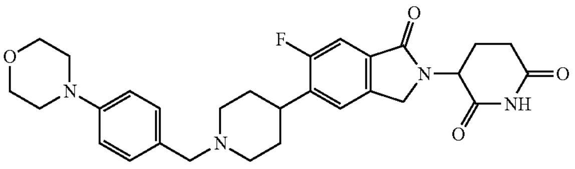

3-(6-Fluoro-1-oxo-5-(1-(3-(quinolin-6-yl)propyl)piperidin-4-yl)isoindolin-2-yl)-piperidine-2,6-dione C1126.

C1126

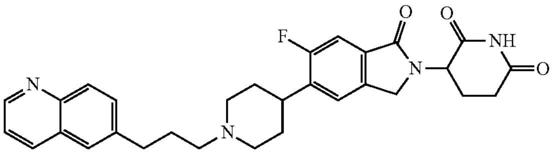

3-(6-Fluoro-1-oxo-5-(1-(thiazol-5-ylmethyl)piperidin-4-yl) isoindolin-2-yl)-piperidine-2,6-dione C1127.

3-(5-(1-((1H-Pyrrol-3-yl)methyl)piperidin-4-yl)-6-fluoro-1-oxoisoindolin-2-yl)-piperidine-2,6-dione C1128.

C1127

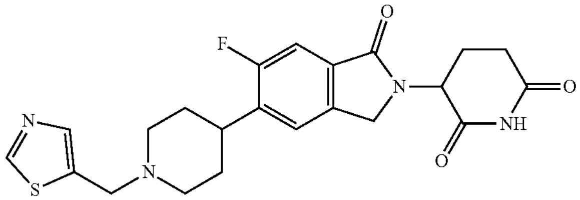

-continued

C1128

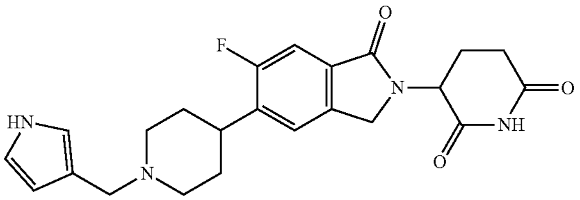

3-(6-Fluoro-5-(1-((6-(methylsulfonyl)pyridin-2-yl)methyl)piperidin-4-yl)-1-oxoisoindolin-2-yl)piperidine-2,6-dione C1129.

C1129

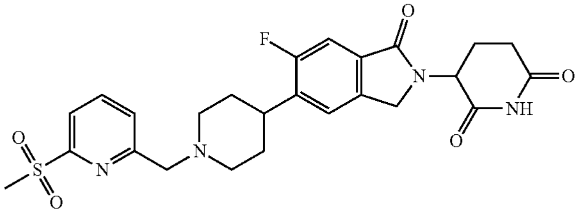

3-(6-Fluoro-1-oxo-5-(1-(3-(pyridin-4-yl)benzyl)piperidin-4-yl)isoindolin-2-yl)piperidine-2,6-dione C1130.

C1130

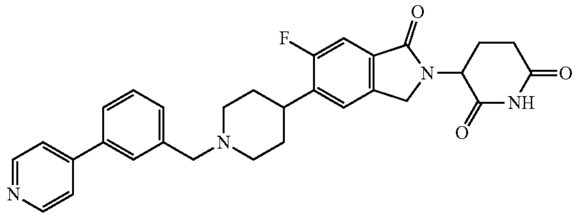

3-(5-(1-([1,1'-Biphenyl]-4-ylmethyl)piperidin-4-yl)-6-fluoro-1-oxoisoindolin-2-yl)piperidine-2,6-dione C1131.

3-(6-Fluoro-5-(1-((6-fluorochroman-8-yl)methyl)piperidin-4-yl)-1-oxoisoindolin-2-yl)piperidine-2,6-dione C1132.

C1131

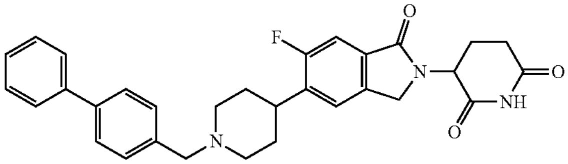

-continued

C1132

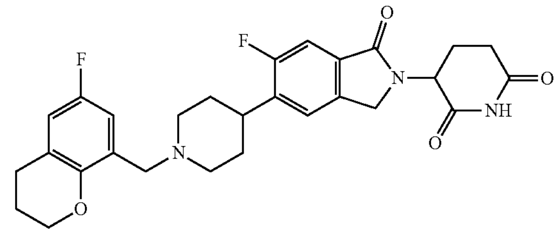

3-(6-Fluoro-1-oxo-5-(1-((6-(pyrrolidin-1-yl)pyridin-3-yl)methyl)piperidin-4-yl)-isoindolin-2-yl)piperidine-2,6-dione C1133.

C1133

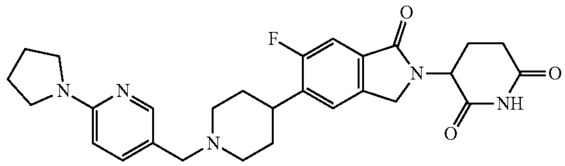

3-(6-Fluoro-1-oxo-5-(1-(3-(pyrrolidin-1-yl)benzyl)piperidin-4-yl)isoindolin-2-yl)-piperidine-2,6-dione C1134.

C1134

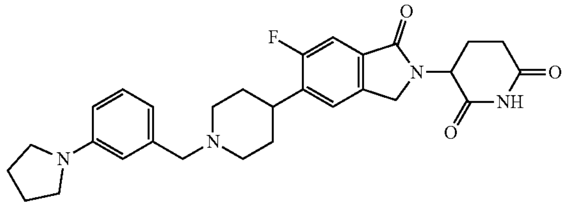

3-(6-Fluoro-1-oxo-5-(1-(4-(pyrrolidin-1-yl)benzyl)piperidin-4-yl)isoindolin-2-yl)-piperidine-2,6-dione C1135.

C1135

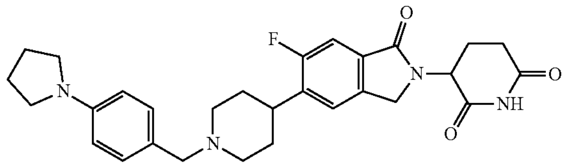

3-(5-(1-(3-(1H-1,2,4-Triazol-1-yl)benzyl)piperidin-4-yl)-6-fluoro-1-oxoisoindolin-2-yl)piperidine-2,6-dione C1136.

C1136

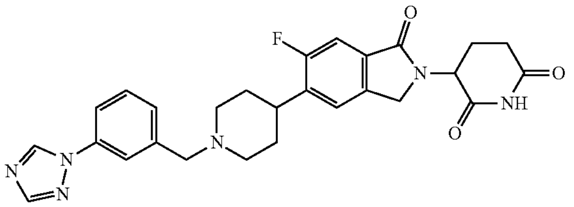

3-(5-(1-(2-(1H-1,2,4-Triazol-1-yl)benzyl)piperidin-4-yl)-6-fluoro-1-oxoisoindolin-2-yl)piperidine-2,6-dione C1137.

3-(5-(1-(4-(1H-1,2,4-Triazol-1-yl)benzyl)piperidin-4-yl)-6-fluoro-1-oxoisoindolin-2-yl)piperidine-2,6-dione C1138.

C1137

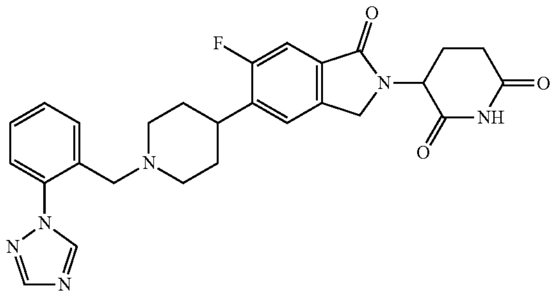

C1138

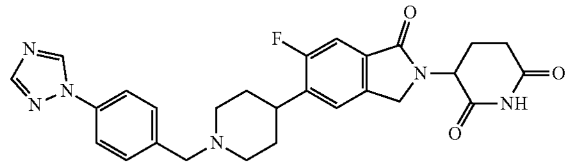

3-(6-Fluoro-1-oxo-5-(1-(thiazol-4-ylmethyl)piperidin-4-yl)isoindolin-2-yl)-piperidine-2,6-dione C1139.

3-(6-Fluoro-1-oxo-5-(1-((1-phenyl-1H-pyrazol-3-yl)methyl)piperidin-4-yl)-isoindolin-2-yl)piperidine-2,6-dione C1140.

C1139

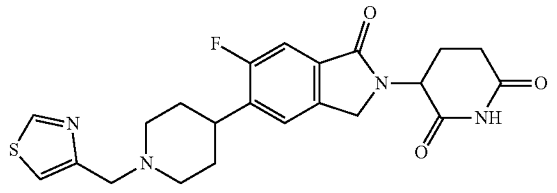

C1140

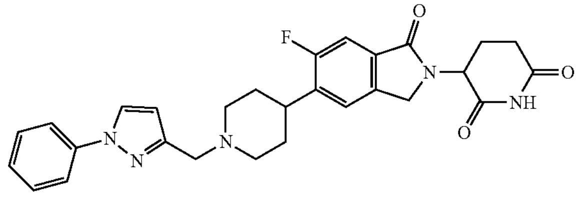

3-(6-Fluoro-1-oxo-5-(1-((5-phenyl-1H-imidazol-2-yl)methyl)piperidin-4-yl)-isoindolin-2-yl)piperidine-2,6-dione C1141.

C1141

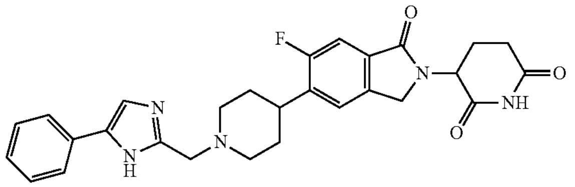

3-(5-(1-(3-(1H-Imidazol-1-yl)benzyl)piperidin-4-yl)-6-fluoro-1-oxoisoindolin-2-yl)piperidine-2,6-dione C1142.

C1142

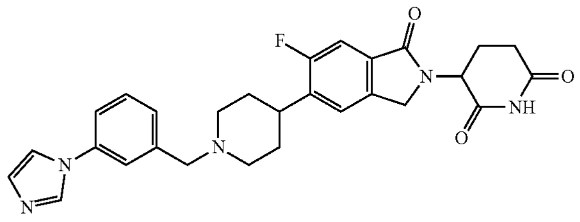

3-(6-Fluoro-1-oxo-5-(1-((2-phenyl-1H-imidazol-5-yl)methyl)piperidin-4-yl)-isoindolin-2-yl)piperidine-2,6-dione C1143.

C1143

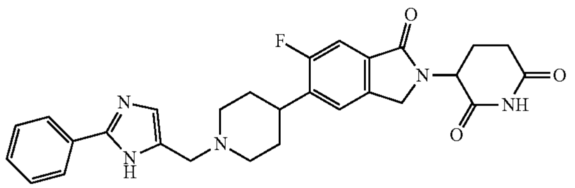

3-(5-(1-(4-(1H-Imidazol-1-yl)benzyl)piperidin-4-yl)-6-fluoro-1-oxoisoindolin-2-yl)piperidine-2,6-dione C1144.

C1144

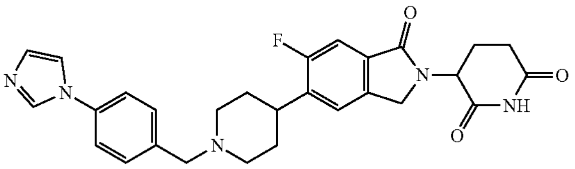

3-(5-(1-(4-(1H-Pyrazol-1-yl)benzyl)piperidin-4-yl)-6-fluoro-1-oxoisoindolin-2-yl)piperidine-2,6-dione C1145.

C1145

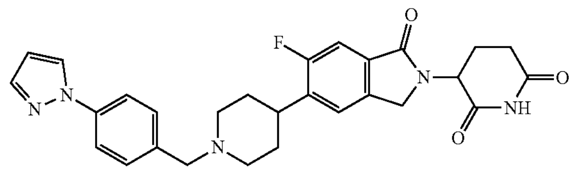

2-((4-(2-(2,6-Dioxopiperidin-3-yl)-6-fluoro-1-oxoisoindolin-5-yl)piperidin-1-yl)-methyl)-1H-indole-6-carbonitrile C1146.

C1146

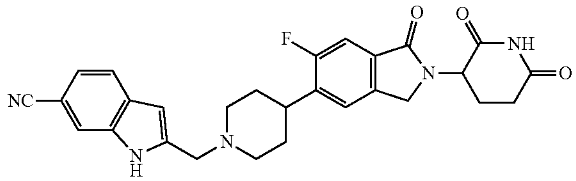

3-((4-(2-(2,6-Dioxopiperidin-3-yl)-6-fluoro-1-oxoisoindolin-5-yl)piperidin-1-yl)-methyl)-1H-indole-6-carbonitrile C1147.

C1147

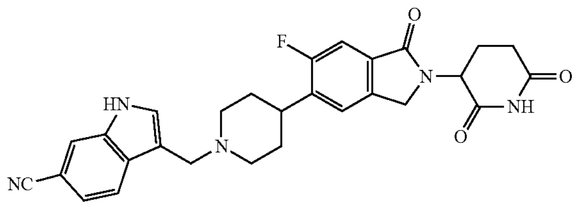

3-(5-(1-((2,3-Dihydro[1,4]dioxino[2,3-b]pyridin-6-yl)methyl)piperidin-4-yl)-6-fluoro-1-oxoisoindolin-2-yl)piperidine-2,6-dione C1148.

C1148

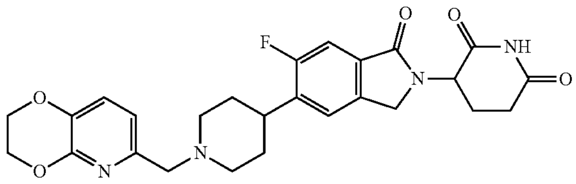

3-(5-(1-((Adamantan-1-yl)methyl)piperidin-4-yl)-6-fluoro-1-oxoisoindolin-2-yl)-piperidine-2,6-dione C1149.

3-(6-Fluoro-1-oxo-5-(1-(thiophen-2-ylmethyl)piperidin-4-yl)isoindolin-2-yl)-piperidine-2,6-dione C1150.

C1149

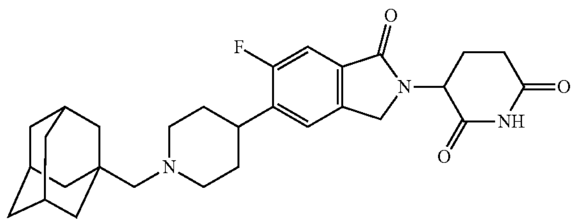

C1150

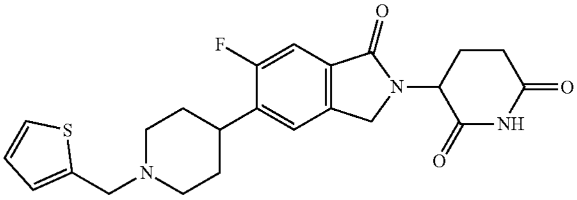

3-(5-(1-(3-(Benzyloxy)propyl)piperidin-4-yl)-6-fluoro-1-oxoisoindolin-2-yl)-piperidine-2,6-dione C1151.

C1151

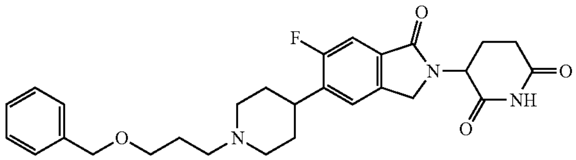

3-(6-Fluoro-5-(1-(3-(2-methoxyphenyl)propyl)piperidin-4-yl)-1-oxoisoindolin-2-yl)piperidine-2,6-dione C1152.

C1152

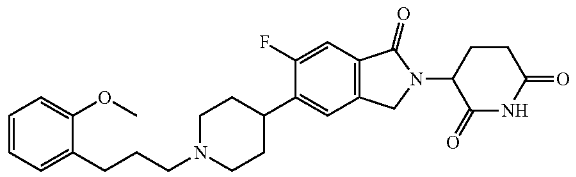

3-(5-(1-((2,3-Dihydrobenzo[b][1,4]dioxin-6-yl)methyl)piperidin-4-yl)-6-fluoro-1-oxoisoindolin-2-yl)piperidine-2,6-dione C1153.

3-(6-Fluoro-5-(1-((5-fluoro-1H-benzo[d]imidazol-2-yl)methyl)piperidin-4-yl)-1-oxoisoindolin-2-yl)piperidine-2,6-dione C1154.

C1153

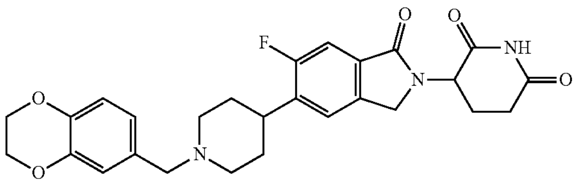

-continued

C1154

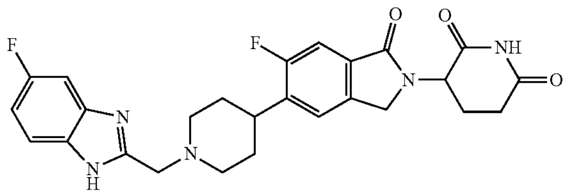

3-(6-Fluoro-5-(1-((4-fluorobenzofuran-7-yl)methyl)piperidin-4-yl)-1-oxoisoindolin-2-yl)piperidine-2,6-dione C1155.

3-(5-(1-(4-(Dimethylamino)-3-methylbenzyl)piperidin-4-yl)-6-fluoro-1-oxoisoindolin-2-yl)piperidine-2,6-dione C1156.

C1155

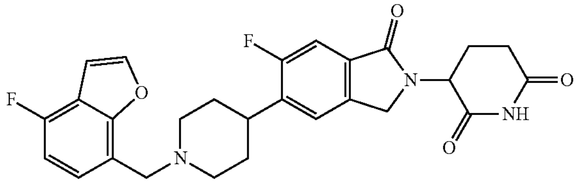

C1156

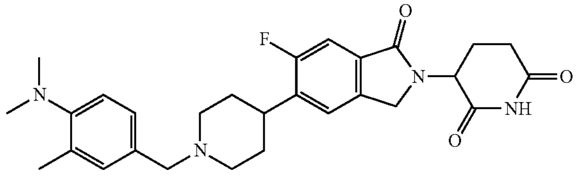

3-(5-(1-((2-(Tert-butyl)pyridin-4-yl)methyl)piperidin-4-yl)-6-fluoro-1-oxoisoindolin-2-yl)piperidine-2,6-dione C1157.

3-(5-(1-(4-((Dimethylamino)methyl)benzyl)piperidin-4-yl)-6-fluoro-1-oxoisoindolin-2-yl)piperidine-2,6-dione C1158.

C1157

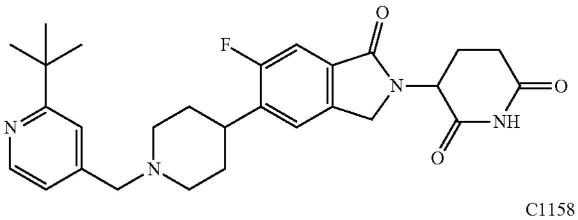

C1158

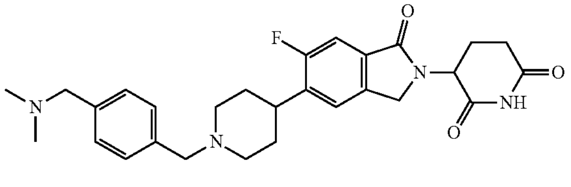

3-(6-Fluoro-1-oxo-5-(1-(thieno[3,2-c]pyridin-2-ylmethyl)piperidin-4-yl)-isoindolin-2-yl)piperidine-2,6-dione C1159.

3-(5-(1-(Benzo[d]thiazol-4-ylmethyl)piperidin-4-yl)-6-fluoro-1-oxoisoindolin-2-yl)piperidine-2,6-dione C1160.

C1159

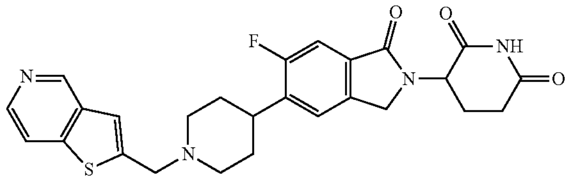

C1160

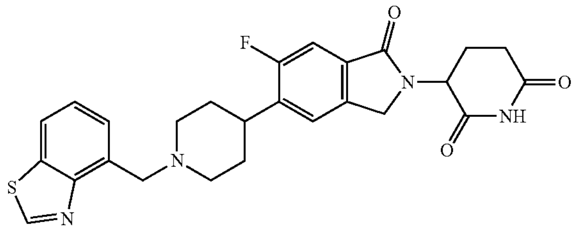

3-(6-Fluoro-1-oxo-5-(1-(thiophen-3-ylmethyl)piperidin-4-yl)isoindolin-2-yl)-piperidine-2,6-dione C1161.

3-(6-Fluoro-1-oxo-5-(1-(thieno[2,3-b]pyridin-2-ylmethyl)piperidin-4-yl)-isoindolin-2-yl)piperidine-2,6-dione C1162.

C1161

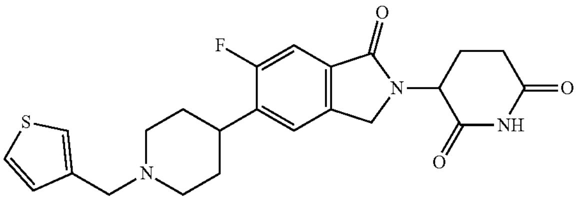

C1162

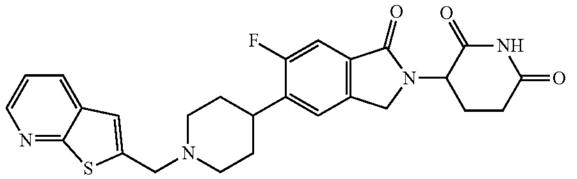

3-(5-(1-((3,4-Dihydro-2H-pyrano[2,3-c]pyridin-6-yl)methyl)piperidin-4-yl)-6-fluoro-1-oxoisoindolin-2-yl)piperidine-2,6-dione C1163.

3-(6-Fluoro-5-(1-(3-methyl-3-phenylbutyl)piperidin-4-yl)-1-oxoisoindolin-2-yl)-piperidine-2,6-dione C1164.

C1163

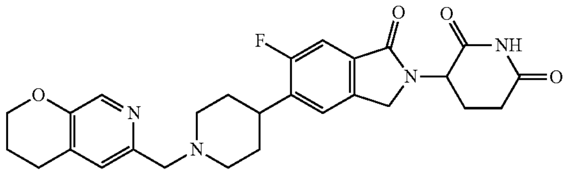

-continued

C1164

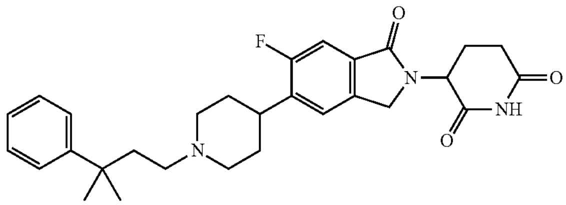

3-(5-(1-(Benzo[b]thiophen-3-ylmethyl)piperidin-4-yl)-6-fluoro-1-oxoisoindolin-2-yl)piperidine-2,6-dione C1165.

3-(5-(1-(Benzo[b]thiophen-2-ylmethyl)piperidin-4-yl)-6-fluoro-1-oxoisoindolin-2-yl)piperidine-2,6-dione C1166.

C1165

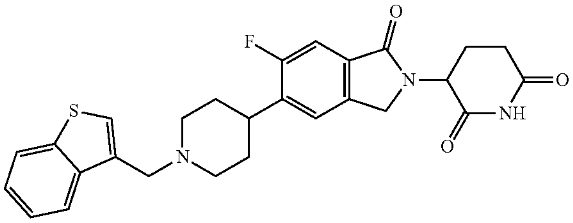

C1166

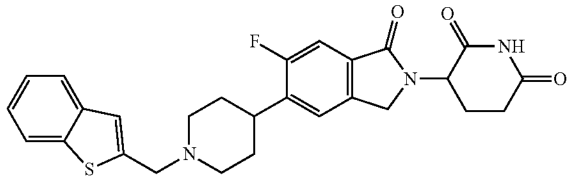

3-(5-(1-(Chroman-6-ylmethyl)piperidin-4-yl)-6-fluoro-1-oxoisoindolin-2-yl)-piperidine-2,6-dione C1167.

3-(6-Fluoro-5-(1-((1-methyl-1H-imidazo[4,5-b]pyridin-2-yl)methyl)piperidin-4-yl)-1-oxoisoindolin-2-yl)piperidine-2,6-dione C1168.

C1167

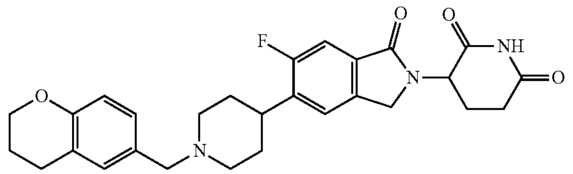

C1168

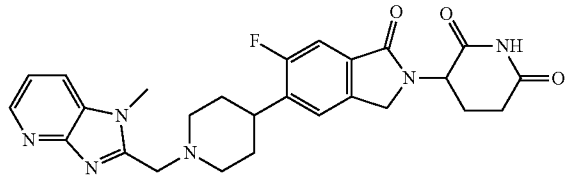

4-((4-(2-(2,6-Dioxopiperidin-3-yl)-6-fluoro-1-oxoisoindolin-5-yl)piperidin-1-yl)-methyl)-2-methoxybenzonitrile C1169.

4-((4-(2-(2,6-Dioxopiperidin-3-yl)-6-fluoro-1-oxoisoindolin-5-yl)piperidin-1-yl)-methyl)-3-methoxybenzonitrile C1170.

C1169

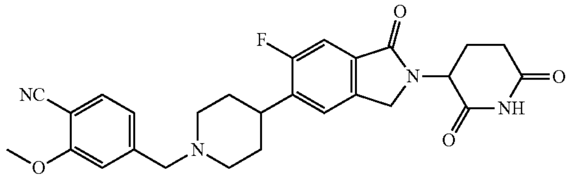

C1170

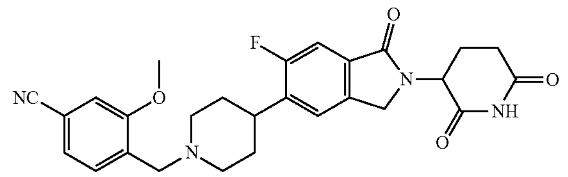

2-((4-(2-(2,6-Dioxopiperidin-3-yl)-6-fluoro-1-oxoisoindolin-5-yl)piperidin-1-yl)-methyl)-5-methoxybenzonitrile C1171.

3-(6-Fluoro-5-(1-((2-methyl-2H-tetrazol-5-yl)methyl)piperidin-4-yl)-1-oxoisoindolin-2-yl)piperidine-2,6-dione C1172.

C1171

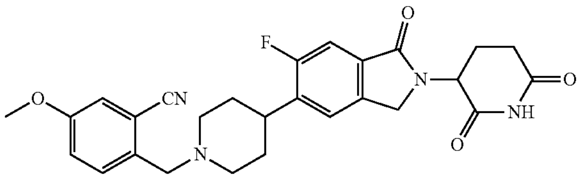

C1172

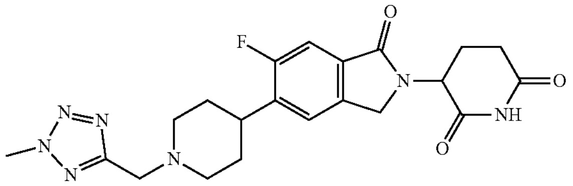

3-(6-Fluoro-5-(1-((2-methylbenzo[d]oxazol-6-yl)methyl)piperidin-4-yl)-1-oxoisoindolin-2-yl)piperidine-2,6-dione C1173.

3-(6-Fluoro-1-oxo-5-(1-((3-oxoisoindolin-5-yl)methyl)piperidin-4-yl)isoindolin-2-yl)piperidine-2,6-dione C1174.

C1173

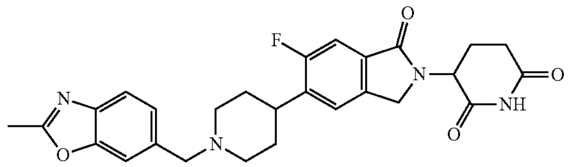

-continued

C1174

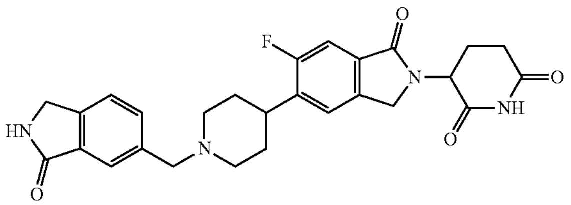

3-(6-Fluoro-1-oxo-5-(1-((1-oxoisoindolin-5-yl)methyl)piperidin-4-yl)isoindolin-2-yl)piperidine-2,6-dione C1175.

3-(6-Fluoro-1-oxo-5-(1-((5,6,7,8-tetrahydronaphthalen-1-yl)methyl)piperidin-4-yl)isoindolin-2-yl)piperidine-2,6-dione C1176.

C1175

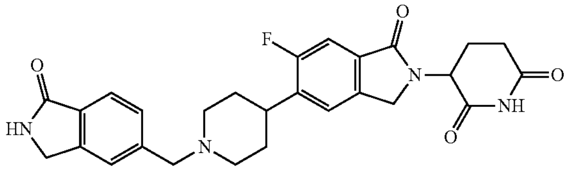

C1176

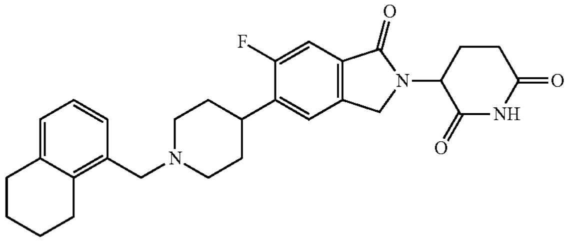

3-(6-Fluoro-5-(1-((3-methylimidazo[1,2-a]pyridin-2-yl)methyl)piperidin-4-yl)-1-oxoisoindolin-2-yl)piperidine-2,6-dione C1177.

3-(6-Fluoro-5-(1-((1-methyl-1H-indazol-6-yl)methyl)piperidin-4-yl)-1-oxoisoindolin-2-yl)piperidine-2,6-dione C1178.

C1177

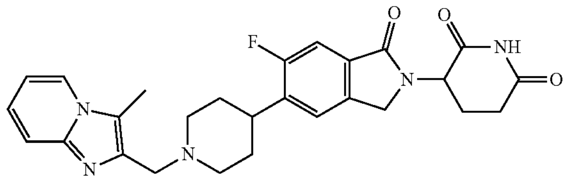

C1178

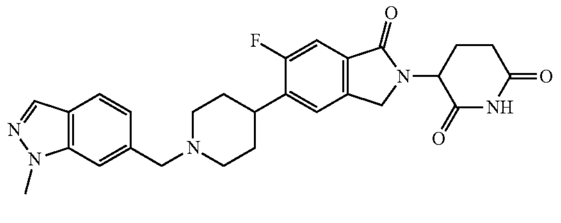

3-(6-Fluoro-5-(1-((2-methyl-2H-indazol-5-yl)methyl)piperidin-4-yl)-1-oxoisoindolin-2-yl)piperidine-2,6-dione C1179.

3-(6-Fluoro-5-(1-((6-methylimidazo[1,2-a]pyridin-2-yl)methyl)piperidin-4-yl)-1-oxoisoindolin-2-yl)piperidine-2,6-dione C1180.

C1179

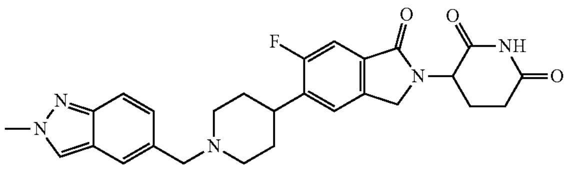

C1180

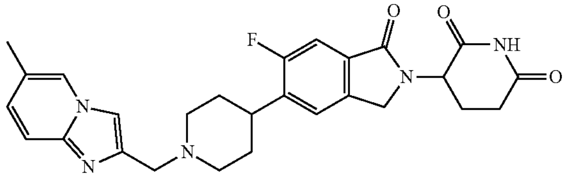

3-(6-Fluoro-5-(1-((5-methylimidazo[1,2-a]pyridin-3-yl)methyl)piperidin-4-yl)-1-oxoisoindolin-2-yl)piperidine-2,6-dione C1181.

3-(6-Fluoro-5-(1-((7-methylimidazo[1,2-a]pyridin-3-yl)methyl)piperidin-4-yl)-1-oxoisoindolin-2-yl)piperidine-2,6-dione C1182.

C1181

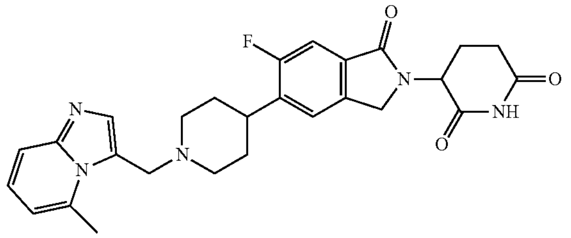

C1182

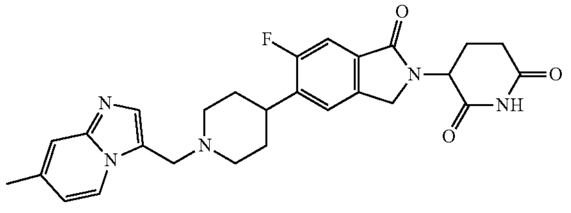

3-(6-Fluoro-5-(1-((5-methyl-4H-1,2,4-triazol-3-yl)methyl)piperidin-4-yl)-1-oxoisoindolin-2-yl)piperidine-2,6-dione C1183.

3-(6-Fluoro-5-(1-((1-methyl-1H-indazol-4-yl)methyl)piperidin-4-yl)-1-oxoisoindolin-2-yl)piperidine-2,6-dione C1184.

C1183

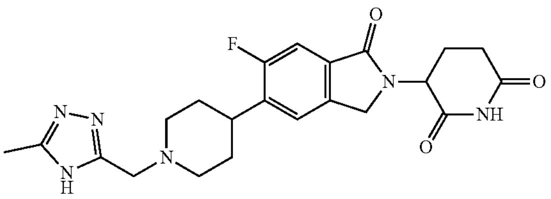

C1184

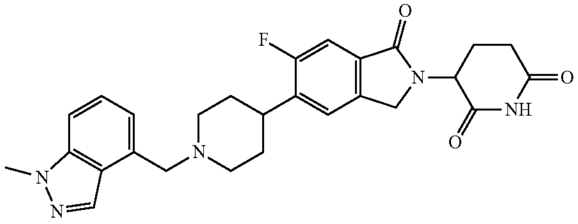

3-(6-Fluoro-5-(1-((5-methyl-1H-pyrrolo[2,3-b]pyridin-3-yl)methyl)piperidin-4-yl)-1-oxoisoindolin-2-yl)piperidine-2,6-dione C1185.

3-(6-Fluoro-5-(1-((1-methyl-1H-benzo[d]imidazol-2-yl)methyl)piperidin-4-yl)-1-oxoisoindolin-2-yl)piperidine-2,6-dione C1186.

C1185

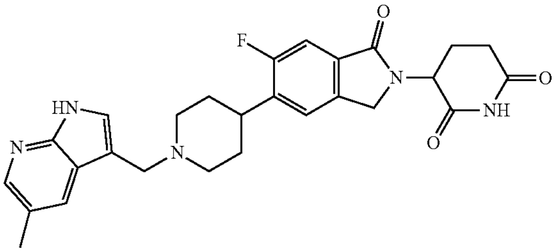

C1186

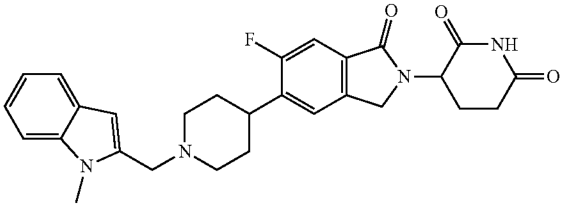

3-(6-Fluoro-5-(1-((2-methylimidazo[1,2-a]pyridin-3-yl)methyl)piperidin-4-yl)-1-oxoisoindolin-2-yl)piperidine-2,6-dione C1187.

3-(6-Fluoro-5-(1-((2-methyl-2H-indazol-3-yl)methyl)piperidin-4-yl)-1-oxoisoindolin-2-yl)piperidine-2,6-dione C1188.

C1187

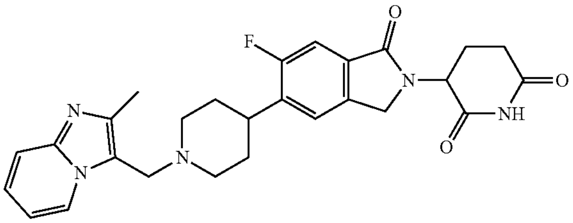

C1188

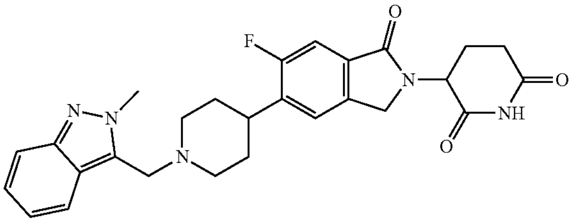

3-(6-Fluoro-5-(1-((7-methyl-1H-indol-3-yl)methyl)piperidin-4-yl)-1-oxoisoindolin-2-yl)piperidine-2,6-dione C1189.

3-(6-Fluoro-5-(1-((1-methyl-1H-indol-5-yl)methyl)piperidin-4-yl)-1-oxoisoindolin-2-yl)piperidine-2,6-dione C1190.

C1189

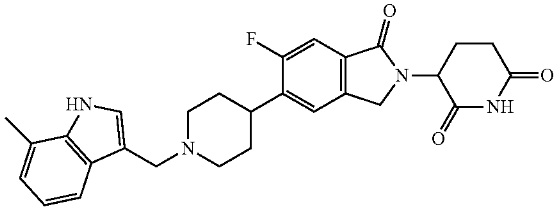

C1190

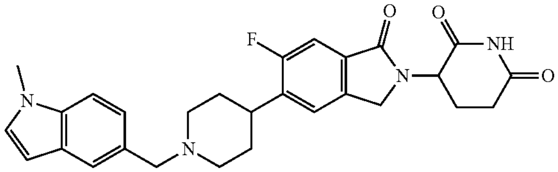

3-(6-Fluoro-5-(1-((2-methyl-1H-indol-4-yl)methyl)piperidin-4-yl)-1-oxoisoindolin-2-yl)piperidine-2,6-dione C1191.

3-(6-Fluoro-5-(1-((1-methyl-1H-indol-6-yl)methyl)piperidin-4-yl)-1-oxoisoindolin-2-yl)piperidine-2,6-dione C1192.

C1191

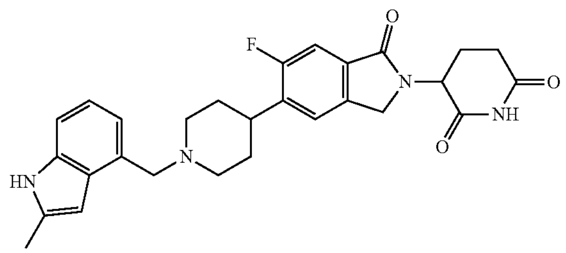

C1192

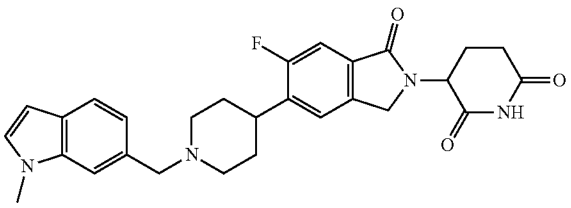

3-(6-Fluoro-5-(1-((4-methyl-1H-indol-3-yl)methyl)piperidin-4-yl)-1-oxoisoindolin-2-yl)piperidine-2,6-dione C1193.

3-(6-Fluoro-5-(1-((4-methyloxazol-5-yl)methyl)piperidin-4-yl)-1-oxoisoindolin-2-yl)piperidine-2,6-dione C1194.

C1193

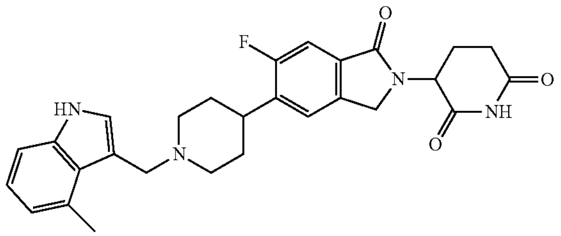

C1194

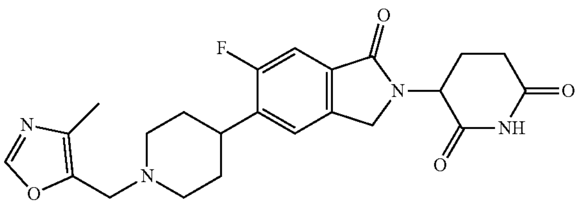

3-(6-Fluoro-5-(1-((3-methyl-1H-indol-2-yl)methyl)piperidin-4-yl)-1-oxoisoindolin-2-yl)piperidine-2,6-dione C1195.

3-(6-Fluoro-5-(1-((6-methyl-1H-indol-3-yl)methyl)piperidin-4-yl)-1-oxoisoindolin-2-yl)piperidine-2,6-dione C1196.

C1195

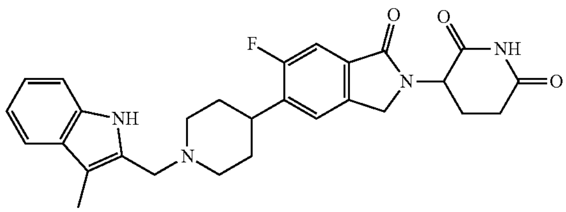

C1196

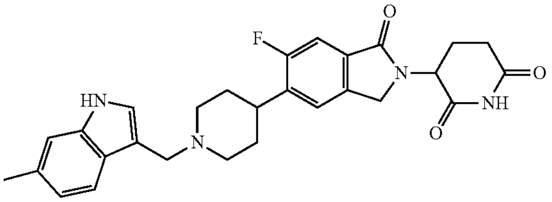

Tert-butyl (2-(4-(2-(2,6-dioxopiperidin-3-yl)-6-fluoro-1-oxoisoindolin-5-yl)-piperidin-1-yl)ethyl)carbamate C1197.

3-(6-Fluoro-1-oxo-5-(1-(quinoxalin-6-ylmethyl)piperidin-4-yl)isoindolin-2-yl)piperidine-2,6-dione C1198.

C1197

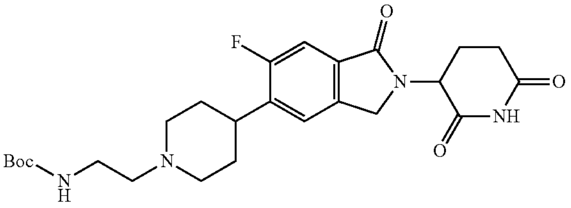

C1198

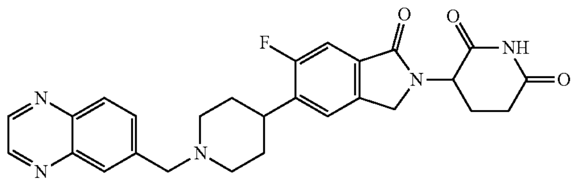

3-(5-(1-((1,8-Naphthyridin-2-yl)methyl)piperidin-4-yl)-6-fluoro-1-oxoisoindolin-2-yl)piperidine-2,6-dione C1199.

3-(6-Fluoro-1-oxo-5-(1-(quinoxalin-2-ylmethyl)piperidin-4-yl)isoindolin-2-yl)-piperidine-2,6-dione C1200.

C1199

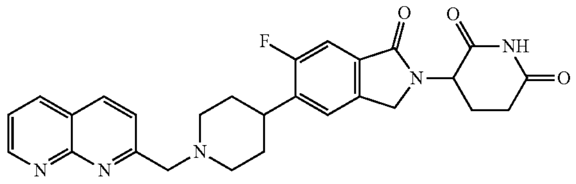

-continued

C1200

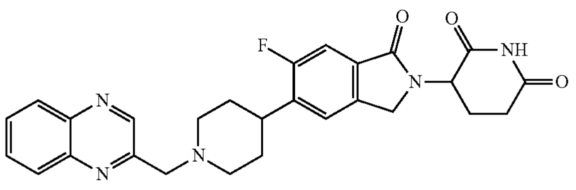

3-(6-Fluoro-1-oxo-5-(1-(quinoxalin-5-ylmethyl)piperidin-4-yl)isoindolin-2-yl)-piperidine-2,6-dione C1201.

3-(6-Fluoro-1-oxo-5-(1-(quinolin-8-ylmethyl)piperidin-4-yl)isoindolin-2-yl)-piperidine-2,6-dione C1202.

C1201

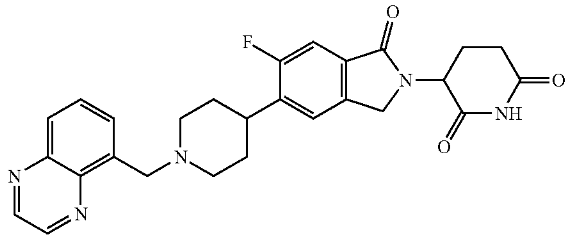

C1201

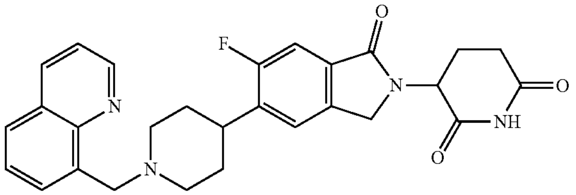

3-(6-Fluoro-5-(1-(isoquinolin-4-ylmethyl)piperidin-4-yl)-1-oxoisoindolin-2-yl)-piperidine-2,6-dione C1203.

3-(6-Fluoro-5-(1-(isoquinolin-3-ylmethyl)piperidin-4-yl)-1-oxoisoindolin-2-yl)-piperidine-2,6-dione C1204.

C1203

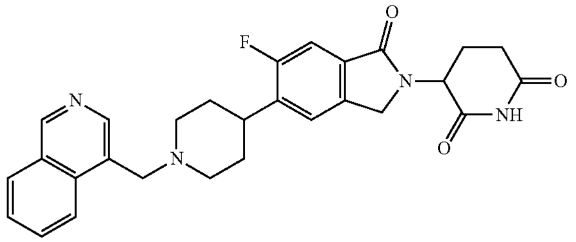

C1204

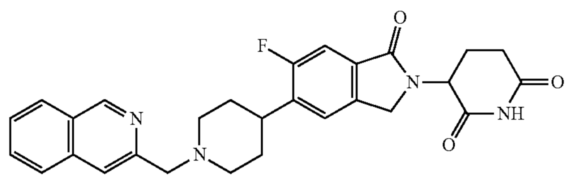

3-(6-Fluoro-5-(1-((2-methyloxazol-4-yl)methyl)piperidin-4-yl)-1-oxoisoindolin-2-yl)piperidine-2,6-dione C1205.

3-(6-Fluoro-5-(1-(isoquinolin-8-ylmethyl)piperidin-4-yl)-1-oxoisoindolin-2-yl)-piperidine-2,6-dione C1206.

C1205

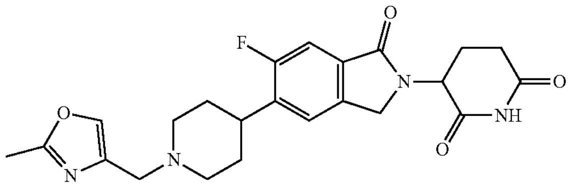

C1206

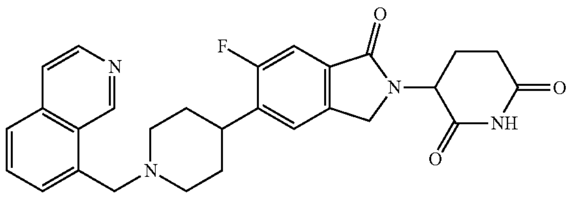

3-(6-Fluoro-5-(1-(isoquinolin-5-ylmethyl)piperidin-4-yl)-1-oxoisoindolin-2-yl)-piperidine-2,6-dione C1207.

3-(6-Fluoro-1-oxo-5-(1-(quinolin-4-ylmethyl)piperidin-4-yl)isoindolin-2-yl)-piperidine-2,6-dione C1208.

C1207

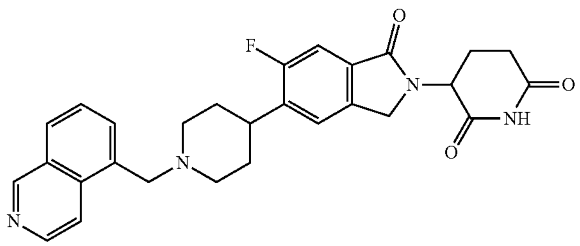

C1208

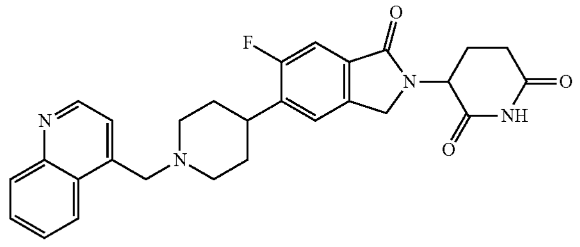

3-(6-Fluoro-1-oxo-5-(1-(quinolin-6-ylmethyl)piperidin-4-yl)isoindolin-2-yl)-piperidine-2,6-dione C1209.

3-(6-Fluoro-5-(1-(naphthalen-2-ylmethyl)piperidin-4-yl)-1-oxoisoindolin-2-yl)-piperidine-2,6-dione C1210.

C1209

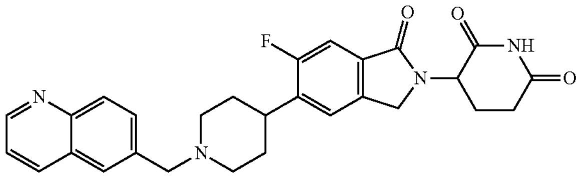

-continued

C1210

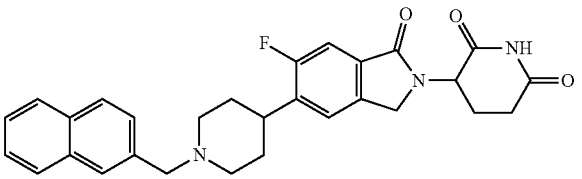

3-(5-(1-(2-Amino-6-chlorobenzyl)piperidin-4-yl)-6-fluoro-1-oxoisoindolin-2-yl)-piperidine-2,6-dione C1211.

3-(5-(1-(2-Amino-4-chlorobenzyl)piperidin-4-yl)-6-fluoro-1-oxoisoindolin-2-yl)-piperidine-2,6-dione C1212.

C1211

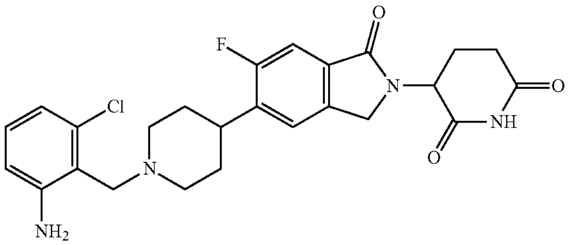

C1212

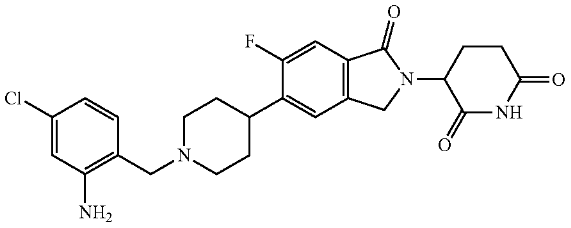

3-(5-(1-(2-Amino-3-chlorobenzyl)piperidin-4-yl)-6-fluoro-1-oxoisoindolin-2-yl)-piperidine-2,6-dione C1213.

3-(5-(1-((5-(Dimethylamino)thiophen-2-yl)methyl)piperidin-4-yl)-6-fluoro-1-oxoisoindolin-2-yl)piperidine-2,6-dione C1214.

C1213

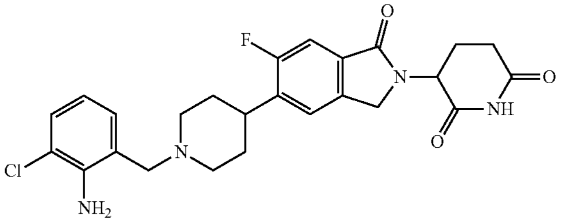

C1214

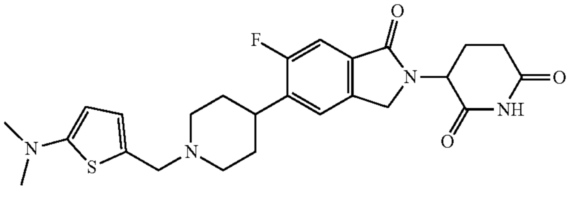

3-(5-(1-(4-Chlorophenethyl)piperidin-4-yl)-6-fluoro-1-oxoisoindolin-2-yl)-piperidine-2,6-dione C1215.

3-(6-Fluoro-5-(1-((2-methyloxazol-5-yl)methyl)piperidin-4-yl)-1-oxoisoindolin-2-yl)piperidine-2,6-dione C1216.

C1215

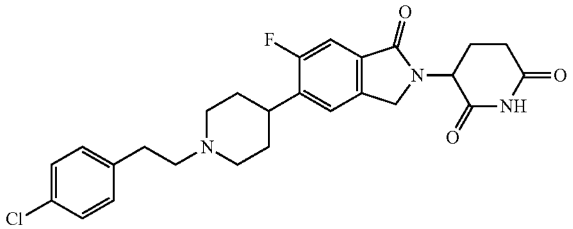

C1216

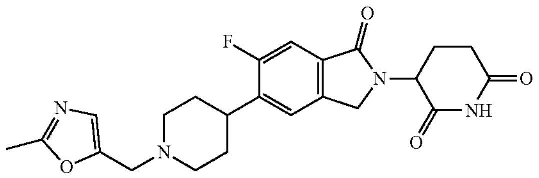

3-(6-Fluoro-5-(1-((4-hydroxybicyclo[2.2.2]octan-1-yl)methyl)piperidin-4-yl)-1-oxoisoindolin-2-yl)piperidine-2,6-dione C1217.

3-(6-Fluoro-5-(1-((2-(methylthio)pyrimidin-4-yl)methyl)piperidin-4-yl)-1-oxoisoindolin-2-yl)piperidine-2,6-dione C1218.

C1217

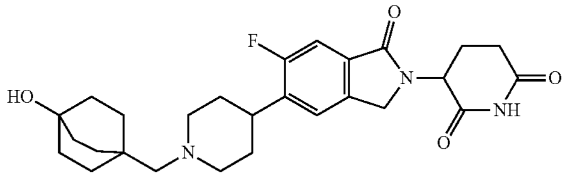

C1218

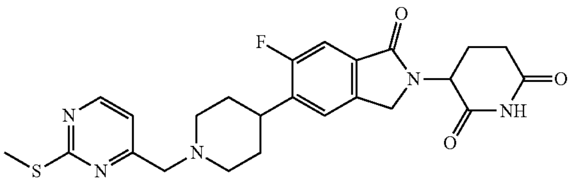

3-(5-(1-((2-Cyclopropylthiazol-5-yl)methyl)piperidin-4-yl)-6-fluoro-1-oxoisoindolin-2-yl)piperidine-2,6-dione C1219.

3-(5-(1-((1-(Tert-butyl)-1H-1,2,3-triazol-4-yl)methyl)piperidin-4-yl)-6-fluoro-1-oxoisoindolin-2-yl)piperidine-2,6-dione C1220.

C1219

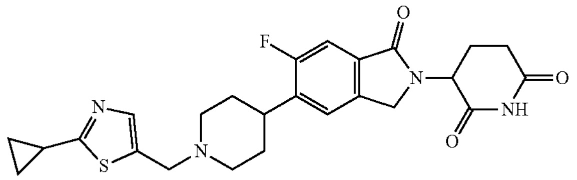

C1220

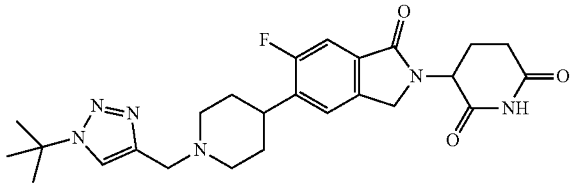

3-(6-Fluoro-5-(1-((1-isobutyl-1H-pyrazol-4-yl)methyl)piperidin-4-yl)-1-oxoisoindolin-2-yl)piperidine-2,6-dione C1221.

3-(5-(1-((5,6-Dihydro-8H-imidazo[2,1-c][1,4]oxazin-3-yl)methyl)piperidin-4-yl)-6-fluoro-1-oxoisoindolin-2-yl)piperidine-2,6-dione C1222.

C1221

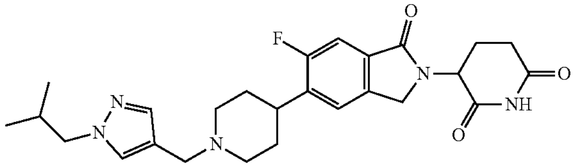

C1222

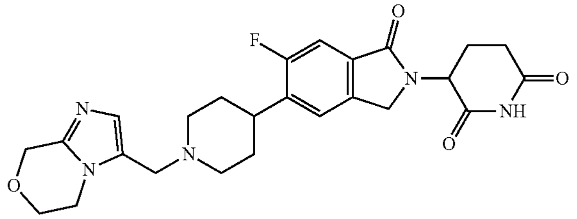

3-(5-(1-((5,6-Dihydro-8H-imidazo[2,1-c][1,4]oxazin-2-yl)methyl)piperidin-4-yl)-6-fluoro-1-oxoisoindolin-2-yl)piperidine-2,6-dione C1223.

3-(5-(1-((5-(Tert-butyl)-1H-pyrrol-2-yl)methyl)piperidin-4-yl)-6-fluoro-1-oxoisoindolin-2-yl)piperidine-2,6-dione C1224.

C1223

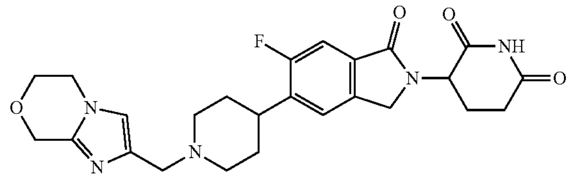

-continued

C1224

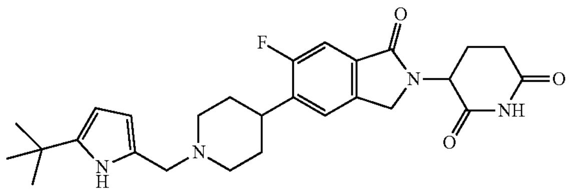

3-(5-(1-((2-(Dimethylamino)pyrimidin-5-yl)methyl)piperidin-4-yl)-6-fluoro-1-oxoisoindolin-2-yl)piperidine-2,6-dione C1225.

3-(6-Fluoro-5-(1-(4-methoxy-3-methylbenzyl)piperidin-4-yl)-1-oxoisoindolin-2-yl)piperidine-2,6-dione C1226.

C1225

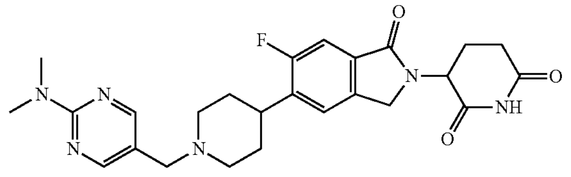

C1226

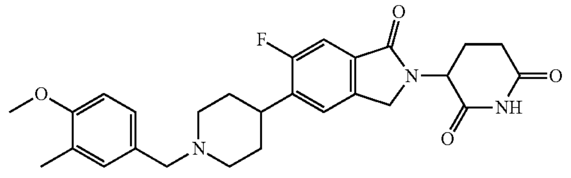

3-(6-Fluoro-5-(1-((1-methyl-1H-imidazol-5-yl)methyl)piperidin-4-yl)-1-oxoisoindolin-2-yl)piperidine-2,6-dione C1227.

3-(6-Fluoro-5-(1-(2-methoxy-3-methylbenzyl)piperidin-4-yl)-1-oxoisoindolin-2-yl)piperidine-2,6-dione C1228.

C1227

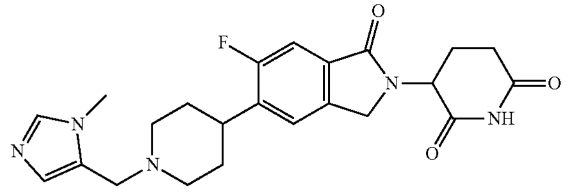

C1228

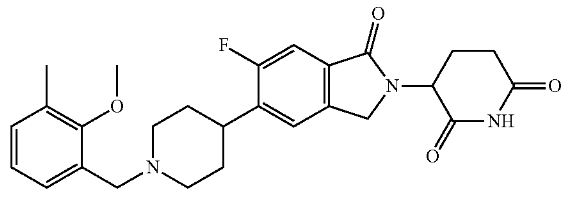

3-(6-Fluoro-5-(1-(3-methoxy-2-methylbenzyl)piperidin-4-yl)-1-oxoisoindolin-2-yl)piperidine-2,6-dione C1229.

3-(6-Fluoro-5-(1-(2-methoxy-6-methylbenzyl)piperidin-4-yl)-1-oxoisoindolin-2-yl)piperidine-2,6-dione C1230.

C1229

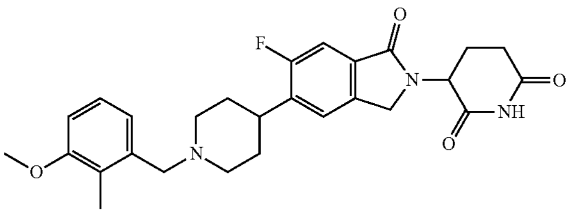

C1230

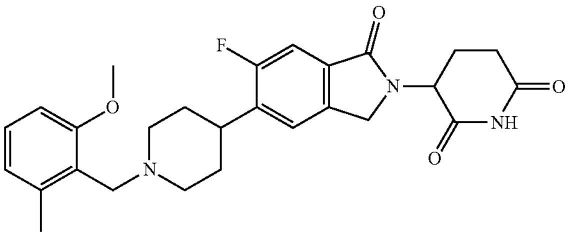

3-(6-Fluoro-5-(1-(3-methoxy-5-methylbenzyl)piperidin-4-yl)-1-oxoisoindolin-2-yl)piperidine-2,6-dione C1231.

3-(6-Fluoro-5-(1-(4-methoxyphenethyl)piperidin-4-yl)-1-oxoisoindolin-2-yl)-piperidine-2,6-dione C1232.

C1231

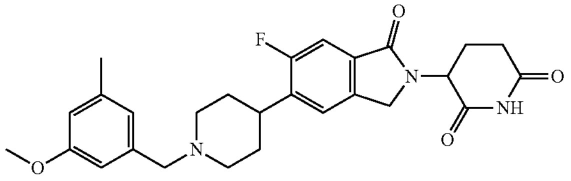

C1232

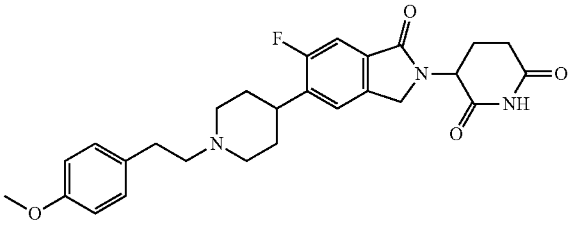

3-(6-Fluoro-5-(1-(3-methoxyphenethyl)piperidin-4-yl)-1-oxoisoindolin-2-yl)-piperidine-2,6-dione C1233.

3-(6-Fluoro-5-(1-(4-methoxy-2-methylbenzyl)piperidin-4-yl)-1-oxoisoindolin-2-yl)piperidine-2,6-dione C1234.

C1233

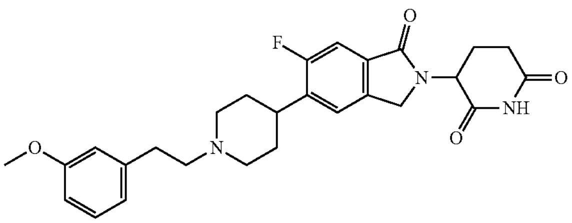

-continued

C1234

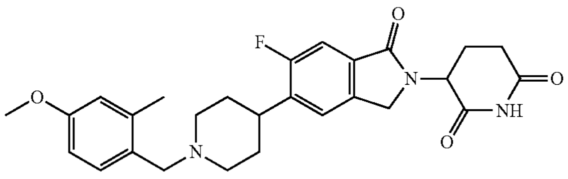

3-(6-Fluoro-5-(1-(4-hydroxy-3,5-dimethylbenzyl)piperidin-4-yl)-1-oxoisoindolin-2-yl)piperidine-2,6-dione C1235.

3-(5-(1-(4-Ethoxybenzyl)piperidin-4-yl)-6-fluoro-1-oxoisoindolin-2-yl)-piperidine-2,6-dione C1236.

C1235

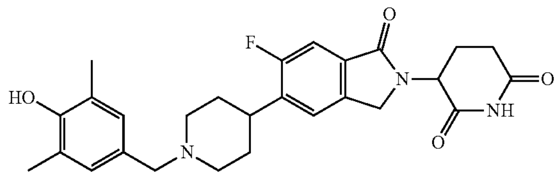

C1236

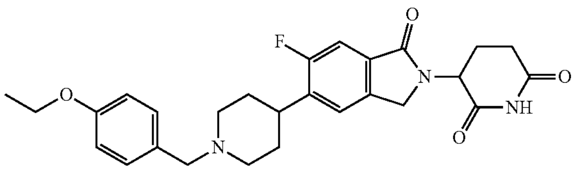

3-(6-Fluoro-5-(1-(3-methoxy-4-methylbenzyl)piperidin-4-yl)-1-oxoisoindolin-2-yl)piperidine-2,6-dione C1237.

3-(6-Fluoro-5-(1-((1-methyl-1H-pyrazol-5-yl)methyl)piperidin-4-yl)-1-oxoisoindolin-2-yl)piperidine-2,6-dione C1238.

C1237

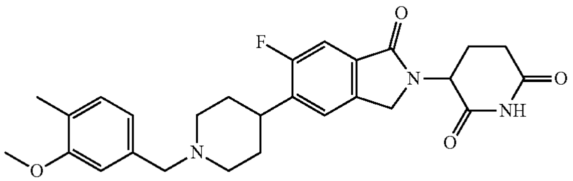

C1238

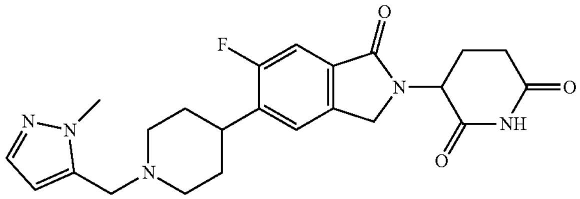

3-(5-(1-((1H-Pyrrol-2-yl)methyl)piperidin-4-yl)-6-fluoro-1-oxoisoindolin-2-yl)-piperidine-2,6-dione C1239.

3-(6-Fluoro-5-(1-(2-methoxy-4-methylbenzyl)piperidin-4-yl)-1-oxoisoindolin-2-yl)piperidine-2,6-dione C1240.

C1239

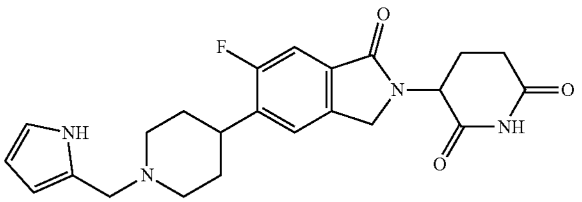

C1240

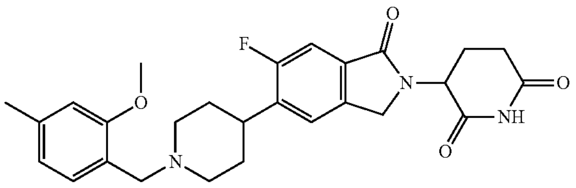

3-(5-(1-(2-(Benzyloxy)ethyl)piperidin-4-yl)-6-fluoro-1-oxoisoindolin-2-yl)-piperidine-2,6-dione C1241.

3-(5-(1-(Benzo[d][1,3]dioxol-4-ylmethyl)piperidin-4-yl)-6-fluoro-1-oxoisoindolin-2-yl)piperidine-2,6-dione C1242.

C1241

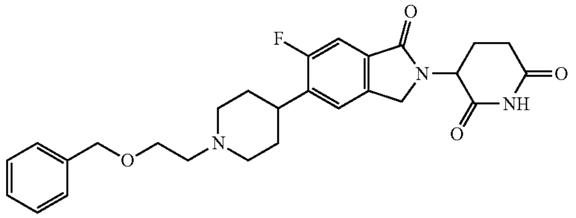

C1242

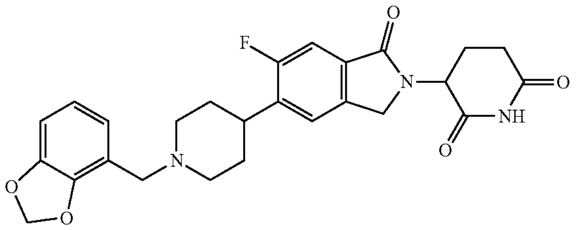

3-(5-(1-(2-(Dimethylamino)benzyl)piperidin-4-yl)-6-fluoro-1-oxoisoindolin-2-yl)piperidine-2,6-dione C1243.

3-(6-Fluoro-5-(1-((5-isopropylpyridin-3-yl)methyl)piperidin-4-yl)-1-oxoisoindolin-2-yl)piperidine-2,6-dione C1244.

C1243

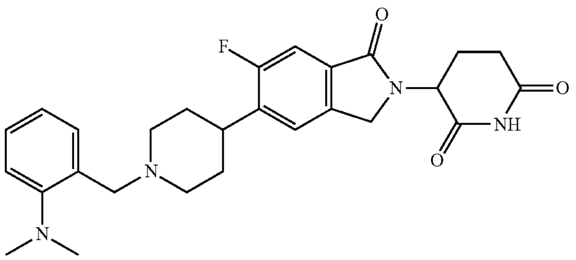

-continued

C1244

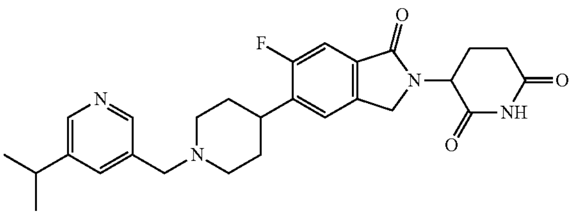

3-(5-(1-(4-(Ethylamino)benzyl)piperidin-4-yl)-6-fluoro-1-oxoisoindolin-2-yl)-piperidine-2,6-dione C1245.

3-(5-(1-(3-(Dimethylamino)benzyl)piperidin-4-yl)-6-fluoro-1-oxoisoindolin-2-yl)piperidine-2,6-dione C1246.

C1245

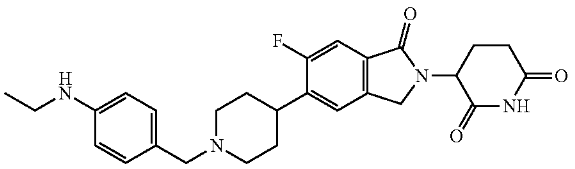

C1246

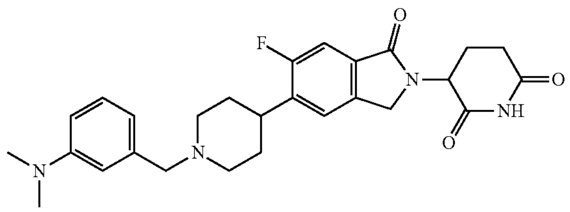

3-((4-(2-(2,6-Dioxopiperidin-3-yl)-6-fluoro-1-oxoisoindolin-5-yl)piperidin-1-yl)-methyl)benzamide C1247.

2-((4-(2-(2,6-Dioxopiperidin-3-yl)-6-fluoro-1-oxoisoindolin-5-yl)piperidin-1-yl)-methyl)-4-fluorobenzonitrile C1248.

C1247

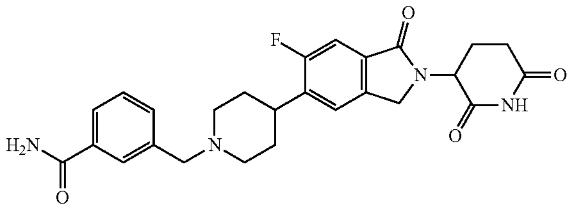

C1248

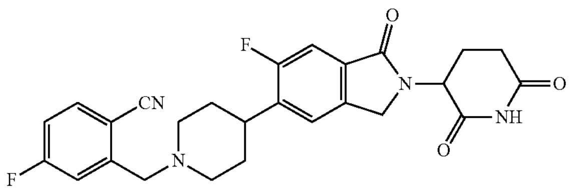

2-((4-(2-(2,6-Dioxopiperidin-3-yl)-6-fluoro-1-oxoisoindolin-5-yl)piperidin-1-yl)-methyl)-5-fluorobenzonitrile C1249.

3-(6-Fluoro-5-(1-((1-methyl-1H-pyrazol-3-yl)methyl)piperidin-4-yl)-1-oxoisoindolin-2-yl)piperidine-2,6-dione C1250.

C1249

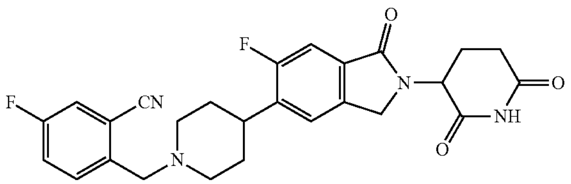

C1250

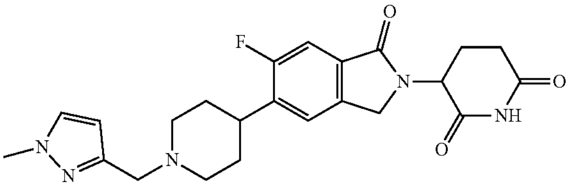

4-((4-(2-(2,6-Dioxopiperidin-3-yl)-6-fluoro-1-oxoisoindolin-5-yl)piperidin-1-yl)-methyl)-3-fluorobenzonitrile C1251.

3-((4-(2-(2,6-Dioxopiperidin-3-yl)-6-fluoro-1-oxoisoindolin-5-yl)piperidin-1-yl)-methyl)-5-fluorobenzonitrile C1252.

C1251

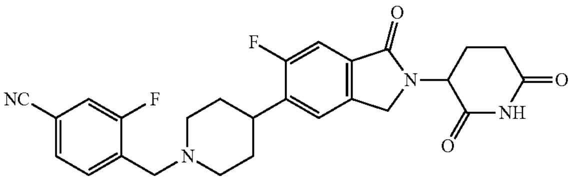

C1252

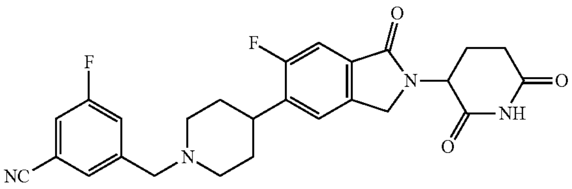

4-((4-(2-(2,6-Dioxopiperidin-3-yl)-6-fluoro-1-oxoisoindolin-5-yl)piperidin-1-yl)-methyl)-2-fluorobenzonitrile C1253.

5-((4-(2-(2,6-Dioxopiperidin-3-yl)-6-fluoro-1-oxoisoindolin-5-yl)piperidin-1-yl)-methyl)-2-fluorobenzonitrile C1254.

C1253

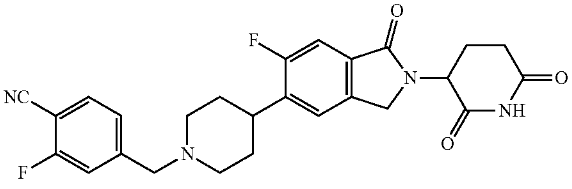

-continued

C1254

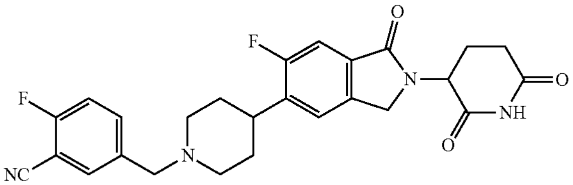

3-(6-Fluoro-1-oxo-5-(1-(2,4,6-trimethylbenzyl)piperidin-4-yl)isoindolin-2-yl)-piperidine-2,6-dione C1255.

3-(6-Fluoro-5-(1-(4-isopropylbenzyl)piperidin-4-yl)-1-oxoisoindolin-2-yl)-piperidine-2,6-dione C1256.

C1255

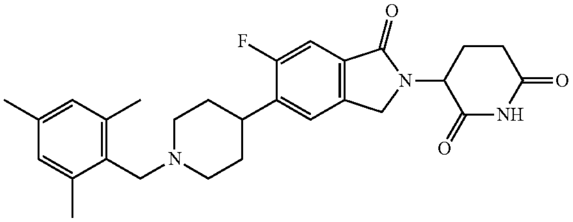

C1256

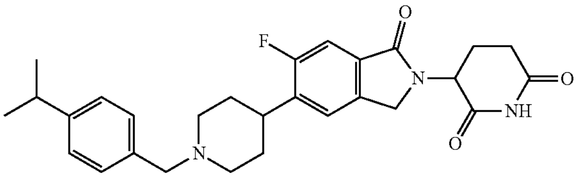

3-(6-Fluoro-1-oxo-5-(1-(4-phenylbutyl)piperidin-4-yl)isoindolin-2-yl)piperidine-2,6-dione C1257.

3-(5-(1-((4,4-Difluorocyclohexyl)methyl)piperidin-4-yl)-6-fluoro-1-oxoisoindolin-2-yl)piperidine-2,6-dione C1258.

C1257

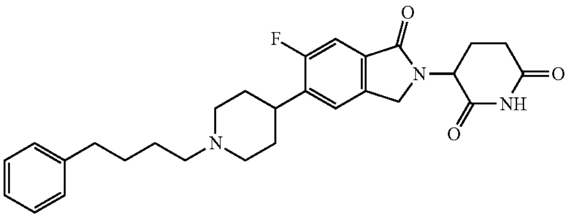

C1258

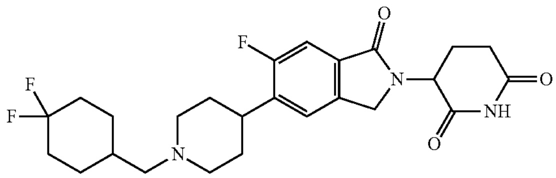

3-(5-(1-(2-Ethynyl-4-fluorobenzyl)piperidin-4-yl)-6-fluoro-1-oxoisoindolin-2-yl)-piperidine-2,6-dione C1259.

3-(5-(1-([1,2,4]Triazolo[1,5-a]pyridin-7-ylmethyl)piperidin-4-yl)-6-fluoro-1-oxoisoindolin-2-yl)piperidine-2,6-dione C1260.

C1259

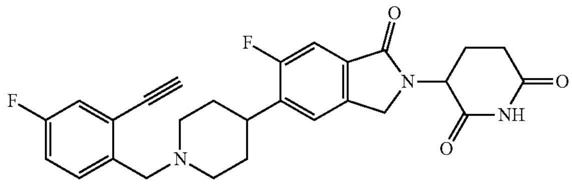

C1260

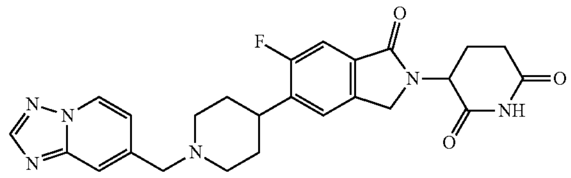

3-(6-Fluoro-5-(1-((1-methyl-1H-imidazol-4-yl)methyl)piperidin-4-yl)-1-oxoisoindolin-2-yl)piperidine-2,6-dione C1261.

3-(6-Fluoro-5-(1-(imidazo[1,2-a]pyrimidin-3-ylmethyl)piperidin-4-yl)-1-oxoisoindolin-2-yl)piperidine-2,6-dione C1262.

C1261

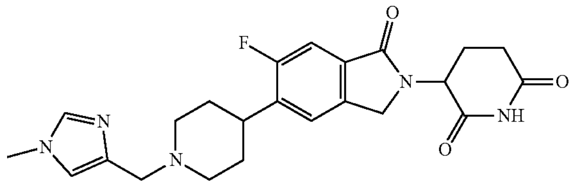

C1262

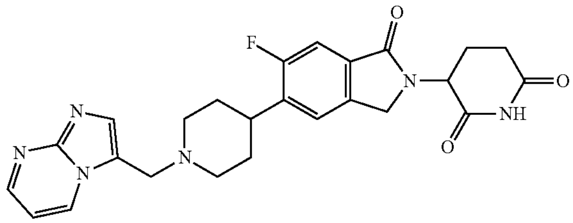

6-Amino-5-((4-(2-(2,6-dioxopiperidin-3-yl)-6-fluoro-1-oxoisoindolin-5-yl)-piperidin-1-yl)methyl)nicotinonitrile C1263.

3-(6-Fluoro-5-(1-(imidazo[1,2-a]pyrimidin-7-ylmethyl)piperidin-4-yl)-1-oxoisoindolin-2-yl)piperidine-2,6-dione C1264.

C1263

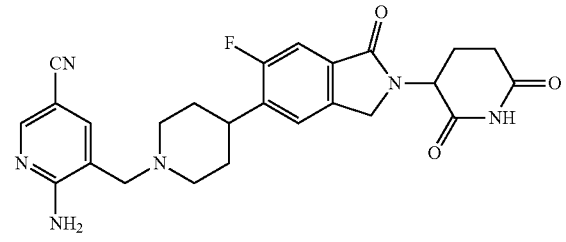

-continued

C1264

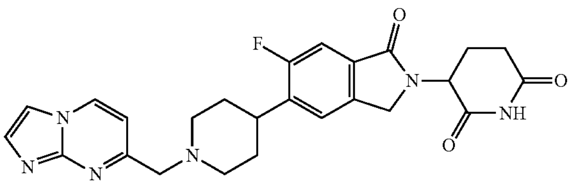

3-(5-(1-((4H-Pyrrolo[2,3-b]pyrazin-7-yl)methyl)piperidin-4-yl)-6-fluoro-1-oxoisoindolin-2-yl)piperidine-2,6-dione C1265.

4-((4-(2-(2,6-Dioxopiperidin-3-yl)-6-fluoro-1-oxoisoindolin-5-yl)piperidin-1-yl)-methyl)-3-hydroxybenzonitrile C1266.

C1265

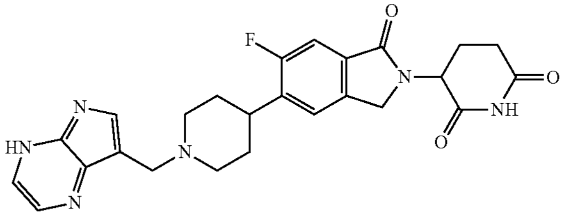

C1266

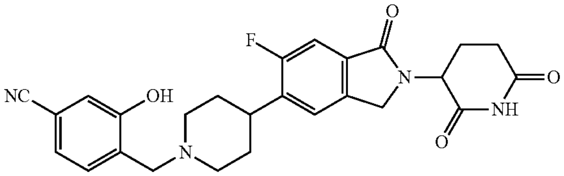

5-((4-(2-(2,6-Dioxopiperidin-3-yl)-6-fluoro-1-oxoisoindolin-5-yl)piperidin-1-yl)-methyl)-2-hydroxybenzonitrile C1267.

3-(6-Fluoro-5-(1-(furo[2,3-c]pyridin-5-ylmethyl)piperidin-4-yl)-1-oxoisoindolin-2-yl)piperidine-2,6-dione C1268.

C1267

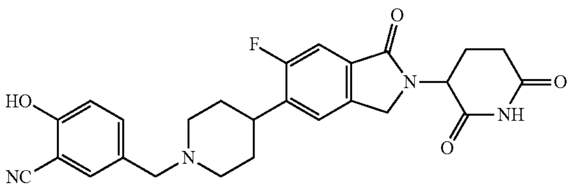

C1268

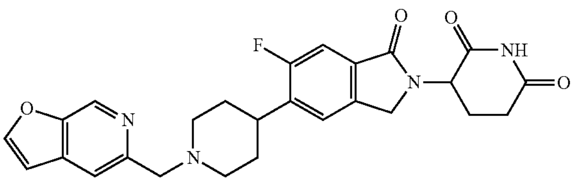

3-(5-(1-(Benzo[d]oxazol-5-ylmethyl)piperidin-4-yl)-6-fluoro-1-oxoisoindolin-2-yl)piperidine-2,6-dione C1269.

3-(5-(1-(Benzo[d]oxazol-6-ylmethyl)piperidin-4-yl)-6-fluoro-1-oxoisoindolin-2-yl)piperidine-2,6-dione C1270.

C1269

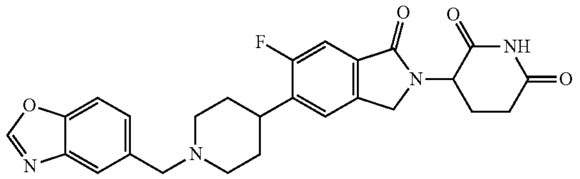

C1270

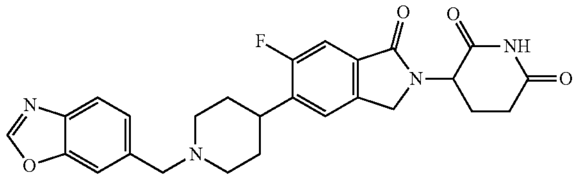

3-(5-(1-((5-Chlorothiophen-2-yl)methyl)piperidin-4-yl)-6-fluoro-1-oxoisoindolin-2-yl)piperidine-2,6-dione C1271.

3-(6-Fluoro-5-(1-((1-methyl-1H-imidazol-2-yl)methyl)piperidin-4-yl)-1-oxoisoindolin-2-yl)piperidine-2,6-dione C1272.

C1271

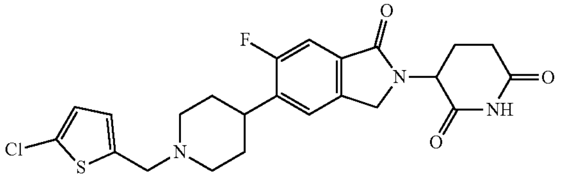

C1272

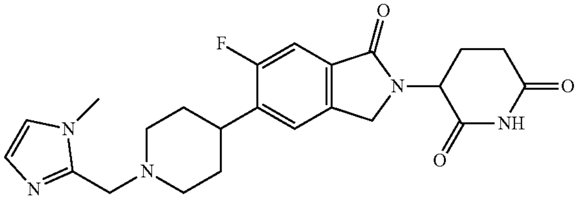

3-(5-(1-((2-Chlorothiophen-3-yl)methyl)piperidin-4-yl)-6-fluoro-1-oxoisoindolin-2-yl)piperidine-2,6-dione C1273.

3-(5-(1-(4-Cyclopropylbenzyl)piperidin-4-yl)-6-fluoro-1-oxoisoindolin-2-yl)-piperidine-2,6-dione C1274.

C1273

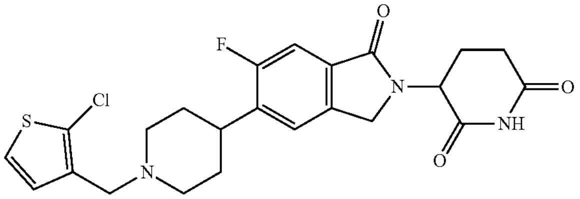

-continued

C1274

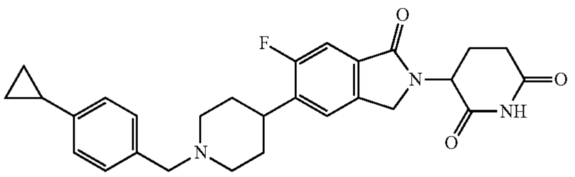

3-(5-(1-(2-Cyclopropylbenzyl)piperidin-4-yl)-6-fluoro-1-oxoisoindolin-2-yl)-piperidine-2,6-dione C1275.

3-(6-Fluoro-1-oxo-5-(1-(pyrazolo[1,5-a]pyridin-7-ylmethyl)piperidin-4-yl)-isoindolin-2-yl)piperidine-2,6-dione C1276.

C1275

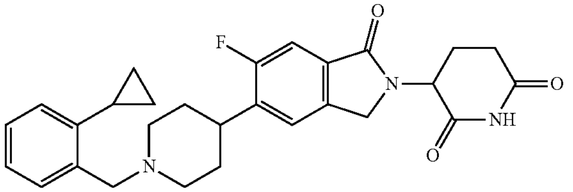

C1276

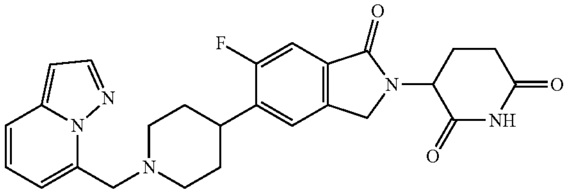

3-(5-(1-((1H-Pyrrolo[2,3-c]pyridin-3-yl)methyl)piperidin-4-yl)-6-fluoro-1-oxoisoindolin-2-yl)piperidine-2,6-dione C1277.

3-(6-Fluoro-5-(1-(imidazo[1,2-a]pyridin-5-ylmethyl)piperidin-4-yl)-1-oxoisoindolin-2-yl)piperidine-2,6-dione C1278.

C1277

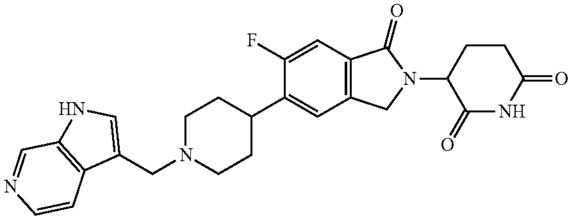

C1278

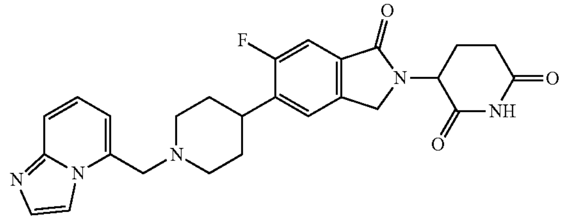

3-(6-Fluoro-1-oxo-5-(1-(pyrazolo[1,5-a]pyridin-3-ylmethyl)piperidin-4-yl)-isoindolin-2-yl)piperidine-2,6-dione C1279.

3-(5-(1-((2H-Indazol-6-yl)methyl)piperidin-4-yl)-6-fluoro-1-oxoisoindolin-2-yl)-piperidine-2,6-dione C1280.

C1279

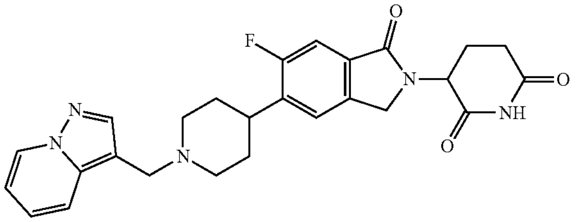

C1280

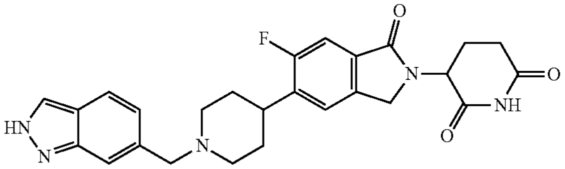

3-(5-(1-((1H-Pyrrolo[3,2-b]pyridin-3-yl)methyl)piperidin-4-yl)-6-fluoro-1-oxoisoindolin-2-yl)piperidine-2,6-dione C1281.

3-(6-Fluoro-5-(1-(imidazo[1,5-a]pyridin-1-ylmethyl)piperidin-4-yl)-1-oxoisoindolin-2-yl)piperidine-2,6-dione C1282.

C1281

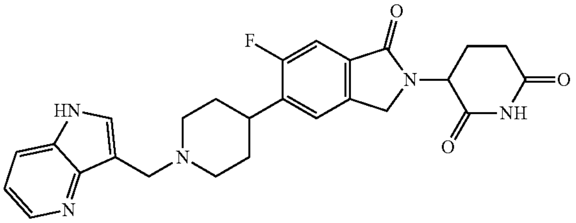

C1282

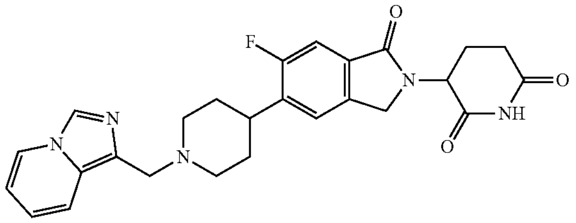

3-(6-Fluoro-5-(1-((5-methyl-1H-pyrazol-3-yl)methyl)piperidin-4-yl)-1-oxoisoindolin-2-yl)piperidine-2,6-dione C1283.

3-(5-(1-((1H-Pyrrolo[2,3-b]pyridin-6-yl)methyl)piperidin-4-yl)-6-fluoro-1-oxoisoindolin-2-yl)piperidine-2,6-dione C1284.

C1283

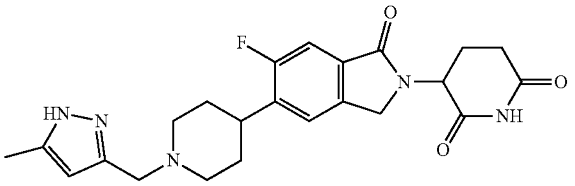

C1284

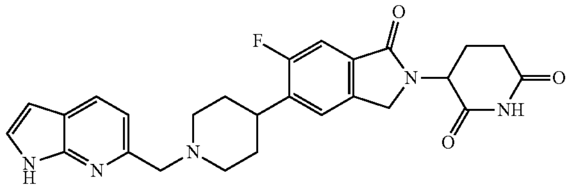

3-(5-(1-((1H-Benzo[d]imidazol-7-yl)methyl)piperidin-4-yl)-6-fluoro-1-oxoisoindolin-2-yl)piperidine-2,6-dione C1285.

3-(6-Fluoro-5-(1-(imidazo[1,2-a]pyridin-6-ylmethyl)piperidin-4-yl)-1-oxoisoindolin-2-yl)piperidine-2,6-dione C1286.

C1285

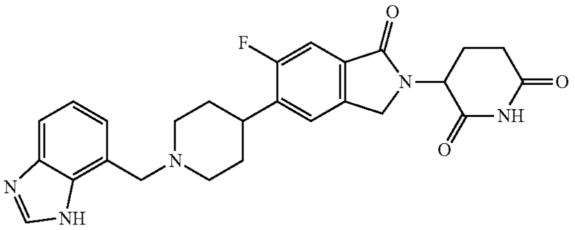

C1286

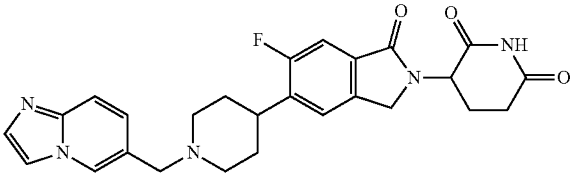

3-(6-Fluoro-5-(1-(imidazo[1,2-a]pyridin-8-ylmethyl)piperidin-4-yl)-1-oxoisoindolin-2-yl)piperidine-2,6-dione C1287.

3-(6-Fluoro-5-(1-(imidazo[1,2-a]pyridin-7-ylmethyl)piperidin-4-yl)-1-oxoisoindolin-2-yl)piperidine-2,6-dione C1288.

C1287

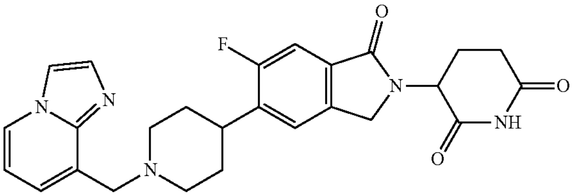

-continued

C1288

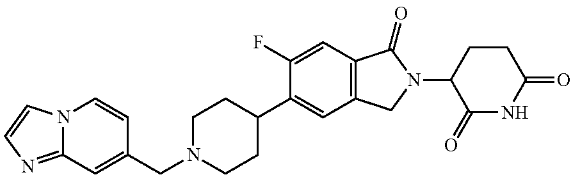

3-(5-(1-((1H-Pyrrolo[3,2-b]pyridin-6-yl)methyl)piperidin-4-yl)-6-fluoro-1-oxoisoindolin-2-yl)piperidine-2,6-dione C1289.

3-(5-(1-((1H-Benzo[d]imidazol-2-yl)methyl)piperidin-4-yl)-6-fluoro-1-oxoisoindolin-2-yl)piperidine-2,6-dione C1290.

C1289

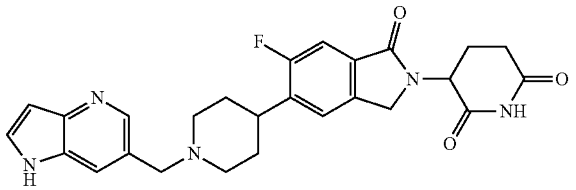

C1290

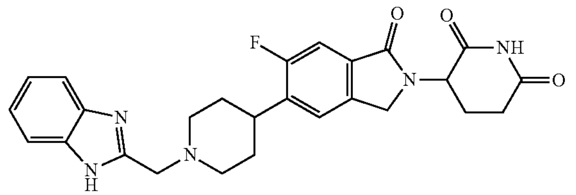

3-(6-Fluoro-5-(1-(imidazo[1,2-a]pyridin-3-ylmethyl)piperidin-4-yl)-1-oxoisoindolin-2-yl)piperidine-2,6-dione C1291.

3-(6-Fluoro-5-(1-(imidazo[1,2-a]pyridin-2-ylmethyl)piperidin-4-yl)-1-oxoisoindolin-2-yl)piperidine-2,6-dione C1292.

C1291

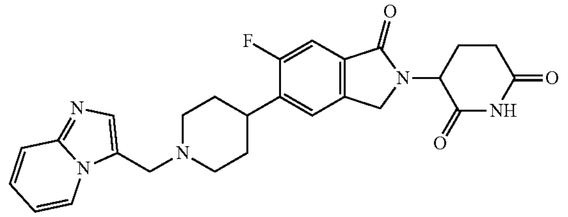

C1292

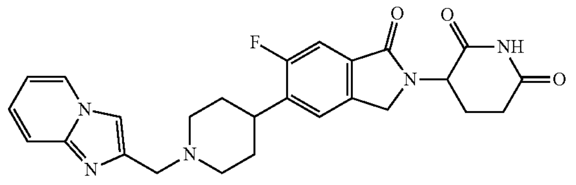

3-(5-(1-(Benzofuran-4-ylmethyl)piperidin-4-yl)-6-fluoro-1-oxoisoindolin-2-yl)-piperidine-2,6-dione C1293.

3-(6-Fluoro-5-(1-((5-methylfuran-2-yl)methyl)piperidin-4-yl)-1-oxoisoindolin-2-yl)-piperidine-2,6-dione C1294.

C1293

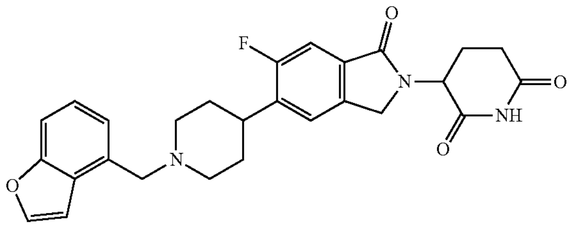

C1294

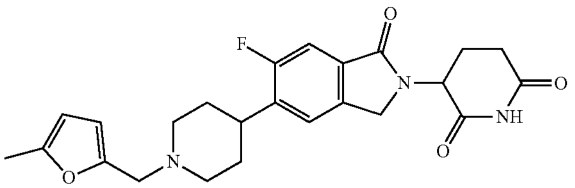

3-(5-(1-(Benzofuran-7-ylmethyl)piperidin-4-yl)-6-fluoro-1-oxoisoindolin-2-yl)-piperidine-2,6-dione C1295.

3-(5-(1-(Benzofuran-5-ylmethyl)piperidin-4-yl)-6-fluoro-1-oxoisoindolin-2-yl)-piperidine-2,6-dione C1296.

C1295

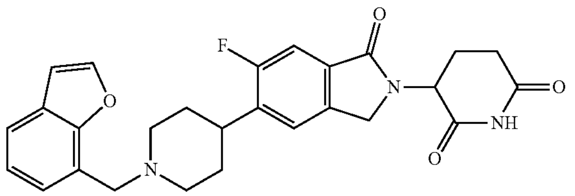

C1296

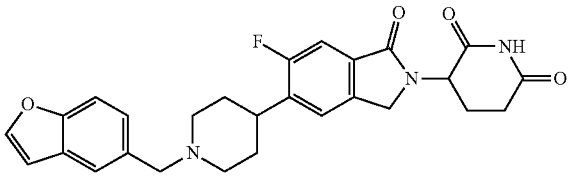

2-((4-(2-(2,6-Dioxopiperidin-3-yl)-6-fluoro-1-oxoisoindolin-5-yl)piperidin-1-yl)-methyl)-5-methylbenzonitrile C1297.

3-((4-(2-(2,6-Dioxopiperidin-3-yl)-6-fluoro-1-oxoisoindolin-5-yl)piperidin-1-yl)-methyl)-2-methylbenzonitrile C1298.

C1297

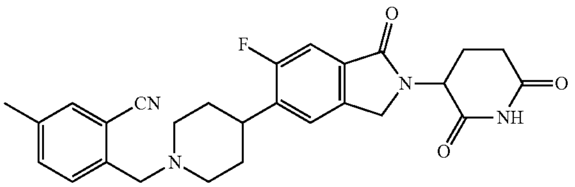

-continued

C1298

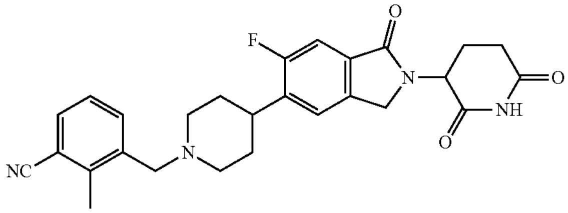

3-((4-(2-(2,6-Dioxopiperidin-3-yl)-6-fluoro-1-oxoisoindolin-5-yl)piperidin-1-yl)-methyl)-5-methylbenzonitrile C1299.

2-((4-(2-(2,6-Dioxopiperidin-3-yl)-6-fluoro-1-oxoisoindolin-5-yl)piperidin-1-yl)-methyl)-6-methylbenzonitrile C1300.

C1299

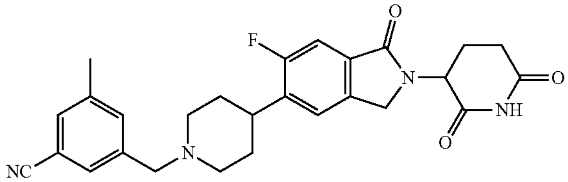

C1300

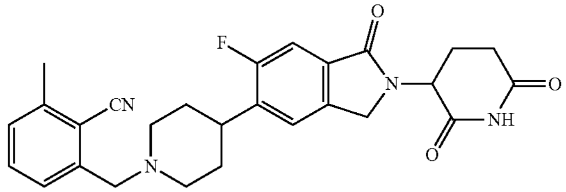

4-((4-(2-(2,6-Dioxopiperidin-3-yl)-6-fluoro-1-oxoisoindolin-5-yl)piperidin-1-yl)-methyl)-3-methylbenzonitrile C1301.

3-(5-(1-((1H-Indol-3-yl)methyl)piperidin-4-yl)-6-fluoro-1-oxoisoindolin-2-yl)-piperidine-2,6-dione C1302.

C1301

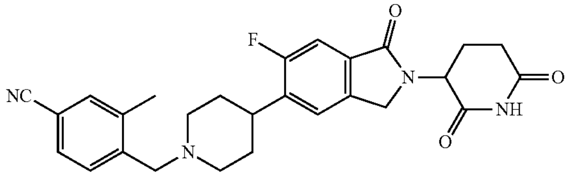

C1302

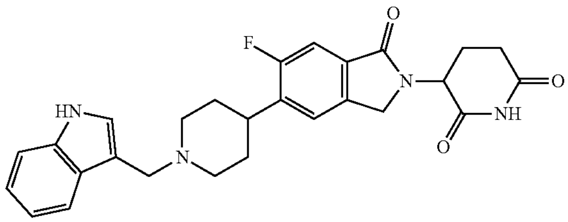

3-(6-Fluoro-5-(1-(indolizin-1-ylmethyl)piperidin-4-yl)-1-oxoisoindolin-2-yl)-piperidine-2,6-dione C1303.

3-(5-(1-((1H-Indol-7-yl)methyl)piperidin-4-yl)-6-fluoro-1-oxoisoindolin-2-yl)-piperidine-2,6-dione C1304.

C1303

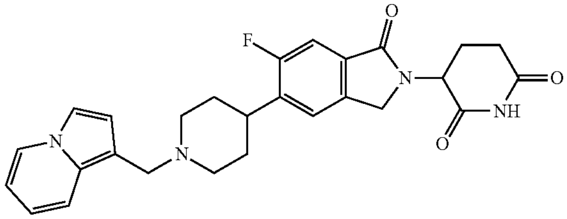

C1304

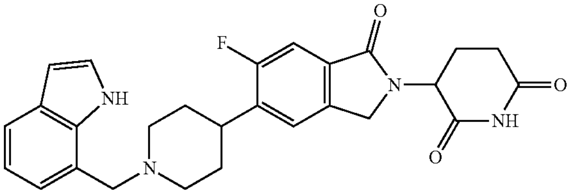

3-(6-Fluoro-5-(1-((3-methyl-1H-pyrrol-2-yl)methyl)piperidin-4-yl)-1-oxoisoindolin-2-yl)piperidine-2,6-dione C1305.

3-(5-(1-((1H-Indol-2-yl)methyl)piperidin-4-yl)-6-fluoro-1-oxoisoindolin-2-yl)-piperidine-2,6-dione C1306.

C1305

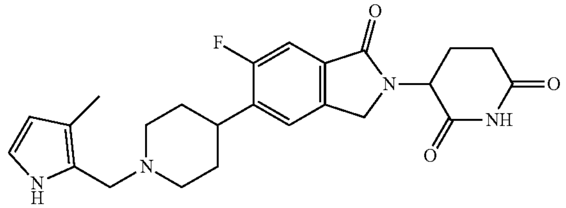

C1306

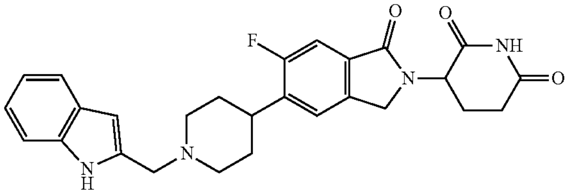

3-(5-(1-((1H-Indol-6-yl)methyl)piperidin-4-yl)-6-fluoro-1-oxoisoindolin-2-yl)-piperidine-2,6-dione C1307.

3-(5-(1-((4-Chloro-1-methyl-1H-pyrazol-3-yl)methyl)piperidin-4-yl)-6-fluoro-1-oxoisoindolin-2-yl)piperidine-2,6-dione C1308.

C1307

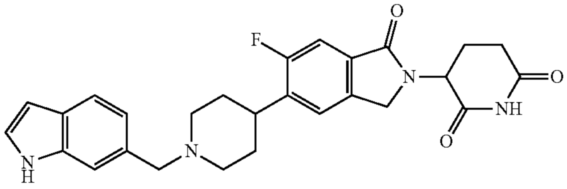

-continued

C1308

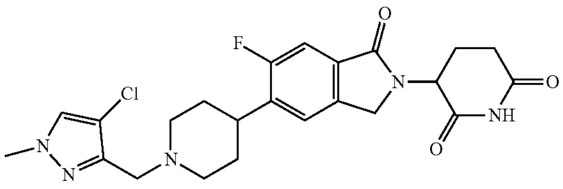

3-(5-(1-((3-Chloropyrazin-2-yl)methyl)piperidin-4-yl)-6-fluoro-1-oxoisoindolin-2-yl)piperidine-2,6-dione C1309.

3-(5-(1-((3-Chloropyridin-4-yl)methyl)piperidin-4-yl)-6-fluoro-1-oxoisoindolin-2-yl)piperidine-2,6-dione C1310.

C1309

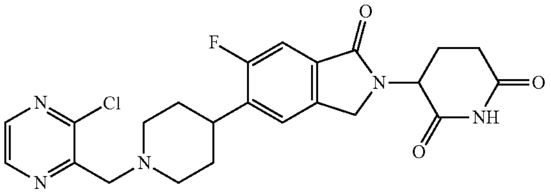

C1310

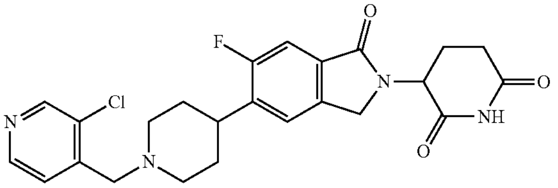

3-(5-(1-((6-Chloropyridin-2-yl)methyl)piperidin-4-yl)-6-fluoro-1-oxoisoindolin-2-yl)piperidine-2,6-dione C1311.

3-(6-Fluoro-5-(1-((5-fluoro-2-oxo-1,2-dihydropyridin-3-yl)methyl)piperidin-4-yl)-1-oxoisoindolin-2-yl)piperidine-2,6-dione C1312.

C1311

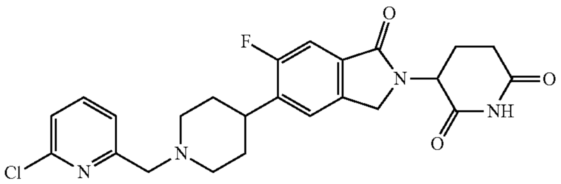

C1312

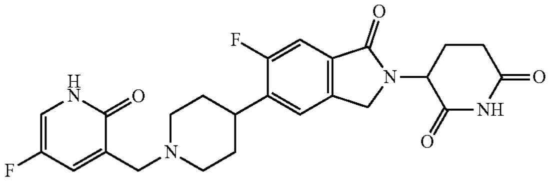

3-(5-(1-(2-Chlorobenzyl)piperidin-4-yl)-6-fluoro-1-oxoisoindolin-2-yl)piperidine-2,6-dione C1313.

3-(5-(1-(4-Chlorobenzyl)piperidin-4-yl)-6-fluoro-1-oxoisoindolin-2-yl)piperidine-2,6-dione C1314.

C1313

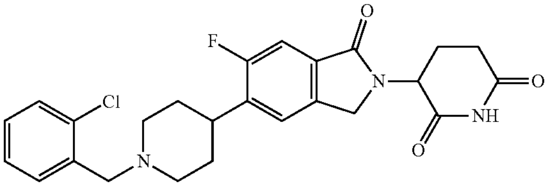

C1314

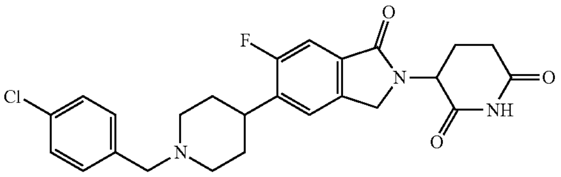

3-(5-(1-(3-Chlorobenzyl)piperidin-4-yl)-6-fluoro-1-oxoisoindolin-2-yl)piperidine-2,6-dione C1315.

3-(6-Fluoro-5-(1-((5-methyl-1H-pyrrol-2-yl)methyl)piperidin-4-yl)-1-oxoisoindolin-2-yl)piperidine-2,6-dione C1316.

C1315

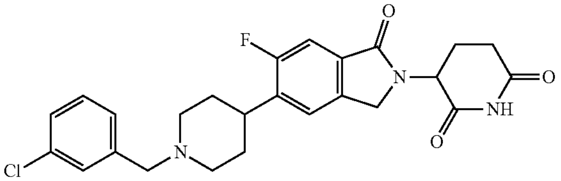

C1316

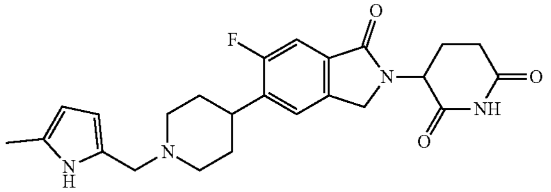

3-(5-(1-(2-Amino-5-fluorobenzyl)piperidin-4-yl)-6-fluoro-1-oxoisoindolin-2-yl)-piperidine-2,6-dione C1317.

3-(6-Fluoro-5-(1-((1-isopropyl-1H-pyrazol-4-yl)methyl)piperidin-4-yl)-1-oxoisoindolin-2-yl)piperidine-2,6-dione C1318.

C1317

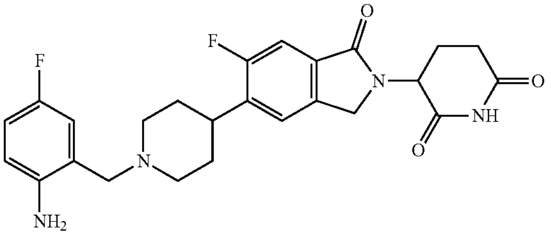

-continued

C1318

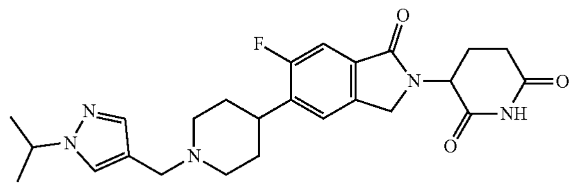

3-(6-Fluoro-5-(1-((4-isopropylfuran-2-yl)methyl)piperidin-4-yl)-1-oxoisoindolin-2-yl)piperidine-2,6-dione C1319.

C1319

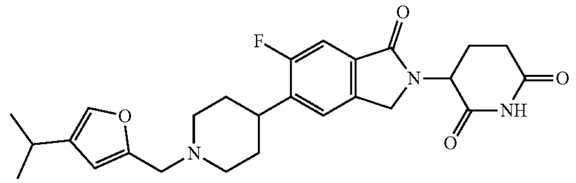

3-(6-Fluoro-5-(1-(3-(5-methylfuran-2-yl)propyl)piperidin-4-yl)-1-oxoisoindolin-2-yl)piperidine-2,6-dione C1320.

C1320

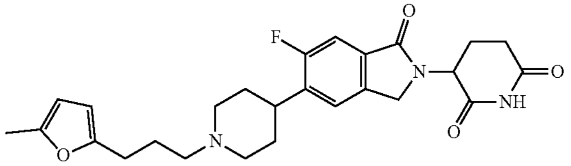

3-(6-Fluoro-5-(1-(4-fluorophenethyl)piperidin-4-yl)-1-oxoisoindolin-2-yl)-piperidine-2,6-dione C1321.

3-(6-Fluoro-5-(1-(3-fluoro-2-methylbenzyl)piperidin-4-yl)-1-oxoisoindolin-2-yl)-piperidine-2,6-dione C1322.

C1321

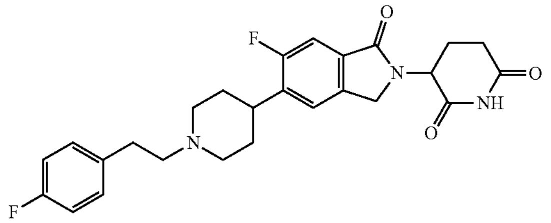

C1322

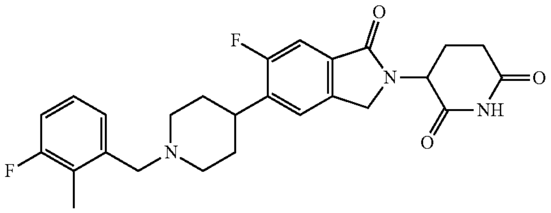

3-(6-Fluoro-5-(1-(2-fluoro-5-methylbenzyl)piperidin-4-yl)-1-oxoisoindolin-2-yl)-piperidine-2,6-dione C1323.

3-(6-Fluoro-5-(1-(4-fluoro-3-methylbenzyl)piperidin-4-yl)-1-oxoisoindolin-2-yl)-piperidine-2,6-dione C1324.

C1323

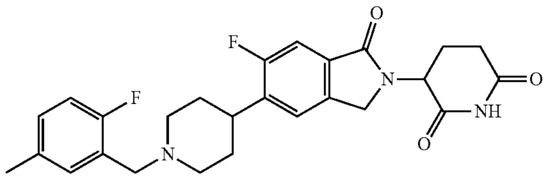

C1324

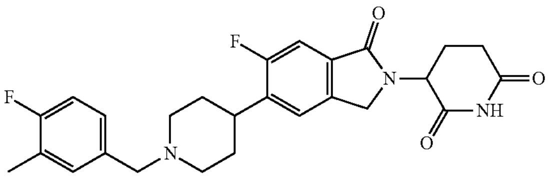

3-(6-Fluoro-5-(1-(3-fluoro-5-methylbenzyl)piperidin-4-yl)-1-oxoisoindolin-2-yl)-piperidine-2,6-dione C1325.

3-(6-Fluoro-5-(1-(4-fluoro-2-methylbenzyl)piperidin-4-yl)-1-oxoisoindolin-2-yl)-piperidine-2,6-dione C1326.

C1325

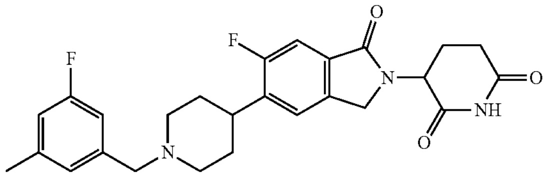

C1326

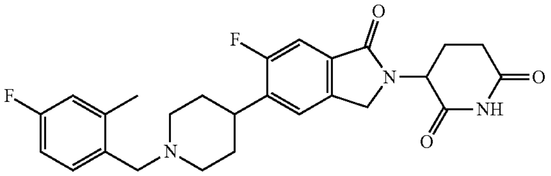

3-(6-Fluoro-5-(1-((1-methyl-1H-pyrrol-2-yl)methyl)piperidin-4-yl)-1-oxoisoindolin-2-yl)piperidine-2,6-dione C1327.

3-(6-Fluoro-5-(1-(5-fluoro-2-methylbenzyl)piperidin-4-yl)-1-oxoisoindolin-2-yl)-piperidine-2,6-dione C1328.

C1327

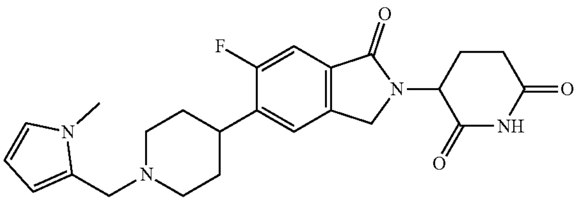

-continued

C1328

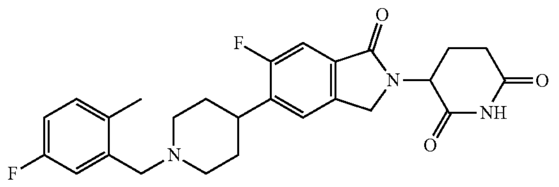

3-(6-Fluoro-5-(1-((5-methoxypyrazin-2-yl)methyl)piperidin-4-yl)-1-oxoisoindolin-2-yl)piperidine-2,6-dione C1329.

3-(6-Fluoro-5-(1-((2-methoxypyrimidin-4-yl)methyl)piperidin-4-yl)-1-oxoisoindolin-2-yl)piperidine-2,6-dione C1330.

C1329

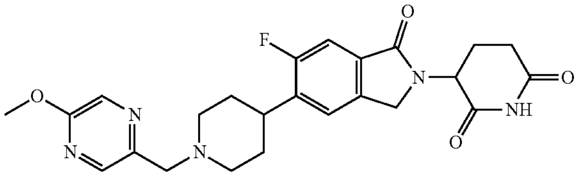

C1330

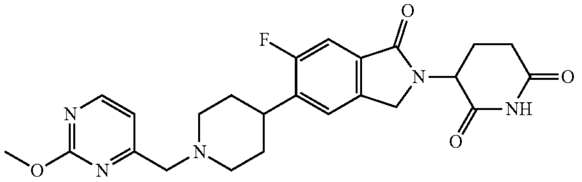

5-((4-(2-(2,6-Dioxopiperidin-3-yl)-6-fluoro-1-oxoisoindolin-5-yl)piperidin-1-yl)-methyl)thiophene-2-carbonitrile C1331.

3-(6-Fluoro-5-(1-((2-methoxypyridin-4-yl)methyl)piperidin-4-yl)-1-oxoisoindolin-2-yl)piperidine-2,6-dione C1332.

C1331

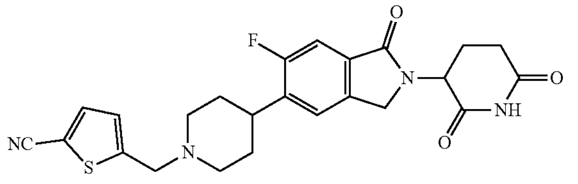

C1332

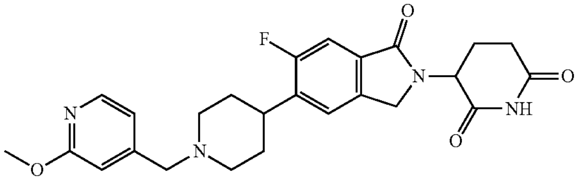

3-(6-Fluoro-5-(1-((2-methoxypyridin-3-yl)methyl)piperidin-4-yl)-1-oxoisoindolin-2-yl)piperidine-2,6-dione C1333.

3-(6-Fluoro-5-(1-((3-methoxypyridin-4-yl)methyl)piperidin-4-yl)-1-oxoisoindolin-2-yl)piperidine-2,6-dione C1334.

C1333

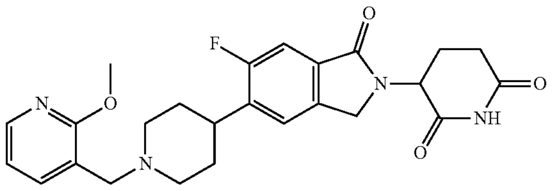

C1334

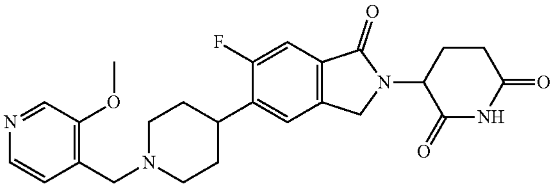

3-(6-Fluoro-5-(1-((6-methoxypyridin-3-yl)methyl)piperidin-4-yl)-1-oxoisoindolin-2-yl)piperidine-2,6-dione C1335.

3-(6-Fluoro-5-(1-((4-methoxypyridin-2-yl)methyl)piperidin-4-yl)-1-oxoisoindolin-2-yl)piperidine-2,6-dione C1336.

C1335

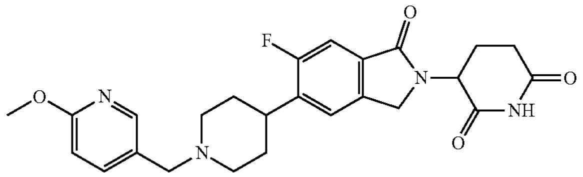

C1336

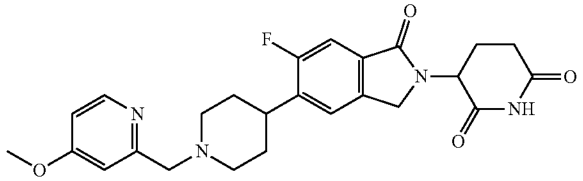

3-(6-Fluoro-5-(1-((5-methoxypyridin-2-yl)methyl)piperidin-4-yl)-1-oxoisoindolin-2-yl)piperidine-2,6-dione C1337.

3-(6-Fluoro-1-oxo-5-(1-(pyrimidin-5-ylmethyl)piperidin-4-yl)isoindolin-2-yl)piperidine-2,6-dione C1338.

C1337

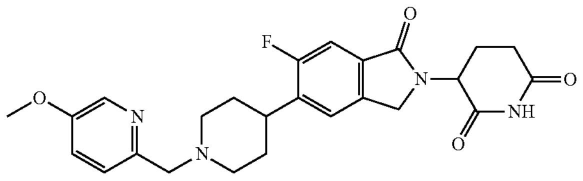

-continued

C1338

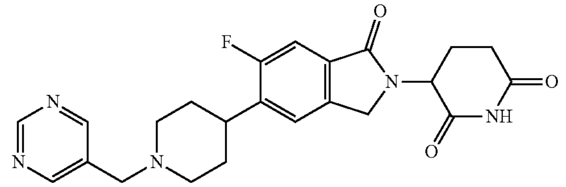

3-(6-Fluoro-5-(1-((3-methoxypyridin-2-yl)methyl)piperidin-4-yl)-1-oxoisoindolin-2-yl)piperidine-2,6-dione C1339.

3-(6-Fluoro-5-(1-((4-methoxypyridin-3-yl)methyl)piperidin-4-yl)-1-oxoisoindolin-2-yl)piperidine-2,6-dione C1340.

C1339

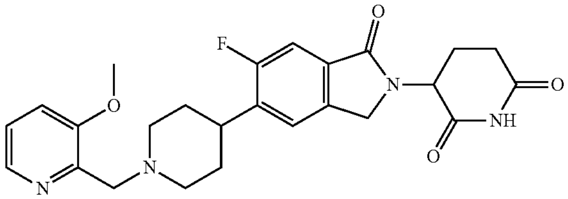

C1340

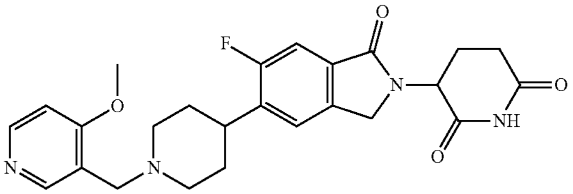

3-(6-Fluoro-5-(1-((6-methoxypyridin-2-yl)methyl)piperidin-4-yl)-1-oxoisoindolin-2-yl)piperidine-2,6-dione C1341.

3-(6-Fluoro-5-(1-((5-methoxypyridin-3-yl)methyl)piperidin-4-yl)-1-oxoisoindolin-2-yl)piperidine-2,6-dione C1342.

C1341

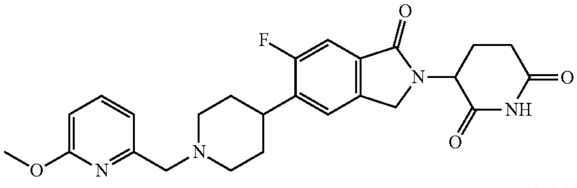

C1342

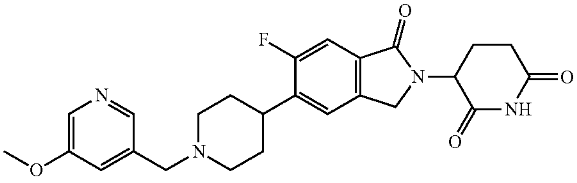

3-(6-Fluoro-5-(1-((1-methyl-6-oxo-1,6-dihydropyridin-2-yl)methyl)piperidin-4-yl)-1-oxoisoindolin-2-yl)piperidine-2,6-dione C1343.

3-(6-Fluoro-5-(1-((1-methyl-2-oxo-1,2-dihydropyridin-4-yl)methyl)piperidin-4-yl)-1-oxoisoindolin-2-yl)piperidine-2,6-dione C1344.

C1343

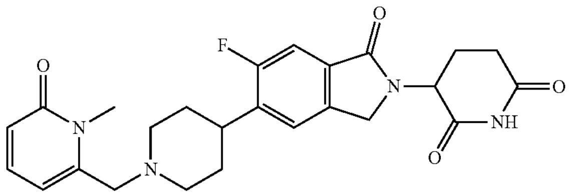

C1344

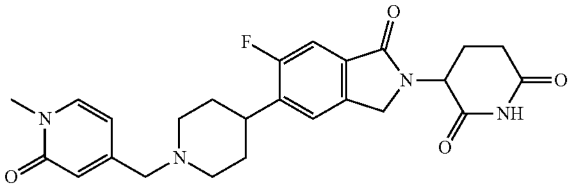

3-(5-(1-((2-Amino-5-methylpyridin-3-yl)methyl)piperidin-4-yl)-6-fluoro-1-oxoisoindolin-2-yl)piperidine-2,6-dione C1345.

3-(6-Fluoro-5-(1-(2-methoxybenzyl)piperidin-4-yl)-1-oxoisoindolin-2-yl)-piperidine-2,6-dione C1346.

C1345

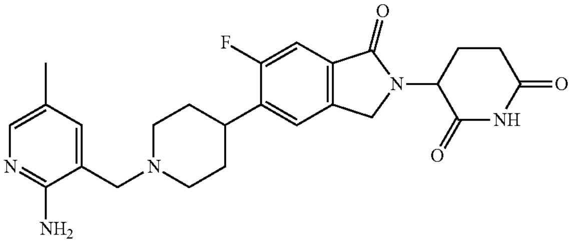

C1346

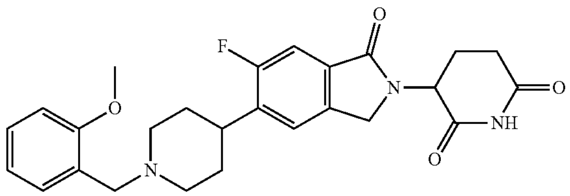

3-(6-Fluoro-5-(1-(4-methoxybenzyl)piperidin-4-yl)-1-oxoisoindolin-2-yl)-piperidine-2,6-dione C1347.

3-(6-Fluoro-5-(1-(3-hydroxy-5-methylbenzyl)piperidin-4-yl)-1-oxoisoindolin-2-yl)piperidine-2,6-dione C1348.

C1347

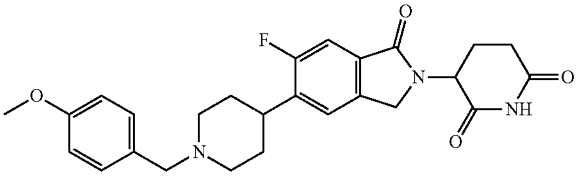

-continued

C1348

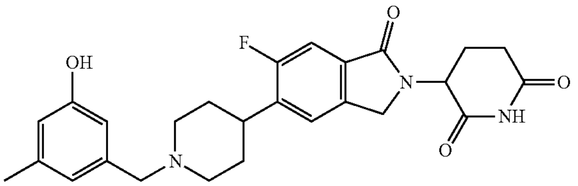

3-(6-Fluoro-1-oxo-5-(1-(pyridin-2-ylmethyl)piperidin-4-yl)isoindolin-2-yl)-piperidine-2,6-dione C1349.

3-(5-(1-(Cyclobutylmethyl)piperidin-4-yl)-6-fluoro-1-oxoisoindolin-2-yl)-piperidine-2,6-dione C1350.

C1349

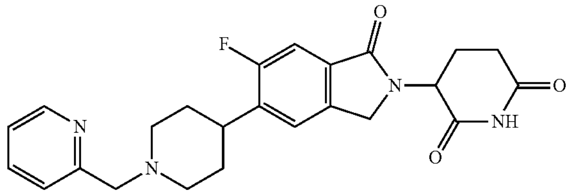

C1350

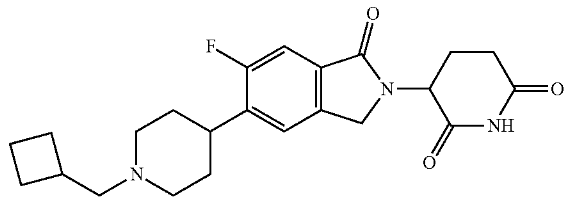

3-(5-(1-(Cyclopropylsulfonyl)piperidin-4-yl)-6-fluoro-1-oxoisoindolin-2-yl)-piperidine-2,6-dione C2001.

3-(6-Fluoro-1-oxo-5-(1-(propylsulfonyl)piperidin-4-yl)isoindolin-2-yl)piperidine-2,6-dione C2002.

C2001

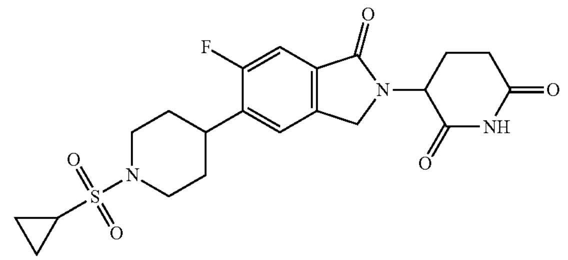

C2002

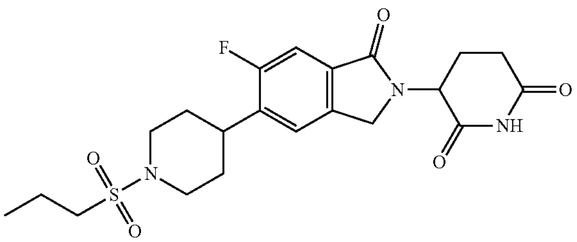

3-(6-Fluoro-5-(1-(isopropylsulfonyl)piperidin-4-yl)-1-oxoisoindolin-2-yl)-piperidine-2,6-dione C2003.

3-(6-Fluoro-5-(1-(isobutylsulfonyl)piperidin-4-yl)-1-oxoisoindolin-2-yl)-piperidine-2,6-dione C2004.

C2003

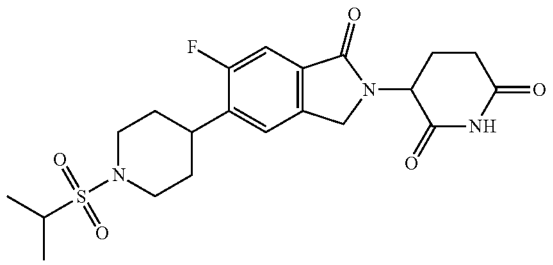

C2004

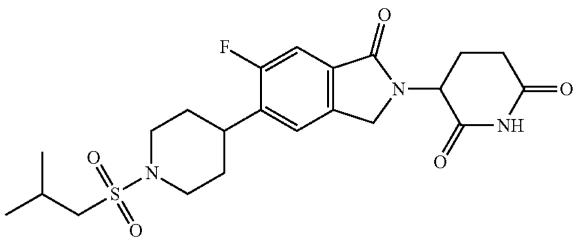

3-(6-Fluoro-5-(1-(furan-3-ylsulfonyl)piperidin-4-yl)-1-oxoisoindolin-2-yl)-piperidine-2,6-dione C2005.

3-(5-(1-((1H-Pyrazol-4-yl)sulfonyl)piperidin-4-yl)-6-fluoro-1-oxoisoindolin-2-yl)piperidine-2,6-dione C2006.

C2005

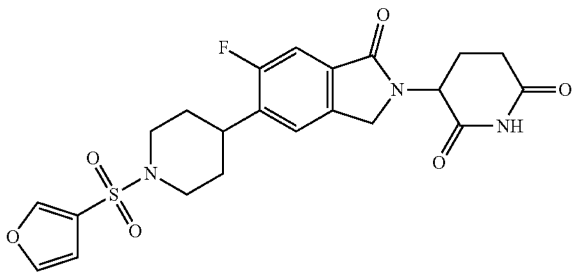

C2006

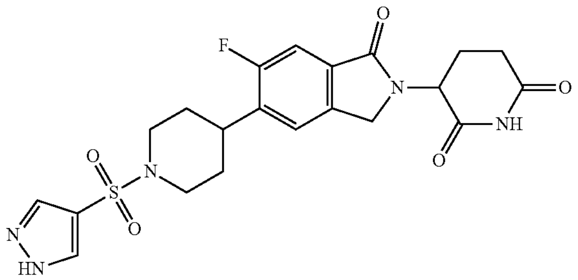

3-(6-Fluoro-1-oxo-5-(1-((trifluoromethyl)sulfonyl)piperidin-4-yl)isoindolin-2-yl)-piperidine-2,6-dione C2007.

3-(5-(1-(((Cyclobutylmethyl)sulfonyl)piperidin-4-yl)-6-fluoro-1-oxoisoindolin-2-yl)piperidine-2,6-dione C2008.

C2007

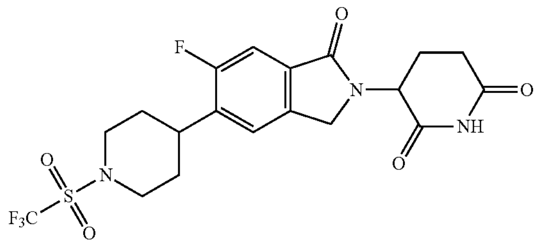

C2008

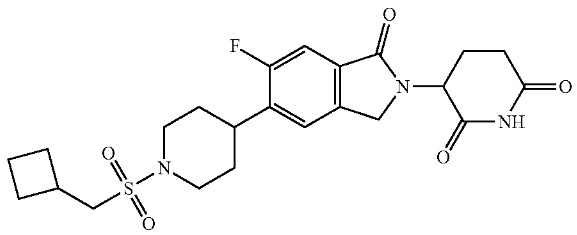

3-(5-(1-((3-Chloropropyl)sulfonyl)piperidin-4-yl)-6-fluoro-1-oxoisoindolin-2-yl)-piperidine-2,6-dione C2009.

3-(6-Fluoro-1-oxo-5-(1-(pyridin-3-ylsulfonyl)piperidin-4-yl)isoindolin-2-yl)-piperidine-2,6-dione C2010.

C2009

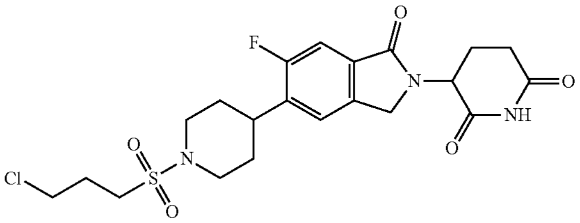

C2010

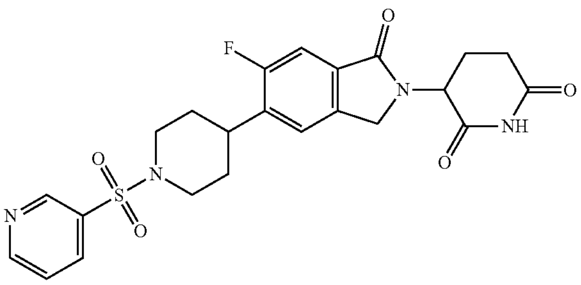

3-(6-Fluoro-5-(1-((1-methyl-1H-pyrazol-4-yl)sulfonyl)piperidin-4-yl)-1-oxoisoindolin-2-yl)piperidine-2,6-dione C2011.

3-(6-Fluoro-5-(1-((1-methyl-1H-pyrazol-3-yl)sulfonyl)piperidin-4-yl)-1-oxoisoindolin-2-yl)piperidine-2,6-dione C2012.

C2011

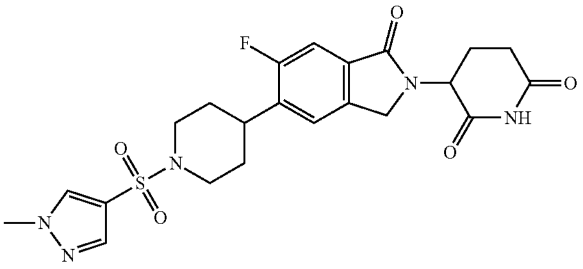

C2012

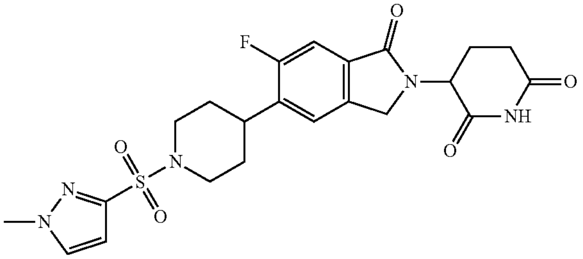

3-(6-Fluoro-5-(1-((1-methyl-1H-imidazol-4-yl)sulfonyl)piperidin-4-yl)-1-oxoisoindolin-2-yl)piperidine-2,6-dione C2013.

3-(6-Fluoro-1-oxo-5-(1-(thiophen-2-ylsulfonyl)piperidin-4-yl)isoindolin-2-yl)-piperidine-2,6-dione C2014.

C2013

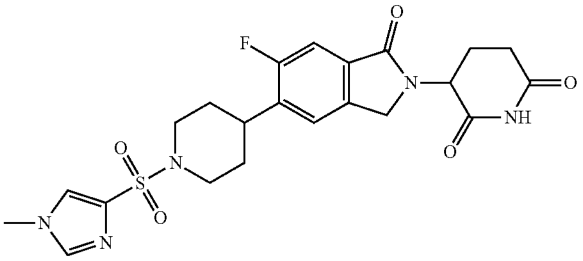

C2014

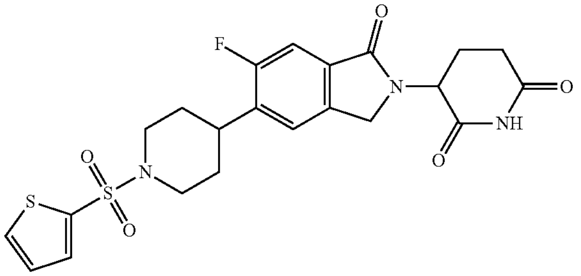

3-(5-(1-(Cyclohexylsulfonyl)piperidin-4-yl)-6-fluoro-1-oxoisoindolin-2-yl)-piperidine-2,6-dione C2015.

3-(6-Fluoro-1-oxo-5-(1-((tetrahydro-2H-pyran-4-yl)sulfonyl)piperidin-4-yl)-isoindolin-2-yl)piperidine-2,6-dione C2016.

C2015

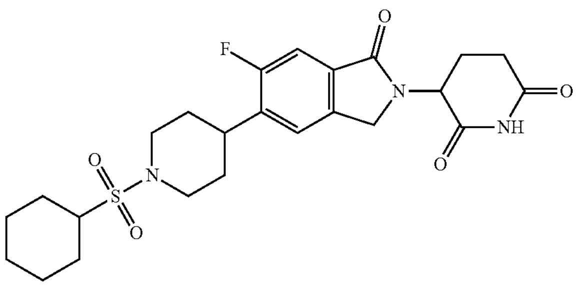

C2016

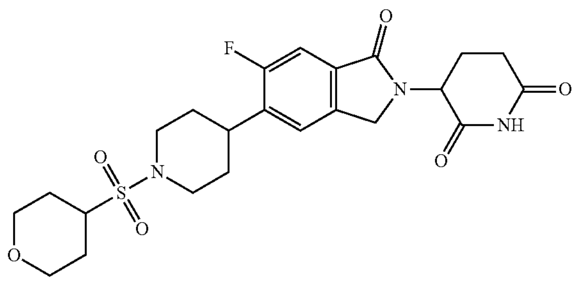

3-(6-Fluoro-1-oxo-5-(1-(m-tolylsulfonyl)piperidin-4-yl)isoindolin-2-yl)-piperidine-2,6-dione C2017.

3-(6-Fluoro-5-(1-((6-methylpyridin-3-yl)sulfonyl)piperidin-4-yl)-1-oxoisoindolin-2-yl)piperidine-2,6-dione C2018.

C2017

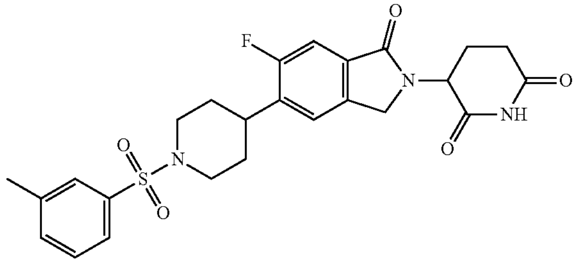

C2018

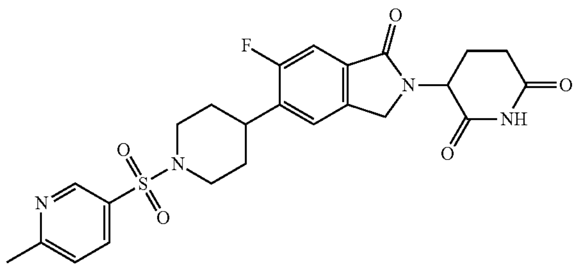

3-(6-Fluoro-5-(1-((4-hydroxyphenyl)sulfonyl)piperidin-4-yl)-1-oxoisoindolin-2-yl)piperidine-2,6-dione C2019.

3-(6-Fluoro-5-(1-((4-fluorophenyl)sulfonyl)piperidin-4-yl)-1-oxoisoindolin-2-yl)-piperidine-2,6-dione C2020.

C2019

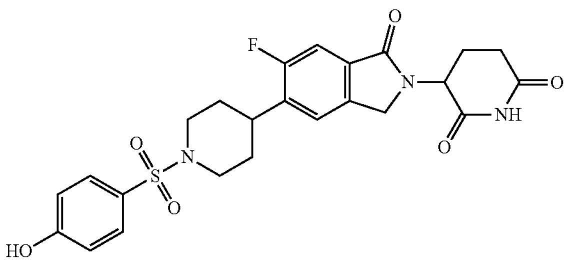

C2020

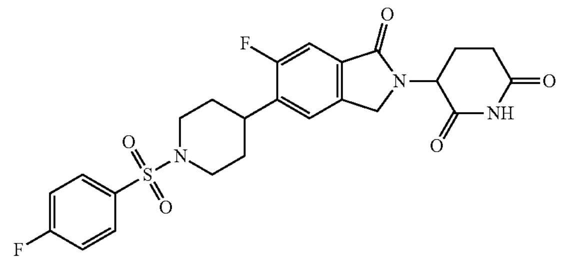

3-(6-Fluoro-5-(1-((3-fluorophenyl)sulfonyl)piperidin-4-yl)-1-oxoisoindolin-2-yl)-piperidine-2,6-dione C2021.

3-(6-Fluoro-5-(1-((2-fluorophenyl)sulfonyl)piperidin-4-yl)-1-oxoisoindolin-2-yl)-piperidine-2,6-dione C2022.

C2021

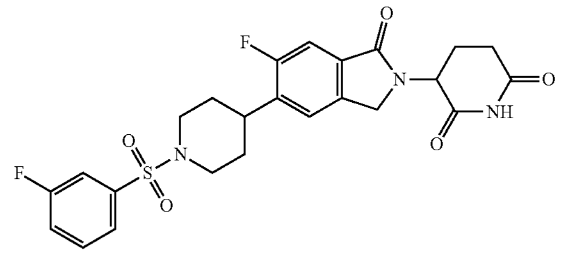

C2022

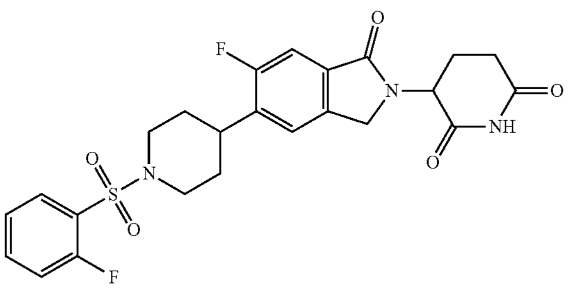

3-(6-Fluoro-1-oxo-5-(1-((3,3,3-trifluoropropyl)sulfonyl)piperidin-4-yl)isoindolin-2-yl)piperidine-2,6-dione C2023.

3-(6-Fluoro-5-(1-((4-methylbenzyl)sulfonyl)piperidin-4-yl)-1-oxoisoindolin-2-yl)-piperidine-2,6-dione C2024.

C2023

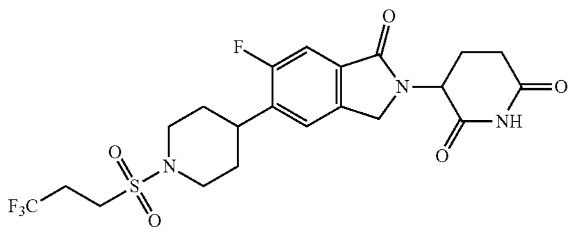

C2024

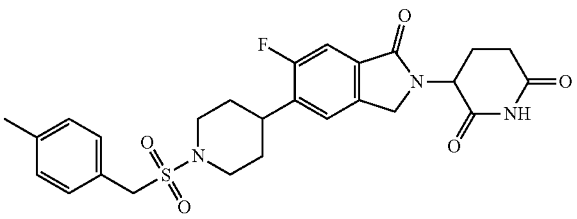

3-(6-Fluoro-1-oxo-5-(1-(phenethylsulfonyl)piperidin-4-yl) isoindolin-2-yl)-piperidine-2,6-dione C2025.

3-(5-(1-((2,6-Dimethylphenyl)sulfonyl)piperidin-4-yl)-6-fluoro-1-oxoisoindolin-2-yl)piperidine-2,6-dione C2026.

C2025

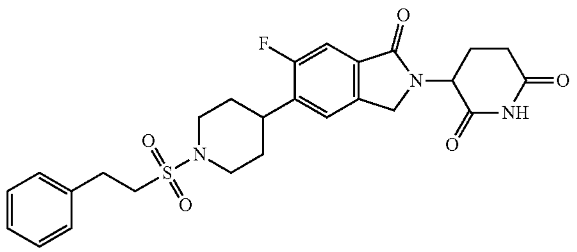

C2026

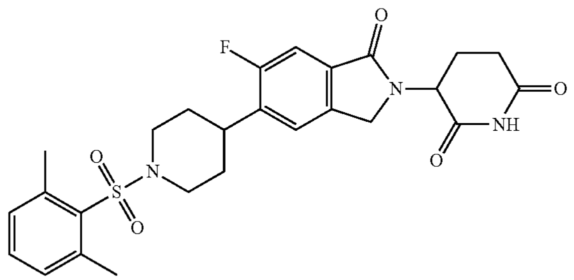

3-(6-Fluoro-5-(1-((4-methoxyphenyl)sulfonyl)piperidin-4-yl)-1-oxoisoindolin-2-yl)piperidine-2,6-dione C2027.

3-(6-Fluoro-5-(1-((3-methoxyphenyl)sulfonyl)piperidin-4-yl)-1-oxoisoindolin-2-yl)piperidine-2,6-dione C2028.

C2027

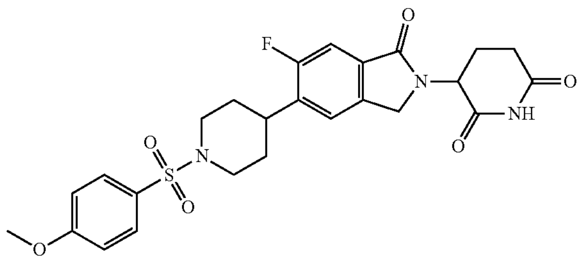

C2028

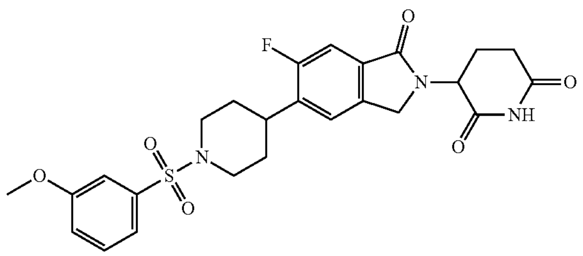

3-(6-Fluoro-5-(1-((6-methoxypyridin-3-yl)sulfonyl)piperidin-4-yl)-1-oxoisoindolin-2-yl)piperidine-2,6-dione C2029.

3-(6-Fluoro-5-(1-((2-fluoro-5-methylphenyl)sulfonyl)piperidin-4-yl)-1-oxoisoindolin-2-yl)piperidine-2,6-dione C2030.

C2029

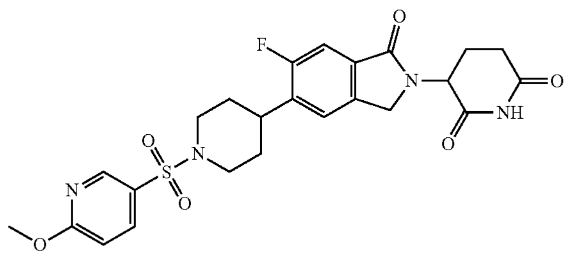

C2030

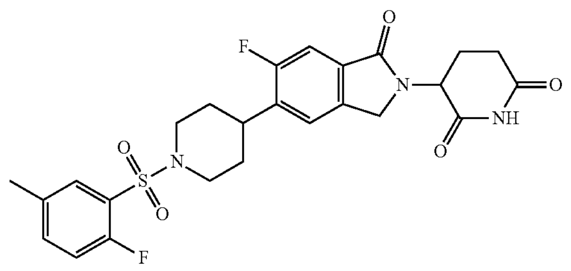

3-(6-Fluoro-5-(1-((4-fluoro-2-methylphenyl)sulfonyl)piperidin-4-yl)-1-oxoisoindolin-2-yl)piperidine-2,6-dione C2031.

3-(6-Fluoro-5-(1-((2-fluoro-4-methylphenyl)sulfonyl)piperidin-4-yl)-1-oxoisoindolin-2-yl)piperidine-2,6-dione C2032.

C2031

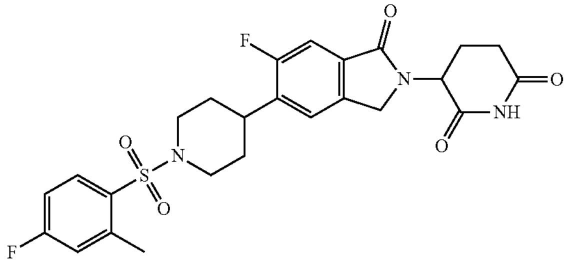

C2032

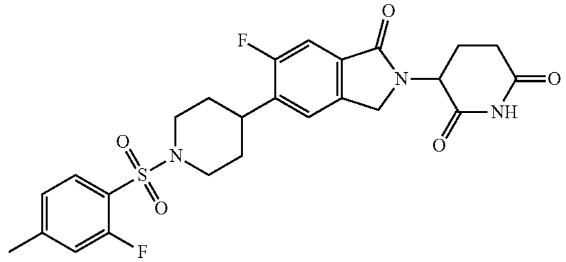

3-(5-(1-((3-Chlorophenyl)sulfonyl)piperidin-4-yl)-6-fluoro-1-oxoisoindolin-2-yl)-piperidine-2,6-dione C2033.

3-(5-(1-((2-Chlorophenyl)sulfonyl)piperidin-4-yl)-6-fluoro-1-oxoisoindolin-2-yl)-piperidine-2,6-dione C2034.

C2033

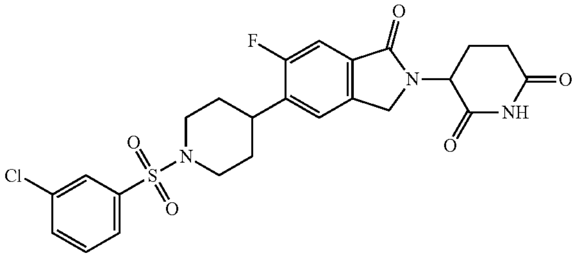

C2034

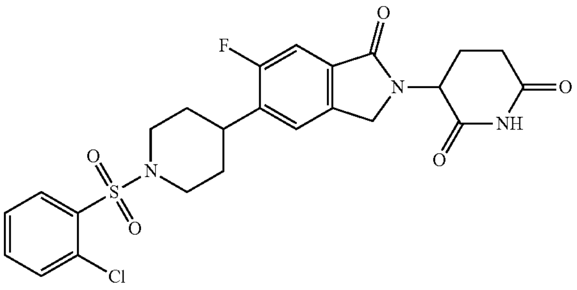

3-(5-(1-((4-Chlorophenyl)sulfonyl)piperidin-4-yl)-6-fluoro-1-oxoisoindolin-2-yl)-piperidine-2,6-dione C2035.

3-(5-(1-((3,4-Difluorophenyl)sulfonyl)piperidin-4-yl)-6-fluoro-1-oxoisoindolin-2-yl)piperidine-2,6-dione C2036.

C2035

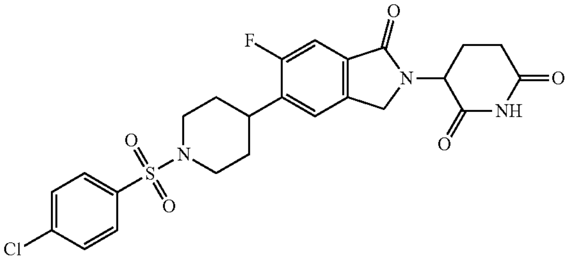

C2036

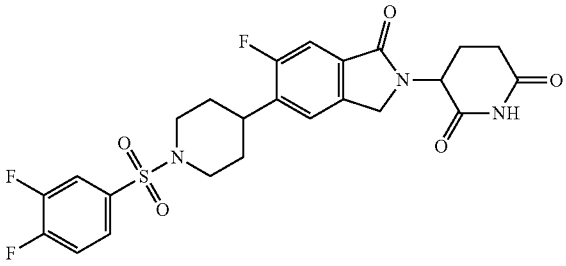

3-(5-(1-((2,4-Difluorophenyl)sulfonyl)piperidin-4-yl)-6-fluoro-1-oxoisoindolin-2-yl)piperidine-2,6-dione C2037.

3-(5-(1-((2,5-Difluorophenyl)sulfonyl)piperidin-4-yl)-6-fluoro-1-oxoisoindolin-2-yl)piperidine-2,6-dione C2038.

C2037

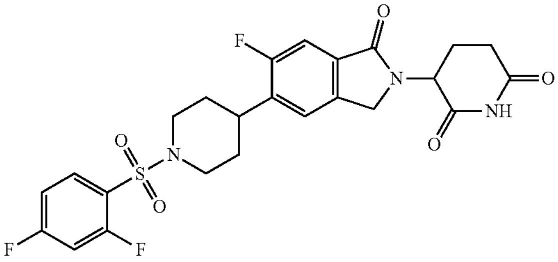

C2038

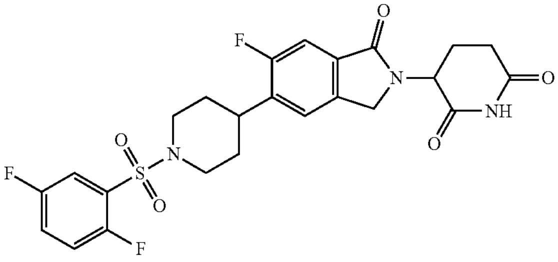

3-(5-(1-((3,5-Difluorophenyl)sulfonyl)piperidin-4-yl)-6-fluoro-1-oxoisoindolin-2-yl)piperidine-2,6-dione C2039.

3-(6-Fluoro-1-oxo-5-(1-(pyridin-3-ylsulfonyl)piperidin-4-yl)isoindolin-2-yl)-piperidine-2,6-dione C2040.

C2039

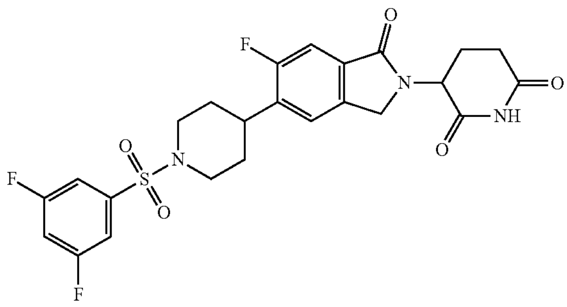

C2040

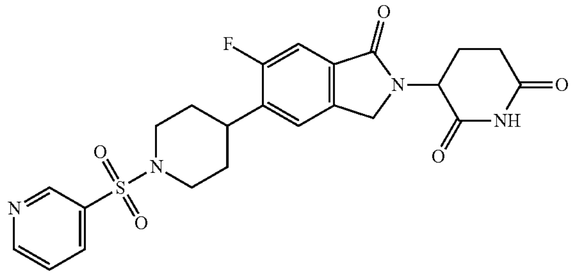

2-((4-(2-(2,6-Dioxopiperidin-3-yl)-6-fluoro-1-oxoisoindolin-5-yl)piperidin-1-yl)sulfonyl)-5-methylbenzonitrile C2041.

3-(5-(1-((1H-Indol-5-yl)sulfonyl)piperidin-4-yl)-6-fluoro-1-oxoisoindolin-2-yl)-piperidine-2,6-dione C2042.

C2041

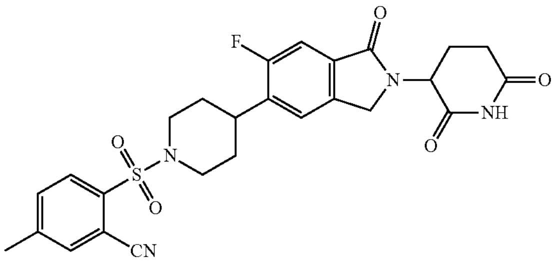

C2042

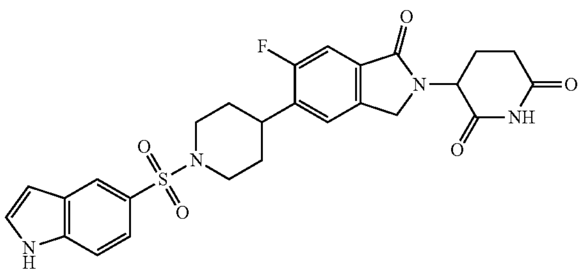

3-(5-(1-(Benzofuran-5-ylsulfonyl)piperidin-4-yl)-6-fluoro-1-oxoisoindolin-2-yl)-piperidine-2,6-dione C2043.

3-(5-(1-((2,3-Dihydrobenzofuran-5-yl)sulfonyl)piperidin-4-yl)-6-fluoro-1-oxoisoindolin-2-yl)piperidine-2,6-dione C2044.

C2043

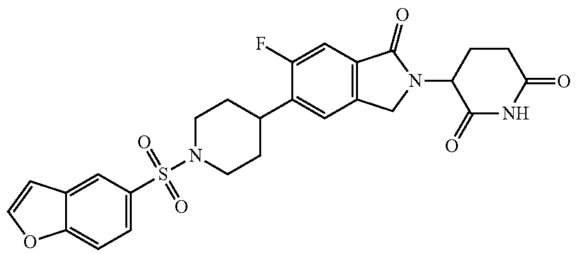

C2044

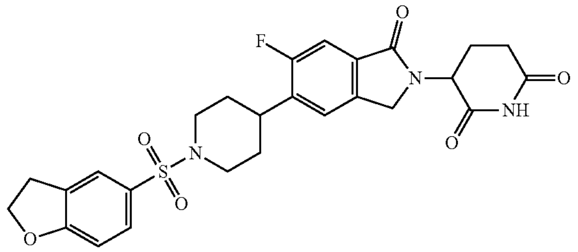

3-(6-Fluoro-5-(1-((4-isopropylphenyl)sulfonyl)piperidin-4-yl)-1-oxoisoindolin-2-yl)piperidine-2,6-di one C2045.

3-(6-Fluoro-5-(1-((3-isopropylphenyl)sulfonyl)piperidin-4-yl)-1-oxoisoindolin-2-yl)piperidine-2,6-dione C2046.

C2045

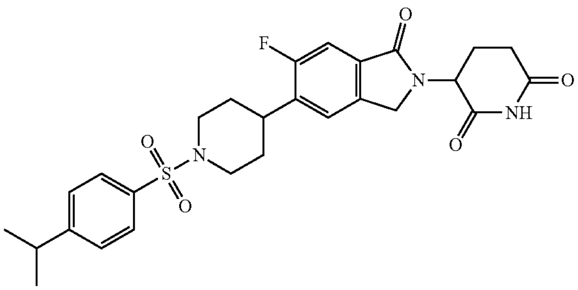

C2046

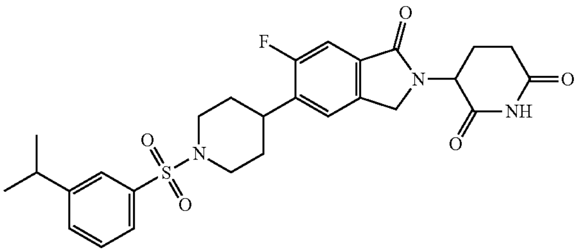

3-((4-(2-(2,6-Dioxopiperidin-3-yl)-6-fluoro-1-oxoisoindolin-5-yl)piperidin-1-yl)-sulfonyl)-4-fluorobenzonitrile C2047.

5-((4-(2-(2,6-Dioxopiperidin-3-yl)-6-fluoro-1-oxoisoindolin-5-yl)piperidin-1-yl)-sulfonyl)-2-fluorobenzonitrile C2048.

C2047

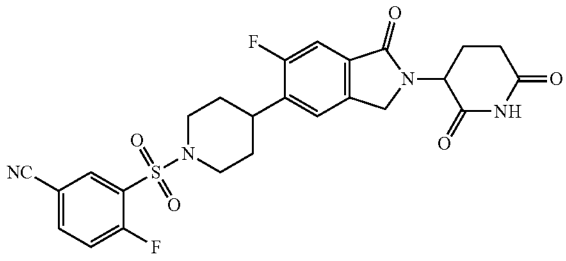

C2048

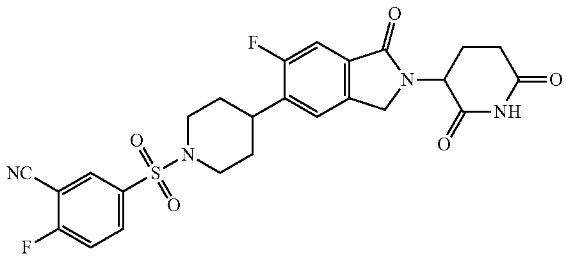

4-((4-(2-(2,6-Dioxopiperidin-3-yl)-6-fluoro-1-oxoisoindolin-5-yl)piperidin-1-yl)-sulfonyl)benzamide C2049.

C2049

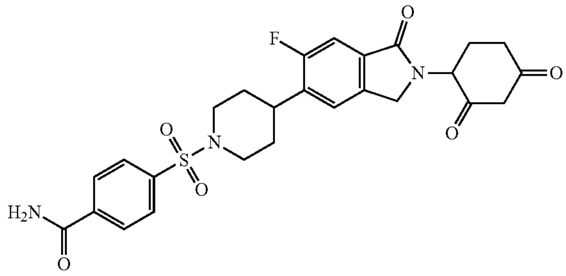

3-(6-Fluoro-5-(1-((3-methoxybenzyl)sulfonyl)piperidin-4-yl)-1-oxoisoindolin-2-yl)piperidine-2,6-dione C2050.

C2050

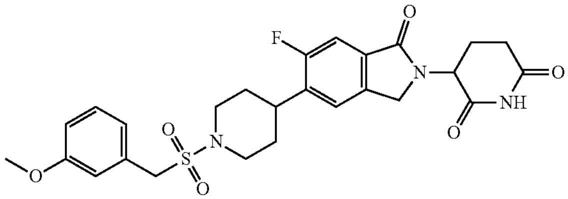

3-(6-Fluoro-5-(1-((3-methoxy-4-methylphenyl)sulfonyl)piperidin-4-yl)-1-oxoisoindolin-2-yl)piperidine-2,6-dione C2051.

3-(6-Fluoro-5-(1-((5-fluoro-2-methoxyphenyl)sulfonyl)piperidin-4-yl)-1-oxoisoindolin-2-yl)piperidine-2,6-dione C2052.

C2051

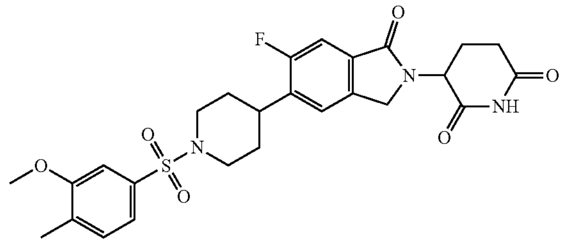

C2052

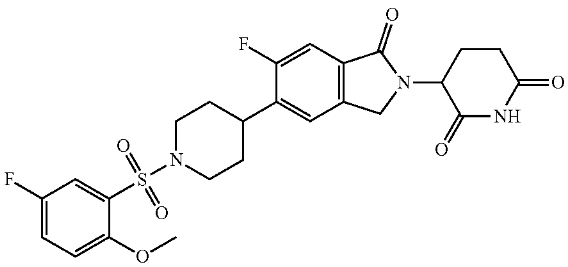

3-(6-Fluoro-5-(1-((3-fluoro-4-methoxyphenyl)sulfonyl)piperidin-4-yl)-1-oxoisoindolin-2-yl)piperidine-2,6-dione C2053.

3-(6-Fluoro-1-oxo-5-(1-((5,6,7,8-tetrahydronaphthalen-2-yl)sulfonyl)piperidin-4-yl)isoindolin-2-yl)piperidine-2,6-dione C2054.

C2053

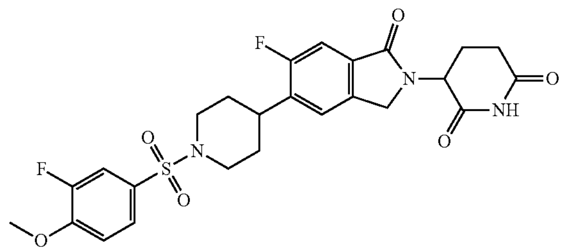

C2054

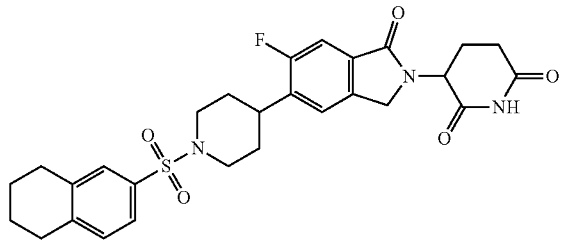

3-(6-Fluoro-5-(1-((2-hydroxy-1H-benzo[d]imidazol-6-yl)sulfonyl)piperidin-4-yl)-1-oxoisoindolin-2-yl)piperidine-2,6-dione C2055.

C2055

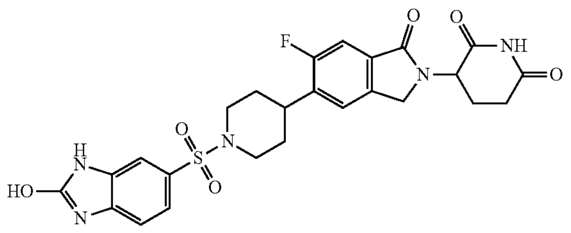

3-(5-(1-((4-(Tert-butyl)phenyl)sulfonyl)piperidin-4-yl)-6-fluoro-1-oxoisoindolin-2-yl)piperidine-2,6-dione C2056.

C2056

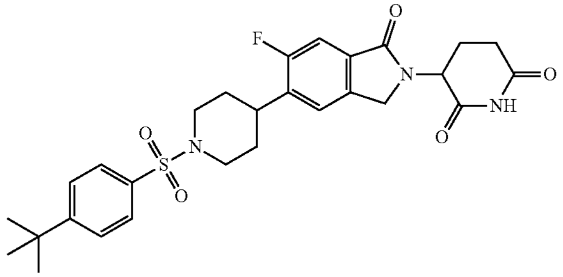

3-(5-(1-((3-(Tert-butyl)phenyl)sulfonyl)piperidin-4-yl)-6-fluoro-1-oxoisoindolin-2-yl)piperidine-2,6-dione C2057.

C2057

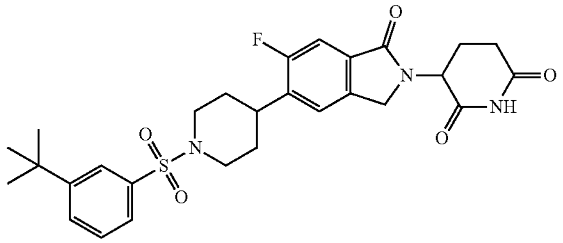

N-(3-((4-(2-(2,6-Dioxopiperidin-3-yl)-6-fluoro-1-oxoisoindolin-5-yl)piperidin-1-yl)sulfonyl)phenyl)acetamide C2058.

C2058

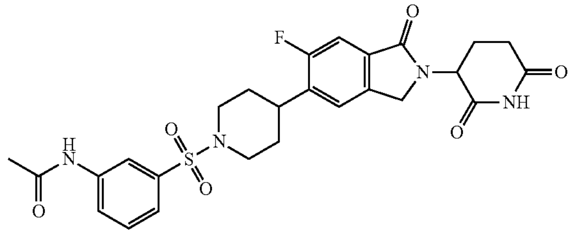

N-(4-((4-(2-(2,6-Dioxopiperidin-3-yl)-6-fluoro-1-oxoisoindolin-5-yl)piperidin-1-yl)sulfonyl)phenyl)acetamide C2059.

C2059

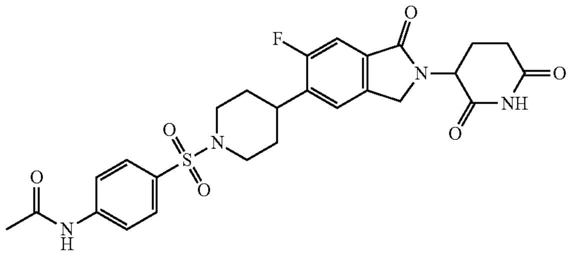

4-((4-(2-(2,6-Dioxopiperidin-3-yl)-6-fluoro-1-oxoisoindolin-5-yl)piperidin-1-yl)-sulfonyl)-N-methylbenzamide C2060.

C2060

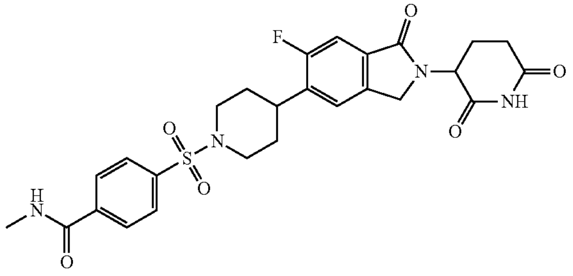

2-Chloro-4-((4-(2-(2,6-dioxopiperidin-3-yl)-6-fluoro-1-oxoisoindolin-5-yl)-piperidin-1-yl)sulfonyl)benzonitrile C2061.

3-(5-(1-((5-Chloro-2-methoxypyridin-3-yl)sulfonyl)piperidin-4-yl)-6-fluoro-1-oxoisoindolin-2-yl)piperidine-2,6-dione C2062.

C2061

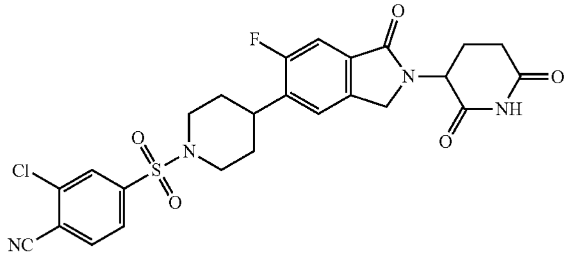

C2062

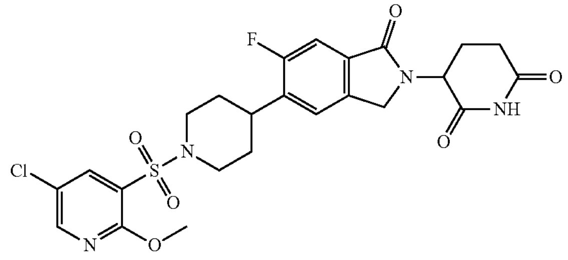

3-(5-(1-((4-(Difluoromethoxy)phenyl)sulfonyl)piperidin-4-yl)-6-fluoro-1-oxoisoindolin-2-yl)piperidine-2,6-dione C2063.

C2063

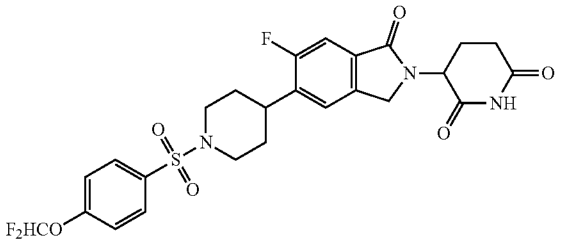

3-(6-Fluoro-5-(1-((4-(oxazol-5-yl)phenyl)sulfonyl)piperidin-4-yl)-1-oxoisoindolin-2-yl)piperidine-2,6-dione C2064.

C2064

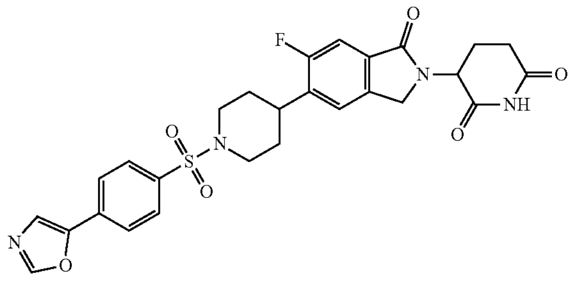

3-(6-Fluoro-1-oxo-5-(1-((4-(trifluoromethyl)phenyl)sulfonyl)piperidin-4-yl)-isoindolin-2-yl)piperidine-2,6-dione C2065.

3-(6-Fluoro-1-oxo-5-(1-((3-(trifluoromethyl)phenyl)sulfonyl)piperidin-4-yl)-isoindolin-2-yl)piperidine-2,6-dione C2066.

C2065

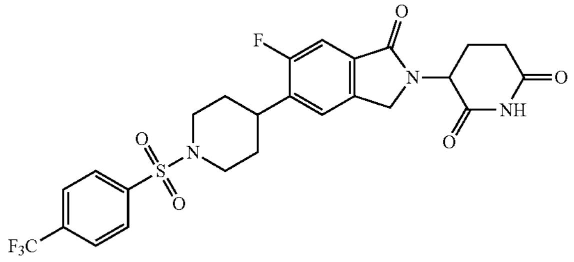

C2066

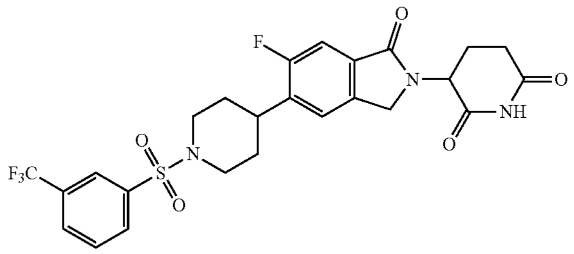

3-(6-Fluoro-1-oxo-5-(1-((2-(trifluoromethyl)phenyl)sulfonyl)piperidin-4-yl)-isoindolin-2-yl)piperidine-2,6-dione C2067.

3-(6-Fluoro-1-oxo-5-(1-((6-(trifluoromethyl)pyridin-3-yl)sulfonyl)piperidin-4-yl)-isoindolin-2-yl)piperidine-2,6-dione C2068.

C2067

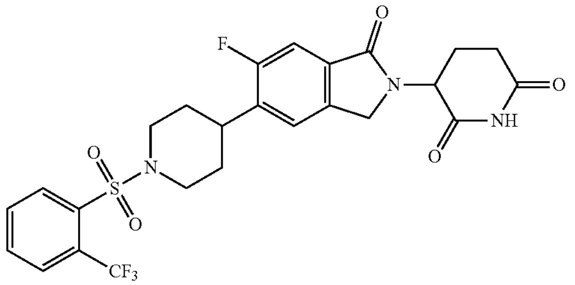

C2068

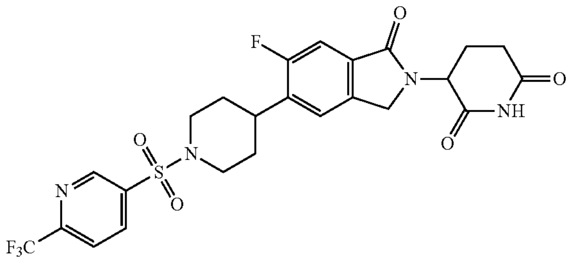

3-(6-Fluoro-1-oxo-5-(1-((2-oxo-1,2,3,4-tetrahydroquinolin-6-yl)sulfonyl)-piperidin-4-yl)isoindolin-2-yl)piperidine-2,6-dione C2069.

2-((4-(2-(2,6-Dioxopiperidin-3-yl)-6-fluoro-1-oxoisoindolin-5-yl)piperidin-1-yl)-sulfonyl)-N,N-dimethylbenzamide C2070.

C2069

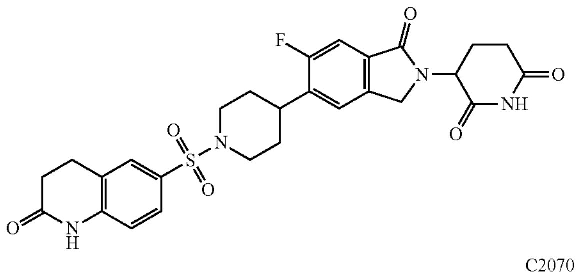

C2070

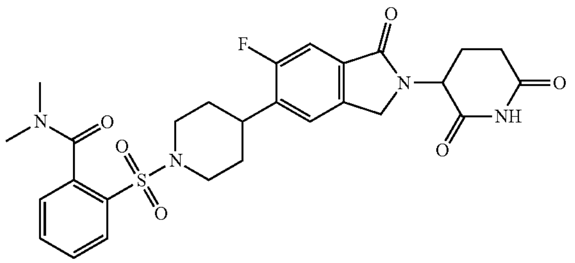

3-(5-(1-((3-Bromophenyl)sulfonyl)piperidin-4-yl)-6-fluoro-1-oxoisoindolin-2-yl)-piperidine-2,6-dione C2071.

3-(5-(1-((2-Bromophenyl)sulfonyl)piperidin-4-yl)-6-fluoro-1-oxoisoindolin-2-yl)-piperidine-2,6-dione C2072.

C2071

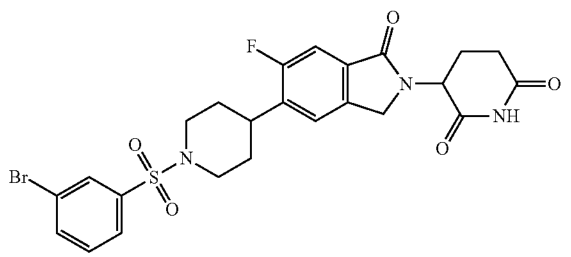

C2072

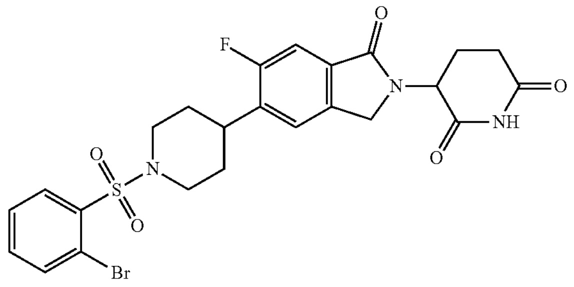

3-(6-Fluoro-1-oxo-5-(1-((1-(o-tolyl)-1H-pyrazol-4-yl)sulfonyl)piperidin-4-yl)-isoindolin-2-yl)piperidine-2,6-dione C2073.

C2073

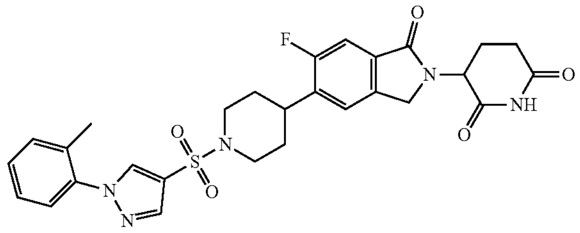

3-(6-Fluoro-1-oxo-5-(1-((4-(trifluoromethyl)benzyl)sulfonyl)piperidin-4-yl)-isoindolin-2-yl)piperidine-2,6-dione C2074.

C2074

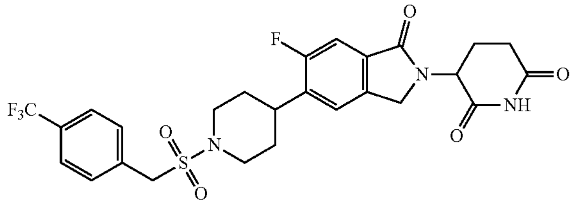

3-(6-Fluoro-1-oxo-5-(1-((2-(trifluoromethoxy)phenyl)sulfonyl)piperidin-4-yl)-isoindolin-2-yl)piperidine-2,6-dione C2075.

3-(5-(1-((1-Chloroisoquinolin-5-yl)sulfonyl)piperidin-4-yl)-6-fluoro-1-oxoisoindolin-2-yl)piperidine-2,6-dione C2076.

C2075

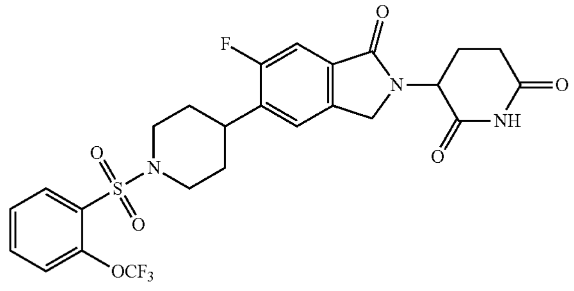

C2076

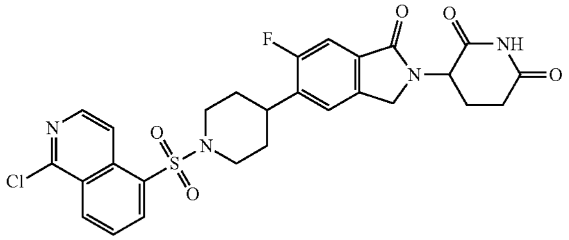

3-(6-Fluoro-5-(1-(isoquinolin-5-ylsulfonyl)piperidin-4-yl)-1-oxoisoindolin-2-yl)-piperidine-2,6-dione C2077.

C2077

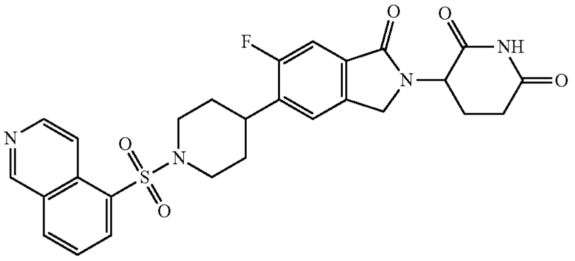

3-(6-Fluoro-1-oxo-5-(1-((4-(pyridin-2-yloxy)phenyl)sulfonyl)piperidin-4-yl)-isoindolin-2-yl)piperidine-2,6-dione C2078.

C2078

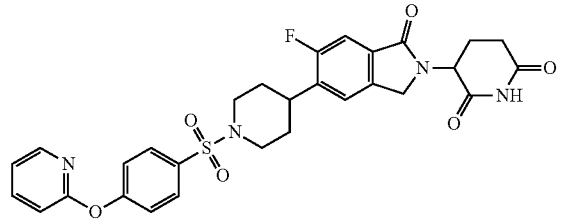

3-(6-Fluoro-1-oxo-5-(1-((6-phenoxypyridin-3-yl)sulfonyl)piperidin-4-yl)-isoindolin-2-yl)piperidine-2,6-dione C2079.

C2079

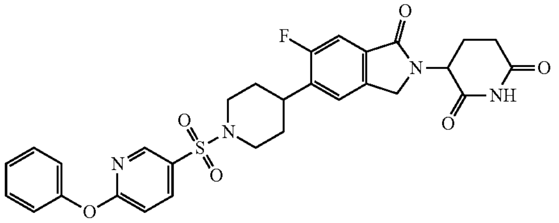

3-(5-(1-((5-(Dimethylamino)naphthalen-1-yl)sulfonyl)piperidin-4-yl)-6-fluoro-1-oxoisoindolin-2-yl)piperidine-2,6-dione C2080.

C2080

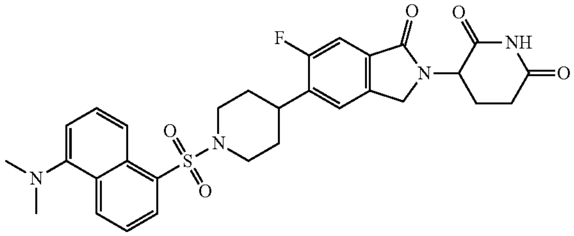

3-(5-(1-((6-(Dimethylamino)naphthalen-2-yl)sulfonyl)piperidin-4-yl)-6-fluoro-1-oxoisoindolin-2-yl)piperidine-2,6-dione C2081.

C2081

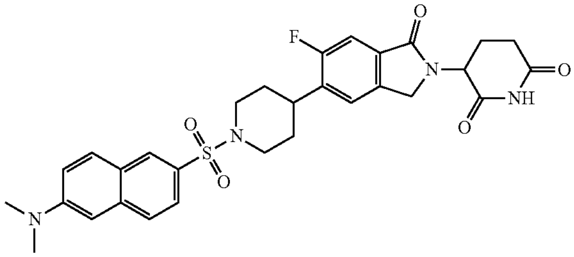

3-(5-(1-((4-(Benzyloxy)phenyl)sulfonyl)piperidin-4-yl)-6-fluoro-1-oxoisoindolin-2-yl)piperidine-2,6-dione C2082.

C2082

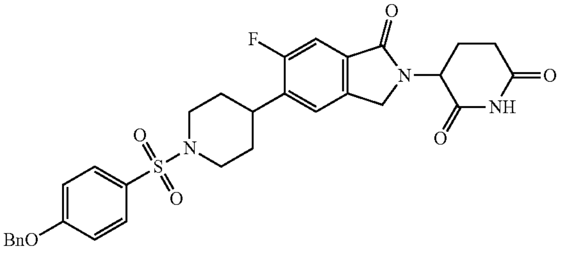

Tert-butyl 4-((4-(2-(2,6-dioxopiperidin-3-yl)-6-fluoro-1-oxoisoindolin-5-yl)-piperidin-1-yl)sulfonyl)piperidine-1-carboxylate C2083.

Benzyl 4-((4-(2-(2,6-dioxopiperidin-3-yl)-6-fluoro-1-oxoisoindolin-5-yl)-piperidin-1-yl)sulfonyl)piperidine-1-carboxylate C2084.

C2083

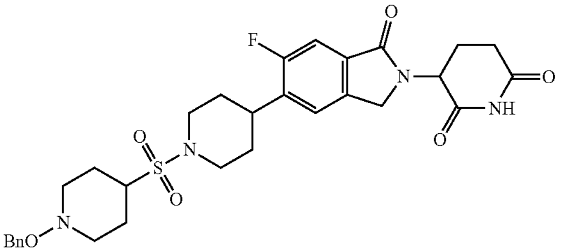

C2084

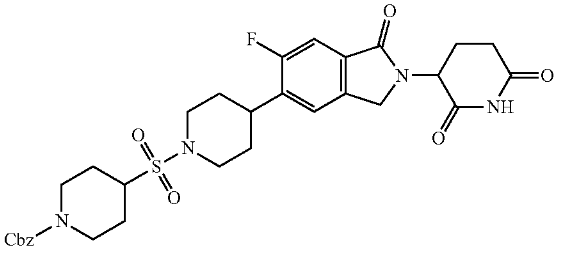

3-(6-Fluoro-1-oxo-5-(1-((2-(2,2,2-trifluoroacetyl)-1,2,3,4-tetrahydroisoquinolin-7-yl)sulfonyl)piperidin-4-yl)isoindolin-2-yl)piperidine-2,6-dione C2085.

C2085

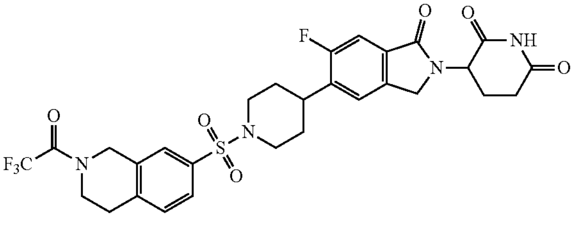

Benzyl 4-(((4-(2-(2,6-dioxopiperidin-3-yl)-6-fluoro-1-oxoisoindolin-5-yl)-piperidin-1-yl)sulfonyl)methyl)piperidine-1-carboxylate C2086.

C2086

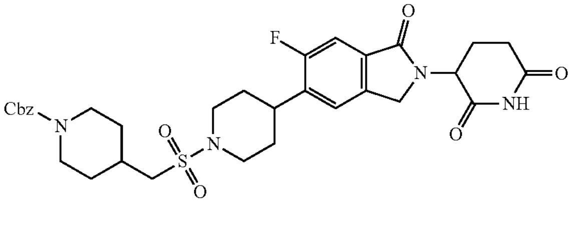

3-(5-(1-(Ethylsulfonyl)piperidin-4-yl)-6-fluoro-1-oxoisoindolin-2-yl)piperidine-2,6-dione C2087.

3-(5-(1-((5-Chlorothiophen-2-yl)sulfonyl)piperidin-4-yl)-6-fluoro-1-oxoisoindolin-2-yl)piperidine-2,6-dione C2088.

C2087

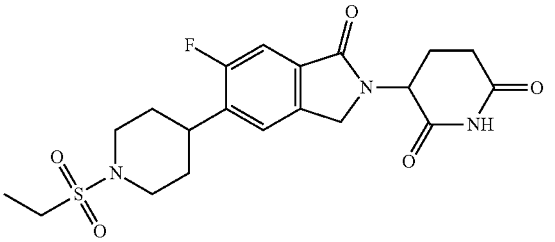

C2088

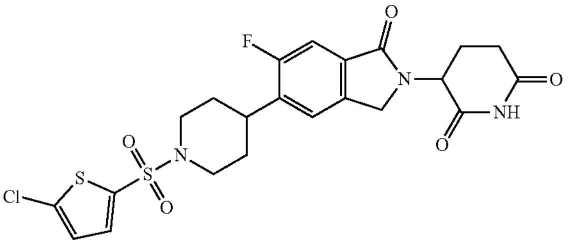

3-(5-(1-((3-Chloro-4-methylphenyl)sulfonyl)piperidin-4-yl)-6-fluoro-1-oxoisoindolin-2-yl)piperidine-2,6-dione C2089.

3-(5-(1-((2-Chloro-6-methylphenyl)sulfonyl)piperidin-4-yl)-6-fluoro-1-oxoisoindolin-2-yl)piperidine-2,6-dione C2090.

C2089

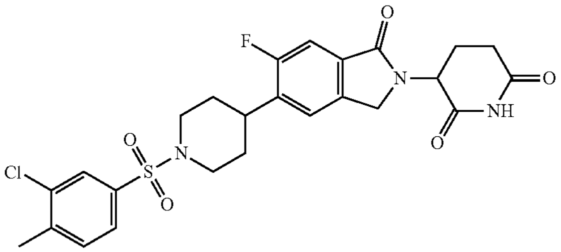

C2090

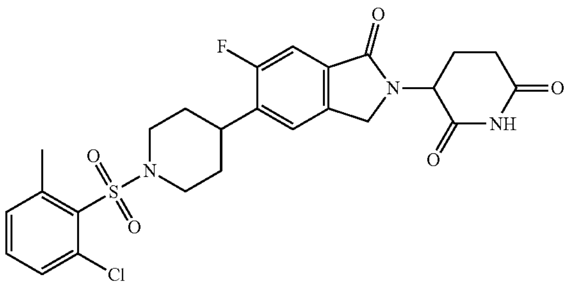

3-(5-(1-((3,5-Difluorobenzyl)sulfonyl)piperidin-4-yl)-6-fluoro-1-oxoisoindolin-2-yl)piperidine-2,6-dione C2091.

3-(6-Fluoro-5-(1-(naphthalen-2-ylsulfonyl)piperidin-4-yl)-1-oxoisoindolin-2-yl)-piperidine-2,6-dione C2092.

C2091

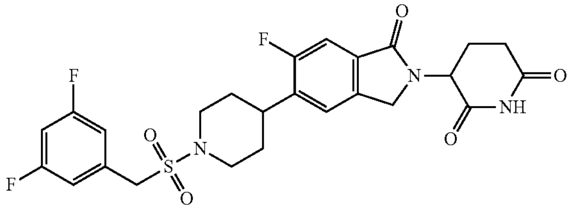

C2092

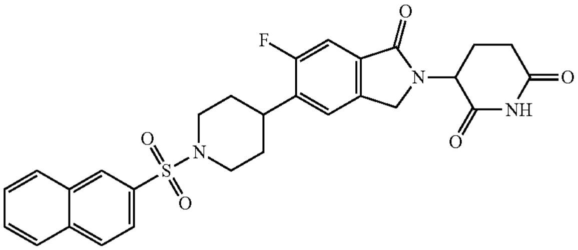

3-(6-Fluoro-1-oxo-5-(1-(quinolin-8-ylsulfonyl)piperidin-4-yl)isoindolin-2-yl)-piperidine-2,6-dione C2093.

3-(6-Fluoro-5-(1-(isoquinolin-5-ylsulfonyl)piperidin-4-yl)-1-oxoisoindolin-2-yl)-piperidine-2,6-dione C2094.

C2093

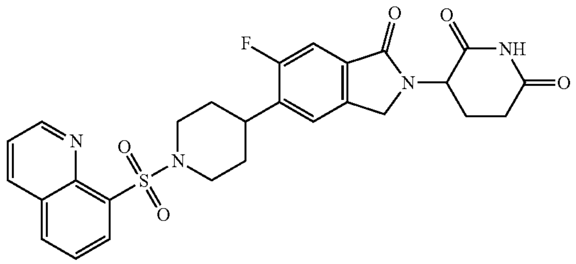

C2094

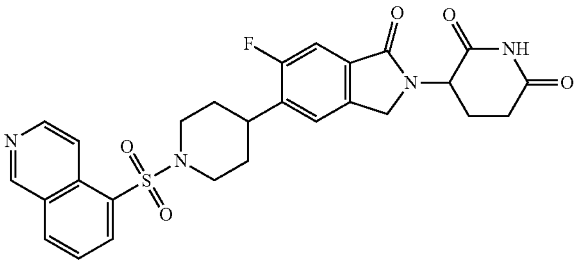

3-(6-Fluoro-1-oxo-5-(1-(quinoxalin-5-ylsulfonyl)piperidin-4-yl)isoindolin-2-yl)-piperidine-2,6-dione C2095.

3-Chloro-4-((4-(2-(2,6-dioxopiperidin-3-yl)-6-fluoro-1-oxoisoindolin-5-yl)-piperidin-1-yl)sulfonyl)benzonitrile C2096.

C2095

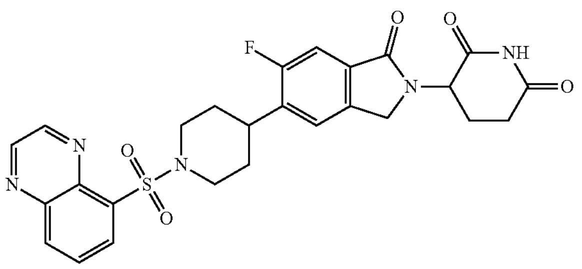

C2096

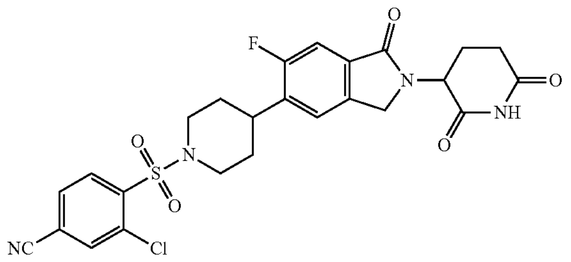

3-(5-(1-(Benzo[d][1,3]dioxol-5-ylsulfonyl)piperidin-4-yl)-6-fluoro-1-oxoisoindolin-2-yl)piperidine-2,6-dione C2097.

3-(5-(1-(Benzo[d]thiazol-6-ylsulfonyl)piperidin-4-yl)-6-fluoro-1-oxoisoindolin-2-yl)piperidine-2,6-dione C2098.

C2097

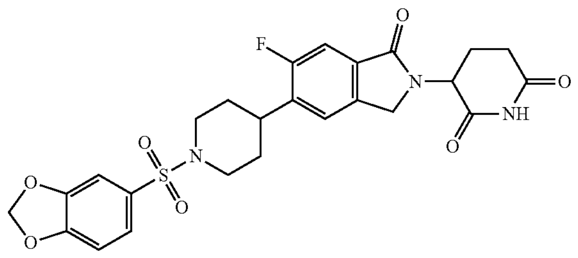

C2098

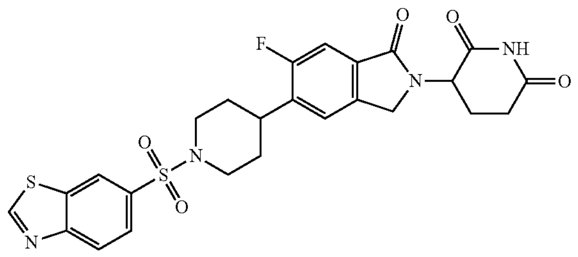

3-(5-(1-((2,4-Dichlorophenyl)sulfonyl)piperidin-4-yl)-6-fluoro-1-oxoisoindolin-2-yl)piperidine-2,6-dione C2099.

3-(5-(1-((2,5-Dichlorophenyl)sulfonyl)piperidin-4-yl)-6-fluoro-1-oxoisoindolin-2-yl)piperidine-2,6-dione C2100.

C2099

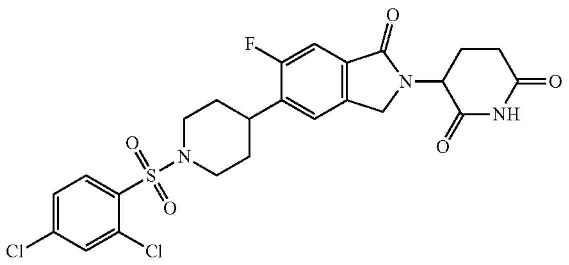

C2100

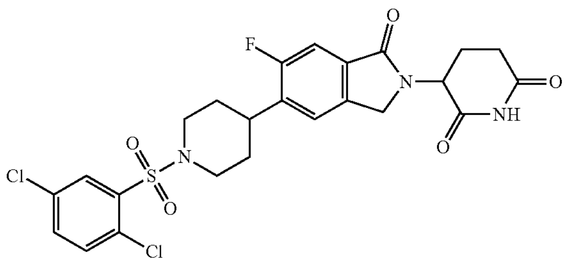

3-(6-Fluoro-1-oxo-5-(4-(5,6,7,8-tetrahydronaphthalene-1-carbonyl)piperazin-1-yl)isoindolin-2-yl)piperidine-2,6-dione D0001.

3-(6-Fluoro-5-(4-(1-methyl-1H-indole-5-carbonyl)piperazin-1-yl)-1-oxoisoindolin-2-yl)piperidine-2,6-dione D0002.

D0001

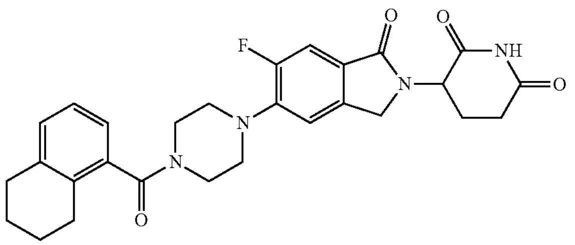

D0002

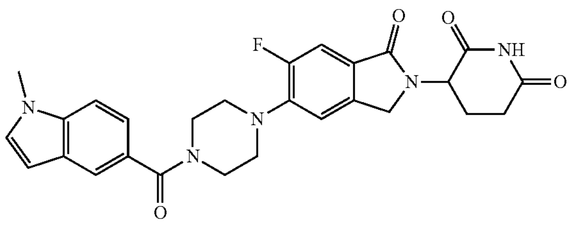

3-(6-Fluoro-1-oxo-5-(4-(quinoxaline-5-carbonyl)piperazin-1-yl)isoindolin-2-yl)-piperidine-2,6-dione D0003.

3-(6-Fluoro-1-oxo-5-(4-(quinazoline-6-carbonyl)piperazin-1-yl)isoindolin-2-yl)-piperidine-2,6-dione D0004.

D0003

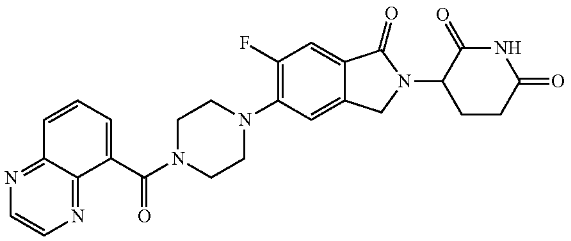

D0004

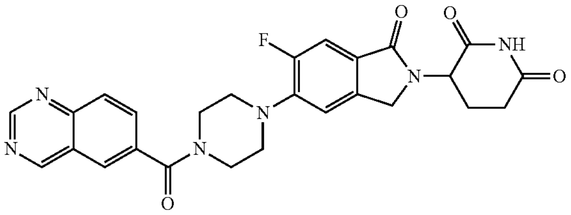

3-(5-(4-(2-(Dimethylamino)benzoyl)piperazin-1-yl)-6-fluoro-1-oxoisoindolin-2-yl)piperidine-2,6-dione D0005.

3-(5-(4-(4-(Dimethylamino)benzoyl)piperazin-1-yl)-6-fluoro-1-oxoisoindolin-2-yl)piperidine-2,6-dione D0006.

D0005

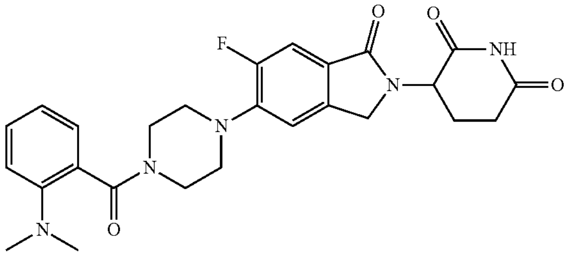

D0006

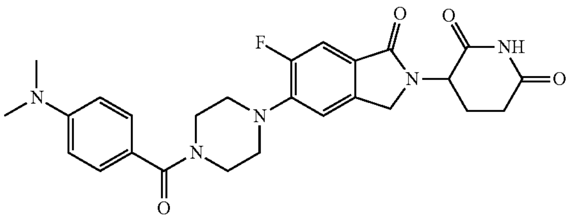

3-(5-(4-(2,3-Dihydrobenzofuran-7-carbonyl)piperazin-1-yl)-6-fluoro-1-oxoisoindolin-2-yl)piperidine-2,6-dione D0007.

3-(5-(4-(Benzo[d]oxazole-5-carbonyl)piperazin-1-yl)-6-fluoro-1-oxoisoindolin-2-yl)piperidine-2,6-dione D0008.

D0007

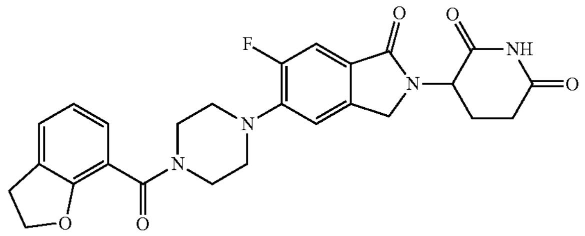

D0008

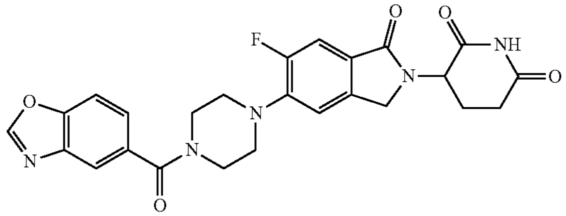

3-(5-(4-(1H-Benzo[d]imidazole-7-carbonyl)piperazin-1-yl)-6-fluoro-1-oxoisoindolin-2-yl)piperidine-2,6-dione D0009.

3-(6-Fluoro-5-(4-(imidazo[1,2-a]pyridin-2-carbonyl)piperazin-1-yl)-1-oxoisoindolin-2-yl)piperidine-2,6-dione D0010.

D0009

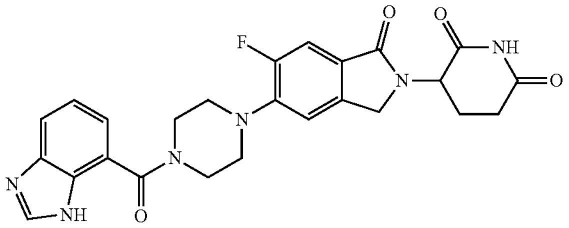

D0010

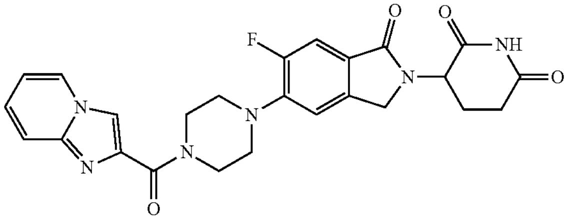

3-(5-(4-(1H-Pyrrolo[3,2-b]pyridin-6-carbonyl)piperazin-1-yl)-6-fluoro-1-oxoisoindolin-2-yl)piperidine-2,6-dione D0011.

3-(6-Fluoro-5-(4-(imidazo[1,2-a]pyridin-3-carbonyl)piperazin-1-yl)-1-oxoisoindolin-2-yl)piperidine-2,6-dione D0012.

D0011

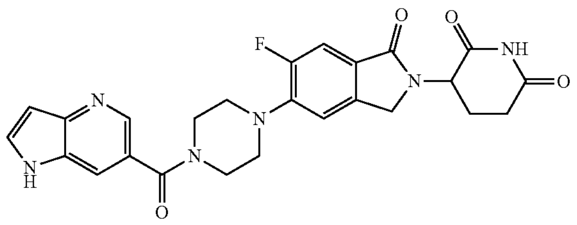

D0012

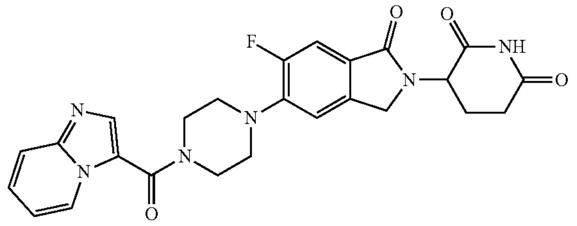

3-(5-(4-(Benzofuran-6-carbonyl)piperazin-1-yl)-6-fluoro-1-oxoisoindolin-2-yl)-piperidine-2,6-dione D0013.

3-(6-Fluoro-1-oxo-5-(4-(2-(piperidin-1-yl)acetyl)piperazin-1-yl)isoindolin-2-yl)-piperidine-2,6-dione D0014.

D0013

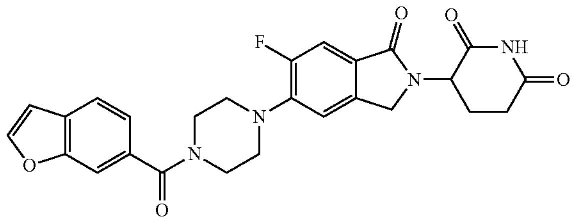

D0014

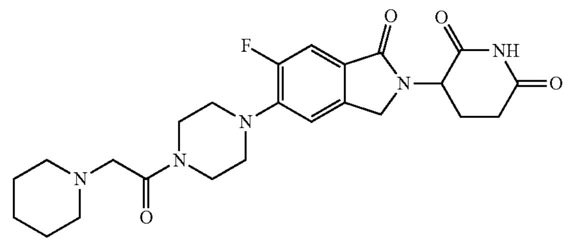

2-(2-(4-(2-(2,6-Dioxopiperidin-3-yl)-6-fluoro-1-oxoisoindolin-5-yl)piperazin-1-yl)-2-oxoethyl)benzonitrile D0015.

3-(2-(4-(2-(2,6-Dioxopiperidin-3-yl)-6-fluoro-1-oxoisoindolin-5-yl)piperazin-1-yl)-2-oxoethyl)benzonitrile D0016.

D0015

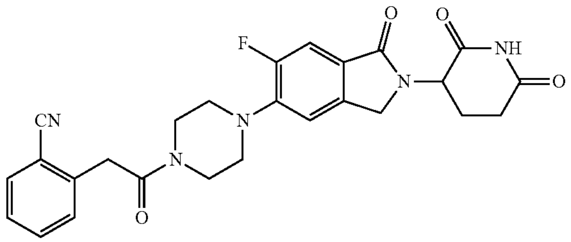

D0016

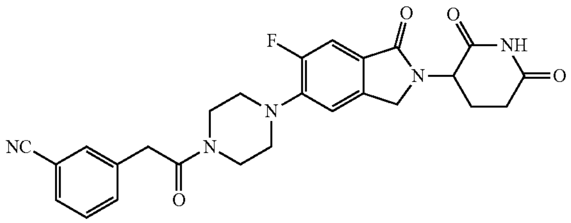

4-(2-(4-(2-(2,6-Dioxopiperidin-3-yl)-6-fluoro-1-oxoisoindolin-5-yl)piperazin-1-yl)-2-oxoethyl)benzonitrile D0017.

3-(5-(4-(1H-Indole-7-carbonyl)piperazin-1-yl)-6-fluoro-1-oxoisoindolin-2-yl)-piperidine-2,6-dione D0018.

D0017

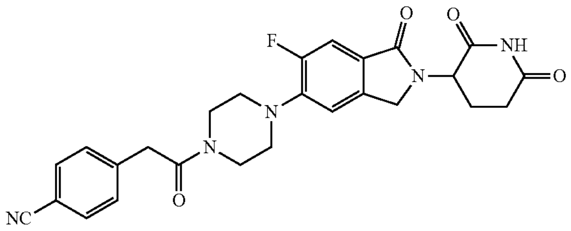

D0018

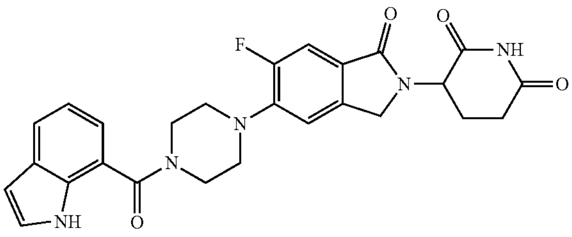

3-(5-(4-(1-Ethylpiperidine-4-carbonyl)piperazin-1-yl)-6-fluoro-1-oxoisoindolin-2-yl)piperidine-2,6-dione D0019.

3-(6-Fluoro-1-oxo-5-(4-(2-(p-tolyl)acetyl)piperazin-1-yl)isoindolin-2-yl)-piperidine-2,6-dione D0020.

D0019

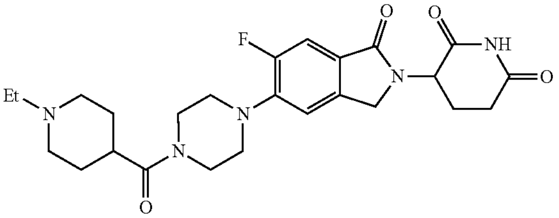

D0020

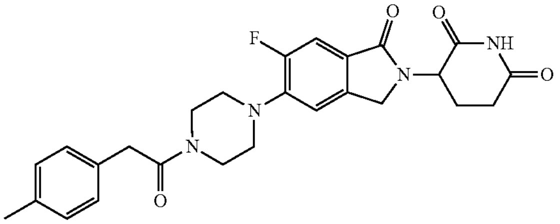

2-(4-(2-(2,6-Dioxopiperidin-3-yl)-6-fluoro-1-oxoisoindolin-5-yl)piperazine-1-carbonyl)benzonitrile D0021.

3-(4-(2-(2,6-Dioxopiperidin-3-yl)-6-fluoro-1-oxoisoindolin-5-yl)piperazine-1-carbonyl)benzonitrile D0022.

D0021

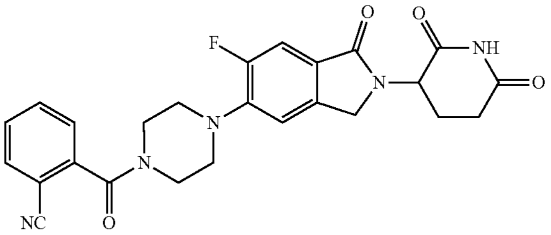

D0022

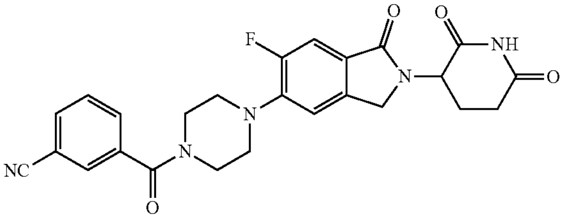

3-(6-Fluoro-5-(4-(4-fluorobenzoyl)piperazin-1-yl)-1-oxoisoindolin-2-yl)-piperidine-2,6-dione D0023.

3-(6-Fluoro-5-(4-(3-fluorobenzoyl)piperazin-1-yl)-1-oxoisoindolin-2-yl)-piperidine-2,6-dione D0024.

D0023

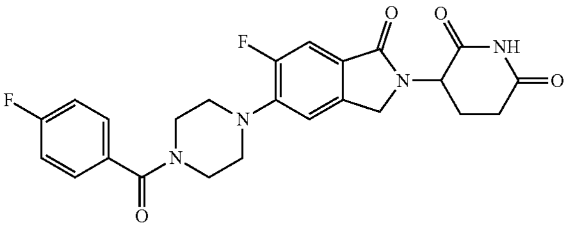

-continued

D0024

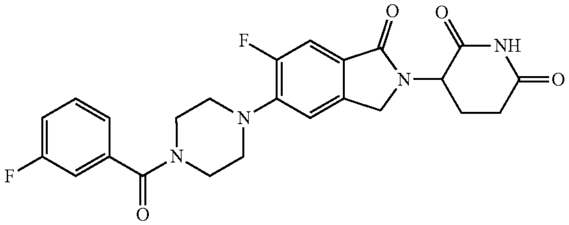

3-(6-Fluoro-5-(4-(2-fluorobenzoyl)piperazin-1-yl)-1-oxoisoindolin-2-yl)-piperidine-2,6-dione D0025.

3-(6-Fluoro-5-(4-(2-methylbenzoyl)piperazin-1-yl)-1-oxoisoindolin-2-yl)-piperidine-2,6-dione D0026.

D0025

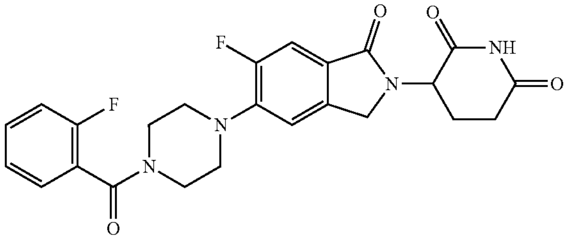

D0026

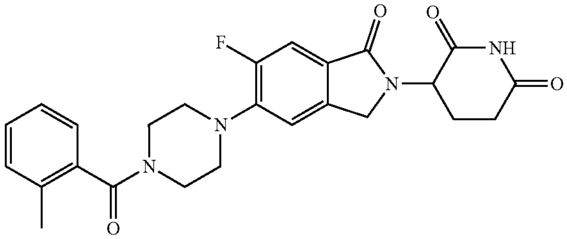

3-(6-Fluoro-5-(4-(3-methylbenzoyl)piperazin-1-yl)-1-oxoisoindolin-2-yl)-piperidine-2,6-dione D0027.

3-(6-Fluoro-5-(4-(4-methylbenzoyl)piperazin-1-yl)-1-oxoisoindolin-2-yl)-piperidine-2,6-dione D0028.

D0027

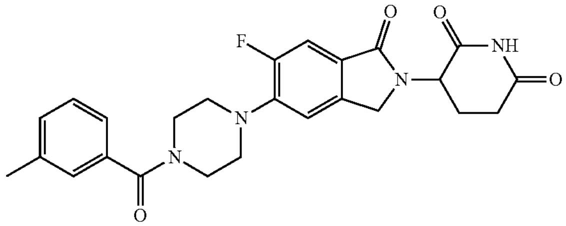

-continued

D0028

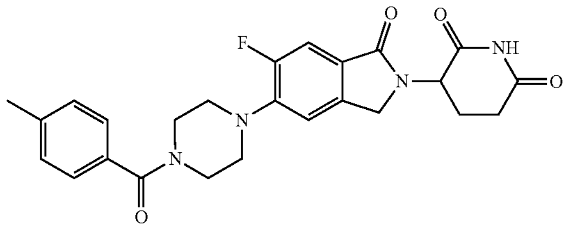

3-(5-(4-(2-Cyclopentylacetyl)piperazin-1-yl)-6-fluoro-1-oxoisoindolin-2-yl)piperidine-2,6-dione D0029.

3-(5-(4-(Cyclohexanecarbonyl)piperazin-1-yl)-6-fluoro-1-oxoisoindolin-2-yl)piperidine-2,6-dione D0030.

D0029

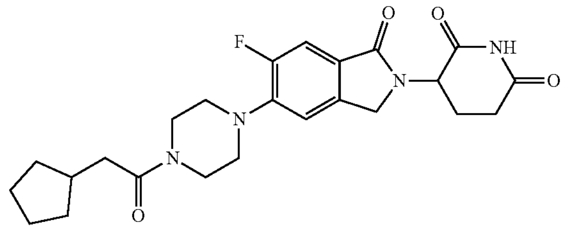

D0030

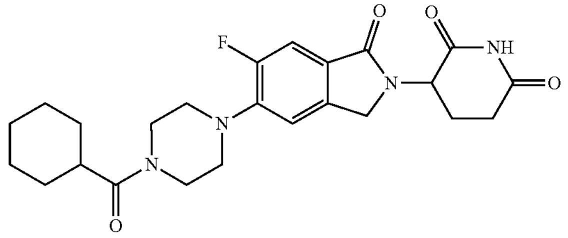

3-(5-(-(3,3-Dimethylcyclobutane-1-carbonyl)piperazin-1-yl)-6-fluoro-1-oxoisoindolin-2-yl)piperidine-2,6-dione D0031.

3-(6-Fluoro-1-oxo-5-(4-(pyrimidine-5-carbonyl)piperazin-1-yl)isoindolin-2-yl)piperidine-2,6-dione D0032.

D0031

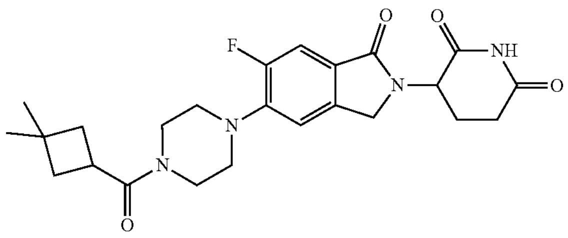

-continued

D0032

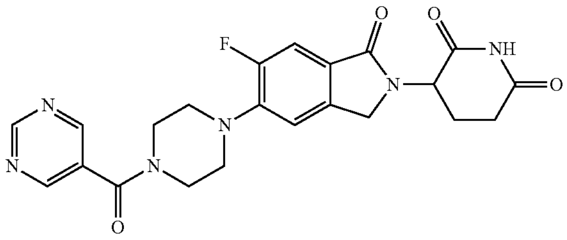

3-(6-Fluoro-1-oxo-5-(4-(pyridazine-4-carbonyl)piperazin-1-yl)isoindolin-2-yl)-piperidine-2,6-dione D0033.

3-(6-Fluoro-1-oxo-5-(4-(pyrimidine-4-carbonyl)piperazin-1-yl)isoindolin-2-yl)-piperidine-2,6-dione D0034.

D0033

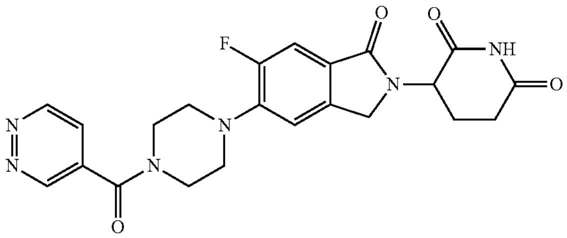

D0034

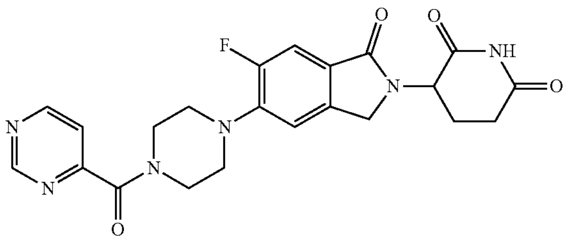

3-(6-Fluoro-1-oxo-5-(4-picolinoylpiperazin-1-yl)isoindolin-2-yl)piperidine-2,6-dione D0035.

3-(6-Fluoro-5-(4-isonicotinoylpiperazin-1-yl)-1-oxoisoindolin-2-yl)piperidine-2,6-dione D0036.

D0035

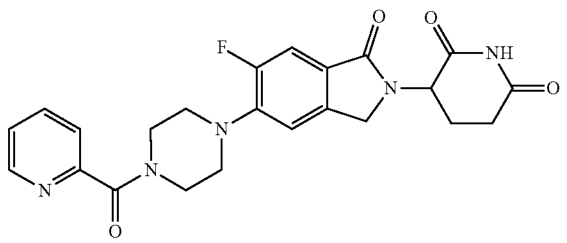

-continued

D0036

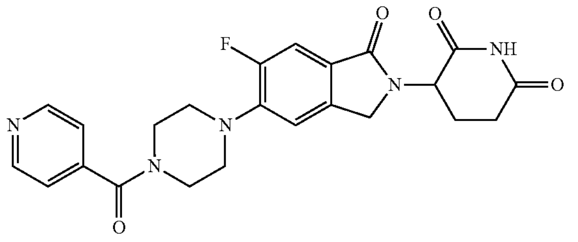

3-(6-Fluoro-5-(4-nicotinoylpiperazin-1-yl)-1-oxoisoindolin-2-yl)piperidine-2,6-dione D0037.

3-(5-(4-Benzoylpiperazin-1-yl)-6-fluoro-1-oxoisoindolin-2-yl)piperidine-2,6-dione D0038.

D0037

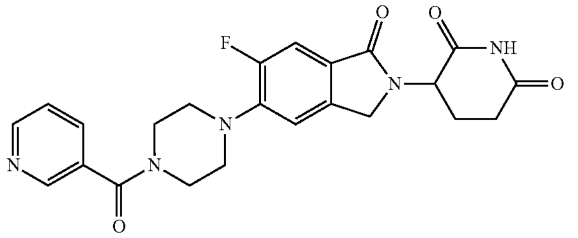

D0038

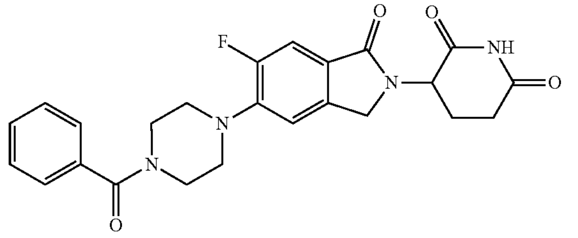

3-(5-(4-(1-Aminocyclobutane-1-carbonyl)piperazin-1-yl)-6-fluoro-1-oxoisoindolin-2-yl)piperidine-2,6-dione D0039.

3-(6-Fluoro-5-(4-(1-methylazetidine-3-carbonyl)piperazin-1-yl)-1-oxoisoindolin-2-yl)piperidine-2,6-dione D0040.

D0039

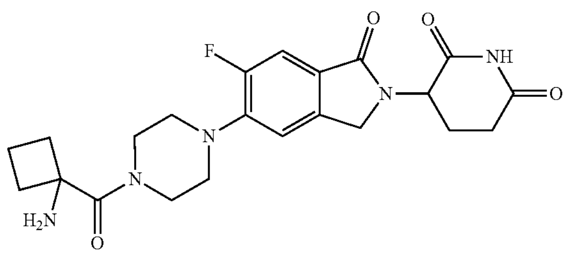

-continued

D0040

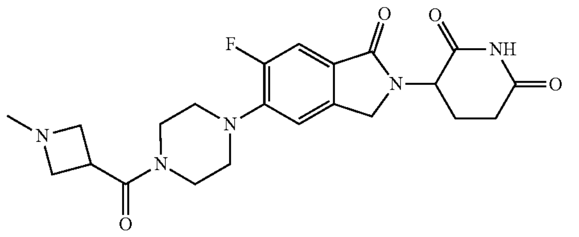

3-(5-(4-(1H-Pyrazole-5-carbonyl)piperazin-1-yl)-6-fluoro-1-oxoisoindolin-2-yl)-piperidine-2,6-dione D0041.

3-(5-(4-(1H-Imidazole-5-carbonyl)piperazin-1-yl)-6-fluoro-1-oxoisoindolin-2-yl)-piperidine-2,6-dione D0042.

D0041

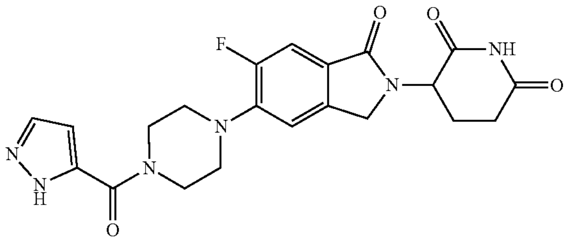

D0042

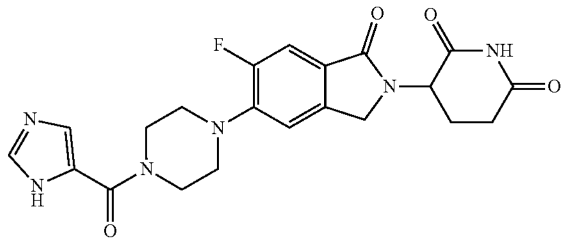

3-(6-Fluoro-5-(4-(furan-3-carbonyl)piperazin-1-yl)-1-oxoisoindolin-2-yl)-piperidine-2,6-dione D0043.

3-(6-Fluoro-5-(4-(furan-2-carbonyl)piperazin-1-yl)-1-oxoisoindolin-2-yl)-piperidine-2,6-dione D0044.

D0043

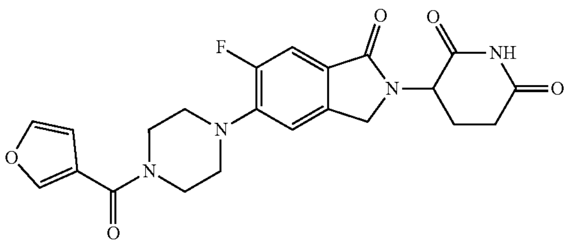

-continued

D0044

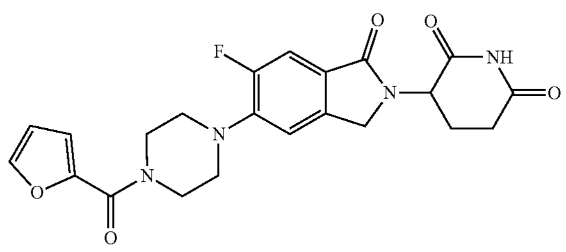

3-(6-Fluoro-5-(4-(1-fluorocyclopropane-1-carbonyl)piperazin-1-yl)-1-oxoisoindolin-2-yl)piperidine-2,6-dione D0045.

3-(6-Fluoro-5-(4-(3-methylbutanoyl)piperazin-1-yl)-1-oxoisoindolin-2-yl)-piperidine-2,6-dione D0046.

D0045

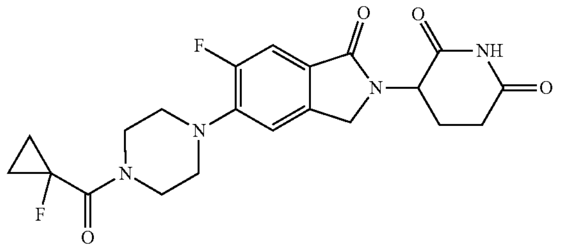

D0046

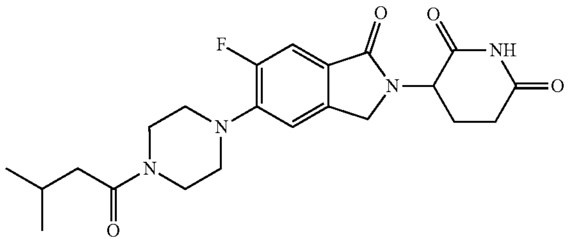

3-(6-Fluoro-5-(4-(oxetane-3-carbonyl)piperazin-1-yl)-1-oxoisoindolin-2-yl)-piperidine-2,6-dione D0047.

3-(5-(4-(Cyclobutanecarbonyl)piperazin-1-yl)-6-fluoro-1-oxoisoindolin-2-yl)-piperidine-2,6-dione D0048.

D0047

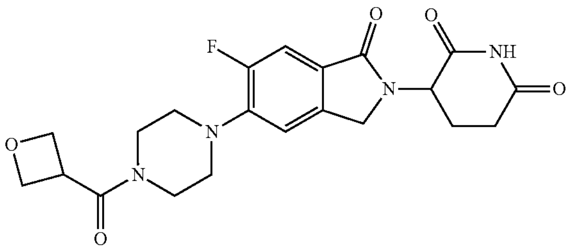

-continued

D0048

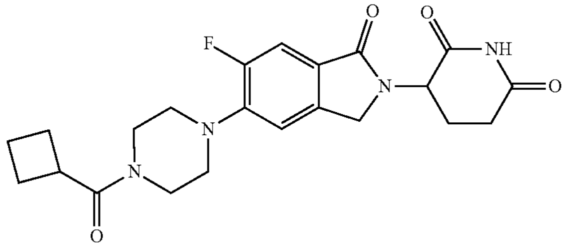

3-(6-Fluoro-5-(4-(methylglycyl)piperazin-1-yl)-1-oxoisoindolin-2-yl)piperidine-2,6-dione D0049.

3-(5-(4-(Cyclopropanecarbonyl)piperazin-1-yl)-6-fluoro-1-oxoisoindolin-2-yl)-piperidine-2,6-dione D0050.

D0049

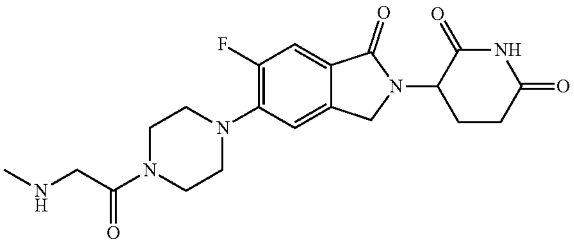

D0050

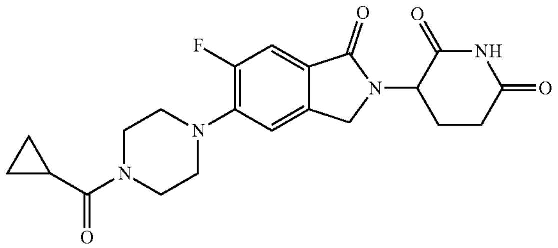

3-(6-Fluoro-5-(4-(3-methoxybenzyl)piperazin-1-yl)-1-oxoisoindolin-2-yl)-piperidine-2,6-dione D1001.

3-(6-Fluoro-5-(4-(2-hydroxy-4-methylbenzyl)piperazin-1-yl)-1-oxoisoindolin-2-yl)piperidine-2,6-dione D1002.

D1001

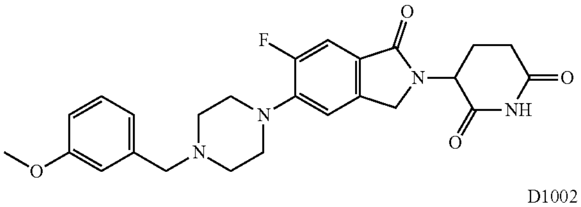

D1002

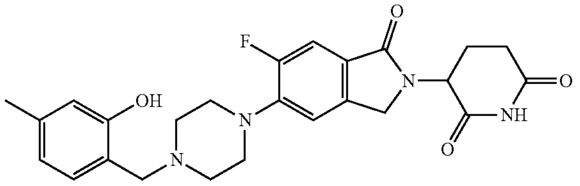

3-(6-Fluoro-5-(4-(4-(hydroxymethyl)benzyl)piperazin-1-yl)-1-oxoisoindolin-2-yl)piperidine-2,6-dione D1003.

3-(5-(4-((2,6-Dimethylpyridin-4-yl)methyl)piperazin-1-yl)-6-fluoro-1-oxoisoindolin-2-yl)piperidine-2,6-dione D1004.

D1003

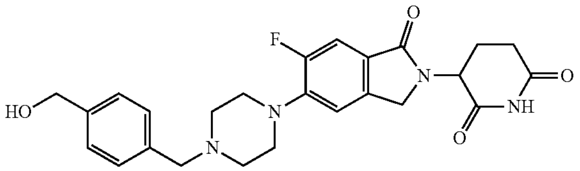

D1004

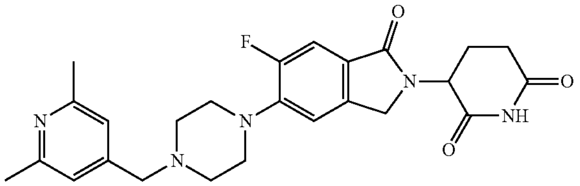

3-(6-Fluoro-5-(4-(2-(methylamino)benzyl)piperazin-1-yl)-1-oxoisoindolin-2-yl)-piperidine-2,6-dione D1005.

3-(5-(4-(2,6-Dimethylbenzyl)piperazin-1-yl)-6-fluoro-1-oxoisoindolin-2-yl)-piperidine-2,6-dione D1006.

D1005

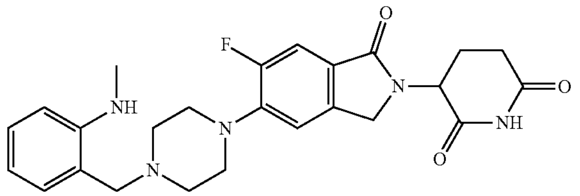

D1006

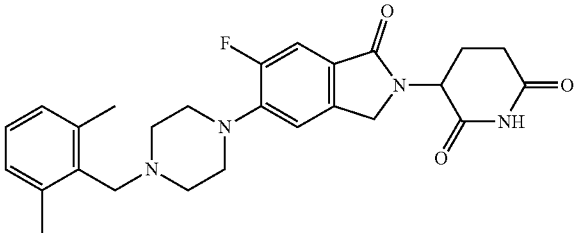

3-(5-(4-(2,4-Dimethylbenzyl)piperazin-1-yl)-6-fluoro-1-oxoisoindolin-2-yl)-piperidine-2,6-dione D1007.

3-(5-(4-(2,5-Dimethylbenzyl)piperazin-1-yl)-6-fluoro-1-oxoisoindolin-2-yl)-piperidine-2,6-dione D1008.

D1007

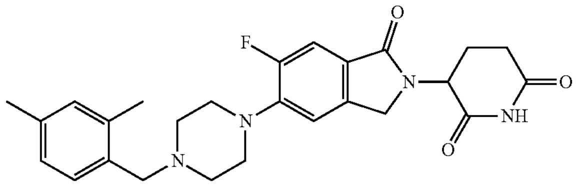

-continued

D1008

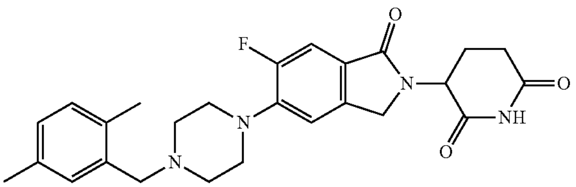

3-(6-Fluoro-5-(4-(2-methylphenethyl)piperazin-1-yl)-1-oxoisoindolin-2-yl)-piperidine-2,6-dione D1009.

3-(5-(4-(3,5-Dimethylbenzyl)piperazin-1-yl)-6-fluoro-1-oxoisoindolin-2-yl)-piperidine-2,6-dione D1010.

D1009

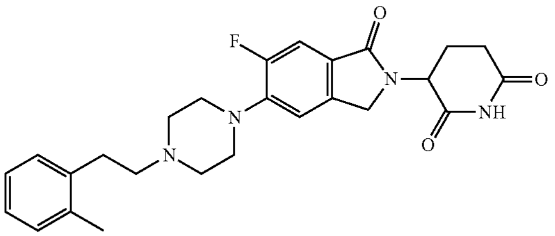

D1010

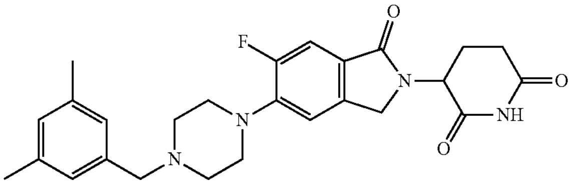

3-(6-Fluoro-1-oxo-5-(4-(pyridin-3-ylmethyl)piperazin-1-yl)isoindolin-2-yl)-piperidine-2,6-dione D1011.

3-(6-Fluoro-1-oxo-5-(4-(3-phenylpropyl)piperazin-1-yl)isoindolin-2-yl)-piperidine-2,6-dione D1012.

D1011

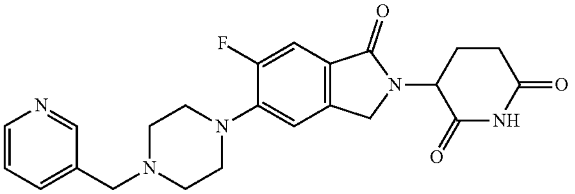

D1012

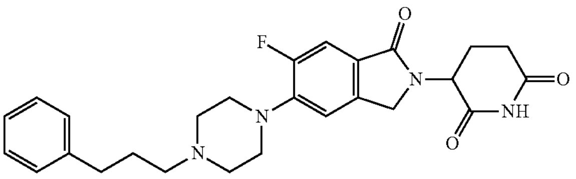

4-((4-(2-(2,6-Dioxopiperidin-3-yl)-6-fluoro-1-oxoisoindolin-5-yl)piperazin-1-yl)-methyl)-1-methyl-1H-pyrrole-2-carbonitrile D1013.

3-(5-(4-(Bicyclo[4.2.0]octa-1(6),2,4-trien-3-ylmethyl)piperazin-1-yl)-6-fluoro-1-oxoisoindolin-2-yl)piperidine-2,6-dione D1014.

D1013

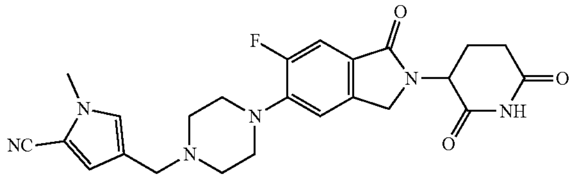

D1014

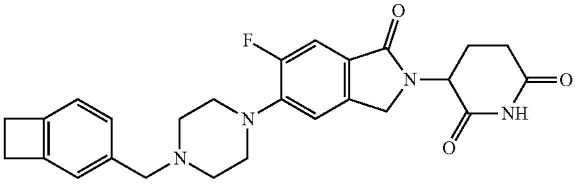

5-((4-(2-(2,6-Dioxopiperidin-3-yl)-6-fluoro-1-oxoisoindolin-5-yl)piperazin-1-yl)-methyl)picolinonitrile D1015.

5-((4-(2-(2,6-Dioxopiperidin-3-yl)-6-fluoro-1-oxoisoindolin-5-yl)piperazin-1-yl)-methyl)nicotinonitrile D1016.

D1015

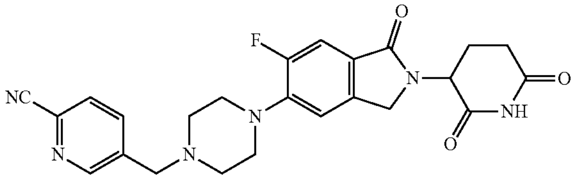

D1016

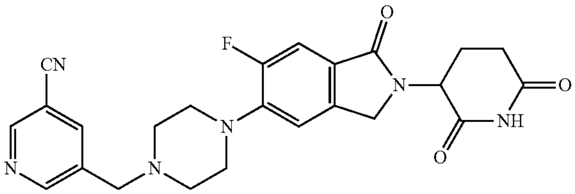

6-((4-(2-(2,6-Dioxopiperidin-3-yl)-6-fluoro-1-oxoisoindolin-5-yl)piperazin-1-yl)-methyl)picolinonitrile D1017.

2-((4-(2-(2,6-Dioxopiperidin-3-yl)-6-fluoro-1-oxoisoindolin-5-yl)piperazin-1-yl)-methyl)isonicotinonitrile D1018.

D1017

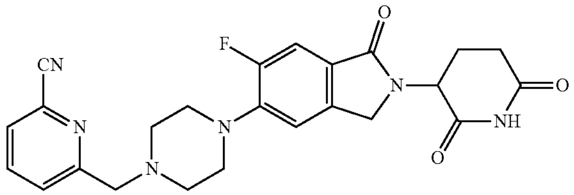

-continued

D1018

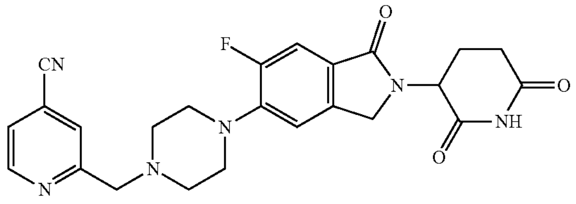

3-((4-(2-(2,6-Dioxopiperidin-3-yl)-6-fluoro-1-oxoisoindolin-5-yl)piperazin-1-yl)-methyl)benzonitrile D1019.

3-(5-(4-((5-Ethynylpyridin-2-yl)methyl)piperazin-1-yl)-6-fluoro-1-oxoisoindolin-2-yl)piperidine-2,6-dione D1020.

D1019

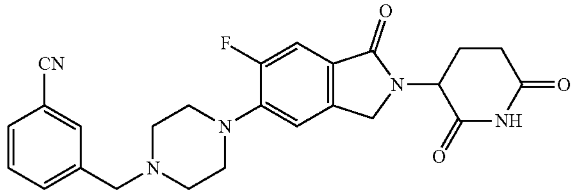

D1020

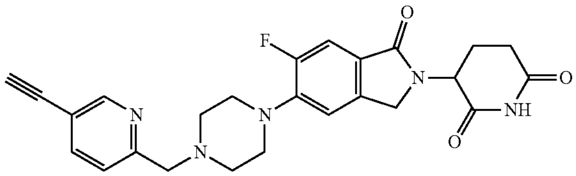

4-((4-(2-(2,6-Dioxopiperidin-3-yl)-6-fluoro-1-oxoisoindolin-5-yl)piperazin-1-yl)-methyl)benzonitrile D1021.

3-(6-Fluoro-5-(4-(3-hydroxy-2,2-dimethylpropyl)piperazin-1-yl)-1-oxoisoindolin-2-yl)piperidine-2,6-dione D1022.

D1021

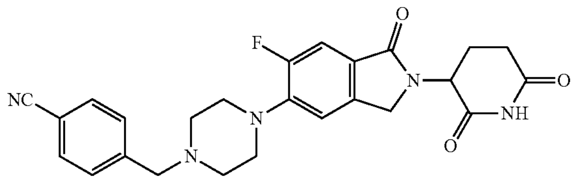

D1022

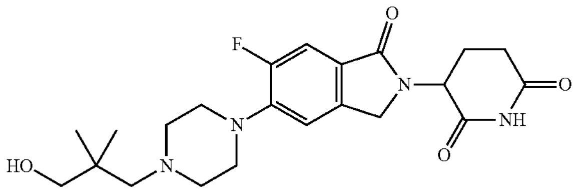

2-((4-(2-(2,6-Dioxopiperidin-3-yl)-6-fluoro-1-oxoisoindolin-5-yl)piperazin-1-yl)-methyl)benzonitrile D1023.

3-(5-(4-(4-Ethynylbenzyl)piperazin-1-yl)-6-fluoro-1-oxoisoindolin-2-yl)-piperidine-2,6-dione D1024.

D1023

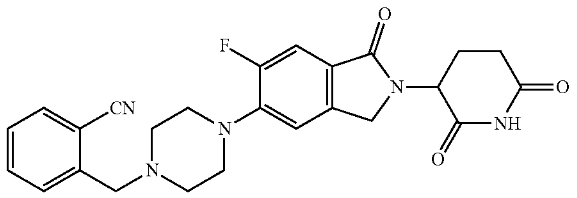

D1024

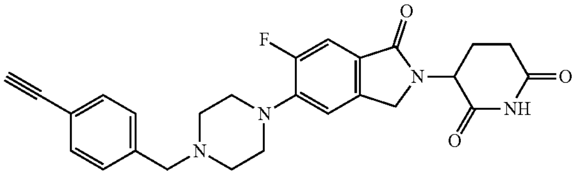

3-(5-(4-(2-Ethynylbenzyl)piperazin-1-yl)-6-fluoro-1-oxoisoindolin-2-yl)-piperidine-2,6-dione D1025.

3-(5-(4-(3-Ethynylbenzyl)piperazin-1-yl)-6-fluoro-1-oxoisoindolin-2-yl)-piperidine-2,6-dione D1026.

D1025

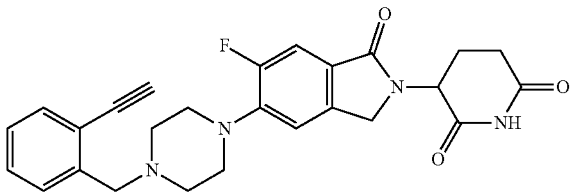

D1026

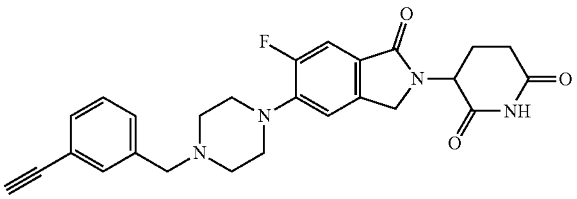

3-(6-Fluoro-5-(4-((5-methylthiazol-2-yl)methyl)piperazin-1-yl)-1-oxoisoindolin-2-yl)piperidine-2,6-dione D1027.

3-(6-Fluoro-5-(4-((2-methylthiazol-5-yl)methyl)piperazin-1-yl)-1-oxoisoindolin-2-yl)piperidine-2,6-dione D1028.

D1027

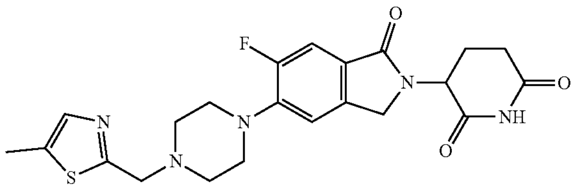

-continued

D1028

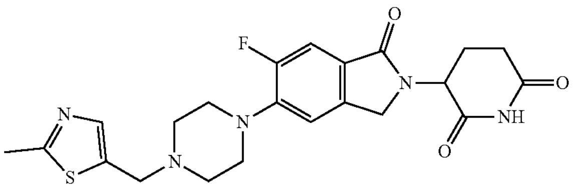

3-(6-Fluoro-5-(4-((4-methylthiazol-5-yl)methyl)piperazin-1-yl)-1-oxoisoindolin-2-yl)piperidine-2,6-dione D1029.

3-(5-(4-(2-Cyclohexylethyl)piperazin-1-yl)-6-fluoro-1-oxoisoindolin-2-yl)-piperidine-2,6-dione D1030.

D1029

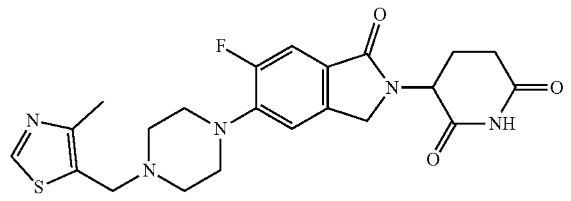

D1030

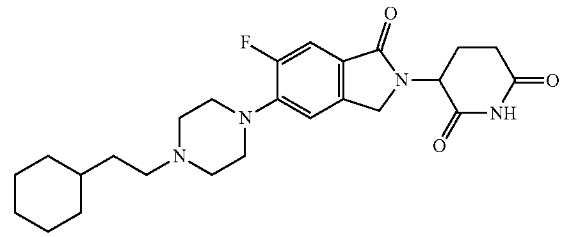

3-(6-Fluoro-5-(4-((3-methylthiophen-2-yl)methyl)piperazin-1-yl)-1-oxoisoindolin-2-yl)piperidine-2,6-dione D1031.

3-(6-Fluoro-5-(4-((3-methoxyfuran-2-yl)methyl)piperazin-1-yl)-1-oxoisoindolin-2-yl)piperidine-2,6-dione D1032.

D1031

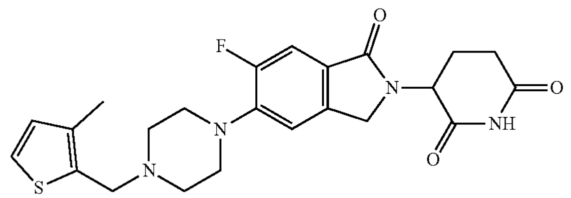

D1032

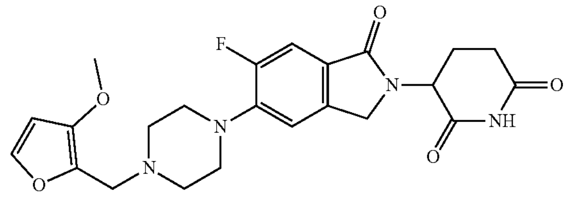

3-(6-Fluoro-5-(4-((3-methyloxetan-3-yl)methyl)piperazin-1-yl)-1-oxoisoindolin-2-yl)piperidine-2,6-dione D1033.

3-(6-Fluoro-5-(4-((5-(hydroxymethyl)furan-2-yl)methyl)piperazin-1-yl)-1-oxoisoindolin-2-yl)piperidine-2,6-dione D1034.

D1033

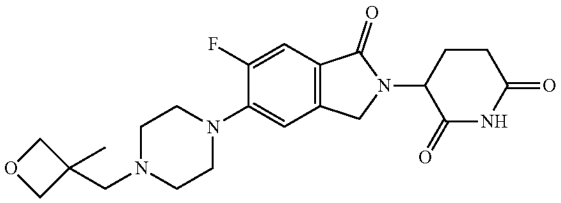

D1034

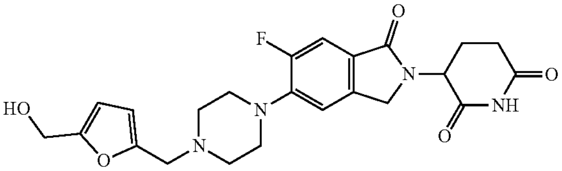

3-(5-(4-((5-Amino-1-methyl-1H-pyrazol-4-yl)methyl)piperazin-1-yl)-6-fluoro-1-oxoisoindolin-2-yl)piperidine-2,6-dione D1035.

3-(6-Fluoro-5-(4-((5-(hydroxymethyl)-1H-pyrrol-2-yl)methyl)piperazin-1-yl)-1-oxoisoindolin-2-yl)piperidine-2,6-dione D1036.

D1035

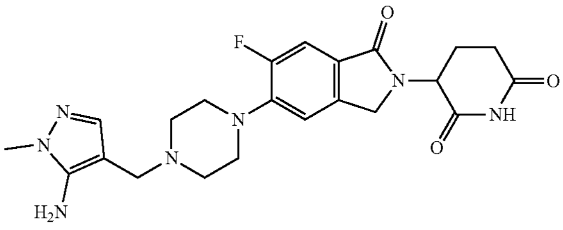

D1036

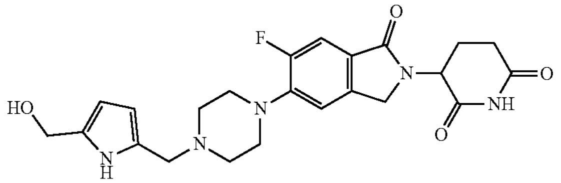

3-(6-Fluoro-5-(4-((6-fluoropyridin-3-yl)methyl)piperazin-1-yl)-1-oxoisoindolin-2-yl)piperidine-2,6-dione D1037.

3-(6-Fluoro-5-(4-((3-fluoropyridin-4-yl)methyl)piperazin-1-yl)-1-oxoisoindolin-2-yl)piperidine-2,6-dione D1038.

D1037

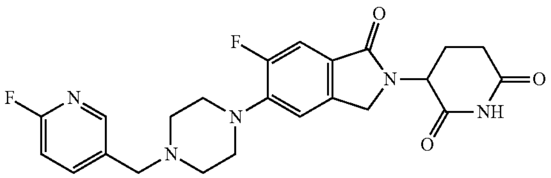

-continued

D1038

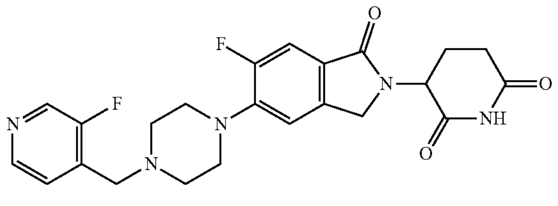

3-(6-Fluoro-5-(4-((5-fluoropyridin-2-yl)methyl)piperazin-1-yl)-1-oxoisoindolin-2-yl)piperidine-2,6-dione D1039.

3-(6-Fluoro-5-(4-((5-fluoropyridin-3-yl)methyl)piperazin-1-yl)-1-oxoisoindolin-2-yl)piperidine-2,6-dione D1040.

D1039

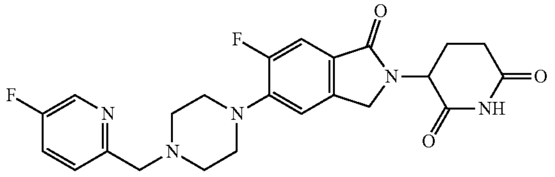

D1040

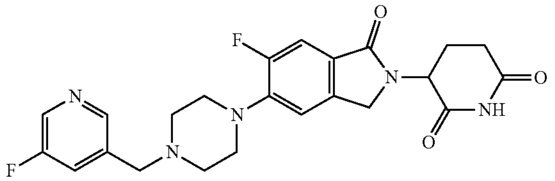

3-(6-Fluoro-5-(4-((4-fluoropyridin-2-yl)methyl)piperazin-1-yl)-1-oxoisoindolin-2-yl)piperidine-2,6-dione D1041.

3-(6-Fluoro-5-(4-((6-fluoropyridin-2-yl)methyl)piperazin-1-yl)-1-oxoisoindolin-2-yl)piperidine-2,6-dione D1042.

D1041

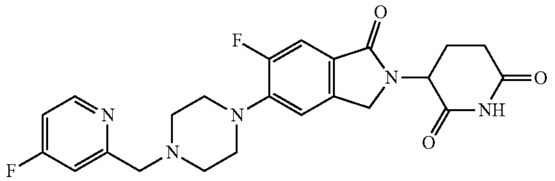

D1042

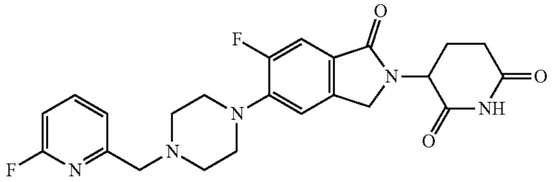

3-(5-(4-((2,5-Dimethyl-1H-imidazol-4-yl)methyl)piperazin-1-yl)-6-fluoro-1-oxoisoindolin-2-yl)piperidine-2,6-dione D1043.

3-(6-Fluoro-5-(4-(oxazol-2-ylmethyl)piperazin-1-yl)-1-oxoisoindolin-2-yl)-piperidine-2,6-dione D1044.

D1043

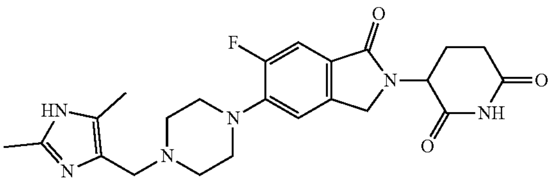

D1044

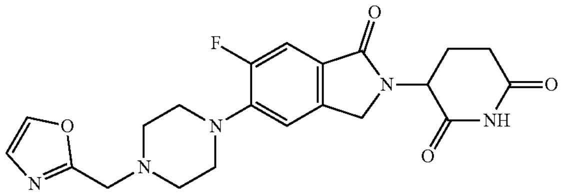

3-(5-(4-((1,4-Dimethyl-1H-pyrazol-5-yl)methyl)piperazin-1-yl)-6-fluoro-1-oxoisoindolin-2-yl)piperidine-2,6-dione D1045.

3-(6-Fluoro-5-(4-(4-fluorobenzyl)piperazin-1-yl)-1-oxoisoindolin-2-yl)piperidine-2,6-dione D1046.

D1045

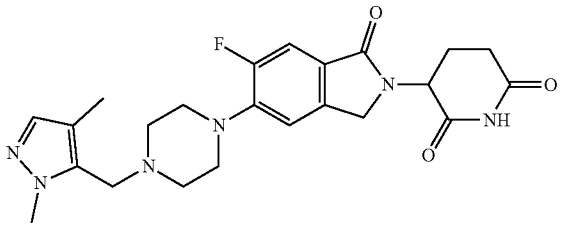

D1046

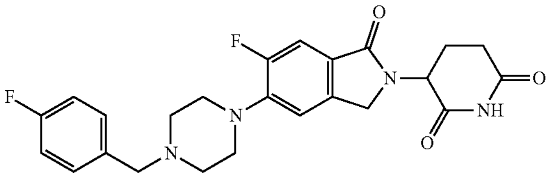

3-(6-Fluoro-5-(4-(3-fluorobenzyl)piperazin-1-yl)-1-oxoisoindolin-2-yl)piperidine-2,6-dione D1047.

3-(6-Fluoro-5-(4-((2-hydroxypyridin-3-yl)methyl)piperazin-1-yl)-1-oxoisoindolin-2-yl)piperidine-2,6-dione D1048.

D1047

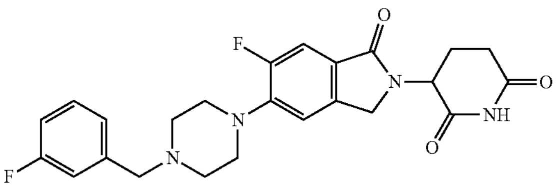

-continued

D1048

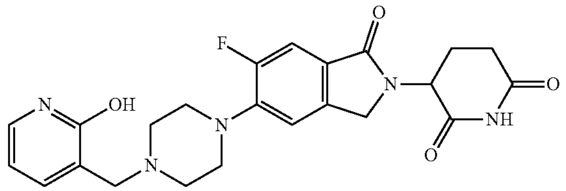

3-(6-Fluoro-5-(4-((5-methylpyrazin-2-yl)methyl)piperazin-1-yl)-1-oxoisoindolin-2-yl)piperidine-2,6-dione D1049.

3-(6-Fluoro-5-(4-((3-methylpyrazin-2-yl)methyl)piperazin-1-yl)-1-oxoisoindolin-2-yl)piperidine-2,6-dione D1050.

D1049

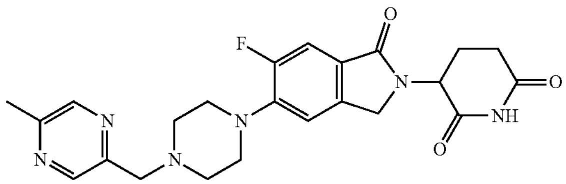

D1050

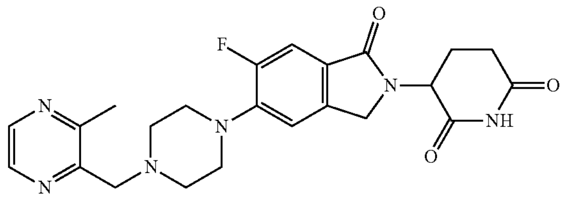

3-(6-Fluoro-5-(4-((2-methylpyrimidin-4-yl)methyl)piperazin-1-yl)-1-oxoisoindolin-2-yl)piperidine-2,6-dione D1051.

3-(6-Fluoro-5-(4-((2-methylpyrimidin-5-yl)methyl)piperazin-1-yl)-1-oxoisoindolin-2-yl)piperidine-2,6-dione D1052.

D1051

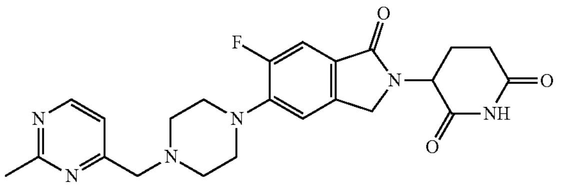

D1052

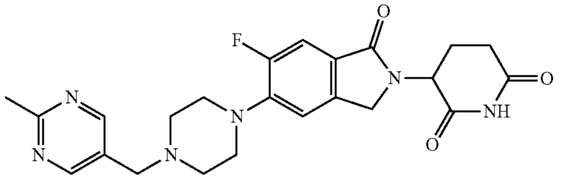

3-(5-(4-((2-Aminopyridin-3-yl)methyl)piperazin-1-yl)-6-fluoro-1-oxoisoindolin-2-yl)piperidine-2,6-dione D1053.

3-(5-(4-((3-Aminopyridin-4-yl)methyl)piperazin-1-yl)-6-fluoro-1-oxoisoindolin-2-yl)piperidine-2,6-dione D1054.

D1053

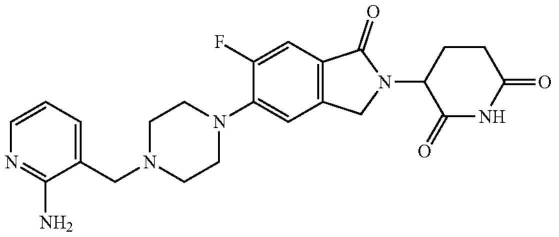

D1054

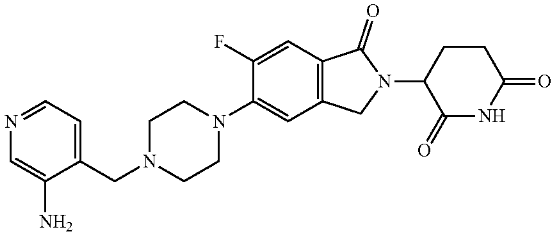

3-(5-(4-((1H-Pyrazol-5-yl)methyl)piperazin-1-yl)-6-fluoro-1-oxoisoindolin-2-yl)-piperidine-2,6-dione D1055.

3-(6-Fluoro-5-(4-(3-hydroxybenzyl)piperazin-1-yl)-1-oxoisoindolin-2-yl)-piperidine-2,6-dione D1056.

D1055

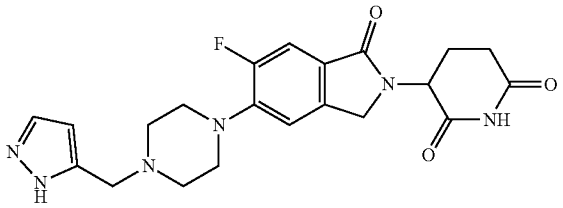

D1056

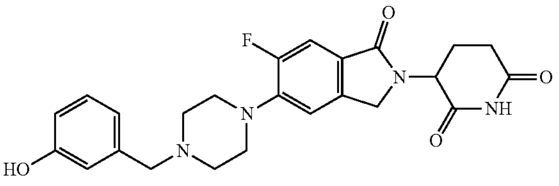

3-(6-Fluoro-5-(4-(4-hydroxybenzyl)piperazin-1-yl)-1-oxoisoindolin-2-yl)-piperidine-2,6-dione D1057.

3-(6-Fluoro-5-(4-((4-methylpyridin-2-yl)methyl)piperazin-1-yl)-1-oxoisoindolin-2-yl)piperidine-2,6-dione D1058.

D1057

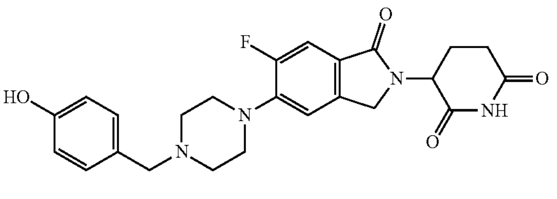

-continued

D1058

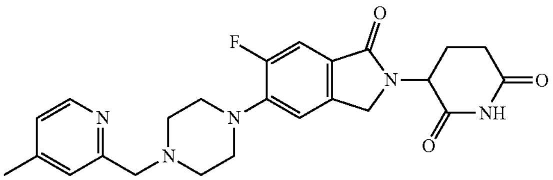

3-(6-Fluoro-5-(4-((3-methylpyridin-2-yl)methyl)piperazin-1-yl)-1-oxoisoindolin-2-yl)piperidine-2,6-dione D1059.

3-(6-Fluoro-5-(4-((2-methylpyridin-3-yl)methyl)piperazin-1-yl)-1-oxoisoindolin-2-yl)piperidine-2,6-dione D1060.

D1059

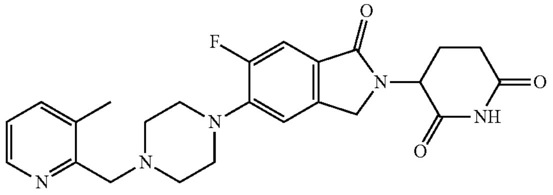

D1060

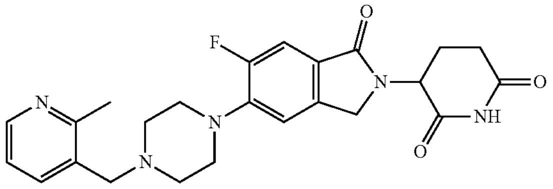

3-(6-Fluoro-5-(4-((2-methylpyridin-4-yl)methyl)piperazin-1-yl)-1-oxoisoindolin-2-yl)piperidine-2,6-dione D1061.

3-(6-Fluoro-5-(4-((5-methylpyridin-2-yl)methyl)piperazin-1-yl)-1-oxoisoindolin-2-yl)piperidine-2,6-dione D1062.

D1061

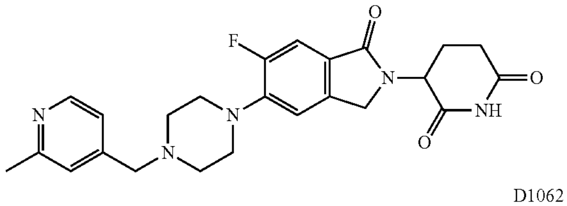

D1062

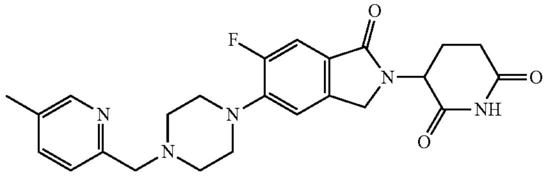

3-(6-Fluoro-5-(4-((6-methylpyridin-2-yl)methyl)piperazin-1-yl)-1-oxoisoindolin-2-yl)piperidine-2,6-dione D1063.

3-(6-Fluoro-5-(4-((4-methylpyridin-3-yl)methyl)piperazin-1-yl)-1-oxoisoindolin-2-yl)piperidine-2,6-dione D1064.

D1063

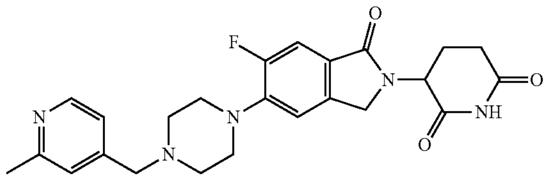

D1064

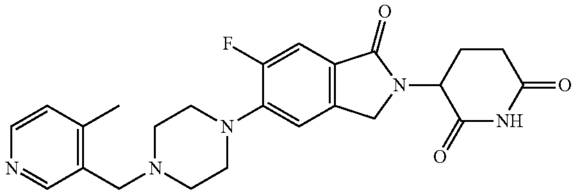

3-(6-Fluoro-5-(4-((5-methylpyridin-3-yl)methyl)piperazin-1-yl)-1-oxoisoindolin-2-yl)piperidine-2,6-dione D1065.

3-(5-(4-((1H-Imidazol-5-yl)methyl)piperazin-1-yl)-6-fluoro-1-oxoisoindolin-2-yl)piperidine-2,6-dione D1066.

D1065

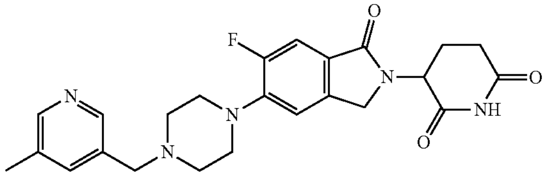

D1066

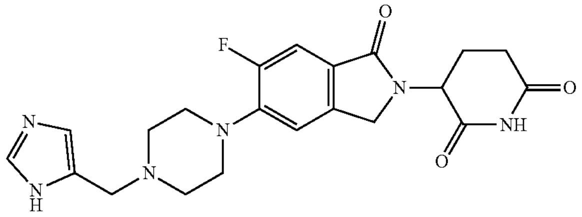

3-(5-(4-(4-Aminobenzyl)piperazin-1-yl)-6-fluoro-1-oxoisoindolin-2-yl)-piperidine-2,6-dione D1067.

3-(5-(4-(2-Aminobenzyl)piperazin-1-yl)-6-fluoro-1-oxoisoindolin-2-yl)-piperidine-2,6-dione D1068.

D1067

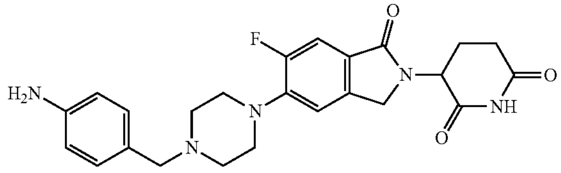

D1068

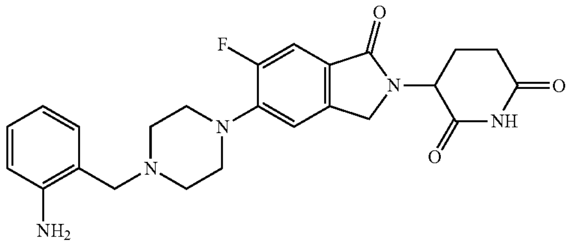

3-(6-Fluoro-5-(4-(4-methylbenzyl)piperazin-1-yl)-1-oxoisoindolin-2-yl)-piperidine-2,6-dione D1069.

3-(6-Fluoro-5-(4-(2-methylbenzyl)piperazin-1-yl)-1-oxoisoindolin-2-yl)-piperidine-2,6-dione D1070.

D1069

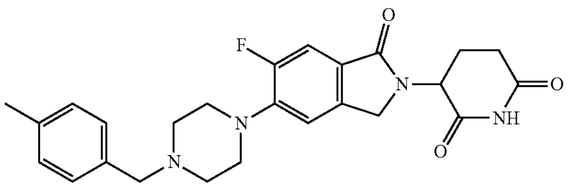

D1070

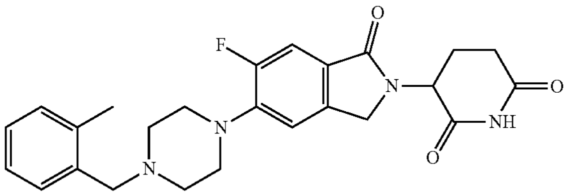

4-(4-Bromo-3-((4-(2-(2,6-dioxopiperidin-3-yl)-6-fluoro-1-oxoisoindolin-5-yl)-piperazin-1-yl)methyl)phenoxy)benzonitrile D1071.

D1071

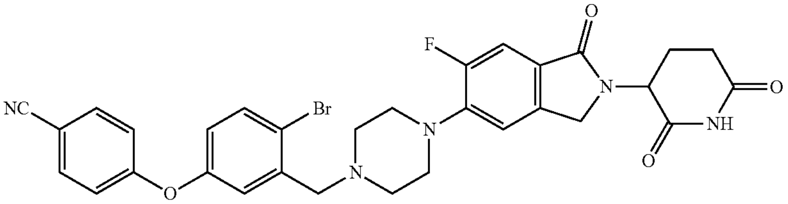

3-(6-Fluoro-1-oxo-5-(4-phenethylpiperazin-1-yl)isoindolin-2-yl)piperidine-2,6-dione D1072.

D1072

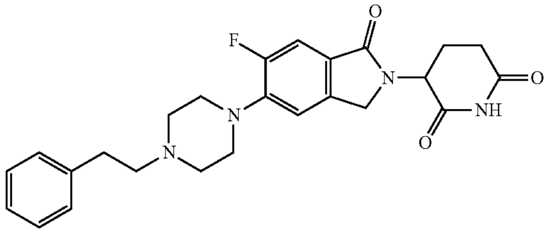

3-(5-(4-(3-Bromo-4-(4-methylpiperazin-1-yl)benzyl)piperazin-1-yl)-6-fluoro-1-oxoisoindolin-2-yl)piperidine-2,6-dione D1073.

D1073

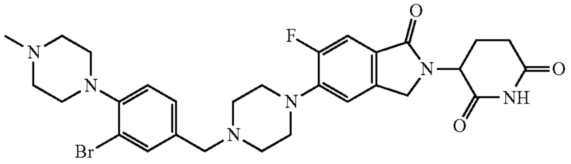

Tert-butyl 4-(4-((4-(2-(2,6-dioxopiperidin-3-yl)-6-fluoro-1-oxoisoindolin-5-yl)-piperazin-1-yl)methyl)-1H-1,2,3-triazol-1-yl)piperidine-1-carboxylate D1074.

D1074

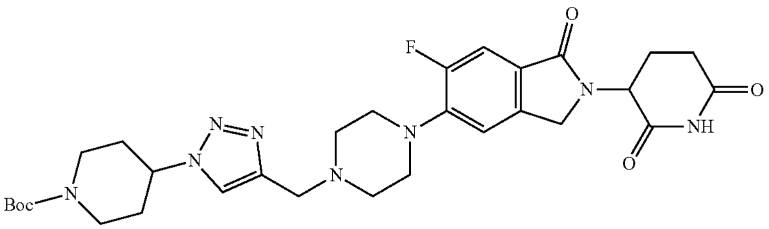

3-(5-(4-(3-Bromo-4-morpholinobenzyl)piperazin-1-yl)-6-fluoro-1-oxoisoindolin-2-yl)piperidine-2,6-dione D1075.

D1075

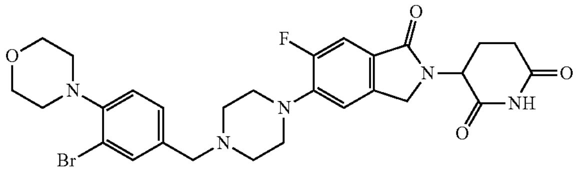

3-(6-Fluoro-1-oxo-5-(4-(4-(4-(trifluoromethyl)phenoxy) benzyl)piperazin-1-yl)-isoindolin-2-yl)piperidine-2,6-dione D1076.

D1076

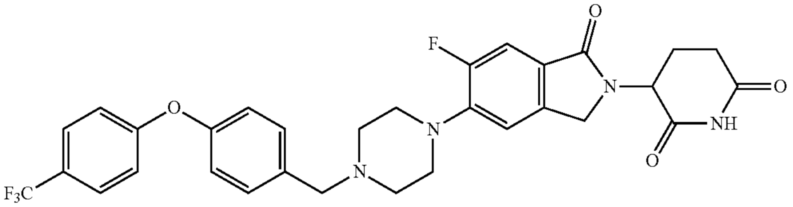

3-(5-(4-(4-(Benzyloxy)-3-ethoxybenzyl)piperazin-1-yl)-6-fluoro-1-oxoisoindolin-2-yl)piperidine-2,6-dione D1077.

D1077

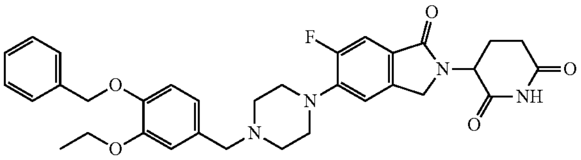

Tert-butyl 4-(1-(4-(2-(2,6-dioxopiperidin-3-yl)-6-fluoro-1-oxoisoindolin-5-yl)-piperazin-1-yl)-2-methylpropan-2-yl)piperidine-1-carboxylate D1078.

D1078

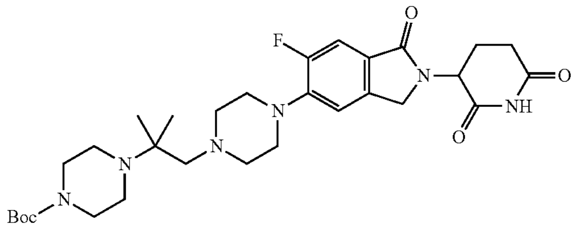

Benzyl (4-((4-(2-(2,6-dioxopiperidin-3-yl)-6-fluoro-1-oxoisoindolin-5-yl)-piperazin-1-yl)methyl)phenyl)carbamate D1079.

D1079

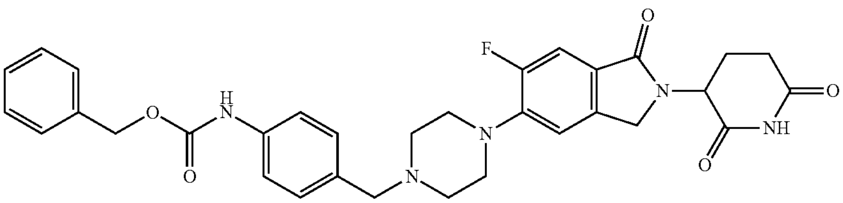

Tert-butyl 6-((4-(2-(2,6-dioxopiperidin-3-yl)-6-fluoro-1-oxoisoindolin-5-yl)-piperazin-1-yl)methyl)indoline-1-carboxylate D1080.

D1080

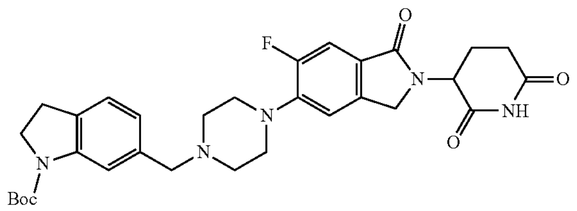

Tert-butyl (((1r,4r)-4-((4-(2-(2,6-dioxopiperidin-3-yl)-6-fluoro-1-oxoisoindolin-5-yl)piperazin-1-yl)methyl)cyclohexyl)methyl)carbamate D1081.

D1081

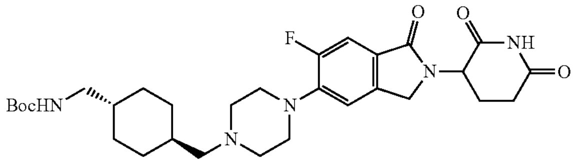

4-(4-((4-(2-(2,6-Dioxopiperidin-3-yl)-6-fluoro-1-oxoisoindolin-5-yl)piperazin-1-yl)methyl)phenoxy)-3-fluorobenzonitrile D1082.

D1082

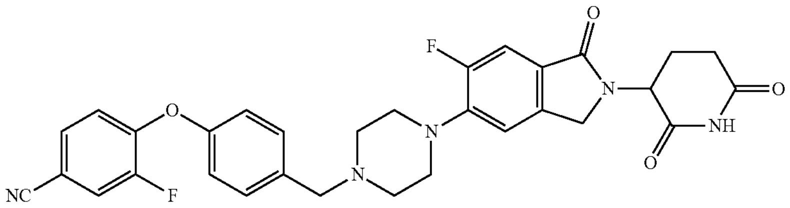

3-(6-Fluoro-5-(4-(3-methylbenzyl)piperazin-1-yl)-1-oxoisoindolin-2-yl)-piperidine-2,6-dione D1083.

Tert-butyl 4-((4-(2-(2,6-dioxopiperidin-3-yl)-6-fluoro-1-oxoisoindolin-5-yl)-piperazin-1-yl)methyl)-4-fluoropiperidine-1-carboxylate D1084.

D1083

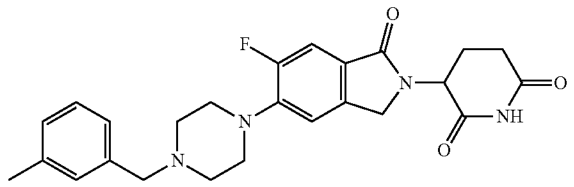

-continued

D1084

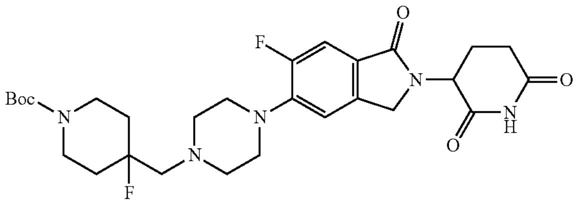

Tert-butyl 4-(2-(4-(2-(2,6-dioxopiperidin-3-yl)-6-fluoro-1-oxoisoindolin-5-yl)-piperazin-1-yl)ethyl)piperazine-1-carboxylate D1085.

3-(5-(4-((2-Chloro-4-morpholinopyrimidin-5-yl)methyl)piperazin-1-yl)-6-fluoro-1-oxoisoindolin-2-yl)piperidine-2,6-dione D1086.

D1085

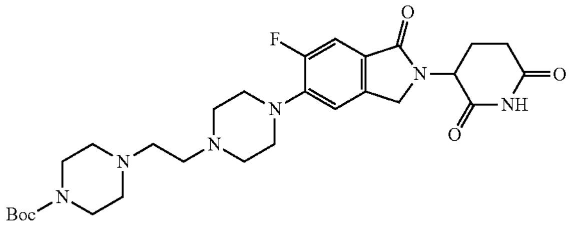

-continued

D1086

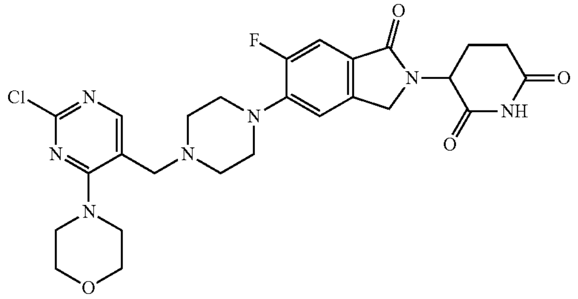

Tert-butyl ((1r,4r)-4-((4-(2-(2,6-dioxopiperidin-3-yl)-6-fluoro-1-oxoisoindolin-5-yl)piperazin-1-yl)methyl)cyclohexyl)carbamate D1087.

D1087

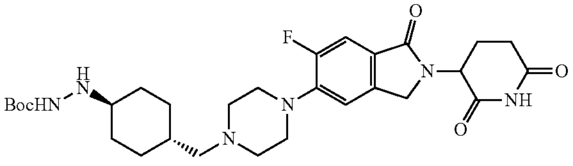

Tert-butyl 4-(2-(4-(2-(2,6-dioxopiperidin-3-yl)-6-fluoro-1-oxoisoindolin-5-yl)-piperazin-1-yl)ethyl)piperidine-1-carboxylate D1088.

D1088

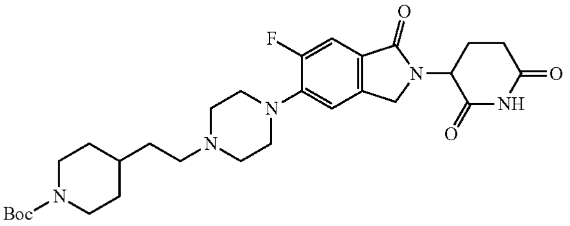

3-(5-(4-(2-(Benzyloxy)-4-methylbenzyl)piperazin-1-yl)-6-fluoro-1-oxoisoindolin-2-yl)piperidine-2,6-dione D1089.

3-(5-(4-(4-(Benzyloxy)-2-methylbenzyl)piperazin-1-yl)-6-fluoro-1-oxoisoindolin-2-yl)piperidine-2,6-dione D1090.

D1089

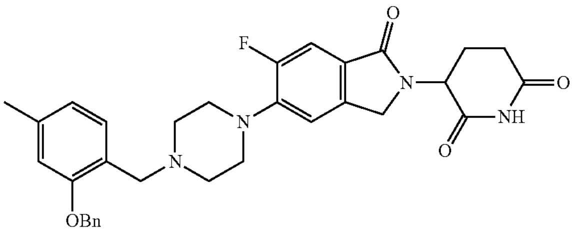

-continued

D1090

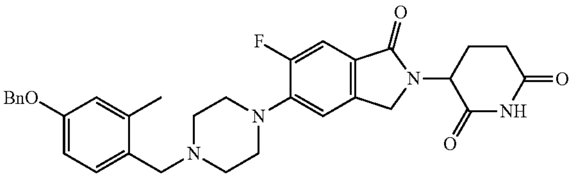

3-(5-(4-(3-Chloro-4-morpholinobenzyl)piperazin-1-yl)-6-fluoro-1-oxoisoindolin-2-yl)piperidine-2,6-dione D1091.

D1091

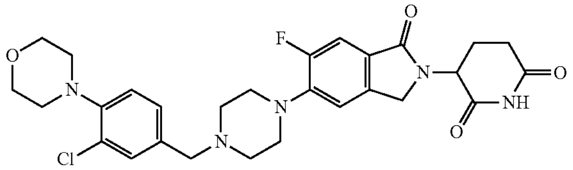

4-(4-((4-(2-(2,6-Dioxopiperidin-3-yl)-6-fluoro-1-oxoisoindolin-5-yl)piperazin-1-yl)methyl)phenoxy)benzonitrile D1092.

D1092

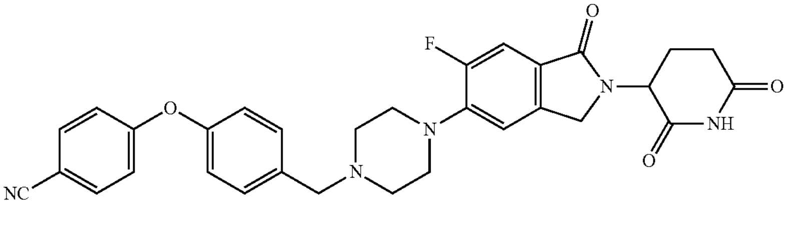

4-(3-((4-(2-(2,6-Dioxopiperidin-3-yl)-6-fluoro-1-oxoisoindolin-5-yl)piperazin-1-yl)methyl)phenoxy)benzonitrile D1093.

D1093

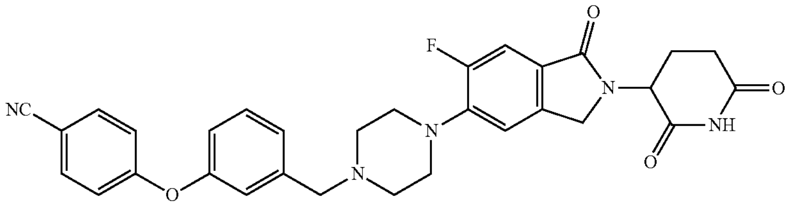

2-((4-(2-(2,6-Dioxopiperidin-3-yl)-6-fluoro-1-oxoisoindolin-5-yl)piperazin-1-yl)methyl)-1H-pyrrole-3-carbonitrile D1094.

D1094

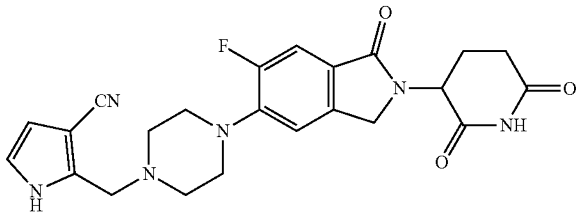

3-(5-(4-(3-(Cyclohexylmethoxy)benzyl)piperazin-1-yl)-6-fluoro-1-oxoisoindolin-2-yl)piperidine-2,6-dione D1095.

D1095

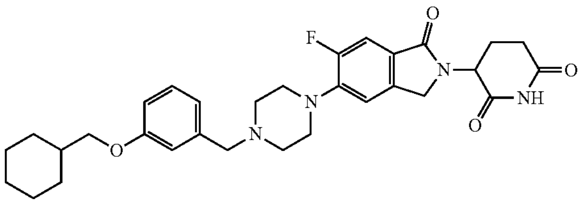

3-(5-(4-(3-(3-Bromophenyl)propyl)piperazin-1-yl)-6-fluoro-1-oxoisoindolin-2-yl)piperidine-2,6-dione D1096.

D1096

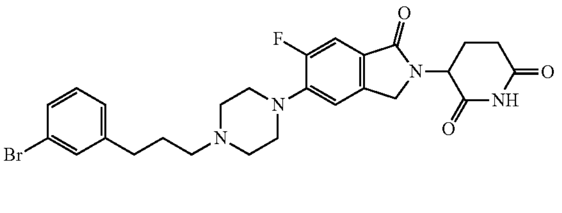

3-(5-(4-(4-(Benzyloxy)benzyl)piperazin-1-yl)-6-fluoro-1-oxoisoindolin-2-yl)-piperidine-2,6-dione D1097.

3-(5-(4-(3-(Benzyloxy)benzyl)piperazin-1-yl)-6-fluoro-1-oxoisoindolin-2-yl)-piperidine-2,6-dione D1098.

D1097

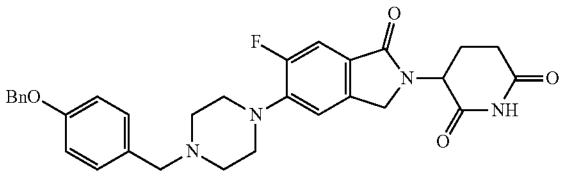

D1098

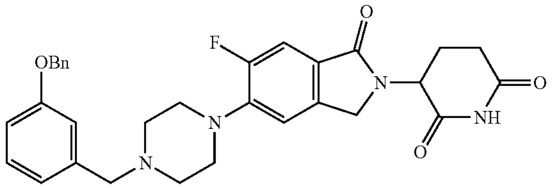

5-((4-(2-(2,6-Dioxopiperidin-3-yl)-6-fluoro-1-oxoisoindolin-5-yl)piperazin-1-yl)-methyl)-2-(4-methyl-1H-imidazol-1-yl)benzonitrile D1099.

D1099

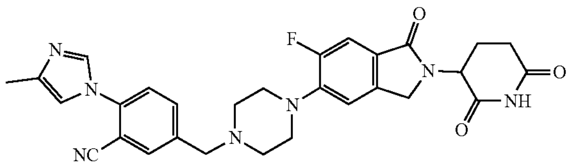

3-(5-(4-(3-Chloro-4-(trifluoromethyl)benzyl)piperazin-1-yl)-6-fluoro-1-oxoisoindolin-2-yl)piperidine-2,6-dione D1100.

D1100

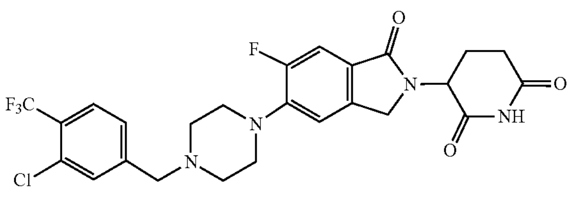

3-(5-(4-(2-Chloro-4-(trifluoromethyl)benzyl)piperazin-1-yl)-6-fluoro-1-oxoisoindolin-2-yl)piperidine-2,6-dione D1101.

3-(5-(4-(4-Chloro-2-(trifluoromethyl)benzyl)piperazin-1-yl)-6-fluoro-1-oxoisoindolin-2-yl)piperidine-2,6-dione D1102.

D1101

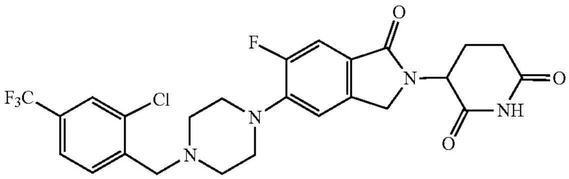

D1102

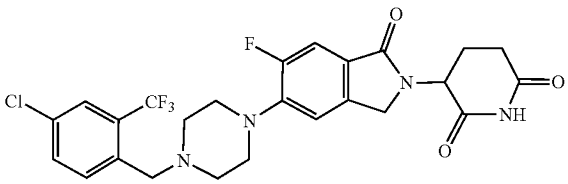

3-(5-(4-(5-Chloro-2-(trifluoromethyl)benzyl)piperazin-1-yl)-6-fluoro-1-oxoisoindolin-2-yl)piperidine-2,6-dione D1103.

3-(5-(4-(2-Chloro-5-(trifluoromethyl)benzyl)piperazin-1-yl)-6-fluoro-1-oxoisoindolin-2-yl)piperidine-2,6-dione D1104.

D1103

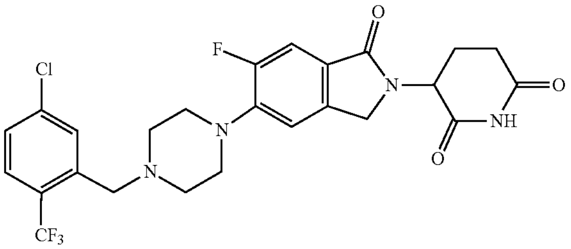

D1104

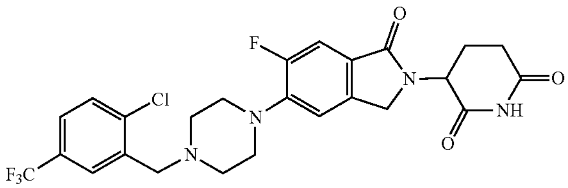

3-(6-Fluoro-1-oxo-5-(4-((tetrahydro-2H-pyran-4-yl)methyl)piperazin-1-yl)-isoindolin-2-yl)piperidine-2,6-dione D1105.

3-(5-(4-((1-Benzylpiperidin-4-yl)methyl)piperazin-1-yl)-6-fluoro-1-oxoisoindolin-2-yl)piperidine-2,6-dione D1106.

D1105

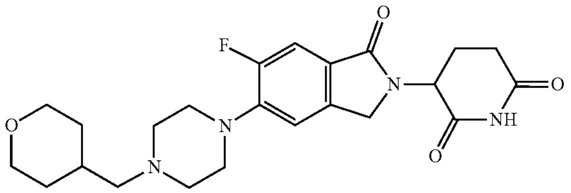

D1106

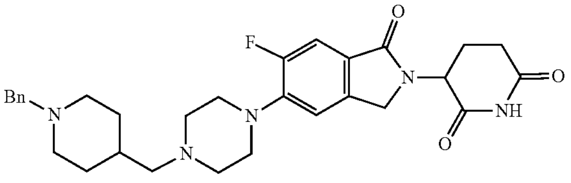

2-(3-(4-(2-(2,6-Dioxopiperidin-3-yl)-6-fluoro-1-oxoisoindolin-5-yl)piperazin-1-yl)propyl)isoindoline-1,3-dione D1107.

D1107

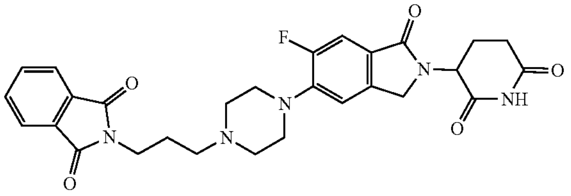

3-(6-Fluoro-1-oxo-5-(4-(3-(3-(trifluoromethyl)phenyl)propyl)piperazin-1-yl)-isoindolin-2-yl)piperidine-2,6-dione D1108.

D1108

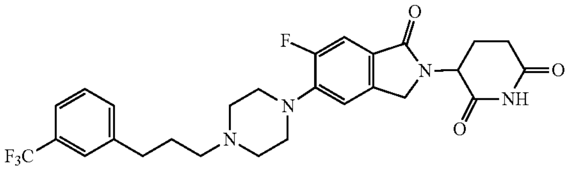

3-(5-(4-((6-(Dimethylamino)naphthalen-2-yl)methyl)piperazin-1-yl)-6-fluoro-1-oxoisoindolin-2-yl)piperidine-2,6-dione D1109.

N-(2-((4-(2-(2,6-Dioxopiperidin-3-yl)-6-fluoro-1-oxoisoindolin-5-yl)piperazin-1-yl)methyl)phenyl)methanesulfonamide D1110.

D1109

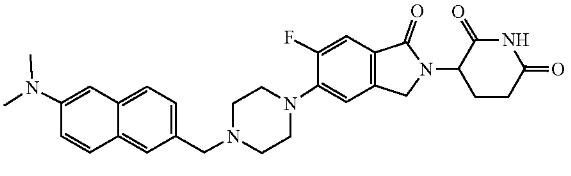

-continued

D1110

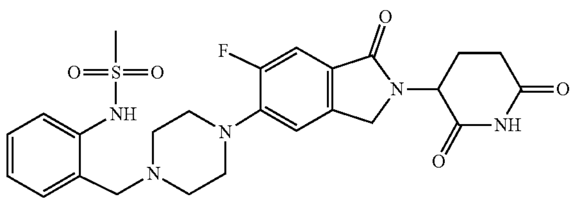

N-(4-((4-(2-(2,6-Dioxopiperidin-3-yl)-6-fluoro-1-oxoisoindolin-5-yl)piperazin-1-yl)methyl)phenyl)methanesulfonamide D1111.

D1111

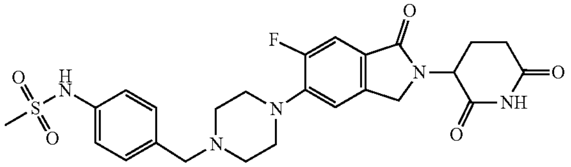

N-(3-((4-(2-(2,6-Dioxopiperidin-3-yl)-6-fluoro-1-oxoisoindolin-5-yl)piperazin-1-yl)methyl)phenyl)methanesulfonamide D1112.

D1112

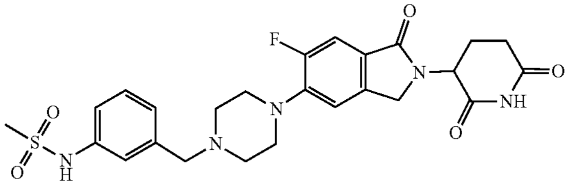

3-(6-Fluoro-1-oxo-5-(4-(2-(pyridin-2-yloxy)benzyl)piperazin-1-yl)isoindolin-2-yl)piperidine-2,6-dione D1113.

3-(5-(4-(4-Bromophenethyl)piperazin-1-yl)-6-fluoro-1-oxoisoindolin-2-yl)-piperidine-2,6-dione D1114.

D1113

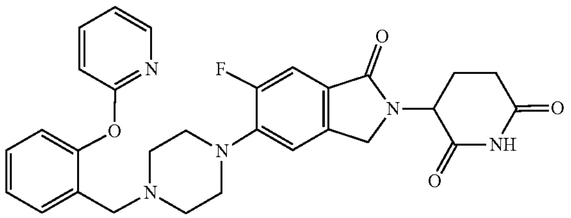

-continued

D1114

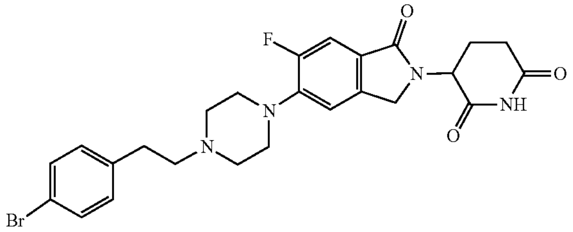

3-(6-Fluoro-5-(4-((2-morpholinothiazol-5-yl)methyl)piperazin-1-yl)-1-oxoisoindolin-2-yl)piperidine-2,6-dione D1115.

3-(6-Fluoro-1-oxo-5-(4-(thiazol-2-ylmethyl)piperazin-1-yl)isoindolin-2-yl)-piperidine-2,6-dione D1116.

D1115

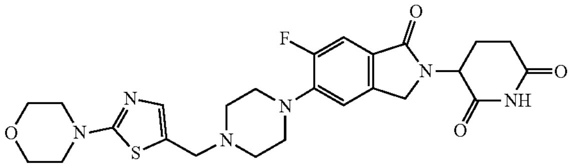

D1116

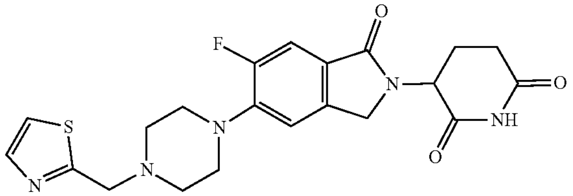

3-(5-(4-(4-(Ethylsulfonyl)benzyl)piperazin-1-yl)-6-fluoro-1-oxoisoindolin-2-yl)-piperidine-2,6-dione D1117.

D1117

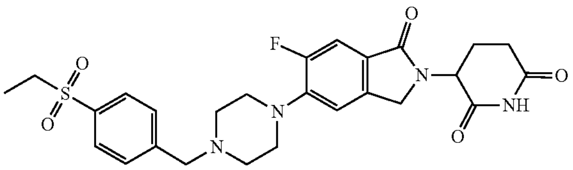

3-(6-Fluoro-5-(4-((4'-methyl-[2,2'-bipyridin]-4-yl)methyl)piperazin-1-yl)-1-oxoisoindolin-2-yl)piperidine-2,6-dione D1118.

D1118

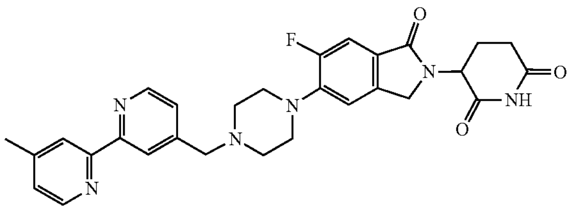

3-(6-Fluoro-1-oxo-5-(4-(4-phenoxybenzyl)piperazin-1-yl)isoindolin-2-yl)-piperidine-2,6-dione D1119.

D1119

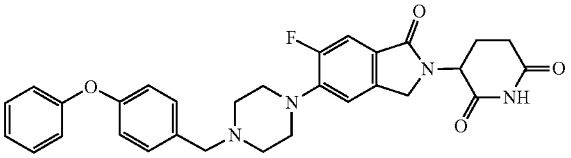

3-(6-Fluoro-1-oxo-5-(4-(3-phenoxybenzyl)piperazin-1-yl)isoindolin-2-yl)-piperidine-2,6-dione D1120.

D1120

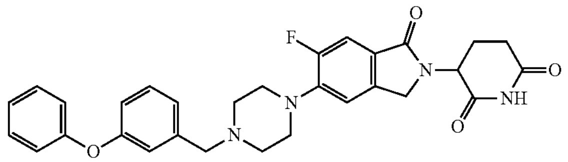

3-(6-Fluoro-1-oxo-5-(4-((6-(p-tolyl)pyridin-3-yl)methyl)piperazin-1-yl)-isoindolin-2-yl)piperidine-2,6-dione D1121.

D1121

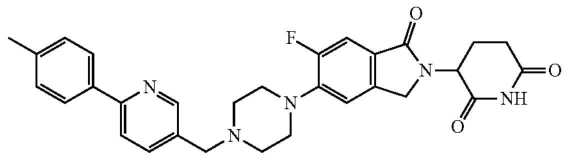

4-((4-(2-(2,6-Dioxopiperidin-3-yl)-6-fluoro-1-oxoisoindolin-5-yl)piperazin-1-yl)-methyl)-N-isopropylbenzamide D1122.

D1122

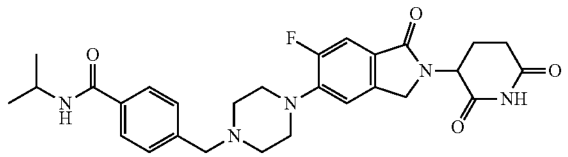

3-(6-Fluoro-5-(4-(2-morpholinobenzyl)piperazin-1-yl)-1-oxoisoindolin-2-yl)-piperidine-2,6-dione D1123.

3-(6-Fluoro-5-(4-(3-morpholinobenzyl)piperazin-1-yl)-1-oxoisoindolin-2-yl)-piperidine-2,6-dione D1124.

D1123

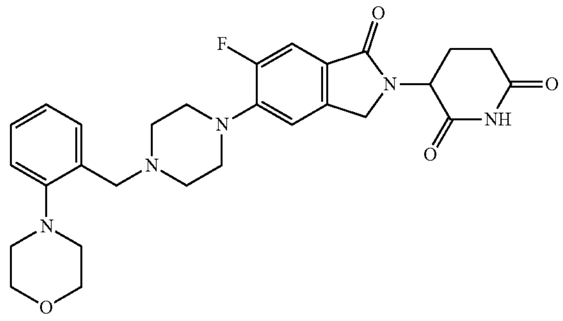

D1124

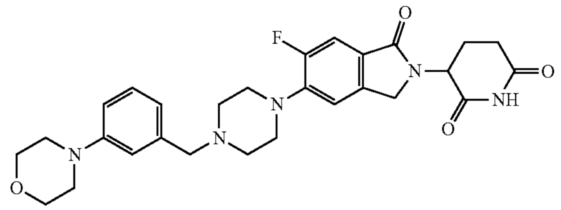

3-(6-Fluoro-5-(4-(4-morpholinobenzyl)piperazin-1-yl)-1-oxoisoindolin-2-yl)-piperidine-2,6-dione D1125.

D1125

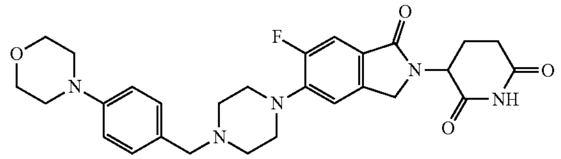

3-(6-Fluoro-1-oxo-5-(4-(3-(quinolin-6-yl)propyl)piperazin-1-yl)isoindolin-2-yl)-piperidine-2,6-dione D1126.

D1126

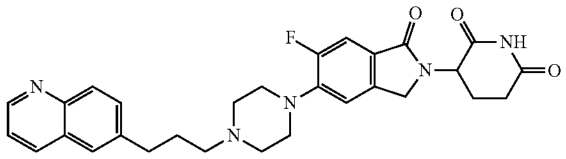

3-(6-Fluoro-1-oxo-5-(4-(thiazol-5-ylmethyl)piperazin-1-yl)isoindolin-2-yl)-piperidine-2,6-dione D1127.

3-(5-(4-((1H-Pyrrol-3-yl)methyl)piperazin-1-yl)-6-fluoro-1-oxoisoindolin-2-yl)-piperidine-2,6-dione D1128.

D1127

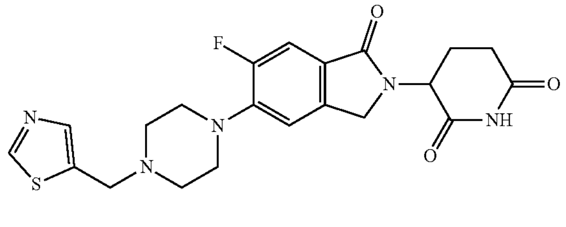

-continued

D1128

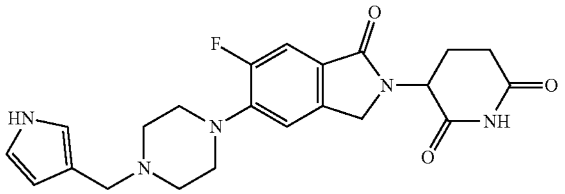

3-(6-Fluoro-5-(4-((6-(methylsulfonyl)pyridin-2-yl)methyl)piperazin-1-yl)-1-oxoisoindolin-2-yl)piperidine-2,6-dione D1129.

D1129

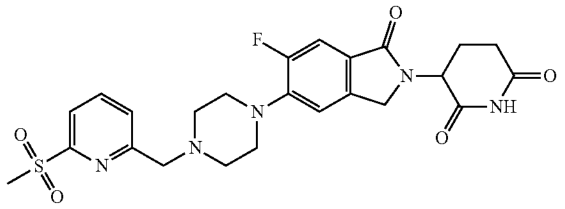

3-(6-Fluoro-1-oxo-5-(4-(3-(pyridin-4-yl)benzyl)piperazin-1-yl)isoindolin-2-yl)-piperidine-2,6-dione D1130.

D1130

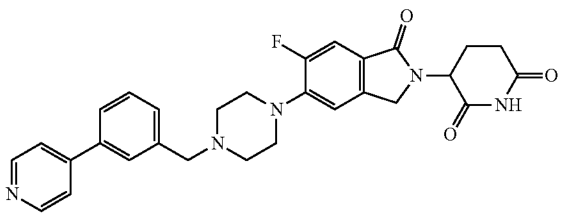

3-(5-(4-([1,1'-Biphenyl]-4-ylmethyl)piperazin-1-yl)-6-fluoro-1-oxoisoindolin-2-yl)piperidine-2,6-dione D1131.

3-(6-Fluoro-5-(4-((6-fluorochroman-8-yl)methyl)piperazin-1-yl)-1-oxoisoindolin-2-yl)piperidine-2,6-dione D1132.

D1131

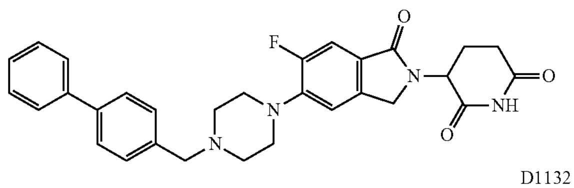

D1132

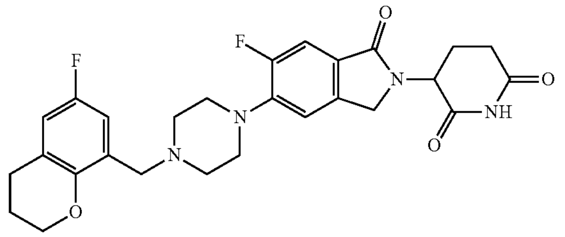

3-(6-Fluoro-1-oxo-5-(4-((6-(pyrrolidin-1-yl)pyridin-3-yl)methyl)piperazin-1-yl)-isoindolin-2-yl)piperidine-2,6-dione D1133.

D1133

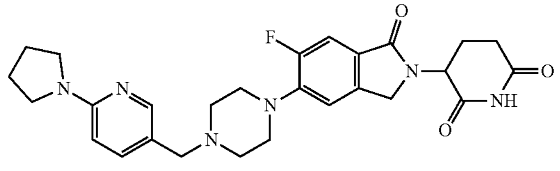

3-(6-Fluoro-1-oxo-5-(4-(3-(pyrrolidin-1-yl)benzyl)piperazin-1-yl)isoindolin-2-yl)piperidine-2,6-dione D1134.

D1134

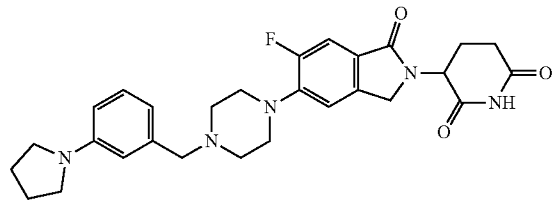

3-(6-Fluoro-1-oxo-5-(4-(4-(pyrrolidin-1-yl)benzyl)piperazin-1-yl)isoindolin-2-yl)piperidine-2,6-dione D1135.

D1135

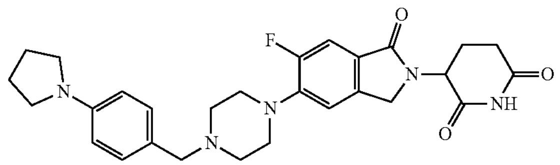

3-(5-(4-(3-(1H-1,2,4-Triazol-1-yl)benzyl)piperazin-1-yl)-6-fluoro-1-oxoisoindolin-2-yl)piperidine-2,6-dione D1136.

D1136

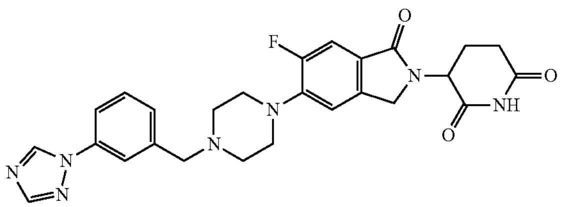

3-(5-(4-(2-(1H-1,2,4-Triazol-1-yl)benzyl)piperazin-1-yl)-6-fluoro-1-oxoisoindolin-2-yl)piperidine-2,6-dione D1137.

3-(5-(4-(4-(1H-1,2,4-Triazol-1-yl)benzyl)piperazin-1-yl)-6-fluoro-1-oxoisoindolin-2-yl)piperidine-2,6-dione D1138.

D1137

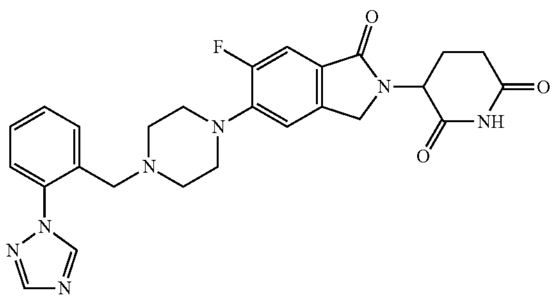

D1138

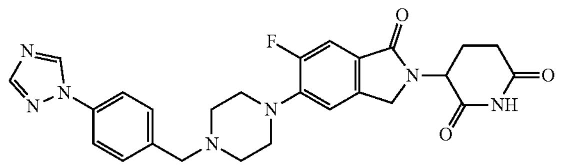

3-(6-Fluoro-1-oxo-5-(4-(thiazol-4-ylmethyl)piperazin-1-yl)isoindolin-2-yl)-piperidine-2,6-dione D1139.

3-(6-Fluoro-1-oxo-5-(4-((1-phenyl-1H-pyrazol-3-yl)methyl)piperazin-1-yl)-isoindolin-2-yl)piperidine-2,6-dione D1140.

D1139

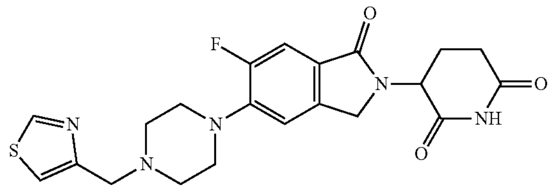

D1140

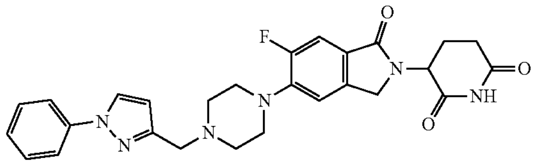

3-(6-Fluoro-1-oxo-5-(4-((5-phenyl-1H-imidazol-2-yl)methyl)piperazin-1-yl)-isoindolin-2-yl)piperidine-2,6-dione D1141.

D1141

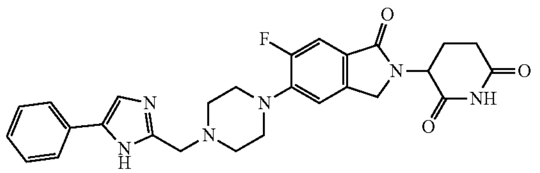

3-(5-(4-(3-(1H-Imidazol-1-yl)benzyl)piperazin-1-yl)-6-fluoro-1-oxoisoindolin-2-yl)piperidine-2,6-dione D1142.

D1142

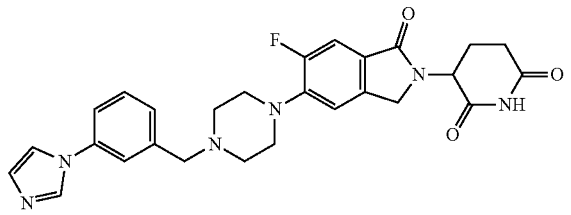

3-(6-Fluoro-1-oxo-5-(4-((2-phenyl-1H-imidazol-5-yl)methyl)piperazin-1-yl)-isoindolin-2-yl)piperidine-2,6-dione D1143.

D1143

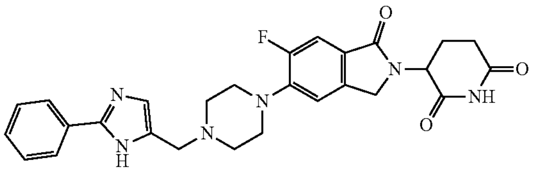

3-(5-(4-(4-(1H-Imidazol-1-yl)benzyl)piperazin-1-yl)-6-fluoro-1-oxoisoindolin-2-yl)piperidine-2,6-dione D1144.

D1144

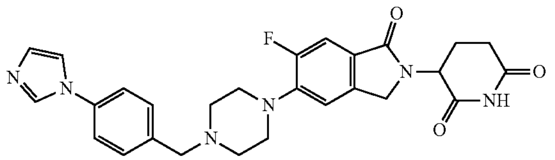

3-(5-(4-(4-(1H-Pyrazol-1-yl)benzyl)piperazin-1-yl)-6-fluoro-1-oxoisoindolin-2-yl)piperidine-2,6-dione D1145.

D1145

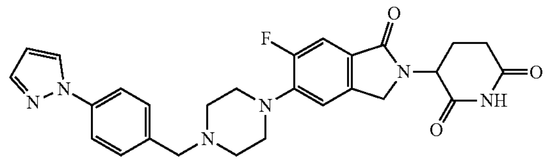

2-((4-(2-(2,6-Dioxopiperidin-3-yl)-6-fluoro-1-oxoisoindolin-5-yl)piperazin-1-yl)-methyl)-1H-indole-6-carbonitrile D1146.

D1146

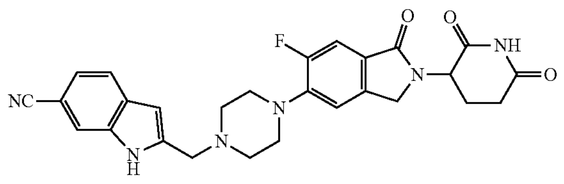

3-((4-(2-(2,6-Dioxopiperidin-3-yl)-6-fluoro-1-oxoisoindolin-5-yl)piperazin-1-yl)-methyl)-1H-indole-6-carbonitrile D1147.

D1147

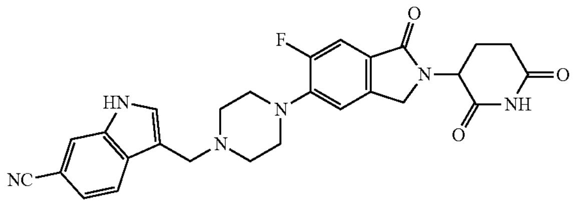

3-(5-(4-((2,3-Dihydro-[1,4]dioxino[2,3-b]pyridin-6-yl)methyl)piperazin-1-yl)-6-fluoro-1-oxoisoindolin-2-yl)piperidine-2,6-dione D1148.

D1148

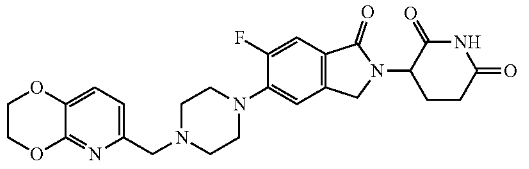

3-(5-(4-((Adamantan-1-yl)methyl)piperazin-1-yl)-6-fluoro-1-oxoisoindolin-2-yl)-piperidine-2,6-dione D1149.

3-(6-Fluoro-1-oxo-5-(4-(thiophen-2-ylmethyl)piperazin-1-yl)isoindolin-2-yl)-piperidine-2,6-dione D1150.

D1149

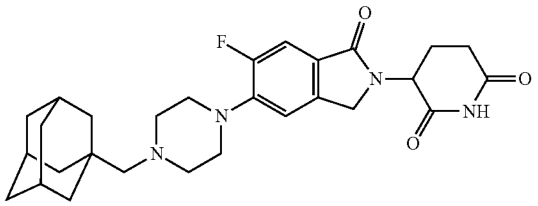

D1150

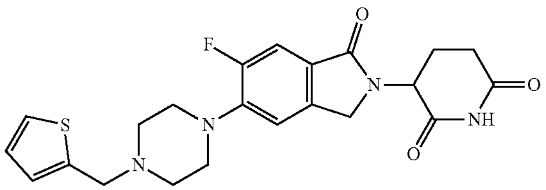

3-(5-(4-(3-(Benzyloxy)propyl)piperazin-1-yl)-6-fluoro-1-oxoisoindolin-2-yl)-piperidine-2,6-dione D1151.

D1151

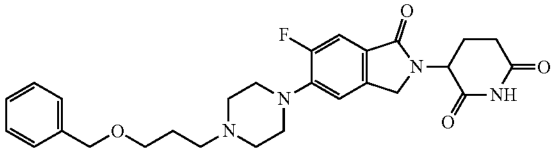

3-(6-Fluoro-5-(4-(3-(2-methoxyphenyl)propyl)piperazin-1-yl)-1-oxoisoindolin-2-yl)piperidine-2,6-dione D1152.

D1152

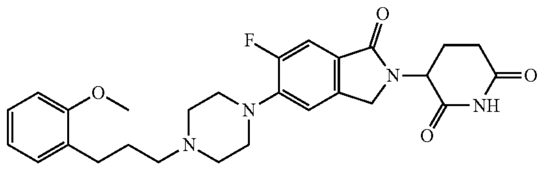

3-(5-(4-((2,3-Dihydrobenzo[b][1,4]dioxin-6-yl)methyl)piperazin-1-yl)-6-fluoro-1-oxoisoindolin-2-yl)piperidine-2,6-dione D1153.

3-(6-Fluoro-5-(4-((5-fluoro-1H-benzo[d]imidazol-2-yl)methyl)piperazin-1-yl)-1-oxoisoindolin-2-yl)piperidine-2,6-dione D1154.

D1153

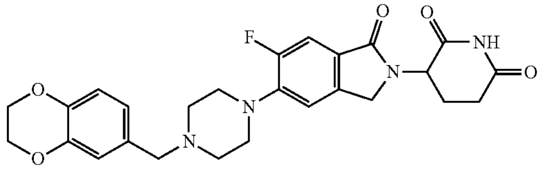

D1154

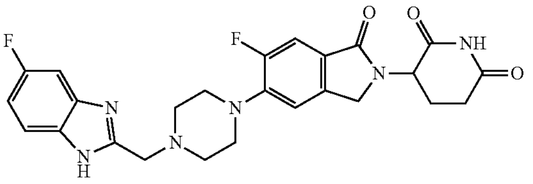

3-(6-Fluoro-5-(4-((4-fluorobenzofuran-7-yl)methyl)piperazin-1-yl)-1-oxoisoindolin-2-yl)piperidine-2,6-dione D1155.

3-(5-(4-(4-(Dimethylamino)-3-methylbenzyl)piperazin-1-yl)-6-fluoro-1-oxoisoindolin-2-yl)piperidine-2,6-dione D1156.

D1155

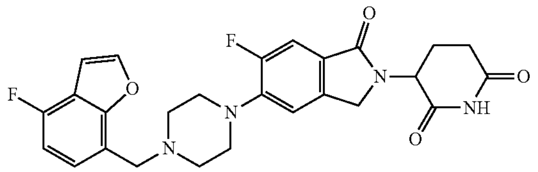

-continued

D1156

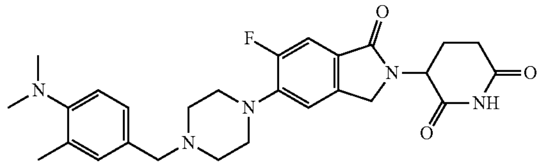

3-(5-(4-((2-(Tert-butyl)pyridin-4-yl)methyl)piperazin-1-yl)-6-fluoro-1-oxoisoindolin-2-yl)piperidine-2,6-dione D1157.

3-(5-(4-(4-((Dimethylamino)methyl)benzyl)piperazin-1-yl)-6-fluoro-1-oxoisoindolin-2-yl)piperidine-2,6-dione D1158.

D1157

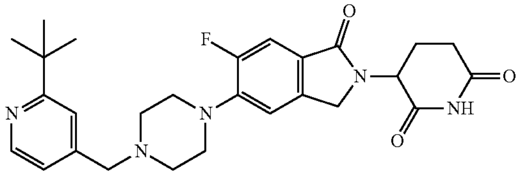

D1158

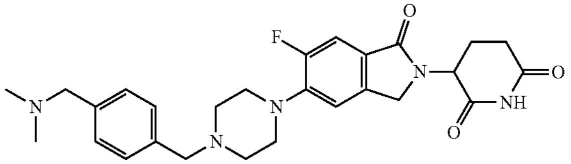

3-(6-Fluoro-1-oxo-5-(4-(thieno[3,2-c]pyridin-2-ylmethyl)piperazin-1-yl)-isoindolin-2-yl)piperidine-2,6-dione D1159.

3-(5-(4-(Benzo[d]thiazol-4-ylmethyl)piperazin-1-yl)-6-fluoro-1-oxoisoindolin-2-yl)piperidine-2,6-dione D1160.

D1159

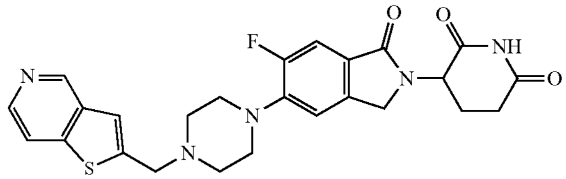

D1160

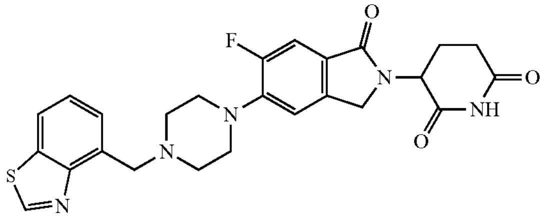

3-(6-Fluoro-1-oxo-5-(4-(thiophen-3-ylmethyl)piperazin-1-yl)isoindolin-2-yl)-piperidine-2,6-dione D1161.

3-(6-Fluoro-1-oxo-5-(4-(thieno[2,3-b]pyridin-2-ylmethyl)piperazin-1-yl)-isoindolin-2-yl)piperidine-2,6-dione D1162.

D1161

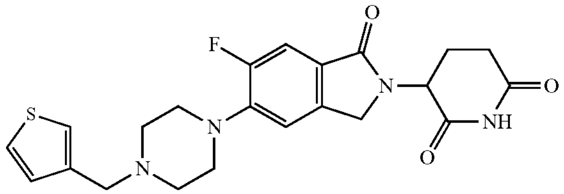

D1162

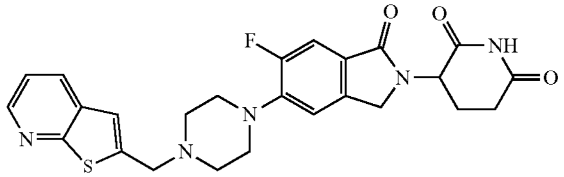

3-(5-(4-((3,4-Dihydro-2H-pyrano[2,3-c]pyridin-6-yl)methyl)piperazin-1-yl)-6-fluoro-1-oxoisoindolin-2-yl)piperidine-2,6-dione D1163.

3-(6-Fluoro-5-(4-(3-methyl-3-phenylbutyl)piperazin-1-yl)-1-oxoisoindolin-2-yl)-piperidine-2,6-dione D1164.

D1163

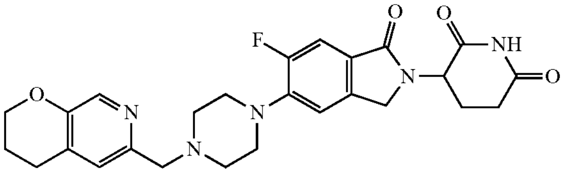

D1164

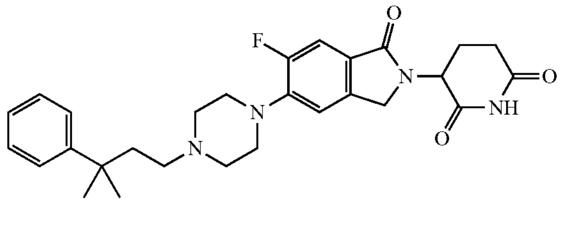

3-(5-(4-(Benzo[b]thiophen-3-ylmethyl)piperazin-1-yl)-6-fluoro-1-oxoisoindolin-2-yl)piperidine-2,6-dione D1165.

3-(5-(4-(Benzo[b]thiophen-2-ylmethyl)piperazin-1-yl)-6-fluoro-1-oxoisoindolin-2-yl)piperidine-2,6-dione D1166.

D1165

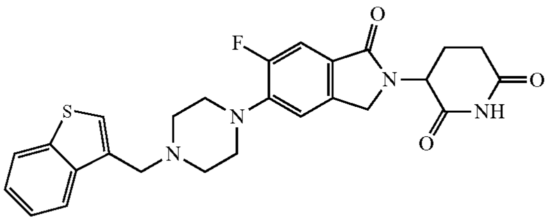

-continued

D1166

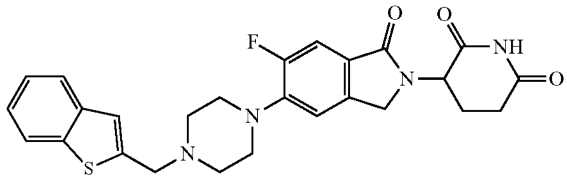

3-(5-(4-(Chroman-6-ylmethyl)piperazin-1-yl)-6-fluoro-1-oxoisoindolin-2-yl)-piperidine-2,6-dione D1167.

3-(6-Fluoro-5-(4-((1-methyl-1H-imidazo[4,5-b]pyridin-2-yl)methyl)piperazin-1-yl)-1-oxoisoindolin-2-yl)piperidine-2,6-dione D1168.

D1167

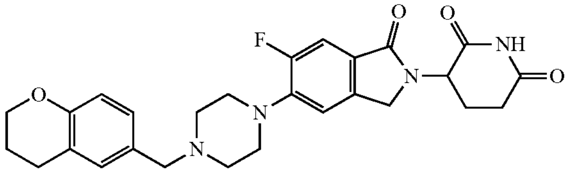

D1168

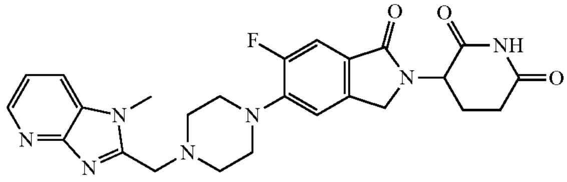

4-((4-(2-(2,6-Dioxopiperidin-3-yl)-6-fluoro-1-oxoisoindolin-5-yl)piperazin-1-yl)methyl)-2-methoxybenzonitrile D1169.

4-((4-(2-(2,6-Dioxopiperidin-3-yl)-6-fluoro-1-oxoisoindolin-5-yl)piperazin-1-yl)methyl)-3-methoxybenzonitrile D1170.

D1169

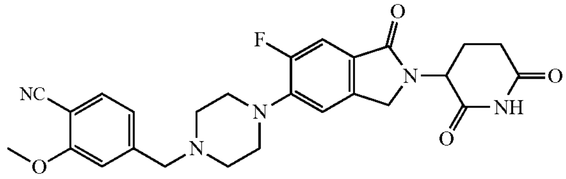

D1170

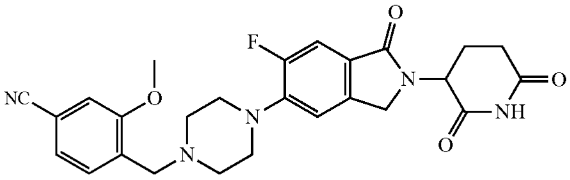

2-((4-(2-(2,6-Dioxopiperidin-3-yl)-6-fluoro-1-oxoisoindolin-5-yl)piperazin-1-yl)-methyl)-5-methoxybenzonitrile D1171.

3-(6-Fluoro-5-(4-((2-methyl-2H-tetrazol-5-yl)methyl)piperazin-1-yl)-1-oxoisoindolin-2-yl)piperidine-2,6-dione D1172.

D1171

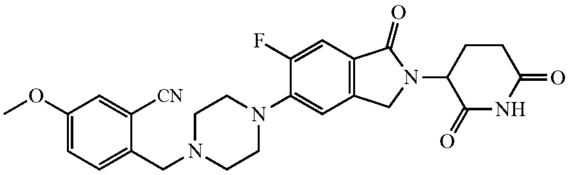

D1172

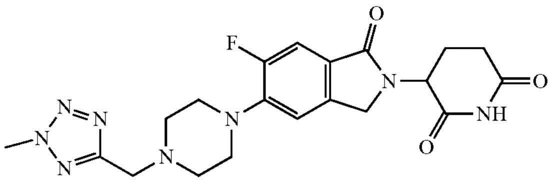

3-(6-Fluoro-5-(4-((2-methylbenzo[d]oxazol-6-yl)methyl)piperazin-1-yl)-1-oxoisoindolin-2-yl)piperidine-2,6-dione D1173.

3-(6-Fluoro-1-oxo-5-(4-((3-oxoisoindolin-5-yl)methyl)piperazin-1-yl)isoindolin-2-yl)piperidine-2,6-dione D1174.

D1173

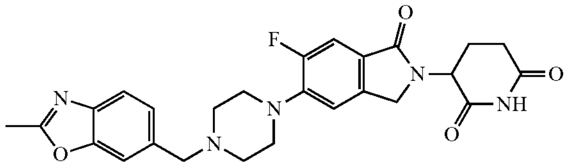

D1174

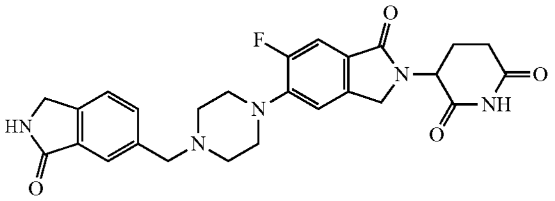

3-(6-Fluoro-1-oxo-5-(4-((1-oxoisoindolin-5-yl)methyl)piperazin-1-yl)isoindolin-2-yl)piperidine-2,6-dione D1175.

3-(6-Fluoro-1-oxo-5-(4-((5,6,7,8-tetrahydronaphthalen-1-yl)methyl)piperazin-1-yl)isoindolin-2-yl)piperidine-2,6-dione D1176.

D1175

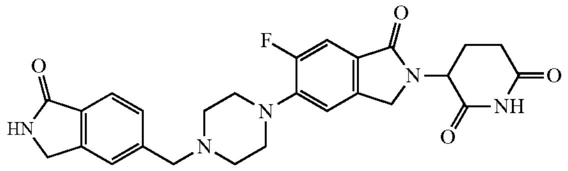

-continued

D1176

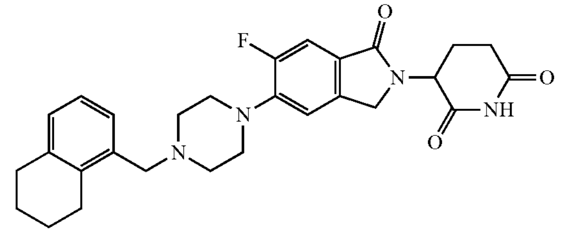

3-(6-Fluoro-5-(4-((3-methylimidazo[1,2-a]pyridin-2-yl)methyl)piperazin-1-yl)-1-oxoisoindolin-2-yl)piperidine-2,6-dione D1177.

3-(6-Fluoro-5-(4-((1-methyl-1H-indazol-6-yl)methyl)piperazin-1-yl)-1-oxoisoindolin-2-yl)piperidine-2,6-dione D1178.

D1177

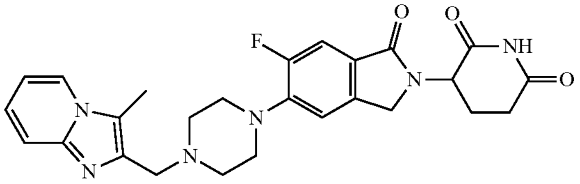

D1178

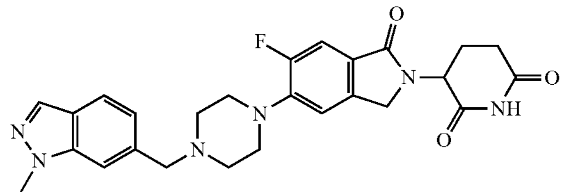

3-(6-Fluoro-5-(4-((2-methyl-2H-indazol-5-yl)methyl)piperazin-1-yl)-1-oxoisoindolin-2-yl)piperidine-2,6-dione D1179.

3-(6-Fluoro-5-(4-((6-methylimidazo[1,2-a]pyridin-2-yl)methyl)piperazin-1-yl)-1-oxoisoindolin-2-yl)piperidine-2,6-dione D1180.

D1179

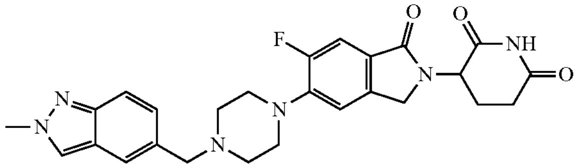

D1180

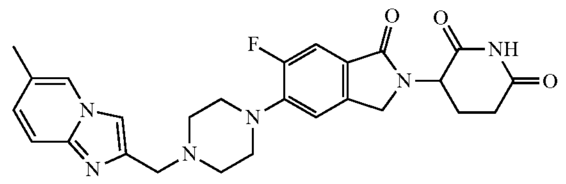

3-(6-Fluoro-5-(4-((5-methylimidazo[1,2-a]pyridin-3-yl)methyl)piperazin-1-yl)-1-oxoisoindolin-2-yl)piperidine-2,6-dione D1181.

3-(6-Fluoro-5-(4-((7-methylimidazo[1,2-a]pyridin-3-yl)methyl)piperazin-1-yl)-1-oxoisoindolin-2-yl)piperidine-2,6-dione D1182.

D1181

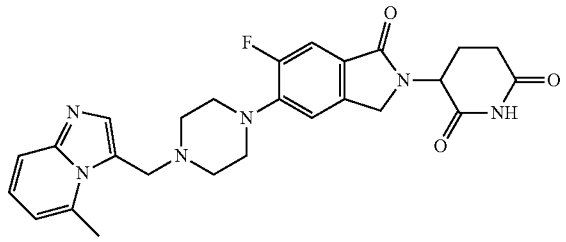

D1182

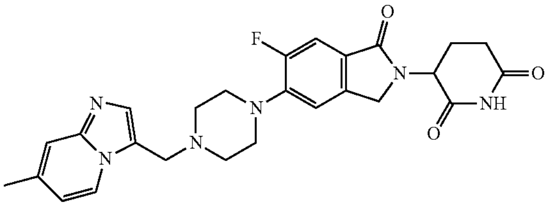

3-(6-Fluoro-5-(4-((5-methyl-4H-1,2,4-triazol-3-yl)methyl)piperazin-1-yl)-1-oxoisoindolin-2-yl)piperidine-2,6-dione D1183.

3-(6-Fluoro-5-(4-((1-methyl-1H-indazol-4-yl)methyl)piperazin-1-yl)-1-oxoisoindolin-2-yl)piperidine-2,6-dione D1184.

D1183

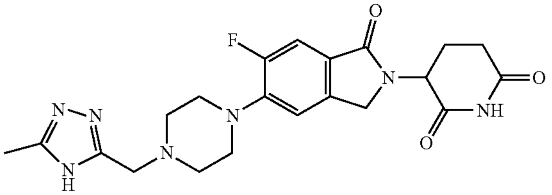

D1184

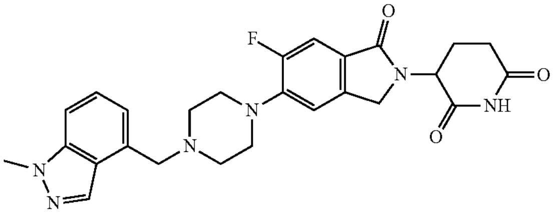

3-(6-Fluoro-5-(4-((5-methyl-1H-pyrrolo[2,3-b]pyridin-3-yl)methyl)piperazin-1-yl)-1-oxoisoindolin-2-yl)piperidine-2,6-dione D1185.

3-(6-Fluoro-5-(4-((1-methyl-1H-benzo[d]imidazol-2-yl)methyl)piperazin-1-yl)-1-oxoisoindolin-2-yl)piperidine-2,6-dione D1186.

D1185

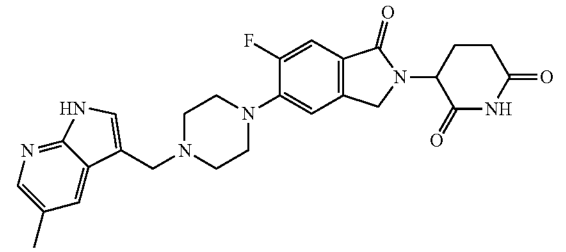

D1186

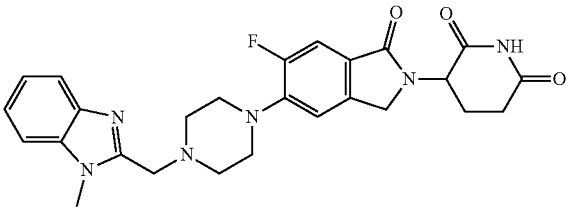

3-(6-Fluoro-5-(4-((2-methylimidazo[1,2-a]pyridin-3-yl)methyl)piperazin-1-yl)-1-oxoisoindolin-2-yl)piperidine-2,6-dione D1187.

3-(6-Fluoro-5-(4-((2-methyl-2H-indazol-3-yl)methyl)piperazin-1-yl)-1-oxoisoindolin-2-yl)piperidine-2,6-dione D1188.

D1187

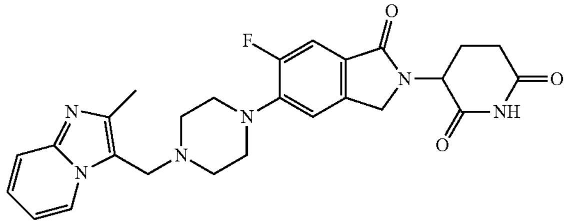

D1188

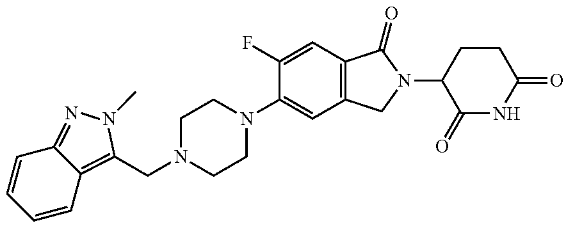

3-(6-Fluoro-5-(4-((7-methyl-1H-indol-3-yl)methyl)piperazin-1-yl)-1-oxoisoindolin-2-yl)piperidine-2,6-dione D1189.

3-(6-Fluoro-5-(4-((1-methyl-1H-indol-5-yl)methyl)piperazin-1-yl)-1-oxoisoindolin-2-yl)piperidine-2,6-dione D1190.

D1189

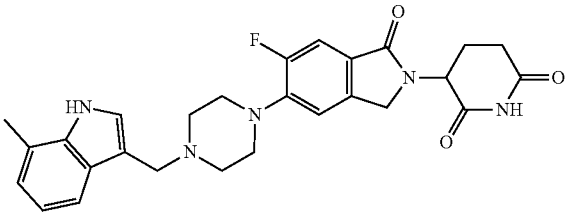

D1190

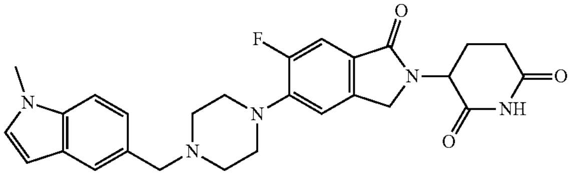

3-(6-Fluoro-5-(4-((2-methyl-1H-indol-4-yl)methyl)piperazin-1-yl)-1-oxoisoindolin-2-yl)piperidine-2,6-dione D1191.

3-(6-Fluoro-5-(4-((1-methyl-1H-indol-6-yl)methyl)piperazin-1-yl)-1-oxoisoindolin-2-yl)piperidine-2,6-dione D1192.

D1191

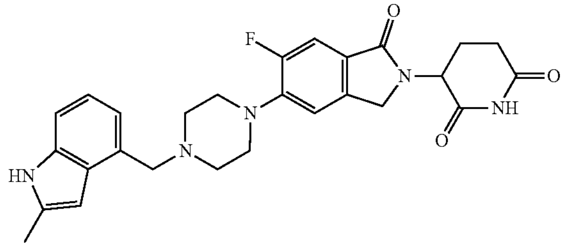

D1192

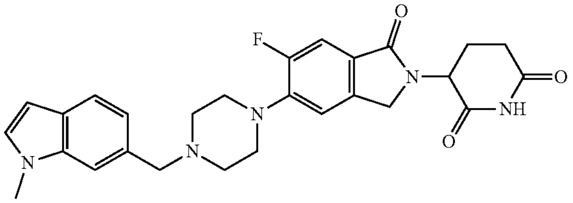

3-(6-Fluoro-5-(4-((4-methyl-1H-indol-3-yl)methyl)piperazin-1-yl)-1-oxoisoindolin-2-yl)piperidine-2,6-dione D1193.

3-(6-Fluoro-5-(4-((4-methyloxazol-5-yl)methyl)piperazin-1-yl)-1-oxoisoindolin-2-yl)piperidine-2,6-dione D1194.

D1193

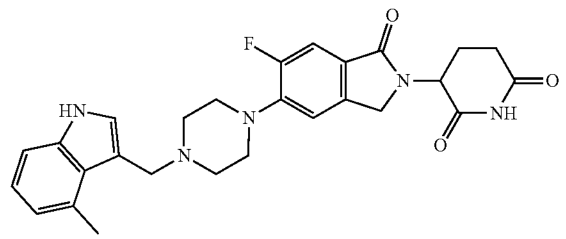

D1194

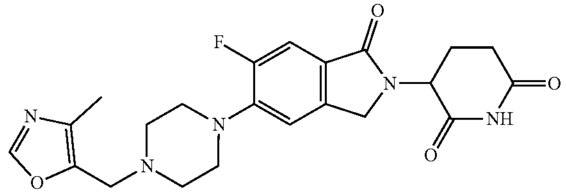

3-(6-Fluoro-5-(4-((3-methyl-1H-indol-2-yl)methyl)piperazin-1-yl)-1-oxoisoindolin-2-yl)piperidine-2,6-dione D1195.

3-(6-Fluoro-5-(4-((6-methyl-1H-indol-3-yl)methyl)piperazin-1-yl)-1-oxoisoindolin-2-yl)piperidine-2,6-dione D1196.

D1195

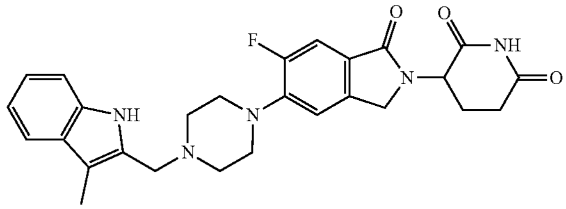

D1196

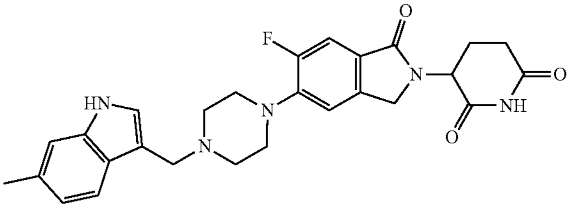

Tert-butyl (2-(4-(2-(2,6-dioxopiperidin-3-yl)-6-fluoro-1-oxoisoindolin-5-yl)-piperazin-1-yl)ethyl)carbamate D1197.

3-(6-Fluoro-1-oxo-5-(4-(quinoxalin-6-ylmethyl)piperazin-1-yl)isoindolin-2-yl)-piperidine-2,6-dione D1198.

D1197

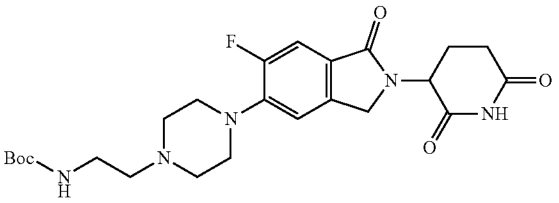

-continued

D1198

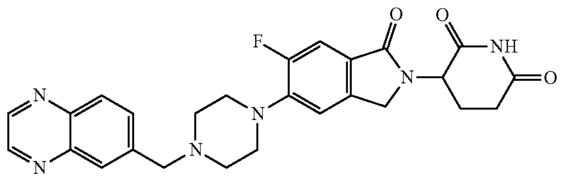

3-(5-(4-((1,8-Naphthyridin-2-yl)methyl)piperazin-1-yl)-6-fluoro-1-oxoisoindolin-2-yl)piperidine-2,6-dione D1199.

3-(6-Fluoro-1-oxo-5-(4-(quinoxalin-6-ylmethyl)piperazin-1-yl)isoindolin-2-yl)-piperidine-2,6-dione D1200.

D1199

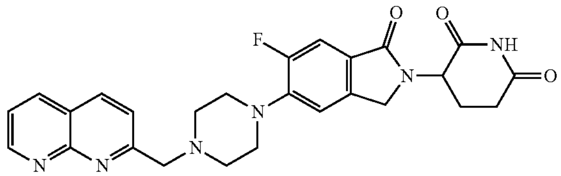

D1200

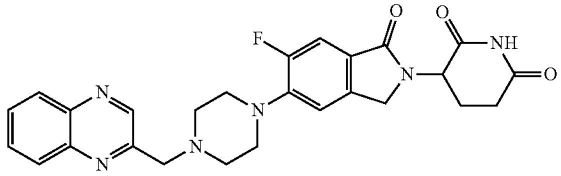

3-(6-Fluoro-1-oxo-5-(4-(quinoxalin-5-ylmethyl)piperazin-1-yl)isoindolin-2-yl)-piperidine-2,6-dione D1201.

3-(6-Fluoro-1-oxo-5-(4-(quinolin-8-ylmethyl)piperazin-1-yl)isoindolin-2-yl)-piperidine-2,6-dione D1202.

D1201

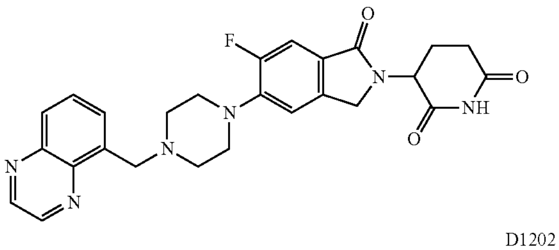

D1202

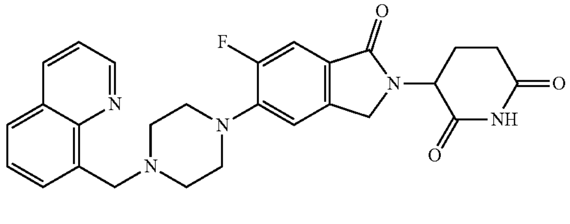

3-(6-Fluoro-5-(4-(isoquinolin-4-ylmethyl)piperazin-1-yl)-1-oxoisoindolin-2-yl)-piperidine-2,6-dione D1203.

3-(6-Fluoro-5-(4-(isoquinolin-3-ylmethyl)piperazin-1-yl)-1-oxoisoindolin-2-yl)-piperidine-2,6-dione D1204.

D1203

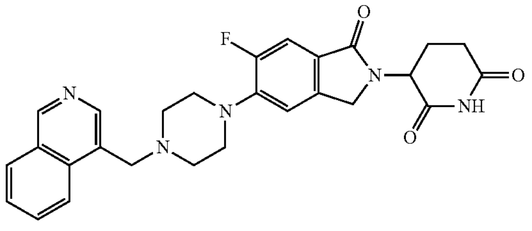

D1204

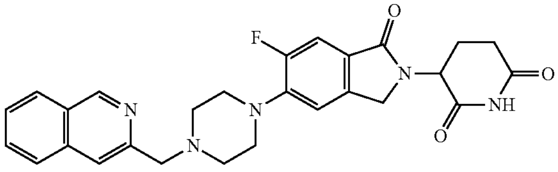

3-(6-Fluoro-5-(4-((2-methyloxazol-4-yl)methyl)piperazin-1-yl)-1-oxoisoindolin-2-yl)piperidine-2,6-dione D1205.

3-(6-Fluoro-5-(4-(isoquinolin-8-ylmethyl)piperazin-1-yl)-1-oxoisoindolin-2-yl)-piperidine-2,6-dione D1206.

D1205

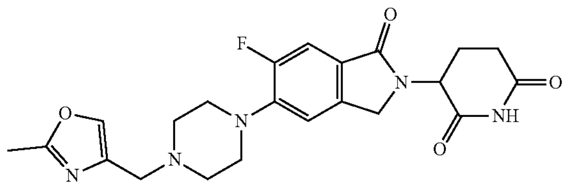

D1206

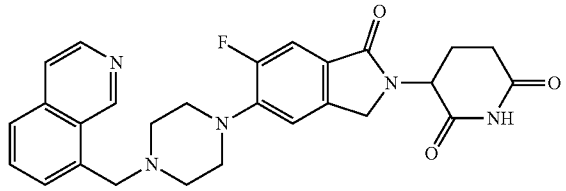

3-(6-Fluoro-5-(4-(isoquinolin-5-ylmethyl)piperazin-1-yl)-1-oxoisoindolin-2-yl)-piperidine-2,6-dione D1207.

3-(6-Fluoro-1-oxo-5-(4-(quinolin-4-ylmethyl)piperazin-1-yl)isoindolin-2-yl)piperidine-2,6-dione D1208.

D1207

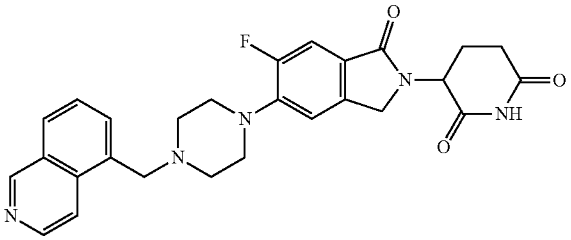

-continued

D1208

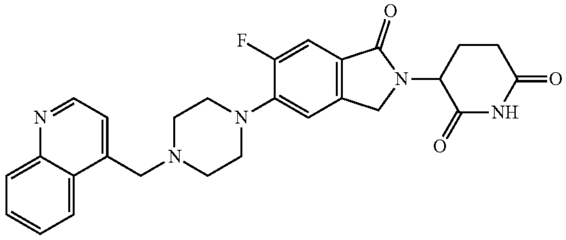

3-(6-Fluoro-1-oxo-5-(4-(quinolin-6-ylmethyl)piperazin-1-yl)isoindolin-2-yl)-piperidine-2,6-dione D1209.

3-(6-Fluoro-5-(4-(naphthalen-2-ylmethyl)piperazin-1-yl)-1-oxoisoindolin-2-yl)-piperidine-2,6-dione D1210.

D1209

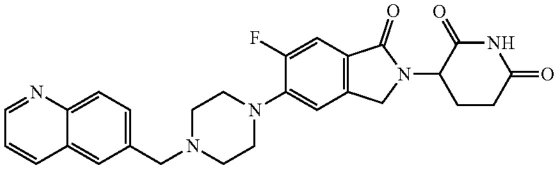

D1210

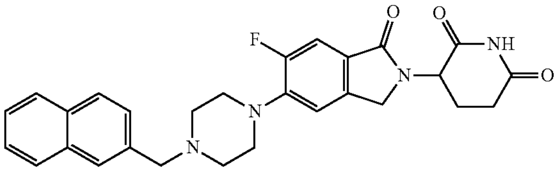

3-(5-(4-(2-Amino-6-chlorobenzyl)piperazin-1-yl)-6-fluoro-1-oxoisoindolin-2-yl)-piperidine-2,6-dione D1211.

3-(5-(4-(2-Amino-4-chlorobenzyl)piperazin-1-yl)-6-fluoro-1-oxoisoindolin-2-yl)-piperidine-2,6-dione D1212.

D1211

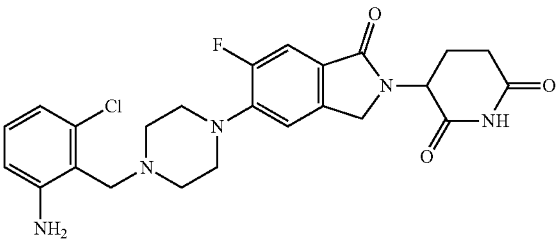

D1212

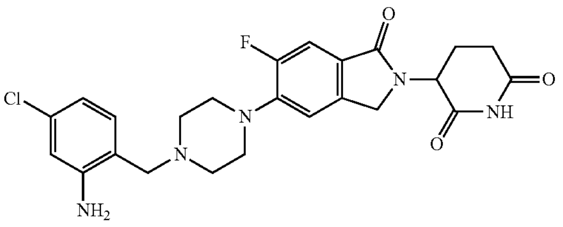

3-(5-(4-(2-Amino-3-chlorobenzyl)piperazin-1-yl)-6-fluoro-1-oxoisoindolin-2-yl)-piperidine-2,6-dione D1213.

3-(5-(4-((5-(Dimethylamino)thiophen-2-yl)methyl)piperazin-1-yl)-6-fluoro-1-oxoisoindolin-2-yl)piperidine-2,6-dione D1214.

D1213

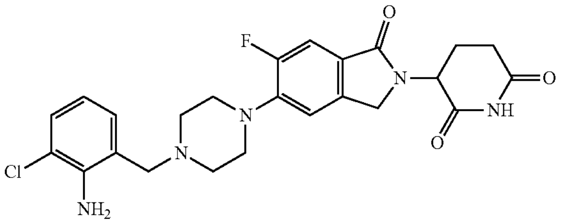

D1214

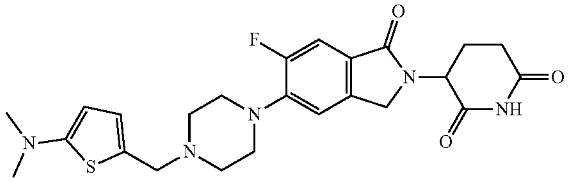

3-(5-(4-(4-Chlorophenethyl)piperazin-1-yl)-6-fluoro-1-oxoisoindolin-2-yl)-piperidine-2,6-dione D1215.

3-(6-Fluoro-5-(4-((2-methyloxazol-5-yl)methyl)piperazin-1-yl)-1-oxoisoindolin-2-yl)piperidine-2,6-dione D1216.

D1215

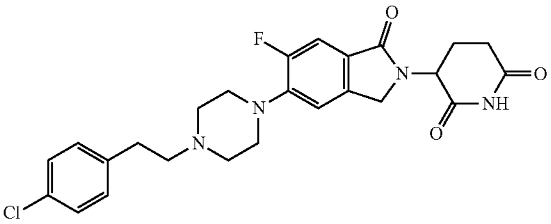

D1216

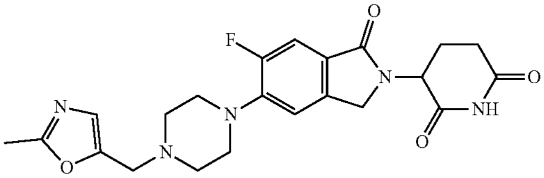

3-(6-Fluoro-5-(4-((4-hydroxybicyclo[2.2.2]octan-1-yl)methyl)piperazin-1-yl)-1-oxoisoindolin-2-yl)piperidine-2,6-dione D1217.

3-(6-Fluoro-5-(4-((2-(methylthio)pyrimidin-4-yl)methyl)piperazin-1-yl)-1-oxoisoindolin-2-yl)piperidine-2,6-dione D1218.

D1217

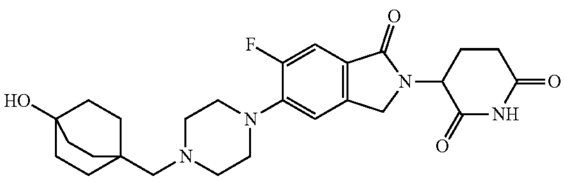

-continued

D1218

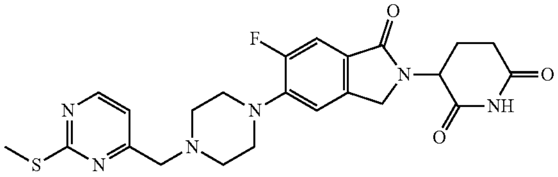

3-(5-(4-((2-Cyclopropylthiazol-5-yl)methyl)piperazin-1-yl)-6-fluoro-1-oxoisoindolin-2-yl)piperidine-2,6-dione D1219.

3-(5-(4-((1-(Tert-butyl)-1H-1,2,3-triazol-4-yl)methyl)piperazin-1-yl)-6-fluoro-1-oxoisoindolin-2-yl)piperidine-2,6-dione D1220.

D1219

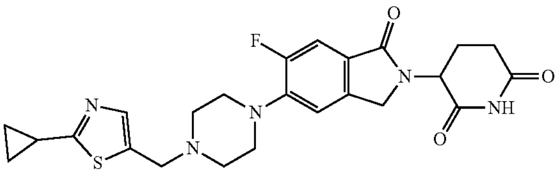

D1220

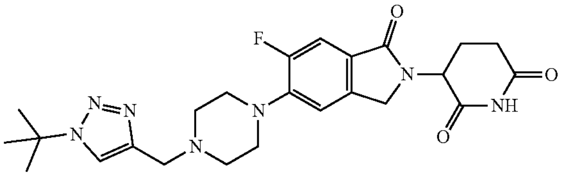

3-(6-Fluoro-5-(4-((1-isobutyl-1H-pyrazol-4-yl)methyl)piperazin-1-yl)-1-oxoisoindolin-2-yl)piperidine-2,6-dione D1221.

3-(5-(4-((5,6-Dihydro-8H-imidazo[2,1-c][1,4]oxazin-3-yl)methyl)piperazin-1-yl)-6-fluoro-1-oxoisoindolin-2-yl)piperidine-2,6-dione D1222.

D1221

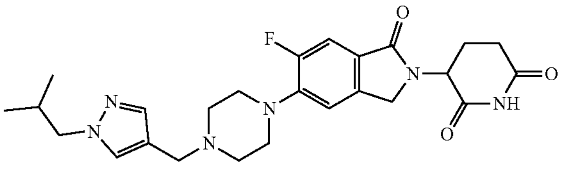

D1222

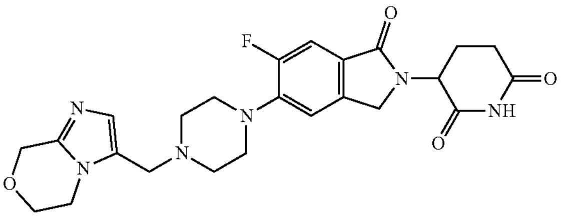

3-(5-(4-((5,6-Dihydro-8H-imidazo[2,1-c][1,4]oxazin-2-yl)methyl)piperazin-1-yl)-6-fluoro-1-oxoisoindolin-2-yl)piperidine-2,6-dione D1223.

3-(5-(4-((5-(Tert-butyl)-1H-pyrrol-2-yl)methyl)piperazin-1-yl)-6-fluoro-1-oxoisoindolin-2-yl)piperidine-2,6-dione D1224.

D1223

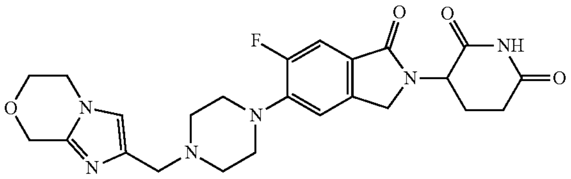

D1224

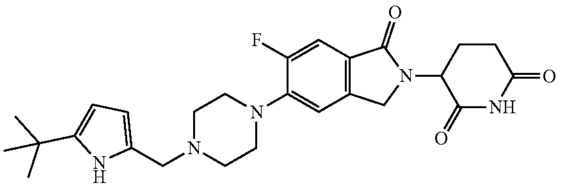

3-(5-(4-((2-(Dimethylamino)pyrimidin-5-yl)methyl)piperazin-1-yl)-6-fluoro-1-oxoisoindolin-2-yl)piperidine-2,6-dione D1225.

3-(6-Fluoro-5-(4-(4-methoxy-3-methylbenzyl)piperazin-1-yl)-1-oxoisoindolin-2-yl)piperidine-2,6-dione D1226.

D1225

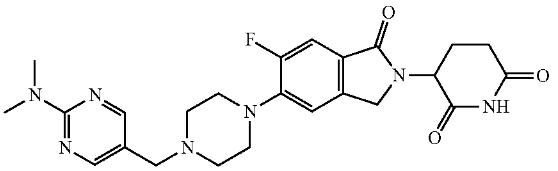

D1226

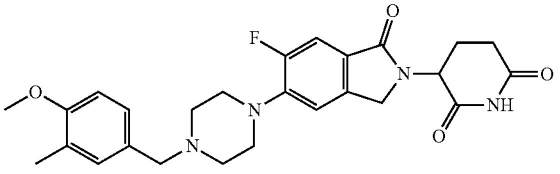

3-(6-Fluoro-5-(4-((1-methyl-1H-imidazol-5-yl)methyl)piperazin-1-yl)-1-oxoisoindolin-2-yl)piperidine-2,6-dione D1227.

3-(6-Fluoro-5-(4-(2-methoxy-3-methylbenzyl)piperazin-1-yl)-1-oxoisoindolin-2-yl)piperidine-2,6-dione D1228.

D1227

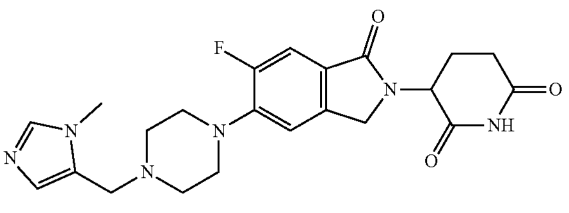

-continued

D1228

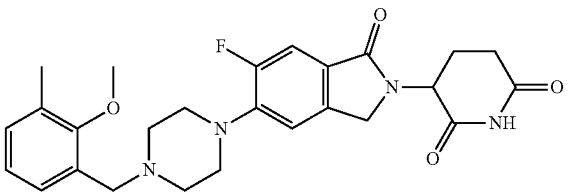

3-(6-Fluoro-5-(4-(3-methoxy-2-methylbenzyl)piperazin-1-yl)-1-oxoisoindolin-2-yl)piperidine-2,6-dione D1229.

3-(6-Fluoro-5-(4-(2-methoxy-6-methylbenzyl)piperazin-1-yl)-1-oxoisoindolin-2-yl)piperidine-2,6-dione D1230.

D1229

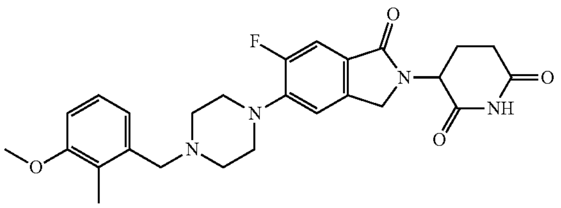

D1230

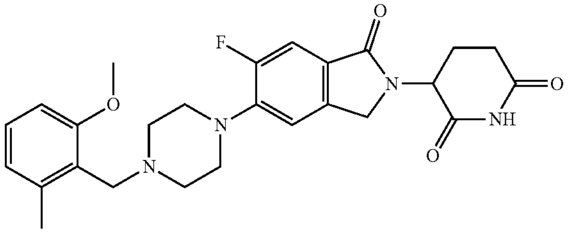

3-(6-Fluoro-5-(4-(3-methoxy-5-methylbenzyl)piperazin-1-yl)-1-oxoisoindolin-2-yl)-piperidine-2,6-dione D1231.

3-(6-Fluoro-5-(4-(4-methoxyphenethyl)piperazin-1-yl)-1-oxoisoindolin-2-yl)-piperidine-2,6-dione D1232.

D1231

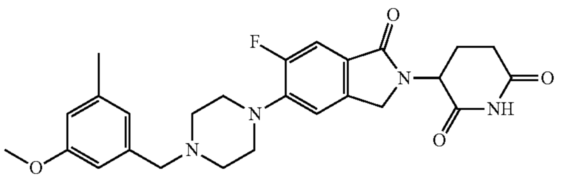

D1232

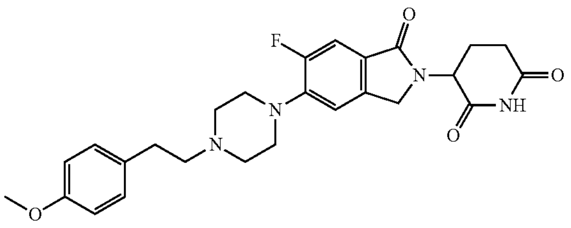

3-(6-Fluoro-5-(4-(3-methoxyphenethyl)piperazin-1-yl)-1-oxoisoindolin-2-yl)-piperidine-2,6-dione D1233.

3-(6-Fluoro-5-(4-(4-methoxy-2-methylbenzyl)piperazin-1-yl)-1-oxoisoindolin-2-yl)piperidine-2,6-dione D1234.

D1233

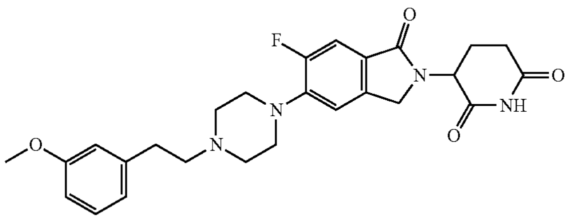

D1234

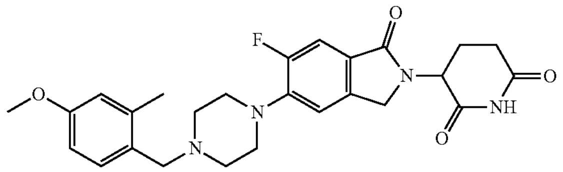

3-(6-Fluoro-5-(4-(4-hydroxy-3,5-dimethylbenzyl)piperazin-1-yl)-1-oxoisoindolin-2-yl)piperidine-2,6-dione D1235.

3-(5-(4-(4-Ethoxybenzyl)piperazin-1-yl)-6-fluoro-1-oxoisoindolin-2-yl)=piperidine-2,6-dione D1236.

D1235

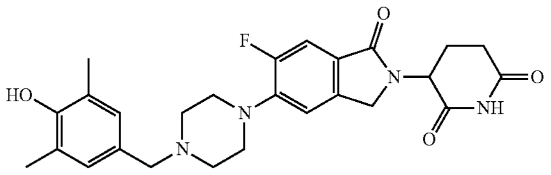

D1236

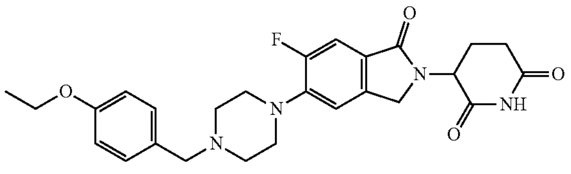

3-(6-Fluoro-5-(4-(3-methoxy-4-methylbenzyl)piperazin-1-yl)-1-oxoisoindolin-2-yl)piperidine-2,6-dione D1237.

3-(6-Fluoro-5-(4-((1-methyl-1H-pyrazol-5-yl)methyl)piperazin-1-yl)-1-oxoisoindolin-2-yl)piperidine-2,6-dione D1238.

D1237

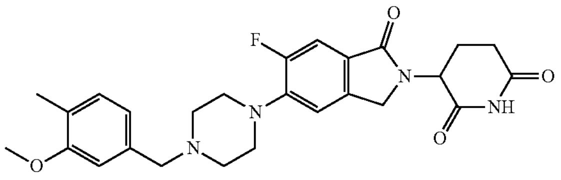

-continued

D1238

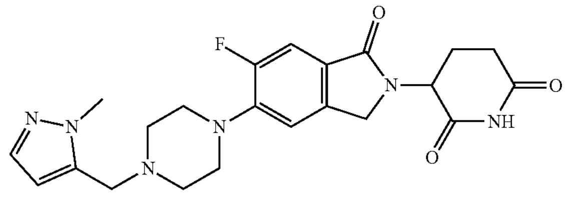

3-(5-(4-((1H-Pyrrol-2-yl)methyl)piperazin-1-yl)-6-fluoro-1-oxoisoindolin-2-yl)-piperidine-2,6-dione D1239.

3-(6-Fluoro-5-(4-(2-methoxy-4-methylbenzyl)piperazin-1-yl)-1-oxoisoindolin-2-yl)piperidine-2,6-dione D1240.

D1239

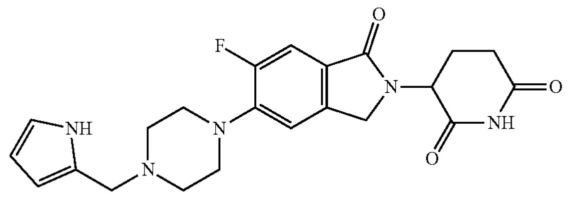

D1240

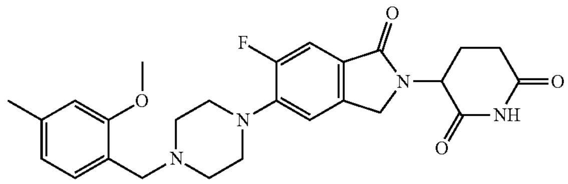

3-(5-(4-(2-(Benzyloxy)ethyl)piperazin-1-yl)-6-fluoro-1-oxoisoindolin-2-yl)-piperidine-2,6-dione D1241.

3-(5-(4-(Benzo[d][1,3]dioxol-4-ylmethyl)piperazin-1-yl)-6-fluoro-1-oxoisoindolin-2-yl)piperidine-2,6-dione D1242.

D1241

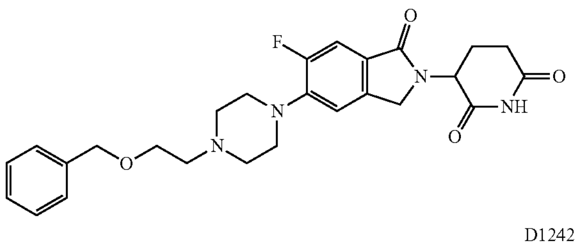

D1242

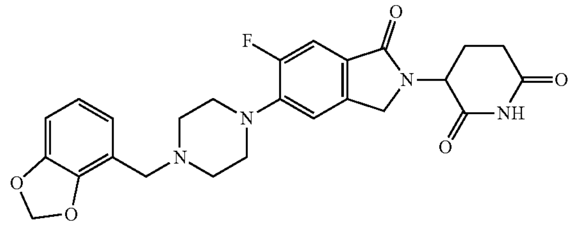

3-(5-(4-(2-(Dimethylamino)benzyl)piperazin-1-yl)-6-fluoro-1-oxoisoindolin-2-yl)piperidine-2,6-dione D1243.

3-(6-Fluoro-5-(4-((5-isopropylpyridin-3-yl)methyl)piperazin-1-yl)-1-oxoisoindolin-2-yl)piperidine-2,6-dione D1244.

D1243

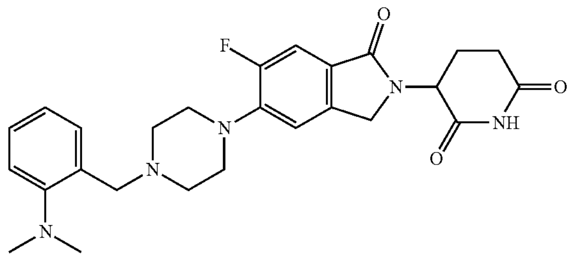

D1244

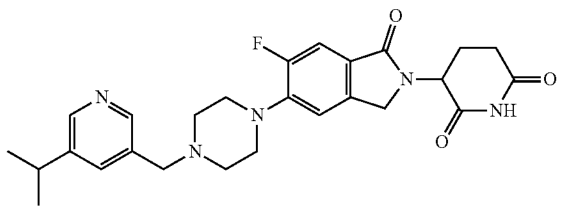

3-(5-(4-(4-(Ethylamino)benzyl)piperazin-1-yl)-6-fluoro-1-oxoisoindolin-2-yl)-piperidine-2,6-dione D1245.

3-(5-(4-(3-(Dimethylamino)benzyl)piperazin-1-yl)-6-fluoro-1-oxoisoindolin-2-yl)piperidine-2,6-dione D1246.

D1245

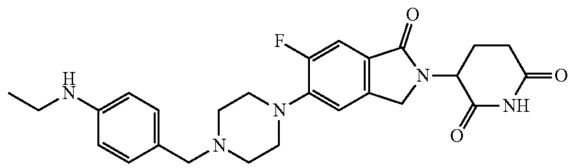

D1246

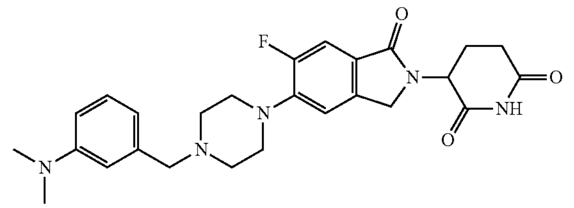

3-((4-(2-(2,6-Dioxopiperidin-3-yl)-6-fluoro-1-oxoisoindolin-5-yl)piperazin-1-yl)-methyl)benzamide D1247.

2-((4-(2-(2,6-Dioxopiperidin-3-yl)-6-fluoro-1-oxoisoindolin-5-yl)piperazin-1-yl)-methyl)-4-fluorobenzonitrile D1248.

D1247

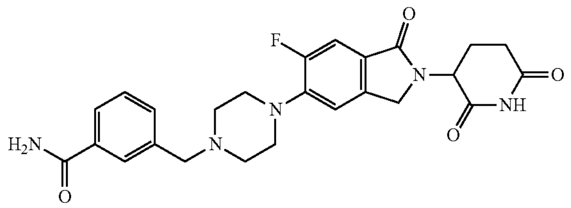

D1248

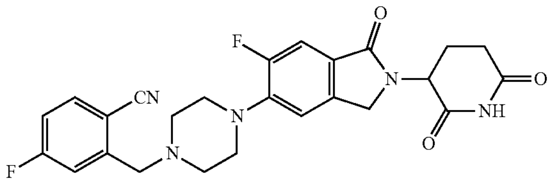

2-((4-(2-(2,6-Dioxopiperidin-3-yl)-6-fluoro-1-oxoisoindolin-5-yl)piperazin-1-yl)-methyl)-5-fluorobenzonitrile D1249.

3-(6-Fluoro-5-(4-((1-methyl-1H-pyrazol-3-yl)methyl)piperazin-1-yl)-1-oxoisoindolin-2-yl)piperidine-2,6-dione D1250.

D1249

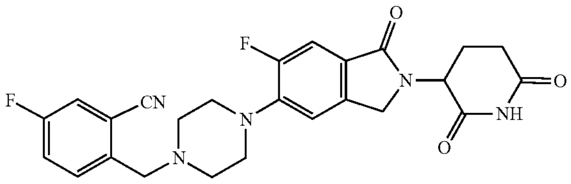

D1250

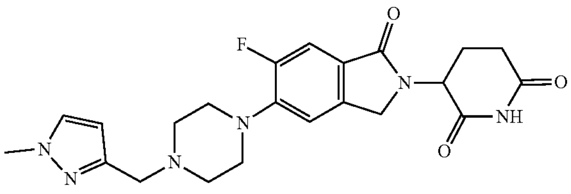

4-((4-(2-(2,6-Dioxopiperidin-3-yl)-6-fluoro-1-oxoisoindolin-5-yl)piperazin-1-yl)-methyl)-3-fluorobenzonitrile D1251.

3-((4-(2-(2,6-Dioxopiperidin-3-yl)-6-fluoro-1-oxoisoindolin-5-yl)piperazin-1-yl)-methyl)-5-fluorobenzonitrile D1252.

D1251

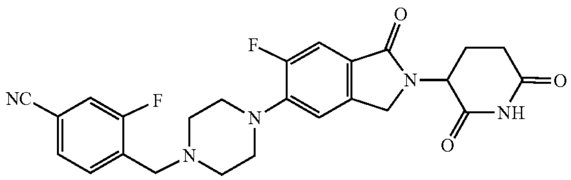

-continued

D1252

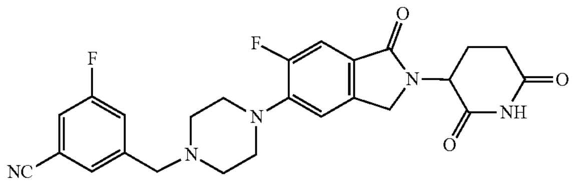

4-((4-(2-(2,6-Dioxopiperidin-3-yl)-6-fluoro-1-oxoisoindolin-5-yl)piperazin-1-yl)-methyl)-2-fluorobenzonitrile D1253.

5-((4-(2-(2,6-Dioxopiperidin-3-yl)-6-fluoro-1-oxoisoindolin-5-yl)piperazin-1-yl)-methyl)-2-fluorobenzonitrile D1254.

D1253

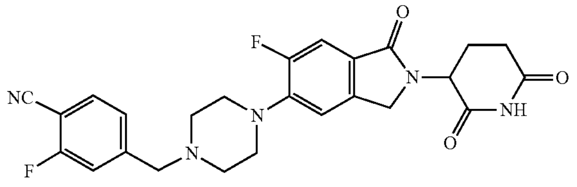

D1254

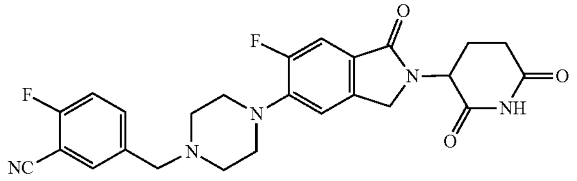

3-(6-Fluoro-1-oxo-5-(4-(2,4,6-trimethylbenzyl)piperazin-1-yl)isoindolin-2-yl)-piperidine-2,6-dione D1255.

3-(6-Fluoro-5-(4-(4-isopropylbenzyl)piperazin-1-yl)-1-oxoisoindolin-2-yl)-piperidine-2,6-dione D1256.

D1255

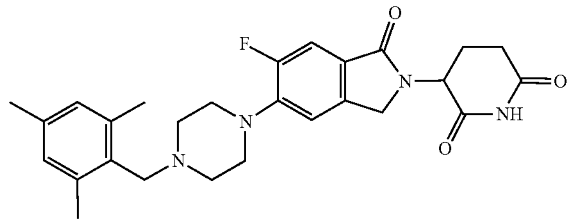

D1256

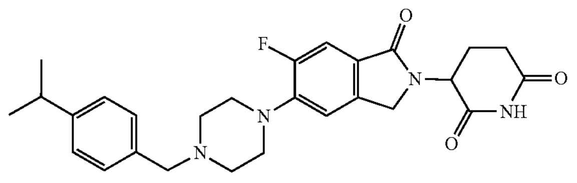

3-(6-Fluoro-1-oxo-5-(4-(4-phenylbutyl)piperazin-1-yl)isoindolin-2-yl)piperidine-2,6-dione D1257.

3-(5-(4-((4,4-Difluorocyclohexyl)methyl)piperazin-1-yl)-6-fluoro-1-oxoisoindolin-2-yl)piperidine-2,6-dione D1258.

D1257

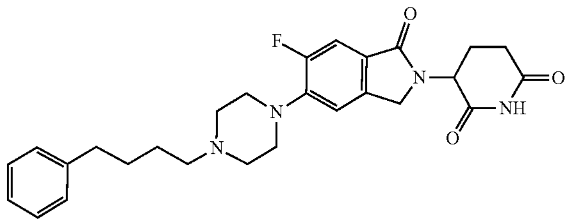

D1258

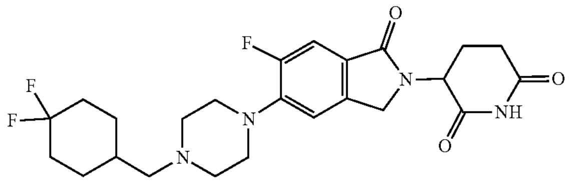

3-(5-(4-(2-Ethynyl-4-fluorobenzyl)piperazin-1-yl)-6-fluoro-1-oxoisoindolin-2-yl)-piperidine-2,6-dione D1259.

3-(5-(4-([1,2,4]Triazolo[1,5-a]pyridin-7-ylmethyl)piperazin-1-yl)-6-fluoro-1-oxoisoindolin-2-yl)piperidine-2,6-dione D1260.

D1259

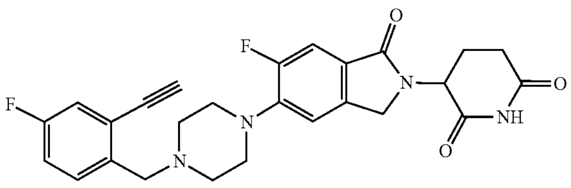

D1260

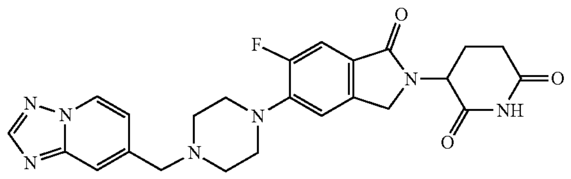

3-(6-Fluoro-5-(4-((1-methyl-1H-imidazol-4-yl)methyl)piperazin-1-yl)-1-oxoisoindolin-2-yl)piperidine-2,6-dione D1261.

3-(6-Fluoro-5-(4-(imidazo[1,2-a]pyrimidin-3-ylmethyl)piperazin-1-yl)-1-oxoisoindolin-2-yl)piperidine-2,6-dione D1262.

D1261

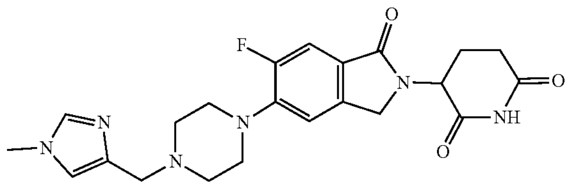

-continued

D1262

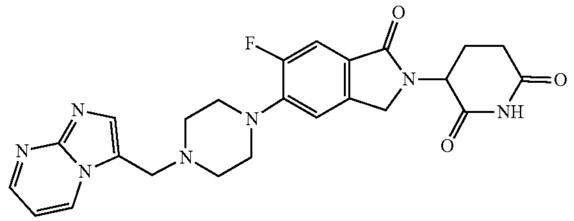

6-Amino-5-((4-(2-(2,6-dioxopiperidin-3-yl)-6-fluoro-1-oxoisoindolin-5-yl)-piperazin-1-yl)methyl)nicotinonitrile D1263.

3-(6-Fluoro-5-(4-(imidazo[1,2-a]pyrimidin-7-ylmethyl)piperazin-1-yl)-1-oxoisoindolin-2-yl)piperidine-2,6-dione D1264.

D1263

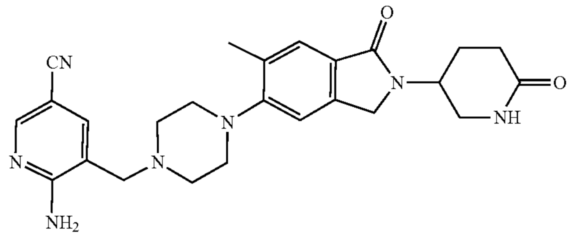

D1264

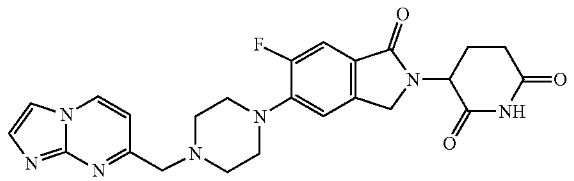

3-(5-(4-((4H-Pyrrolo[2,3-b]pyrazin-7-yl)methyl)piperazin-1-yl)-6-fluoro-1-oxoisoindolin-2-yl)piperidine-2,6-dione D1265.

4-((4-(2-(2,6-Dioxopiperidin-3-yl)-6-fluoro-1-oxoisoindolin-5-yl)piperazin-1-yl)-methyl)-3-hydroxybenzonitrile D1266.

D1265

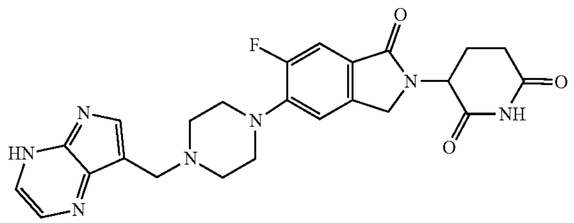

-continued

D1266

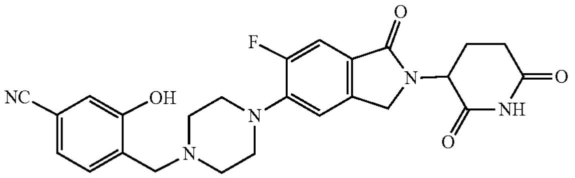

5-((4-(2-(2,6-Dioxopiperidin-3-yl)-6-fluoro-1-oxoisoindolin-5-yl)piperazin-1-yl)-methyl)-2-hydroxybenzonitrile D1267.

3-(6-Fluoro-5-(4-(furo[2,3-c]pyridin-5-ylmethyl)piperazin-1-yl)-1-oxoisoindolin-2-yl)piperidine-2,6-dione D1268.

D1267

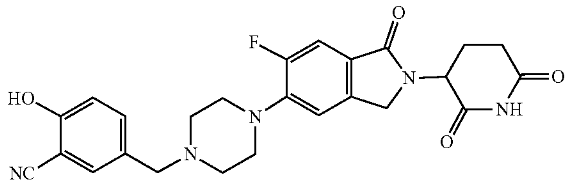

D1268

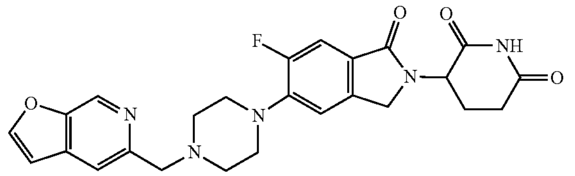

3-(5-(4-(Benzo[d]oxazol-5-ylmethyl)piperazin-1-yl)-6-fluoro-1-oxoisoindolin-2-yl)piperidine-2,6-dione D1269.

3-(5-(4-(Benzo[d]oxazol-6-ylmethyl)piperazin-1-yl)-6-fluoro-1-oxoisoindolin-2-yl)piperidine-2,6-dione C1270.

D1269

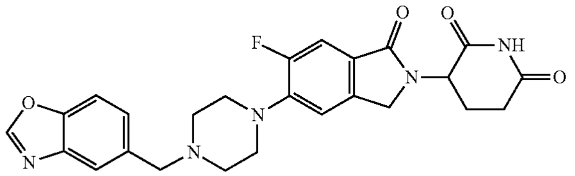

D1270

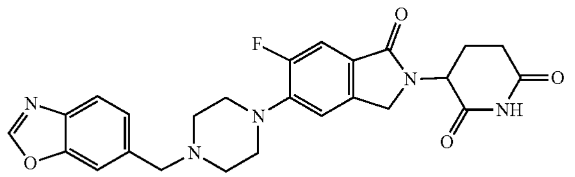

3-(5-(4-((5-Chlorothiophen-2-yl)methyl)piperazin-1-yl)-6-fluoro-1-oxoisoindolin-2-yl)piperidine-2,6-dione D1271.

3-(6-Fluoro-5-(4-((1-methyl-1H-imidazol-2-yl)methyl)piperazin-1-yl)-1-oxoisoindolin-2-yl)piperidine-2,6-dione D1272.

-continued

D1271

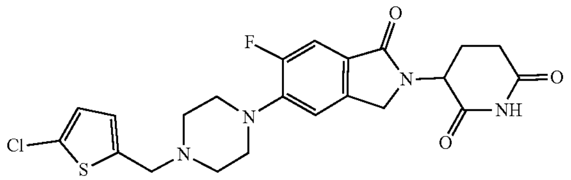

D1272

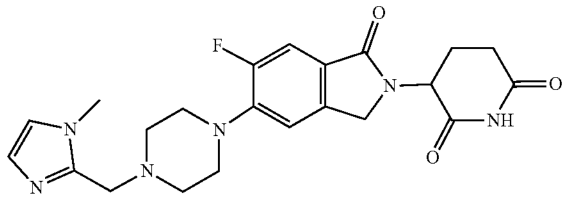

3-(5-(4-((2-Chlorothiophen-3-yl)methyl)piperazin-1-yl)-6-fluoro-1-oxoisoindolin-2-yl)piperidine-2,6-dione D1273.

3-(5-(4-(4-Cyclopropylbenzyl)piperazin-1-yl)-6-fluoro-1-oxoisoindolin-2-yl)-piperidine-2,6-dione D1274.

D1273

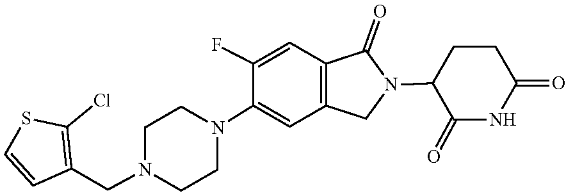

D1274

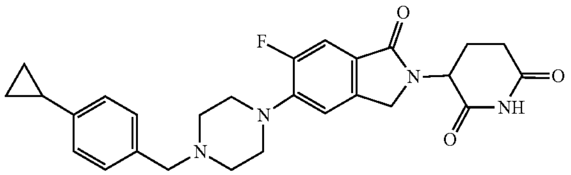

3-(5-(4-(2-Cyclopropylbenzyl)piperazin-1-yl)-6-fluoro-1-oxoisoindolin-2-yl)-piperidine-2,6-dione D1275.

3-(6-Fluoro-1-oxo-5-(4-(pyrazolo[1,5-a]pyridin-7-ylmethyl)piperazin-1-yl)-isoindolin-2-yl)piperidine-2,6-dione D1276.

D1275

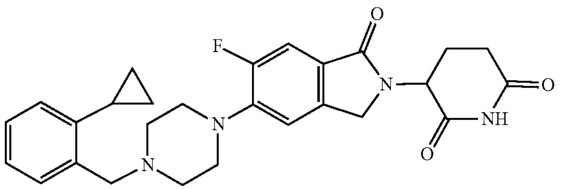

D1276

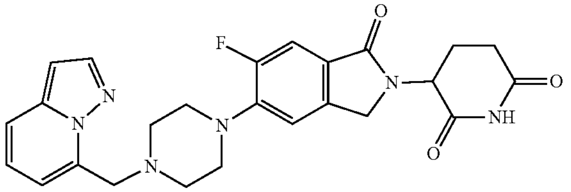

3-(5-(4-((1H-Pyrrolo[2,3-c]pyridin-3-yl)methyl)piperazin-1-yl)-6-fluoro-1-oxoisoindolin-2-yl)piperidine-2,6-dione D1277.

3-(6-Fluoro-5-(4-(imidazo[1,2-a]pyridin-5-ylmethyl)piperazin-1-yl)-1-oxoisoindolin-2-yl)piperidine-2,6-dione D1278.

D1277

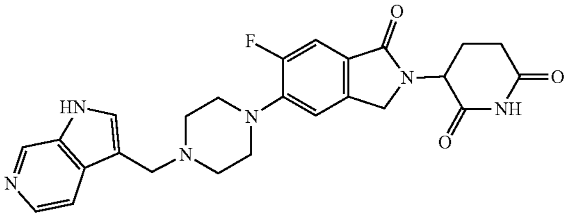

D1278

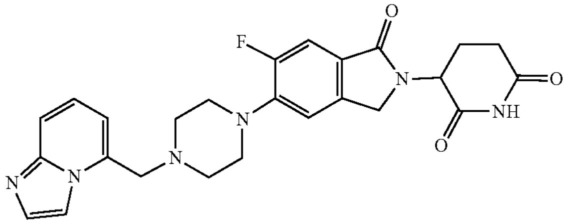

3-(6-Fluoro-1-oxo-5-(4-(pyrazolo[1,5-a]pyridin-3-ylmethyl)piperazin-1-yl)-isoindolin-2-yl)piperidine-2,6-dione D1279.

3-(5-(4-((2H-Indazol-6-yl)methyl)piperazin-1-yl)-6-fluoro-1-oxoisoindolin-2-yl)-piperidine-2,6-dione D1280.

D1279

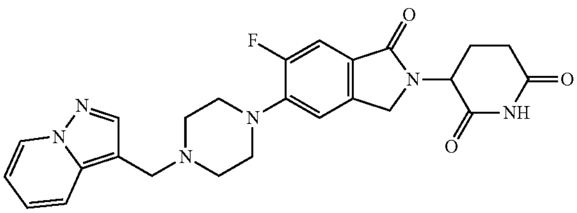

D1280

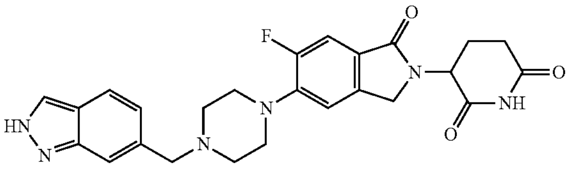

3-(5-(4-((1H-Pyrrolo[3,2-b]pyridin-3-yl)methyl)piperazin-1-yl)-6-fluoro-1-oxoisoindolin-2-yl)piperidine-2,6-dione D1281.

3-(6-Fluoro-5-(4-(imidazo[1,5-a]pyridin-1-ylmethyl)piperazin-1-yl)-1-oxoisoindolin-2-yl)piperidine-2,6-dione D1282.

D1281

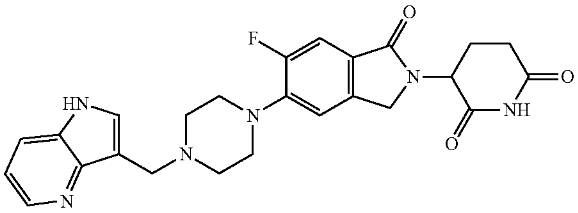

D1282

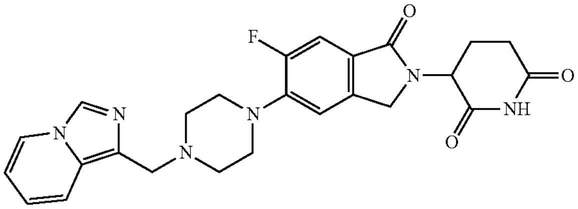

3-(6-Fluoro-5-(4-((5-methyl-1H-pyrazol-3-yl)methyl)piperazin-1-yl)-1-oxoisoindolin-2-yl)piperidine-2,6-dione D1283.

3-(5-(4-((1H-Pyrrolo[2,3-b]pyridin-6-yl)methyl)piperazin-1-yl)-6-fluoro-1-oxoisoindolin-2-yl)piperidine-2,6-dione D1284.

D1283

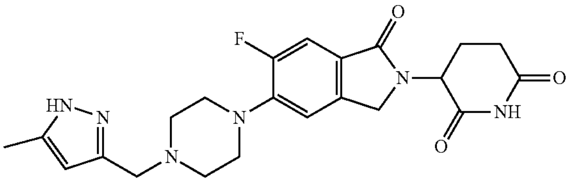

D1284

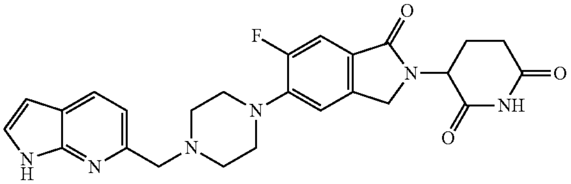

3-(5-(4-((1H-Benzo[d]imidazol-7-yl)methyl)piperazin-1-yl)-6-fluoro-1-oxoisoindolin-2-yl)piperidine-2,6-dione D1285.

3-(6-Fluoro-5-(4-(imidazo[1,2-a]pyridin-6-ylmethyl)piperazin-1-yl)-1-oxoisoindolin-2-yl)piperidine-2,6-dione D1286.

D1285

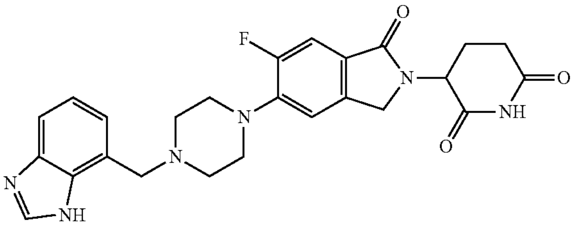

D1286

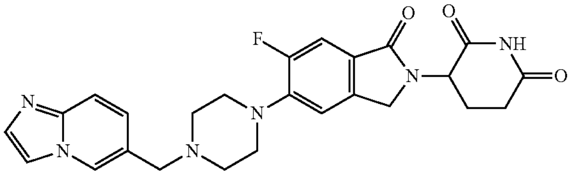

3-(6-Fluoro-5-(4-(imidazo[1,2-a]pyridin-8-ylmethyl)piperazin-1-yl)-1-oxoisoindolin-2-yl)piperidine-2,6-dione D1287.

3-(6-Fluoro-5-(4-(imidazo[1,2-a]pyridin-7-ylmethyl)piperazin-1-yl)-1-oxoisoindolin-2-yl)piperidine-2,6-dione D1288.

D1287

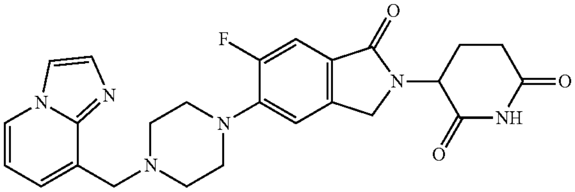

D1288

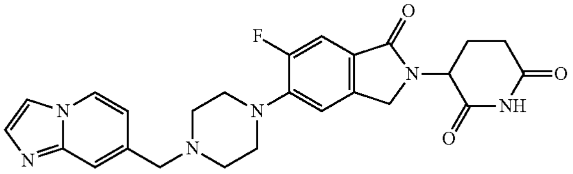

3-(5-(4-((1H-Pyrrolo[3,2-b]pyridin-6-yl)methyl)piperazin-1-yl)-6-fluoro-1-oxoisoindolin-2-yl)piperidine-2,6-dione D1289.

3-(5-(4-((1H-Benzo[d]imidazol-2-yl)methyl)piperazin-1-yl)-6-fluoro-1-oxoisoindolin-2-yl)piperidine-2,6-dione D1290.

D1289

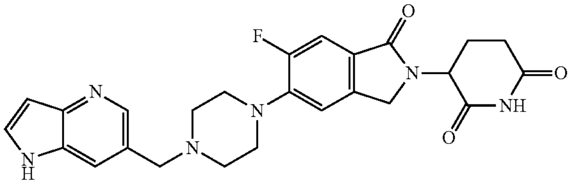

-continued

D1290

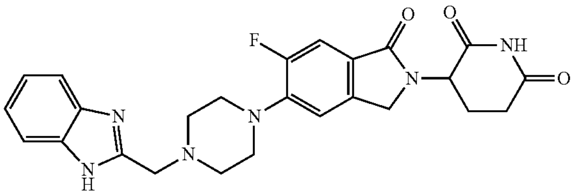

3-(6-Fluoro-5-(4-(imidazo[1,2-a]pyridin-3-ylmethyl)piperazin-1-yl)-1-oxoisoindolin-2-yl)piperidine-2,6-dione D1291.

3-(6-Fluoro-5-(4-(imidazo[1,2-a]pyridin-2-ylmethyl)piperazin-1-yl)-1-oxoisoindolin-2-yl)piperidine-2,6-dione D1292.

D1291

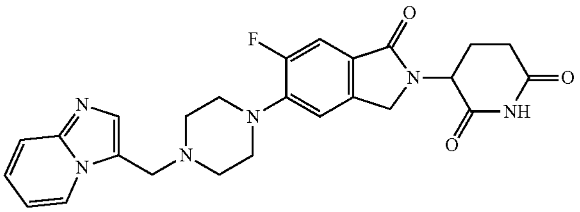

D1292

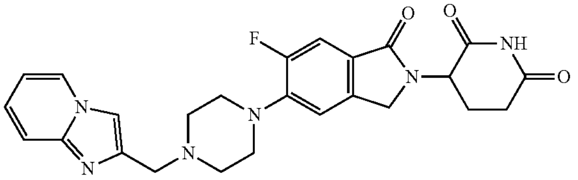

3-(5-(4-(Benzofuran-4-ylmethyl)piperazin-1-yl)-6-fluoro-1-oxoisoindolin-2-yl)-piperidine-2,6-dione D1293.

3-(6-Fluoro-5-(4-((5-methylfuran-2-yl)methyl)piperazin-1-yl)-1-oxoisoindolin-2-yl)piperidine-2,6-dione D1294.

D1293

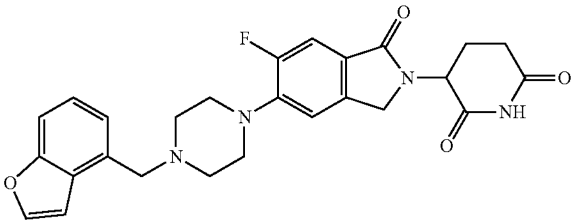

D1294

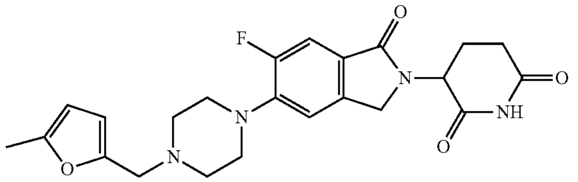

3-(5-(4-(Benzofuran-7-ylmethyl)piperazin-1-yl)-6-fluoro-1-oxoisoindolin-2-yl)-piperidine-2,6-dione D1295.

3-(5-(4-(Benzofuran-5-ylmethyl)piperazin-1-yl)-6-fluoro-1-oxoisoindolin-2-yl)-piperidine-2,6-dione D1296.

D1295

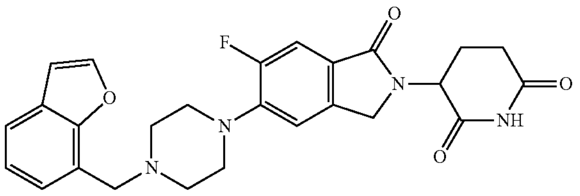

D1296

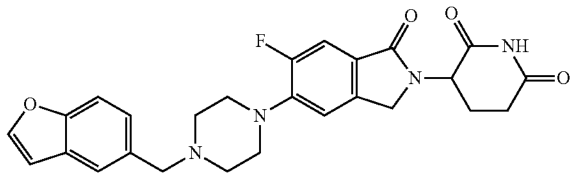

2-((4-(2-(2,6-Dioxopiperidin-3-yl)-6-fluoro-1-oxoisoindolin-5-yl)piperazin-1-yl)-methyl)-5-methylbenzonitrile D1297.

3-((4-(2-(2,6-Dioxopiperidin-3-yl)-6-fluoro-1-oxoisoindolin-5-yl)piperazin-1-yl)-methyl)-2-methylbenzonitrile D1298.

D1297

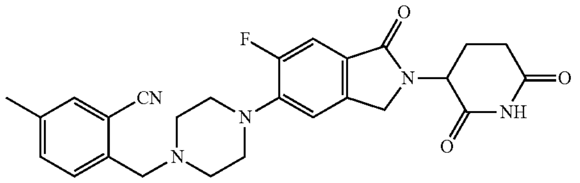

D1298

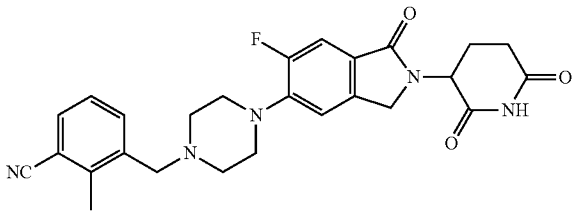

3-((4-(2-(2,6-Dioxopiperidin-3-yl)-6-fluoro-1-oxoisoindolin-5-yl)piperazin-1-yl)-methyl)-5-methylbenzonitrile D1299.

2-((4-(2-(2,6-Dioxopiperidin-3-yl)-6-fluoro-1-oxoisoindolin-5-yl)piperazin-1-yl)-methyl)-6-methylbenzonitrile D1300.

D1299

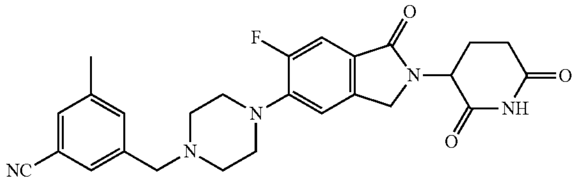

-continued

D1300

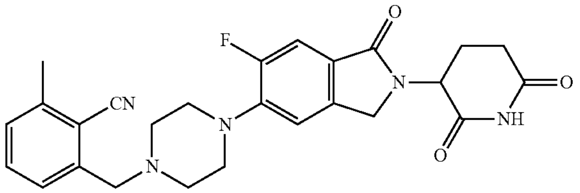

4-((4-(2-(2,6-Dioxopiperidin-3-yl)-6-fluoro-1-oxoisoindolin-5-yl)piperazin-1-yl)-methyl)-3-methylbenzonitrile D1301.

3-(5-(4-((1H-Indol-3-yl)methyl)piperazin-1-yl)-6-fluoro-1-oxoisoindolin-2-yl)-piperidine-2,6-dione D1302.

D1301

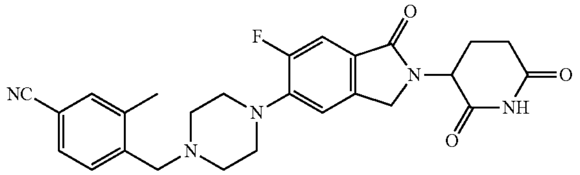

D1302

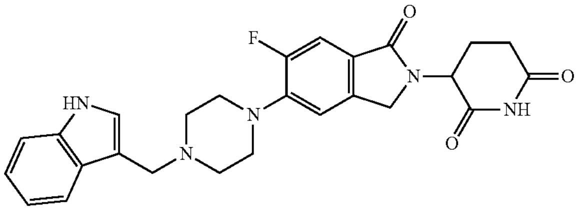

3-(6-Fluoro-5-(4-(indolizin-1-ylmethyl)piperazin-1-yl)-1-oxoisoindolin-2-yl)-piperidine-2,6-dione D1303.

3-(5-(4-((1H-Indol-7-yl)methyl)piperazin-1-yl)-6-fluoro-1-oxoisoindolin-2-yl)-piperidine-2,6-dione D1304.

D1303

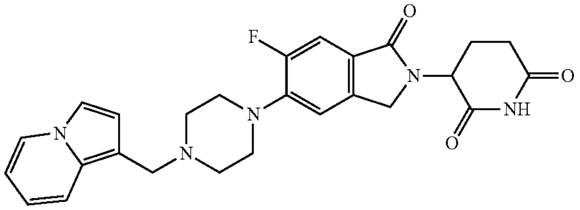

D1304

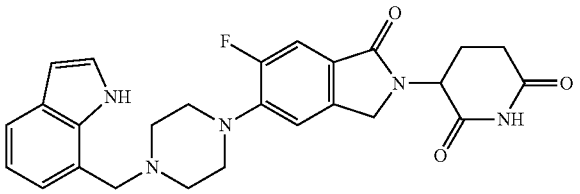

3-(6-Fluoro-5-(4-((3-methyl-1H-pyrrol-2-yl)methyl)piperazin-1-yl)-1-oxoisoindolin-2-yl)piperidine-2,6-dione D1305.

3-(5-(4-((1H-Indol-2-yl)methyl)piperazin-1-yl)-6-fluoro-1-oxoisoindolin-2-yl)-piperidine-2,6-dione D1306.

D1305

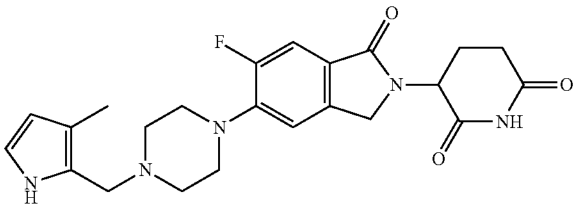

D1306

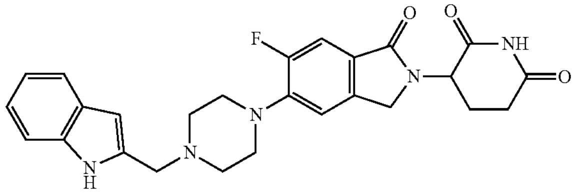

3-(5-(4-((1H-Indol-6-yl)methyl)piperazin-1-yl)-6-fluoro-1-oxoisoindolin-2-yl)-piperidine-2,6-dione D1307.

3-(5-(4-((4-Chloro-1-methyl-1H-pyrazol-3-yl)methyl)piperazin-1-yl)-6-fluoro-1-oxoisoindolin-2-yl)piperidine-2,6-dione D1308.

D1307

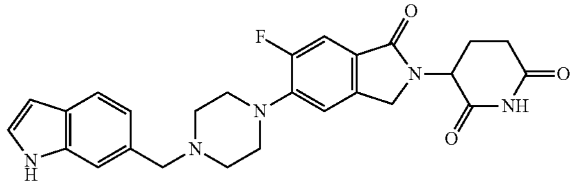

D1308

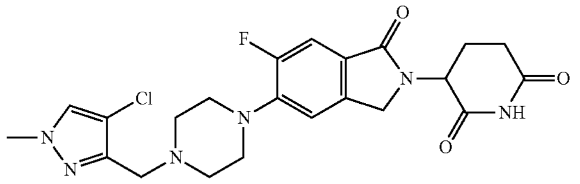

3-(5-(4-((3-Chloropyrazin-2-yl)methyl)piperazin-1-yl)-6-fluoro-1-oxoisoindolin-2-yl)piperidine-2,6-dione D1309.

3-(5-(4-((3-Chloropyridin-4-yl)methyl)piperazin-1-yl)-6-fluoro-1-oxoisoindolin-2-yl)piperidine-2,6-dione D1310.

D1309

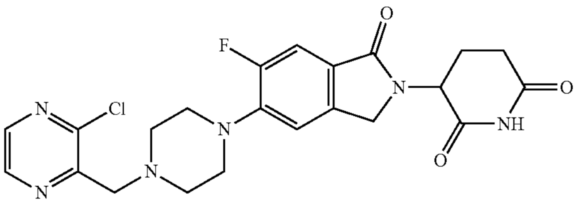

-continued

D1310

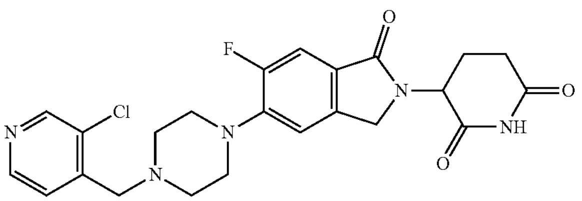

3-(5-(4-((6-Chloropyridin-2-yl)methyl)piperazin-1-yl)-6-fluoro-1-oxoisoindolin-2-yl)piperidine-2,6-dione D1311.

3-(6-Fluoro-5-(4-((5-fluoro-2-oxo-1,2-dihydropyridin-3-yl)methyl)piperazin-1-yl)-1-oxoisoindolin-2-yl)piperidine-2,6-dione D1312.

D1311

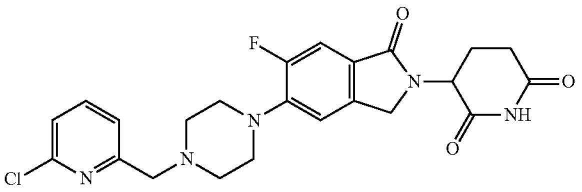

D1312

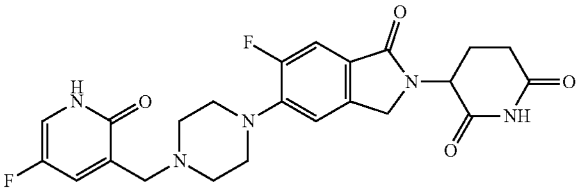

3-(5-(4-(2-Chlorobenzyl)piperazin-1-yl)-6-fluoro-1-oxoisoindolin-2-yl)-piperidine-2,6-dione D1313.

3-(5-(4-(4-Chlorobenzyl)piperazin-1-yl)-6-fluoro-1-oxoisoindolin-2-yl)-piperidine-2,6-dione D1314.

D1313

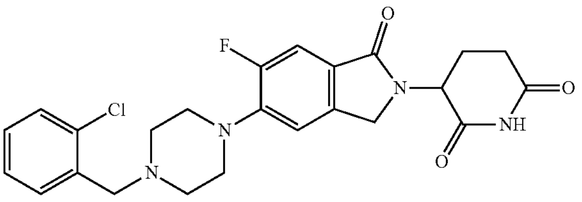

D1314

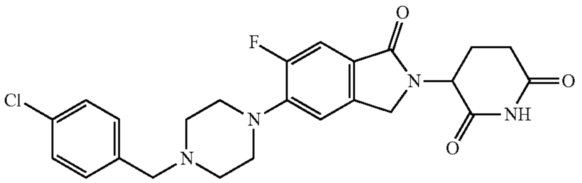

3-(5-(4-(3-Chlorobenzyl)piperazin-1-yl)-6-fluoro-1-oxoisoindolin-2-yl)-piperidine-2,6-dione D1315.

3-(6-Fluoro-5-(4-((5-methyl-1H-pyrrol-2-yl)methyl)piperazin-1-yl)-1-oxoisoindolin-2-yl)piperidine-2,6-dione D1316.

D1315

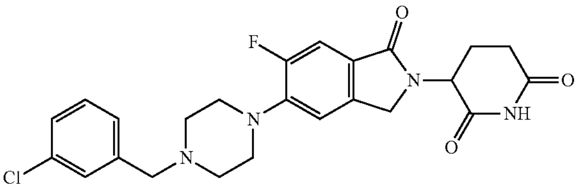

D1316

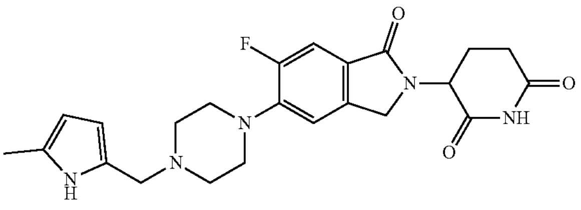

3-(5-(4-(2-Amino-5-fluorobenzyl)piperazin-1-yl)-6-fluoro-1-oxoisoindolin-2-yl)-piperidine-2,6-dione D1317.

3-(6-Fluoro-5-(4-((1-isopropyl-1H-pyrazol-4-yl)methyl)piperazin-1-yl)-1-oxoisoindolin-2-yl)piperidine-2,6-dione D1318.

D1317

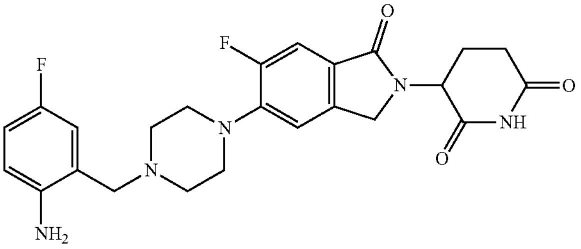

D1318

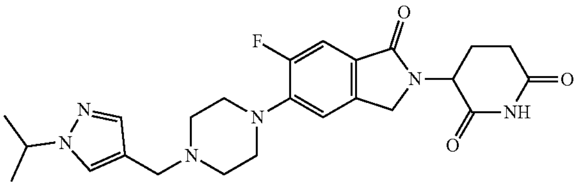

3-(6-Fluoro-5-(4-((4-isopropylfuran-2-yl)methyl)piperazin-1-yl)-1-oxoisoindolin-2-yl)piperidine-2,6-dione D1319.

D1319

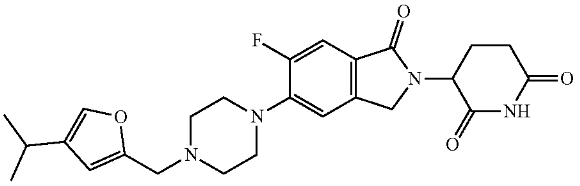

3-(6-Fluoro-5-(4-(3-(5-methylfuran-2-yl)propyl)piperazin-1-yl)-1-oxoisoindolin-2-yl)piperidine-2,6-dione D1320.

D1320

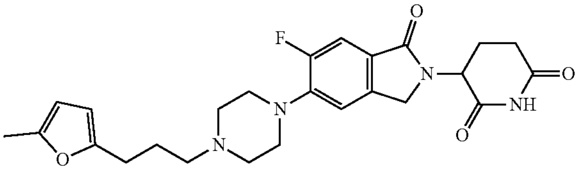

3-(6-Fluoro-5-(4-(4-fluorophenethyl)piperazin-1-yl)-1-oxoisoindolin-2-yl)-piperidine-2,6-dione D1321.

3-(6-Fluoro-5-(4-(3-fluoro-2-methylbenzyl)piperazin-1-yl)-1-oxoisoindolin-2-yl)-piperidine-2,6-dione D1322.

D1321

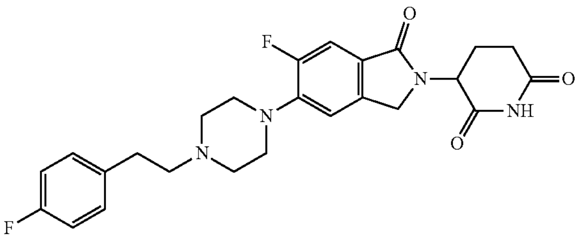

D1322

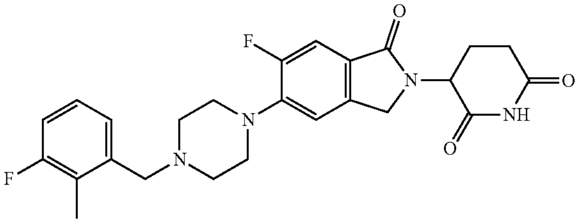

3-(6-Fluoro-5-(4-(2-fluoro-5-methylbenzyl)piperazin-1-yl)-1-oxoisoindolin-2-yl)-piperidine-2,6-dione D1323.

3-(6-Fluoro-5-(4-(4-fluoro-3-methylbenzyl)piperazin-1-yl)-1-oxoisoindolin-2-yl)-piperidine-2,6-dione D1324.

D1323

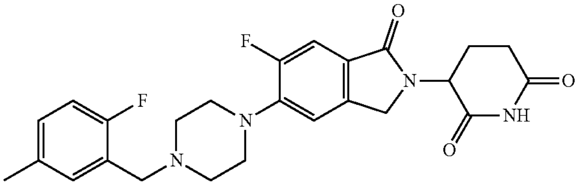

D1324

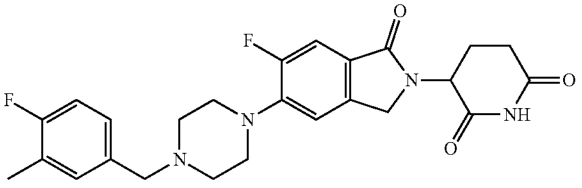

3-(6-Fluoro-5-(4-(3-fluoro-5-methylbenzyl)piperazin-1-yl)-1-oxoisoindolin-2-yl)-piperidine-2,6-dione D1325.

3-(6-Fluoro-5-(4-(4-fluoro-2-methylbenzyl)piperazin-1-yl)-1-oxoisoindolin-2-yl)-piperidine-2,6-dione D1326.

D1325

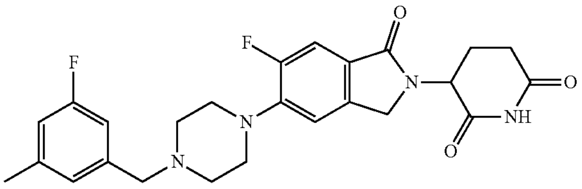

D1326

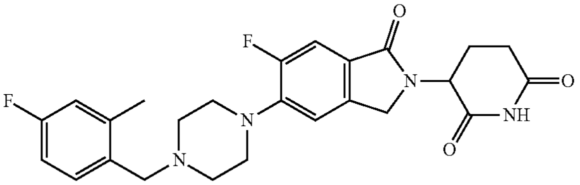

3-(6-Fluoro-5-(4-((1-methyl-1H-pyrrol-2-yl)methyl)piperazin-1-yl)-1-oxoisoindolin-2-yl)piperidine-2,6-dione D1327.

3-(6-Fluoro-5-(4-(5-fluoro-2-methylbenzyl)piperazin-1-yl)-1-oxoisoindolin-2-yl)-piperidine-2,6-dione D1328.

D1327

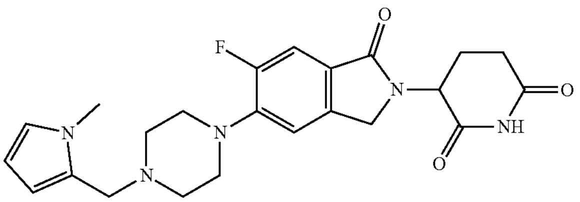

D1328

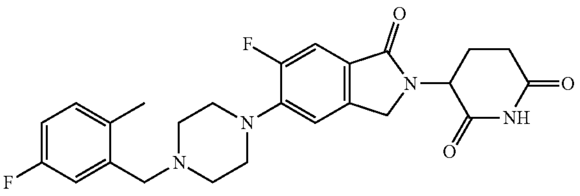

3-(6-Fluoro-5-(4-((5-methoxypyrazin-2-yl)methyl)piperazin-1-yl)-1-oxoisoindolin-2-yl)piperidine-2,6-dione D1329.

3-(6-Fluoro-5-(4-((2-methoxypyrimidin-4-yl)methyl)piperazin-1-yl)-1-oxoisoindolin-2-yl)piperidine-2,6-dione D1330.

D1329

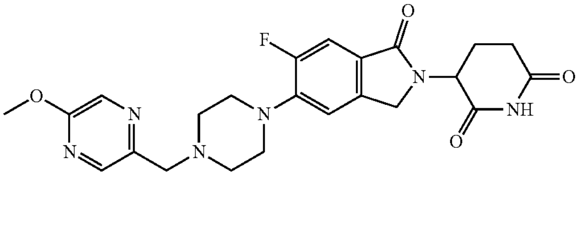

-continued

D1330

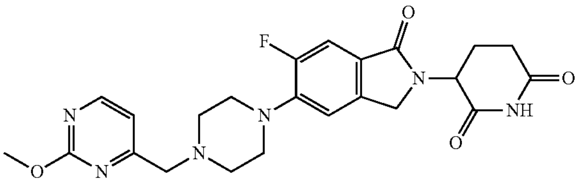

5-((4-(2-(2,6-Dioxopiperidin-3-yl)-6-fluoro-1-oxoisoindolin-5-yl)piperazin-1-yl)-methyl)thiophene-2-carbonitrile D1331.

3-(6-Fluoro-5-(4-((2-methoxypyridin-4-yl)methyl)piperazin-1-yl)-1-oxoisoindolin-2-yl)piperidine-2,6-dione D1332.

D1331

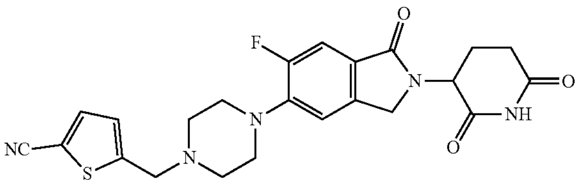

D1332

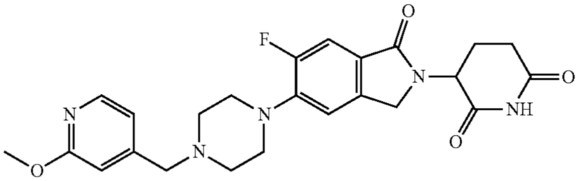

3-(6-Fluoro-5-(4-((2-methoxypyridin-3-yl)methyl)piperazin-1-yl)-1-oxoisoindolin-2-yl)piperidine-2,6-dione D1333.

3-(6-Fluoro-5-(4-((3-methoxypyridin-4-yl)methyl)piperazin-1-yl)-1-oxoisoindolin-2-yl)piperidine-2,6-dione D1334.

D1333

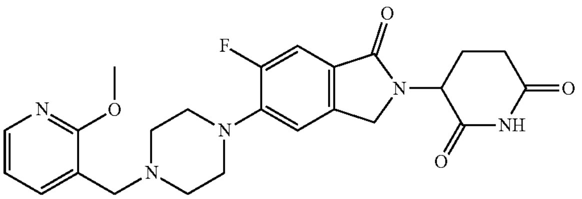

D1334

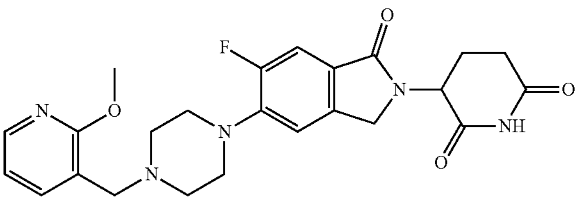

3-(6-Fluoro-5-(4-((6-methoxypyridin-3-yl)methyl)piperazin-1-yl)-1-oxoisoindolin-2-yl)piperidine-2,6-dione D1335.

3-(6-Fluoro-5-(4-((4-methoxypyridin-2-yl)methyl)piperazin-1-yl)-1-oxoisoindolin-2-yl)piperidine-2,6-dione D1336.

D1335

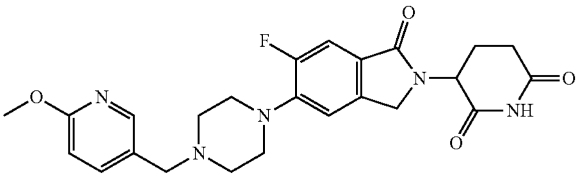

D1336

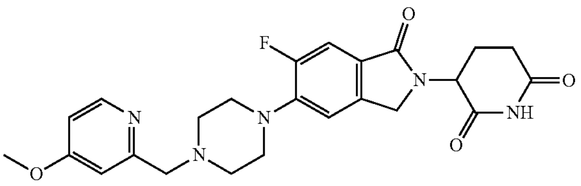

3-(6-Fluoro-5-(4-((5-methoxypyridin-2-yl)methyl)piperazin-1-yl)-1-oxoisoindolin-2-yl)piperidine-2,6-dione D1337.

3-(6-Fluoro-1-oxo-5-(4-(pyrimidin-5-ylmethyl)piperazin-1-yl)isoindolin-2-yl)piperidine-2,6-dione D1338.

D1137

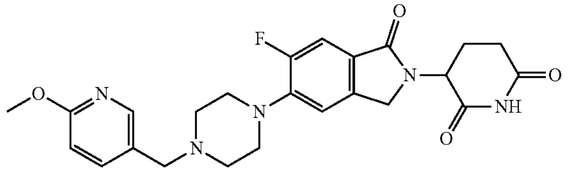

D1138

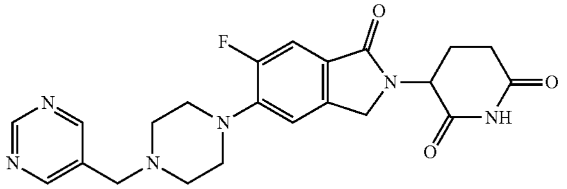

3-(6-Fluoro-5-(4-((3-methoxypyridin-2-yl)methyl)piperazin-1-yl)-1-oxoisoindolin-2-yl)piperidine-2,6-dione D1339.

3-(6-Fluoro-5-(4-((4-methoxypyridin-3-yl)methyl)piperazin-1-yl)-1-oxoisoindolin-2-yl)piperidine-2,6-dione D1340.

D1339

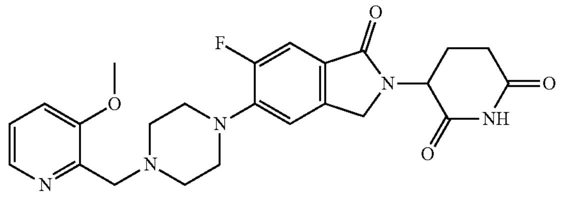

-continued

D1340

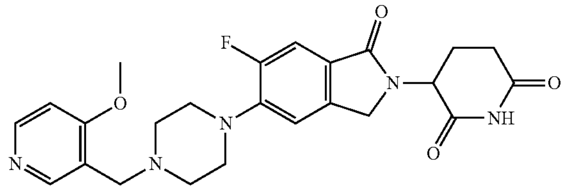

3-(6-Fluoro-5-(4-((6-methoxypyridin-2-yl)methyl)piperazin-1-yl)-1-oxoisoindolin-2-yl)piperidine-2,6-dione D1341.

3-(6-Fluoro-5-(4-((5-methoxypyridin-3-yl)methyl)piperazin-1-yl)-1-oxoisoindolin-2-yl)piperidine-2,6-dione D1342.

D1341

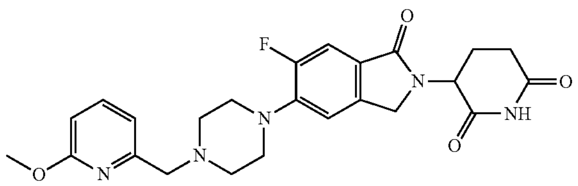

D1342

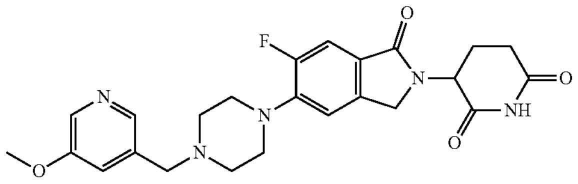

3-(6-Fluoro-5-(4-((1-methyl-6-oxo-1,6-dihydropyridin-2-yl)methyl)piperazin-1-yl)-1-oxoisoindolin-2-yl)piperidine-2,6-dione D1343.

3-(6-Fluoro-5-(4-((1-methyl-2-oxo-1,2-dihydropyridin-4-yl)methyl)piperazin-1-yl)-1-oxoisoindolin-2-yl)piperidine-2,6-dione D1344.

D1343

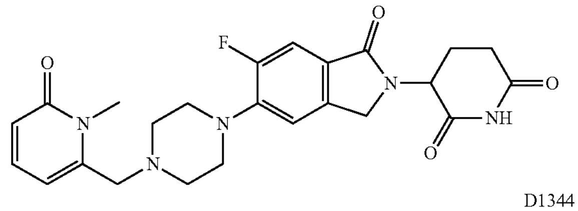

D1344

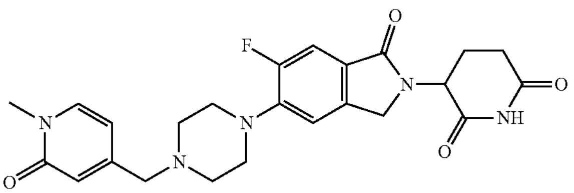

3-(5-(4-((2-Amino-5-methylpyridin-3-yl)methyl)piperazin-1-yl)-6-fluoro-1-oxoisoindolin-2-yl)piperidine-2,6-dione D1345.

3-(6-Fluoro-5-(4-(2-methoxybenzyl)piperazin-1-yl)-1-oxoisoindolin-2-yl)-piperidine-2,6-dione D1346.

D1345

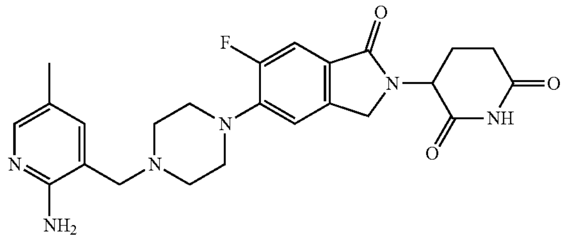

D1346

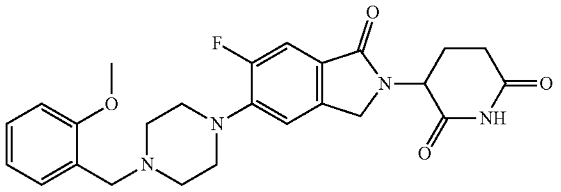

3-(6-Fluoro-5-(4-(4-methoxybenzyl)piperazin-1-yl)-1-oxoisoindolin-2-yl)-piperidine-2,6-dione D1347.

3-(6-Fluoro-5-(4-(3-hydroxy-5-methylbenzyl)piperazin-1-yl)-1-oxoisoindolin-2-yl)piperidine-2,6-dione D1348.

D1347

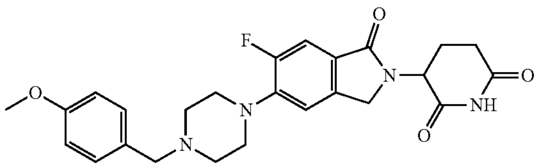

D1348

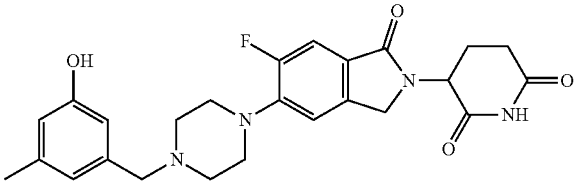

3-(6-Fluoro-1-oxo-5-(4-(pyridin-2-ylmethyl)piperazin-1-yl)isoindolin-2-yl)-piperidine-2,6-dione D1349.

3-(5-(4-(Cyclobutylmethyl)piperazin-1-yl)-6-fluoro-1-oxoisoindolin-2-yl)-piperidine-2,6-dione D1350.

D1349

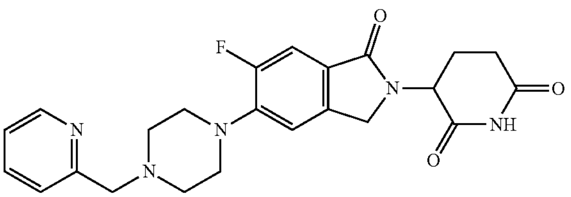

-continued

D1350

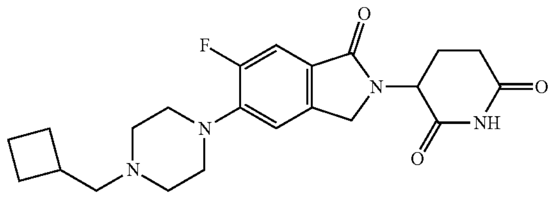

3-(5-(4-(Cyclopropylsulfonyl)piperazin-1-yl)-6-fluoro-1-oxoisoindolin-2-yl)-piperidine-2,6-dione D2001.

3-(6-Fluoro-1-oxo-5-(4-(propylsulfonyl)piperazin-1-yl) isoindolin-2-yl)piperidine-2,6-dione D2002.

D2001

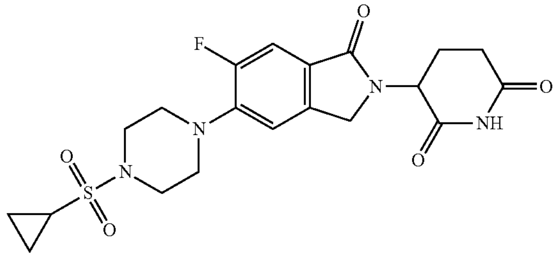

D2002

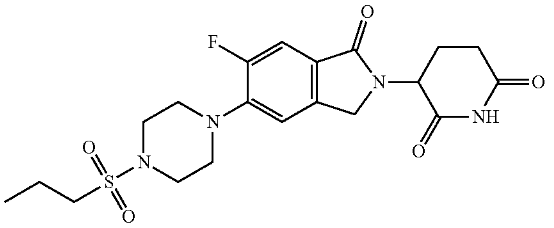

3-(6-Fluoro-5-(4-(isopropylsulfonyl)piperazin-1-yl)-1-oxoisoindolin-2-yl)-piperidine-2,6-dione D2003.

3-(6-Fluoro-5-(4-(isobutylsulfonyl)piperazin-1-yl)-1-oxoisoindolin-2-yl)-piperidine-2,6-dione D2004.

D2003

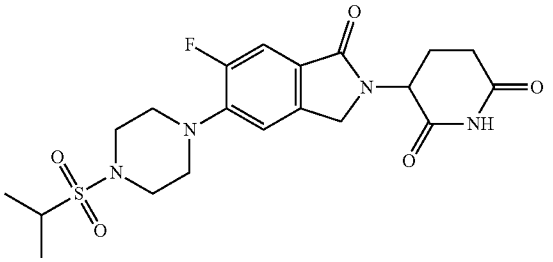

-continued

D2004

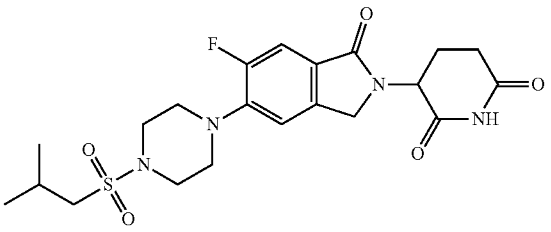

3-(6-Fluoro-5-(4-(furan-3-ylsulfonyl)piperazin-1-yl)-1-oxoisoindolin-2-yl)-piperidine-2,6-dione D2005.

3-(5-(4-((1H-Pyrazol-4-yl)sulfonyl)piperazin-1-yl)-6-fluoro-1-oxoisoindolin-2-yl)piperidine-2,6-dione D2006.

D2005

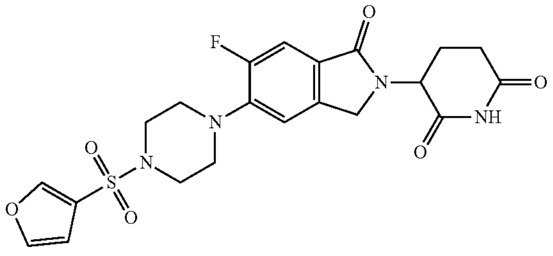

D2006

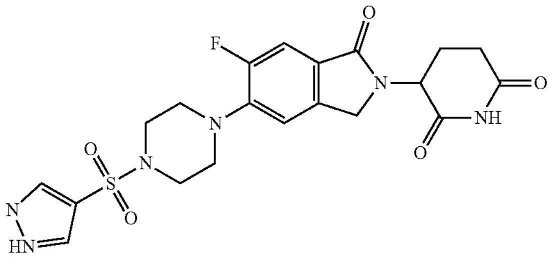

3-(6-Fluoro-1-oxo-5-(4-((trifluoromethyl)sulfonyl)piperazin-1-yl)isoindolin-2-yl)-piperidine-2,6-dione D2007.

3-(5-(4-((Cyclobutylmethyl)sulfonyl)piperazin-1-yl)-6-fluoro-1-oxoisoindolin-2-yl)piperidine-2,6-dione D2008.

D2007

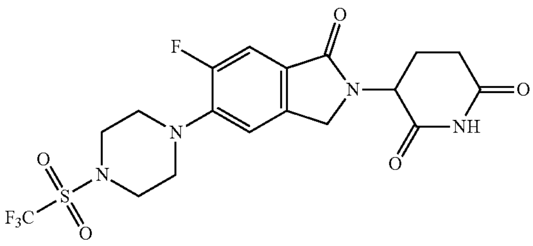

-continued

D2008

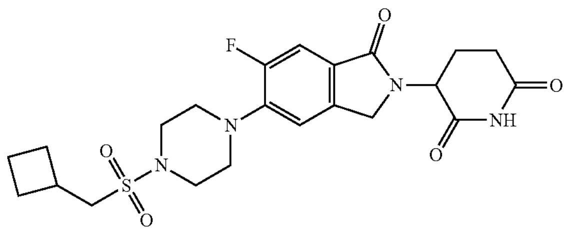

3-(5-(4-((3-Chloropropyl)sulfonyl)piperazin-1-yl)-6-fluoro-1-oxoisoindolin-2-yl)-piperidine-2,6-dione D2009.

3-(6-Fluoro-1-oxo-5-(4-(pyridin-3-ylsulfonyl)piperazin-1-yl)isoindolin-2-yl)-piperidine-2,6-dione D2010.

D2009

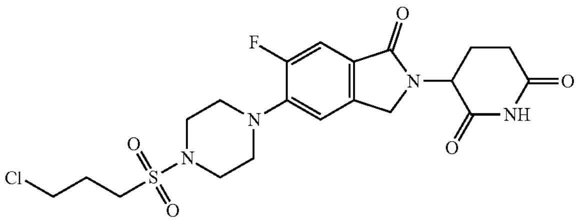

D2010

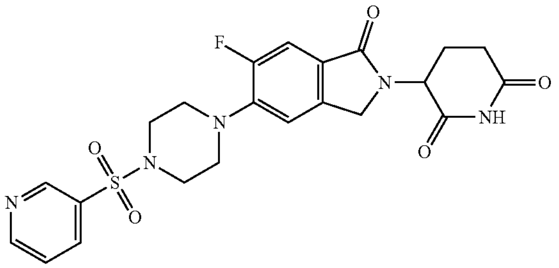

3-(6-Fluoro-5-(4-((1-methyl-1H-pyrazol-4-yl)sulfonyl)piperazin-1-yl)-1-oxoisoindolin-2-yl)piperidine-2,6-dione D2011.

3-(6-Fluoro-5-(4-((1-methyl-1H-pyrazol-3-yl)sulfonyl)piperazin-1-yl)-1-oxoisoindolin-2-yl)piperidine-2,6-dione D2012.

D2011

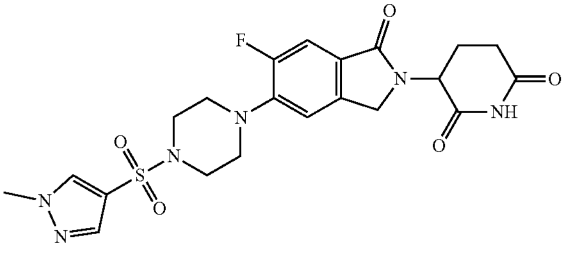

-continued

D2012

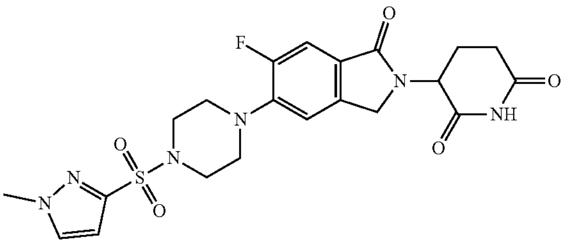

3-(6-Fluoro-5-(4-((1-methyl-1H-imidazol-4-yl)sulfonyl)piperazin-1-yl)-1-oxoisoindolin-2-yl)piperidine-2,6-dione D2013.

3-(6-Fluoro-1-oxo-5-(4-(thiophen-2-ylsulfonyl)piperazin-1-yl)isoindolin-2-yl)-piperidine-2,6-dione D2014.

D2013

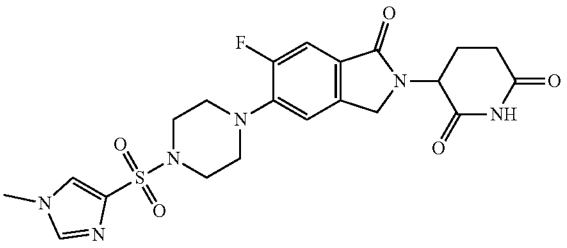

D2014

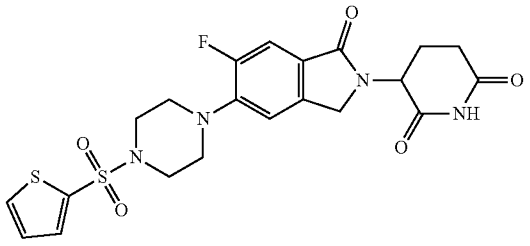

3-(5-(4-(Cyclohexylsulfonyl)piperazin-1-yl)-6-fluoro-1-oxoisoindolin-2-yl)-piperidine-2,6-dione D2015.

3-(6-Fluoro-1-oxo-5-(4-((tetrahydro-2H-pyran-4-yl)sulfonyl)piperazin-1-yl)-isoindolin-2-yl)piperidine-2,6-dione D2016.

D2015

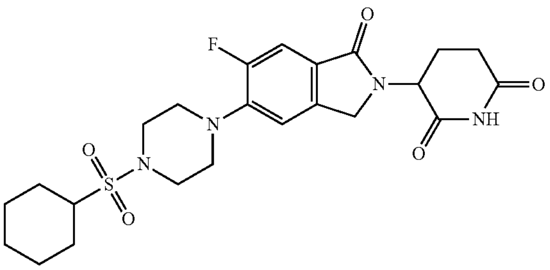

-continued

D2016

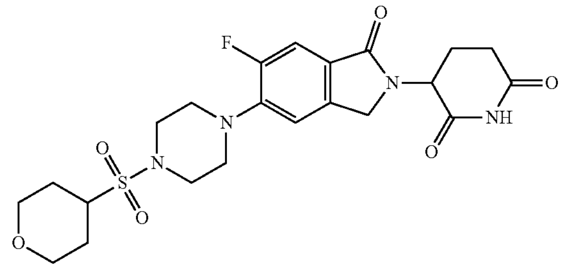

3-(6-Fluoro-1-oxo-5-(4-(m-tolylsulfonyl)piperazin-1-yl) isoindolin-2-yl)-piperidine-2,6-dione D2017.

3-(6-Fluoro-5-(4-((6-methylpyridin-3-yl)sulfonyl)piperazin-1-yl)-1-oxoisoindolin-2-yl)piperidine-2,6-dione D2018.

D2017

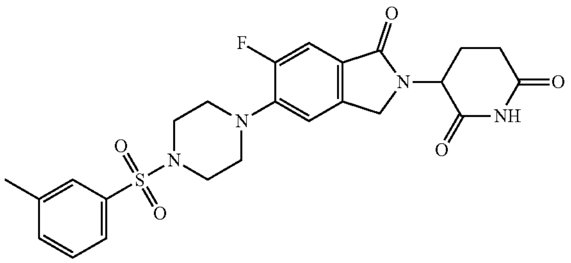

D2018

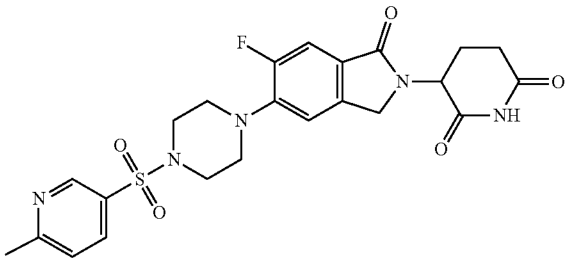

3-(6-Fluoro-5-(4-((4-hydroxyphenyl)sulfonyl)piperazin-1-yl)-1-oxoisoindolin-2-yl)piperidine-2,6-dione D2019.

3-(6-Fluoro-5-(4-((4-fluorophenyl)sulfonyl)piperazin-1-yl)-1-oxoisoindolin-2-yl)-piperidine-2,6-dione D2020.

D2019

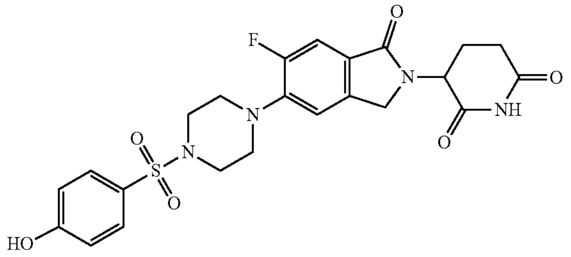

-continued

D2020

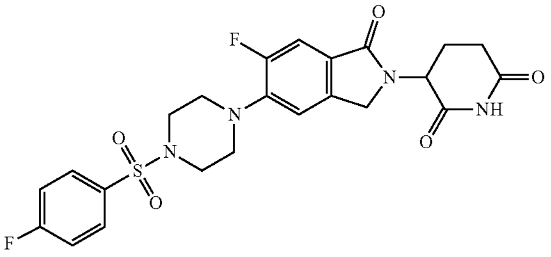

3-(6-Fluoro-5-(4-((3-fluorophenyl)sulfonyl)piperazin-1-yl)-1-oxoisoindolin-2-yl)-piperidine-2,6-dione D2021.

3-(6-Fluoro-5-(4-((2-fluorophenyl)sulfonyl)piperazin-1-yl)-1-oxoisoindolin-2-yl)-piperidine-2,6-dione D2022.

D2021

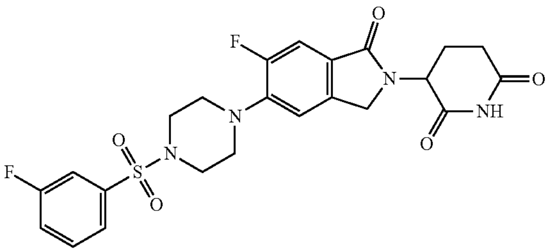

D2022

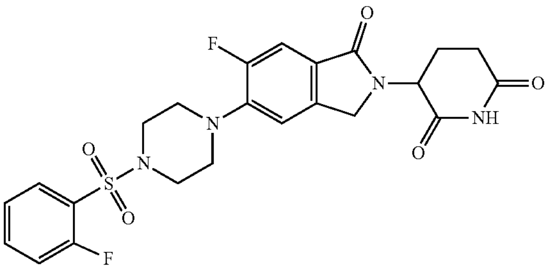

3-(6-Fluoro-1-oxo-5-(4-((3,3,3-trifluoropropyl)sulfonyl) piperazin-1-yl)isoindolin-2-yl)piperidine-2,6-dione D2023.

3-(6-Fluoro-5-(4-((4-methylbenzyl)sulfonyl)piperazin-1-yl)-1-oxoisoindolin-2-yl)piperidine-2,6-dione D2024.

D2023

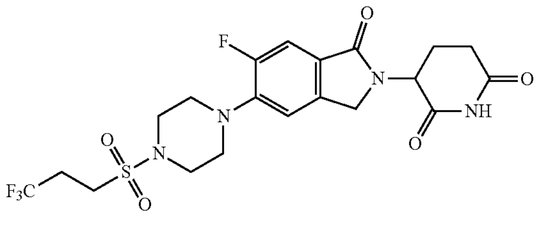

-continued

D2024

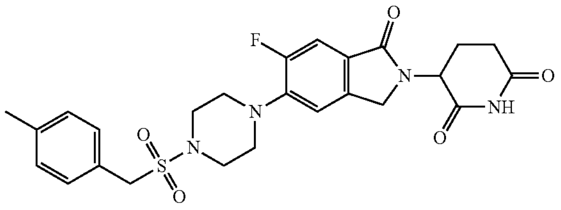

3-(6-Fluoro-1-oxo-5-(4-(phenethylsulfonyl)piperazin-1-yl) isoindolin-2-yl)-piperidine-2,6-dione D2025.

3-(5-(4-((2,6-Dimethylphenyl)sulfonyl)piperazin-1-yl)-6-fluoro-1-oxoisoindolin-2-yl)piperidine-2,6-dione D2026.

D2025

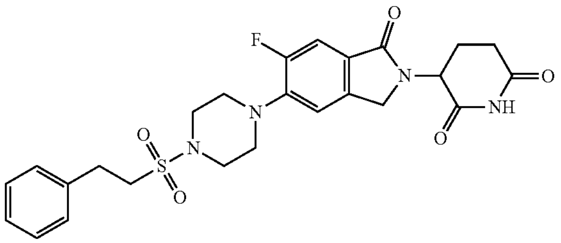

D2026

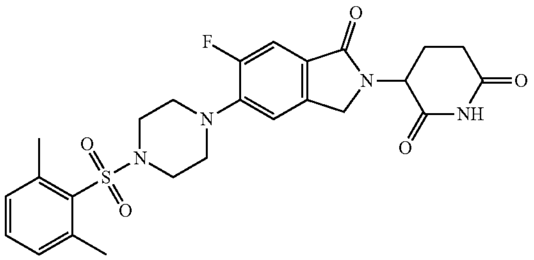

3-(6-Fluoro-5-(4-((4-methoxyphenyl)sulfonyl)piperazin-1-yl)-1-oxoisoindolin-2-yl)piperidine-2,6-dione D2027.

3-(6-Fluoro-5-(4-((3-methoxyphenyl)sulfonyl)piperazin-1-yl)-1-oxoisoindolin-2-yl)piperidine-2,6-dione D2028.

D2027

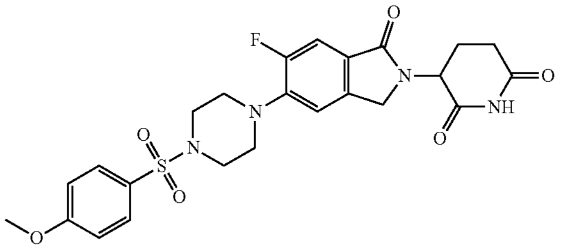

-continued

D2028

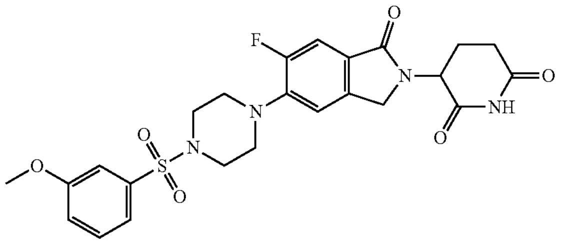

3-(6-Fluoro-5-(4-((6-methoxypyridin-3-yl)sulfonyl)piperazin-1-yl)-1-oxoisoindolin-2-yl)piperidine-2,6-dione D2029.

3-(6-Fluoro-5-(4-((2-fluoro-5-methylphenyl)sulfonyl)piperazin-1-yl)-1-oxoisoindolin-2-yl)piperidine-2,6-dione D2030.

D2029

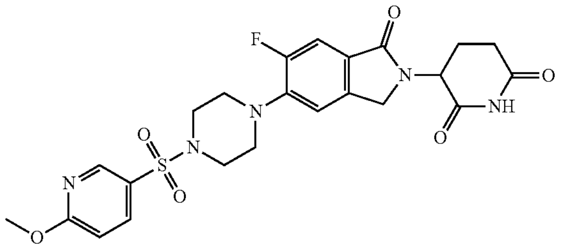

D2030

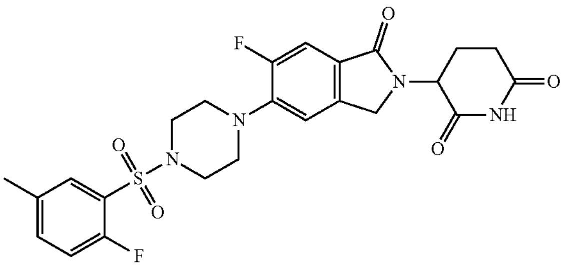

3-(6-Fluoro-5-(4-((4-fluoro-2-methylphenyl)sulfonyl)piperazin-1-yl)-1-oxoisoindolin-2-yl)piperidine-2,6-dione D2031.

3-(6-Fluoro-5-(4-((2-fluoro-4-methylphenyl)sulfonyl)piperazin-1-yl)-1-oxoisoindolin-2-yl)piperidine-2,6-dione D2032.

D2031

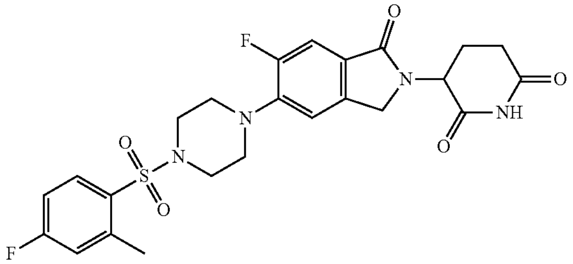

-continued

D2032

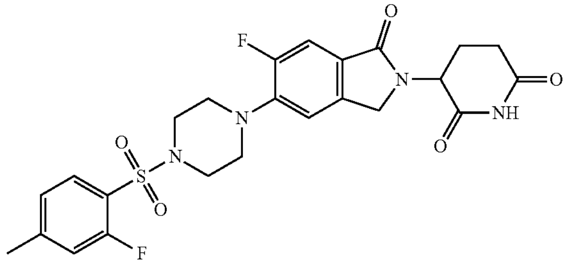

3-(5-(4-((3-Chlorophenyl)sulfonyl)piperazin-1-yl)-6-fluoro-1-oxoisoindolin-2-yl)-piperidine-2,6-dione D2033.

3-(5-(4-((2-Chlorophenyl)sulfonyl)piperazin-1-yl)-6-fluoro-1-oxoisoindolin-2-yl)-piperidine-2,6-dione D2034.

D2033

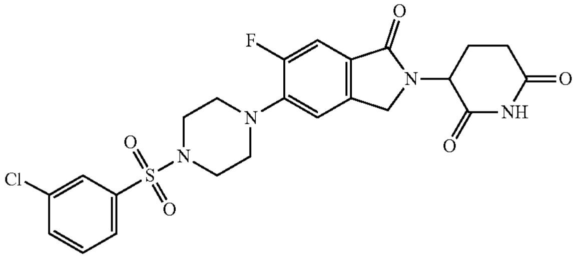

D2034

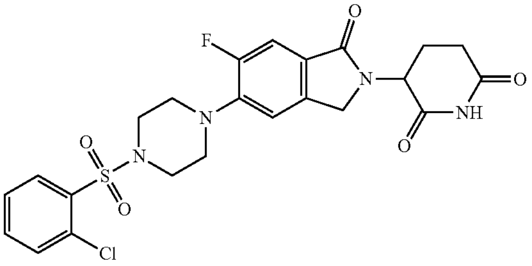

3-(5-(4-((4-Chlorophenyl)sulfonyl)piperazin-1-yl)-6-fluoro-1-oxoisoindolin-2-yl)-piperidine-2,6-dione D2035.

3-(5-(4-((3,4-Difluorophenyl)sulfonyl)piperazin-1-yl)-6-fluoro-1-oxoisoindolin-2-yl)piperidine-2,6-dione D2036.

D2035

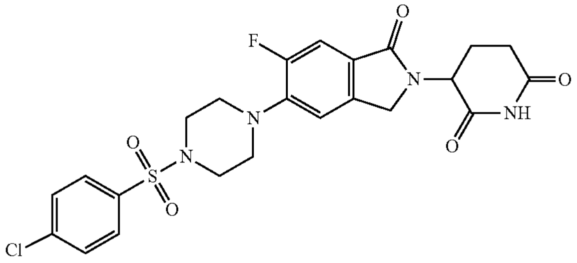

-continued

D2036

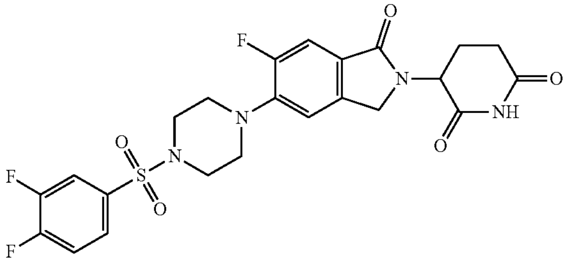

3-(5-(4-((2,4-Difluorophenyl)sulfonyl)piperazin-1-yl)-6-fluoro-1-oxoisoindolin-2-yl)piperidine-2,6-dione D2037.

3-(5-(4-((2,5-Difluorophenyl)sulfonyl)piperazin-1-yl)-6-fluoro-1-oxoisoindolin-2-yl)piperidine-2,6-dione D2038.

D2037

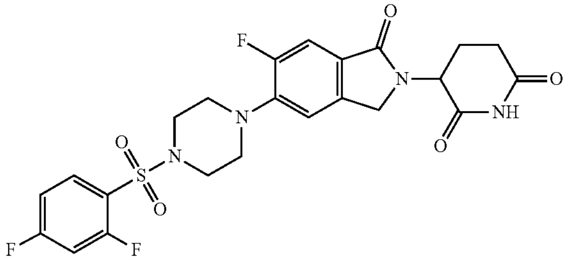

D2038

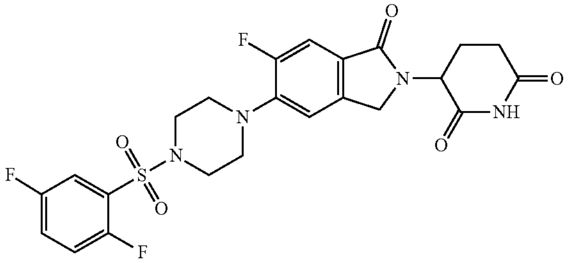

3-(5-(4-((3,5-Difluorophenyl)sulfonyl)piperazin-1-yl)-6-fluoro-1-oxoisoindolin-2-yl)piperidine-2,6-dione D2039.

3-(6-Fluoro-1-oxo-5-(4-(pyridin-3-ylsulfonyl)piperazin-1-yl)isoindolin-2-yl)-piperidine-2,6-dione D2040.

D2039

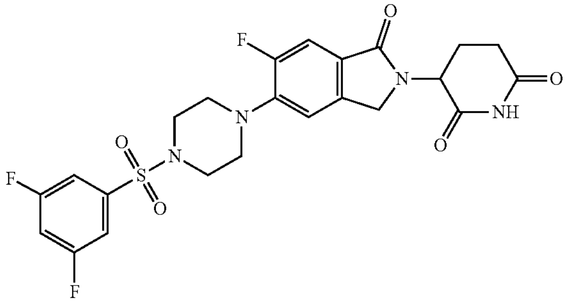

-continued

D2040

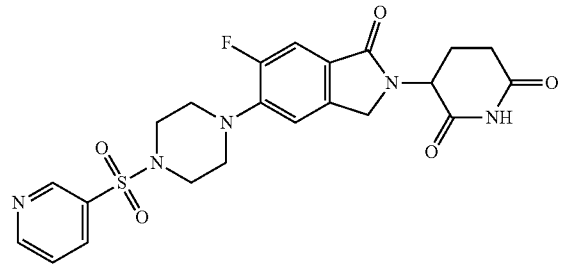

2-((4-(2-(2,6-Dioxopiperidin-3-yl)-6-fluoro-1-oxoisoindolin-5-yl)piperazin-1-yl)-sulfonyl)-5-methylbenzonitrile D2041.

3-(5-(4-((1H-Indol-5-yl)sulfonyl)piperazin-1-yl)-6-fluoro-1-oxoisoindolin-2-yl)-piperidine-2,6-dione D2042.

D2041

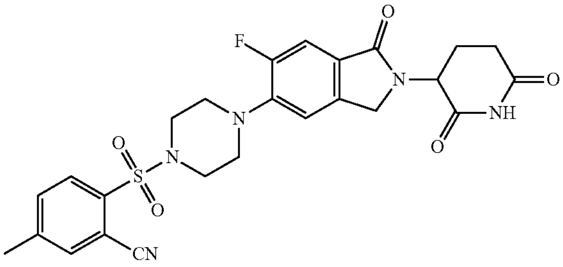

D2042

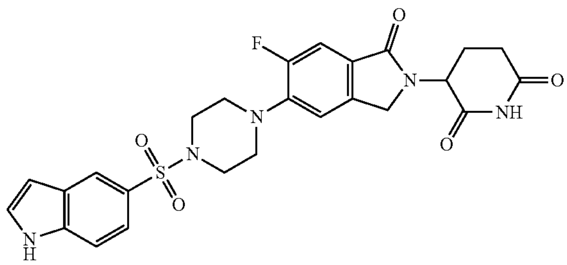

3-(5-(4-(Benzofuran-5-ylsulfonyl)piperazin-1-yl)-6-fluoro-1-oxoisoindolin-2-yl)-piperidine-2,6-dione D2043.

3-(5-(4-((2,3-Dihydrobenzofuran-5-yl)sulfonyl)piperazin-1-yl)-6-fluoro-1-oxoisoindolin-2-yl)piperidine-2,6-dione D2044.

D2043

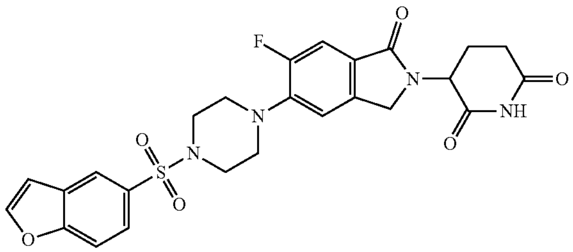

-continued

D2044

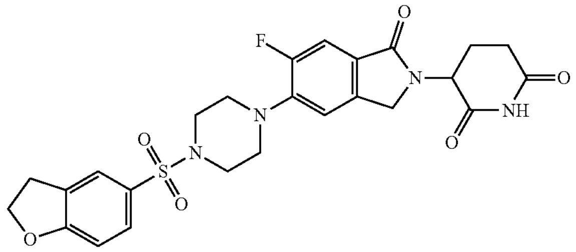

3-(6-Fluoro-5-(4-((4-isopropylphenyl)sulfonyl)piperazin-1-yl)-1-oxoisoindolin-2-yl)piperidine-2,6-dione D2045.

3-(6-Fluoro-5-(4-((3-isopropylphenyl)sulfonyl)piperazin-1-yl)-1-oxoisoindolin-2-yl)piperidine-2,6-dione D2046.

D2045

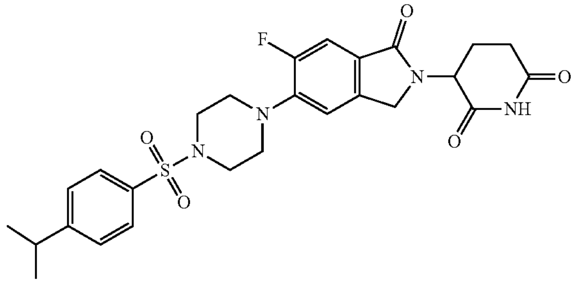

D2046

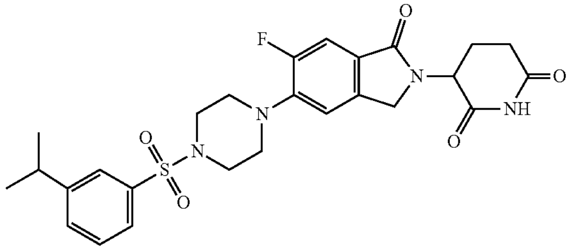

3-((4-(2-(2,6-Dioxopiperidin-3-yl)-6-fluoro-1-oxoisoindolin-5-yl)piperazin-1-yl)-sulfonyl)-4-fluorobenzonitrile D2047.

5-((4-(2-(2,6-Dioxopiperidin-3-yl)-6-fluoro-1-oxoisoindolin-5-yl)piperazin-1-yl)-sulfonyl)-2-fluorobenzonitrile D2048.

D2047

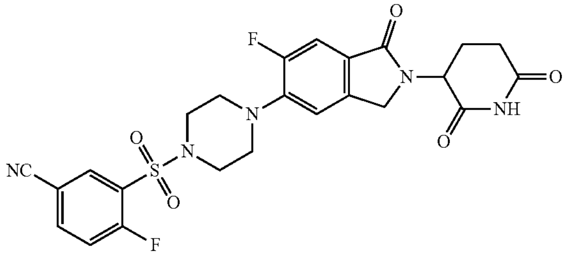

-continued

D2048

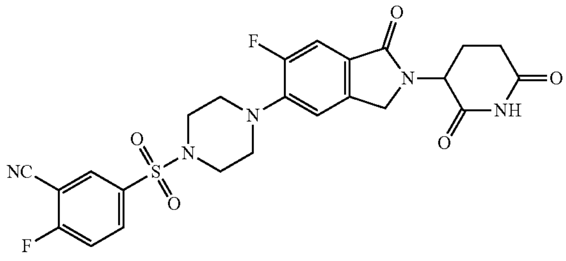

4-((4-(2-(2,6-Dioxopiperidin-3-yl)-6-fluoro-1-oxoisoindolin-5-yl)piperazin-1-yl)-sulfonyl)benzamide D2049.

D2049

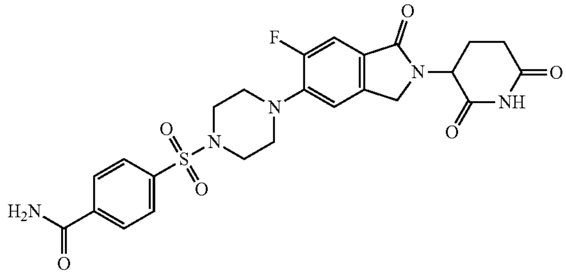

3-(6-Fluoro-5-(4-((3-methoxybenzyl)sulfonyl)piperazin-1-yl)-1-oxoisoindolin-2-yl)piperidine-2,6-dione D2050.

D2050

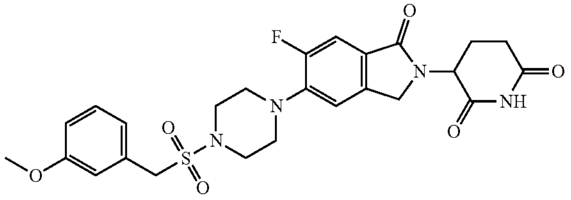

3-(6-Fluoro-5-(4-((3-methoxy-4-methylphenyl)sulfonyl)piperazin-1-yl)-1-oxoisoindolin-2-yl)piperidine-2,6-dione D2051.

3-(6-Fluoro-5-(4-((5-fluoro-2-methoxyphenyl)sulfonyl)piperazin-1-yl)-1-oxoisoindolin-2-yl)piperidine-2,6-dione D2052.

D2051

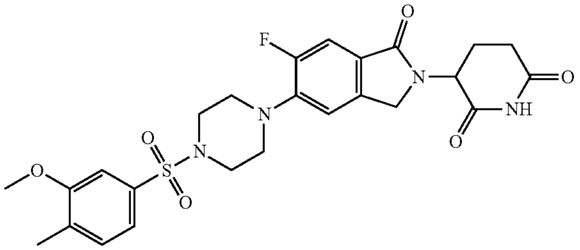

-continued

D2052

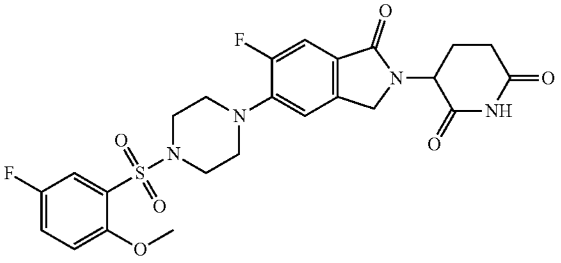

3-(6-Fluoro-5-(4-((3-fluoro-4-methoxyphenyl)sulfonyl)piperazin-1-yl)-1-oxoisoindolin-2-yl)piperidine-2,6-dione D2053.

3-(6-Fluoro-1-oxo-5-(4-((5,6,7,8-tetrahydronaphthalen-2-yl)sulfonyl)piperazin-1-yl)isoindolin-2-yl)piperidine-2,6-dione D2054.

D2053

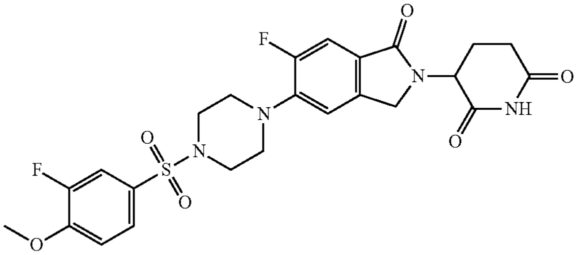

D2054

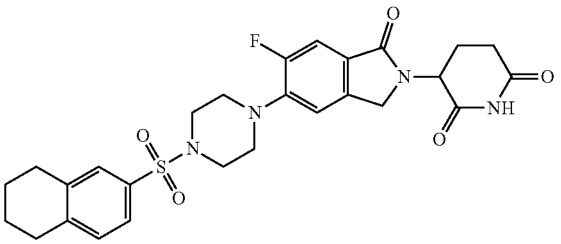

3-(6-Fluoro-5-(4-((2-hydroxy-1H-benzo[d]imidazol-6-yl)sulfonyl)piperazin-1-yl)-1-oxoisoindolin-2-yl)piperidine-2,6-dione D2055.

D2055

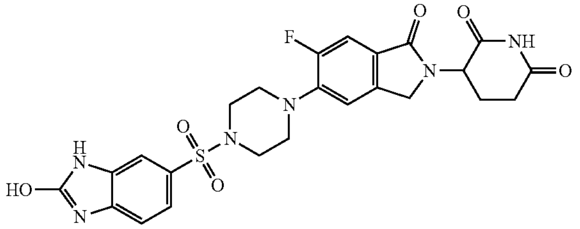

3-(5-(4-((4-(Tert-butyl)phenyl)sulfonyl)piperazin-1-yl)-6-fluoro-1-oxoisoindolin-2-yl)piperidine-2,6-dione D2056.

D2056

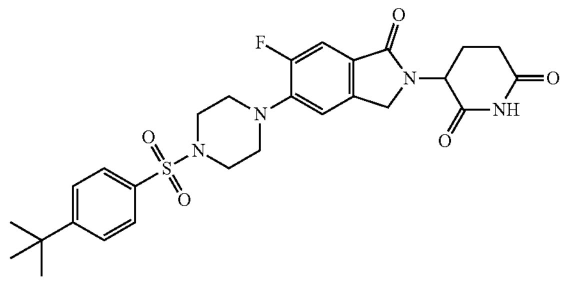

3-(5-(4-((3-(Tert-butyl)phenyl)sulfonyl)piperazin-1-yl)-6-fluoro-1-oxoisoindolin-2-yl)piperidine-2,6-dione D2057.

D2057

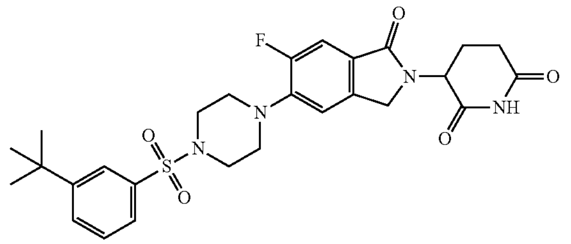

N-(3-((4-(2-(2,6-Dioxopiperidin-3-yl)-6-fluoro-1-oxoisoindolin-5-yl)piperazin-1-yl)sulfonyl)phenyl)acetamide D2058.

D2058

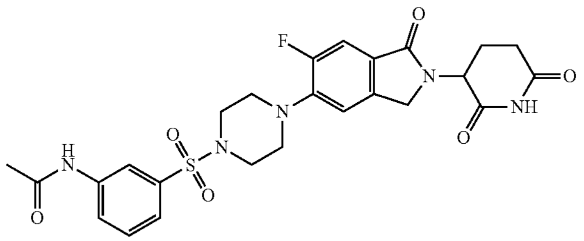

N-(4-((4-(2-(2,6-Dioxopiperidin-3-yl)-6-fluoro-1-oxoisoindolin-5-yl)piperazin-1-yl)sulfonyl)phenyl)acetamide D2059.

D2059

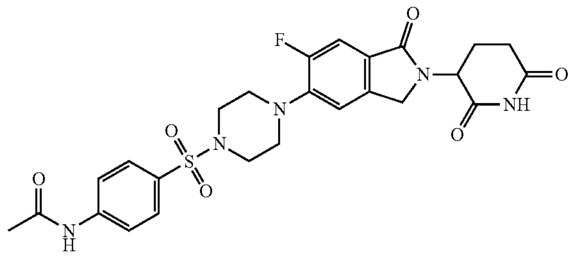

4-((4-(2-(2,6-Dioxopiperidin-3-yl)-6-fluoro-1-oxoisoindolin-5-yl)piperazin-1-yl)-sulfonyl)-N-methylbenzamide D2060.

D2060

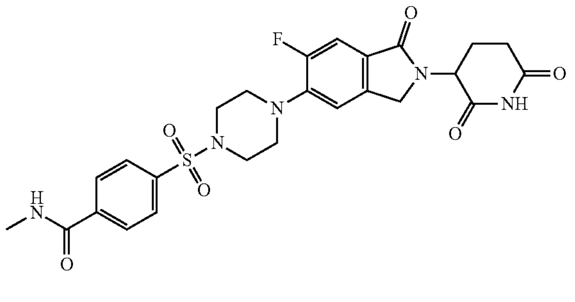

2-Chloro-4-((4-(2-(2,6-dioxopiperidin-3-yl)-6-fluoro-1-oxoisoindolin-5-yl)-piperazin-1-yl)sulfonyl)benzonitrile D2061.

3-(5-(4-((5-Chloro-2-methoxypyridin-3-yl)sulfonyl)piperazin-1-yl)-6-fluoro-1-oxoisoindolin-2-yl)piperidine-2,6-dione D2062.

D2061

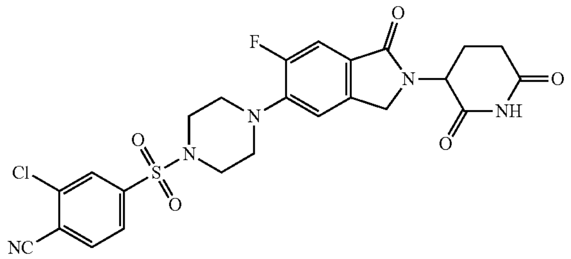

D2062

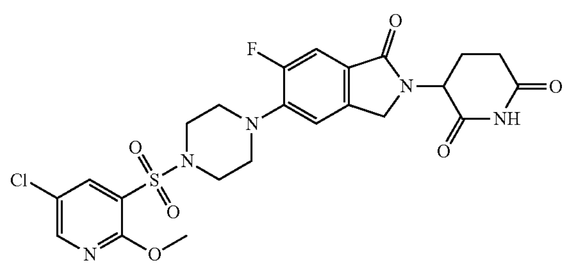

3-(5-(4-((4-(Difluoromethoxy)phenyl)sulfonyl)piperazin-1-yl)-6-fluoro-1-oxoisoindolin-2-yl)piperidine-2,6-dione D2063.

D2063

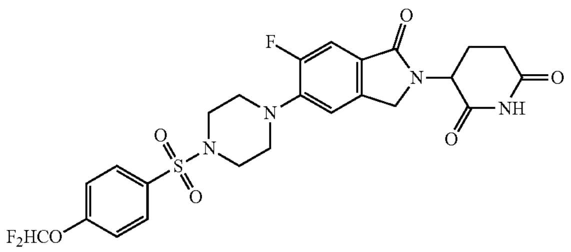

3-(6-Fluoro-5-(4-((4-(oxazol-5-yl)phenyl)sulfonyl)piperazin-1-yl)-1-oxoisoindolin-2-yl)piperidine-2,6-dione D2064.

D2064

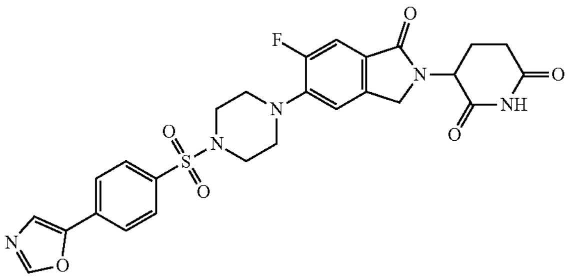

3-(6-Fluoro-1-oxo-5-(4-((4-(trifluoromethyl)phenyl)sulfonyl)piperazin-1-yl)-isoindolin-2-yl)piperidine-2,6-dione D2065.

3-(6-Fluoro-1-oxo-5-(4-((3-(trifluoromethyl)phenyl)sulfonyl)piperazin-1-yl)-isoindolin-2-yl)piperidine-2,6-dione D2066.

D2065

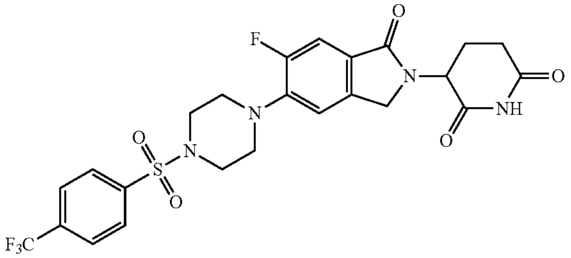

D2066

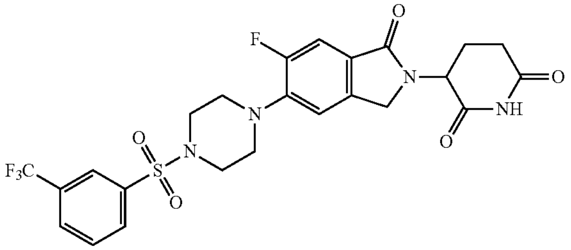

3-(6-Fluoro-1-oxo-5-(4-((2-(trifluoromethyl)phenyl)sulfonyl)piperazin-1-yl)-isoindolin-2-yl)piperidine-2,6-dione D2067.

3-(6-Fluoro-1-oxo-5-(4-((6-(trifluoromethyl)pyridin-3-yl)sulfonyl)piperazin-1-yl)isoindolin-2-yl)piperidine-2,6-dione D2068.

D2067

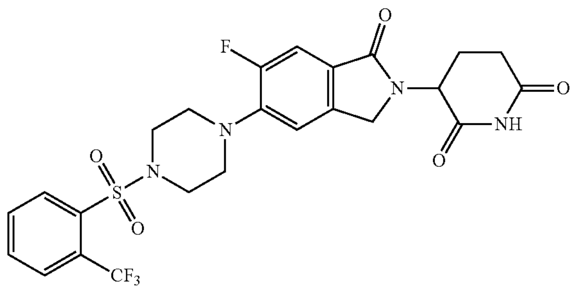

D2068

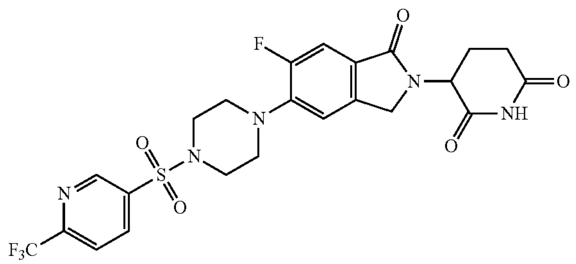

3-(6-Fluoro-1-oxo-5-(4-((2-oxo-1,2,3,4-tetrahydroquinolin-6-yl)sulfonyl)-piperazin-1-yl)isoindolin-2-yl)piperidine-2,6-dione D2069.

2-((4-(2-(2,6-Dioxopiperidin-3-yl)-6-fluoro-1-oxoisoindolin-5-yl)piperazin-1-yl)-sulfonyl)-N,N-dimethylbenzamide D2070.

D2069

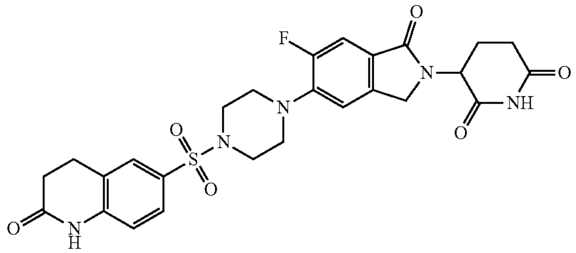

D2070

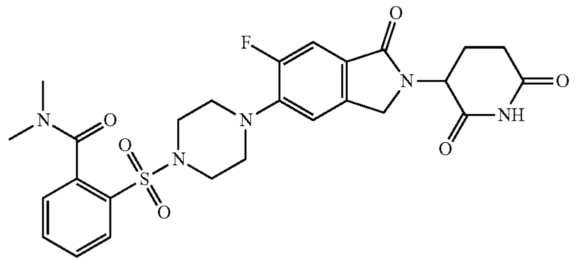

3-(5-(4-((3-Bromophenyl)sulfonyl)piperazin-1-yl)-6-fluoro-1-oxoisoindolin-2-yl)-piperidine-2,6-dione D2071.

3-(5-(4-((2-Bromophenyl)sulfonyl)piperazin-1-yl)-6-fluoro-1-oxoisoindolin-2-yl)-piperidine-2,6-dione D2072.

D2071

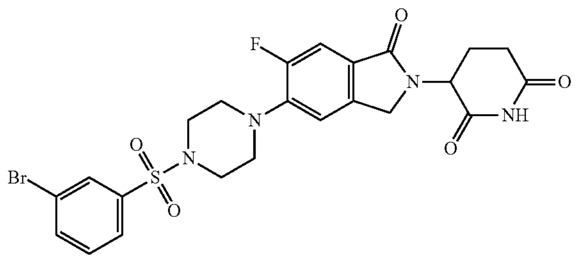

D2072

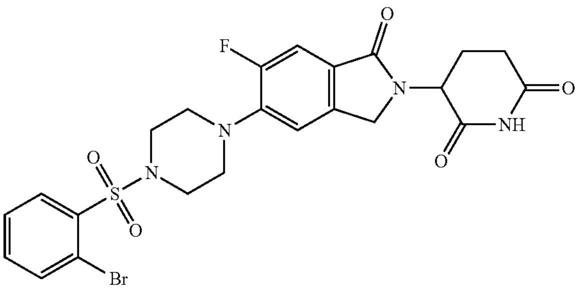

3-(6-Fluoro-1-oxo-5-(4-((1-(o-tolyl)-1H-pyrazol-4-yl)sulfonyl)piperazin-1-yl)-isoindolin-2-yl)piperidine-2,6-dione D2073.

D2073

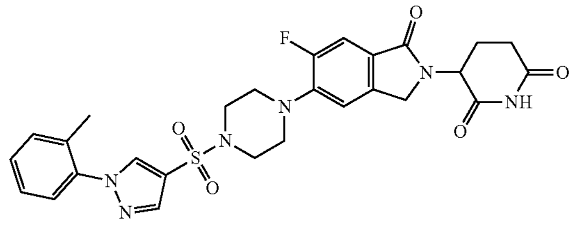

3-(6-Fluoro-1-oxo-5-(4-((4-(trifluoromethyl)benzyl)sulfonyl)piperazin-1-yl)-isoindolin-2-yl)piperidine-2,6-dione D2074.

D2074

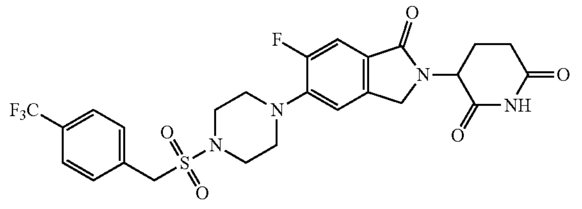

3-(6-Fluoro-1-oxo-5-(4-((2-(trifluoromethoxy)phenyl) sulfonyl)piperazin-1-yl)-isoindolin-2-yl)piperidine-2,6-dione D2075.

3-(5-(4-((1-Chloroisoquinolin-5-yl)sulfonyl)piperazin-1-yl)-6-fluoro-1-oxoisoindolin-2-yl)piperidine-2,6-dione D2076.

D2075

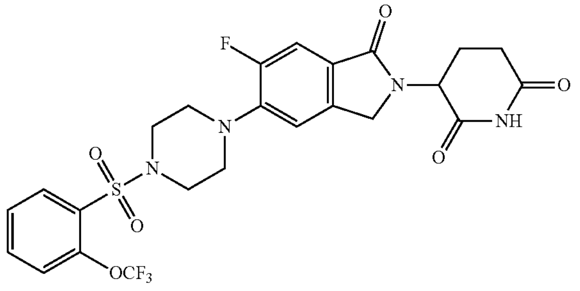

D2076

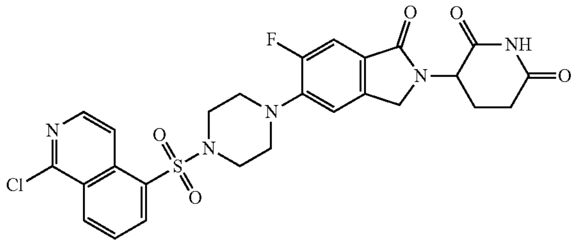

3-(6-Fluoro-5-(4-(isoquinolin-5-ylsulfonyl)piperazin-1-yl)-1-oxoisoindolin-2-yl)-piperidine-2,6-dione D2077.

3-(6-Fluoro-1-oxo-5-(4-((4-(pyridin-2-yloxy)phenyl)sulfonyl)piperazin-1-yl)-isoindolin-2-yl)piperidine-2,6-dione D2078.

D2077

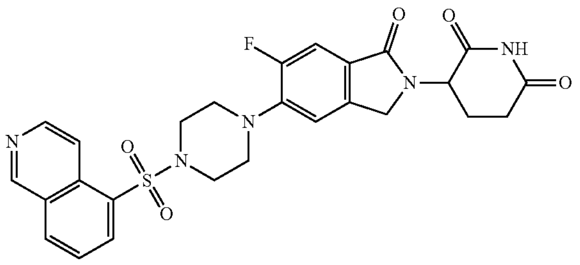

D2078

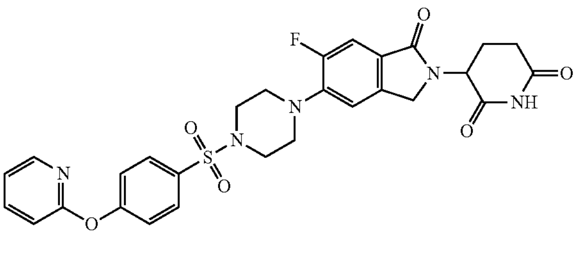

3-(6-Fluoro-1-oxo-5-(4-((6-phenoxypyridin-3-yl)sulfonyl) piperazin-1-yl)-isoindolin-2-yl)piperidine-2,6-dione D2079.

D2079

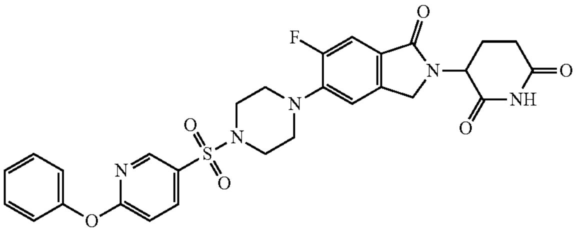

3-(5-(4-((5-(Dimethylamino)naphthalen-1-yl)sulfonyl)piperazin-1-yl)-6-fluoro-1-oxoisoindolin-2-yl)piperidine-2,6-dione D2080.

D2080

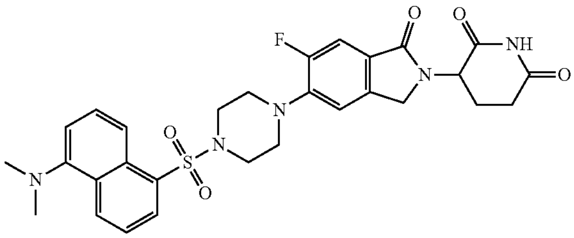

3-(5-(4-((6-(Dimethylamino)naphthalen-2-yl)sulfonyl)piperazin-1-yl)-6-fluoro-1-oxoisoindolin-2-yl)piperidine-2,6-dione D2081.

D2081

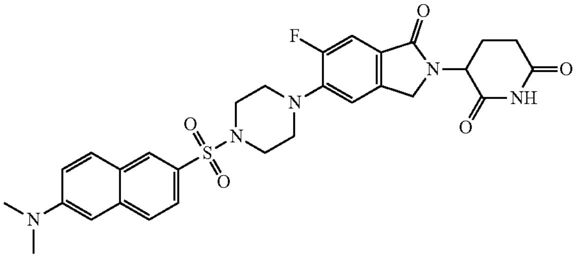

3-(5-(4-((4-(Benzyloxy)phenyl)sulfonyl)piperazin-1-yl)-6-fluoro-1-oxoisoindolin-2-yl)piperidine-2,6-dione D2082.

D2082

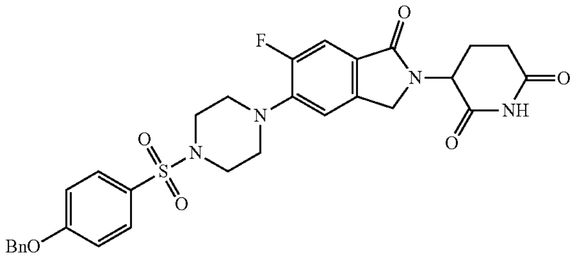

Tert-butyl 4-((4-(2-(2,6-dioxopiperidin-3-yl)-6-fluoro-1-oxoisoindolin-5-yl)-piperazin-1-yl)sulfonyl)piperidine-1-carboxylate D2083.

Benzyl 4-((4-(2-(2,6-dioxopiperidin-3-yl)-6-fluoro-1-oxoisoindolin-5-yl)-piperazin-1-yl)sulfonyl)piperidine-1-carboxylate D2084.

D2083

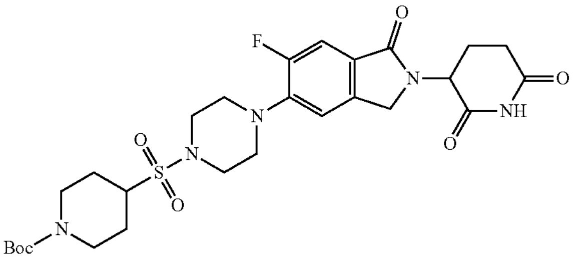

D2084

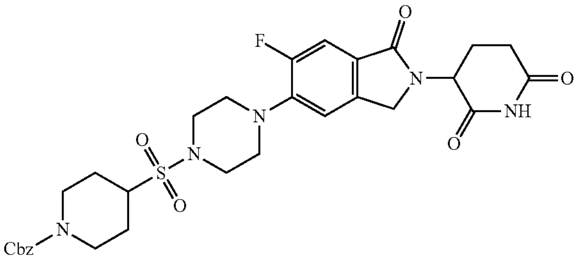

3-(6-Fluoro-1-oxo-5-(4-((2-(2,2,2-trifluoroacetyl)-1,2,3,4-tetrahydroisoquinolin-7-yl)sulfonyl)piperazin-1-yl)isoindolin-2-yl)piperidine-2,6-di one D2085.

D2085

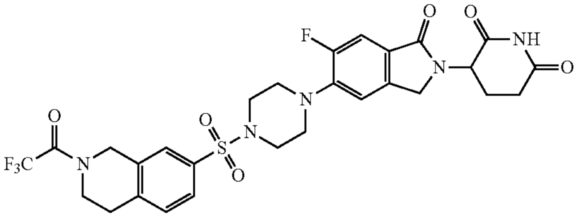

Benzyl 4-(((4-(2-(2,6-dioxopiperidin-3-yl)-6-fluoro-1-oxoisoindolin-5-yl)-piperazin-1-yl)sulfonyl)methyl)piperidine-1-carboxylate D2086.

D2086

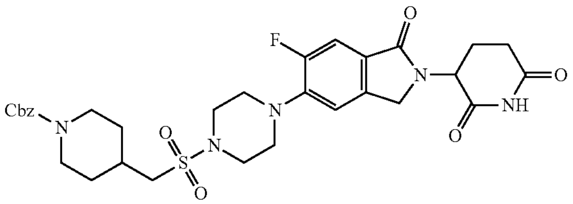

3-(5-(4-(Ethylsulfonyl)piperazin-1-yl)-6-fluoro-1-oxoisoindolin-2-yl)piperidine-2,6-dione D2087.

3-(5-(4-((5-Chlorothiophen-2-yl)sulfonyl)piperazin-1-yl)-6-fluoro-1-oxoisoindolin-2-yl)piperidine-2,6-dione D2088.

D2087

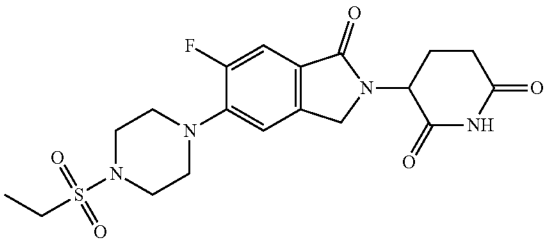

D2088

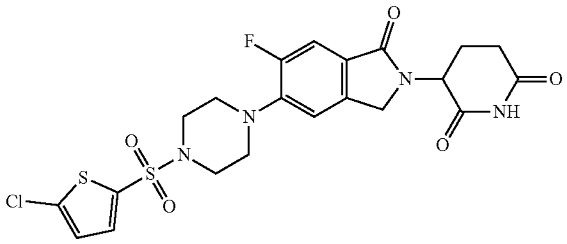

3-(5-(4-((3-Chloro-4-methylphenyl)sulfonyl)piperazin-1-yl)-6-fluoro-1-oxoisoindolin-2-yl)piperidine-2,6-dione D2089.

3-(5-(4-((2-Chloro-6-methylphenyl)sulfonyl)piperazin-1-yl)-6-fluoro-1-oxoisoindolin-2-yl)piperidine-2,6-dione D2090.

D2089

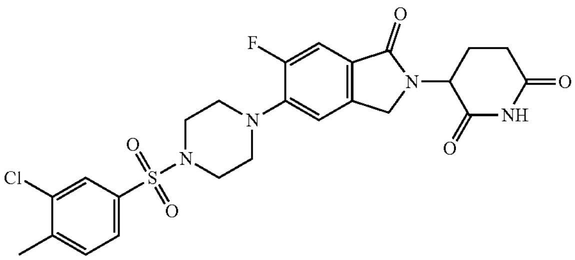

D2090

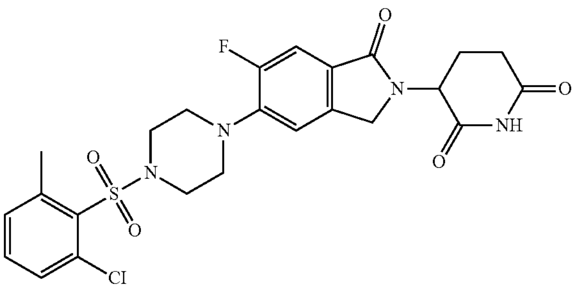

3-(5-(4-((3,5-Difluorobenzyl)sulfonyl)piperazin-1-yl)-6-fluoro-1-oxoisoindolin-2-yl)piperidine-2,6-dione D2091.

3-(6-Fluoro-5-(4-(naphthalen-2-ylsulfonyl)piperazin-1-yl)-1-oxoisoindolin-2-yl)-piperidine-2,6-dione D2092.

D2091

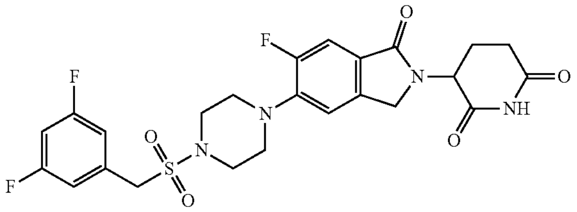

D2092

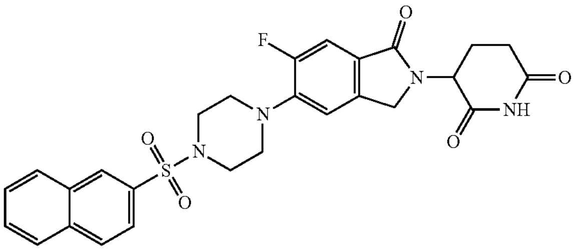

3-(6-Fluoro-1-oxo-5-(4-(quinolin-8-ylsulfonyl)piperazin-1-yl)isoindolin-2-yl)-piperidine-2,6-dione D2093.

3-(6-Fluoro-5-(4-(isoquinolin-5-ylsulfonyl)piperazin-1-yl)-1-oxoisoindolin-2-yl)-piperidine-2,6-dione D2094.

D2093

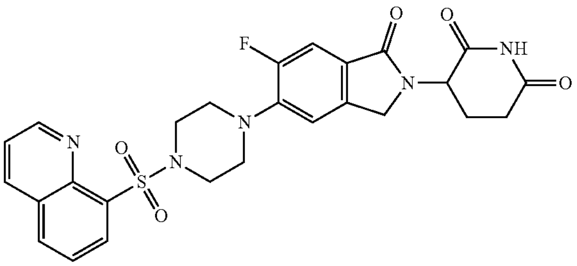

D2094

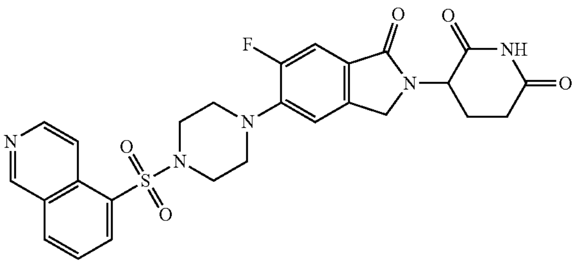

3-(6-Fluoro-1-oxo-5-(4-(quinoxalin-5-ylsulfonyl)piperazin-1-yl)isoindolin-2-yl)-piperidine-2,6-dione D2095.

3-Chloro-4-((4-(2-(2,6-dioxopiperidin-3-yl)-6-fluoro-1-oxoisoindolin-5-yl)-piperazin-1-yl)sulfonyl)benzonitrile D2096.

D2095

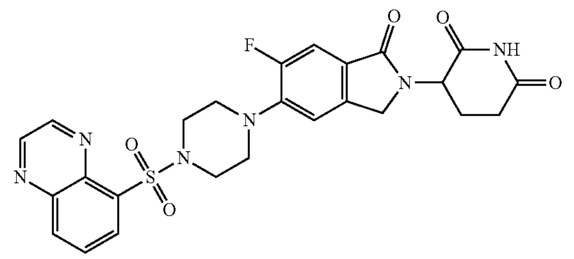

D2096

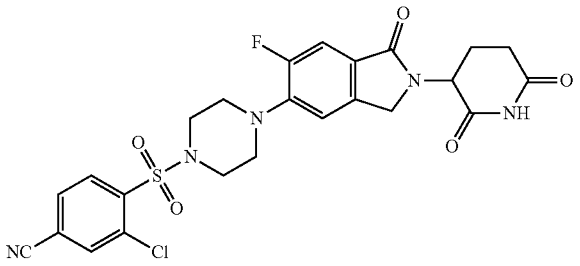

3-(5-(4-(Benzo[d][1,3]dioxol-5-ylsulfonyl)piperazin-1-yl)-6-fluoro-1-oxoisoindolin-2-yl)piperidine-2,6-dione D2097.

3-(5-(4-(Benzo[d]thiazol-6-ylsulfonyl)piperazin-1-yl)-6-fluoro-1-oxoisoindolin-2-yl)piperidine-2,6-dione D2098.

D2097

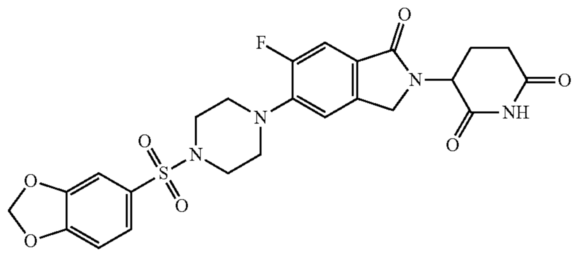

D2098

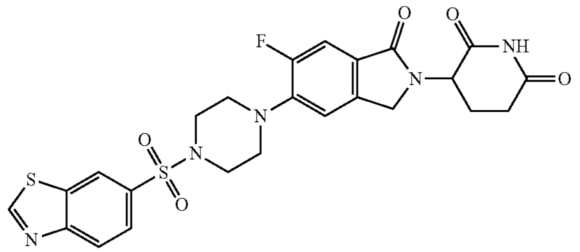

3-(5-(4-((2,4-Dichlorophenyl)sulfonyl)piperazin-1-yl)-6-fluoro-1-oxoisoindolin-2-yl)piperidine-2,6-dione D2099.

3-(5-(4-((2,5-Dichlorophenyl)sulfonyl)piperazin-1-yl)-6-fluoro-1-oxoisoindolin-2-yl)piperidine-2,6-dione D2100.

D2099

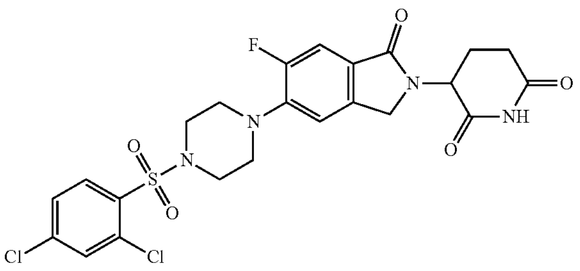

D2100

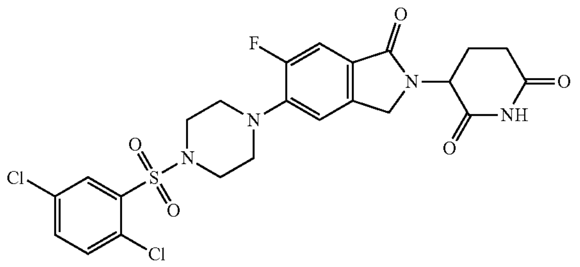

3-(4-(7-(Furan-2-carbonyl)-2,7-diazaspiro[3.5]nonan-2-yl)-1-oxoisoindolin-2-yl)-piperidine-2,6-dione E0001.

3-(4-(7-(Furan-3-carbonyl)-2,7-diazaspiro[3.5]nonan-2-yl)-1-oxoisoindolin-2-yl)-piperidine-2,6-dione E0002.

E001

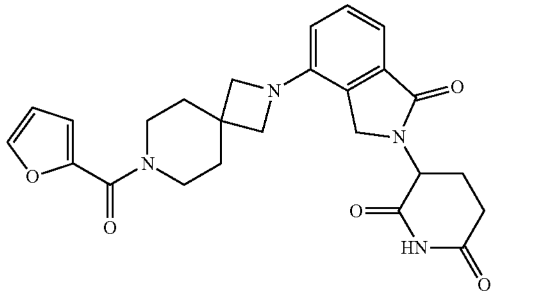

E002

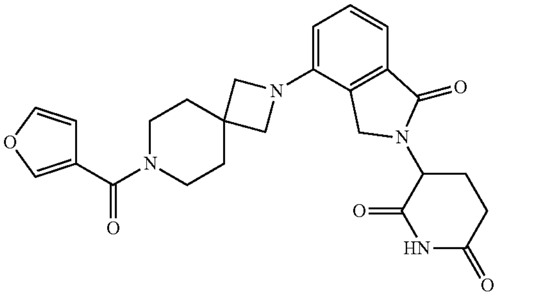

3-(4-(7-(2-(1H-Pyrrol-2-yl)acetyl)-2,7-diazaspiro[3.5]nonan-2-yl)-1-oxoisoindolin-2-yl)piperidine-2,6-dione E0003.

3-(4-(7-(2-(1H-Pyrazol-1-yl)acetyl)-2,7-diazaspiro[3.5]nonan-2-yl)-1-oxoisoindolin-2-yl)piperidine-2,6-dione E0004.

E003

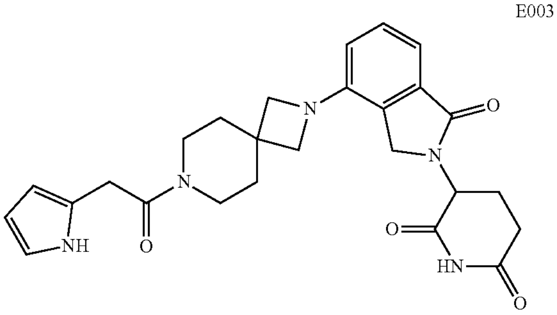

E004

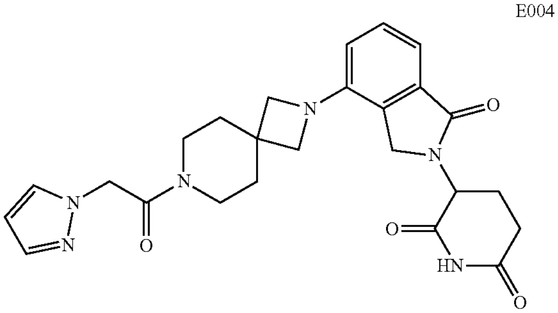

3-(1-Oxo-4-(7-(2-(pyrrolidin-1-yl)acetyl)-2,7-diazaspiro[3.5]nonan-2-yl)-isoindolin-2-yl)piperidine-2,6-dione E0005.

3-(1-Oxo-4-(7-(tetrahydro-2H-pyran-4-carbonyl)-2,7-diazaspiro[3.5]nonan-2-yl)-isoindolin-2-yl)piperidine-2,6-dione E0006.

E005

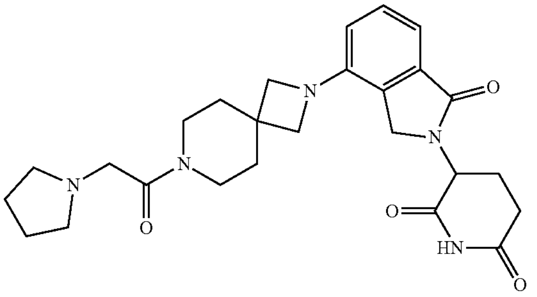

E006

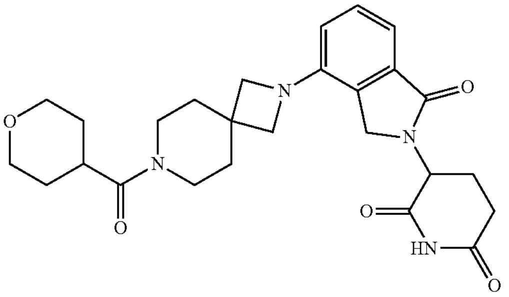

3-(4-(7-(2-Morpholinoacetyl)-2,7-diazaspiro[3.5]nonan-2-yl)-1-oxoisoindolin-2-yl)piperidine-2,6-dione E0007.

3-(2-(2-(2,6-Dioxopiperidin-3-yl)-1-oxoisoindolin-4-yl)-2,7-diazaspiro[3.5]-nonane-7-carbonyl)benzonitrile E0008.

E007

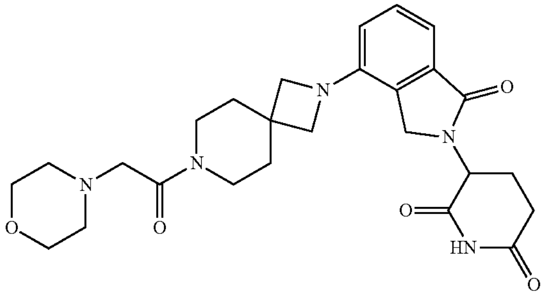

E008

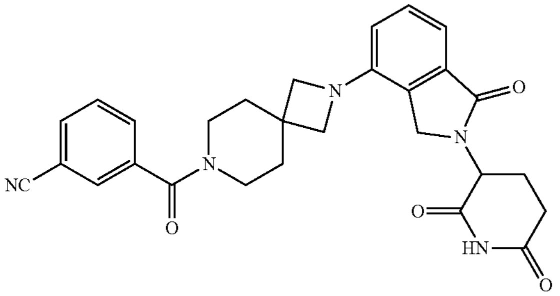

3-(1-Oxo-4-(7-(2-(m-tolyl)acetyl)-2,7-diazaspiro[3.5]nonan-2-yl)isoindolin-2-yl)-piperidine-2,6-dione E0009.

3-(1-Oxo-4-(7-(3-phenylpropanoyl)-2,7-diazaspiro[3.5]nonan-2-yl)isoindolin-2-yl)piperidine-2,6-dione E0010.

E0009

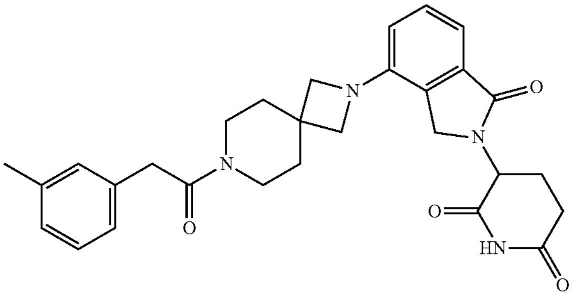

E0010

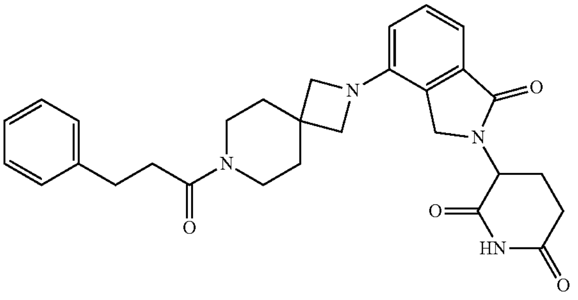

3-(1-Oxo-4-(7-(3-(pyridin-2-yl)propanoyl)-2,7-diazaspiro[3.5]nonan-2-yl)-isoindolin-2-yl)piperidine-2,6-dione E0011.

3-(4-(7-(3-(Hydroxymethyl)benzoyl)-2,7-diazaspiro[3.5]nonan-2-yl)-1-oxoisoindolin-2-yl)piperidine-2,6-dione E0012.

E0011

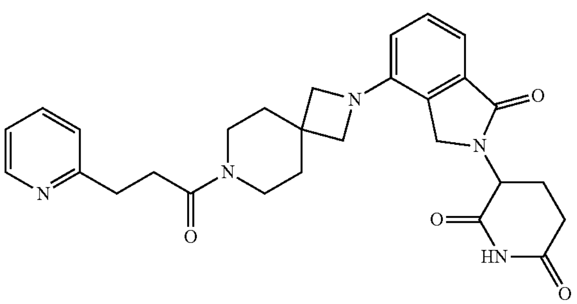

E0012

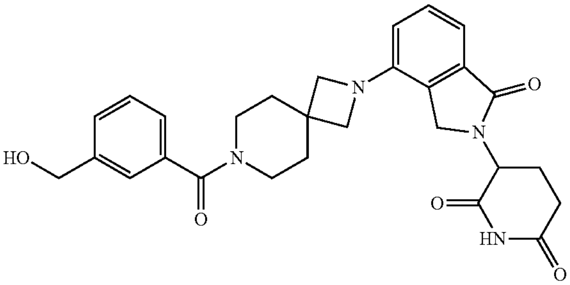

3-(4-(7-(1H-Pyrrole-2-carbonyl)-2,7-diazaspiro[3.5]nonan-2-yl)-1-oxoisoindolin-2-yl)piperidine-2,6-dione E0013.

3-(1-Oxo-4-(7-(2-(m-tolyloxy)acetyl)-2,7-diazaspiro[3.5]nonan-2-yl)isoindolin-2-yl)piperidine-2,6-dione E0014.

E0013

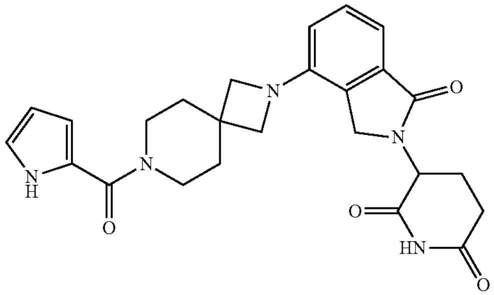

E0014

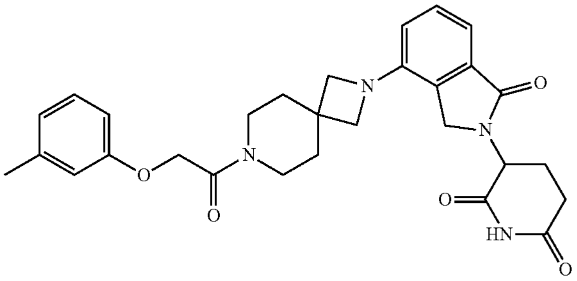

3-(4-(7-(2-(2-Methoxypyridin-3-yl)acetyl)-2,7-diazaspiro[3.5]nonan-2-yl)-1-oxoisoindolin-2-yl)piperidine-2,6-dione E0015.

2-Chloro-5-(2-(2-(2,6-dioxopiperidin-3-yl)-1-oxoisoindolin-4-yl)-2,7-diazaspiro[3.5]nonane-7-carbonyl)benzonitrile E0016.

E0015

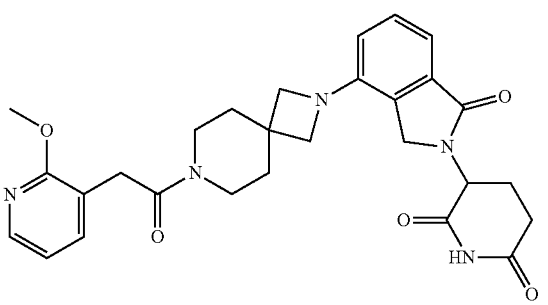

E0016

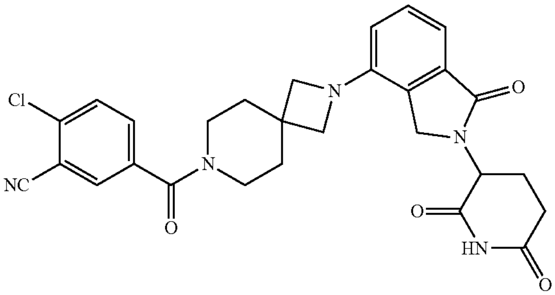

2-Chloro-4-(2-(2-(2,6-dioxopiperidin-3-yl)-1-oxoisoindolin-4-yl)-2,7-diazaspiro[3.5]nonane-7-carbonyl)benzonitrile E0017.

3-(1-Oxo-4-(7-(3-(pyridin-3-yl)propanoyl)-2,7-diazaspiro[3.5]nonan-2-yl)-isoindolin-2-yl)piperidine-2,6-dione E0018.

E0017

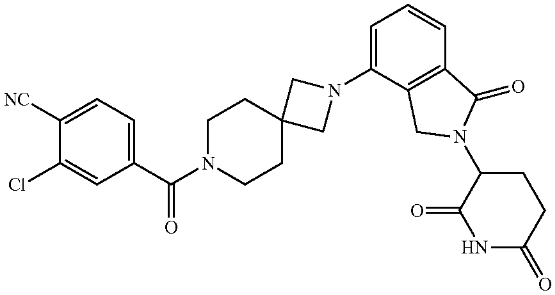

E0018

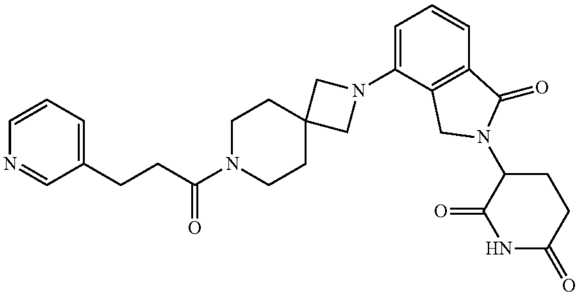

3-(4-(7-(2,6-Difluorobenzoyl)-2,7-diazaspiro[3.5]nonan-2-yl)-1-oxoisoindolin-2-yl)piperidine-2,6-dione E0019.

3-(4-(7-(2,5-Difluorobenzoyl)-2,7-diazaspiro[3.5]nonan-2-yl)-1-oxoisoindolin-2-yl)piperidine-2,6-dione E0020.

E0019

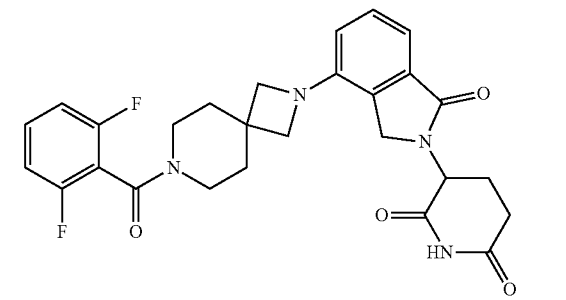

E0020

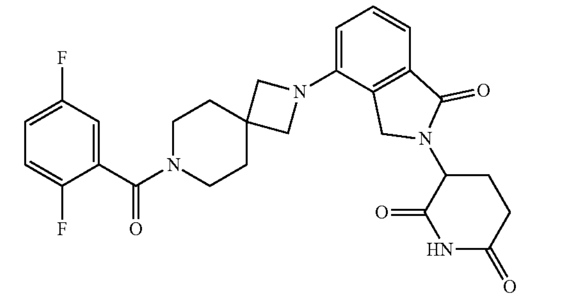

3-(4-(7-(3,5-Difluorobenzoyl)-2,7-diazaspiro[3.5]nonan-2-yl)-1-oxoisoindolin-2-yl)piperidine-2,6-dione E0021.

3-(4-(7-(2-Methyl-2-phenylpropanoyl)-2,7-diazaspiro[3.5]nonan-2-yl)-1-oxoisoindolin-2-yl)piperidine-2,6-dione E0022.

E0021

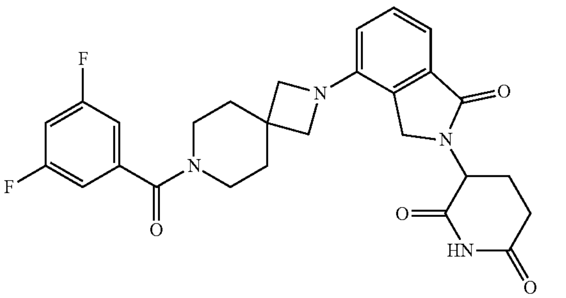

E0022

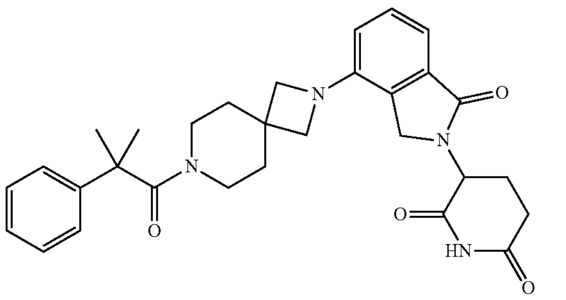

3-(1-Oxo-4-(7-(pyrimidine-4-carbonyl)-2,7-diazaspiro[3.5]nonan-2-yl)isoindolin-2-yl)piperidine-2,6-dione E0023.

3-(4-(7-(1-Methyl-1H-pyrrole-2-carbonyl)-2,7-diazaspiro[3.5]nonan-2-yl)-1-oxoisoindolin-2-yl)piperidine-2,6-dione E0024.

E0023

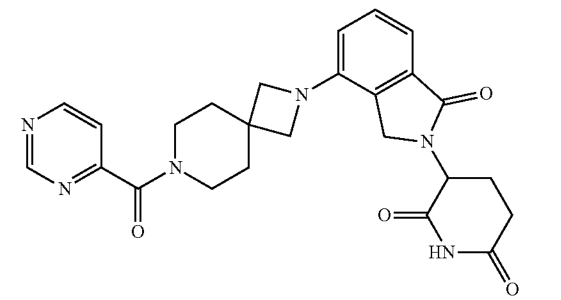

E0024

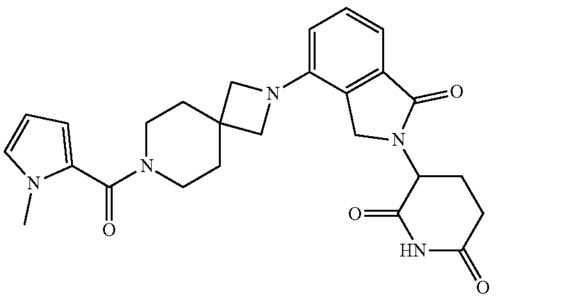

3-(4-(7-(2-Methyl-1H-imidazole-5-carbonyl)-2,7-diazaspiro[3.5]nonan-2-yl)-1-oxoisoindolin-2-yl)piperidine-2,6-dione E0025.

3-(4-(7-(2-(1H-1,2,3-Triazol-1-yl)acetyl)-2,7-diazaspiro[3.5]nonan-2-yl)-1-oxoisoindolin-2-yl)piperidine-2,6-dione E0026.

E0025

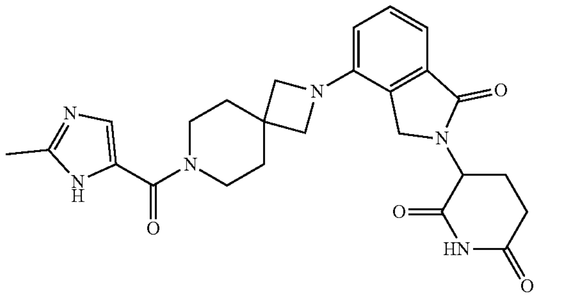

E0026

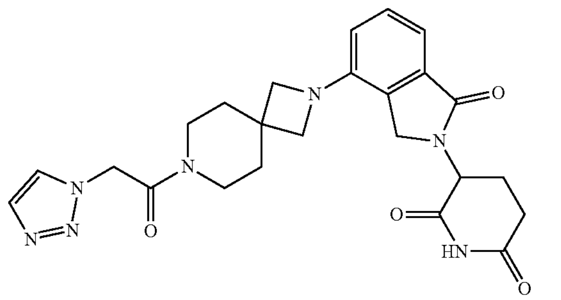

3-(4-(7-(2-Cyclopentylacetyl)-2,7-diazaspiro[3.5]nonan-2-yl)-1-oxoisoindolin-2-yl)piperidine-2,6-dione E0027.

5-(2-(2-(2,6-Dioxopiperidin-3-yl)-1-oxoisoindolin-4-yl)-2,7-diazaspiro[3.5]nonane-7-carbonyl)-1H-pyrrole-2-carbonitrile E0028.

E0027

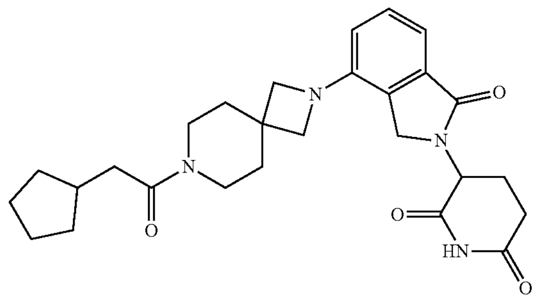

E0028

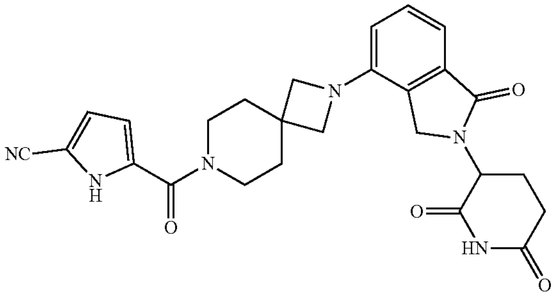

5-(2-(2-(2,6-Dioxopiperidin-3-yl)-1-oxoisoindolin-4-yl)-2,7-diazaspiro[3.5]-nonane-7-carbonyl)-1H-pyrrole-3-carbonitrile E0029.

3-(1-Oxo-4-(7-(2-(pyrimidin-2-yl)acetyl)-2,7-diazaspiro[3.5]nonan-2-yl)-isoindolin-2-yl)piperidine-2,6-dione E0030.

E0029

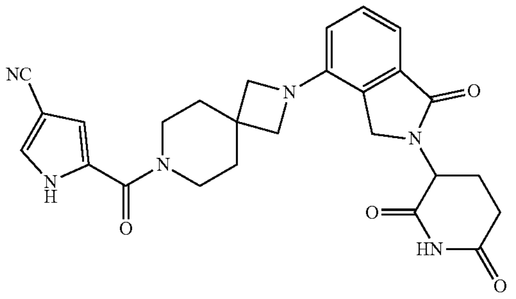

E0030

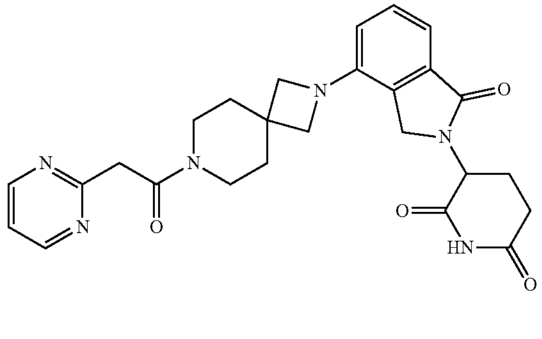

3-(1-Oxo-4-(7-(2-(pyrimidin-5-yl)acetyl)-2,7-diazaspiro[3.5]nonan-2-yl)-isoindolin-2-yl)piperidine-2,6-dione E0031.

3-(4-(7-(3-(1H-Pyrrol-2-yl)propanoyl)-2,7-diazaspiro[3.5]nonan-2-yl)-1-oxoisoindolin-2-yl)piperidine-2,6-dione E0032.

E0031

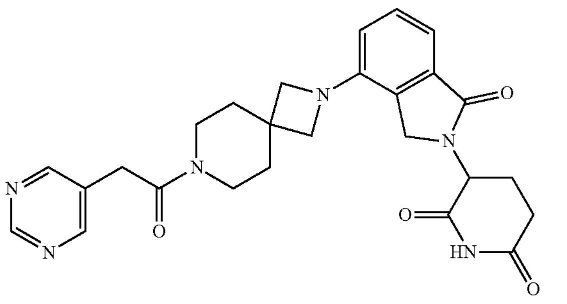

E0032

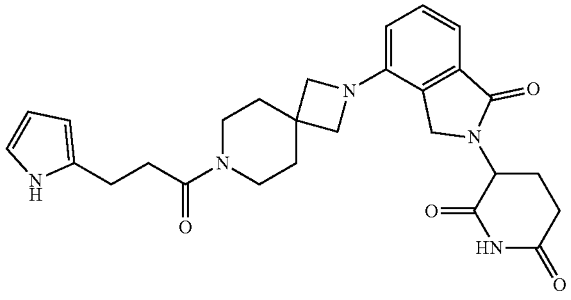

3-(4-(7-(1-Methylpiperidine-4-carbonyl)-2,7-diazaspiro[3.5]nonan-2-yl)-1-oxoisoindolin-2-yl)piperidine-2,6-dione E0033.

3-(1-Oxo-4-(7-(2-(piperidin-1-yl)acetyl)-2,7-diazaspiro[3.5]nonan-2-yl)-isoindolin-2-yl)piperidine-2,6-dione E0034.

E0033

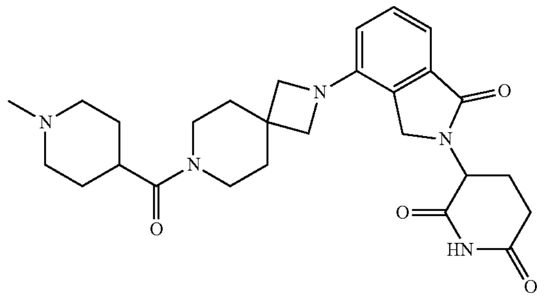

E0034

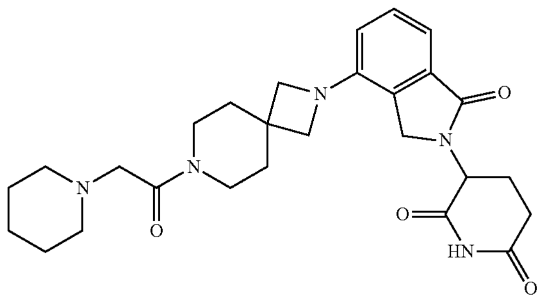

3-(1-Oxo-4-(7-(2-(tetrahydro-2H-pyran-4-yl)acetyl)-2,7-diazaspiro[3.5]nonan-2-yl)isoindolin-2-yl)piperidine-2,6-dione E0035.

E0035

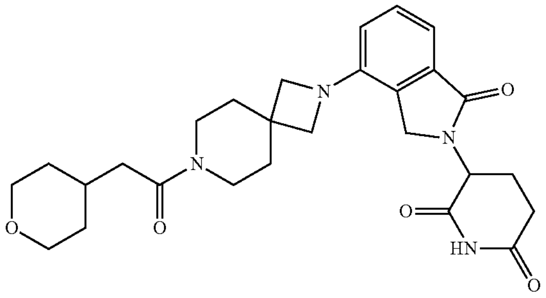

3-(4-(7-Benzyl-2,7-diazaspiro[3.5]nonan-2-yl)-1-oxoisoindolin-2-yl)piperidine-2,6-dione E1001.

3-(1-Oxo-4-(7-(pyridin-3-ylmethyl)-2,7-diazaspiro[3.5]nonan-2-yl)isoindolin-2-yl)piperidine-2,6-dione E1002.

E1001

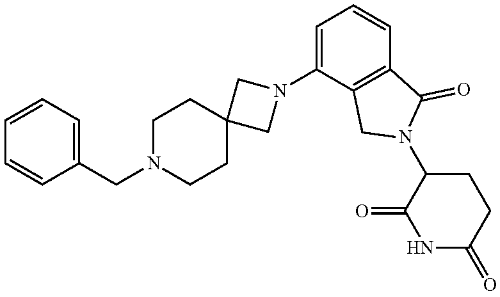

E1002

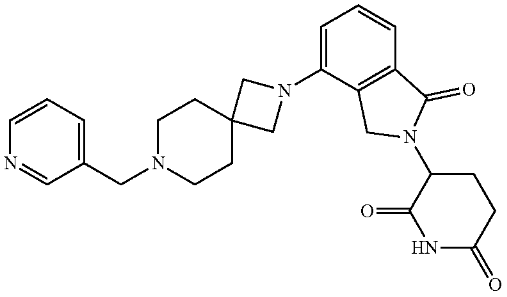

3-(1-Oxo-4-(7-(pyridin-4-ylmethyl)-2,7-diazaspiro[3.5]nonan-2-yl)isoindolin-2-yl)piperidine-2,6-dione E1003.

3-(1-Oxo-4-(7-(pyridin-2-ylmethyl)-2,7-diazaspiro[3.5]nonan-2-yl)isoindolin-2-yl)piperidine-2,6-dione E1004.

E1003

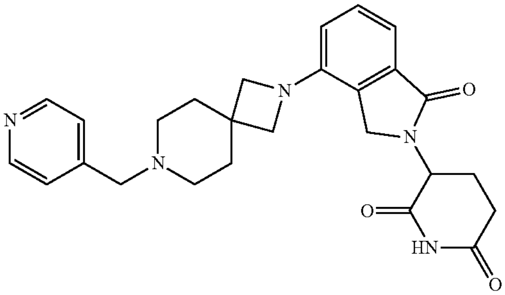

E1004

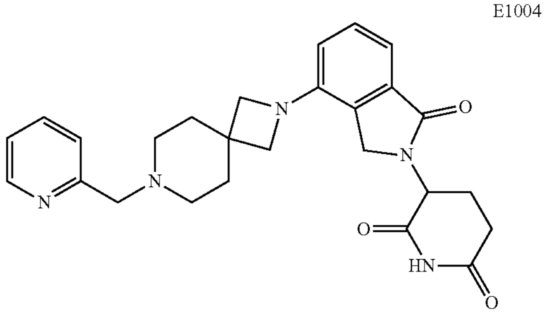

3-(1-Oxo-4-(7-(pyrimidin-5-ylmethyl)-2,7-diazaspiro[3.5]nonan-2-yl)isoindolin-2-yl)piperidine-2,6-dione E1005.

3-(4-(7-((1-Methyl-1H-imidazol-5-yl)methyl)-2,7-diazaspiro[3.5]nonan-2-yl)-1-oxoisoindolin-2-yl)piperidine-2,6-dione E1006.

E1005

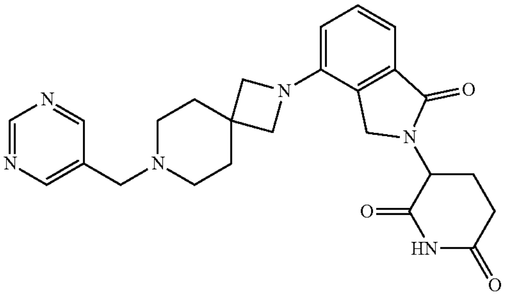

E1006

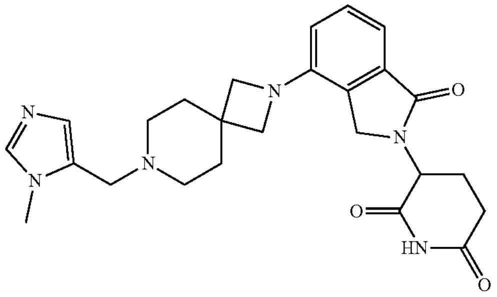

3-(1-Oxo-4-(7-phenethyl-2,7-diazaspiro[3.5]nonan-2-yl)isoindolin-2-yl)-piperidine-2,6-dione E1007.

3-((2-(2-(2,6-Dioxopiperidin-3-yl)-1-oxoisoindolin-4-yl)-2,7-diazaspiro[3.5]-nonan-7-yl)methyl)benzonitrile E1008.

E1007

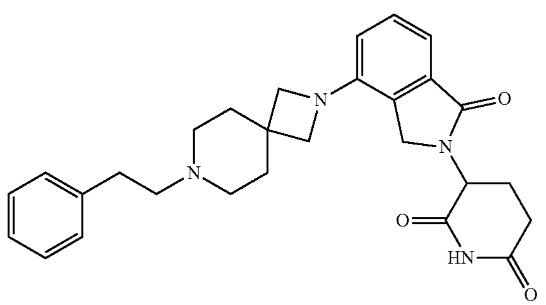

E1008

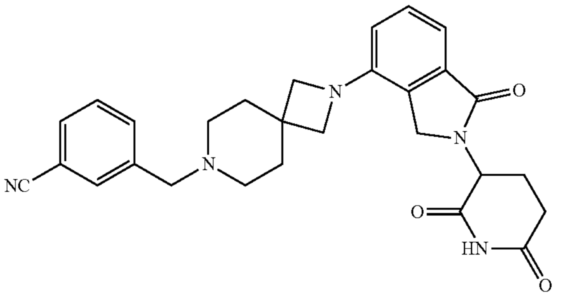

2-((2-(2-(2,6-Dioxopiperidin-3-yl)-1-oxoisoindolin-4-yl)-2,7-diazaspiro[3.5]-nonan-7-yl)methyl)benzonitrile E1009.

6-((2-(2-(2,6-Dioxopiperidin-3-yl)-1-oxoisoindolin-4-yl)-2,7-diazaspiro[3.5]-nonan-7-yl)methyl)nicotinonitrile E1010.

E1009

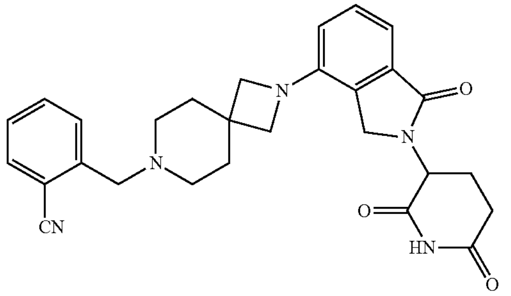

E1010

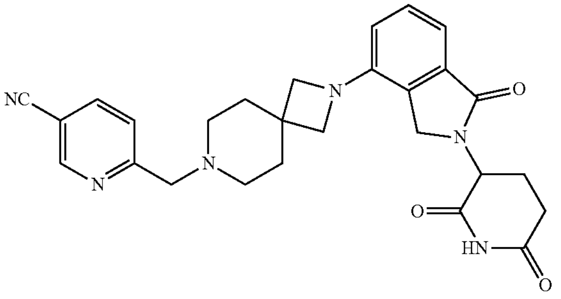

3-(1-Oxo-4-(7-(3-phenylpropyl)-2,7-diazaspiro[3.5]nonan-2-yl)isoindolin-2-yl)-piperidine-2,6-dione E1011.

3-(4-(7-(4-(Hydroxymethyl)benzyl)-2,7-diazaspiro[3.5]nonan-2-yl)-1-oxoisoindolin-2-yl)piperidine-2,6-dione E1012.

E1011

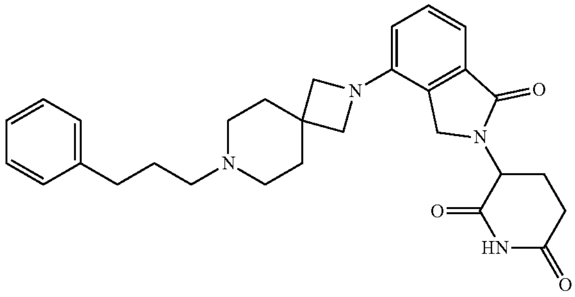

E1012

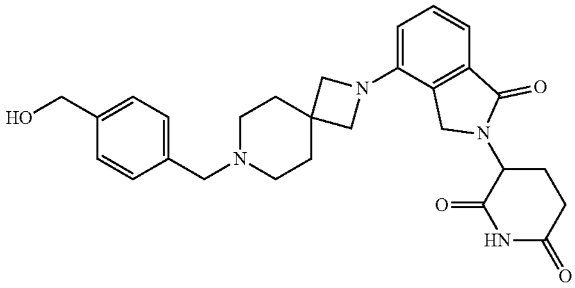

2-((2-(2-(2,6-Dioxopiperidin-3-yl)-1-oxoisoindolin-4-yl)-2,7-diazaspiro[3.5]-nonan-7-yl)methyl)-5-methoxybenzonitrile E1013.

3-Chloro-5-((2-(2-(2,6-dioxopiperidin-3-yl)-1-oxoisoindolin-4-yl)-2,7-diazaspiro[3.5]nonan-7-yl)methyl)benzonitrile E1014.

E1013

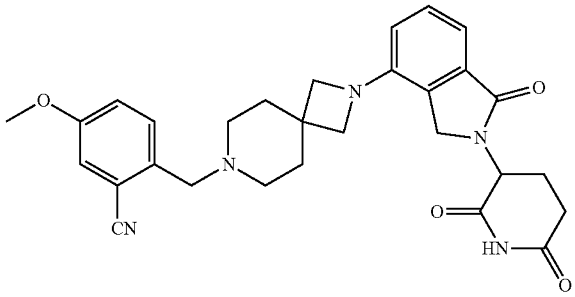

E1014

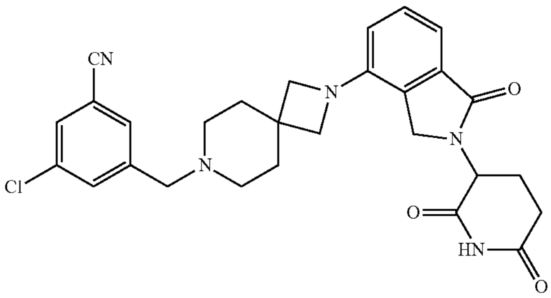

2-Chloro-4-((2-(2-(2,6-dioxopiperidin-3-yl)-1-oxoisoindolin-4-yl)-2,7-diazaspiro[3.5]nonan-7-yl)methyl)benzonitrile E1015.

3-(1-Oxo-4-(7-((2-phenyl-1H-imidazol-5-yl)methyl)-2,7-diazaspiro[3.5]nonan-2-yl)isoindolin-2-yl)piperidine-2,6-dione E1016.

E1015

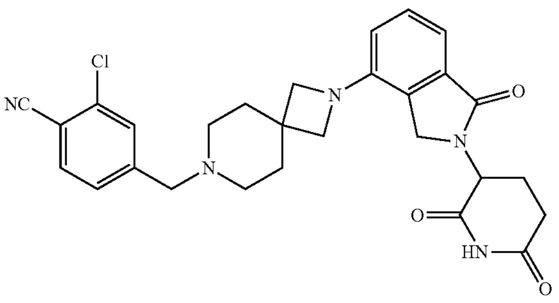

E1016

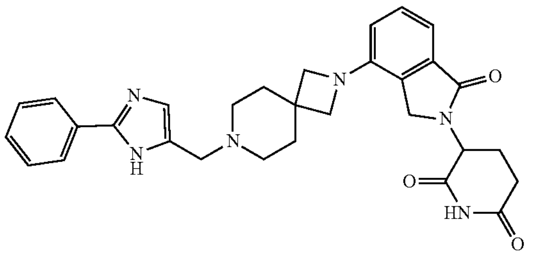

3-(1-Oxo-4-(7-(4-(pyrrolidin-1-yl)benzyl)-2,7-diazaspiro[3.5]nonan-2-yl)-isoindolin-2-yl)piperidine-2,6-dione E1017.

3-(4-(7-(4-((2-Hydroxyethyl)(methyl)amino)benzyl)-2,7-diazaspiro[3.5]nonan-2-yl)-1-oxoisoindolin-2-yl)piperidine-2,6-dione E1018.

E1017

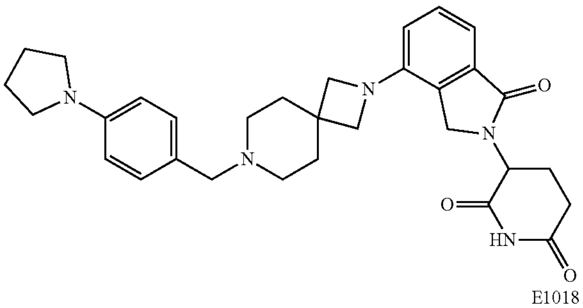

E1018

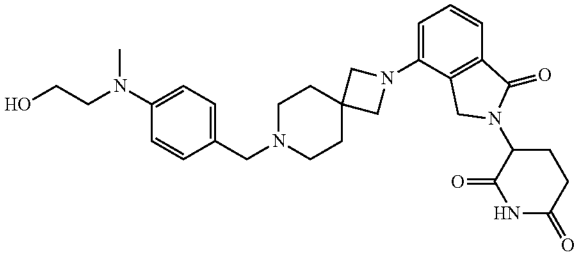

3-(4-(7-(4-(Cyclopentyloxy)benzyl)-2,7-diazaspiro[3.5]nonan-2-yl)-1-oxoisoindolin-2-yl)piperidine-2,6-dione E1019.

3-(4-(7-(4-Morpholinobenzyl)-2,7-diazaspiro[3.5]nonan-2-yl)-1-oxoisoindolin-2-yl)piperidine-2,6-dione E1020.

E1019

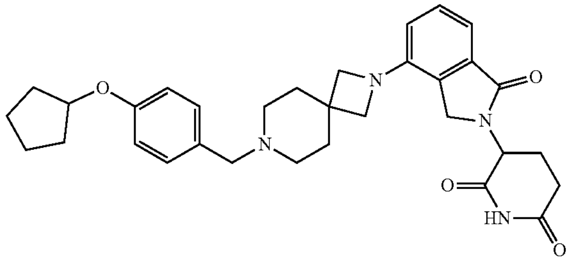

E1020

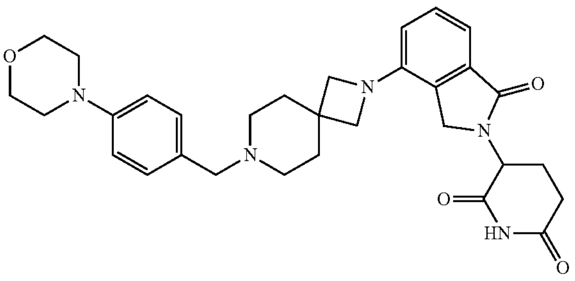

3-(4-(7-(3-Morpholinobenzyl)-2,7-diazaspiro[3.5]nonan-2-yl)-1-oxoisoindolin-2-yl)piperidine-2,6-dione E1021.

3-(4-(7-(4-Benzylbenzyl)-2,7-diazaspiro[3.5]nonan-2-yl)-1-oxoisoindolin-2-yl)piperidine-2,6-dione E1022.

E1021

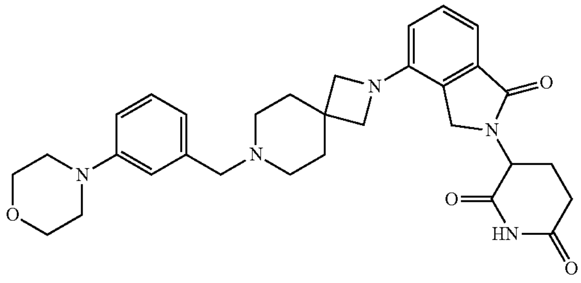

E1022

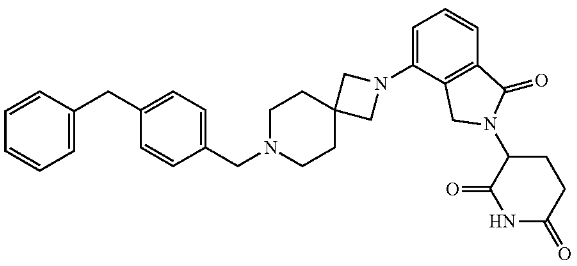

3-(1-Oxo-4-(7-(4-(pyridin-3-yloxy)benzyl)-2,7-diazaspiro[3.5]nonan-2-yl)-isoindolin-2-yl)piperidine-2,6-dione E1023.

3-(1-Oxo-4-(7-(pyrimidin-4-ylmethyl)-2,7-diazaspiro[3.5]nonan-2-yl)isoindolin-2-yl)piperidine-2,6-dione E1024.

E1023

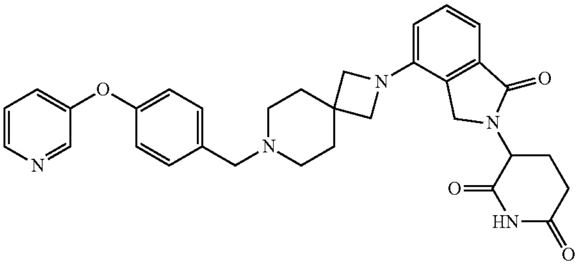

E1024

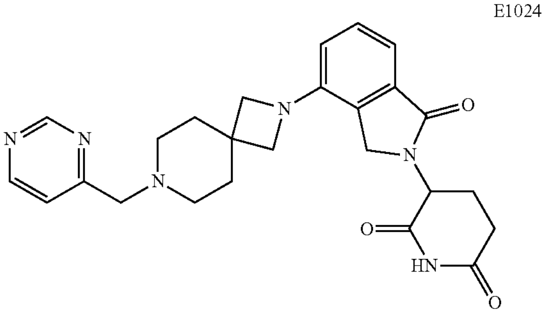

3-(4-(7-(Cyclohexylmethyl)-2,7-diazaspiro[3.5]nonan-2-yl)-1-oxoisoindolin-2-yl)piperidine-2,6-dione E1025.

3-(1-Oxo-4-(7-((tetrahydro-2H-pyran-4-yl)methyl)-2,7-diazaspiro[3.5]nonan-2-yl)isoindolin-2-yl)piperidine-2,6-dione E1026.

E1025

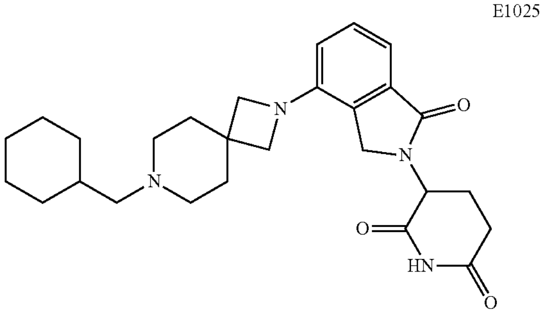

E1026

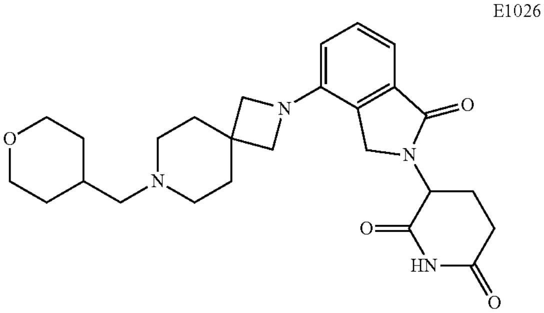

3-(4-(7-(4-Methoxybenzyl)-2,7-diazaspiro[3.5]nonan-2-yl)-1-oxoisoindolin-2-yl)piperidine-2,6-dione E1027.

3-(4-(7-(3-Methoxybenzyl)-2,7-diazaspiro[3.5]nonan-2-yl)-1-oxoisoindolin-2-yl)piperidine-2,6-dione E1028.

E1027

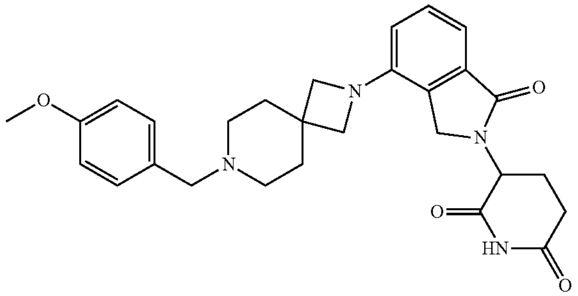

E1028

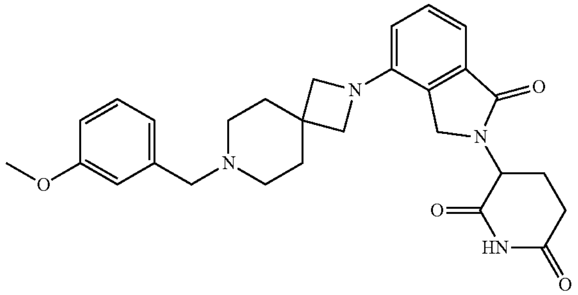

3-(4-(7-((6-Methoxypyridin-3-yl)methyl)-2,7-diazaspiro[3.5]nonan-2-yl)-1-oxoisoindolin-2-yl)piperidine-2,6-dione E1029.

3-(4-(7-((1H-Indol-3-yl)methyl)-2,7-diazaspiro[3.5]nonan-2-yl)-1-oxoisoindolin-2-yl)piperidine-2,6-dione E1030.

E1029

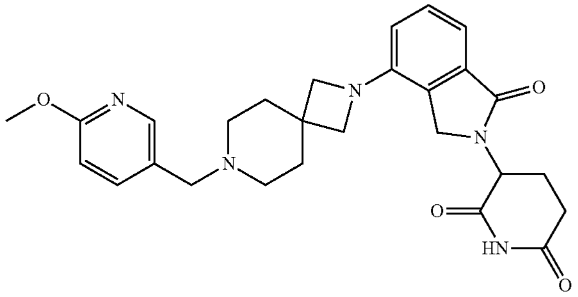

E1030

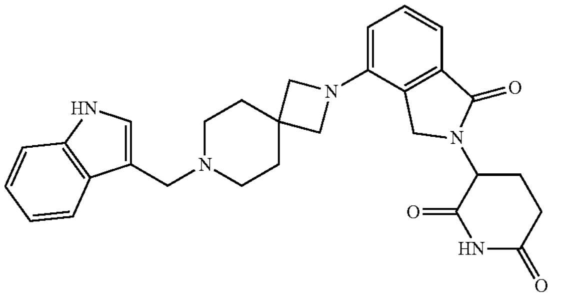

3-(4-(7-(2-Methoxyphenethyl)-2,7-diazaspiro[3.5]nonan-2-yl)-1-oxoisoindolin-2-yl)piperidine-2,6-dione E1031.

3-(1-Oxo-4-(7-((6-(pyrrolidin-1-yl)pyridin-3-yl)methyl)-2,7-diazaspiro[3.5]-nonan-2-yl)isoindolin-2-yl)piperidine-2,6-dione E1032.

E1031

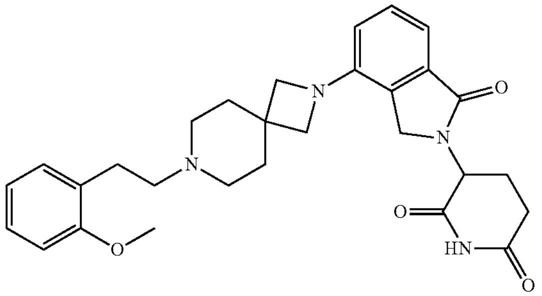

E1032

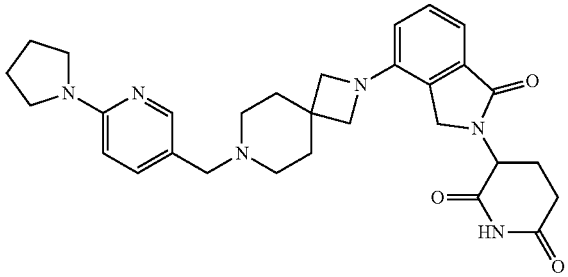

3-(4-(7-((5-(Morpholinomethyl)furan-2-yl)methyl)-2,7-diazaspiro[3.5]nonan-2-yl)-1-oxoisoindolin-2-yl)piperidine-2,6-dione E1033.

3-(4-(7-((1-Benzylpiperidin-4-yl)methyl)-2,7-diazaspiro[3.5]nonan-2-yl)-1-oxoisoindolin-2-yl)piperidine-2,6-dione E1034.

E1033

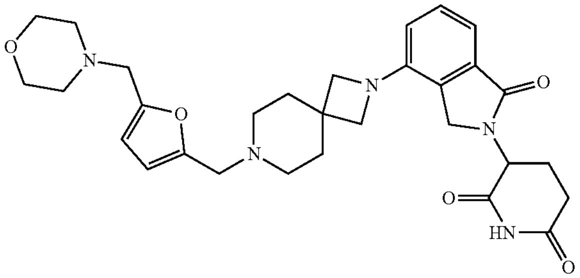

E1034

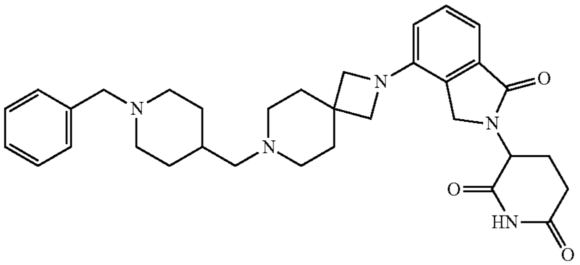

3-(4-(7-((4-(Benzyloxy)pyridin-2-yl)methyl)-2,7-diazaspiro[3.5]nonan-2-yl)-1-oxoisoindolin-2-yl)piperidine-2,6-dione E1035.

E1035

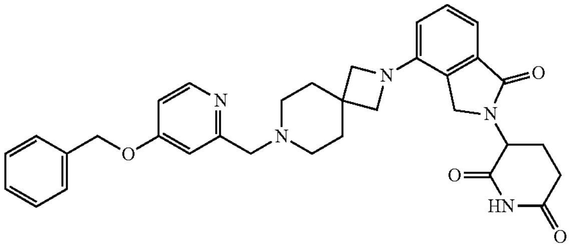

3-(1-Oxo-4-(7-(4-((pyridin-2-yloxy)methyl)benzyl)-2,7-diazaspiro[3.5]nonan-2-yl)isoindolin-2-yl)piperidine-2,6-dione E1036.

E1036

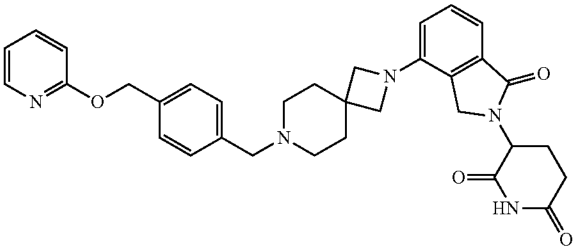

3-(4-(7-(2-Chloro-4-morpholinobenzyl)-2,7-diazaspiro[3.5]nonan-2-yl)-1-oxoisoindolin-2-yl)piperidine-2,6-dione E1037.

3-(4-(7-(Furan-3-ylmethyl)-2,7-diazaspiro[3.5]nonan-2-yl)-1-oxoisoindolin-2-yl)-piperidine-2,6-dione E1038.

E1037

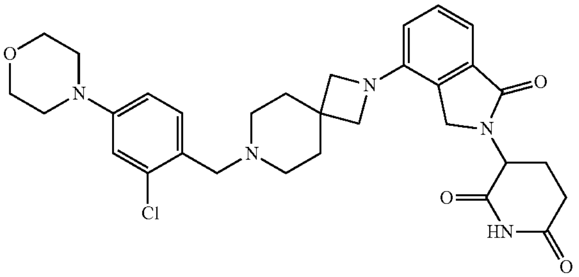

E1038

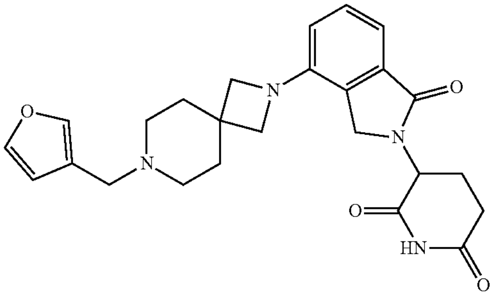

3-(4-(7-(Furan-2-ylmethyl)-2,7-diazaspiro[3.5]nonan-2-yl)-1-oxoisoindolin-2-yl)-piperidine-2,6-dione E1039.

3-(4-(7-((1H-Pyrazol-4-yl)methyl)-2,7-diazaspiro[3.5]nonan-2-yl)-1-oxoisoindolin-2-yl)piperidine-2,6-dione E1040.

E1039

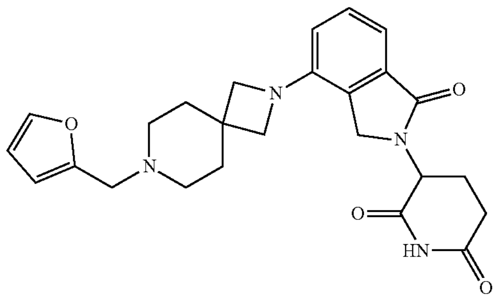

E1040

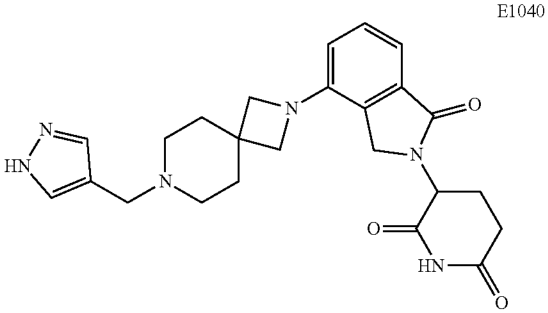

3-(5-(7-(Furan-2-carbonyl)-2,7-diazaspiro[3.5]nonan-2-yl)-1-oxoisoindolin-2-yl)-piperidine-2,6-dione F0001.

3-(5-(7-(Furan-3-carbonyl)-2,7-diazaspiro[3.5]nonan-2-yl)-1-oxoisoindolin-2-yl)-piperidine-2,6-dione F0002.

F0001

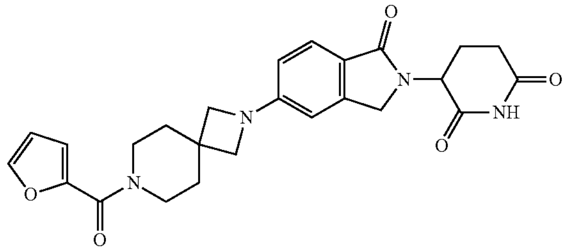

F0002

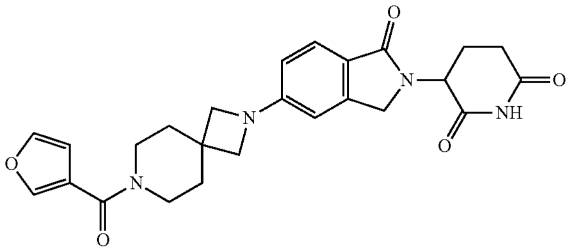

3-(5-(7-(2-(1H-Pyrrol-2-yl)acetyl)-2,7-diazaspiro[3.5]nonan-2-yl)-1-oxoisoindolin-2-yl)piperidine-2,6-dione F0003.

3-(5-(7-(2-(1H-Pyrazol-1-yl)acetyl)-2,7-diazaspiro[3.5]nonan-2-yl)-1-oxoisoindolin-2-yl)piperidine-2,6-dione F0004.

F0003

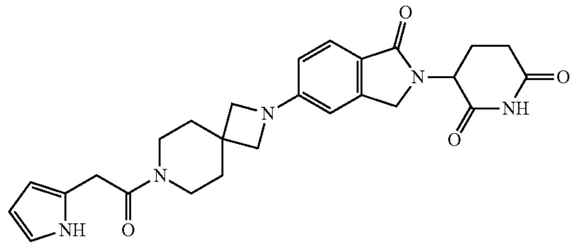

F0004

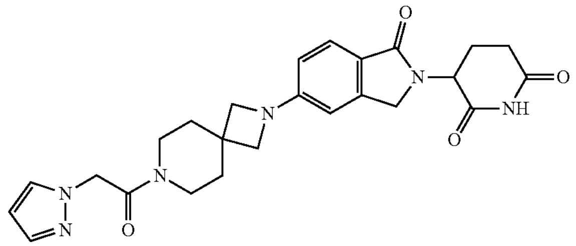

3-(1-Oxo-5-(7-(2-(pyrrolidin-1-yl)acetyl)-2,7-diazaspiro[3.5]nonan-2-yl)-isoindolin-2-yl)piperidine-2,6-dione F0005.

3-(1-Oxo-5-(7-(tetrahydro-2H-pyran-4-carbonyl)-2,7-diazaspiro[3.5]nonan-2-yl)-isoindolin-2-yl)piperidine-2,6-dione F0006.

F0005

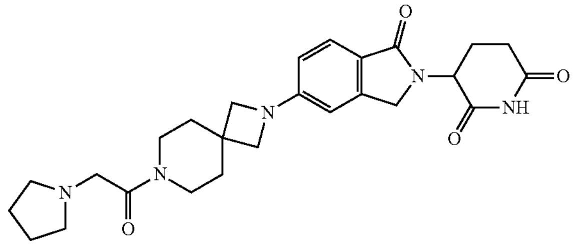

F0006

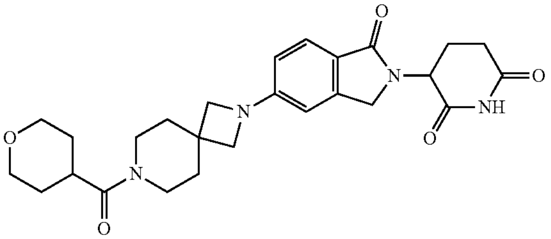

3-(5-(7-(2-Morpholinoacetyl)-2,7-diazaspiro[3.5]nonan-2-yl)-1-oxoisoindolin-2-yl)piperidine-2,6-dione F0007.

F0007

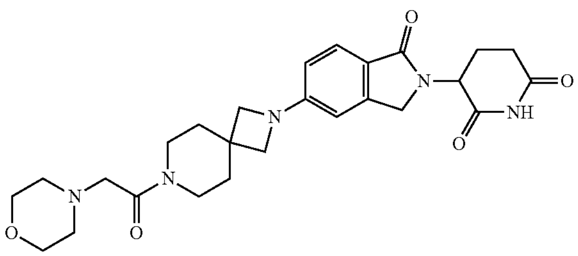

3-(2-(2-(2,6-Dioxopiperidin-3-yl)-1-oxoisoindolin-5-yl)-2,7-diazaspiro[3.5]-nonane-7-carbonyl)benzonitrile F0008.

F0008

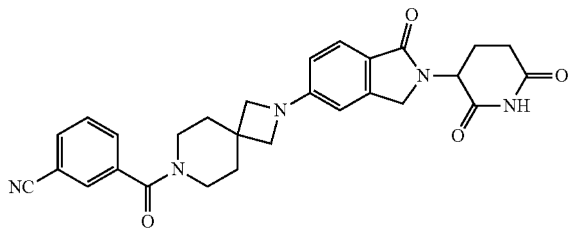

3-(1-Oxo-5-(7-(2-(m-tolyl)acetyl)-2,7-diazaspiro[3.5]nonan-2-yl)isoindolin-2-yl)-piperidine-2,6-dione F0009.

F0009

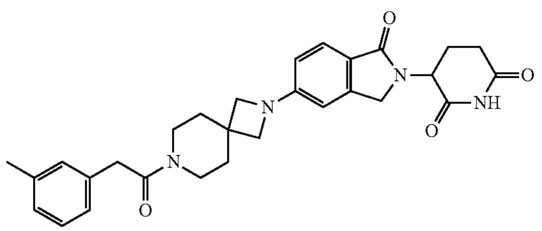

3-(1-Oxo-5-(7-(3-phenylpropanoyl)-2,7-diazaspiro[3.5]nonan-2-yl)isoindolin-2-yl)-piperidine-2,6-dione F0010.

F0010

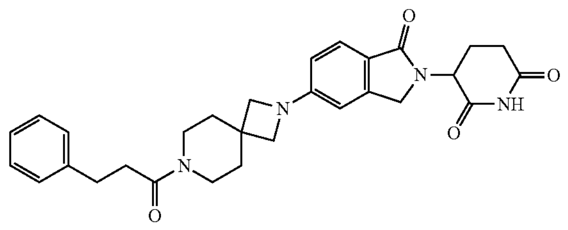

3-(1-Oxo-5-(7-(3-(pyridin-2-yl)propanoyl)-2,7-diazaspiro[3.5]nonan-2-yl)-isoindolin-2-yl)piperidine-2,6-dione F0011.

F0011

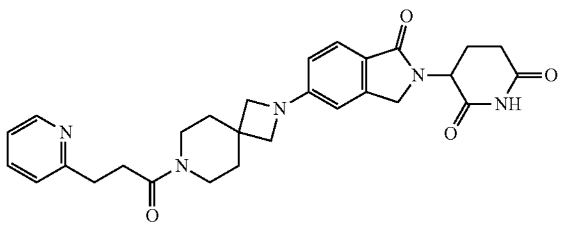

3-(5-(7-(3-(Hydroxymethyl)benzoyl)-2,7-diazaspiro[3.5]nonan-2-yl)-1-oxoisoindolin-2-yl)piperidine-2,6-dione F0012.

F0012

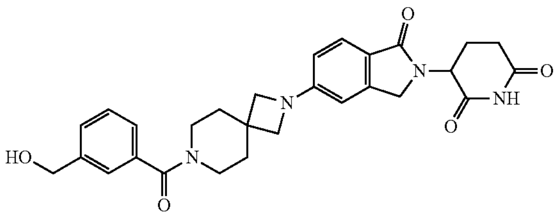

3-(5-(7-(1H-Pyrrole-2-carbonyl)-2,7-diazaspiro[3.5]nonan-2-yl)-1-oxoisoindolin-2-yl)piperidine-2,6-dione F0013.

F0013

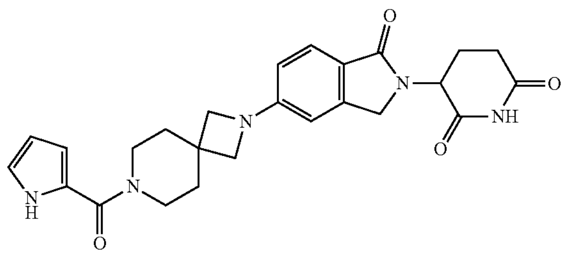

3-(1-Oxo-5-(7-(2-(m-tolyloxy)acetyl)-2,7-diazaspiro[3.5]nonan-2-yl)isoindolin-2-yl)piperidine-2,6-dione F0014.

F0014

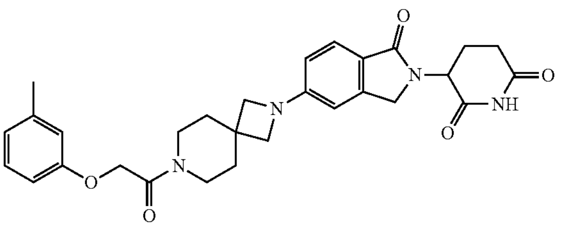

3-(5-(7-(2-(2-Methoxypyridin-3-yl)acetyl)-2,7-diazaspiro[3.5]nonan-2-yl)-1-oxoisoindolin-2-yl)piperidine-2,6-dione F0015.

F0015

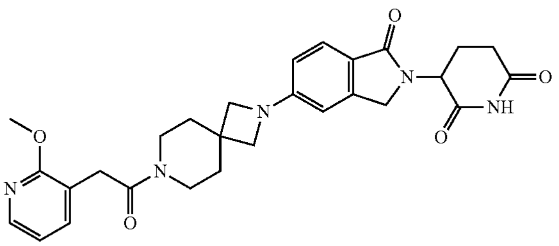

2-Chloro-5-(2-(2-(2,6-dioxopiperidin-3-yl)-1-oxoisoindolin-5-yl)-2,7-diazaspiro[3.5]nonane-7-carbonyl)benzonitrile F0016.

F0016

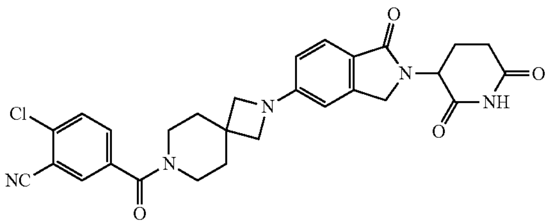

2-Chloro-4-(2-(2-(2,6-dioxopiperidin-3-yl)-1-oxoisoindolin-5-yl)-2,7-diazaspiro[3.5]nonane-7-carbonyl)benzonitrile F0017.

F0017

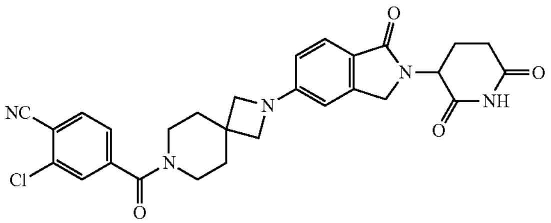

3-(1-Oxo-5-(7-(3-(pyridin-3-yl)propanoyl)-2,7-diazaspiro[3.5]nonan-2-yl)-isoindolin-2-yl)piperidine-2,6-dione F0018.

F0018

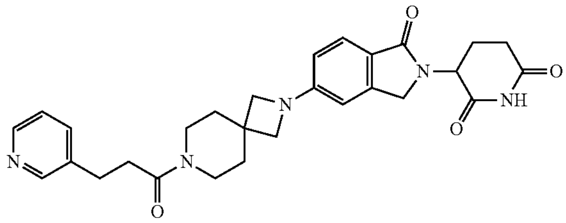

3-(5-(7-(2,6-Difluorobenzoyl)-2,7-diazaspiro[3.5]nonan-2-yl)-1-oxoisoindolin-2-yl)piperidine-2,6-dione F0019.

3-(5-(7-(2,5-Difluorobenzoyl)-2,7-diazaspiro[3.5]nonan-2-yl)-1-oxoisoindolin-2-yl)piperidine-2,6-dione F0020.

F0019

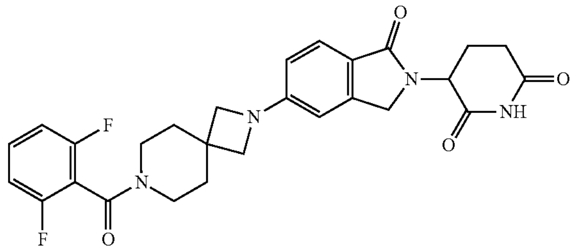

F0020

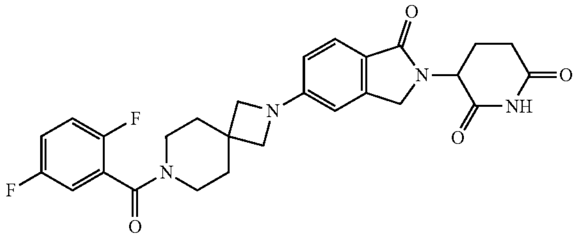

3-(5-(7-(3,5-Difluorobenzoyl)-2,7-diazaspiro[3.5]nonan-2-yl)-1-oxoisoindolin-2-yl)piperidine-2,6-dione F0021.

F0021

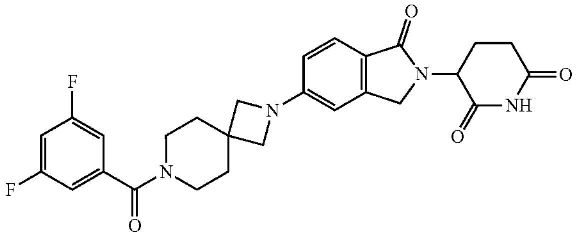

3-(5-(7-(2-Methyl-2-phenylpropanoyl)-2,7-diazaspiro[3.5]nonan-2-yl)-1-oxoisoindolin-2-yl)piperidine-2,6-dione F0022.

F0022

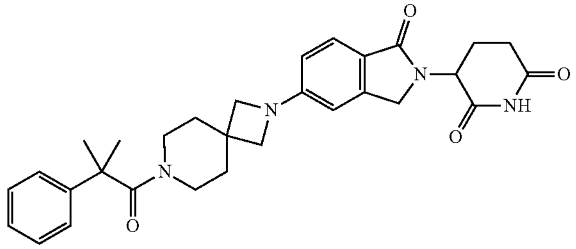

3-(1-Oxo-5-(7-(pyrimidine-4-carbonyl)-2,7-diazaspiro[3.5]nonan-2-yl)isoindolin-2-yl)piperidine-2,6-dione F0023.

3-(5-(7-(1-Methyl-1H-pyrrole-2-carbonyl)-2,7-diazaspiro[3.5]nonan-2-yl)-1-oxoisoindolin-2-yl)piperidine-2,6-dione F0024.

F0023

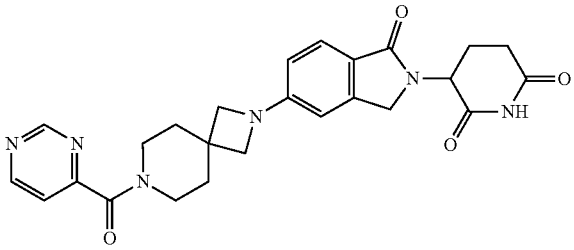

F0024

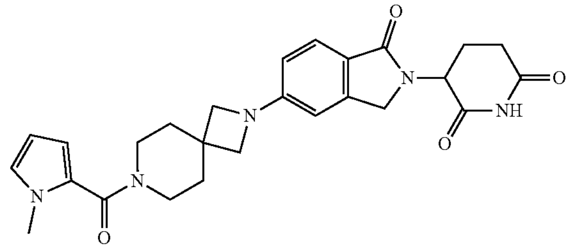

3-(5-(7-(2-Methyl-1H-imidazole-5-carbonyl)-2,7-diazaspiro[3.5]nonan-2-yl)-1-oxoisoindolin-2-yl)piperidine-2,6-dione F0025.

F0025

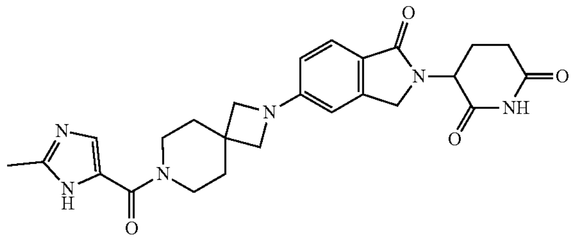

3-(5-(7-(2-(1H-1,2,3-Triazol-1-yl)acetyl)-2,7-diazaspiro[3.5]nonan-2-yl)-1-oxoisoindolin-2-yl)piperidine-2,6-dione F0026.

F0026

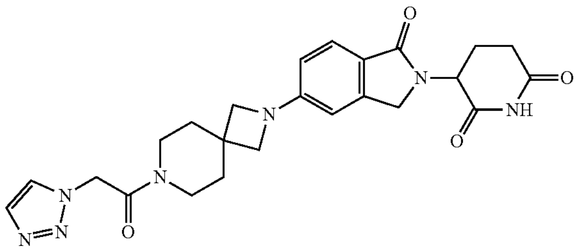

3-(5-(7-(2-Cyclopentylacetyl)-2,7-diazaspiro[3.5]nonan-2-yl)-1-oxoisoindolin-2-yl)piperidine-2,6-dione F0027.

5-(2-(2-(2,6-Dioxopiperidin-3-yl)-1-oxoisoindolin-5-yl)-2,7-diazaspiro[3.5]-nonane-7-carbonyl)-1H-pyrrole-2-carbonitrile F0028.

F0027

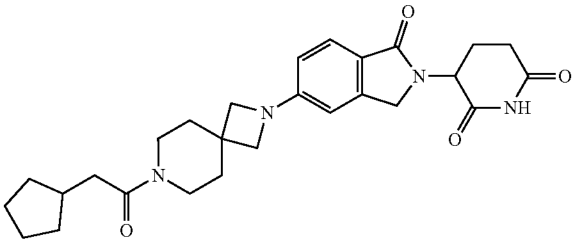

F0028

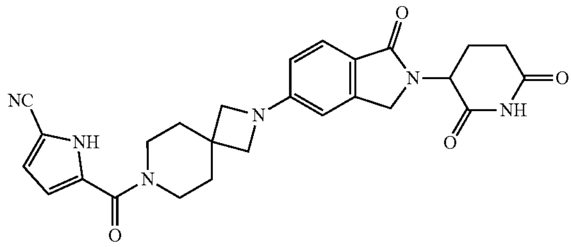

5-(2-(2-(2,6-Dioxopiperidin-3-yl)-1-oxoisoindolin-5-yl)-2,7-diazaspiro[3.5]-nonane-7-carbonyl)-1H-pyrrole-3-carbonitrile F0029.

3-(1-Oxo-5-(7-(2-(pyrimidin-2-yl)acetyl)-2,7-diazaspiro[3.5]nonan-2-yl)-isoindolin-2-yl)piperidine-2,6-dione F0030.

F0029

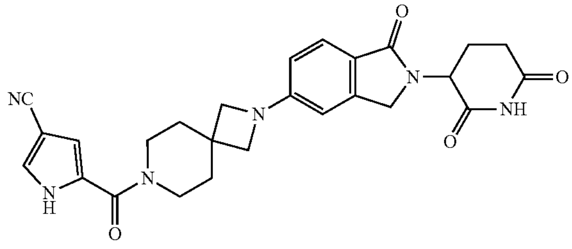

F0030

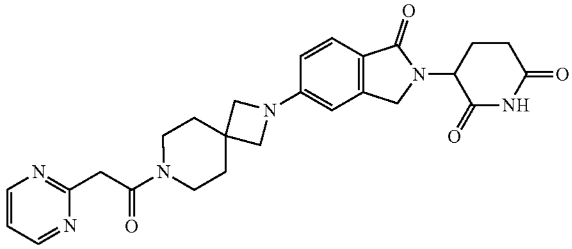

3-(1-Oxo-5-(7-(2-(pyrimidin-5-yl)acetyl)-2,7-diazaspiro[3.5]nonan-2-yl)-isoindolin-2-yl)piperidine-2,6-dione F0031.

F0031

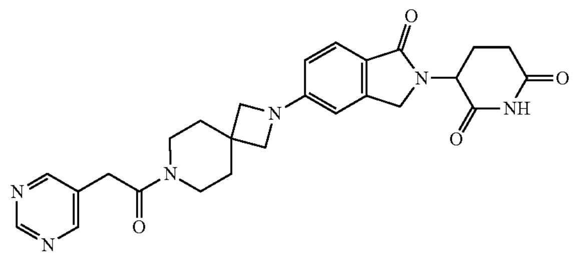

3-(5-(7-(3-(1H-Pyrrol-2-yl)propanoyl)-2,7-diazaspiro[3.5]nonan-2-yl)-1-oxoisoindolin-2-yl)piperidine-2,6-dione F0032.

F0032

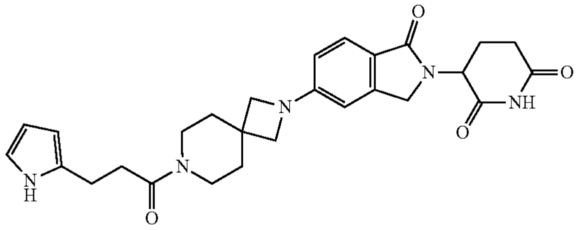

3-(5-(7-(1-Methylpiperidine-4-carbonyl)-2,7-diazaspiro[3.5]nonan-2-yl)-1-oxoisoindolin-2-yl)piperidine-2,6-dione F0033.

F0033

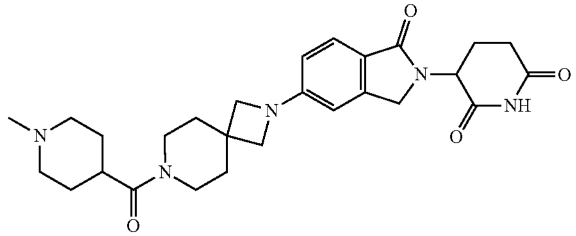

3-(1-Oxo-5-(7-(2-(piperidin-1-yl)acetyl)-2,7-diazaspiro[3.5]nonan-2-yl)-isoindolin-2-yl)piperidine-2,6-dione F0034.

F0034

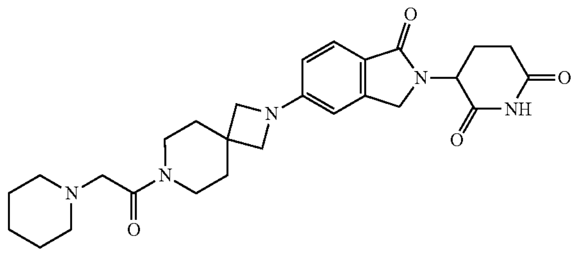

3-(1-Oxo-5-(7-(2-(tetrahydro-2H-pyran-4-yl)acetyl)-2,7-diazaspiro[3.5]nonan-2-yl)isoindolin-2-yl)piperidine-2,6-dione F0035.

F0035

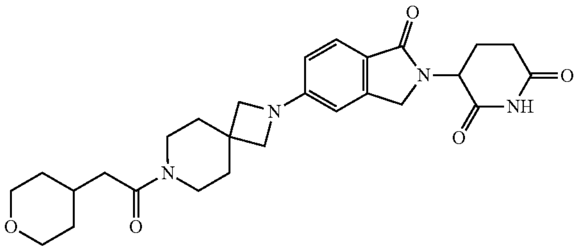

3-(5-(7-Benzyl-2,7-diazaspiro[3.5]nonan-2-yl)-1-oxoisoindolin-2-yl)piperidine-2,6-dione F1001.

3-(1-Oxo-5-(7-(pyridin-3-ylmethyl)-2,7-diazaspiro[3.5]nonan-2-yl)isoindolin-2-yl)piperidine-2,6-dione F1002.

F1001

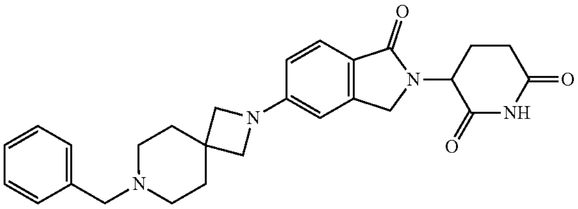

F1002

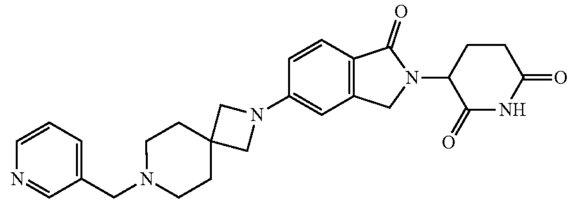

3-(1-Oxo-5-(7-(pyridin-4-ylmethyl)-2,7-diazaspiro[3.5]nonan-2-yl)isoindolin-2-yl)piperidine-2,6-dione F1003.

3-(1-Oxo-5-(7-(pyridin-2-ylmethyl)-2,7-diazaspiro[3.5]nonan-2-yl)isoindolin-2-yl)piperidine-2,6-dione F1004.

F1003

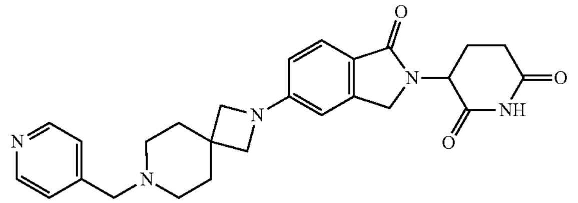

F1004

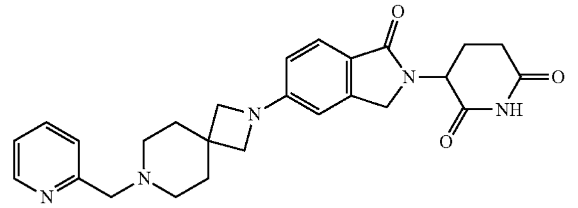

3-(1-Oxo-5-(7-(pyrimidin-5-ylmethyl)-2,7-diazaspiro[3.5]nonan-2-yl)isoindolin-2-yl)piperidine-2,6-dione F1005.

3-(5-(7-((1-Methyl-1H-imidazol-5-yl)methyl)-2,7-diazaspiro[3.5]nonan-2-yl)-1-oxoisoindolin-2-yl)piperidine-2,6-dione F1006.

F1005

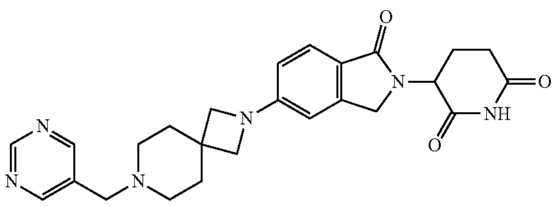

F1006

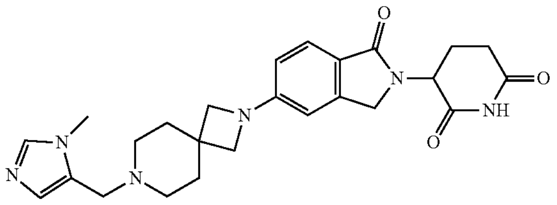

3-(1-Oxo-5-(7-phenethyl-2,7-diazaspiro[3.5]nonan-2-yl)isoindolin-2-yl)-piperidine-2,6-dione F1007.

3-((2-(2-(2,6-Dioxopiperidin-3-yl)-1-oxoisoindolin-5-yl)-2,7-diazaspiro[3.5]-nonan-7-yl)methyl)benzonitrile F1008.

F1007

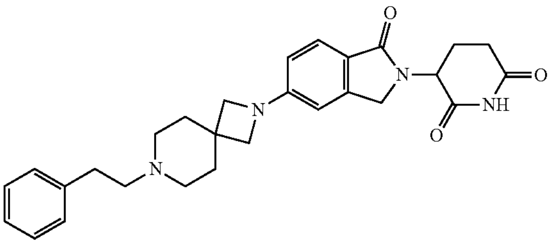

F1008

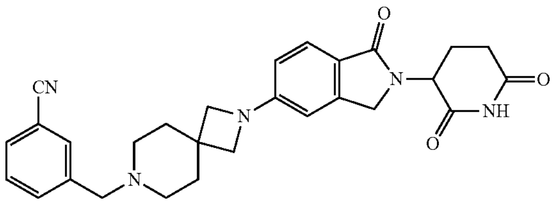

2-((2-(2-(2,6-Dioxopiperidin-3-yl)-1-oxoisoindolin-5-yl)-2,7-diazaspiro[3.5]-nonan-7-yl)methyl)benzonitrile F1009.

F1009

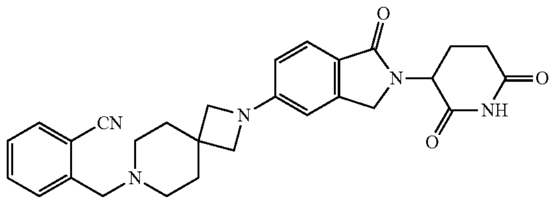

6-((2-(2-(2,6-Dioxopiperidin-3-yl)-1-oxoisoindolin-5-yl)-2,7-diazaspiro[3.5]-nonan-7-yl)methyl)nicotinonitrile F1010.

F1010

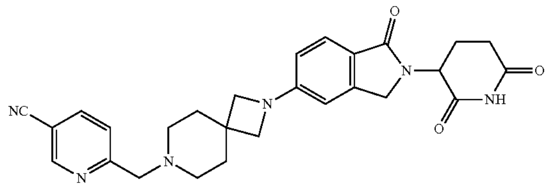

3-(1-Oxo-5-(7-(3-phenylpropyl)-2,7-diazaspiro[3.5]nonan-2-yl)isoindolin-2-yl)-piperidine-2,6-dione F1011.

F1011

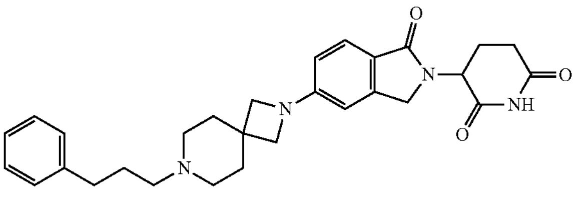

3-(5-(7-(4-(Hydroxymethyl)benzyl)-2,7-diazaspiro[3.5]nonan-2-yl)-1-oxoisoindolin-2-yl)piperidine-2,6-dione F1012.

F1012

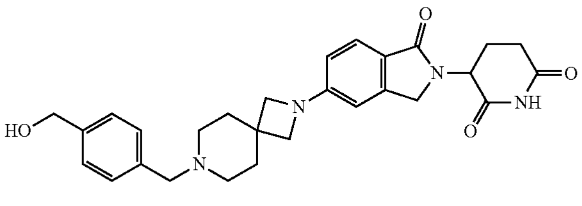

2-((2-(2-(2,6-Dioxopiperidin-3-yl)-1-oxoisoindolin-5-yl)-2,7-diazaspiro[3.5]-nonan-7-yl)methyl)-5-methoxybenzonitrile F1013.

F1013

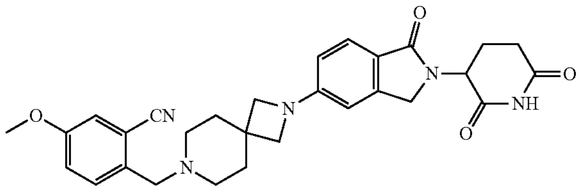

3-Chloro-5-((2-(2-(2,6-dioxopiperidin-3-yl)-1-oxoisoindolin-5-yl)-2,7-diazaspiro[3.5]nonan-7-yl)methyl)benzonitrile F1014.

F1014

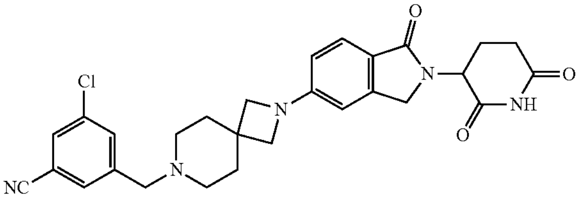

2-Chloro-4-((2-(2-(2,6-dioxopiperidin-3-yl)-1-oxoisoindolin-5-yl)-2,7-diazaspiro[3.5]nonan-7-yl)methyl)benzonitrile F1015.

F1015

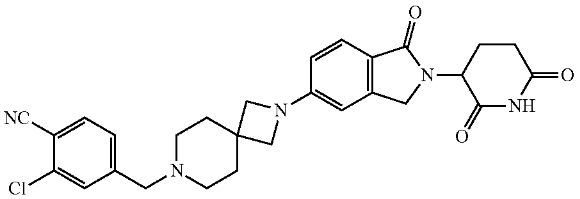

3-(1-Oxo-5-(7-((2-phenyl-1H-imidazol-5-yl)methyl)-2,7-diazaspiro[3.5]nonan-2-yl)isoindolin-2-yl)piperidine-2,6-dione F1016.

F1016

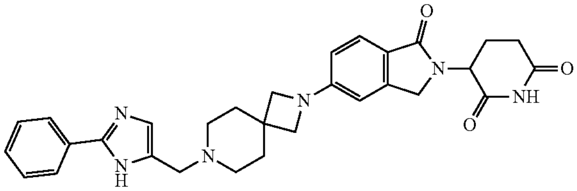

3-(1-Oxo-5-(7-(4-(pyrrolidin-1-yl)benzyl)-2,7-diazaspiro[3.5]nonan-2-yl)-isoindolin-2-yl)piperidine-2,6-dione F1017.

F1017

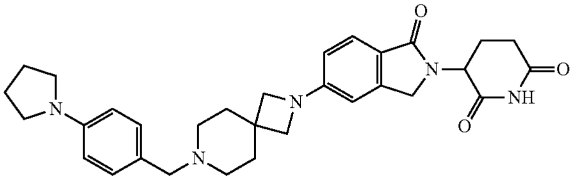

3-(5-(7-(4-((2-Hydroxyethyl)(methyl)amino)benzyl)-2,7-diazaspiro[3.5]nonan-2-yl)-1-oxoisoindolin-2-yl)piperidine-2,6-dione F1018.

F1018

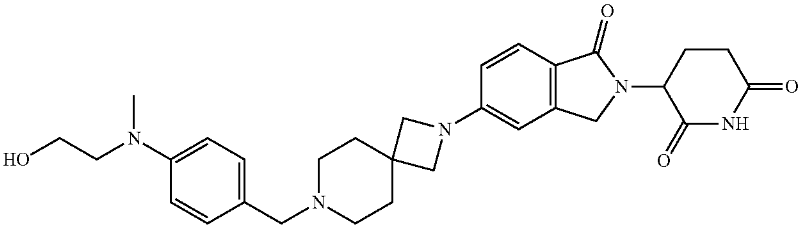

3-(5-(7-(4-(Cyclopentyloxy)benzyl)-2,7-diazaspiro[3.5]nonan-2-yl)-1-oxoisoindolin-2-yl)piperidine-2,6-dione F1019.

F1019

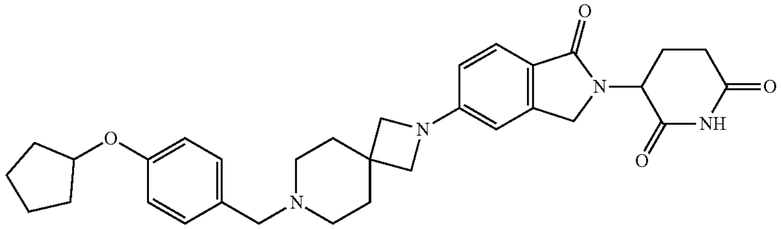

3-(5-(7-(4-Morpholinobenzyl)-2,7-diazaspiro[3.5]nonan-2-yl)-1-oxoisoindolin-2-yl)piperidine-2,6-dione F1020.
F1020
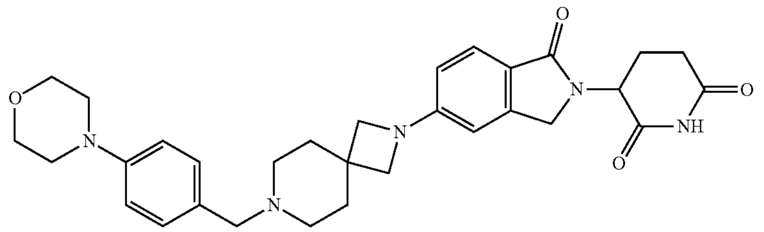
3-(5-(7-(3-Morpholinobenzyl)-2,7-diazaspiro[3.5]nonan-2-yl)-1-oxoisoindolin-2-yl)piperidine-2,6-dione F1021.
F1021
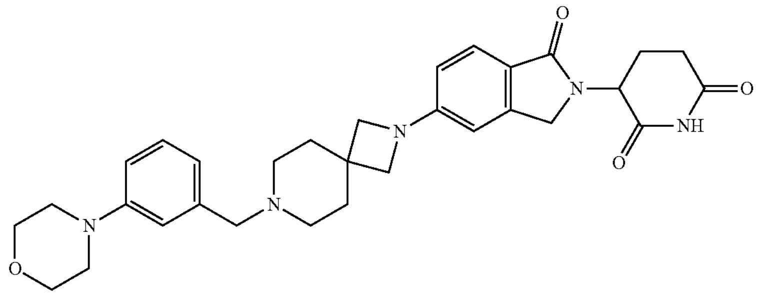
3-(5-(7-(4-Benzylbenzyl)-2,7-diazaspiro[3.5]nonan-2-yl)-1-oxoisoindolin-2-yl)-piperidine-2,6-dione F1022.
F1022
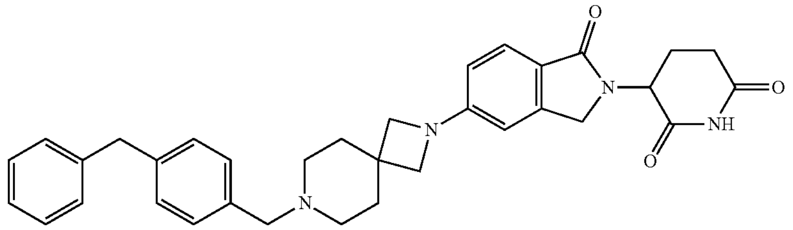
3-(1-Oxo-5-(7-(4-(pyridin-3-yloxy)benzyl)-2,7-diazaspiro[3.5]nonan-2-yl)-isoindolin-2-yl)piperidine-2,6-dione F1023.

F1023

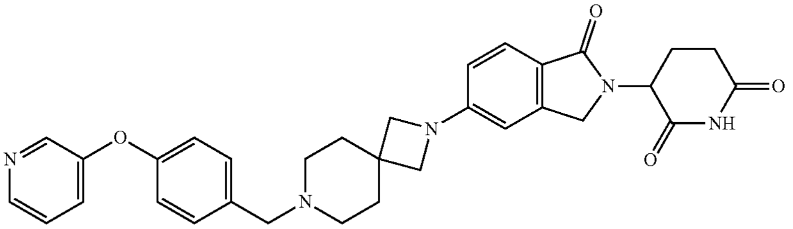

3-(1-Oxo-5-(7-(pyrimidin-4-ylmethyl)-2,7-diazaspiro[3.5]nonan-2-yl)isoindolin-2-yl)piperidine-2,6-dione F1024.

3-(5-(7-(Cyclohexylmethyl)-2,7-diazaspiro[3.5]nonan-2-yl)-1-oxoisoindolin-2-yl)piperidine-2,6-dione F1025.

F1024

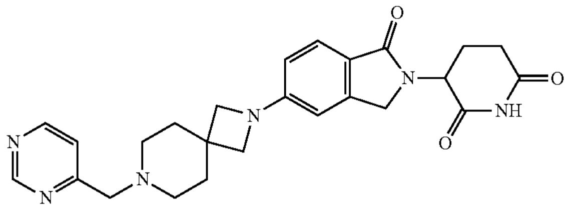

F1025

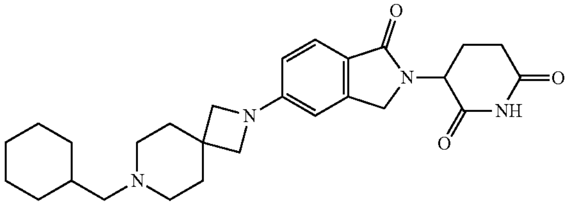

3-(1-Oxo-5-(7-((tetrahydro-2H-pyran-4-yl)methyl)-2,7-diazaspiro[3.5]nonan-2-yl)isoindolin-2-yl)piperidine-2,6-dione F1026.

F1026

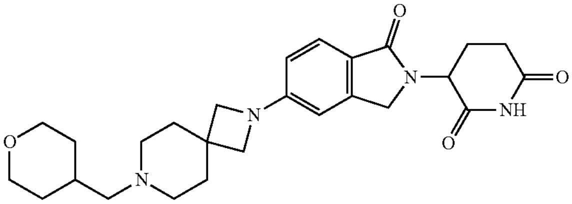

3-(5-(7-(4-Methoxybenzyl)-2,7-diazaspiro[3.5]nonan-2-yl)-1-oxoisoindolin-2-yl)-piperidine-2,6-dione F1027.

F1027

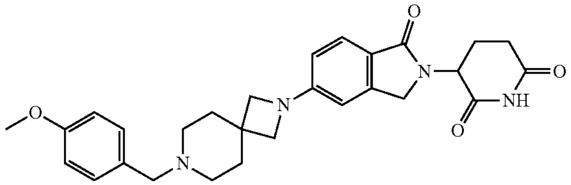

3-(5-(7-(3-Methoxybenzyl)-2,7-diazaspiro[3.5]nonan-2-yl)-1-oxoisoindolin-2-yl)-piperidine-2,6-dione F1028.

F1028

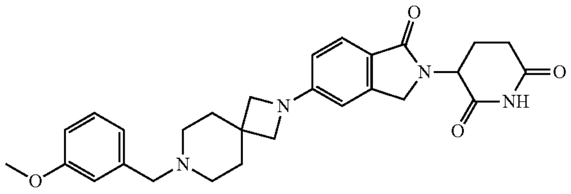

3-(5-(7-((6-Methoxypyridin-3-yl)methyl)-2,7-diazaspiro[3.5]nonan-2-yl)-1-oxoisoindolin-2-yl)piperidine-2,6-dione F1029.

F1029

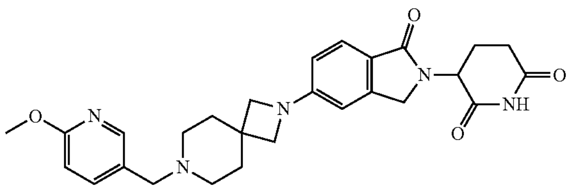

3-(5-(7-((1H-Indol-3-yl)methyl)-2,7-diazaspiro[3.5]nonan-2-yl)-1-oxoisoindolin-2-yl)piperidine-2,6-dione F1030.

F1030

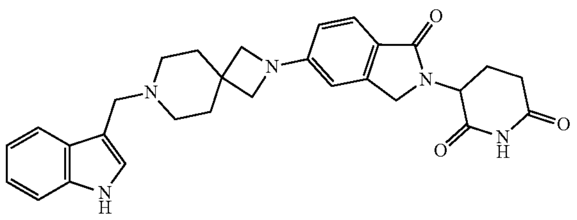

3-(5-(7-(2-Methoxyphenethyl)-2,7-diazaspiro[3.5]nonan-2-yl)-1-oxoisoindolin-2-yl)piperidine-2,6-dione F1031.

F1031

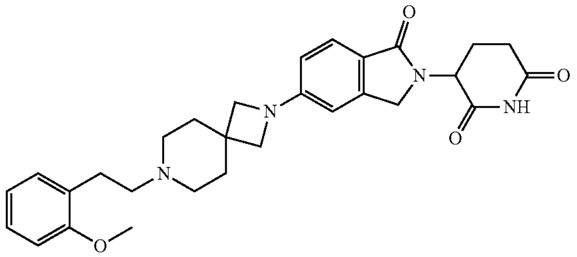

3-(1-Oxo-5-(7-((6-(pyrrolidin-1-yl)pyridin-3-yl)methyl)-2,7-diazaspiro[3.5]-nonan-2-yl)isoindolin-2-yl)piperidine-2,6-dione F1032.

F1032

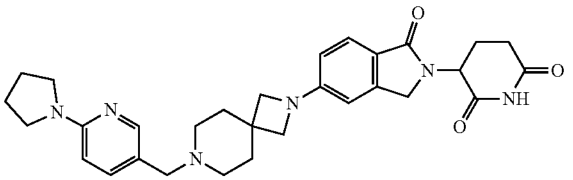

3-(5-(7-((5-(Morpholinomethyl)furan-2-yl)methyl)-2,7-diazaspiro[3.5]nonan-2-yl)-1-oxoisoindolin-2-yl)piperidine-2,6-dione F1033.

F1033

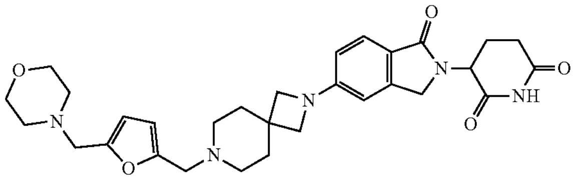

3-(5-(7-((1-Benzylpiperidin-4-yl)methyl)-2,7-diazaspiro[3.5]nonan-2-yl)-1-oxoisoindolin-2-yl)piperidine-2,6-dione F1034.

F1034

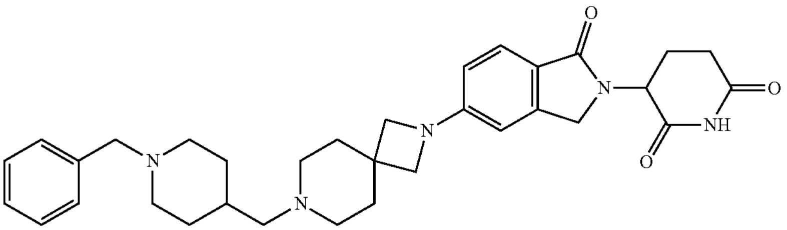

3-(5-(7-((4-(Benzyloxy)pyridin-2-yl)methyl)-2,7-diazaspiro[3.5]nonan-2-yl)-1-oxoisoindolin-2-yl)piperidine-2,6-dione F1035.

F1035

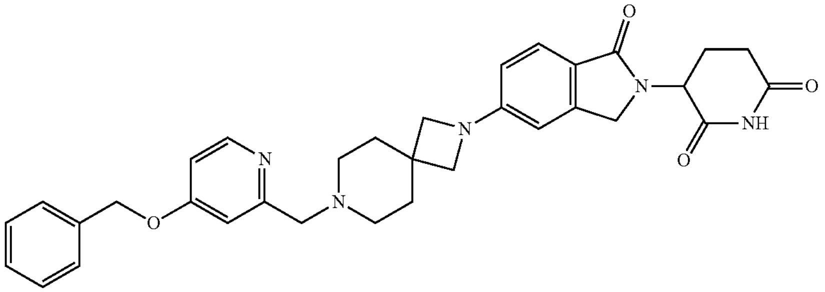

3-(1-Oxo-5-(7-(4-((pyridin-2-yloxy)methyl)benzyl)-2,7-diazaspiro[3.5]nonan-2-yl)isoindolin-2-yl)piperidine-2,6-dione F1036.

F1036

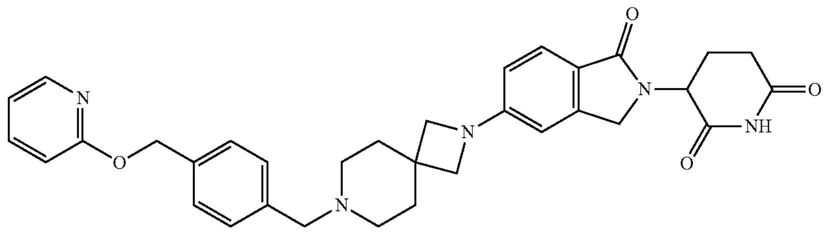

3-(5-(7-(2-Chloro-4-morpholinobenzyl)-2,7-diazaspiro[3.5]nonan-2-yl)-1-oxoisoindolin-2-yl)piperidine-2,6-dione F1037.

F1037

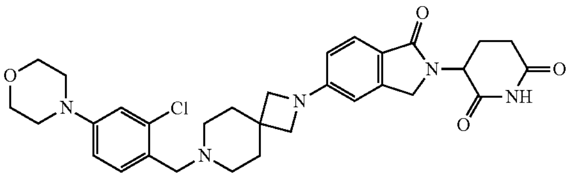

3-(5-(7-(Furan-3-ylmethyl)-2,7-diazaspiro[3.5]nonan-2-yl)-1-oxoisoindolin-2-yl)-piperidine-2,6-dione F1038.

3-(5-(7-(Furan-2-ylmethyl)-2,7-diazaspiro[3.5]nonan-2-yl)-1-oxoisoindolin-2-yl)-piperidine-2,6-dione F1039.

F1038

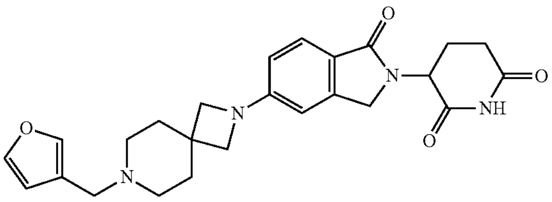

F1039

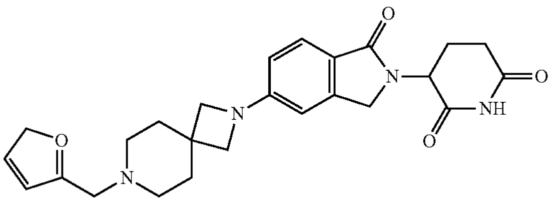

3-(5-(7-((1H-Pyrazol-4-yl)methyl)-2,7-diazaspiro[3.5]nonan-2-yl)-1-oxoisoindolin-2-yl)piperidine-2,6-dione F1040.

F1040

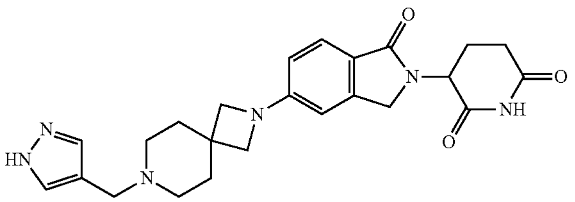

Example B1

Protein Degradation Assays

A compound provided herein is assessed for its activity in degrading CK1α, GSPT1, and Ikaros in cancerous cells (e.g., MV-4-11 cells) via a western blot. The cells are grown at 37° C. in a humidified 5% $CO_2$ environment in RPMI 1640 media supplemented with 10% fetal bovine serum, streptomycin, and penicillin. The cells are cultured at approximately $10^6$ cells per mL. The cells are treated with a compound or DMSO (control) for about 8 h. Whole cell extracts are prepared using a radioimmunoprecipitation assay (RIPA) buffer. Briefly, $3\times10^6$ cells are washed once in PBS, and the cell pellets are resuspended in the RIPA buffer and incubated for 15 min on ice. Cells debris is removed by centrifugation and the cleared whole cell lysates are transferred to new tubes for further analysis.

For a western blot analysis, the whole cell protein extracts are separated on 12% SDS-polyacrylamide gels, transferred to nitrocellulose, and probed with primary antibodies, including an anti-hPD-L1 antibody. Membranes are subsequently washed and probed with IRDYE® secondary antibodies. The signals are detected using an ODYSSEY® Imaging System.

For Western blot analysis, the whole cell protein extracts are separated on 4-12% SDS-polyacrylamide gels, transferred to nitrocellulose, and probed with primary antibodies, including anti-eRF3/GSPT1, anti-Ikaros, anti-CK1α, and β-actin (8H10D10) mouse monoclonal antibody. Membranes are subsequently washed and probed with IRDYE® secondary antibodies, including IRDYE® 680RD goat anti-rabbit antibody, and IRDYE® 800CW goat anti-mouse antibody. The signals are detected using an ODYSSEY® Imaging System.

Example B2

Cytokine Modulation Assays

Frozen primary blood mononuclear cells (PBMCs) or frozen CD14+ mobilized peripheral blood monocytes are quick thawed, washed once with RPMI 1640 media supplemented with 10% fetal bovine serum, streptomycin, and penicillin, and plated in 96 well plates at 200,000 cells per well. The cells are pretreated with a compound or DMSO (control) for 1 h and then induced with 100 ng/mL lipopolysaccharide (LPS) for 18-24 h. The supernatant is analyzed for IL-1β, IL-6, and TNFα using Meso Scale assays. The negative control wells are treated with DMSO.

For the IL-2 analysis, a 96 well plate is precoated with 1 μg/mL anti-human CD3 antibody. After washed with PBS, a compound or DMSO (control) is added (50 μL/well), followed by addition of PBMCs diluted at 3-4 million cells/mL (150 μL/well). The plate is incubated for 24 h and the supernatants are collected for IL-2 analysis. IL-2 activity is measured as fold difference from the DMSO control.

Example B3

Cell Viability Assays

MOLM-13 cells were cultured in RPMI 1640 media supplemented with 10% fetal bovine serum, streptomycin, and penicillin. The cells were plated in white walled 96-well plates at 2,500 cells/well. The cells were incubated in DMSO (control) or an indicated compound for 3 days at 37° C. and 5% $CO_2$. Following the incubation period, 100 μL of CELLTITER-GLO® (CTG) reagent was added to each well. Following a 10-min incubation with shaking, luminescence was measured using an ENVISION® Multimode plate reader.

The examples set forth above are provided to give those of ordinary skill in the art with a complete disclosure and description of how to make and use the claimed embodiments and are not intended to limit the scope of what is disclosed herein. Modifications that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

What is claimed is:

1. A compound of Formula (I):

(I)

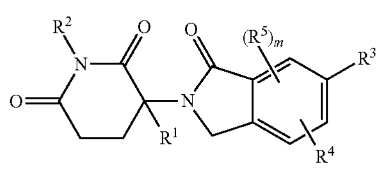

or an enantiomer, a mixture of enantiomers, a diastereomer, a mixture of two or more diastereomers, a tautomer, or a mixture of two or more tautomers thereof; or a pharmaceutically acceptable salt, solvate, or hydrate thereof; wherein:

$R^1$ is hydrogen or $C_{1-6}$ alkyl;

$R^2$ is hydrogen;

$R^3$ is hydrogen or fluoro;

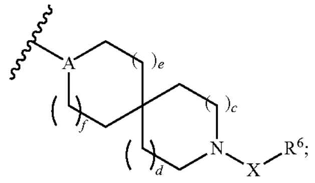

$R^4$ is $R^5$ is absent;

$R^6$ is:

(i) ethyl, propyl, isopropyl, isobutyl, trifluoromethyl, 2,2,2-trifluoroethyl, 3,3,3-trifluoropropyl, 3-chloropropyl, cyclobutylmethyl, cyclopentyl-methyl, cyclohexylmethyl, (3-methylphenoxy)methyl, benzyl, 2-phenyl-ethyl, 3-phenylpropyl, 2-(3-bromophenyl)ethyl, 2-methyl-2-phenylpropyl, 2-(3-trifluoromethylphenyl)ethyl, 2-(2-methoxyphenyl)ethyl, 2-benzoxy-ethyl, 2-(5-methylfuran-2-yl)ethyl, pyrazol-1-ylmethyl, pyrrol-2-ylmethyl, 2-(pyrrol-2-yl)ethyl, 1,2,3-triazol-1-ylmethyl, pyrimidin-2-ylmethyl, pyrimidin-5-ylmethyl, 2-methoxypyridin-3-ylmethyl, 2-(pyridin-2-yl)-ethyl, 2-(pyridin-3-yl)ethyl, 2-(quinolin-6-yl)ethyl, pyrrolidin-1-ylmethyl, tetrahydropyran-4-ylmethyl, piperidin-1-ylmethyl, 1-benzoxycarbonyl-piperidin-4-ylmethyl, 1-(tert-butoxycarbonyl)piperidin-4-ylmethyl, 2-(1-(tert-butoxycarbonyl)piperidin-4-yl) prop-2-yl, 4-(tert-butoxycarbonyl)-piperazin-1-ylmethyl, morpholinomethyl, 3-hydroxy-2-methylprop-2-yl, benzoxymethyl, 2-benzoxyethyl, methylaminomethyl, or (tert-butoxy-carbonyl)aminomethyl;

(ii) cyclopropyl, cyclobutyl, 3,3-dimethylcyclobut-1-yl, cyclopentyl, cyclo-hexyl, adamantan-1-yl, 1-fluorocyclopropyl, 4,4-difluorocyclohexyl, 3,3-dimethylcyclobutyl, 4-hydroxybicyclo[2.2.2]octan-1-yl, 1-aminocyclo-butyl, 4-(tert-butoxycarbonylamino)cyclohexyl, or 4-(tert-butoxycarbonylaminomethyl)cyclohexyl;

(iii) phenyl, optionally substituted with one, two, or three substituents, each of which is independently cyano, fluoro, chloro, bromo, oxo, methyl, ethyl, isopropyl, isobutyl, tert-butyl, trifluoromethyl, morpholinomethyl, hydroxymethyl, (dimethylamino)methyl, (tert-butoxycarbonylamino)-methyl, ethynyl, cyclopropyl, cyclobutyl, cyclopentyl, cyclohexyl, phenyl, 3-bromophenyl, 4-methylphenyl, 3-trifluoromethylphenyl, 2-methoxy-phenyl, benzyl, 5-methylfuran-2-yl, imidazol-1-yl, oxazol-5-yl, pyrazol-1-yl, pyrrol-2-yl, 1,2,3-triazol-1-yl, 1,2,4-triazol-1-yl, pyrimidin-2-yl, pyrimidin-5-yl, pyridin-3-yl, pyridin-4-yl, 4-methylpyridin-2-yl, 2-methoxypyridin-3-yl, quinolin-6-yl, pyrrolidin-1-yl, morpholino, piperidin-1-yl, 1-benzoxycarbonylpiperidin-4-yl, 1-(tert-butoxycarbonyl)-piperidin-4-yl, 4-methylpiperazin-1-yl, 4-(tert-butoxycarbonyl)piperazin-1-yl, 2,2,2-trifluoroacetyl, benzoxycarbonyl, tert-butoxycarbonyl, amino-carbonyl, methylaminocarbonyl, dimethylaminocarbonyl, isopropylamino-carbonyl, hydroxyl, methoxy, ethoxy, difluoromethoxy, trifluoromethoxy, cyclohexylmethoxy, cyclopentoxy, phenoxy, 4-cyanophenoxy, 3-methyl-phenoxy, 4-trifluoromethylphenoxy, 4-cyano-2-fluorophenoxy, benzoxy, 4-cyanobenzoxy, pyridin-2-yloxy, pyridin-3-yloxy, amino, methylamino, ethylamino, dimethylamino, (2-hydroxyethyl)(methyl)amino), acetamido, benzoxycarbonylamino, tert-butoxycarbonylamino, methylsulfonylamino, methylthio, methylsulfonyl, or ethylsulfonyl;

(iv) bicyclo[4.2.0]octa-1 (6),2,4-trien-3-yl, naphthalen-1-yl, naphthalen-2-yl, 5-(dimethylamino)naphthalen-1-yl, 6-(dimethylamino)naphthalen-2-yl, 5,6,7,8-tetrahydronaphthalen-1-yl, or 5,6,7,8-tetrahydronaphthalen-2-yl;

(v) benzyl, 2-cyanobenzyl, 3-cyanobenzyl, 4-cyanobenzyl, 4-fluorobenzyl, 4-chlorobenzyl, 4-bromobenzyl, 2-methylbenzyl, 3-methylbenzyl, 4-methyl-benzyl, 4-trifluoromethylbenzyl, 2-methoxybenzyl, 3-methoxybenzyl, 4-methoxybenzyl, 2-phenylethyl, 3-phenylpropyl, 2-phenylprop-2-yl, 2-(3-bromophenyl)ethyl, 2-methyl-2-phenylpropyl, 2-(3-trifluoromethyl-phenyl)ethyl, or 2-(2-methoxyphenyl)ethyl;

(vi) furanyl, imidazolyl, oxazolyl, pyrazolyl, pyrrolyl, thiazolyl, thienyl, 1,2,4-triazolyl, tetrazolyl, pyridinyl, 1,2-dihydropyridinyl, 1,6-dihydropyridinyl, pyridazinyl, or pyrimidinyl, each optionally substituted with one, two, or three substituents, each of which is independently cyano, fluoro, chloro, bromo, oxo, methyl, ethyl, isopropyl, isobutyl, tert-butyl, trifluoromethyl, morpholinomethyl, hydroxymethyl, (dimethylamino)methyl, (tert-butoxy-carbonylamino)methyl, ethynyl, cyclopropyl, cyclobutyl, cyclopentyl, cyclohexyl, phenyl, 3-bromophenyl, 4-methylphenyl, 3-trifluoromethyl-phenyl, 2-methoxyphenyl, benzyl, 5-methylfuran-2-yl, imidazol-1-yl, oxazol-5-yl, pyrazol-1-yl, pyrrol-2-yl, 1,2,3-triazol-1-yl, 1,2,4-triazol-1-yl, pyrimidin-2-yl, pyrimidin-5-yl, pyridin-3-yl, pyridin-4-yl, 4-methylpyridin-2-yl, 2-methoxypyridin-3-yl, quinolin-6-yl, pyrrolidin-1-yl, morpholino, piperidin-1-yl, 1-benzoxycarbonylpiperidin-4-yl, 1-(tert-butoxycarbonyl)piperidin-4-yl, 4-methylpiperazin-1-yl, 4-(tert-butoxy-carbonyl)piperazin-1-yl, 2,2,2-trifluoroacetyl, benzoxycarbonyl, tert-butoxycarbonyl, aminocarbonyl, methylaminocarbonyl, dimethylamino-carbonyl, isopropylaminocarbonyl, hydroxyl, methoxy, ethoxy, difluoro-methoxy, trifluoromethoxy, cyclohexylmethoxy, cyclopentoxy, phenoxy, 4-cyanophenoxy, 3-methylphenoxy, 4-trifluoromethylphenoxy, 4-cyano-2-fluorophenoxy, benzoxy, 4-cyanobenzoxy, pyridin-2-yloxy, pyridin-3-yl-oxy, amino, methylamino, ethylamino, dimethylamino, (2-hydroxyethyl)-(methyl)amino), acetamido, benzoxycarbonylamino, tert-butoxycarbonyl-amino, methylsulfonylamino, methylthio, methylsulfonyl, or ethylsulfonyl;

(vii) benzo[d][1,3]dioxolyl, benzofuranyl, benzo[d]imidazolyl, benzo[d]oxazol-yl, benzo[d]thiazolyl, benzo[b]thienyl, chromanyl, 2,3-dihydrobenzo[b]-[1,4]dioxinyl, 2,3-dihydrobenzofuranyl, 2,3-dihydro[1,4]dioxino[2,3-b]-pyridinyl, 5,6-dihydroimidazo[2,1-c][1,4]oxazinyl, 3,4-dihydropyrano-[2,3-c]pyridinyl, furo[2,3-c]pyridinyl, imidazo[1,2-a]pyridinyl, imidazo-[1,5-a]pyridinyl, imidazo[4,5-b]pyridinyl, imidazo[1,2-a]pyrimidinyl, indazolyl, indolyl, indolinyl, indolizinyl, isoindolinyl, isoquinolinyl, 1,8-naphthyridinyl, pyrazolo[1,5-a]pyridinyl, pyrrolo[2,3-b]pyrazinyl, pyrrolo[2,3-b]pyridinyl, pyrrolo[2,3-c]pyridinyl, pyrrolo[3,2-b]pyridinyl, quinazolinyl, quinolinyl, quinoxalinyl, 1,2,3,4-tetrahydroisoquinolinyl, 1,2,3,4-tetrahydroquinolinyl, thieno[2,3-b]pyridinyl, thieno[3,2-c]-pyridinyl, or [1,2,4]triazolo[1,5-a]pyridinyl, each optionally substituted with one, two, or three substituents, each of which is independently cyano, fluoro, chloro, bromo, oxo, methyl, ethyl, isopropyl, tert-butyl, trifluoro-methyl, morpholinomethyl, hydroxymethyl, (dimethylamino)methyl, (tert-butoxycarbonylamino)methyl, ethynyl, cyclopropyl, cyclobutyl, cyclo-pentyl, cyclohexyl, phenyl, 3-bromophenyl, 4-methylphenyl, 3-trifluoro-methylphenyl, 2-methoxyphenyl, benzyl, 5-methylfuran-2-yl, imidazol-1-yl, oxazol-5-yl, pyrazol-1-yl, pyrrol-2-yl, 1,2,3-triazol-1-yl, 1,2,4-triazol-1-yl, pyrimidin-2-yl, pyrimidin-5-yl, pyridin-3-yl, pyridin-4-yl, 4-methylpyridin-2-yl, 2-methoxypyridin-3-yl, quinolin-6-yl, pyrrolidin-1-yl, morpholino, piperidin-1-yl, 1-benzoxycarbonyl-piperidin-4-yl, 1-(tert-butoxycarbonyl)piperidin-4-yl, 4-methylpiperazin-1-yl, 4-(tert-butoxy-carbonyl)piperazin-1-yl, 2,2,2-trifluoroacetyl, benzoxycarbonyl, tert-butoxycarbonyl, aminocarbonyl, methylaminocarbonyl, dimethylamino-carbonyl, isopropylaminocarbonyl, hydroxyl, methoxy, ethoxy, difluoro-methoxy, trifluoromethoxy, cyclohexylmethoxy, cyclopentoxy, phenoxy, 4-cyanophenoxy, 3-methylphenoxy, 4-trifluoromethylphenoxy, 4-cyano-2-fluorophenoxy, benzoxy, 4-cyanobenzoxy, pyridin-2-yloxy, pyridin-3-yl-oxy, amino, methylamino, ethylamino, dimethylamino, (2-hydroxyethyl)-(methyl)amino), acetamido, benzoxycarbonylamino, tert-butoxycarbonyl-amino, methylsulfonylamino, methylthio, methylsulfonyl, or ethylsulfonyl; or (viii) 1-methylazetidin-3-yl, oxetan-3-yl, 3-methyloxetan-3-yl, tetrahydro-pyran-4-yl, ethylpiperidin-4-yl, 1-benzylpiperidin-4-yl, 1-benzoxy-carbonylpiperidin-4-yl, 1-(tert-butoxycarbonyl)piperidin-4-yl, 1-(ethyl-sulfonyl)piperidin-4-yl, 1-(tert-butoxycarbonyl)-4-fluoropiperidin-4-yl, or 4-(tert-butoxycarbonyl)piperazin-1-yl;

A is N;

X is $-(CH_2)_n-$, $-C(O)-$, $-S(O)-$, or $-S(O_2)-$; wherein n is an integer of 1, 2, 3, 4, or 5; and c and d are:

(i) c and d are each independently an integer of 1; and e and f are each independently an integer of 0 or 1; or (ii) c and d are each independently an integer of 0 or 1; and e and f are each independently an integer of 1.

2. The compound of claim 1, having the structure of Formula (XI):

(XI)

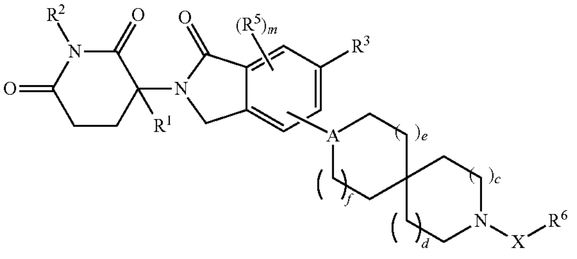

or an enantiomer, a mixture of enantiomers, a diastereomer, a mixture of two or more diastereomers, a tautomer, or a mixture of two or more tautomers thereof; or a pharmaceutically acceptable salt, solvate, or hydrate thereof.

3. The compound of claim 1, having the structure of Formula (XII):

(XII)

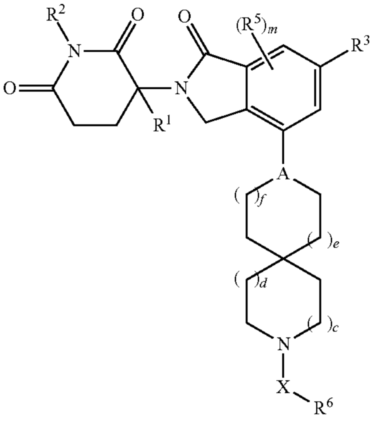

or an enantiomer, a mixture of enantiomers, a diastereomer, a mixture of two or more diastereomers, a tautomer, or a mixture of two or more tautomers thereof; or a pharmaceutically acceptable salt, solvate, or hydrate thereof.

4. The compound of claim 1, having the structure of (XVI)

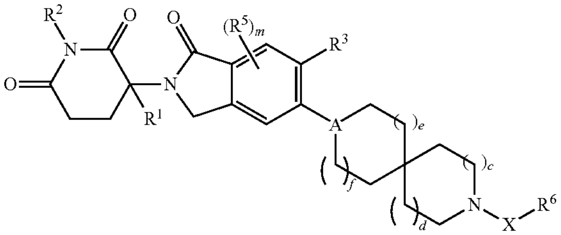

or an enantiomer, a mixture or enantiomers, a diastereomer, a mixture or two or more diastereomers, a tautomer, or a mixture of two or more tautomers thereof; or a pharmaceutically acceptable salt, solvate, or hydrate thereof.

5. The compound of claim 1, having the structure of Formula (XIII):

(XIII)

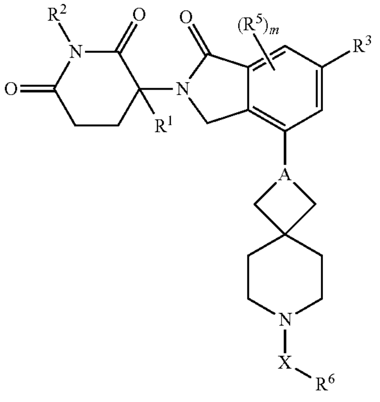

or an enantiomer, a mixture of enantiomers, a diastereomer, a mixture of two or more diastereomers, a tautomer, or a mixture of two or more tautomers thereof; or a pharmaceutically acceptable salt, solvate, or hydrate thereof.

6. The compound of claim 1, having the structure of Formula (XVII):

(XVII)

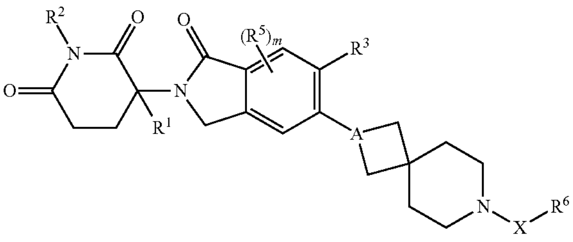

or an enantiomer, a mixture of enantiomers, a diastereomer, a mixture of two or more diastereomers, a tautomer, or a mixture of two or more tautomers thereof; or a pharmaceutically acceptable salt, solvate, or hydrate thereof.

7. The compound of claim 1, wherein $R^1$ is hydrogen.

8. The compound of claim 1, wherein X is —C(O)—.

9. The compound of claim 1, wherein X is —$S(O_2)$—.

10. The compound of claim 1, wherein $R^6$ is ethyl, propyl, isopropyl, isobutyl, trifluoromethyl, 2,2,2-trifluoroethyl, 3,3,3-trifluoropropyl, 3-chloropropyl, cyclobutylmethyl, cyclopentylmethyl, cyclohexylmethyl, (3-methylphenoxy)methyl, benzyl, 2-phenylethyl, 3-phenylpropyl, 2-(3-bromophenyl)ethyl, 2-methyl-2-phenylpropyl, 2-(3-trifluoro-methylphenyl)ethyl, 2-(2-methoxyphenyl)ethyl, 2-benzoxyethyl, 2-(5-methylfuran-2-yl)ethyl, pyrazol-1-ylmethyl, pyrrol-2-ylmethyl, 2-(pyrrol-2-yl)ethyl, 1,2,3-triazol-1-ylmethyl, pyrimidin-2-yl-methyl, pyrimidin-5-ylmethyl, 2-methoxypyridin-3-ylmethyl, 2-(pyridin-2-yl)ethyl, 2-(pyridin-3-yl)ethyl, 2-(quinolin-6-yl)ethyl, pyrrolidin-1-ylmethyl, tetrahydropyran-4-ylmethyl, piperidin-1-ylmethyl, 1-benzoxycarbonylpiperidin-4-ylmethyl, 1-(tert-butoxycarbonyl)piperidin-4-ylmethyl, 2-(1-(tert-butoxycarbonyl)piperidin-4-yl) prop-2-yl, 4-(tert-butoxycarbonyl)-piperazin-1-yl-methyl, morpholinomethyl, 3-hydroxy-2-methylprop-2-yl, benzoxymethyl, 2-benzoxyethyl, methylaminomethyl, or (tert-butoxycarbonyl)aminomethyl.

11. The compound of claim 1, wherein $R^6$ is cyclopropyl, cyclobutyl, 3,3-dimethylcyclobut-1-yl, cyclopentyl, cyclohexyl, adamantan-1-yl, 1-fluorocyclo-propyl, 4,4-difluorocyclohexyl, 3,3-dimethylcyclobutyl, 4-hydroxybicyclo[2.2.2]octan-1-yl, 1-aminocyclobutyl, 4-(tert-butoxycarbonylamino)cyclohexyl, or 4-(tert-butoxycarbonylamino-methyl)cyclohexyl.

12. The compound of claim 1, wherein $R^6$ is 2-fluorophenyl, 3-fluorophenyl, 4-fluorophenyl, 2-chlorophenyl, 3-chlorophenyl, 4-chlorophenyl, 2-bromo-phenyl, 3-bromophenyl, 2-cyanophenyl, 3-cyanophenyl, 4-cyanophenyl, 2-methylphenyl, 3-methylphenyl, 4-methylphenyl, 3-isopropylphenyl, 4-isopropylphenyl, 3-tert-butylphenyl, 4-tert-butylphenyl, 2-trifluoromethylphenyl, 3-trifluoromethylphenyl, 4-trifluoromethylphenyl, 3-hydroxymethylphenyl, 4-hydroxymethylphenyl, 4-((dimethylamino)methyl)phenyl, 2-ethynyl-phenyl, 3-ethynylphenyl, 4-ethynylphenyl, 2-cyclopropylphenyl, 4-cyclopropylphenyl, 4-phenyl-phenyl, 4-benzylphenyl, 3-(imidazol-1-yl)phenyl, 4-(imidazol-1-yl)phenyl, 4-(oxazol-5-yl)-phenyl, 4-(pyrazol-1-yl)phenyl, 2-(1,2,4-triazol-1-yl)phenyl, 3-(1,2,4-triazol-1-yl)phenyl, 4-(1,2,4-triazol-1-yl)phenyl, 3-(pyridin-4-yl)phenyl, 3-(pyrrolidin-1-yl)phenyl, 4-(pyrrolidin-1-yl)-phenyl, 2-(morpholino)phenyl, 3-(morpholino)phenyl, 4-(morpholino)phenyl, 3-aminocarbonyl-phenyl, 4-aminocarbonylphenyl, 4-(methylaminocarbonyl)phenyl, 2-(dimethylaminocarbonyl)-phenyl, 4-(isopropylaminocarbonyl)phenyl, 3-hydroxyphenyl, 4-hydroxyphenyl, 2-methoxyphenyl, 3-methoxyphenyl, 4-methoxyphenyl, 4-ethoxyphenyl, 4-difluoromethoxyphenyl, 2-trifluoromethoxyphenyl, 4-cyclopentoxyphenyl, 3-(cyclohexylmethoxy)phenyl, 3-phenoxy-phenyl, 4-phenoxyphenyl, 3-(4-cyanophenoxy)phenyl, 4-(4-cyanophenoxy)phenyl, 4-(4-trifluoromethylphenoxy)phenyl, 4-(4-cyano-2-fluorophenoxy)phenyl, 3-benzoxyphenyl, 4-benzoxyphenyl, 3-(4-cyanobenzoxy)phenyl, 4-(4-cyanobenzoxy)phenyl, 2-(pyridin-2-yloxy)-phenyl, 4-(pyridin-2-yl-oxy)phenyl, 4-(pyridin-3-yloxy)phenyl, 3-morpholinophenyl, 4-morpholinophenyl, 2-aminophenyl, 4-aminophenyl, 2-methylaminophenyl, 4-ethylaminophenyl, 2-(dimethylamino)phenyl, 3-(dimethylamino)phenyl, 4-(dimethylamino)phenyl, 4-(2-hydroxy-ethyl)(methyl)amino)phenyl, 3-acetamidophenyl, 4-acetamidophenyl, 4-benzoxycarbonylamino-phenyl, 4-methylsulfonylaminophenyl, 2-methylsulfonylaminophenyl, 3-methylsulfonylamino-phenyl, or 4-(ethylsulfonyl)phenyl.

13. The compound of claim 1, wherein $R^6$ is 2-amino-3-chlorophenyl, 2-amino-4-chlorophenyl, 2-amino-6-chlorophenyl, 2-amino-5-fluorophenyl, 2-benzoxy-4-methylphenyl, 4-benzoxy-2-methylphenyl, 2-bromo-4-(4-cyanophenoxy)phenyl, 2-bromo-5-(4-cyanophenoxy)phenyl, 3-bromo-4-(4-methylpiperazin-1-yl)phenyl, 3-bromo-4-morpholinophenyl, 2-chloro-4-cyanophenyl, 3-chloro-4-cyanophenyl, 3-chloro-5-cyanophenyl, 4-chloro-3-cyanophenyl, 2-chloro-6-methylphenyl, 3-chloro-4-methylphenyl, 2-chloro-4-morpholinophenyl, 3-chloro-4-morpholinophenyl, 2-chloro-4-trifluoromethylphenyl, 2-chloro-5-trifluoromethylphenyl, 3-chloro-4-trifluoromethylphenyl, 4-chloro-2-trifluoromethylphenyl, 5-chloro-2-trifluoromethylphenyl, 2-cyano-4-fluorophenyl, 2-cyano-5-fluorophenyl, 3-cyano-4-fluorophenyl, 3-cyano-5-fluorophenyl, 4-cyano-3-fluorophenyl, 4-cyano-2-fluorophenyl, 5-cyano-2-fluorophenyl, 3-cyano-4-(4-methylimidazol-1-yl)phenyl, 3-cyano-4-hydroxyphenyl, 4-cyano-2-hydroxyphenyl, 2-cyano-4-methoxyphenyl, 4-cyano-2-methoxyphenyl, 4-cyano-3-methoxyphenyl, 4-cyano-3-methoxyphenyl, 2-cyano-3-methylphenyl, 2-cyano-4-methylphenyl, 3-cyano-2-methylphenyl, 3-cyano-5-methylphenyl, 4-cyano-2-methylphenyl, 2,4-dichloro-phenyl, 2,5-dichlorophenyl, 2,4-difluorophenyl, 2,5-difluorophenyl, 2,6-difluorophenyl, 3,4-difluorophenyl, 3,5-difluorophenyl, 4-(dimethylamino)-3-methylphenyl, 2,4-dimethylphenyl, 2,5-dimethylphenyl, 2,6-dimethylphenyl, 3,5-dimethylphenyl, 2-ethynyl-4-fluorophenyl, 3-fluoro-4-methoxyphenyl, 5-fluoro-2-methoxyphenyl, 2-fluoro-4-methylphenyl, 2-fluoro-5-methylphenyl, 3-fluoro-2-methylphenyl, 3-fluoro-4-methylphenyl, 3-fluoro-5-methylphenyl, 4-fluoro-2-methylphenyl, 4-fluoro-3-methylphenyl, 5-fluoro-2-methylphenyl, 2-hydroxy-4-methyl-phenyl, 3-hydroxy-5-methylphenyl, 2-methoxy-3-methylphenyl, 2-methoxy-4-methylphenyl, 2-methoxy-6-methylphenyl, 3-methoxy-2-methylphenyl, 3-methoxy-4-methylphenyl, 3-methoxy-5-methylphenyl, 4-methoxy-2-methylphenyl, or 4-methoxy-3-methylphenyl.

14. The compound of claim 1, wherein $R^6$ is 4-hydroxy-3,5-dimethylphenyl or 2,4,6-trimethylphenyl.

15. The compound of claim 1, wherein $R^6$ is bicyclo[4.2.0]-octa-1(6),2,4-trien-3-yl, naphthalen-1-yl, naphthalen-2-yl, 5-(dimethylamino)naphthalen-1-yl, 6-(dimethylamino)naphthalen-2-yl, 5,6,7,8-tetrahydronaphthalen-1-yl, or 5,6,7,8-tetrahydro-naphthalen-2-yl.

16. The compound of claim 1, wherein $R^6$ is benzyl, 2-cyanobenzyl, 3-cyanobenzyl, 4-cyanobenzyl, 4-fluorobenzyl, 4-chlorobenzyl, 4-bromobenzyl, 2-methylbenzyl, 3-methylbenzyl, 4-methylbenzyl, 4-trifluoromethylbenzyl, 2-methoxybenzyl, 3-methoxybenzyl, 4-methoxybenzyl, 2-phenylethyl, 3-phenylpropyl, 2-phenylprop-2-yl, 2-(3-bromophenyl)ethyl, 2-methyl-2-phenylpropyl, 2-(3-trifluoromethylphenyl)ethyl, or 2-(2-methoxyphenyl)ethyl.

17. The compound of claim 1, wherein $R^6$ is furan-2-yl, furan-3-yl, 5-methylfuran-2-yl, 4-isopropylfuran-2-yl, 5-(morpholinomethyl)furan-2-yl, 5-(hydroxymethyl)furan-2-yl, 3-methoxyfuran-2-yl, imidazol-4-yl, 1-methylimidazol-2-yl, 1-methylimidazol-4-yl, 1-methylimidazol-5-yl, 2-methylimidazol-4-yl, 2,5-dimethylimidazol-4-yl, 2-phenylimidazol-4-yl, 4-phenylimidazol-2-yl, oxazol-2-yl, 2-methyloxazol-4-yl, 2-methyl-oxazol-5-yl, 4-methyloxazol-5-yl, pyrazol-3-yl, pyrazol-4-yl, 1-methylpyrazol-3-yl, 1-methyl-pyrazol-4-yl, 1-methylpyrazol-5-yl, 5-methylpyrazol-3-yl, 1-isopropylpyrazol-4-yl, 1-isobutyl-pyrazol-4-yl, 5-amino-1-methylpyrazol-4-yl, 4-chloro-1-methylpyrazol-3-yl, 2-cyano-1-methyl-pyrazol-4-yl, 1,4-dimethylpyrazol-5-yl, 1-phenylpyrazol-3-yl, 1-(2-methylphenyl)pyrazol-4-yl, pyrrol-2-yl, pyrrol-3-yl, 3-cyanopyrrol-2-yl, 4-cyanopyrrol-2-yl, 1-methylpyrrol-2-yl, 3-methyl-pyrrol-2-yl, 5-methylpyrrol-2-yl, 5-(hydroxymethyl)pyrrol-2-yl, 5-(tert-butyl)pyrrol-2-yl, 2-cyano-1-methylpyrrol-4-yl, thiazol-2-yl, thiazol-4-yl, thiazol-5-yl, 2-methylthiazol-5-yl, 4-methylthiazol-5-yl, 5-methylthiazol-2-yl, 2-cyclopropylthiazol-5-yl, 2-(morpholino)thiazol-5-yl, thien-2-yl, thien-3-yl, 2-chlorothien-3-yl, 5-chlorothien-2-yl, 5-cyanothien-2-yl, 5-cyanothien-3-yl, 3-methylthien-2-yl, 5-(dimethylamino)thien-2-yl, 5-methyl-1,2,4-triazol-3-yl, 1-(tert-butyl)-1,2,3-triazol-4-yl, 1-(1-tert-butoxycarbonylpiperidin-4-yl)-1,2,3-triazol-4-yl, 2-methyltetrazol-5-yl, chloropyrazin-2-yl, 3-methylpyrazin-2-yl, 5-methylpyrazin-2-yl, 5-methoxypyrazin-2-yl, pyridin-2-yl, pyridin-3-yl, pyridin-4-yl, 4-cyanopyridin-2-yl, 5-cyanopyridin-2-yl, 5-cyano-pyridin-3-yl, 6-cyanopyridin-2-yl, 6-cyanopyridin-3-yl, 3-fluoropyridin-4-yl, 4-fluoropyridin-2-yl, 5-fluoropyridin-2-yl, 5-fluoropyridin-3-yl, 6-fluoropyridin-2-yl, 6-fluoropyridin-3-yl, 3-chloropyridin-4-yl, 6-chloro-pyridin-2-yl, 2-methylpyridin-3-yl, 2-methylpyridin-4-yl, 3-methyl-pyridin-2-yl, 4-methylpyridin-2-yl, 4-methylpyridin-3-yl, 5-methylpyridin-2-yl, 5-methyl-pyridin-3-yl, 6-methylpyridin-2-yl, 5-isopropylpyridin-3-yl, 2-trifluoromethylpyridin-5-yl, 6-(trifluoromethyl)pyridin-3-yl, 2-(tert-butyl)pyridin-4-yl, 5-ethynylpyridin-2-yl, 6-(4-methyl-phenyl)pyridin-3-yl, 6-(pyrrolidin-1-yl)pyridin-3-yl, 2-(4-methylpyridin-2-yl)pyridine-4-yl, 2-hydroxypyridin-3-yl, 2-methoxypyridin-3-yl, 2-methoxypyridin-4-yl, 3-methoxypyridin-2-yl, 3-methoxypyridin-4-yl, 4-methoxy-pyridin-2-yl, 4-methoxypyridin-3-yl, 5-methoxypyridin-2-yl, 5-methoxypyridin-3-yl, 6-methoxypyridin-2-yl, 6-methoxypyridin-3-yl, 6-phenoxypyridin-3-yl, 2-amino-pyridin-3-yl, 3-aminopyridin-4-yl, 6-(methylsulfonyl)pyridin-2-yl, 2-amino-5-cyano-pyridin-3-yl, 2-amino-5-methylpyridin-3-yl, 5-chloro-2-methoxypyridin-3-yl, 2,6-dimethyl-pyridin-4-yl, 5-fluoro-2-oxo-1,2-dihydropyridin-3-yl, 1-methyl-2-oxo-1,2-dihydropyridin-4-yl, 1-methyl-6-oxo-1,6-dihydropyridin-2-yl, pyridazin-4-yl, pyrimidin-4-yl, pyrimidin-5-yl, 2-methylpyrimidin-4-yl, 2-methylpyrimidin-5-yl, 2-methoxypyrimidin-4-yl, 2-(methylthio)-pyrimidin-4-yl, or 2-chloro-4-(morpholino)pyrimidin-5-yl.

18. The compound of claim 1, wherein $R^6$ is benzo[d][1,3]-dioxol-4-yl, benzo[d][1,3]dioxol-5-yl, benzofuran-4-yl, benzofuran-5-yl, benzofuran-6-yl, benzofuran-7-yl, 4-fluorobenzofuran-7-yl, benzo[d]imidazol-2-yl, benzo[d]imidazol-4-yl, 5-fluorobenzo[d]imidazol-2-yl, 1-methylbenzo[d]imidazol-2-yl, 2-hydroxybenzo[d]imidazol-6-yl, benzo[d]oxazol-5-yl, benzo[d]oxazol-6-yl, 2-methylbenzo[d]oxazol-6-yl, benzo[d]thiazol-4-yl, benzo[d]thiazol-6-yl, benzo[b]thien-2-yl, benzo[b]thien-3-yl, chroman-6-yl, 6-fluorochroman-8-yl, 2,3-dihydrobenzo[b][1,4]dioxin-6-yl, 2,3-dihydro[1,4]dioxino[2,3-b]pyridin-6-yl, 5,6-dihydro-imidazo[2,1-c][1,4]oxazin-2-yl, 2,3-dihydrobenzofuran-5-yl, 2,3-dihydrobenzofuran-7-yl, 5,6-dihydroimidazo[2,1-c][1,4]oxazin-3-yl, 3,4-dihydropyrano[2,3-c]pyridin-6-yl, furo[2,3-c]pyridin-5-yl, imidazo[1,2-a]pyridin-2-yl, imidazo[1,2-a]pyridin-3-yl, imidazo[1,2-a]pyridin-5-yl, imidazo[1,2-a]pyridin-6-yl, imidazo[1,2-a]pyridin-7-yl, imidazo[1,2-a]pyridin-8-yl, 2-methylimidazo[1,2-a]pyridin-3-yl, 3-methylimidazo[1,2-a]pyridin-2-yl, 5-methylimidazo[1,2-a]-pyridin-3-yl, 6-methylimidazo[1,2-a]pyridin-2-yl, 7-methylimidazo[1,2-a]pyridin-3-yl, imidazo-[1,5-a]pyridin-1-yl, 1-methylimidazo[4,5-b]pyridin-2-yl, imidazo[1,2-a]pyrimidin-3-yl, imidazo-[1,2-a]pyrimidin-7-yl, indazol-6-yl, 1-methylindazol-4-yl, 1-methylindazol-6-yl, 2-methyl-indazol-3-yl, 2-methylindazol-5-yl, indol-2-yl, indol-3-yl, indol-5-yl, indol-6-yl, indol-7-yl, 6-cyanoindol-2-yl, 6-cyanoindol-3-yl, 1-methylindol-5-yl, 1-methylindol-6-yl, 2-methylindol-4-yl, 3-methylindol-2-yl, 4-methylindol-3-yl, 6-methylindol-3-yl, 7-methylindol-3-yl, 1-tert-butoxy-carbonylindolin-6-yl, indolizin-1-yl, 1,3-dioxoisoindolin-2-yl, 1-oxoisoindolin-5-yl, 3-oxo-isoindolin-5-yl, isoquinolin-3-yl, isoquinolin-4-yl, isoquinolin-5-yl, isoquinolin-8-yl, 1-chloro-isoquinolin-5-yl, 1,8-naphthyridin-2-yl, pyrazolo[1,5-a]pyridin-3-yl, pyrazolo[1,5-a]pyridin-7-yl, pyrrolo[2,3-b]pyrazin-7-yl, pyrrolo[2,3-b]pyridin-6-yl, 5-methylpyrrolo[2,3-b]pyridin-3-yl, pyrrolo[2,3-c]pyridin-3-yl, pyrrolo[3,2-b]pyridin-3-yl, pyrrolo[3,2-b]pyridin-6-yl, quinazolin-6-yl, quinolin-4-yl, quinolin-6-yl, quinolin-8-yl, quinoxalin-2-yl, quinoxalin-5-yl, quinoxalin-6-yl, 1,2,3,4-tetrahydroisoquinolin-7-yl, 2-(2,2,2-trifluoroacetyl)-1,2,3,4-tetrahydroisoquinolin-7-yl, 2-oxo-1,2,3,4-tetrahydroquinolin-6-yl, thieno[2,3-b]pyridin-2-yl, thieno[3,2-c]pyridin-2-yl, or [1,2,4]triazolo[1,5-a]pyridin-7-yl.

19. The compound of claim 1, wherein Re is 1-methyl-azetidin-3-yl, oxetan-3-yl, 3-methyloxetan-3-yl, tetrahydro-pyran-4-yl, ethylpiperidin-4-yl, 1-benzylpiperidin-4-yl, 1-benzoxycarbonylpiperidin-4-yl, 1-(tert-butoxycarbonyl)piperidin-4-yl, 1-(ethylsulfonyl)-piperidin-4-yl, 1-(tert-butoxycarbonyl)-4-fluoropiperidin-4-yl, or 4-(tert-butoxy-carbonyl)-piperazin-1-yl.

20. The compound of claim 1, wherein c and d are each an integer of 1; and e and f are each an integer of 0.

21. The compound of claim 1, wherein c and d are each an integer of 0; and e and f are each an integer of 1.

22. The compound of claim 1, wherein the compound is:

3-(4-(7-(furan-2-carbonyl)-2,7-diazaspiro[3.5]nonan-2-yl)-1-oxoisoindolin-2-yl)-piperidine-2,6-dione E0001;

3-(4-(7-(furan-3-carbonyl)-2,7-diazaspiro[3.5]nonan-2-yl)-1-oxoisoindolin-2-yl)-piperidine-2,6-dione E0002;

3-(4-(7-(2-(1H-pyrrol-2-yl)acetyl)-2,7-diazaspiro[3.5]nonan-2-yl)-1-oxoisoindo-lin-2-yl)piperidine-2,6-dione E0003;

3-(4-(7-(2-(1H-pyrazol-1-yl)acetyl)-2,7-diazaspiro[3.5]nonan-2-yl)-1-oxoisoindo-lin-2-yl)piperidine-2,6-dione E0004;

3-(1-oxo-4-(7-(2-(pyrrolidin-1-yl)acetyl)-2,7-diazaspiro[3.5]nonan-2-yl)isoindo-lin-2-yl)piperidine-2,6-dione E0005;

3-(1-oxo-4-(7-(tetrahydro-2H-pyran-4-carbonyl)-2,7-diazaspiro[3.5]nonan-2-yl)-isoindolin-2-yl)piperidine-2,6-dione E0006;

3-(4-(7-(2-morpholinoacetyl)-2,7-diazaspiro[3.5]nonan-2-yl)-1-oxoisoindolin-2-yl)piperidine-2,6-dione E0007;

3-(2-(2-(2,6-dioxopiperidin-3-yl)-1-oxoisoindolin-4-yl)-2,7-diazaspiro[3.5]-nonane-7-carbonyl)benzonitrile E0008;

3-(1-oxo-4-(7-(2-(m-tolyl)acetyl)-2,7-diazaspiro[3.5]nonan-2-yl)isoindolin-2-yl)-piperidine-2,6-dione E0009;

3-(1-oxo-4-(7-(3-phenylpropanoyl)-2,7-diazaspiro[3.5]nonan-2-yl)isoindolin-2-yl)piperidine-2,6-dione E0010;

3-(1-oxo-4-(7-(3-(pyridin-2-yl)propanoyl)-2,7-diazaspiro[3.5]nonan-2-yl)iso-indolin-2-yl)piperidine-2,6-dione E0011;

3-(4-(7-(3-(hydroxymethyl)benzoyl)-2,7-diazaspiro[3.5]nonan-2-yl)-1-oxoiso-indolin-2-yl)piperidine-2,6-dione E0012;

3-(4-(7-(1H-pyrrole-2-carbonyl)-2,7-diazaspiro[3.5]nonan-2-yl)-1-oxoisoindolin-2-yl)piperidine-2,6-dione E0013;

3-(1-oxo-4-(7-(2-(m-tolyloxy)acetyl)-2,7-diazaspiro[3.5]nonan-2-yl)isoindolin-2-yl)piperidine-2,6-dione E0014;

3-(4-(7-(2-(2-methoxypyridin-3-yl)acetyl)-2,7-diazaspiro[3.5]nonan-2-yl)-1-oxo-isoindolin-2-yl)piperidine-2,6-dione E0015;

2-chloro-5-(2-(2-(2,6-dioxopiperidin-3-yl)-1-oxoisoindo-lin-4-yl)-2,7-diazaspiro-[3.5]nonane-7-carbonyl)benzonitrile E0016;

2-chloro-4-(2-(2-(2,6-dioxopiperidin-3-yl)-1-oxoisoindo-lin-4-yl)-2,7-diazaspiro-[3.5]nonane-7-carbonyl)benzonitrile E0017;

3-(1-oxo-4-(7-(3-(pyridin-3-yl)propanoyl)-2,7-diazaspiro[3.5]nonan-2-yl)iso-indolin-2-yl)piperidine-2,6-dione E0018;

3-(4-(7-(2,6-difluorobenzoyl)-2,7-diazaspiro[3.5]nonan-2-yl)-1-oxoisoindolin-2-yl)piperidine-2,6-dione E0019;

3-(4-(7-(2,5-difluorobenzoyl)-2,7-diazaspiro[3.5]nonan-2-yl)-1-oxoisoindolin-2-yl)piperidine-2,6-dione E0020;

3-(4-(7-(3,5-difluorobenzoyl)-2,7-diazaspiro[3.5]nonan-2-yl)-1-oxoisoindolin-2-yl)piperidine-2,6-dione E0021;

3-(4-(7-(2-methyl-2-phenylpropanoyl)-2,7-diazaspiro[3.5]nonan-2-yl)-1-oxoiso-indolin-2-yl)piperidine-2,6-dione E0022;

3-(1-oxo-4-(7-(pyrimidine-4-carbonyl)-2,7-diazaspiro[3.5]nonan-2-yl)isoindolin-2-yl)piperidine-2,6-dione E0023;

3-(4-(7-(1-methyl-1H-pyrrole-2-carbonyl)-2,7-diazaspiro[3.5]nonan-2-yl)-1-oxo-isoindolin-2-yl)piperidine-2,6-dione E0024;

3-(4-(7-(2-methyl-1H-imidazole-5-carbonyl)-2,7-diazaspiro[3.5]nonan-2-yl)-1-oxoisoindolin-2-yl)piperidine-2,6-dione E0025;

3-(4-(7-(2-(1H-1,2,3-triazol-1-yl)acetyl)-2,7-diazaspiro[3.5]nonan-2-yl)-1-oxo-isoindolin-2-yl)piperidine-2,6-dione E0026;

3-(4-(7-(2-cyclopentylacetyl)-2,7-diazaspiro[3.5]nonan-2-yl)-1-oxoisoindolin-2-yl)piperidine-2,6-dione E0027;

5-(2-(2-(2,6-dioxopiperidin-3-yl)-1-oxoisoindolin-4-yl)-2,7-diazaspiro[3.5]-nonane-7-carbonyl)-1H-pyrrole-2-carbonitrile E0028;

5-(2-(2-(2,6-dioxopiperidin-3-yl)-1-oxoisoindolin-4-yl)-2,7-diazaspiro[3.5]-nonane-7-carbonyl)-1H-pyrrole-3-carbonitrile E0029;

3-(1-oxo-4-(7-(2-(pyrimidin-2-yl)acetyl)-2,7-diazaspiro[3.5]nonan-2-yl)isoindo-lin-2-yl)piperidine-2,6-dionee E0030;

3-(1-oxo-4-(7-(2-(pyrimidin-5-yl)acetyl)-2,7-diazaspiro[3.5]nonan-2-yl)isoindo-lin-2-yl)piperidine-2,6-dione E0031;

3-(4-(7-(3-(1H-pyrrol-2-yl)propanoyl)-2,7-diazaspiro[3.5]nonan-2-yl)-1-oxoiso-indolin-2-yl)piperidine-2,6-dione E0032;

3-(4-(7-(1-methylpiperidine-4-carbonyl)-2,7-diazaspiro[3.5]nonan-2-yl)-1-oxoiso-indolin-2-yl)piperidine-2,6-dione E0033;

3-(1-oxo-4-(7-(2-(piperidin-1-yl)acetyl)-2,7-diazaspiro[3.5]nonan-2-yl)isoindo-lin-2-yl)piperidine-2,6-dione E0034;

3-(1-oxo-4-(7-(2-(tetrahydro-2H-pyran-4-yl)acetyl)-2,7-diazaspiro[3.5]nonan-2-yl)isoindolin-2-yl)piperidine-2,6-dione E0035;

3-(4-(7-benzyl-2,7-diazaspiro[3.5]nonan-2-yl)-1-oxoisoindolin-2-yl)piperidine-2,6-dione E1001;

3-(1-oxo-4-(7-(pyridin-3-ylmethyl)-2,7-diazaspiro[3.5]nonan-2-yl)isoindolin-2-yl)piperidine-2,6-dione E1002;

3-(1-oxo-4-(7-(pyridin-4-ylmethyl)-2,7-diazaspiro[3.5]nonan-2-yl)isoindolin-2-yl)piperidine-2,6-dione E1003;

3-(1-oxo-4-(7-(pyridin-2-ylmethyl)-2,7-diazaspiro[3.5]nonan-2-yl)isoindolin-2-yl)piperidine-2,6-dione E1004;

3-(1-oxo-4-(7-(pyrimidin-5-ylmethyl)-2,7-diazaspiro[3.5]nonan-2-yl)isoindolin-2-yl)piperidine-2,6-dione E1005;

3-(4-(7-((1-methyl-1H-imidazol-5-yl)methyl)-2,7-diazaspiro[3.5]nonan-2-yl)-1-oxoisoindolin-2-yl)piperidine-2,6-dione E1006;

3-(1-oxo-4-(7-phenethyl-2,7-diazaspiro[3.5]nonan-2-yl)isoindolin-2-yl)piperi-dine-2,6-dione E1007;

3-((2-(2-(2,6-dioxopiperidin-3-yl)-1-oxoisoindolin-4-yl)-2,7-diazaspiro[3.5]-nonan-7-yl)methyl)benzonitrile E1008;

2-((2-(2-(2,6-dioxopiperidin-3-yl)-1-oxoisoindolin-4-yl)-2,7-diazaspiro[3.5]-nonan-7-yl)methyl)benzonitrile E1009;

6-((2-(2-(2,6-dioxopiperidin-3-yl)-1-oxoisoindolin-4-yl)-2,7-diazaspiro[3.5]-nonan-7-yl)methyl) nicotinonitrile E1010;

3-(1-oxo-4-(7-(3-phenylpropyl)-2,7-diazaspiro[3.5]nonan-2-yl)isoindolin-2-yl)-piperidine-2,6-dione E1011;

3-(4-(7-(4-(hydroxymethyl)benzyl)-2,7-diazaspiro[3.5]nonan-2-yl)-1-oxoisoindo-lin-2-yl)piperidine-2,6-dione E1012;

2-((2-(2-(2,6-dioxopiperidin-3-yl)-1-oxoisoindolin-4-yl)-2,7-diazaspiro[3.5]-nonan-7-yl)methyl)-5-methoxybenzonitrile E1013;

3-chloro-5-((2-(2-(2,6-dioxopiperidin-3-yl)-1-oxoisoindolin-4-yl)-2,7-diazaspiro-[3.5]nonan-7-yl)methyl)benzonitrile E1014;

2-chloro-4-((2-(2-(2,6-dioxopiperidin-3-yl)-1-oxoisoindolin-4-yl)-2,7-diazaspiro-[3.5]nonan-7-yl)methyl)benzonitrile E1015;

3-(1-oxo-4-(7-((2-phenyl-1H-imidazol-5-yl)methyl)-2,7-diazaspiro[3.5]nonan-2-yl)isoindolin-2-yl)piperidine-2,6-dione E1016;

3-(1-oxo-4-(7-(4-(pyrrolidin-1-yl)benzyl)-2,7-diazaspiro[3.5]nonan-2-yl)isoindo-lin-2-yl)piperidine-2,6-dione E1017;

3-(4-(7-(4-((2-hydroxyethyl)(methyl)amino)benzyl)-2,7-diazaspiro[3.5]nonan-2-yl)-1-oxoisoindolin-2-yl)piperidine-2,6-dione E1018;

3-(4-(7-(4-(cyclopentyloxy)benzyl)-2,7-diazaspiro[3.5]nonan-2-yl)-1-oxoisoindo-lin-2-yl)piperidine-2,6-dione E1019;

3-(4-(7-(4-morpholinobenzyl)-2,7-diazaspiro[3.5]nonan-2-yl)-1-oxoisoindolin-2-yl)piperidine-2,6-dione E1020;

3-(4-(7-(3-morpholinobenzyl)-2,7-diazaspiro[3.5]nonan-2-yl)-1-oxoisoindolin-2-yl)piperidine-2,6-dione E1021;

3-(4-(7-(4-benzylbenzyl)-2,7-diazaspiro[3.5]nonan-2-yl)-1-oxoisoindolin-2-yl)-piperidine-2,6-dione E1022;

3-(1-oxo-4-(7-(4-(pyridin-3-yloxy)benzyl)-2,7-diazaspiro[3.5]nonan-2-yl)iso-indolin-2-yl)piperidine-2,6-dione E1023;

3-(1-oxo-4-(7-(pyrimidin-4-ylmethyl)-2,7-diazaspiro[3.5]nonan-2-yl)isoindolin-2-yl)piperidine-2,6-dione E1024;

3-(4-(7-(cyclohexylmethyl)-2,7-diazaspiro[3.5]nonan-2-yl)-1-oxoisoindolin-2-yl)-piperidine-2,6-dione E1025;

3-(1-oxo-4-(7-((tetrahydro-2H-pyran-4-yl)methyl)-2,7-diazaspiro[3.5]nonan-2-yl)isoindolin-2-yl)piperidine-2,6-dione E1026;

3-(4-(7-(4-methoxybenzyl)-2,7-diazaspiro[3.5]nonan-2-yl)-1-oxoisoindolin-2-yl)-piperidine-2,6-dione E1027;

3-(4-(7-(3-methoxybenzyl)-2,7-diazaspiro[3.5]nonan-2-yl)-1-oxoisoindolin-2-yl)-piperidine-2,6-dione E1028;

3-(4-(7-((6-methoxypyridin-3-yl)methyl)-2,7-diazaspiro[3.5]nonan-2-yl)-1-oxo-isoindolin-2-yl)piperidine-2,6-dione E1029;

3-(4-(7-((1H-indol-3-yl)methyl)-2,7-diazaspiro[3.5]nonan-2-yl)-1-oxoisoindolin-2-yl)piperidine-2,6-dione E1030;

3-(4-(7-(2-methoxyphenethyl)-2,7-diazaspiro[3.5]nonan-2-yl)-1-oxoisoindolin-2-yl)piperidine-2,6-dione E1031;

3-(1-oxo-4-(7-((6-(pyrrolidin-1-yl)pyridin-3-yl)methyl)-2,7-diazaspiro[3.5]-nonan-2-yl)isoindolin-2-yl)piperidine-2,6-dione E1032;

3-(4-(7-((5-(morpholinomethyl)furan-2-yl)methyl)-2,7-diazaspiro[3.5]nonan-2-yl)-1-oxoisoindolin-2-yl)piperidine-2,6-dione E1033;

3-(4-(7-((1-benzylpiperidin-4-yl)methyl)-2,7-diazaspiro[3.5]nonan-2-yl)-1-oxo-isoindolin-2-yl)piperidine-2,6-dione E1034;

3-(4-(7-((4-(benzyloxy)pyridin-2-yl)methyl)-2,7-diazaspiro[3.5]nonan-2-yl)-1-oxoisoindolin-2-yl)piperidine-2,6-dione E1035;

3-(1-oxo-4-(7-(4-((pyridin-2-yloxy)methyl)benzyl)-2,7-diazaspiro[3.5]nonan-2-yl)isoindolin-2-yl)piperidine-2,6-dione E1036;

3-(4-(7-(2-chloro-4-morpholinobenzyl)-2,7-diazaspiro[3.5]nonan-2-yl)-1-oxoiso-indolin-2-yl)piperidine-2,6-dione E1037;

3-(4-(7-(furan-3-ylmethyl)-2,7-diazaspiro[3.5]nonan-2-yl)-1-oxoisoindolin-2-yl)-piperidine-2,6-dione E1038;

3-(4-(7-(furan-2-ylmethyl)-2,7-diazaspiro[3.5]nonan-2-yl)-1-oxoisoindolin-2-yl)-piperidine-2,6-dione E1039;

3-(4-(7-((1H-pyrazol-4-yl)methyl)-2,7-diazaspiro[3.5]nonan-2-yl)-1-oxoisoindo-lin-2-yl)piperidine-2,6-dione E1040;

3-(5-(7-(furan-2-carbonyl)-2,7-diazaspiro[3.5]nonan-2-yl)-1-oxoisoindolin-2-yl)-piperidine-2,6-dione F0001;

3-(5-(7-(furan-3-carbonyl)-2,7-diazaspiro[3.5]nonan-2-yl)-1-oxoisoindolin-2-yl)-piperidine-2,6-dione F0002;

3-(5-(7-(2-(1H-pyrrol-2-yl)acetyl)-2,7-diazaspiro[3.5]nonan-2-yl)-1-oxoisoindo-lin-2-yl)piperidine-2,6-dione F0003;

3-(5-(7-(2-(1H-pyrazol-1-yl)acetyl)-2,7-diazaspiro[3.5]nonan-2-yl)-1-oxoisoindo-lin-2-yl)piperidine-2,6-dione F0004;

3-(1-oxo-5-(7-(2-(pyrrolidin-1-yl)acetyl)-2,7-diazaspiro[3.5]nonan-2-yl)-isoindo-lin-2-yl)piperidine-2,6-dione F0005;

3-(1-pxo-5-(7-(tetrahydro-2H-pyran-4-carbonyl)-2,7-diazaspiro[3.5]nonan-2-yl)-isoindolin-2-yl)piperidine-2,6-dione F0006;

3-(5-(7-(2-morpholinoacetyl)-2,7-diazaspiro[3.5]nonan-2-yl)-1-oxoisoindolin-2-yl)piperidine-2,6-dione F0007;

3-(2-(2-(2,6-dioxopiperidin-3-yl)-1-oxoisoindolin-5-yl)-2,7-diazaspiro[3.5]-nonane-7-carbonyl)benzonitrile F0008;

3-(1-oxo-5-(7-(2-(m-tolyl)acetyl)-2,7-diazaspiro[3.5]nonan-2-yl)isoindolin-2-yl)-piperidine-2,6-dione F0009;

3-(1-oxo-5-(7-(3-phenylpropanoyl)-2,7-diazaspiro[3.5]nonan-2-yl)isoindolin-2-yl)piperidine-2,6-dione F0010;

3-(1-oxo-5-(7-(3-(pyridin-2-yl)propanoyl)-2,7-diazaspiro[3.5]nonan-2-yl)iso-indolin-2-yl)piperidine-2,6-dione F0011;

3-(5-(7-(3-(hydroxymethyl)benzoyl)-2,7-diazaspiro[3.5]nonan-2-yl)-1-oxoiso-indolin-2-yl)piperidine-2,6-dione F0012;

3-(5-(7-(1H-pyrrole-2-carbonyl)-2,7-diazaspiro[3.5]nonan-2-yl)-1-oxoisoindolin-2-yl)piperidine-2,6-dione F0013;

3-(1-oxo-5-(7-(2-(m-tolyloxy)acetyl)-2,7-diazaspiro[3.5]nonan-2-yl)isoindolin-2-yl)piperidine-2,6-dione F0014;

3-(5-(7-(2-(2-methoxypyridin-3-yl)acetyl)-2,7-diazaspiro[3.5]nonan-2-yl)-1-oxo-isoindolin-2-yl)piperidine-2,6-dione F0015;

2-chloro-5-(2-(2-(2,6-dioxopiperidin-3-yl)-1-oxoisoindolin-5-yl)-2,7-diazaspiro-[3.5]nonane-7-carbonyl)benzonitrile F0016;

2-chloro-4-(2-(2-(2,6-dioxopiperidin-3-yl)-1-oxoisoindolin-5-yl)-2,7-diazaspiro-[3.5]nonane-7-carbonyl)benzonitrile F0017;

3-(1-oxo-5-(7-(3-(pyridin-3-yl)propanoyl)-2,7-diazaspiro[3.5]nonan-2-yl)iso-indolin-2-yl)piperidine-2,6-dione F0018;

3-(5-(7-(2,6-difluorobenzoyl)-2,7-diazaspiro[3.5]nonan-2-yl)-1-oxoisoindolin-2-yl)piperidine-2,6-dione F0019;

3-(5-(7-(2,5-difluorobenzoyl)-2,7-diazaspiro[3.5]nonan-2-yl)-1-oxoisoindolin-2-yl)piperidine-2,6-dione F0020;

3-(5-(7-(3,5-difluorobenzoyl)-2,7-diazaspiro[3.5]nonan-2-yl)-1-oxoisoindolin-2-yl)piperidine-2,6-dione F0021;

3-(5-(7-(2-methyl-2-phenylpropanoyl)-2,7-diazaspiro[3.5]nonan-2-yl)-1-oxoiso-indolin-2-yl)piperidine-2,6-dione F0022;

3-(1-oxo-5-(7-(pyrimidine-4-carbonyl)-2,7-diazaspiro[3.5]nonan-2-yl)isoindolin-2-yl)piperidine-2,6-dione F0023;

3-(5-(7-(1-methyl-1H-pyrrole-2-carbonyl)-2,7-diazaspiro[3.5]nonan-2-yl)-1-oxo-isoindolin-2-yl)piperidine-2,6-dione F0024;

3-(5-(7-(2-methyl-1H-imidazole-5-carbonyl)-2,7-diazaspiro[3.5]nonan-2-yl)-1-oxoisoindolin-2-yl)piperidine-2,6-dione F0025;

3-(5-(7-(2-(1H-1,2,3-triazol-1-yl)acetyl)-2,7-diazaspiro[3.5]nonan-2-yl)-1-oxo-isoindolin-2-yl)piperidine-2,6-dione F0026;

3-(5-(7-(2-cyclopentylacetyl)-2,7-diazaspiro[3.5]nonan-2-yl)-1-oxoisoindolin-2-yl)piperidine-2,6-dione F0027;

5-(2-(2-(2,6-dioxopiperidin-3-yl)-1-oxoisoindolin-5-yl)-2,7-diazaspiro[3.5]-nonane-7-carbonyl)-1H-pyrrole-2-carbonitrile F0028;

5-(2-(2-(2,6-dioxopiperidin-3-yl)-1-oxoisoindolin-5-yl)-2,7-diazaspiro[3.5]-nonane-7-carbonyl)-1H-pyrrole-3-carbonitrile F0029;

3-(1-oxo-5-(7-(2-(pyrimidin-2-yl)acetyl)-2,7-diazaspiro[3.5]nonan-2-yl)iso-indolin-2-yl)piperidine-2,6-dione F0030;

3-(1-oxo-5-(7-(2-(pyrimidin-5-yl)acetyl)-2,7-diazaspiro[3.5]nonan-2-yl)iso-indolin-2-yl)piperidine-2,6-dione F0031;

3-(5-(7-(3-(1H-pyrrol-2-yl)propanoyl)-2,7-diazaspiro[3.5]nonan-2-yl)-1-oxo-isoindolin-2-yl)piperidine-2,6-dione F0032;

3-(5-(7-(1-methylpiperidine-4-carbonyl)-2,7-diazaspiro[3.5]nonan-2-yl)-1-oxo-isoindolin-2-yl)piperidine-2,6-dione F0033;

3-(1-oxo-5-(7-(2-(piperidin-1-yl)acetyl)-2,7-diazaspiro[3.5]nonan-2-yl)isoindo-lin-2-yl)piperidine-2,6-dione F0034;

3-(1-oxo-5-(7-(2-(tetrahydro-2H-pyran-4-yl)acetyl)-2,7-diazaspiro[3.5]nonan-2-yl)isoindolin-2-yl)piperidine-2,6-dione F0035;

3-(5-(7-benzyl-2,7-diazaspiro[3.5]nonan-2-yl)-1-oxoisoindolin-2-yl)piperidine-2,6-dione F1001;

3-(1-oxo-5-(7-(pyridin-3-ylmethyl)-2,7-diazaspiro[3.5]nonan-2-yl)isoindolin-2-yl)piperidine-2,6-dione F1002;

3-(1-oxo-5-(7-(pyridin-4-ylmethyl)-2,7-diazaspiro[3.5]nonan-2-yl)isoindolin-2-yl)piperidine-2,6-dione F1003;

3-(1-oxo-5-(7-(pyridin-2-ylmethyl)-2,7-diazaspiro[3.5]nonan-2-yl)isoindolin-2-yl)piperidine-2,6-dione F1004;

3-(1-oxo-5-(7-(pyrimidin-5-ylmethyl)-2,7-diazaspiro[3.5]nonan-2-yl)isoindolin-2-yl)piperidine-2,6-dione F1005;

3-(5-(7-((1-methyl-1H-imidazol-5-yl)methyl)-2,7-diazaspiro[3.5]nonan-2-yl)-1-oxoisoindolin-2-yl)piperidine-2,6-dione F1006;

3-(1-oxo-5-(7-phenethyl-2,7-diazaspiro[3.5]nonan-2-yl)isoindolin-2-yl)piperi-dine-2,6-dione F1007;

3-((2-(2-(2,6-dioxopiperidin-3-yl)-1-oxoisoindolin-5-yl)-2,7-diazaspiro[3.5]-nonan-7-yl)methyl)benzonitrile F1008;

2-((2-(2-(2,6-dioxopiperidin-3-yl)-1-oxoisoindolin-5-yl)-2,7-diazaspiro[3.5]-nonan-7-yl)methyl)benzonitrile F1009;

6-((2-(2-(2,6-dioxopiperidin-3-yl)-1-oxoisoindolin-5-yl)-2,7-diazaspiro[3.5]-nonan-7-yl)methyl) nicotinonitrile F1010;

3-(1-oxo-5-(7-(3-phenylpropyl)-2,7-diazaspiro[3.5]nonan-2-yl)isoindolin-2-yl)-piperidine-2,6-dione F1011;

3-(5-(7-(4-(hydroxymethyl)benzyl)-2,7-diazaspiro[3.5]nonan-2-yl)-1-oxoisoindo-lin-2-yl)piperidine-2,6-dione F1012;

2-((2-(2-(2,6-dioxopiperidin-3-yl)-1-oxoisoindolin-5-yl)-2,7-diazaspiro[3.5]-nonan-7-yl)methyl)-5-methoxybenzonitrile F1013;

3-chloro-5-((2-(2-(2,6-dioxopiperidin-3-yl)-1-oxoisoindolin-5-yl)-2,7-diazaspiro-[3.5]nonan-7-yl)methyl)benzonitrile F1014;

2-chloro-4-((2-(2-(2,6-dioxopiperidin-3-yl)-1-oxoisoindolin-5-yl)-2,7-diazaspiro-[3.5]nonan-7-yl)methyl)benzonitrile F1015;

3-(1-oxo-5-(7-((2-phenyl-1H-imidazol-5-yl)methyl)-2,7-diazaspiro[3.5]nonan-2-yl)isoindolin-2-yl)piperidine-2,6-dione F1016;

3-(1-oxo-5-(7-(4-(pyrrolidin-1-yl)benzyl)-2,7-diazaspiro[3.5]nonan-2-yl)isoindo-lin-2-yl)piperidine-2,6-dione F1017;

3-(5-(7-(4-((2-hydroxyethyl)(methyl)amino)benzyl)-2,7-diazaspiro[3.5]nonan-2-yl)-1-oxoisoindolin-2-yl)piperidine-2,6-dione F1018;

3-(5-(7-(4-(cyclopentyloxy)benzyl)-2,7-diazaspiro[3.5]nonan-2-yl)-1-oxoisoindo-lin-2-yl)piperidine-2,6-dione F1019;

3-(5-(7-(4-morpholinobenzyl)-2,7-diazaspiro[3.5]nonan-2-yl)-1-oxoisoindolin-2-yl)piperidine-2,6-dione F1020;

3-(5-(7-(3-morpholinobenzyl)-2,7-diazaspiro[3.5]nonan-2-yl)-1-oxoisoindolin-2-yl)piperidine-2,6-dione F1021;

3-(5-(7-(4-benzylbenzyl)-2,7-diazaspiro[3.5]nonan-2-yl)-1-oxoisoindolin-2-yl)-piperidine-2,6-dione F1022;

3-(1-oxo-5-(7-(4-(pyridin-3-yloxy)benzyl)-2,7-diazaspiro[3.5]nonan-2-yl)iso-indolin-2-yl)piperidine-2,6-dione F1023;

3-(1-oxo-5-(7-(pyrimidin-4-ylmethyl)-2,7-diazaspiro[3.5]nonan-2-yl)isoindolin-2-yl)piperidine-2,6-dione F1024;

3-(5-(7-(cyclohexylmethyl)-2,7-diazaspiro[3.5]nonan-2-yl)-1-oxoisoindolin-2-yl)-piperidine-2,6-dione F1025;

3-(1-oxo-5-(7-((tetrahydro-2H-pyran-4-yl)methyl)-2,7-diazaspiro[3.5]nonan-2-yl)isoindolin-2-yl)piperidine-2,6-dione F1026;

3-(5-(7-(4-methoxybenzyl)-2,7-diazaspiro[3.5]nonan-2-yl)-1-oxoisoindolin-2-yl)-piperidine-2,6-dione F1027;

3-(5-(7-(3-methoxybenzyl)-2,7-diazaspiro[3.5]nonan-2-yl)-1-oxoisoindolin-2-yl)-piperidine-2,6-dione F1028;

3-(5-(7-((6-methoxypyridin-3-yl)methyl)-2,7-diazaspiro[3.5]nonan-2-yl)-1-oxo-isoindolin-2-yl)piperidine-2,6-dione F1029;

3-(5-(7-((1H-indol-3-yl)methyl)-2,7-diazaspiro[3.5]nonan-2-yl)-1-oxoisoindolin-2-yl)piperidine-2,6-dione F1030;

3-(5-(7-(2-methoxyphenethyl)-2,7-diazaspiro[3.5]nonan-2-yl)-1-oxoisoindolin-2-yl)piperidine-2,6-dione F1031;

3-(1-oxo-5-(7-((6-(pyrrolidin-1-yl)pyridin-3-yl)methyl)-2,7-diazaspiro[3.5]-nonan-2-yl)isoindolin-2-yl)piperidine-2,6-dione F1032;

3-(5-(7-((5-(morpholinomethyl)furan-2-yl)methyl)-2,7-diazaspiro[3.5]nonan-2-yl)-1-oxoisoindolin-2-yl)piperidine-2,6-dione F1033;

3-(5-(7-((1-benzylpiperidin-4-yl)methyl)-2,7-diazaspiro[3.5]nonan-2-yl)-1-oxo-isoindolin-2-yl)piperidine-2,6-dione F1034;

3-(5-(7-((4-(benzyloxy)pyridin-2-yl)methyl)-2,7-diazaspiro[3.5]nonan-2-yl)-1-oxoisoindolin-2-yl)piperidine-2,6-dione F1035;

3-(1-oxo-5-(7-(4-((pyridin-2-yloxy)methyl)benzyl)-2,7-diazaspiro[3.5]nonan-2-yl)isoindolin-2-yl)piperidine-2,6-dione F1036;

3-(5-(7-(2-chloro-4-morpholinobenzyl)-2,7-diazaspiro[3.5]nonan-2-yl)-1-oxo-isoindolin-2-yl)piperidine-2,6-dione F1037;

3-(5-(7-(furan-3-ylmethyl)-2,7-diazaspiro[3.5]nonan-2-yl)-1-oxoisoindolin-2-yl)-piperidine-2,6-dione F1038;

3-(5-(7-(furan-2-ylmethyl)-2,7-diazaspiro[3.5]nonan-2-yl)-1-oxoisoindolin-2-yl)-piperidine-2,6-dione F1039; or 3-(5-(7-((1H-pyrazol-4-yl)methyl)-2,7-diazaspiro[3.5]nonan-2-yl)-1-oxoisoindo-lin-2-yl)piperidine-2,6-dione F1040;

or an enantiomer, a mixture of enantiomers, a diastereomer, a mixture of two or more diastereomers, a tautomer, or a mixture of two or more tautomers thereof, or a pharmaceutically acceptable salt, solvate, or hydrate thereof.

23. A pharmaceutical composition comprising an effective amount of the compound of claim 1, or an enantiomer, a mixture of enantiomers, a diastereomer, a mixture of two or more diastereomers, a tautomer, or a mixture of two or more tautomers thereof; or a pharmaceutically acceptable salt, solvate, or hydrate thereof; and a pharmaceutically acceptable excipient.

* * * * *